US012473304B2

(12) United States Patent
Selvakumar et al.

(10) Patent No.: US 12,473,304 B2
(45) Date of Patent: Nov. 18, 2025

(54) HETEROCYCLIC PAD4 INHIBITORS

(71) Applicant: BRISTOL-MYERS SQUIBB COMPANY, Princeton, NJ (US)

(72) Inventors: Kumaravel Selvakumar, Bangalore (IN); Venkatram Reddy Paidi, Kamareddy (IN); Srinivasan Thangathirupathy, Hosur (IN); Vijaya Kumar Cm, Hosur (IN); Tirupathi Rao Alajangi, Vizianagaram (IN); Mallikarjun Reddy Sura, Kadapa (IN); Krishna Mahadevu, Mandya (IN); Ramesh Kumar Sistla, Bangalore (IN); Piyush Agarwal, Jodhpur (IN); Arul Mozhi Subbiah Karuppiah, Bangalore (IN); Jalathi S. Nair, Bangalore (IN); Ooha Morampudi, Khammam (IN); Manoranjan Panda, Bangalore (IN); Joseph A. Tino, Lawrenceville, NJ (US); Robert J. Cherney, Newtown, PA (US); John V. Duncia, Newtown, PA (US); Daniel S. Gardner, Furlong, PA (US); T. G. Murali Dhar, Newtown, PA (US); Audrey Graham Ross, Cambridge, MA (US); Paul E. Gormisky, Belmont, MA (US); Xiao Zhu, Winchester, MA (US); Boris M. Seletsky, Andover, MA (US); Alyssa H. Antropow, Boston, MA (US); Deqiang Niu, Lexington, MA (US); Zhengdong Zhu, Westborough, MA (US); Guobin Miao, Lexington, MA (US); Julio Hernan Cuervo, Arlington, MA (US)

(73) Assignee: Bristol-Myers Squibb Company, Princeton, NJ (US)

(*) Notice: Subject to any disclaimer, the term of this patent is extended or adjusted under 35 U.S.C. 154(b) by 658 days.

(21) Appl. No.: 17/799,028

(22) PCT Filed: Feb. 11, 2021

(86) PCT No.: PCT/US2021/017554
§ 371 (c)(1),
(2) Date: Aug. 11, 2022

(87) PCT Pub. No.: WO2021/163254
PCT Pub. Date: Aug. 19, 2021

(65) Prior Publication Data
US 2023/0167131 A1 Jun. 1, 2023

(30) Foreign Application Priority Data
Feb. 12, 2020 (IN) ............................ 202041006146

(51) Int. Cl.
*C07D 519/00* (2006.01)
*C07D 405/14* (2006.01)
(Continued)

(52) U.S. Cl.
CPC ......... *C07D 519/00* (2013.01); *C07D 405/14* (2013.01); *C07D 409/14* (2013.01);
(Continued)

(58) Field of Classification Search
CPC .. C07D 519/00; C07D 405/14; C07D 409/14; C07D 413/14; C07D 471/04;
(Continued)

(56) References Cited

U.S. PATENT DOCUMENTS

2007/0112048 A1 5/2007 Bavari et al.
2019/0276440 A1 9/2019 Zhao

FOREIGN PATENT DOCUMENTS

CN 103030627 A 4/2013
CN 108689942 A 10/2018
(Continued)

OTHER PUBLICATIONS

Berge et al Pharmaceutical Salts Journal of Pharmaceutical Sciences, vol. 66(1), pp. 1-19 (1977).
(Continued)

*Primary Examiner* — Joseph K McKane
*Assistant Examiner* — Meghan C Heasley
(74) *Attorney, Agent, or Firm* — Hong Liu

(57) ABSTRACT

(Ia)

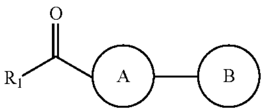

wherein

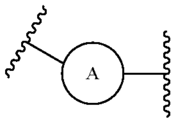

is

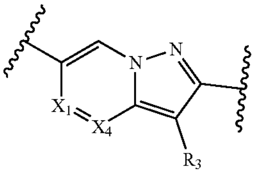

or

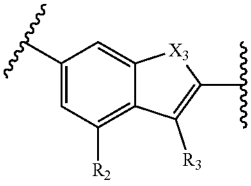

;

(Continued)

-continued

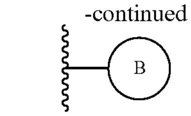

is

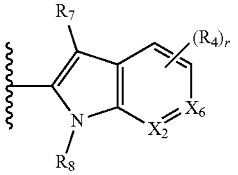

or

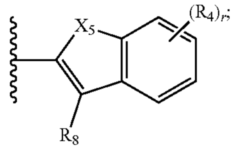

and $X_1$-$X_6$ and $R_1$-$R_8$, along with other variables are as defined herein.

The disclosure generally relates to substituted heterocyclic compounds of Formula (Ia), which are inhibitors of PAD4, method for preparing these compounds, pharmaceutical compositions comprising these compounds and use of these compounds in the treatment of a disease or a disorder associated with PAD4 enzyme activity.

29 Claims, No Drawings

(51) Int. Cl.

| | |
|---|---|
| ***C07D 409/14*** | (2006.01) |
| ***C07D 413/14*** | (2006.01) |
| ***C07D 471/04*** | (2006.01) |
| ***C07D 487/04*** | (2006.01) |

(52) U.S. Cl.
CPC ......... *C07D 413/14* (2013.01); *C07D 471/04* (2013.01); *C07D 487/04* (2013.01)

(58) Field of Classification Search
CPC .. C07D 487/04; C07D 403/14; C07D 407/14; C07D 401/14; A61K 45/06; A61K 31/437; A61P 19/02; A61P 25/28; A61P 29/00; A61P 35/00; A61P 37/00
See application file for complete search history.

(56) References Cited

FOREIGN PATENT DOCUMENTS

| | | | | |
|---|---|---|---|---|
| JP | 2010013386 | A | 1/2010 | |
| JP | 2018140974 | A | 9/2018 | |
| KR | 10150109111 | A | 10/2015 | |
| WO | 2000075117 | A1 | 12/2000 | |
| WO | 2006091972 | A2 | 8/2006 | |
| WO | 2007118137 | A1 | 10/2007 | |
| WO | 2008089125 | A2 | 7/2008 | |
| WO | 2009079011 | A1 | 6/2009 | |
| WO | 2013040528 | A1 | 3/2013 | |
| WO | 2013052263 | A2 | 4/2013 | |
| WO | WO-2014015905 | A1 * | 1/2014 | ........... A61K 31/407 |
| WO | 2014177593 | A1 | 11/2014 | |
| WO | 2016004513 | A1 | 1/2016 | |
| WO | 2016185279 | A1 | 11/2016 | |
| WO | 2017075694 | A1 | 5/2017 | |
| WO | 2017/100601 | A1 | 6/2017 | |
| WO | 2017108282 | A1 | 6/2017 | |
| WO | 2017/100594 | A1 | 7/2017 | |
| WO | 2017147102 | A1 | 8/2017 | |
| WO | 2018022897 | A1 | 2/2018 | |
| WO | 2018049296 | A1 | 3/2018 | |
| WO | 2019038195 | A1 | 2/2019 | |
| WO | 2019077631 | A1 | 4/2019 | |
| WO | 2020033488 | A1 | 2/2020 | |
| WO | 2020033490 | A1 | 2/2020 | |
| WO | 2020033514 | A1 | 2/2020 | |
| WO | 2020033520 | A1 | 2/2020 | |
| WO | 2021158840 | A1 | 8/2021 | |
| WO | 2021163254 | A1 | 8/2021 | |

OTHER PUBLICATIONS

Brinkmann et al., Neutrophil extracellular traps kill bacteria, Science vol. 303(5663) pp. 1532-1535 (2004).

Chang, et al., "Increased PADI4 expression in blood and tissues of patients with malignant tumors", BMC Cancer, vol. 9(40), pp. 1-11 (2009).

Chumanevich, et al., "Suppression of colitis in mice by CI-amidine: a novel peptidylarginine deiminase inhibitor", American J of Physiology, Gastrointestinal and Liver Physiology, vol. 300(6), pp. G929-G938 (2011).

Clark, et al., "Platelet TLR4 activates neutrophil extracellular traps to ensnare bacteria in septic blood", Nature Medicine, vol. 13(4), pp. 463-469 (2007).

Dworski et al., "Eosinophil and neutrophil extracellular DNA traps in human allergic asthmatic airways", The Journal of Allergy and Clinical Immunology, vol. 127(5), pp. 1260-1266 (2011).

Fuchs, et al., "Extracellular DNA traps promote thrombosis", PNAS, vol. 107(36), pp. 15880-15885 (2010).

Guo, et al., Synthesis of reversible PAD4 inhibitors via copper-catalyzed C—H arylation of benzimidazole Science China Chemistry the Frontiers of Chemical Biology and Synthesis vol. 62(5) pp. 592-596 (2019).

Hakkim et al., "Impairment of neutrophil extracellular trap degradation is associated with lupus nephritis", PNAS, vol. 107(21), pp. 9813-9818 (2010).

ISR issued by USPTO for Application No. PCT/US2016/065857 mailed Apr. 17, 2017 (10 pages).

Jones et al., "Protein arginine deiminase 4 (PAD4): current understanding and future therapeutic potential", Current Opinion in Drug Discovery & Development, vol. 12(5), pp. 616-627 (2009).

Kessenbrock et al., "Netting neutrophils in autoimmune small-vessel vasculitis", Nature Medicine, vol. 15(6), pp. 623-625 (2009).

Kochi et al., "PADI4 polymorphism predisposes male smokers to rheumatoid arthritis", Annals of the Rheumatic Diseases, vol. 70(3), pp. 512-515 (2011).

Lange et al., Peptidylarginine Deiminases as Mediators of Microvesicular Release Novel Therapeutic Interventions 2017.

Lange et al., "Protein deiminases: New players in the developmentally regulated loss of neutral regenerative ability", Developmental Biology, vol. 355(2), 205-214 (2011).

Lewis et al., "Inhibition of PAD4 activity is sufficient to disrupt mouse and human NET formation", Nature Chemical Biology, vol. 11(3) pp. 189-191 (2015).

Li et al., "PAD4 is essential for antibacterial innate immunity mediated by neutrophil extracellular traps", JEM, vol. 207 (9), pp. 1853-1862 (2010).

Li et al., "Regulation of p53 Target Gene Expression by Peptidylarginine Deiminase 4", Molecular and Cellular Biology, vol. 28(15), pp. 4745-4758 (2008).

Lin et al., "Mast Cells and Neutrophils Release IL-17 through Extracellular Trip Formation in Psoriasis", The Journal of Immunology, vol. 187(1), pp. 490-500 (2011).

Neeli et al., "Histone Deimination as a Response to Inflammatory Stimuli in Neutrophils", The Journal of Immunology, vol. 108(3), pp. 1895-1902 (2008).

Pubchem, "Substance Record for SID 1730220505," retrieved from http://pubchem.ncbi.nim.nih.gov/substance/173022050#section=Top accessed on Mar. 24, 2018 (5 pages).

(56) References Cited

OTHER PUBLICATIONS

Savchenko et al., "Long pentraxin 3 (PTX3) expression and release by neutrophils in nitro and in ulcerative colitis", Pathology International, 2011, vol. 61, pp. 290-297.
Slack et al., "Protein Arginine Deiminase 4: a target for an epigenetic cancer therapy", Cellular and Molecular Life Sciences, vol. 68(4), pp. 709-720 (2011).
Villanueva et al., "Netting Neutrophils Induce Endothelial Damage, Infiltrate Tissues, and Expose Immunostimulatory Molecules in Systemic Lupus Erythematosus", The Journal of Immunology, vol. 187(1), pp. 538-552 (2011).
Vitkov et al., "Neutrophil Fate in Gingival Crevicular Fluid", Ultrastructrual Pathology, vol. 34(1), pp. 1-6 (2010).
Wegner et al., "Autoimmunity to specific citrullinated proteins gives the first clues to the etiology of rheumatoid arthritis", Immunological Reviews, vol. 233(1), pp. 34-54 (2010).
Willis et al., "N-a-Benzoyl-N5-(2-Chloro-1-Iminoethyl)-L-Ornithine Amide, a Protein Arginine Deiminase Inhibitor, Reduces the Severity of Murine Collagen-Induced Arthritis", The J. of Immunology, vol. 186(7), pp. 4396-4404 (2011).

* cited by examiner

HETEROCYCLIC PAD4 INHIBITORS

CROSS-REFERENCE TO RELATED APPLICATIONS

This application is a 371 application of PCT/US2021/017554, filed on Feb. 11, 2021, which claims the benefit of Indian Provisional Application No. 202041006146, filed Feb. 12, 2020, the contents of which are specifically incorporated by reference herein their entireties.

FIELD OF THE INVENTION

The invention generally relates to substituted heterocyclic compounds, methods for preparing these compounds, pharmaceutical compositions comprising these compounds, and use of these compounds in the treatment of a disease or a disorder associated with PAD4 enzyme activity.

BACKGROUND OF THE INVENTION

PAD4 is a member of the peptidylarginine deiminase (PAD) family of enzymes capable of catalysing the citrullination of arginine into citrulline within peptide sequences. PAD4 is responsible for the deimination or citrullination of a variety of proteins in vitro and in vivo, with consequences of diverse functional responses in a variety of diseases (Jones J. E. et al, *Curr. Opin. Drug Discov. Devel.,* 12(5), (2009), 616-627). Examples of exemplar diseases or disorders include rheumatoid arthritis, diseases with neutrophilic contributions to pathogenesis (for example vasculitis, systemic lupus erythematosus, ulcerative colitis) in addition to oncology indications. PAD4 inhibitors also have wider applicability as tools and therapeutics for human diseases and disorders through epigenetic mechanisms.

Inhibitors of PAD4 have utility against Rheumatoid Arthritis (RA). RA is an autoimmune disease affecting approximately 1% of the population (Wegner N. et al, *Immunol. Rev.,* 233(1), (2010), 34-54). It is characterized by inflammation of articular joints leading to debilitating destruction of bone and cartilage. A weak genetic association between PAD4 polymorphisms and susceptibility to RA has been suggested, albeit inconsistently, in a number of population studies (Kochi Y. et al, *Ann. Rheum. Dis.,* 70, (2011), 512-515). PAD4 (along with family member PAD2) has been detected in synovial tissue where it is responsible for the deimination of a variety of joint proteins. This process is presumed to lead to a break of tolerance to, and initiation of immune responses to, citrullinated substrates such as fibrinogen, vimentin and collagen in RA joints. These anti-citrullinated protein antibodies (ACPA) contribute to disease pathogenesis and may also be used as a diagnostic test for RA (e.g. the commercially available CCP2 or cyclic citrullinated protein 2 test). In addition, increased citrullination may also offer additional direct contributions to disease pathogenesis through its ability to affect directly the function of several joint and inflammatory mediators (e.g. fibrinogen, anti-thrombin, and multiple chemokines). In a smaller subset of RA patients, anti-PAD4 antibodies can be measured and may correlate with a more erosive form of the disease.

PAD4 inhibitors are also useful for the reduction of pathological neutrophil activity in a variety of diseases. Studies suggest that the process of Neutrophil Extracellular Trap (NET) formation, an innate defense mechanism by which neutrophils are able to immobilize and kill pathogens, is associated with histone citrullination and is deficient in a PAD4 knockout mice (Neeli I. et al, *J. Immunol.,* 180, (2008), 1895-1902, and Li P. et al, *J. Exp. Med.,* 207(9), (2010), 1853-1862). PAD4 inhibitors may therefore have applicability for diseases where NET formation in tissues contributes to local injury and disease pathology. Such diseases include, but are not limited to, small vessel vasculitis (Kessenbrock K. et al, *Nat. Med.,* 15(6), (2009), 623-625), systemic lupus erythematosus (Hakkim A. et al, *Proc. Natl. Acad. Sci. USA,* 107(21), (2010), 9813-9818, and Villanueva E. et al, *J. Immunol.,* 187(1), (2011), 538-52), ulcerative colitis (Savchenko A. et al, *Pathol. Int.,* 61(5), (2011), 290-7), cystic fibrosis, asthma (Dworski R. et al, *J. Allergy Clin. Immunol.,* 127(5), (2011), 1260-6), deep vein thrombosis (Fuchs T. et al, *Proc. Natl. Acad. Sci. USA,* 107(36), (2010), 15880-5), periodontitis (Vitkov L. et al, *Ultrastructural Pathol.,* 34(1), (2010), 25-30), sepsis (Clark S. R. et al, *Nat. Med.,* 13(4), (2007), 463-9), appendicitis (Brinkmann V. et al, *Science,* 303, (2004), 1532-5), and stroke. In addition, there is evidence that NETs may contribute to pathology in diseases affecting the skin, e.g., in cutaneous lupus erythematosis (Villanueva E. et al, *J. Immunol.,* 187(1), (2011), 538-52) and psoriasis (Lin A. M. et al., *J. Immunol.,* 187(1), (2011), 490-500), so a PAD4 inhibitor may show benefit to tackle NET skin diseases, when administered by a systemic or cutaneous route. PAD4 inhibitors may affect additional functions within neutrophils and have wider applicability to neutrophilic diseases.

Studies have demonstrated efficacy of tool PAD inhibitors (for example, chloro-amidine) in a number of animal models of disease, including collagen-induced arthritis (Willis V. C. et al, *J. Immunol.,* 186(7), (2011), 4396-4404), dextran sulfate sodium (DSS)-induced experimental colitis (Chumanevich A. A. et al, *Am. J. Physiol. Gastrointest. Liver Physiol.,* 300(6), (2011), G929-G938), spinal cord repair (Lange S. et al, *Dev. Biol.,* 355(2), (2011), 205-14), and experimental autoimmune encephalomyelitis (EAE). The DSS colitis report also demonstrates that chloro-amidine drives apoptosis of inflammatory cells both in vitro and in vivo, suggesting that PAD4 inhibitors may be effective more generally in widespread inflammatory diseases.

PAD4 inhibitors are also useful in the treatment of cancers (Slack J. L. et al, *Cell. Mol. Life Sci.,* 68(4), (2011), 709-720). Over-expression of PAD4 has been demonstrated in numerous cancers (Chang X. et al, *BMC Cancer,* 9, (2009), 40). An anti-proliferative role has been suggested for PAD4 inhibitors from the observation that PAD4 citrullinates arginine residues in histones at the promoters of p53-target genes such as p21, which are involved in cell cycle arrest and induction of apoptosis (Li P. et al, *Mol. Cell Biol.,* 28(15), (2008), 4745-4758).

The aforementioned role of PAD4 in deiminating arginine residues in histones may be indicative of a role for PAD4 in epigenetic regulation of gene expression. PAD4 is the primary PAD family member observed to be resident in the nucleus as well as the cytoplasm. Early evidence that PAD4 may act as a histone demethyliminase as well as a deiminase is inconsistent and unproven. However, it may reduce histone arginine methylation (and hence epigenetic regulation associated with this mark) indirectly via depletion of available arginine residues by conversion to citrulline. PAD4 inhibitors are useful as epigenetic tools or therapeutics for affecting expression of varied target genes in additional disease settings. Through such mechanisms, PAD4 inhibitors may also be effective in controlling citrullination levels in stem cells and may therefore therapeutically affect the pluripotency status and differentiation potential of diverse stem cells including, but not limited to, embryonic stem cells, neural stem cells, haematopoietic stem cells and cancer stem cells. Accordingly, there remains an unmet need to identify and develop PAD4 inhibitors for the treatment of PAD4-mediated diseases or disorders.

SUMMARY OF THE INVENTION

Accordingly, there are provided compounds of Formula (Ia):

(Ia)

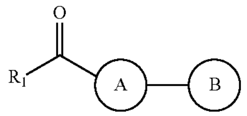

or a stereoisomer, an enantiomer, a diastereomer, a tautomer, or a pharmaceutically acceptable salt thereof.

In another general aspect, there are provided pharmaceutical compositions comprising at least one compound of Formula (I), or a stereoisomer, an enantiomer, a diastereomer, a tautomer, or a pharmaceutically acceptable salt thereof, and one or more pharmaceutically acceptable carriers.

In another general aspect, there is provided a method of treating a disease or a disorder associated with PAD4 enzyme activity, comprising administering to a subject in need of such treatment, a therapeutically effective amount of at least one compound of Formula (I), or a stereoisomer, an enantiomer, a diastereomer, a tautomer, or a pharmaceutically acceptable salt thereof.

The details of one or more embodiments of the invention are set forth in the description below. Other features, objects and advantages of the invention will be apparent from the following description including claims.

DETAILED DESCRIPTION OF THE INVENTION

1. Definitions

The following are definitions of terms used in this specification. The initial definition provided for a group or term herein applies to that group or term throughout the specification, individually or as part of another group, unless otherwise indicated. Although the invention is described with reference to exemplary embodiments, it should nevertheless be understood that no limitation of the scope of the invention is thereby intended. Numerous alterations and further modifications of the inventive features of the invention can be envisaged by one skilled in the relevant art, and having possession of this disclosure. All such alterations and modifications are to be considered within the scope of the invention. It must be noted that, as used in this specification and the appended claims, the singular forms "a", "an", and "the" include plural references unless the content clearly dictates otherwise. All references including patents, patent applications, and literature cited in the specification are expressly incorporated herein by reference in their entirety.

The term "$C_{1-6}$ alkyl" as used herein refers to and includes cyclic, straight and branched chain hydrocarbon groups containing 1 to 6 carbon atoms. Typical, non-limiting examples of $C_{1-6}$ alkyl include methyl, ethyl, propyl, isopropyl, butyl, t-butyl, isobutyl, pentyl, hexyl, isohexyl, cyclopropyl, cyclobutyl, cyclopentyl, cyclohexyl, and the like.

The term "alkenyl" as used herein refers to and includes straight or branched chain hydrocarbon groups containing 2 to 20 carbons, which include 1 to 6 double bonds. Typical, non-limiting examples of alkenyl include vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, and the like.

The term "alkynyl" as used herein refers to and includes straight or branched chain hydrocarbon groups containing 2 to 12 carbon atoms, and at least one carbon to carbon triple bond. Typical, non-limiting examples of alkynyl include ethynyl, 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, and the like.

The term "cycloalkyl" as used herein refers to and includes a saturated or partially unsaturated (containing 1 or 2 double bonds) cyclic hydrocarbon group containing 1 to 3 rings (for example, monocyclic, bicyclic, or tricyclic), and containing a total of 3 to 20 carbon atoms forming the rings. The cycloalkyl may be optionally substituted. The rings of multi-ring cycloalkyls may exist as fused, bridged and/or joined through one or more spiro union to 1 or 2 aromatic cycloalkyl or heterocyclic rings. Typical, non-limiting examples of cycloalkyl groups include cyclopropyl, cyclobutyl, cyclopentyl, cyclohexyl, cycloheptyl, cyclooctyl, cyclodecyl, cyclododecyl, cyclopentenyl, cyclohexenyl, cycloheptenyl, cyclooctenyl, cyclohexadienyl, cycloheptadienyl, and the like.

The terms "heterocyclic", "heterocyclyl" or "heterocyclo" as used herein refers to and includes optionally substituted, saturated, unsaturated or partially unsaturated 3 to 20 member cyclic groups (for example, 3 to 13 member monocyclic, 7 to 17 member bicyclic, or 10 to 20 member tricyclic ring systems), which have at least one heteroatom in at least one carbon atom-containing ring. The heteroatom is selected from nitrogen, oxygen and/or sulfur atoms. Each ring of the heterocyclic group may have 1, 2, 3, 4 or 5 heteroatoms, subject to a condition that that at least one ring contains at least one heteroatom. The nitrogen and sulfur heteroatoms may optionally be oxidized and the nitrogen heteroatoms may optionally be quaternized. The rings of multi-ring heterocycles may be fused, bridged and/or joined through one or more spiro unions. Typical, non-limiting examples of heterocyclic groups include azetidinyl, pyrrolidinyl, oxetanyl, imidazolinyl, oxazolidinyl, isoxazolinyl, thiazolidinyl, isothiazolidinyl, tetrahydrofuranyl, piperidinyl, piperazinyl, 2-oxopiperazinyl, 2-oxopiperidinyl, 2-oxopyrrolodinyl, 2-oxoazepinyl, azepinyl, 4-piperidonyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, and the like.

The term "aryl" as used herein refers to and includes aromatic homocyclic (i.e., hydrocarbon) monocyclic, bicyclic or tricyclic aromatic groups containing 6 to 14 carbons in the ring portion, and may optionally include one to three additional rings (either cycloalkyl, heterocyclo or heteroaryl) fused thereto. Typical, non-limiting examples of aryl groups includes phenyl, biphenyl, naphthyl (including 1-naphthyl, and 2-naphthyl), anthracenyl, and the like.

The above-defined groups may optionally have one or more hydrogen atoms that are attached to a carbon atom substituted with any group known to one of skill in the art. Throughout the specification, groups and substituents thereof may be chosen to provide stable moieties and compounds.

The term "subject" as used herein refers to and includes any human or non-human organism that could potentially benefit from treatment with a PAD4 inhibitor. Exemplary subjects include humans and animals.

The terms "treating" or "treatment" as used herein refer to and include treatment of a disease-state in a subject, for example in a human or animal, and include: (a) inhibiting the disease-state, i.e., arresting it's development; (b) relieving the disease-state, i.e., causing regression of the disease state; and/or (c) preventing the disease-state from occurring in a subject.

The terms "preventing" or "prevention" as used herein refer to and include preventive treatment (i.e. prophylaxis and/or risk reduction) of a sub clinical disease-state in a subject, for example in a human or animal, aimed at reducing the probability of the occurrence of a clinical disease-state. Subjects may be selected for preventative therapy based on factors that are known to increase risk of suffering a clinical disease state compared to the general population. "Prophylaxis" therapies can be divided into (a) primary prevention, and (b) secondary prevention. Primary prevention is defined as treatment in a subject that has not yet presented with a clinical disease state, whereas secondary prevention is defined as preventing a second occurrence of the same or similar clinical disease state.

The term "therapeutically effective amount" refers to and includes an amount of a compound or a composition according to the invention that is effective when administered alone or in combination to prevent or treat the disease or disorder associated with PAD4 enzyme activity. When applied to a combination, the term refers to combined amounts of the active ingredients that result in the preventive or therapeutic effect, whether administered in combination, serially, or simultaneously.

A "pharmaceutically acceptable carrier" refers to media generally accepted in the art for the delivery of biologically active agents to humans and/or animals. Pharmaceutically acceptable carriers are formulated according to a number of factors well within the purview of those of ordinary skill in the art. These include, without limitation, the type and nature of the active agent being formulated, the subject to which the agent-containing composition is to be administered, the intended route of administration of the compound or composition, and, the therapeutic indication being targeted. Pharmaceutically acceptable carriers include both aqueous and non-aqueous liquid media. Such carriers can include a number of different ingredients and additives in addition to the active agent, such additional ingredients being included in the formulation for a variety of reasons, e.g., stabilization of the active agent, binders, etc., well known to those of ordinary skill in the art. Typical, non-limiting examples of such carriers include diluents, preserving agents, fillers, flow regulating agents, disintegrating agents, wetting agents, emulsifying agents, suspending agents, sweetening agents, flavouring agents, perfuming agents, anti-bacterial agents, anti-fungal agents, lubricating agents, dispensing agents, coating agents, and the like. Descriptions of suitable pharmaceutically acceptable carriers, and factors involved in their selection, are found in a variety of readily available sources such as, for example, Allen, L. V., Jr. et al., *Remington: The Science and Practice of Pharmacy* (*2 Volumes*), *22nd Edition, Pharmaceutical Press* (2012).

Prodrugs and solvates of the compounds of the invention are also contemplated herein. The term "prodrug", as employed herein, denotes a compound, which, upon administration to a subject, undergoes chemical conversion by metabolic or chemical processes to yield a compound of Formula (I), or a salt and/or solvate thereof. Solvates of the compounds of Formula (Ia) include hydrates.

Any tautomer, which may exist, is also contemplated herein as a part of the present invention. All stereoisomers of the compound of Formula (Ia), such as those, which may exist due to asymmetric carbons, including enantiomeric forms (which may exist even in the absence of asymmetric carbons, e.g., atropisomers) and diastereomeric forms are contemplated within the scope of this invention. Individual stereoisomers of the compound of Formula (Ia) may, for example, be substantially free of other isomers, or may be admixed, for example, as racemates or with all other, or other selected, stereoisomers. The chiral centres in these compounds may have the S or R configuration as defined by the IUPAC 1974 Recommendations. In general, the compounds according to the invention may be described herein without specific stereochemistry for convenience, however all stereoisomeric forms are included within the scope of the invention.

The present invention is intended to include all isotopes of atoms occurring in the present compounds. Isotopes include those atoms having the same atomic number but different mass numbers. By way of general example and without limitation, isotopes of hydrogen include deuterium (symbol D or $^{2}H$) and tritium (symbol T or $^{3}H$). For example, a methyl group may be represented by $CH_3$ or $CD_3$. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

The compound of Formula (I) forms salts which are also within the scope of this invention. Reference to a compound of the Formula (I) herein is understood to include reference to salts thereof, unless otherwise indicated. The term "salt (s)", as employed herein, denotes acidic and/or basic salts formed with inorganic and/or organic acids and bases. In addition, when a compound of Formula (I) contains both a basic moiety and an acidic moiety, zwitterions ("inner salts") may be formed and are included within the term "salt(s)" as used herein. Pharmaceutically acceptable salts include those generally acceptable in the art of pharmaceutical sciences for administration in a subject, including humans and animals. In general, the pharmaceutically acceptable salts are non-toxic and physiologically acceptable salts. Salts of the compounds according to the invention may be formed, for example, by reacting the compound with an amount of acid or base, such as an equivalent amount, in a medium such as one in which the salt precipitates or in an aqueous medium followed by lyophilization.

The compounds of Formula (Ia) which contain a basic moiety may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecyl sulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

The compounds of Formula (Ia) which contain an acidic moiety may form salts with a variety of organic and inorganic bases. Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines (formed with N,N-bis(dehydroabietyl)-ethylenediamine), N-methyl-D-glucamines, N-methyl-D-glucamides, t-butyl amines, and salts with amino acids such as arginine, lysine and the like. Basic nitrogen-containing groups may be quaternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

The invention encompasses compounds of Formula (I), including their stereoisomers, enantiomers, diastereomers, tautomers, and pharmaceutically acceptable salts, methods for preparing these compounds, pharmaceutical compositions comprising these compounds, and use of these compounds in the treatment of diseases or disorders associated with PAD4 enzyme activity.

2. Description of Certain Aspects of the Invention

In a first aspect, the invention provides a compound of Formula (I):

(I)

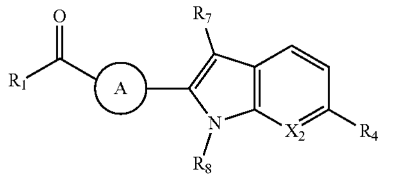

or a pharmaceutically acceptable salt thereof, wherein:

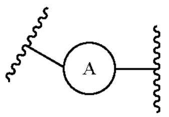

is independently selected from

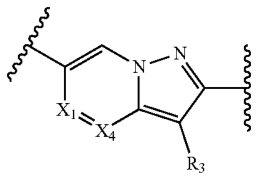

or

-continued

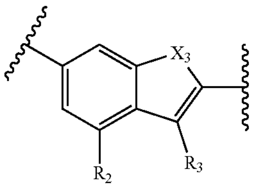

;

$X_1$ and $X_2$ are independently selected from CH and N;

$X_3$ is independently selected from O and S;

$X_4$ is independently selected from $CR_2$ and N; provided $X_1$ and $X_4$ are not both N;

$R_1$ is independently selected from —NH—$C_{1-5}$ alkyl optionally substituted with one or more substituents selected from F, Cl, and $NH_2$, 4-10 membered heterocyclyl, and —NH-4-10 membered heterocyclyl, wherein said heterocyclyl is optionally substituted with one or more substituents selected from F, Cl, CN, $C_{1-3}$ alkyl, =N—$OR_b$, —$(CH_2)_rOR_b$, —$(CH_2)_rNR_aR_a$, —$NR_aC$(=NH)$C_{1-3}$alkyl, —$NR_aC$(=O)$OR_b$, carbocyclyl, and heterocyclyl;

$R_2$ is independently selected from H, F, Cl, $C_{1-4}$ alkyl, and —$OC_{1-4}$ alky;

$R_3$ is independently selected from H, F, Cl, —CN, —C(=O)$OR_b$, and $C_{1-3}$ alkyl optionally substituted with one or more substituents selected from F, Cl, and OH;

$R_4$ is independently selected from H, F, Cl, Br, —C(=O)$R_b$, $C_{1-6}$ alkyl optionally substituted with one or more substituents selected from F, Cl, —OH, —NH—$C_{1-6}$ alkyl optionally substituted with one or more substituents selected from F, Cl, and OH, and $C_{3-6}$ cycloalkyl, —$(CH_2)_r$-aryl substituted with one or more $R_5$, —$(CH_2)_r$—$C_{3-12}$ cycloalkyl substituted with one or more $R_5$, and —$(CH_2)_r$-4-10 membered heterocyclyl comprising carbon atoms and 1-5 heteroatoms selected from N, $NR_6$, O, and S and substituted with one or more $R_5$;

$R_5$ is independently selected from H, F, Cl, Br, —CN, =O, $C_{1-4}$alkyl optionally substituted with one or more $R_e$, $C_{2-4}$alkenyl optionally substituted with one or more $R_e$, $C_{2-4}$alkynyl optionally substituted with one or more $R_e$, —$(CR_dR_d)_rOR_b$, —$(CR_dR_d)_rS(O)_pR_c$, —$(CR_dR_d)_rS(O)_pNR_aR_a$, —$(CR_dR_d)_rNR_aS(O)_pR_c$, —$(CR_dR_d)_rNR_aR_a$, —$(CR_dR_d)_rNR_aC$(=O)$R_b$, —$(CR_dR_d)_rNR_aC$(=O)$OR_b$, —$(CR_dR_d)_rNR_aC$(=O)$NR_aR_a$, —$(CR_dR_d)_rC$(=O)$R_b$, —$(CR_dR_d)_rC$(=O)$OR_b$, —$(CR_dR_d)_rC$(=O)$NR_aR_a$, —$(CR_dR_d)_rOC$(=O)$R_b$, —$(CR_dR_d)_rOC$(=O)$OR_b$, —$(CR_dR_d)_rO(CH_2)_rC$(=O)$NR_aR_a$, $C_{3-6}$cycloalkyl optionally substituted with one or more $R_e$, aryl optionally substituted with one or more $R_e$, and heterocyclyl optionally substituted with one or more $R_e$;

$R_6$ is independently selected from H, $C_{1-6}$alkyl optionally substituted with one or more $R_e$, —$S(O)_pR_c$, —$S(O)_pNR_aR_a$, —C(=O)$R_b$, —C(=O)$OR_b$, —C(=O)$NR_aR_a$, $C_{3-6}$cycloalkyl optionally substituted with one or more $R_e$, aryl optionally substituted with one or more $R_e$, and heterocyclyl optionally substituted with one or more $R_e$;

$R_7$ is independently selected from H, F, and Cl;

$R_8$ is independently selected from H and $C_{1-6}$ alkyl optionally substituted with one or more substituents selected from F, Cl, and $C_{3-6}$ cycloalkyl;

$R_a$ is independently selected from H, $C_{1-6}$ alkyl optionally substituted with one or more $R_e$, $C_{2-6}$ alkenyl optionally substituted with one or more $R_e$, $C_{2-6}$ alkynyl optionally substituted with one or more $R_e$, —$(CH_2)_r$—$C_{3-10}$carbocyclyl optionally substituted with one or more $R_e$, and —$(CH_2)_r$-heterocyclyl optionally substituted with one or more $R_e$; or $R_a$ and $R_a$ together with the nitrogen atom to which they are both attached form a heterocyclic ring optionally substituted with one or more $R_e$;

$R_b$ is independently selected from H, $C_{1-6}$ alkyl optionally substituted with one or more $R_e$, $C_{2-6}$ alkenyl optionally substituted with one or more $R_e$, $C_{2-6}$ alkynyl optionally substituted with one or more $R_e$, —$(CH_2)_r$—$C_{3-10}$carbocyclyl optionally substituted with one or more $R_e$, and —$(CH_2)_r$-heterocyclyl optionally substituted with one or more $R_e$;

$R_e$ is independently selected from $C_{1-6}$ alkyl optionally substituted with one or more $R_e$, $C_{2-6}$alkenyl optionally substituted with one or more $R_e$, $C_{2-6}$ alkynyl optionally substituted with one or more $R_e$, —$(CH_2)_r$—$C_{3-6}$ carbocyclyl optionally substituted with one or more $R_e$, and —$(CH_2)_r$-heterocyclyl optionally substituted with one or more $R_e$;

$R_d$ is independently selected from H, $C_{1-6}$ alkyl optionally substituted with one or more $R_e$, $R_e$ is independently selected from F, Cl, Br, —CN, —$NH_2$, —$NHC_{1-4}$alkyl, —$N(C_{1-4}alkyl)_2$, =O, OH, $OC_{1-6}$ alkyl, —$CO_2H$, $C_{1-6}$ alkyl optionally substituted with one or more $R_f$, $C_{2-6}$ alkenyl, $C_{2-6}$ alkynyl, —$(CH_2)_r$—$C_{3-6}$ cycloalkyl optionally substituted with one or more $R_f$, —$(CH_2)_r$-aryl optionally substituted with one or more $R_f$, —$(CH_2)_r$-heterocyclyl optionally substituted with one or more $R_f$;

$R_f$ is independently selected from F, Cl, Br, —CN, —OH, $C_{1-5}$ alkyl optionally substituted with —OH, $C_{2-5}$ alkenyl, $C_{2-5}$ alkynyl, $C_{3-6}$ cycloalkyl, and phenyl;

p, at each occurrence, is independently selected from zero, 1, and 2; and r, at each occurrence, is independently selected from zero, 1, 2, 3, and 4.

In a second aspect, the invention provides a compound of Formula (II):

(II)

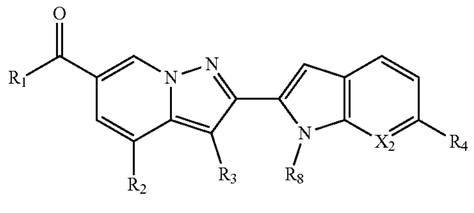

or a pharmaceutically acceptable salt thereof, within the scope of the first aspect, wherein:

$X_2$ is independently selected from CH and N;

$R_1$ is independently selected from

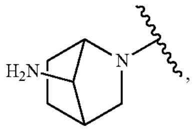
,
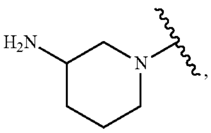
,

-continued

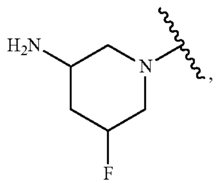
,
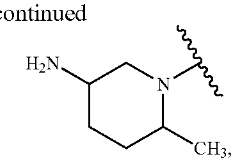
and
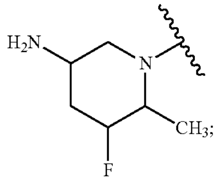
;

$R_2$ is independently selected from H, F, Cl, —$CH_3$, and —$OCH_3$;

$R_3$ is independently selected from H, F, Cl, —CN, —$CH_3$, and —$CH_2OH$;

$R_4$ is independently selected from H, $C_{1-5}$ alkyl optionally substituted with one or more substituents selected from F, Cl, and —OH, phenyl substituted with one or more $R_5$, $C_{3-6}$ cycloalkyl, and a 4-10 membered heterocyclyl comprising carbon atoms and 1-5 heteroatoms selected from N, $NR_6$, O, and S and substituted with one or more $R_5$;

$R_5$ is independently selected from H, F, Cl, Br, —CN, =O, $C_{1-4}$alkyl optionally substituted with one or more $R_e$, $C_{2-4}$alkenyl optionally substituted with one or more $R_e$, —$(CHR_d)_rOR_b$, —$(CHR_d)_rS(O)_pR_c$—$(CHR_d)_rN$-$R_aS(O)_pR_c$, —$(CHR_d)_rNR_aR_a$, —$(CHR_d)_rNR_aC$(=O)$R_b$, —$(CHR_d)_rNR_aC$(=O)$OR_b$, —$(CHR_d)_rC$(=O)$R_b$, —$(CHR_d)_rC$(=O)$OR_b$, —$(CHR_d)_rC$(=O)$NR_aR_a$, —$(CHR_d)_rOC$(=O)$R_b$, —$(CHR_d)_rOC$(=O)$OR_b$, —$(CHR_d)_rO(CH_2)_rC$(=O)$NR_aR_a$;

$R_6$ is independently selected from H and $C_{1-4}$alkyl optionally substituted with one or more $R_e$;

$R_8$ is independently selected from H and —$CH_2$—$C_{3-6}$ cycloalkyl;

$R_a$ is independently selected from H, $C_{1-6}$ alkyl optionally substituted with one or more $R_e$, —$(CH_2)_r$—$C_{3-10}$carbocyclyl optionally substituted with one or more $R_e$, and —$(CH_2)_r$-heterocyclyl optionally substituted with one or more $R_e$; or $R_a$ and $R_a$ together with the nitrogen atom to which they are both attached form a heterocyclic ring optionally substituted with one or more $R_e$;

$R_b$ is independently selected from H, $C_{1-6}$ alkyl optionally substituted with one or more $R_e$, —$(CH_2)_r$—$C_{3-10}$carbocyclyl optionally substituted with one or more $R_e$, and —$(CH_2)_r$-heterocyclyl optionally substituted with one or more $R_e$;

$R_c$ is independently selected from $C_{1-6}$ alkyl optionally substituted with one or more $R_e$, —$(CH_2)_r$—$C_{3-6}$ carbocyclyl optionally substituted with one or more $R_e$, and —$(CH_2)_r$-heterocyclyl optionally substituted with one or more $R_e$;

$R_d$ is independently selected from H and $C_{1-4}$ alkyl optionally substituted with one or more $R_e$;

$R_e$ is independently selected from F, Cl, Br, —CN, —$NO_2$, =O, OH, $OC_{1-4}$ alkyl, $C_{1-4}$ alkyl optionally substituted with one or more $R_f$, $C_{3-6}$ cycloalkyl optionally substituted with one or more $R_f$, —$(CH_2)_r$-aryl optionally substituted with one or more $R_f$, $-(CH_2)_r$-heterocyclyl optionally substituted with one or more $R_f$;

$R_f$ is independently selected from F, Cl, Br, —CN, and —OH;

p, at each occurrence, is independently selected from zero, 1, and 2; and r, at each occurrence, is independently selected from zero, 1, 2, 3, and 4.

In a third aspect, the invention provides a compound within the scope of the second aspect, or a pharmaceutically acceptable salt thereof, wherein:

$R_1$ is independently selected from

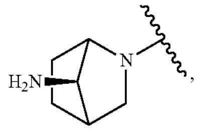, 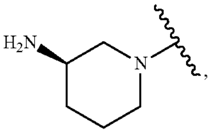, 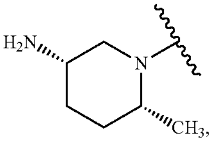, and 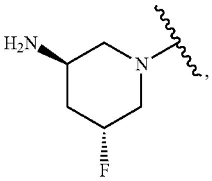, 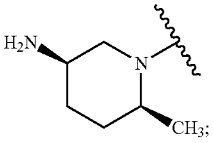;

$R_2$ is independently selected from H, F, $-CH_3$, and $-OCH_3$;

$R_3$ is independently selected from H, Cl, $-CH_3$, and $-CH_2OH$;

$R_4$ is independently selected from H, $C_{1-5}$ alkyl optionally substituted with one or more substituents selected from F, Cl, and —OH, phenyl substituted with one or more $R_5$, $C_{3-6}$ cycloalkyl, and a 4-10 membered heterocyclyl comprising carbon atoms and 1-5 heteroatoms selected from N, $NR_6$, O, and S and substituted with one or more $R_5$;

$R_5$, at each occurrence, is independently selected from H, F, Cl, —CN, =O, $C_{1-4}$alkyl optionally substituted with one or more $R_e$, $-(CH_2)_rOR_b$, $-(CH_2)_rNR_aS(O)_pR_c$, $-(CH_2)_rNR_aR_a$, $-(CH_2)_rNR_aC(=O)R_b$, $-(CH_2)_rNR_aC(=O)OR_b$, $-(CH_2)_rNR_aC(=O)NR_aR_a$, $-(CH_2)_rC(=O)R_b$, $-(CH_2)_rC(=O)OR_b$, $-(CH_2)_rC(=O)NR_aR_a$, $-(CH_2)_rOC(=O)R_b$, $-(CH_2)_rOC(=O)OR_b$, and $-(CH_2)_rO(CH_2)_rC(=O)NR_aR_a$;

$R_6$ is independently selected from H and $C_{1-3}$alkyl optionally substituted with one or more $R_e$;

$R_8$ is $-CH_2$-cyclopropyl;

$R_a$ is independently selected from H and $C_{1-6}$ alkyl optionally substituted with one or more $R_e$; or $R_a$ and $R_a$ together with the nitrogen atom to which they are both attached form a heterocyclic ring optionally substituted with one or more $R_e$;

$R_b$ is independently selected from H and $C_{1-6}$ alkyl optionally substituted with one or more $R_e$;

$R_c$ is $C_{1-6}$ alkyl optionally substituted with one or more $R_e$;

$R_e$ is independently selected from F, Cl, Br, —CN, =O, OH, $OC_{1-3}$ alkyl, $C_{1-3}$ alkyl optionally substituted with one or more $R_f$, $C_{3-6}$ cycloalkyl optionally substituted with one or more $R_f$, $-(CH_2)_r$-aryl optionally substituted with one or more $R_f$, $-(CH_2)_r$-heterocyclyl optionally substituted with one or more $R_f$;

$R_f$ is independently selected from F, Cl, Br, —CN, and —OH;

p, at each occurrence, is independently selected from zero, 1, and 2; and r, at each occurrence, is independently selected from zero, 1, 2, 3, and 4.

In a fourth aspect, the invention provides a compound within the scope of the third aspect, or a pharmaceutically acceptable salt thereof, wherein:

$R_1$ is independently selected from

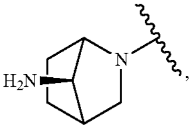, 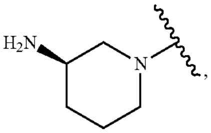, and 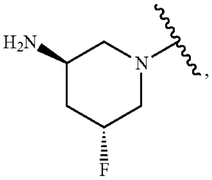, $R_2$ is independently selected from H, F, and $-OCH_3$;

$R_3$ is $CH_3$;

$R_4$ is selected from F, Cl, $C_{1-3}$ alkyl,

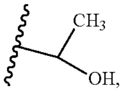 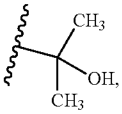 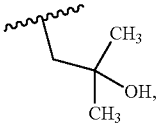

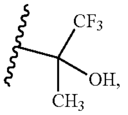 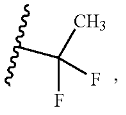 , 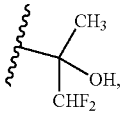

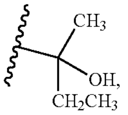 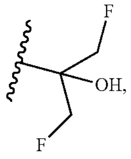 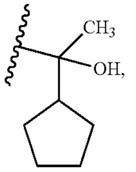

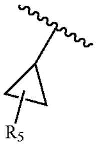 , 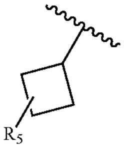 , 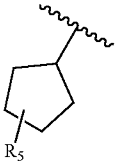 ,

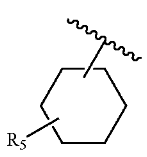 , 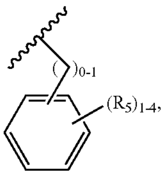 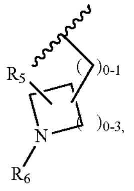

-continued
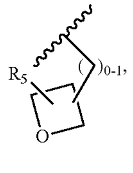
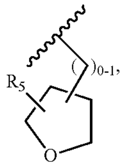
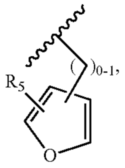
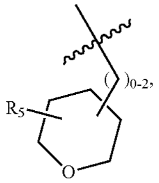
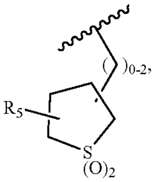
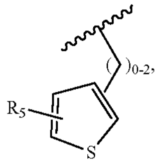
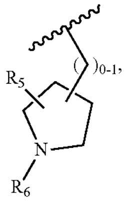
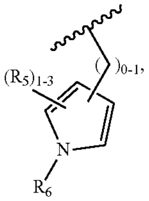
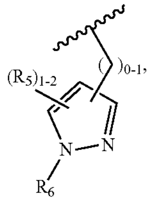
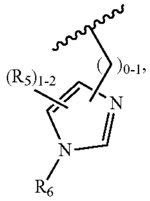
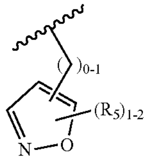
,
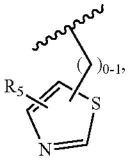
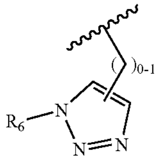
,
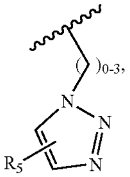
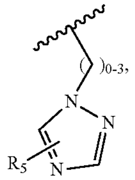
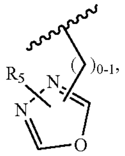
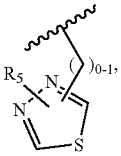
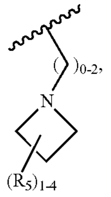
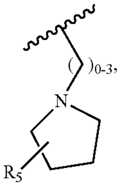
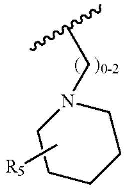
,
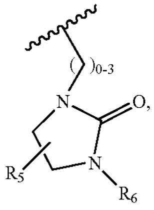
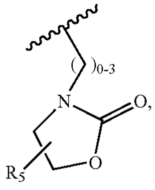
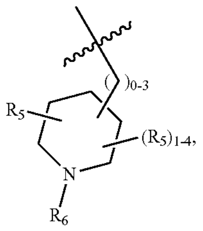
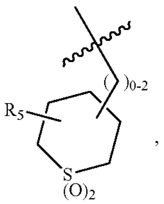
,
-continued
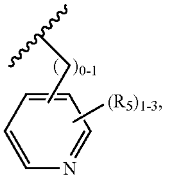
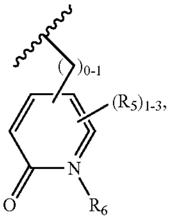
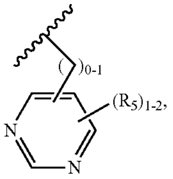
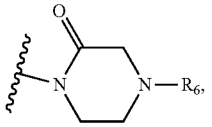
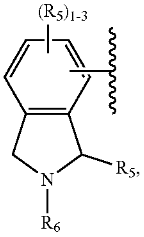
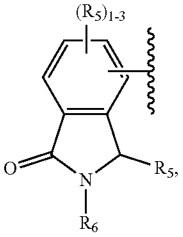
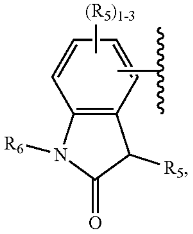
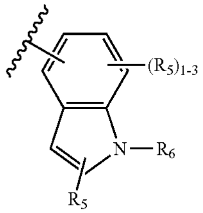
,
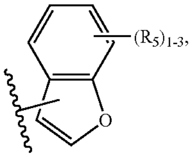
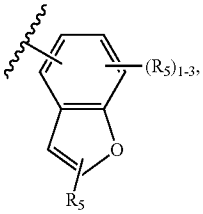
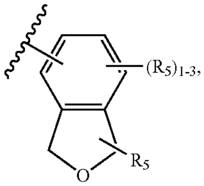
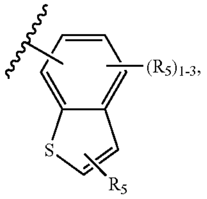
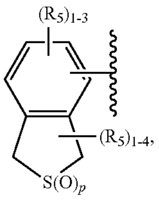
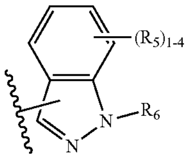
,
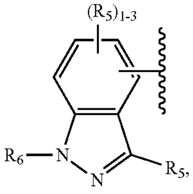
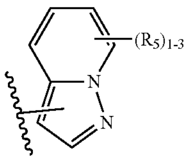
, -continued
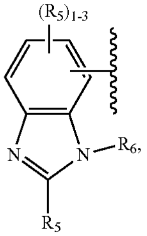
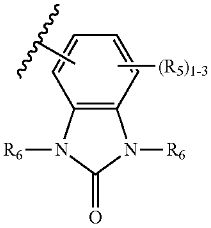
,
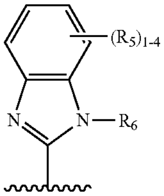
,
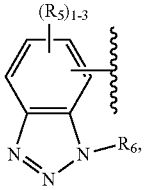
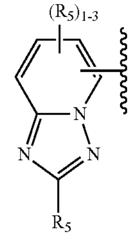
,
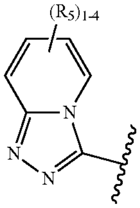
,
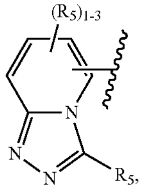
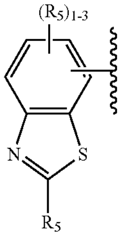
,
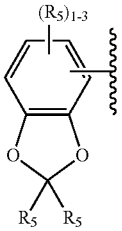
,
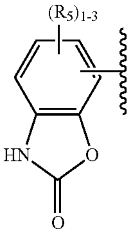
,
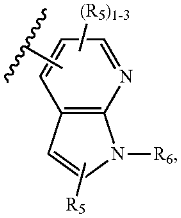
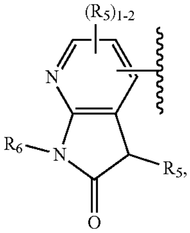
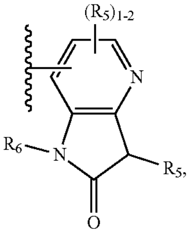
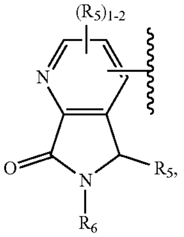
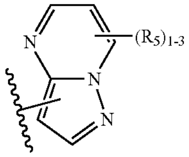
,
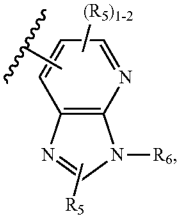
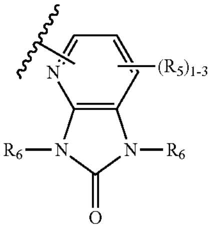
,
-continued
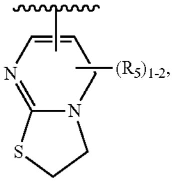
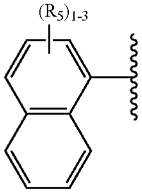
,
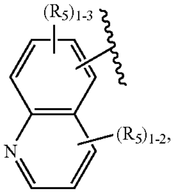
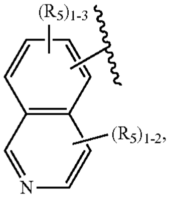
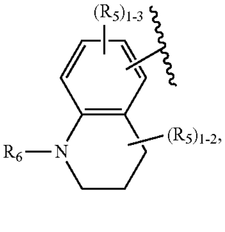
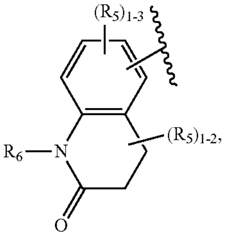
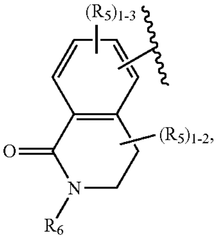
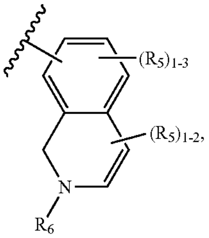
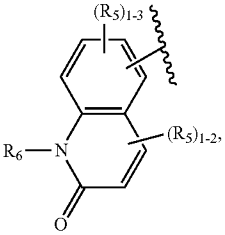
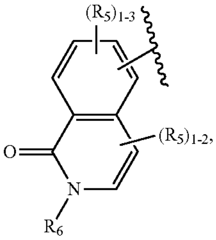
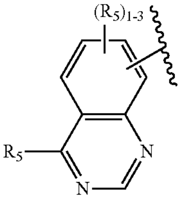
,
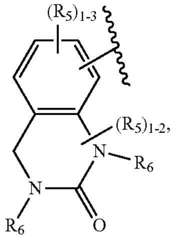
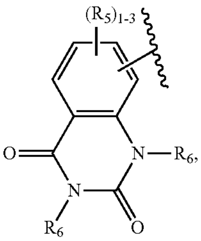
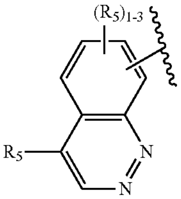
, -continued

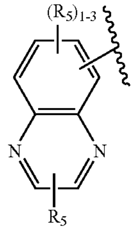, 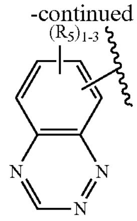, 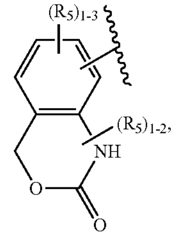

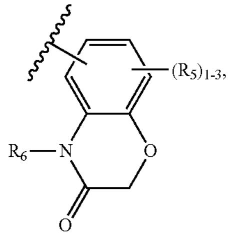 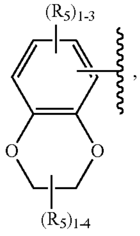, and

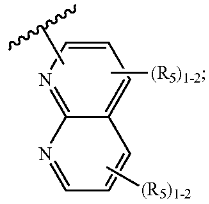

$R_5$, at each occurrence, is independently selected from H, F, Cl, —CN, =O, $C_{1-4}$alkyl optionally substituted with one or more $R_e$, —$OR_b$, —$NR_aS(O)_2R_c$, —$NR_aR_a$, —$NR_aC(=O)R_b$, —$NR_aC(=O)OR_b$, —$NR_aC(=O)NR_aR_a$, —$C(=O)R_b$, —$C(=O)OR_b$, —$C(=O)NR_aR_a$, —$OC(=O)R_b$, and —$OC(=O)OR_b$;

$R_6$ is independently selected from H and $C_{1-3}$alkyl;

$R_a$ is independently selected from H and $C_{1-5}$ alkyl; or $R_a$ and $R_a$ together with the nitrogen atom to which they are both attached form a heterocyclic ring optionally substituted with one or more $R_e$;

$R_b$ is independently selected from H and $C_{1-5}$ alkyl optionally substituted with one or more $R_e$;

$R_c$ is $C_{1-5}$ alkyl optionally substituted with one or more $R_e$;

$R_e$ is independently selected from F, Cl, Br, —CN, =O, OH, $C_{1-4}$ alkyl optionally substituted with one or more $R_f$, $C_{3-6}$ cycloalkyl optionally substituted with one or more $R_f$, aryl optionally substituted with one or more $R_f$, heterocyclyl optionally substituted with one or more $R_f$; and $R_f$ is independently selected from F, Cl, Br, —CN, and —OH.

In a fifth aspect, the invention provides a compound within the scope of the fourth aspect, or a pharmaceutically acceptable salt thereof, wherein:

$R_4$ is selected from $C_{1-2}$ alkyl,

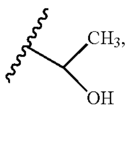 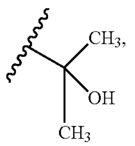 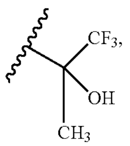

-continued

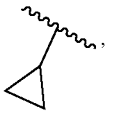, 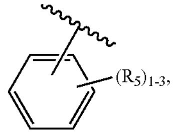, 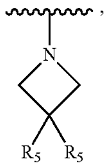,

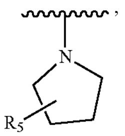, 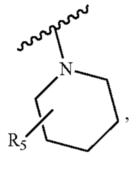, 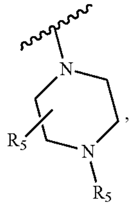,

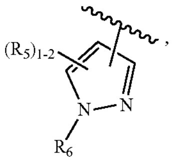, 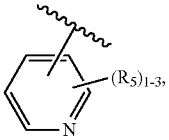

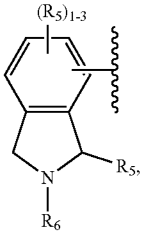 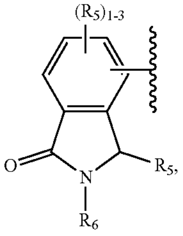

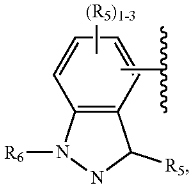 and 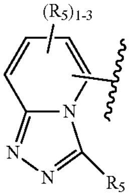;

$R_5$ is independently selected from H, F, Cl, =O, $C_{1-4}$alkyl optionally substituted with one or more $R_e$, —$OR_b$, —$NR_aS(O)_2R_c$—$NR_aR_a$, —$NR_aC(=O)R_b$, and $C(=O)NR_aR_a$;

$R_6$ is independently selected from H and $C_{1-4}$alkyl optionally substituted with one or more substituents selected from F, Cl, and OH;

$R_a$ is independently selected from H and $C_{1-4}$ alkyl optionally substituted with one or more $R_e$;

$R_b$ is independently selected from H and $C_{1-4}$ alkyl optionally substituted with one or more $R_e$;

$R_c$ is independently selected from H and $C_{1-4}$ alkyl optionally substituted with one or more $R_e$; and $R_e$ is independently selected from F, Cl, Br, —CN, =O, OH, and $C_{1-6}$ alkyl.

In a sixth aspect, the invention provides a compound within the scope of the fifth aspect, or a pharmaceutically acceptable salt thereof, wherein:

$R_4$ is independently selected from $CH_3$,

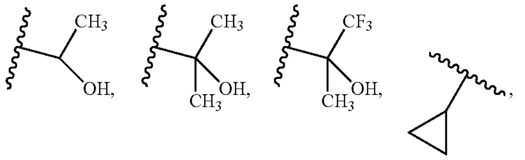

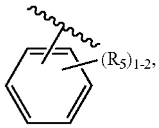

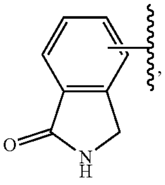

and

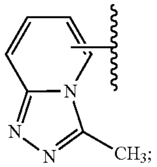

$R_5$ is independently selected from F, Cl, —OH, and C(=O)$NH_2$.

In a seventh aspect, the invention provides a compound of Formula (III):

(III)

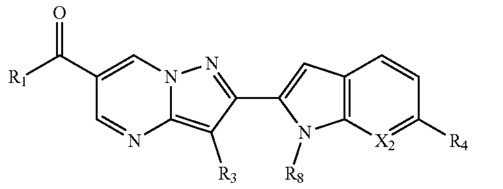

or a pharmaceutically acceptable salt thereof, within the scope of the first aspect, wherein:

$X_2$ is independently selected from CH and N;

$R_1$ is independently selected from

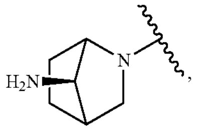

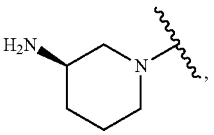

and

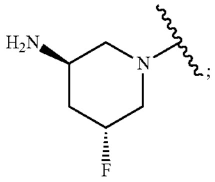

$R_2$ is independently selected from H, F, Cl, —$CH_3$, and —$OCH_3$;

$R_3$ is independently selected from H, F, Cl, —CN, —$CH_3$, and —$CH_2OH$;

$R_4$ is independently selected from H, F, Cl, $C_{1-3}$ alkyl,

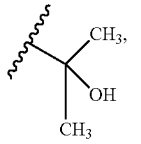

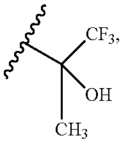

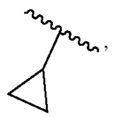

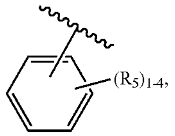

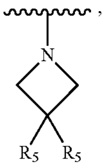

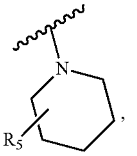

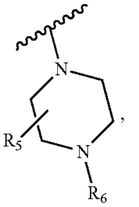

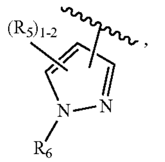

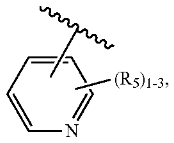

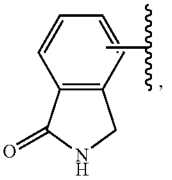

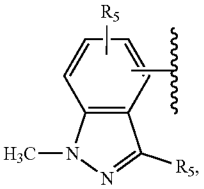

and

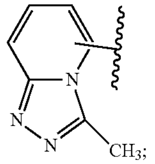

$R_5$ is independently selected from H, F, Cl, =O, —OH, —$OCHF_2$, C(=O)$NH_2$, and —$NHS(O)_2C_{1-4}$alkyl;

$R_6$ is independently selected from H and $C_{1-4}$alkyl optionally substituted with one or more substituents selected from F, Cl, and OH;

$R_8$ is —$CH_2$-cyclopropyl;

$R_a$ is independently selected from H and $C_{1-4}$ alkyl optionally substituted with one or more $R_e$;

$R_b$ is independently selected from H and $C_{1-4}$ alkyl optionally substituted with one or more $R_e$; and $R_e$ is independently selected from F, Cl, Br, —CN, =O, OH, and $C_{1-6}$ alkyl.

In an eighth aspect, the invention provides a compound of Formula (IV):

(III)

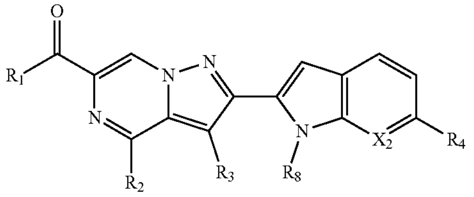

or a pharmaceutically acceptable salt thereof, within the scope of the first aspect, wherein:

$X_2$ is independently selected from CH and N;

$R_1$ is independently selected from $-NHCH_2CHFCH_2NH_2$,

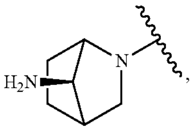,
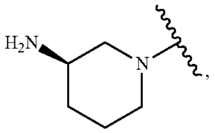, and
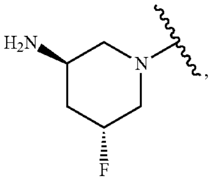, and
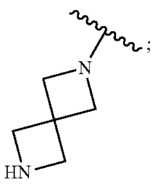;

$R_2$ is independently selected from H, F, Cl, $-CH_3$, and $-OCH_3$;

$R_3$ is independently selected from H, F, Cl, $-CN$, $-CH_3$, and $-CH_2OH$;

$R_4$ is independently selected from H, F, Cl, and $C_{1-3}$ alkyl; and $R_8$ is $-CH_2$-cyclopropyl.

In a ninth aspect, the invention provides a compound of Formula (V):

(V)

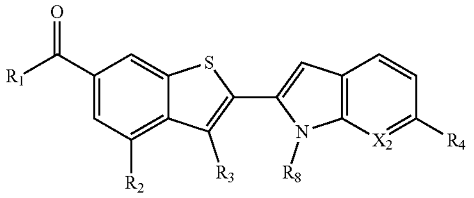

or a pharmaceutically acceptable salt thereof, within the scope of the first aspect, wherein:

$X_2$ is independently selected from CH and N;

$R_1$ is independently selected from

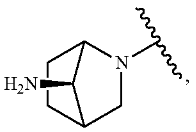,
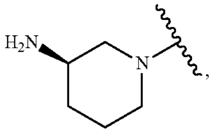, and

-continued

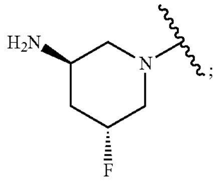;

$R_2$ is independently selected from H, F, Cl, $-CH_3$, and $-OCH_3$;

$R_3$ is independently selected from H, F, Cl, $-CN$, $-CH_3$, and $-CH_2OH$;

$R_4$ is independently selected from H, F, Cl, Br, $C_{1-3}$ alkyl,

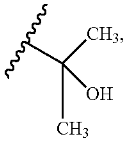
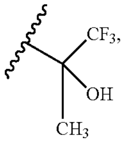
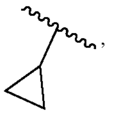
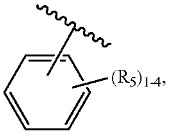
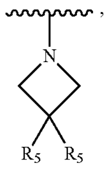
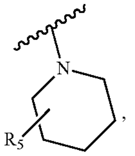
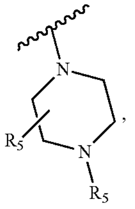
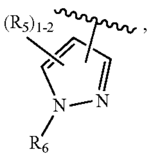
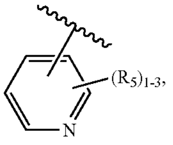
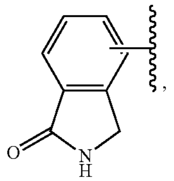
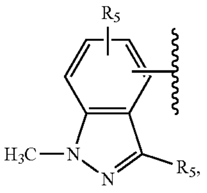, and
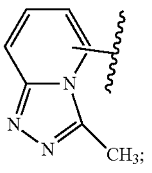

$R_5$ is independently selected from H, F, Cl, $=O$, $-OH$, $-OCHF_2$, $NH_2$, and $C(=O)NH_2$;

$R_6$ is independently selected from H and $C_{1-4}$alkyl optionally substituted with one or more substituents selected from F, Cl, and OH;

$R_8$ is $-CH_2$-cyclopropyl;

$R_a$ is independently selected from H and $C_{1-4}$ alkyl optionally substituted with one or more $R_e$;

$R_b$ is independently selected from H and $C_{1-4}$ alkyl optionally substituted with one or more $R_e$; and $R_e$ is independently selected from F, Cl, Br, $-CN$, $=O$, OH, and $C_{1-6}$ alkyl.

In a tenth aspect, the invention provides a compound of Formula (VI):

(V)

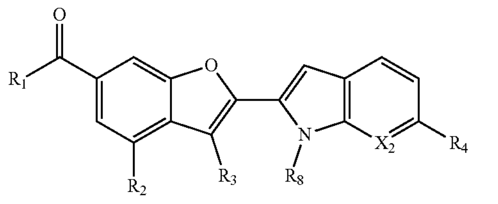

or a pharmaceutically acceptable salt thereof, within the scope of the first aspect, wherein:

$X_2$ is independently selected from CH and N;

$R_1$ is independently selected from

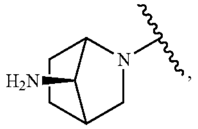, 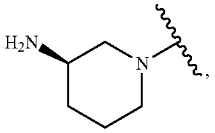, and 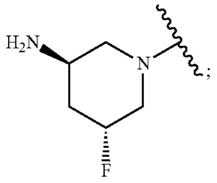;

$R_2$ is independently selected from H, F, Cl, —$CH_3$, and —$OCH_3$;

$R_3$ is independently selected from H, F, Cl, —CN, —$CH_3$, and —$CH_2OH$;

$R_4$ is independently selected from H, F, Cl, $C_{1-3}$ alkyl,

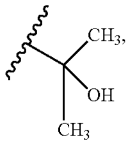 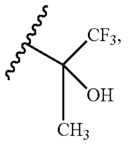 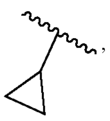, 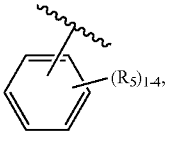 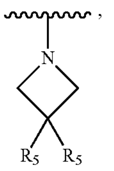, 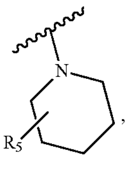, 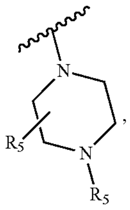, 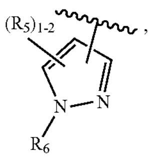, -continued

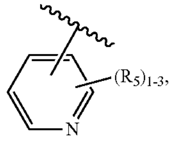 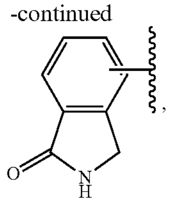, 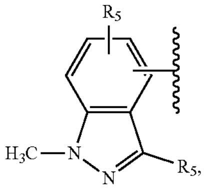 and 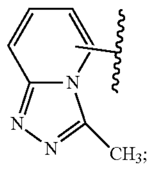

$R_5$ is independently selected from H, F, Cl, =O, —OH, —$OCHF_2$, and —C(=O)$NH_2$;

$R_6$ is independently selected from H and $C_{1-4}$alkyl optionally substituted with one or more substituents selected from F, Cl, and OH;

$R_8$ is —$CH_2$-cyclopropyl;

$R_a$ is independently selected from H and $C_{1-4}$ alkyl optionally substituted with one or more $R_e$;

$R_b$ is independently selected from H and $C_{1-4}$ alkyl optionally substituted with one or more $R_e$; and $R_e$ is independently selected from F, Cl, Br, —CN, =O, OH, and $C_{1-6}$ alkyl.

In an eleventh aspect, the invention provides a compound within the scope of the tenth aspect, or a pharmaceutically acceptable salt thereof, wherein:

$R_1$ is independently selected from

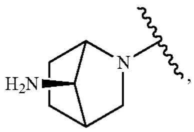, and 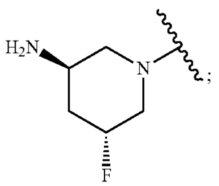;

$R_2$ is independently selected from H, F, and —$OCH_3$;

$R_3$ is —$CH_3$;

$R_4$ is independently selected from

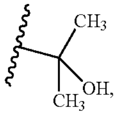 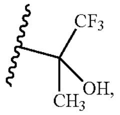 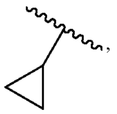, 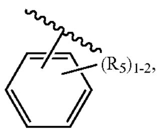 and 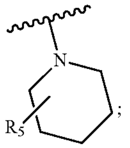;

and $R_5$ is independently selected from F, Cl, —OH, —$NH_2$, —$OC_{1-4}$alkyl, and C(=O)$NH_2$.

In one aspect, the invention provides a compound of Formula (Ia):

(Ia)

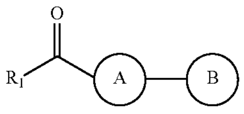

or a stereoisomer, an enantiomer, a diastereomer, a tautomer, or a pharmaceutically acceptable salt thereof, wherein:

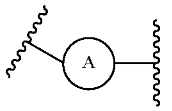

is selected from

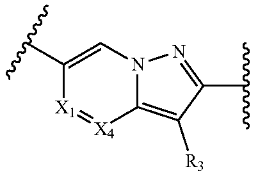

and

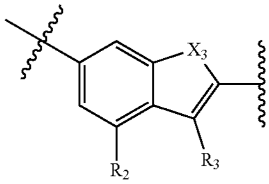

,

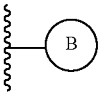

is selected from

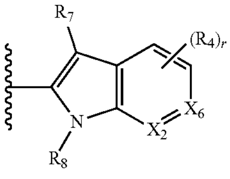

and

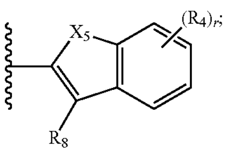

$X_1$ is independently selected from $CR_2$ and N;

$X_2$ is independently selected from $CR_4$ and N;

$X_3$ is independently selected from O and S;

$X_4$ is independently selected from $CR_2$ and N; provided $X_1$ and $X_4$ are not both N;

$X_5$ is independently selected from O and S;

$X_6$ is independently selected from $CR_4$, and N; provided 1) $X_2$ and $X_6$ are not both N; 2) when $X_2$ and $X_6$ are both $CR_4$, one of $R_4$ is H;

$R_1$ is independently selected from —NH—$C_{1-5}$ alkyl optionally substituted with one or more substituents selected from F, Cl, and $NH_2$, 4-10 membered heterocyclyl, and —NH-4-10 membered heterocyclyl, wherein said heterocyclyl is optionally substituted with one or more substituents selected from F, Cl, CN, $C_{1-3}$ alkyl, =N—$OR_b$, —$(CH_2)_r OR_b$, —$(CH_2)_r NR_aR_a$, —$NR_aC(=NH)C_{1-3}$ alkyl, —$NR_aC(=O)OR_b$, carbocyclyl, and heterocyclyl;

$R_2$ is independently selected from H, F, Cl, $C_{1-4}$ alkyl optionally substituted with one or more substituents selected from F, Cl, and OH, and —$OC_{1-4}$ alkyl;

$R_3$ is independently selected from H, F, Cl, CN, —C(=O)$OR_b$, and $C_{1-3}$ alkyl optionally substituted with one or more substituents selected from F, Cl, OH, $NH_2$, and $N_3$;

$R_4$ is independently selected from H, F, Cl, Br, —C(=O)$R_b$, $C_{1-6}$ alkyl optionally substituted with one or more substituents selected from F, Cl, OH, and $C_{3-6}$ cycloalkyl, —NH—$C_{1-6}$ alkyl optionally substituted with one or more substituents selected from F, Cl, OH, and $C_{3-6}$ cycloalkyl, —$(CH_2)_r$-aryl substituted with one or more $R_5$, —O—$C_{1-6}$ alkyl substituted with one or more $R_5$, —$(CH_2)_r$—$C_{3-12}$ cycloalkyl substituted with one or more $R_5$, and —$(CH_2)_r$-4-10 membered heterocyclyl comprising carbon atoms and 1-5 heteroatoms selected from N, $NR_6$, O, and S and substituted with one or more $R_5$;

$R_5$ is independently selected from H, F, Cl, Br, CN, =O, $C_{1-4}$ alkyl optionally substituted with one or more $R_e$, $C_{2-4}$ alkenyl optionally substituted with one or more $R_e$, $C_{2-4}$ alkynyl optionally substituted with one or more $R_e$, —$(CR_dR_d)_r OR_b$, —$(CR_dR_d)_r S(O)_p R_c$, —$(CR_dR_d)_r S(O)_p NR_aR_a$, —$(CR_dR_d)_r NR_aS(O)_p R_c$, —$(CR_dR_d)_r NR_aR_a$, —$(CR_dR_d)_r NR_aC(=O)R_b$, —$(CR_dR_d)_r NR_aC(=O)OR_b$, —$(CR_dR_d)_r NR_aC(=O)NR_aR_a$, —$(CR_dR_d)_r C(=O)R_b$, —$(CR_dR_d)_r C(=O)OR_b$, —$(CR_dR_d)_r C(=O)NR_aR_a$, —$(CR_dR_d)_r OC(=O)R_b$, —$(CR_dR_d)_r OC(=O)OR_b$, —$(CR_dR_d)_r O(CH_2)_r C(=O)NR_aR_a$, $C_{3-6}$ cycloalkyl optionally substituted with one or more $R_e$, aryl optionally substituted with one or more $R_e$, and heterocyclyl optionally substituted with one or more $R_e$;

$R_6$ is independently selected from H, $C_{1-6}$ alkyl optionally substituted with one or more $R_e$, —$S(O)_p R_c$, —$S(O)_p NR_aR_a$, —C(=O)$R_b$, —C(=O)$OR_b$, —C(=O)$NR_aR_a$, $C_{3-6}$ cycloalkyl optionally substituted with one or more $R_e$, aryl optionally substituted with one or more $R_e$, and heterocyclyl optionally substituted with one or more $R_e$;

$R_7$ is independently selected from H, F, and Cl;

$R_8$ is independently selected from H, and $C_{1-6}$ alkyl optionally substituted with one or more substituents selected from F, Cl, and $C_{3-6}$ cycloalkyl;

$R_a$ is independently selected from H, $C_{1-6}$ alkyl optionally substituted with one or more $R_e$, $C_{2-6}$ alkenyl optionally substituted with one or more $R_e$, $C_{2-6}$ alkynyl optionally substituted with one or more $R_e$, —$(CH_2)_r$—$C_{3-10}$ carbocyclyl optionally substituted with one or more $R_e$, and —$(CH_2)_r$-heterocyclyl optionally substituted with one or more $R_e$; or $R_a$ and $R_a$ together with the nitrogen atom to which they are both attached form a heterocyclic ring optionally substituted with one or more $R_e$;

$R_b$ is independently selected from H, $C_{1-6}$ alkyl optionally substituted with one or more $R_e$, $C_{2-6}$ alkenyl optionally substituted with one or more $R_e$, $C_{2-6}$ alkynyl optionally substituted with one or more $R_e$, —$(CH_2)_r$—$C_{3-10}$ carbocyclyl optionally substituted with one or more $R_e$, and —$(CH_2)_r$-heterocyclyl optionally substituted with one or more $R_e$;

$R_c$ is independently selected from $C_{1-6}$ alkyl optionally substituted with one or more $R_e$, $C_{2-6}$ alkenyl optionally substituted with one or more $R_e$, $C_{2-6}$ alkynyl optionally substituted with one or more $R_e$, —$(CH_2)_r$—$C_{3-10}$ carbocyclyl optionally substituted with one or more $R_e$, and —$(CH_2)_r$-heterocyclyl optionally substituted with one or more $R_e$;

$R_d$ is independently selected from H, and $C_{1-6}$ alkyl optionally substituted with one or more $R_e$;

$R_e$ is independently selected from F, Cl, Br, CN, $NH_2$, —NH—$C_{1-4}$ alkyl, —N($C_{1-4}$ alkyl)$_2$, =O, OH, —O$C_{1-6}$ alkyl, —$CO_2$H, $C_{1-6}$ alkyl optionally substituted with one or more $R_f$, $C_{2-6}$ alkenyl, $C_{2-6}$ alkynyl, —$(CH_2)_r$—$C_{3-6}$ cycloalkyl optionally substituted with one or more $R_f$, —$(CH_2)_r$-aryl optionally substituted with one or more $R_f$, and —$(CH_2)_r$-heterocyclyl optionally substituted with one or more $R_f$;

$R_f$ is independently selected from F, Cl, Br, CN, OH, O$C_{1-5}$ alkyl, $C_{1-5}$ alkyl optionally substituted with OH, $C_{2-5}$ alkenyl, $C_{2-5}$ alkynyl, $C_{3-6}$ cycloalkyl, and phenyl;

p, at each occurrence, is independently selected from zero, 1, and 2; and r, at each occurrence, is independently selected from zero, 1, 2, 3, and 4.

In another aspect, the invention provides a compound of Formulae (IIa)-(XIII):

(IIa)

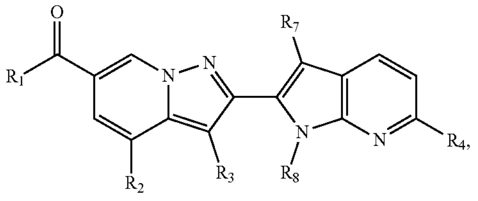

(IIIa)

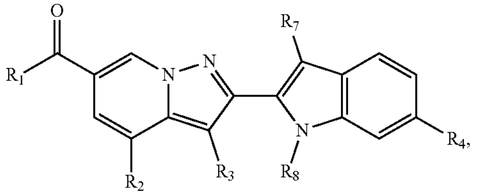

(IVa)

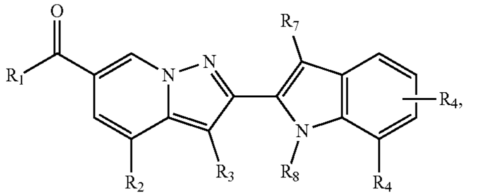

(Va)

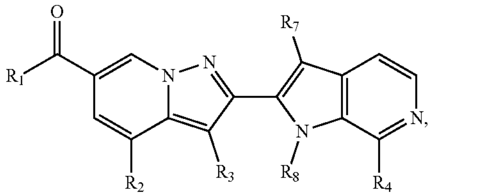

(VIa)

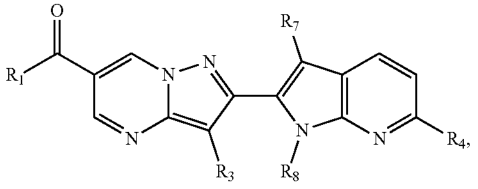

-continued (VII)

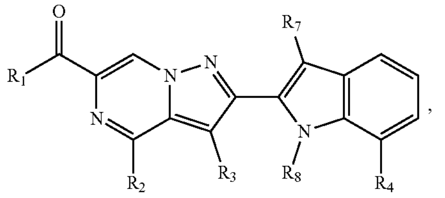

(VIII)

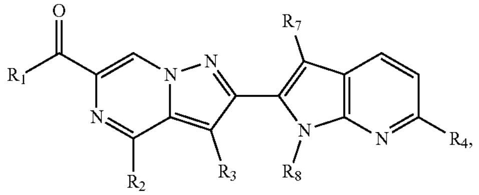

(IX)

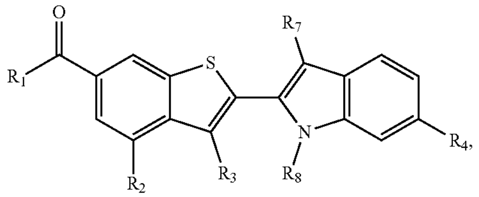

(X)

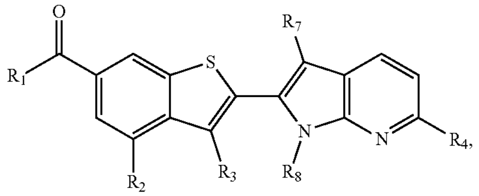

(XI)

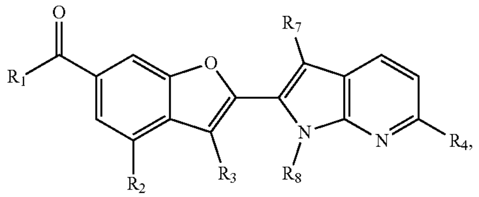

(XII)

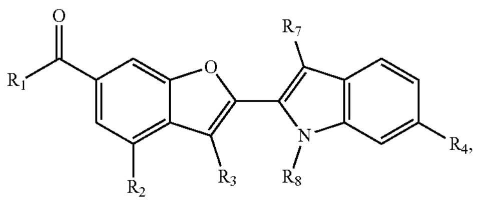

or (XIII)

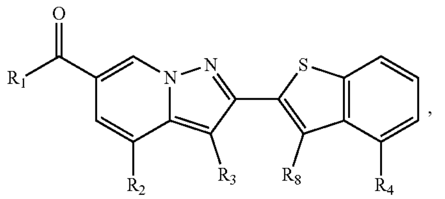

or a stereoisomer, an enantiomer, a diastereomer, a tautomer, or a pharmaceutically acceptable salt thereof. $R_1$, $R_2$, $R_3$, $R_4$, $R_7$, and $R_8$ are as defined in Formula (Ia).

In another aspect, the invention provides a compound having Formula (IIa):

(IIa)

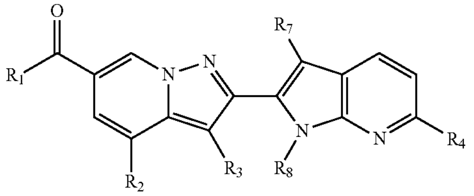

or a stereoisomer, an enantiomer, a diastereomer, a tautomer, or a pharmaceutically acceptable salt thereof, wherein:

$R_1$ is independently selected from

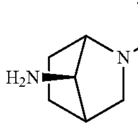,
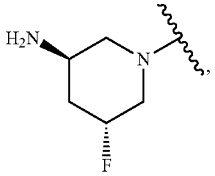,
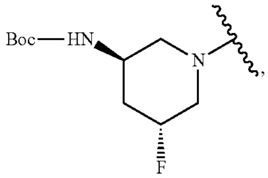,
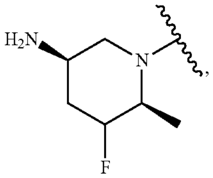,
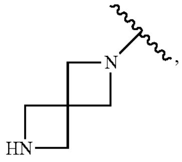,
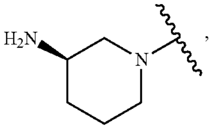, and
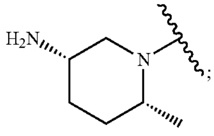;

$R_2$ is independently selected from H, F, Cl, $C_{1-3}$ alkyl optionally substituted with one or more substituents selected from F, Cl, and OH, and $OC_{1-3}$ alkyl;

$R_3$ is independently selected from H, F, Cl, $CH_3$, and $CH_2OH$;

$R_4$ is independently selected from H, F, Cl, $—C(═O)R_b$, $C_{1-6}$ alkyl optionally substituted with one or more substituents selected from F, Cl, OH, and $C_{3-6}$ cycloalkyl, $—NH—C_{1-6}$ alkyl optionally substituted with one or more substituents selected from F, Cl, OH, and $C_{3-6}$ cycloalkyl, $—(CH_2)_r$-aryl substituted with one or more $R_5$, $—O—C_{1-6}$ alkyl substituted with one or more $R_5$, $—(CH_2)_r—C_{3-12}$ cycloalkyl substituted with one or more $R_5$, and $—(CH_2)_r$-4-10 membered heterocyclyl comprising carbon atoms and 1-5 heteroatoms selected from N, $NR_6$, O, and S and substituted with one or more $R_5$;

$R_5$ is independently selected from H, F, Cl, ═O, $C_{1-4}$ alkyl optionally substituted with one or more $R_e$, $—(CH_2)_rOR_b$, $—(CH_2)_rS(O)_pR_c$, $—(CH_2)_rS(O)_pNR_aR_a$, $—(CH_2)_rNR_aS(O)_pR_c$, $—(CH_2)_rNR_aR_a$, $—(CH_2)_rNR_aC(═O)R_b$, $—(CH_2)_rNR_aC(═O)OR_b$, $—(CH_2)_rNR_aC(═O)NR_aR_a$, $—(CH_2)_rC(═O)R_b$, $—(CH_2)_rC(═O)OR_b$, $—(CH_2)_rC(═O)NR_aR_a$, $—(CH_2)_rOC(═O)R_b$, $—(CH_2)_rOC(═O)OR_b$, $—(CH_2)_rO(CH_2)_rC(═O)NR_aR_a$, $C_{3-6}$ cycloalkyl optionally substituted with one or more $R_e$, aryl optionally substituted with one or more $R_e$, and heterocyclyl optionally substituted with one or more $R_e$;

$R_6$ is independently selected from H, $C_{1-6}$ alkyl optionally substituted with one or more $R_e$, $C(═O)R_b$, $—C(═O)NR_aR_a$, $C_{3-6}$ cycloalkyl optionally substituted with one or more $R_e$, aryl optionally substituted with one or more $R_e$, and heterocyclyl optionally substituted with one or more $R_e$;

$R_7$ is independently selected from H, F, and Cl;

$R_8$ is independently selected from H, and $C_{1-6}$ alkyl optionally substituted with one or more substituents selected from F, Cl, and $C_{3-6}$ cycloalkyl;

$R_a$ is independently selected from H, and $C_{1-6}$ alkyl optionally substituted with one or more $R_e$; or $R_a$ and $R_a$ together with the nitrogen atom to which they are both attached form a heterocyclic ring optionally substituted with one or more $R_e$;

$R_b$ is independently selected from H, $C_{1-6}$ alkyl optionally substituted with one or more $R_e$, $—(CH_2)_r—C_{3-10}$ carbocyclyl optionally substituted with one or more $R_e$, and $—(CH_2)_r$ heterocyclyl optionally substituted with one or more $R_e$;

$R_c$ is independently selected from $C_{1-6}$ alkyl optionally substituted with one or more $R_e$, $—(CH_2)_r—C_{3-10}$ carbocyclyl optionally substituted with one or more $R_e$, and $—(CH_2)_r$-heterocyclyl optionally substituted with one or more $R_e$;

$R_e$ is independently selected from F, Cl, Br, $NH_2$, $—NH—C_{1-4}$ alkyl, $—N(C_{1-4}\ alkyl)_2$, ═O, OH, $—OC_{1-6}$ alkyl, $C_{1-6}$ alkyl optionally substituted with one or more $R_f$, $—(CH_2)_r—C_{3-6}$ cycloalkyl optionally substituted with one or more $R_f$, $—(CH_2)_r$-aryl optionally substituted with one or more $R_f$, and $—(CH_2)_r$-heterocyclyl optionally substituted with one or more $R_f$;

$R_f$ is independently selected from F, Cl, OH, $OC_{1-5}$ alkyl, $C_{1-5}$ alkyl optionally substituted with OH, $C_{3-6}$ cycloalkyl, and phenyl;

p, at each occurrence, is independently selected from zero, 1, and 2; and r, at each occurrence, is independently selected from zero, 1, 2, 3, and 4.

In another aspect, the invention provides a compound having Formula (IIIa):

(IIIa)

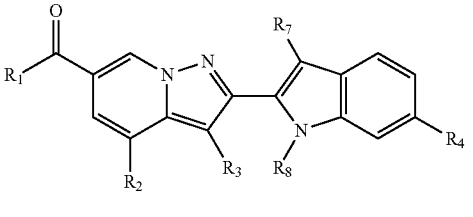

or a stereoisomer, an enantiomer, a diastereomer, a tautomer, or a pharmaceutically acceptable salt thereof, wherein:

$R_1$ is independently selected from

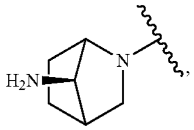, 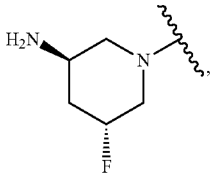, 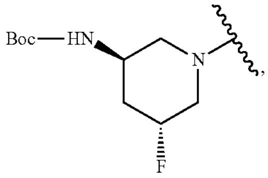, 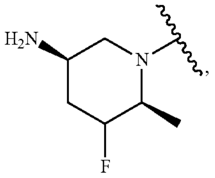, 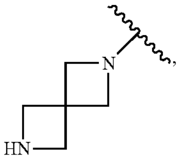, 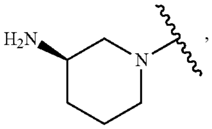, and 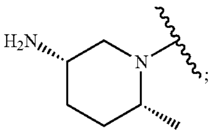;

$R_2$ is independently selected from H, F, Cl, $C_{1-3}$ alkyl optionally substituted with one or more substituents selected from F, Cl, and OH, and $OC_{1-3}$ alkyl;

$R_3$ is independently selected from H, F, Cl, and $C_{1-3}$ alkyl optionally substituted with one or more substituents selected from F, Cl, and OH;

$R_4$ is independently selected from H, F, Cl, $—C(═O)R_b$, $C_{1-6}$ alkyl optionally substituted with one or more substituents selected from F, Cl, OH, and $C_{3-6}$ cycloalkyl, $—NH—C_{1-6}$ alkyl optionally substituted with one or more substituents selected from F, Cl, OH, and $C_{3-6}$ cycloalkyl, $—(CH_2)_r$-aryl substituted with one or more $R_5$, $—O—C_{1-6}$ alkyl substituted with one or more $R_5$, $—(CH_2)_r—C_{3-12}$ cycloalkyl substituted with one or more $R_5$, and $—(CH_2)_r$-4-10 membered heterocyclyl comprising carbon atoms and 1-5 heteroatoms selected from N, $NR_6$, O, and S and substituted with one or more $R_5$;

$R_5$ is independently selected from H, F, Cl, ═O, $C_{1-4}$ alkyl optionally substituted with one or more $R_e$, $—(CH_2)_rOR_b$, $—(CH_2)_rS(O)_pR_c$, $—(CH_2)_rS(O)_pNR_aR_a$, $—(CH_2)_rNR_aS(O)_pR_c$, $—(CH_2)_rNR_aR_a$, $—(CH_2)_rNR_aC(═O)R_b$, $—(CH_2)_rNR_aC(═O)OR_b$, $—(CH_2)_rNR_aC(═O)NR_aR_a$, $—(CH_2)_rC(═O)R_b$, $—(CH_2)_rC(═O)OR_b$, $—(CH_2)_rC(═O)NR_aR_a$, $—(CH_2)_rOC(═O)R_b$, $—(CH_2)_rOC(═O)OR_b$, $—(CH_2)_rO(CH_2)_rC(═O)NR_aR_a$, $C_{3-6}$ cycloalkyl optionally substituted with one or more $R_e$, aryl optionally substituted with one or more $R_e$, and heterocyclyl optionally substituted with one or more $R_e$;

$R_6$ is independently selected from H, $C_{1-6}$ alkyl optionally substituted with one or more $R_e$, $—C(═O)R_b$, $—C(═O)OR_b$, $—C(═O)NR_aR_a$, $C_{3-6}$ cycloalkyl optionally substituted with one or more $R_e$, aryl optionally substituted with one or more $R_e$, and heterocyclyl optionally substituted with one or more $R_e$;

$R_7$ is independently selected from H, F, and Cl;

$R_8$ is independently selected from H, and $C_{1-6}$ alkyl optionally substituted with one or more substituents selected from F, Cl, and $C_{3-6}$ cycloalkyl;

$R_a$ is independently selected from H, and $C_{1-6}$ alkyl optionally substituted with one or more $R_e$; or $R_a$ and $R_a$ together with the nitrogen atom to which they are both attached form a heterocyclic ring optionally substituted with one or more $R_e$;

$R_b$ is independently selected from H, $C_{1-6}$ alkyl optionally substituted with one or more $R_e$, $—(CH_2)_r—C_{3-10}$ carbocyclyl optionally substituted with one or more $R_e$, and $—(CH_2)_r$ heterocyclyl optionally substituted with one or more $R_e$;

$R_c$ is independently selected from $C_{1-6}$ alkyl optionally substituted with one or more $R_e$, $—(CH_2)_r—C_{3-10}$ carbocyclyl optionally substituted with one or more $R_e$, and $—(CH_2)_r$-heterocyclyl optionally substituted with one or more $R_e$;

$R_e$ is independently selected from F, Cl, Br, CN, $NH_2$, $—NH—C_{1-4}$ alkyl, $—N(C_{1-4}\ alkyl)_2$, ═O, OH, $—OC_{1-6}$ alkyl, $C_{1-6}$ alkyl optionally substituted with one or more $R_f$, $—(CH_2)_r—C_{3-6}$ cycloalkyl optionally substituted with one or more $R_f$, $—(CH_2)_r$-aryl optionally substituted with one or more $R_f$, and $—(CH_2)_r$-heterocyclyl optionally substituted with one or more $R_f$;

$R_f$ is independently selected from F, Cl, OH, $OC_{1-5}$ alkyl, $C_{1-5}$ alkyl optionally substituted with OH, $C_{3-6}$ cycloalkyl, and phenyl;

p, at each occurrence, is independently selected from zero, 1, and 2; and r, at each occurrence, is independently selected from zero, 1, 2, 3, and 4.

In another aspect, the invention provides a compound having Formulae (IIa)-(IIIa), or a stereoisomer, an enantiomer, a diastereomer, a tautomer, or a pharmaceutically acceptable salt thereof, wherein:

$R_1$ is independently selected from

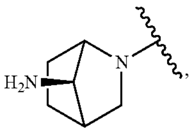, 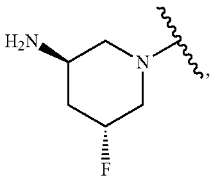, and 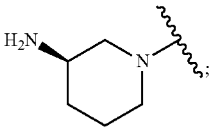;

$R_2$ is independently selected from H, F, Cl, $CH_3$, and $OCH_3$;

$R_3$ is independently selected from H, F, Cl, $CH_3$, and $CH_2OH$;

$R_4$ is independently selected from H, F, Cl, $C_{1-5}$ alkyl optionally substituted with one or more substituents selected from F, Cl, OH, and $C_{3-6}$ cycloalkyl, $—(CH_2)_r$-aryl substituted with one or more $R_5$, $—O—C_{1-6}$ alkyl substituted with one or more $R_5$, $—(CH_2)_r—C_{3-12}$ cycloalkyl substituted with one or more $R_5$, and $—(CH_2)_r$-4-10 membered heterocyclyl comprising carbon atoms and 1-5 heteroatoms selected from N, $NR_6$, O, and S and substituted with one or more $R_5$;

$R_5$ is independently selected from H, F, Cl, ═O, $C_{1-4}$ alkyl optionally substituted with one or more $R_e$, —$(CH_2)_rOR_b$, —$(CH_2)_rS(O)_2R_c$, —$(CH_2)_rS(O)_pNR_aR_a$, —$(CH_2)_rNR_aS(O)_2R_c$, —$(CH_2)_rNR_aR_a$, —$(CH_2)_rNR_aC(=O)R_b$, —$(CH_2)_rNR_aC(=O)OR_b$, —$(CH_2)_rNR_aC(=O)NR_aR_a$, —$(CH_2)_rC(=O)R_b$, —$(CH_2)_rC(=O)OR_b$, —$(CH_2)_rC(=O)NR_aR_a$, —$(CH_2)_rOC(=O)R_b$, —$(CH_2)_rOC(=O)OR_b$, —$(CH_2)_rO(CH_2)_rC(=O)NR_aR_a$, $C_{3-6}$ cycloalkyl optionally substituted with one or more $R_e$, aryl optionally substituted with one or more $R_e$, and heterocyclyl optionally substituted with one or more $R_e$;

$R_6$ is independently selected from H and $C_{1-65}$ alkyl optionally substituted with one or more $R_e$;

$R_7$ is H;

$R_8$ is $C_{1-3}$ alkyl substituted with one $C_{3-6}$ cycloalkyl;

$R_a$ is independently selected from H, and $C_{1-4}$ alkyl;

$R_b$ is independently selected from H, $C_{1-4}$ alkyl;

$R_c$ is $C_{1-4}$ alkyl; and r, at each occurrence, is independently selected from zero, 1, and 2.

In another aspect, the invention provides a compound having Formulae (IIa)-(IIIa), or a stereoisomer, an enantiomer, a diastereomer, a tautomer, or a pharmaceutically acceptable salt thereof, wherein:

$R_4$ is independently selected from H, F, Cl, $C_{1-5}$ alkyl optionally substituted with one or more substituents selected from F, Cl, and OH, $C_{3-6}$ cycloalkyl,

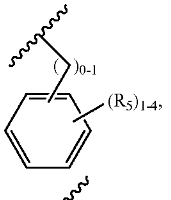
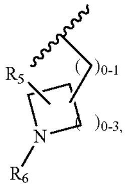
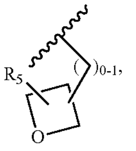
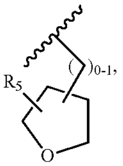
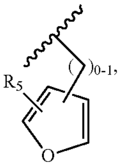
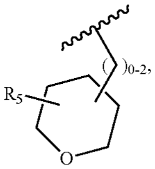
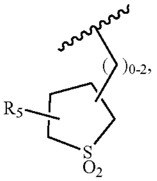
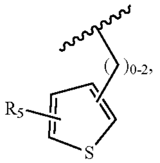
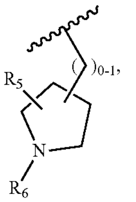
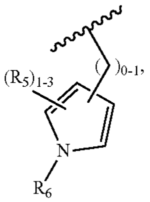
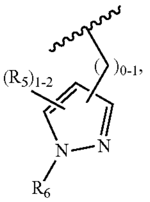
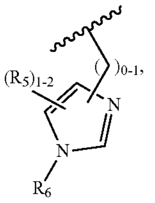
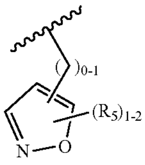
,
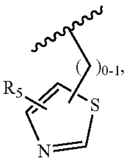

-continued

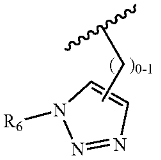
,
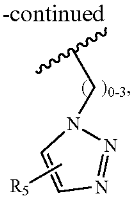
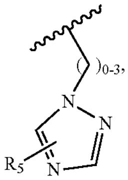
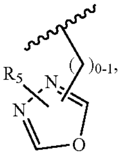
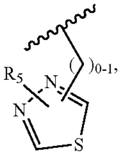
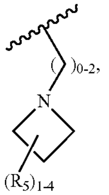
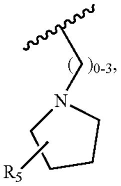
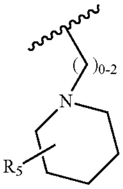
,
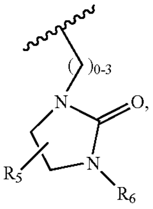
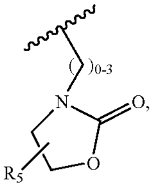
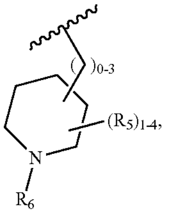
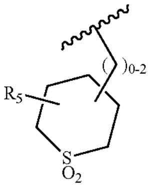
,
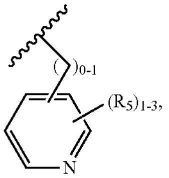
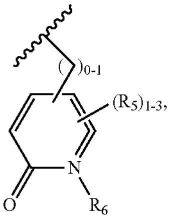
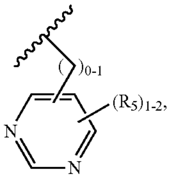
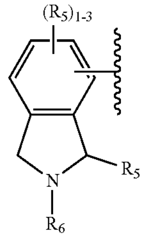
,
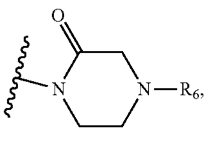
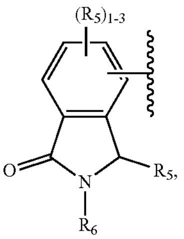
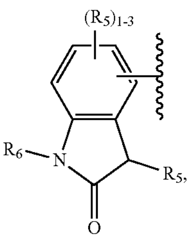
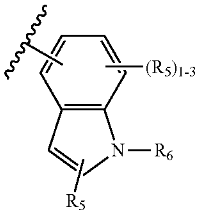
, -continued
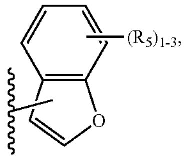
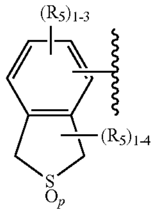
,
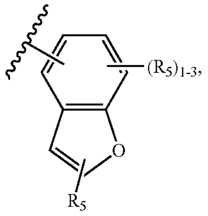
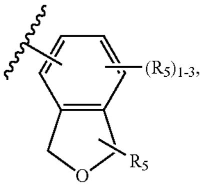
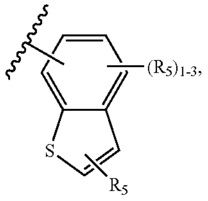
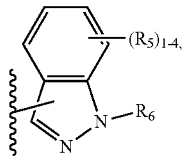
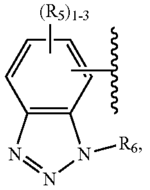
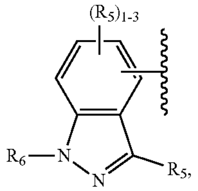
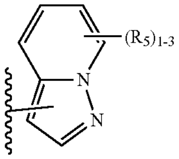
,
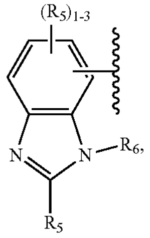
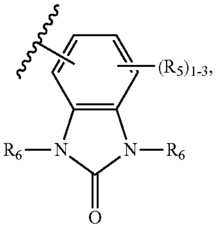
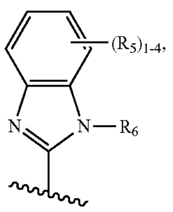
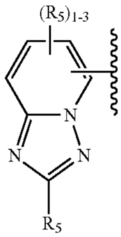
,
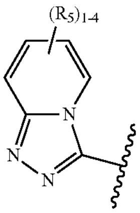
,
-continued
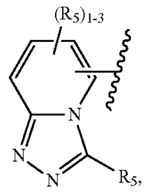
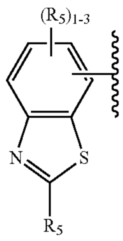
,
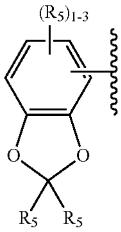
,
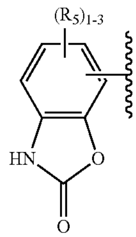
,
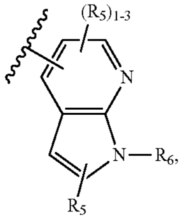
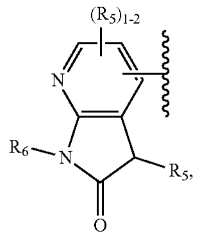
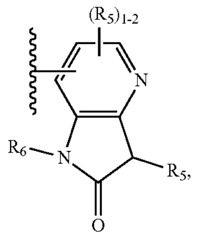
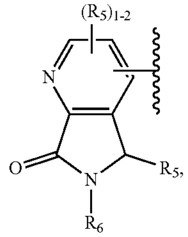
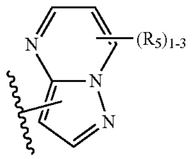
,
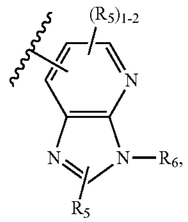
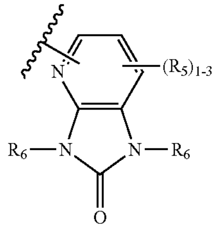
,
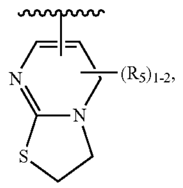
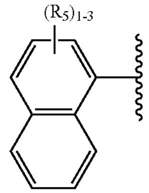
,
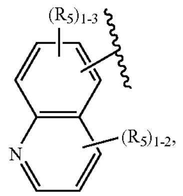
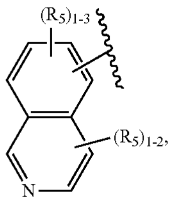

-continued

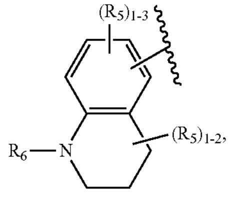 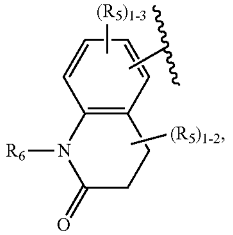

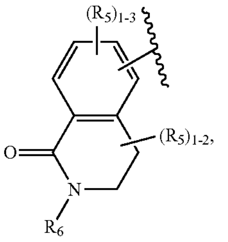 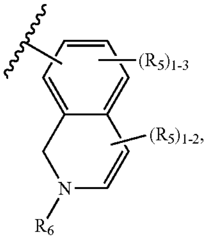

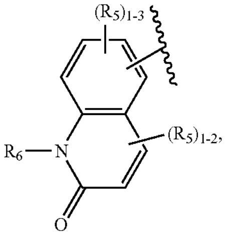 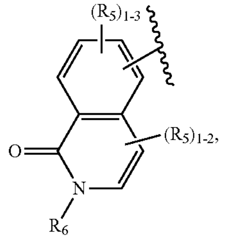

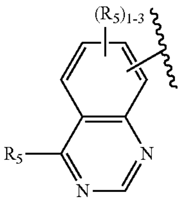 , 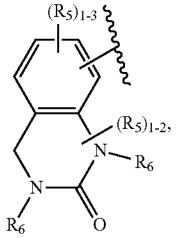

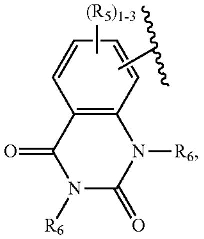 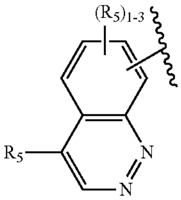 ,

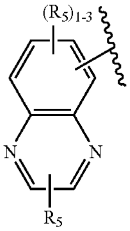 , 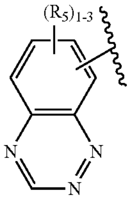 , 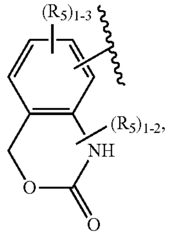

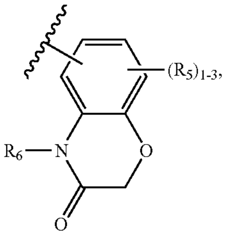 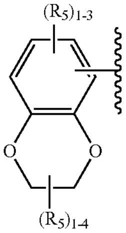 , and

-continued

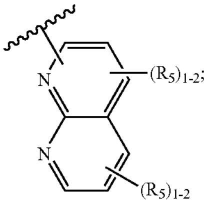

$R_5$ is independently selected from H, F, Cl, $=O$, $C_{1-4}$ alkyl optionally substituted with one or more $R_e$, $-(CH_2)_rOR_b$, $-(CH_2)_rS(O)_pR_c$, $-(CH_2)_rS(O)_pNR_aR_a$, $-(CH_2)_rNR_aS(O)_pR_c$, $-(CH_2)_rNR_aR_a$, $-(CH_2)_rNR_aC(=O)R_b$, $-(CH_2)_rNR_aC(=O)OR_b$, $-(CH_2)_rNR_aC(=O)NR_aR_a$, $-(CH_2)_rC(=O)R_b$, $-(CH_2)_rC(=O)OR_b$, $-(CH_2)_rC(=O)NR_aR_a$, $-(CH_2)_rOC(=O)R_b$, $-(CH_2)_rOC(=O)OR_b$, $-(CH_2)_rO(CH_2)_rC(=O)NR_aR_a$, $C_{3-6}$ cycloalkyl optionally substituted with one or more $R_e$, aryl optionally substituted with one or more $R_e$, and heterocyclyl optionally substituted with one or more $R_e$; and $R_6$ is independently selected from H and $C_{1-5}$ alkyl; and other variables are as defined in Formulae (IIa)-(IIIa).

In another aspect, the invention provides a compound having Formulae (IIa)-(IIIa), or a stereoisomer, an enantiomer, a diastereomer, a tautomer, or a pharmaceutically acceptable salt thereof, wherein:

$R_4$ is independently selected from

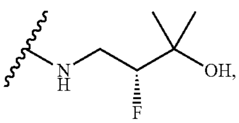 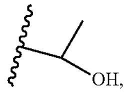

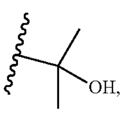 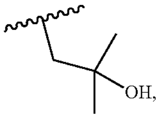 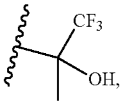

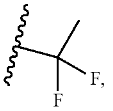 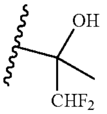 , 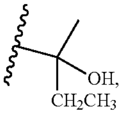

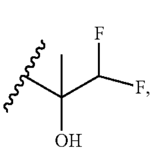 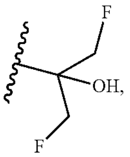 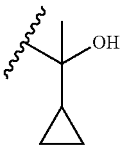 ,

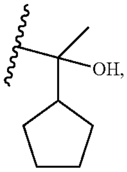 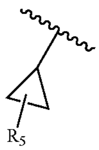 , 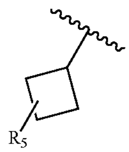 ,

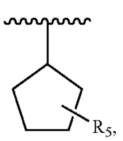 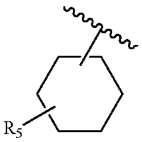 ,

-continued
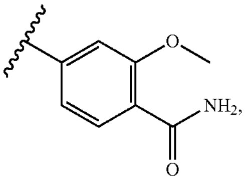,
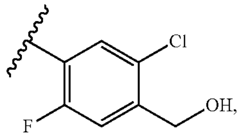,
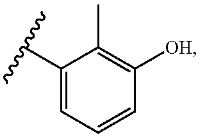,
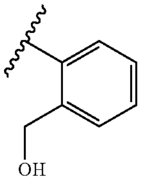,
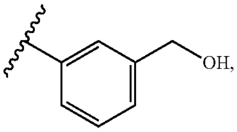,
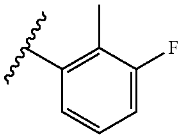,
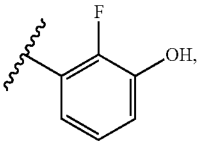,
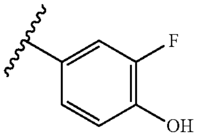,
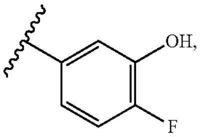,
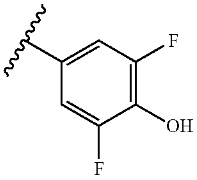,
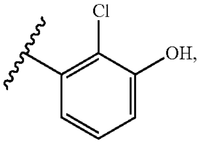,
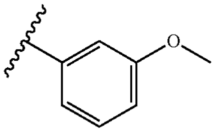,
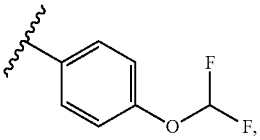,
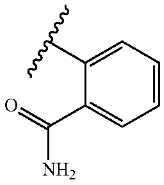,
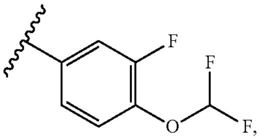,
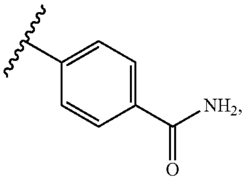,
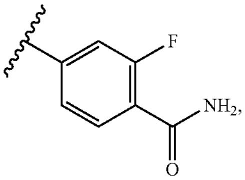,
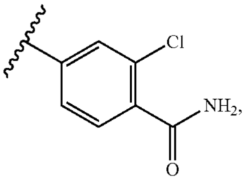,
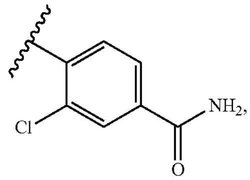,
-continued
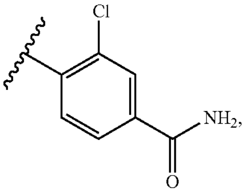,
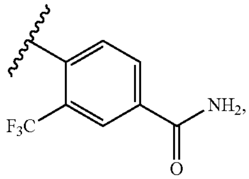,
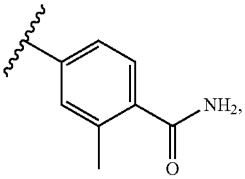,
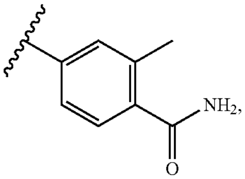,
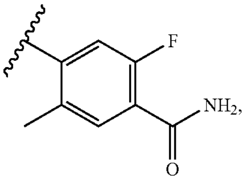,
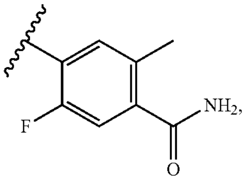,
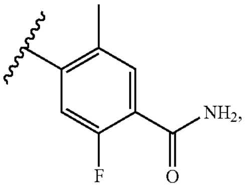,
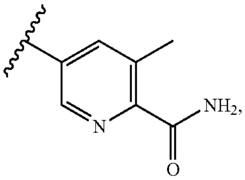,
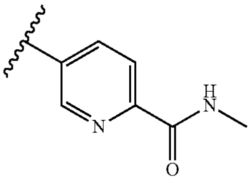,
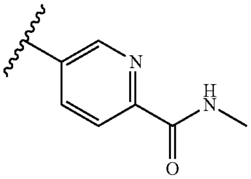,
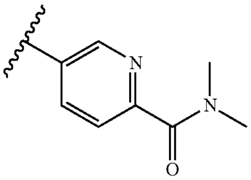,
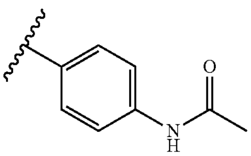,
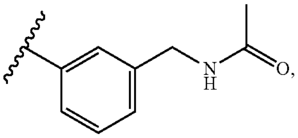

-continued
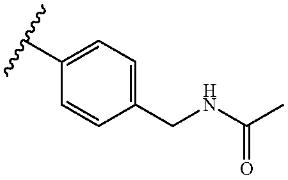,
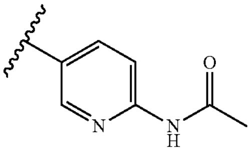,
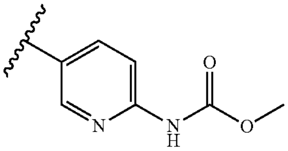,
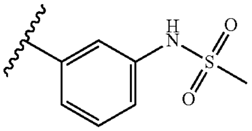,
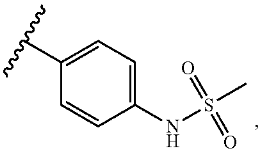,
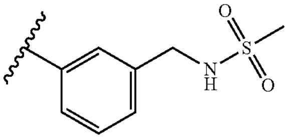,
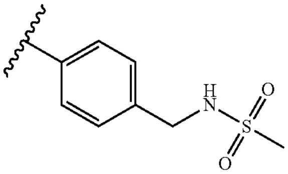, 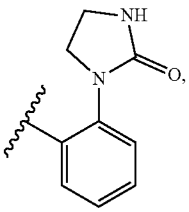
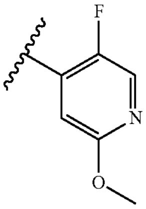, 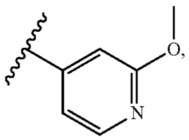
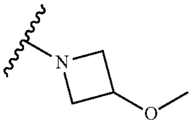, 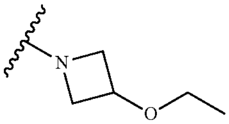,
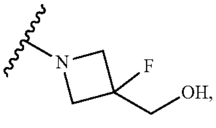 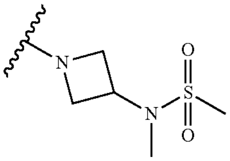,
-continued
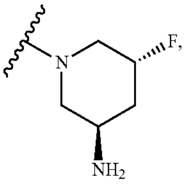 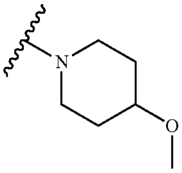,
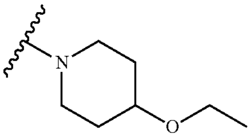, 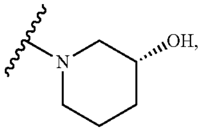
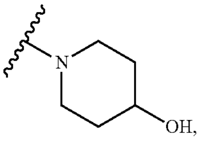 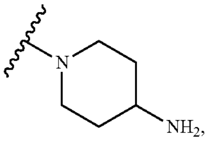
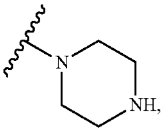
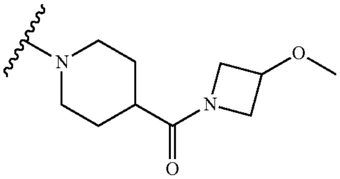,
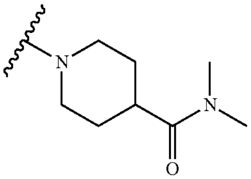,
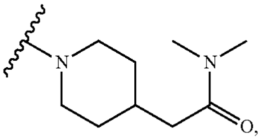
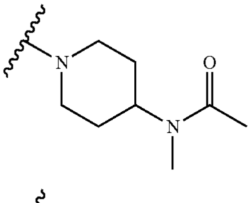,
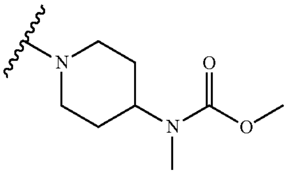,
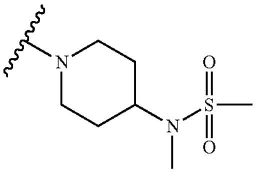, 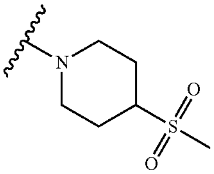, -continued
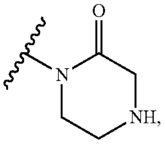 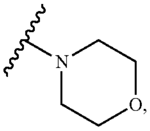 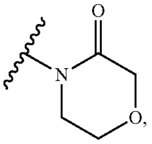
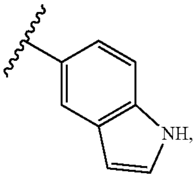 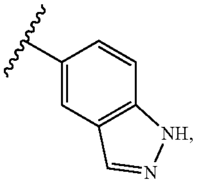
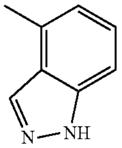, 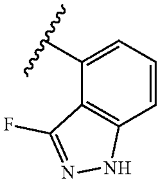,
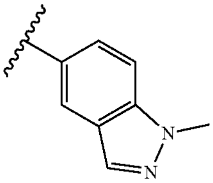, 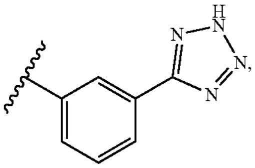
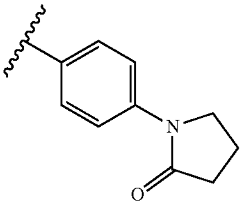, 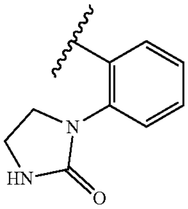,
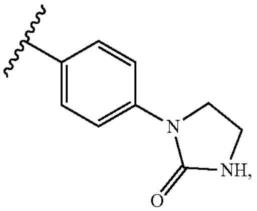 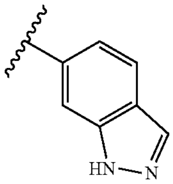,
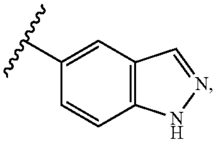 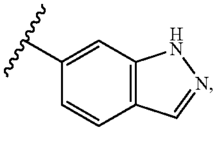
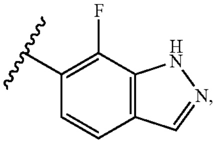 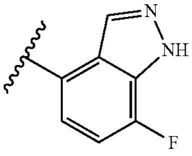,
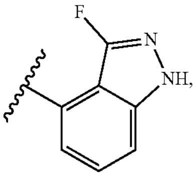 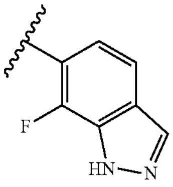,
-continued
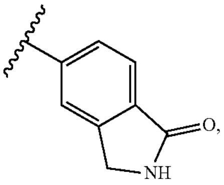 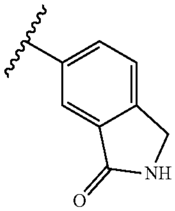,
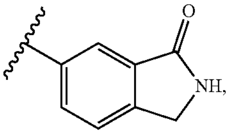 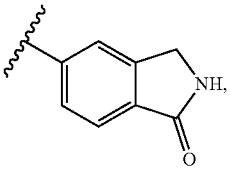
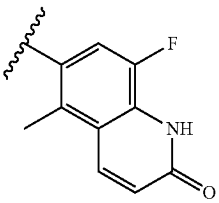, 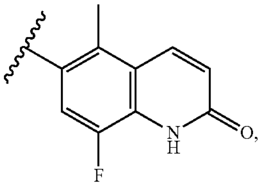
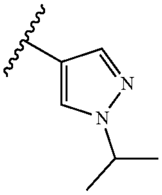, 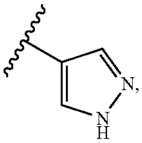
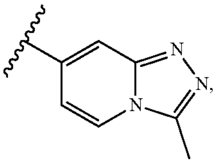
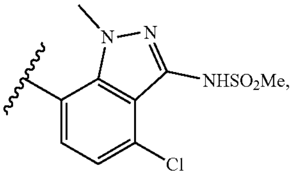
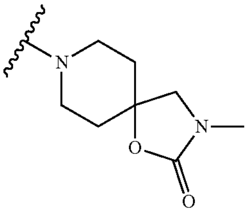,
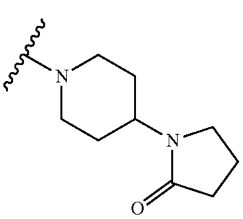, 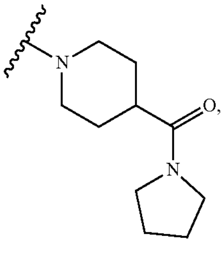

-continued

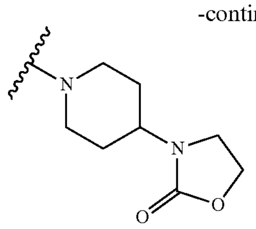

, and

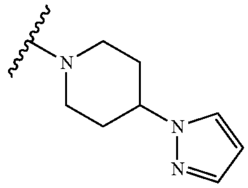

;

and other variables are as defined in Formulae (IIa)-(IIIa).

In another aspect, the invention provides a compound having Formula (IVa):

(IVa)

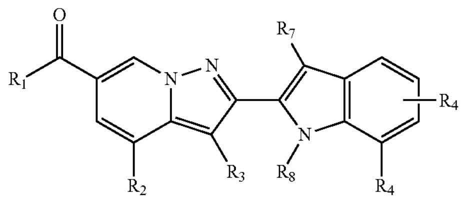

or a stereoisomer, an enantiomer, a diastereomer, a tautomer, or a pharmaceutically acceptable salt thereof, wherein:

$R_1$ is independently selected from

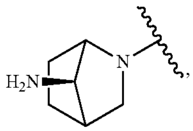

,

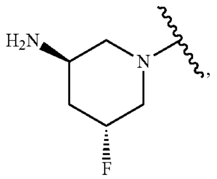

,

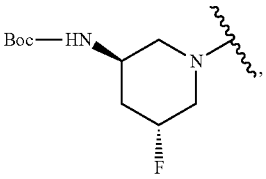

,

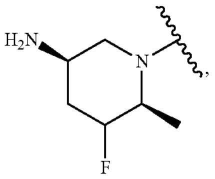

,

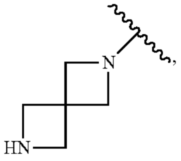

,

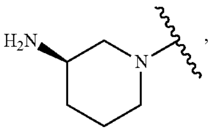

, and

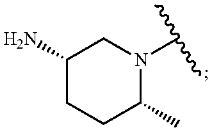

;

$R_2$ is independently selected from H, F, Cl, $C_{1-3}$ alkyl optionally substituted with one or more substituents selected from F, Cl, and OH, and $OC_{1-3}$ alkyl;

$R_3$ is independently selected from H, F, Cl, and $C_{1-3}$ alkyl optionally substituted with one or more substituents selected from F, Cl, and OH;

$R_4$ is independently selected from H, F, Cl, —C(=O)$R_b$, $C_{1-6}$ alkyl optionally substituted with one or more substituents selected from F, Cl, OH, and $C_{3-6}$ cycloalkyl, —NH—$C_{1-6}$ alkyl optionally substituted with one or more substituents selected from F, Cl, OH, and $C_{3-6}$ cycloalkyl, —$(CH_2)_r$-aryl substituted with one or more $R_5$, —O—$C_{1-6}$ alkyl substituted with one or more $R_5$, —$(CH_2)_r$—$C_{3-12}$ cycloalkyl substituted with one or more $R_5$, and —$(CH_2)_r$-4-10 membered heterocyclyl comprising carbon atoms and 1-5 heteroatoms selected from N, $NR_6$, O, and S and substituted with one or more $R_5$;

$R_5$ is independently selected from H, F, Cl, =O, $C_{1-4}$ alkyl optionally substituted with one or more $R_e$, —$(CH_2)_r$O$R_b$, —$(CH_2)_r$S$(O)_p$$R_c$, —$(CH_2)_r$S$(O)_p$N$R_a$$R_a$, —$(CH_2)_r$N$R_a$S$(O)_p$$R_c$, —$(CH_2)_r$N$R_a$$R_a$, —$(CH_2)_r$N$R_a$C(=O)$R_b$, —$(CH_2)_r$N$R_a$C(=O)O$R_b$, —$(CH_2)_r$N$R_a$C(=O)N$R_a$$R_a$, —$(CH_2)_r$C(=O)$R_b$, —$(CH_2)_r$C(=O)O$R_b$, —$(CH_2)_r$C(=O)N$R_a$$R_a$, —$(CH_2)_r$OC(=O)$R_b$, —$(CH_2)_r$OC(=O)O$R_b$, —$(CH_2)_r$O$(CH_2)_r$C(=O)N$R_a$$R_a$, $C_{3-6}$ cycloalkyl optionally substituted with one or more $R_e$, aryl optionally substituted with one or more $R_e$, and heterocyclyl optionally substituted with one or more $R_e$;

$R_6$ is independently selected from H, $C_{1-6}$ alkyl optionally substituted with one or more $R_e$, —S$(O)_p$$R_c$, —S$(O)_p$N$R_a$$R_a$, —C(=O)$R_b$, —C(=O)O$R_b$, —C(=O)N$R_a$$R_a$, $C_{3-6}$ cycloalkyl optionally substituted with one or more $R_e$, aryl optionally substituted with one or more $R_e$, and heterocyclyl optionally substituted with one or more $R_e$;

$R_7$ is independently selected from H, F, and Cl;

$R_8$ is independently selected from H, and $C_{1-6}$ alkyl optionally substituted with one or more substituents selected from F, Cl, and $C_{3-6}$ cycloalkyl;

$R_a$ is independently selected from H, $C_{1-6}$ alkyl optionally substituted with one or more $R_e$, —$(CH_2)_r$—$C_{3-10}$ carbocyclyl optionally substituted with one or more $R_e$, and —$(CH_2)_r$-heterocyclyl optionally substituted with one or more $R_e$; or $R_a$ and $R_a$ together with the nitrogen atom to which they are both attached form a heterocyclic ring optionally substituted with one or more $R_e$;

$R_b$ is independently selected from H, $C_{1-6}$ alkyl optionally substituted with one or more $R_e$, —$(CH_2)_r$—$C_{3-10}$ carbocyclyl optionally substituted with one or more $R_e$, and —$(CH_2)_r$ heterocyclyl optionally substituted with one or more $R_e$;

$R_c$ is independently selected from $C_{1-6}$ alkyl optionally substituted with one or more $R_e$, —$(CH_2)_r$—$C_{3-10}$ carbocyclyl optionally substituted with one or more $R_e$, and —$(CH_2)_r$-heterocyclyl optionally substituted with one or more $R_e$;

$R_e$ is independently selected from F, Cl, Br, $NH_2$, —NH—$C_{1-4}$ alkyl, —N$(C_{1-4}$ alkyl$)_2$, =O, OH, —$OC_{1-6}$ alkyl, $C_{1-6}$ alkyl optionally substituted with one or more $R_f$, —$(CH_2)_r$—$C_{3-6}$ cycloalkyl optionally substituted with one or more $R_f$, —$(CH_2)_r$-aryl optionally substituted with one or more $R_f$, and —$(CH_2)_r$-heterocyclyl optionally substituted with one or more $R_f$;

$R_f$ is independently selected from F, Cl, OH, $OC_{1-5}$ alkyl, $C_{1-5}$ alkyl optionally substituted with OH, $C_{2-5}$ alkenyl, $C_{2-5}$ alkynyl, $C_{3-6}$ cycloalkyl, and phenyl;

p, at each occurrence, is independently selected from zero, 1, and 2; and r, at each occurrence, is independently selected from zero, 1, 2, 3, and 4.

In another aspect, the invention provides a compound having Formulae (IVa), or a stereoisomer, an enantiomer, a diastereomer, a tautomer, or a pharmaceutically acceptable salt thereof, wherein:

$R_1$ is independently selected from

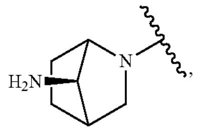

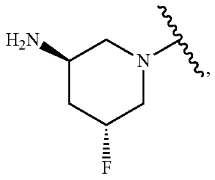

and

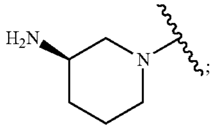

$R_2$ is independently selected from H, F, Cl, and $OCH_3$;

$R_3$ is independently selected from F, Cl, and $CH_3$;

$R_4$ is independently selected from H,

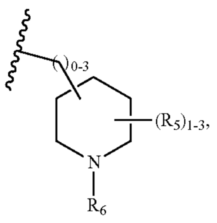

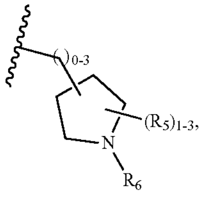

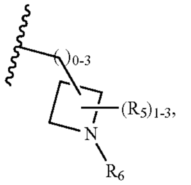

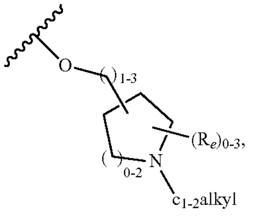

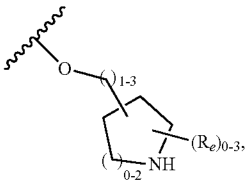

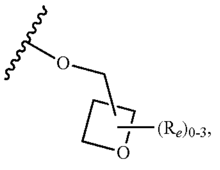

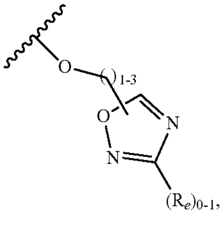

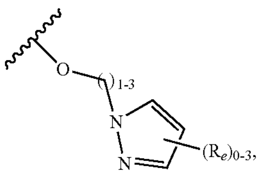

-continued

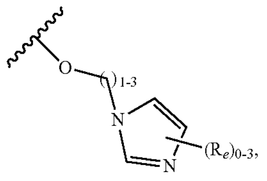

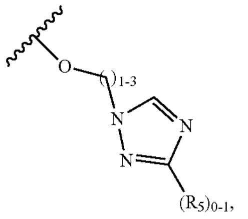

and

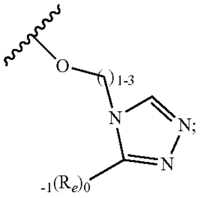

$R_5$ is independently selected from H, =O, $C_{1-4}$ alkyl, OH, and $NH_2$;

$R_6$ is independently selected from H, $C_{1-5}$ alkyl optionally substituted with one or more $R_e$, and —C(=O)$R_b$;

$R_7$ is H;

$R_8$ is $C_{1-2}$ alkyl optionally substituted with cyclopropyl;

$R_b$ is independently selected from H, $C_{1-6}$ alkyl optionally substituted with one or more $R_e$, —$(CH_2)_r$—$C_{3-10}$ carbocyclyl optionally substituted with one or more $R_e$, and —$(CH_2)_r$- heterocyclyl optionally substituted with one or more $R_e$;

$R_e$ is independently selected from $NH_2$ and $C_{1-5}$ alkyl optionally substituted with one or more $R_f$; and $R_f$ is independently selected from F, Cl, OH, and $OC_{1-5}$ alkyl.

In another aspect, the invention provides a compound having Formulae (IIa)-(IIIa), or a stereoisomer, an enantiomer, a diastereomer, a tautomer, or a pharmaceutically acceptable salt thereof, wherein:

$R_4$ is independently selected from

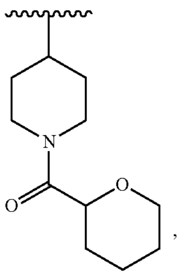

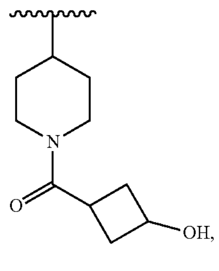

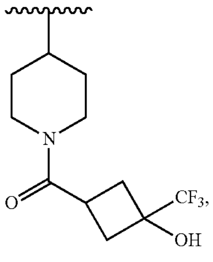

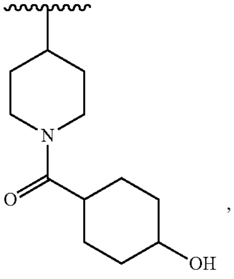

-continued
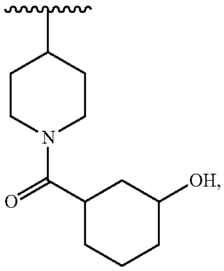,
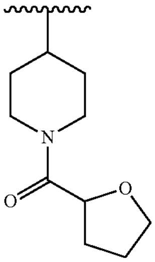,
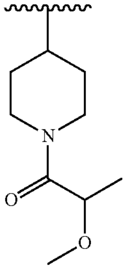,
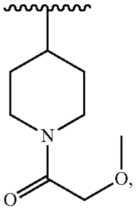,
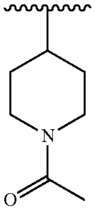,
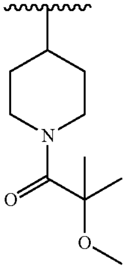,
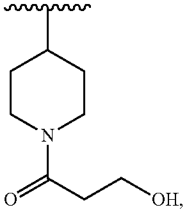,
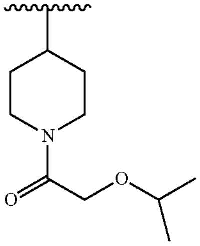,
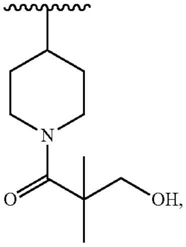,
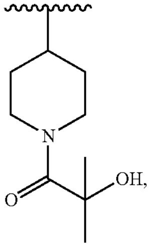,
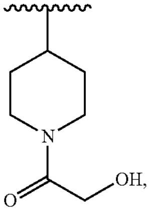,
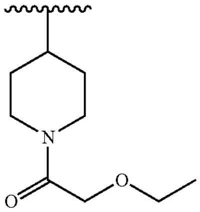,
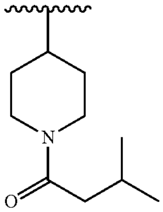,
-continued
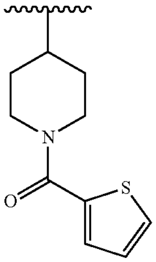,
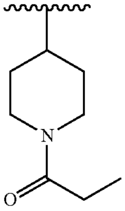,
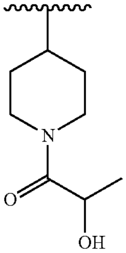,
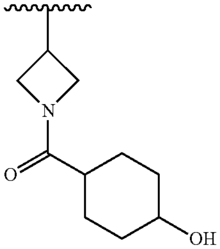,
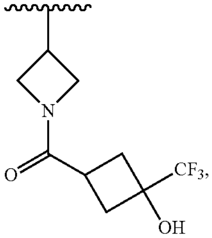,
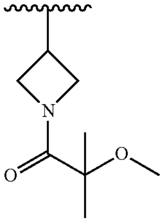,
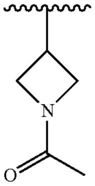,
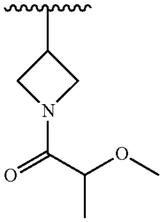,
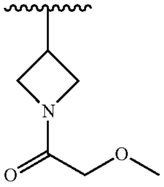,
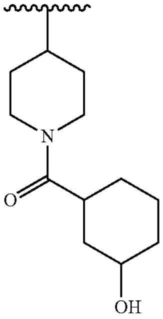,
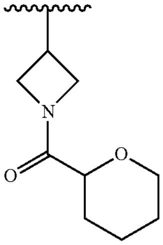,
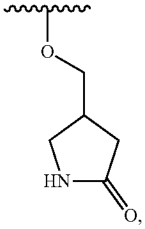,
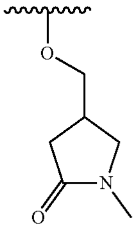,
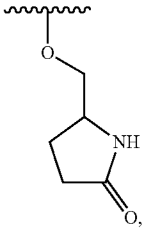,
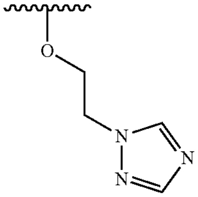, -continued

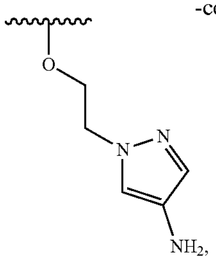

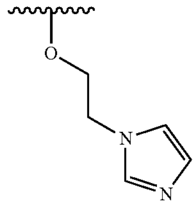
,

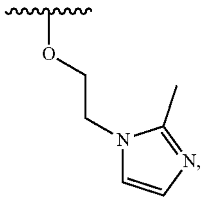

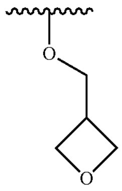
, and

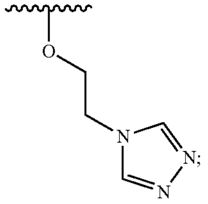

and other variables are as defined in Formulae (IIa)-(IIIa).

In another aspect, the invention provides a compound having Formula (Va):

(Va)

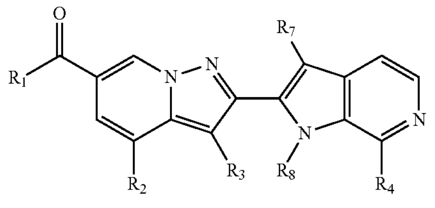

or a stereoisomer, an enantiomer, a diastereomer, a tautomer, or a pharmaceutically acceptable salt thereof, wherein:

$R_1$ is independently selected from

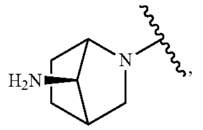
,

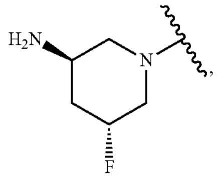
, and

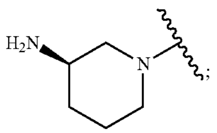

$R_2$ is independently selected from H, F, Cl, $CH_3$, and $OCH_3$;

$R_3$ is independently selected from H, F, Cl, CN, $CH_3$, and $CH_2OH$;

$R_4$ is independently selected from H, F, Cl, —C(═O)$R_b$, $C_{1-6}$ alkyl optionally substituted with one or more substituents selected from F, Cl, OH, and $C_{3-6}$ cycloalkyl, —NH—$C_{1-6}$ alkyl optionally substituted with one or more substituents selected from F, Cl, OH, and $C_{3-6}$ cycloalkyl, —$(CH_2)_r$-aryl substituted with one or more $R_5$, —O—$C_{1-6}$ alkyl substituted with one or more $R_5$, —$(CH_2)_r$—$C_{3-12}$ cycloalkyl substituted with one or more $R_5$, and —$(CH_2)_r$-4-10 membered heterocyclyl comprising carbon atoms and 1-5 heteroatoms selected from N, $NR_6$, O, and S and substituted with one or more $R_5$;

$R_5$ is independently selected from H, F, Cl, ═O, $C_{1-4}$ alkyl optionally substituted with one or more $R_e$, —$(CH_2)_r$O$R_b$, —$(CH_2)_r$S(O)$_p$$R_c$, —$(CH_2)_r$S(O)$_p$N$R_a$$R_a$, —$(CH_2)_r$N$R_a$S(O)$_p$$R_c$, —$(CH_2)_r$N$R_a$$R_a$, —$(CH_2)_r$N$R_a$C(═O)$R_b$, —$(CH_2)_r$N$R_a$C(═O)O$R_b$, —$(CH_2)_r$N$R_a$C(═O)N$R_a$$R_a$, —$(CH_2)_r$C(═O)$R_b$, —$(CH_2)_r$C(═O)O$R_b$, —$(CH_2)_r$C(═O)N$R_a$$R_a$, —$(CH_2)_r$OC(═O)$R_b$, —$(CH_2)_r$OC(═O)O$R_b$, —$(CH_2)_r$O$(CH_2)_r$C(═O)N$R_a$$R_a$, $C_{3-6}$ cycloalkyl optionally substituted with one or more $R_e$, aryl optionally substituted with one or more $R_e$, and heterocyclyl optionally substituted with one or more $R_e$;

$R_6$ is independently selected from H, $C_{1-6}$ alkyl optionally substituted with one or more $R_e$, —C(═O)$R_b$, —C(═O)O$R_b$, —C(═O)N$R_a$$R_a$, $C_{3-6}$ cycloalkyl optionally substituted with one or more $R_e$, aryl optionally substituted with one or more $R_e$, and heterocyclyl optionally substituted with one or more $R_e$;

$R_7$ is independently selected from H, F, and Cl;

$R_8$ is independently selected from H, and $C_{1-6}$ alkyl optionally substituted with one or more substituents selected from F, Cl, and $C_{3-6}$ cycloalkyl;

$R_a$ is independently selected from H, $C_{1-6}$ alkyl optionally substituted with one or more $R_e$, —$(CH_2)_r$—$C_{3-10}$ carbocyclyl optionally substituted with one or more $R_e$, and —$(CH_2)_r$-heterocyclyl optionally substituted with one or more $R_e$; or $R_a$ and $R_a$ together with the nitrogen atom to which they are both attached form a heterocyclic ring optionally substituted with one or more $R_e$;

$R_b$ is independently selected from H, $C_{1-6}$ alkyl optionally substituted with one or more $R_e$, —$(CH_2)_r$—$C_{3-10}$ carbocyclyl optionally substituted with one or more $R_e$, and —$(CH_2)_r$ heterocyclyl optionally substituted with one or more $R_e$;

$R_c$ is independently selected from $C_{1-6}$ alkyl optionally substituted with one or more $R_e$, —$(CH_2)_r$—$C_{3-10}$ carbocyclyl optionally substituted with one or more $R_e$, and —$(CH_2)_r$-heterocyclyl optionally substituted with one or more $R_e$;

$R_e$ is independently selected from F, Cl, Br, $NH_2$, —NH—$C_{1-4}$ alkyl, —N($C_{1-4}$ alkyl)$_2$, ═O, OH, —O$C_{1-6}$ alkyl, —$CO_2$H, $C_{1-6}$ alkyl optionally substituted with one or more $R_f$, —$(CH_2)_r$—$C_{3-6}$ cycloalkyl optionally substituted with one or more $R_f$, —$(CH_2)_r$-aryl optionally substituted with one or more $R_f$, and —$(CH_2)_r$-heterocyclyl optionally substituted with one or more $R_f$;

$R_f$ is independently selected from F, Cl, Br, CN, OH, $C_{1-5}$ alkyl optionally substituted with OH, $C_{2-5}$ alkenyl, $C_{2-5}$ alkynyl, $C_{3-6}$ cycloalkyl, and phenyl;

p, at each occurrence, is independently selected from zero, 1, and 2; and r, at each occurrence, is independently selected from zero, 1, 2, 3, and 4.

In another aspect, the invention provides a compound having Formula (Va), or a stereoisomer, an enantiomer, a diastereomer, a tautomer, or a pharmaceutically acceptable salt thereof, wherein:

$R_1$ is independently selected from
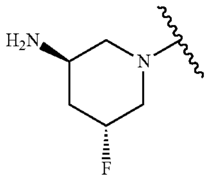
and
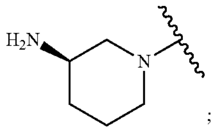
;
$R_2$ is $CH_3$;
$R_3$ is $CH_3$; and
$R_4$ is independently selected from,
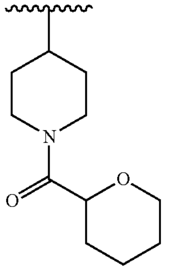
,
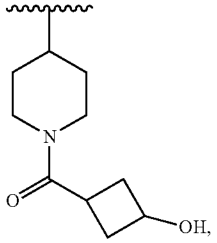
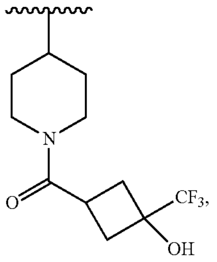
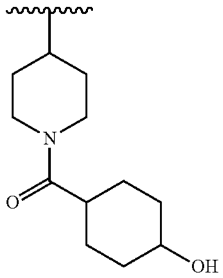
,
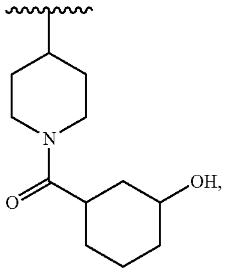
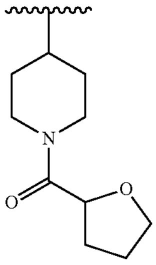
,
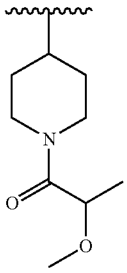
,
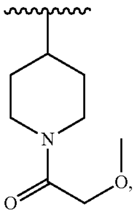
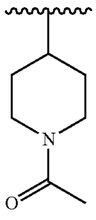
,
-continued
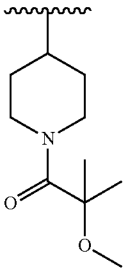
,
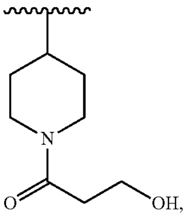
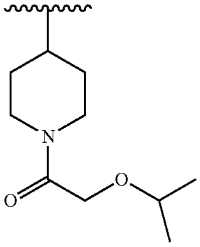
,
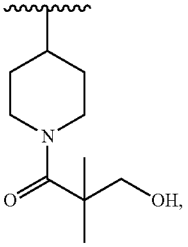
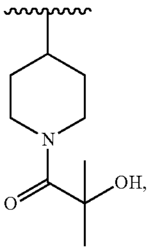
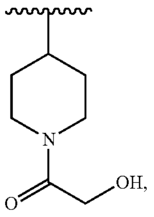
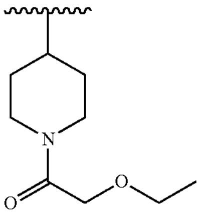
,
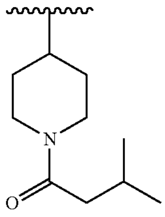
,
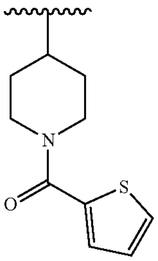
,
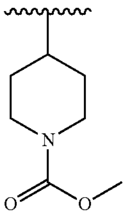
,
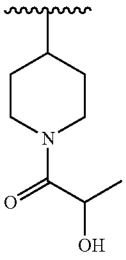
,
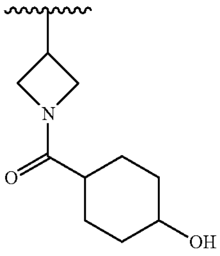
, -continued

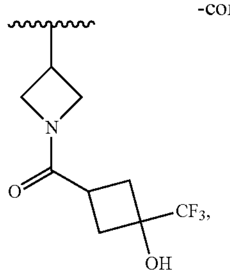 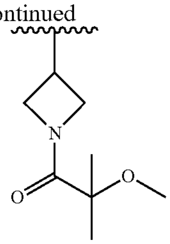 ,

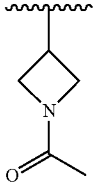 , 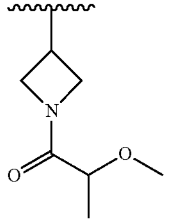 , 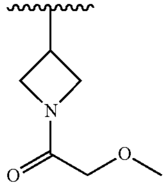 ,

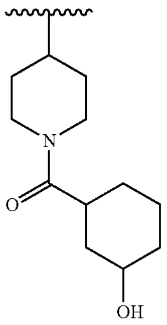 , 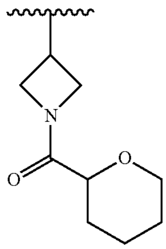 ,

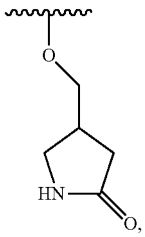 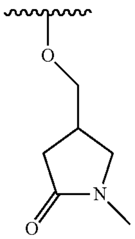 , 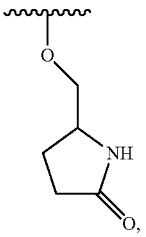

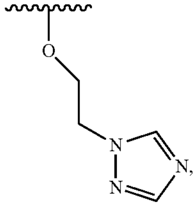 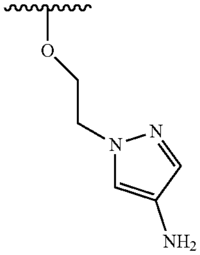 ,

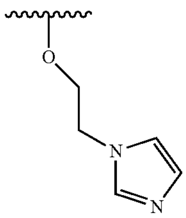 , 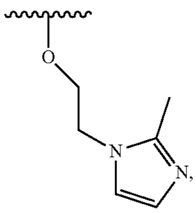

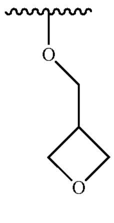 , 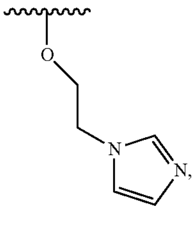 and

-continued

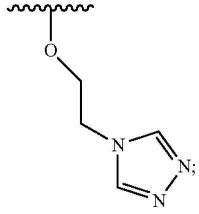

$R_7$ is H; and $R_8$ is $C_{1-2}$ alkyl optionally substituted with cyclopropyl.

In another aspect, the invention provides a compound having Formula (VIa):

(VIa)

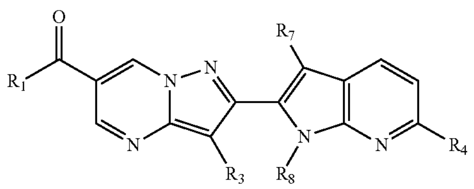

or a stereoisomer, an enantiomer, a diastereomer, a tautomer, or a pharmaceutically acceptable salt thereof, wherein:

$R_1$ is independently selected from

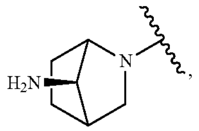

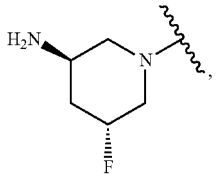 and

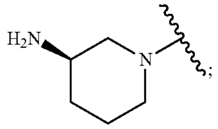

$R_3$ is independently selected from H, F, and $CH_3$;

$R_4$ is independently selected from H, F, Cl, —C(═O)$R_b$, $C_{1-6}$ alkyl optionally substituted with one or more substituents selected from F, Cl, OH, and $C_{3-6}$ cycloalkyl, —NH—$C_{1-6}$ alkyl optionally substituted with one or more substituents selected from F, Cl, OH, and $C_{3-6}$ cycloalkyl, —$(CH_2)_r$-aryl substituted with one or more $R_5$, —O—$C_{1-6}$ alkyl substituted with one or more $R_5$, —$(CH_2)_r$—$C_{3-12}$ cycloalkyl substituted with one or more $R_5$, and —$(CH_2)_r$-4-10 membered heterocyclyl comprising carbon atoms and 1-5 heteroatoms selected from N, $NR_6$, O, and S and substituted with one or more $R_5$;

$R_5$ is independently selected from H, F, Cl, Br, CN, ═O, $C_{1-4}$ alkyl optionally substituted with one or more $R_e$, $C_{2-4}$ alkenyl optionally substituted with one or more $R_e$, $C_{2-4}$ alkynyl optionally substituted with one or more $R_e$, $—(CH_2)_rOR_b$, $—(CH_2)_rS(O)_pR_c$, $—(CH_2)_rS(O)_pNR_aR_a$, $—(CH_2)_rNR_aS(O)_pR_c$, $—(CH_2)_rNR_aR_a$, $—(CH_2)_rNR_rC(=O)R_b$, $—(CH_2)_rNR_aC(=O)OR_b$, $—(CH_2)_rNR_aC(=O)NR_aR_a$, $—(CH_2)_rC(=O)R_b$, $—(CH_2)_rC(=O)OR_b$, $—(CH_2)_rC(=O)NR_aR_a$, $—(CH_2)_rOC(=O)R_b$, $—(CH_2)_rOC(=O)OR_b$, $—(CH_2)_rO(CH_2)_rC(=O)NR_aR_a$, $C_{3-6}$ cycloalkyl optionally substituted with one or more $R_e$, aryl optionally substituted with one or more $R_e$, and heterocyclyl optionally substituted with one or more $R_e$;

$R_6$ is independently selected from H, $C_{1-6}$ alkyl optionally substituted with one or more $R_e$, $—C(=O)R_b$, $—C(=O)OR_b$, $—C(=O)NR_aR_a$, $C_{3-6}$ cycloalkyl optionally substituted with one or more $R_e$, aryl optionally substituted with one or more $R_e$, and heterocyclyl optionally substituted with one or more $R_e$;

$R_7$ is independently selected from H, F, and Cl;

$R_8$ is independently selected from H, and $C_{1-6}$ alkyl optionally substituted with one or more substituents selected from F, Cl, and $C_{3-6}$ cycloalkyl;

$R_a$ is independently selected from H, $C_{1-6}$ alkyl optionally substituted with one or more $R_e$, $C_{2-6}$ alkenyl optionally substituted with one or more Re, $C_{2-6}$ alkynyl optionally substituted with one or more $R_e$, $—(CH_2)_r—C_{3-10}$ carbocyclyl optionally substituted with one or more $R_e$, and $—(CH_2)_r$-heterocyclyl optionally substituted with one or more $R_e$; or $R_a$ and $R_a$ together with the nitrogen atom to which they are both attached form a heterocyclic ring optionally substituted with one or more $R_e$;

$R_b$ is independently selected from H, $C_{1-6}$ alkyl optionally substituted with one or more $R_e$, $C_{2-6}$ alkenyl optionally substituted with one or more $R_e$, $C_{2-6}$ alkynyl optionally substituted with one or more $R_e$, $—(CH_2)_r—C_{3-10}$ carbocyclyl optionally substituted with one or more $R_e$, and $—(CH_2)_r$ heterocyclyl optionally substituted with one or more $R_e$;

$R_c$ is independently selected from $C_{1-6}$ alkyl optionally substituted with one or more $R_e$, $C_{2-6}$ alkenyl optionally substituted with one or more $R_e$, $C_{2-6}$ alkynyl optionally substituted with one or more $R_e$, $—(CH_2)_r—C_{3-10}$ carbocyclyl optionally substituted with one or more $R_e$, and $—(CH_2)_r$-heterocyclyl optionally substituted with one or more $R_e$;

$R_e$ is independently selected from F, Cl, Br, CN, $NH_2$, $—NH—C_{1-4}$ alkyl, $—N(C_{1-4}\ alkyl)_2$, $=O$, OH, $—OC_{1-6}$ alkyl, $—CO_2H$, $C_{1-6}$ alkyl optionally substituted with one or more $R_f$, $C_{2-6}$ alkenyl, $C_{2-6}$ alkynyl, $—(CH_2)_r—C_{3-6}$ cycloalkyl optionally substituted with one or more $R_f$, $—(CH_2)_r$-aryl optionally substituted with one or more $R_f$, and $—(CH_2)_r$-heterocyclyl optionally substituted with one or more $R_f$;

$R_f$ is independently selected from F, Cl, Br, CN, OH, $C_{1-5}$ alkyl optionally substituted with OH, $C_{2-5}$ alkenyl, $C_{2-5}$ alkynyl, $C_{3-6}$ cycloalkyl, and phenyl;

p, at each occurrence, is independently selected from zero, 1, and 2; and r, at each occurrence, is independently selected from zero, 1, 2, 3, and 4.

In another aspect, the invention provides a compound having Formula (VIa), or a stereoisomer, an enantiomer, a diastereomer, a tautomer, or a pharmaceutically acceptable salt thereof, wherein:

$R_1$ is independently selected from

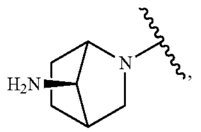

and

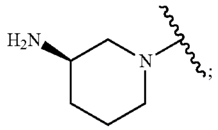

$R_3$ is $CH_3$;

$R_4$ is independently selected from F, Cl,

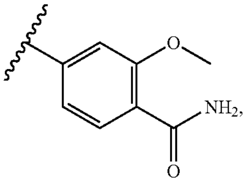

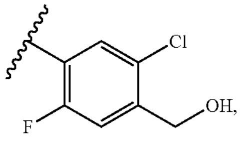

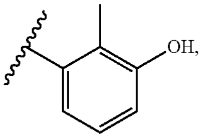

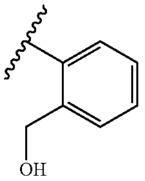

,

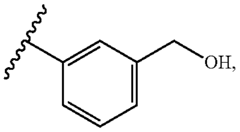

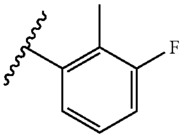

,

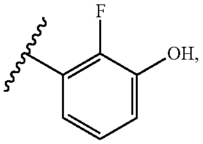

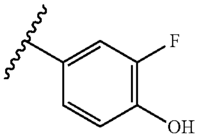

,

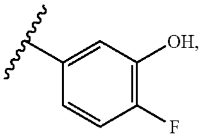

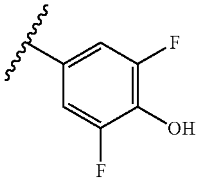

,

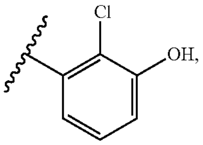

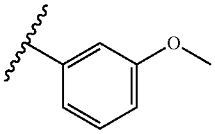

,

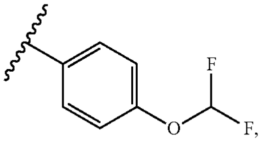

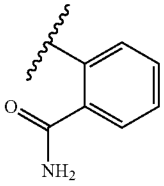

,

-continued
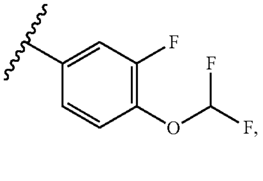
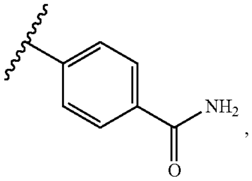
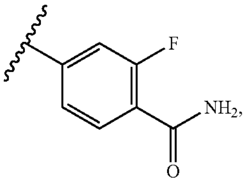
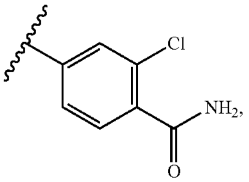
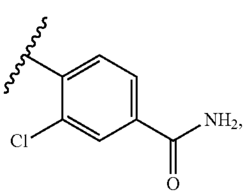
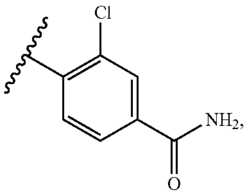
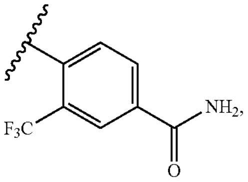
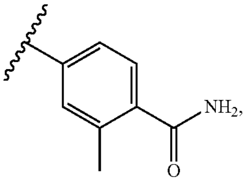
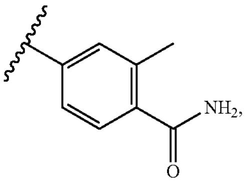
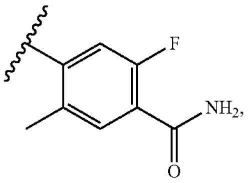
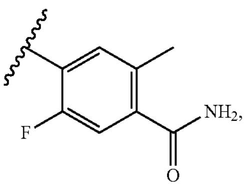
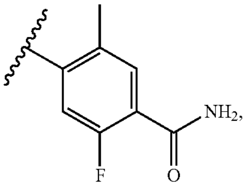
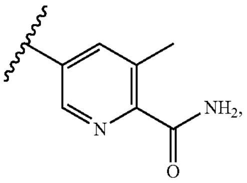
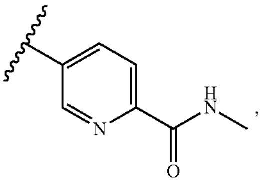
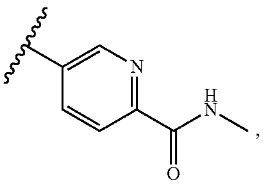
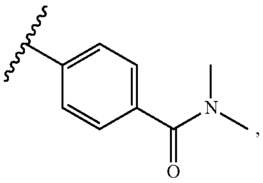
-continued
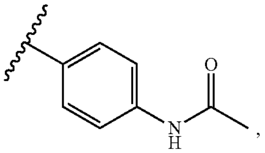
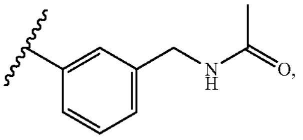
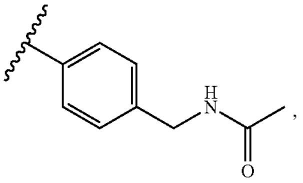
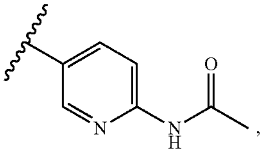
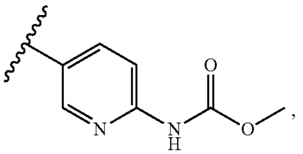
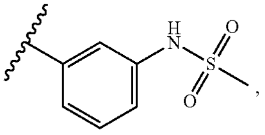
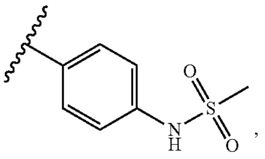
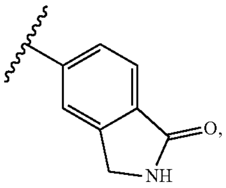
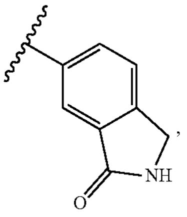
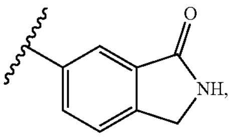
and
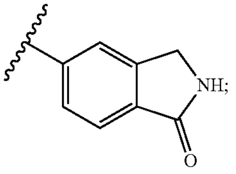
$R_7$ is H; and
$R_8$ is $C_{1-2}$ alkyl optionally substituted with cyclopropyl.
In another aspect, the invention provides a compound having Formula (VII):

(VII)

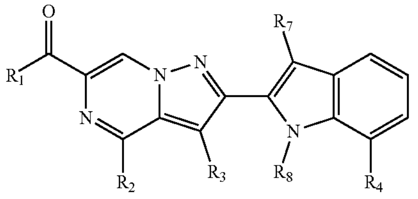

or a stereoisomer, an enantiomer, a diastereomer, a tautomer, or a pharmaceutically acceptable salt thereof, wherein:

$R_1$ is independently selected from

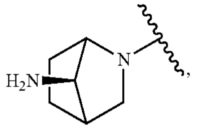

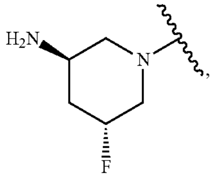

and

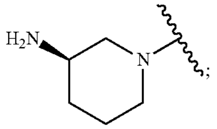

$R_2$ is independently selected from H, F, Cl, $CH_3$, and $OCH_3$;

$R_3$ is independently selected from H, F, and $CH_3$;

$R_4$ is independently selected from H, F, Cl, Br, —C(=O)$R_b$, $C_{1-6}$ alkyl optionally substituted with one or more substituents selected from F, Cl, OH, and $C_{3-6}$ cycloalkyl, —NH—$C_{1-6}$ alkyl optionally substituted with one or more substituents selected from F, Cl, OH, and $C_{3-6}$ cycloalkyl, —$(CH_2)_r$-aryl substituted with one or more $R_5$, —O—$C_{1-6}$ alkyl substituted with one or more $R_5$, —$(CH_2)_r$—$C_{3-12}$ cycloalkyl substituted with one or more $R_5$, and —$(CH_2)_r$-4-10 membered heterocyclyl comprising carbon atoms and 1-5 heteroatoms selected from N, $NR_6$, O, and S and substituted with one or more $R_5$;

$R_5$ is independently selected from H, F, Cl, Br, CN, =O, $C_{1-4}$ alkyl optionally substituted with one or more $R_e$, $C_{2-4}$ alkenyl optionally substituted with one or more $R_e$, $C_{2-4}$ alkynyl optionally substituted with one or more $R_e$, —$(CH_2)_r$$OR_b$, —$(CH_2)_r$$S(O)_pR_c$, —$(CH_2)_r$$S(O)_pNR_aR_a$, —$(CH_2)_r$$NR_aS(O)_pR_c$, —$(CH_2)_r$$NR_aR_a$, —$(CH_2)_r$$NR_aC$(=O)$R_b$, —$(CH_2)_r$$NR_aC$(=O)$OR_b$, —$(CH_2)_r$$NR_aC$(=O)$NR_aR_a$, —$(CH_2)_r$C(=O)$R_b$, —$(CH_2)_r$C(=O)$OR_b$, —$(CH_2)_r$C(=O)$NR_aR_a$, —$(CH_2)_r$OC(=O)$R_b$, —$(CH_2)_r$OC(=O)$OR_b$, —$(CH_2)_r$O$(CH_2)_r$C(=O)$NR_aR_a$, $C_{3-6}$ cycloalkyl optionally substituted with one or more $R_e$, aryl optionally substituted with one or more $R_e$, and heterocyclyl optionally substituted with one or more $R_e$;

$R_6$ is independently selected from H, $C_{1-6}$ alkyl optionally substituted with one or more $R_e$, —$S(O)_pR_c$, —$S(O)_pNR_aR_a$, —C(=O)$R_b$, —C(=O)$OR_b$, —C(=O)$NR_aR_a$, $C_{3-6}$ cycloalkyl optionally substituted with one or more $R_e$, aryl optionally substituted with one or more $R_e$, and heterocyclyl optionally substituted with one or more $R_e$;

$R_7$ is independently selected from H, F, and Cl;

$R_8$ is independently selected from H, and $C_{1-6}$ alkyl optionally substituted with one or more substituents selected from F, Cl, and $C_{3-6}$ cycloalkyl;

$R_a$ is independently selected from H, $C_{1-6}$ alkyl optionally substituted with one or more $R_e$, $C_{2-6}$ alkenyl optionally substituted with one or more Re, $C_{2-6}$ alkynyl optionally substituted with one or more $R_e$, —$(CH_2)_r$—$C_{3-10}$ carbocyclyl optionally substituted with one or more $R_e$, and —$(CH_2)_r$-heterocyclyl optionally substituted with one or more $R_e$; or $R_a$ and $R_a$ together with the nitrogen atom to which they are both attached form a heterocyclic ring optionally substituted with one or more $R_e$;

$R_b$ is independently selected from H, $C_{1-6}$ alkyl optionally substituted with one or more $R_e$, $C_{2-6}$ alkenyl optionally substituted with one or more $R_e$, $C_{2-6}$ alkynyl optionally substituted with one or more $R_e$, —$(CH_2)_r$—$C_{3-10}$ carbocyclyl optionally substituted with one or more $R_e$, and —$(CH_2)_r$ heterocyclyl optionally substituted with one or more $R_e$;

$R_c$ is independently selected from $C_{1-6}$ alkyl optionally substituted with one or more $R_e$, $C_{2-6}$ alkenyl optionally substituted with one or more $R_e$, $C_{2-6}$ alkynyl optionally substituted with one or more $R_e$, —$(CH_2)_r$—$C_{3-10}$ carbocyclyl optionally substituted with one or more $R_e$, and —$(CH_2)_r$-heterocyclyl optionally substituted with one or more $R_e$;

$R_e$ is independently selected from F, Cl, Br, CN, $NH_2$, —NH—$C_{1-4}$ alkyl, —N($C_{1-4}$ alkyl)$_2$, =O, OH, —$OC_{1-6}$ alkyl, —$CO_2H$, $C_{1-6}$ alkyl optionally substituted with one or more $R_f$, $C_{2-6}$ alkenyl, $C_{2-6}$ alkynyl, —$(CH_2)_r$—$C_{3-6}$ cycloalkyl optionally substituted with one or more $R_f$, —$(CH_2)_r$-aryl optionally substituted with one or more $R_f$, and —$(CH_2)_r$-heterocyclyl optionally substituted with one or more $R_f$;

$R_f$ is independently selected from F, Cl, Br, CN, OH, $C_{1-5}$ alkyl optionally substituted with OH, $C_{2-5}$ alkenyl, $C_{2-5}$ alkynyl, $C_{3-6}$ cycloalkyl, and phenyl;

p, at each occurrence, is independently selected from zero, 1, and 2; and r, at each occurrence, is independently selected from zero, 1, 2, 3, and 4.

In another aspect, the invention provides a compound having Formula (VIII):

(VIII)

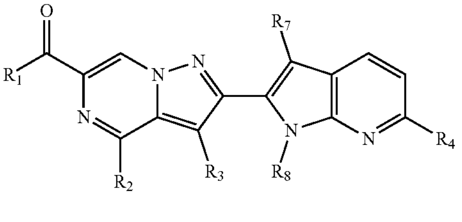

or a stereoisomer, an enantiomer, a diastereomer, a tautomer, or a pharmaceutically acceptable salt thereof, wherein:

$R_1$ is independently selected from

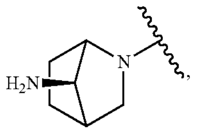,

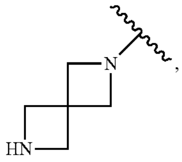, and

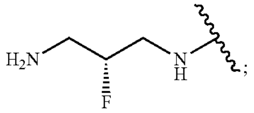;

$R_2$ is independently selected from H, F, and $OCH_3$;

$R_3$ is independently selected from H, F, and $CH_3$;

$R_4$ is independently selected from H, F, Cl, Br, —C(=O)$R_b$, $C_{1-6}$ alkyl optionally substituted with one or more substituents selected from F, Cl, OH, and $C_{3-6}$ cycloalkyl, —NH—$C_{1-6}$ alkyl optionally substituted with one or more substituents selected from F, Cl, OH, and $C_{3-6}$ cycloalkyl, —$(CH_2)_r$-aryl substituted with one or more $R_5$, —O—$C_{1-6}$ alkyl substituted with one or more $R_5$, —$(CH_2)_r$—$C_{3-12}$ cycloalkyl substituted with one or more $R_5$, and —$(CH_2)_r$-4-10 membered heterocyclyl comprising carbon atoms and 1-5 heteroatoms selected from N, $NR_6$, O, and S and substituted with one or more $R_5$;

$R_5$ is independently selected from H, F, Cl, Br, CN, =O, $C_{1-4}$ alkyl optionally substituted with one or more $R_e$, $C_{2-4}$ alkenyl optionally substituted with one or more $R_e$, $C_{2-4}$ alkynyl optionally substituted with one or more $R_e$, —$(CH_2)_rOR_b$, —$(CH_2)_rS(O)_pR_e$, —$(CH_2)_rS(O)_pNR_aR_a$, —$(CH_2)_rNR_aS(O)_pR_c$, —$(CH_2)_rNR_aR_a$, —$(CH_2)_rNR_rC(=O)R_b$, —$(CH_2)_rNR_aC(=O)OR_b$, —$(CH_2)_rNR_aC(=O)NR_aR_a$, —$(CH_2)_rC(=O)R_b$, —$(CH_2)_rC(=O)OR_b$, —$(CH_2)_rC(=O)NR_aR_a$, —$(CH_2)_rOC(=O)R_b$, —$(CH_2)_rOC(=O)OR_b$, —$(CH_2)_rO(CH_2)_rC(=O)NR_aR_a$, $C_{3-6}$ cycloalkyl optionally substituted with one or more $R_e$, aryl optionally substituted with one or more $R_e$, and heterocyclyl optionally substituted with one or more $R_e$;

$R_6$ is independently selected from H, $C_{1-6}$ alkyl optionally substituted with one or more $R_e$, —C(=O)$R_b$, —C(=O)$OR_b$, —C(=O)$NR_aR_a$, $C_{3-6}$ cycloalkyl optionally substituted with one or more $R_e$, aryl optionally substituted with one or more $R_e$, and heterocyclyl optionally substituted with one or more $R_e$;

$R_7$ is independently selected from H, F, and Cl;

$R_8$ is independently selected from H, and $C_{1-6}$ alkyl optionally substituted with one or more substituents selected from F, Cl, and $C_{3-6}$ cycloalkyl;

$R_a$ is independently selected from H, $C_{1-6}$ alkyl optionally substituted with one or more $R_e$, $C_{2-6}$ alkenyl optionally substituted with one or more Re, $C_{2-6}$ alkynyl optionally substituted with one or more $R_e$, —$(CH_2)_r$—$C_{3-10}$ carbocyclyl optionally substituted with one or more $R_e$, and —$(CH_2)_r$-heterocyclyl optionally substituted with one or more $R_e$; or $R_a$ and $R_a$ together with the nitrogen atom to which they are both attached form a heterocyclic ring optionally substituted with one or more $R_e$;

$R_b$ is independently selected from H, $C_{1-6}$ alkyl optionally substituted with one or more $R_e$, $C_{2-6}$ alkenyl optionally substituted with one or more $R_e$, $C_{2-6}$ alkynyl optionally substituted with one or more $R_e$, —$(CH_2)_r$—$C_{3-10}$ carbocyclyl optionally substituted with one or more $R_e$, and —$(CH_2)_r$ heterocyclyl optionally substituted with one or more $R_e$;

$R_c$ is independently selected from $C_{1-6}$ alkyl optionally substituted with one or more $R_e$, $C_{2-6}$ alkenyl optionally substituted with one or more $R_e$, $C_{2-6}$ alkynyl optionally substituted with one or more $R_e$, —$(CH_2)_r$—$C_{3-10}$ carbocyclyl optionally substituted with one or more $R_e$, and —$(CH_2)_r$-heterocyclyl optionally substituted with one or more $R_e$;

$R_d$ is independently selected from H, and $C_{1-6}$ alkyl optionally substituted with one or more $R_e$;

$R_e$ is independently selected from F, Cl, Br, CN, $NH_2$, —NH—$C_{1-4}$ alkyl, —N($C_{1-4}$ alkyl)$_2$, =O, OH, —$OC_{1-6}$ alkyl, —$CO_2H$, $C_{1-6}$ alkyl optionally substituted with one or more $R_f$, $C_{2-6}$ alkenyl, $C_{2-6}$ alkynyl, —$(CH_2)_r$—$C_{3-6}$ cycloalkyl optionally substituted with one or more $R_f$, —$(CH_2)_r$-aryl optionally substituted with one or more $R_f$, and —$(CH_2)_r$-heterocyclyl optionally substituted with one or more $R_f$;

$R_f$ is independently selected from F, Cl, Br, CN, OH, $C_{1-5}$ alkyl optionally substituted with OH, $C_{2-5}$ alkenyl, $C_{2-5}$ alkynyl, $C_{3-6}$ cycloalkyl, and phenyl;

p, at each occurrence, is independently selected from zero, 1, and 2; and r, at each occurrence, is independently selected from zero, 1, 2, 3, and 4.

In another aspect, the invention provides a compound having Formula (IX):

(IX)

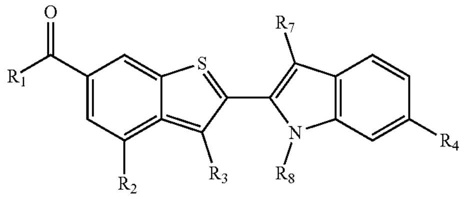

or a stereoisomer, an enantiomer, a diastereomer, a tautomer, or a pharmaceutically acceptable salt thereof, wherein:

$R_1$ is independently selected from

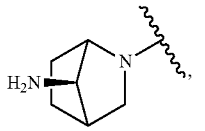,

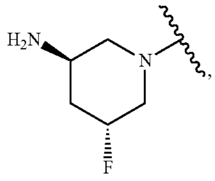, and

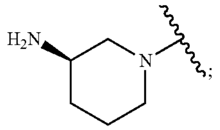;

$R_2$ is independently selected from H, F, $CH_3$, $CH_2OH$, $CH_2CH_2OH$, and $OCH_3$;

$R_3$ is independently selected from H, F, Cl, $CH_3$, $CH_2OH$, $CH_2CH_2OH$, $CH_2NH_3$, $CH_2CH_2NH_2$, and $CH_2CH_2N_3$;

$R_4$ is independently selected from H, F, Cl, Br, —C(=O)$R_b$, $C_{1-6}$ alkyl optionally substituted with one or more substituents selected from F, Cl, OH, and $C_{3-6}$ cycloalkyl, —NH—$C_{1-6}$ alkyl optionally substituted with one or more substituents selected from F, Cl, OH, and $C_{3-6}$ cycloalkyl, —$(CH_2)_r$-aryl substituted with one or more $R_5$, —O—$C_{1-6}$ alkyl substituted with one or more $R_5$, —$(CH_2)_r$—$C_{3-12}$ cycloalkyl substituted with one or more $R_5$, and —$(CH_2)_r$-4-10 membered heterocyclyl comprising carbon atoms and 1-5 heteroatoms selected from N, $NR_6$, O, and S and substituted with one or more $R_5$;

$R_5$ is independently selected from H, F, Cl, Br, CN, =O, $C_{1-4}$ alkyl optionally substituted with one or more $R_e$, $C_{2-4}$ alkenyl optionally substituted with one or more $R_e$, $C_{2-4}$ alkynyl optionally substituted with one or more $R_e$, —$(CH_2)_r$$OR_b$, —$(CH_2)_r$$S(O)_pR_c$, —$(CH_2)_r$$S(O)_pNR_aR_a$, —$(CH_2)_r$$NR_aS(O)_pR_c$, —$(CH_2)_r$$NR_aR_a$, —$(CH_2)_r$$NR_aC(=O)R_b$, —$(CH_2)_r$$NR_aC(=O)OR_b$, —$(CH_2)_r$$NR_aC(=O)NR_aR_a$, —$(CH_2)_r$$C(=O)R_b$, —$(CH_2)_r$$C(=O)OR_b$, —$(CH_2)_r$$C(=O)NR_aR_a$, —$(CH_2)_r$$OC(=O)R_b$, —$(CH_2)_r$$OC(=O)OR_b$, —$(CH_2)_r$$O(CH_2)_r$$C(=O)NR_aR_a$, $C_{3-6}$ cycloalkyl optionally substituted with one or more $R_e$, aryl optionally substituted with one or more $R_e$, and heterocyclyl optionally substituted with one or more $R_e$;

$R_6$ is independently selected from H, $C_{1-6}$ alkyl optionally substituted with one or more $R_e$, —$S(O)_pR_c$, —$S(O)_pNR_aR_a$, —$C(=O)R_b$, —$C(=O)OR_b$, —$C(=O)NR_aR_a$, $C_{3-6}$ cycloalkyl optionally substituted with one or more $R_e$, aryl optionally substituted with one or more $R_e$, and heterocyclyl optionally substituted with one or more $R_e$;

$R_7$ is independently selected from H, F, and Cl;

$R_8$ is independently selected from H, and $C_{1-6}$ alkyl optionally substituted with one or more substituents selected from F, Cl, and $C_{3-6}$ cycloalkyl;

$R_a$ is independently selected from H, $C_{1-6}$ alkyl optionally substituted with one or more $R_e$, $C_{2-6}$ alkenyl optionally substituted with one or more Re, $C_{2-6}$ alkynyl optionally substituted with one or more $R_e$, —$(CH_2)_r$—$C_{3-10}$ carbocyclyl optionally substituted with one or more $R_e$, and —$(CH_2)_r$-heterocyclyl optionally substituted with one or more $R_e$; or $R_a$ and $R_a$ together with the nitrogen atom to which they are both attached form a heterocyclic ring optionally substituted with one or more $R_e$;

$R_b$ is independently selected from H, $C_{1-6}$ alkyl optionally substituted with one or more $R_e$, $C_{2-6}$ alkenyl optionally substituted with one or more $R_e$, $C_{2-6}$ alkynyl optionally substituted with one or more $R_e$, —$(CH_2)_r$—$C_{3-10}$ carbocyclyl optionally substituted with one or more $R_e$, and —$(CH_2)_r$ heterocyclyl optionally substituted with one or more $R_e$;

$R_c$ is independently selected from $C_{1-6}$ alkyl optionally substituted with one or more $R_e$, $C_{2-6}$ alkenyl optionally substituted with one or more $R_e$, $C_{2-6}$ alkynyl optionally substituted with one or more $R_e$, —$(CH_2)_r$—$C_{3-10}$ carbocyclyl optionally substituted with one or more $R_e$, and —$(CH_2)_r$-heterocyclyl optionally substituted with one or more $R_e$;

$R_e$ is independently selected from F, Cl, Br, CN, $NH_2$, —NH—$C_{1-4}$ alkyl, —$N(C_{1-4}\text{ alkyl})_2$, =O, OH, —$OC_{1-6}$ alkyl, —$CO_2H$, $C_{1-6}$ alkyl optionally substituted with one or more $R_f$, $C_{2-6}$ alkenyl, $C_{2-6}$ alkynyl, —$(CH_2)_r$—$C_{3-6}$ cycloalkyl optionally substituted with one or more $R_f$, —$(CH_2)_r$-aryl optionally substituted with one or more $R_f$, and —$(CH_2)_r$-heterocyclyl optionally substituted with one or more $R_f$;

$R_f$ is independently selected from F, Cl, Br, CN, OH, $C_{1-5}$ alkyl optionally substituted with OH, $C_{2-5}$ alkenyl, $C_{2-5}$ alkynyl, $C_{3-6}$ cycloalkyl, and phenyl;

p, at each occurrence, is independently selected from zero, 1, and 2; and r, at each occurrence, is independently selected from zero, 1, 2, 3, and 4.

In another aspect, the invention provides a compound having Formula (X):

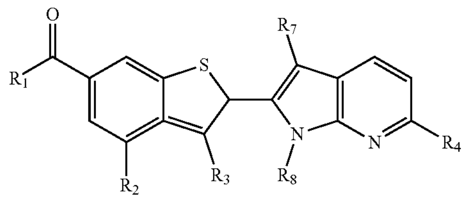

(X)

or a stereoisomer, an enantiomer, a diastereomer, a tautomer, or a pharmaceutically acceptable salt thereof, wherein:

$R_1$ is independently selected from

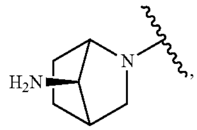

,

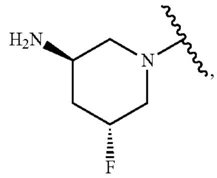

, and

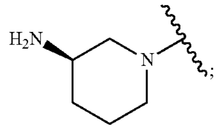

;

$R_2$ is independently selected from H, F, $CH_3$, $CH_2OH$, $CH_2CH_2OH$, and $OCH_3$;

$R_3$ is independently selected from H, F, $CH_3$, $CH_2OH$, $CH_2CH_2OH$, $CH_2NH_3$, $CH_2CH_2NH_2$, and $CH_2CH_2N_3$;

$R_4$ is independently selected from H, F, Cl, Br, —C(=O)$R_b$, $C_{1-6}$ alkyl optionally substituted with one or more substituents selected from F, Cl, OH, and $C_{3-6}$ cycloalkyl, —NH—$C_{1-6}$ alkyl optionally substituted with one or more substituents selected from F, Cl, OH, and $C_{3-6}$ cycloalkyl, —$(CH_2)_r$-aryl substituted with one or more $R_5$, —O—$C_{1-6}$ alkyl substituted with one or more $R_5$, —$(CH_2)_r$—$C_{3-12}$ cycloalkyl substituted with one or more $R_5$, and —$(CH_2)_r$-4-10 membered heterocyclyl comprising carbon atoms and 1-5 heteroatoms selected from N, $NR_6$, O, and S and substituted with one or more $R_5$;

$R_5$ is independently selected from H, F, Cl, Br, CN, =O, $C_{1-4}$ alkyl optionally substituted with one or more $R_e$, $C_{2-4}$ alkenyl optionally substituted with one or more $R_e$, $C_{2-4}$ alkynyl optionally substituted with one or more $R_e$, —$(CH_2)_rOR_b$, —$(CH_2)_rS(O)_pR_c$, —$(CH_2)_rS(O)_pNR_aR_a$, —$(CH_2)_rNR_aS(O)_pR_c$, —$(CH_2)_rNR_aR_a$, —$(CH_2)_rNR_aC(=O)R_b$, —$(CH_2)_rNR_aC(=O)OR_b$, —$(CH_2)_rNR_aC(=O)NR_aR_a$, —$(CH_2)_rC(=O)R_b$, —$(CH_2)_rC(=O)OR_b$, —$(CH_2)_rC(=O)NR_aR_a$, —$(CH_2)_rOC(=O)R_b$, —$(CH_2)_rOC(=O)OR_b$, —$(CH_2)_rO(CH_2)_rC(=O)NR_aR_a$, $C_{3-6}$ cycloalkyl optionally substituted with one or more $R_e$, aryl optionally substituted with one or more $R_e$, and heterocyclyl optionally substituted with one or more $R_e$;

$R_6$ is independently selected from H, $C_{1-6}$ alkyl optionally substituted with one or more $R_e$, —$S(O)_pR_c$, —$S(O)_pNR_aR_a$, —$C(=O)R_b$, —$C(=O)OR_b$, —$C(=O)NR_aR_a$, $C_{3-6}$ cycloalkyl optionally substituted with one or more $R_e$, aryl optionally substituted with one or more $R_e$, and heterocyclyl optionally substituted with one or more $R_e$;

$R_7$ is independently selected from H, F, and Cl;

$R_8$ is independently selected from H, and $C_{1-6}$ alkyl optionally substituted with one or more substituents selected from F, Cl, and $C_{3-6}$ cycloalkyl;

$R_a$ is independently selected from H, $C_{1-6}$ alkyl optionally substituted with one or more $R_e$, $C_{2-6}$ alkenyl optionally substituted with one or more Re, $C_{2-6}$ alkynyl optionally substituted with one or more $R_e$, —$(CH_2)_r$—$C_{3-10}$ carbocyclyl optionally substituted with one or more $R_e$, and —$(CH_2)_r$-heterocyclyl optionally substituted with one or more $R_e$; or $R_a$ and $R_a$ together with the nitrogen atom to which they are both attached form a heterocyclic ring optionally substituted with one or more $R_e$;

$R_b$ is independently selected from H, $C_{1-6}$ alkyl optionally substituted with one or more $R_e$, $C_{2-6}$ alkenyl optionally substituted with one or more $R_e$, $C_{2-6}$ alkynyl optionally substituted with one or more $R_e$, —$(CH_2)_r$—$C_{3-10}$ carbocyclyl optionally substituted with one or more $R_e$, and —$(CH_2)_r$ heterocyclyl optionally substituted with one or more $R_e$;

$R_c$ is independently selected from $C_{1-6}$ alkyl optionally substituted with one or more $R_e$, $C_{2-6}$ alkenyl optionally substituted with one or more $R_e$, $C_{2-6}$ alkynyl optionally substituted with one or more $R_e$, —$(CH_2)_r$—$C_{3-10}$ carbocyclyl optionally substituted with one or more $R_e$, and —$(CH_2)_r$-heterocyclyl optionally substituted with one or more $R_e$;

$R_e$ is independently selected from F, Cl, Br, CN, $NH_2$, —NH—$C_{1-4}$ alkyl, —$N(C_{1-4}\ alkyl)_2$, =O, OH, —$OC_{1-6}$ alkyl, —$CO_2H$, $C_{1-6}$ alkyl optionally substituted with one or more $R_f$, $C_{2-6}$ alkenyl, $C_{2-6}$ alkynyl, —$(CH_2)_r$—$C_{3-6}$ cycloalkyl optionally substituted with one or more $R_f$, —$(CH_2)_r$-aryl optionally substituted with one or more $R_f$, and —$(CH_2)_r$-heterocyclyl optionally substituted with one or more $R_f$;

$R_f$ is independently selected from F, Cl, Br, CN, OH, $C_{1-5}$ alkyl optionally substituted with OH, $C_{2-5}$ alkenyl, $C_{2-5}$ alkynyl, $C_{3-6}$ cycloalkyl, and phenyl;

p, at each occurrence, is independently selected from zero, 1, and 2; and r, at each occurrence, is independently selected from zero, 1, 2, 3, and 4.

In another aspect, the invention provides a compound having Formula (XI):

(XI)

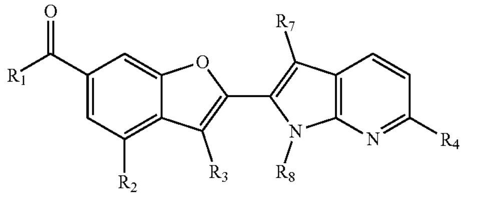

or a stereoisomer, an enantiomer, a diastereomer, a tautomer, or a pharmaceutically acceptable salt thereof, wherein:

$R_1$ is independently selected from

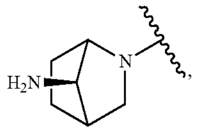

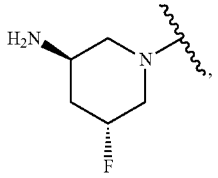

and

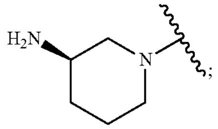

$R_2$ is independently selected from H, F, $CH_3$, $CH_2OH$, $CH_2CH_2OH$, and $OCH_3$;

$R_3$ is independently selected from H, F, $CH_3CH_2OH$, $CH_2CH_2OH$, $CH_2NH_3$, $CH_2CH_2NH_2$, and $CH_2CH_2N_3$;

$R_4$ is independently selected from H, F, Cl, Br, —$C(=O)R_b$, $C_{1-6}$ alkyl optionally substituted with one or more substituents selected from F, Cl, OH, and $C_{3-6}$ cycloalkyl, —NH—$C_{1-6}$ alkyl optionally substituted with one or more substituents selected from F, Cl, OH, and $C_{3-6}$ cycloalkyl, —$(CH_2)_r$-aryl substituted with one or more $R_5$, —O—$C_{1-6}$ alkyl substituted with one or more $R_5$, —$(CH_2)_r$—$C_{3-12}$ cycloalkyl substituted with one or more $R_5$, and —$(CH_2)_r$-4-10 membered heterocyclyl comprising carbon atoms and 1-5 heteroatoms selected from N, $NR_6$, O, and S and substituted with one or more $R_5$;

$R_5$ is independently selected from H, F, Cl, Br, CN, =O, $C_{1-4}$ alkyl optionally substituted with one or more $R_e$, $C_{2-4}$ alkenyl optionally substituted with one or more $R_e$, $C_{2-4}$ alkynyl optionally substituted with one or more $R_e$, —$(CH_2)_rOR_b$, —$(CH_2)_rS(O)_pR_c$, —$(CH_2)_rS(O)_pNR_aR_a$, —$(CH_2)_rNR_aS(O)_pR_c$, —$(CH_2)_rNR_aR_a$, —$(CH_2)_rNR_aC(=O)R_b$, —$(CH_2)_rNR_aC(=O)OR_b$, —$(CH_2)_rNR_aC(=O)NR_aR_a$, —$(CH_2)_rC(=O)R_b$, —$(CH_2)_rC(=O)OR_b$, —$(CH_2)_rC(=O)NR_aR_a$, —$(CH_2)_rOC(=O)R_b$, —$(CH_2)_rOC(=O)OR_b$, —$(CH_2)_rO(CH_2)_rC(=O)NR_aR_a$, $C_{3-6}$ cycloalkyl optionally substituted with one or more $R_e$, aryl optionally substituted with one or more $R_e$, and heterocyclyl optionally substituted with one or more $R_e$;

$R_6$ is independently selected from H, $C_{1-6}$ alkyl optionally substituted with one or more $R_e$, —$S(O)_pR_c$, —$S(O)_pNR_aR_a$, —C(═O)$R_b$, —C(═O)$OR_b$, —C(═O)$NR_aR_a$, $C_{3-6}$ cycloalkyl optionally substituted with one or more $R_e$, aryl optionally substituted with one or more $R_e$, and heterocyclyl optionally substituted with one or more $R_e$;

$R_7$ is independently selected from H, F, and Cl;

$R_8$ is independently selected from H, and $C_{1-6}$ alkyl optionally substituted with one or more substituents selected from F, Cl, and $C_{3-6}$ cycloalkyl;

$R_a$ is independently selected from H, $C_{1-6}$ alkyl optionally substituted with one or more $R_e$, $C_{2-6}$ alkenyl optionally substituted with one or more Re, $C_{2-6}$ alkynyl optionally substituted with one or more $R_e$, —$(CH_2)_r$—$C_{3-10}$ carbocyclyl optionally substituted with one or more $R_e$, and —$(CH_2)_r$-heterocyclyl optionally substituted with one or more $R_e$; or $R_a$ and $R_a$ together with the nitrogen atom to which they are both attached form a heterocyclic ring optionally substituted with one or more $R_e$;

$R_b$ is independently selected from H, $C_{1-6}$ alkyl optionally substituted with one or more $R_e$, $C_{2-6}$ alkenyl optionally substituted with one or more $R_e$, $C_{2-6}$ alkynyl optionally substituted with one or more $R_e$, —$(CH_2)_r$—$C_{3-10}$ carbocyclyl optionally substituted with one or more $R_e$, and —$(CH_2)_r$ heterocyclyl optionally substituted with one or more $R_e$;

$R_c$ is independently selected from $C_{1-6}$ alkyl optionally substituted with one or more $R_e$, $C_{2-6}$ alkenyl optionally substituted with one or more $R_e$, $C_{2-6}$ alkynyl optionally substituted with one or more $R_e$, —$(CH_2)_r$—$C_{3-10}$ carbocyclyl optionally substituted with one or more $R_e$, and —$(CH_2)_r$-heterocyclyl optionally substituted with one or more $R_e$;

$R_d$ is independently selected from H, and $C_{1-6}$ alkyl optionally substituted with one or more $R_e$;

$R_e$ is independently selected from F, Cl, Br, CN, $NH_2$, —NH—$C_{1-4}$ alkyl, —$N(C_{1-4}\ alkyl)_2$, ═O, OH, —$OC_{1-6}$ alkyl, —$CO_2H$, $C_{1-6}$ alkyl optionally substituted with one or more $R_f$, $C_{2-6}$ alkenyl, $C_{2-6}$ alkynyl, —$(CH_2)_r$—$C_{3-6}$ cycloalkyl optionally substituted with one or more $R_f$, —$(CH_2)_r$-aryl optionally substituted with one or more $R_f$, and —$(CH_2)_r$-heterocyclyl optionally substituted with one or more $R_f$;

$R_f$ is independently selected from F, Cl, Br, CN, OH, $C_{1-5}$ alkyl optionally substituted with OH, $C_{2-5}$ alkenyl, $C_{2-5}$ alkynyl, $C_{3-6}$ cycloalkyl, and phenyl;

p, at each occurrence, is independently selected from zero, 1, and 2; and r, at each occurrence, is independently selected from zero, 1, 2, 3, and 4.

In another aspect, the invention provides a compound having Formula (XII):

(XII)

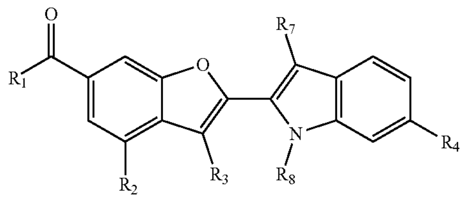

or a stereoisomer, an enantiomer, a diastereomer, a tautomer, or a pharmaceutically acceptable salt thereof, wherein:

$R_1$ is independently selected from

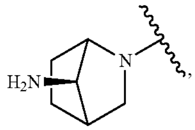,
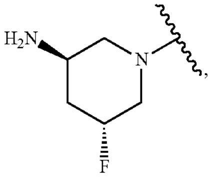,
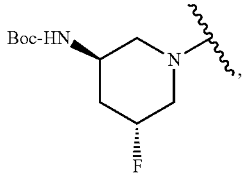, and
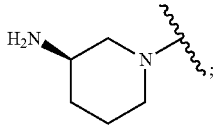;

$R_2$ is independently selected from H, F, $CH_3$, $CH_2OH$, $CH_2CH_2OH$ and $OCH_3$;

$R_3$ is independently selected from H, F, $CH_3$ $CH_2OH$, $CH_2CH_2OH$, $CH_2NH_3$, $CH_2CH_2NH_2$, and $CH_2CH_2N_3$;

$R_4$ is independently selected from H, F, Cl, Br, —C(═O)$R_b$, $C_{1-6}$ alkyl optionally substituted with one or more substituents selected from F, Cl, OH, and $C_{3-6}$ cycloalkyl, —NH—$C_{1-6}$ alkyl optionally substituted with one or more substituents selected from F, Cl, OH, and $C_{3-6}$ cycloalkyl, —$(CH_2)_r$-aryl substituted with one or more $R_5$, —O—$C_{1-6}$ alkyl substituted with one or more $R_5$, —$(CH_2)_r$—$C_{3-12}$ cycloalkyl substituted with one or more $R_5$, and —$(CH_2)_r$-4-10 membered heterocyclyl comprising carbon atoms and 1-5 heteroatoms selected from N, $NR_6$, O, and S and substituted with one or more $R_5$;

$R_5$ is independently selected from H, F, Cl, Br, CN, ═O, $C_{1-4}$ alkyl optionally substituted with one or more $R_e$, $C_{2-4}$ alkenyl optionally substituted with one or more $R_e$, $C_{2-4}$ alkynyl optionally substituted with one or more $R_e$, —$(CH_2)_rOR_b$, —$(CH_2)_rS(O)_pR_e$, —$(CH_2)_rS(O)_pNR_aR_a$, —$(CH_2)_rNR_aS(O)_pR_c$, —$(CH_2)_rNR_aR_a$, —$(CH_2)_rNR_aC$(═O)$R_b$, —$(CH_2)_rNR_aC$(═O)$OR_b$, —$(CH_2)_rNR_aC$(═O)$NR_aR_a$, —$(CH_2)_rC$(═O)$R_b$, —$(CH_2)_rC$(═O)$OR_b$, —$(CH_2)_rC$(═O)$NR_aR_a$, —$(CH_2)_rOC$(═O)$R_b$, —$(CH_2)_rOC$(═O)$OR_b$, —$(CH_2)_rO(CH_2)_rC$(═O)$NR_aR_a$, $C_{3-6}$ cycloalkyl optionally substituted with one or more $R_e$, aryl optionally substituted with one or more $R_e$, and heterocyclyl optionally substituted with one or more $R_e$;

$R_6$ is independently selected from H, $C_{1-6}$ alkyl optionally substituted with one or more $R_e$, —$S(O)_pR_c$, —$S(O)_pNR_aR_a$, —C(═O)$R_b$, —C(═O)$OR_b$, —C(═O)$NR_aR_a$, $C_{3-6}$ cycloalkyl optionally substituted with one or more $R_e$, aryl optionally substituted with one or more $R_e$, and heterocyclyl optionally substituted with one or more $R_e$;

$R_7$ is independently selected from H, F, and Cl;

$R_8$ is independently selected from H, and $C_{1-6}$ alkyl optionally substituted with one or more substituents selected from F, Cl, and $C_{3-6}$ cycloalkyl;

$R_a$ is independently selected from H, $C_{1-6}$ alkyl optionally substituted with one or more $R_e$, $C_{2-6}$ alkenyl optionally substituted with one or more Re, $C_{2-6}$ alkynyl optionally substituted with one or more $R_e$, —$(CH_2)_r$—$C_{3-10}$ carbocyclyl optionally substituted with one or more $R_e$, and —$(CH_2)_r$-heterocyclyl optionally substituted with one or more $R_e$; or $R_a$ and $R_a$ together with the nitrogen atom to which they are both attached form a heterocyclic ring optionally substituted with one or more $R_e$;

$R_b$ is independently selected from H, $C_{1-6}$ alkyl optionally substituted with one or more $R_e$, $C_{2-6}$ alkenyl optionally substituted with one or more $R_e$, $C_{2-6}$ alkynyl optionally substituted with one or more $R_e$, —$(CH_2)_r$—$C_{3-10}$ carbocyclyl optionally substituted with one or more $R_e$, and —$(CH_2)_r$ heterocyclyl optionally substituted with one or more $R_e$;

$R_c$ is independently selected from $C_{1-6}$ alkyl optionally substituted with one or more $R_e$, $C_{2-6}$ alkenyl optionally substituted with one or more $R_e$, $C_{2-6}$ alkynyl optionally substituted with one or more $R_e$, —$(CH_2)_r$—$C_{3-10}$ carbocyclyl optionally substituted with one or more $R_e$, and —$(CH_2)_r$-heterocyclyl optionally substituted with one or more $R_e$;

$R_d$ is independently selected from H, and $C_{1-6}$ alkyl optionally substituted with one or more $R_e$;

$R_e$ is independently selected from F, Cl, Br, CN, $NH_2$, —NH—$C_{1-4}$ alkyl, —N$(C_{1-4}$ alkyl$)_2$, =O, OH, —$OC_{1-6}$ alkyl, —$CO_2H$, $C_{1-6}$ alkyl optionally substituted with one or more $R_f$, $C_{2-6}$ alkenyl, $C_{2-6}$ alkynyl, —$(CH_2)_r$—$C_{3-6}$ cycloalkyl optionally substituted with one or more $R_f$, —$(CH_2)_r$-aryl optionally substituted with one or more $R_f$, and —$(CH_2)_r$-heterocyclyl optionally substituted with one or more $R_f$;

$R_f$ is independently selected from F, Cl, Br, CN, OH, $C_{1-5}$ alkyl optionally substituted with OH, $C_{2-5}$ alkenyl, $C_{2-5}$ alkynyl, $C_{3-6}$ cycloalkyl, and phenyl;

p, at each occurrence, is independently selected from zero, 1, and 2; and r, at each occurrence, is independently selected from zero, 1, 2, 3, and 4.

In another aspect, the invention provides a compound having Formulae (IX)-(XII), or a stereoisomer, an enantiomer, a diastereomer, a tautomer, or a pharmaceutically acceptable salt thereof, wherein;

$R_4$ is independently selected from H, F, Cl, Br,

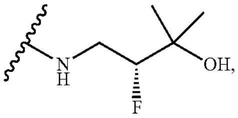 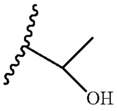 , 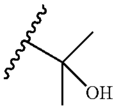 ,

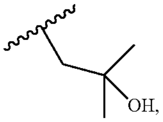 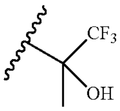 , 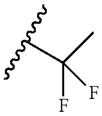 ,

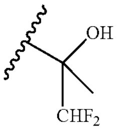 , 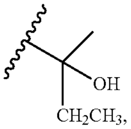 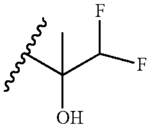 ,

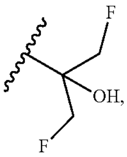 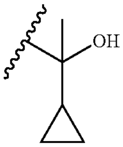 , 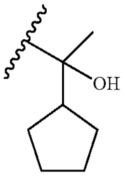 ,

-continued

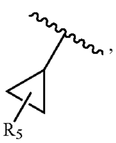 , 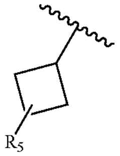 , 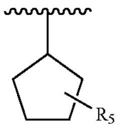 ,

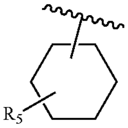 , 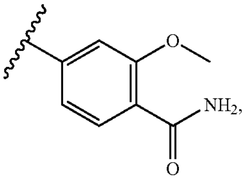

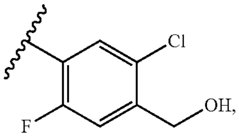 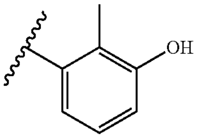 ,

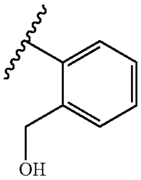 , 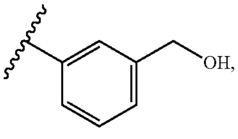

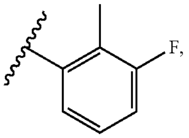 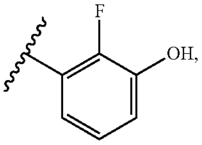

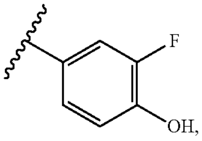 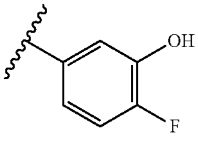 ,

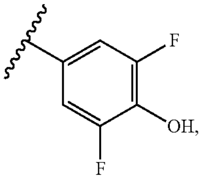 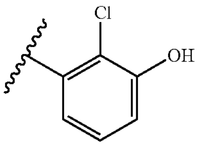 ,

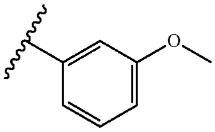 , 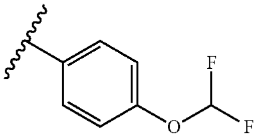 ,

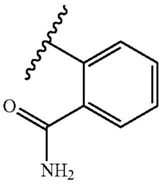 , 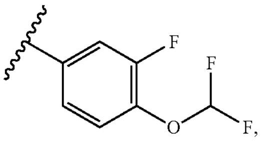

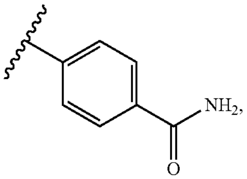 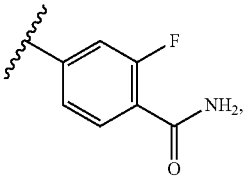

-continued
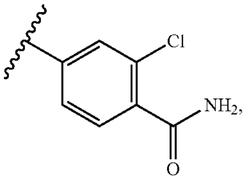
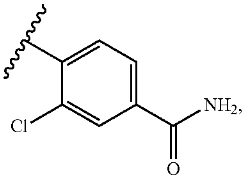
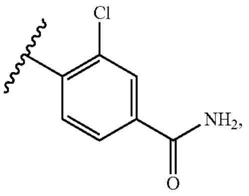
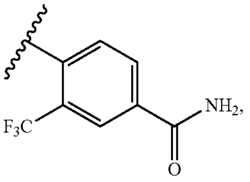
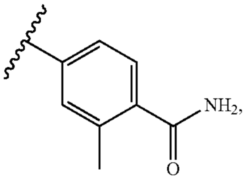
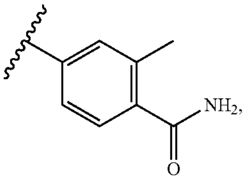
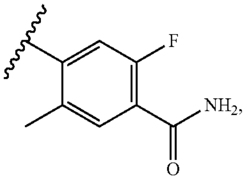
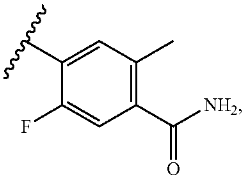
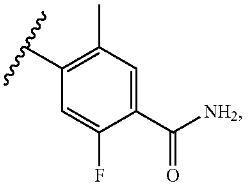
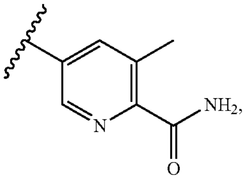
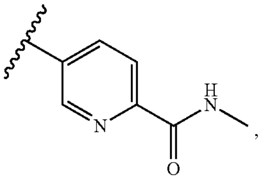
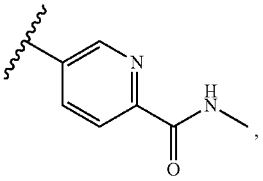
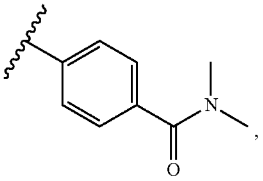
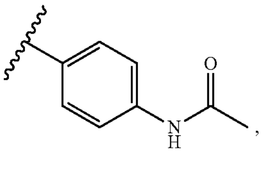
-continued
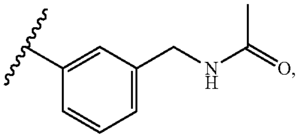
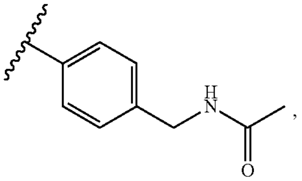
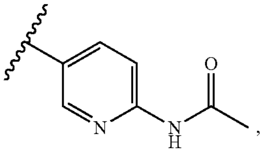
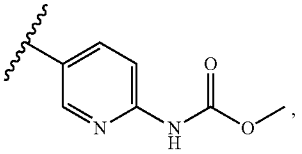
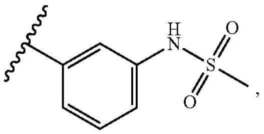
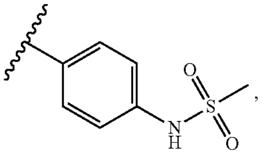
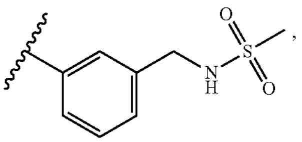
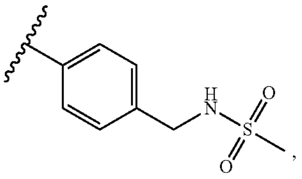
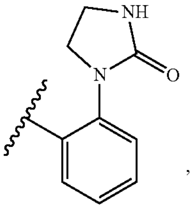
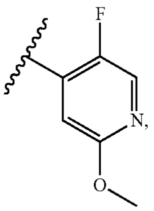
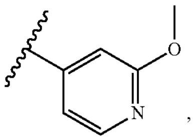
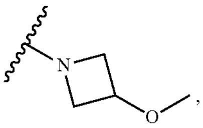
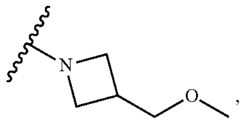

-continued
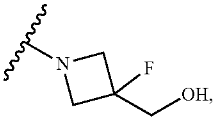 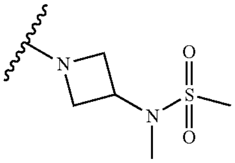,
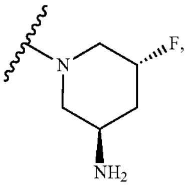 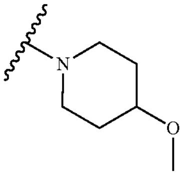,
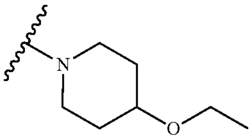, 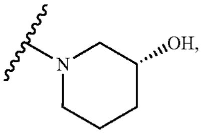
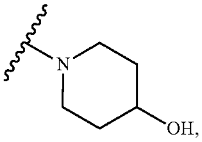 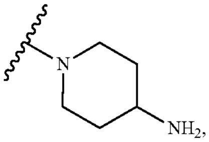
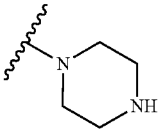 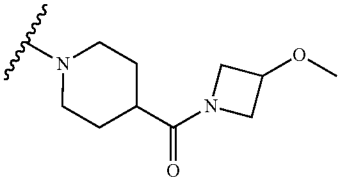,
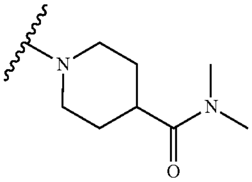
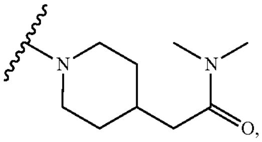
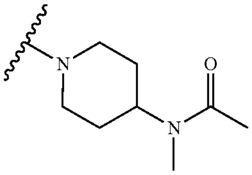
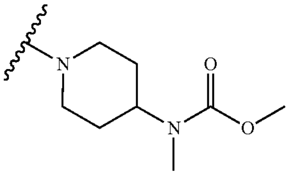
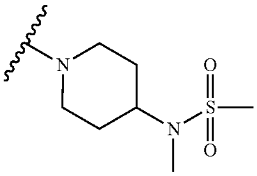 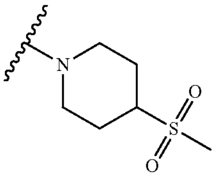,
-continued
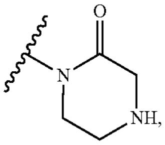 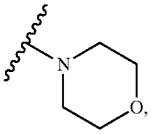 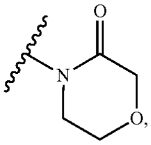
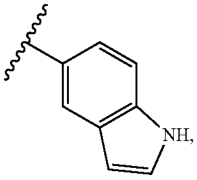 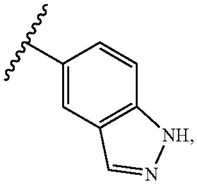
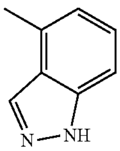, 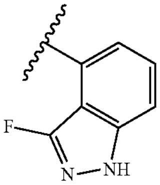,
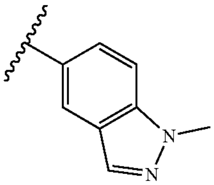, 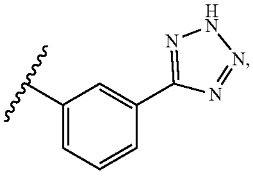
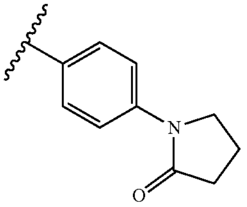, 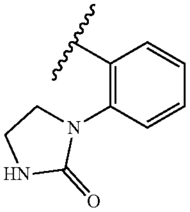,
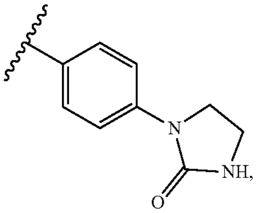 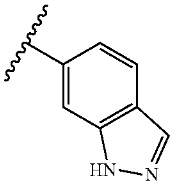,
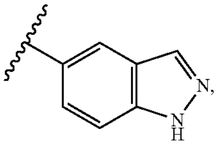 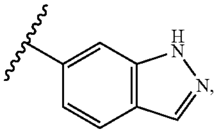
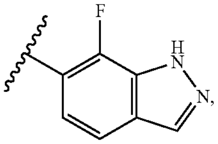 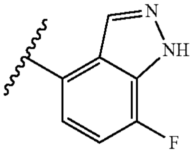,
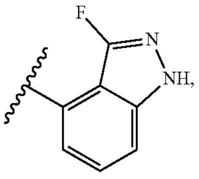 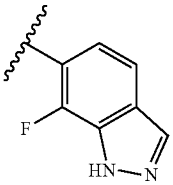, -continued

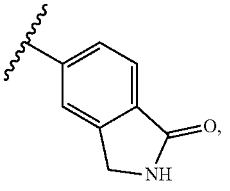

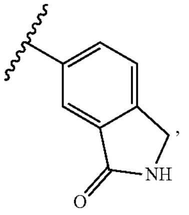

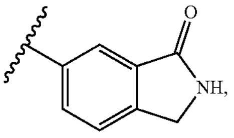

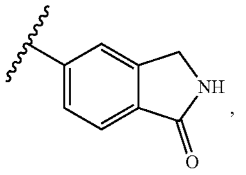

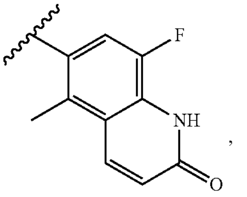

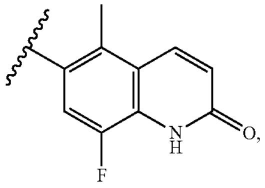

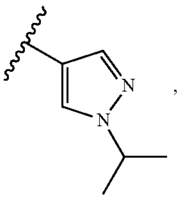

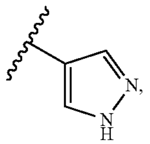

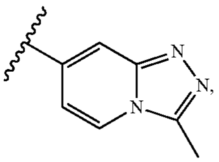

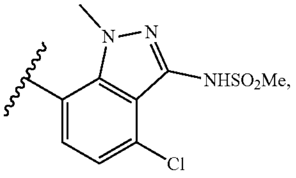

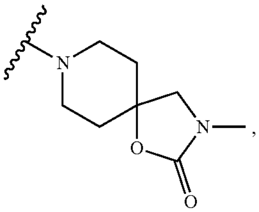

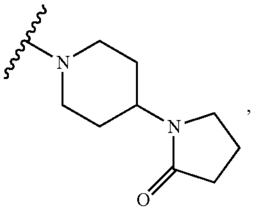

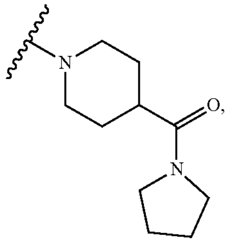

-continued

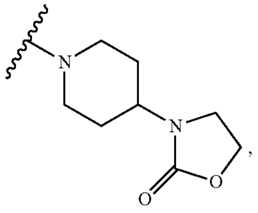

and

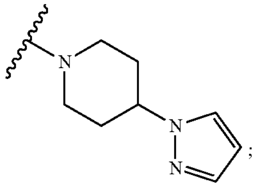

and other variables are as defined in Formulae (IX)-(XII).

In another aspect, the invention provides a compound having Formula (XIII):

(XIII)

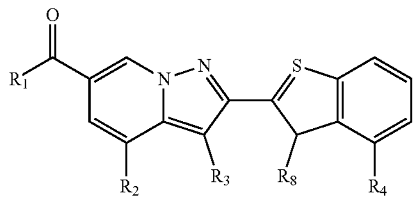

or a stereoisomer, an enantiomer, a diastereomer, a tautomer, or a pharmaceutically acceptable salt thereof, wherein:

$R_1$ is independently selected from

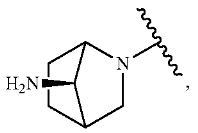

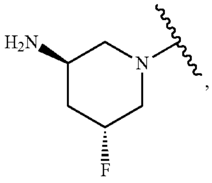

and

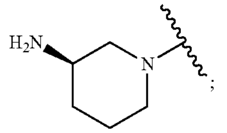

$R_2$ is independently selected from H, F, $CH_3$, and $OCH_3$;

$R_3$ is independently selected from H, F, and $CH_3$;

$R_4$ is independently selected from H, F, Cl, Br, —C(═O)$R_b$, $C_{1-6}$ alkyl optionally substituted with one or more substituents selected from F, Cl, OH, and $C_{3-6}$ cycloalkyl, —NH—$C_{1-6}$ alkyl optionally substituted with one or more substituents selected from F, Cl, OH, and $C_{3-6}$ cycloalkyl, —$(CH_2)_r$-aryl substituted with one or more $R_5$, —O—$C_{1-6}$ alkyl substituted with one or more $R_5$, —$(CH_2)_r$—$C_{3-12}$ cycloalkyl substituted with one or more $R_5$, and —$(CH_2)_r$-4-10 membered heterocyclyl comprising carbon atoms and 1-5 heteroatoms selected from N, $NR_6$, O, and S and substituted with one or more $R_5$;

$R_5$ is independently selected from H, F, Cl, Br, CN, ═O, $C_{1-4}$ alkyl optionally substituted with one or more $R_e$, $C_{2-4}$ alkenyl optionally substituted with one or more $R_e$, $C_{2-4}$ alkynyl optionally substituted with one or more $R_e$, $-(CH_2)_rOR_b$, $-(CH_2)_rS(O)_pR_c$, $-(CH_2)_rS(O)_pNR_aR_a$, $-(CH_2)_rNR_aS(O)_pR_c$, $-(CH_2)_rNR_aR_a$, $-(CH_2)_rNR_aC(=O)R_b$, $-(CH_2)_rNR_aC(=O)OR_b$, $-(CH_2)_rNR_aC(=O)NR_aR_a$, $-(CH_2)_rC(=O)R_b$, $-(CH_2)_rC(=O)OR_b$, $-(CH_2)_rC(=O)NR_aR_a$, $-(CH_2)_rOC(=O)R_b$, $-(CH_2)_rOC(=O)OR_b$, $-(CH_2)_rO(CH_2)_rC(=O)NR_aR_a$, $C_{3-6}$ cycloalkyl optionally substituted with one or more $R_e$, aryl optionally substituted with one or more $R_e$, and heterocyclyl optionally substituted with one or more $R_e$;

$R_6$ is independently selected from H, $C_{1-6}$ alkyl optionally substituted with one or more $R_e$, $-S(O)_pR_c$, $-S(O)_pNR_aR_a$, $-C(=O)R_b$, $-C(=O)OR_b$, $-C(=O)NR_aR_a$, $C_{3-6}$ cycloalkyl optionally substituted with one or more $R_e$, aryl optionally substituted with one or more $R_e$, and heterocyclyl optionally substituted with one or more $R_e$;

$R_8$ is independently selected from H, and $C_{1-6}$ alkyl optionally substituted with one or more substituents selected from F, Cl, and $C_{3-6}$ cycloalkyl;

$R_a$ is independently selected from H, $C_{1-6}$ alkyl optionally substituted with one or more $R_e$, $C_{2-6}$ alkenyl optionally substituted with one or more Re, $C_{2-6}$ alkynyl optionally substituted with one or more $R_e$, $-(CH_2)_r-C_{3-10}$ carbocyclyl optionally substituted with one or more $R_e$, and $-(CH_2)_r$-heterocyclyl optionally substituted with one or more $R_e$; or $R_a$ and $R_a$ together with the nitrogen atom to which they are both attached form a heterocyclic ring optionally substituted with one or more $R_e$;

$R_b$ is independently selected from H, $C_{1-6}$ alkyl optionally substituted with one or more $R_e$, $C_{2-6}$ alkenyl optionally substituted with one or more $R_e$, $C_{2-6}$ alkynyl optionally substituted with one or more $R_e$, $-(CH_2)_r-C_{3-10}$ carbocyclyl optionally substituted with one or more $R_e$, and $-(CH_2)_r$ heterocyclyl optionally substituted with one or more $R_e$;

$R_c$ is independently selected from $C_{1-6}$ alkyl optionally substituted with one or more $R_e$, $C_{2-6}$ alkenyl optionally substituted with one or more $R_e$, $C_{2-6}$ alkynyl optionally substituted with one or more $R_e$, $-(CH_2)_r-C_{3-10}$ carbocyclyl optionally substituted with one or more $R_e$, and $-(CH_2)_r$-heterocyclyl optionally substituted with one or more $R_e$;

$R_d$ is independently selected from H, and $C_{1-6}$ alkyl optionally substituted with one or more $R_e$;

$R_e$ is independently selected from F, Cl, Br, CN, $NH_2$, $-NH-C_{1-4}$ alkyl, $-N(C_{1-4}\ alkyl)_2$, $=O$, OH, $-OC_{1-6}$ alkyl, $-CO_2H$, $C_{1-6}$ alkyl optionally substituted with one or more $R_f$, $C_{2-6}$ alkenyl, $C_{2-6}$ alkynyl, $-(CH_2)_r-C_{3-6}$ cycloalkyl optionally substituted with one or more $R_f$, $-(CH_2)_r$-aryl optionally substituted with one or more $R_f$, and $-(CH_2)_r$-heterocyclyl optionally substituted with one or more $R_f$;

$R_f$ is independently selected from F, Cl, Br, CN, OH, $C_{1-5}$ alkyl optionally substituted with OH, $C_{2-5}$ alkenyl, $C_{2-5}$ alkynyl, $C_{3-6}$ cycloalkyl, and phenyl;

p, at each occurrence, is independently selected from zero, 1, and 2; and r, at each occurrence, is independently selected from zero, 1, 2, 3, and 4.

In another aspect, the invention provides a compound having Formula (XIV):

(XIV)

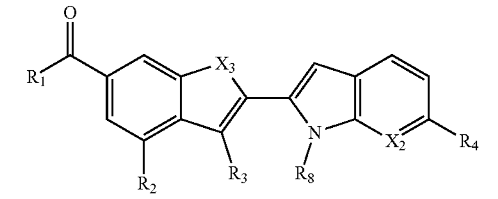

or a stereoisomer, an enantiomer, a diastereomer, a tautomer, or a pharmaceutically acceptable salt thereof, wherein:

$X_2$ is independently selected from $CR_4$ and N;

$X_3$ is independently selected from O and S;

$R_1$ is independently selected from

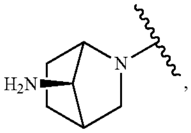
,
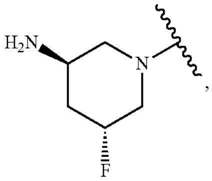
, and
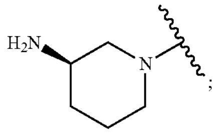
;

$R_2$ is independently selected from $CH_2OH$, $CH_2CH_2OH$ and $OCH_3$;

$R_3$ is independently selected from $CH_2OH$, $CH_2CH_2OH$, $CH_2NH_2$, $CH_2CH_2NH_2$, and $CH_2CH_2N_3$;

$R_4$ is independently selected from H and $-O-C_{1-4}$ alkyl substituted with one or more $R_5$; provided $R_4$ is not both $-O-C_{1-4}$ alkyl substituted with one or more $R_5$;

$R_5$ is independently selected from OH and heterocyclyl optionally substituted with one or more $R_e$;

$R_8$ is independently selected from H, and $C_{1-6}$ alkyl optionally substituted with $C_{3-6}$ cycloalkyl; and $R_e$ is independently selected from $NH_2$ and $C_{1-3}$ alkyl.

In another aspect, the invention provides a compound having Formula (XV):

(XV)

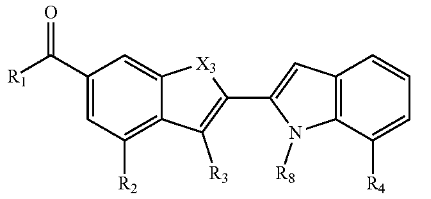

or a stereoisomer, an enantiomer, a diastereomer, a tautomer, or a pharmaceutically acceptable salt thereof, wherein:

$R_4$ is independently selected from H, $OCH_3$, $OCH_2CH_2OH$,

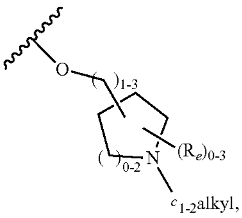,

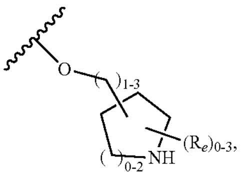,

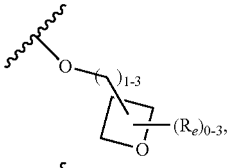,

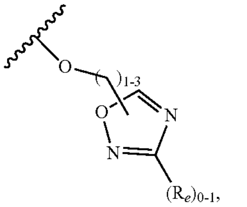,

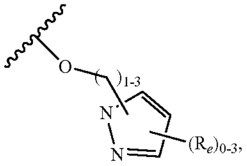,

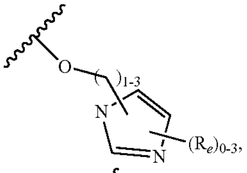,

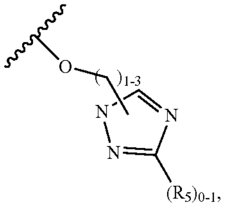, and

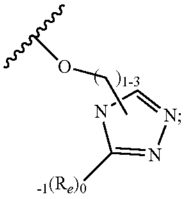;

$R_8$ is $C_{1-3}$ alkyl substituted with $C_{3-6}$ cycloalkyl; and $R_e$ is independently selected from $NH_2$ and $C_{1-3}$ alkyl; and other variables are as defined in Formula (XIV).

Typical, non-limiting examples of the compounds according to the invention include:

((7R)-7-Amino-2-azabicyclo[2.2.1]heptan-2-yl)(2-(1-(cyclopropylmethyl)-1H-pyrrolo[2,3-b]pyridin-2-yl)-4-methoxy-3-methylpyrazolo[1,5-a]pyridin-6-yl)methanone (1);

((7R)-7-Amino-2-azabicyclo[2.2.1]heptan-2-yl)(2-(6-chloro-1-(cyclopropylmethyl)-1H-pyrrolo[2,3-b]pyridin-2-yl)-4-methoxy-3-methylpyrazolo[1,5-a]pyridin-6-yl)methanone (2);

6-(2-(6-((7R)-7-Amino-2-azabicyclo[2.2.1]heptane-2-carbonyl)-4-methoxy-3-methylpyrazolo[1,5-a]pyridin-2-yl)-1-(cyclopropylmethyl)-1H-pyrrolo[2,3-b]pyridin-6-yl)isoindolin-1-one (3);

((7R)-7-Amino-2-azabicyclo[2.2.1]heptan-2-yl)(2-(1-(cyclopropylmethyl)-6-methyl-1H-pyrrolo[2,3-b]pyridin-2-yl)-4-methoxy-3-methylpyrazolo[1,5-a]pyridin-6-yl)methanone (4);

5-(2-(6-((7R)-7-Amino-2-azabicyclo[2.2.1]-heptane-2-carbonyl)-4-methoxy-3-methylpyrazolo[1,5-a]pyridin-2-yl)-1-(cyclopropylmethyl)-1H-pyrrolo[2,3-b]pyridin-6-yl)isoindolin-1-one (5);

((7R)-7-Amino-2-azabicyclo[2.2.1]heptan-2-yl)(2-(6-cyclopropyl-1-(cyclopropylmethyl)-1H-pyrrolo[2,3-b]pyridin-2-yl)-4-methoxy-3-methylpyrazolo[1,5-a]pyridin-6-yl)methanone (6);

((7R)-7-Amino-2-azabicyclo[2.2.1]heptan-2-yl)(2-(1-(cyclopropylmethyl)-6-(1-isopropyl-1H-pyrazol-4-yl)-1H-pyrrolo[2,3-b]pyridin-2-yl)-4-methoxy-3-methylpyrazolo[1,5-a]pyridin-6-yl)methanone (7);

((7R)-7-Amino-2-azabicyclo[2.2.1]heptan-2-yl)(2-(1-(cyclopropylmethyl)-6-(3-methyl-[1,2,4]triazolo[4,3-a]pyridin-7-yl)-1H-pyrrolo[2,3-b]pyridin-2-yl)-4-methoxy-3-methylpyrazolo[1,5-a]pyridin-6-yl)methanone (8);

((7R)-7-Amino-2-azabicyclo[2.2.1]heptan-2-yl)(2-(1-(cyclopropylmethyl)-6-(2-fluoro-3-hydroxyphenyl)-1H-pyrrolo[2,3-b]pyridin-2-yl)-4-methoxy-3-methylpyrazolo[1,5-a]pyridin-6-yl)methanone (9);

((7R)-7-Amino-2-azabicyclo[2.2.1]heptan-2-yl)(2-(1-(cyclopropylmethyl)-6-(3-fluoro-4-hydroxyphenyl)-1H-pyrrolo[2,3-b]pyridin-2-yl)-4-methoxy-3-methylpyrazolo[1,5-a]pyridin-6-yl)methanone (10);

((7R)-7-Amino-2-azabicyclo[2.2.1]heptan-2-yl)(2-(1-(cyclopropylmethyl)-6-(4-(difluoromethoxy)phenyl)-1H-pyrrolo[2,3-b]pyridin-2-yl)-4-methoxy-3-methylpyrazolo[1,5-a]pyridin-6-yl)methanone (11);

((7R)-7-Amino-2-azabicyclo[2.2.1]heptan-2-yl)(2-(1-(cyclopropylmethyl)-6-(4-(difluoromethoxy)-3-fluorophenyl)-1H-pyrrolo[2,3-b]pyridin-2-yl)-4-methoxy-3-methylpyrazolo[1,5-a]pyridin-6-yl)methanone (12);

((7R)-7-Amino-2-azabicyclo[2.2.1]heptan-2-yl)(2-(1-(cyclopropylmethyl)-6-(3-methoxyazetidin-1-yl)-1H-pyrrolo[2,3-b]pyridin-2-yl)-4-methoxy-3-methylpyrazolo[1,5-a]pyridin-6-yl)methanone (13);

((3R,5R)-3-Amino-5-fluoropiperidin-1-yl)(2-(1-(cyclopropylmethyl)-1H-pyrrolo[2,3-b]pyridin-2-yl)-4-methoxy-3-methylpyrazolo[1,5-a]pyridin-6-yl)methanone (14);

((3R,5R)-3-Amino-5-fluoropiperidin-1-yl)(2-(6-chloro-1-(cyclopropylmethyl)-1H-pyrrolo[2,3-b]pyridin-2-yl)-4-methoxy-3-methylpyrazolo[1,5-a]pyridin-6-yl)methanone (15);

6-(2-(6-((3R,5R)-3-Amino-5-fluoropiperidine-1-carbonyl)-4-methoxy-3-methylpyrazolo[1,5-a]pyridin-2-yl)-1-(cyclopropylmethyl)-1H-pyrrolo[2,3-b]pyridin-6-yl)isoindolin-1-one (16);

((3R,5R)-3-Amino-5-fluoropiperidin-1-yl)(2-(1-(cyclopropylmethyl)-6-methyl-1H-pyrrolo[2,3-b]pyridin-2-yl)-4-methoxy-3-methylpyrazolo[1,5-a]pyridin-6-yl)-methanone (17);

((3R,5R)-3-Amino-5-fluoropiperidin-1-yl)(2-(1-(cyclopropylmethyl)-6-(1-isopropyl-1H-pyrazol-4-yl)-1H-indol-2-yl)-4-methoxy-3-methylpyrazolo[1,5-a]pyridin-6-yl)methanone (18);

((3R,5R)-3-Amino-5-fluoropiperidin-1-yl)(2-(6-cyclopropyl-1-(cyclopropylmethyl)-1H-pyrrolo[2,3-b]pyridin-2-yl)-4-methoxy-3-methylpyrazolo[1,5-a]pyridin-6-yl)methanone (19);

5-(2-(6-((3R,5R)-3-Amino-5-fluoropiperidine-1-carbonyl)-4-methoxy-3-methylpyrazolo[1,5-a]pyridin-2-yl)-1-(cyclopropylmethyl)-1H-pyrrolo[2,3-b]pyridin-6-yl)isoindolin-1-one (20);

((3R,5R)-3-Amino-5-fluoropiperidin-1-yl)(2-(1-(cyclopropylmethyl)-6-(3-methyl-[1,2,4]triazolo[4,3-a]pyridin-7-yl)-1H-pyrrolo[2,3-b]pyridin-2-yl)-4-methoxy-3-methylpyrazolo[1,5-a]pyridin-6-yl)methanone (21);

((7R)-7-Amino-2-azabicyclo[2.2.1]heptan-2-yl)(2-(1-(cyclopropylmethyl)-1H-indol-2-yl)-4-methoxy-3-methylpyrazolo[1,5-a]pyridin-6-yl)methanone (22);

6-(2-(6-((7R)-7-Amino-2-azabicyclo[2.2.1]heptane-2-carbonyl)-4-methoxy-3-methylpyrazolo[1,5-a]pyridin-2-yl)-1-(cyclopropylmethyl)-1H-indol-6-yl)isoindolin-1-one (23);

5-(2-(6-((7R)-7-Amino-2-azabicyclo[2.2.1]heptane-2-carbonyl)-4-methoxy-3-methylpyrazolo[1,5-a]pyridin-2-yl)-1-(cyclopropylmethyl)-1H-indol-6-yl)isoindolin-1-one (24);

((7R)-7-Amino-2-azabicyclo[2.2.1]heptan-2-yl)(2-(1-(cyclopropylmethyl)-6-(3-methyl-[1,2,4]triazolo[4,3-a]pyridin-7-yl)-1H-indol-2-yl)-4-methoxy-3-methylpyrazolo[1,5-a]pyridin-6-yl)methanone (25);

((7R)-7-Amino-2-azabicyclo[2.2.1]heptan-2-yl)(2-(1-(cyclopropylmethyl)-6-(4-(difluoromethoxy)phenyl)-1H-indol-2-yl)-4-methoxy-3-methylpyrazolo[1,5-a]pyridin-6-yl)methanone (26);

((7R)-7-Amino-2-azabicyclo[2.2.1]heptan-2-yl)(2-(1-(cyclopropylmethyl)-6-methyl-1H-indol-2-yl)-4-methoxy-3-methylpyrazolo[1,5-a]pyridin-6-yl)methanone (27);

((7R)-7-Amino-2-azabicyclo[2.2.1]heptan-2-yl)(2-(6-cyclopropyl-1-(cyclopropylmethyl)-1H-indol-2-yl)-4-methoxy-3-methylpyrazolo[1,5-a]pyridin-6-yl)methanone (28);

6-(2-(6-((3R,5R)-3-Amino-5-fluoropiperidine-1-carbonyl)-4-methoxy-3-methylpyrazolo[1,5-a]pyridin-2-yl)-1-(cyclopropylmethyl)-1H-indol-6-yl)isoindolin-1-one (29);

5-(2-(6-((3R,5R)-3-Amino-5-fluoropiperidine-1-carbonyl)-4-methoxy-3-methylpyrazolo[1,5-a]pyridin-2-yl)-1-(cyclopropylmethyl)-1H-indol-6-yl)isoindolin-1-one (30);

((3R,5R)-3-Amino-5-fluoropiperidin-1-yl)(2-(1-(cyclopropylmethyl)-6-(3-methyl-[1,2,4]triazolo[4,3-a]pyridin-7-yl)-1H-indol-2-yl)-4-methoxy-3-methylpyrazolo[1,5-a]pyridin-6-yl)methanone (31);

((3R,5R)-3-Amino-5-fluoropiperidin-1-yl)(2-(1-(cyclopropylmethyl)-6-(2-fluoro-3-hydroxyphenyl)-1H-indol-2-yl)-4-methoxy-3-methylpyrazolo[1,5-a]pyridin-6-yl)methanone (32);

((3R,5R)-3-Amino-5-fluoropiperidin-1-yl)(2-(1-(cyclopropylmethyl)-6-(3-(methoxymethyl)-azetidin-1-yl)-1H-indol-2-yl)-4-methoxy-3-methylpyrazolo[1,5-a]pyridin-6-yl)methanone (33);

((3R,5R)-3-Amino-5-fluoropiperidin-1-yl)(2-(6-((3R,5R)-3-amino-5-fluoropiperidin-1-yl)-1-(cyclopropylmethyl)-1H-indol-2-yl)-4-methoxy-3-methylpyrazolo[1,5-a]pyridin-6-yl)methanone (34);

((3R,5R)-3-Amino-5-fluoropiperidin-1-yl)(2-(1-(cyclopropylmethyl)-6-(4-methoxypiperidin-1-yl)-1H-indol-2-yl)-4-methoxy-3-methylpyrazolo[1,5-a]pyridin-6-yl)methanone (35);

((3R,5R)-3-Amino-5-fluoropiperidin-1-yl)(2-(1-(cyclopropylmethyl)-6-(((R)-2-fluoro-3-hydroxy-3-methylbutyl)amino)-1H-indol-2-yl)-4-methoxy-3-methylpyrazolo[1,5-a]pyridin-6-yl)methanone (36);

((3R,5R)-3-Amino-5-fluoropiperidin-1-yl)(2-(1-(cyclopropylmethyl)-6-(3-fluoro-3-(hydroxymethyl)azetidin-1-yl)-1H-indol-2-yl)-4-methoxy-3-methylpyrazolo[1,5-a]pyridin-6-yl)methanone (37);

((7R)-7-Amino-2-azabicyclo[2.2.1]heptan-2-yl)(2-(1-(cyclopropylmethyl)-1H-pyrrolo[2,3-b]pyridin-2-yl)-4-fluoro-3-methylpyrazolo[1,5-a]pyridin-6-yl)methanone (38);

((7R)-7-Amino-2-azabicyclo[2.2.1]heptan-2-yl)(2-(6-chloro-1-(cyclopropylmethyl)-1H-pyrrolo[2,3-b]pyridin-2-yl)-4-fluoro-3-methylpyrazolo[1,5-a]pyridin-6-yl)methanone (39);

3((7R)-7-Amino-2-azabicyclo[2.2.1]heptan-2-yl)(2-(1-(cyclopropylmethyl)-6-methyl-1H-pyrrolo[2,3-b]pyridin-2-yl)-4-fluoro-3-methylpyrazolo[1,5-a]pyridin-6-yl)methanone (40);

((7R)-7-Amino-2-azabicyclo[2.2.1]heptan-2-yl)(2-(6-cyclopropyl-1-(cyclopropylmethyl)-1H-pyrrolo[2,3-b]pyridin-2-yl)-4-fluoro-3-methylpyrazolo[1,5-a]pyridin-6-yl)methanone (41);

5-(2-(6-((7R)-7-Amino-2-azabicyclo[2.2.1]heptane-2-carbonyl)-4-fluoro-3-methylpyrazolo[1,5-a]pyridin-2-yl)-1-(cyclopropylmethyl)-1H-pyrrolo[2,3-b]pyridin-6-yl)isoindolin-1-one (42);

((7R)-7-Amino-2-azabicyclo[2.2.1]heptan-2-yl)(2-(1-(cyclopropylmethyl)-6-(3-methyl-[1,2,4]triazolo[4,3-a]pyridin-7-yl)-1H-pyrrolo[2,3-b]pyridin-2-yl)-4-fluoro-3-methylpyrazolo[1,5-a]pyridin-6-yl)methanone (43);

((7R)-7-Amino-2-azabicyclo[2.2.1]heptan-2-yl)(2-(1-(cyclopropylmethyl)-6-(4-(difluoromethoxy)-3-fluorophenyl)-1H-pyrrolo[2,3-b]pyridin-2-yl)-4-fluoro-3-methylpyrazolo[1,5-a]pyridin-6-yl)methanone (44);

((7R)-7-Amino-2-azabicyclo[2.2.1]heptan-2-yl)(2-(1-(cyclopropylmethyl)-6-(5-fluoro-2-methoxypyridin-4-yl)-1H-pyrrolo[2,3-b]pyridin-2-yl)-4-fluoro-3-methylpyrazolo[1,5-a]pyridin-6-yl)methanone (45);

6-(2-(6-((7R)-7-Amino-2-azabicyclo[2.2.1]heptane-2-carbonyl)-4-fluoro-3-methylpyrazolo[1,5-a]pyridin-2-yl)-1-(cyclopropylmethyl)-1H-pyrrolo[2,3-b]pyridin-6-yl)isoindolin-1-one (46);

((7R)-7-Amino-2-azabicyclo[2.2.1]heptan-2-yl)(2-(1-(cyclopropylmethyl)-6-(4-(difluoromethoxy)phenyl)-1H-pyrrolo[2,3-b]pyridin-2-yl)-4-fluoro-3-methylpyrazolo[1,5-a]pyridin-6-yl)methanone (47);

((7R)-7-Amino-2-azabicyclo[2.2.1]heptan-2-yl)(2-(1-(cyclopropylmethyl)-6-(3-fluoro-4-hydroxyphenyl)-1H-pyrrolo[2,3-b]pyridin-2-yl)-4-fluoro-3-methylpyrazolo[1,5-a]pyridin-6-yl)methanone (48);

((7R)-7-Amino-2-azabicyclo[2.2.1]heptan-2-yl)(2-(1-(cyclopropylmethyl)-6-(2-fluoro-3-hydroxyphenyl)-1H-pyrrolo[2,3-b]pyridin-2-yl)-4-fluoro-3-methylpyrazolo[1,5-a]pyridin-6-yl)methanone (49);

((7R)-7-Amino-2-azabicyclo[2.2.1]heptan-2-yl)(2-(1-(cyclopropylmethyl)-6-(3-methoxyazetidin-1-yl)-1H-pyrrolo[2,3-b]pyridin-2-yl)-4-fluoro-3-methylpyrazolo[1,5-a]pyridin-6-yl)methanone (50);

((7R)-7-Amino-2-azabicyclo[2.2.1]heptan-2-yl)(2-(1-(cyclopropylmethyl)-6-(R)-3-hydroxypiperidin-1-yl)-1H-pyrrolo[2,3-b]pyridin-2-yl)-4-fluoro-3-methylpyrazolo[1,5-a]pyridin-6-yl)methanone (51);

((3R,5R)-3-Amino-5-fluoropiperidin-1-yl)(2-(1-(cyclopropylmethyl)-1H-pyrrolo[2,3-b]pyridin-2-yl)-4-fluoro-3-methylpyrazolo[1,5-a]pyridin-6-yl)methanone (52);

((3R,5R)-3-Amino-5-fluoropiperidin-1-yl)(2-(6-chloro-1-(cyclopropylmethyl)-1H-pyrrolo[2,3-b]pyridin-2-yl)-4-fluoro-3-methylpyrazolo[1,5-a]pyridin-6-yl)methanone (53);

((3R,5R)-3-Amino-5-fluoropiperidin-1-yl)(2-(1-(cyclopropylmethyl)-6-methyl-1H-pyrrolo[2,3-b]pyridin-2-yl)-4-fluoro-3-methylpyrazolo[1,5-a]pyridin-6-yl)methanone (54);

((3R,5R)-3-Amino-5-fluoropiperidin-1-yl)(2-(1-(cyclopropylmethyl)-6-(2-fluoro-3-hydroxyphenyl)-1H-pyrrolo[2,3-b]pyridin-2-yl)-4-fluoro-3-methylpyrazolo[1,5-a]pyridin-6-yl)methanone (55);

4-(2-(6-((3R,5R)-3-Amino-5-fluoropiperidine-1-carbonyl)-4-fluoro-3-methylpyrazolo[1,5-a]pyridin-2-yl)-1-(cyclopropylmethyl)-1H-pyrrolo[2,3-b]pyridin-6-yl)-2-fluorobenzamide (56);

((3R,5R)-3-Amino-5-fluoropiperidin-1-yl)(2-(6-cyclopropyl-1-(cyclopropylmethyl)-1H-pyrrolo[2,3-b]pyridin-2-yl)-4-fluoro-3-methylpyrazolo[1,5-a]pyridin-6-yl)methanone (57);

N-(7-(2-(6-((7R)-7-Amino-2-azabicyclo[2.2.1]heptane-2-carbonyl)-4-fluoro-3-methylpyrazolo[1,5-a]pyridin-2-yl)-1-(cyclopropylmethyl)-1H-indol-6-yl)-4-chloro-1-methyl-1H-indazol-3-yl)methanesulfonamide (58);

((7R)-7-Amino-2-azabicyclo[2.2.1]heptan-2-yl)(2-(1-(cyclopropylmethyl)-6-(2-fluoro-3-hydroxyphenyl)-1H-indol-2-yl)-4-fluoro-3-methylpyrazolo[1,5-a]pyridin-6-yl)methanone (59);

((7R)-7-Amino-2-azabicyclo[2.2.1]heptan-2-yl)(2-(1-(cyclopropylmethyl)-6-(3-fluoro-4-hydroxyphenyl)-1H-indol-2-yl)-4-fluoro-3-methylpyrazolo[1,5-a]pyridin-6-yl)methanone (60);

((7R)-7-Amino-2-azabicyclo[2.2.1]heptan-2-yl)(2-(1-(cyclopropylmethyl)-6-(4-fluoro-3-hydroxyphenyl)-1H-indol-2-yl)-4-fluoro-3-methylpyrazolo[1,5-a]pyridin-6-yl)methanone (61);

((7R)-7-Amino-2-azabicyclo[2.2.1]heptan-2-yl)(2-(1-(cyclopropylmethyl)-6-(3-methyl-[1,2,4]triazolo[4,3-a]pyridin-7-yl)-1H-indol-2-yl)-4-fluoro-3-methylpyrazolo[1,5-a]pyridin-6-yl)methanone (62);

((7R)-7-Amino-2-azabicyclo[2.2.1]heptan-2-yl)(2-(1-(cyclopropylmethyl)-1H-pyrrolo[2,3-b]pyridin-2-yl)-3-methylpyrazolo[1,5-a]pyridin-6-yl)methanone (63);

5-(2-(6-((7R)-7-Amino-2-azabicyclo[2.2.1]heptane-2-carbonyl)-3-methylpyrazolo[1,5-a]pyridin-2-yl)-1-(cyclopropylmethyl)-1H-pyrrolo[2,3-b]pyridin-6-yl)isoindolin-1-one (64);

6-(2-(6-((7R)-7-Amino-2-azabicyclo[2.2.1]heptane-2-carbonyl)-3-methylpyrazolo[1,5-a]pyridin-2-yl)-1-(cyclopropylmethyl)-1H-pyrrolo[2,3-b]pyridin-6-yl)isoindolin-1-one (65);

((7R)-7-Amino-2-azabicyclo[2.2.1]heptan-2-yl)(2-(1-(cyclopropylmethyl)-6-methyl-1H-pyrrolo[2,3-b]pyridin-2-yl)-3-methylpyrazolo[1,5-a]pyridin-6-yl)methanone (66);

((7R)-7-Amino-2-azabicyclo[2.2.1]heptan-2-yl)(2-(1-(cyclopropylmethyl)-6-(3-fluoro-4-hydroxyphenyl)-1H-pyrrolo[2,3-b]pyridin-2-yl)-3-methylpyrazolo[1,5-a]pyridin-6-yl)methanone (67);

((7R)-7-Amino-2-azabicyclo[2.2.1]heptan-2-yl)(2-(1-(cyclopropylmethyl)-6-(2-fluoro-3-hydroxyphenyl)-1H-pyrrolo[2,3-b]pyridin-2-yl)-3-methylpyrazolo[1,5-a]pyridin-6-yl)methanone (68);

4-(2-(6-((7R)-7-Amino-2-azabicyclo[2.2.1]heptane-2-carbonyl)-3-methylpyrazolo[1,5-a]pyridin-2-yl)-1-(cyclopropylmethyl)-1H-pyrrolo[2,3-b]pyridin-6-yl)-2-fluorobenzamide (69);

((7R)-7-Amino-2-azabicyclo[2.2.1]heptan-2-yl)(2-(1-(cyclopropylmethyl)-6-(3-methyl-[1,2,4]triazolo[4,3-a]pyridin-7-yl)-1H-pyrrolo[2,3-b]pyridin-2-yl)-3-methylpyrazolo[1,5-a]pyridin-6-yl)methanone (70);

((7R)-7-Amino-2-azabicyclo[2.2.1]heptan-2-yl)(2-(6-cyclopropyl-1-(cyclopropylmethyl)-1H-pyrrolo[2,3-b]pyridin-2-yl)-3-methylpyrazolo[1,5-a]pyridin-6-yl)methanone (71);

((7R)-7-Amino-2-azabicyclo[2.2.1]heptan-2-yl)(2-(1-(cyclopropylmethyl)-6-(5-fluoro-2-methoxypyridin-4-yl)-1H-pyrrolo[2,3-b]pyridin-2-yl)-3-methylpyrazolo[1,5-a]pyridin-6-yl)methanone (72);

((7R)-7-Amino-2-azabicyclo[2.2.1]heptan-2-yl)(2-(1-(cyclopropylmethyl)-6-(4-(difluoromethoxy)-3-fluorophenyl)-1H-pyrrolo[2,3-b]pyridin-2-yl)-3-methylpyrazolo[1,5-a]pyridin-6-yl)methanone (73);

((7R)-7-Amino-2-azabicyclo[2.2.1]heptan-2-yl)(2-(1-(cyclopropylmethyl)-6-(3,5-difluoro-4-hydroxyphenyl)-1H-pyrrolo[2,3-b]pyridin-2-yl)-3-methylpyrazolo[1,5-a]pyridin-6-yl)methanone (74);

((7R)-7-Amino-2-azabicyclo[2.2.1]heptan-2-yl)(2-(1-(cyclopropylmethyl)-6-(4-fluoro-3-hydroxyphenyl)-1H-pyrrolo[2,3-b]pyridin-2-yl)-3-methylpyrazolo[1,5-a]pyridin-6-yl)methanone (75);

((7R)-7-Amino-2-azabicyclo[2.2.1]heptan-2-yl)(2-(1-(cyclopropylmethyl)-6-(4-methoxypiperidin-1-yl)-1H-pyrrolo[2,3-b]pyridin-2-yl)-3-methylpyrazolo[1,5-a]pyridin-6-yl)methanone (76);

((7R)-7-Amino-2-azabicyclo[2.2.1]heptan-2-yl)(2-(1-(cyclopropylmethyl)-6-(4-hydroxypiperidin-1-yl)-1H-pyrrolo[2,3-b]pyridin-2-yl)-3-methylpyrazolo[1,5-a]pyridin-6-yl)methanone (77);

((7R)-7-Amino-2-azabicyclo[2.2.1]heptan-2-yl)(2-(1-(cyclopropylmethyl)-6-((R)-3-hydroxypiperidin-1-yl)-1H-pyrrolo[2,3-b]pyridin-2-yl)-3-methylpyrazolo[1,5-a]pyridin-6-yl)methanone (78);

((7R)-7-Amino-2-azabicyclo[2.2.1]heptan-2-yl)(2-(1-(cyclopropylmethyl)-6-(3-methoxyazetidin-1-yl)-1H-pyrrolo[2,3-b]pyridin-2-yl)-3-methylpyrazolo[1,5-a]pyridin-6-yl)methanone (79);

((3R,5R)-3-Amino-5-fluoropiperidin-1-yl)(2-(1-(cyclopropylmethyl)-1H-pyrrolo[2,3-b]pyridin-2-yl)-3-methylpyrazolo[1,5-a]pyridin-6-yl)methanone (80);

5-(2-(6-((3R,5R)-3-Amino-5-fluoropiperidine-1-carbonyl)-3-methylpyrazolo[1,5-a]pyridin-2-yl)-1-(cyclopropylmethyl)-1H-pyrrolo[2,3-b]pyridin-6-yl)isoindolin-1-one (81);

((3R,5R)-3-Amino-5-fluoropiperidin-1-yl)(2-(1-(cyclopropylmethyl)-6-methyl-1H-pyrrolo[2,3-b]pyridin-2-yl)-3-methylpyrazolo[1,5-a]pyridin-6-yl)methanone (82);

6-(2-(6-((3R,5R)-3-Amino-5-fluoropiperidine-1-carbonyl)-3-methylpyrazolo[1,5-a]pyridin-2-yl)-1-(cyclopropylmethyl)-1H-pyrrolo[2,3-b]pyridin-6-yl)isoindolin-1-one (83);

4-(2-(6-((3R,5R)-3-Amino-5-fluoropiperidine-1-carbonyl)-3-methylpyrazolo[1,5-a]pyridin-2-yl)-1-(cyclopropylmethyl)-1H-pyrrolo[2,3-b]pyridin-6-yl)-2-fluorobenzamide (84);

4-(2-(6-((3R,5R)-3-Amino-5-fluoropiperidine-1-carbonyl)-3-methylpyrazolo[1,5-a]pyridin-2-yl)-1-(cyclopropylmethyl)-1H-pyrrolo[2,3-b]pyridin-6-yl)-2-chlorobenzamide (85);

((3R,5R)-3-Amino-5-fluoropiperidin-1-yl)(2-(1-(cyclopropylmethyl)-6-(2-fluoro-3-hydroxyphenyl)-1H-pyrrolo[2,3-b]pyridin-2-yl)-3-methylpyrazolo[1,5-a]pyridin-6-yl)methanone (86);

((3R,5R)-3-Amino-5-fluoropiperidin-1-yl)(2-(1-(cyclopropylmethyl)-6-(4-methoxypiperidin-1-yl)-1H-pyrrolo[2,3-b]pyridin-2-yl)-3-methylpyrazolo[1,5-a]pyridin-6-yl)methanone (87);

((3R,5R)-3-Amino-5-fluoropiperidin-1-yl)(2-(1-(cyclopropylmethyl)-6-(4-hydroxypiperidin-1-yl)-1H-pyrrolo[2,3-b]pyridin-2-yl)-3-methylpyrazolo[1,5-a]pyridin-6-yl)methanone (88);

6-(2-(6-((7R)-7-Amino-2-azabicyclo[2.2.1]heptane-2-carbonyl)-3-methylpyrazolo[1,5-a]pyridin-2-yl)-1-(cyclopropylmethyl)-1H-indol-6-yl)isoindolin-1-one (89);

5-(2-(6-((7R)-7-Amino-2-azabicyclo[2.2.1]heptane-2-carbonyl)-3-methylpyrazolo[1,5-a]pyridin-2-yl)-1-(cyclopropylmethyl)-1H-indol-6-yl)isoindolin-1-one (90);

((7R)-7-Amino-2-azabicyclo[2.2.1]heptan-2-yl)(2-(1-(cyclopropylmethyl)-6-(3-fluoro-3-(hydroxymethyl)azetidin-1-yl)-1H-indol-2-yl)-3-methylpyrazolo[1,5-a]pyridin-6-yl)methanone (91);

((3R,5R)-3-Amino-5-fluoropiperidin-1-yl)(2-(1-(cyclopropylmethyl)-6-(2-fluoro-3-hydroxyphenyl)-1H-indol-2-yl)-3-methylpyrazolo[1,5-a]pyridin-6-yl)methanone (92);

4-(2-(6-((3R,5R)-3-Amino-5-fluoropiperidine-1-carbonyl)-3-methylpyrazolo[1,5-a]pyridin-2-yl)-1-(cyclopropylmethyl)-1H-indol-6-yl)-2-fluorobenzamide (93);

((3R,5R)-3-Amino-5-fluoropiperidin-1-yl)(2-(1-(cyclopropylmethyl)-6-(3-fluoro-4-hydroxyphenyl)-1H-indol-2-yl)-3-methylpyrazolo[1,5-a]pyridin-6-yl)methanone (94);

5-(2-(6-((3R,5R)-3-Amino-5-fluoropiperidine-1-carbonyl)-3-methylpyrazolo[1,5-a]pyridin-2-yl)-1-(cyclopropylmethyl)-1H-indol-6-yl)isoindolin-1-one (95);

6-(2-(6-((3R,5R)-3-Amino-5-fluoropiperidine-1-carbonyl)-3-methylpyrazolo[1,5-a]pyridin-2-yl)-1-(cyclopropylmethyl)-1H-indol-6-yl)isoindolin-1-one (96);

((7R)-7-Amino-2-azabicyclo[2.2.1]heptan-2-yl)(2-(1-(cyclopropylmethyl)-6-(2-hydroxypropan-2-yl)-1H-indol-2-yl)-4-methoxy-3-methylpyrazolo[1,5-a]pyridin-6-yl)methanone (97);

((3R,5R)-3-Amino-5-fluoropiperidin-1-yl)(2-(1-(cyclopropylmethyl)-6-(2-hydroxypropan-2-yl)-1H-indol-2-yl)-4-methoxy-3-methylpyrazolo[1,5-a]pyridin-6-yl)methanone (98);

((3R,5R)-3-Amino-5-fluoropiperidin-1-yl)(2-(1-(cyclopropylmethyl)-6-(1,1,1-trifluoro-2-hydroxypropan-2-yl)-1H-indol-2-yl)-4-methoxy-3-methylpyrazolo[1,5-a]pyridin-6-yl)methanone (99);

((7R)-7-Amino-2-azabicyclo[2.2.1]heptan-2-yl)(2-(1-(cyclopropylmethyl)-6-(2-hydroxypropan-2-yl)-1H-indol-2-yl)-3-methylpyrazolo[1,5-a]pyridin-6-yl)methanone (100);

((7R)-7-Amino-2-azabicyclo[2.2.1]heptan-2-yl)(2-(1-(cyclopropylmethyl)-6-(1,1,1-trifluoro-2-hydroxypropan-2-yl)-1H-indol-2-yl)-3-methylpyrazolo[1,5-a]pyridin-6-yl)methanone (101);

((7R)-7-Amino-2-azabicyclo[2.2.1]heptan-2-yl)(2-(1-(cyclopropylmethyl)-6-(2-hydroxypropan-2-yl)-1H-pyrrolo[2,3-b]pyridin-2-yl)-3-methylpyrazolo[1,5-a]pyridin-6-yl)methanone (102);

((7R)-7-Amino-2-azabicyclo[2.2.1]heptan-2-yl)(2-(1-(cyclopropylmethyl)-6-(1,1,1-trifluoro-2-hydroxypropan-2-yl)-1H-pyrrolo[2,3-b]pyridin-2-yl)-3-methylpyrazolo[1,5-a]pyridin-6-yl)methanone (103);

((7R)-7-Amino-2-azabicyclo[2.2.1]heptan-2-yl)(2-(1-(cyclopropylmethyl)-6-(1-hydroxyethyl)-1H-pyrrolo[2,3-b]pyridin-2-yl)-3-methylpyrazolo[1,5-a]pyridin-6-yl)methanone (104);

((3R,5R)-3-Amino-5-fluoropiperidin-1-yl)(2-(1-(cyclopropylmethyl)-6-(2-hydroxypropan-2-yl)-1H-pyrrolo[2,3-b]pyridin-2-yl)-3-methylpyrazolo[1,5-a]pyridin-6-yl)methanone (105);

((3R,5R)-3-Amino-5-fluoropiperidin-1-yl)(2-(1-(cyclopropylmethyl)-6-(1,1,1-trifluoro-2-hydroxypropan-2-yl)-1H-pyrrolo[2,3-b]pyridin-2-yl)-3-methylpyrazolo[1,5-a]pyridin-6-yl)methanone (106, 107 as diastereomers);

((7R)-7-Amino-2-azabicyclo[2.2.1]heptan-2-yl)(2-(6-chloro-1-(cyclopropylmethyl)-1H-pyrrolo[2,3-b]pyridin-2-yl)-3-methylpyrazolo[1,5-a]pyrimidin-6-yl)methanone (108);

((7R)-7-Amino-2-azabicyclo[2.2.1]heptan-2-yl)(2-(1-(cyclopropylmethyl)-6-(2-fluoro-3-hydroxyphenyl)-1H-pyrrolo[2,3-b]pyridin-2-yl)-3-methylpyrazolo[1,5-a]pyrimidin-6-yl)methanone (109);

6-(2-(6-((7R)-7-Amino-2-azabicyclo[2.2.1]heptane-2-carbonyl)-3-methylpyrazolo[1,5-a]pyrimidin-2-yl)-1-(cyclopropylmethyl)-1H-pyrrolo[2,3-b]pyridin-6-yl)isoindolin-1-one (110);

((7R)-7-Amino-2-azabicyclo[2.2.1]heptan-2-yl)(2-(1-(cyclopropylmethyl)-6-(3-fluoro-4-hydroxyphenyl)-1H-pyrrolo[2,3-b]pyridin-2-yl)-3-methylpyrazolo[1,5-a]pyrimidin-6-yl)methanone (111);

4-(2-(6-((7R)-7-Amino-2-azabicyclo[2.2.1]heptane-2-carbonyl)-3-methylpyrazolo[1,5-a]pyrimidin-2-yl)-1-(cyclopropylmethyl)-1H-pyrrolo[2,3-b]pyridin-6-yl)-2-fluorobenzamide (112);

((7R)-7-Amino-2-azabicyclo[2.2.1]heptan-2-yl)(2-(1-(cyclopropylmethyl)-1H-indol-2-yl)-4-methoxy-3-methylpyrazolo[1,5-a]pyrazin-6-yl)methanone (113);

((3R,5R)-3-Amino-5-fluoropiperidin-1-yl)(2-(1-(cyclopropylmethyl)-1H-indol-2-yl)-4-methoxy-3-methylpyrazolo[1,5-a]pyrazin-6-yl)methanone (114);

((7R)-7-Amino-2-azabicyclo[2.2.1]heptan-2-yl)(2-(1-(cyclopropylmethyl)-1H-pyrrolo[2,3-b]pyridin-2-yl)-4-methoxy-3-methylpyrazolo[1,5-a]pyrazin-6-yl)methanone (115);

(2-(1-(Cyclopropylmethyl)-1H-pyrrolo[2,3-b]pyridin-2-yl)-4-methoxy-3-methylpyrazolo[1,5-a]pyrazin-6-yl)(2,6-diazaspiro[3.3]heptan-2-yl)methanone (116);

(R)—N-(3-Amino-2-fluoropropyl)-2-(1-(cyclopropylmethyl)-1H-pyrrolo[2,3-b]pyridin-2-yl)-4-methoxy-3-methylpyrazolo[1,5-a]pyrazine-6-carboxamide (117);

((7R)-7-Amino-2-azabicyclo[2.2.1]heptan-2-yl)(2-(1-(cyclopropylmethyl)-1H-indol-2-yl)-4-methoxy-3-methylbenzo[b]thiophen-6-yl)methanone (118);

((7R)-7-Amino-2-azabicyclo[2.2.1]heptan-2-yl)(2-(1-(cyclopropylmethyl)-1H-pyrrolo[2,3-b]pyridin-2-yl)-4-methoxy-3-methylbenzo[b]thiophen-6-yl)methanone (119);

6-(2-(6-((7R)-7-Amino-2-azabicyclo[2.2.1]heptane-2-carbonyl)-4-methoxy-3-methylbenzo[b]thiophen-2-yl)-1-(cyclopropylmethyl)-1H-indol-6-yl)isoindolin-1-one (120);

((7R)-7-Amino-2-azabicyclo[2.2.1]heptan-2-yl)(2-(1-(cyclopropylmethyl)-6-(2-fluoro-3-hydroxyphenyl)-1H-indol-2-yl)-4-methoxy-3-methylbenzo[b]thiophen-6-yl)methanone (121);

((7R)-7-Amino-2-azabicyclo[2.2.1]heptan-2-yl)(2-(1-(cyclopropylmethyl)-6-(3-methyl-[1,2,4]triazolo[4,3-a]pyridin-7-yl)-1H-indol-2-yl)-4-methoxy-3-methylbenzo[b]thiophen-6-yl)methanone (122);

((7R)-7-Amino-2-azabicyclo[2.2.1]heptan-2-yl)(2-(1-(cyclopropylmethyl)-6-(3-fluoro-4-hydroxyphenyl)-1H-indol-2-yl)-4-methoxy-3-methylbenzo[b]thiophen-6-yl)methanone (123);

4-(2-(6-((7R)-7-Amino-2-azabicyclo[2.2.1]heptane-2-carbonyl)-4-methoxy-3-methylbenzo[b]thiophen-2-yl)-1-(cyclopropylmethyl)-1H-indol-6-yl)-2-fluorobenzamide (124);

4-(2-(6-((7R)-7-Amino-2-azabicyclo[2.2.1]heptane-2-carbonyl)-4-methoxy-3-methylbenzo[b]thiophen-2-yl)-1-(cyclopropylmethyl)-1H-indol-6-yl)-2-chlorobenzamide (125);

5-(2-(6-((7R)-7-Amino-2-azabicyclo[2.2.1]heptane-2-carbonyl)-4-methoxy-3-methylbenzo[b]thiophen-2-yl)-1-(cyclopropylmethyl)-1H-indol-6-yl)isoindolin-1-one (126);

((7R)-7-Amino-2-azabicyclo[2.2.1]heptan-2-yl)(2-(1-(cyclopropylmethyl)-6-methyl-1H-indol-2-yl)-4-methoxy-3-methylbenzo[b]thiophen-6-yl)methanone (127);

((7R)-7-Amino-2-azabicyclo[2.2.1]heptan-2-yl)(2-(1-(cyclopropylmethyl)-6-(3-fluoro-2-methylphenyl)-1H-indol-2-yl)-4-methoxy-3-methylbenzo[b]thiophen-6-yl)methanone (128);

((7R)-7-Amino-2-azabicyclo[2.2.1]heptan-2-yl)(2-(1-(cyclopropylmethyl)-6-(2-methoxypyridin-4-yl)-1H-indol-2-yl)-4-methoxy-3-methylbenzo[b]thiophen-6-yl)methanone (129);

((7R)-7-Amino-2-azabicyclo[2.2.1]heptan-2-yl)(2-(6-(4-aminopiperidin-1-yl)-1-(cyclopropylmethyl)-1H-indol-2-yl)-4-methoxy-3-methylbenzo[b]thiophen-6-yl)methanone (130);

((7R)-7-Amino-2-azabicyclo[2.2.1]heptan-2-yl)(2-(1-(cyclopropylmethyl)-6-(4-methoxypiperidin-1-yl)-1H-indol-2-yl)-4-methoxy-3-methylbenzo[b]thiophen-6-yl)methanone (131);

5-(2-(6-((7R)-7-Amino-2-azabicyclo[2.2.1]heptane-2-carbonyl)-4-methoxy-3-methylbenzo-[b]thiophen-2-yl)-1-(cyclopropylmethyl)-1H-pyrrolo[2,3-b]pyridin-6-yl)isoindolin-1-one (132);

4-(2-(6-((7R)-7-Amino-2-azabicyclo[2.2.1]heptane-2-carbonyl)-4-methoxy-3-methylbenzo[b]thiophen-2-yl)-1-(cyclopropylmethyl)-1H-pyrrolo[2,3-b]pyridin-6-yl)-2-fluorobenzamide (133);

((7R)-7-Amino-2-azabicyclo[2.2.1]heptan-2-yl)(2-(1-(cyclopropylmethyl)-6-(2-fluoro-3-hydroxyphenyl)-1H-pyrrolo[2,3-b]pyridin-2-yl)-4-methoxy-3-methylbenzo[b]thiophen-6-yl)methanone (134);

6-(2-(6-((7R)-7-Amino-2-azabicyclo[2.2.1]heptane-2-carbonyl)-4-methoxy-3-methylbenzo[b]thiophen-2-yl)-1-(cyclopropylmethyl)-1H-pyrrolo[2,3-b]pyridin-6-yl)isoindolin-1-one (135);

((7R)-7-Amino-2-azabicyclo[2.2.1]heptan-2-yl)(2-(1-(cyclopropylmethyl)-6-(3-fluoro-4-hydroxyphenyl)-1H-pyrrolo[2,3-b]pyridin-2-yl)-4-methoxy-3-methylbenzo[b]thiophen-6-yl)methanone (136);

((7R)-7-Amino-2-azabicyclo[2.2.1]heptan-2-yl)(2-(1-(cyclopropylmethyl)-6-(4-methoxypiperidin-1-yl)-1H-pyrrolo[2,3-b]pyridin-2-yl)-4-methoxy-3-methylbenzo[b]thiophen-6-yl)methanone (137);

((3R,5R)-3-Amino-5-fluoropiperidin-1-yl)(2-(1-(cyclopropylmethyl)-1H-pyrrolo[2,3-b]pyridin-2-yl)-4-methoxy-3-methylbenzo[b]thiophen-6-yl)methanone (138);

5-(2-(6-((3R,5R)-3-Amino-5-fluoropiperidine-1-carbonyl)-4-methoxy-3-methylbenzo[b]thiophen-2-yl)-1-(cyclopropylmethyl)-1H-pyrrolo[2,3-b]pyridin-6-yl)isoindolin-1-one (139);

6-(2-(6-((3R,5R)-3-Amino-5-fluoropiperidine-1-carbonyl)-4-methoxy-3-methylbenzo[b]thiophen-2-yl)-1-(cyclopropylmethyl)-1H-pyrrolo[2,3-b]pyridin-6-yl)isoindolin-1-one (140);

4-(2-(6-((3R,5R)-3-Amino-5-fluoropiperidine-1-carbonyl)-4-methoxy-3-methylbenzo[b]thiophen-2-yl)-1-(cyclopropylmethyl)-1H-pyrrolo[2,3-b]pyridin-6-yl)-2-fluorobenzamide (141);

((3R,5R)-3-Amino-5-fluoropiperidin-1-yl)(2-(1-(cyclopropylmethyl)-6-(4-methoxypiperidin-1-yl)-1H-pyrrolo[2,3-b]pyridin-2-yl)-4-methoxy-3-methylbenzo[b]thiophen-6-yl)methanone (142);

6-(2-(6-((3R,5R)-3-Amino-5-fluoropiperidine-1-carbonyl)-4-methoxy-3-methylbenzo[b]thiophen-2-yl)-1-(cyclopropylmethyl)-1H-indol-6-yl)isoindolin-1-one (143);

5-(2-(6-((3R,5R)-3-Amino-5-fluoropiperidine-1-carbonyl)-4-methoxy-3-methylbenzo[b]thiophen-2-yl)-1-(cyclopropylmethyl)-1H-indol-6-yl)isoindolin-1-one (144);

((7R)-7-Amino-2-azabicyclo[2.2.1]heptan-2-yl)(2-(1-(cyclopropylmethyl)-1H-pyrrolo[2,3-b]pyridin-2-yl)-4-methoxy-3-methylbenzofuran-6-yl)methanone (145);

((7R)-7-Amino-2-azabicyclo[2.2.1]heptan-2-yl)(2-(6-chloro-1-(cyclopropylmethyl)-1H-pyrrolo[2,3-b]pyridin-2-yl)-4-methoxy-3-methylbenzofuran-6-yl)methanone (146);

((3R,5R)-3-Amino-5-fluoropiperidin-1-yl)(2-(1-(cyclopropylmethyl)-1H-pyrrolo[2,3-b]pyridin-2-yl)-4-methoxy-3-methylbenzofuran-6-yl)methanone (147);

((7R)-7-Amino-2-azabicyclo[2.2.1]heptan-2-yl)(2-(1-(cyclopropylmethyl)-1H-indol-2-yl)-4-methoxy-3-methylbenzofuran-6-yl)methanone (148);

5-(2-(6-((7R)-7-Amino-2-azabicyclo[2.2.1]heptane-2-carbonyl)-4-methoxy-3-methylbenzofuran-2-yl)-1-(cyclopropylmethyl)-1H-indol-6-yl)isoindolin-1-one (149);

6-(2-(6-((7R)-7-Amino-2-azabicyclo[2.2.1]-heptane-2-carbonyl)-4-methoxy-3-methylbenzofuran-2-yl)-1-(cyclopropylmethyl)-1H-indol-6-yl)isoindolin-1-one (150);

((7R)-7-Amino-2-azabicyclo[2.2.1]heptan-2-yl)(2-(1-(cyclopropylmethyl)-6-methyl-1H-indol-2-yl)-4-methoxy-3-methylbenzofuran-6-yl)methanone (151);

4-(2-(6-((7R)-7-Amino-2-azabicyclo[2.2.1]heptane-2-carbonyl)-4-methoxy-3-methylbenzofuran-2-yl)-1-(cyclopropylmethyl)-1H-indol-6-yl)-2-fluorobenzamide (152);

4-(2-(6-((7R)-7-Amino-2-azabicyclo[2.2.1]heptane-2-carbonyl)-4-methoxy-3-methylbenzofuran-2-yl)-1-(cyclopropylmethyl)-1H-indol-6-yl)-2-chlorobenzamide (153);

((7R)-7-Amino-2-azabicyclo[2.2.1]heptan-2-yl)(2-(1-(cyclopropylmethyl)-6-(3-fluoro-4-hydroxyphenyl)-1H-indol-2-yl)-4-methoxy-3-methylbenzofuran-6-yl)methanone (154);

((7R)-7-Amino-2-azabicyclo[2.2.1]heptan-2-yl)(2-(1-(cyclopropylmethyl)-6-(3-methyl-[1,2,4]triazolo[4,3-a]pyridin-7-yl)-1H-pyrrolo[2,3-b]pyridin-2-yl)-4-methoxy-3-methylpyrazolo[1,5-a]pyridin-6-yl)methanone (155);

((7R)-7-Amino-2-azabicyclo[2.2.1]heptan-2-yl)(2-(6-cyclopropyl-1-(cyclopropylmethyl)-1H-indol-2-yl)-4-methoxy-3-methylbenzofuran-6-yl)methanone (156);

((7R)-7-Amino-2-azabicyclo[2.2.1]heptan-2-yl)(2-(1-(cyclopropylmethyl)-6-(3-methyl-[1,2,4]triazolo[4,3-a]pyridin-7-yl)-1H-indol-2-yl)-4-methoxy-3-methylbenzofuran-6-yl)methanone (157);

3-((7R)-7-Amino-2-azabicyclo[2.2.1]heptan-2-yl)(2-(1-(cyclopropylmethyl)-6-(4-ethoxypiperidin-1-yl)-1H-indol-2-yl)-4-methoxy-3-methylbenzofuran-6-yl)methanone (158);

((7R)-7-Amino-2-azabicyclo[2.2.1]heptan-2-yl)(2-(1-(cyclopropylmethyl)-6-(4-methoxypiperidin-1-yl)-1H-indol-2-yl)-4-methoxy-3-methylbenzofuran-6-yl)methanone (159);

((7R)-7-Amino-2-azabicyclo[2.2.1]heptan-2-yl)(2-(6-(4-aminopiperidin-1-yl)-1-(cyclopropylmethyl)-1H-indol-2-yl)-4-methoxy-3-methylbenzofuran-6-yl)methanone (160);

((3R,5R)-3-Amino-5-fluoropiperidin-1-yl)(2-(1-(cyclopropylmethyl)-1H-indol-2-yl)-4-methoxy-3-methylbenzofuran-6-yl)methanone (161);

4-(2-(6-((3R,5R)-3-Amino-5-fluoropiperidine-1-carbonyl)-4-methoxy-3-methylbenzofuran-2-yl)-1-(cyclopropylmethyl)-1H-indol-6-yl)-2-chlorobenzamide (162);

((3R,5R)-3-Amino-5-fluoropiperidin-1-yl)(2-(1-(cyclopropylmethyl)-6-(2-fluoro-3-hydroxyphenyl)-1H-indol-2-yl)-4-methoxy-3-methylbenzofuran-6-yl)methanone (163);

((7R)-7-Amino-2-azabicyclo[2.2.1]heptan-2-yl)(2-(1-(cyclopropylmethyl)-1H-pyrrolo[2,3-b]pyridin-2-yl)-3-methylbenzofuran-6-yl)methanone (164);

((7R)-7-Amino-2-azabicyclo[2.2.1]heptan-2-yl)(2-(6-chloro-1-(cyclopropylmethyl)-1H-pyrrolo[2,3-b]pyridin-2-yl)-3-methylbenzofuran-6-yl)methanone (165);

6-(2-(6-((7R)-7-Amino-2-azabicyclo[2.2.1]heptane-2-carbonyl)-3-methylbenzofuran-2-yl)-1-(cyclopropylmethyl)-1H-pyrrolo[2,3-b]pyridin-6-yl)isoindolin-1-one (166);

((7R)-7-Amino-2-azabicyclo[2.2.1]heptan-2-yl)(2-(1-(cyclopropylmethyl)-6-(3-methyl-[1,2,4]triazolo[4,3-a]pyridin-7-yl)-1H-pyrrolo[2,3-b]pyridin-2-yl)-3-methylbenzofuran-6-yl)methanonecyclopropylmethyl)-1H-indol-6-yl)isoindolin-1-one (167);

5-(2-(6-((7R)-7-Amino-2-azabicyclo[2.2.1]heptane-2-carbonyl)-3-methylbenzofuran-2-yl)-1-(cyclopropylmethyl)-1H-pyrrolo[2,3-b]pyridin-6-yl)isoindolin-1-one (168);

((7R)-7-Amino-2-azabicyclo[2.2.1]heptan-2-yl)(2-(1-(cyclopropylmethyl)-6-(2-fluoro-3-hydroxyphenyl)-1H-pyrrolo[2,3-b]pyridin-2-yl)-3-methylbenzofuran-6-yl)methanone (169);

4-(2-(6-((7R)-7-amino-2-azabicyclo[2.2.1]heptane-2-carbonyl)-3-methylbenzofuran-2-yl)-1-(cyclopropylmethyl)-1H-pyrrolo[2,3-b]pyridin-6-yl)-2-fluorobenzamide (170);

((7R)-7-Amino-2-azabicyclo[2.2.1]heptan-2-yl)(2-(1-(cyclopropylmethyl)-6-methyl-1H-pyrrolo[2,3-b]pyridin-2-yl)-3-methylbenzofuran-6-yl)methanone (171);

((7R)-7-Amino-2-azabicyclo[2.2.1]heptan-2-yl)(2-(1-(cyclopropylmethyl)-6-(2-methoxypyridin-4-yl)-1H-pyrrolo[2,3-b]pyridin-2-yl)-3-methylbenzofuran-6-yl)methanone (172);

((7R)-7-Amino-2-azabicyclo[2.2.1]heptan-2-yl)(2-(1-(cyclopropylmethyl)-6-(3-methoxyazetidin-1-yl)-1H-pyrrolo[2,3-b]pyridin-2-yl)-3-methylbenzofuran-6-yl)methanone (173);

((3R,5R)-3-Amino-5-fluoropiperidin-1-yl)(2-(1-(cyclopropylmethyl)-1H-pyrrolo[2,3-b]pyridin-2-yl)-3-methylbenzofuran-6-yl)methanone (174);

6-(2-(6-((3R,5R)-3-Amino-5-fluoropiperidine-1-carbonyl)-3-methylbenzofuran-2-yl)-1-(cyclopropylmethyl)-1H-pyrrolo[2,3-b]pyridin-6-yl)isoindolin-1-one (175);

((7R)-7-Amino-2-azabicyclo[2.2.1]heptan-2-yl)(2-(1-(cyclopropylmethyl)-1H-indol-2-yl)-3-methylbenzofuran-6-yl)methanone (176);

6-(2-(6-((7R)-7-Amino-2-azabicyclo[2.2.1]heptane-2-carbonyl)-3-methylbenzofuran-2-yl)-1-(cyclopropylmethyl)-1H-indol-6-yl)isoindolin-1-one (177);

5-(2-(6-((7R)-7-Amino-2-azabicyclo[2.2.1]heptane-2-carbonyl)-3-methylbenzofuran-2-yl)-1-(cyclopropylmethyl)-1H-indol-6-yl)isoindolin-1-one (178);

((7R)-7-Amino-2-azabicyclo[2.2.1]heptan-2-yl)(2-(1-(cyclopropylmethyl)-6-(3-methyl-[1,2,4]triazolo[4,3a]pyridin-7-yl)-1H-indol-2-yl)-3-methylbenzofuran-6-yl)methanone (179);

((7R)-7-Amino-2-azabicyclo[2.2.1]heptan-2-yl)(2-(1-(cyclopropylmethyl)-6-(1-isopropyl-1H-pyrazol-4-yl)-1H-indol-2-yl)-3-methylbenzofuran-6-yl)methanone (180);

((7R)-7-Amino-2-azabicyclo[2.2.1]heptan-2-yl)(2-(1-(cyclopropylmethyl)-6-(2-fluoro-3-hydroxyphenyl)-1H-indol-2-yl)-3-methylbenzofuran-6-yl)methanone (181);

((7R)-7-Amino-2-azabicyclo[2.2.1]heptan-2-yl)(2-(1-(cyclopropylmethyl)-6-(3-fluoro-4-hydroxyphenyl)-1H-indol-2-yl)-3-methylbenzofuran-6-yl)methanone (182);

4-(2-(6-((7R)-7-Amino-2-azabicyclo[2.2.1]heptane-2-carbonyl)-3-methylbenzofuran-2-yl)-1-(cyclopropylmethyl)-1H-indol-6-yl)-2-chlorobenzamide (183);

((7R)-7-Amino-2-azabicyclo[2.2.1]heptan-2-yl)(2-(1-(cyclopropylmethyl)-6-methyl-1H-indol-2-yl)-3-methylbenzofuran-6-yl)methanone (184);

4-(2-(6-((7R)-7-Amino-2-azabicyclo[2.2.1]heptane-2-carbonyl)-3-methylbenzofuran-2-yl)-1-(cyclopropylmethyl)-1H-indol-6-yl)-2-fluorobenzamide (185);

((7R)-7-Amino-2-azabicyclo[2.2.1]heptan-2-yl)(2-(1-(cyclopropylmethyl)-6-(2-methoxypyridin-4-yl)-1H-indol-2-yl)-3-methylbenzofuran-6-yl)methanone (186);

((7R)-7-Amino-2-azabicyclo[2.2.1]heptan-2-yl)(2-(6-cyclopropyl-1-(cyclopropylmethyl)-1H-indol-2-yl)-3-methylbenzofuran-6-yl)methanone (187);

5-(2-(6-((7R)-7-Amino-2-azabicyclo[2.2.1]heptane-2-carbonyl)-3-methylbenzofuran-2-yl)-1-(cyclopropylmethyl)-1H-indol-6-yl)-3-methylpicolinamide (188);

((7R)-7-Amino-2-azabicyclo[2.2.1]heptan-2-yl)(2-(1-(cyclopropylmethyl)-6-(4-methoxypiperidin-1-yl)-1H-indol-2-yl)-3-methylbenzofuran-6-yl)methanone (189);

((7R)-7-Amino-2-azabicyclo[2.2.1]heptan-2-yl)(2-(1-(cyclopropylmethyl)-6-(3-methoxyazetidin-1-yl)-1H-indol-2-yl)-3-methylbenzofuran-6-yl)methanone (190);

((7R)-7-Amino-2-azabicyclo[2.2.1]heptan-2-yl)(2-(6-(4-aminopiperidin-1-yl)-1-(cyclopropylmethyl)-1H-indol-2-yl)-3-methylbenzofuran-6-yl)methanone (191);

((7R)-7-Amino-2-azabicyclo[2.2.1]heptan-2-yl)(2-(1-(cyclopropylmethyl)-6-(piperazin-1-yl)-1H-indol-2-yl)-3-methylbenzofuran-6-yl)methanone (192);

1-(2-(6-((7R)-7-Amino-2-azabicyclo[2.2.1]heptane-2-carbonyl)-3-methylbenzofuran-2-yl)-1-(cyclopropylmethyl)-1H-indol-6-yl)piperazin-2-one (193);

((3R,5R)-3-Amino-5-fluoropiperidin-1-yl)(2-(1-(cyclopropylmethyl)-1H-indol-2-yl)-3-methylbenzofuran-6-yl)methanone (194);

5-(2-(6-((3R,5R)-3-Amino-5-fluoropiperidine-1-carbonyl)-3-methylbenzofuran-2-yl)-1-(cyclopropylmethyl)-1H-indol-6-yl)isoindolin-1-one (195);

4-(2-(6-((3R,5R)-3-Amino-5-fluoropiperidine-1-carbonyl)-3-methylbenzofuran-2-yl)-1-(cyclopropylmethyl)-1H-indol-6-yl)-2-fluorobenzamide (196);

((3R,5R)-3-Amino-5-fluoropiperidin-1-yl)(2-(1-(cyclopropylmethyl)-6-(3-methyl-[1,2,4]triazolo[4,3-a]pyridin-7-yl)-1H-indol-2-yl)-3-methylbenzofuran-6-yl)methanone (197);

((3R,5R)-3-Amino-5-fluoropiperidin-1-yl)(2-(1-(cyclopropylmethyl)-6-(2-fluoro-3-hydroxyphenyl)-1H-indol-2-yl)-3-methylbenzofuran-6-yl)methanone (198);

4-(2-(6-((3R,5R)-3-Amino-5-fluoropiperidine-1-carbonyl)-3-methylbenzofuran-2-yl)-1-(cyclopropylmethyl)-1H-indol-6-yl)-2-chlorobenzamide (199);

((3R,5R)-3-Amino-5-fluoropiperidin-1-yl)(2-(1-(cyclopropylmethyl)-6-(4-methoxypiperidin-1-yl)-1H-indol-2-yl)-3-methylbenzofuran-6-yl)methanone (200);

((3R,5R)-3-Amino-5-fluoropiperidin-1-yl)(2-(1-(cyclopropylmethyl)-6-(piperazin-1-yl)-1H-indol-2-yl)-3-methylbenzofuran-6-yl)methanone (201);

((3R,5R)-3-Amino-5-fluoropiperidin-1-yl)(2-(6-(4-aminopiperidin-1-yl)-1-(cyclopropylmethyl)-1H-indol-2-yl)-3-methylbenzofuran-6-yl)methanone (202);

((7R)-7-Amino-2-azabicyclo[2.2.1]heptan-2-yl)(2-(1-(cyclopropylmethyl)-6-(2-hydroxypropan-2-yl)-1H-pyrrolo[2,3-b]pyridin-2-yl)-4-methoxy-3-methylbenzofuran-6-yl)methanone (203);

((7R)-7-Amino-2-azabicyclo[2.2.1]heptan-2-yl)(2-(1-(cyclopropylmethyl)-6-(2-hydroxypropan-2-yl)-1H-indol-2-yl)-3-methylbenzofuran-6-yl)methanone (204);

1-[2-(2-{6-[(7R)-7-Amino-2-azabicyclo[2.2.1]heptane-2-carbonyl]-4-methoxy-3-methylpyrazolo[1,5-a]pyridin-2-yl}-1-(cyclopropylmethyl)-1H-pyrrolo[2,3-b]pyridin-6-yl)phenyl]imidazolidin-2-one (205);

4-(2-{6-[(7R)-7-Amino-2-azabicyclo[2.2.1]heptane-2-carbonyl]-4-methoxy-3-methylpyrazolo[1,5-a]pyridin-2-yl}-1-(cyclopropylmethyl)-1H-pyrrolo[2,3-b]pyridin-6-yl)-2-methylbenzamide (206);

4-(2-{6-[(3R,5R)-3-Amino-5-fluoropiperidine-1-carbonyl]-4-methoxy-3-methylpyrazolo[1,5-a]pyridin-2-yl}-1-(cyclopropylmethyl)-1H-pyrrolo[2,3-b]pyridin-6-yl)-2-fluoro-5-methylbenzamide (207);

4-(2-{6-[(3R)-3-Aminopiperidine-1-carbonyl]-4-methoxy-3-methylpyrazolo[1,5-a]pyridin-2-yl}-1-(cyclopropylmethyl)-1H-pyrrolo[2,3-b]pyridin-6-yl)-2-fluoro-5-methylbenzamide (208);

[2-(2-{6-[(3R,5R)-3-Amino-5-fluoropiperidine-1-carbonyl]-4-methoxy-3-methylpyrazolo[1,5-a]pyridin-2-yl}-1-(cyclopropylmethyl)-1H-indol-6-yl)phenyl]methanol (209);

[3-(2-{6-[(3R,5R)-3-Amino-5-fluoropiperidine-1-carbonyl]-4-methoxy-3-methylpyrazolo[1,5-a]pyridin-2-yl}-1-(cyclopropylmethyl)-1H-indol-6-yl)phenyl]methanol (210);

N-{[3-(2-{6-[(3R,5R)-3-Amino-5-fluoropiperidine-1-carbonyl]-4-methoxy-3-methylpyrazolo[1,5-a]pyridin-2-yl}-1-(cyclopropylmethyl)-1H-indol-6-yl)phenyl]methyl}methanesulfonamide (211);

(3R,5R)-1-{2-[1-(Cyclopropylmethyl)-6-(3-methoxyphenyl)-1H-indol-2-yl]-4-methoxy-3-methylpyrazolo[1,5-a]pyridine-6-carbonyl}-5-fluoropiperidin-3-amine (212);

N-[3-(2-{6-[(3R,5R)-3-Amino-5-fluoropiperidine-1-carbonyl]-4-methoxy-3-methylpyrazolo[1,5-a]pyridin-2-yl}-1-(cyclopropylmethyl)-1H-indol-6-yl)phenyl]methanesulfonamide (213);

N-[4-(2-{6-[(3R,5R)-3-Amino-5-fluoropiperidine-1-carbonyl]-4-methoxy-3-methylpyrazolo[1,5-a]pyridin-2-yl}-1-(cyclopropylmethyl)-1H-indol-6-yl)phenyl]acetamide (214);

N-{[3-(2-{6-[(3R,5R)-3-Amino-5-fluoropiperidine-1-carbonyl]-4-methoxy-3-methylpyrazolo[1,5-a]pyridin-2-yl}-1-(cyclopropylmethyl)-1H-indol-6-yl)phenyl]methyl}acetamide (215);

N-[4-(2-{6-[(3R,5R)-3-Amino-5-fluoropiperidine-1-carbonyl]-4-methoxy-3-methylpyrazolo[1,5-a]pyridin-2-yl}-1-(cyclopropylmethyl)-1H-indol-6-yl)phenyl]methanesulfonamide (216);

4-(2-{6-[(3R,5R)-3-Amino-5-fluoropiperidine-1-carbonyl]-4-methoxy-3-methylpyrazolo[1,5-a]pyridin-2-yl}-1-(cyclopropylmethyl)-1H-indol-6-yl)-N,N-dimethylbenzamide (217);

(3R,5R)-1-{2-[1-(Cyclopropylmethyl)-6-(1H-indazol-5-yl)-1H-indol-2-yl]-4-methoxy-3-methylpyrazolo[1,5-a]pyridine-6-carbonyl}-5-fluoropiperidin-3-amine (218);

(3R,5R)-1-{2-[1-(Cyclopropylmethyl)-6-(1-methyl-1H-indazol-5-yl)-1H-indol-2-yl]-4-methoxy-3-methylpyrazolo[1,5-a]pyridine-6-carbonyl}-5-fluoropiperidin-3-amine (219);

(3R,5R)-1-{2-[1-(Cyclopropylmethyl)-6-[3-(2H-1,2,3,4-tetrazol-5-yl)phenyl]-1H-indol-2-yl]-4-methoxy-3-methylpyrazolo[1,5-a]pyridine-6-carbonyl}-5-fluoropiperidin-3-amine (220);

N-{[4-(2-{6-[(3R,5R)-3-Amino-5-fluoropiperidine-1-carbonyl]-4-methoxy-3-methylpyrazolo[1,5-a]pyridin-2-yl}-1-(cyclopropylmethyl)-1H-indol-6-yl)phenyl]methyl}acetamide (221);

(3R,5R)-1-{2-[1-(Cyclopropylmethyl)-6-(1H-indazol-4-yl)-1H-indol-2-yl]-4-methoxy-3-methylpyrazolo[1,5-a]pyridine-6-carbonyl}-5-fluoropiperidin-3-amine (222);

2-(2-{6-[(3R,5R)-3-Amino-5-fluoropiperidine-1-carbonyl]-4-methoxy-3-methylpyrazolo[1,5-a]pyridin-2-yl}-1-(cyclopropylmethyl)-1H-indol-6-yl)benzamide (223);

N-{[4-(2-{6-[(3R,5R)-3-Amino-5-fluoropiperidine-1-carbonyl]-4-methoxy-3-methylpyrazolo[1,5-a]pyridin-2-yl}-1-(cyclopropylmethyl)-1H-indol-6-yl)phenyl]methyl}methanesulfonamide (224);

6-(2-{6-[(3R,5R)-3-Amino-5-fluoropiperidine-1-carbonyl]-4-methoxy-3-methylpyrazolo[1,5-a]pyridin-2-yl}-1-(cyclopropylmethyl)-1H-indol-6-yl)-8-fluoro-5-methyl-1,2-dihydroquinolin-2-one (225);

N-[5-(2-{6-[(3R,5R)-3-Amino-5-fluoropiperidine-1-carbonyl]-4-methoxy-3-methylpyrazolo[1,5-a]pyridin-2-yl}-1-(cyclopropylmethyl)-1H-indol-6-yl)pyridin-2-yl]acetamide (226);

[3-(2-{6-[(3R)-3-Aminopiperidine-1-carbonyl]-4-methoxy-3-methylpyrazolo[1,5-a]pyridin-2-yl}-1-(cyclopropylmethyl)-1H-indol-6-yl)phenyl]methanol (227);

N-{[4-(2-{6-[(3R)-3-Aminopiperidine-1-carbonyl]-4-methoxy-3-methylpyrazolo[1,5-a]pyridin-2-yl}-1-(cyclopropylmethyl)-1H-indol-6-yl)phenyl]methyl}acetamide (228);

4-(2-{6-[(3R)-3-Aminopiperidine-1-carbonyl]-4-methoxy-3-methylpyrazolo[1,5-a]pyridin-2-yl}-1-(cyclopropylmethyl)-1H-indol-6-yl)benzamide (229);

4-(2-{6-[(3R)-3-Aminopiperidine-1-carbonyl]-4-methoxy-3-methylpyrazolo[1,5-a]pyridin-2-yl}-1-(cyclopropylmethyl)-1H-indol-6-yl)-N,N-dimethylbenzamide (230);

N-[4-(2-{6-[(3R)-3-Aminopiperidine-1-carbonyl]-4-methoxy-3-methylpyrazolo[1,5-a]pyridin-2-yl}-1-(cyclopropylmethyl)-1H-indol-6-yl)phenyl]methanesulfonamide (231);

N-{[3-(2-{6-[(3R)-3-Aminopiperidine-1-carbonyl]-4-methoxy-3-methylpyrazolo[1,5-a]pyridin-2-yl}-1-(cyclopropylmethyl)-1H-indol-6-yl)phenyl]methyl}acetamide (232);

[2-(2-{6-[(3R)-3-Aminopiperidine-1-carbonyl]-4-methoxy-3-methylpyrazolo[1,5-a]pyridin-2-yl}-1-(cyclopropylmethyl)-1H-indol-6-yl)phenyl]methanol (233);

N-{[4-(2-{6-[(3R)-3-Aminopiperidine-1-carbonyl]-4-methoxy-3-methylpyrazolo[1,5-a]pyridin-2-yl}-1-(cyclopropylmethyl)-1H-indol-6-yl)phenyl]methyl}methanesulfonamide (234);

N-{[3-(2-{6-[(3R)-3-Aminopiperidine-1-carbonyl]-4-methoxy-3-methylpyrazolo[1,5-a]pyridin-2-yl}-1-(cyclopropylmethyl)-1H-indol-6-yl)phenyl]methyl}methanesulfonamide (235);

[3-(2-{6-[(3R)-3-Aminopiperidine-1-carbonyl]-4-methoxy-3-methylpyrazolo[1,5-a]pyridin-2-yl}-1-(cyclopropylmethyl)-1H-indol-6-yl)phenyl]methanol (236);

2-(2-{6-[(3R)-3-Aminopiperidine-1-carbonyl]-4-methoxy-3-methylpyrazolo[1,5-a]pyridin-2-yl}-1-(cyclopropylmethyl)-1H-indol-6-yl)benzamide (237);

(3R)-1-{2-[1-(Cyclopropylmethyl)-6-(1H-indazol-4-yl)-1H-indol-2-yl]-4-methoxy-3-methylpyrazolo[1,5-a]pyridine-6-carbonyl}piperidin-3-amine (238);

6-(2-{6-[(3R)-3-Aminopiperidine-1-carbonyl]-4-methoxy-3-methylpyrazolo[1,5-a]pyridin-2-yl}-1-(cyclopropylmethyl)-1H-indol-6-yl)-8-fluoro-5-methyl-1,2-dihydroquinolin-2-one (239);

N-[5-(2-{6-[(3R)-3-Aminopiperidine-1-carbonyl]-4-methoxy-3-methylpyrazolo[1,5-a]pyridin-2-yl}-1-(cyclopropylmethyl)-1H-indol-6-yl)pyridin-2-yl]acetamide (240);

(3R,5R)-1-{2-[1-(Cyclopropylmethyl)-6-(4-methanesulfonylpiperidin-1-yl)-1H-indol-2-yl]-4-methoxy-3-methylpyrazolo[1,5-a]pyridine-6-carbonyl}-5-fluoropiperidin-3-amine (241);

1-(2-{6-[(3R,5R)-3-Amino-5-fluoropiperidine-1-carbonyl]-4-methoxy-3-methylpyrazolo[1,5-a]pyridin-2-yl}-1-(cyclopropylmethyl)-1H-indol-6-yl)-N,N-dimethylpiperidine-4-carboxamide (242);

N-[1-(2-{6-[(3R,5R)-3-Amino-5-fluoropiperidine-1-carbonyl]-4-methoxy-3-methylpyrazolo[1,5-a]pyridin-2-yl}-1-(cyclopropylmethyl)-1H-indol-6-yl)piperidin-4-yl]-N-methylacetamide (243);

N-[1-(2-{6-[(3R,5R)-3-Amino-5-fluoropiperidine-1-carbonyl]-4-methoxy-3-methylpyrazolo[1,5-a]pyridin-2-yl}-1-(cyclopropylmethyl)-1H-indol-6-yl)piperidin-4-yl]-N-methylacetamide (244);

Methyl N-[1-(2-{6-[(3R,5R)-3-amino-5-fluoropiperidine-1-carbonyl]-4-methoxy-3-methylpyrazolo[1,5-a]pyridin-2-yl}-1-(cyclopropylmethyl)-1H-indol-6-yl)piperidin-4-yl]-N-methylcarbamate (245);

N-[1-(2-{6-[(3R,5R)-3-Amino-5-fluoropiperidine-1-carbonyl]-4-methoxy-3-methylpyrazolo[1,5-a]pyridin-2-yl}-1-(cyclopropylmethyl)-1H-indol-6-yl)piperidin-4-yl]-N-methylmethanesulfonamide (246);

N-[1-(2-{6-[(3R,5R)-3-Amino-5-fluoropiperidine-1-carbonyl]-4-methoxy-3-methylpyrazolo[1,5-a]pyridin-2-yl}-1-(cyclopropylmethyl)-1H-indol-6-yl)azetidin-3-yl]-N-methylmethanesulfonamide (247);

(3R)-1-{2-[1-(Cyclopropylmethyl)-6-(4-methanesulfonylpiperidin-1-yl)-1H-indol-2-yl]-4-methoxy-3-methylpyrazolo[1,5-a]pyridine-6-carbonyl}piperidin-3-amine (248);

(3R)-1-{2-[1-(Cyclopropylmethyl)-6-(4-methoxypiperidin-1-yl)-1H-indol-2-yl]-4-methoxy-3-methylpyrazolo[1,5-a]pyridine-6-carbonyl}piperidin-3-amine (249);

2-[1-(2-{6-[(3R)-3-Aminopiperidine-1-carbonyl]-4-methoxy-3-methylpyrazolo[1,5-a]pyridin-2-yl}-1-(cyclopropylmethyl)-1H-indol-6-yl)piperidin-4-yl]-N,N-dimethylacetamide (250);

(3R)-1-{2-[1-(Cyclopropylmethyl)-6-[4-(3-methoxyazetidine-1-carbonyl)piperidin-1-yl]-1H-indol-2-yl]-4-methoxy-3-methylpyrazolo[1,5-a]pyridine-6-carbonyl}piperidin-3-amine (251);

N-[1-(2-{6-[(3R)-3-Aminopiperidine-1-carbonyl]-4-methoxy-3-methylpyrazolo[1,5-a]pyridin-2-yl}-1-(cyclopropylmethyl)-1H-indol-6-yl)piperidin-4-yl]-N-methylacetamide (252);

N-[1-(2-{6-[(3R)-3-Aminopiperidine-1-carbonyl]-4-methoxy-3-methylpyrazolo[1,5-a]pyridin-2-yl}-1-(cyclopropylmethyl)-1H-indol-6-yl)piperidin-4-yl]-N-methylacetamide (253);

N-[1-(2-{6-[(3R)-3-Aminopiperidine-1-carbonyl]-4-methoxy-3-methylpyrazolo[1,5-a]pyridin-2-yl}-1-(cyclopropylmethyl)-1H-indol-6-yl)piperidin-4-yl]-N-methylmethanesulfonamide (254);

Methyl N-[1-(2-{6-[(3R)-3-aminopiperidine-1-carbonyl]-4-methoxy-3-methylpyrazolo[1,5-a]pyridin-2-yl}-1-(cyclopropylmethyl)-1H-indol-6-yl)piperidin-4-yl]-N-methylcarbamate (255);

N-[1-(2-{6-[(3R)-3-Aminopiperidine-1-carbonyl]-4-methoxy-3-methylpyrazolo[1,5-a]pyridin-2-yl}-1-(cyclopropylmethyl)-1H-indol-6-yl)azetidin-3-yl]-N-methylmethanesulfonamide (256);

1-[2-(2-{6-[(7R)-7-Amino-2-azabicyclo[2.2.1]heptane-2-carbonyl]-4-fluoro-3-methylpyrazolo[1,5-a]pyridin-2-yl}-1-(cyclopropylmethyl)-1H-pyrrolo[2,3-b]pyridin-6-yl)phenyl]imidazolidin-2-one (257);

1-[4-(2-{6-[(7R)-7-Amino-2-azabicyclo[2.2.1]heptane-2-carbonyl]-4-fluoro-3-methylpyrazolo[1,5-a]pyridin-2-yl}-1-(cyclopropylmethyl)-1H-pyrrolo[2,3-b]pyridin-6-yl)phenyl]pyrrolidin-2-one (258);

3-(2-{6-[(7R)-7-Amino-2-azabicyclo[2.2.1]heptane-2-carbonyl]-4-fluoro-3-methylpyrazolo[1,5-a]pyridin-2-yl}-1-(cyclopropylmethyl)-1H-pyrrolo[2,3-b]pyridin-6-yl)-2-methylphenol (259);

4-(2-{6-[(7R)-7-Amino-2-azabicyclo[2.2.1]heptane-2-carbonyl]-4-fluoro-3-methylpyrazolo[1,5-a]pyridin-2-yl}-1-(cyclopropylmethyl)-1H-pyrrolo[2,3-b]pyridin-6-yl)-2-fluoro-5-methylbenzamide (260);

1-[4-(2-{6-[(7R)-7-Amino-2-azabicyclo[2.2.1]heptane-2-carbonyl]-4-fluoro-3-methylpyrazolo[1,5-a]pyridin-2-yl}-1-(cyclopropylmethyl)-1H-pyrrolo[2,3-b]pyridin-6-yl)phenyl]imidazolidin-2-one (261);

4-(2-{6-[(7R)-7-Amino-2-azabicyclo[2.2.1]heptane-2-carbonyl]-4-fluoro-3-methylpyrazolo[1,5-a]pyridin-2-yl}-1-(cyclopropylmethyl)-1H-pyrrolo[2,3-b]pyridin-6-yl)-2-methylbenzamide (262);

4-(2-{6-[(7R)-7-Amino-2-azabicyclo[2.2.1]heptane-2-carbonyl]-4-fluoro-3-methylpyrazolo[1,5-a]pyridin-2-yl}-1-(cyclopropylmethyl)-1H-pyrrolo[2,3-b]pyridin-6-yl)benzamide (263);

5-(2-{6-[(7R)-7-Amino-2-azabicyclo[2.2.1]heptane-2-carbonyl]-4-fluoro-3-methylpyrazolo[1,5-a]pyridin-2-yl}-1-(cyclopropylmethyl)-1H-pyrrolo[2,3-b]pyridin-6-yl)-N-methylpyridine-2-carboxamide (264);

((7R)-7-Amino-2-azabicyclo[2.2.1]heptan-2-yl)(2-(1-(cyclopropylmethyl)-6-((R)-3-hydroxypiperidin-1-yl)-1H-pyrrolo[2,3-b]pyridin-2-yl)-4-fluoro-3-methylpyrazolo[1,5-a]pyridin-6-yl)methanone (265);

(7R)-2-{2-[1-(Cyclopropylmethyl)-6-(morpholin-4-yl)-1H-pyrrolo[2,3-b]pyridin-2-yl]-4-fluoro-3-methylpyrazolo[1,5-a]pyridine-6-carbonyl}-2-azabicyclo[2.2.1]heptan-7-amine (266);

4-(2-{6-[(7R)-7-Amino-2-azabicyclo[2.2.1]heptane-2-carbonyl]-4-fluoro-3-methylpyrazolo[1,5-a]pyridin-2-yl}-1-(cyclopropylmethyl)-1H-pyrrolo[2,3-b]pyridin-6-yl)morpholin-3-one (267);

(7R)-2-{2-[1-(Cyclopropylmethyl)-6-(4-methanesulfonylpiperidin-1-yl)-1H-pyrrolo[2,3-b]pyridin-2-yl]-4-fluoro-3-methylpyrazolo[1,5-a]pyridine-6-carbonyl}-2-azabicyclo[2.2.1]heptan-7-amine (268);

8-(2-{6-[(3R)-3-Aminopiperidine-1-carbonyl]-4-fluoro-3-methylpyrazolo[1,5-a]pyridin-2-yl}-1-(cyclopropylmethyl)-1H-pyrrolo[2,3-b]pyridin-6-yl)-3-methyl-1-oxa-3,8-diazaspiro[4.5]decan-2-one (269);

(3R)-1-{2-[1-(Cyclopropylmethyl)-6-(4-methanesulfonylpiperidin-1-yl)-1H-pyrrolo[2,3-b]pyridin-2-yl]-4-fluoro-3-methylpyrazolo[1,5-a]pyridine-6-carbonyl}piperidin-3-amine (270);

N-[1-(2-{6-[(3R)-3-Aminopiperidine-1-carbonyl]-4-fluoro-3-methylpyrazolo[1,5-a]pyridin-2-yl}-1-(cyclopropylmethyl)-1H-pyrrolo[2,3-b]pyridin-6-yl)piperidin-4-yl]-N-methylacetamide (271);

Methyl N-[1-(2-{6-[(3R)-3-aminopiperidine-1-carbonyl]-4-fluoro-3-methylpyrazolo[1,5-a]pyridin-2-yl}-1-(cyclopropylmethyl)-1H-pyrrolo[2,3-b]pyridin-6-yl)piperidin-4-yl]-N-methylcarbamate (272);

1-[1-(2-{6-[(3R)-3-Aminopiperidine-1-carbonyl]-4-fluoro-3-methylpyrazolo[1,5-a]pyridin-2-yl}-1-(cyclopropylmethyl)-1H-pyrrolo[2,3-b]pyridin-6-yl)piperidin-4-yl]pyrrolidin-2-one (273);

(5S)-5-{[(2-{6-[(7R)-7-Amino-2-azabicyclo[2.2.1]heptane-2-carbonyl]-4-fluoro-3-methylpyrazolo[1,5-a]pyridin-2-yl}-1-(cyclopropylmethyl)-1H-pyrrolo[2,3-b]pyridin-6-yl)oxy]methyl}pyrrolidin-2-one (274);

4-{[(2-{6-[(7R)-7-Amino-2-azabicyclo[2.2.1]heptane-2-carbonyl]-4-fluoro-3-methylpyrazolo[1,5-a]pyridin-2-yl}-1-(cyclopropylmethyl)-1H-pyrrolo[2,3-b]pyridin-6-yl)oxy]methyl}pyrrolidin-2-one (275);

(3R)-1-{4-Chloro-2-[1-(cyclopropylmethyl)-6-(4-methoxypiperidin-1-yl)-1H-pyrrolo[2,3-b]pyridin-2-yl]-3-methylpyrazolo[1,5-a]pyridine-6-carbonyl}piperidin-3-amine (276);

4-(2-{6-[(3R)-3-Aminopiperidine-1-carbonyl]-4-fluoro-3-methylpyrazolo[1,5-a]pyridin-2-yl}-1-(cyclopropylmethyl)-1H-pyrrolo[2,3-b]pyridin-6-yl)-2-fluoro-5-methylbenzamide (277);

3-(2-{6-[(3R)-3-Aminopiperidine-1-carbonyl]-4-fluoro-3-methylpyrazolo[1,5-a]pyridin-2-yl}-1-(cyclopropylmethyl)-1H-pyrrolo[2,3-b]pyridin-6-yl)-2-chlorophenol (278);

4-(2-{6-[(3R)-3-Aminopiperidine-1-carbonyl]-4-fluoro-3-methylpyrazolo[1,5-a]pyridin-2-yl}-1-(cyclopropylmethyl)-1H-pyrrolo[2,3-b]pyridin-6-yl)-2-fluorobenzamide (279);

1-[4-(2-{6-[(3R)-3-Aminopiperidine-1-carbonyl]-4-fluoro-3-methylpyrazolo[1,5-a]pyridin-2-yl}-1-(cyclopropylmethyl)-1H-pyrrolo[2,3-b]pyridin-6-yl)phenyl]imidazolidin-2-one (280);

1-[2-(2-{6-[(3R)-3-Aminopiperidine-1-carbonyl]-4-fluoro-3-methylpyrazolo[1,5-a]pyridin-2-yl}-1-(cyclopropylmethyl)-1H-pyrrolo[2,3-b]pyridin-6-yl)phenyl]imidazolidin-2-one (281);

3-(2-{6-[(3R)-3-Aminopiperidine-1-carbonyl]-4-fluoro-3-methylpyrazolo[1,5-a]pyridin-2-yl}-1-(cyclopropylmethyl)-1H-pyrrolo[2,3-b]pyridin-6-yl)-2-methylphenol (282);

3-(2-{6-[(3R)-3-Aminopiperidine-1-carbonyl]-4-fluoro-3-methylpyrazolo[1,5-a]pyridin-2-yl}-1-(cyclopropylmethyl)-1H-pyrrolo[2,3-b]pyridin-6-yl)-2-fluorophenol (283);

5-(2-{6-[(3R)-3-Aminopiperidine-1-carbonyl]-4-fluoro-3-methylpyrazolo[1,5-a]pyridin-2-yl}-1-(cyclopropylmethyl)-1H-pyrrolo[2,3-b]pyridin-6-yl)-2,3-dihydro-1H-isoindol-1-one (284);

6-(2-{6-[(3R)-3-Aminopiperidine-1-carbonyl]-4-fluoro-3-methylpyrazolo[1,5-a]pyridin-2-yl}-1-(cyclopropylmethyl)-1H-pyrrolo[2,3-b]pyridin-6-yl)-2,3-dihydro-1H-isoindol-1-one (285);

4-(2-{6-[(3R)-3-Aminopiperidine-1-carbonyl]-4-fluoro-3-methylpyrazolo[1,5-a]pyridin-2-yl}-1-(cyclopropylmethyl)-1H-pyrrolo[2,3-b]pyridin-6-yl)-2-methylbenzamide (286);

5-(2-{6-[(3R)-3-Aminopiperidine-1-carbonyl]-4-fluoro-3-methylpyrazolo[1,5-a]pyridin-2-yl}-1-(cyclopropylmethyl)-1H-pyrrolo[2,3-b]pyridin-6-yl)-N-methylpyridine-2-carboxamide (287);

(3R)-1-{2-[1-(Cyclopropylmethyl)-6-{3-methyl-[1,2,4]triazolo[4,3-a]pyridin-7-yl}-1H-pyrrolo[2,3-b]pyridin-2-yl]-4-fluoro-3-methylpyrazolo[1,5-a]pyridine-6-carbonyl}piperidin-3-amine (288);

(3R,5R)-1-{4-Chloro-2-[6-chloro-1-(cyclopropylmethyl)-1H-pyrrolo[2,3-b]pyridin-2-yl]-3-methylpyrazolo[1,5-a]pyridine-6-carbonyl}-5-fluoropiperidin-3-amine (289);

(3R,5R)-1-{4-Chloro-2-[1-(cyclopropylmethyl)-6-(1H-indazol-5-yl)-1H-pyrrolo[2,3-b]pyridin-2-yl]-3-methylpyrazolo[1,5-a]pyridine-6-carbonyl}-5-fluoropiperidin-3-amine (290);

(3R)-1-{4-Chloro-2-[6-chloro-1-(cyclopropylmethyl)-1H-pyrrolo[2,3-b]pyridin-2-yl]-3-methylpyrazolo[1,5-a]pyridine-6-carbonyl}piperidin-3-amine (291);

(3R)-1-{4-chloro-2-[1-(Cyclopropylmethyl)-6-(1H-indazol-5-yl)-1H-pyrrolo[2,3-b]pyridin-2-yl]-3-methylpyrazolo[1,5-a]pyridine-6-carbonyl}piperidin-3-amine (292);

5-(2-{6-[(7R)-7-Amino-2-azabicyclo[2.2.1]heptane-2-carbonyl]-4-fluoro-3-methylpyrazolo[1,5-a]pyridin-2-yl}-1-(cyclopropylmethyl)-1H-indol-6-yl)-2,3-dihydro-1H-isoindol-1-one (293);

4-(2-{6-[(7R)-7-Amino-2-azabicyclo[2.2.1]heptane-2-carbonyl]-4-fluoro-3-methylpyrazolo[1,5-a]pyridin-2-yl}-1-(cyclopropylmethyl)-1H-indol-6-yl)-3-chlorobenzamide (294);

(7R)-2-{2-[1-(Cyclopropylmethyl)-6-{3-methyl-[1,2,4]triazolo[4,3-a]pyridin-7-yl}-1H-indol-2-yl]-4-fluoro-3-methylpyrazolo[1,5-a]pyridine-6-carbonyl}-2-azabicyclo[2.2.1]heptan-7-amine (295);

(7R)-2-{2-[1-(Cyclopropylmethyl)-6-(3-methoxyazetidin-1-yl)-1H-indol-2-yl]-4-fluoro-3-methylpyrazolo[1,5-a]pyridine-6-carbonyl}-2-azabicyclo[2.2.1]heptan-7-amine (296);

(7R)-2-{2-[1-(Cyclopropylmethyl)-6-(3-fluoro-1H-indazol-4-yl)-1H-pyrrolo[2,3-b]pyridin-2-yl]-3-methylpyrazolo[1,5-a]pyridine-6-carbonyl}-2-azabicyclo[2.2.1]heptan-7-amine (297);

(7R)-2-{2-[1-(Cyclopropylmethyl)-6-(1H-indazol-6-yl)-1H-pyrrolo[2,3-b]pyridin-2-yl]-3-methylpyrazolo[1,5-a]pyridine-6-carbonyl}-2-azabicyclo[2.2.1]heptan-7-amine (298);

(7R)-2-{2-[1-(Cyclopropylmethyl)-6-(1H-indazol-4-yl)-1H-pyrrolo[2,3-b]pyridin-2-yl]-3-methylpyrazolo[1,5-a]pyridine-6-carbonyl}-2-azabicyclo[2.2.1]heptan-7-amine (299);

(7R)-2-{2-[1-(Cyclopropylmethyl)-6-(1H-indazol-5-yl)-1H-pyrrolo[2,3-b]pyridin-2-yl]-3-methylpyrazolo[1,5-a]pyridine-6-carbonyl}-2-azabicyclo[2.2.1]heptan-7-amine (300);

3-(2-{6-[(7R)-7-Amino-2-azabicyclo[2.2.1]heptane-2-carbonyl]-3-methylpyrazolo[1,5-a]pyridin-2-yl}-1-(cyclopropylmethyl)-1H-pyrrolo[2,3-b]pyridin-6-yl)-2-methylphenol (301);

1-[2-(2-{6-[(7R)-7-Amino-2-azabicyclo[2.2.1]heptane-2-carbonyl]-3-methylpyrazolo[1,5-a]pyridin-2-yl}-1-(cyclopropylmethyl)-1H-pyrrolo[2,3-b]pyridin-6-yl)phenyl]imidazolidin-2-one (302);

4-(2-{6-[(7R)-7-Amino-2-azabicyclo[2.2.1]heptane-2-carbonyl]-3-methylpyrazolo[1,5-a]pyridin-2-yl}-1-(cyclopropylmethyl)-1H-pyrrolo[2,3-b]pyridin-6-yl)-2-methoxybenzamide (303);

1-[4-(2-{6-[(7R)-7-Amino-2-azabicyclo[2.2.1]heptane-2-carbonyl]-3-methylpyrazolo[1,5-a]pyridin-2-yl}-1-(cyclopropylmethyl)-1H-pyrrolo[2,3-b]pyridin-6-yl)phenyl]pyrrolidin-2-one (304);

4-(2-{6-[(7R)-7-Amino-2-azabicyclo[2.2.1]heptane-2-carbonyl]-3-methylpyrazolo[1,5-a]pyridin-2-yl}-1-(cyclopropylmethyl)-1H-pyrrolo[2,3-b]pyridin-6-yl)-2-fluoro-5-methylbenzamide (305);

(7R)-2-{2-[1-(Cyclopropylmethyl)-6-(7-fluoro-1H-indazol-6-yl)-1H-pyrrolo[2,3-b]pyridin-2-yl]-3-methylpyrazolo[1,5-a]pyridine-6-carbonyl}-2-azabicyclo[2.2.1]heptan-7-amine (306);

5-(2-{6-[(7R)-7-Amino-2-azabicyclo[2.2.1]heptane-2-carbonyl]-3-methylpyrazolo[1,5-a]pyridin-2-yl}-1-(cyclopropylmethyl)-1H-pyrrolo[2,3-b]pyridin-6-yl)-N-methylpyridine-2-carboxamide (307);

Methyl N-[5-(2-{6-[(7R)-7-amino-2-azabicyclo[2.2.1]heptane-2-carbonyl]-3-methylpyrazolo[1,5-a]pyridin-2-yl}-1-(cyclopropylmethyl)-1H-pyrrolo[2,3-b]pyridin-6-yl)pyridin-2-yl]carbamate (308);

(3R)-1-{2-[1-(Cyclopropylmethyl)-6-(1H-indazol-5-yl)-1H-pyrrolo[2,3-b]pyridin-2-yl]-3-methylpyrazolo[1,5-a]pyridine-6-carbonyl}piperidin-3-amine (309);

(3R)-1-{2-[1-(Cyclopropylmethyl)-6-(1H-indazol-6-yl)-1H-pyrrolo[2,3-b]pyridin-2-yl]-3-methylpyrazolo[1,5-a]pyridine-6-carbonyl}piperidin-3-amine (310);

(3R)-1-{2-[1-(Cyclopropylmethyl)-6-(1H-indazol-4-yl)-1H-pyrrolo[2,3-b]pyridin-2-yl]-3-methylpyrazolo[1,5-a]pyridine-6-carbonyl}piperidin-3-amine (311);

6-(2-{6-[(3R)-3-Aminopiperidine-1-carbonyl]-3-methylpyrazolo[1,5-a]pyridin-2-yl}-1-(cyclopropylmethyl)-1H-pyrrolo[2,3-b]pyridin-6-yl)-8-fluoro-5-methyl-1,2-dihydroquinolin-2-one (312);

3-(2-{6-[(3R)-3-Aminopiperidine-1-carbonyl]-3-methylpyrazolo[1,5-a]pyridin-2-yl}-1-(cyclopropylmethyl)-1H-pyrrolo[2,3-b]pyridin-6-yl)-2-chlorophenol (313);

3-(2-{6-[(3R)-3-Aminopiperidine-1-carbonyl]-3-methylpyrazolo[1,5-a]pyridin-2-yl}-1-(cyclopropylmethyl)-1H-pyrrolo[2,3-b]pyridin-6-yl)-2-fluorophenol (314);

6-(2-{6-[(3R)-3-Aminopiperidine-1-carbonyl]-3-methylpyrazolo[1,5-a]pyridin-2-yl}-1-(cyclopropylmethyl)-1H-pyrrolo[2,3-b]pyridin-6-yl)-2,3-dihydro-1H-isoindol-1-one (315);

4-(2-{6-[(3R)-3-Aminopiperidine-1-carbonyl]-3-methylpyrazolo[1,5-a]pyridin-2-yl}-1-(cyclopropylmethyl)-1H-pyrrolo[2,3-b]pyridin-6-yl)-2-methylbenzamide (316);

5-(2-{6-[(3R)-3-Aminopiperidine-1-carbonyl]-3-methylpyrazolo[1,5-a]pyridin-2-yl}-1-(cyclopropylmethyl)-1H-pyrrolo[2,3-b]pyridin-6-yl)-2,3-dihydro-1H-isoindol-1-one (317);

(7R)-2-{2-[1-(Cyclopropylmethyl)-6-(morpholin-4-yl)-1H-pyrrolo[2,3-b]pyridin-2-yl]-3-methylpyrazolo[1,5-a]pyridine-6-carbonyl}-2-azabicyclo[2.2.1]heptan-7-amine (318);

4-(2-{6-[(7R)-7-Amino-2-azabicyclo[2.2.1]heptane-2-carbonyl]-3-methylpyrazolo[1,5-a]pyridin-2-yl}-1-(cyclopropylmethyl)-1H-pyrrolo[2,3-b]pyridin-6-yl)morpholin-3-one (319);

(7R)-2-{2-[1-(Cyclopropylmethyl)-6-(4-methanesulfonylpiperidin-1-yl)-1H-pyrrolo[2,3-b]pyridin-2-yl]-3-methylpyrazolo[1,5-a]pyridine-6-carbonyl}-2-azabicyclo[2.2.1]heptan-7-amine (320);

(3R,5R)-1-{2-[1-(Cyclopropylmethyl)-6-(1H-indazol-6-yl)-1H-pyrrolo[2,3-b]pyridin-2-yl]-3-methylpyrazolo[1,5-a]pyridine-6-carbonyl}-5-fluoropiperidin-3-amine (321);

(3R,5R)-1-{2-[1-(Cyclopropylmethyl)-6-(1H-indazol-4-yl)-1H-pyrrolo[2,3-b]pyridin-2-yl]-3-methylpyrazolo[1,5-a]pyridine-6-carbonyl}-5-fluoropiperidin-3-amine (322);

(3R,5R)-1-{2-[1-(Cyclopropylmethyl)-6-(1H-indazol-5-yl)-1H-pyrrolo[2,3-b]pyridin-2-yl]-3-methylpyrazolo[1,5-a]pyridine-6-carbonyl}-5-fluoropiperidin-3-amine (323);

6-(2-{6-[(3R,5R)-3-Amino-5-fluoropiperidine-1-carbonyl]-3-methylpyrazolo[1,5-a]pyridin-2-yl}-1-(cyclopropylmethyl)-1H-pyrrolo[2,3-b]pyridin-6-yl)-8-fluoro-5-methyl-1,2-dihydroquinolin-2-one (324);

Methyl N-[1-(2-{6-[(3R,5R)-3-amino-5-fluoropiperidine-1-carbonyl]-3-methylpyrazolo[1,5-a]pyridin-2-yl}-1-(cyclopropylmethyl)-1H-pyrrolo[2,3-b]pyridin-6-yl)piperidin-4-yl]-N-methylcarbamate (325);

(7R)-2-{2-[1-(Cyclopropylmethyl)-6-(7-fluoro-1H-indazol-4-yl)-1H-indol-2-yl]-3-methylpyrazolo[1,5-a]pyridine-6-carbonyl}-2-azabicyclo[2.2.1]heptan-7-amine (326);

(7R)-2-{2-[1-(Cyclopropylmethyl)-6-(3-fluoro-1H-indazol-4-yl)-1H-indol-2-yl]-3-methylpyrazolo[1,5-a]pyridine-6-carbonyl}-2-azabicyclo[2.2.1]heptan-7-amine (327);

1-[4-(2-{6-[(7R)-7-Amino-2-azabicyclo[2.2.1]heptane-2-carbonyl]-3-methylpyrazolo[1,5-a]pyridin-2-yl}-1-(cyclopropylmethyl)-1H-indol-6-yl)phenyl]imidazolidin-2-one (328);

1-[4-(2-{6-[(7R)-7-Amino-2-azabicyclo[2.2.1]heptane-2-carbonyl]-3-methylpyrazolo[1,5-a]pyridin-2-yl}-1-(cyclopropylmethyl)-1H-indol-6-yl)phenyl]pyrrolidin-2-one (329);

(7R)-2-{2-[1-(Cyclopropylmethyl)-6-(7-fluoro-1H-indazol-6-yl)-1H-indol-2-yl]-3-methylpyrazolo[1,5-a]pyridine-6-carbonyl}-2-azabicyclo[2.2.1]heptan-7-amine (330);

4-(2-{6-[(7R)-7-Amino-2-azabicyclo[2.2.1]heptane-2-carbonyl]-3-methylpyrazolo[1,5-a]pyridin-2-yl}-1-(cyclopropylmethyl)-1H-indol-6-yl)-5-fluoro-2-methylbenzamide (331);

(7R)-2-{2-[1-(Cyclopropylmethyl)-6-(1H-indazol-6-yl)-1H-indol-2-yl]-3-methylpyrazolo[1,5-a]pyridine-6-carbonyl}-2-azabicyclo[2.2.1]heptan-7-amine (332);

(7R)-2-{2-[1-(Cyclopropylmethyl)-6-(1H-indazol-5-yl)-1H-indol-2-yl]-3-methylpyrazolo[1,5-a]pyridine-6-carbonyl}-2-azabicyclo[2.2.1]heptan-7-amine (333);

4-(2-{6-[(7R)-7-Amino-2-azabicyclo[2.2.1]heptane-2-carbonyl]-3-methylpyrazolo[1,5-a]pyridin-2-yl}-1-(cyclopropylmethyl)-1H-indol-6-yl)-2-methylbenzamide (334);

4-(2-{6-[(7R)-7-Amino-2-azabicyclo[2.2.1]heptane-2-carbonyl]-3-methylpyrazolo[1,5-a]pyridin-2-yl}-1-(cyclopropylmethyl)-1H-indol-6-yl)-3-(trifluoromethyl)benzamide (335);

(7R)-2-{2-[1-(Cyclopropylmethyl)-6-(7-fluoro-1H-indazol-6-yl)-1H-indol-2-yl]-3-methylpyrazolo[1,5-a]pyridine-6-carbonyl}-2-azabicyclo[2.2.1]heptan-7-amine (336);

N-[7-(2-{6-[(7R)-7-Amino-2-azabicyclo[2.2.1]heptane-2-carbonyl]-3-methylpyrazolo[1,5-a]pyridin-2-yl}-1-(cyclopropylmethyl)-1H-indol-6-yl)-4-chloro-1-methyl-1H-indazol-3-yl]methanesulfonamide (337);

1-[2-(2-{6-[(7R)-7-Amino-2-azabicyclo[2.2.1]heptane-2-carbonyl]-3-methylpyrazolo[1,5-a]pyridin-2-yl}-1-(cyclopropylmethyl)-1H-indol-6-yl)phenyl]imidazolidin-2-one (338);

4-(2-{6-[(7R)-7-Amino-2-azabicyclo[2.2.1]heptane-2-carbonyl]-3-methylpyrazolo[1,5-a]pyridin-2-yl}-1-(cyclopropylmethyl)-1H-indol-6-yl)-2-chlorobenzamide (339);

5-(2-{6-[(7R)-7-Amino-2-azabicyclo[2.2.1]heptane-2-carbonyl]-3-methylpyrazolo[1,5-a]pyridin-2-yl}-1-(cyclopropylmethyl)-1H-indol-6-yl)-N-methylpyridine-2-carboxamide (340);

(7R)-2-{2-[1-(Cyclopropylmethyl)-6-(1H-pyrazol-4-yl)-1H-indol-2-yl]-3-methylpyrazolo[1,5-a]pyridine-6-carbonyl}-2-azabicyclo[2.2.1]heptan-7-amine (341);

N-{[4-(2-{6-[(3R)-3-Aminopiperidine-1-carbonyl]-3-methylpyrazolo[1,5-a]pyridin-2-yl}-1-(cyclopropylmethyl)-1H-indol-6-yl)phenyl]methyl}methanesulfonamide (342);

N-{[3-(2-{6-[(3R)-3-Aminopiperidine-1-carbonyl]-3-methylpyrazolo[1,5-a]pyridin-2-yl}-1-(cyclopropylmethyl)-1H-indol-6-yl)phenyl]methyl}acetamide (343);

[3-(2-{6-[(3R)-3-Aminopiperidine-1-carbonyl]-3-methylpyrazolo[1,5-a]pyridin-2-yl}-1-(cyclopropylmethyl)-1H-indol-6-yl)phenyl]methanol (344);

(3R)-1-{2-[1'-(Cyclopropylmethyl)-1H,1'H-[5,6'-biindole]-2'-yl]-3-methylpyrazolo[1,5-a]pyridine-6-carbonyl}piperidin-3-amine (345);

6-(2-{6-[(3R)-3-Aminopiperidine-1-carbonyl]-3-methylpyrazolo[1,5-a]pyridin-2-yl}-1-(cyclopropylmethyl)-1H-indol-6-yl)-8-fluoro-5-methyl-1,2-dihydroquinolin-2-one (346);

N-[4-(2-{6-[(3R)-3-Aminopiperidine-1-carbonyl]-3-methylpyrazolo[1,5-a]pyridin-2-yl}-1-(cyclopropylmethyl)-1H-indol-6-yl)phenyl]methanesulfonamide (347);

N-[5-(2-{6-[(3R)-3-Aminopiperidine-1-carbonyl]-3-methylpyrazolo[1,5-a]pyridin-2-yl}-1-(cyclopropylmethyl)-1H-indol-6-yl)pyridin-2-yl]acetamide (348);

(R)-(3-Aminopiperidin-1-yl)(2-(1-(cyclopropylmethyl)-6-(3-methyl-[1,2,4]triazolo[4,3-a]pyridin-7-yl)-1H-indol-2-yl)-3-methylpyrazolo[1,5-a]pyridin-6-yl)methanone (349);

(7R)-2-{2-[1-(Cyclopropylmethyl)-6-(morpholin-4-yl)-1H-indol-2-yl]-3-methylpyrazolo[1,5-a]pyridine-6-carbonyl}-2-azabicyclo[2.2.1]heptan-7-amine (350);

(7R)-2-{2-[1-(Cyclopropylmethyl)-6-(4-methanesulfonylpiperidin-1-yl)-1H-indol-2-yl]-3-methylpyrazolo[1,5-a]pyridine-6-carbonyl}-2-azabicyclo[2.2.1]heptan-7-amine (351);

Methyl N-[1-(2-{6-[(3R,5R)-3-amino-5-fluoropiperidine-1-carbonyl]-3-methylpyrazolo[1,5-a]pyridin-2-yl}-1-(cyclopropylmethyl)-1H-indol-6-yl)piperidin-4-yl]-N-methylcarbamate (352);

N-[1-(2-{6-[(3R,5R)-3-Amino-5-fluoropiperidine-1-carbonyl]-3-methylpyrazolo[1,5-a]pyridin-2-yl}-1-(cyclopropylmethyl)-1H-indol-6-yl)piperidin-4-yl]-N-methylacetamide (353);

N-[1-(2-{6-[(3R,5R)-3-Amino-5-fluoropiperidine-1-carbonyl]-3-methylpyrazolo[1,5-a]pyridin-2-yl}-1-(cyclopropylmethyl)-1H-indol-6-yl)piperidin-4-yl]-N-methylmethanesulfonamide (354);

(3R,5R)-1-{2-[1-(Cyclopropylmethyl)-6-[4-(pyrrolidine-1-carbonyl)piperidin-1-yl]-1H-indol-2-yl]-3-methylpyrazolo[1,5-a]pyridine-6-carbonyl}-5-fluoropiperidin-3-amine (355);

1-[1-(2-{6-[(3R,5R)-3-Amino-5-fluoropiperidine-1-carbonyl]-3-methylpyrazolo[1,5-a]pyridin-2-yl}-1-(cyclopropylmethyl)-1H-indol-6-yl)piperidin-4-yl]pyrrolidin-2-one (356);

3-[1-(2-{6-[(3R,5R)-3-Amino-5-fluoropiperidine-1-carbonyl]-3-methylpyrazolo[1,5-a]pyridin-2-yl}-1-(cyclopropylmethyl)-1H-indol-6-yl)piperidin-4-yl]-1,3-oxazolidin-2-one (357);

Methyl N-[1-(2-{6-[(3R)-3-aminopiperidine-1-carbonyl]-3-methylpyrazolo[1,5-a]pyridin-2-yl}-1-(cyclopropylmethyl)-1H-indol-6-yl)piperidin-4-yl]-N-methylcarbamate (358);

N-[1-(2-{6-[(3R)-3-Aminopiperidine-1-carbonyl]-3-methylpyrazolo[1,5-a]pyridin-2-yl}-1-(cyclopropylmethyl)-1H-indol-6-yl)piperidin-4-yl]-N-methylacetamide (359);

N-[1-(2-{6-[(3R)-3-Aminopiperidine-1-carbonyl]-3-methylpyrazolo[1,5-a]pyridin-2-yl}-1-(cyclopropylmethyl)-1H-indol-6-yl)piperidin-4-yl]-N-methylmethanesulfonamide (360);

(3R)-1-{2-[1-(Cyclopropylmethyl)-6-[4-(pyrrolidine-1-carbonyl)piperidin-1-yl]-1H-indol-2-yl]-3-methylpyrazolo[1,5-a]pyridine-6-carbonyl}piperidin-3-amine (361);

N-[1-(2-{6-[(3R)-3-Aminopiperidine-1-carbonyl]-3-methylpyrazolo[1,5-a]pyridin-2-yl}-1-(cyclopropylmethyl)-1H-indol-6-yl)piperidin-4-yl]-N-methylmethanesulfonamide (362);

1-[1-(2-{6-[(3R)-3-Aminopiperidine-1-carbonyl]-3-methylpyrazolo[1,5-a]pyridin-2-yl}-1-(cyclopropylmethyl)-1H-indol-6-yl)piperidin-4-yl]pyrrolidin-2-one (363);

3-[1-(2-{6-[(3R)-3-Aminopiperidine-1-carbonyl]-3-methylpyrazolo[1,5-a]pyridin-2-yl}-1-(cyclopropylmethyl)-1H-indol-6-yl)piperidin-4-yl]-1,3-oxazolidin-2-one (364);

(3R)-1-{2-[1-(Cyclopropylmethyl)-6-[4-(1H-pyrazol-1-yl)piperidin-1-yl]-1H-indol-2-yl]-3-methylpyrazolo[1,5-a]pyridine-6-carbonyl}piperidin-3-amine (365);

N-[1-(2-{6-[(3R)-3-Aminopiperidine-1-carbonyl]-3-methylpyrazolo[1,5-a]pyridin-2-yl}-1-(cyclopropylmethyl)-1H-indol-6-yl)azetidin-3-yl]-N-methylmethanesulfonamide (366);

N-{[3-(2-{6-[(3R,5R)-3-Amino-5-fluoropiperidine-1-carbonyl]-3-methylpyrazolo[1,5-a]pyridin-2-yl}-1-(cyclopropylmethyl)-1H-indol-6-yl)phenyl]methyl}methanesulfonamide (367);

(3R,5R)-1-{2-[1-(Cyclopropylmethyl)-6-[3-(2H-1,2,3,4-tetrazol-5-yl)phenyl]-1H-indol-2-yl]-3-methylpyrazolo[1,5-a]pyridine-6-carbonyl}-5-fluoropiperidin-3-amine (368);

N-[4-(2-{6-[(3R,5R)-3-Amino-5-fluoropiperidine-1-carbonyl]-3-methylpyrazolo[1,5-a]pyridin-2-yl}-1-(cyclopropylmethyl)-1H-indol-6-yl)phenyl]methanesulfonamide (369);

N-{[4-(2-{6-[(3R,5R)-3-Amino-5-fluoropiperidine-1-carbonyl]-3-methylpyrazolo[1,5-a]pyridin-2-yl}-1-(cyclopropylmethyl)-1H-indol-6-yl)phenyl]methyl}methanesulfonamide (370);

[3-(2-{6-[(3R,5R)-3-Amino-5-fluoropiperidine-1-carbonyl]-3-methylpyrazolo[1,5-a]pyridin-2-yl}-1-(cyclopropylmethyl)-1H-indol-6-yl)phenyl]methanol (371);

2-(2-{6-[(3R,5R)-3-Amino-5-fluoropiperidine-1-carbonyl]-3-methylpyrazolo[1,5-a]pyridin-2-yl}-1-(cyclopropylmethyl)-1H-indol-6-yl)benzamide (372);

4-(2-{6-[(3R,5R)-3-Amino-5-fluoropiperidine-1-carbonyl]-3-methylpyrazolo[1,5-a]pyridin-2-yl}-1-(cyclopropylmethyl)-1H-indol-6-yl)benzamide (373);

(3R,5R)-1-{2-[1'-(Cyclopropylmethyl)-1H,1'H-[5,6'-biindole]-2'-yl]-3-methylpyrazolo[1,5-a]pyridine-6-carbonyl}-5-fluoropiperidin-3-amine (374);

[4-(2-{6-[(3R,5R)-3-Amino-5-fluoropiperidine-1-carbonyl]-3-methylpyrazolo[1,5-a]pyridin-2-yl}-1-(cyclopropylmethyl)-1H-indol-6-yl)-2-chloro-5-fluorophenyl]methanol (375);

6-(2-{6-[(3R,5R)-3-Amino-5-fluoropiperidine-1-carbonyl]-3-methylpyrazolo[1,5-a]pyridin-2-yl}-1-(cyclopropylmethyl)-1H-indol-6-yl)-8-fluoro-5-methyl-1,2-dihydroquinolin-2-one (376);

4-(2-{6-[(3R,5R)-3-Amino-5-fluoropiperidine-1-carbonyl]-3-methylpyrazolo[1,5-a]pyridin-2-yl}-1-(cyclopropylmethyl)-1H-indol-6-yl)-3-chlorobenzamide (377);

4-(2-{6-[(3R,5R)-3-Amino-5-fluoropiperidine-1-carbonyl]-3-methylpyrazolo[1,5-a]pyridin-2-yl}-1-(cyclopropylmethyl)-1H-indol-6-yl)-2-methylbenzamide (378);

(3R,5R)-1-{2-[1-(Cyclopropylmethyl)-6-{3-methyl-[1,2,4]triazolo[4,3-a]pyridin-7-yl}-1H-indol-2-yl]-3-methylpyrazolo[1,5-a]pyridine-6-carbonyl}-5-fluoropiperidin-3-amine (379);

2-(2-{6-[(3R)-3-Aminopiperidine-1-carbonyl]-3-methylpyrazolo[1,5-a]pyridin-2-yl}-1-(cyclopropylmethyl)-1H-pyrrolo[2,3-b]pyridin-6-yl)propan-2-ol6-yl)propan-2-ol (Homochiral) (380);

2-(2-{6-[(7R)-7-Amino-2-azabicyclo[2.2.1]heptane-2-carbonyl]-3-methylpyrazolo[1,5-a]pyridin-2-yl}-1-(cyclopropylmethyl)-1H-pyrrolo[2,3-b]pyridin-6-yl)-1,1-difluoropropan-2-ol (Diastereomeric mixture) (381);

2-(2-{6-[(3R)-3-Aminopiperidine-1-carbonyl]-3-methylpyrazolo[1,5-a]pyridin-2-yl}-1-(cyclopropylmethyl)-1H-pyrrolo[2,3-b]pyridin-6-yl)-1,1,1-trifluoropropan-2-trifluoropropan-2-ol (Diastereomeric mixture) (382);

2-(2-{6-[(7R)-7-Amino-2-azabicyclo[2.2.1]heptane-2-carbonyl]-4-fluoro-3-methylpyrazolo[1,5-a]pyridin-2-yl}-1-(cyclopropylmethyl)-1H-pyrrolo[2,3-b]pyridin-6-yl)-1,1,1-trifluoropropan-2-ol (383);

1-(2-{6-[(7R)-7-Amino-2-azabicyclo[2.2.1]heptane-2-carbonyl]-4-fluoro-3-methylpyrazolo[1,5-a]pyridin-2-yl}-1-

(cyclopropylmethyl)-1H-pyrrolo[2,3-b]pyridin-6-yl)-1-cyclopropylethan-1-ol (384);

1-(2-{6-[(3R)-3-Aminopiperidine-1-carbonyl]-3-methylpyrazolo[1,5-a]pyridin-2-yl}-1-(cyclopropylmethyl)-1H-pyrrolo[2,3-b]pyridin-6-yl)ethan-1-ol-6-yl)ethan-1-ol (Diastereomeric mixture) (385);

((R)-3-Aminopiperidin-1-yl)(2-(1-(cyclopropylmethyl)-7-(1-(tetrahydro-2H-pyran-2-carbonyl)piperidin-4-yl)-1H-indol-2-yl)-4-methoxy-3-methylpyrazolo[1,5-a]pyridin-6-yl)methanone (386);

((R)-3-Aminopiperidin-1-yl)(2-(1-(cyclopropylmethyl)-7-(1-(tetrahydro-2H-pyran-2-carbonyl)piperidin-4-yl)-1H-indol-2-yl)-4-methoxy-3-methylpyrazolo[1,5-a]pyridin-6-yl)methanone (387);

((3R,5R)-3-Amino-5-fluoropiperidin-1-yl)(2-(1-(cyclopropylmethyl)-7-(1-(tetrahydro-2H-pyran-2-carbonyl)piperidin-4-yl)-1H-indol-2-yl)-4-methoxy-3-methylpyrazolo[1,5-a]pyridin-6-yl)methanone (388);

((3R,5R)-3-Amino-5-fluoropiperidin-1-yl)(2-(1-(cyclopropylmethyl)-7-(1-(tetrahydro-2H-pyran-2-carbonyl)piperidin-4-yl)-1H-indol-2-yl)-4-methoxy-3-methylpyrazolo[1,5-a]pyridin-6-yl)methanone (389);

((3R,5R)-3-Amino-5-fluoropiperidin-1-yl)(2-(1-(cyclopropylmethyl)-7-(1-(3-hydroxycyclobutane-1-carbonyl)piperidin-4-yl)-1H-indol-2-yl)-4-methoxy-3-methylpyrazolo[1,5-a]pyridin-6-yl)methanone (390);

((3R,5R)-3-Amino-5-fluoropiperidin-1-yl)(2-(1-(cyclopropylmethyl)-7-(1-((1r,4r)-4-hydroxycyclohexane-1-carbonyl)piperidin-4-yl)-1H-indol-2-yl)-4-methoxy-3-methylpyrazolo[1,5-a]pyridin-6-yl)methanone (391);

(R)-(3-Aminopiperidin-1-yl)(2-(1-(cyclopropylmethyl)-7-(1-(3-hydroxycyclobutane-1-carbonyl)piperidin-4-yl)-1H-indol-2-yl)-4-methoxy-3-methylpyrazolo[1,5-a]pyridin-6-yl)methanone (392);

((3R,5R)-3-Amino-5-fluoropiperidin-1-yl)(2-(1-(cyclopropylmethyl)-7-(1-(3-hydroxycyclobutane-1-carbonyl)piperidin-4-yl)-1H-indol-2-yl)-4-methoxy-3-methylpyrazolo[1,5-a]pyridin-6-yl)methanone (393);

((3R,5R)-3-Amino-5-fluoropiperidin-1-yl)(2-(1-(cyclopropylmethyl)-7-(1-(tetrahydrofuran-2-carbonyl)piperidin-4-yl)-1H-indol-2-yl)-4-methoxy-3-methylpyrazolo[1,5-a]pyridin-6-yl)methanone (394);

(R)-1-(4-(2-(6-((3R,5R)-3-Amino-5-fluoropiperidine-1-carbonyl)-4-methoxy-3-methylpyrazolo[1,5-a]pyridin-2-yl)-1-(cyclopropylmethyl)-1H-indol-7-yl)piperidin-1-yl)-2-methoxypropan-1-one (395);

(R)-(3-Aminopiperidin-1-yl)(2-(1-(cyclopropylmethyl)-7-(1-(3-hydroxycyclobutane-1-carbonyl)piperidin-4-yl)-1H-indol-2-yl)-4-methoxy-3-methylpyrazolo[1,5-a]pyridin-6-yl)methanone (396);

((3R,5R)-3-Amino-5-fluoropiperidin-1-yl)(2-(1-(cyclopropylmethyl)-7-(1-(tetrahydrofuran-2-carbonyl)piperidin-4-yl)-1H-indol-2-yl)-4-methoxy-3-methylpyrazolo[1,5-a]pyridin-6-yl)methanone (397);

(R)-(3-Aminopiperidin-1-yl)(2-(1-(cyclopropylmethyl)-7-(1-(3-hydroxy-3-(trifluoromethyl)cyclobutane-1-carbonyl)piperidin-4-yl)-1H-indol-2-yl)-4-methoxy-3-methylpyrazolo[1,5-a]pyridin-6-yl)methanone (398);

((3R,5R)-3-Amino-5-fluoropiperidin-1-yl)(2-(1-(cyclopropylmethyl)-7-(1-(3-hydroxy-3-(trifluoromethyl)cyclobutane-1-carbonyl)piperidin-4-yl)-1H-indol-2-yl)-4-methoxy-3-methylpyrazolo[1,5-a]pyridin-6-yl)methanone (399);

((R)-3-Aminopiperidin-1-yl)(2-(1-(cyclopropylmethyl)-7-(1-(tetrahydrofuran-2-carbonyl)piperidin-4-yl)-1H-indol-2-yl)-4-methoxy-3-methylpyrazolo[1,5-a]pyridin-6-yl)methanone (400);

(R)-1-(4-(2-(6-(3-Aminopiperidine-1-carbonyl)-4-methoxy-3-methylpyrazolo[1,5-a]pyridin-2-yl)-1-(cyclopropylmethyl)-1H-indol-7-yl)piperidin-1-yl)-2-methoxyethan-1-one (401);

(R)-1-(4-(2-(6-((R)-3-Aminopiperidine-1-carbonyl)-4-methoxy-3-methylpyrazolo[1,5-a]pyridin-2-yl)-1-(cyclopropylmethyl)-1H-indol-7-yl)piperidin-1-yl)-2-methoxypropan-1-one (402);

(S)-1-(4-(2-(6-((R)-3-Aminopiperidine-1-carbonyl)-4-methoxy-3-methylpyrazolo[1,5-a]pyridin-2-yl)-1-(cyclopropylmethyl)-1H-indol-7-yl)piperidin-1-yl)-2-methoxypropan-1-one (403);

(S)-1-(4-(2-(6-((3R,5R)-3-Amino-5-fluoropiperidine-1-carbonyl)-4-methoxy-3-methylpyrazolo[1,5-a]pyridin-2-yl)-1-(cyclopropylmethyl)-1H-indol-7-yl)piperidin-1-yl)-2-methoxypropan-1-one (404);

1-(4-(2-(6-((3R,5R)-3-Amino-5-fluoropiperidine-1-carbonyl)-4-methoxy-3-methylpyrazolo[1,5-a]pyridin-2-yl)-1-(cyclopropylmethyl)-1H-indol-7-yl)piperidin-1-yl)-2-methoxyethan-1-one (405);

((R)-3-Aminopiperidin-1-yl)(2-(1-(cyclopropylmethyl)-7-(14(1s,4s)-4-hydroxycyclohexane-1-carbonyl)piperidin-4-yl)-1H-indol-2-yl)-4-methoxy-3-methylpyrazolo[1,5-a]pyridin-6-yl)methanone (406);

((3R,5R)-3-Amino-5-fluoropiperidin-1-yl)(2-(1-(cyclopropylmethyl)-7-(1-((1s,4s)-4-hydroxycyclohexane-1-carbonyl)piperidin-4-yl)-1H-indol-2-yl)-4-methoxy-3-methylpyrazolo[1,5-a]pyridin-6-yl)methanone (407);

((R)-3-Aminopiperidin-1-yl)(2-(1-(cyclopropylmethyl)-7-(14(1r,4r)-4-hydroxycyclohexane-1-carbonyl)piperidin-4-yl)-1H-indol-2-yl)-4-methoxy-3-methylpyrazolo[1,5-a]pyridin-6-yl)methanone (408);

((3R,5R)-3-Amino-5-fluoropiperidin-1-yl)(2-(1-(cyclopropylmethyl)-7-(1-((1r,4r)-4-hydroxycyclohexane-1-carbonyl)piperidin-4-yl)-1H-indol-2-yl)-4-methoxy-3-methylpyrazolo[1,5-a]pyridin-6-yl)methanone (409);

(R)-1-(4-(2-(6-(3-Aminopiperidine-1-carbonyl)-4-methoxy-3-methylpyrazolo[1,5-a]pyridin-2-yl)-1-(cyclopropylmethyl)-1H-indol-7-yl)piperidin-1-yl)ethan-1-one (410);

1-(4-(2-(6-((3R,5R)-3-Amino-5-fluoropiperidine-1-carbonyl)-4-methoxy-3-methylpyrazolo[1,5-a]pyridin-2-yl)-1-(cyclopropylmethyl)-1H-indol-7-yl)piperidin-1-yl)ethan-1-one (411);

1-(4-(2-(6-((7R)-7-Amino-2-azabicyclo[2.2.1]heptane-2-carbonyl)-4-methoxy-3-methylpyrazolo[1,5-a]pyridin-2-yl)-1-(cyclopropylmethyl)-1H-indol-7-yl)piperidin-1-yl)ethan-1-one (412);

(R)-1-(4-(2-(6-(3-Aminopiperidine-1-carbonyl)-4-fluoro-3-methylpyrazolo[1,5-a]pyridin-2-yl)-1-(cyclopropylmethyl)-1H-indol-7-yl)piperidin-1-yl)ethan-1-one (413);

((3R,5R)-3-Amino-5-fluoropiperidin-1-yl)(2-(1-(cyclopropylmethyl)-7-(1-((1r,4r)-4-hydroxycyclohexane-1-carbonyl)piperidin-4-yl)-1H-indol-2-yl)-4-fluoro-3-methylpyrazolo[1,5-a]pyridin-6-yl)methanone (414);

((R)-3-Aminopiperidin-1-yl)(2-(1-(cyclopropylmethyl)-7-(14(1r,4r)-4-hydroxycyclohexane-1-carbonyl)piperidin-4-yl)-1H-indol-2-yl)-4-fluoro-3-methylpyrazolo[1,5-a]pyridin-6-yl)methanone (415);

((3R,5R)-3-Amino-5-fluoropiperidin-1-yl)(2-(1-(cyclopropylmethyl)-7-(1-((1s,4s)-4-hydroxycyclohexane-1-carbonyl)piperidin-4-yl)-1H-indol-2-yl)-4-fluoro-3-methylpyrazolo[1,5-a]pyridin-6-yl)methanone (416);

1-(4-(2-(6-((3R,5R)-3-Amino-5-fluoropiperidine-1-carbonyl)-4-fluoro-3-methylpyrazolo[1,5-a]pyridin-2-yl)-1-(cyclopropylmethyl)-1H-indol-7-yl)piperidin-1-yl)-2-methoxy-2-methylpropan-1-one (417);

(R)-1-(4-(2-(6-(3-Aminopiperidine-1-carbonyl)-4-fluoro-3-methylpyrazolo[1,5-a]pyridin-2-yl)-1-(cyclopropylmethyl)-1H-indol-7-yl)piperidin-1-yl)-2-methoxy-2-methylpropan-1-one (418);

((3R,5R)-3-Amino-5-fluoropiperidin-1-yl)(2-(1-(cyclopropylmethyl)-7-(1-(3-hydroxycyclobutane-1-carbonyl)piperidin-4-yl)-1H-indol-2-yl)-4-fluoro-3-methylpyrazolo[1,5-a]pyridin-6-yl)methanone (419);

(R)-(3-Aminopiperidin-1-yl)(2-(1-(cyclopropylmethyl)-7-(1-(3-hydroxycyclobutane-1-carbonyl)piperidin-4-yl)-1H-indol-2-yl)-4-fluoro-3-methylpyrazolo[1,5-a]pyridin-6-yl)methanone (420);

((3R,5R)-3-Amino-5-fluoropiperidin-1-yl)(2-(1-(cyclopropylmethyl)-7-(1-(3-hydroxy-3-(trifluoromethyl)cyclobutane-1-carbonyl)piperidin-4-yl)-1H-indol-2-yl)-4-fluoro-3-methylpyrazolo[1,5-a]pyridin-6-yl)methanone (421);

(R)-(3-Aminopiperidin-1-yl)(2-(1-(cyclopropylmethyl)-7-(1-(3-hydroxy-3-(trifluoromethyl)cyclobutane-1-carbonyl)piperidin-4-yl)-1H-indol-2-yl)-4-fluoro-3-methylpyrazolo[1,5-a]pyridin-6-yl)methanone (422);

(S)-1-(4-(2-(6-((3R,5R)-3-Amino-5-fluoropiperidine-1-carbonyl)-4-fluoro-3-methylpyrazolo[1,5-a]pyridin-2-yl)-1-(cyclopropylmethyl)-1H-indol-7-yl)piperidin-1-yl)-2-methoxypropan-1-one (423);

(S)-1-(4-(2-(6-((R)-3-Aminopiperidine-1-carbonyl)-4-fluoro-3-methylpyrazolo[1,5-a]pyridin-2-yl)-1-(cyclopropylmethyl)-1H-indol-7-yl)piperidin-1-yl)-2-methoxypropan-1-one (424);

(R)-1-(4-(2-(6-((3R,5R)-3-Amino-5-fluoropiperidine-1-carbonyl)-4-fluoro-3-methylpyrazolo[1,5-a]pyridin-2-yl)-1-(cyclopropylmethyl)-1H-indol-7-yl)piperidin-1-yl)-2-methoxypropan-1-one (425);

(R)-1-(4-(2-(6-((R)-3-Aminopiperidine-1-carbonyl)-4-fluoro-3-methylpyrazolo[1,5-a]pyridin-2-yl)-1-(cyclopropylmethyl)-1H-indol-7-yl)piperidin-1-yl)-2-methoxypropan-1-one (426);

1-(4-(2-(6-((3R,5R)-3-Amino-5-fluoropiperidine-1-carbonyl)-4-fluoro-3-methylpyrazolo[1,5-a]pyridin-2-yl)-1-(cyclopropylmethyl)-1H-indol-7-yl)piperidin-1-yl)ethan-1-one (427);

1-(4-(2-(6-((3R,5R)-3-Amino-5-fluoropiperidine-1-carbonyl)-4-fluoro-3-methylpyrazolo[1,5-a]pyridin-2-yl)-1-(cyclopropylmethyl)-1H-indol-7-yl)piperidin-1-yl)-2-methoxyethan-1-one (428);

(R)-1-(4-(2-(6-(3-Aminopiperidine-1-carbonyl)-4-fluoro-3-methylpyrazolo[1,5-a]pyridin-2-yl)-1-(cyclopropylmethyl)-1H-indol-7-yl)piperidin-1-yl)-2-methoxyethan-1-one (429);

Ethyl 2-(7-(1-(tert-butoxycarbonyl)piperidin-4-yl)-1-(cyclopropylmethyl)-1H-indol-2-yl)-3-methylpyrazolo[1,5-a]pyridine-6-carboxylate (430);

1-(4-(2-(6-((3R,5R)-3-amino-5-fluoropiperidine-1-carbonyl)-3-methylpyrazolo[1,5-a]pyridin-2-yl)-1-(cyclopropylmethyl)-1H-indol-7-yl)piperidin-1-yl)-3-hydroxypropan-1-one (430);

1-(4-(2-(6-((3R,5R)-3-amino-5-fluoropiperidine-1-carbonyl)-3-methylpyrazolo[1,5-a]pyridin-2-yl)-1-(cyclopropylmethyl)-1H-indol-7-yl)piperidin-1-yl)-2-isopropoxyethan-1-one (431);

(R)-1-(4-(2-(6-(3-aminopiperidine-1-carbonyl)-3-methylpyrazolo[1,5-a]pyridin-2-yl)-1-(cyclopropylmethyl)-1H-indol-7-yl)piperidin-1-yl)-2-isopropoxyethan-1-one (432);

1-(4-(2-(6-((3R,5R)-3-amino-5-fluoropiperidine-1-carbonyl)-3-methylpyrazolo[1,5-a]pyridin-2-yl)-1-(cyclopropylmethyl)-1H-indol-7-yl)piperidin-1-yl)-3-hydroxy-2,2-dimethylpropan-1-one (433);

(R)-1-(4-(2-(6-(3-aminopiperidine-1-carbonyl)-3-methylpyrazolo[1,5-a]pyridin-2-yl)-1-(cyclopropylmethyl)-1H-indol-7-yl)piperidin-1-yl)-3-hydroxy-2,2-dimethylpropan-1-one (434);

1-(4-(2-(6-((3R,5R)-3-amino-5-fluoropiperidine-1-carbonyl)-3-methylpyrazolo[1,5-a]pyridin-2-yl)-1-(cyclopropylmethyl)-1H-indol-7-yl)piperidin-1-yl)-2-hydroxy-2-methylpropan-1-one (435);

(R)-1-(4-(2-(6-(3-aminopiperidine-1-carbonyl)-3-methylpyrazolo[1,5-a]pyridin-2-yl)-1-(cyclopropylmethyl)-1H-indol-7-yl)piperidin-1-yl)-2-hydroxy-2-methylpropan-1-one (436);

(R)-1-(4-(2-(6-(3-aminopiperidine-1-carbonyl)-3-methylpyrazolo[1,5-a]pyridin-2-yl)-1-(cyclopropylmethyl)-1H-indol-7-yl)piperidin-1-yl)-3-hydroxypropan-1-one (437);

1-(4-(2-(6-((3R,5R)-3-amino-5-fluoropiperidine-1-carbonyl)-3-methylpyrazolo[1,5-a]pyridin-2-yl)-1-(cyclopropylmethyl)-1H-indol-7-yl)piperidin-1-yl)-2-hydroxyethan-1-one (438);

(R)-1-(4-(2-(6-(3-aminopiperidine-1-carbonyl)-3-methylpyrazolo[1,5-a]pyridin-2-yl)-1-(cyclopropylmethyl)-1H-indol-7-yl)piperidin-1-yl)-2-hydroxyethan-1-one (439);

((R)-3-aminopiperidin-1-yl)(2-(1-(cyclopropylmethyl)-7-(14(1R,3 S)-3-hydroxycyclohexane-1-carbonyl)piperidin-4-yl)-1H-indol-2-yl)-3-methylpyrazolo[1,5-a]pyridin-6-yl)methanone (440);

(R)-1-(4-(2-(6-(3-aminopiperidine-1-carbonyl)-3-methylpyrazolo[1,5-a]pyridin-2-yl)-1-(cyclopropylmethyl)-1H-indol-7-yl)piperidin-1-yl)-2-ethoxyethan-1-one (441);

1-(4-(2-(6-((3R,5R)-3-amino-5-fluoropiperidine-1-carbonyl)-3-methylpyrazolo[1,5-a]pyridin-2-yl)-1-(cyclopropylmethyl)-1H-indol-7-yl)piperidin-1-yl)-2-ethoxyethan-1-one (442);

((R)-3-aminopiperidin-1-yl)(2-(1-(cyclopropylmethyl)-7-(1-((1r,4r)-4-hydroxycyclohexane-1-carbonyl)piperidin-4-yl)-1H-indol-2-yl)-3-methylpyrazolo[1,5-a]pyridin-6-yl)methanone (443);

((3R,5R)-3-amino-5-fluoropiperidin-1-yl)(2-(1-(cyclopropylmethyl)-7-(1-(1s,4s)-4-hydroxycyclohexane-1-carbonyl)piperidin-4-yl)-1H-indol-2-yl)-3-methylpyrazolo[1,5-a]pyridin-6-yl)methanone (444);

1-(4-(2-(6-((3R,5R)-3-amino-5-fluoropiperidine-1-carbonyl)-3-methylpyrazolo[1,5-a]pyridin-2-yl)-1-(cyclopropylmethyl)-1H-indol-7-yl)piperidin-1-yl)-3-methylbutan-1-one (445);

(R)-1-(4-(2-(6-(3-aminopiperidine-1-carbonyl)-3-methylpyrazolo[1,5-a]pyridin-2-yl)-1-(cyclopropylmethyl)-1H-indol-7-yl)piperidin-1-yl)-3-methylbutan-1-one (446);

((R)-3-aminopiperidin-1-yl)(2-(1-(cyclopropylmethyl)-7-(1-(1S,3R)-3-hydroxycyclohexane-1-carbonyl)piperidin-4-yl)-1H-indol-2-yl)-3-methylpyrazolo[1,5-a]pyridin-6-yl)methanone (447);

((3R,5R)-3-amino-5-fluoropiperidin-1-yl)(2-(1-(cyclopropylmethyl)-7-(1-((1S,3R)-3-hydroxycyclohexane-1-carbonyl)piperidin-4-yl)-1H-indol-2-yl)-3-methylpyrazolo[1,5-a]pyridin-6-yl)methanone (448);

((3R,5R)-3-amino-5-fluoropiperidin-1-yl)(2-(1-(cyclopropylmethyl)-7-(1-((1R,3 S)-3-hydroxycyclohexane-1-carbonyl)piperidin-4-yl)-1H-indol-2-yl)-3-methylpyrazolo[1,5-a]pyridin-6-yl)methanone (449);

((R)-3-aminopiperidin-1-yl)(2-(1-(cyclopropylmethyl)-7-(1-((1 s,4s)-4-hydroxycyclohexane-1-carbonyl)piperidin-4-yl)-1H-indol-2-yl)-3-methylpyrazolo[1,5-a]pyridin-6-yl)methanone (450);

((3R,5R)-3-amino-5-fluoropiperidin-1-yl)(2-(1-(cyclopropylmethyl)-7-(14(1r,4r)-4-hydroxycyclohexane-1-carbonyl)piperidin-4-yl)-1H-indol-2-yl)-3-methylpyrazolo[1,5-a]pyridin-6-yl)methanone (451);

1-(4-(2-(6-((3R,5R)-3-amino-5-fluoropiperidine-1-carbonyl)-3-methylpyrazolo[1,5-a]pyridin-2-yl)-1-(cyclopropylmethyl)-1H-indol-7-yl)piperidin-1-yl)ethan-1-one (452);

1-(4-(2-(6-((7R)-7-amino-2-azabicyclo[2.2.1]heptane-2-carbonyl)-3-methylpyrazolo[1,5-a]pyridin-2-yl)-1-(cyclopropylmethyl)-1H-indol-7-yl)piperidin-1-yl)-2-methoxyethan-1-one (453);

(S)-1-(4-(2-(6-((R)-3-aminopiperidine-1-carbonyl)-3-methylpyrazolo[1,5-a]pyridin-2-yl)-1-(cyclopropylmethyl)-1H-indol-7-yl)piperidin-1-yl)-2-methoxypropan-1-one (454);

(R)-1-(4-(2-(6-(3-aminopiperidine-1-carbonyl)-3-methylpyrazolo[1,5-a]pyridin-2-yl)-1-(cyclopropylmethyl)-1H-indol-7-yl)piperidin-1-yl)-2-methoxyethan-1-one (455);

(R)-(3-aminopiperidin-1-yl)(2-(1-(cyclopropylmethyl)-7-(1-(3-hydroxy-3-(trifluoromethyl)cyclobutane-1-carbonyl)piperidin-4-yl)-1H-indol-2-yl)-3-methylpyrazolo[1,5-a]pyridin-6-yl)methanone (456);

((R)-3-aminopiperidin-1-yl)(2-(1-(cyclopropylmethyl)-7-(1-(tetrahydro-2H-pyran-2-carbonyl)piperidin-4-yl)-1H-indol-2-yl)-3-methylpyrazolo[1,5-a]pyridin-6-yl)methanone (457);

((3R,5R)-3-amino-5-fluoropiperidin-1-yl)(2-(1-(cyclopropylmethyl)-7-(1-(tetrahydro-2H-pyran-2-carbonyl)piperidin-4-yl)-1H-indol-2-yl)-3-methylpyrazolo[1,5-a]pyridin-6-yl)methanone (458);

(S)-1-(4-(2-(6-((3R,5R)-3-amino-5-fluoropiperidine-1-carbonyl)-3-methylpyrazolo[1,5-a]pyridin-2-yl)-1-(cyclopropylmethyl)-1H-indol-7-yl)piperidin-1-yl)-2-methoxypropan-1-one (459);

(R)-1-(4-(2-(6-((R)-3-aminopiperidine-1-carbonyl)-3-methylpyrazolo[1,5-a]pyridin-2-yl)-1-(cyclopropylmethyl)-1H-indol-7-yl)piperidin-1-yl)-2-methoxypropan-1-one (460);

(R)-1-(4-(2-(6-((3R,5R)-3-amino-5-fluoropiperidine-1-carbonyl)-3-methylpyrazolo[1,5-a]pyridin-2-yl)-1-(cyclopropylmethyl)-1H-indol-7-yl)piperidin-1-yl)-2-methoxypropan-1-one (461);

((R)-3-aminopiperidin-1-yl)(2-(1-(cyclopropylmethyl)-7-(1-(tetrahydrofuran-2-carbonyl)piperidin-4-yl)-1H-indol-2-yl)-3-methylpyrazolo[1,5-a]pyridin-6-yl)methanone (462);

((3R,5R)-3-amino-5-fluoropiperidin-1-yl)(2-(1-(cyclopropylmethyl)-7-(1-(tetrahydrofuran-2-carbonyl)piperidin-4-yl)-1H-indol-2-yl)-3-methylpyrazolo[1,5-a]pyridin-6-yl)methanone (463);

(R)-(3-aminopiperidin-1-yl)(2-(1-(cyclopropylmethyl)-7-(1-(thiophene-2-carbonyl)piperidin-4-yl)-1H-indol-2-yl)-3-methylpyrazolo[1,5-a]pyridin-6-yl)methanone (464);

(R)-(3-aminopiperidin-1-yl)(2-(1-(cyclopropylmethyl)-7-(1-(3-hydroxycyclobutane-1-carbonyl)piperidin-4-yl)-1H-indol-2-yl)-3-methylpyrazolo[1,5-a]pyridin-6-yl)methanone (465);

((3R,5R)-3-amino-5-fluoropiperidin-1-yl)(2-(1-(cyclopropylmethyl)-7-(1-(3-hydroxycyclobutane-1-carbonyl)piperidin-4-yl)-1H-indol-2-yl)-3-methylpyrazolo[1,5-a]pyridin-6-yl)methanone (466);

(4-(2-(6-((7R)-7-amino-2-azabicyclo[2.2.1]heptane-2-carbonyl)-3-methylpyrazolo[1,5-a]pyridin-2-yl)-1-(cyclopropylmethyl)-1H-indol-7-yl)piperidin-1-yl)(3-hydroxycyclobutyl)methanone (467);

Methyl (R)-4-(2-(6-(3-aminopiperidine-1-carbonyl)-3-methylpyrazolo[1,5-a]pyridin-2-yl)-1-(cyclopropylmethyl)-1H-indol-7-yl)piperidine-1-carboxylate (468);

Methyl 4-(2-(6-((3R,5R)-3-amino-5-fluoropiperidine-1-carbonyl)-3-methylpyrazolo[1,5-a]pyridin-2-yl)-1-(cyclopropylmethyl)-1H-indol-7-yl)piperidine-1-carboxylate (469);

Methyl 4-(2-(6-((7R)-7-amino-2-azabicyclo[2.2.1]heptane-2-carbonyl)-3-methylpyrazolo[1,5-a]pyridin-2-yl)-1-(cyclopropylmethyl)-1H-indol-7-yl)piperidine-1-carboxylate (470);

(R)-1-(4-(2-(6-((R)-3-aminopiperidine-1-carbonyl)-3-methylpyrazolo[1,5-a]pyridin-2-yl)-1-(cyclopropylmethyl)-1H-indol-7-yl)piperidin-1-yl)-2-hydroxypropan-1-one (471);

(R)-1-(4-(2-(6-((3R,5R)-3-amino-5-fluoropiperidine-1-carbonyl)-3-methylpyrazolo[1,5-a]pyridin-2-yl)-1-(cyclopropylmethyl)-1H-indol-7-yl)piperidin-1-yl)-2-hydroxypropan-1-one (472);

(2R)-1-(4-(2-(6-((7R)-7-Amino-2-azabicyclo[2.2.1]heptane-2-carbonyl)-3-methylpyrazolo[1,5-a]pyridin-2-yl)-1-(cyclopropylmethyl)-1H-indol-7-yl)piperidin-1-yl)-2-hydroxypropan-1-one (473);

((3R,5R)-3-Amino-5-fluoropiperidin-1-yl)(2-(1-(cyclopropylmethyl)-7-(1-(thiophene-2-carbonyl)piperidin-4-yl)-1H-indol-2-yl)-3-methylpyrazolo[1,5-a]pyridin-6-yl)methanone (474);

(4-(2-(6-((7R)-7-Amino-2-azabicyclo[2.2.1]heptane-2-carbonyl)-3-methylpyrazolo[1,5-a]pyridin-2-yl)-1-(cyclopropylmethyl)-1H-indol-7-yl)piperidin-1-yl)(thiophen-2-yl)methanone (475);

1-(4-(2-(6-((3R,5R)-3-Amino-5-fluoropiperidine-1-carbonyl)-3-methylpyrazolo[1,5-a]pyridin-2-yl)-1-(cyclopropylmethyl)-1H-indol-7-yl)piperidin-1-yl)ethan-1-one (476);

1-(4-(2-(6-((7R)-7-Amino-2-azabicyclo[2.2.1]heptane-2-carbonyl)-3-methylpyrazolo[1,5-a]pyridin-2-yl)-1-(cyclopropylmethyl)-1H-indol-7-yl)piperidin-1-yl)ethan-1-one (477);

1-(4-(2-(6-((3R,5R)-3-Amino-5-fluoropiperidine-1-carbonyl)-3-methylpyrazolo[1,5-a]pyridin-2-yl)-1-(cyclopropylmethyl)-1H-indol-7-yl)piperidin-1-yl)-2-methoxyethan-1-one (478);

(R)-1-(4-(2-(6-(3-Aminopiperidine-1-carbonyl)-3-methylpyrazolo[1,5-a]pyridin-2-yl)-1-(cyclopropylmethyl)-1H-indol-7-yl)piperidin-1-yl)ethan-1-one (479);

(R)-1-(4-(2-(6-(3-aminopiperidine-1-carbonyl)-4-methoxy-3-methylpyrazolo[1,5-a]pyridin-2-yl)-1-(cyclopropylmethyl)-5-fluoro-1H-indol-7-yl)piperidin-1-yl)-2-methoxyethan-1-one (480);

1-(4-(2-(6-((3R,5R)-3-Amino-5-fluoropiperidine-1-carbonyl)-4-methoxy-3-methylpyrazolo[1,5-a]pyridin-2-yl)-1-(cyclopropylmethyl)-5-fluoro-1H-indol-7-yl)piperidin-1-yl)-2-methoxyethan-1-one (481);

1-(4-(2-(6-((3R,5R)-3-Amino-5-fluoropiperidine-1-carbonyl)-4-methoxy-3-methylpyrazolo[1,5-a]pyridin-2-yl)-1-(cyclopropylmethyl)-5-fluoro-1H-indol-7-yl)piperidin-1-yl)ethan-1-one (482);

(R)-1-(4-(2-(6-(3-Aminopiperidine-1-carbonyl)-4-methoxy-3-methylpyrazolo[1,5-a]pyridin-2-yl)-1-(cyclopropylmethyl)-5-fluoro-1H-indol-7-yl)piperidin-1-yl)ethan-1-one (483);

((R)-3-Aminopiperidin-1-yl)(2-(1-(cyclopropylmethyl)-5-fluoro-7-(1-((1r,4r)-4-hydroxycyclohexane-1-carbonyl)piperidin-4-yl)-1H-indol-2-yl)-3-methylpyrazolo[1,5-a]pyridin-6-yl)methanone (484);

((R)-3-Aminopiperidin-1-yl)(2-(1-(cyclopropylmethyl)-5-fluoro-7-(1-((1s,4s)-4-hydroxycyclohexane-1-carbonyl)piperidin-4-yl)-1H-indol-2-yl)-3-methylpyrazolo[1,5-a]pyridin-6-yl)methanone (485);

((3R,5R)-3-Amino-5-fluoropiperidin-1-yl)(2-(1-(cyclopropylmethyl)-5-fluoro-7-(1-((1s,4s)-4-hydroxycyclohexane-1-carbonyl)piperidin-4-yl)-1H-indol-2-yl)-3-methylpyrazolo[1,5-a]pyridin-6-yl)methanone (486);

((3R,5R)-3-Amino-5-fluoropiperidin-1-yl)(2-(1-(cyclopropylmethyl)-5-fluoro-7-(1-((1r,4r)-4-hydroxycyclohexane-1-carbonyl)piperidin-4-yl)-1H-indol-2-yl)-3-methylpyrazolo[1,5-a]pyridin-6-yl)methanone (487);

((R)-3-Aminopiperidin-1-yl)(2-(1-(cyclopropylmethyl)-5-fluoro-7-(1-(tetrahydrofuran-2-carbonyl)piperidin-4-yl)-1H-indol-2-yl)-3-methylpyrazolo[1,5-a]pyridin-6-yl)methanone (488);

((R)-3-Aminopiperidin-1-yl)(2-(1-(cyclopropylmethyl)-5-fluoro-7-(1-(tetrahydrofuran-2-carbonyl)piperidin-4-yl)-1H-indol-2-yl)-3-methylpyrazolo[1,5-a]pyridin-6-yl)methanone (489);

((3R,5R)-3-Amino-5-fluoropiperidin-1-yl)(2-(1-(cyclopropylmethyl)-5-fluoro-7-(1-(tetrahydrofuran-2-carbonyl)piperidin-4-yl)-1H-indol-2-yl)-3-methylpyrazolo[1,5-a]pyridin-6-yl)methanone (490);

((3R,5R)-3-Amino-5-fluoropiperidin-1-yl)(2-(1-(cyclopropylmethyl)-5-fluoro-7-(1-(tetrahydrofuran-2-carbonyl)piperidin-4-yl)-1H-indol-2-yl)-3-methylpyrazolo[1,5-a]pyridin-6-yl)methanone (491);

(R)-(3-Aminopiperidin-1-yl)(2-(1-(cyclopropylmethyl)-5-fluoro-7-(1-(3-hydroxycyclobutane-1-carbonyl)piperidin-4-yl)-1H-indol-2-yl)-3-methylpyrazolo[1,5-a]pyridin-6-yl)methanone (492);

(R)-1-(4-(2-(6-(3-Aminopiperidine-1-carbonyl)-3-methylpyrazolo[1,5-a]pyridin-2-yl)-1-(cyclopropylmethyl)-5-fluoro-1H-indol-7-yl)piperidin-1-yl)-2-methoxy-2-methylpropan-1-one (493);

1-(4-(2-(6-((3R,5R)-3-Amino-5-fluoropiperidine-1-carbonyl)-3-methylpyrazolo[1,5-a]pyridin-2-yl)-1-(cyclopropylmethyl)-5-fluoro-1H-indol-7-yl)piperidin-1-yl)-3-methylbutan-1-one (494);

1-(4-(2-(6-((3R,5R)-3-Amino-5-fluoropiperidine-1-carbonyl)-3-methylpyrazolo[1,5-a]pyridin-2-yl)-1-(cyclopropylmethyl)-5-fluoro-1H-indol-7-yl)piperidin-1-yl)-3-methylbutan-1-one (495);

((3R,5R)-3-Amino-5-fluoropiperidin-1-yl)(2-(1-(cyclopropylmethyl)-5-fluoro-7-(1-(3-hydroxycyclobutane-1-carbonyl)piperidin-4-yl)-1H-indol-2-yl)-3-methylpyrazolo[1,5-a]pyridin-6-yl)methanone (496);

(R)-1-(4-(2-(6-((R)-3-Aminopiperidine-1-carbonyl)-3-methylpyrazolo[1,5-a]pyridin-2-yl)-1-(cyclopropylmethyl)-5-fluoro-1H-indol-7-yl)piperidin-1-yl)-2-methoxypropan-1-one (497);

(R)-1-(4-(2-(6-((3R,5R)-3-Amino-5-fluoropiperidine-1-carbonyl)-3-methylpyrazolo[1,5-a]pyridin-2-yl)-1-(cyclopropylmethyl)-5-fluoro-1H-indol-7-yl)piperidin-1-yl)-2-methoxypropan-1-one (498);

(S)-1-(4-(2-(6-((R)-3-Aminopiperidine-1-carbonyl)-3-methylpyrazolo[1,5-a]pyridin-2-yl)-1-(cyclopropylmethyl)-5-fluoro-1H-indol-7-yl)piperidin-1-yl)-2-methoxypropan-1-one (499);

(S)-1-(4-(2-(6-((3R,5R)-3-Amino-5-fluoropiperidine-1-carbonyl)-3-methylpyrazolo[1,5-a]pyridin-2-yl)-1-(cyclopropylmethyl)-5-fluoro-1H-indol-7-yl)piperidin-1-yl)-2-methoxypropan-1-one (500);

1-(4-(2-(6-((3R,5R)-3-Amino-5-fluoropiperidine-1-carbonyl)-3-methylpyrazolo[1,5-a]pyridin-2-yl)-1-(cyclopropylmethyl)-5-fluoro-1H-indol-7-yl)piperidin-1-yl)-2-methoxy-2-methylpropan-1-one (501);

(R)-1-(4-(2-(6-(3-Aminopiperidine-1-carbonyl)-3-methylpyrazolo[1,5-a]pyridin-2-yl)-1-(cyclopropylmethyl)-5-fluoro-1H-indol-7-yl)piperidin-1-yl)-2-methoxyethan-1-one (502);

1-(4-(2-(6-((3R,5R)-3-Amino-5-fluoropiperidine-1-carbonyl)-3-methylpyrazolo[1,5-a]pyridin-2-yl)-1-(cyclopropylmethyl)-5-fluoro-1H-indol-7-yl)piperidin-1-yl)-2-methoxyethan-1-one (503);

(R)-(3-Aminopiperidin-1-yl)(2-(1-(cyclopropylmethyl)-5-fluoro-7-(1-(3-hydroxy-3-(trifluoromethyl)cyclobutane-1-carbonyl)piperidin-4-yl)-1H-indol-2-yl)-3-methylpyrazolo[1,5-a]pyridin-6-yl)methanone (504);

((3R,5R)-3-Amino-5-fluoropiperidin-1-yl)(2-(1-(cyclopropylmethyl)-5-fluoro-7-(1-(3-hydroxy-3-(trifluoromethyl)cyclobutane-1-carbonyl)piperidin-4-yl)-1H-indol-2-yl)-3-methylpyrazolo[1,5-a]pyridin-6-yl)methanone (505);

(R)-1-(4-(2-(6-(3-Aminopiperidine-1-carbonyl)-3-methylpyrazolo[1,5-a]pyridin-2-yl)-1-(cyclopropylmethyl)-5-fluoro-1H-indol-7-yl)piperidin-1-yl)ethan-1-one (506);

1-(4-(2-(6-((3R,5R)-3-Amino-5-fluoropiperidine-1-carbonyl)-3-methylpyrazolo[1,5-a]pyridin-2-yl)-1-(cyclopropylmethyl)-5-fluoro-1H-indol-7-yl)piperidin-1-yl)ethan-1-one (507);

((R)-3-Aminopiperidin-1-yl)(2-(1-(cyclopropylmethyl)-5-fluoro-7-(1-(tetrahydro-2H-pyran-2-carbonyl)piperidin-4-yl)-1H-indol-2-yl)-3-methylpyrazolo[1,5-a]pyridin-6-yl)methanone (508);

((3R,5R)-3-Amino-5-fluoropiperidin-1-yl)(2-(1-(cyclopropylmethyl)-5-fluoro-7-(1-(tetrahydro-2H-pyran-2-carbonyl)piperidin-4-yl)-1H-indol-2-yl)-3-methylpyrazolo[1,5-a]pyridin-6-yl)methanone (509);

(R)-1-(4-(2-(6-(3-Aminopiperidine-1-carbonyl)-4-methoxy-3-methylpyrazolo[1,5-a]pyridin-2-yl)-1-(cyclopropylmethyl)-1H-pyrrolo[2,3-c]pyridin-7-yl)piperidin-1-yl)-2-methoxyethan-1-one (510);

1-(4-(2-(6-((3R,5R)-3-Amino-5-fluoropiperidine-1-carbonyl)-4-methoxy-3-methylpyrazolo[1,5-a]pyridin-2-yl)-1-(cyclopropylmethyl)-1H-pyrrolo[2,3-c]pyridin-7-yl)piperidin-1-yl)-2-methoxyethan-1-one (511);

(R)-1-(4-(2-(6-(3-Aminopiperidine-1-carbonyl)-3-methylpyrazolo[1,5-a]pyridin-2-yl)-1-(cyclopropylmethyl)-1H-pyrrolo[2,3-c]pyridin-7-yl)piperidin-1-yl)-2-methoxyethan-1-one (512);

1-(4-(2-(6-((3R,5R)-3-Amino-5-fluoropiperidine-1-carbonyl)-3-methylpyrazolo[1,5-a]pyridin-2-yl)-1-(cyclopropylmethyl)-1H-pyrrolo[2,3-c]pyridin-7-yl)piperidin-1-yl)-2-methoxyethan-1-one (513);

((3R,5R)-3-Amino-5-fluoropiperidin-1-yl)(2-(1-(cyclopropylmethyl)-7-(1-((1r,4r)-4-hydroxycyclohexane-1-carbonyl)azetidin-3-yl)-1H-indol-2-yl)-4-methoxy-3-methylpyrazolo[1,5-a]pyridin-6-yl)methanone (514);

(R)-(3-Aminopiperidin-1-yl)(2-(1-(cyclopropylmethyl)-7-(1-(3-hydroxy-3-(trifluoromethyl)cyclobutane-1-carbonyl)azetidin-3-yl)-1H-indol-2-yl)-4-methoxy-3-methylpyrazolo[1,5-a]pyridin-6-yl)methanone (515);

(R)-1-(3-(2-(6-(3-Aminopiperidine-1-carbonyl)-4-methoxy-3-methylpyrazolo[1,5-a]pyridin-2-yl)-1-(cyclopropylmethyl)-1H-indol-7-yl)azetidin-1-yl)-2-methoxy-2-methylpropan-1-one (516);

((R)-3-Aminopiperidin-1-yl)(2-(1-(cyclopropylmethyl)-7-(14(1r,4r)-4-hydroxycyclohexane-1-carbonyl)azetidin-3-yl)-1H-indol-2-yl)-4-methoxy-3-methylpyrazolo[1,5-a]pyridin-6-yl)methanone (517);

1-(3-(2-(6-((3R,5R)-3-Amino-5-fluoropiperidine-1-carbonyl)-4-methoxy-3-methylpyrazolo[1,5-a]pyridin-2-yl)-1-(cyclopropylmethyl)-1H-indol-7-yl)azetidin-1-yl)-2-methoxy-2-methylpropan-1-one (518);

((3R,5R)-3-Amino-5-fluoropiperidin-1-yl)(2-(1-(cyclopropylmethyl)-7-(1-((1s,4 s)-4-hydroxycyclohexane-1-carbonyl)azetidin-3-yl)-1H-indol-2-yl)-4-methoxy-3-methylpyrazolo[1,5-a]pyridin-6-yl)methanone (519);

((R)-3-Aminopiperidin-1-yl)(2-(1-(cyclopropylmethyl)-7-(1-((1s,4s)-4-hydroxycyclohexane-1-carbonyl)azetidin-3-yl)-1H-indol-2-yl)-4-methoxy-3-methylpyrazolo[1,5-a]pyridin-6-yl)methanone (520);

(R)-1-(3-(2-(6-(3-Aminopiperidine-1-carbonyl)-4-methoxy-3-methylpyrazolo[1,5-a]pyridin-2-yl)-1-(cyclopropylmethyl)-1H-indol-7-yl)azetidin-1-yl)ethan-1-one (521);

1-(3-(2-(6-((3R,5R)-3-Amino-5-fluoropiperidine-1-carbonyl)-4-methoxy-3-methylpyrazolo[1,5-a]pyridin-2-yl)-1-(cyclopropylmethyl)-1H-indol-7-yl)azetidin-1-yl)ethan-1-one (522);

(S)-1-(3-(2-(6-((R)-3-Aminopiperidine-1-carbonyl)-4-methoxy-3-methylpyrazolo[1,5-a]pyridin-2-yl)-1-(cyclopropylmethyl)-1H-indol-7-yl)azetidin-1-yl)-2-methoxypropan-1-one (523);

(S)-1-(3-(2-(6-((3R,5R)-3-Amino-5-fluoropiperidine-1-carbonyl)-4-methoxy-3-methylpyrazolo[1,5-a]pyridin-2-yl)-1-(cyclopropylmethyl)-1H-indol-7-yl)azetidin-1-yl)-2-methoxypropan-1-one (524);

(R)-1-(3-(2-(6-((R)-3-Aminopiperidine-1-carbonyl)-4-methoxy-3-methylpyrazolo[1,5-a]pyridin-2-yl)-1-(cyclopropylmethyl)-1H-indol-7-yl)azetidin-1-yl)-2-methoxypropan-1-one (525);

(R)-1-(3-(2-(6-((3R,5R)-3-Amino-5-fluoropiperidine-1-carbonyl)-4-methoxy-3-methylpyrazolo[1,5-a]pyridin-2-yl)-1-(cyclopropylmethyl)-1H-indol-7-yl)azetidin-1-yl)-2-methoxypropan-1-one (526);

1-(3-(2-(6-((3R,5R)-3-Amino-5-fluoropiperidine-1-carbonyl)-4-methoxy-3-methylpyrazolo[1,5-a]pyridin-2-yl)-1-(cyclopropylmethyl)-1H-indol-7-yl)azetidin-1-yl)-2-methoxyethan-1-one (527);

(R)-1-(3-(2-(6-(3-Aminopiperidine-1-carbonyl)-4-methoxy-3-methylpyrazolo[1,5-a]pyridin-2-yl)-1-(cyclopropylmethyl)-1H-indol-7-yl)azetidin-1-yl)-2-methoxyethan-1-one (528);

(R)-1-(3-(2-(6-(3-Aminopiperidine-1-carbonyl)-4-methoxy-3-methylpyrazolo[1,5-a]pyridin-2-yl)-1-(cyclopropylmethyl)-1H-indol-7-yl)azetidin-1-yl)-2-methoxyethan-1-one (529);

((R)-3-Aminopiperidin-1-yl)(2-(1-(cyclopropylmethyl)-7-(1-((1r,4r)-4-hydroxycyclohexane-1-carbonyl)azetidin-3-yl)-1H-indol-2-yl)-3-methylpyrazolo[1,5-a]pyridin-6-yl)methanone (530);

((3R,5R)-3-Amino-5-fluoropiperidin-1-yl)(2-(1-(cyclopropylmethyl)-7-(1-((1R,3 S)-3-hydroxycyclohexane-1-carbonyl)azetidin-3-yl)-1H-indol-2-yl)-3-methylpyrazolo[1,5-a]pyridin-6-yl)methanone (531);

((R)-3-Aminopiperidin-1-yl)(2-(1-(cyclopropylmethyl)-7-(1-((1R,3S)-3-hydroxycyclohexane-1-carbonyl)azetidin-3-yl)-1H-indol-2-yl)-3-methylpyrazolo[1,5-a]pyridin-6-yl)methanone (532);

((3R,5R)-3-Amino-5-fluoropiperidin-1-yl)(2-(1-(cyclopropylmethyl)-7-(1-((1S,3R)-3-hydroxycyclohexane-1-carbonyl)azetidin-3-yl)-1H-indol-2-yl)-3-methylpyrazolo[1,5-a]pyridin-6-yl)methanone (533);

((R)-3-Aminopiperidin-1-yl)(2-(1-(cyclopropylmethyl)-7-(1-((1S,3R)-3-hydroxycyclohexane-1-carbonyl)azetidin-3-yl)-1H-indol-2-yl)-3-methylpyrazolo[1,5-a]pyridin-6-yl)methanone (534);

(R)-(3-Aminopiperidin-1-yl)(2-(1-(cyclopropylmethyl)-7-(1-(3-hydroxy-3-(trifluoromethyl)cyclobutane-1-carbonyl)azetidin-3-yl)-1H-indol-2-yl)-3-methylpyrazolo[1,5-a]pyridin-6-yl)methanone (535);

(R)-1-(3-(2-(6-(3-Aminopiperidine-1-carbonyl)-3-methylpyrazolo[1,5-a]pyridin-2-yl)-1-(cyclopropylmethyl)-1H-indol-7-yl)azetidin-1-yl)-2-methoxy-2-methylpropan-1-one (536);

((3R,5R)-3-Amino-5-fluoropiperidin-1-yl)(2-(1-(cyclopropylmethyl)-7-(1-((1r,4r)-4-hydroxycyclohexane-1-carbonyl)azetidin-3-yl)-1H-indol-2-yl)-3-methylpyrazolo[1,5-a]pyridin-6-yl)methanone (537);

((3R,5R)-3-Amino-5-fluoropiperidin-1-yl)(2-(1-(cyclopropylmethyl)-7-(1-((1s,4s)-4-hydroxycyclohexane-1-carbonyl)azetidin-3-yl)-1H-indol-2-yl)-3-methylpyrazolo[1,5-a]pyridin-6-yl)methanone (538);

((R)-3-Aminopiperidin-1-yl)(2-(1-(cyclopropylmethyl)-7-(1-(1s,4s)-4-hydroxycyclohexane-1-carbonyl)azetidin-3-yl)-1H-indol-2-yl)-3-methylpyrazolo[1,5-a]pyridin-6-yl)methanone (539);

(R)-1-(3-(2-(6-((3R,5R)-3-Amino-5-fluoropiperidine-1-carbonyl)-3-methylpyrazolo[1,5-a]pyridin-2-yl)-1-(cyclopropylmethyl)-1H-indol-7-yl)azetidin-1-yl)-2-methoxypropan-1-one (540);

(R)-1-(3-(2-(6-((R)-3-Aminopiperidine-1-carbonyl)-3-methylpyrazolo[1,5-a]pyridin-2-yl)-1-(cyclopropylmethyl)-1H-indol-7-yl)azetidin-1-yl)-2-methoxypropan-1-one (541);

(S)-1-(3-(2-(6-((3R,5R)-3-Amino-5-fluoropiperidine-1-carbonyl)-3-methylpyrazolo[1,5-a]pyridin-2-yl)-1-(cyclopropylmethyl)-1H-indol-7-yl)azetidin-1-yl)-2-methoxypropan-1-one (542);

(S)-1-(3-(2-(6-((R)-3-aminopiperidine-1-carbonyl)-3-methylpyrazolo[1,5-a]pyridin-2-yl)-1-(cyclopropylmethyl)-1H-indol-7-yl)azetidin-1-yl)-2-methoxypropan-1-one (543);

((3R,5R)-3-Amino-5-fluoropiperidin-1-yl)(2-(1-(cyclopropylmethyl)-7-(1-(tetrahydro-2H-pyran-2-carbonyl)azetidin-3-yl)-1H-indol-2-yl)-3-methylpyrazolo[1,5-a]pyridin-6-yl)methanone (544);

((R)-3-Aminopiperidin-1-yl)(2-(1-(cyclopropylmethyl)-7-(1-(tetrahydro-2H-pyran-2-carbonyl)azetidin-3-yl)-1H-indol-2-yl)-3-methylpyrazolo[1,5-a]pyridin-6-yl)methanone (545);

(R)-1-(3-(2-(6-(3-Aminopiperidine-1-carbonyl)-3-methylpyrazolo[1,5-a]pyridin-2-yl)-1-(cyclopropylmethyl)-1H-indol-7-yl)azetidin-1-yl)-2-methoxyethan-1-one (546);

1-(3-(2-(6-((3R,5R)-3-Amino-5-fluoropiperidine-1-carbonyl)-3-methylpyrazolo[1,5-a]pyridin-2-yl)-1-(cyclopropylmethyl)-1H-indol-7-yl)azetidin-1-yl)-2-methoxyethan-1-one (547);

1-(3-(2-(6-((3R,5R)-3-Amino-5-fluoropiperidine-1-carbonyl)-3-methylpyrazolo[1,5-a]pyridin-2-yl)-1-(cyclopropylmethyl)-1H-indol-7-yl)azetidin-1-yl)ethan-1-one (548);

1-(3-(2-(6-((7R)-7-Amino-2-azabicyclo[2.2.1]heptane-2-carbonyl)-3-methylpyrazolo[1,5-a]pyridin-2-yl)-1-(cyclopropylmethyl)-1H-indol-7-yl)azetidin-1-yl)ethan-1-one (549);

4-(((2-(6-((R)-3-Aminopiperidine-1-carbonyl)-4-methoxy-3-methylpyrazolo[1,5-a]pyridin-2-yl)-1-(cyclopropylmethyl)-1H-indol-7-yl)oxy)methyl)pyrrolidin-2-one (550);

4-(((2-(6-((R)-3-Aminopiperidine-1-carbonyl)-4-methoxy-3-methylpyrazolo[1,5-a]pyridin-2-yl)-1-(cyclopropylmethyl)-1H-indol-7-yl)oxy)methyl)-1-methylpyrrolidin-2-one (551);

4-(((2-(6-((R)-3-Aminopiperidine-1-carbonyl)-4-methoxy-3-methylpyrazolo[1,5-a]pyridin-2-yl)-1-(cyclopropylmethyl)-1H-indol-7-yl)oxy)methyl)-1-methylpyrrolidin-2-one (552);

4-(((2-(6-((3R,5R)-3-Amino-5-fluoropiperidine-1-carbonyl)-4-methoxy-3-methylpyrazolo[1,5-a]pyridin-2-yl)-1-(cyclopropylmethyl)-1H-indol-7-yl)oxy)methyl)-1-methylpyrrolidin-2-one (553);

4-(((2-(6-((3R,5R)-3-Amino-5-fluoropiperidine-1-carbonyl)-4-methoxy-3-methylpyrazolo[1,5-a]pyridin-2-yl)-1-(cyclopropylmethyl)-1H-indol-7-yl)oxy)methyl)-1-methylpyrrolidin-2-one (554);

(R)-(2-(7-(2-(1H-1,2,4-Triazol-1-yl)ethoxy)-1-(cyclopropylmethyl)-1H-indol-2-yl)-4-methoxy-3-methylpyrazolo[1,5-a]pyridin-6-yl)(3-aminopiperidin-1-yl)methanone (555);

(2-(7-(2-(1H-1,2,4-Triazol-1-yl)ethoxy)-1-(cyclopropylmethyl)-1H-indol-2-yl)-4-methoxy-3-methylpyrazolo[1,5-a]pyridin-6-yl)((3R,5R)-3-amino-5-fluoropiperidin-1-yl)methanone (556);

(2-(7-(2-(4-Amino-1H-pyrazol-1-yl)ethoxy)-1-(cyclopropylmethyl)-1H-indol-2-yl)-4-methoxy-3-methylpyrazolo[1,5-a]pyridin-6-yl)((3R,5R)-3-amino-5-fluoropiperidin-1-yl)methanone (557);

(R)-(2-(7-(2-(4-Amino-1H-pyrazol-1-yl)ethoxy)-1-(cyclopropylmethyl)-1H-indol-2-yl)-4-methoxy-3-methylpyrazolo[1,5-a]pyridin-6-yl)(3-aminopiperidin-1-yl)methanone (558);

(S)-5-(((2-(6-((R)-3-Aminopiperidine-1-carbonyl)-4-methoxy-3-methylpyrazolo[1,5-a]pyridin-2-yl)-1-(cyclopropylmethyl)-1H-indol-7-yl)oxy)methyl)pyrrolidin-2-one (559);

(S)-5-(((2-(6-((3R,5R)-3-Amino-5-fluoropiperidine-1-carbonyl)-4-methoxy-3-methylpyrazolo[1,5-a]pyridin-2-yl)-1-(cyclopropylmethyl)-1H-indol-7-yl)oxy)methyl)pyrrolidin-2-one (560);

(R)-5-(((2-(6-((R)-3-Aminopiperidine-1-carbonyl)-4-methoxy-3-methylpyrazolo[1,5-a]pyridin-2-yl)-1-(cyclopropylmethyl)-1H-indol-7-yl)oxy)methyl)pyrrolidin-2-one (561);

4-(((2-(6-((R)-3-Aminopiperidine-1-carbonyl)-4-methoxy-3-methylpyrazolo[1,5-a]pyridin-2-yl)-1-(cyclopropylmethyl)-1H-indol-7-yl)oxy)methyl)pyrrolidin-2-one (562);

4-(((2-(6-((3R,5R)-3-Amino-5-fluoropiperidine-1-carbonyl)-4-methoxy-3-methylpyrazolo[1,5-a]pyridin-2-yl)-1-(cyclopropylmethyl)-1H-indol-7-yl)oxy)methyl)pyrrolidin-2-one (563);

4-(((2-(6-((R)-3-Aminopiperidine-1-carbonyl)-4-methoxy-3-methylpyrazolo[1,5-a]pyridin-2-yl)-1-(cyclopropylmethyl)-1H-indol-7-yl)oxy)methyl)pyrrolidin-2-one (564);

4-(((2-(6-((3R,5R)-3-Amino-5-fluoropiperidine-1-carbonyl)-4-methoxy-3-methylpyrazolo[1,5-a]pyridin-2-yl)-1-(cyclopropylmethyl)-1H-indol-7-yl)oxy)methyl)pyrrolidin-2-one (565);

4-(((2-(6-((R)-3-Aminopiperidine-1-carbonyl)-4-fluoro-3-methylpyrazolo[1,5-a]pyridin-2-yl)-1-(cyclopropylmethyl)-1H-indol-7-yl)oxy)methyl)pyrrolidin-2-one (566);

4-(((2-(6-((3R,5R)-3-Amino-5-fluoropiperidine-1-carbonyl)-4-fluoro-3-methylpyrazolo[1,5-a]pyridin-2-yl)-1-(cyclopropylmethyl)-1H-indol-7-yl)oxy)methyl)pyrrolidin-2-one (567);

(S)-5-(((2-(6-((3R,5R)-3-Amino-5-fluoropiperidine-1-carbonyl)-4-fluoro-3-methylpyrazolo[1,5-a]pyridin-2-yl)-1-(cyclopropylmethyl)-1H-indol-7-yl)oxy)methyl)pyrrolidin-2-one (568);

(S)-5-(((2-(6-((R)-3-Aminopiperidine-1-carbonyl)-4-fluoro-3-methylpyrazolo[1,5-a]pyridin-2-yl)-1-(cyclopropylmethyl)-1H-indol-7-yl)oxy)methyl)pyrrolidin-2-one (569);

(R)-5-(((2-(6-((R)-3-Aminopiperidine-1-carbonyl)-4-fluoro-3-methylpyrazolo[1,5-a]pyridin-2-yl)-1-(cyclopropylmethyl)-1H-indol-7-yl)oxy)methyl)pyrrolidin-2-one (570);

4-(((2-(6-((R)-3-Aminopiperidine-1-carbonyl)-4-fluoro-3-methylpyrazolo[1,5-a]pyridin-2-yl)-1-(cyclopropylmethyl)-1H-indol-7-yl)oxy)methyl)pyrrolidin-2-one (571);

4-(((2-(6-((3R,5R)-3-Amino-5-fluoropiperidine-1-carbonyl)-4-fluoro-3-methylpyrazolo[1,5-a]pyridin-2-yl)-1-(cyclopropylmethyl)-1H-indol-7-yl)oxy)methyl)pyrrolidin-2-one (572);

4-(((2-(6-((3R,5R)-3-Amino-5-fluoropiperidine-1-carbonyl)-3-methylpyrazolo[1,5-a]pyridin-2-yl)-1-(cyclopropylmethyl)-1H-indol-7-yl)oxy)methyl)pyrrolidin-2-one (573);

(2-(7-(2-(1H-Imidazol-1-yl)ethoxy)-1-(cyclopropylmethyl)-1H-indol-2-yl)-3-methylpyrazolo[1,5-a]pyridin-6-yl)((3R,5R)-3-amino-5-fluoropiperidin-1-yl)methanone (574);

(R)-(2-(7-(2-(1H-Imidazol-1-yl)ethoxy)-1-(cyclopropylmethyl)-1H-indol-2-yl)-3-methylpyrazolo[1,5-a]pyridin-6-yl)(3-aminopiperidin-1-yl)methanone (575);

4-(((2-(6-((R)-3-Aminopiperidine-1-carbonyl)-3-methylpyrazolo[1,5-a]pyridin-2-yl)-1-(cyclopropylmethyl)-1H-indol-7-yl)oxy)methyl)-1-methylpyrrolidin-2-one (576);

4-(((2-(6-((3R,5R)-3-Amino-5-fluoropiperidine-1-carbonyl)-3-methylpyrazolo[1,5-a]pyridin-2-yl)-1-(cyclopropylmethyl)-1H-indol-7-yl)oxy)methyl)-1-methylpyrrolidin-2-one (577);

4-(((2-(6-((R)-3-Aminopiperidine-1-carbonyl)-3-methylpyrazolo[1,5-a]pyridin-2-yl)-1-(cyclopropylmethyl)-1H-indol-7-yl)oxy)methyl)-1-methylpyrrolidin-2-one (578);

4-(((2-(6-((3R,5R)-3-Amino-5-fluoropiperidine-1-carbonyl)-3-methylpyrazolo[1,5-a]pyridin-2-yl)-1-(cyclopropylmethyl)-1H-indol-7-yl)oxy)methyl)-1-methylpyrrolidin-2-one (579);

(R)-(2-(7-(2-(1H-1,2,4-Triazol-1-yl)ethoxy)-1-(cyclopropylmethyl)-1H-indol-2-yl)-3-methylpyrazolo[1,5-a]pyridin-6-yl)(3-aminopiperidin-1-yl)methanone (580);

(2-(7-(2-(1H-1,2,4-Triazol-1-yl)ethoxy)-1-(cyclopropylmethyl)-1H-indol-2-yl)-3-methylpyrazolo[1,5-a]pyridin-6-yl)((3R,5R)-3-amino-5-fluoropiperidin-1-yl)methanone (581);

(R)-(2-(7-(2-(4-Amino-1H-pyrazol-1-yl)ethoxy)-1-(cyclopropylmethyl)-1H-indol-2-yl)-3-methylpyrazolo[1,5-a]pyridin-6-yl)(3-aminopiperidin-1-yl)methanone (582);

(2-(7-(2-(4-Amino-1H-pyrazol-1-yl)ethoxy)-1-(cyclopropylmethyl)-1H-indol-2-yl)-3-methylpyrazolo[1,5-a]pyridin-6-yl)((3R,5R)-3-amino-5-fluoropiperidin-1-yl)methanone (583);

(S)-5-(((2-(6-((R)-3-Aminopiperidine-1-carbonyl)-3-methylpyrazolo[1,5-a]pyridin-2-yl)-1-(cyclopropylmethyl)-1H-indol-7-yl)oxy)methyl)pyrrolidin-2-one (584);

(S)-5-(((2-(6-((3R,5R)-3-Amino-5-fluoropiperidine-1-carbonyl)-3-methylpyrazolo[1,5-a]pyridin-2-yl)-1-(cyclopropylmethyl)-1H-indol-7-yl)oxy)methyl)pyrrolidin-2-one (585);

(R)-5-(((2-(6-((R)-3-Aminopiperidine-1-carbonyl)-3-methylpyrazolo[1,5-a]pyridin-2-yl)-1-(cyclopropylmethyl)-1H-indol-7-yl)oxy)methyl)pyrrolidin-2-one (586);

(R)-5-(((2-(6-((3R,5R)-3-Amino-5-fluoropiperidine-1-carbonyl)-3-methylpyrazolo[1,5-a]pyridin-2-yl)-1-(cyclopropylmethyl)-1H-indol-7-yl)oxy)methyl)pyrrolidin-2-one (587);

4-(((2-(6-((R)-3-Aminopiperidine-1-carbonyl)-3-methylpyrazolo[1,5-a]pyridin-2-yl)-1-(cyclopropylmethyl)-1H-indol-7-yl)oxy)methyl)pyrrolidin-2-one (588);

4-(((2-(6-((R)-3-Aminopiperidine-1-carbonyl)-3-methylpyrazolo[1,5-a]pyridin-2-yl)-1-(cyclopropylmethyl)-1H-indol-7-yl)oxy)methyl)pyrrolidin-2-one (589);

4-(((2-(6-((3R,5R)-3-Amino-5-fluoropiperidine-1-carbonyl)-3-methylpyrazolo[1,5-a]pyridin-2-yl)-1-(cyclopropylmethyl)-1H-indol-7-yl)oxy)methyl)pyrrolidin-2-one (590);

4-(((2-(6-((R)-3-Aminopiperidine-1-carbonyl)-4-methoxy-3-methylpyrazolo[1,5-a]pyridin-2-yl)-1-(cyclopropylmethyl)-1H-pyrrolo[2,3-c]pyridin-7-yl)oxy)methyl)pyrrolidin-2-one (591);

(2-(7-(2-(1H-1,2,4-Triazol-1-yl)ethoxy)-1-(cyclopropylmethyl)-1H-pyrrolo[2,3-c]pyridin-2-yl)-4-methoxy-3-methylpyrazolo[1,5-a]pyridin-6-yl)((3R,5R)-3-amino-5-fluoropiperidin-1-yl)methanone (592);

(R)-(2-(7-(2-(1H-1,2,4-Triazol-1-yl)ethoxy)-1-(cyclopropylmethyl)-1H-pyrrolo[2,3-c]pyridin-2-yl)-4-methoxy-3-methylpyrazolo[1,5-a]pyridin-6-yl)(3-aminopiperidin-1-yl)methanone (593);

((3R,5R)-3-Amino-5-fluoropiperidin-1-yl)(2-(1-(cyclopropylmethyl)-7-(2-(2-methyl-1H-imidazol-1-yl)ethoxy)-1H-pyrrolo[2,3-c]pyridin-2-yl)-4-methoxy-3-methylpyrazolo[1,5-a]pyridin-6-yl)methanone (594);

(R)-(3-Aminopiperidin-1-yl)(2-(1-(cyclopropylmethyl)-7-(2-(2-methyl-1H-imidazol-1-yl)ethoxy)-1H-pyrrolo[2,3-c]pyridin-2-yl)-4-methoxy-3-methylpyrazolo[1,5-a]pyridin-6-yl)methanone (595);

(R)-(3-Aminopiperidin-1-yl)(2-(1-(cyclopropylmethyl)-7-(oxetan-3-ylmethoxy)-1H-pyrrolo[2,3-c]pyridin-2-yl)-4-methoxy-3-methylpyrazolo[1,5-a]pyridin-6-yl)methanone (596);

(2-(7-(2-(1H-Imidazol-1-yl)ethoxy)-1-(cyclopropylmethyl)-1H-pyrrolo[2,3-c]pyridin-2-yl)-4-methoxy-3-methylpyrazolo[1,5-a]pyridin-6-yl)((3R,5R)-3-amino-5-fluoropiperidin-1-yl)methanone (597);

(R)-(2-(7-(2-(1H-Imidazol-1-yl)ethoxy)-1-(cyclopropylmethyl)-1H-pyrrolo[2,3-c]pyridin-2-yl)-4-methoxy-3-methylpyrazolo[1,5-a]pyridin-6-yl)(3-aminopiperidin-1-yl)methanone (598);

(R)-(2-(7-(2-(4H-1,2,4-Triazol-4-yl)ethoxy)-1-(cyclopropylmethyl)-1H-pyrrolo[2,3-c]pyridin-2-yl)-4-methoxy-3-methylpyrazolo[1,5-a]pyridin-6-yl)(3-aminopiperidin-1-yl)methanone (599);

(2-(7-(2-(4H-1,2,4-Triazol-4-yl)ethoxy)-1-(cyclopropylmethyl)-1H-pyrrolo[2,3-c]pyridin-2-yl)-4-methoxy-3-methylpyrazolo[1,5-a]pyridin-6-yl)((3R,5R)-3-amino-5-fluoropiperidin-1-yl)methanone (600);

4-(((2-(6-((3R,5R)-3-Amino-5-fluoropiperidine-1-carbonyl)-4-methoxy-3-methylpyrazolo[1,5-a]pyridin-2-yl)-1-(cyclopropylmethyl)-1H-pyrrolo[2,3-c]pyridin-7-yl)oxy)methyl)pyrrolidin-2-one (601);

4-(((2-(6-((3R,5R)-3-Amino-5-fluoropiperidine-1-carbonyl)-4-methoxy-3-methylpyrazolo[1,5-a]pyridin-2-yl)-1-(cyclopropylmethyl)-1H-pyrrolo[2,3-c]pyridin-7-yl)oxy)methyl)pyrrolidin-2-one (602);

4-(((2-(6-((R)-3-Aminopiperidine-1-carbonyl)-4-methoxy-3-methylpyrazolo[1,5-a]pyridin-2-yl)-1-(cyclopropylmethyl)-1H-pyrrolo[2,3-c]pyridin-7-yl)oxy)methyl)pyrrolidin-2-one (603);

(5R)-5-(((2-(6-((7R)-7-Amino-2-azabicyclo[2.2.1]heptane-2-carbonyl)-4-methoxy-3-methylpyrazolo[1,5-a]pyridin-2-yl)-1-(cyclopropylmethyl)-1H-pyrrolo[2,3-c]pyridin-7-yl)oxy)methyl)pyrrolidin-2-one (604);

4-(((2-(6-((7R)-7-Amino-2-azabicyclo[2.2.1]heptane-2-carbonyl)-4-methoxy-3-methylpyrazolo[1,5-a]pyridin-2-yl)-1-(cyclopropylmethyl)-1H-pyrrolo[2,3-c]pyridin-7-yl)oxy)methyl)pyrrolidin-2-one (605);

4-(((2-(6-((7R)-7-Amino-2-azabicyclo[2.2.1]heptane-2-carbonyl)-4-methoxy-3-methylpyrazolo[1,5-a]pyridin-2-yl)-1-(cyclopropylmethyl)-1H-pyrrolo[2,3-c]pyridin-7-yl)oxy)methyl)pyrrolidin-2-one (606);

(5R)-5-(((2-(6-((7S)-7-Amino-2-azabicyclo[2.2.1]heptane-2-carbonyl)-4-methoxy-3-methylpyrazolo[1,5-a]pyridin-2-yl)-1-(cyclopropylmethyl)-1H-pyrrolo[2,3-c]pyridin-7-yl)oxy)methyl)pyrrolidin-2-one (607);

4-(((2-(6-((7R)-7-Amino-2-azabicyclo[2.2.1]heptane-2-carbonyl)-4-methoxy-3-methylpyrazolo[1,5-a]pyridin-2-yl)-1-(cyclopropylmethyl)-1H-pyrrolo[2,3-c]pyridin-7-yl)oxy)methyl)pyrrolidin-2-one (608);

(R)-(2-(7-(2-(4H-1,2,4-Triazol-4-yl)ethoxy)-1-(cyclopropylmethyl)-1H-pyrrolo[2,3-c]pyridin-2-yl)-3-methylpyrazolo[1,5-a]pyridin-6-yl)(3-aminopiperidin-1-yl)methanone (609);

(2-(7-(2-(1H-1,2,4-Triazol-1-yl)ethoxy)-1-(cyclopropylmethyl)-1H-pyrrolo[2,3-c]pyridin-2-yl)-3-methylpyrazolo[1,5-a]pyridin-6-yl)((3R,5R)-3-amino-5-fluoropiperidin-1-yl)methanone (610);

((3R,5R)-3-Amino-5-fluoropiperidin-1-yl)(2-(1-(cyclopropylmethyl)-7-(2-(2-methyl-1H-imidazol-1-yl)ethoxy)-1H-pyrrolo[2,3-c]pyridin-2-yl)-3-methylpyrazolo[1,5-a]pyridin-6-yl)methanone (611);

(R)-(3-Aminopiperidin-1-yl)(2-(1-(cyclopropylmethyl)-7-(2-(2-methyl-1H-imidazol-1-yl)ethoxy)-1H-pyrrolo[2,3-c]pyridin-2-yl)-3-methylpyrazolo[1,5-a]pyridin-6-yl)methanone (612);

(2-(7-(2-(4H-1,2,4-Triazol-4-yl)ethoxy)-1-(cyclopropylmethyl)-1H-pyrrolo[2,3-c]pyridin-2-yl)-3-methylpyrazolo[1,5-a]pyridin-6-yl)((3R,5R)-3-amino-5-fluoropiperidin-1-yl)methanone (613);

4-(((2-(6-((3R,5R)-3-Amino-5-fluoropiperidine-1-carbonyl)-3-methylpyrazolo[1,5-a]pyridin-2-yl)-1-(cyclopropylmethyl)-1H-pyrrolo[2,3-c]pyridin-7-yl)oxy)methyl)pyrrolidin-2-one (614);

4-(((2-(6-((3R,5R)-3-Amino-5-fluoropiperidine-1-carbonyl)-3-methylpyrazolo[1,5-a]pyridin-2-yl)-1-(cyclopropylmethyl)-1H-pyrrolo[2,3-c]pyridin-7-yl)oxy)methyl)pyrrolidin-2-one (615);

(2-(7-(2-(1H-Imidazol-1-yl)ethoxy)-1-(cyclopropylmethyl)-1H-pyrrolo[2,3-c]pyridin-2-yl)-3-methylpyrazolo[1,5-a]pyridin-6-yl)((3R,5R)-3-amino-5-fluoropiperidin-1-yl)methanone (616);

(R)-(2-(7-(2-(1H-Imidazol-1-yl)ethoxy)-1-(cyclopropylmethyl)-1H-pyrrolo[2,3-c]pyridin-2-yl)-3-methylpyrazolo[1,5-a]pyridin-6-yl)(3-aminopiperidin-1-yl)methanone (617);

4-(((2-(6-((R)-3-Aminopiperidine-1-carbonyl)-3-methylpyrazolo[1,5-a]pyridin-2-yl)-1-(cyclopropylmethyl)-1H-pyrrolo[2,3-c]pyridin-7-yl)oxy)methyl)pyrrolidin-2-one (618);

4-(((2-(6-((R)-3-Aminopiperidine-1-carbonyl)-3-methylpyrazolo[1,5-a]pyridin-2-yl)-1-(cyclopropylmethyl)-1H-pyrrolo[2,3-c]pyridin-7-yl)oxy)methyl)pyrrolidin-2-one (619);

(2-(7-(2-(4H-1,2,4-Triazol-4-yl)ethoxy)-1-methyl-1H-pyrrolo[2,3-c]pyridin-2-yl)-4-methoxy-3-methylpyrazolo[1,5-a]pyridin-6-yl)((3R,5R)-3-amino-5-fluoropiperidin-1-yl)methanone (620); and ((3R,5R)-3-Amino-5-fluoropiperidin-1-yl) (2-(3-(cyclopropylmethyl)-4-(1-(2-hydroxyethyl)-1H-pyrazol-4-yl) benzo[b]thiophen-2-yl)-4-methoxy-3-methylpyrazolo[1,5-a]pyridin-6-yl)methanone (621);

or a stereoisomer, an enantiomer, a diastereomer, a tautomer, or a pharmaceutically acceptable salt thereof.

In one embodiment, the present invention provides compounds with $IC_{50}$ values≤4.000 μM, using the RFMS PAD4 functional assay disclosed herein, preferably, $IC_{50}$ values≤1.000 μM, preferably, $IC_{50}$ values≤0.500 μM, preferably, $IC_{50}$ values≤0.100 μM, more preferably, $IC_{50}$ values≤0.050 μM, more preferably, $IC_{50}$ values≤0.03 μM, more preferably, $IC_{50}$ values≤0.02 μM, even more preferably, $IC_{50}$ values≤0.01 μM.

As defined above and described herein, $X_2$ is selected from N and $CR_4$. In some embodiments, $X_2$ is N. In some embodiments, $X_2$ is $CR_4$. In certain embodiments, $X_2$ is selected from those functional groups depicted in the examples below.

As defined above, $R_1$ is selected from

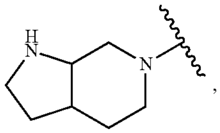
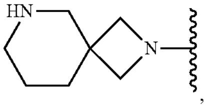
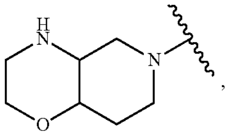
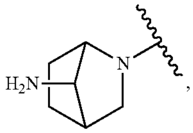
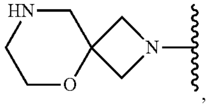
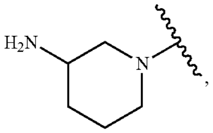
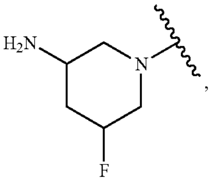
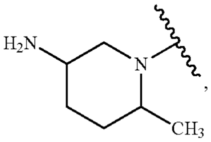

and

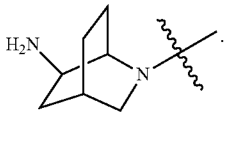

In some embodiments, $R_1$ is

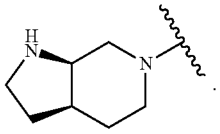 [SMILES: *N1CC[C@H]2CCN[C@H]2C1]

In some embodiments, $R_1$ is

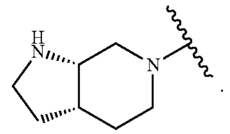 [SMILES: *N1CC[C@@H]2CCN[C@@H]2C1]

In some embodiments, $R_1$ is

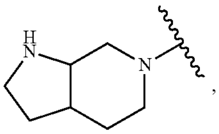
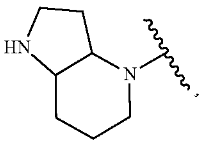
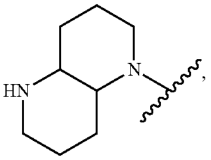
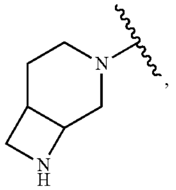
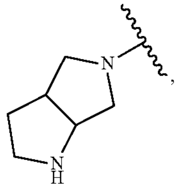
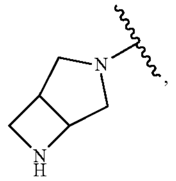
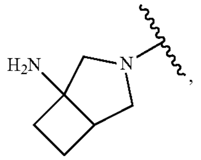
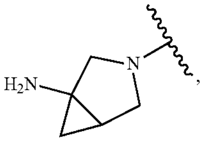

or

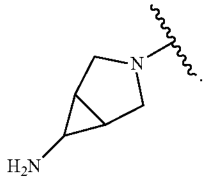

In some embodiments, $R_1$ is selected from

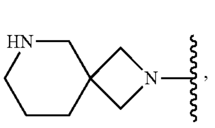
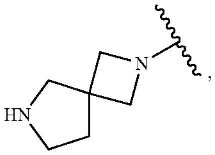
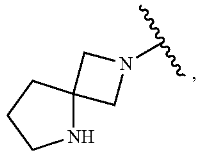
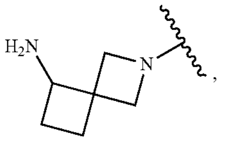

-continued
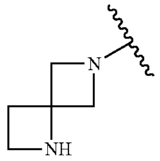, 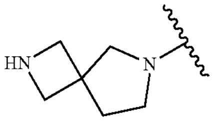,
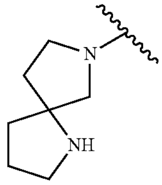, 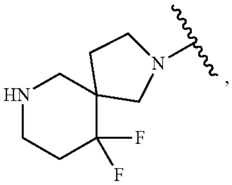,
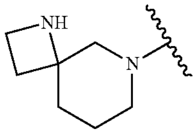, 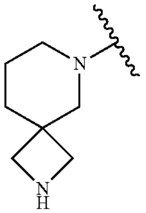,
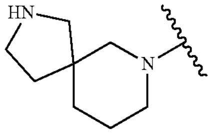, 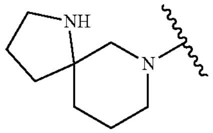,
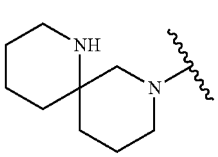, 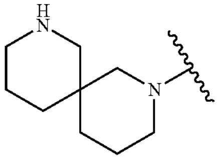, and
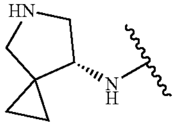.
In some embodiments, $R_1$ is selected from
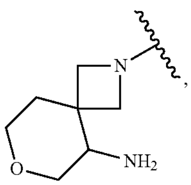, 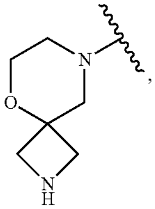,
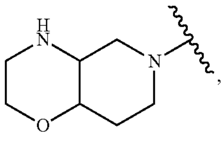, 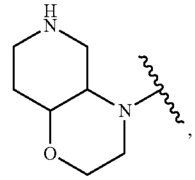,
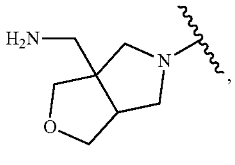, 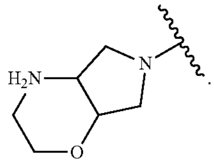.
In some embodiments, $R_1$ is selected from
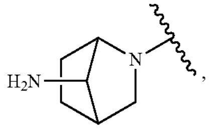, 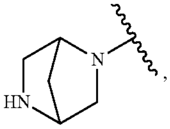,
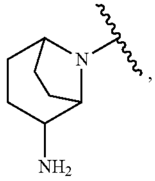, 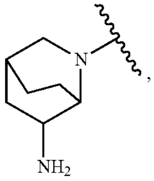,
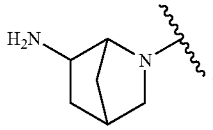, 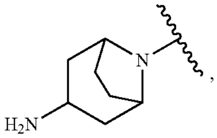,
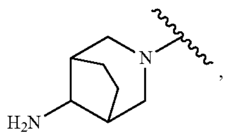, 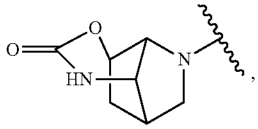,
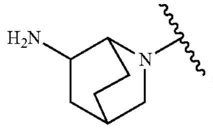, 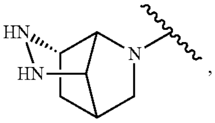,
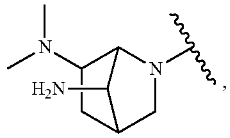, 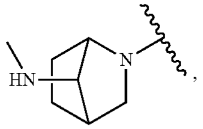,
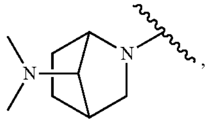, 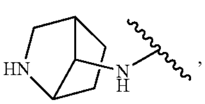,
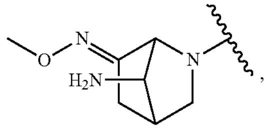, 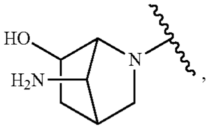,
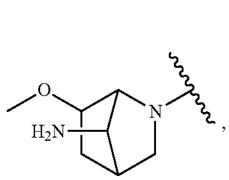, 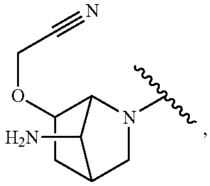,
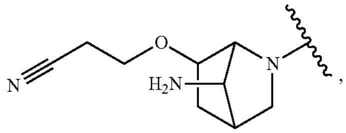,
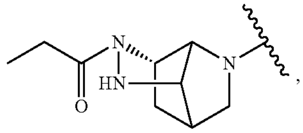, -continued
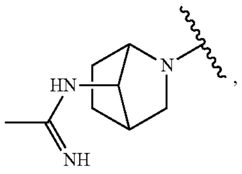
and
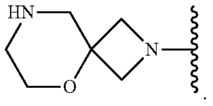 [SMILES: *N1CC2(CNCCO2)C1]
In some embodiments, $R_1$ is selected from
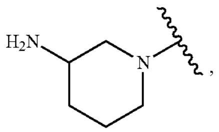
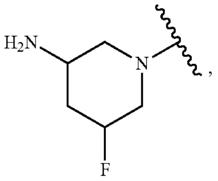
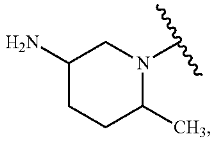
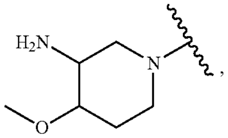
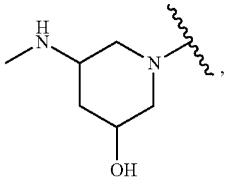
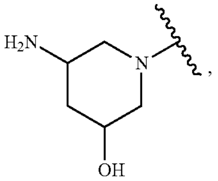
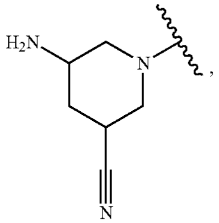
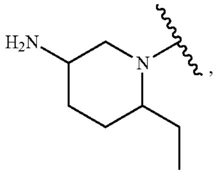
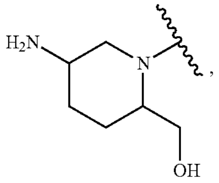
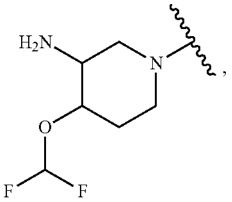
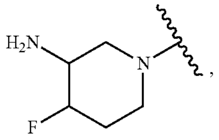
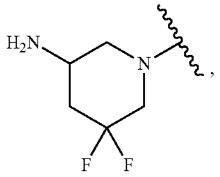
-continued
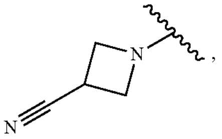
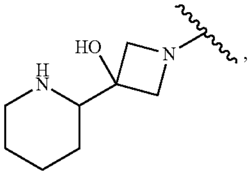
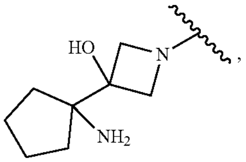
and
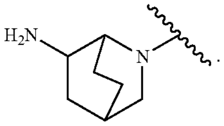
In some embodiments, $R_1$ is
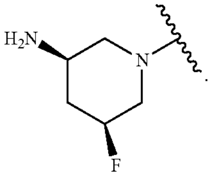 [SMILES: *N1C[C@H](N)C[C@H](F)C1]
In some embodiments, $R_1$ is
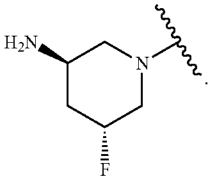 [SMILES: *N1C[C@H](N)C[C@@H](F)C1]
In some embodiments, $R_1$ is
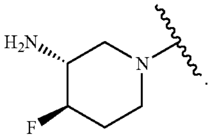 [SMILES: *N1CC[C@@H](F)[C@H](N)C1]
In some embodiments, $R_1$ is
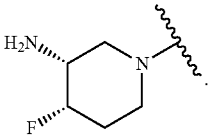 [SMILES: *N1CC[C@H](F)[C@H](N)C1]

In some embodiments, $R_1$ is
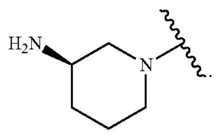 [SMILES: *N1CCC[C@@H](N)C1]
In some embodiments, $R_1$ is
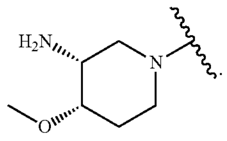 [SMILES: *N1CC[C@H](OC)[C@H](N)C1]
In some embodiments, $R_1$ is
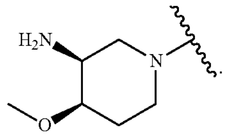 [SMILES: *N1CC[C@@H](OC)[C@@H](N)C1]
In some embodiments, $R_1$ is
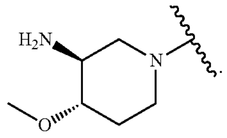 [SMILES: *N1CC[C@H](OC)[C@@H](N)C1]
In some embodiments, $R_1$ is
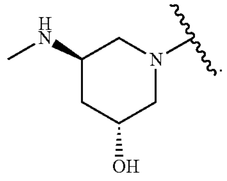 [SMILES: *N1C[C@H](O)C[C@@H](NC)C1]
In some embodiments, $R_1$ is
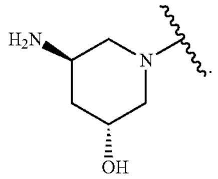 [SMILES: *N1C[C@H](N)C[C@@H](O)C1]
In some embodiments, $R_1$ is
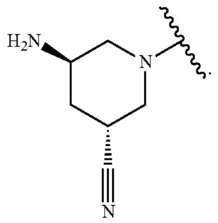 [SMILES: *N1C[C@H](N)C[C@@H](C#N)C1]
In some embodiments, $R_1$ is
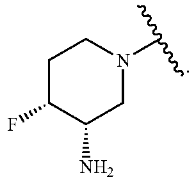
In some embodiments, $R_1$ is
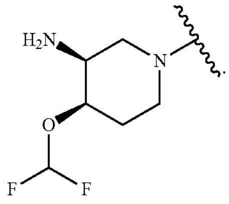 [SMILES: *N1CC[C@@H](OC(F)F)[C@@H](N)C1]
In some embodiments, $R_1$ is
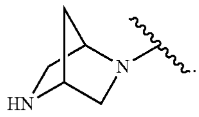 [SMILES: *N1CC2CC1CN2]
In some embodiments, $R_1$ is
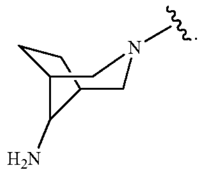
In some embodiments, $R_1$ is
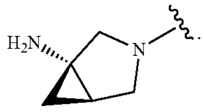

In some embodiments, $R_1$ is
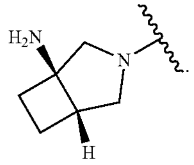 [SMILES: *N1C[C@@H]2CC[C@]2(N)C1]
In some embodiments, $R_1$ is
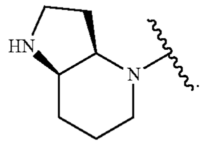 [SMILES: *N1CCC[C@H]2NCC[C@H]21]
In some embodiments, $R_1$ is
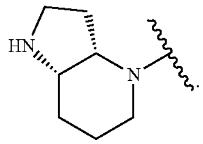 [SMILES: *N1CCC[C@@H]2NCC[C@@H]21]
In some embodiments, $R_1$ is
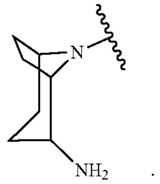 [SMILES: *N1C2CCC23CCC(N)CC13]
In some embodiments, $R_1$ is
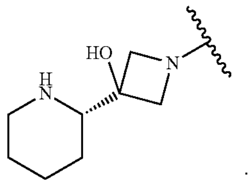 [SMILES: *N1CC(O)([C@@H]2CCCCN2)C1]
In some embodiments, $R_1$ is
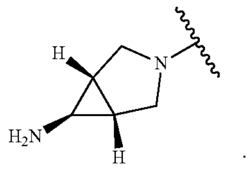 [SMILES: *N1C[C@@H]2[C@@H](N)[C@@H]2C1]
In some embodiments, $R_1$ is
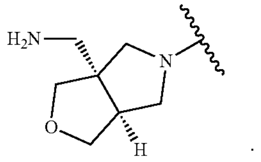 [SMILES: *N1C[C@H]2COC[C@@]2(CN)C1]
In some embodiments, $R_1$ is
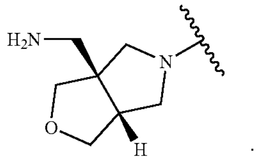 [SMILES: *N1C[C@@H]2COC[C@]2(CN)C1]
In some embodiments, $R_1$ is
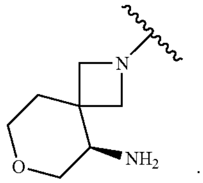 [SMILES: *N1CC2(CCOC[C@@H]2N)C1]
In some embodiments, $R_1$ is
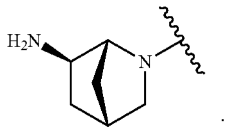 [SMILES: *N1C[C@@H]2C[C@@H](N)[C@H]1C2]
In some embodiments, $R_1$ is
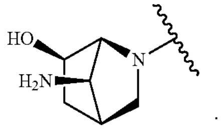 [SMILES: *N1C[C@H]2C[C@@H](O)[C@@H]1[C@@H]2N]
In some embodiments, $R_1$ is
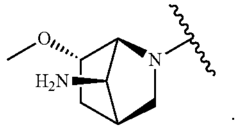 [SMILES: *N1C[C@H]2C[C@H](OC)[C@@H]1[C@@H]2N]

In some embodiments, $R_1$ is

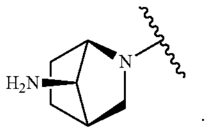 [SMILES: *N1C[C@H]2CC[C@@H]1[C@@H]2N]

In some embodiments, $R_1$ is

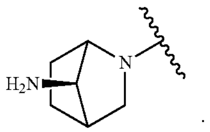 [SMILES: *N1CC2CCC1[C@@H]2N]

In some embodiments, $R_1$ is

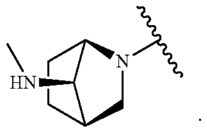 [SMILES: *N1C[C@H]2CC[C@@H]1[C@@H]2NC]

In some embodiments, $R_1$ is

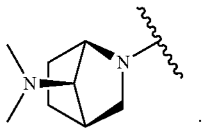 [SMILES: *N1C[C@H]2CC[C@@H]1[C@@H]2N(C)C]

In some embodiments, $R_1$ is

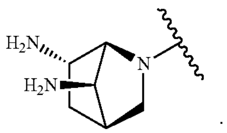 [SMILES: *N1C[C@H]2C[C@H](N)[C@@H]1[C@@H]2N]

In some embodiments, $R_1$ is

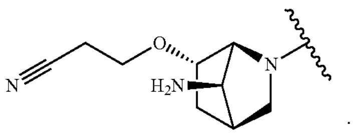 [SMILES: *N1C[C@H]2C[C@H](OCCC#N)[C@@H]1[C@@H]2N]

In some embodiments, $R_1$ is

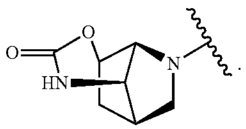 [SMILES: *N1C[C@H]2CC3OC(=O)N[C@H]2[C@@H]31]

In some embodiments, $R_1$ is

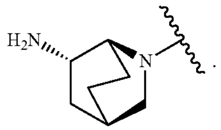 [SMILES: *N1C[C@@H]2CC[C@H]1[C@@H](N)C2]

In some embodiments, $R_1$ is

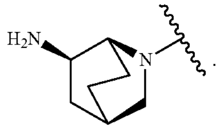 [SMILES: *N1C[C@@H]2CC[C@H]1[C@H](N)C2]

In some embodiments, $R_1$ is

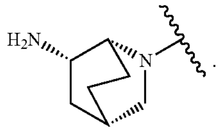 [SMILES: *N1C[C@H]2CC[C@@H]1[C@@H](N)C2]

In some embodiments, $R_1$ is

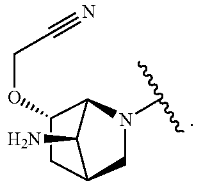 [SMILES: *N1C[C@H]2C[C@H](OCC#N)[C@@H]1[C@@H]2N]

In some embodiments, $R_1$ is

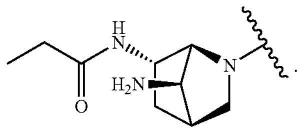 [SMILES: *N1C[C@H]2C[C@H](NC(=O)CC)[C@@H]1[C@@H]2N]

In some embodiments, $R_1$ is

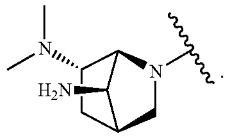 [SMILES: *N1C[C@H]2C[C@H](N(C)C)[C@@H]1[C@@H]2N]

In some embodiments, $R_1$ is

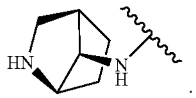 [SMILES: *N[C@@H]1[C@@H]2CC[C@H]1NC2]

In some embodiments, $R_1$ is
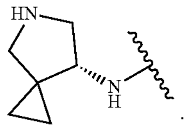 [SMILES: *N[C@H]1CNCC12CC2]
In some embodiments, $R_1$ is
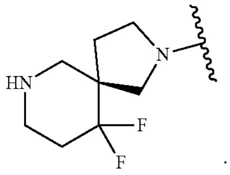 [SMILES: *N1CC[C@]2(CNCCC2(F)F)C1]
In some embodiments, $R_1$ is
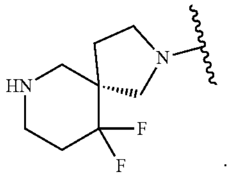 [SMILES: *N1CC[C@@]2(CNCCC2(F)F)C1]
In some embodiments, $R_1$ is
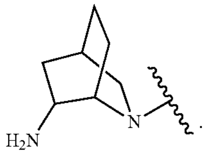
In some embodiments, $R_1$ is
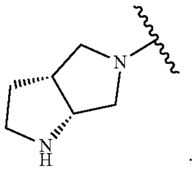 [SMILES: *N1C[C@H]2CCN[C@H]2C1]
In some embodiments, $R_1$ is
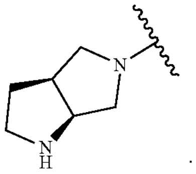 [SMILES: *N1C[C@@H]2CCN[C@@H]2C1]
In some embodiments, $R_1$ is
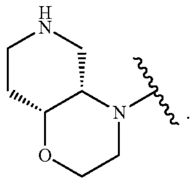 [SMILES: *N1CCO[C@@H]2CCNC[C@@H]21]
In some embodiments, $R_1$ is
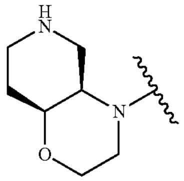 [SMILES: *N1CCO[C@H]2CCNC[C@H]21]
In some embodiments, $R_1$ is
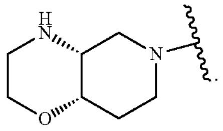 [SMILES: *N1CC[C@@H]2OCCN[C@@H]2C1]
In some embodiments, $R_1$ is
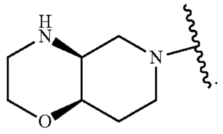 [SMILES: *N1CC[C@H]2OCCN[C@H]2C1]
In some embodiments, $R_1$ is
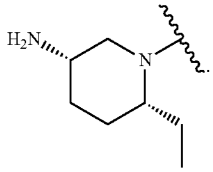 [SMILES: *N1C[C@@H](N)CC[C@H]1CC]
In some embodiments, $R_1$ is
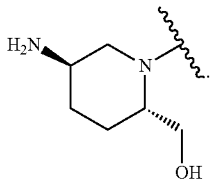 [SMILES: *N1C[C@H](N)CC[C@H]1CO]

In some embodiments, $R_1$ is

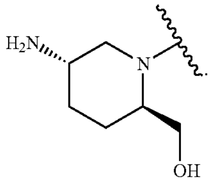 [SMILES: *N1C[C@@H](N)CC[C@@H]1CO]

In some embodiments, $R_1$ is

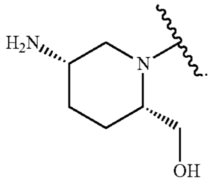 [SMILES: *N1C[C@@H](N)CC[C@H]1CO]

In some embodiments, $R_1$ is

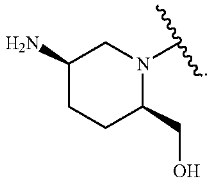 [SMILES: *N1C[C@H](N)CC[C@@H]1CO]

In some embodiments, $R_1$ is

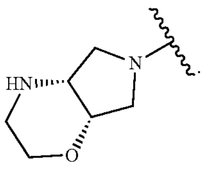 [SMILES: *N1C[C@@H]2OCCN[C@@H]2C1]

In some embodiments, $R_1$ is

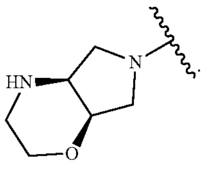 [SMILES: *N1C[C@@H]2NCCO[C@@H]2C1]

In certain embodiments, $R_1$ is selected from those functional groups depicted in the examples below. $R_1$ is preferably selected from

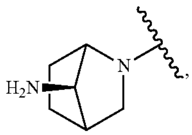,

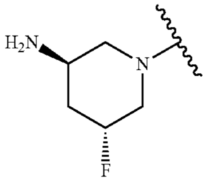,

-continued

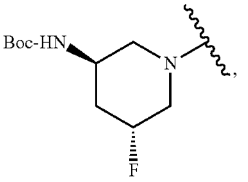,

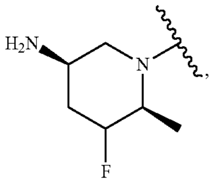,

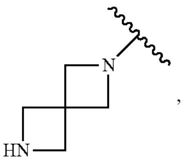,

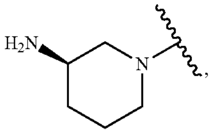,

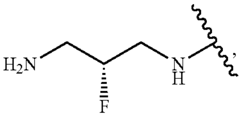, and

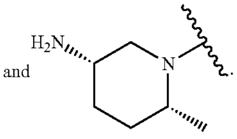.

As defined above and described herein, $R_2$ is selected from H, F, Cl, Br, —$OR_b$, and $C_{1-3}$ alkyl optionally substituted with one or more $R_e$. In some embodiments, $R_2$ is H. In some embodiments, $R_2$ is F, Cl, Br. In some embodiments, $R_2$ is F, In some embodiments, $R_2$ is $C_{1-3}$ alkyl. In some embodiments, $R_2$ is methyl. In some embodiments, $R_2$ is ethyl. In some embodiments, $R_2$ is propyl. In some embodiments, $R_2$ is $OR_b$. In some embodiments, $R_2$ is —$OCH_3$. In some embodiments, $R_2$ is —$OCH_2CH_3$. In some embodiments, $R_2$ is —$OCH_2CH_2CH_3$. In certain embodiments, $R_2$ is —$OCH(F)_2$. In certain embodiments, $R_2$ is selected from those functional groups depicted in the examples below. $R_2$ is preferably selected from H, F, Cl, $CH_3$, and $OCH_3$.

As defined above and described herein, $R_3$ is selected from $CH_3$ and $CD_3$. In some embodiments, $R_3$ is $CH_3$. In some embodiments, $R_3$ is $CD_3$. In certain embodiments, $R_3$ is selected from those functional groups depicted in the examples below. $R_3$ is preferably selected from H, F, Cl, $CH_3$, and $CH_2OH$.

As defined above and described herein, $R_4$ is selected from H, F, Cl, Br, $C_{1-4}$ alkyl, $OC_{1-4}$ alkyl substituted with one or more $R_5$,

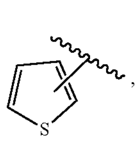,

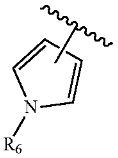,

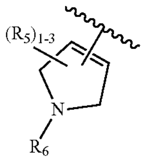,

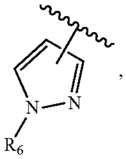,

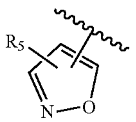,

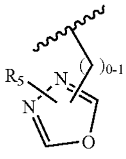,

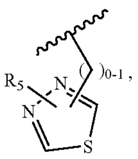,

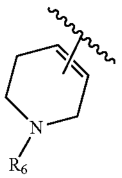,

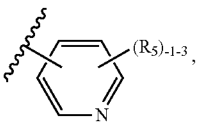,

-continued
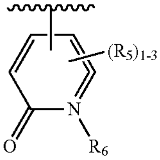 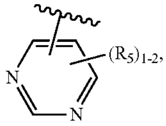 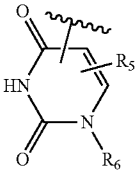 ,
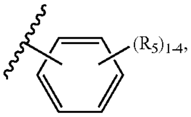 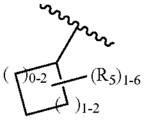 ,
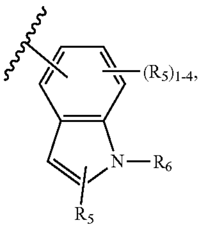 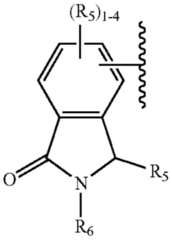 ,
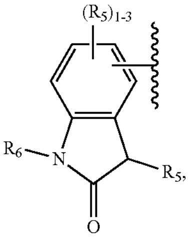 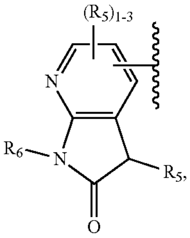
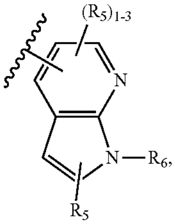 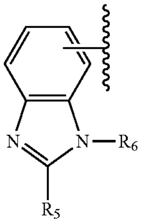 ,
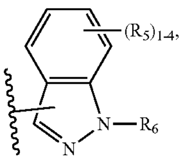 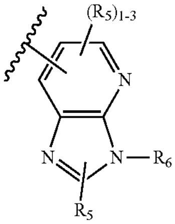 ,
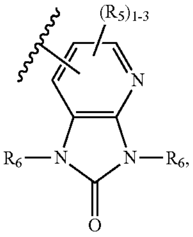 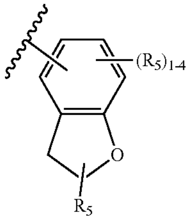 ,
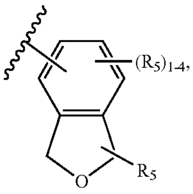 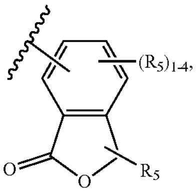
-continued
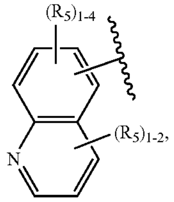 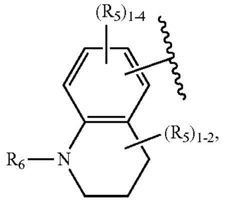
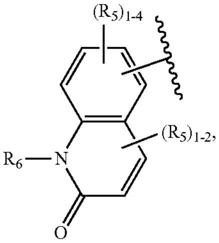 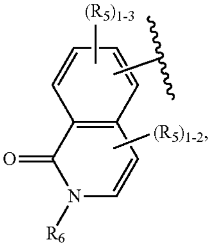
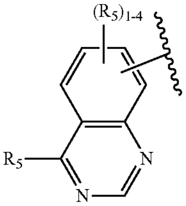 , 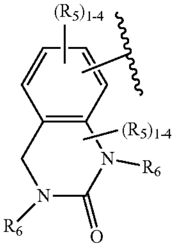 ,
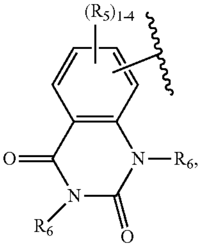 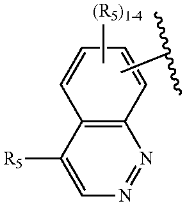 ,
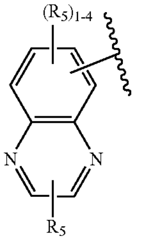 and 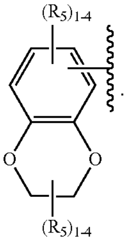 .
In some embodiments, $R_4$ is H. In some embodiments, $R_4$ is selected from F, Cl, and Br.
In some embodiments, $R_4$ is $C_{1-3}$ alkyl. In some embodiments, $R_4$ is $CH_3$.
In some embodiments, $R_4$ is selected from
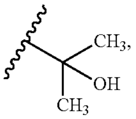 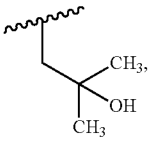 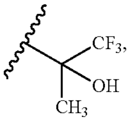
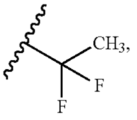 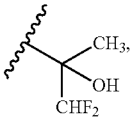 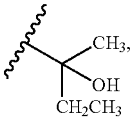

-continued
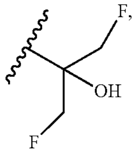
and
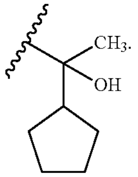
In some embodiments, $R_4$ is
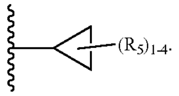
In some embodiments, $R_4$ is
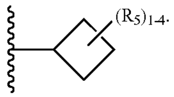
In some embodiments, $R_4$ is
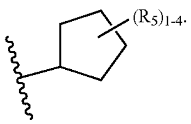
In some embodiments, $R_4$ is
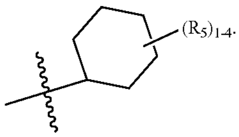
In some embodiments, $R_4$ is
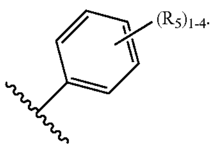
In some embodiments, $R_4$ is
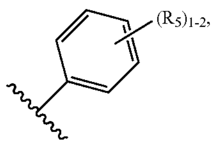
wherein $R_5$ is selected from F, Cl, —OH, —C(═O)$NH_2$. In some embodiments, $R_4$ is
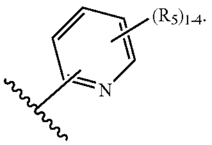
In some embodiments, $R_4$ is
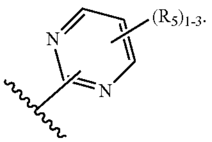
In some embodiments, $R_4$ is selected from
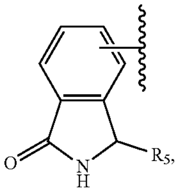
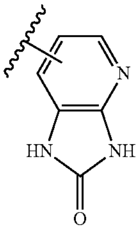
,
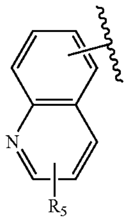
,
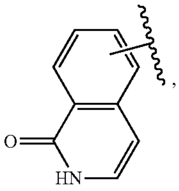
,
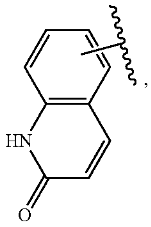
,
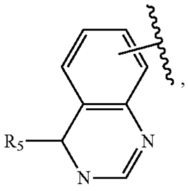
,
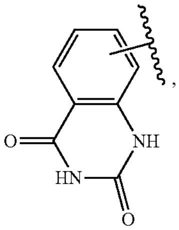
,
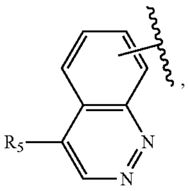
, and
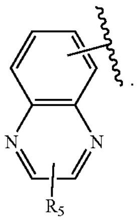
.

In some embodiments, $R_4$ is

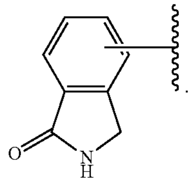

In some embodiments, $R_4$ is

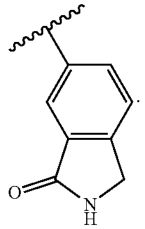 [SMILES: *c1ccc2c(c1)C(=O)NC2]

In some embodiments, $R_4$ is

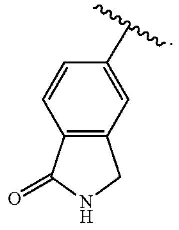 [SMILES: *c1ccc2c(c1)CNC2=O]

In some embodiments, $R_4$ is selected from

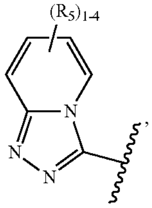, 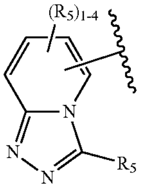 and 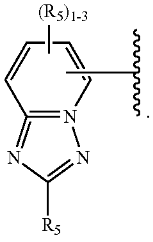

In some embodiments, $R_4$ is

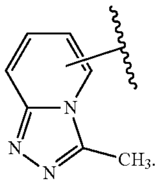

In some embodiments, $R_4$ is selected from

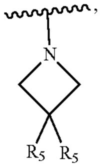, 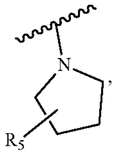, and 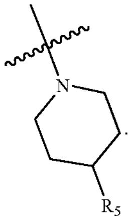

In some embodiments, $R_4$ is

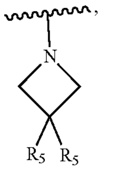

wherein $R_5$ is selected from F, Cl, and $CH_2OH$. In some embodiments, $R_4$ is

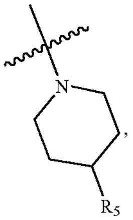

wherein $R_5$ is selected from F, Cl, —OH, —$OCH_3$—$OCH_2CH_3$, and $NH_2$. In certain embodiments, $R_4$ is selected from those functional groups depicted in the examples below.

$R_4$, alone or together with $R_5$ and $R_6$, is preferably selected from H, F, Cl, $C_{1-5}$ alkyl optionally substituted with one or more substituents selected from F, Cl, and OH, $C_{3-6}$ cycloalkyl,

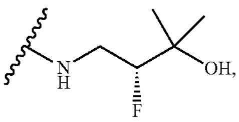 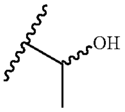,

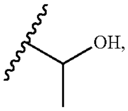 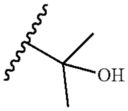, 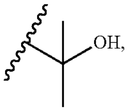

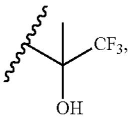 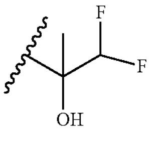 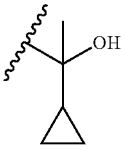,

-continued
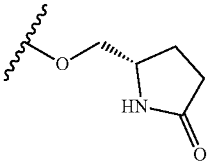
,
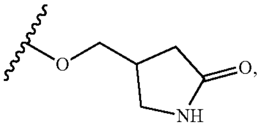
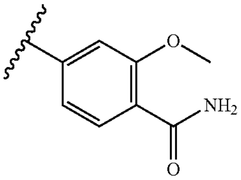
,
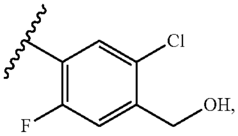
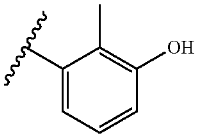
,
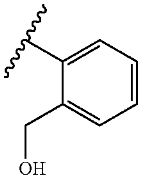
,
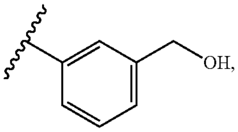
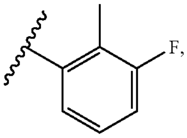
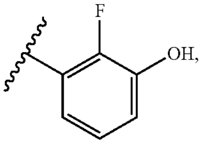
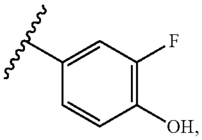
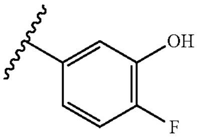
,
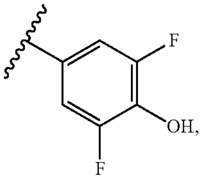
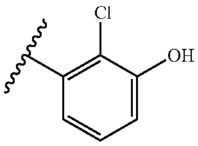
,
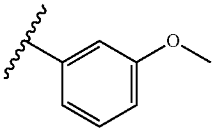
,
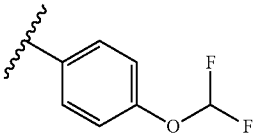
,
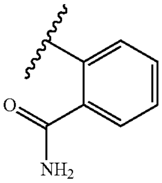
,
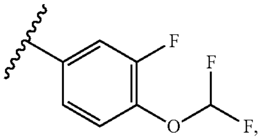
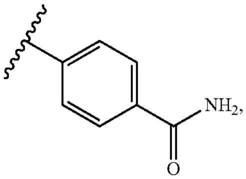
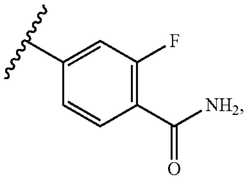
-continued
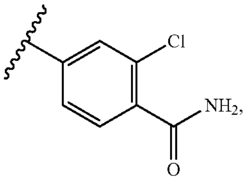
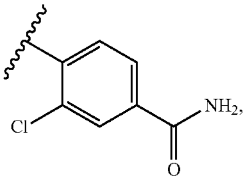
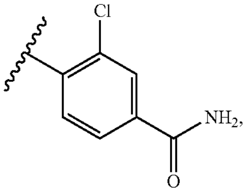
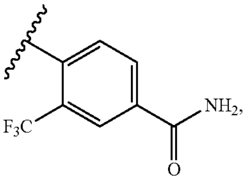
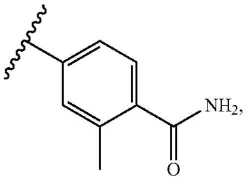
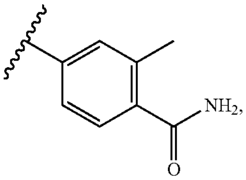
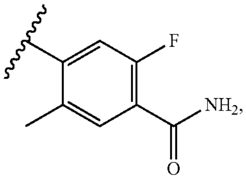
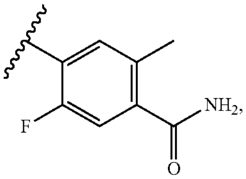
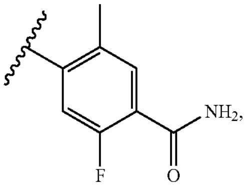
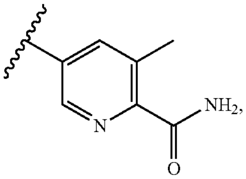
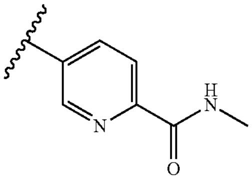
,
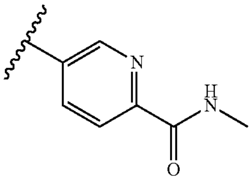
,
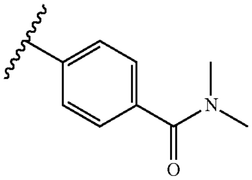
,
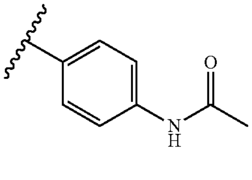
, -continued
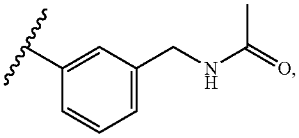
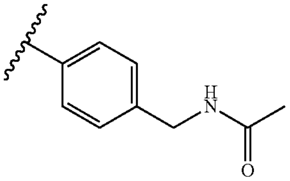
,
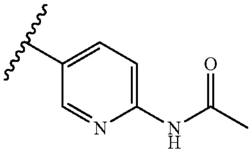
,
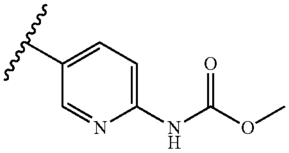
,
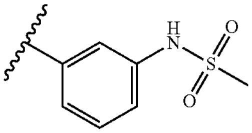
,
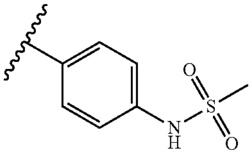
,
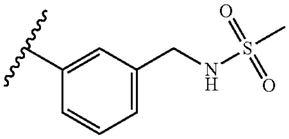
,
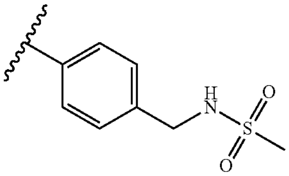
,
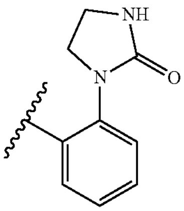
,
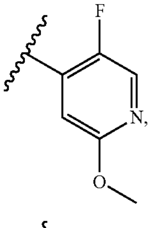
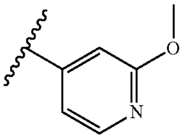
,
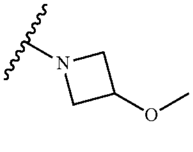
,
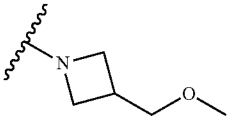
,
-continued
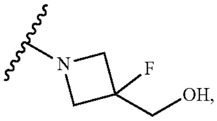
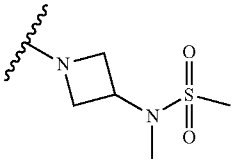
,
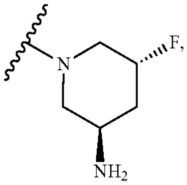
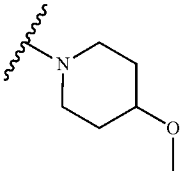
,
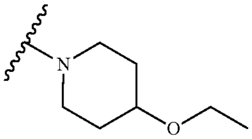
,
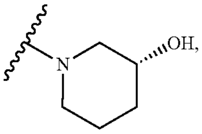
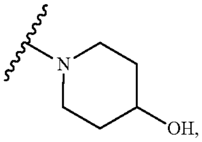
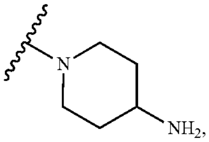
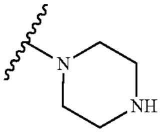
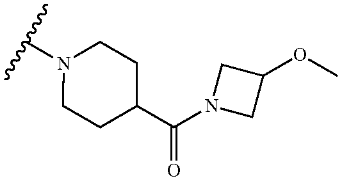
,
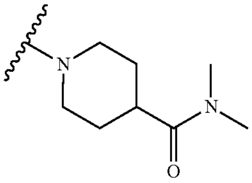
,
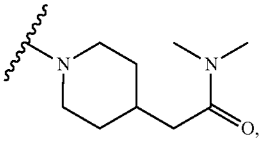
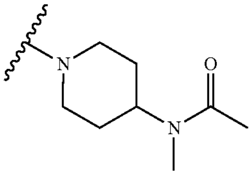
,
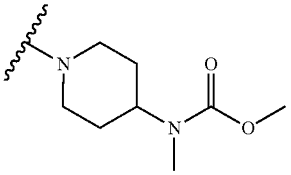
,
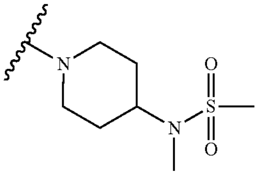
,
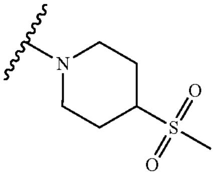
, -continued
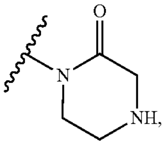
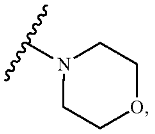
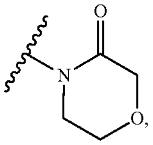
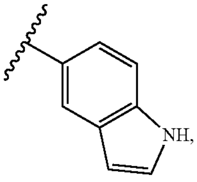
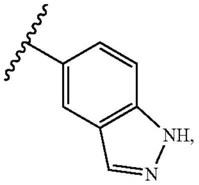
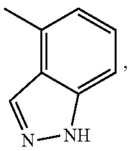
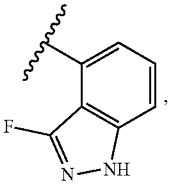
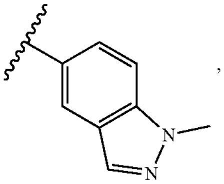
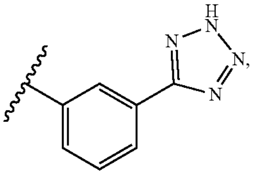
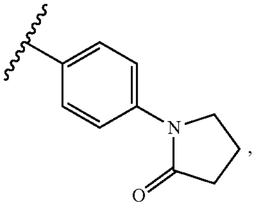
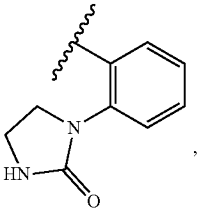
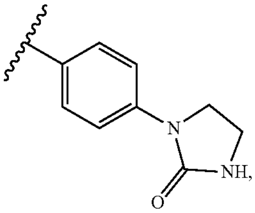
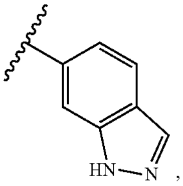
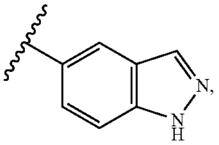
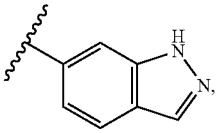
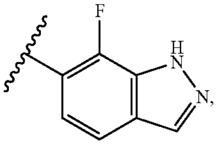
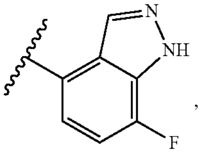
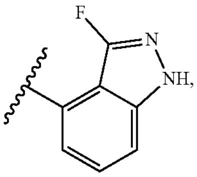
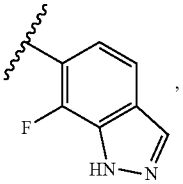
-continued
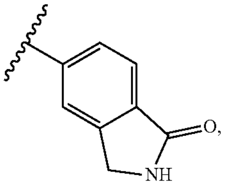
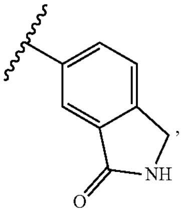
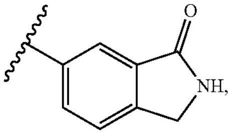
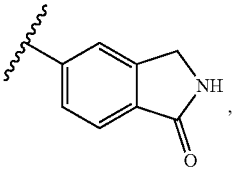
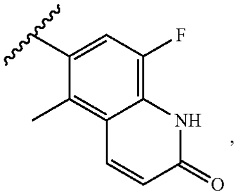
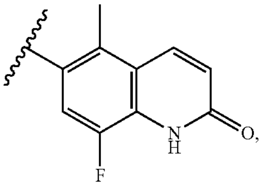
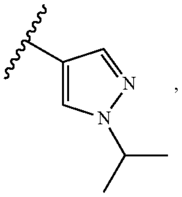
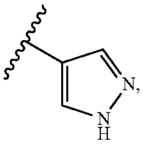
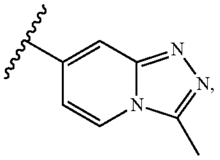
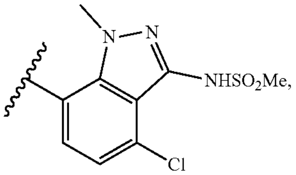
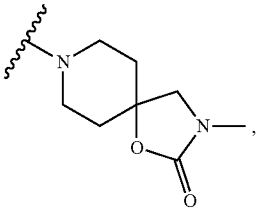
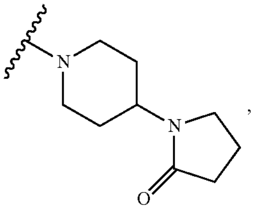
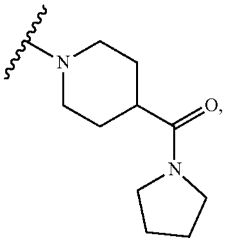

-continued
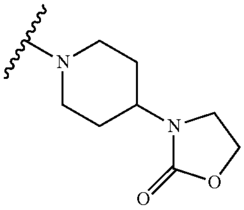,
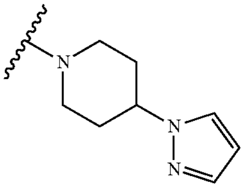,
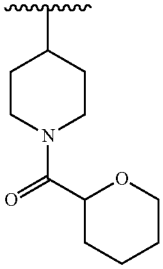,
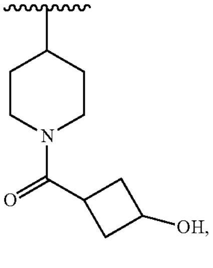
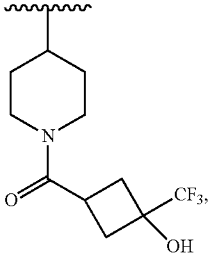
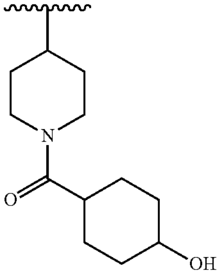,
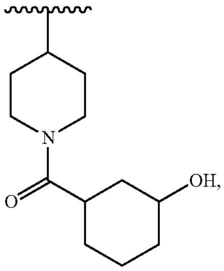
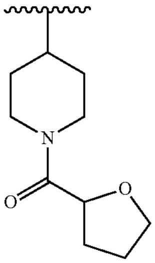,
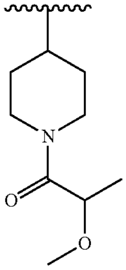,
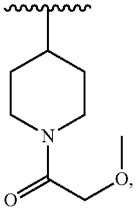
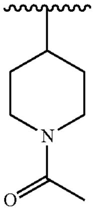,
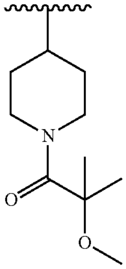,
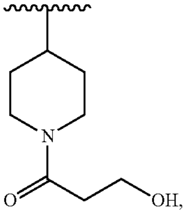
-continued
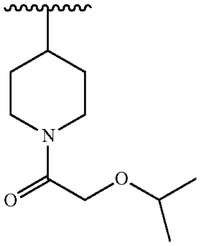,
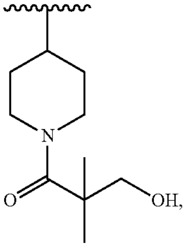
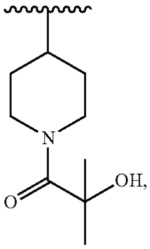
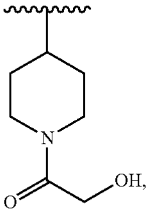
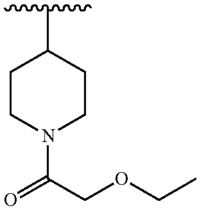,
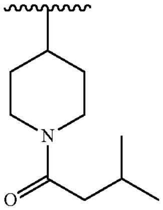,
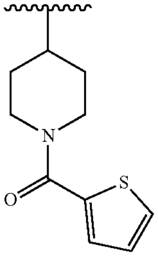,
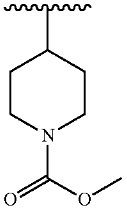,
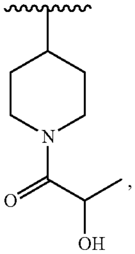,
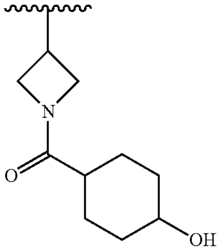,
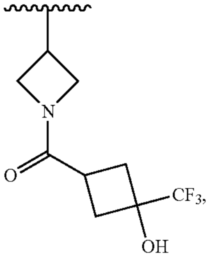
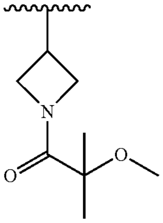,
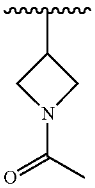,
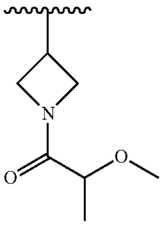,
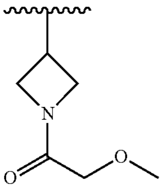, -continued

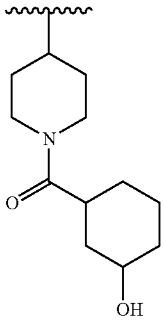,
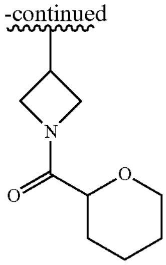,
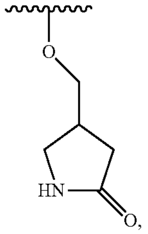,
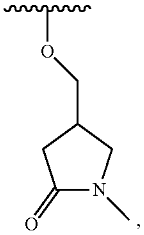,
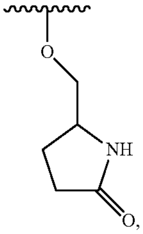,
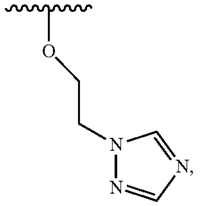,
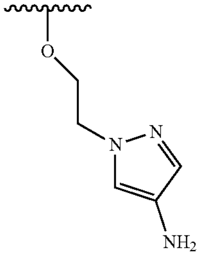,
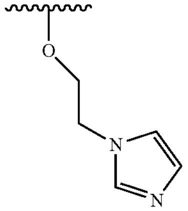,
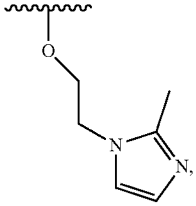,
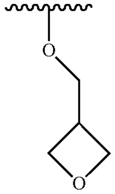,
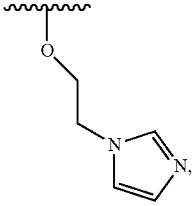 and
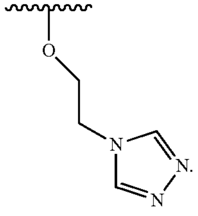

As defined above and described herein, $R_5$ is independently selected from H, F, Cl, Br, CN, =O, $C_{1-4}$ alkyl optionally substituted with one or more $R_e$, $C_{2-4}$ alkenyl optionally substituted with one or more $R_e$, $C_{2-4}$ alkynyl optionally substituted with one or more $R_e$, $—(CR_dR_d)_rOR_b$, $—(CR_dR_d)_rS(O)_pR_c$, $—(CR_dR_d)_rS(O)_pNR_aR_a$, $—(CR_dR_d)_rNR_aS(O)_pR_c$, $—(CR_dR_d)_rNR_aR_a$, $—(CR_dR_d)_rNR_aC(=O)R_b$, $—(CR_dR_d)_rNR_aC(=O)OR_b$, $—(CR_dR_d)_rNR_aC(=O)NR_aR_a$, $—(CR_dR_d)_rC(=O)R_b$, $—(CR_dR_d)_rC(=O)OR_b$, $—(CR_dR_d)_rC(=O)NR_aR_a$, $—(CR_dR_d)_rOC(=O)R_b$, $—(CR_dR_d)_rOC(=O)OR_b$, $—(CR_dR_d)_rO(CH_2)_rC(=O)NR_aR_a$, $C_{3-6}$ cycloalkyl optionally substituted with one or more $R_e$, aryl optionally substituted with one or more $R_e$, and heterocyclyl optionally substituted with one or more $R_e$.

In some embodiments, $R_5$ is selected from H, F, Cl, CN, $C_{1-4}$alkyl (optionally substituted with OH, $NH_2$, and COOH), $SC_{1-4}$alkyl, $S(O)_2C_{1-4}$alkyl, $S(O)_2$NH-cyclopropyl, $—(CH_2)_{0-1}NHS(O)_2C_{1-4}$alkyl, $—NR_aS(O)_2C_{2-4}$alkenyl, $—(CH_2)_{0-1}OH$, $OC_{1-4}$alkyl, $—(CH_2)_{0-1}NH_2$, $—(CH_2)_{0-1}NHC(=O)C_{1-4}$alkyl, $—NR_aC(=O)C_{2-4}$alkenyl, $—NHC(=O)C_{2-4}$alkynyl, $—(CH_2)_{0-1}C(=O)OH$, $—C(=O)OC_{1-4}$alkyl, $—NHC(=O)OC_{1-4}$alkyl, $—NHC(=O)O(CH_2)_2OC_{1-4}$alkyl, $—NHC(=O)OCH_2$-cyclopropyl, $—NHC(=O)NH_2$, $C(=O)NHC_{1-4}$alkyl, $CONH(CH_2)_{1-2}C(=O)OH$, $—(CH_2)_{0-1}C(=O)NH_2$, $—(CH_2)_{0-1}C(=O)NHC_{1-4}$alkyl, C(=O)NH-pyridine, $—C(=O)NH(CH_2)_2N(C_{1-4}alkyl)_2$, $—C(=O)NH(CH_2)_2OH$, $—C(=O)NH(CH_2)_2S(O)_2C_{1-4}$alkyl, and $—OC(=O)C_{1-4}$alkyl.

In some embodiments, $R_5$ is F. In some embodiments, $R_5$ is $C_{1-4}$alkyl. In some embodiments, $R_5$ is —OH or $—OC_{1-3}$alkyl. In some embodiments, $R_5$ is $—NHS(O)_2C_{1-4}$alkyl. In certain embodiments, $R_5$ is selected from those functional groups depicted in the examples below.

In some embodiments, $R_4$ is $OC_{1-3}$ alkyl substituted with one or more $R_5$; $R_5$ is

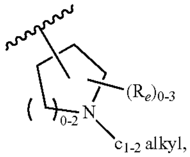,
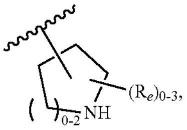,
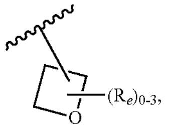,
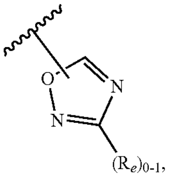,
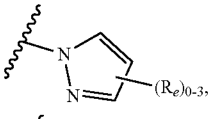,
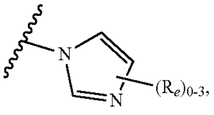,
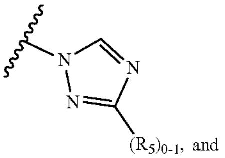, and
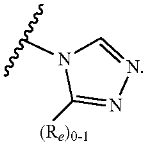.

As defined above and described herein, $R_6$ is selected from H and $C_{1-3}$alkyl optionally substituted with one or more $R_e$, $—S(O)_pR_c$, $—C(=O)R_b$, $—(CH_2)_r—C(=O)NR_aR_a$, $—C(=O)(CH_2)_rNR_aC(=O)R_b$, $—C(=O)OR_b$, $—S(O)_pNR_aR_a$, aryl optionally substituted with one or more $R_e$, or heterocyclyl optionally substituted with one or more $R_e$. In some embodiments, $R_6$ is H. In some embodiments, $R_6$ is methyl or isopropyl. In some embodiments, $R_6$ is $—(CH_2)_2OH$. In certain embodiments, $R_6$ is selected from those functional groups depicted in the examples below. $R_6$ is preferably selected from H, $C_{1-6}$ alkyl optionally substituted with one or more $R_e$, $—S(O)_pR_c$, $—S(O)_pNR_aR_a$, —C(═O)$R_b$, —C(═O)O$R_b$, —C(═O)N$R_aR_a$, $C_{3-6}$ cycloalkyl optionally substituted with one or more $R_e$, aryl optionally substituted with one or more $R_e$, and heterocyclyl optionally substituted with one or more $R_e$. In some embodiments, $R_4$, $R_5$, and $R_6$ together are selected from

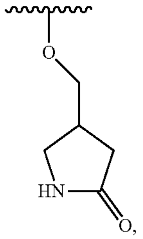

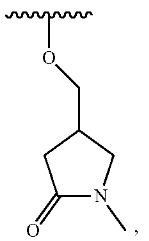

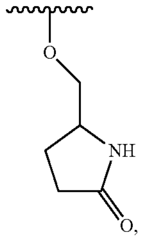

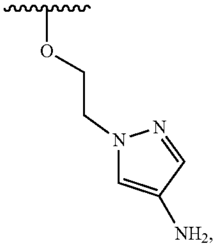

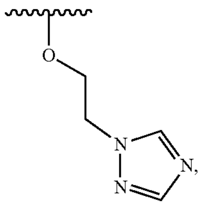

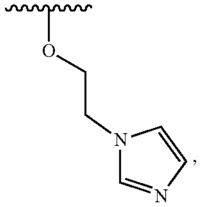

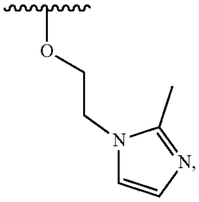

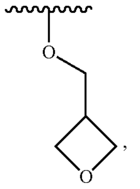

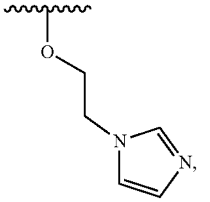

and

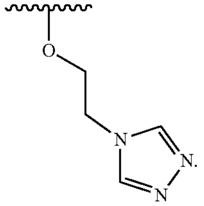

As defined above and described herein, $R_7$ is selected from H, F, Cl, Br, and $C_{1-4}$alkyl. In some embodiments, $R_7$ is H. In some embodiments, $R_7$ is $C_{1-3}$alkyl. In certain embodiments, $R_7$ is selected from those functional groups depicted in the examples below. $R_7$ is preferably selected from H, F, and Cl.

As defined above and described herein, $R_8$ is selected from H and $C_{1-3}$ alkyl optionally substituted with one or more substitutents selected from F, Cl, and $C_{3-6}$ cycloalkyl. In some embodiments, $R_8$ is hydrogen. In some embodiments, $R_8$ is $C_{1-2}$ alkyl substituted with $C_{3-6}$ cycloalkyl. In some embodiments, $R_8$ is methyl. In some embodiments, $R_8$ is ethyl. In some embodiments, $R_8$ is cyclopropyl. Preferably, $R_8$ is —$CH_2$-cyclopropyl or —$CH_2$-cyclobutyl. In some embodiments, $R_8$ is —$CH_2$-cyclobutyl optionally substituted with methyl and —OH. In certain embodiments, $R_8$ is selected from those functional groups depicted in the examples below.

As defined above and described herein, $R_a$ is independently selected from H, $C_{1-6}$ alkyl optionally substituted with one or more $R_e$, $C_{2-6}$ alkenyl optionally substituted with one or more $R_e$, $C_{2-6}$ alkynyl optionally substituted with one or more $R_e$, —$(CH_2)_r$—$C_{3-10}$ carbocyclyl optionally substituted with one or more $R_e$, and —$(CH_2)_r$-heterocyclyl optionally substituted with one or more $R_e$; or $R_a$ and $R_a$ together with the nitrogen atom to which they are both attached form a heterocyclic ring optionally substituted with one or more $R_e$.

As defined above and described herein, $R_b$ is independently selected from H, $C_{1-6}$ alkyl optionally substituted with one or more $R_e$, $C_{2-6}$ alkenyl optionally substituted with one or more $R_e$, $C_{2-6}$ alkynyl optionally substituted with one or more $R_e$, —$(CH_2)_r$—$C_{3-10}$ carbocyclyl optionally substituted with one or more $R_e$, and —$(CH_2)_r$-heterocyclyl optionally substituted with one or more $R_e$.

As defined above and described herein, $R_c$, is independently selected from $C_{1-6}$ alkyl optionally substituted with one or more $R_e$, $C_{2-6}$ alkenyl optionally substituted with one or more $R_e$, $C_{2-6}$ alkynyl optionally substituted with one or more $R_e$, —$(CH_2)_r$—$C_{3-10}$ carbocyclyl optionally substituted with one or more $R_e$, and —$(CH_2)_r$-heterocyclyl optionally substituted with one or more $R_e$.

As defined above and described herein, $R_d$ is independently selected from H, and $C_{1-6}$ alkyl optionally substituted with one or more $R_e$.

As defined above and described herein, $R_e$ is independently selected from F, Cl, Br, CN, $NH_2$, —NH—$C_{1-4}$ alkyl, —N($C_{1-4}$ alkyl)$_2$, ═O, OH, —O$C_{1-6}$ alkyl, —$CO_2$H, $C_{1-6}$ alkyl optionally substituted with one or more $R_f$, $C_{2-6}$ alkenyl, $C_{2-6}$ alkynyl, —$(CH)_r$—$C_{3-6}$ cycloalkyl optionally substituted with one or more $R_f$, —$(CH_2)_r$-aryl optionally substituted with one or more $R_f$, and —$(CH_2)_r$-heterocyclyl optionally substituted with one or more $R_f$.

As defined above and described herein, $R_f$ is independently selected from F, Cl, Br, CN, OH, $C_{1-5}$ alkyl optionally substituted with OH, $C_{2-5}$ alkenyl, $C_{2-5}$ alkynyl, $C_{3-6}$ cycloalkyl, and phenyl.

As defined above and described herein, p, at each occurrence, is independently selected from zero, 1, and 2.

As defined above and described herein, r is 0-4. In some embodiments, r is 0. In some embodiments, r is 1. In some embodiments, r is 2. In some embodiments, r is 3. In some embodiments, r is 4.

In some embodiments, the compound of Formula (Ia) is selected from examples depicted below. In certain embodiments, the present invention provides any compound described above and herein, or a pharmaceutically acceptable salt thereof or a composition for use in therapy. In some embodiments, the present invention provides any compound described above and herein in isolated form. In some embodiments, the present invention provides the compounds according to any one of claims presented below.

3. Pharmaceutical Compositions

In another aspect, the invention provides a composition comprising a compound of this invention or a stereoisomer, an enantiomer, a diastereomer, a tautomer, or a pharmaceutically acceptable salt thereof, and a pharmaceutically acceptable carrier, adjuvant, or vehicle. The amount of a compound in the compositions of this invention is such that it is effective to measurably inhibit PAD4 in a biological sample or in a patient. In certain embodiments, the amount of compound in compositions of this invention is such that it is effective to measurably inhibit PAD4, in a biological sample or in a patient. In certain embodiments, a composition of this invention is formulated for administration to a patient in need of such composition. In some embodiments, a composition of this invention is formulated for oral administration to a patient.

The term "subject," as used herein, is used interchangeably with the term "patient" and means an animal, preferably a mammal. In some embodiments, a subject or patient is a human. In other embodiments, a subject (or patient) is a veterinary subject (or patient). In some embodiments, a veterinary subject (or patient) is a canine, a feline, or an equine subject.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs. Topical application for the lower intestinal tract can be effected in a rectal suppository formulation (see above) or in a suitable enema formulation. Topically-transdermal patches may also be used. For topical applications, provided pharmaceutically acceptable compositions may be formulated in a suitable ointment containing the active component suspended or dissolved in one or more carriers. Carriers for topical administration of compounds of this invention include, but are not limited to, mineral oil, liquid petrolatum, white petrolatum, propylene glycol, polyoxyethylene, polyoxypropylene compound, emulsifying wax and water.

Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Preferably, pharmaceutically acceptable compositions of this invention are formulated for oral administration. Such formulations may be administered with or without food. In some embodiments, pharmaceutically acceptable compositions of this invention are administered without food. In other embodiments, pharmaceutically acceptable compositions of this invention are administered with food.

Pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, as required. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid may also be used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature, and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar-agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

The amount of compounds of the present invention that may be combined with the carrier materials to produce a composition in a single dosage form will vary depending upon the host treated, the particular mode of administration. Preferably, provided compositions should be formulated so that a dosage of between 0.01-100 mg/kg body weight/day of the inhibitor can be administered to a patient receiving these compositions.

A compound of the current invention can be administered alone or in combination with one or more other therapeutic compounds, possible combination therapy taking the form of fixed combinations or the administration of a compound of the invention and one or more other therapeutic compounds being staggered or given independently of one another, or the combined administration of fixed combinations and one or more other therapeutic compounds. Exemplary of such other therapeutic agents include corticosteroids, rolipram, calphostin, cytokine-suppressive anti-inflammatory drugs (CSAIDs), Interleukin-10, glucocorticoids, salicylates, nitric oxide, and other immunosuppressants; nuclear translocation inhibitors, such as deoxyspergualin (DSG); non-steroidal antiinflammatory drugs (NSAIDs) such as ibuprofen, celecoxib and rofecoxib; steroids such as prednisone or dexamethasone; antiviral agents such as abacavir; antiproliferative agents such as methotrexate, leflunomide, FK506 (tacrolimus, Prograf); cytotoxic drugs such as azathiprine and cyclophosphamide; TNF-α inhibitors such as tenidap, anti-TNF antibodies or soluble TNF receptor, and rapamycin (sirolimus or Rapamune) or derivatives thereof. A compound of the current invention can besides or in addition be administered especially for tumor therapy in combination with chemotherapy, radiotherapy, immunotherapy, phototherapy, surgical intervention, or a combination of these. Long-term therapy is equally possible as is adjuvant therapy in the context of other treatment strategies, as described above. Other possible treatments are therapy to maintain the patient's status after tumor regression, or even chemopreventive therapy, for example in patients at risk.

Those additional agents may be administered separately from an inventive compound-containing composition, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another normally within five hours from one another.

As used herein, the term "combination," "combined," and related terms refer to the simultaneous or sequential administration of therapeutic agents in accordance with this invention. For example, a compound of the present invention may be administered with another therapeutic agent simultaneously or sequentially in separate unit dosage forms or together in a single unit dosage form. Accordingly, the present invention provides a single unit dosage form comprising a compound of the current invention, an additional therapeutic agent, and a pharmaceutically acceptable carrier, adjuvant, or vehicle.

The amount of both an inventive compound and additional therapeutic agent (in those compositions which comprise an additional therapeutic agent as described above) that may be combined with the carrier materials to produce a single dosage form will vary depending upon the host treated and the particular mode of administration. Preferably, compositions of this invention should be formulated so that a dosage of between 0.01-100 mg/kg body weight/day of an inventive compound can be administered.

In those compositions which comprise an additional therapeutic agent, that additional therapeutic agent and the compound of this invention may act synergistically. Therefore, the amount of additional therapeutic agent in such compositions will be less than that required in a monotherapy utilizing only that therapeutic agent.

The amount of additional therapeutic agent present in the compositions of this invention will be no more than the amount that would normally be administered in a composition comprising that therapeutic agent as the only active agent. Preferably, the amount of additional therapeutic agent in the presently disclosed compositions will range from about 50% to 100% of the amount normally present in a composition comprising that agent as the only therapeutically active agent.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease or disorder being treated. The amount of a compound of the present invention in the composition will also depend upon the particular compound in the composition.

4. Uses of Compounds

Compounds and compositions described herein are generally useful for the inhibition of PAD4.

The activity of a compound utilized in this invention as an inhibitor of PAD4, may be assayed in vitro, in vivo or in a cell line. In vitro assays include assays that determine the inhibition of PAD4. Detailed conditions for assaying a compound utilized in this invention as an inhibitor of PAD4 are set forth in the Examples below. In some embodiments, a provided compound inhibits PAD4 selectively as compared to PAD2.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

Provided compounds are inhibitors of PAD4 and are therefore useful for treating one or more diseases or disorders associated with PAD4 enzyme activity. Thus, in certain embodiments, the present invention provides a method for treating a disease or a disorder associated with PAD4 enzyme activity, comprising the step of administering to a patient in need thereof a compound of the present invention, or a pharmaceutically acceptable composition thereof.

In one embodiment, a disease or a disorder associated with PAD4 enzyme activity is a disease, condition, or disorder mediated by inappropriate PAD4 activity. In some embodiments, a disease or a disorder associated with PAD4 enzyme activity is selected from the group consisting of rheumatoid arthritis, vasculitis, systemic lupus erythematosus, ulcerative colitis, cancer, cystic fibrosis, asthma, cutaneous lupus erythematosus, and psoriasis. In a further embodiment, the disease or a disorder associated with PAD4 enzyme activity is rheumatoid arthritis. In a further embodiment, the disease or a disorder associated with PAD4 enzyme activity is systemic lupus. In a further embodiment, the disease or a disorder associated with PAD4 enzyme activity is vasculitis. In a further embodiment, the disease or a disorder associated with PAD4 enzyme activity cutaneous lupus erythematosus. In a further embodiment, the disease or a disorder associated with PAD4 enzyme activity is psoriasis.

In one embodiment there is provided a method of treatment of rheumatoid arthritis, vasculitis, systemic lupus erythematosus, ulcerative colitis, cancer, cystic fibrosis, asthma, cutaneous lupus erythematosus, or psoriasis, which method comprises administering to a human subject in need thereof, a therapeutically effective amount of a provided compound or a stereoisomer, an enantiomer, a diastereomer, a tautomer, or a pharmaceutically acceptable salt thereof.

In one embodiment there is provided a method of treatment of rheumatoid arthritis, which method comprises administering to a human subject in need thereof, a therapeutically effective amount of a provided compound, a stereoisomer, an enantiomer, a diastereomer, a tautomer, or a pharmaceutically acceptable salt thereof. In one embodiment there is provided a method of treatment of systemic lupus, which method comprises administering to a human subject in need thereof, a therapeutically effective amount of a provided compound, a stereoisomer, an enantiomer, a diastereomer, a tautomer, or a pharmaceutically acceptable salt thereof. In one embodiment there is provided a method of treatment of vasculitis, which method comprises administering to a human subject in need thereof, a therapeutically effective amount of a provided compound, a stereoisomer, an enantiomer, a diastereomer, a tautomer, or a pharmaceutically acceptable salt thereof. In one embodiment there is provided a method of treatment of cutaneous lupus erythematosus, which method comprises administering to a human subject in need thereof, a therapeutically effective amount of a provided compound, a stereoisomer, an enantiomer, a diastereomer, a tautomer, or a pharmaceutically acceptable salt thereof. In one embodiment there is provided a method of treatment of psoriasis, which method comprises administering to a human subject in need thereof, a therapeutically effective amount of a provided compound, a stereoisomer, an enantiomer, a diastereomer, a tautomer, or a pharmaceutically acceptable salt thereof.

In some embodiments, a disease or a disorder associated with PAD4 enzyme activity is selected from the group consisting of acid-induced lung injury, acne (PAPA), acute lymphocytic leukemia, acute respiratory distress syndrome, Addison's disease, adrenal hyperplasia, adrenocortical insufficiency, ageing, AIDS, alcoholic hepatitis, alcoholic liver disease, allergen induced asthma, allergic bronchopulmonary, aspergillosis, allergic conjunctivitis, alopecia, Alzheimer's disease, amyloidosis, amyotropic lateral sclerosis, weight loss, angina pectoris, angioedema, anhidrotic ecodermal dysplasia-ID, ankylosing spondylitis, anterior segment, inflammation, antiphospholipid syndrome, aphthous stomatitis, appendicitis, arthritis, asthma, atherosclerosis, atopic dermatitis, autoimmune diseases, autoimmune hepatitis, bee sting-induced inflammation, Bechet's disease, Bechet's syndrome, Bells Palsey, berylliosis, Blau syndrome, bone pain, bronchiolitis, burns, bursitis, cancer, cardiac hypertrophy, carpal tunnel syndrome, catabolic disorders, cataracts, cerebral aneurysm, chemical irritant-induced inflammation, chorioretinitis, chronic heart failure, chronic lung disease of prematurity, chronic lymphocytic leukemia, chronic obstructive pulmonary disease, colitis, complex regional pain syndrome, connective tissue disease, corneal ulcer, crohn's disease, cryopyrin-associated periodic syndromes, cyrptococcosis, cystic fibrosis, deficiency of the interleukin-1-receptor antagonist (DIRA), dermatitis, dermatitis endotoxemia, dermatomyositis, diffuse intrinsic pontine glioma, endometriosis, endotoxemia, epicondylitis, erythroblastopenia, familial amyloidotic polyneuropathy, familial cold urticarial, familial Mediterranean fever, fetal growth retardation, glaucoma, glomerular disease, glomerular nephritis, gout, gouty arthritis, graft-versus-host disease, gut diseases, head injury, headache, hearing loss, heart disease, hemolytic anemia, Henoch-Scholein purpura, hepatitis, hereditary periodic fever syndrome, herpes zoster and simplex, HIV-1, Hodgkin's disease, Huntington's disease, hyaline membrane disease, hyperammonemia, hypercalcemia, hypercholesterolemia, hyperimmunoglobulinemia D with recurrent fever (HIDS), hypoplastic and other anemias, hypoplastic anemia, idiopathic thrombocytopenic purpura, incontinentia pigmenti, infectious mononucleosis, inflammatory bowel disease, inflammatory lung disease, inflammatory neuropathy, inflammatory pain, insect bite-induced inflammation, iritis, irritant-induced inflammation, ischemia/reperfusion, juvenile rheumatoid arthritis, keratitis, kidney disease, kidney injury caused by parasitic infections, kidney injury caused by parasitic infections, kidney transplant rejection prophylaxis, leptospiriosis, leukemia, Loeffler's syndrome, lung injury, lupus, lupus nephritis, lymphoma, meningitis, mesothelioma, mixed connective tissue disease, Muckle-Wells syndrome (urticaria deafness amyloidosis), multiple sclerosis, muscle wasting, muscular dystrophy, myasthenia gravis, myocarditis, mycosis fungoides, myelodysplastic syndrome, myositis, nasal sinusitis, necrotizing enterocolitis, neonatal onset multisystem inflammatory disease (NOMID), nephrotic syndrome, neuritis, neuropathological diseases, non-allergen induced asthma, obesity, ocular allergy, optic neuritis, organ transplant, osteoarthritis, otitis media, Paget's disease, pain, pancreatitis, Parkinson's disease, pemphigus, pericarditis, periodic fever, periodontitis, peritoneal endometriosis, pertussis, pharyngitis and adenitis (PFAPA syndrome), plant irritant-induced inflammation, pneumonia, pneumonitis, pneumosysts infection, poison ivy/urushiol oil-induced inflammation, polyarteritis nodosa, polychondritis, polycystic kidney disease, polymyositis, psoriasis, psychosocial stress diseases, pulmonary disease, pulmonary hypertension, pulmonary fibrosis, pyoderma gangrenosum, pyogenic sterile arthritis, renal disease, retinal disease, rheumatic carditis, rheumatic disease, rheumatoid arthritis, sarcoidosis, seborrhea, sepsis, severe pain, sickle cell, sickle cell anemia, silica-induced disease, Sjogren's syndrome, skin diseases, sleep apnea, solid tumors, spinal cord injury, Stevens-Johnson syndrome, stroke, subarachnoid hemorrhage, sunburn, temporal arteritis, tenosynovitis, thrombocytopenia, thyroiditis, tissue transplant, TNF receptor associated periodic syndrome (TRAPS), toxoplasmosis, transplant, traumatic brain injury, tuberculosis, type 1 diabetes, type 2 diabetes, ulcerative colitis, urticarial, uveitis, Wegener's granulomatosis, interstitial lung disease, psoriatic arthritis, juvenile idiopathic arthritis, Sjögren's syndrome, antineutrophil cytoplasmic antibody (ANCA)-associated vasculitis, antiphospholipid antibody syndrome, sepsis, deep vein thrombosis, fibrosis, Alzheimer's, scleroderma and CREST syndrome.

In one embodiment, the invention provides a compound, or a pharmaceutically acceptable salt thereof, for use in therapy. In another embodiment, the invention provides a compound, or a pharmaceutically acceptable salt thereof, for use in the treatment of a disease or a disorder mediated by inappropriate PAD4 activity. In another embodiment, the invention provides a compound, or a stereoisomer, an enantiomer, a diastereomer, a tautomer, or a pharmaceutically acceptable salt thereof, for use in the treatment of rheumatoid arthritis, vasculitis, systemic lupus erythematosus, ulcerative colitis, cancer, cystic fibrosis, asthma, cutaneous lupus erythematosus, or psoriasis. In another embodiment, the invention provides a compound, or a stereoisomer, an enantiomer, a diastereomer, a tautomer, or a pharmaceutically acceptable salt thereof, for use in the treatment of rheumatoid arthritis. In another embodiment, the invention provides a compound, or a stereoisomer, an enantiomer, a diastereomer, a tautomer, or a pharmaceutically acceptable salt thereof, for use in the treatment of systemic lupus. In another embodiment, the invention provides a compound, or a stereoisomer, an enantiomer, a diastereomer, a tautomer, or a pharmaceutically acceptable salt thereof, for use in the treatment of vasculitis. In another embodiment, the invention provides a compound, or a stereoisomer, an enantiomer, a diastereomer, a tautomer, or a pharmaceutically acceptable salt thereof, for use in the treatment of cutaneous lupus erythematosus. In another embodiment, the invention provides a compound, or a stereoisomer, an enantiomer, a diastereomer, a tautomer, or a pharmaceutically acceptable salt thereof, for use in the treatment of psoriasis. In another embodiment, the invention provides the use of a compound, or a stereoisomer, an enantiomer, a diastereomer, a tautomer, or a pharmaceutically acceptable salt thereof, in the manufacture of a medicament for use in the treatment of a disorder mediated by inappropriate PAD4 activity. In another embodiment, the invention provides the use of a compound, or a stereoisomer, an enantiomer, a diastereomer, a tautomer, or a pharmaceutically acceptable salt thereof, in the manufacture of a medicament for use in the treatment of rheumatoid arthritis, vasculitis, systemic lupus erythematosus, ulcerative colitis, cancer, cystic fibrosis, asthma, cutaneous lupus erythematosus, or psoriasis. In another embodiment, the invention provides the use of a compound, or a stereoisomer, an enantiomer, a diastereomer, a tautomer, or a pharmaceutically acceptable salt thereof, in the manufacture of a medicament for use in the treatment of rheumatoid arthritis. In another embodiment, the invention provides the use of a compound, or a stereoisomer, an enantiomer, a diastereomer, a tautomer, or a pharmaceutically acceptable salt thereof, in the manufacture of a medicament for use in the treatment of systemic lupus. In another embodiment, the invention provides the use of a compound, or a stereoisomer, an enantiomer, a diastereomer, a tautomer, or a pharmaceutically acceptable salt thereof, in the manufacture of a medicament for use in the treatment of vasculitis. In another embodiment, the invention provides the use of a compound, or a stereoisomer, an enantiomer, a diastereomer, a tautomer, or a pharmaceutically acceptable salt thereof, in the manufacture of a medicament for use in the treatment of cutaneous lupus erythematosus. In another embodiment, the invention provides the use of a compound, or a stereoisomer, an enantiomer, a diastereomer, a tautomer, or a pharmaceutically acceptable salt thereof, in the manufacture of a medicament for use in the treatment of psoriasis. In a further embodiment, the invention provides a pharmaceutical composition for the treatment or prophylaxis of a disease or a disorder mediated by inappropriate PAD4 activity comprising a provided compound, or a stereoisomer, an enantiomer, a diastereomer, a tautomer, or a pharmaceutically acceptable salt thereof. In a further embodiment, the invention provides a pharmaceutical composition for the treatment or prophylaxis of rheumatoid arthritis, vasculitis, systemic lupus erythematosus, ulcerative colitis, cancer, cystic fibrosis, asthma, cutaneous lupus erythematosus, or psoriasis, comprising a provided compound, or a stereoisomer, an enantiomer, a diastereomer, a tautomer, or a pharmaceutically acceptable salt thereof. In a further embodiment, the invention provides a pharmaceutical composition for the treatment or prophylaxis of rheumatoid arthritis comprising a provided compound, or a stereoisomer, an enantiomer, a diastereomer, a tautomer, or a pharmaceutically acceptable salt thereof. In a further embodiment, the invention provides a pharmaceutical composition for the treatment or prophylaxis of systemic lupus comprising a provided compound, or a stereoisomer, an enantiomer, a diastereomer, a tautomer, or a pharmaceutically acceptable salt thereof. In a further embodiment, the invention provides a pharmaceutical composition for the treatment or prophylaxis of vasculitis comprising a provided compound, or a stereoisomer, an enantiomer, a diastereomer, a tautomer, or a pharmaceutically acceptable salt thereof. In a further embodiment, the invention provides a pharmaceutical composition for the treatment or prophylaxis of cutaneous lupus erythematosus comprising a provided compound, or a stereoisomer, an enantiomer, a diastereomer, a tautomer, or a pharmaceutically acceptable salt thereof. In a further embodiment, the invention provides a pharmaceutical composition for the treatment or prophylaxis of psoriasis comprising a provided compound, or a stereoisomer, an enantiomer, a diastereomer, a tautomer, or a pharmaceutically acceptable salt thereof.

All features of each of the aspects of the invention apply to all other aspects mutatis mutandis. In order that the invention described herein may be more fully understood, the following examples are set forth. It should be understood that these examples are for illustrative purposes only and are not to be construed as limiting this invention in any manner.

5. Examples

The following Examples have been prepared, isolated and characterized using the methods disclosed herein. The following examples demonstrate a partial scope of the invention and are not meant to be limiting of the scope of the invention.

Details of various HPLC/LC-MS methods used in the analysis of compounds and intermediates is provided below.

Method A: SUNFIRE C18 (4.6×150) mm, 3.5 μm column; flow rate 1 ml/min; gradient time 15 min; 10-100% solvent B; monitoring at 254 nm and 220 nm (solvent A: 5% acetonitrile (ACN), 95% water, 0.05% trifluoroacetic acid (TFA); solvent B: 95% ACN, 5% water, 0.05% TFA).

Method B: X-Bridge Phenyl (4.6×150) mm, 3.5 μm column; flow rate 1 ml/min; gradient time 15 min;% 10-100% solvent B; monitoring at 254 nm and 220 nm (solvent A: 5% ACN, 95% water, 0.05% TFA; solvent B: 95% ACN, 5% water, 0.05% TFA).

Method C: Kinetex EVO C18 (4.6×100) mm, 2.6 μm, buffer: 0.05% TFA in water, mobile phase C: buffer:ACN (95:5), mobile phase D: ACN:buffer (95:5).

Method D: Kinetex Biphenyl (4.6×100) mm, 2.6 μm, buffer: 0.05% TFA in water, mobile phase C: buffer:ACN (95:5), mobile phase D: ACN:buffer (95:5).

Method E: XBridge BEH XP C18 (50×2.1) mm, 2.5 μm, Time (min): 0-3% B: 0-100 buffer A: 95% water:5% ACN; 10 mM ammonium acetate ($NH_4OAc$) B: 5% water:95% ACN; 10 mM $NH_4OAc$, flow: 1.1 ml/min, temperature: 50° C.

Method F: XBridge BEH XP C18 (50×2.1) mm, 2.5 μm, time (min): 0-3%, B: 0-100, A: 95% water:5% ACN; 0.1% TFA, B: 5% water:95% ACN; 0.1% TFA, flow: 1.1 ml/min, temperature: 50° C.

Method G: ACQUITY UPLC® BEH C18 (3×50) mm, 1.7 μm, buffer: 10 mM $NH_4OAc$, mobile phase A: buffer:ACN (95:5), mobile phase B: buffer:ACN (5:95), flow: 0.7 ml/min, method: 0 min-20% B, 20% to 100% B 2 min, 2 to 2.3 min-100%.

Method H: Kinetex XB C18 (75×3) mm, 2.6 μm, mobile phase A: 10 mM $NH_4OAc$ in water, water:ACN (98:02), mobile phase B: 10 mM $NH_4OAc$ in water:ACN (02:98), gradient: 20-100% B over 4 min, flow: 1.0 ml/min.

Method I: ACQUITY UPLC® BEH C18 (3×50) mm, 1.7 μm, buffer: 0.05% TFA in water, mobile phase A: buffer: ACN (95:5), mobile phase B: ACN:buffer (95:5).

Method J: Column: HALO C18, 3×30 mm, 2.7 μm; Mobile Phase A: water+0.05% TFA, Mobile Phase B: acetonitrile+0.05% TFA; Flow rate: 1.5 mL/min; Gradient: 5% B to 95% B in 2.5 min, hold at 95% for 1 min, 95% B to 5% B in 0.05 min; Detection: MS and UV (254 nm).

Method K: Column: Shim-pack XR-ODS, 3×50 mm, 2.2 μm; Mobile Phase A: water/0.05% TFA, Mobile Phase B: acetonitrile/0.05% TFA; Flow Rate: 1.2000 mL/min; Gradient: 5% B to 95% B in 3.3 min, hold at 95% for 0.7 min, 95% B to 5% B in 0.1 min; Detection: MS and UV (254 nm).

General procedure for purification using Reverse Phase HPLC (RP-HPLC) is as follows. Typically, the sample to be purified was dissolved in DCM:MeOH (2:1), 20% by weight of poly(4-vinylpyridine) (Aldrich #226963) was added to this solution, and the container containing the solution was placed on a shaker for 2 hours. Thereafter, the contents were filtered through a 25 mm syringe filter fitted with a 0.45 μm nylon membrane (VWR #28145-489) into a clean vial, and dried using centrifugal evaporation to afford the purified sample.

General Synthetic Procedures:

Intermediate 1

1-Amino-3-methoxy-5-(methoxycarbonyl)pyridin-1-ium 2,4-dinitrophenolate

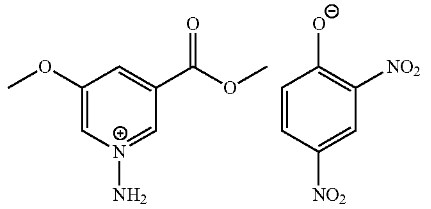

O-(2,4-dinitrophenyl)hydroxylamine (10.01 g, 50.3 mmol) was added to a stirred solution of methyl 5-methoxynicotinate (7 g, 41.9 mmol) in tetrahydrofuran (THF, 50 ml) and water (50 ml). The reaction mixture was heated to 40° C., stirred for 12 hours, and filtered to afford 1-amino-3-methoxy-5-(methoxycarbonyl)pyridin-1-ium (10 g, 130%) as yellowish brown solid, which was used in the next step without further purification. Liquid chromatography—mass spectrometry (LC-MS) m/z: 183.1 $[M+H]^+$.

Intermediate 2 tert-Butyl-3-(1-(cyclopropylmethyl)-1H-pyrrolo[2,3-b]pyridin-2-yl)propiolate

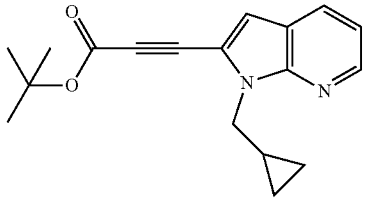 [SMILES: CC(C)(C)OC(=O)C#Cc1cc2cccnc2n1CC1CC1]

tert-Butyl propiolate (0.605 g, 4.80 mmol) and bis(triphenylphosphine)palladium(II) dichloride (0.153 g, 0.218 mmol) were added to a stirred solution of 1-(cyclopropylmethyl)-2-iodo-1H-pyrrolo[2,3-b]pyridine (1.3 g, 4.36 mmol) in a mixture of triethylamine (TEA, 5 ml) and THF (5 ml). The reaction mixture was heated to 65° C., stirred for 1 hour, and filtered through a celite bed. The filtrate was concentrated under reduced pressure to obtain a crude product, which was purified using a silica gel column (40 g, Redisep® $SiO_2$ column, eluting with 20% ethyl acetate (EtOAc) in hexane) to afford the title compound (1.2 g, 93%) as a brown liquid. LC-MS m/z: 297.1 $[M+H]^+$. $^1H$ NMR (300 MHz, chloroform-d) δ ppm: 8.55-8.38 (m, 1H), 7.99-7.87 (m, 1H), 7.26-6.99 (m, 1H), 7.04-6.99 (m, 1H), 4.43-4.06 (m, 2H), 3.26-3.16 (m, 1H), 1.65-1.38 (m, 10H), 1.34-1.07 (m, 1H), 0.59-0.39 (m, 4H).

Intermediate 3

6-Chloro-1-(cyclopropylmethyl)-2-iodo-1H-pyrrolo[2,3-b]pyridine

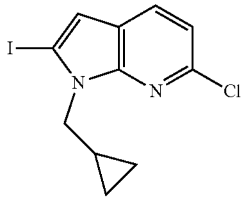 [SMILES: Clc1ccc2cc(I)n(CC3CC3)c2n1]

Sodium hydride (2.87 g, 71.8 mmol) was added to a stirred solution of 6-chloro-2-iodo-1H-pyrrolo[2,3-b]pyridine (10 g, 35.9 mmol) in dimethylformamide (DMF, 200 ml) at 0° C. and the reaction mixture was stirred for 0.5 hours, followed by addition of (bromomethyl)cyclopropane (4.50 ml, 46.7 mmol). The reaction mixture was stirred for 1 hour, poured into ice water (200 ml), and extracted with ethyl acetate (3×200 ml). The combined organic fractions were washed with water (2×300 ml) and brine (2×200 ml), dried over sodium sulfate ($Na_2SO_4$), filtered, and concentrated to obtain a crude product, which was purified using a silica gel column (80 g, Redisep® Silica column, 0-50% EtOAc in hexane as an eluent) to afford the title compound (8 g, 67%) as yellow solid. LC-MS m/z: 332.9 $[M+H]^+$. $^1H$ NMR (400 MHz, chloroform-d) δ ppm: 7.75 (d, J=8.1 Hz, 1H), 7.04 (d, J=8.3 Hz, 1H), 6.79 (s, 1H), 1.46-1.26 (m, 1H), 0.61-0.44 (m, 4H).

Intermediate 4 tert-Butyl-3-(6-chloro-1-(cyclopropylmethyl)-1H-pyrrolo[2,3-b]pyridin-2-yl)propiolate

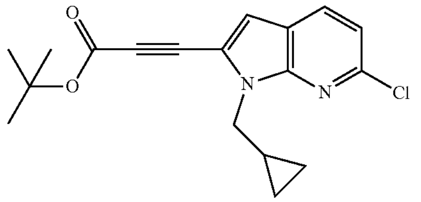 [SMILES: CC(C)(C)OC(=O)C#Cc1cc2ccc(Cl)nc2n1CC1CC1]

tert-Butyl propiolate (1.669 g, 13.23 mmol) and bis(triphenylphosphine)palladium(II) dichloride (0.422 g, 0.601 mmol) were added to a stirred solution of 6-chloro-1-(cyclopropyl-methyl)-2-iodo-1H-pyrrolo[2,3-b]pyridine (Intermediate 3, 4 g, 12.03 mmol) in a mixture of TEA (10 ml) and THF (10 ml). The reaction mixture was stirred at 50° C. for 1 hour, and filtered through a celite bed. The filtrate was concentrated under reduced pressure to obtain a crude compound, which was purified using a silica gel column (40 g, Redisep® $SiO_2$ column, eluting with 20% EtOAc in hexane) to afford the title compound (2.5 g, 63%) as yellow liquid. LC-MS m/z: 331.1 $[M+H]^+$.

Intermediate 5

6-Bromo-1-(cyclopropylmethyl)-2-ethynyl-1H-indole

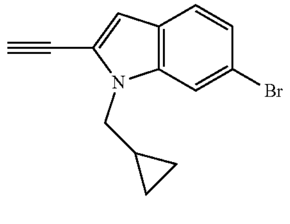 [SMILES: C#Cc1cc2ccc(Br)cc2n1CC1CC1]

Potassium carbonate ($K_2CO_3$, 11.18 g, 81 mmol) was added to a stirred solution of dimethyl (1-diazo-2-oxopropyl)phosphonate (51.8 g, 27.0 mmol, 10% solution in acetonitrile) in methanol (MeOH, 50 ml), followed by the addition of 6-bromo-1-(cyclopropylmethyl)-1H-indole-2-carbaldehyde (7.5 g, 27.0 mmol) at 0° C. The reaction mixture was allowed to warm to a room temperature, stirred for 6 hours, and concentrated under vacuum to afford a crude residue, which was diluted with water and extracted with EtOAc (2×100 ml). The combined organic layers were dried over $Na_2SO_4$, filtered, and the filtrate was concentrated under reduced pressure to obtain a crude product, which was purified using a silica gel column (40 g, Redisep® $SiO_2$ column, eluting with 0-5% EtOAc in hexane) to afford the title compound (6.3 g, 85%) as a brown liquid. LC-MS m/z: 276.1 $[M+^2H]^+$.

Intermediate 6 tert-Butyl-3-(6-bromo-1-(cyclopropylmethyl)-1H-indol-2-yl)propiolate

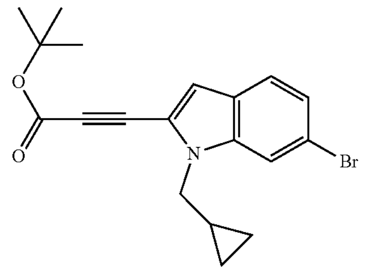 [SMILES: CC(C)(C)OC(=O)C#Cc1cc2ccc(Br)cc2n1CC1CC1]

Lithium diisopropylamide (LDA, 17.23 ml, 34.5 mmol) was added to a stirred solution of 6-bromo-1-(cyclopropylmethyl)-2-ethynyl-1H-indole (Intermediate 5, 6.3 g, 22.98 mmol) in THF (10 ml) at 0° C., and the reaction mixture was stirred for 30 min, followed by the addition of $Boc_2O$ (5.34 ml, 22.98 mmol) slowly. The reaction mixture was stirred for 1 hour, quenched with water, and extracted with EtOAc (2×100 ml). The combined organic layers were washed with water (2×300 ml) and brine (2×200 ml), dried over $Na_2SO_4$, filtered, and the filtrate was concentrated under reduced pressure. The crude product obtained was purified using a silica gel column (80 g, Redisep® Silica column, 0-5% EtOAc in hexane as an eluent) to afford the title compound (6.2 g, 72%). LC-MS m/z: 318.0 $[M\text{-isobutene}+H]^+$. $^1H$ NMR (400 MHz, DMSO-$d_6$) δ ppm: 7.94 (s, 1H), 7.58 (d, J=8.5 Hz, 1H), 7.26 (dd, J=1.5, 8.5 Hz, 1H), 7.21 (s, 1H), 4.17 (d, J=7.0 Hz, 2H), 1.51 (s, 9H), 1.27-1.18 (m, 1H), 0.52-0.40 (m, 4H).

Intermediate 7

1-(Cyclopropylmethyl)-2-(trimethylstannyl)-1H-pyrrolo[2,3-b]pyridine

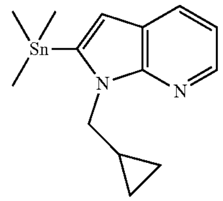 [SMILES: [CH3][Sn]([CH3])([CH3])[c]1cc2cccnc2n1CC1CC1]

Hexamethylditin (0.278 ml, 1.342 mmol) was added to a stirred solution of 1-(cyclopropyl-methyl)-2-iodo-1H-pyrrolo[2,3-b]pyridine (0.2 g, 0.671 mmol) in 1,4-dioxane (1.5 ml), and the reaction mixture was degassed with argon for 5 min, followed by the addition of [1,1'-bis(di-tert-butylphosphino)-ferrocene]-dichloropalladium(II) (0.031 g, 0.047 mmol). The reaction mixture was stirred at 70° C. for 2 hours, filtered through a celite bed, and the filtrate was concentrated to afford a crude product (250 mg), which was used in the next steps without further purification. LC-MS m/z: 337 [M+H]+.

Intermediate 8

1-Amino-3-(ethoxycarbonyl)pyridin-1-ium 2,4-dinitrophenolate

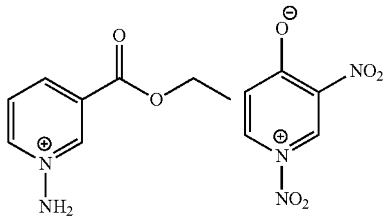

Intermediate 8 was prepared following a procedure similar to the preparation of Intermediate 1 (10 g, 28.5 mmol, 100%). LC-MS m/z: 168 [M+H]+.

Intermediate 9

1-Amino-3-fluoro-5-(methoxycarbonyl)pyridin-1-ium 2,4,6-trimethylbenzenesulfonate

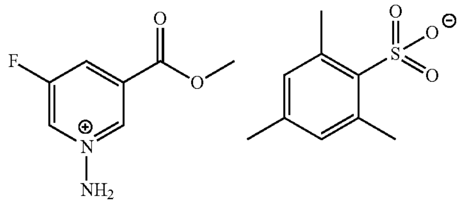

O-(mesitylsulfonyl)hydroxylamine (8.33 g, 38.7 mmol) was added to a stirred solution of methyl 5-fluoronicotinate (5 g, 32.2 mmol) in dichloromethane (DCM, 20 ml) at 0° C. The reaction mixture was stirred for 2 hours, and concentrated to afford 1-amino-3-fluoro-5-(methoxycarbonyl)pyridin-1-ium (5 g, 91%) as a brown solid, which was used in the next step without further purification. LC-MS m/z: 171.0 [M+H]+.

Intermediate 10

1-(Cyclopropylmethyl)-2-(4,4,5,5-tetramethyl-1,3,2-dioxaborolan-2-yl)-1H-indole

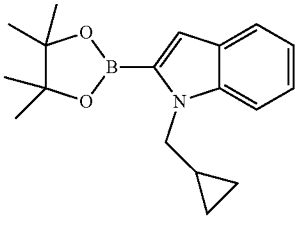 [SMILES: CC1(C)OB(c2cc3ccccc3n2CC2CC2)OC1(C)C]

sec-Butyllithium (16.68 ml, 23.36 mmol) was added drop wise to a stirred solution of 1-(cyclopropylmethyl)-1H-indole (2 g, 11.68 mmol) in THF (20 ml) under argon atmosphere at −78° C. The reaction mixture was stirred further for 30 min, followed by the addition of 2-isopropoxy-4,4,5,5-tetramethyl-1,3,2-dioxaborolane (2.173 g, 11.68 mmol). The reaction mixture was stirred at a room temperature for 2 hours, quenched with drop wise addition of water (50 ml), and extracted with EtOAc (2×50 ml). The combined organic extracts were washed with water (100 ml) and brine (100 ml), dried over $Na_2SO_4$, filtered, and the filtrate was evaporated to dryness under reduced pressure. The crude product thus obtained was purified using a silica gel column column (EtOAc in hexane), and the purified product was isolated at 15% EtOAc in hexane. Required fractions were collected and volatiles were evaporated to dryness under reduced pressure to afford the title compound (2 g, 58%). $^1H$ NMR (400 MHz, DMSO-$d_6$) δ ppm: 0.32-0.44 (m, 4H), 1.16-1.34 (m, 13H), 4.32 (d, J=6.85 Hz, 2H), 6.94-7.05 (m, 2H), 7.16-7.25 (m, 1H), 7.51-7.60 (m, 2H).

Intermediate 11

1-(Cyclopropylmethyl)-2-(4,4,5,5-tetramethyl-1,3,2-dioxaborolan-2-yl)-1H-pyrrolo[2,3-b]pyridine

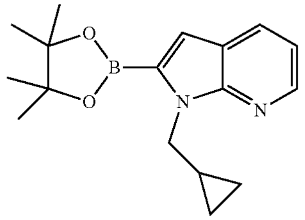 [SMILES: CC1(C)OB(c2cc3cccnc3n2CC2CC2)OC1(C)C]

Intermediate 11 was prepared following a procedure similar to the preparation of Intermediate 10 (1.3 g, 31%). LC-MS (ESI) m/z: 300.3 [M+H]+.

Intermediate 12

6-Bromo-1-(cyclopropylmethyl)-2-iodo-1H-indole

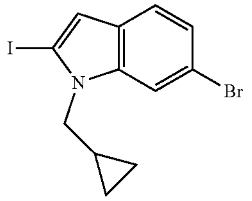 [SMILES: Brc1ccc2cc(I)n(CC3CC3)c2c1]

Sodium hydride (NaH, 1.372 g, 34.3 mmol) was added lot wise to a stirred solution of 6-bromo-2-iodo-1H-indole (5.52 g, 17.15 mmol, Ref: *Bioorg. Med. Chem.* 22(5), 2014, 1708) in DMF (20 ml) at 0° C., and the reaction mixture was stirred for 10 minutes followed by drop wise the addition of (bromomethyl)-cyclopropane (2.498 ml, 25.7 mmol). The reaction mixture was stirred at a room temperature for 16 hours, diluted with cold water (50 ml), and extracted with EtOAc (3×50 ml). The combined organic layers were dried over anhydrous sodium sulphate, filtered, and the filtrate was evaporated under reduced pressure. The crude product thus obtained was purified using a silica gel column (24 g, Redisep® $SiO_2$ column, eluting with 10% EtOAc in n-hexane) to afford the title compound (5 g, 78%). LC-MS m/z: 377 $[M+H]^+$. $^1H$ NMR (400 MHz, DMSO-$d_6$) δ ppm: 7.83 (s, 1H), 7.43 (d, J=8.3 Hz, 1H), 7.14 (dd, J=1.8, 8.5 Hz, 1H), 6.82 (s, 1H), 4.13 (d, J=6.8 Hz, 2H), 1.31-1.13 (m, 1H), 0.51-0.41 (m, 4H).

Intermediate 13

1-Amino-3-chloro-5-(methoxycarbonyl)pyridin-1-ium-2,4,6-trimethylbenzenesulfonate

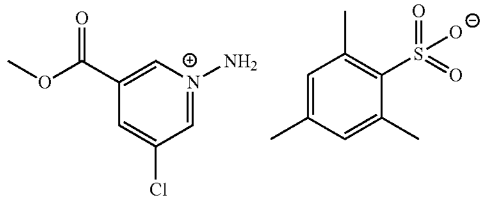

O-(mesitylsulfonyl)hydroxylamine (2.6 g, 11.66 mmol) was added to a stirred solution of methyl 5-chloronicotinate (2 g, 11.66 mmol) in DCM (40 ml) at 0° C. The reaction mixture was stirred at a room temperature for 2 hours, and evaporated under reduced pressure to afford crude 1-amino-3-chloro-5-(methoxycarbonyl)pyridin-1-ium (2.1 g, 96%) as a white solid, which was used in the next step without further purification. LC-MS m/z: 187.2 $[M+H]^+$.

Intermediate 14

Ethyl 6-bromo-1-(cyclopropylmethyl)-1H-indole-2-carboxylate

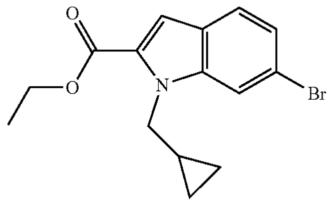 [SMILES: CCOC(=O)c1cc2ccc(Br)cc2n1CC1CC1]

Potassium carbonate (10.3 g, 74.6 mmol) was added to a stirred solution of ethyl 6-bromo-1H-indole-2-carboxylate (10 g, 37.3 mmol) in DMF (60 ml), followed by the addition of (bromomethyl)cyclopropane (5.0 g, 37.3 mmol). The reaction mixture was stirred for 16 hours, and potassium carbonate (5 g) and (bromomethyl)cyclopropane (2.5 g) were added. The resulting reaction mixture was heated to 50° C. for 2 hours, diluted with water (150 ml), and extracted with ethyl acetate (3×150 ml). The combined organic layers were concentrated in vacuo to afford ethyl 6-bromo-1-(cyclopropylmethyl)-1H-indole-2-carboxylate (10 g, 83%) as a brown solid, which was used further without purification. LC-MS m/z: 322.0 $[M+H]^+$.

Intermediate 15

(6-Bromo-1-(cyclopropylmethyl)-1H-indol-2-yl) methanol

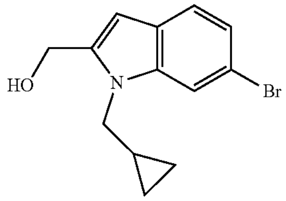 [SMILES: OCc1cc2ccc(Br)cc2n1CC1CC1]

$LiBH_4$ (15.52 ml, 62.1 mmol, 4 M in THF) was added to a stirred solution of Intermediate 14 (10 g, 31 mmol) in THF (50 ml) at 0° C. The reaction mixture was allowed to warm to a room temperature over 1 hour, stirred for 16 hours, cooled to 0° C. and additional amount of $LiBH_4$ (15.52 ml, 62.1 mmol, 4 M in THF) was added dropwise. The reaction mixture was stirred for 6 hours at a room temperature, cooled to 0° C., quenched by slow addition of saturated ammonium chloride solution (need to add carefully, sudden evolution of gas was noticed), stirred for ~45 minutes, and extracted with ethyl acetate (4×100 ml). The organic layers were separated, dried over $Na_2SO_4$, filtered and concentrated to obtain a crude product, which was further purified using a silica gel column (0-30% ethyl acetate/pet ether) to afford 6-bromo-1-(cyclopropylmethyl)-1H-indol-2-yl) methanol (8.5 g, 98%). LC-MS m/z: 280.1 $[M+H]^+$.

Intermediate 16

6-Bromo-1-(cyclopropylmethyl)-1H-indole-2-carbaldehyde

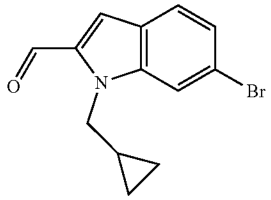 [SMILES: O=Cc1cc2ccc(Br)cc2n1CC1CC1]

Manganese dioxide (10.3 g, 119 mmol) was added to a stirred solution of Intermediate 15 (8.3 g, 29.6 mmol) in THF (50 ml). The reaction mixture was stirred at 45° C. for 2 hours, and filtered through a celite bed. The filtrate was concentrated in vacuo to obtain 6-bromo-1-(cyclopropylmethyl)-1H-indole-2-carbaldehyde (7.6 g, 92%) as a brown syrup, which was used further without purification. LC-MS m/z: 278.1 $[M+H]^+$.

Intermediate 17

(E)-6-Bromo-1-(cyclopropylmethyl)-2-(2-nitroprop-1-en-1-yl)-1H-indole

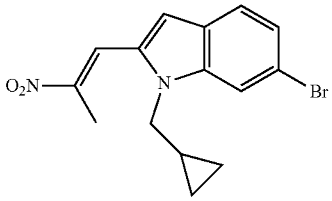 [SMILES: C/C(=C\c1cc2ccc(Br)cc2n1CC1CC1)[N+](=O)[O-]]

Ammonium acetate (122 mg, 1.582 mmol) was added to a stirred solution of Intermediate 16 (400 mg, 1.438 mmol) in nitroethane (2 ml, 28.0 mmol). The reaction mixture was stirred at 90° C. for 2 hours, diluted with water (5 ml), and extracted with ethyl acetate (2×10 ml). The combined organic layers were washed with brine, dried over sodium sulfate, filtered, and concentrated in vacuum to afford (E)-6-bromo-1-(cyclopropylmethyl)-2-(2-nitroprop-1-en-1-yl)-1H-indole as yellow liquid (420 mg), which was used in the next step without purification. LC-MS retention time: 1.26 min., m/z=335.1 $[M+H]^+$ Intermediate 18

Ethyl 2-(6-bromo-1-(cyclopropylmethyl)-1H-indol-2-yl)-3-methylpyrazolo[1,5-a]pyridine-6-carboxylate

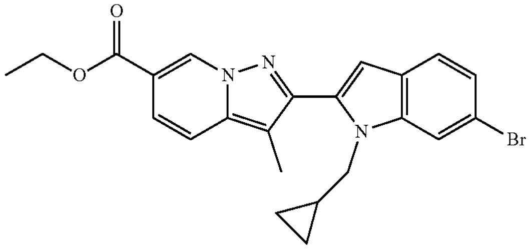 [SMILES: CCOC(=O)c1ccc2c(C)c(-c3cc4ccc(Br)cc4n3CC3CC3)nn2c1]

Intermediate 8 (75 mg, 0.447 mmol) and copper (I) iodide (6 mg, 0.03 mmol) were added to a stirred solution of Intermediate 17 (50 mg, 0.149 mmol) in DMF (1 ml). The reaction mixture was stirred at 80° C. for 30 hours, concentrated to remove DMF, and water (10 ml) was added, and the contents were extracted with ethyl acetate (3×50 ml). The combined organic layers were washed with brine, dried over sodium sulfate, filtered, and concentrated in vacuum to obtain a crude product, which was purified using a silica gel column (0-5% methanol in dichloromethane) to afford ethyl 2-(6-bromo-1-(cyclopropylmethyl)-1H-indol-2-yl)-3-methylpyrazolo[1,5-a]pyridine-6-carboxylate (20 mg, 30%). LC-MS (ES): m/z=452.1 $[M+H]^+$. $^1H$ NMR (400 MHz, DMSO-$d_6$) δ ppm: 9.19 (s, 1H), 7.90 (s, 1H), 7.83 (d, J=9.5 Hz, 1H), 7.62-7.58 (m, 2H), 7.24-7.20 (m, 1H), 6.91 (s, 1H), 4.50 (d, J=7.0 Hz, 2H), 4.36 (q, J=7.0 Hz, 2H), 2.42 (s, 3H), 1.36 (t, J=7.0 Hz, 3H), 1.11 (m, 1H), 0.32-0.26 (m, 2H), 0.18-0.13 (m, 2H).

Intermediate 19

Ethyl 2-(6-bromo-1-(cyclopropylmethyl)-1H-indol-2-yl)-4-methoxy-3-methylpyrazolo[1,5-a]pyridine-6-carboxylate

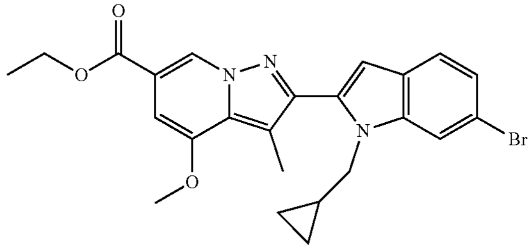 [SMILES: CCOC(=O)c1cc(OC)c2c(C)c(-c3cc4ccc(Br)cc4n3CC3CC3)nn2c1]

Intermediate 19 was prepared following a procedure similar to the preparation of Intermediate 18 using appropriate reactants. LC-MS retention time: 1.76 min, m/z: 468.2 [M+H] (Method G). $^1H$ NMR (400 MHz, chloroform-d) δ ppm: 8.91 (s, 1H), 8.50 (s, 1H), 7.80 (dd, J=3.01, 1.51 Hz, 1H), 7.43-7.60 (m, 1H), 6.85-6.91 (m, 1H), 6.75 (s, 1H), 4.37 (d, J=6.5 Hz, 2H), 4.02 (s, 3H), 3.93 (s, 3H), 2.56-2.62 (m, 3H), 1.15-1.34 (m, 1H), 0.33-0.46 (m, 2H), 0.13-0.18 (m, 2H).

Intermediate 20

6-Chloro-1-(cyclopropylmethyl)-1H-pyrrolo[2,3-b]pyridine

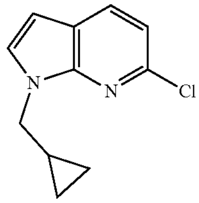 [SMILES: Clc1ccc2ccn(CC3CC3)c2n1]

Sodium hydride in mineral oil (60% w/w, 1.31 g, 32.8 mmol) was added portion wise to a stirred solution of 6-chloro-1H-pyrrolo[2,3-b]pyridine (5 g, 32.8 mmol) in DMF (25 ml) at 0° C., the reaction mixture was stirred for 15 minutes, followed by the slow addition of (bromomethyl) cyclopropane (4.42 g, 32.8 mmol) over 5 minutes. The reaction mixture was allowed to warm to a room temperature, stirred for 16 hours, quenched with water (50 ml), and extracted with ethyl acetate (3×50 ml). The combined organic layers were concentrated in vacuo to obtain a crude product, which was purified using a silica gel column (0-5% ethyl acetate/pet ether) to afford 6-chloro-1-(cyclopropylmethyl)-1H-pyrrolo[2,3-b]pyridine (6.5 g, 96%). LC-MS retention time: 1.85 min, m/z: 207.0 [M+H] (Method G).

Intermediate 21

6-Chloro-1-(cyclopropylmethyl)-1H-pyrrolo[2,3-b]pyridine-2-carbaldehyde

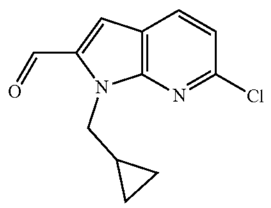 [SMILES: O=Cc1cc2ccc(Cl)nc2n1CC1CC1]

sec-Butyllithium (10.37 ml, 14.52 mmol, 1.4 M in cyclohexane) was added to a stirred solution of Intermediate 20 (2 g, 9.68 mmol) in THF (20 ml) at −78° C., the contents were stirred for 30 minutes, followed by the addition of DMF (2 ml, 25.8 mmol). The reaction mixture was allowed to warm to −20° C., then to a room temperature, stirred for 12 hours, cooled to −10° C., and quenched by addition of saturated ammonium chloride solution. The reaction mixture was diluted with water (100 ml) and extracted with ethylacetate (3×100 ml). The combined organic layers were dried over sodium sulphate, filtered and the filtrate was concentrated in vacuo to obtain a crude product, which was purified using a silica gel column (0 to 15% ethyl acetate/pet ether) to afford 6-chloro-1-(cyclopropylmethyl)-1H-pyrrolo[2,3-b]pyridine-2-carbaldehyde (1.45 g, 64%) as an off-white crystalline solid. LC-MS retention time: 1.85 min., m/z: 235.0 [M+H] (Method G).

Intermediate 22

(E)-6-Chloro-1-(cyclopropylmethyl)-2-(2-nitroprop-1-en-1-yl)-1H-pyrrolo[2,3-b]pyridine

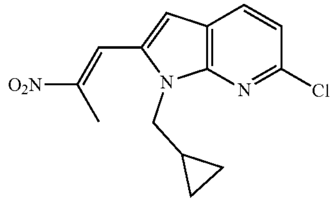 [SMILES: C/C(=C\c1cc2ccc(Cl)nc2n1CC1CC1)[N+](=O)[O-]]

Intermediate 22 was prepared following a procedure similar to the preparation of Intermediate 17 using Intermediate 21. LC-MS retention time: 1.17 min, m/z: 292.2 [M+H] (Method G).

Intermediate 23

Ethyl 2-(6-chloro-1-(cyclopropylmethyl)-1H-pyrrolo[2,3-b]pyridin-2-yl)-3-methylpyrazolo[1,5-a]pyridine-6-carboxylate

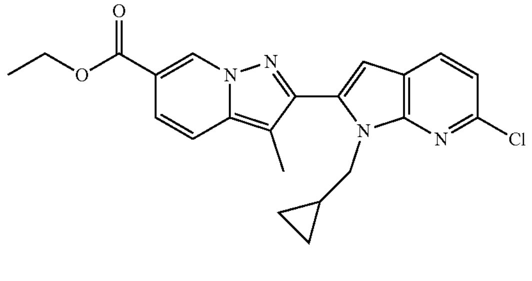 [SMILES: CCOC(=O)c1ccc2c(C)c(-c3cc4ccc(Cl)nc4n3CC3CC3)nn2c1]

Intermediate 23 was prepared following a procedure similar to the preparation of Intermediate 18 using Intermediate 22 and Intermediate 8. LC-MS retention time: 1.66 min, m/z: 409.1 [M+H] (Method G).

Intermediate 24

Methyl 2-(6-chloro-1-(cyclopropylmethyl)-1H-pyrrolo[2,3-b]pyridin-2-yl)-4-chloro-3-methylpyrazolo[1,5-a]pyridine-6-carboxylate

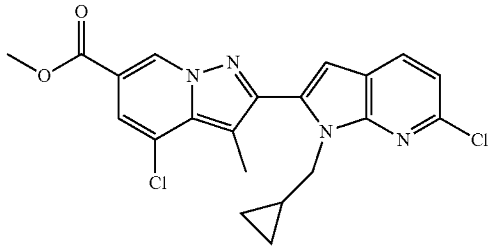 [SMILES: COC(=O)c1cc(Cl)c2c(C)c(-c3cc4ccc(Cl)nc4n3CC3CC3)nn2c1]

Intermediate 24 was prepared as a gummy liquid following a procedure similar to the preparation of Intermediate 18 using Intermediate 13 and Intermediate 22. LC-MS (ES): m/z: 429.1 $[M+H]^+$.

Intermediate 25

Ethyl 7-(1-(tert-butoxycarbonyl)-1,2,3,6-tetrahydropyridin-4-yl)-1H-indole-2-carboxylate

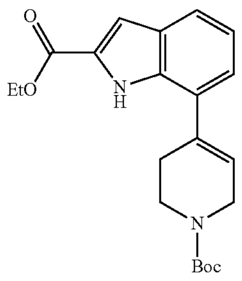 [SMILES: CCOC(=O)c1cc2cccc(C3=CCN(C(=O)OC(C)(C)C)CC3)c2[nH]1]

$K_2CO_3$ (15.46 g, 112 mmol) and $PdCl_2(dppf)\cdot CH_2Cl_2$ (3.05 g, 3.73 mmol) were added to a stirred solution of tert-butyl 4-(4,4,5,5-tetramethyl-1,3,2-dioxaborolan-2-yl)-3,6-dihydropyridine-1(2H)-carboxylate (11.53 g, 37.3 mmol) and ethyl 7-bromo-1H-indole-2-carboxylate (10 g, 37.3 mmol) in dioxane (200 ml). The reaction mixture was purged with nitrogen for 2 minutes, stirred at 100° C. for 3 hours thereafter, filtered through a celite bed, and the celite bed was thoroughly washed with ethyl acetate. The combined filtrate was concentrated under reduced pressure to obtain a crude product, which was purified using a silica gel column (0-30% ethyl acetate in pet ether) to afford the title compound (11.3 g, 82%) as a gummy liquid. LC-MS m/z: 369.4 $[M-H]^+$. 1H NMR (300 MHz, DMSO-$d_6$) δ ppm: 11.43 (s, 1H), 7.57 (d, J=7.2 Hz, 1H), 7.21 (d, J=4.0 Hz, 1H), 7.24-7.04 (m, 2H), 5.96 (br, s, 1H), 4.34 (q, J=7.1 Hz, 2H), 4.08-3.99 (m, 2H), 3.62 (t, J=5.7 Hz, 2H), 1.51-1.45 (m, 2H), 1.46 (s, 9H), 1.34 (t, J=7.2 Hz, 3H).

Intermediate 26

Ethyl 7-(1-(tert-butoxycarbonyl)piperidin-4-yl)-1H-indole-2-carboxylate

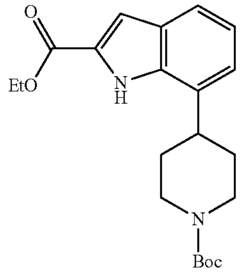 [SMILES: CCOC(=O)c1cc2cccc(C3CCN(C(=O)OC(C)(C)C)CC3)c2[nH]1]

Pd/C (7.18 g, 6.75 mmol, 50% wet) was added to a stirred solution of Intermediate 25 (5.0 g, 13.50 mmol) in methanol (100 ml) purged with nitrogen, and the reaction mixture was stirred under $H_2$ atmosphere for 4 hours. The reaction mixture was filtered through a celite bed, and the filtrate was concentrated under reduced pressure to obtain ethyl 7-(1-(tert-butoxycarbonyl)piperidin-4-yl)-1H-indole-2-carboxylate (4.95 g, 98%). LC-MS m/z: 371.4 $[M-H]^+$. $^1H$ NMR (300 MHz, DMSO-$d_6$) δ ppm: 11.84 (s, 1H), 7.49 (d, J=7.6 Hz, 1H), 7.21-7.01 (m, 3H), 4.36 (q, J=7.1 Hz, 2H), 4.16-4.04 (m, 4H), 3.61-3.42 (m, 1H), 1.90-1.74 (m, 2H), 1.59-1.47 (m, 2H), 1.43 (s, 9H), 1.35 (t, J=7.2 Hz, 3H).

Intermediate 27

Ethyl 7-(1-(tert-butoxycarbonyl)piperidin-4-yl)-1-(cyclopropylmethyl)-1H-indole-2-carboxylate

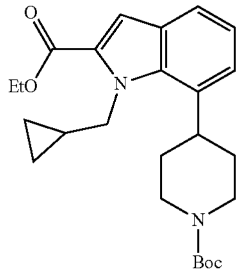 [SMILES: CCOC(=O)c1cc2cccc(C3CCN(C(=O)OC(C)(C)C)CC3)c2n1CC1CC1]

$K_2CO_3$ (14.47 g, 105 mmol) and (bromomethyl)cyclopropane (14.14 g, 105 mmol) were added to a stirred solution of Intermediate 26 (13 g, 34.9 mmol) in DMF (100 ml). The reaction mixture was stirred at 50° C. for 12 hours, allowed to cool to a room temperature, diluted with water, and extracted with ethyl acetate (3×150 ml). The combined organic layers were washed with water and brine solution, dried over anhydrous sodium sulphate, and the volatiles were evaporated under reduced pressure to obtain a crude product, which was purified using a silica gel column (0-20% ethyl acetate in pet ether) to afford ethyl 7-(1-(tert-butoxycarbonyl)piperidin-4-yl)-1-(cyclopropylmethyl)-1H-indole-2-carboxylate (4.8 g, 32%) as a gummy liquid. LC-MS m/z: 427.5 $[M+H]^+$.

Intermediate 28 tert-Butyl 4-(1-(cyclopropylmethyl)-2-(hydroxymethyl)-1H-indol-7-yl)piperidine-1-carboxylate

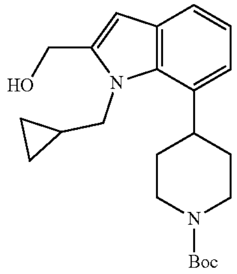 [SMILES: CC(C)(C)OC(=O)N1CCC(c2cccc3cc(CO)n(CC4CC4)c23)CC1]

$LiBH_4$ in tetrahydrofuran (10.08 ml, 40.3 mmol) was added to a stirred solution of Intermediate 27 (4.3 g, 10.08 mmol) in tetrahydrofuran (80 ml) at 0° C. The reaction mixture was allowed to warm to a room temperature, stirred for 48 hours, quenched with saturated ammonium chloride solution, and extracted with ethyl acetate (4×50 ml). The combined organic layers were washed with water and brine solution, dried over anhydrous sodium sulphate, and evaporated under reduced pressure to obtain a crude product, which was purified using a silica gel column (0-70% ethyl acetate in pet ether) to afford tert-butyl 4-(1-(cyclopropylmethyl)-2-(hydroxymethyl)-1H-indol-7-yl)piperidine-1-carboxylate (3.7 g, 95%) as a gummy liquid. LC-MS m/z: 385.4 $[M+H]^+$. $^1H$ NMR (300 MHz, DMSO-$d_6$) δ ppm: 7.33 (d, J=6.8 Hz, 1H), 7.03-6.90 (m, 2H), 6.38 (s, 1H), 5.24 (br, t, 1H), 4.60 (s, 2H), 4.30 (d, J=5.3 Hz, 2H), 4.22-3.98 (m, 2H), 3.59-3.38 (m, 1H), 3.02-2.74 (m, 2H), 1.88-1.80 (m, 2H), 1.74-1.50 (m, 2H), 1.43 (s, 9H), 1.19-1.01 (m, 1H), 0.55-0.37 (m, 2H), 0.36-0.19 (m, 2H).

Intermediate 29 tert-Butyl 4-(1-(cyclopropylmethyl)-2-formyl-1H-indol-7-yl)piperidine-1-carboxylate

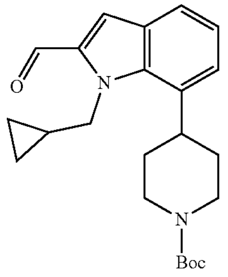 [SMILES: CC(C)(C)OC(=O)N1CCC(c2cccc3cc(C=O)n(CC4CC4)c23)CC1]

Manganese dioxide (9.04 g, 104 mmol) was added to a stirred solution of Intermediate 28 (4 g, 10.40 mmol) in tetrahydrofuran (60 ml). The reaction mixture was heated to 40° C., stirred for 2 hours, filtered through a celite bed, and washed with ethyl acetate. The combined filtrate was concentrated under reduced pressure to obtain tert-butyl 4-(1-(cyclopropylmethyl)-2-formyl-1H-indol-7-yl)piperidine-1-carboxylate (3.8 g, 96%). LC-MS m/z: 383.4 $[M+H]^+$. $^1H$ NMR (400 MHz, chloroform-d) δ ppm: 9.84 (s, 1H), 7.63 (dd, J=1.3, 7.8 Hz, 1H), 7.42-7.33 (m, 1H), 7.30 (s, 1H), 7.32

(s, 1H), 7.18 (t, J=7.6 Hz, 1H), 5.32 (s, 1H), 4.83 (d, J=6.0 Hz, 2H), 4.47-4.23 (m, 2H), 3.81-3.72 (m, 1H), 3.64-3.48 (m, 1H), 2.93 (br, t, J=12.3 Hz, 2H), 2.01-1.95 (m, 2H), 1.84-1.78 (m, 2H), 1.52 (s, 9H), 1.18-1.08 (m, 1H), 0.50-0.42 (m, 2H), 0.42-0.35 (m, 2H).

Intermediate 30 tert-Butyl (E)-4-(1-(cyclopropylmethyl)-2-(2-nitroprop-1-en-1-yl)-1H-indol-7-yl)piperidine-1-carboxylate

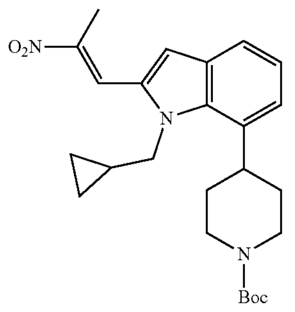 [SMILES: C/C(=C\c1cc2cccc(C3CCN(C(=O)OC(C)(C)C)CC3)c2n1CC1CC1)[N+](=O)[O-]]

Ammonium acetate (0.937 g, 12.16 mmol) was added to a stirred solution of Intermediate 29 (3.1 g, 8.10 mmol) in nitroethane (20 ml, 280 mmol). The reaction mixture was heated to 80° C., stirred for 2 hours, diluted with water and extracted with ethyl acetate (2×50 ml). The combined organic layers were washed with water and brine solution, dried over anhydrous sodium sulphate, and evaporated under reduced pressure to obtain tert-butyl (E)-4-(1-(cyclopropylmethyl)-2-(2-nitroprop-1-en-1-yl)-1H-indol-7-yl)piperidine-1-carboxylate (3.5 g, 98%). LC-MS m/z: 440.4 $[M+H]^+$. $^1$H NMR (300 MHz, chloroform-d) δ ppm: 8.23 (s, 1H), 7.53 (d, J=6.80 Hz, 1H), 7.07-7.24 (m, 2H), 6.89 (s, 1H), 4.37 (br, s, 1H), 4.33 (br, d, J=5.3 Hz, 2H), 3.46-3.59 (m, 1H), 2.78-2.98 (m, 2H), 2.59 (s, 3H), 2.00-1.90 (m, 2H), 1.86-1.77 (m, 1H), 1.53-1.63 (m, 9H), 1.22-1.32 (m, 1H), 1.07-1.21 (m, 1H), 0.83 (br, d, J=2.27 Hz, 1H), 0.53-0.62 (m, 2H), 0.31 (q, J=5.16 Hz, 2H).

Intermediate 31

Ethyl 7-(1-(tert-butoxycarbonyl)-1,2,3,6-tetrahydropyridin-4-yl)-5-fluoro-1H-indole-2-carboxylate

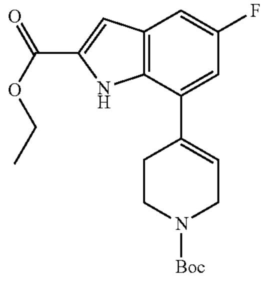 [SMILES: CCOC(=O)c1cc2cc(F)cc(C3=CCN(C(=O)OC(C)(C)C)CC3)c2[nH]1]

tert-Butyl 4-(4,4,5,5-tetramethyl-1,3,2-dioxaborolan-2-yl)-3,6-dihydropyridine-1(2H)-carboxylate (5.40 g, 17.48 mmol) and potassium carbonate (6.04 g, 43.7 mmol) were added to a stirred solution of ethyl 7-bromo-5-fluoro-1H-indole-2-carboxylate (5 g, 17.48 mmol) in 1,4-dioxane (45 ml) and water (5 ml). The reaction mixture was degassed with nitrogen for 2 min, followed by addition of $PdCl_2$(dppf) (1.279 g, 1.748 mmol). The reaction mixture was degassed for additional 2 min, heated to 100° C. for 3 hours, filtered through a celite bed, and the celite bed was washed with ethyl acetate (300 ml). The combined filtrates were concentrated under reduced pressure to obtain a crude product, which was purified using a silica gel column (0-30% ethyl acetate in hexane) to afford ethyl 7-(1-(tert-butoxycarbonyl)-1,2,3,6-tetrahydropyridin-4-yl)-5-fluoro-1H-indole-2-carboxylate (5.7 g, 84%). LC-MS m/z: 387.5 $[M-H]^+$. $^1$H NMR (300 MHz, chloroform-d) δ ppm: 8.92 (br, s, 1H), 7.25-7.20 (m, 1H), 7.18 (d, J=2.2 Hz, 1H), 6.95 (dd, J=2.3, 10.2 Hz, 1H), 6.12 (br, s, 1H), 4.42 (q, J=7.2 Hz, 2H), 4.16 (br, d, J=3.0 Hz, 2H), 3.71 (t, J=5.5 Hz, 2H), 2.63-2.42 (m, 2H), 1.53 (s, 9H), 1.42 (t, J=7.2 Hz, 3H).

Intermediate 32

Ethyl 7-(1-(tert-butoxycarbonyl)piperidin-4-yl)-5-fluoro-1H-indole-2-carboxylate

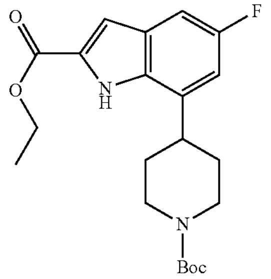 [SMILES: CCOC(=O)c1cc2cc(F)cc(C3CCN(C(=O)OC(C)(C)C)CC3)c2[nH]1]

Pd/C (3.29 g, 15.45 mmol) was added to a solution of Intermediate 31 (6.0 g, 15.45 mmol) in methanol (60 ml) purged with nitrogen for 2 min. The reaction mixture was stirred under hydrogen atmosphere at 1 atmospheric pressure for 3 hours, filtered through a celite bed, and washed with ethyl acetate (300 ml). The combined organic layers were concentrated under reduced pressure to obtain ethyl 7-(1-(tert-butoxycarbonyl)piperidin-4-yl)-5-fluoro-1H-indole-2-carboxylate (5.5 g, 91%). LC-MS m/z: 389.2 $[M-H]^+$. $^1$H NMR (300 MHz, DMSO-$d_6$) δ ppm: 12.00 (s, 1H), 7.25 (dd, J=2.3, 9.1 Hz, 1H), 7.15 (d, J=1.9 Hz, 1H), 7.00 (dd, J=2.5, 10.8 Hz, 1H), 4.36 (q, J=7.2 Hz, 2H), 4.11 (br d, J=12.5 Hz, 2H), 3.52 (br s, 1H), 3.34 (s, 1H), 3.07-2.74 (m, 2H), 1.81 (br d, J=11.7 Hz, 2H), 1.62-1.50 (m, 1H), 1.43 (s, 9H), 1.34 (t, J=7.0 Hz, 3H).

Intermediate 33

Ethyl 7-(1-(tert-butoxycarbonyl)piperidin-4-yl)-1-(cyclopropylmethyl)-5-fluoro-1H-indole-2-carboxylate

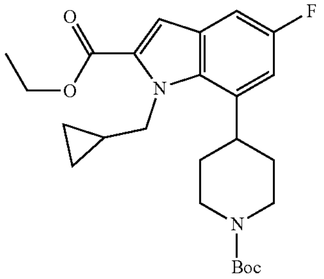 [SMILES: CCOC(=O)c1cc2cc(F)cc(C3CCN(C(=O)OC(C)(C)C)CC3)c2n1CC1CC1]

Cesium carbonate (10.43 g, 32.0 mmol), TBAI (4.73 g, 12.81 mmol) and (bromomethyl)cyclopropane (3.46 g, 25.6 mmol) were added to a stirred solution of Intermediate 32 (5 g, 12.81 mmol) in DMF (50 ml). The reaction mixture was heated to 55° C. for 16 hours, quenched with water (100 ml), and extracted with ethyl acetate (2×100 ml). The combined organic layers were dried over sodium sulphate, filtered, and concentrated under reduced pressure to obtain a crude product, which was purified using a silica gel column (0-20% ethyl acetate in hexane) to afford ethyl 7-(1-(tert-butoxycarbonyl)piperidin-4-yl)-1-(cyclopropylmethyl)-5-fluoro-1H-indole-2-carboxylate (4.8 g, 84%). LC-MS m/z: 389.3 $[M+H]^+$. $^1$H NMR (400 MHz, chloroform-d) δ ppm: 7.32 (s, 1H), 7.18 (dd, J=2.5, 8.5 Hz, 1H), 6.99 (dd, J=2.8, 10.8 Hz, 1H), 4.79 (d, J=6.0 Hz, 2H), 4.44-4.34 (m, 2H), 3.55 (br, s, 1H), 2.92 (br, s, 2H), 2.00 (br, d, J=13.0 Hz, 2H), 1.76 (br, dd, J=4.0, 12.5 Hz, 2H), 1.52 (s, 9H), 1.45-1.40 (m, 3H), 1.05 (s, 1H), 0.48-0.39 (m, 2H), 0.38-0.30 (m, 2H).

Intermediate 34 tert-Butyl 4-(1-(cyclopropylmethyl)-5-fluoro-2-(hydroxymethyl)-1H-indol-7-yl)piperidine-1-carboxylate

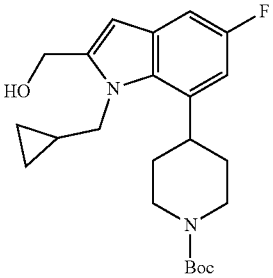 [SMILES: CC(C)(C)OC(=O)N1CCC(c2cc(F)cc3cc(CO)n(CC4CC4)c23)CC1]

$LiBH_4$ (9.84 ml, 39.4 mmol) was added to a stirred solution of Intermediate 33 (3.5 g, 7.87 mmol) in THF (35 ml) at 0° C. The reaction mixture was stirred for 16 hours at a room temperature, filtered through a celite bed, and washed with ethyl acetate (70 ml). The combined organic layers were concentrated under reduced pressure to obtain crude tert-butyl 4-(1-(cyclopropylmethyl)-5-fluoro-2-(hydroxymethyl)-1H-indol-7-yl)piperidine-1-carboxylate (2.5 g, 79%). LC-MS m/z: 403.4 $[M+H]^+$. $^1$H NMR (300 MHz, DMSO-$d_6$) δ ppm: 7.10 (dd, J=9.07, 2.64 Hz, 1H), 6.74-6.92 (m, 1H), 6.38 (s, 1H), 5.29 (t, J=5.48 Hz, 1H), 4.59 (d, J=5.67 Hz, 1H), 4.28 (br d, J=5.29 Hz, 2H), 4.13 (br d, J=12.46 Hz, 1H), 3.51 (br t, J=10.58 Hz, 1H), 3.13-3.32 (m, 1H), 2.35 (s, 2H), 2.27 (d, J=5.29 Hz, 1H), 1.84 (br d, J=12.84 Hz, 2H), 1.51-1.74 (m, 2H), 1.35-1.51 (m, 9H), 0.74-1.04 (m, 1H), 0.21-0.51 (m, 4H).

Intermediate 35 tert-Butyl 4-(1-(cyclopropylmethyl)-5-fluoro-2-formyl-1H-indol-7-yl)piperidine-1-carboxylate

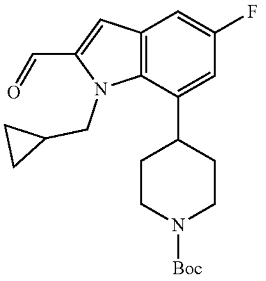 [SMILES: CC(C)(C)OC(=O)N1CCC(c2cc(F)cc3cc(C=O)n(CC4CC4)c23)CC1]

Manganese dioxide (0.691 g, 7.95 mmol) was added to a stirred solution of Intermediate 34 (3.2 g, 7.95 mmol) in tetrahydrofuran (32 ml). The reaction mixture was stirred for 16 hours, filtered through a celite bed, and washed with ethyl acetate (70 ml). The organic layers were concentrated under reduced pressure to obtain tert-butyl 4-(1-(cyclopropylmethyl)-5-fluoro-2-formyl-1H-indol-7-yl)piperidine-1-carboxylate (2.7 g, 85%). LC-MS m/z: 345.1 $[M-tBu]^+$. $^1$H NMR (300 MHz, chloroform-d) δ ppm: 9.81 (s, 1H), 7.25-7.20 (m, 2H), 7.05 (dd, J=2.3, 11.0 Hz, 1H), 4.78 (d, J=6.0 Hz, 2H), 4.48-4.22 (m, 2H), 3.52 (br, t, J=11.5 Hz, 1H), 3.02-2.77 (m, 2H), 2.05-1.89 (m, 2H), 1.86-1.64 (m, 2H), 1.50 (s, 9H), 1.15-1.01 (m, 1H), 0.49-0.31 (m, 4H).

Intermediate 36 tert-Butyl (E)-4-(1-(cyclopropylmethyl)-5-fluoro-2-(2-nitroprop-1-en-1-yl)-1H-indol-7-yl)piperidine-1-carboxylate

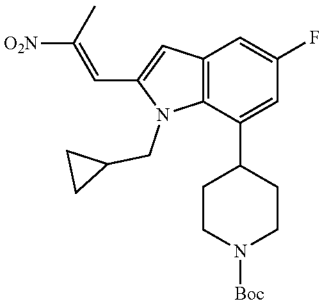 [SMILES: C/C(=C\c1cc2cc(F)cc(C3CCN(C(=O)OC(C)(C)C)CC3)c2n1CC1CC1)[N+](=O)[O-]]

Intermediate 36 was prepared following a procedure similar to the preparation of Intermediate 30, using appropriate reactants. LC-MS m/z: 402.3 $[M+H]^+$. $^1$H NMR (300 MHz, chloroform-d) δ ppm: 8.18 (s, 1H), 7.15 (dd, J=2.5, 8.1 Hz, 1H), 6.94 (dd, J=2.3, 11.0 Hz, 1H), 6.82 (s, 1H), 4.47-4.26 (m, 4H), 3.60-3.44 (m, 1H), 3.01-2.79 (m, 2H), 2.58 (s, 3H), 2.01-1.90 (m, 2H), 1.84-1.70 (m, 2H), 1.50 (s, 9H), 1.15-1.05 (m, 1H), 0.62-0.52 (m, 2H), 0.29 (q, J=5.3 Hz, 2H).

Intermediate 37

Ethyl 3-(2-chloro-3-nitropyridin-4-yl)-2-hydroxyacrylate

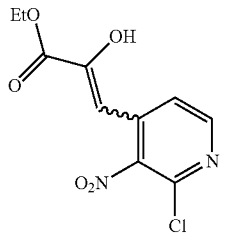 [SMILES: CCOC(=O)C(O)=Cc1ccnc(Cl)c1[N+](=O)[O-]]

Sodium ethoxide in ethanol (28.2 g, 87 mmol) was added to diethyl oxalate (12.70 g, 87 mmol) in toluene (50 ml). The reaction mixture was stirred for 10 min at a room temperature, followed by the addition of 2-chloro-4-methyl-3-nitropyridine (10 g, 57.9 mmol). The reaction mixture was stirred at a room temperature for 16 hours, concentrated, the residue thus obtained was diluted with water (20 ml), and acidified with acetic acid (10 ml) to bring pH to about 4. The solids thus obtained were filtered and dried to afford ethyl 3-(2-chloro-3-nitropyridin-4-yl)-2-hydroxyacrylate (15 g, 95%) as an off-white solid. LC-MS m/z: 273.0 $[M+H]^+$. $^1H$ NMR (300 MHz, DMSO-$d_6$) δ ppm: 8.61 (d, J=5.7 Hz, 1H), 8.31 (d, J=5.7 Hz, 1H), 5.92 (s, 1H), 4.30 (q, J=7.1 Hz, 2H), 1.28 (t, J=7.0 Hz, 3H).

Intermediate 38

Ethyl 7-chloro-1H-pyrrolo[2,3-c]pyridine-2-carboxylate

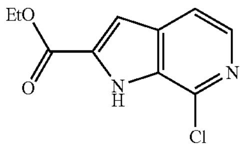 [SMILES: CCOC(=O)c1cc2ccnc(Cl)c2[nH]1]

Iron (15.36 g, 275 mmol) and ammonium chloride (23.54 g, 440 mmol) in water (30 ml) were added to a stirred solution of Intermediate 37 (15.0 g, 55.0 mmol) in ethanol (50 ml) and THF (100 ml). The reaction mixture was stirred at 65° C. for 3 hours, filtered through a celite bed, the filtrate obtained was diluted with water (50 ml), and quenched with saturated $NaHCO_3$ solution, followed by extraction with ethyl acetate (2×100 ml). The combined organic layers were dried over sodium sulphate, filtered, and concentrated under reduced pressure to obtain a crude product, which was purified using a silica gel column (0-50% ethyl acetate in hexane) to afford ethyl 7-chloro-1H-pyrrolo[2,3-c]pyridine-2-carboxylate (6.5 g, 53%). LC-MS m/z: 225.0 $[M+H]^+$. $^1H$ NMR (400 MHz, DMSO-$d_6$) δ ppm: 12.73 (br, s, 1H), 7.99 (d, J=5.5 Hz, 1H), 7.68 (d, J=5.5 Hz, 1H), 7.30 (s, 1H), 4.39 (q, J=7.0 Hz, 2H), 1.36 (t, J=7.0 Hz, 3H).

Intermediate 39

Ethyl 7-(1-(tert-butoxycarbonyl)-1,2,3,6-tetrahydropyridin-4-yl)-1H-pyrrolo[2,3-c]pyridine-2-carboxylate

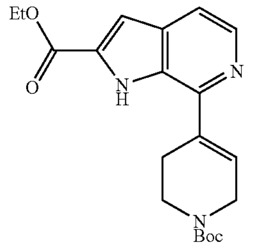 [SMILES: CCOC(=O)c1cc2ccnc(C3=CCN(C(=O)OC(C)(C)C)CC3)c2[nH]1]

tert-Butyl 4-(4,4,5,5-tetramethyl-1,3,2-dioxaborolan-2-yl)-3,6-dihydropyridine-1(2H)-carboxylate (11.63 g, 37.6 mmol) and $K_2CO_3$ in water (36.2 ml, 72.3 mmol) were added to a stirred solution of Intermediate 38 (6.5 g, 28.9 mmol) in 1,4-dioxane (65 ml). The reaction mixture was degassed with argon for 10 min, followed by the addition of $PdCl_2(dppf)-CH_2Cl_2$ adduct (1.418 g, 1.736 mmol), and stirred at 110° C. for 16 hours. The reaction mixture was filtered through a celite bed, the filtrate was diluted with water (50 ml) and extracted with ethyl acetate (2×100 ml). The combined organic layers were dried over sodium sulphate, filtered, and concentrated under reduced pressure to obtain a crude product, which was purified using a silica gel column (0-60% ethyl acetate in hexane) to afford ethyl 7-(1-(tert-butoxycarbonyl)-1,2,3,6-tetrahydropyridin-4-yl)-1H-pyrrolo[2,3-c]pyridine-2-carboxylate (10.2 g, 95%). LC-MS m/z: 372.2 $[M+H]^+$. $^1H$ NMR (300 MHz, DMSO-$d_6$) δ ppm: 11.95 (br, s, 1H), 8.16 (d, J=5.3 Hz, 1H), 7.53 (d, J=5.7 Hz, 1H), 7.23 (s, 1H), 6.36 (br s, 1H), 4.38 (q, J=7.1 Hz, 2H), 4.15-4.08 (m, 2H), 4.03 (d, J=7.2 Hz, 1H), 3.94 (s, 2H), 3.59 (br t, J=5.3 Hz, 2H), 2.72-2.62 (m, 2H), 1.46 (s, 9H), 1.35 (t, J=7.2 Hz, 3H).

Intermediate 40

Ethyl 7-(1-(tert-butoxycarbonyl)piperidin-4-yl)-1H-pyrrolo[2,3-c]pyridine-2-carboxylate

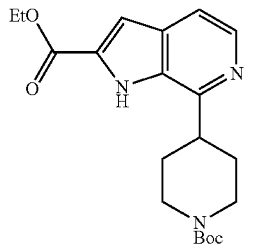 [SMILES: CCOC(=O)c1cc2ccnc(C3CCN(C(=O)OC(C)(C)C)CC3)c2[nH]1]

Pd/C (50% wet, 2.92 g, 2.75 mmol) was added to a stirred solution of Intermediate 39 (10.2 g, 27.5 mmol) in ethanol (10 ml). The reaction mixture was stirred under hydrogen atmosphere for 16 hours, filtered through a celite bed, and the filtrate was concentrated to obtain ethyl 7-(1-(tert-butoxycarbonyl)piperidin-4-yl)-1H-pyrrolo[2,3-c]pyridine-2-carboxylate (8.1 g, 79%). LC-MS m/z: 374.1 $[M+H]^+$. $^1$H NMR (300 MHz, DMSO-$d_6$) δ ppm: 12.38 (s, 1H), 8.09 (d, J=5.3 Hz, 1H), 7.46 (d, J=5.7 Hz, 1H), 7.18 (d, J=1.5 Hz, 1H), 4.43-4.34 (m, 2H), 4.16-4.05 (m, 2H), 3.94 (s, 2H), 3.80-3.62 (m, 2H), 3.44-3.42 (m, 2H), 1.76 (br, s, 1H), 1.43 (s, 9H), 1.39-1.23 (m, 3H).

Intermediate 41

Ethyl 7-(1-(tert-butoxycarbonyl)piperidin-4-yl)-1-(cyclopropylmethyl)-1H-pyrrolo[2,3-c]pyridine-2-carboxylate

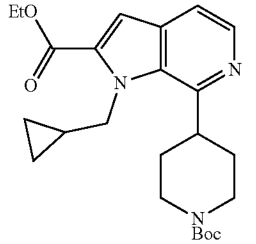 [SMILES: CCOC(=O)c1cc2ccnc(C3CCN(C(=O)OC(C)(C)C)CC3)c2n1CC1CC1]

Cesium carbonate (4.45 g, 13.66 mmol) and TBAI (0.841 g, 2.276 mmol) were added to a stirred solution of Intermediate 40 (1.7 g, 4.55 mmol) in DMF (10 ml), followed by the addition of (bromomethyl)cyclopropane (1.229 g, 9.10 mmol). The reaction mixture was stirred at 60° C. for 3 hours, diluted with water (20 ml), and extracted with ethyl acetate (3×20 ml). The combined organic layers were washed with brine, dried over sodium sulfate, filtered, and concentrated in vacuum to obtain a crude product, which was purified using a silica gel column (0-20% ethyl acetate in hexane) to afford ethyl 7-(1-(tert-butoxycarbonyl)piperidin-4-yl)-1-(cyclopropylmethyl)-1H-pyrrolo[2,3-c]pyridine-2-carboxylate (1.3 g, 67%). LC-MS m/z: 428.2 $[M+H]^+$. $^1$H NMR (300 MHz, DMSO-$d_6$) δ ppm: 8.18 (d, J=5.3 Hz, 1H), 7.53 (d, J=5.3 Hz, 1H), 7.33 (s, 1H), 4.80 (br, d, J=6.4 Hz, 2H), 4.35 (q, J=7.2 Hz, 2H), 4.19-3.98 (m, 2H), 3.68-3.52 (m, 1H), 2.94 (br, s, 2H), 1.85 (br, s, 4H), 1.43 (s, 9H), 1.36-1.32 (m, 3H), 1.27-0.99 (m, 1H), 0.53-0.35 (m, 2H), 0.33-0.17 (m, 2H).

Intermediate 42 tert-Butyl 4-(1-(cyclopropylmethyl)-2-(hydroxymethyl)-1H-pyrrolo[2,3-c]pyridin-7-yl)piperidine-1-carboxylate

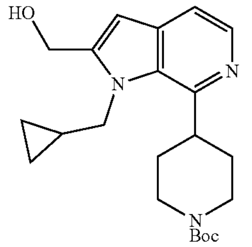 [SMILES: CC(C)(C)OC(=O)N1CCC(c2nccc3cc(CO)n(CC4CC4)c23)CC1]

$LiBH_4$ (4.56 ml, 18.24 mmol) was added to a stirred solution of Intermediate 41 (1.3 g, 3.04 mmol) in THF (30 ml). The reaction mixture was stirred at a room temperature for 36 hours, quenched with saturated ammonium chloride solution (10 ml), diluted with water (20 ml), and extracted with ethyl acetate (3×20 ml). The combined organic layers were washed with brine, dried over sodium sulfate, filtered, and concentrated in vacuum to obtain a crude product, which was purified using a silica gel column (0-20% ethyl acetate in hexane) to afford tert-butyl 4-(1-(cyclopropylmethyl)-2-(hydroxymethyl)-1H-pyrrolo[2,3-c]pyridin-7-yl)piperidine-1-carboxylate (1.02 g, 87%). LC-MS m/z: 386.2 $[M+H]^+$. $^1$H NMR (300 MHz, DMSO-$d_6$) δ ppm: 8.04 (d, J=5.3 Hz, 1H), 7.32 (d, J=5.3 Hz, 1H), 6.45 (s, 1H), 5.42 (t, J=5.3 Hz, 1H), 4.65 (d, J=5.7 Hz, 2H), 4.34 (br d, J=6.0 Hz, 2H), 4.11 (br d, J=10.6 Hz, 2H), 3.57 (br d, J=11.0 Hz, 1H), 2.90 (br s, 2H), 1.88 (br d, J=9.8 Hz, 2H), 1.83-1.64 (m, 2H), 1.43 (s, 9H), 1.24 (br s, 1H), 0.53-0.42 (m, 2H), 0.31 (q, J=4.9 Hz, 2H).

Intermediate 43 tert-Butyl 4-(1-(cyclopropylmethyl)-2-formyl-1H-pyrrolo[2,3-c]pyridin-7-yl)piperidine-1-carboxylate

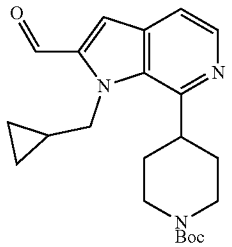 [SMILES: CC(C)(C)OC(=O)N1CCC(c2nccc3cc(C=O)n(CC4CC4)c23)CC1]

Manganese dioxide (2.255 g, 25.9 mmol) was added to a stirred solution of Intermediate 42 (1 g, 2.59 mmol) in THF (10 ml). The reaction mixture was stirred at 40° C. for 3 hours, filtered through a celite bed, and the filtrate was concentrated to obtain tert-butyl 4-(1-(cyclopropylmethyl)-2-formyl-1H-pyrrolo[2,3-c]pyridin-7-yl)piperidine-1-carboxylate (0.9 g, 90%). LC-MS m/z: 384.2$[M+H]^+$. $^1$H NMR (300 MHz, DMSO-$d_6$) δ ppm: 10.03 (s, 1H), 8.22 (d, J=5.3 Hz, 1H), 7.61 (d, J=5.3 Hz, 1H), 7.56 (s, 1H), 4.80 (d, J=6.0 Hz, 2H), 4.18-4.00 (m, 2H), 3.67-3.55 (m, 1H), 3.13-2.81 (m, 2H), 1.94-1.75 (m, 4H), 1.47-1.35 (m, 9H), 1.29-1.12 (m, 1H), 0.51-0.37 (m, 2H), 0.36-0.23 (m, 2H).

Intermediate 44 tert-Butyl (E)-4-(1-(cyclopropylmethyl)-2-(2-nitroprop-1-en-1-yl)-1H-pyrrolo[2,3-c]pyridin-7-yl)piperidine-1-carboxylate

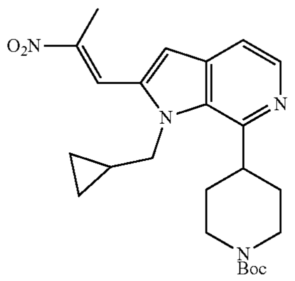 [SMILES: C/C(=C\c1cc2ccnc(C3CCN(C(=O)OC(C)(C)C)CC3)c2n1CC1CC1)[N+](=O)[O-]]

Ammonium acetate (0.271 g, 3.52 mmol) was added to a stirred solution of Intermediate 43 (0.9 g, 2.347 mmol) in nitroethane (1.678 ml, 23.47 mmol). The reaction mixture was stirred at 90° C. for 2 hours, diluted with water (50 ml), and extracted with ethyl acetate (2×100 ml). The combined organic layers were dried over sodium sulphate, filtered, and concentrated under reduced pressure to obtain tert-butyl (E)-4-(1-(cyclopropylmethyl)-2-(2-nitroprop-1-en-1-yl)-1H-pyrrolo[2,3-c]pyridin-7-yl)piperidine-1-carboxylate (0.85 g, 82%). LC-MS m/z: 441.2 $[M+H]^+$.

Intermediate 45

Ethyl 7-bromo-1-(cyclopropylmethyl)-1H-indole-2-carboxylate

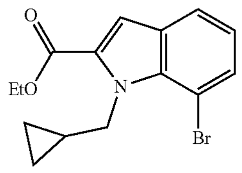 [SMILES: CCOC(=O)c1cc2cccc(Br)c2n1CC1CC1]

Potassium carbonate (41.2 g, 298 mmol) was added to a stirred solution of ethyl 7-bromo-1H-indole-2-carboxylate (20 g, 74.6 mmol) in DMF (80 ml), followed by addition of (bromomethyl)cyclopropane (14.47 ml, 149 mmol). The reaction mixture was stirred at 50° C. for 16 hours, diluted with water (100 ml), and extracted with ethyl acetate (2×200 ml). The combined organic layers were washed with brine, dried over sodium sulfate, filtered, and concentrated in vacuum to obtain a crude product, which was purified using a silica gel column (0-10% ethyl acetate in hexane) to afford (22 g, 92%) of ethyl 7-bromo-1-(cyclopropylmethyl)-1H-indole-2-carboxylate as off white solid. LC-MS m/z: 322.0 $[M+H]^+$. $^1H$ NMR (400 MHz, DMSO-$d_6$) δ ppm: 7.76 (d, J=8.0 Hz, 1H), 7.59 (d, J=8.0 Hz, 1H), 7.41 (s, 1H), 7.07 (t, J=8.0 Hz, 1H), 5.01 (d, J=8.0 Hz, 2H), 4.34 (q, J=8.0 Hz, 2H), 2.33 (br, s, 1H), 1.34 (t, J=8.00 Hz, 3H), 1.27-1.15 (m, 1H), 0.42-0.29 (m, 4H).

Intermediate 46

Ethyl 7-(1-(tert-butoxycarbonyl)azetidin-3-yl)-1-(cyclopropylmethyl)-1H-indole-2-carboxylate

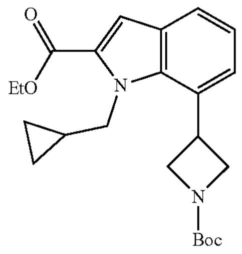 [SMILES: CCOC(=O)c1cc2cccc(C3CN(C(=O)OC(C)(C)C)C3)c2n1CC1CC1]

Tris(trimethylsilyl)silane (5.67 g, 22.81 mmol) and sodium carbonate (4.61 g, 43.5 mmol) were added to a stirred solution of Intermediate 45 (9.84 g, 34.8 mmol) in 1,2-dimethoxyethane (35 ml) in a first vial, and the reaction mixture was purged with argon followed by the addition of $Ir[DF(CF_3)PPY]_2(DTBBPY)PF_6$ (0.244 g, 0.217 mmol). A mixture of 4,4'-di-tert-butyl-2,2'-dipyridyl (0.292 g, 1.086 mmol) and Nickel(II) chloride ethylene glycol dimethyl ether complex (0.239 g, 1.086 mmol) in 1,2-dimethoxy ethane (0.5 ml) was prepared in another vial and the contents were sonicated for 10 min to obtain a catalyst (green suspension). The catalyst was added into the reaction mixture in the first vial, and the vial containing the reaction mixture was placed under Blue LED light (34 W) for 16 hours. The reaction mixture was diluted with water (100 ml), and extracted with ethyl acetate (2×200 ml). The combined organic layers were washed with brine, dried over sodium sulfate, filtered, and concentrated in vacuum to obtain a crude product, which was purified using a silica gel column (0-20% ethyl acetate in hexane) to afford (5.6 g, 64%) of ethyl 7-(1-(tert-butoxycarbonyl)azetidin-3-yl)-1-(cyclopropylmethyl)-1H-indole-2-carboxylate as pale yellow liquid. LC-MS m/z: 343.3 $[M-56]^+$. $^1H$ NMR (400 MHz, DMSO-$d_6$) δ ppm: 7.63 (d, J=8.0 Hz, 1H), 7.49 (d, J=8.0 Hz, 1H), 7.36 (s, 1H), 7.19 (t, J=8.0 Hz, 1H), 4.63 (d, J=8.0 Hz, 2H), 4.57-4.52 (m, 1H), 4.41-4.29 (m, 2H), 4.12-3.94 (m, 2H), 3.82-3.80 (m, 2H), 2.12 (quin, J=7.5 Hz, 1H), 1.41 (s, 9H), 1.33(t, J=8.0 Hz, 3H), 0.94-0.84 (m, 1H), 0.39-0.27 (m, 2H), 0.21-0.02 (m, 2H).

Intermediate 47 tert-Butyl 3-(1-(cyclopropylmethyl)-2-(hydroxymethyl)-1H-indol-7-yl)azetidine-1-carboxylate

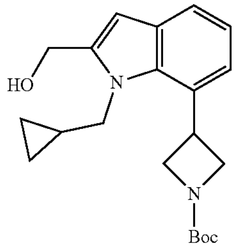 [SMILES: CC(C)(C)OC(=O)N1CC(c2cccc3cc(CO)n(CC4CC4)c23)C1]

$LiBH_4$ (14.05 ml, 56.2 mmol) was added to a stirred solution of Intermediate 46 (5.6 g, 14.05 mmol) in THF (50 ml). The reaction mixture was stirred at a room temperature for 4 days, quenched with saturated ammonium chloride solution (10 ml), diluted with water (20 ml), and extracted with ethyl acetate (3×50 ml). The combined organic layers were washed with brine, dried over sodium sulfate, filtered, and concentrated in vacuum to obtain a crude product, which was purified using a silica gel column (0-20% ethyl acetate in hexane) to afford (2.0 g, 39%) of tert-butyl 3-(1-(cyclopropylmethyl)-2-(hydroxymethyl)-1H-indol-7-yl)azetidine-1-carboxylate. LC-MS m/z: 357.0 $[M+H]^+$. $^1H$ NMR (400 MHz, DMSO-$d_6$) δ ppm: 7.41 (d, J=8.0 Hz, 1H), 7.29 (d, J=8.0 Hz, 1H), 7.06 (t, J=8.0 Hz, 1H), 6.41 (s, 1H), 5.23 (t, J=4.0 Hz, 1H), 4.66-4.55 (m, 2H), 4.36 (br, t, J=8.5 Hz, 2H), 4.24 (d, J=6.0 Hz, 2H), 3.96 (br, t, J=8.0 Hz, 2H), 1.99 (s, 1H), 1.46-1.38 (m, 9H), 1.09-1.00 (m, 1H), 0.47-0.37 (m, 2H), 0.24 (q, J=5.0 Hz, 2H).

Intermediate 48 tert-Butyl 3-(1-(cyclopropylmethyl)-2-formyl-1H-indol-7-yl)azetidine-1-carboxylate

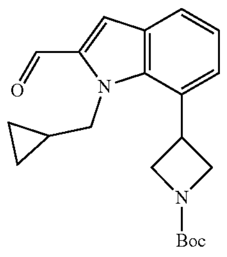 [SMILES: CC(C)(C)OC(=O)N1CC(c2cccc3cc(C=O)n(CC4CC4)c23)C1]

Manganese dioxide (4.88 g, 56.1 mmol) was added to a stirred solution of Intermediate 47 (2 g, 5.61 mmol) in THF (10 ml). The reaction mixture was stirred at 40° C. for 3 hours, filtered through a celite bed, and the filtrate was concentrated to obtain (1.9 g, 96%) of tert-butyl 3-(1-(cyclopropylmethyl)-2-formyl-1H-indol-7-yl)azetidine-1-carboxylate. LC-MS m/z: 299 $[M-56]^+$. $^1H$ NMR (400 MHz, DMSO-$d_6$) δ ppm: 9.86 (s, 1H), 7.72 (d, J=8.0 Hz, 1H), 7.60 (d, J=8.0 Hz, 1H), 7.56 (s, 1H), 7.23 (t, J=8.0 Hz, 1H), 4.65 (d, J=8.0 Hz, 2H), 4.38 (br t, J=8.0 Hz, 2H), 4.06-3.96 (m, 2H), 1.77 (td, J=3.4, 6.3 Hz, 1H), 1.41 (s, 9H), 1.02-0.99 (m, 1H), 0.41-0.30 (m, 2H), 0.26-0.15 (m, 2H).

Intermediate 49 tert-Butyl (E)-3-(1-(cyclopropylmethyl)-2-(2-nitroprop-1-en-1-yl)-1H-indol-7-yl)azetidine-1-carboxylate

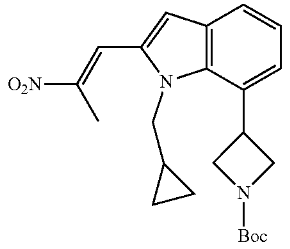 [SMILES: C/C(=C\c1cc2cccc(C3CN(C(=O)OC(C)(C)C)C3)c2n1CC1CC1)[N+](=O)[O-]]

Ammonium acetate (0.620 g, 8.04 mmol) was added to a stirred solution of Intermediate 48 (1.9 g, 5.36 mmol) in nitroethane (3.83 ml, 53.6 mmol). The reaction mixture was stirred at 90° C. for 2 hours, diluted with water (20 ml), and extracted with ethyl acetate (3×20 ml). The combined organic layers were washed with brine, dried over sodium sulfate, filtered, and concentrated in vacuum to afford (2.2 g, 100%) of tert-butyl (E)-3-(1-(cyclopropylmethyl)-2-(2-nitroprop-1-en-1-yl)-1H-indol-7-yl)azetidine-1-carboxylate. LC-MS m/z: 412.3 $[M+H]^+$. $^1H$ NMR (400 MHz, DMSO-$d_6$) δ ppm: 8.21 (s, 1H), 7.60 (d, J=8.0 Hz, 1H), 7.45 (d, J=8.0 Hz, 1H), 7.18 (t, J=8.0 Hz, 1H), 7.09 (s, 1H), 4.58-4.53 (m, 1H), 4.43-4.33 (m, 2H), 4.30 (d, J=6.0 Hz, 2H), 4.09-3.95 (m, 2H), 2.48-2.38 (m, 1H), 1.47-1.37 (m, 9H), 1.06-0.96 (m, 1H), 0.49-0.39 (m, 2H), 0.29-0.15 (m, 2H).

Intermediate 50

(E)-7-(benzyloxy)-1-(cyclopropylmethyl)-2-(2-nitroprop-1-en-1-yl)-1H-indole

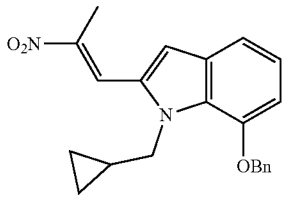 [SMILES: C/C(=C\c1cc2cccc(OCc3ccccc3)c2n1CC1CC1)[N+](=O)[O-]]

Ammonium acetate (0.606 g, 7.86 mmol) was added to a stirred solution of 7-(benzyloxy)-1-(cyclopropylmethyl)-1H-indole-2-carbaldehyde (2 g, 6.55 mmol) in nitroethane (18.73 ml, 262 mmol). The reaction mixture was heated to 90° C. for 2 hours, allowed to cool to a room temperature, diluted with water (100 ml), and extracted with ethyl acetate (2×100 ml). The combined organic layers were dried over sodium sulphate, filtered, and concentrated under reduced pressure to obtain crude (E)-7-(benzyloxy)-1-(cyclopropylmethyl)-2-(2-nitroprop-1-en-1-yl)-1H-indole (1.9 g, 80%) LC-MS m/z: 361.7 $[M+H]^+$.

Intermediate 51

7-Chloro-1H-pyrrolo[2,3-c]pyridine

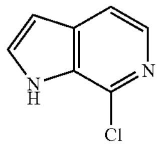

Vinyl magnesium bromide (189 ml, 189 mmol) was added to a stirred solution of 2-chloro-3-nitropyridine (10 g, 63.1 mmol) in THF (80 ml) at −78° C. The reaction mixture was stirred for 1 hour, warmed to −20° C., and the resulting solution was stirred at −20° C. for 12 hours. The reaction mixture was quenched with saturated ammonium chloride solution (20 ml), diluted with water (2×50 ml), and extracted with ethyl acetate (3×50 ml). The combined organic layers were washed with brine, dried over sodium sulfate, filtered, and concentrated in vacuum to obtain a crude product, which was purified using a silica gel column (0-50% ethyl acetate in hexane) to afford 7-chloro-1H-pyrrolo[2,3-c]pyridine (3.4 g, 35%) as brown solid. LC-MS m/z: 153.1 $[M+H]^+$. $^1H$ NMR (300 MHz, DMSO-$d_6$) δ ppm: 8.35-8.30 (m, 1H), 8.29 (s, 1H), 7.88-7.78 (m, 1H), 7.78-7.70 (m, 1H), 7.66 (s, 1H).

Intermediate 52

7-Chloro-1-(cyclopropylmethyl)-1H-pyrrolo[2,3-c] pyridine

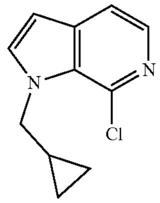 [SMILES: Clc1nccc2ccn(CC3CC3)c12]

Sodium hydride (1.049 g, 26.2 mmol) was added to a stirred solution of Intermediate 51 (2 g, 13.11 mmol) in DMF (20 ml) at 0° C., the contents were stirred for 20 minutes, followed by the addition of (bromomethyl)cyclopropane (1.910 ml, 19.66 mmol). The resulting reaction mixture was stirred for 16 hours, quenched with ice-flakes and cold water (20 ml), and extracted with ethyl acetate (3×30 ml). The combined organic layers were washed with brine, dried over sodium sulfate, filtered, and concentrated in vacuum to obtain a crude product, which was purified using a silica gel column (0-20% ethyl acetate in hexane) to afford 7-chloro-1-(cyclopropylmethyl)-1H-pyrrolo[2,3-c] pyridine (2.2 g, 81%) of. LC-MS m/z: 207.1 $[M+H]^+$. $^1H$ NMR (300 MHz, DMSO-$d_6$) δ ppm: 7.90 (d, J=5.3 Hz, 1H), 7.76 (d, J=3.0 Hz, 1H), 7.58 (d, J=5.3 Hz, 1H), 6.63 (d, J=3.4 Hz, 1H), 4.40 (d, J=6.8 Hz, 2H), 1.40-1.22 (m, 1H), 0.53-0.39 (m, 4H).

Intermediate 53

7-Chloro-1-(cyclopropylmethyl)-1H-pyrrolo[2,3-c] pyridine-2-carbaldehyde

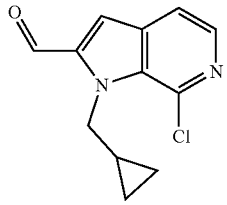 [SMILES: O=Cc1cc2ccnc(Cl)c2n1CC1CC1]

sec-Butyllithium (11.41 ml, 15.97 mmol) was added to a stirred solution of Intermediate 52 (2.2 g, 10.64 mmol) in tetrahydrofuran (30 ml) at −78° C., the contents were stirred for 1 hour, followed by the addition of DMF (1.236 ml, 15.97 mmol). The resulting reaction mixture was stirred at the same temperature for 1 hour, quenched with saturated ammonium chloride solution (10 ml), diluted with water (20 ml), and extracted with ethyl acetate (3×20 ml). The combined organic layers were washed with brine, dried over sodium sulfate, filtered, and concentrated in vacuum to obtain a crude product, which was purified using a silica gel column (eluting with 0-20% ethyl acetate in hexane) to afford 7-chloro-1-(cyclopropylmethyl)-1H-pyrrolo[2,3-c] pyridine-2-carbaldehyde (1.2 g, 78%) as an off white solid. LC-MS m/z: 235.0 $[M+H]^+$. $^1H$ NMR (400 MHz, DMSO-$d_6$) δ ppm: 10.10 (s, 1H), 8.08 (d, J=5.0 Hz, 1H), 7.84 (d, J=5.5 Hz, 1H), 7.67 (s, 1H), 4.92 (d, J=7.0 Hz, 2H), 1.35-1.24 (m, 1H), 0.47-0.41 (m, 2H), 0.41-0.33 (m, 2H).

Intermediate 54

(E)-7-Chloro-1-(cyclopropylmethyl)-2-(2-nitroprop-1-en-1-yl)-1H-pyrrolo[2,3-c]pyridine

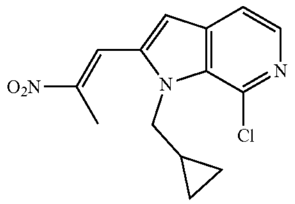 [SMILES: C/C(=C\c1cc2ccnc(Cl)c2n1CC1CC1)[N+](=O)[O-]]

(E)-7-chloro-1-(cyclopropylmethyl)-2-(2-nitroprop-1-en-1-yl)-1H-pyrrolo[2,3-c]pyridine (1.2 g, 97%) was prepared following a procedure similar to the preparation of Intermediate 57. LC-MS m/z 292.2 $[M+H]^+$. $^1H$ NMR (400 MHz, DMSO-$d_6$) δ ppm: 8.18 (s, 1H), 8.01 (d, J=5.5 Hz, 1H), 7.69 (d, J=5.5 Hz, 1H), 7.14 (s, 1H), 4.64 (d, J=7.0 Hz, 2H), 2.54-2.52 (m, 3H), 1.33-1.09 (m, 1H), 0.43-0.23 (m, 4H).

Intermediate 55

7-Chloro-1-methyl-1H-pyrrolo[2,3-c]pyridine

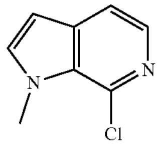

Sodium hydride (1.311 g, 32.8 mmol) was added to a stirred solution of Intermediate 51 (5 g, 32.8 mmol) in DMF (100 ml) at 0° C., the contents were stirred for 5 min, followed by the addition of iodomethane (2.049 ml, 32.8 mmol). The resulting reaction mixture was stirred at a room temperature for 16 hours, quenched with ice water, and extracted with ethyl acetate (3×100 ml). The combined organic layers were dried over $Na_2SO_4$, and concentrated to obtain a crude product, which was purified using a silica gel column (0-50% ethyl acetate in hexane) to afford 7-chloro-1-methyl-1H-pyrrolo[2,3-c]pyridine (4 g, 73%) as off-white solid. LC-MS m/z: 167.0 $[M+H]^+$.

Intermediate 56

7-Chloro-1-methyl-1H-pyrrolo[2,3-c]pyridine-2-carbaldehyde

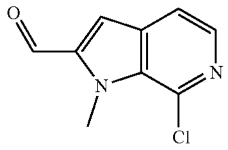

sec-Butyl lithium (6.43 ml, 9 mmol) was added to a solution of Intermediate 55 (1 g, 6 mmol) in tetrahydrofuran (10 ml) at −78° C., the contents were stirred for 0.5 hours, followed by the addition of DMF (0.697 ml, 9 mmol). The resulting reaction mixture was stirred for 1 hour, quenched with saturated $NH_4Cl$ solution (50 ml), extracted with ethyl acetate (3×50 ml), dried over $Na_2SO_4$, and concentrated to obtain a crude product, which was purified using a silica gel column (0-50% ethyl acetate in hexane) to afford 7-chloro-1-methyl-1H-pyrrolo[2,3-c]pyridine-2-carbaldehyde (1.0 g, 86%) as a brown oil. LC-MS m/z: 195.0 $[M+H]^+$.

Intermediate 57

(E)-7-Chloro-1-methyl-2-(2-nitroprop-1-en-1-yl)-1H-pyrrolo[2,3-c]pyridine

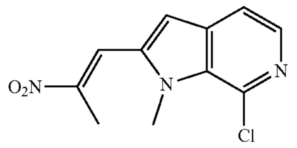 [SMILES: C/C(=C\c1cc2ccnc(Cl)c2n1C)[N+](=O)[O-]]

Ammonium acetate (0.594 g, 7.71 mmol) was added to a solution of Intermediate 56 (1 g, 5.14 mmol) in nitroethane (10 ml). The reaction mixture was heated to 90° C., stirred for 2 hours, diluted with ethyl acetate (50 ml), washed with saturated $NH_4Cl$, dried over $Na_2SO_4$, and concentrated to obtain a crude product, which was purified using a silica gel column (0-50% ethyl acetate in hexane) to afford (E)-7-chloro-1-methyl-2-(2-nitroprop-1-en-1-yl)-1H-pyrrolo[2,3-c]pyridine (1.1 g, 85%) as a yellow solid. LC-MS m/z: 252.3 $[M+H]^+$.

Intermediate 58

4-Bromobenzo[b]thiophene-3-carbaldehyde

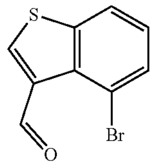 [SMILES: O=Cc1csc2cccc(Br)c12]

A solution of 4-bromobenzo[b]thiophene (10 g, 46.9 mmol) and dichloro(methoxy)methane (5.39 g, 46.9 mmol) in DCM (500 ml) was stirred and cooled to 0° C., followed by the addition of $TiCl_4$ (65.17 ml, 591 mmol) dropwise at a room temperature. The resulting reaction mixture was stirred for 16 hours at a room temperature. Thereafter, saturated ammonium chloride (500 ml) was added dropwise to the reaction mixture, and the contents were extracted with DCM (2×500 ml). The combined organic layers were washed with water (200 ml) and brine solution (200 ml), followed by drying over sodium sulphate. The organic layers were filtered, and volatiles were evaporated to dryness under reduced pressure to obtain a crude product, which was purified using a silica gel column (0-20% ethyl acetate in hexane) to afford 4-bromobenzo[b]thiophene-3-carbaldehyde (6 g, 53%). $^1H$ NMR (300 MHz, DMSO-$d_6$) δ ppm: 10.80-10.95 (m, 1H), 8.80 (s, 1H), 8.21 (dd, J=8.31, 0.76 Hz, 1H), 7.79-7.85 (m, 1H), 7.41 (t, J=7.93 Hz, 1H).

Intermediate 59

(4-Bromobenzo[b]thiophen-3-yl)(cyclopropyl)methanol

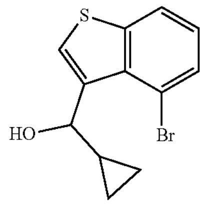 [SMILES: OC(c1csc2cccc(Br)c12)C1CC1]

Cyclopropylmagnesium bromide (12.44 ml, 12.44 mmol) was added dropwise under nitrogen atmosphere to a stirred solution of Intermediate 58 (2 g, 8.30 mmol) in THF (30 ml) cooled to −20° C. The reaction mixture stirred for 2 hours, diluted with water (50 ml), and extracted with ethyl acetate (2×50 ml). The combined organic layers were washed with water (100 ml) and brine solution (100 ml), followed by drying over sodium sulphate. The organic layers were filtered, and volatiles were evaporated to dryness under reduced pressure to afford (4-bromobenzo[b]thiophen-3-yl)(cyclopropyl)methanol (2.2 g, 94%). $^1H$ NMR (300 MHz, DMSO-$d_6$) δ ppm: 7.99-8.08 (m, 1H), 7.84-7.90 (m, 1H), 7.60-7.68 (m, 1H), 7.19-7.28 (m, 1H), 5.52-5.65 (m, 1H), 5.11-5.23 (m, 1H), 1.33-1.48 (m, 1H), 0.27-0.49 (m, 4H).

Intermediate 60

4-Bromo-3-(cyclopropylmethyl)benzo[b]thiophene

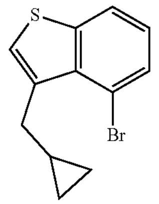 [SMILES: Brc1cccc2scc(CC3CC3)c12]

Triethylsilane (14 ml, 49.4 mmol) was added to a stirred solution of Intermediate 50 (14 g, 49.4 mmol) in DCM (200 ml), followed by the addition of TFA (14 ml, 182 mmol) after 5 minutes. The resulting reaction mixture was stirred for 1 hour at a room temperature. Thereafter, the volatiles were evaporated to dryness under reduced pressure, saturated $NaHCO_3$ (100 ml) was added, and the contents were extracted with DCM (2×150 ml). The combined organic extracts were washed with water (100 ml) and brine solution (100 ml), dried over sodium sulphate, filtered, and volatiles were evaporated to dryness under reduced pressure to obtain a crude product, which was purified using a silica gel column (0-10% ethyl acetate in hexane) to afford 4-bromo-3-(cyclopropylmethyl)benzo[b]thiophene (6 g, 45%). $^1H$ NMR (300 MHz, DMSO-$d_6$) δ ppm: 8.02 (dd, J=7.93, 0.76 Hz, 1H), 7.70 (s, 1H), 7.63 (dd, J=7.55, 1.13 Hz, 1H), 7.24 (t, J=7.74 Hz, 1H), 3.05 (d, J=6.80 Hz, 2H), 1.24 (br, d, J=3.78 Hz, 1H), 0.54-0.44 (m, 2H), 0.31-0.17 (m, 2H).

Intermediate 61

4-Bromo-3-(cyclopropylmethyl)benzo[b]thiophene-2-carbaldehyde

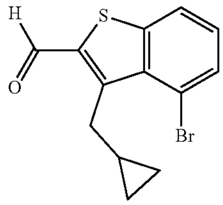 [SMILES: O=Cc1sc2cccc(Br)c2c1CC1CC1]

LDA (2M in THF, 11.23 ml, 22.46 mmol) was added dropwise to a stirred solution of Intermediate 60 (3 g, 11.23 mmol) in THF (30 ml) cooled to −78° C., the contents were stirred for 1 hour at −78° C., followed by the addition of DMF (1.739 ml, 22.46 mmol). The resulting reaction mixture was stirred for 3 hours, water (100 ml) was added, and the contents were extracted with ethyl acetate (2×100 ml). The combined organic layers were washed with water (100 ml) and brine solution (100 ml), dried over sodium sulphate, filtered, and volatiles were evaporated to dryness under reduced pressure to afford 4-bromo-3-(cyclopropylmethyl)benzo[b]thiophene-2-carbaldehyde (3 g, 91%). $^1$H NMR (300 MHz, DMSO-$d_6$) δ ppm: 10.32 (s, 1H), 8.15 (dd, J=8.3, 0.70 Hz, 1H), 8.07-7.92 (m, 1H), 7.45 (t, J=8.0 Hz, (1H), 3.57 (d, J=6.4 Hz, 2H), 1.24-1.03 (m, 1H), 0.54-0.23 (m, 4H). LC-MS m/z: 295.31 [M+H]$^+$.

Intermediate 62

(E)-4-Bromo-3-(cyclopropylmethyl)-2-(2-nitroprop-1-en-1-yl)benzo[b]thiophene

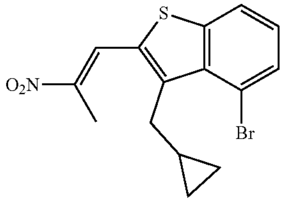 [SMILES: C/C(=C\c1sc2cccc(Br)c2c1CC1CC1)[N+](=O)[O-]]

Ammonium acetate (0.261 g, 3.39 mmol) was added to a stirred solution of Intermediate 61 (1 g, 3.39 mmol) in nitroethane (0.242 ml, 3.39 mmol). The reaction mixture was stirred for 2 hours at 90° C., water (100 ml) was added to the reaction mixture, and the contents were extracted with ethyl acetate (2×100 ml). The combined organic layers were washed with water (100 ml), dried over sodium sulphate, filtered, and volatiles were evaporated to dryness under reduced pressure to afford (E)-4-bromo-3-(cyclopropylmethyl)-2-(2-nitroprop-1-en-1-yl)benzo[b]thiophene (1 g, 84%) as a yellow solid. $^1$H NMR (300 MHz, DMSO-$d_6$) δ ppm: 8.39 (s, 1H), 8.14 (d, J=8.3 Hz, 1H), 7.76 (d, J=7.6 Hz, 1H), 7.44-7.34 (m, 1H), 3.34 (m, 2H), 1.29-1.2 (m, 1H), 0.47-0.42 (m, 2H), 0.27 (d, J=4.5 Hz, 2H).

Example 1

((7R)-7-Amino-2-azabicyclo[2.2.1]heptan-2-yl)(2-(1-(cyclopropylmethyl)-1H-pyrrolo[2,3-b]pyridin-2-yl)-4-methoxy-3-methylpyrazolo[1,5-a]pyridin-6-yl)methanone

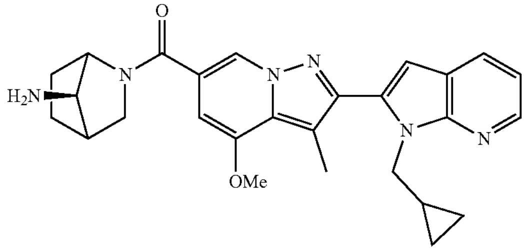 [SMILES: COc1cc(C(=O)N2CC3CCC2[C@@H]3N)cn2nc(-c3cc4cccnc4n3CC3CC3)c(C)c12]

Intermediate 1A 3-(tert-Butyl)-6-methyl 2-(1-(cyclopropylmethyl)-1H-pyrrolo[2,3-b]pyridin-2-yl)-4-methoxypyrazolo[1,5-a]pyridine-3,6-dicarboxylate

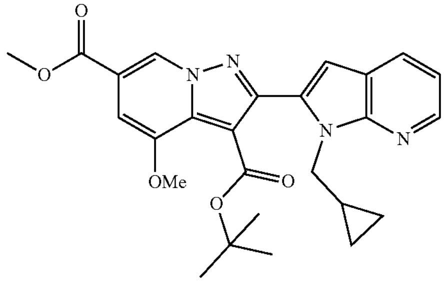 [SMILES: COC(=O)c1cc(OC)c2c(C(=O)OC(C)(C)C)c(-c3cc4cccnc4n3CC3CC3)nn2c1]

1-Amino-3-methoxy-5-(methoxycarbonyl)pyridin-1-ium (Intermediate 1, 0.618 g, 3.37 mmol) and $K_2CO_3$ (0.933 g, 6.75 mmol) were added to a stirred solution of tert-butyl 3-(1-(cyclopropylmethyl)-1H-pyrrolo[2,3-b]pyridin-2-yl) propiolate (Intermediate 2, 1 g, 3.37 mmol) in DMF (20 ml). The reaction mixture was stirred at a room temperature for 16 hours, diluted with EtOAc (50 ml), washed with water (3×50 ml) and brine (3×50 ml), dried over $Na_2SO_4$, and concentrated under reduced pressure to obtain a crude product. The crude product was purified using a silica gel column (24 g, Redisep $SiO_2$ column, eluting with 30% EtOAc in hexane) to afford the title compound (650 mg, 40%) as a yellow solid. LC-MS m/z: 477.2 [M+H]$^+$. $^1$H NMR (400 MHz, chloroform-d) δ ppm: 8.92 (d, J=1.0 Hz, 1H), 8.39 (d, J=4.8 Hz, 1H), 7.98-7.93 (m, 1H), 7.16-7.08 (m, 2H), 6.82 (s, 1H), 4.48 (d, J=7.0 Hz, 2H), 4.04 (s, 3H), 3.99 (s, 3H), 1.43 (m, 9H), 1.37-1.21 (m, 5H), 0.38-0.25 (m, 4H).

Intermediate 1B 2-(1-(Cyclopropylmethyl)-1H-pyrrolo[2,3-b]pyridin-2-yl)-4-methoxy-6-(methoxycarbonyl)pyrazolo[1,5-a]pyridine-3-carboxylic acid

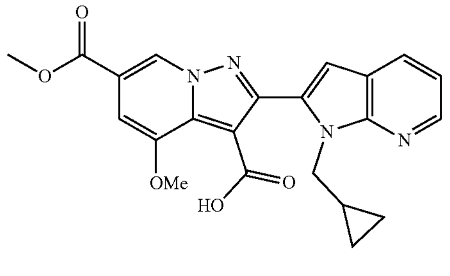 [SMILES: COC(=O)c1cc(OC)c2c(C(=O)O)c(-c3cc4cccnc4n3CC3CC3)nn2c1]

TFA (0.210 ml, 2.73 mmol) was added to a stirred solution of Intermediate 1A (650 mg, 1.364 mmol) in DCM (5 ml). The reaction mixture was stirred at a room temperature for 1 hour, and concentrated to afford the title compound (600 mg, 73%) as a brown solid. The crude compound was used in the next steps without further purification. LC-MS m/z: 421.1 $[M+H]^+$.

Intermediate 1C

Methyl 2-(1-(cyclopropylmethyl)-1H-pyrrolo-[2,3-b]pyridin-2-yl)-4-methoxy-3-methylpyrazolo[1,5-a]pyridine-6-carboxylate

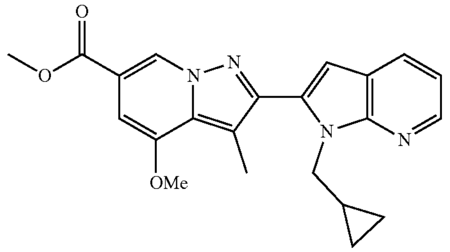 [SMILES: COC(=O)c1cc(OC)c2c(C)c(-c3cc4cccnc4n3CC3CC3)nn2c1]

Borane dimethyl sulfide complex (3.57 ml, 7.14 mmol) was added to a stirred solution of Intermediate 1B (600 mg, 1.427 mmol) in THF (10 ml) at 0° C. The reaction mixture was stirred for 30 min, followed by heating to 65° C. and stirring for 5 hours, quenched with methanol (5 ml) at 0° C., and concentrated to afford the title compound (520 mg, 93%) as a brown solid. The crude compound was used in the next steps without further purification. LC-MS m/z: 391.2 $[M+H]^+$. $^1$H NMR (400 MHz, chloroform-d) δ ppm: 8.88-8.76 (m, 1H), 8.44-8.27 (m, 1H), 7.99-7.85 (m, 1H), 7.13-6.90 (m, 1H), 6.89-6.85 (m, 1H), 6.76-6.69 (m, 1H), 4.62-4.44 (m, 2H), 4.07-3.96 (m, 6H), 2.58 (s, 3H), 1.05-0.78 (m, 1H), 0.45-0.11 (m, 4H).

Intermediate 1D 2-(1-(Cyclopropylmethyl)-1H-pyrrolo[2,3-b]pyridin-2-yl)-4-methoxy-3-methylpyrazolo[1,5-a]pyridine-6-carboxylic acid

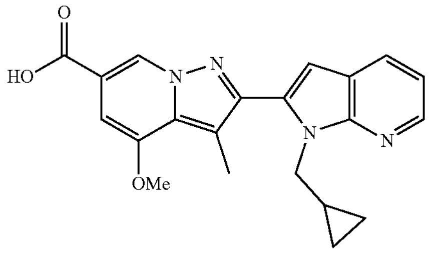 [SMILES: COc1cc(C(=O)O)cn2nc(-c3cc4cccnc4n3CC3CC3)c(C)c12]

Lithium hydroxide (LiOH, 153 mg, 6.40 mmol) was added to a stirred solution of Intermediate 1C (500 mg, 1.281 mmol) in a mixture of THF (3 ml), methanol (3 ml) and water (3 ml). The reaction mixture was stirred at a room temperature for 30 min, concentrated, and the crude residue was acidified with 1.5 N HCl. The solid product obtained was filtered, and dried under vacuum to afford the title compound (360 mg, 75%) as an off-white solid. LC-MS m/z: 377.1 $[M+H]^+$.

Intermediate 1E tert-Butyl-((7R)-2-(2-(1-(cyclopropylmethyl)-1H-pyrrolo[2,3-b]pyridin-2-yl)-4-methoxy-3-methylpyrazolo[1,5-a]pyridine-6-carbonyl)-2-azabicyclo[2.2.1]heptan-7-yl)carbamate

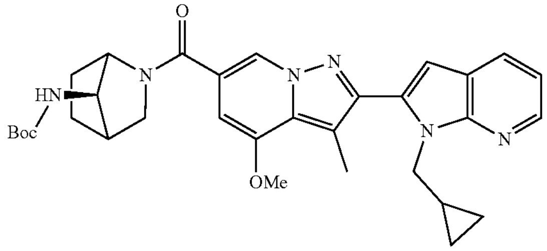 [SMILES: COc1cc(C(=O)N2CC3CCC2[C@@H]3NC(=O)OC(C)(C)C)cn2nc(-c3cc4cccnc4n3CC3CC3)c(C)c12]

(1-[Bis(dimethylamino)methylene]-1H-1,2,3-triazolo[4,5-b]pyridinium 3-oxide hexafluorophosphate (HATU, 707 mg, 1.860 mmol) and N,N-diisopropylethylamine (DIPEA, 0.487 ml, 2.79 mmol) were added to a stirred solution of Intermediate 1D (350 mg, 0.930 mmol) and tert-butyl ((7R)-2-azabicyclo[2.2.1]-heptan-7-yl)carbamate (197 mg, 0.930 mmol) in DMF (5 ml). The reaction mixture was stirred at a room temperature for 12 hours, poured into ice water (10 ml), and the solid product separated was filtered and dried under vacuum to obtain a crude product, which was purified using a silica gel column (24 g, Redisep®) $SiO_2$ column, eluting with 50% EtOAc in hexane) to afford the title compound (300 mg, 57%) as an off-white solid. LC-MS m/z: 571.2 $[M+H]^+$.

Example 1

TFA (0.364 ml, 4.73 mmol) was added to a stirred solution of Intermediate 1E (270 mg, 0.473 mmol) in DCM (5 ml).

The reaction mixture was stirred at a room temperature for 1 hour, concentrated, and the crude compound obtained was purified using Prep-HPLC. The purified sample was further purified using RP-HPLC to afford the title compound (76 mg, 34%). LC-MS m/z: 471.2 $[M+H]^+$. LC-MS retention time: 1.76 min (Method E). $^1H$ NMR (400 MHz, DMSO-$d_6$) δ ppm: 8.55 (s, 0.5H), 8.39 (s, 0.5H), 8.31-8.33 (m, 1H), 8.03-8.05 (m, 1H), 7.14-7.17(m, 1H), 6.81 (s, 1H), 6.59-6.65 (m, 1H), 4.47 (br, d, J=7.03 Hz, 2H), 4.09 (br, s, 0.5H), 3.94-4.04 (m, 3H), 3.82 (br s, 0.5H), 3.62-3.77 (m, 0.5H), 3.03-3.29 (m, 3.5H), 2.52-2.55 (m, 3H), 2.13-2.32 (m, 2H), 1.88-2.08 (m, 3H), 1.58-1.70 (m, 1H), 1.33-1.47 (m, 1H), 1.09-1.19 (m, 1H), 0.17-0.30 (m, 4H).

Example 2

((7R)-7-Amino-2-azabicyclo[2.2.1]heptan-2-yl)(2-(6-chloro-1-(cyclopropylmethyl)-1H-pyrrolo[2,3-b]pyridin-2-yl)-4-methoxy-3-methylpyrazolo[1,5-a]pyridin-6-yl)methanone

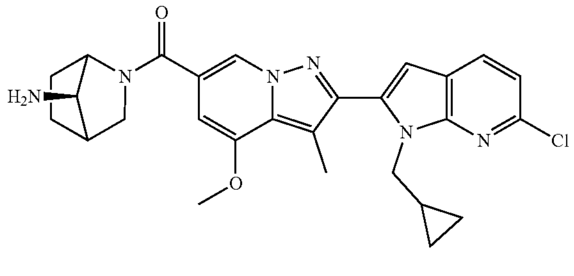 [SMILES: COc1cc(C(=O)N2CC3CCC2[C@@H]3N)cn2nc(-c3cc4ccc(Cl)nc4n3CC3CC3)c(C)c12]

Intermediate 2A 3-(tert-Butyl)-6-methyl 2-(6-chloro-1-(cyclopropylmethyl)-1H-pyrrolo[2,3-b]pyridin-2-yl)-4-methoxy-pyrazolo[1,5-a]pyridine-3,6-dicarboxylate

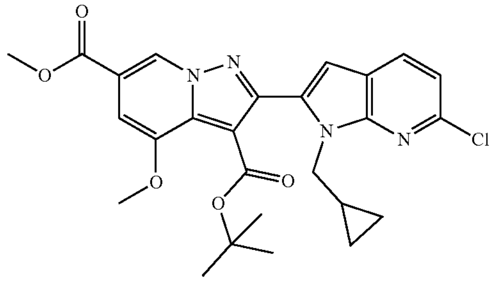 [SMILES: COC(=O)c1cc(OC)c2c(C(=O)OC(C)(C)C)c(-c3cc4ccc(Cl)nc4n3CC3CC3)nn2c1]

1-Amino-3-methoxy-5-(methoxycarbonyl)pyridin-1-ium (Intermediate 1, 1.384 g, 7.56 mmol) and $K_2CO_3$ (2.089 g, 15.11 mmol) were added to a stirred solution of tert-butyl 3-(6-chloro-1-(cyclopropylmethyl)-1H-pyrrolo[2,3-b]pyridin-2-yl)propiolate (Intermediate 4, 2.5 g, 7.56 mmol) in DMF (5 ml). The reaction mixture was stirred at a room temperature for 16 hours, diluted with EtOAc (50 ml), washed with water (3×50 ml), dried over $Na_2SO_4$, and concentrated to obtain a crude product, which was purified using a silica gel column (40 g, Redisep® $SiO_2$ column, eluting with 30% EtOAc in hexane) to afford the title compound (1.5 g, 39%) as a yellow liquid. LC-MS m/z: 511.2 $[M+H]^+$.

Intermediate 2B 2-(6-Chloro-1-(cyclopropylmethyl)-1H-pyrrolo[2,3-b]pyridin-2-yl)-4-methoxy-6-(methoxycarbonyl)pyrazolo[1,5-a]pyridine-3-carboxylic acid

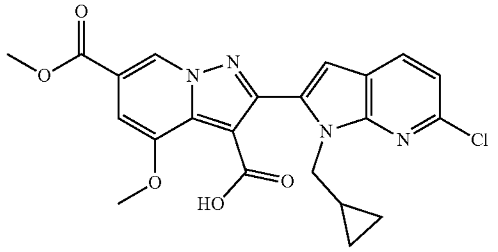 [SMILES: COC(=O)c1cc(OC)c2c(C(=O)O)c(-c3cc4ccc(Cl)nc4n3CC3CC3)nn2c1]

2,6-Lutidine (0.684 ml, 5.87 mmol) and trimethylsilyl trifluoromethanesulfonate (0.530 ml, 2.94 mmol) were added to a solution of Intermediate 2A (1.5 g, 2.94 mmol) in DCM (20 ml). The reaction mixture was stirred at a room temperature for 30 min, diluted with DCM (30 ml), washed with 10% $NaHCO_3$ solution (3×50 ml), dried over $Na_2SO_4$, and concentrated to afford the title compound (1.5 g, 79%) as a brown solid. LC-MS m/z: 455.1 $[M+H]^+$.

Intermediate 2C

Methyl-2-(6-chloro-1-(cyclopropylmethyl)-1H-pyrrolo[2,3-b]pyridin-2-yl)-4-methoxy-3-methylpyrazolo[1,5-a]pyridine-6-carboxylate

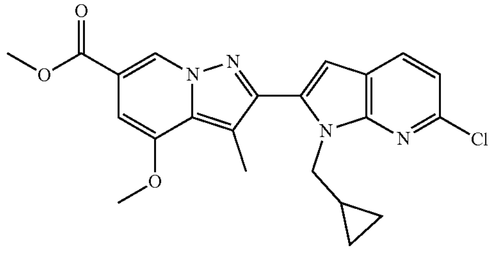 [SMILES: COC(=O)c1cc(OC)c2c(C)c(-c3cc4ccc(Cl)nc4n3CC3CC3)nn2c1]

Borane dimethyl sulphide complex (3.30 ml, 6.60 mmol) was added to a stirred solution of Intermediate 2B (1 g, 2.198 mmol) in THF (10 ml) at 0° C. The reaction mixture was stirred at the same temperature for 30 min, then heated to 65° C. and stirred for 5 hours, quenched with methanol (5 ml), and the reaction contents were concentrated to afford the title compound as an off-white solid (200 mg, 22%). The crude compound was used in the next steps without further purification. LC-MS m/z: 425.1 $[M+H]^+$.

Intermediate 2D 2-(6-Chloro-1-(cyclopropylmethyl)-1H-pyrrolo[2,3-b]pyridin-2-yl)-4-methoxy-3-methylpyrazolo[1,5-a]pyridine-6-carboxylic acid

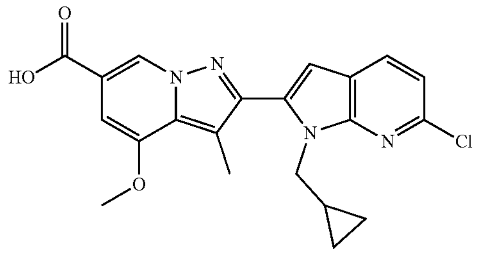 [SMILES: COc1cc(C(=O)O)cn2nc(-c3cc4ccc(Cl)nc4n3CC3CC3)c(C)c12]

LiOH (141 mg, 5.88 mmol) was added to a stirred solution of Intermediate 2C (500 mg, 1.177 mmol) in a mixture of THF (3 ml), methanol (3 ml) and water (3 ml), and the reaction mixture was stirred at a room temperature for 30 min. The reaction mixture was concentrated under reduced pressure and the residue obtained was acidified with 1.5 N HCl. The separated solids were filtered, and dried under vacuum to afford the title compound (400 mg, 83%) as an off-white solid. LC-MS m/z: 411.1 $[M+H]^+$.

Intermediate 2E tert-Butyl-((7R)-2-(2-(6-chloro-1-(cyclopropylmethyl)-1H-pyrrolo[2,3-b]pyridin-2-yl)-4-methoxy-3-methylpyrazolo[1,5-a]pyridine-6-carbonyl)-2-azabicyclo[2.2.1]heptan-7-yl)carbamate

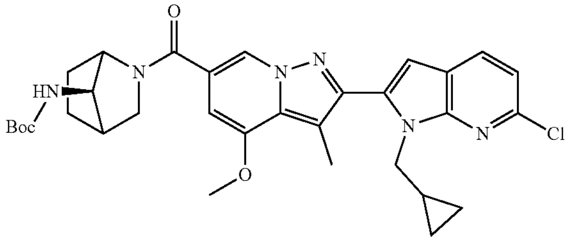

HATU (555 mg, 1.460 mmol) and DIPEA (0.383 ml, 2.191 mmol) were added to a stirred solution of Intermediate 2D (300 mg, 0.730 mmol) and tert-butyl ((7R)-2-azabicyclo [2.2.1]-heptan-7-yl)carbamate (155 mg, 0.730 mmol) in DMF (5 ml). The reaction mixture was stirred at a room temperature for 12 hours, poured into ice water (10 ml), the solid product thus obtained was filtered, and dried under vacuum to afford the title compound (400 mg, 91%). LC-MS m/z: 605.4 $[M+H]^+$.

Example 2

TFA (0.127 ml, 1.653 mmol) was added to a solution of Intermediate 2E (100 mg, 0.165 mmol) in DCM (5 ml). The reaction mixture was stirred at a room temperature for 1 hour, concentrated under reduced pressure, and the crude product obtained was purified using Prep-HPLC. The product was further purified using RP-HPLC to afford the title compound (12 mg, 14%). LC-MS m/z: 505.3 $[M+H]^+$.

LC-MS retention time: 1.79 min ((Method E). $^1$H NMR (400 MHz, DMSO-$d_6$) δ ppm: 8.55 (s, 0.5H), 8.39 (s, 0.5H), 8.11 (d, J=8.03 Hz, 1H), 7.22 (d, J=8.53 Hz, 1H), 6.87 (s, 1H), 6.60-6.66 (m, 1H), 4.42 (br, d, J=7.03 Hz, 2H), 4.09 (s, 0.5H),3.99 (s, 3H), 3.81 (br, s, 0.5H), 3.48-61 (m, 2H), 3.12-3.29 (m, 2H), 3.06-3.25 (m, 2H), 2.57-2.66 (m, 1H), 2.53 (br, s, 3H), 1.60-2.23 (m, 4H), 1.39-1.41 (m, 1H), 1.13-1.15 (m, 1H), 0.31 (br, d, J=8.03 Hz, 2H), 0.20 (br, d, J=4.02 Hz, 2H).

Example 3

6-(2-(6-((7R)-7-Amino-2-azabicyclo[2.2.1]heptane-2-carbonyl)-4-methoxy-3-methylpyrazolo[1,5-a]pyridin-2-yl)-1-(cyclopropylmethyl)-1H-pyrrolo[2,3-b]pyridin-6-yl)isoindolin-1-one

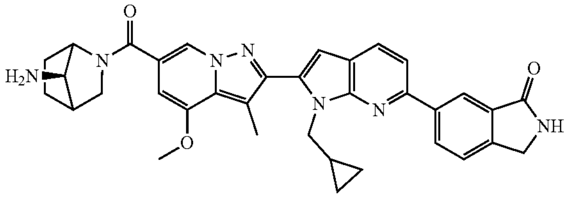 [SMILES: COc1cc(C(=O)N2CC3CCC2[C@@H]3N)cn2nc(-c3cc4ccc(-c5ccc6c(c5)C(=O)NC6)nc4n3CC3CC3)c(C)c12]

Intermediate 3A tert-Butyl-((7R)-2-(2-(1-(cyclopropylmethyl)-6-(3-oxoisoindolin-5-yl)-1H-pyrrolo[2,3-b]pyridin-2-yl)-4-methoxy-3-methylpyrazolo[1,5-a]pyridine-6-carbonyl)-2-azabicyclo[2.2.1]heptan-7-yl)carbamate

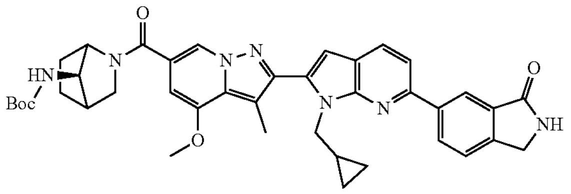 [SMILES: COc1cc(C(=O)N2CC3CCC2[C@@H]3NC(=O)OC(C)(C)C)cn2nc(-c3cc4ccc(-c5ccc6c(c5)C(=O)NC6)nc4n3CC3CC3)c(C)c12]

$PdCl_2(dppf)\cdot CH_2Cl_2$ (13.50 mg, 0.017 mmol) was added to a degasified solution of Intermediate 2E (100 mg, 0.165 mmol), (3-oxoisoindolin-5-yl)boronic acid (43.9 mg, 0.248 mmol) and $K_2CO_3$ (68.5 mg, 0.496 mmol) in dioxane (5 ml) and water (0.556 ml). The reaction mixture was heated to 100° C. and stirred for 12 hours, filtered through a celite bed, and the filtrate was concentrated to afford a crude product, which was purified using Prep-HPLC to afford the title compound (16 mg, 14%). LC-MS m/z: 702.4 $[M+H]^+$. $^1$H NMR (400 MHz, chloroform-d) δ ppm: 8.60 (s, 1H), 8.49-8.46 (m, 1H), 8.28-8.20 (m, 1H), 8.07-7.95 (m, 1H), 7.73-7.64 (m, 1H), 7.62-7.53 (m, 1H), 6.78 (s, 1H), 6.53 (s, 1H), 6.20-6.10 (m, 1H), 4.64-4.41 (m, 5H), 4.01 (s, 3H), 3.89-3.72 (m, 2H), 3.33-3.18 (m, 1H), 2.64-2.50 (m, 4H), 1.95 (br s, 2H), 1.41 (s, 9H), 1.34-1.14 (m, 2H), 0.38-0.25 (m, 4H).

Example 3

TFA (0.016 ml, 0.214 mmol) was added to a solution of Intermediate 3A (15 mg, 0.021 mmol) in DCM (5 ml). The reaction mixture was stirred for 1 hour, concentrated, and the crude product obtained was purified using Prep-HPLC. The purified product was further purified using RP-HPLC to afford the title compound (7.42 mg, 57%). LC-MS m/z: 602.2 $[M+H]^+$. HPLC retention time: 6.364 min (Method C). $^1H$ NMR (400 MHz, DMSO-$d_6$) δ ppm: 8.70-8.57 (m, 1H), 8.46-8.32 (m, 3H), 8.18-8.08 (m, 1H), 7.88-7.77 (m, 1H), 7.72-7.58 (m, 1H), 6.89-6.76 (m, 1H), 6.66-6.52 (m, 1H), 4.71-4.48 (m, 2H), 4.47-4.35 (m, 2H), 4.10-3.88 (m, 5H), 3.87-3.42 (m, 1H), 3.06-3.22 (m, 1H), 2.54-2.41 (m, 3H), 1.76-2.26 (m, 4H), 1.48-1.31 (m, 1H), 1.27-1.15 (m, 1H), 0.44-0.20 (m, 4H).

Compounds of Examples 4 to 12 in Table 1 were prepared following a procedure similar to the preparation of a compound of Example 3, using Suzuki coupling reaction of Intermediate 2E with appropriate boronic acid.

TABLE 1

| Example | Structure, Name, Analytical Data: LC-MS m/z $[M + H]^+$; HPLC retention time (HPLC method) |
|---|---|
| 4 | 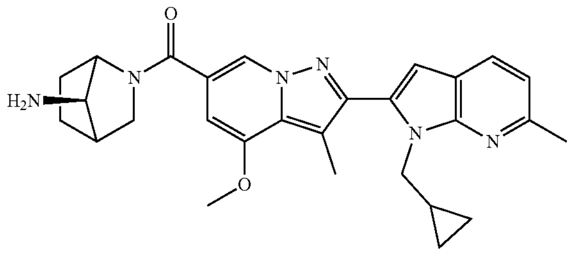 [SMILES: COc1cc(C(=O)N2CC3CCC2[C@@H]3N)cn2nc(-c3cc4ccc(C)nc4n3CC3CC3)c(C)c12] ((7R)-7-Amino-2-azabicyclo[2.2.1]heptan-2-yl)(2-(1-(cyclopropylmethyl)-6-methyl-1H-pyrrolo[2,3-b]pyridin-2-yl)-4-methoxy-3-methylpyrazolo[1,5-a]pyridin-6-yl)methanone. Analytical data: 485.2, 4.452 min (Method C) |
| 5 | 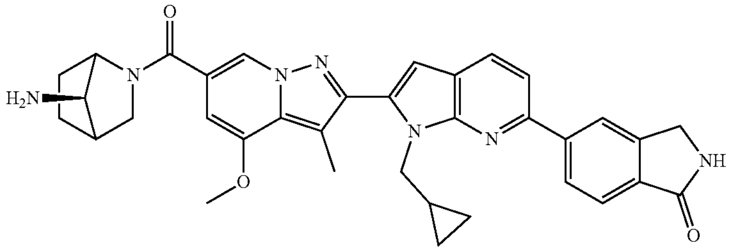 5-(2-(6-((7R)-7-Amino-2-azabicyclo[2.2.1]-heptane-2-carbonyl)-4-methoxy-3-methylpyrazolo[1,5-a]pyridin-2-yl)-1-(cyclopropylmethyl)-1H-pyrrolo[2,3-b]pyridin-6-yl)isoindolin-1-one. Analytical data: 602.2, 6.281 min (Method C) |
| 6 | 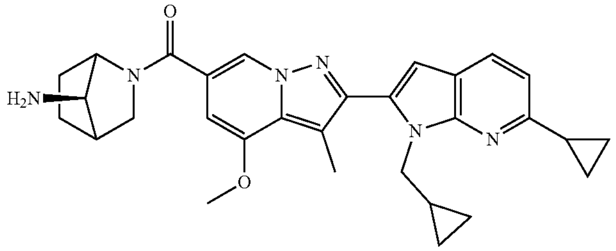 [SMILES: COc1cc(C(=O)N2CC3CCC2[C@@H]3N)cn2nc(-c3cc4ccc(C5CC5)nc4n3CC3CC3)c(C)c12] ((7R)-7-Amino-2-azabicyclo[2.2.1]heptan-2-yl)(2-(6-cyclopropyl-1-(cyclopropylmethyl)-1H-pyrrolo[2,3-b]pyridin-2-yl)-4-methoxy-3-methylpyrazolo[1,5-a]pyridin-6-yl)methanone Analytical data: 511.4, 7.977 min (Method C) |

TABLE 1-continued

| Example | Structure, Name, Analytical Data: LC-MS m/z [M + H]+; HPLC retention time (HPLC method) |
|---|---|
| 7 | 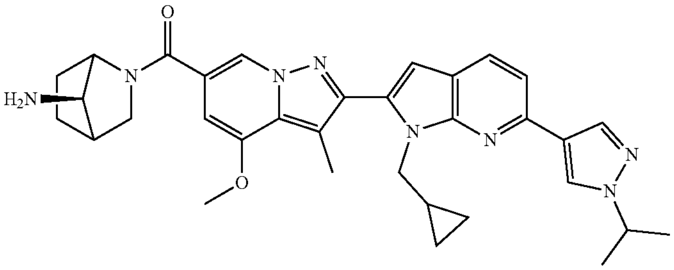 [SMILES: COc1cc(C(=O)N2CC3CCC2[C@@H]3N)cn2nc(-c3cc4ccc(-c5cnn(C(C)C)c5)nc4n3CC3CC3)c(C)c12] ((7R)-7-Amino-2-azabicyclo[2.2.1]heptan-2-yl)(2-(1-(cyclopropylmethyl)-6-(1-isopropyl-1H-pyrazol-4-yl)-1H-pyrrolo[2,3-b]pyridin-2-yl)-4-methoxy-3-methylpyrazolo[1,5-a]pyridin-6-yl)methanone<br>Analytical data: 579.4, 6.603 min (Method C) |
| 8 | 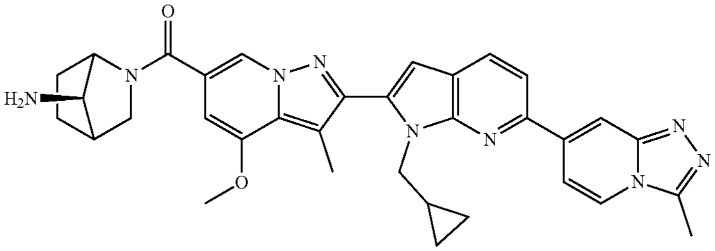 [SMILES: COc1cc(C(=O)N2CC3CCC2[C@@H]3N)cn2nc(-c3cc4ccc(-c5ccn6c(C)nnc6c5)nc4n3CC3CC3)c(C)c12] ((7R)-7-Amino-2-azabicyclo[2.2.1]heptan-2-yl)(2-(1-(cyclopropylmethyl)-6-(3-methyl-[1,2,4]triazolo[4,3-a]pyridin-7-yl)-1H-pyrrolo[2,3-b]pyridin-2-yl)-4-methoxy-3-methylpyrazolo[1,5-a]pyridin-6-yl)methanone.<br>Analytical data: 602.3, 4.761 min (Method C) |
| 9 | 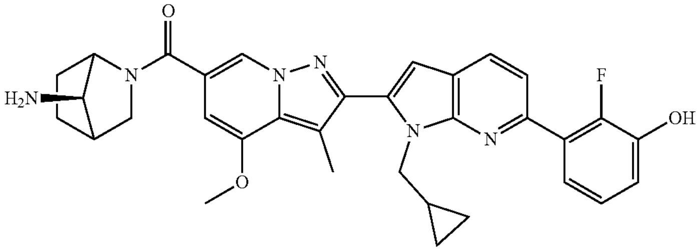 [SMILES: COc1cc(C(=O)N2CC3CCC2[C@@H]3N)cn2nc(-c3cc4ccc(-c5cccc(O)c5F)nc4n3CC3CC3)c(C)c12] ((7R)-7-Amino-2-azabicyclo[2.2.1]heptan-2-yl)(2-(1-(cyclopropylmethyl)-6-(2-fluoro-3-hydroxyphenyl)-1H-pyrrolo[2,3-b]pyridin-2-yl)-4-methoxy-3-methylpyrazolo[1,5-a]pyridin-6-yl)methanone<br>Analytical data: 581.3, 7.259 min (Method C) |
| 10 | 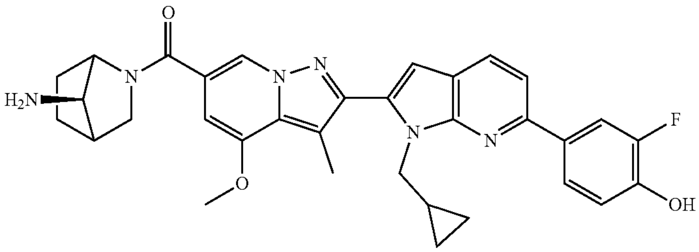 [SMILES: COc1cc(C(=O)N2CC3CCC2[C@@H]3N)cn2nc(-c3cc4ccc(-c5ccc(O)c(F)c5)nc4n3CC3CC3)c(C)c12] ((7R)-7-Amino-2-azabicyclo[2.2.1]heptan-2-yl)(2-(1-(cyclopropylmethyl)-6-(3-fluoro-4-hydroxyphenyl)-1H-pyrrolo[2,3-b]pyridin-2-yl)-4-methoxy-3-methylpyrazolo[1,5-a]pyridin-6-yl)methanone.<br>Analytical data: 581.4, 4.619 min (Method C) |

TABLE 1-continued

| Example | Structure,<br>Name,<br>Analytical Data: LC-MS m/z [M + H]$^+$; HPLC retention time (HPLC method) |
|---|---|
| 11 | 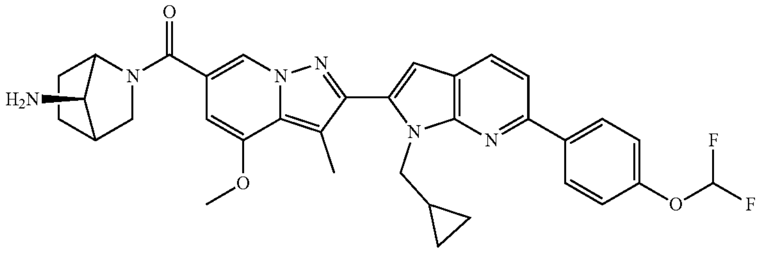 [SMILES: COc1cc(C(=O)N2CC3CCC2[C@@H]3N)cn2nc(-c3cc4ccc(-c5ccc(OC(F)F)cc5)nc4n3CC3CC3)c(C)c12]<br>((7R)-7-Amino-2-azabicyclo[2.2.1]heptan-2-yl)(2-(1-(cyclopropylmethyl)-6-(4-(difluoromethoxy)phenyl)-1H-pyrrolo[2,3-b]pyridin-2-yl)-4-methoxy-3-methylpyrazolo[1,5-a]pyridin-6-yl)methanone<br>Analytical data: 613.2, 5.878 min (Method C) |
| 12 | 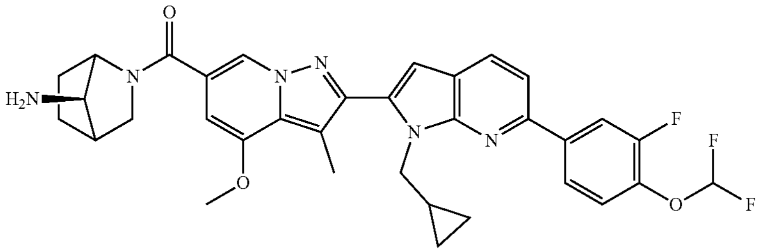 [SMILES: COc1cc(C(=O)N2CC3CCC2[C@@H]3N)cn2nc(-c3cc4ccc(-c5ccc(OC(F)F)c(F)c5)nc4n3CC3CC3)c(C)c12]<br>((7R)-7-Amino-2-azabicyclo[2.2.1]heptan-2-yl)(2-(1-(cyclopropylmethyl)-6-(4-(difluoromethoxy)-3-fluorophenyl)-1H-pyrrolo[2,3-b]pyridin-2-yl)-4-methoxy-3-methylpyrazolo[1,5-a]pyridin-6-yl)methanone.<br>Analytical data: 631.3, 2.417 min (Method E) |

Example 13

((7R)-7-Amino-2-azabicyclo[2.2.1]heptan-2-yl)(2-(1-(cyclopropylmethyl)-6-(3-methoxyazetidin-1-yl)-1H-pyrrolo[2,3-b]pyridin-2-yl)-4-methoxy-3-methylpyrazolo[1,5-a]pyridin-6-yl)methanone

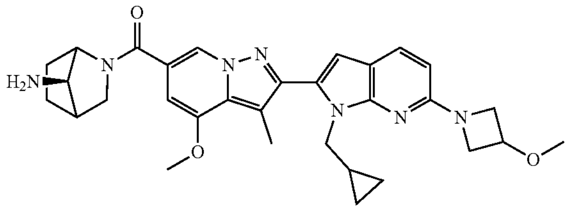 [SMILES: COc1cc(C(=O)N2CC3CCC2[C@@H]3N)cn2nc(-c3cc4ccc(N5CC(OC)C5)nc4n3CC3CC3)c(C)c12]

Intermediate 13A tert-Butyl-((7R)-2-(2-(1-(cyclopropylmethyl)-6-(3-methoxyazetidin-1-yl)-1H-pyrrolo[2,3-b]pyridin-2-yl)-4-methoxy-3-methylpyrazolo[1,5-a]pyridine-6-carbonyl)-2-azabicyclo[2.2.1]heptan-7-yl)carbamate

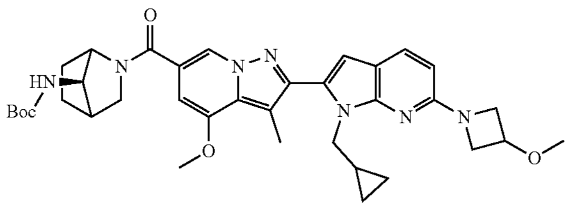 [SMILES: COc1cc(C(=O)N2CC3CCC2[C@@H]3NC(=O)OC(C)(C)C)cn2nc(-c3cc4ccc(N5CC(OC)C5)nc4n3CC3CC3)c(C)c12]

$Pd_2(dba)_3$ (5.67 mg, 6.20 μmol) and 2-Dicyclohexylphosphino-2',6'-diisopropoxybiphenyl (RUPHOS, 15.42 mg, 0.033 mmol) were added to a degassed solution of Intermediate 2E (100 mg, 0.165 mmol), 3-methoxyazetidine (28.8 mg, 0.331 mmol) and caesium carbonate (162 mg, 0.496 mmol) in dioxane (5 ml). The reaction mixture was heated to 85° C. and stirred for 12 hours, filtered, and the filtrate was concentrated under reduced pressure to afford the crude product, which was used in the next step without further purification. LC-MS m/z: 656.5 [M+H]$^+$.

Example 13

TFA (0.117 ml, 1.525 mmol) was added to a stirred solution of Intermediate 13A (100 mg, 0.152 mmol) in DCM (5 ml). The reaction mixture was stirred for 1 hour, concentrated under reduced pressure, and the crude product obtained was purified using Prep-HPLC. The purified sample was further purified using RP-HPLC to afford the title compound (8.5 mg, 10%). LC-MS m/z: 556.4 [M+H]$^+$. HPLC retention time: 7.703 min (Method C). $^1H$ NMR (400 MHz, DMSO-$d_6$) δ ppm: 8.56-8.34 (m, 1H), 7.78 (d, J=8.5 Hz, 1H), 6.62-6.57 (m, 2H), 6.27 (d, J=8.5 Hz, 1H), 4.35 (br, d, J=6.0 Hz, 4H), 4.27-4.13 (m, 2H), 3.98 (s, 6H), 3.84-3.58 (m, 5H), 3.29 3.06 (m, 1H),2.67-2.57 (m, 3H), 2.20-1.40 (m, 5H), 1.24-1.12 (m, 1H), 0.32-0.22 (m, 4H).

Example 14

((3R,5R)-3-Amino-5-fluoropiperidin-1-yl)(2-(1-(cyclopropylmethyl)-1H-pyrrolo[2,3-b]pyridin-2-yl)-4-methoxy-3-methylpyrazolo[1,5-a]pyridin-6-yl)methanone

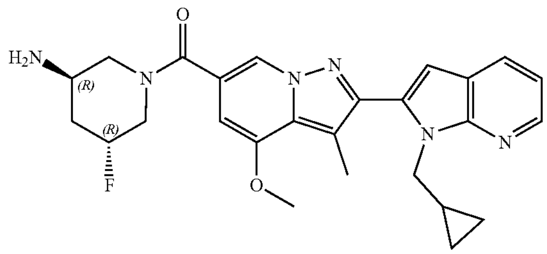

Intermediate 14A tert-Butyl-((3R,5R)-1-(2-(1-(cyclopropylmethyl)-1H-pyrrolo[2,3-b]pyridin-2-yl)-4-methoxy-3-methylpyrazolo[1,5-a]pyridine-6-carbonyl)-5-fluoropiperidin-3-yl)carbamate

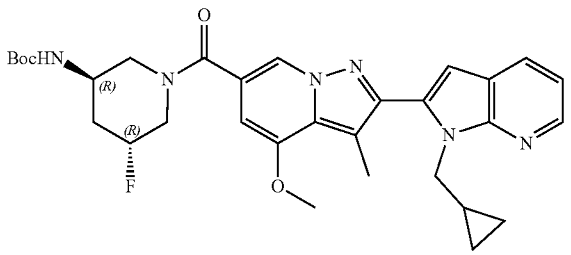

Intermediate 14A was prepared following a procedure similar to the preparation of Intermediate 2E (20 mg, 52%). LC-MS m/z: 577.1 $[M+H]^+$.

Example 14

TFA (0.027 ml, 0.347 mmol) was added to a stirred solution of Intermediate 14A (20 mg, 0.035 mmol) in DCM (1 ml) at a room temperature. The reaction mixture was stirred for 1 hour, concentrated under reduced pressure, and the crude product obtained was purified using Prep-HPLC. The purified product was further purified using RP-HPLC to afford the title compound (6 mg, 36%). LC-MS m/z: 477.1 $[M+H]^+$. LC-MS retention time: 1.374 min (method E). $^1$H NMR (400 MHz, DMSO-$d_6$) δ ppm: 8.39 (s, 1H), 8.32 (dd, J=1.5, 4.6 Hz, 1H), 8.04 (dd, J=1.7, 7.8 Hz, 1H), 7.16 (dd, J=4.6, 7.8 Hz, 1H), 6.81 (s, 1H), 6.56 (s, 1H), 4.89 (br, s, 1H), 4.47 (d, J=7.1 Hz, 2H), 3.98 (s, 4H), 3.03-2.98 (m, 2H), 2.55 (s, 3H), 2.21-2.11 (m, 1H), 1.35-1.09, (m, 3H), 0.32-0.14 (m, 4H).

Example 15

((3R,5R)-3-Amino-5-fluoropiperidin-1-yl)(2-(6-chloro-1-(cyclopropylmethyl)-1H-pyrrolo[2,3-b]pyridin-2-yl)-4-methoxy-3-methylpyrazolo[1,5-a]pyridin-6-yl)methanone

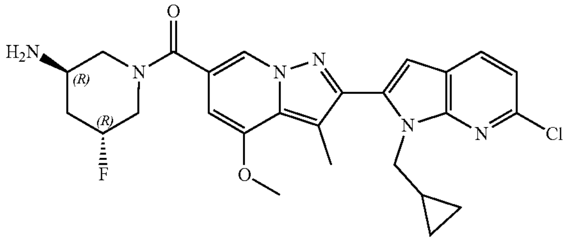

Intermediate 15A tert-Butyl-((3R,5R)-1-(2-(6-chloro-1-(cyclopropylmethyl)-1H-pyrrolo[2,3-b]pyridin-2-yl)-4-methoxy-3-methylpyrazolo[1,5-a]pyridine-6-carbonyl)-5-fluoropiperidin-3-yl)carbamate

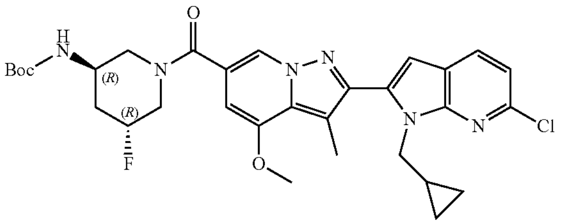

HATU (1296 mg, 3.41 mmol) and DIPEA (0.893 ml, 5.11 mmol) were added to a stirred solution of Intermediate 2D (700 mg, 1.704 mmol) and tert-butyl ((3R,5R)-5-fluoropiperidin-3-yl)carbamate (372 mg, 1.704 mmol) in DMF (5 ml). The reaction mixture was stirred at a room temperature for 12 hours, poured into ice water (40 ml), and the solids obtained were filtered, dried under vacuum to afford the title compound (1 g, 67%) as an off-white solid. LC-MS m/z: 611.4 $[M+H]^+$.

Example 15

TFA (0.252 ml, 3.27 mmol) was added to a stirred solution of Intermediate 15A (200 mg, 0.327 mmol) in DCM (5 ml). The reaction mixture was stirred at a room temperature for 1 hour, concentrated under reduced pressure, and the crude product obtained was purified using Prep-HPLC. The purified product was further purified using RP-HPLC to afford the title compound (21 mg, 12%). LC-MS m/z: 608.4 $[M+H]^+$. LC-MS retention time: 2.054 min (Method E). $^1$H NMR (400 MHz, DMSO-$d_6$) δ ppm: 8.38 (s, 1H), 8.10 (d, J=8.07 Hz, 1H), 7.22 (d, J=8.07 Hz, 1H), 6.87 (s, 1H), 6.56 (s, 1H), 4.96-4.78 (m, 1H), 4.41 (d, J=7.09 Hz, 3H), 3.98 (s, 4H), 2.97 (br, s, 2H), 2.52-2.55 (m, 3H), 2.14 (br, s, 1H), 1.41-1.60 (m, 1H), 1.12-1.20 (m, 1H), 0.27-0.34 (m, 2H), 0.20-0.26 (m, 2H).

Example 16

6-(2-(6-((3R,5R)-3-Amino-5-fluoropiperidine-1-carbonyl)-4-methoxy-3-methylpyrazolo[1,5-a]pyridin-2-yl)-1-(cyclopropylmethyl)-1H-pyrrolo[2,3-b]pyridin-6-yl)isoindolin-1-one

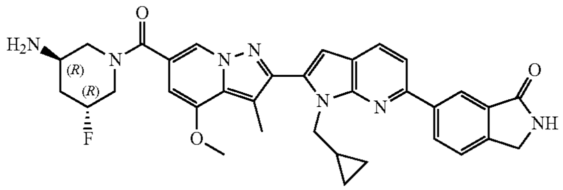

Intermediate 16A tert-Butyl-((3R,5R)-1-(2-(1-(cyclopropylmethyl)-6-(3-oxoisoindolin-5-yl)-1H-pyrrolo[2,3-b]pyridin-2-yl)-4-methoxy-3-methylpyrazolo[1,5-a]pyridine-6-carbonyl)-5-fluoropiperidin-3-yl)carbamate

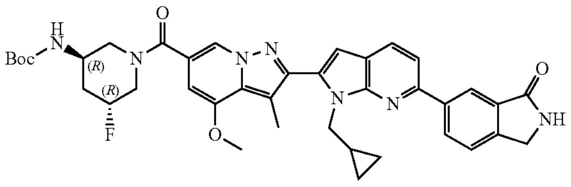

$PdCl_2(dppf)\cdot CH_2Cl_2$ (9.35 mg, 0.011 mmol) was added to a degassed solution of Intermediate 15A (70 mg, 0.115 mmol), (3-oxoisoindolin-5-yl)boronic acid (30.4 mg, 0.172 mmol) and $K_2CO_3$ (47.5 mg, 0.344 mmol) in dioxane (5 ml) and water (0.556 ml). The reaction mixture was stirred at 100° C. for 12 hours, filtered, and the filtrate was concentrated under reduced pressure to afford a crude product. The crude product was used in next the step without further purification. LC-MS m/z: 708.5 $[M+H]^+$.

Example 16

TFA (0.076 ml, 0.989 mmol) was added to a solution of Intermediate 16A (70 mg, 0.099 mmol) in DCM (5 ml). The reaction mixture was stirred for 1 hour, concentrated under reduced pressure, and the crude product obtained was purified using Prep-HPLC. The purified product was further purified using RP-HPLC to afford the title compound (12 mg, 19%). LC-MS m/z: 608.4 $[M+H]^+$. HPLC retention time: 6.559 min (method E). $^1H$ NMR (400 MHz, DMSO-$d_6$) δ ppm: 8.65 (s, 1H), 8.48-8.41 (m, 3H), 8.16 (d, J=8.4 Hz, 1H), 8.10-7.98 (m, 1H), 7.99 (brs, 1H), 7.88 (d, J=8.0 Hz, 1H), 7.73 (d, J=8.0 Hz, 1H), 6.95 (s, 1H), 6.59 (s, 1H), 5.08-4.55 (m, 1H), 4.59 (d, J=6.8 Hz, 3H), 4.46 (s, 3H), 4.00 (s, 3H), 3.20 (br d, J=10.5 Hz, 1H), 2.57-2.53 (m, 3H), 2.49-2.27 (m, 2H), 1.78-1.58 (m, 1H), 1.34-1.11 (m, 2H), 0.34-0.26 (m, 4H).

Compounds of Examples 17 to 21 in Table 2 were prepared following a procedure similar to the preparation of a compound of Example 16, using the Intermediate 15A and the appropriate boronic acid.

TABLE 2

| Example | Structure<br>Name<br>Analytical Data: LC-MS m/z $[M + H]^+$; HPLC retention time (HPLC method) |
|---|---|
| 17 | 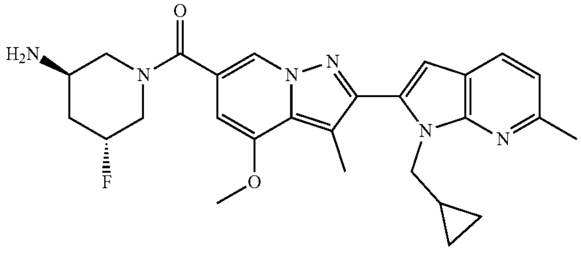 [SMILES: COc1cc(C(=O)N2C[C@H](N)C[C@@H](F)C2)cn2nc(-c3cc4ccc(C)nc4n3CC3CC3)c(C)c12]<br>((3R,5R)-3-Amino-5-fluoropiperidin-1-yl)(2-(1-(cyclopropylmethyl)-6-methyl-1H-pyrrolo[2,3-b]pyridin-2-yl)-4-methoxy-3-methylpyrazolo[1,5-a]pyridin-6-yl)-methanone.<br>Analytical Data: 491.4, 4.563 min (Method C) |

TABLE 2-continued

| Example | Structure<br>Name<br>Analytical Data: LC-MS m/z [M + H]+; HPLC retention time (HPLC method) |
|---|---|
| 18 | 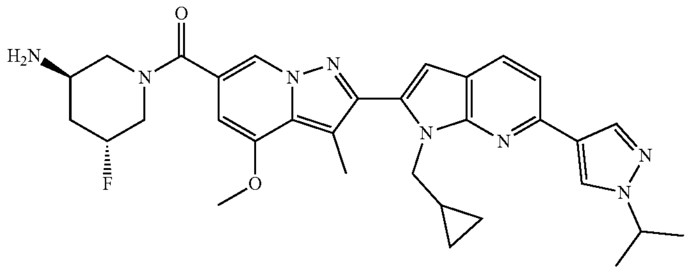 [SMILES: COc1cc(C(=O)N2C[C@H](N)C[C@@H](F)C2)cn2nc(-c3cc4ccc(-c5cnn(C(C)C)c5)nc4n3CC3CC3)c(C)c12]<br>((3R,5R)-3-Amino-5-fluoropiperidin-1-yl)(2-(1-(cyclopropylmethyl)-6-(1-isopropyl-1H-pyrazol-4-yl)-1H-indol-2-yl)-4-methoxy-3-methylpyrazolo[1,5-a]pyridin-6-yl)methanone<br>Analytical Data: 585.5, 7.566 min (Method C) |
| 19 | 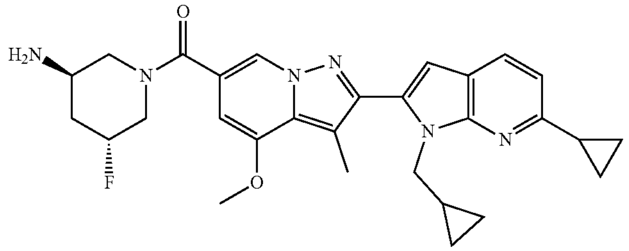 [SMILES: COc1cc(C(=O)N2C[C@H](N)C[C@@H](F)C2)cn2nc(-c3cc4ccc(C5CC5)nc4n3CC3CC3)c(C)c12]<br>((3R,5R)-3-Amino-5-fluoropiperidin-1-yl)(2-(6-cyclopropyl-1-(cyclopropylmethyl)-1H-pyrrolo[2,3-b]pyridin-2-yl)-4-methoxy-3-methylpyrazolo[1,5-a]pyridin-6-yl)methanone<br>Analytical Data: 585.5, 7.566 min (Method C) |
| 20 | 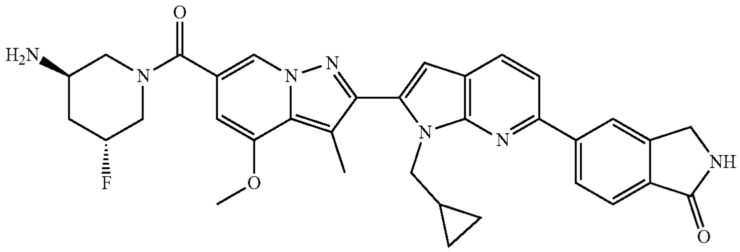 [SMILES: COc1cc(C(=O)N2C[C@H](N)C[C@@H](F)C2)cn2nc(-c3cc4ccc(-c5ccc6c(c5)CNC6=O)nc4n3CC3CC3)c(C)c12]<br>5-(2-(6-((3R,5R)-3-Amino-5-fluoropiperidine-1-carbonyl)-4-methoxy-3-methylpyrazolo[l,5-a]pyridin-2-yl)-1-(cyclopropylmethyl)-1H-pyrrolo[2,3-b]pyridin-6-yl)isoindolin-1-one<br>Analytical Data: 608.3, 5.958 min (Method C) |
| 21 | 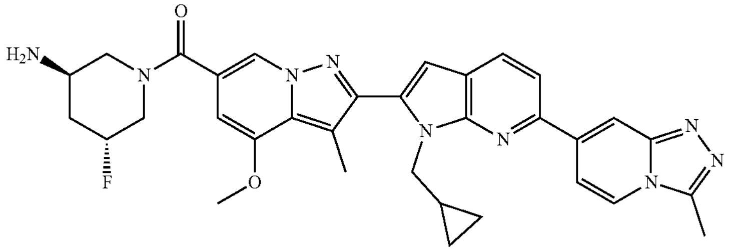 [SMILES: COc1cc(C(=O)N2C[C@H](N)C[C@@H](F)C2)cn2nc(-c3cc4ccc(-c5ccn6c(C)nnc6c5)nc4n3CC3CC3)c(C)c12]<br>((3R,5R)-3-Amino-5-fluoropiperidin-1-yl)(2-(1-(cyclopropylmethyl)-6-(3-methyl-[1,2,4]triazolo[4,3-a]pyridin-7-yl)-1H-pyrrolo[2,3-b]pyridin-2-yl)-4-methoxy-3-methylpyrazolo[1,5-a]pyridin-6-yl)methanone<br>Analytical Data: 608.4, 5.179 min (Method C) |

Example 22

((7R)-7-Amino-2-azabicyclo[2.2.1]heptan-2-yl)(2-(1-(cyclopropylmethyl)-1H-indol-2-yl)-4-methoxy-3-methylpyrazolo[1,5-a]pyridin-6-yl)methanone

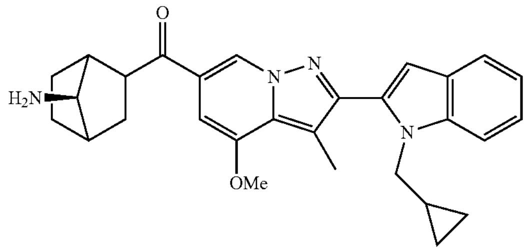 [SMILES: COc1cc(C(=O)C2CC3CCC2[C@@H]3N)cn2nc(-c3cc4ccccc4n3CC3CC3)c(C)c12]

Intermediate 22A 3-(tert-Butyl)-6-methyl 2-(1-(cyclopropylmethyl)-1H-indol-2-yl)-4-methoxypyrazolo[1,5-a]pyridine-3,6-dicarboxylate

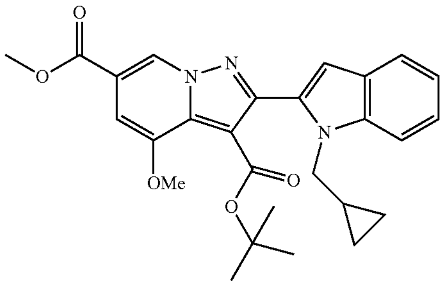 [SMILES: COC(=O)c1cc(OC)c2c(C(=O)OC(C)(C)C)c(-c3cc4ccccc4n3CC3CC3)nn2c1]

tert-Butyl-3-(1-(cyclopropylmethyl)-1H-indol-2-yl)propiolate (1 g, 3.39 mmol) and $K_2CO_3$ (0.468 g, 3.39 mmol) were added to a stirred solution of 1-amino-3-methoxy-5-(methoxy-carbonyl)pyridin-1-ium (Intermediate 1, 0.620 g, 3.39 mmol) in DMF (10 ml). The reaction mixture was stirred at a room temperature for 48 hours, quenched with water (100 ml), and extracted with EtOAc (2×100 ml). The combined organic layers were dried over $Na_2SO_4$, filtered, and concentrated under reduced pressure to obtain a crude product, which was purified using a silica gel column (EtOAc in hexane). The product was isolated at 10-20% EtOAc in hexane, required fractions were collected and volatiles were evaporated to dryness under reduced pressure to afford the title compound (480 mg, 30%). LC-MS m/z: 476.2 $[M+H]^+$.

Intermediate 22B 2-(1-(Cyclopropylmethyl)-1H-indol-2-yl)-4-methoxy-6-(methoxycarbonyl)pyrazolo[1,5-a]pyridine-3-carboxylic acid

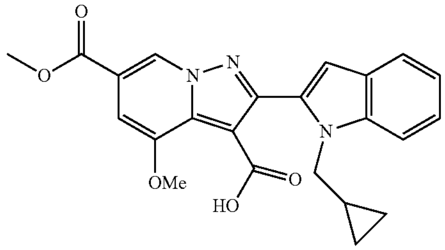 [SMILES: COC(=O)c1cc(OC)c2c(C(=O)O)c(-c3cc4ccccc4n3CC3CC3)nn2c1]

Formic acid (0.028 ml, 0.736 mmol) was added to a solution of Intermediate 22A (350 mg, 0.736 mmol) in DCM (1 ml). The reaction mixture was stirred at a room temperature for 4 hours, quenched with saturated $NaHCO_3$ solution, and extracted with DCM (2×100 ml). The combined the organic layers were dried over $Na_2SO_4$, filtered, and concentrated under reduced pressure to afford the crude title compound (150 mg, 49%) LC-MS m/z: 420.2 $[M+H]^+$.

Intermediate 22C

Methyl-2-(1-(cyclopropylmethyl)-1H-indol-2-yl)-4-methoxy-3-methylpyrazolo[1,5-a]pyridine-6-carboxylate

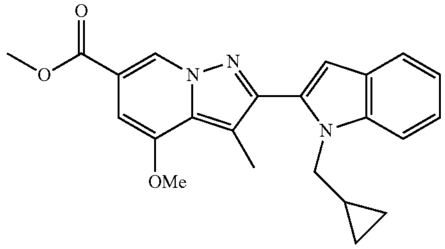 [SMILES: COC(=O)c1cc(OC)c2c(C)c(-c3cc4ccccc4n3CC3CC3)nn2c1]

Borane dimethyl sulfide complex (0.834 ml, 1.669 mmol) was added to a stirred solution of Intermediate 22B (350 mg, 0.834 mmol) in THF (2 ml). The reaction mixture was stirred at 50° C. for 5 hours, cooled to a room temperature, quenched with methanol, and concentrated under reduced pressure to afford a crude product, which was purified using a silica gel column (EtOAc in hexane (10-20%)) to afford the title compound (100 mg, 31%) LC-MS/z: 390.2 $[M+H]^+$.

Intermediate 22D 2-(1-(Cyclopropylmethyl)-1H-indol-2-yl)-4-methoxy-3-methylpyrazolo[1,5-a]pyridine-6-carboxylic acid

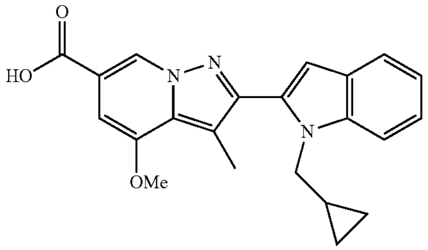 [SMILES: COc1cc(C(=O)O)cn2nc(-c3cc4ccccc4n3CC3CC3)c(C)c12]

LiOH (9.39 mg, 0.392 mmol) was added to a stirred solution of Intermediate 22C (100 mg, 0.131 mmol) in THF (6 ml) and water (6 ml). The reaction mixture was stirred at a room temperature for 16 hours, concentrated under reduced pressure to evaporate THF, and acidified with 1N HCl. The solid product separated was filtered and dried under vacuum to afford the title compound (80 mg, 163%); LC-MS m/z: 376.2 $[M+H]^+$.

Intermediate 22E tert-Butyl-((7R)-2-(2-(1-(cyclopropylmethyl)-1H-indol-2-yl)-4-methoxy-3-methylpyrazolo[1,5-a]pyridine-6-carbonyl)-2-azabicyclo[2.2.1]heptan-7-yl) carbamate

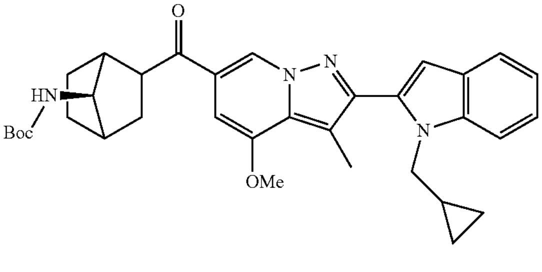 [SMILES: COc1cc(C(=O)C2CC3CCC2[C@@H]3NC(=O)OC(C)(C)C)cn2nc(-c3cc4ccccc4n3CC3CC3)c(C)c12]

HATU (161 mg, 0.424 mmol), DIPEA (0.185 ml, 1.060 mmol) and tert-butyl ((7R)-2-azabicyclo[2.2.1]heptan-7-yl) carbamate (90 mg, 0.424 mmol) were added to a stirred solution of Intermediate 22D (260 mg, 0.353 mmol) in DMF (2 ml) at 0° C. The reaction mixture was stirred at a room temperature for 2 hours, quenched with water (100 ml), and extracted with EtOAc (2×100 ml). The combined the organic layers were dried over sodium sulphate, filtered, and concentrated under reduced pressure to afford the crude product (100 mg, 49%). LC-MS m/z: 570.3 $[M+H]^+$.

Example 22

TFA (0.022 ml, 0.281 mmol) was added to a stirred solution of Intermediate 24E (80 mg, 0.140 mmol) in DCM (2 ml). The reaction mixture was stirred at a room temperature for 16 hours, evaporated completely under reduced pressure, and the crude product obtained was purified using Prep-HPLC. The purified product was further purified using RP-HPLC to afford the title compound (13.4 mg, 20%). LC-MS m/z: 470.3 $[M+H]^+$. LC-MS retention time: 2.0 min (Method E). $^1H$ NMR (400 MHz, DMSO-$d_6$) δ ppm: 8.63-8.40 (m, 1H), 8.32-8.01 (m, 1H), 7.62 (t, J=7.3 Hz, 2H), 7.33-6.93 (m, 2H), 6.76 (s, 1H), 6.67-6.50 (m, 1H), 4.58-4.25 (m, 3H), 4.08-3.96 (m, 3H), 3.90 (s, 1H), 3.87-3.80 (m, 1H), 3.67-3.54 (m, 2H), 3.30-3.14 (m, 1H), 2.97-2.60 (m, 2H), 2.05-1.58 (m, 2H), 1.29-1.13 (m, 2H), 1.13-1.03 (m, 1H), 0.34-0.21 (m, 2H), 0.12 (q, J=4.8 Hz, 2H).

Example 23

6-(2-(6-((7R)-7-Amino-2-azabicyclo[2.2.1]heptane-2-carbonyl)-4-methoxy-3-methylpyrazolo[1,5-a]pyridin-2-yl)-1-(cyclopropylmethyl)-1H-indol-6-yl)isoindolin-1-one

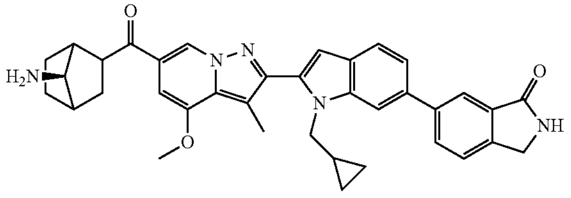 [SMILES: COc1cc(C(=O)C2CC3CCC2[C@@H]3N)cn2nc(-c3cc4ccc(-c5ccc6c(c5)C(=O)NC6)cc4n3CC3CC3)c(C)c12]

Intermediate 23A 3-(tert-Butyl)-6-methyl 2-(6-bromo-1-(cyclopropylmethyl)-1H-indol-2-yl)-4-methoxypyrazolo[1,5-a]pyridine-3,6-dicarboxylate

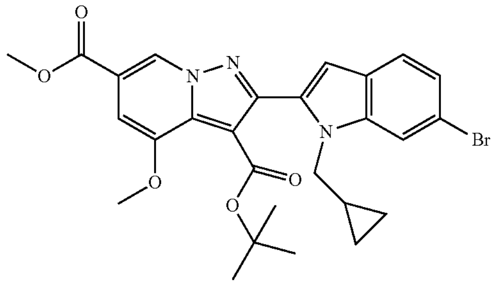 [SMILES: COC(=O)c1cc(OC)c2c(C(=O)OC(C)(C)C)c(-c3cc4ccc(Br)cc4n3CC3CC3)nn2c1]

tert-Butyl 3-(6-bromo-1-(cyclopropylmethyl)-1H-indol-2-yl)propiolate (Intermediate 6, 5.5 g, 14.69 mmol) and $K_2CO_3$ (6.09 g, 44.1 mmol) were added to a solution of 1-amino-3-methoxy-5-(methoxycarbonyl)pyridin-1-ium 2,4-dinitrophenolate (Intermediate 1, 8.07 g, 22.04 mmol) in DMF (50 ml). The reaction mixture was stirred overnight, concentrated under a vacuum at ~45° C. over a period of 1 hour, diluted with EtOAc, and filtered through a celite bed. The filtrate was further washed with water, dried over $Na_2SO_4$, filtered, and the organic layer was concentrated under vacuum to obtain a crude compound, which was purified using a silica gel column (40 g, Redisep®) $SiO_2$ column, eluting with 30% EtOAc in hexane) to afford the title compound (5.3 g, 65%). LC-MS m/z: 500.1 $[M+H]^+$. $^1H$ NMR (400 MHz, DMSO-$d_6$) δ ppm: 9.04-8.91 (m, 1H), 8.56-7.96-7.84 (m, 1H), 7.63-7.53 (m, 1H), 7.30-7.06 (m, 2H), 6.80-6.70 (m, 1H), 4.44-4.30 (m, 2H), 3.96-3.86 (m, 6H), 1.43-1.36 (m, 8H), 1.12-1.02 (m, 1H), 0.34-0.24 (m, 2H), 0.18-0.12 (m, 2H).

Intermediate 23B 2-(6-Bromo-1-(cyclopropylmethyl)-1H-indol-2-yl)-4-methoxy-6-(methoxycarbonyl)pyrazolo[1,5-a]pyridine-3-carboxylic acid

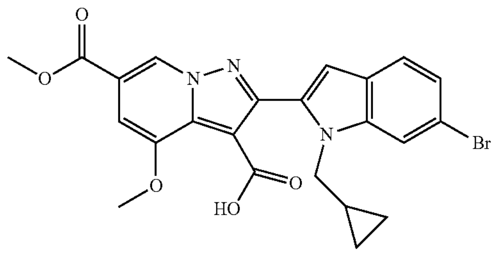 [SMILES: COC(=O)c1cc(OC)c2c(C(=O)O)c(-c3cc4ccc(Br)cc4n3CC3CC3)nn2c1]

2,6-Lutidine (8.91 ml, 76 mmol) was added to a stirred solution of Intermediate 23A (5.3 g, 9.56 mmol) in DCM (50 ml), followed by the addition of trimethylsilyl trifluoromethanesulfonate (6.91 ml, 38.2 mmol) at 0-5° C. The reaction mixture was stirred for 2 hours at the same temperature, quenched with 10% $NaHCO_3$ solution, stirred for 10 min, and diluted with EtOAc (50 ml). The organic layer was separated, and aqueous layer was extracted with EtOAc (3×25 ml). The combined organic layers were dried over $Na_2SO_4$, and concentrated under vacuum at a room temperature to obtain the title compound as a pale yellow syrup (5.5 g, 102%). LC-MS m/z: 500 $[M+H]^+$.

Intermediate 23C

Methyl-2-(6-bromo-1-(cyclopropylmethyl)-1H-indol-2-yl)-4-methoxy-3-methylpyrazolo[1,5-a]pyridine-6-carboxylate

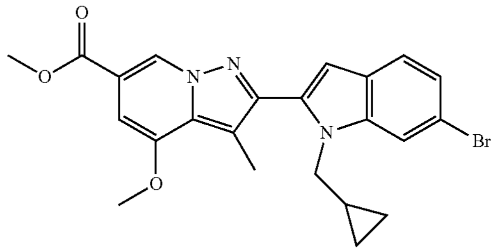 [SMILES: COC(=O)c1cc(OC)c2c(C)c(-c3cc4ccc(Br)cc4n3CC3CC3)nn2c1]

Borane-methyl sulfide complex (2.52 ml, 26.6 mmol) was added to a stirred solution of Intermediate 23B (5.3 g, 10.64 mmol) in THF (50 ml) at 0° C. The reaction mixture was stirred for 30 min, slowly heated to 50° C. and stirred for 4 hours, followed by stirring at a room temperature for 12 hours. The reaction mixture was cooled to 0° C., quenched by careful addition of methanol, and concentrated under vacuum to obtain a crude residue. The crude product was triturated with water (3×25 ml), and the sticky off-white residue was purified using a silica gel column (40 g, Redisep® $SiO_2$ column, eluting with 0 to 50% EtOAc in hexane) to afford the title compound (1.1 g, 22%). LC-MS m/z: 470.1 $[M+H]^+$.

Intermediate 23D 2-(6-Bromo-1-(cyclopropylmethyl)-1H-indol-2-yl)-4-methoxy-3-methylpyrazolo[1,5-a]pyridine-6-carboxylic acid

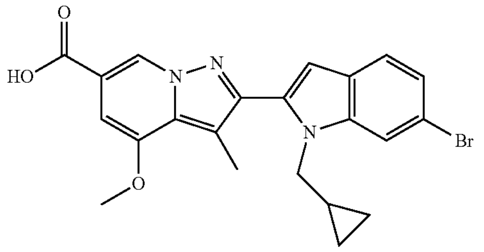 [SMILES: COc1cc(C(=O)O)cn2nc(-c3cc4ccc(Br)cc4n3CC3CC3)c(C)c12]

LiOH (0.169 g, 7.05 mmol) in water (5 ml) was added to a stirred suspension of Intermediate 23C (1.1 g, 2.349 mmol) in a mixture of methanol (20 ml) and THF (5 ml). The reaction mixture was stirred for 4 hours, concentrated under vacuum to obtain a crude salt, which was neutralized using 1.5 N HCl. The solids obtained were filtered and dried under vacuum to afford the title compound (930 mg, 87%) as an off-white solid. LC-MS m/z: 455 $[M+H]^+$.

Intermediate 23E tert-Butyl-((7R)-2-(2-(6-bromo-1-(cyclopropylmethyl)-1H-indol-2-yl)-4-methoxy-3-methylpyrazolo[1,5-a]pyridine-6-carbonyl)-2-azabicyclo[2.2.1]heptan-7-yl)carbamate

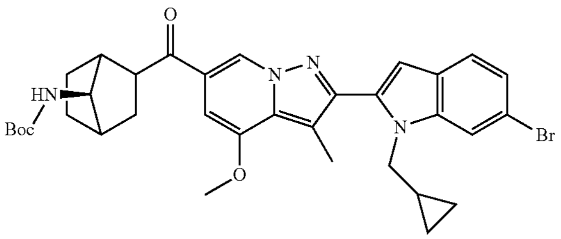 [SMILES: COc1cc(C(=O)C2CC3CCC2[C@@H]3NC(=O)OC(C)(C)C)cn2nc(-c3cc4ccc(Br)cc4n3CC3CC3)c(C)c12]

HATU (250 mg, 0.658 mmol), DIPEA (0.265 ml, 1.519 mmol) and tert-butyl ((7R)-2-azabicyclo[2.2.1]heptan-7-yl) carbamate (107 mg, 0.506 mmol) were successively added to a stirred solution of Intermediate 23D (230 mg, 0.506 mmol) in DMF (2 ml). The reaction mixture was stirred for 3 hours, cooled, and treated with ice-cold water and stirred for 10 min. The solids obtained were filtered, and dried in vacuum to afford the title compound (300 mg, 91%) as an off-white solid. LC-MS m/z: 650.3 [M+H]. $^1H$ NMR (400 MHz, DMSO-$d_6$) δ ppm: 8.59-8.50 (m, 1H), 8.42-8.31 (m, 1H), 7.89 (s, 1H), 7.59 (d, J=8.3 Hz, 1H), 7.22 (d, J=8.8 Hz, 1H), 7.14-7.01 (m, 1H), 6.80 (s, 1H), 6.68-6.60 (m, 1H), 4.40 (br, d, J=6.4 Hz, 2H), 4.25-4.12 (m, 1H), 4.00 (br, s, 3H), 3.84-3.64 (m, 1H), 3.58-3.43 (m, 1H), 3.21-2.86 (m, 2H), 2.44 (br, s, 3H), 2.33 (br, s, 1H), 2.08-1.74 (m, 3H), 1.35 (br, s, 10H), 0.29 (br d,J=7.6 Hz, 2H), 0.11 (br, s, 2H).

Intermediate 23F tert-Butyl-((7R)-2-(2-(1-(cyclopropylmethyl)-6-(3-oxoisoindolin-5-yl)-1H-indol-2-yl)-4-methoxy-3-methylpyrazolo[1,5-a]pyridine-6-carbonyl)-2-azabicyclo[2.2.1]heptan-7-yl)carbamate

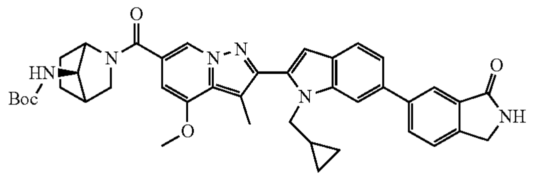

$K_2CO_3$ (29.8 mg, 0.216 mmol) and $PdCl_2$(dppf) (7.90 mg, 10.79 μmol) were added to a solution of Intermediate 23E (70 mg, 0.108 mmol) and 6-(4,4,5,5-tetramethyl-1,3,2-dioxaborolan-2-yl)isoindolin-1-one (28.0 mg, 0.108 mmol) in dioxane (3 ml) in a 8 ml chemglass vial. The reaction mixture was degassed using argon, heated to 85° C. and stirred for 8 hours, filtered, and concentrated under vacuum to afford a crude product, which was purified using Prep-HPLC to obtain the title compound (40 mg, 53%) as a white solid. LC-MS retention time: 0.94 min. LC-MS m/z: 701.5 $[M+H]^+$.

Example 23

TFA (0.1 ml, 1.298 mmol) was added to a solution of Intermediate 23F (40 mg, 0.057 mmol) in DCM (1 ml). The reaction mixture was stirred for 2 hours, concentrated under vacuum, the residue obtained was treated with 28% ammonia solution, and kept on standby for 30 min. The aqueous layer was decanted, and solids left in the flask were dried under vacuum. The crude product was further purified using RP-HPLC to afford the title compound (25 mg, 0.040 mmol, 70%), which was lyophilized to afford a white solid. LC-MS m/z: 601.4 $[M+H]^+$. HPLC retention time: 6.958 min (Method C). $^1H$ NMR (400 MHz, DMSO-$d_6$) δ ppm: 8.63-8.48 (m, 1H), 8.78-8.43 (m, 1H), 8.43-8.35 (m, 1H), 8.05-7.94 (m, 3H), 7.80-7.65 (m, 2H), 7.50-7.40 (m, 1H), 6.85-6.75 (m, 1H), 6.68-6.57 (m, 1H), 4.56-4.46 (m, 2H), 4.46-4.40 (m, 2H), 4.24-4.18 (m, 1H), 4.03-3.85 (m, 3H), 3.82-3.46 (m, 1H), 3.15-3.06 (m, 1H), 2.53 (s, 3H), 2.30-2.20 (m, 1H), 2.10-1.78 (m, 4H), 1.52-1.37 (m, 1H), 1.19-1.10 (m, 1H), 0.36-0.26 (m, 2H), 0.19-0.13 (m, 2H).

Compounds of Examples 24 to 28 in Table 3 were prepared following a procedure similar to the preparation of a compound of Example 23, using Suzuki coupling of Intermediate 23E with appropriate boronic acid.

TABLE 3

| Example | Structure<br>Name<br>Analytical Data: LC-MS m/z $[M + H]^+$; HPLC retention time (HPLC method) |
|---|---|
| 24 | 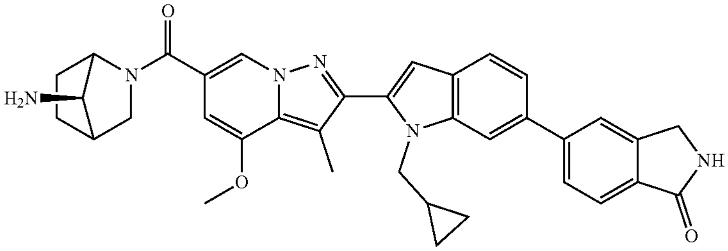 [SMILES: COc1cc(C(=O)N2CC3CCC2[C@@H]3N)cn2nc(-c3cc4ccc(-c5ccc6c(c5)CNC6=O)cc4n3CC3CC3)c(C)c12]<br>5-(2-(6-((7R)-7-Amino-2-azabicyclo[2.2.1]heptane-2-carbonyl)-4-methoxy-3-methylpyrazolo[1,5-a]pyridin-2-yl)-1-(cyclopropylmethyl)-1H-indol-6-yl)isoindolin-1-one<br>Analytical Data: 601.4, 6.779 min (Method C) |
| 25 | 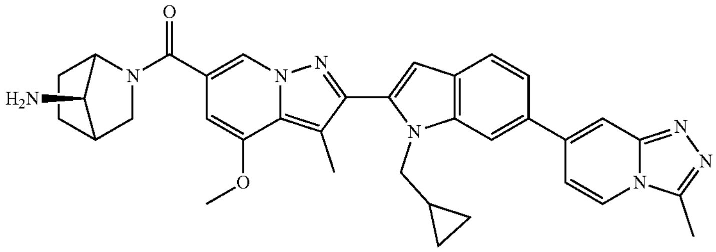 [SMILES: COc1cc(C(=O)N2CC3CCC2[C@@H]3N)cn2nc(-c3cc4ccc(-c5ccn6c(C)nnc6c5)cc4n3CC3CC3)c(C)c12]<br>((7R)-7-Amino-2-azabicyclo[2.2.1]heptan-2-yl)(2-(1-(cyclopropylmethyl)-6-(3-methyl-[1,2,4]triazolo[4,3-a]pyridin-7-yl)-1H-indol-2-yl)-4-methoxy-3-methylpyrazolo[1,5-a]pyridin-6-yl)methanone<br>Analytical Data: 601.4, 5.325 min (Method C) |

TABLE 3-continued

| Example | Structure<br>Name<br>Analytical Data: LC-MS m/z $[M + H]^+$; HPLC retention time (HPLC method) |
|---|---|
| 26 | 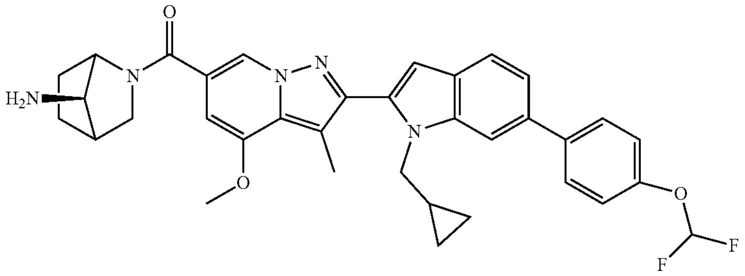 [SMILES: COc1cc(C(=O)N2CC3CCC2[C@@H]3N)cn2nc(-c3cc4ccc(-c5ccc(OC(F)F)cc5)cc4n3CC3CC3)c(C)c12]<br>((7R)-7-Amino-2-azabicyclo[2.2.1]heptan-2-yl)(2-(1-(cyclopropylmethyl)-6-(4-(difluoromethoxy)phenyl)-1H-indol-2-yl)-4-methoxy-3-methylpyrazolo[1,5-a]pyridin-6-yl)methanone<br>Analytical Data: 612.4, 5.954 min (Method C) |
| 27 | 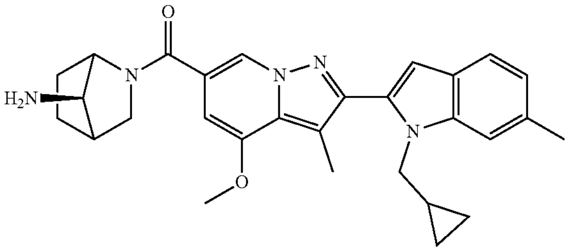 [SMILES: COc1cc(C(=O)N2CC3CCC2[C@@H]3N)cn2nc(-c3cc4ccc(C)cc4n3CC3CC3)c(C)c12]<br>((7R)-7-Amino-2-azabicyclo[2.2.1]heptan-2-yl)(2-(1-(cyclopropylmethyl)-6-methyl-1H-indol-2-yl)-4-methoxy-3-methylpyrazolo[1,5-a]pyridin-6-yl)methanone<br>Analytical Data: 484.3, 5.698 min ( Method C) |
| 28 | 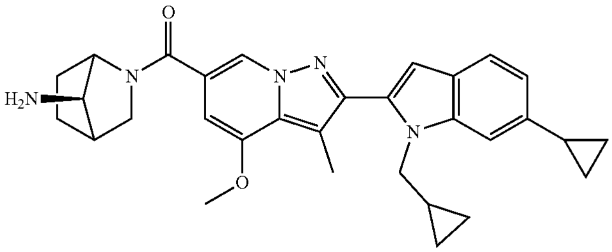 [SMILES: COc1cc(C(=O)N2CC3CCC2[C@@H]3N)cn2nc(-c3cc4ccc(C5CC5)cc4n3CC3CC3)c(C)c12]<br>((7R)-7-Amino-2-azabicyclo[2.2.1]heptan-2-yl)(2-(6-cyclopropyl-1-(cyclopropylmethyl)-1H-indol-2-yl)-4-methoxy-3-methylpyrazolo[1,5-a]pyridin-6-yl)methanone<br>Analytical Data: 511.3, 4.777 min (Method C) |

Example 29

6-(2-(6-((3R,5R)-3-Amino-5-fluoropiperidine-1-carbonyl)-4-methoxy-3-methylpyrazolo[1,5-a]pyridin-2-yl)-1-(cyclopropylmethyl)-1H-indol-6-yl) isoindolin-1-one

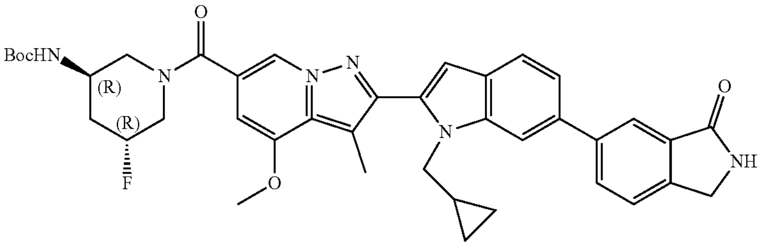

Intermediated 29A tert-Butyl-((3R,5R)-1-(2-(6-bromo-1-(cyclopropylmethyl)-1H-indol-2-yl)-4-methoxy-3-methylpyrazolo[1,5-a]pyridine-6-carbonyl)-5-fluoropiperidin-3-yl) carbamate

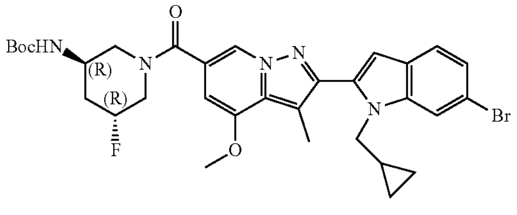

HATU (1742 mg, 4.58 mmol) followed by DIPEA (2.401 ml, 13.74 mmol) were added to a stirred solution of Intermediate 23D (2081 mg, 4.58 mmol) and tert-butyl ((3R,5R)-5-fluoropiperidin-3-yl)carbamate (1000 mg, 4.58 mmol) in DMF (3 ml). The reaction mixture was stirred at a room temperature overnight, cooled to 0° C., and ice-cold water was added. The solids obtained were filtered, washed with water, and purified using a silica gel column (0-1% methanol/chloroform) to afford the title compound (1.4 g, 47%) as an off-white solid. LC-MS m/z: 655.4 $[M+H]^+$.

Intermediate 29B tert-Butyl-((3R,5R)-1-(2-(1-(cyclopropylmethyl)-6-(3-oxoisoindolin-5-yl)-1H-indol-2-yl)-4-methoxy-3-methylpyrazolo[1,5-a]pyridine-6-carbonyl)-5-fluoropiperidin-3-yl)carbamate

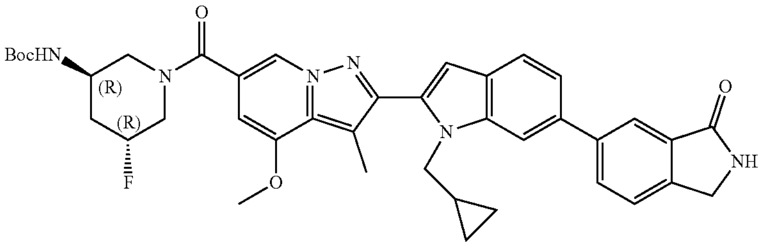

$K_2CO_3$ (29.6 mg, 0.214 mmol) and $PdCl_2$(dppf) (7.82 mg, 10.69 µmol) were added to a solution of Intermediate 29A (70 mg, 0.107 mmol) and 6-(4,4,5,5-tetramethyl-1,3,2-dioxaborolan-2-yl)isoindolin-1-one (27.7 mg, 0.107 mmol) in dioxane (3 ml). The reaction mixture was degassed using argon, heated to 85° C. and stirred for 8 hours, filtered, and the filtrate was concentrated under vacuum to obtain a crude compound, which was purified using Prep-HPLC to afford the title compound (40 mg, 53%) as a white solid. LC-MS m/z: 707.5 $[M+H]^+$.

Example 29

TFA (0.1 ml, 1.298 mmol) was added to a solution of Intermediate 29B (40 mg, 0.057 mmol) in DCM (1 ml). The reaction mixture was stirred for 2 hours, concentrated under vacuum, the crude compound obtained was treated with 28% ammonia solution, and kept on standby for 30 minutes. The aqueous layer was decanted, and the solids left in the flask were dried under vacuum. The product was further purified using RP-HPLC to afford the title compound (18 mg, 51%), which was lyophilized to afford white solid. LC-MS m/z: 607.4 $[M+H]^+$. HPLC retention time: 7.167 min (Method C). $^1$H NMR (400 MHz, DMSO-$d_6$) δ ppm: 8.54 (s, 1H), 8.38 (s, 1H), 7.98 (d, J=5.5 Hz, 2H), 7.89 (d, J=7.5 Hz, 1H), 7.78-7.65 (m, 2H), 7.49 (d, J=8.3 Hz, 1H), 6.81 (s, 1H), 6.56 (s, 1H), 5.02-4.92 (m, 1H), 4.55-4.41 (m, 5H), 4.00 (s, 4H), 3.50-3.36 (m, 1H), 3.28-3.05 (m, 1H), 2.47-2.35 (m, 3H), 1.92-1.89 (m, 1H), 1.69 (br d, J=1.0 Hz, 1H), 1.24-1.20 (m, 1H), 0.40-0.29(m, 2H), 0.21-0.11 (m, 2H).

Compounds of Examples 30 to 33 in Table 4 were prepared following a procedure similar to the preparation of a compound of Example 29, by Suzuki coupling of Intermediate 29A with appropriate boronic acid.

TABLE 4

| Example | Structure<br>Name<br>Analytical Data: LC-MS m/z [M + H]+; HPLC retention time (HPLC method 1) |
|---|---|
| 30 | 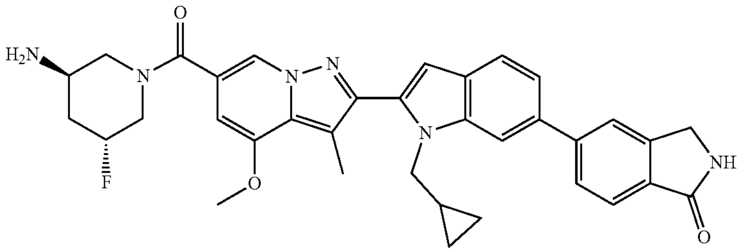 [SMILES: COc1cc(C(=O)N2C[C@H](N)C[C@@H](F)C2)cn2nc(-c3cc4ccc(-c5ccc6c(c5)CNC6=O)cc4n3CC3CC3)c(C)c12]<br>5-(2-(6-((3R,5R)-3-Amino-5-fluoropiperidine-1-carbonyl)-4-methoxy-3-methylpyrazolo[1,5-a]pyridin-2-yl)-1-(cyclopropylmethyl)-1H-indol-6-yl)isoindolin-1-one<br>Analytical Data: 607.2, 6.951 min (Method C) |
| 31 | 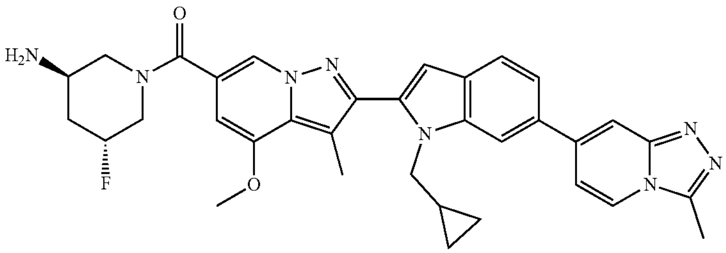 [SMILES: COc1cc(C(=O)N2C[C@H](N)C[C@@H](F)C2)cn2nc(-c3cc4ccc(-c5ccn6c(C)nnc6c5)cc4n3CC3CC3)c(C)c12]<br>((3R,5R)-3-Amino-5-fluoropiperidin-1-yl)(2-(1-(cyclopropylmethyl)-6-(3-methyl-[1,2,4]triazolo[4,3-a]pyridin-7-yl)-1H-indol-2-yl)-4-methoxy-3-methylpyrazolo[1,5-a]pyridin-6-yl)methanone<br>Analytical Data: 674, 5.471 min (Method C) |
| 32 | 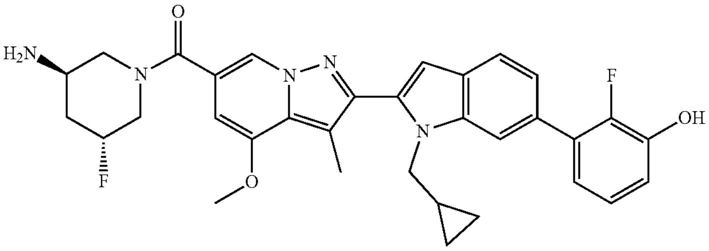 [SMILES: COc1cc(C(=O)N2C[C@H](N)C[C@@H](F)C2)cn2nc(-c3cc4ccc(-c5cccc(O)c5F)cc4n3CC3CC3)c(C)c12]<br>((3R,5R)-3-Amino-5-fluoropiperidin-1-yl)(2-(1-(cyclopropylmethyl)-6-(2-fluoro-3-hydroxyphenyl)-1H-indol-2-yl)-4-methoxy-3-methylpyrazolo[1,5-a]pyridin-6-yl)methanone<br>Analytical Data: 586.4, 1.964 min (Method E) |

Example 33

((3R,5R)-3-Amino-5-fluoropiperidin-1-yl)(2-(1-(cyclopropylmethyl)-6-(3-(methoxymethyl)-azetidin-1-yl)-1H-indol-2-yl)-4-methoxy-3-methylpyrazolo[1,5-a]pyridin-6-yl)methanone

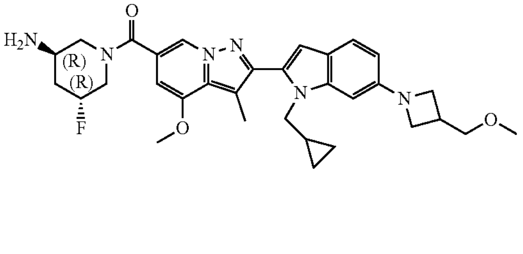

Intermediate 33A tert-Butyl-((3R,5R)-1-(2-(1-(cyclopropylmethyl)-6-(3-(methoxymethyl)azetidin-1-yl)-1H-indol-2-yl)-4-methoxy-3-methylpyrazolo[1,5-a]pyridine-6-carbonyl)-5-fluoropiperidin-3-yl)carbamate

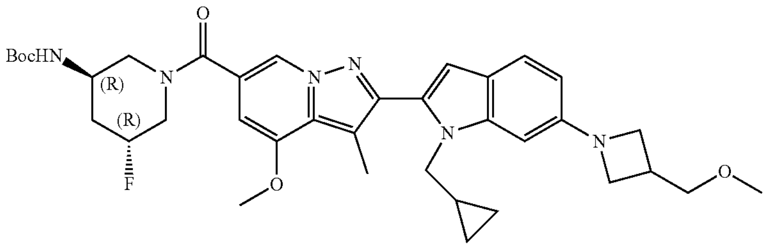

$Pd_2(dba)_3$ (12 mg, 0.013 mmol), $Cs_2CO_3$ (100 mg, 0.307 mmol), and RUPHOS (13 mg, 0.028 mmol) were added to a solution of Intermediate 29A (65 mg, 0.099 mmol) and 3-(methoxymethyl)-azetidine (10.04 mg, 0.099 mmol) in dioxane (3 ml) in a 8 ml chemglass vial. The reaction mixture was degassed using argon, heated to 110° C. and stirred for 14 hours, filtered, and concentrated under vacuum to afford a crude compound (70 mg, 104%), which was used in the next step without further purification. LC-MS m/z: 675.5 $[M+H]^+$.

Example 33

TFA (0.3 ml, 3.89 mmol) was added to a solution of Intermediate 33A (70 mg, 0.104 mmol) in DCM (1 ml). The reaction mixture was stirred for 2 hours, concentrated under vacuum, and the crude product obtained was purified using prep-HPLC. The product was further purified using RP-HPLC to afford the title compound (13 mg, 22%). LC-MS m/z: 575 $[M+H]^+$. LC-MS retention time: 1.963 min (Method E). $^1H$ NMR (400 MHz, methanol-$d_4$) δ ppm: 8.27 (d, J=1.0 Hz, 1H), 7.46 (d, J=8.5 Hz, 1H), 6.59 (s, 1H), 6.55 (s, 2H), 6.45 (dd, J=2.0, 8.5 Hz, 1H), 5.01-4.96 (m, 1H), 4.27 (d, J=6.5 Hz, 2H), 4.09-3.96 (m, 6H), 3.72-3.64 (m, 4H), 3.51-3.35 (m, 1H), 3.31-3.14 (m, 2H), 3.06-2.88(m, 1H), 2.88-2.68 (m, 1H), 2.53 (s, 3H), 2.45-2.19 (m, 1H), 1.75-1.54 (m, 1H), 1.42-1.23 (m, 1H), 1.19-0.99 (m, 1H), 0.35-0.28 (m, 2H), 0.13-0.01 (m, 2H).

Compounds of Examples 34 to 37 in Table 5 were prepared following a procedure similar to the preparation of a compound of Example 33, by Buchwald coupling of Intermediate 29A with appropriate amine.

TABLE 5

| Example | Structure<br>Name<br>Analytical Data: LC-MS m/z $[M + H]^+$; HPLC retention time (HPLC method) |
|---|---|
| 34 | 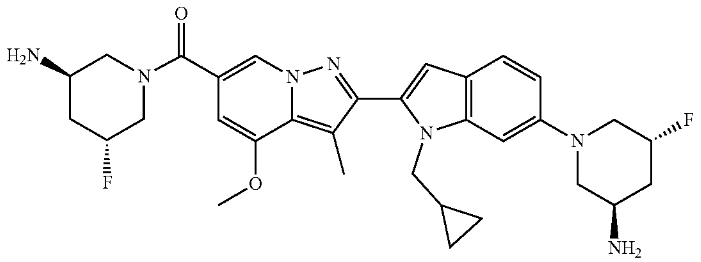 [SMILES: COc1cc(C(=O)N2C[C@H](N)C[C@@H](F)C2)cn2nc(-c3cc4ccc(N5C[C@H](N)C[C@@H](F)C5)cc4n3CC3CC3)c(C)c12]<br>((3R,5R)-3-Amino-5-fluoropiperidin-1-yl)(2-(6-((3R,5R)-3-amino-5-fluoropiperidin-1-yl)-1-(cyclopropylmethyl)-1H-indol-2-yl)-4-methoxy-3-methylpyrazolo[1,5-a]pyridin-6-yl)methanone<br>Analytical Data: 592.4, 1.216 min (Method E) |

TABLE 5-continued

| Example | Structure<br>Name<br>Analytical Data: LC-MS m/z [M + H]$^+$; HPLC retention time (HPLC method) |
|---|---|
| 35 | 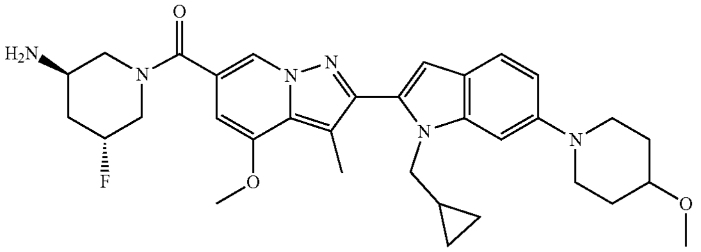 [SMILES: COc1cc(C(=O)N2C[C@H](N)C[C@@H](F)C2)cn2nc(-c3cc4ccc(N5CCC(OC)CC5)cc4n3CC3CC3)c(C)c12]<br>((3R,5R)-3-Amino-5-fluoropiperidin-1-yl)(2-(1-(cyclopropylmethyl)-6-(4-methoxypiperidin-1-yl)-1H-indol-2-yl)-4-methoxy-3-methylpyrazolo[1,5-a]pyridin-6-yl)methanone<br>Analytical Data: 589.4, 1.970 min (Method E) |
| 36 | 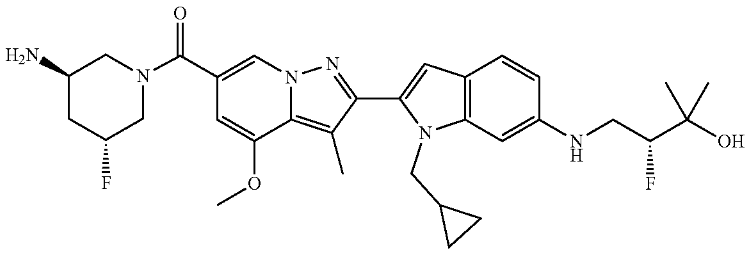 [SMILES: COc1cc(C(=O)N2C[C@H](N)C[C@@H](F)C2)cn2nc(-c3cc4ccc(NC[C@@H](F)C(C)(C)O)cc4n3CC3CC3)c(C)c12]<br>((3R,5R)-3-Amino-5-fluoropiperidin-1-yl)(2-(1-(cyclopropylmethyl)-6-(((R)-2-fluoro-3-hydroxy-3-methylbutyl)amino)-1H-indol-2-yl)-4-methoxy-3-methylpyrazolo[1,5-a]pyridin-6-yl)methanone<br>Analytical Data: 595.4, 1.712 min (Method E) |
| 37 | 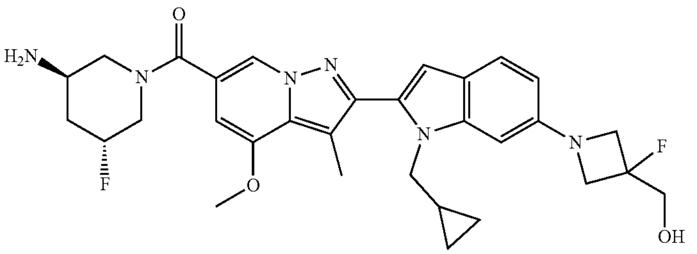 [SMILES: COc1cc(C(=O)N2C[C@H](N)C[C@@H](F)C2)cn2nc(-c3cc4ccc(N5CC(F)(CO)C5)cc4n3CC3CC3)c(C)c12]<br>((3R,5R)-3-Amino-5-fluoropiperidin-1-yl)(2-(1-(cyclopropylmethyl)-6-(3-fluoro-3-(hydroxymethyl)azetidin-1-yl)-1H-indol-2-yl)-4-methoxy-3-methylpyrazolo[1,5-a]pyridin-6-yl)methanone<br>Analytical Data: 579.4, 1.428 min (Method F) |

Example 38

((7R)-7-Amino-2-azabicyclo[2.2.1]heptan-2-yl)(2-(1-(cyclopropylmethyl)-1H-pyrrolo[2,3-b]pyridin-2-yl)-4-fluoro-3-methylpyrazolo[1,5-a]pyridin-6-yl)methanone

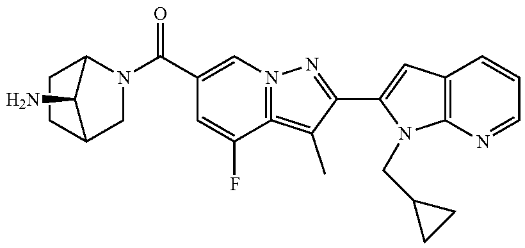

Intermediate 38A 3-(tert-Butyl)-6-methyl 2-(1-(cyclopropylmethyl)-1H-pyrrolo[2,3-b]pyridin-2-yl)-4-fluoropyrazolo[1,5-a]pyridine-3,6-dicarboxylate

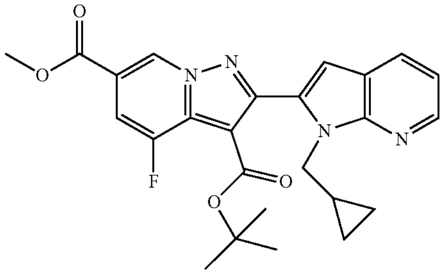

Intermediate 38A was prepared following a procedure similar to the preparation of Intermediate 1A, and using 1-amino-3-fluoro-5-(methoxycarbonyl)pyridin-1-ium 2,4,6-trimethylbenzenesulfonate (Intermediate 9) and tert-butyl 3-(1-(cyclopropylmethyl)-1H-pyrrolo[2,3-b]pyridin-2-yl)propiolate (Intermediate 2), as a pale yellow solid (200 mg, 43%). LC-MS m/z: 465.1 [M+H]$^+$.

Intermediate 38B 2-(1-(Cyclopropylmethyl)-1H-pyrrolo[2,3-b]pyridin-2-yl)-4-fluoro-6-(methoxycarbonyl)pyrazolo[1,5-a]pyridine-3-carboxylic acid

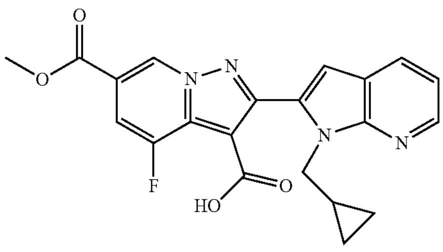

Intermediate 38B was prepared following a procedure similar to the preparation of Intermediate 1B, as a pale yellow solid (170 mg, 56%). LC-MS m/z: 409.2 [M+H]$^+$.

Intermediate 38C

Methyl-2-(1-(cyclopropylmethyl)-1H-pyrrolo[2,3-b]pyridin-2-yl)-4-fluoro-3-methylpyrazolo[1,5-a]pyridine-6-carboxylate

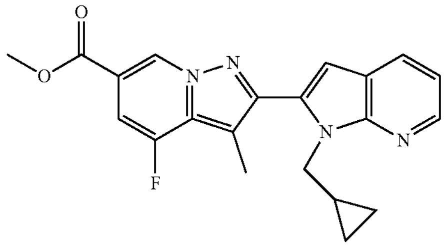

Intermediate 38C was prepared following a procedure similar to the preparation of Intermediate 1C, as a brown solid (142 mg, 90%). LC-MS m/z: 379.2 [M+H]$^+$.

Intermediate 38D 2-(1-(Cyclopropylmethyl)-1H-pyrrolo[2,3-b]pyridin-2-yl)-4-fluoro-3-methylpyrazolo[1,5-a]pyridine-6-carboxylic acid

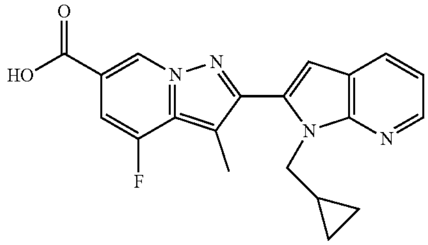

Intermediate 38D was prepared following a procedure similar to the preparation of Intermediate, as an off white solid (125 mg, 93%). LC-MS m/z: 365.2 [M+H]$^+$.

Intermediate 38E tert-Butyl-((7R)-2-(2-(1-(cyclopropylmethyl)-1H-pyrrolo[2,3-b]pyridin-2-yl)-4-fluoro-3-methylpyrazolo[1,5-a]pyridine-6-carbonyl)-2-azabicyclo[2.2.1]heptan-7-yl)carbamate

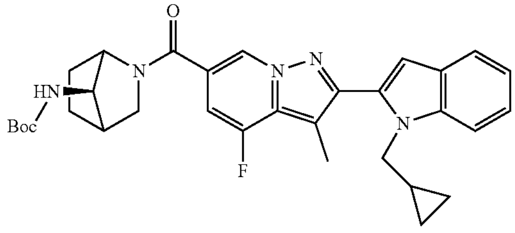

Intermediate 38E was prepared following a procedure similar to preparation of Intermediate 1E, as an off white solid (60 mg, 66%). LC-MS m/z: 559.3 [M+H]+.

Example 38

Compound of Example 38 was prepared following a procedure similar to the preparation of a compound of Example 1 (8.07 mg, 19%). LC-MS m/z: 459.3 [M+H]+. HPLC retention time: 5.349 min (Method C). $^{1}$H NMR (400 MHz, DMSO-$d_6$) δ ppm: 8.87-8.72 (m, 1H), 8.34 (dd, J=4.52, 1.51 Hz, 1H), 8.07 (dd, J=7.78, 1.76 Hz, 1H), 7.13-7.19 (m, 2H), 6.88 (s, 1H), 4.50 (br, d, J=6.53 Hz, 2H), 4.08-3.81 (m, 1H), 3.75-3.45 (m, 2H), 3.10-3.29 (m, 3H), 2.53 (s, 3H), 2.09-2.32 (m, 2H), 1.96 (br, s, 3H), 1.87-1.65 (m, 1H), 1.36-1.46 (m, 1H), 1.24 (s, 1H), 0.21-0.45 (m, 4H).

Example 39

((7R)-7-Amino-2-azabicyclo[2.2.1]heptan-2-yl)(2-(6-chloro-1-(cyclopropylmethyl)-1H-pyrrolo[2,3-b]pyridin-2-yl)-4-fluoro-3-methylpyrazolo[1,5-a]pyridin-6-yl)methanone

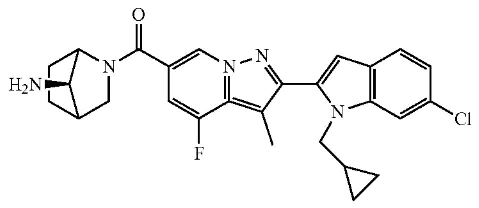

Intermediate 39A 3-(tert-Butyl)-6-methyl 2-(6-chloro-1-(cyclopropylmethyl)-1H-pyrrolo[2,3-b]pyridin-2-yl)-4-fluoropyrazolo[1,5-a]pyridine-3,6-dicarboxylate

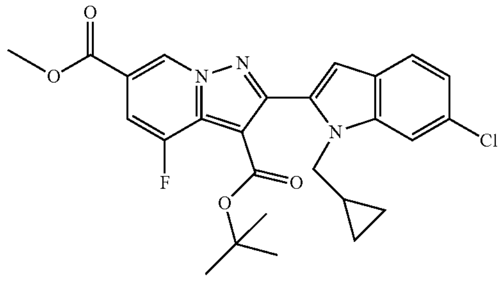

Intermediate 39A was prepared following a procedure similar to the preparation of Intermediate 2A, as a yellow solid (1.5 g, 33%). LC-MS m/z: 499.1 [M+H]+.

Intermediate 39B 2-(6-Chloro-1-(cyclopropylmethyl)-1H-pyrrolo[2,3-b]pyridin-2-yl)-4-fluoro-6-(methoxycarbonyl)pyrazolo[1,5-a]pyridine-3-carboxylic acid

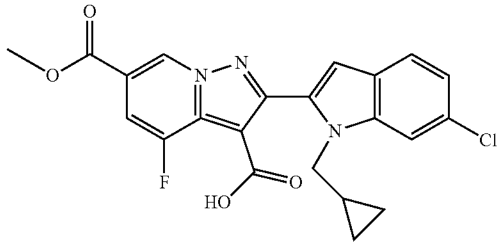

Intermediate 39B was prepared following a procedure similar to preparation of Intermediate 2B, as a brown solid (1.3 g, 98%). LC-MS m/z: 443.1 [M+H]+.

Intermediate 39C

Methyl-2-(6-chloro-1-(cyclopropylmethyl)-1H-pyrrolo[2,3-b]pyridin-2-yl)-4-fluoro-3-methylpyrazolo[1,5-a]pyridine-6-carboxylate

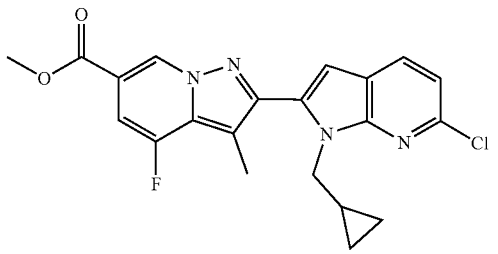 [SMILES: COC(=O)c1cc(F)c2c(C)c(-c3cc4ccc(Cl)nc4n3CC3CC3)nn2c1]

Intermediate 39B was prepared following a procedure similar to the preparation of Intermediate 2C, as a brown solid (1.21 g, 50%). LC-MS m/z: 413.2 [M+H]+.

Intermediate 39D 2-(6-Chloro-1-(cyclopropylmethyl)-1H-pyrrolo[2,3-b]pyridin-2-yl)-4-fluoro-3-methylpyrazolo[1,5-a]pyridine-6-carboxylic acid

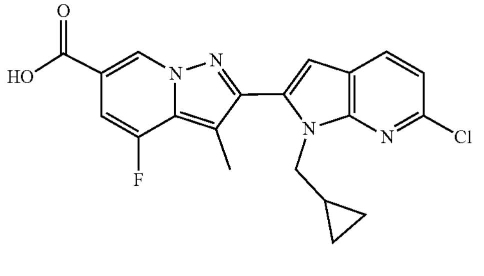 [SMILES: Cc1c(-c2cc3ccc(Cl)nc3n2CC2CC2)nn2cc(C(=O)O)cc(F)c12]

Intermediate 39D was prepared following a procedure similar to the preparation of Intermediate 2D, as a brown solid (1.2 g, 67%) as a brown solid. LC-MS m/z: 399.2 $[M+H]^+$.

Intermediate 39E tert-Butyl-((7R)-2-(2-(6-chloro-1-(cyclopropylmethyl)-1H-pyrrolo[2,3-b]pyridin-2-yl)-4-fluoro-3-methylpyrazolo[1,5-a]pyridine-6-carbonyl)-2-azabicyclo[2.2.1]heptan-7-yl)carbamate

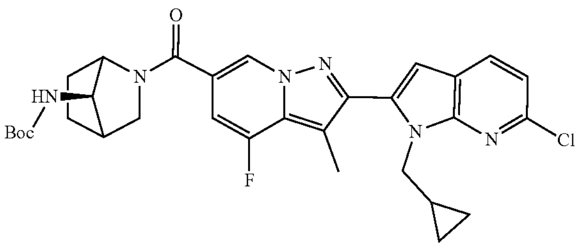 [SMILES: Cc1c(-c2cc3ccc(Cl)nc3n2CC2CC2)nn2cc(C(=O)N3CC4CCC3[C@@H]4NC(=O)OC(C)(C)C)cc(F)c12]

Intermediate 39E was prepared following a procedure similar to the preparation of Intermediate 2E, as a brown solid (700 mg, 78%) as a brown solid. LC-MS m/z: 593.3 $[M+H]^+$.

Example 39

Compound of Example 39 was prepared following a procedure similar to the preparation of a compound of Example 2 (7.2 mg, 8%). LC-MS m/z: 493.3 $[M+H]^+$. LC-MS retention time: 2.105 min (Method E). $^1$H NMR (400 MHz, DMSO-$d_6$) δ ppm: 8.95-8.71 (m, 1H), 8.13 (d, J=8.3 Hz, 1H), 7.29-7.11 (m, 2H), 6.95 (s, 1H), 4.56-4.18 (m, 2.5H), 4.28-4.21 (s, 0.5H), 3.84-3.75 (m, 0.5H), 3.57 (br s, 1.5H), 3.19 (br d, J=10.8 Hz, 0.5H), 2.69-2.58 (m, 1.5H), 2.03-1.81 (m, 3H), 1.69-1.58 (m, 1H), 1.28-1.10 (m, 2H), 0.40-0.14 (m, 4H).

Example 40

3((7R)-7-Amino-2-azabicyclo[2.2.1]heptan-2-yl)(2-(1-(cyclopropylmethyl)-6-methyl-1H-pyrrolo[2,3-b]pyridin-2-yl)-4-fluoro-3-methylpyrazolo[1,5-a]pyridin-6-yl)methanone

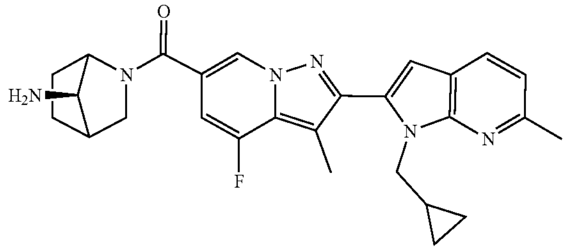 [SMILES: Cc1ccc2cc(-c3nn4cc(C(=O)N5CC6CCC5[C@@H]6N)cc(F)c4c3C)n(CC3CC3)c2n1]

Intermediate 40A tert-Butyl-((7R)-2-(2-(1-(cyclopropylmethyl)-6-methyl-1H-pyrrolo[2,3-b]pyridin-2-yl)-4-fluoro-3-methylpyrazolo[1,5-a]pyridine-6-carbonyl)-2-azabicyclo[2.2.1]heptan-7-yl)carbamate

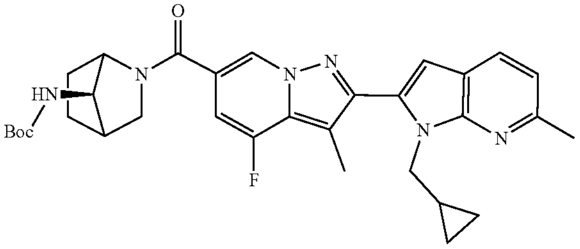 [SMILES: Cc1ccc2cc(-c3nn4cc(C(=O)N5CC6CCC5[C@@H]6NC(=O)OC(C)(C)C)cc(F)c4c3C)n(CC3CC3)c2n1]

$PdCl_2$(dppf). DCM complex (13.77 mg, 0.017 mmol) was added to a degassed and stirred solution of Intermediate 39E (100 mg, 0.169 mmol), trimethylboraxine (31.7 mg, 0.253 mmol), and $K_2CO_3$ (69.9 mg, 0.506 mmol) in dioxane (5 ml) and water (0.556 ml). The reaction mixture was stirred at 100° C. for 12 hours, filtered, and concentrated under reduced pressure to afford a crude compound. The crude compound was used in the next step without further purification. LC-MS m/z: 573.3 $[M+H]^+$.

Example 40

Compound of Example 40 was prepared following a procedure similar to the preparation of Example 3 to obtain the tittle compound as a brown solid (15 mg, 18%). LC-MS m/z: 473.2 $[M+H]^+$. HPLC retention time: 4.76 min (Method C). $^1$H NMR (400 MHz, DMSO-$d_6$) δ ppm: 8.90-8.77 (m, 1H), 8.04-7.93 (m, 1H), 7.23 (s, 1H), 7.08-7.04 (m, 2H), 6.96-6.81(m, 1H), 4.63-4.47 (m, 2.5H), 4.27 (brs, 0.5H), 3.80 (brs, 1H), 3.58 (brs, 2H), 2.62 (s, 3H), 2.53 (s, 3H), 2.02-1.85 (m, 2H), 1.70-1.66 (m, 1H), 1.28-1.02 (m, 3H), 0.41-0.19 (m, 4H).

Compounds of Examples 41 to 49 in Table 6 were prepared following a procedure similar to the preparation of a compound of Example 40, using Suzuki coupling of Intermediate 39E with appropriate boronic acid.

TABLE 6

| Example | Structure<br>Name<br>Analytical Data: LC-MS m/z [M + H]$^+$; HPLC retention time (HPLC method) |
|---|---|
| 41 | 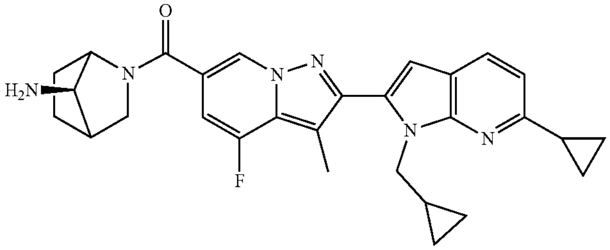 [SMILES: Cc1c(-c2cc3ccc(C4CC4)nc3n2CC2CC2)nn2cc(C(=O)N3CC4CCC3[C@@H]4N)cc(F)c12]<br>((7R)-7-Amino-2-azabicyclo[2.2.1]heptan-2-yl)(2-(6-cyclopropyl-1-(cyclopropylmethyl)-1H-pyrrolo[2,3-b]pyridin-2-yl)-4-fluoro-3-methylpyrazolo[1,5-a]pyridin-6-yl)methanone<br>Analytical Data: 499.4, 6.953 min (Method C) |
| 42 | 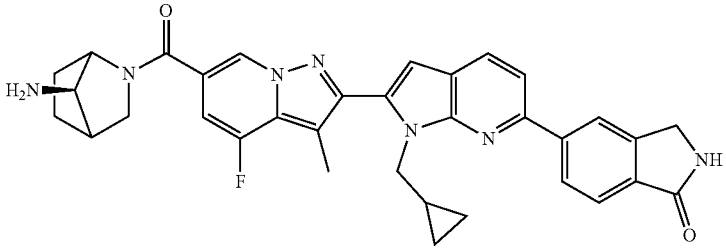 [SMILES: Cc1c(-c2cc3ccc(-c4ccc5c(c4)CNC5=O)nc3n2CC2CC2)nn2cc(C(=O)N3CC4CCC3[C@@H]4N)cc(F)c12]<br>5-(2-(6-((7R)-7-Amino-2-azabicyclo[2.2.1]heptane-2-carbonyl)-4-fluoro-3-methylpyrazolo[1,5-a]pyridin-2-yl)-1-(cyclopropylmethyl)-1H-pyrrolo[2,3-b]pyridin-6-yl)isoindolin-1-one<br>Analytical Data: 590.2, 12.831 min (Method G) |
| 43 | 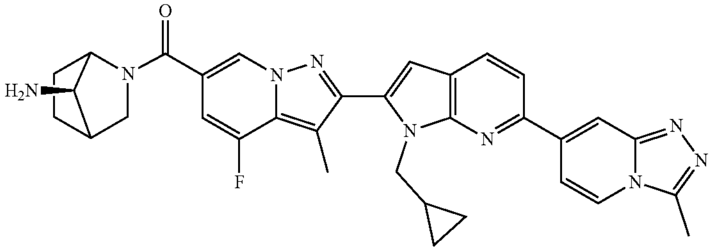 [SMILES: Cc1c(-c2cc3ccc(-c4ccn5c(C)nnc5c4)nc3n2CC2CC2)nn2cc(C(=O)N3CC4CCC3[C@@H]4N)cc(F)c12]<br>((7R)-7-Amino-2-azabicyclo[2.2.1]heptan-2-yl)(2-(1-(cyclopropylmethyl)-6-(3-methyl-[1,2,4]triazolo[4,3-a]pyridin-7-yl)-1H-pyrrolo[2,3-b]pyridin-2-yl)-4-fluoro-3-methylpyrazolo[1,5-a]pyridin-6-yl)methanone<br>Analytical Data: 587.2, 5.439 min (Method C) |
| 44 | 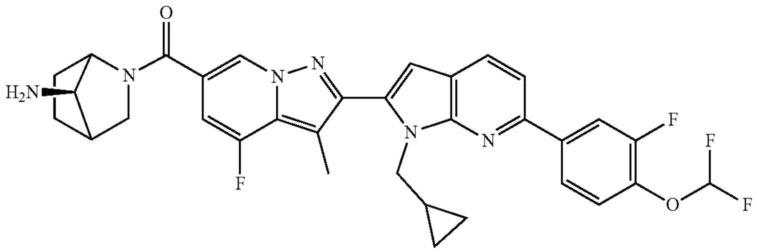 [SMILES: Cc1c(-c2cc3ccc(-c4ccc(OC(F)F)c(F)c4)nc3n2CC2CC2)nn2cc(C(=O)N3CC4CCC3[C@@H]4N)cc(F)c12]<br>((7R)-7-Amino-2-azabicyclo[2.2.1]heptan-2-yl)(2-(1-(cyclopropylmethyl)-6-(4-(difluoromethoxy)-3-fluorophenyl)-1H-pyrrolo[2,3-b]pyridin-2-yl)-4-fluoro-3-methylpyrazolo[1,5-a]pyridin-6-yl)methanone<br>Analytical Data: 619.4, 6.063 min (Method C) |

TABLE 6-continued

| Example | Structure<br>Name<br>Analytical Data: LC-MS m/z [M + H]$^+$; HPLC retention time (HPLC method) |
|---|---|
| 45 | 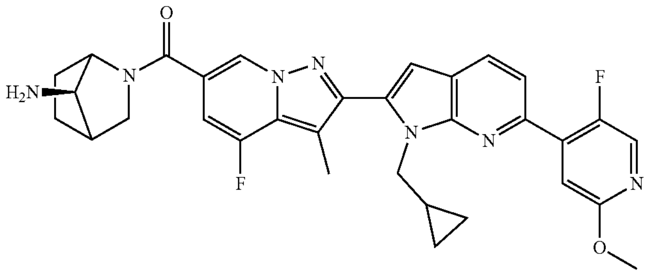 [SMILES: COc1cc(-c2ccc3cc(-c4nn5cc(C(=O)N6CC7CCC6[C@@H]7N)cc(F)c5c4C)n(CC4CC4)c3n2)c(F)cn1]<br>((7R)-7-Amino-2-azabicyclo[2.2.1]heptan-2-yl)(2-(1-(cyclopropylmethyl)-6-(5-fluoro-2-methoxypyridin-4-yl)-1H-pyrrolo[2,3-b]pyridin-2-yl)-4-fluoro-3-methylpyrazolo[1,5-a]pyridin-6-yl)methanone<br>Analytical Data: 584.2, 5.467 min (Method C) |
| 46 | 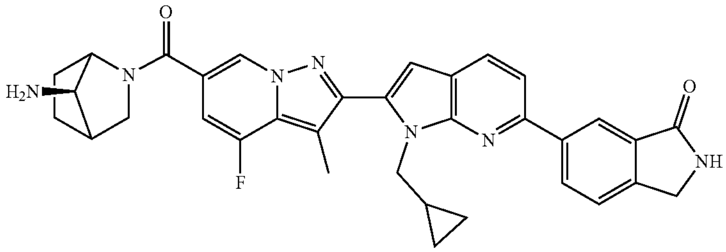 [SMILES: Cc1c(-c2cc3ccc(-c4ccc5c(c4)C(=O)NC5)nc3n2CC2CC2)nn2cc(C(=O)N3CC4CCC3[C@@H]4N)cc(F)c12]<br>6-(2-(6-((7R)-7-Amino-2-azabicyclo[2.2.1]heptane-2-carbonyl)-4-fluoro-3-methylpyrazolo[1,5-a]pyridin-2-yl)-1-(cyclopropylmethyl)-1H-pyrrolo[2,3-b]pyridin-6-yl)isoindolin-1-one<br>Analytical Data: 590.3, 6.629 min (Method C) |
| 47 | 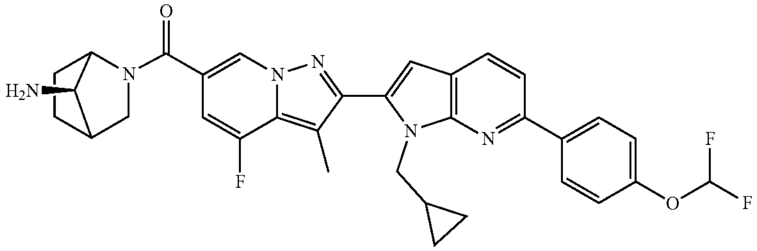 [SMILES: Cc1c(-c2cc3ccc(-c4ccc(OC(F)F)cc4)nc3n2CC2CC2)nn2cc(C(=O)N3CC4CCC3[C@@H]4N)cc(F)c12]<br>((7R)-7-Amino-2-azabicyclo[2.2.1]heptan-2-yl)(2-(1-(cyclopropylmethyl)-6-(4-(difluoromethoxy)phenyl)-1H-pyrrolo[2,3-b]pyridin-2-yl)-4-fluoro-3-methylpyrazolo[1,5-a]pyridin-6-yl)methanone<br>Analytical Data: 601.4, 5.976 min (Method C) |
| 48 | 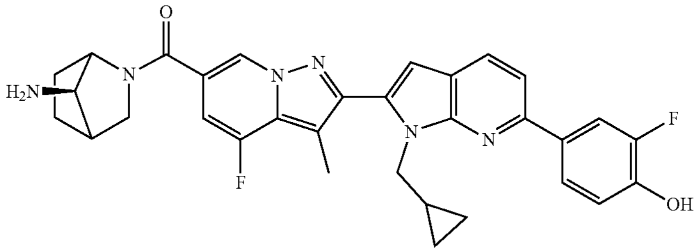 [SMILES: Cc1c(-c2cc3ccc(-c4ccc(O)c(F)c4)nc3n2CC2CC2)nn2cc(C(=O)N3CC4CCC3[C@@H]4N)cc(F)c12]<br>((7R)-7-Amino-2-azabicyclo[2.2.1]heptan-2-yl)(2-(1-(cyclopropylmethyl)-6-(3-fluoro-4-hydroxyphenyl)-1H-pyrrolo[2,3-b]pyridin-2-yl)-4-fluoro-3-methylpyrazolo[1,5-a]pyridin-6-yl)methanone<br>Analytical Data: 567.2, 7.351 min (Method C) |

TABLE 6-continued

| Example | Structure<br>Name<br>Analytical Data: LC-MS m/z [M + H]$^+$; HPLC retention time (HPLC method) |
|---|---|
| 49 | 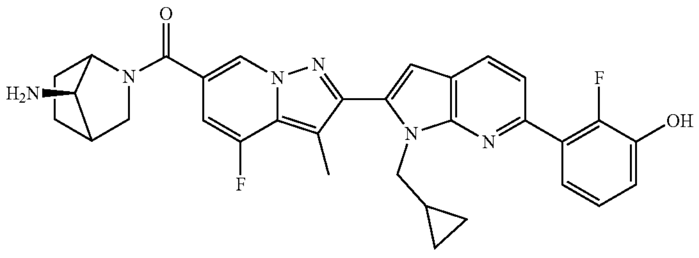 [SMILES: Cc1c(-c2cc3ccc(-c4cccc(O)c4F)nc3n2CC2CC2)nn2cc(C(=O)N3CC4CCC3[C@@H]4N)cc(F)c12]<br>((7R)-7-Amino-2-azabicyclo[2.2.1]heptan-2-yl)(2-(1-(cyclopropylmethyl)-6-(2-fluoro-3-hydroxyphenyl)-1H-pyrrolo[2,3-b]pyridin-2-yl)-4-fluoro-3-methylpyrazolo[1,5-a]pyridin-6-yl)methanone<br>Analytical Data: 569.3, 7.115 min (Method C) |

Example 50

((7R)-7-Amino-2-azabicyclo[2.2.1]heptan-2-yl)(2-(1-(cyclopropylmethyl)-6-(3-methoxyazetidin-1-yl)-1H-pyrrolo[2,3-b]pyridin-2-yl)-4-fluoro-3-methylpyrazolo[1,5-a]pyridin-6-yl)methanone

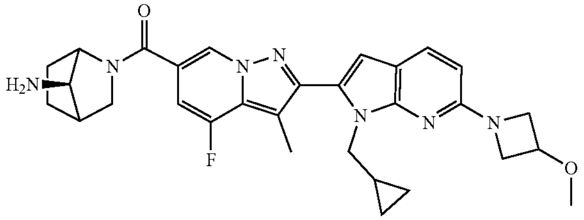 [SMILES: COC1CN(c2ccc3cc(-c4nn5cc(C(=O)N6CC7CCC6[C@@H]7N)cc(F)c5c4C)n(CC4CC4)c3n2)C1]

Intermediate 50A tert-Butyl-((7R)-2-(2-(1-(cyclopropylmethyl)-6-(3-methoxyazetidin-1-yl)-1H-pyrrolo[2,3-b]pyridin-2-yl)-4-fluoro-3-methylpyrazolo[1,5-a]pyridine-6-carbonyl)-2-azabicyclo[2.2.1]heptan-7-yl)carbamate

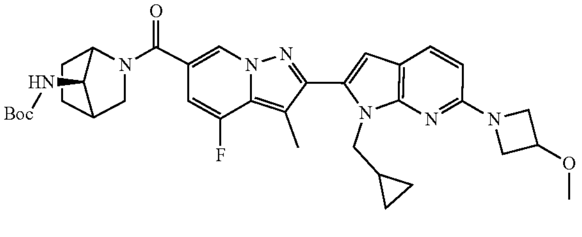 [SMILES: COC1CN(c2ccc3cc(-c4nn5cc(C(=O)N6CC7CCC6[C@@H]7NC(=O)OC(C)(C)C)cc(F)c5c4C)n(CC4CC4)c3n2)C1]

Intermediate 50A was prepared following a procedure similar to the preparation of Intermediate 13A as a brown solid (crude 100 mg, 92%). LC-MS m/z: 644.5 [M+H]$^+$.

Example 50

Compound of Example 50 was prepared following a procedure similar to the preparation of a compound of Example 13, as a brown solid (23 mg, 26%). LC-MS m/z: 544.4 [M+H]$^+$. HPLC retention time: 7.768 min (Method C). $^1$H NMR (400 MHz, DMSO-$d_6$) δ ppm: 8.82 (s, 0.5H), 8.66 (s, 0.5H), 7.80 (d, J=8.5 Hz, 1H), 7.13 (s, 1H), 7.10 (s, 1H), 6.68 (s, 1H), 6.29 (d, J=8.0 Hz, 1H), 4.53-4.28 (m, 4H), 4.27-4.14 (m, 2.5H), 4.08 (br s, 0.5H), 3.80 (dd, J=8.8, 4.3 Hz, 4H), 3.62-3.36 (m, 2H), 3.25-3.13 (m, 2H), 2.53 (m, 3H), 2.32-1.83 (m, 5H), 1.40-1.38 (m, 1H), 1.22-1.20 (m 2H), 0.34-0.24 (m, 4H).

Example 51

((7R)-7-Amino-2-azabicyclo[2.2.1]heptan-2-yl)(2-(1-(cyclopropylmethyl)-6-(R)-3-hydroxypiperidin-1-yl)-1H-pyrrolo[2,3-b]pyridin-2-yl)-4-fluoro-3-methylpyrazolo[1,5-a]pyridin-6-yl)methanone

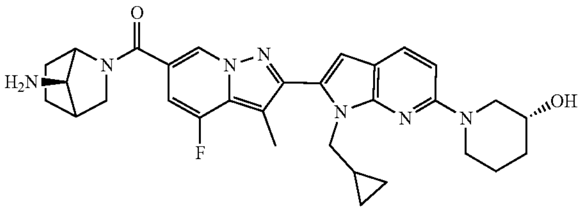 [SMILES: Cc1c(-c2cc3ccc(N4CCC[C@@H](O)C4)nc3n2CC2CC2)nn2cc(C(=O)N3CC4CCC3[C@@H]4N)cc(F)c12]

Compound of Example 51 was prepared following a procedure similar to the preparation of a compound of Example 50, by Buchwald coupling of Intermediate 39E with appropriate amine. LC-MS m/z: 558.4 [M+H]$^+$, HPLC retention time: 5.795 min (method C).

Example 52

((3R,5R)-3-Amino-5-fluoropiperidin-1-yl)(2-(1-(cyclopropylmethyl)-1H-pyrrolo[2,3-b]pyridin-2-yl)-4-fluoro-3-methylpyrazolo[1,5-a]pyridin-6-yl)methanone

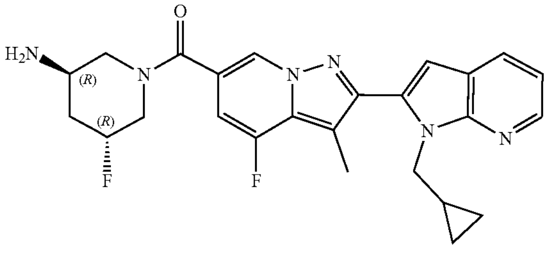

Intermediate 52A tert-Butyl-((3R,5R)-1-(2-(1-(cyclopropylmethyl)-1H-pyrrolo[2,3-b]pyridin-2-yl)-4-fluoro-3-methylpyrazolo[1,5-a]pyridine-6-carbonyl)-5-fluoropiperidin-3-yl)carbamate

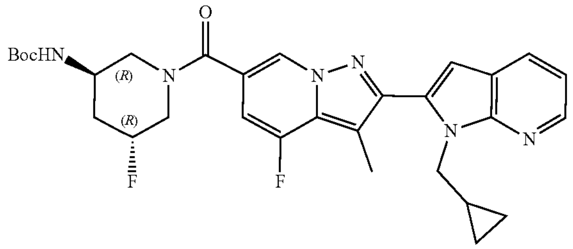

Intermediate 52A was prepared following a procedure similar to the preparation of Intermediate 14A as off-white solid (40 mg, 43%). LC-MS m/z: 565.3 $[M+H]^+$, LC-MS retention time: 2.01 min.

Example 52

Compound of Example 52 was prepared following a procedure similar to the preparation of a compound of Example 14 as off-white solid (7.73 mg, 23%). LC-MS m/z: 465.2 $[M+H]^+$. LC-MS retention time: 7.132 min (Method C). $^1$H NMR (400 MHz, DMSO-$d_6$) δ ppm: 8.65-8.74 (m, 1H), 8.23-8.35 (m, 1H), 7.96-8.06 (m, 1H), 7.00-7.20 (m, 2H), 6.84 (s, 1H), 4.80-5.04 (m, 1H), 4.37-4.56 (m, 4H), 2.84-3.03 (m, 4H), 2.57 (s, 3H), 2.04-2.23 (m, 1H), 1.40-1.64 (m, 1H), 1.12-1.24 (m, 2H), 0.14-0.42 (m, 4H).

Example 53

((3R,5R)-3-Amino-5-fluoropiperidin-1-yl)(2-(6-chloro-1-(cyclopropylmethyl)-1H-pyrrolo[2,3-b]pyridin-2-yl)-4-fluoro-3-methylpyrazolo[1,5-a]pyridin-6-yl)methanone

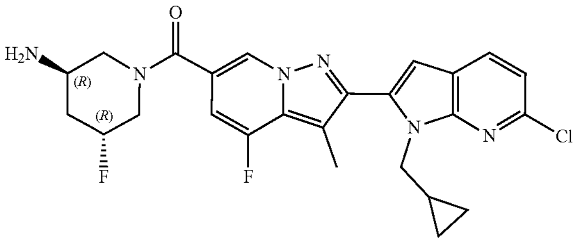

Intermediate 53A tert-Butyl-((3R,5R)-1-(2-(6-chloro-1-(cyclopropylmethyl)-1H-pyrrolo[2,3-b]pyridin-2-yl)-4-fluoro-3-methylpyrazolo[1,5-a]pyridine-6-carbonyl)-5-fluoropiperidin-3-yl)carbamate

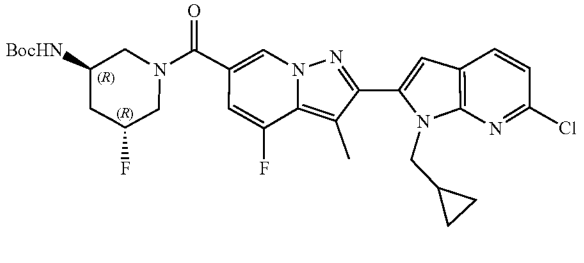

Intermediate 53A was prepared following a procedure similar to the preparation of Intermediate 15A, as off-white solid (130 mg, 87%). LC-MS m/z: 599.2 $[M+H]^+$.

Example 53

Compound of Example 53 was prepared following a procedure similar to the preparation of a compound of Example 15, as off-white solid (10.1 mg, 9%). LC-MS m/z: 499.2 $[M+H]^+$. LC-MS retention time: 2.058 min (Method E). $^1$H NMR (400 MHz, DMSO-$d_6$) δ ppm: 8.79 (br s, 1H), 8.19-7.95 (m, 1H), 7.24 (d, J=8.3 Hz, 1H), 7.20-7.09 (m, 1H), 6.95 (s, 1H), 5.11-4.90 (m, 1H), 4.44 (d,J=7.1 Hz, 2H), 3.46-3.41 (m, 1H), 3.08-2.77 (m, 2H), 2.53 (s, 3H), 2.41-2.34 (m, 1H), 1.96-1.75 (m, 1H), 1.27-1.11 (m, 1H), 0.38-0.19 (m, 4H).

Example 54

((3R,5R)-3-Amino-5-fluoropiperidin-1-yl)(2-(1-(cyclopropylmethyl)-6-methyl-1H-pyrrolo[2,3-b]pyridin-2-yl)-4-fluoro-3-methylpyrazolo[1,5-a]pyridin-6-yl)methanone

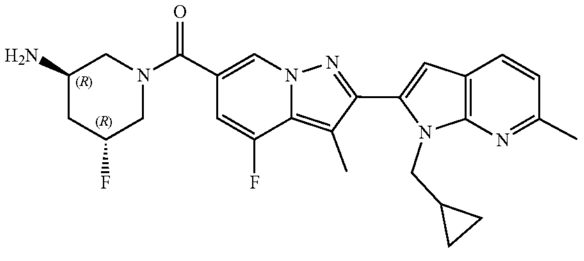

Intermediate 54A tert-Butyl-((3R,5R)-1-(2-(1-(cyclopropylmethyl)-6-methyl-1H-pyrrolo[2,3-b]pyridin-2-yl)-4-fluoro-3-methylpyrazolo[1,5-a]pyridine-6-carbonyl)-5-fluoropiperidin-3-yl)carbamate

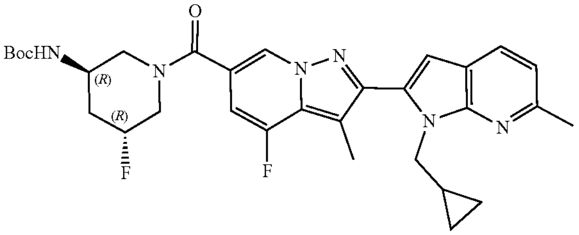

Intermediate 54A was prepared following a procedure similar to the preparation of Intermediate 16A, as off-white solid (70 mg, 91%). LC-MS m/z: 579.3 $[M+H]^+$.

Example 54

Compound of Example 54 was prepared following a procedure similar to the preparation of a compound of Example 16, as off-white solid (9.8 mg, 15%). LC-MS m/z: 479.3 $[M+H]^+$. LC-MS retention time: 1.19 min (Method E). $^1$H NMR (400 MHz, DMSO-$d_6$) δ ppm: 8.76-8.67 (m, 1H), 7.93 (d, J=7.8 Hz, 1H), 7.15-6.98 (m, 2H), 6.80 (s, 1H), 4.94-4.79 (m, 1H); 4.49-4.39 (m, 3H), 4.10 (ddd, J=6.4, 5.0, 2.6 Hz, 1H), 3.04-2.94 (m, 3H), 2.58 (s, 3H), 2.19-2.06 (m, 1H), 1.64-1.45 (m, 1H), 1.27-1.11 (m, 3H), 0.33-0.18 (m, 4H).

Compounds of Examples 55 to 57 in Table 7 were prepared following a procedure similar to the preparation of a compound of Example 54, by Suzuki coupling of Intermediate 53A with appropriate boronic acid.

TABLE 7

| Example | Structure<br>Name<br>Analytical Data: LC-MS m/z $[M + H]^+$; HPLC retention time (HPLC method) |
|---|---|
| 55 | 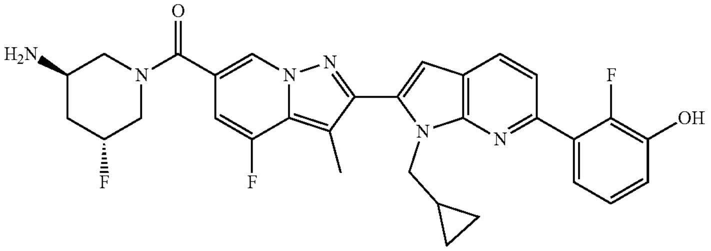 [SMILES: Cc1c(-c2cc3ccc(-c4cccc(O)c4F)nc3n2CC2CC2)nn2cc(C(=O)N3C[C@H](N)C[C@@H](F)C3)cc(F)c12]<br>((3R,5R)-3-Amino-5-fluoropiperidin-1-yl)(2-(1-(cyclopropylmethyl)-6-(2-fluoro-3-hydroxyphenyl)-1H-pyrrolo[2,3-b]pyridin-2-yl)-4-fluoro-3-methylpyrazolo[1,5-a]pyridin-6-yl)methanone<br>Analytical Data: 575.2, 7.279 min (Method C) |
| 56 | 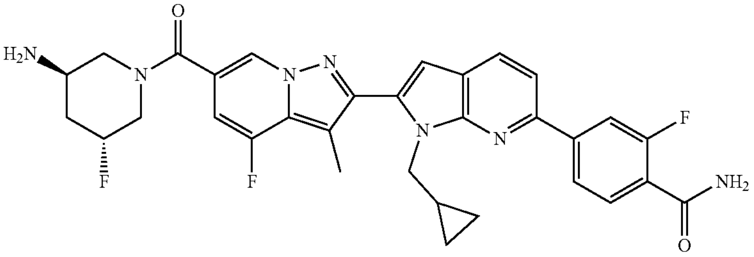 [SMILES: Cc1c(-c2cc3ccc(-c4ccc(C(N)=O)c(F)c4)nc3n2CC2CC2)nn2cc(C(=O)N3C[C@H](N)C[C@@H](F)C3)cc(F)c12]<br>4-(2-(6-((3R,5R)-3-Amino-5-fluoropiperidine-1-carbonyl)-4-fluoro-3-methylpyrazolo[1,5-a]pyridin-2-yl)-1-(cyclopropylmethyl)-1H-pyrrolo[2,3-b]pyridin-6-yl)-2-fluorobenzamide<br>Analytical Data: 602.3, 6.922 min (Method C) |

TABLE 7-continued

| Example | Structure<br>Name<br>Analytical Data: LC-MS m/z [M + H]+; HPLC retention time (HPLC method) |
|---|---|
| 57 | 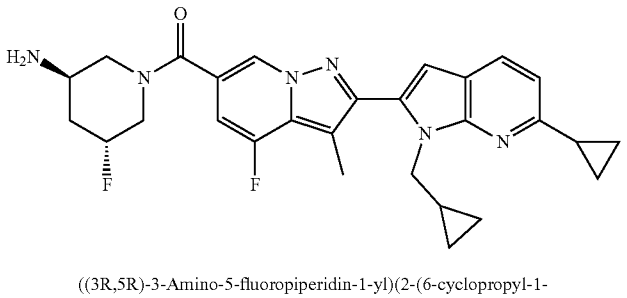<br>((3R,5R)-3-Amino-5-fluoropiperidin-1-yl)(2-(6-cyclopropyl-1-(cyclopropylmethyl)-1H-pyrrolo[2,3-b]pyridin-2-yl)-4-fluoro-3-methylpyrazolo[1,5-a]pyridin-6-yl)methanone<br>Analytical Data: 505.3, 2.265 min (Method E) |

Example 58

N-(7-(2-(6-((7R)-7-Amino-2-azabicyclo[2.2.1]heptane-2-carbonyl)-4-fluoro-3-methylpyrazolo[1,5-a]pyridin-2-yl)-1-(cyclopropylmethyl)-1H-indol-6-yl)-4-chloro-1-methyl-1H-indazol-3-yl)methanesulfonamide

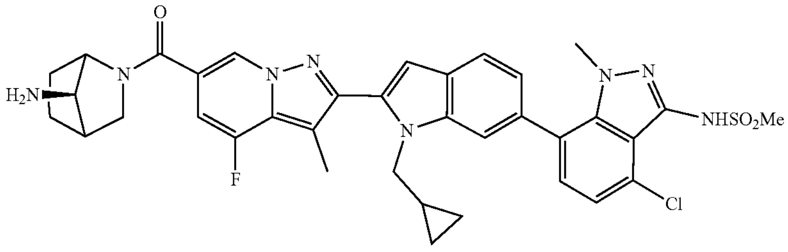

Intermediate 58A 3-(tert-Butyl)-6-methyl 2-(6-bromo-1-(cyclopropylmethyl)-1H-indol-2-yl)-4-fluoropyrazolo[1,5-a]pyridine-3,6-dicarboxylate

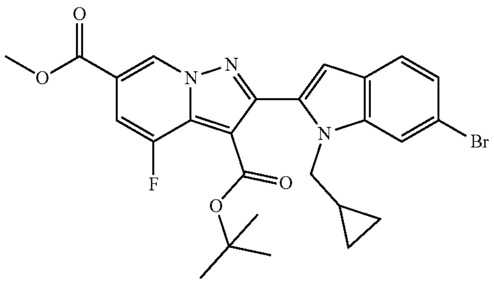 [SMILES: COC(=O)c1cc(F)c2c(C(=O)OC(C)(C)C)c(-c3cc4ccc(Br)cc4n3CC3CC3)nn2c1]

Intermediate 58A was prepared following a procedure similar to the preparation of Intermediate 23A, as a pale yellow solid (2.0 g, 27%). LC-MS m/z: 543.9 [M+H]+.

Intermediate 58B 2-(6-Bromo-1-(cyclopropylmethyl)-1H-indol-2-yl)-4-fluoro-6-(methoxycarbonyl)pyrazolo[1,5-a]pyridine-3-carboxylic acid

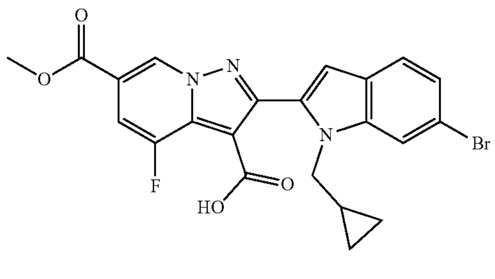 [SMILES: COC(=O)c1cc(F)c2c(C(=O)O)c(-c3cc4ccc(Br)cc4n3CC3CC3)nn2c1]

Intermediate 58B was prepared following a procedure similar to the preparation of Intermediate 23B, as a pale yellow solid (2 g, 3.07 mmol, 89%). LC-MS m/z: 488.0 [M+H]+.

Intermediate 58C

Methyl-2-(6-bromo-1-(cyclopropylmethyl)-1H-indol-2-yl)-4-fluoro-3-methylpyrazolo[1,5-a]pyridine-6-carboxylate

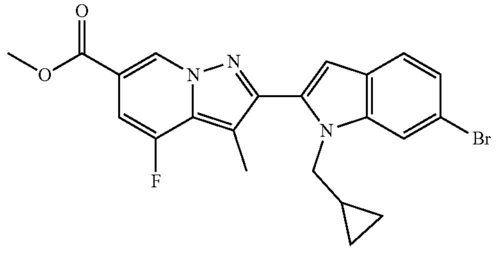 [SMILES: COC(=O)c1cc(F)c2c(C)c(-c3cc4ccc(Br)cc4n3CC3CC3)nn2c1]

Intermediate 58C was prepared following a procedure similar to the preparation of 23C as a pale yellow solid (crude 2.0 g, 75%). LC-MS m/z: 458.1 $[M+H]^+$.

Intermediate 58D 2-(6-Bromo-1-(cyclopropylmethyl)-1H-indol-2-yl)-4-fluoro-3-methylpyrazolo[1,5-a]pyridine-6-carboxylic acid

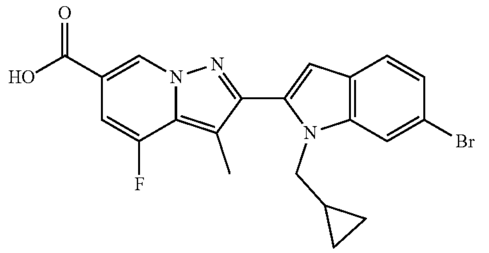 [SMILES: Cc1c(-c2cc3ccc(Br)cc3n2CC2CC2)nn2cc(C(=O)O)cc(F)c12]

Intermediate 58D was prepared following a procedure similar to the preparation of Intermediate 23D, as a pale yellow solid (1.6 g, 83%). LC-MS m/z: 444.1 $[M+H]^+$.

Intermediate 58E tert-Butyl-((7R)-2-(2-(6-bromo-1-(cyclopropylmethyl)-1H-indol-2-yl)-4-fluoro-3-methylpyrazolo[1,5-a]pyridine-6-carbonyl)-2-azabicyclo[2.2.1]heptan-7-yl)carbamate

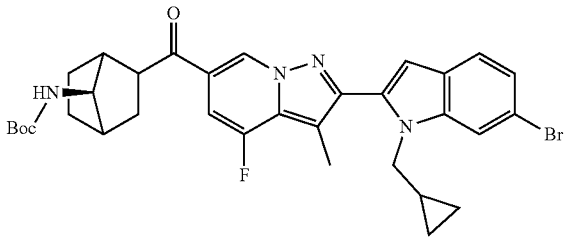 [SMILES: Cc1c(-c2cc3ccc(Br)cc3n2CC2CC2)nn2cc(C(=O)C3CC4CCC3[C@@H]4NC(=O)OC(C)(C)C)cc(F)c12]

Intermediate 58E was prepared following a procedure similar to the preparation of Intermediate 23E, as a pale yellow solid (700 mg, 97%). LC-MS: m/z: 638.2 $[M+H]^+$.

Intermediate 58F tert-Butyl-((7R)-2-(2-(6-(4-chloro-1-methyl-3-(methylsulfonamido)-1H-indazol-7-yl)-1-(cyclopropylmethyl)-1H-indol-2-yl)-4-fluoro-3-methylpyrazolo[1,5-a]pyridine-6-carbonyl)-2-azabicyclo[2.2.1]heptan-7-yl)carbamate

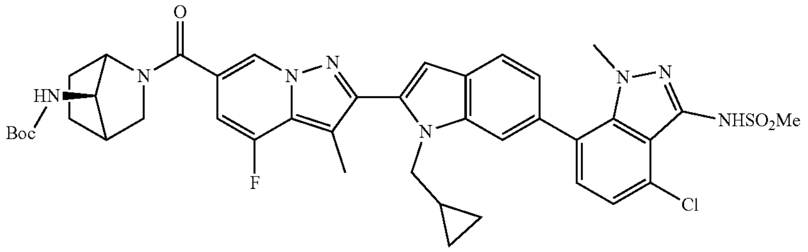

Intermediate 58F was prepared following a procedure similar to the preparation of Intermediate 23F as a pale yellow solid (70 mg, 95%). LC-MS m/z: 668.3 $[M+H]^+$.

Example 58

Compound of Example 58 was prepared following a procedure similar to the preparation of a compound of Example 23, as a pale yellow solid (5 mg, 0.007 mmol, 8%). LC-MS m/z: 715.3 $[M+H]^+$. LC-MS retention time: 0.85 min (Method G).

Compounds of Examples 59 to 62 in Table 8 were prepared following a procedure similar to the preparation of a compound of Example 58, by Suzuki coupling of Intermediate 58E with appropriate boronic acid.

TABLE 8

| Example | Structure<br>Name<br>Analytical Data: LC-MS m/z [M + H]$^+$; HPLC retention time (HPLC method) |
|---|---|
| 59 | 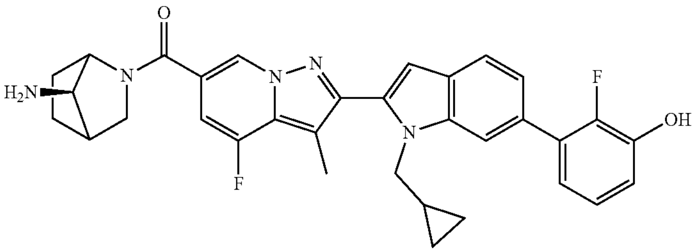 [SMILES: Cc1c(-c2cc3ccc(-c4cccc(O)c4F)cc3n2CC2CC2)nn2cc(C(=O)N3CC4CCC3[C@@H]4N)cc(F)c12]<br>((7R)-7-Amino-2-azabicyclo[2.2.1]heptan-2-yl)(2-(1-(cyclopropylmethyl)-6-(2-fluoro-3-hydroxyphenyl)-1H-indol-2-yl)-4-fluoro-3-methylpyrazolo[1,5-a]pyridin-6-yl)methanone<br>Analytical Data: 568.3, 3.8 min (Method C) |
| 60 | 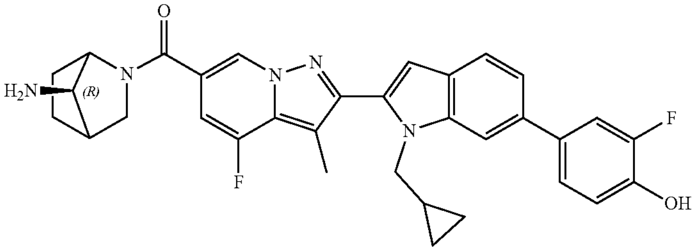<br>((7R)-7-Amino-2-azabicyclo[2.2.1]heptan-2-yl)(2-(1-(cyclopropylmethyl)-6-(3-fluoro-4-hydroxyphenyl)-1H-indol-2-yl)-4-fluoro-3-methylpyrazolo[1,5-a]pyridin-6-yl)methanone<br>Analytical Data: 568.3, 10.01 min (Method A) |
| 61 | 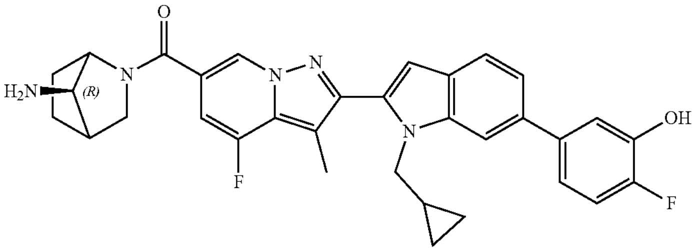<br>((7R)-7-Amino-2-azabicyclo[2.2.1]heptan-2-yl)(2-(1-(cyclopropylmethyl)-6-(4-fluoro-3-hydroxyphenyl)-1H-indol-2-yl)-4-fluoro-3-methylpyrazolo[1,5-a]pyridin-6-yl)methanone<br>Analytical Data: 568.3, 3.5 min (Method C) |
| 62 | 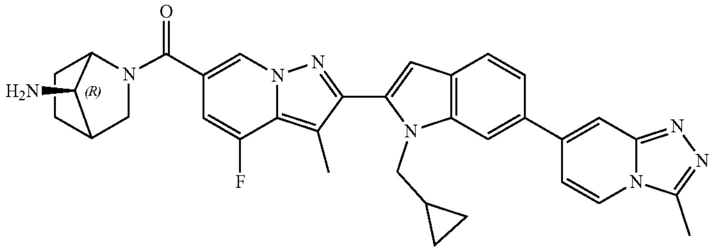<br>((7R)-7-Amino-2-azabicyclo[2.2.1]heptan-2-yl)(2-(1-(cyclopropylmethyl)-6-(3-methyl-[1,2,4]triazolo[4,3-a]pyridin-7-yl)-1H-indol-2-yl)-4-fluoro-3-methylpyrazolo[1,5-a]pyridin-6-yl)methanone<br>Analytical Data: 589.4, 1.16 min (Method C) |

Example 63

((7R)-7-Amino-2-azabicyclo[2.2.1]heptan-2-yl)(2-(1-(cyclopropylmethyl)-1H-pyrrolo[2,3-b]pyridin-2-yl)-3-methylpyrazolo[1,5-a]pyridin-6-yl)methanone

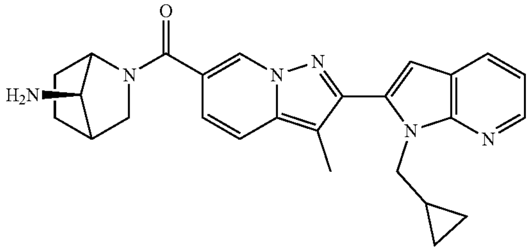 [SMILES: Cc1c(-c2cc3cccnc3n2CC2CC2)nn2cc(C(=O)N3CC4CCC3[C@@H]4N)ccc12]

Intermediate 63A 3-(tert-Butyl)-6-ethyl 2-(1-(cyclopropylmethyl)-1H-pyrrolo[2,3-b]pyridin-2-yl)pyrazolo[1,5-a]pyridine-3,6-dicarboxylate

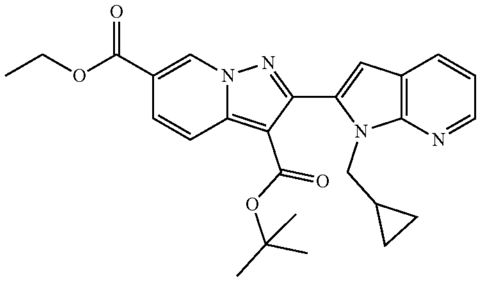 [SMILES: CCOC(=O)c1ccc2c(C(=O)OC(C)(C)C)c(-c3cc4cccnc4n3CC3CC3)nn2c1]

$K_2CO_3$ (839 mg, 6.07 mmol) and tert-butyl 3-(1-(cyclopropylmethyl)-1H-pyrrolo[2,3-b]pyridin-2-yl)propiolate (Intermediate 2, 600 mg, 2.024 mmol) were added to a stirred solution of 1-amino-3-(ethoxycarbonyl)pyridin-1-ium salt (Intermediate 8, 338 mg, 2.024 mmol) in acetone (25 ml). The reaction mixture was bubbled with air for 5 minutes, stirred overnight, filtered, and concentrated in vacuum to afford a crude compound, which was dissolved in EtOAc and washed with water. The organic layer was concentrated under vacuum to afford a crude compound, which was purified using a silica gel column to afford the title compound as a pale yellow solid (300 mg, 32%). LC-MS m/z: 461.2 $[M+H]^+$. $^1H$ NMR (400 MHz, DMSO-$d_6$) δ ppm: 8.73 (s, 1H), 8.15 (d, J=8.0 Hz, 1H), 7.69-7.62 (m, 1H), 7.59-7.50 (m, 4H), 7.36 (t, J=6.8 Hz, 1H), 7.13 (br, t, J=7.3 Hz, 2H), 7.04-7.00 (m, 1H), 6.93 (s, 1H), 4.58-4.47 (m, 4H), 4.41 (d, J=1.5 Hz, 2H), 4.10 (s, 3H), 3.42 (s, 3H), 3.39-3.35 (m, 1H), 3.27 (br, s, 1H), 2.61-1.24 (s, 3H), 0.36-0.32 (m, 5H), 0.15 (s, 2H).

Intermediate 63B 2-(1-(Cyclopropylmethyl)-1H-pyrrolo[2,3-b]pyridin-2-yl)-6-(ethoxycarbonyl)pyrazolo[1,5-a]pyridine-3-carboxylic acid

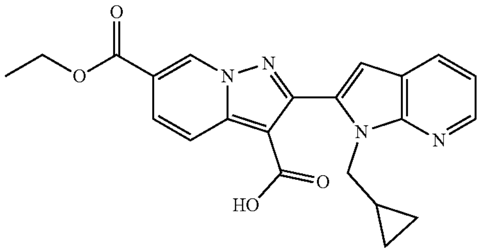 [SMILES: CCOC(=O)c1ccc2c(C(=O)O)c(-c3cc4cccnc4n3CC3CC3)nn2c1]

A solution of Intermediate 63A (300 mg, 0.651 mmol) in DCM (3 ml) and TFA (0.5 m) was stirred for 2 hours, and concentrated under reduced pressure at a room temperature to obtain a pale pink compound, which was dried over high vacuum to afford the title compound (200 mg, 76%). The crude compound was used in the next steps without further purification. LC-MS m/z: 405.2 $[M+H]^+$.

Intermediate 63C

Ethyl-2-(1-(cyclopropylmethyl)-1H-pyrrolo[2,3-b]pyridin-2-yl)-3-methylpyrazolo[1,5-a]pyridine-6-carboxylate

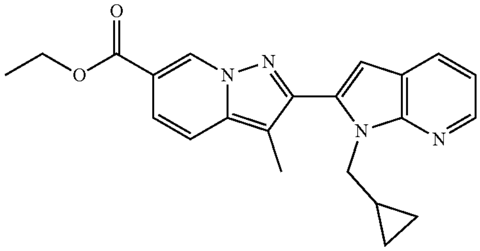 [SMILES: CCOC(=O)c1ccc2c(C)c(-c3cc4cccnc4n3CC3CC3)nn2c1]

Intermediate 63C was prepared following a procedure similar to the preparation of Intermediate 1C, as a pale yellow solid (120 mg, 65%). LC-MS m/z: 375.1 $[M+H]^+$. $^1H$ NMR (400 MHz, DMSO-$d_6$) δ ppm: 9.27-9.22 (m, 1H), 8.35-8.31 (m, 1H), 8.08-8.03 (m, 1H), 7.87-7.81 (m, 1H), 7.62 (d, J=9.3 Hz, 1H), 7.19-7.13 (m, 1H), 6.94 (s, 1H), 4.59 (d, J=7.0 Hz, 2H), 4.40-4.34 (m, 2H), 2.48-2.45 (m, 3H), 1.37 (t, J=7.0 Hz, 3H), 1.29-1.19 (m, 1H), 0.35-0.24 (m, 4H).

Intermediate 63D 2-(1-(Cyclopropylmethyl)-1H-pyrrolo[2,3-b]pyridin-2-yl)-3-methylpyrazolo[1,5-a]pyridine-6-carboxylic acid

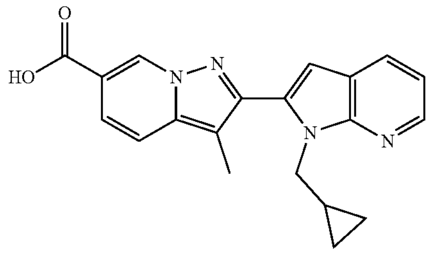 [SMILES: Cc1c(-c2cc3cccnc3n2CC2CC2)nn2cc(C(=O)O)ccc12]

Intermediate 63D was prepared following a procedure similar to the preparation of Intermediate 1D, as off-white solid (110 mg, 99%). LC-MS m/z: 347 $[M+H]^+$.

Intermediate 63E tert-Butyl-((7R)-2-(2-(1-(cyclopropylmethyl)-1H-pyrrolo[2,3-b]pyridin-2-yl)-3-methylpyrazolo[1,5-a]pyridine-6-carbonyl)-2-azabicyclo[2.2.1]heptan-7-yl)carbamate

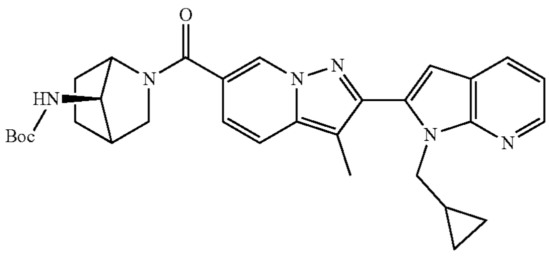 [SMILES: Cc1c(-c2cc3cccnc3n2CC2CC2)nn2cc(C(=O)N3CC4CCC3[C@@H]4NC(=O)OC(C)(C)C)ccc12]

Intermediate 63C was prepared following a procedure similar to the preparation of Intermediate 1E (70 mg, 90%). LC-MS m/z: 541.3 $[M+H]^+$.

Example 63

Compound of Example 63 was prepared following a procedure similar to preparation of Example 1 (9.0 mg, 15%). LC-MS m/z: 441.3 $[M+H]^+$. LC-MS retention time: 1.570 min (Method E). $^1H$ NMR (400 MHz, DMSO-$d_6$) δ ppm: 8.94-8.78 (m, 1H), 8.32 (d, J=4.6 Hz, 1H), 8.05 (dd, J=1.1, 7.7 Hz, 1H), 7.85-7.75 (m, 1H), 7.39-7.24 (m, 1H), 7.16 (dd, J=4.5, 7.7 Hz, 1H), 6.87 (s, 1H), 4.56 (br d, J=7.1 Hz, 2H), 3.93-3.90 (m, 1H), 3.77-3.68 (m, 1H), 3.65-3.46 (m, 2H), 3.32-3.06 (m, 2H), 2.63-2.52 (m, 1H), 2.48-2.36 (m, 3H), 2.02-1.84 (m, 2H), 1.80-1.65 (m, 1H), 1.54-1.37 (m, 1H), 1.30-1.13 (m, 1H), 0.31-0.19 (m, 4H).

Example 64

5-(2-(6-((7R)-7-Amino-2-azabicyclo[2.2.1]heptane-2-carbonyl)-3-methylpyrazolo[1,5-a]pyridin-2-yl)-1-(cyclopropylmethyl)-1H-pyrrolo[2,3-b]pyridin-6-yl)isoindolin-1-one

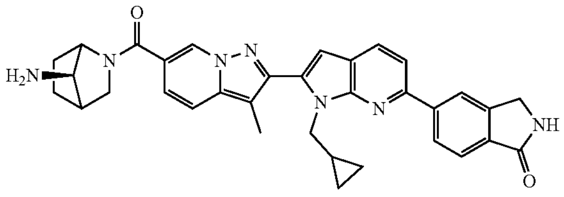 [SMILES: Cc1c(-c2cc3ccc(-c4ccc5c(c4)CNC5=O)nc3n2CC2CC2)nn2cc(C(=O)N3CC4CCC3[C@@H]4N)ccc12]

Intermediate 64A 3-(tert-Butyl)-6-ethyl 2-(6-chloro-1-(cyclopropylmethyl)-1H-pyrrolo[2,3-b]pyridin-2-yl)pyrazolo[1,5-a]pyridine-3,6-dicarboxylate

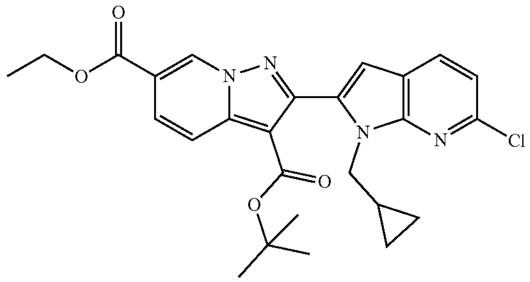 [SMILES: CCOC(=O)c1ccc2c(C(=O)OC(C)(C)C)c(-c3cc4ccc(Cl)nc4n3CC3CC3)nn2c1]

Intermediate 64A was prepared following a procedure similar to the preparation of Intermediate 2A (2 g, 30%). LC-MS m/z: 495.2 $[M+H]^+$.

Intermediate 64B 2-(6-Chloro-1-(cyclopropylmethyl)-1H-pyrrolo[2,3-b]pyridin-2-yl)-6-(ethoxycarbonyl)pyrazolo[1,5-a]pyridine-3-carboxylic acid

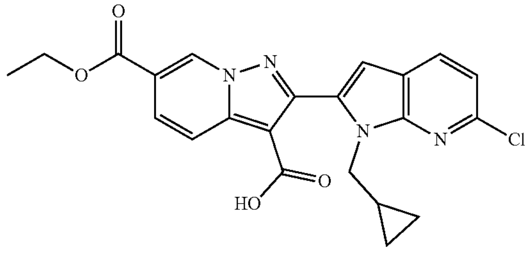 [SMILES: CCOC(=O)c1ccc2c(C(=O)O)c(-c3cc4ccc(Cl)nc4n3CC3CC3)nn2c1]

Intermediate 64B was prepared following a procedure similar to the preparation of Intermediate 2B (1.5 g, 85%). LC-MS m/z: 441.3 $[M+H]^+$.

Intermediate 64C

Ethyl-2-(6-chloro-1-(cyclopropylmethyl)-1H-pyrrolo[2,3-b]pyridin-2-yl)-3-methylpyrazolo[1,5-a]pyridine-6-carboxylate

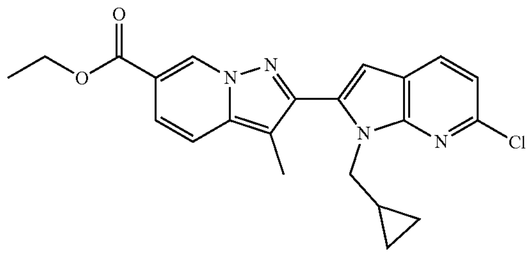 [SMILES: CCOC(=O)c1ccc2c(C)c(-c3cc4ccc(Cl)nc4n3CC3CC3)nn2c1]

Intermediate 64C was prepared following a procedure similar to the preparation of Intermediate 2C (240 mg, 0.05 mmol, 86%). LC-MS m/z: 409.2 [M+H]+.

Intermediate 64D 2-(6-Chloro-1-(cyclopropylmethyl)-1H-pyrrolo[2,3-b]pyridin-2-yl)-3-methylpyrazolo[1,5-a]pyridine-6-carboxylic acid

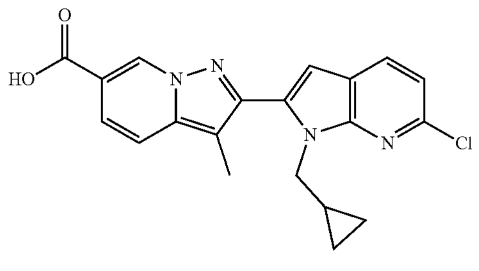 [SMILES: Cc1c(-c2cc3ccc(Cl)nc3n2CC2CC2)nn2cc(C(=O)O)ccc12]

Intermediate 63D was prepared following a procedure similar to the preparation of Intermediate 2D (900 mg, 88%). LC-MS m/z: 381.1 [M+H]+.

Intermediate 64E tert-Butyl-((7R)-2-(2-(6-chloro-1-(cyclopropylmethyl)-1H-pyrrolo[2,3-b]pyridin-2-yl)-3-methylpyrazolo[1,5-a]pyridine-6-carbonyl)-2-azabicyclo[2.2.1]heptan-7-yl)carbamate

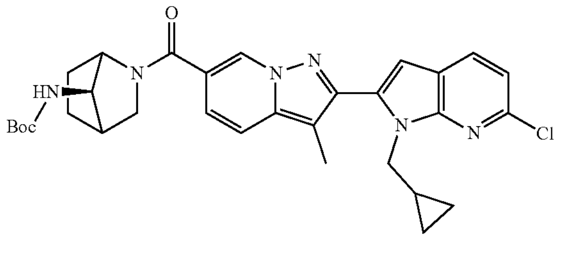 [SMILES: Cc1c(-c2cc3ccc(Cl)nc3n2CC2CC2)nn2cc(C(=O)N3CC4CCC3[C@@H]4NC(=O)OC(C)(C)C)ccc12]

Intermediate 64E was prepared following a procedure similar to the preparation of Intermediate 2E (1.2 g, 88%). LC-MS m/z: 575.3 [M+H]+.

Intermediate 64F tert-Butyl-((7R)-2-(2-(1-(cyclopropylmethyl)-6-(1-oxoisoindolin-5-yl)-1H-pyrrolo[2,3-b]pyridin-2-yl)-3-methylpyrazolo[1,5-a]pyridine-6-carbonyl)-2-azabicyclo[2.2.1]heptan-7-yl)carbamate

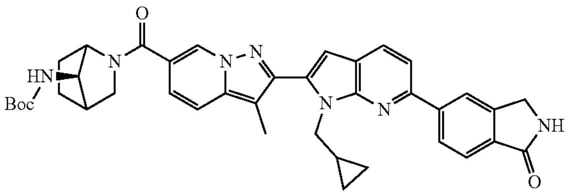 [SMILES: Cc1c(-c2cc3ccc(-c4ccc5c(c4)CNC5=O)nc3n2CC2CC2)nn2cc(C(=O)N3CC4CCC3[C@@H]4NC(=O)OC(C)(C)C)ccc12]

Intermediate 63F was prepared following a procedure similar to the preparation of Intermediate 3A (50 mg, 61%). LC-MS m/z: 672.4 [M+H]+.

Example 64

Compound of Example 64 was prepared following a procedure similar to the preparation of compound of Example 3 (8.88 mg, 17%). LC-MS m/z: 672.4 [M+H]+. HPLC retention time: 5.956 min (Method C). $^1$H NMR (400 MHz, DMSO-$d_6$) δ ppm: 9.01-8.88 (m, 1H), 8.61 (s, 1H), 8.37 (s, 1H), 8.32 (d, J=7.8 Hz, 1H), 8.18 (d, J=8.0 Hz, 1H), 8.12-7.91 (m, 3H), 7.90-7.77 (m, 2H), 7.40-7.28 (m, 1H), 6.95 (s, 1H), 4.69 (br d, J=6.0 Hz, 2H), 4.50 (s, 2H), 4.25 (br s, 1H), 3.82 (br dd, J=3.0, 9.5 Hz, 1H), 3.71-3.51 (m, 2H), 3.48-3.36 (m, 1H), 3.19-3.07 (m, 1H), 2.70-2.53 (m, 1H), 2.46-2.43 (m, 3H), 2.06-1.80 (m, 3H), 1.77-1.60 (m, 1H), 1.34-1.15 (m, 1H), 0.38-0.30 (m, 4H).

Compounds of Examples 65 to 75 in Table 9 were prepared following a procedure similar to the preparation of a compound of Example 64, by Suzuki coupling of Intermediate 64E with appropriate boronic acid.

TABLE 9

| Example | Structure<br>Name<br>Analytical Data: LC-MS m/z [M + H]+; HPLC retention time (HPLC method) |
|---|---|
| 65 | 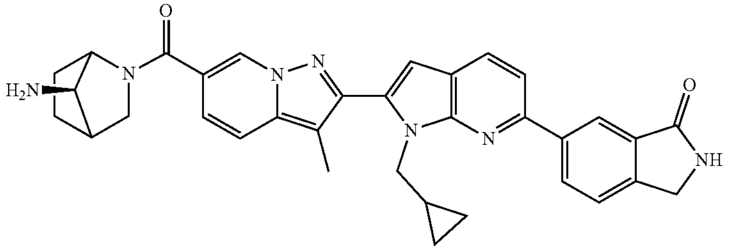 [SMILES: Cc1c(-c2cc3ccc(-c4ccc5c(c4)C(=O)NC5)nc3n2CC2CC2)nn2cc(C(=O)N3CC4CCC3[C@@H]4N)ccc12]<br>6-(2-(6-((7R)-7-Amino-2-azabicyclo[2.2.1]heptane-2-carbonyl)-3-methylpyrazolo[1,5-a]pyridin-2-yl)-1-(cyclopropylmethyl)-1H-pyrrolo[2,3-b]pyridin-6-yl)isoindolin-1-one<br>Analytical Data: 572.3, 6.015 min (Method C) |
| 66 | 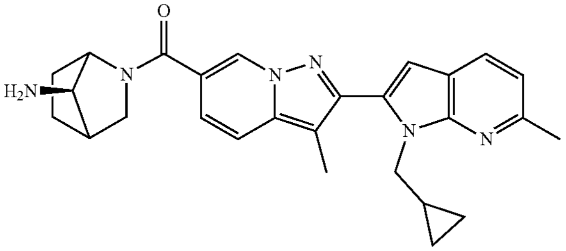 [SMILES: Cc1ccc2cc(-c3nn4cc(C(=O)N5CC6CCC5[C@@H]6N)ccc4c3C)n(CC3CC3)c2n1]<br>((7R)-7-Amino-2-azabicyclo[2.2.1]heptan-2-yl)(2-(1-(cyclopropylmethyl)-6-methyl-1H-pyrrolo[2,3-b]pyridin-2-yl)-3-methylpyrazolo[1,5-a]pyridin-6-yl)methanone<br>Analytical Data: 455.3, 5.696 min (Method C) |
| 67 | 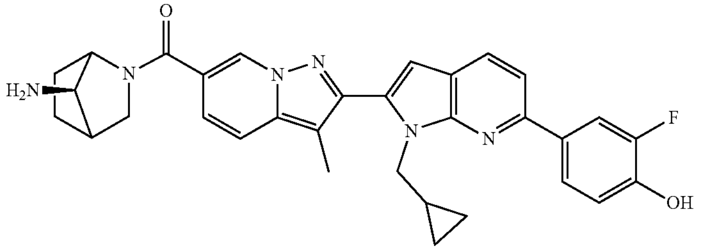 [SMILES: Cc1c(-c2cc3ccc(-c4ccc(O)c(F)c4)nc3n2CC2CC2)nn2cc(C(=O)N3CC4CCC3[C@@H]4N)ccc12]<br>((7R)-7-Amino-2-azabicyclo[2.2.1]heptan-2-yl)(2-(1-(cyclopropylmethyl)-6-(3-fluoro-4-hydroxyphenyl)-1H-pyrrolo[2,3-b]pyridin-2-yl)-3-methylpyrazolo[1,5-a]pyridin-6-yl)methanone<br>Analytical Data: 551.3, 6.268 min (Method C) |
| 68 | 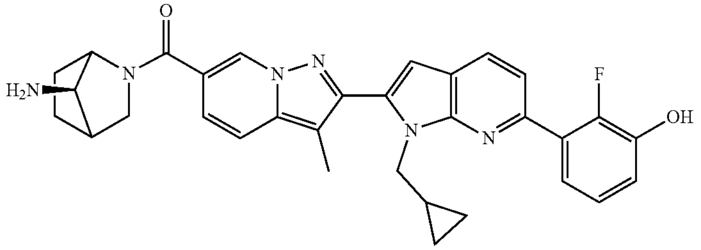 [SMILES: Cc1c(-c2cc3ccc(-c4cccc(O)c4F)nc3n2CC2CC2)nn2cc(C(=O)N3CC4CCC3[C@@H]4N)ccc12]<br>((7R)-7-Amino-2-azabicyclo[2.2.1]heptan-2-yl)(2-(1-(cyclopropylmethyl)-6-(2-fluoro-3-hydroxyphenyl)-1H-pyrrolo[2,3-b]pyridin-2-yl)-3-methylpyrazolo[1,5-a]pyridin-6-yl)methanone<br>Analytical Data: 551.4, 6.502 min (Method C) |

TABLE 9-continued

| Example | Structure<br>Name<br>Analytical Data: LC-MS m/z [M + H]$^+$; HPLC retention time (HPLC method) |
|---|---|
| 69 | 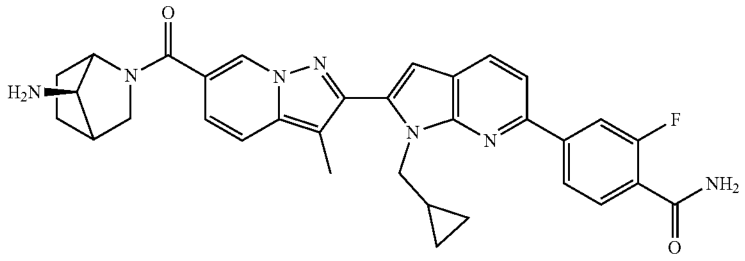 [SMILES: Cc1c(-c2cc3ccc(-c4ccc(C(N)=O)c(F)c4)nc3n2CC2CC2)nn2cc(C(=O)N3CC4CCC3[C@@H]4N)ccc12]<br>4-(2-(6-((7R)-7-Amino-2-azabicyclo[2.2.1]heptane-2-carbonyl)-3-methylpyrazolo[1,5-a]pyridin-2-yl)-1-(cyclopropylmethyl)-1H-pyrrolo[2,3-b]pyridin-6-yl)-2-fluorobenzamide<br>Analytical Data: 578.4, 7.954 min (Method C) |
| 70 | 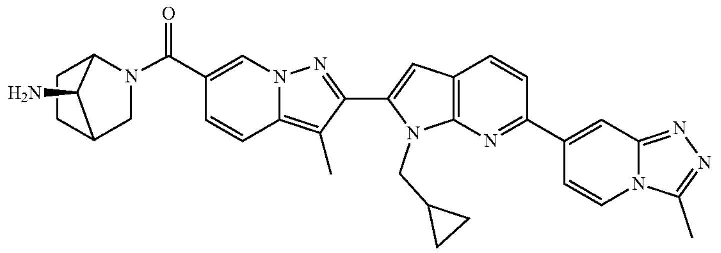 [SMILES: Cc1c(-c2cc3ccc(-c4ccn5c(C)nnc5c4)nc3n2CC2CC2)nn2cc(C(=O)N3CC4CCC3[C@@H]4N)ccc12]<br>((7R)-7-Amino-2-azabicyclo[2.2.1]heptan-2-yl)(2-(1-(cyclopropylmethyl)-6-(3-methyl-[1,2,4]triazolo[4,3-a]pyridin-7-yl)-1H-pyrrolo[2,3-b]pyridin-2-yl)-3-methylpyrazolo[1,5-a]pyridin-6-yl)methanone<br>Analytical Data: 572.4, 5.613 min (Method C) |
| 71 | 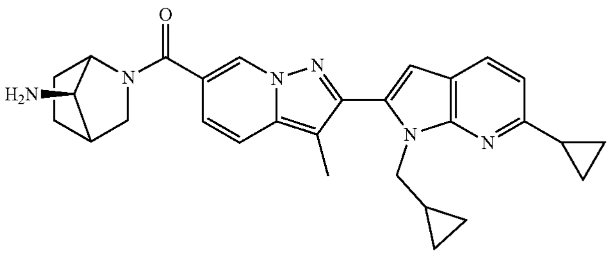 [SMILES: Cc1c(-c2cc3ccc(C4CC4)nc3n2CC2CC2)nn2cc(C(=O)N3CC4CCC3[C@@H]4N)ccc12]<br>((7R)-7-Amino-2-azabicyclo[2.2.1]heptan-2-yl)(2-(6-cyclopropyl-1-(cyclopropylmethyl)-1H-pyrrolo[2,3-b]pyridin-2-yl)-3-methylpyrazolo[1,5-a]pyridin-6-yl)methanone<br>Analytical Data: 481.3, 1.588 min (Method F) |
| 72 | 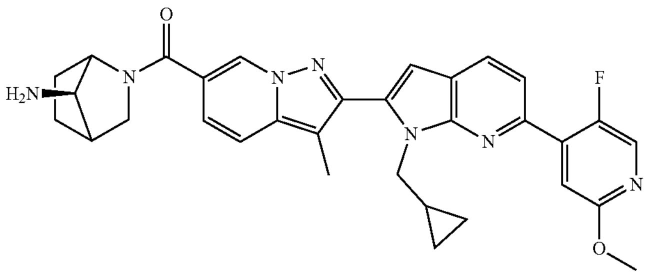 [SMILES: COc1cc(-c2ccc3cc(-c4nn5cc(C(=O)N6CC7CCC6[C@@H]7N)ccc5c4C)n(CC4CC4)c3n2)c(F)cn1]<br>((7R)-7-Amino-2-azabicyclo[2.2.1]heptan-2-yl)(2-(1-(cyclopropylmethyl)-6-(5-fluoro-2-methoxypyridin-4-yl)-1H-pyrrolo[2,3-b]pyridin-2-yl)-3-methylpyrazolo[1,5-a]pyridin-6-yl)methanone<br>Analytical Data: 566.3, 1.893 min (Method F) |

TABLE 9-continued

| Example | Structure<br>Name<br>Analytical Data: LC-MS m/z [M + H]+; HPLC retention time (HPLC method) |
|---|---|
| 73 | 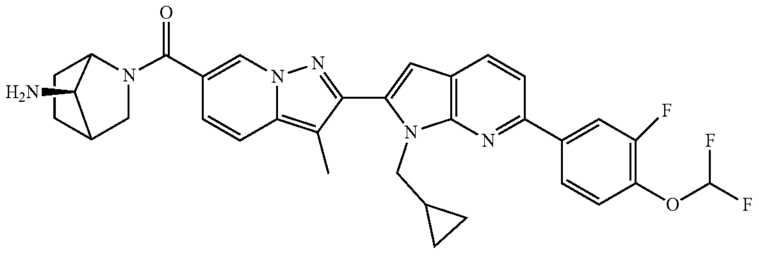 [SMILES: Cc1c(-c2cc3ccc(-c4ccc(OC(F)F)c(F)c4)nc3n2CC2CC2)nn2cc(C(=O)N3CC4CCC3[C@@H]4N)ccc12]<br>((7R)-7-Amino-2-azabicyclo[2.2.1]heptan-2-yl)(2-(1-(cyclopropylmethyl)-6-(4-(difluoromethoxy)-3-fluorophenyl)-1H-pyrrolo[2,3-b]pyridin-2-yl)-3-methylpyrazolo[1,5-a]pyridin-6-yl)methanone<br>Analytical Data: 601.3, 1.987 min (Method F) |
| 74 | 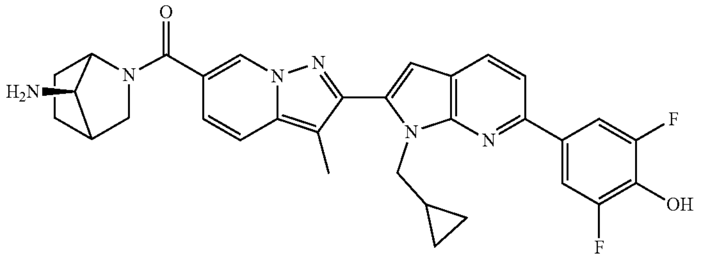 [SMILES: Cc1c(-c2cc3ccc(-c4cc(F)c(O)c(F)c4)nc3n2CC2CC2)nn2cc(C(=O)N3CC4CCC3[C@@H]4N)ccc12]<br>((7R)-7-Amino-2-azabicyclo[2.2.1]heptan-2-yl)(2-(1-(cyclopropylmethyl)-6-(3,5-difluoro-4-hydroxyphenyl)-1H-pyrrolo[2,3-b]pyridin-2-yl)-3-methylpyrazolo[1,5-a]pyridin-6-yl)methanone<br>Analytical Data: 569.3, 1.648 min (Method F) |
| 75 | 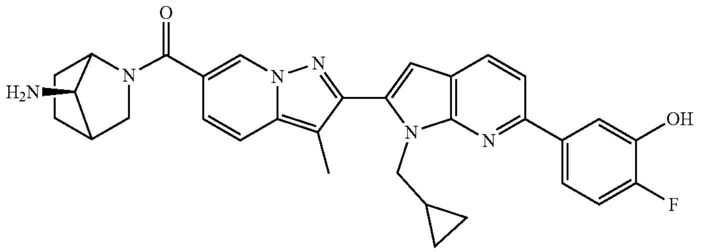 [SMILES: Cc1c(-c2cc3ccc(-c4ccc(F)c(O)c4)nc3n2CC2CC2)nn2cc(C(=O)N3CC4CCC3[C@@H]4N)ccc12]<br>((7R)-7-Amino-2-azabicyclo[2.2.1]heptan-2-yl)(2-(1-(cyclopropylmethyl)-6-(4-fluoro-3-hydroxyphenyl)-1H-pyrrolo[2,3-b]pyridin-2-yl)-3-methylpyrazolo[1,5-a]pyridin-6-yl)methanone<br>Analytical Data: 551.3, 1.639 min (Method F) |

Example 76

((7R)-7-Amino-2-azabicyclo[2.2.1]heptan-2-yl)(2-(1-(cyclopropylmethyl)-6-(4-methoxypiperidin-1-yl)-1H-pyrrolo[2,3-b]pyridin-2-yl)-3-methylpyrazolo[1,5-a]pyridin-6-yl)methanone

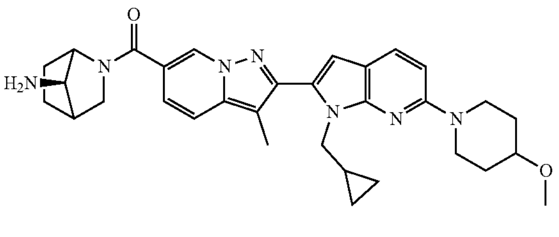 [SMILES: COC1CCN(c2ccc3cc(-c4nn5cc(C(=O)N6CC7CCC6[C@@H]7N)ccc5c4C)n(CC4CC4)c3n2)CC1]

Intermediate 76A tert-Butyl-((7R)-2-(2-(1-(cyclopropylmethyl)-6-(4-methoxypiperidin-1-yl)-1H-pyrrolo[2,3-b]pyridin-2-yl)-3-methylpyrazolo[1,5-a]pyridine-6-carbonyl)-2-azabicyclo[2.2.1]heptan-7-yl)carbamate

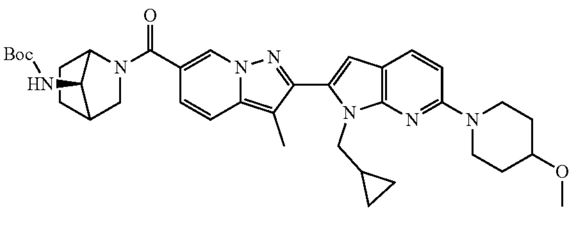 [SMILES: COC1CCN(c2ccc3cc(-c4nn5cc(C(=O)N6CC7CCC6[C@@H]7NC(=O)OC(C)(C)C)ccc5c4C)n(CC4CC4)c3n2)CC1]

Intermediate 76A was prepared following a procedure similar to the preparation of Intermediate 13A (50 mg, 63%). LC-MS m/z: 654.5 $[M+H]^+$.

Example 76

Compound of Example 76 was prepared following a procedure similar to the preparation of compound of Example 13 (9.1 mg, 16%). LC-MS m/z: 554.4 $[M+H]^+$. LC-MS retention time: 1.994 min (Method E). $^1H$ NMR (400 MHz, DMSO-$d_6$) δ ppm: 8.99-8.71 (m, 1H), 8.11-7.93 (m, 2H), 7.87-7.67 (m, 1H), 7.56-7.20 (m, 2H), 6.82-6.72 (m, 1H), 6.66 (s, 1H), 4.48-4.41 (m, 2H), 4.27-4.20 (m, 1H), 4.09-3.98 (m, 3H), 3.65-3.54 (m, 2H), 3.49-3.41 (m, 2H), 3.26-3.22 (m, 3H), 3.24-3.16 (m, 1H), 2.72-2.59 (m, 2H), 2.42 (s, 3H), 2.02-1.84 (m, 5H), 1.76-1.61 (m, 1H), 1.54-1.41 (m, 2H), 1.27-1.24 (m, 1H), 0.39-0.22 (m, 4H).

Compounds of Examples 77 to 79 in Table 10 were prepared following a procedure similar to the preparation of a compound of Example 76, by Buchwald coupling of Intermediate 64E with appropriate amines.

TABLE 10

| Example | Structure<br>Name<br>Analytical Data: LC-MS m/z $[M + H]^+$; HPLC retention time (HPLC method) |
|---|---|
| 77 | 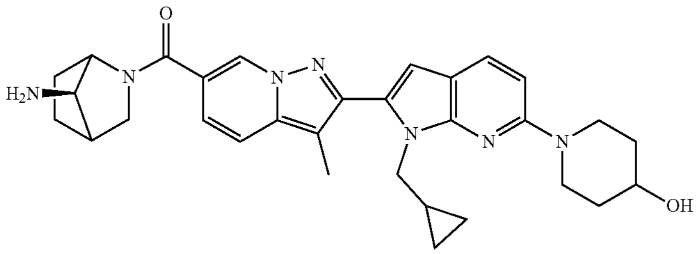 [SMILES: Cc1c(-c2cc3ccc(N4CCC(O)CC4)nc3n2CC2CC2)nn2cc(C(=O)N3CC4CCC3[C@@H]4N)ccc12]<br>((7R)-7-Amino-2-azabicyclo[2.2.1]heptan-2-yl)(2-(1-(cyclopropylmethyl)-6-(4-hydroxypiperidin-1-yl)-1H-pyrrolo[2,3-b]pyridin-2-yl)-3-methylpyrazolo[1,5-a]pyridin-6-yl)methanone<br>Analytical Data: 540.4, 1.078 min (Method F) |
| 78 | 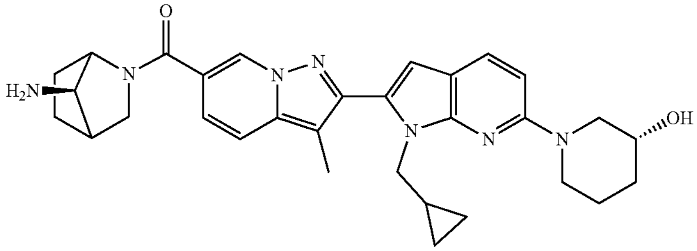 [SMILES: Cc1c(-c2cc3ccc(N4CCC[C@@H](O)C4)nc3n2CC2CC2)nn2cc(C(=O)N3CC4CCC3[C@@H]4N)ccc12]<br>((7R)-7-Amino-2-azabicyclo[2.2.1]heptan-2-yl)(2-(1-(cyclopropylmethyl)-6-((R)-3-hydroxypiperidin-1-yl)-1H-pyrrolo[2,3-b]pyridin-2-yl)-3-methylpyrazolo[1,5-a]pyridin-6-yl)methanone<br>Analytical Data: 540.4, 1.235 min (Method F) |
| 79 | 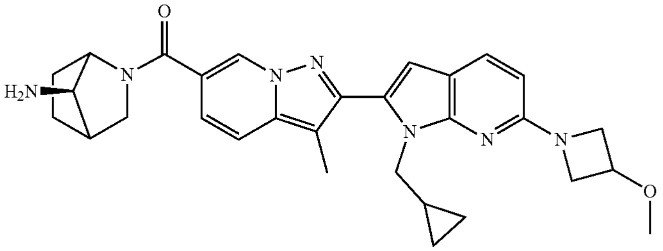 [SMILES: COC1CN(c2ccc3cc(-c4nn5cc(C(=O)N6CC7CCC6[C@@H]7N)ccc5c4C)n(CC4CC4)c3n2)C1]<br>((7R)-7-Amino-2-azabicyclo[2.2.1]heptan-2-yl)(2-(1-(cyclopropylmethyl)-6-(3-methoxyazetidin-1-yl)-1H-pyrrolo[2,3-b]pyridin-2-yl)-3-methylpyrazolo[1,5-a]pyridin-6-yl)methanone<br>Analytical Data: 526.4, 1.393 min (Method F) |

Example 80

((3R,5R)-3-Amino-5-fluoropiperidin-1-yl)(2-(1-(cyclopropylmethyl)-1H-pyrrolo[2,3-b]pyridin-2-yl)-3-methylpyrazolo[1,5-a]pyridin-6-yl)methanone

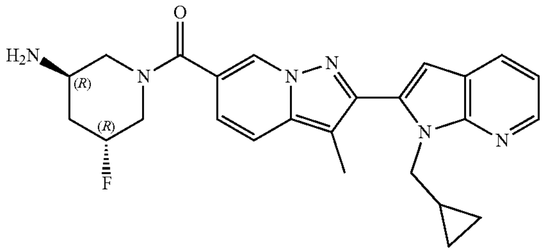

Intermediate 80A tert-Butyl-((3R,5R)-1-(2-(1-(cyclopropylmethyl)-1H-pyrrolo[2,3-b]pyridin-2-yl)-3-methylpyrazolo[1,5-a]pyridine-6-carbonyl)-5-fluoropiperidin-3-yl) carbamate

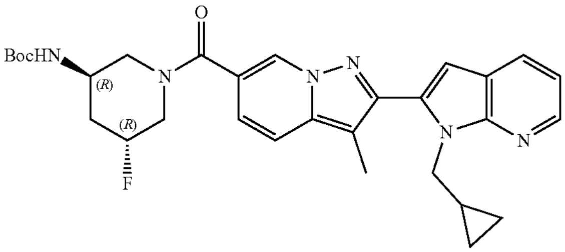

Intermediate 80A was prepared following a procedure similar to the preparation of Intermediate 14A (50 mg, 63%). LC-MS m/z: 547.3 $[M+H]^+$.

Example 80

Compound of Example 80 was prepared following a procedure similar to the preparation of Example 14 (21.2 mg, 43%). LC-MS m/z: 447.3 $[M+H]^+$. $^1H$ NMR (400 MHz, DMSO-$d_6$) δ ppm: 8.79 (s, 1H), 8.33 (dd, J=1.6, 4.8 Hz, 1H), 8.05 (dd, J=1.5, 7.8 Hz, 1H), 7.82 (d, J=9.3 Hz, 1H), 7.23 (dd, J=1.2, 9.3 Hz, 1H), 7.16 (dd, J=4.6, 7.8 Hz, 1H), 6.87 (s, 1H), 5.04-4.80 (m, 1H), 4.55 (d, J=7.1 Hz, 3H), 3.91 (s, 2H), 3.03-2.95 (m, 1H), 2.45 (s, 3H), 2.22-2.09 (m, 1H), 1.65-1.41 (m, 1H), 1.29-1.15 (m, 1H), 0.34-0.21 (m, 4H).

Example 81

5-(2-(6-((3R,5R)-3-Amino-5-fluoropiperidine-1-carbonyl)-3-methylpyrazolo[1,5-a]pyridin-2-yl)-1-(cyclopropylmethyl)-1H-pyrrolo[2,3-b]pyridin-6-yl) isoindolin-1-one

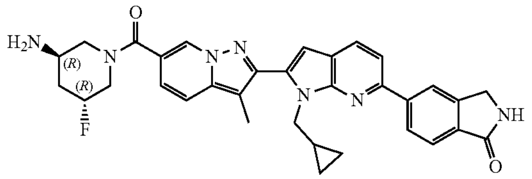

Intermediate 81A tert-Butyl-((3R,5R)-1-(2-(6-chloro-1-(cyclopropylmethyl)-1H-pyrrolo[2,3-b]pyridin-2-yl)-3-methylpyrazolo[1,5-a]pyridine-6-carbonyl)-5-fluoropiperidin-3-yl)carbamate

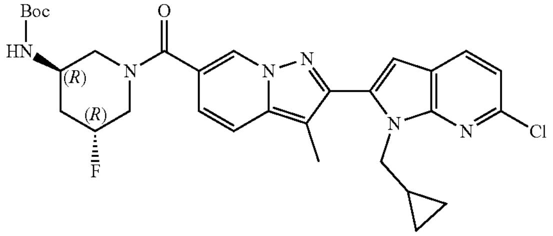

Intermediate 81A was prepared following a procedure similar to the preparation of Intermediate 15A (600 mg, 79%). LC-MS m/z: 581.3 $[M+H]^+$.

Intermediate 81B tert-Butyl-((3R,5R)-1-(2-(1-(cyclopropylmethyl)-6-(1-oxoisoindolin-5-yl)-1H-pyrrolo[2,3-b]pyridin-2-yl)-3-methylpyrazolo[1,5-a]pyridine-6-carbonyl)-5-fluoropiperidin-3-yl)carbamate

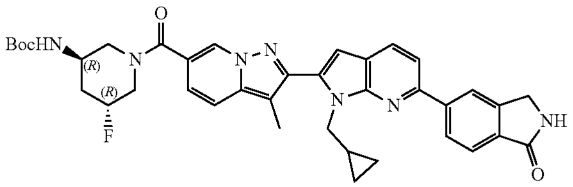

Intermediate 81B was prepared following a procedure similar to the preparation of Intermediate 16A (50 mg, 61%). LC-MS m/z: 678.4 $[M+H]^+$.

Example 81

Compound of Example 81 was prepared following a procedure similar to the preparation of Example 16 (7.1 mg).

LC-MS m/z: 578.4 [M+H]$^+$. LC-MS retention time: 1.576 min (Method E). $^1$H NMR (400 MHz, DMSO-$d_6$) δ ppm: 8.86-8.77 (m, 1H), 8.66-8.56 (m, 1H), 8.42-8.28 (m, 2H), 8.17 (d, J=8.1 Hz, 1H), 7.88-7.76 (m, 3H), 7.24 (d, J=8.4 Hz, 1H), 6.93 (s, 1H), 5.08-4.82 (m, 1H), 4.73-4.59 (m, 2H), 4.56-4.38 (m, 2H), 4.22-4.12 (m, 1H), 4.12-3.85 (m, 1H), 3.09-2.95 (m, 2H), 2.48-2.38 (m, 3H), 2.24-2.11 (m, 1H), 1.98-1.82 (m, 1H), 1.68-1.42 (m, 1H), 1.39-1.14 (m, 1H), 0.37-0.30 (m, 4H).

Compounds of Examples 82 to 86 in Table 11 were prepared following a procedure similar to the preparation of a compound of Example 81, by Suzuki coupling of Intermediate 81A with appropriate boronic acid.

TABLE 11

| Example | Structure<br>Name<br>Analytical Data: LC-MS m/z [M + H]$^+$; HPLC retention time (HPLC method) |
|---|---|
| 82 | 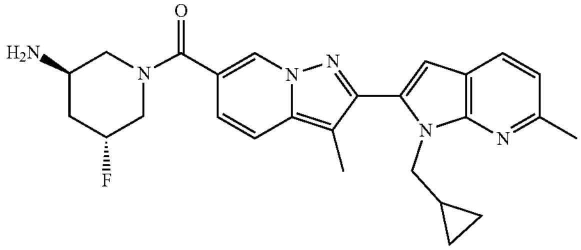 [SMILES: Cc1ccc2cc(-c3nn4cc(C(=O)N5C[C@H](N)C[C@@H](F)C5)ccc4c3C)n(CC3CC3)c2n1]<br>((3R,5R)-3-Amino-5-fluoropiperidin-1-yl)(2-(1-(cyclopropylmethyl)-6-methyl-1H-pyrrolo[2,3-b]pyridin-2-yl)-3-methylpyrazolo[1,5-a]pyridin-6-yl)methanone<br>Analytical Data: 461.4, 1.129 min (Method F) |
| 83 | 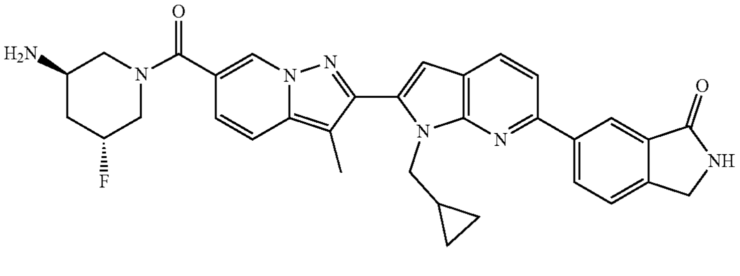 [SMILES: Cc1c(-c2cc3ccc(-c4ccc5c(c4)C(=O)NC5)nc3n2CC2CC2)nn2cc(C(=O)N3C[C@H](N)C[C@@H](F)C3)ccc12]<br>6-(2-(6-((3R,5R)-3-Amino-5-fluoropiperidine-1-carbonyl)-3-methylpyrazolo[1,5-a]pyridin-2-yl)-1-(cyclopropylmethyl)-1H-pyrrolo[2,3-b]pyridin-6-yl)isoindolin-1-one<br>Analytical Data: 578.3, 1.440 min (Method F) |
| 84 | 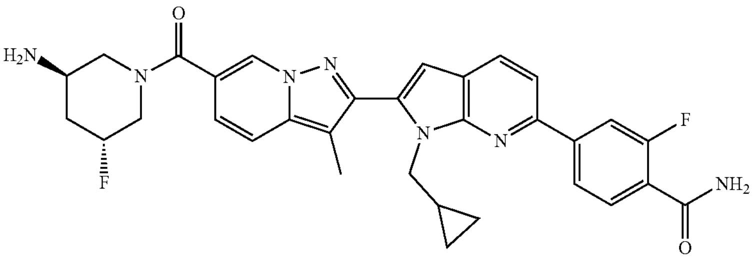 [SMILES: Cc1c(-c2cc3ccc(-c4ccc(C(N)=O)c(F)c4)nc3n2CC2CC2)nn2cc(C(=O)N3C[C@H](N)C[C@@H](F)C3)ccc12]<br>4-(2-(6-((3R,5R)-3-Amino-5-fluoropiperidine-1-carbonyl)-3-methylpyrazolo[1,5-a]pyridin-2-yl)-1-(cyclopropylmethyl)-1H-pyrrolo[2,3-b]pyridin-6-yl)-2-fluorobenzamide<br>Analytical Data: 584.3, 1.623 min (Method F) |

TABLE 11-continued

| Example | Structure<br>Name<br>Analytical Data: LC-MS m/z [M + H]$^+$; HPLC retention time (HPLC method) |
|---|---|
| 85 | 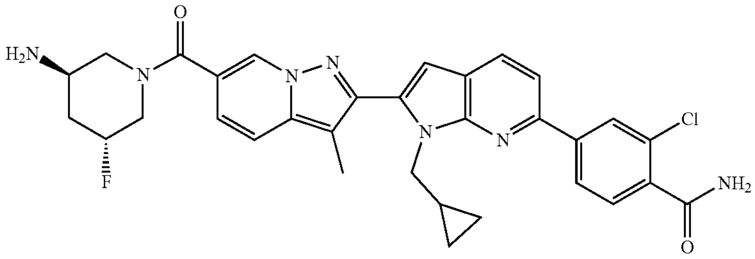 [SMILES: Cc1c(-c2cc3ccc(-c4ccc(C(N)=O)c(Cl)c4)nc3n2CC2CC2)nn2cc(C(=O)N3C[C@H](N)C[C@@H](F)C3)ccc12]<br>4-(2-(6-((3R,5R)-3-Amino-5-fluoropiperidine-1-carbonyl)-3-methylpyrazolo[1,5-a]pyridin-2-yl)-1-(cyclopropylmethyl)-1H-pyrrolo[2,3-b]pyridin-6-yl)-2-chlorobenzamide<br>Analytical Data: 600.3, 1.454 min (Method F) |
| 86 | 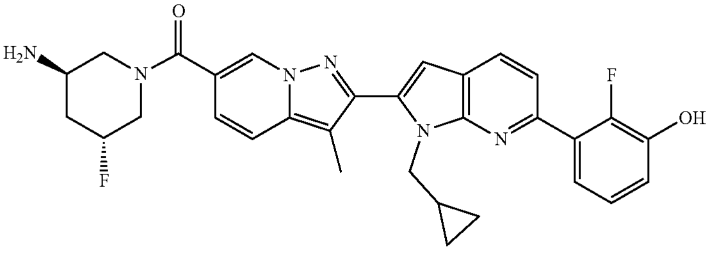 [SMILES: Cc1c(-c2cc3ccc(-c4cccc(O)c4F)nc3n2CC2CC2)nn2cc(C(=O)N3C[C@H](N)C[C@@H](F)C3)ccc12]<br>((3R,5R)-3-Amino-5-fluoropiperidin-1-yl)(2-(1-(cyclopropylmethyl)-6-(2-fluoro-3-hydroxyphenyl)-1H-pyrrolo[2,3-b]pyridin-2-yl)-3-methylpyrazolo[1,5-a]pyridin-6-yl)methanone<br>Analytical Data: 557.4, 1.603 min (Method F) |

Example 87

((3R,5R)-3-Amino-5-fluoropiperidin-1-yl)(2-(1-(cyclopropylmethyl)-6-(4-methoxypiperidin-1-yl)-1H-pyrrolo[2,3-b]pyridin-2-yl)-3-methylpyrazolo[1,5-a]pyridin-6-yl)methanone

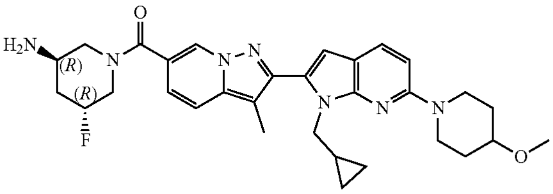

Intermediate 87A tert-Butyl-((3R,5R)-1-(2-(1-(cyclopropylmethyl)-6-(4-methoxypiperidin-1-yl)-1H-pyrrolo[2,3-b]pyridin-2-yl)-3-methylpyrazolo[1,5-a]pyridine-6-carbonyl)-5-fluoropiperidin-3-yl)carbamate

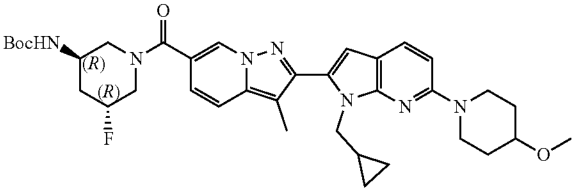

Intermediate 87A was prepared following a procedure similar to the preparation of Intermediate 13A (60 mg, 75%). LC-MS m/z: 660.5 [M+H]$^+$.

Example 87

Compound of Example 87 was prepared following a procedure similar to the preparation of Example 13 (5 mg, 9%). LC-MS m/z: 560.4 [M+H]$^+$. $^1$H NMR (400 MHz, DMSO-$d_6$) δ ppm: 8.72 (s, 1H), 7.79-7.69 (m, 2H), 7.22-7.14 (m, 1H), 6.75 (d, J=8.6 Hz, 1H), 6.65 (s, 1H), 5.10-4.80 (m, 1H), 4.46-4.38 (m, 3H), 4.06-3.97 (m, 4H), 3.28-3.30 (m, 5H), 3.22-3.18 (m, 2H), 2.98-2.93 (m, 1H), 2.41 (s, 3H), 1.99-1.89 (m, 3H), 1.51-1.42 (m, 3H), 1.32-1.09 (m, 1H), 0.96-0.84 (m, 1H), 0.31 (d, J=6.6 Hz, 4H).

Example 88

((3R,5R)-3-Amino-5-fluoropiperidin-1-yl)(2-(1-(cyclopropylmethyl)-6-(4-hydroxypiperidin-1-yl)-1H-pyrrolo[2,3-b]pyridin-2-yl)-3-methylpyrazolo[1,5-a]pyridin-6-yl)methanone

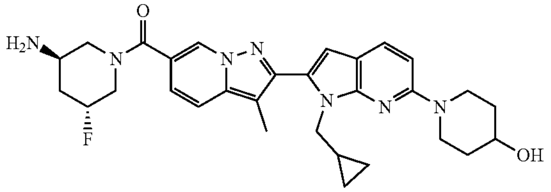 [SMILES: Cc1c(-c2cc3ccc(N4CCC(O)CC4)nc3n2CC2CC2)nn2cc(C(=O)N3C[C@H](N)C[C@@H](F)C3)ccc12]

Compound of Example 88 was prepared following a procedure similar to the preparation of Example 87, by Buchwald coupling of Intermediate 81A with appropriate amine. LC-MS m/z: 546.3 [M+H]+. LC-MS retention time: 1.573 min (Method F).

Example 89

6-(2-(6-((7R)-7-Amino-2-azabicyclo[2.2.1]heptane-2-carbonyl)-3-methylpyrazolo[1,5-a]pyridin-2-yl)-1-(cyclopropylmethyl)-1H-indol-6-yl)isoindolin-1-one

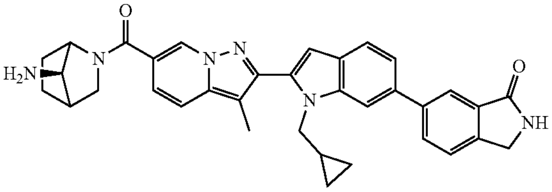 [SMILES: Cc1c(-c2cc3ccc(-c4ccc5c(c4)C(=O)NC5)cc3n2CC2CC2)nn2cc(C(=O)N3CC4CCC3[C@@H]4N)ccc12]

Intermediate 89A 3-(tert-Butyl)-6-ethyl 2-(6-bromo-1-(cyclopropylmethyl)-1H-indol-2-yl)pyrazolo[1,5-a]pyridine-3,6-dicarboxylate

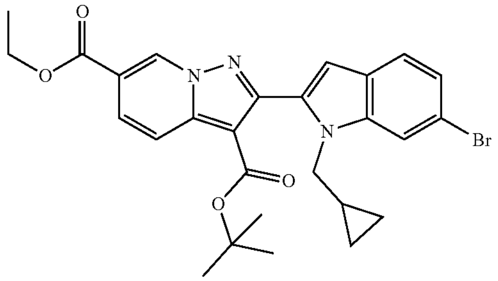 [SMILES: CCOC(=O)c1ccc2c(C(=O)OC(C)(C)C)c(-c3cc4ccc(Br)cc4n3CC3CC3)nn2c1]

Intermediate 89A was prepared following a procedure similar to the preparation of Intermediate 23A, as a pale brown glassy solid (300 mg, 26%). LC-MS m/z: 538.2 [M+H]+.

Intermediate 89B 2-(6-Bromo-1-(cyclopropylmethyl)-1H-indol-2-yl)-6-(ethoxycarbonyl)pyrazolo[1,5-a]pyridine-3-carboxylic acid

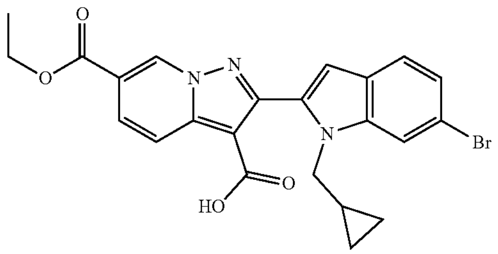 [SMILES: CCOC(=O)c1ccc2c(C(=O)O)c(-c3cc4ccc(Br)cc4n3CC3CC3)nn2c1]

Intermediate 89B was prepared following a procedure similar to the preparation of Intermediate 23B, as pale yellow syrup (300 mg, 99%). LC-MS m/z: 484.0 [M+2H]+.

Intermediate 89C

Ethyl-2-(6-bromo-1-(cyclopropylmethyl)-1H-indol-2-yl)-3-methylpyrazolo[1,5-a]pyridine-6-carboxylate

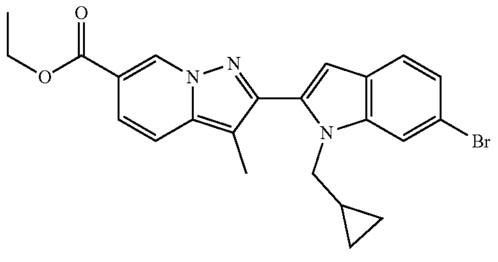 [SMILES: CCOC(=O)c1ccc2c(C)c(-c3cc4ccc(Br)cc4n3CC3CC3)nn2c1]

Intermediate 89C was prepared following a procedure similar to the preparation of Intermediate 23C (250 mg, 89%). LC-MS m/z: 454.1 [M+2H]+.

Intermediate 89D 2-(6-Bromo-1-(cyclopropylmethyl)-1H-indol-2-yl)-3-methylpyrazolo[1,5-a]pyridine-6-carboxylic acid

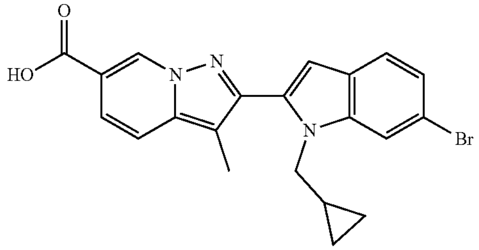 [SMILES: Cc1c(-c2cc3ccc(Br)cc3n2CC2CC2)nn2cc(C(=O)O)ccc12]

Intermediate 89D was prepared following a procedure similar to the preparation of Intermediate 23D, as brown syrup (230 mg, 98%). LC-MS m/z: 426.3 [M+2H]+.

Intermediate 89E tert-Butyl-((7R)-2-(2-(6-bromo-1-(cyclopropylmethyl)-1H-indol-2-yl)-3-methylpyrazolo[1,5-a]pyridine-6-carbonyl)-2-azabicyclo[2.2.1]heptan-7-yl)carbamate

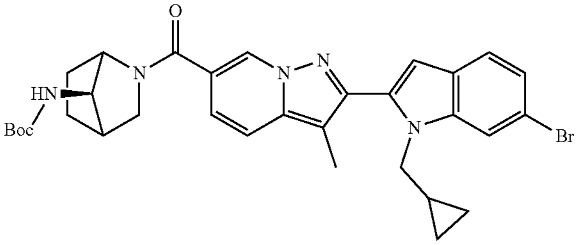 [SMILES: Cc1c(-c2cc3ccc(Br)cc3n2CC2CC2)nn2cc(C(=O)N3CC4CCC3[C@@H]4NC(=O)OC(C)(C)C)ccc12]

Intermediate 89E was prepared following a procedure similar to the preparation of Intermediate 23E, as a glassy solid (180 mg, 54%). LC-MS m/z: 620.3 [M+2H]$^+$.

Intermediate 89F tert-Butyl-((7R)-2-(2-(1-(cyclopropylmethyl)-6-(3-oxoisoindolin-5-yl)-1H-indol-2-yl)-3-methylpyrazolo[1,5-a]pyridine-6-carbonyl)-2-azabicyclo[2.2.1]heptan-7-yl)carbamate

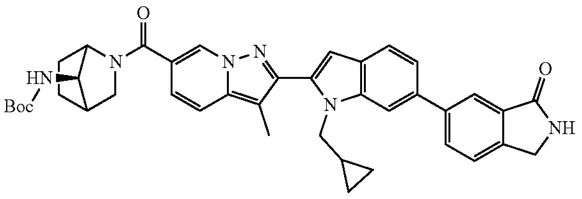 [SMILES: Cc1c(-c2cc3ccc(-c4ccc5c(c4)C(=O)NC5)cc3n2CC2CC2)nn2cc(C(=O)N3CC4CCC3[C@@H]4NC(=O)OC(C)(C)C)ccc12]

Intermediate 89F was prepared following a procedure similar to the preparation of Intermediate 23F, as a white solid (40 mg, 53%). LC-MS m/z: 671.5 [M+H]$^+$.

Example 89

Compound of Example 89 was prepared following a procedure similar to the preparation of the compound of Example 23, as a white solid (4 mg, 11%). LC-MS m/z: 571.3 [M+H]$^+$. $^1$H NMR (400 MHz, methanol-d$_4$) δ ppm: 8.82 (s, 1H), 8.75 (s, 1H), 8.14 (s, 1H), 8.02 (dd, J=1.8, 7.8 Hz, 1H), 7.83 (s, 1H), 7.75-7.64 (m, 3H),7.57-7.42 (m, 1H), 7.40-7.22 (m, 1H), 6.82 (s, 1H), 5.07-4.88 (m, 1H), 4.83-4.80 (m, 1H), 4.59 (s, 1H), 4.56-4.50 (m, 4H), 4.35 (s, 1H), 4.02(s, 1H), 3.85-3.58 (m, 1H), 3.57-3.39 (m, 1H), 3.34 (br, d, J=6.0 Hz, 1H), 3.29-3.22 (m, 1H), 2.50-2.43 (m, 3H), 2.40 (br, s, 1H), 2.34 (br, s, 1H), 2.13-1.89 (m, 3H), 1.71-1.48 (m, 1H), 1.42-1.24 (m, 1H), 1.24-1.11 (m, 1H), 0.41-0.30 (m, 2H), 0.18-0.08 (m, 2H).

Example 90

5-(2-(6-((7R)-7-Amino-2-azabicyclo[2.2.1]heptane-2-carbonyl)-3-methylpyrazolo[1,5-a]pyridin-2-yl)-1-(cyclopropylmethyl)-1H-indol-6-yl)isoindolin-1-one

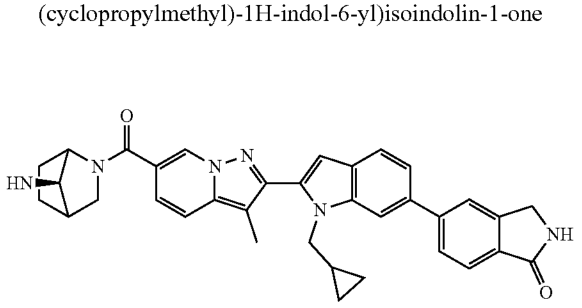

Compound of Example 90 was prepared following a procedure similar to the preparation of the compound of Example 89, by Suzuki coupling of Intermediate 89E with appropriate boronic acid. LC-MS m/z: 571.3 [M+H]$^+$, LC-MS retention time: 7.662 min (Method C).

Example 91

((7R)-7-Amino-2-azabicyclo[2.2.1]heptan-2-yl)(2-(1-(cyclopropylmethyl)-6-(3-fluoro-3-(hydroxymethyl)azetidin-1-yl)-1H-indol-2-yl)-3-methylpyrazolo[1,5-a]pyridin-6-yl)methanone

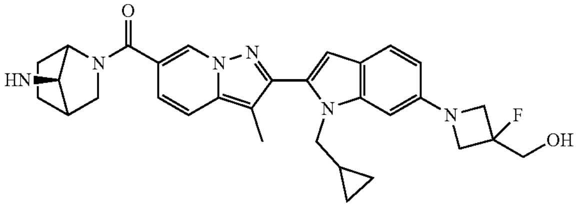 [SMILES: Cc1c(-c2cc3ccc(N4CC(F)(CO)C4)cc3n2CC2CC2)nn2cc(C(=O)N3CC4CCC3[C@@H]4N)ccc12]

Intermediate 91A tert-Butyl-((7R)-2-(2-(1-(cyclopropylmethyl)-6-(3-fluoro-3-(hydroxymethyl)azetidin-1-yl)-1H-indol-2-yl)-3-methylpyrazolo[1,5-a]pyridine-6-carbonyl)-2-azabicyclo[2.2.1]heptan-7-yl)carbamate

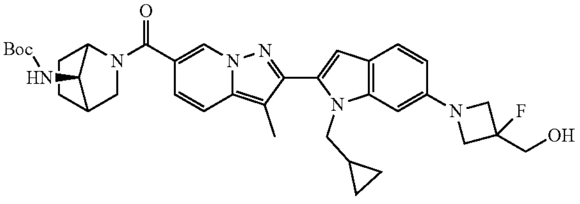 [SMILES: Cc1c(-c2cc3ccc(N4CC(F)(CO)C4)cc3n2CC2CC2)nn2cc(C(=O)N3CC4CCC3[C@@H]4NC(=O)OC(C)(C)C)ccc12]

Intermediate 91A was prepared following a procedure similar to the preparation of Intermediate 33A (45 mg, 62%). LC-MS m/z: 643.5 [M+H]$^+$.

Example 91

Compound of Example 91 was prepared following a procedure similar to the preparation of the compound of 33 (9 mg, 7%). LC-MS m/z: 543.4 [M+H]$^+$. LC-MS retention time: 1.285 min (Method E). $^1$H NMR (400 MHz, DMSO-d$_6$) δ ppm: 8.74 (br, d, J=2.0 Hz, 1H), 7.77-7.66 (m, 1H), 7.45 (d, J=8.6 Hz, 1H), 7.34-7.14 (m, 2H), 6.68 (s, 1H), 6.59 (s,1H), 6.45-6.35 (m, 1H), 5.37-5.27 (m, 1H), 4.48-4.36 (m, 2H), 4.11-3.98 (m, 3H), 3.90-3.73 (m, 5H), 2.39 (s, 3H), 2.03-1.80 (m, 4H), 1.58-1.45 (m, 2H), 1.38-1.07 (m, 3H), 0.34-0.23 (m, 2H), 0.20-0.05 (m, 2H).

Example 92

((3R,5R)-3-Amino-5-fluoropiperidin-1-yl)(2-(1-(cyclopropylmethyl)-6-(2-fluoro-3-hydroxyphenyl)-1H-indol-2-yl)-3-methylpyrazolo[1,5-a]pyridin-6-yl)methanone

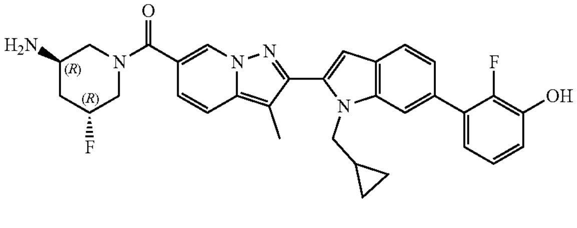

Intermediate 92A tert-Butyl-((3R,5R)-1-(2-(6-bromo-1-(cyclopropylmethyl)-1H-indol-2-yl)-3-methylpyrazolo[1,5-a]pyridine-6-carbonyl)-5-fluoropiperidin-3-yl)carbamate

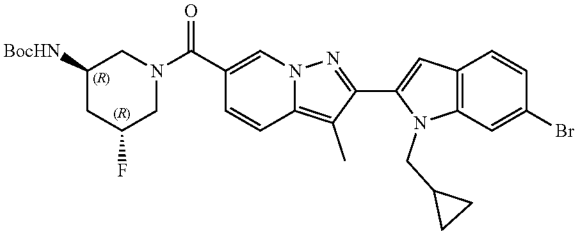

Intermediate 92A was prepared following a procedure similar to the preparation of Intermediate 29A (300 mg, 41%). LC-MS m/z: 657.3 $[M+H]^+$.

Intermediate 92B ((3R,5R)-3-Amino-5-fluoropiperidin-1-yl)(2-(1-(cyclopropylmethyl)-6-(2-fluoro-3-hydroxyphenyl)-1H-indol-2-yl)-3-methylpyrazolo[1,5-a]pyridin-6-yl)methanone

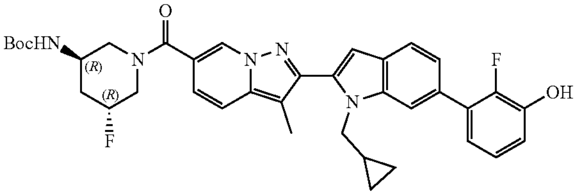

Intermediate 92B was prepared following a procedure similar to the preparation of Intermediate 29B (50 mg, 68%). LC-MS m/z: 557.4 $[M+H]^+$.

Example 92

Compound of Example 92 was prepared following a procedure similar to the preparation of the compound of Example 29 (16.3 mg). LC-MS m/z: 556.3 $[M+H]^+$. LC-MS retention time: 1.843 min (method E). $^1H$ NMR (400 MHz, DMSO-$d_6$) δ ppm: 9.93-9.83 (m, 1H), 8.82 (s, 1H), 8.11-7.89 (m, 1H), 7.83 (d, J=9.3 Hz, 1H), 7.76-7.65 (m, 2H), 7.30-7.18 (m,2H), 7.11-7.04 (m, 1H), 7.01-6.92 (m, 2H), 6.87 (s, 1H), 5.11-4.93 (m, 1H), 4.54-4.40 (m, 3H), 3.28-3.20 (m, 2H), 2.43 (s, 3H), 2.42-2.35 (m, 2H), 1.97-1.75 (m, 1H), 1.19-1.07 (m, 1H), 0.36-0.27 (m, 2H), 0.25-0.13 (m, 2H).

Compounds of Examples 93 to 96 in Table 12 were prepared following a procedure similar to the preparation of a compound of Example 92, by Suzuki coupling of Intermediate 92A with appropriate boronic acid.

TABLE 12

| Example | Structure<br>Name<br>Analytical Data: LC-MS m/z $[M + H]^+$; HPLC retention time (HPLC method) |
|---|---|
| 93 | 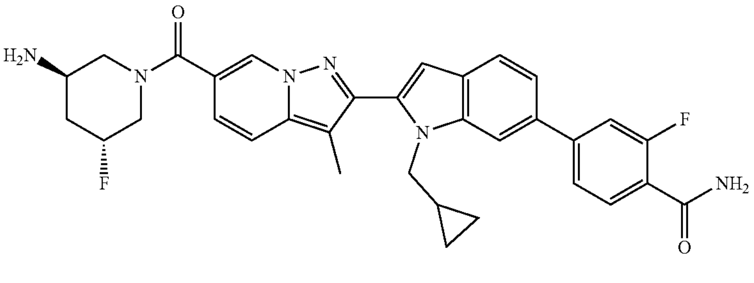 [SMILES: Cc1c(-c2cc3ccc(-c4ccc(C(N)=O)c(F)c4)cc3n2CC2CC2)nn2cc(C(=O)N3C[C@H](N)C[C@@H](F)C3)ccc12]<br>4-(2-(6-((3R,5R)-3-Amino-5-fluoropiperidine-1-carbonyl)-3-methylpyrazolo[1,5-a]pyridin-2-yl)-1-(cyclopropylmethyl)-1H-indol-6-yl)-2-fluorobenzamide<br>Analytical Data: 583.3, 1.530 min (Method F) |

TABLE 12-continued

| Example | Structure<br>Name<br>Analytical Data: LC-MS m/z [M + H]$^+$; HPLC retention time (HPLC method) |
|---|---|
| 94 | 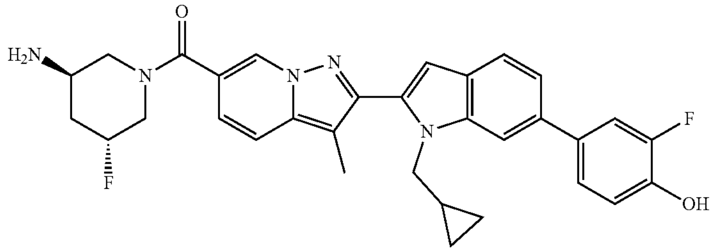 [SMILES: Cc1c(-c2cc3ccc(-c4ccc(O)c(F)c4)cc3n2CC2CC2)nn2cc(C(=O)N3C[C@H](N)C[C@@H](F)C3)ccc12]<br>((3R,5R)-3-Amino-5-fluoropiperidin-1-yl)(2-(1-(cyclopropylmethyl)-6-(3-fluoro-4-hydroxyphenyl)-1H-indol-2-yl)-3-methylpyrazolo[1,5-a]pyridin-6-yl)methanone<br>Analytical Data: 556.3, 1.668 min (Method F) |
| 95 | 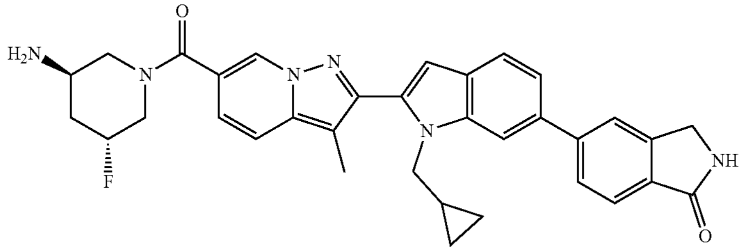 [SMILES: Cc1c(-c2cc3ccc(-c4ccc5c(c4)CNC5=O)cc3n2CC2CC2)nn2cc(C(=O)N3C[C@H](N)C[C@@H](F)C3)ccc12]<br>5-(2-(6-((3R,5R)-3-Amino-5-fluoropiperidine-1-carbonyl)-3-methylpyrazolo[1,5-a]pyridin-2-yl)-1-(cyclopropylmethyl)-1H-indol-6-yl)isoindolin-1-one<br>Analytical Data: 577.4, 1.460 min (Method F) |
| 96 | 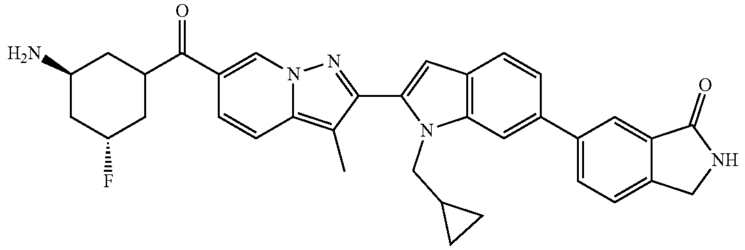 [SMILES: Cc1c(-c2cc3ccc(-c4ccc5c(c4)C(=O)NC5)cc3n2CC2CC2)nn2cc(C(=O)C3C[C@H](N)C[C@@H](F)C3)ccc12]<br>6-(2-(6-((3R,5R)-3-Amino-5-fluoropiperidine-1-carbonyl)-3-methylpyrazolo[1,5-a]pyridin-2-yl)-1-(cyclopropylmethyl)-1H-indol-6-yl)isoindolin-1-one<br>Analytical Data: 577.3, 7.422 min (Method F) |

Example 97

((7R)-7-Amino-2-azabicyclo[2.2.1]heptan-2-yl)(2-(1-(cyclopropylmethyl)-6-(2-hydroxypropan-2-yl)-1H-indol-2-yl)-4-methoxy-3-methylpyrazolo[1,5-a]pyridin-6-yl)methanone

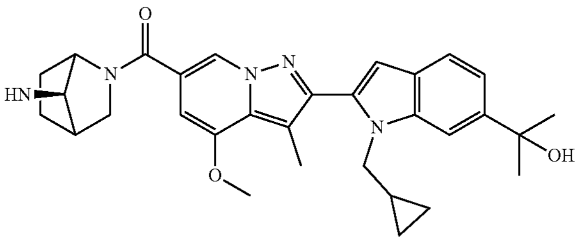 [SMILES: COc1cc(C(=O)N2CC3CCC2[C@@H]3N)cn2nc(-c3cc4ccc(C(C)(C)O)cc4n3CC3CC3)c(C)c12]

Intermediate 97A ((7R)-7-Amino-2-azabicyclo[2.2.1]heptan-2-yl)(2-(6-bromo-1-(cyclopropylmethyl)-1H-indol-2-yl)-4-methoxy-3-methylpyrazolo[1,5-a]pyridin-6-yl)methanone

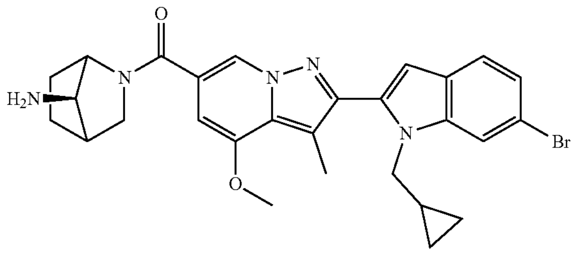 [SMILES: COc1cc(C(=O)N2CC3CCC2[C@@H]3N)cn2nc(-c3cc4ccc(Br)cc4n3CC3CC3)c(C)c12]

TFA (0.3 ml, 3.89 mmol) was added to a solution of Intermediate 23E (200 mg, 0.308 mmol) in DCM (1 ml). The reaction mixture was stirred for 2 hours, and concentrated under vacuum to afford the crude title compound (180 mg, 100%), which was used in next step without further purification. LC-MS m/z: 548 $[M+H]^+$.

Intermediate 97B (9H-Fluoren-9-yl)methyl-((7R)-2-(2-(6-bromo-1-(cyclopropylmethyl)-1H-indol-2-yl)-4-methoxy-3-methylpyrazolo[1,5-a]pyridine-6-carbonyl)-2-azabicyclo[2.2.1]heptan-7-yl)carbamate

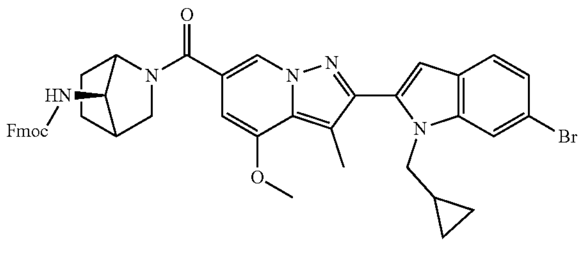

Sodium bicarbonate (115 mg, 1.367 mmol) was added to a stirred solution of Intermediate 97A (250 mg, 0.456 mmol) in a mixture of solvents dioxane (1 ml) and water (1 ml), followed by the addition of (9H-fluoren-9-yl)methyl carbonochloridate (118 mg, 0.456 mmol). The reaction mixture was diluted with DCM and stirred for about 5 min. The organic layer was separated and concentrated under reduced pressure to afford crude compound, which was purified using a silica gel column (eluting with 0-60% EtOAc in hexane) to afford the title compound (70 mg, 20%) as off-white solid. LC-MS m/z: 772.3 $[M+H]^+$.

Intermediate 97C (9H-Fluoren-9-yl)methyl-((7R)-2-(2-(6-acetyl-1-(cyclopropylmethyl)-1H-indol-2-yl)-4-methoxy-3-methylpyrazolo[1,5-a]pyridine-6-carbonyl)-2-azabicyclo[2.2.1]heptan-7-yl)carbamate

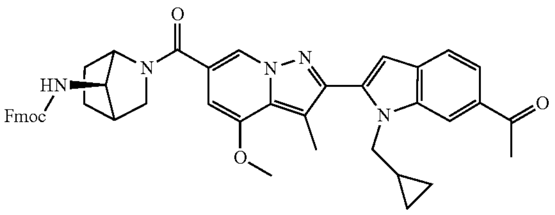

Tributyl(1-ethoxyvinyl)stannane (46.9 mg, 0.130 mmol) and $Pd(PPh_3)_2Cl_2$ (9.11 mg, 0.013 mmol) were added to a solution of Intermediate 97B (100 mg, 0.130 mmol) in toluene (3 m) in a vial. The reaction mixture was degassed with argon for 2 min, heated to 85° C. and stirred for 16 hours, diluted in minimum amount of DCM and loaded onto a silica gel column for purification. Eluting with 0-100% EtOAc/pet ether afforded the ether cleaved title compound (70 mg, 74%) as a colourless syrup. LC-MS m/z: 734.4 $[M+H]^+$.

Intermediate 97D (9H-Fluoren-9-yl)methyl-((7R)-2-(2-(1-(cyclopropylmethyl)-6-(2-hydroxypropan-2-yl)-1H-indol-2-yl)-4-methoxy-3-methylpyrazolo[1,5-a]pyridine-6-carbonyl)-2-azabicyclo[2.2.1]heptan-7-yl)carbamate

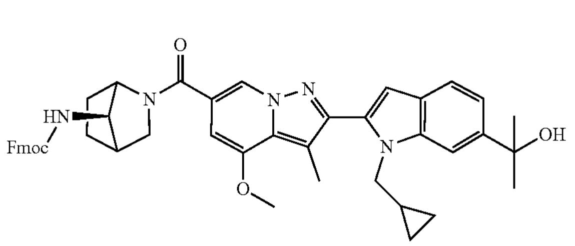

Methyl magnesium bromide (0.127 ml, 0.382 mmol, 3 M in THF) was added to a stirred solution of Intermediate 97C (70 mg, 0.095 mmol) in THF (3 ml) at 0° C. The reaction mixture was stirred for 1 hour, quenched with saturated $NH_4Cl$ solution at 0° C., extracted with EtOAc, dried over $Na_2SO_4$, and concentrated under reduced pressure to afford a crude compound. Purification by prep-HPLC of the crude compound afforded the title compound (40 mg, 56%) as a white solid. LC-MS m/z: 750.4 $[M+H]^+$.

Example 97

Piperidine (10.56 μL, 0.107 mmol) was added drop wise to a stirred solution of Intermediate 97D (40 mg, 0.053 mmol) in DCM. The reaction mixture was stirred for 2 hours, and concentrated to afford a crude compound as off-white solid. Purification by Prep-HPLC afforded the title compound. The purified compound was further purified using RP-HPLC to afford the title compound (3 mg, 10%) as off-white solid. LC-MS m/z: 534.4 $[M+H]^+$. HPLC retention time: 6.983 (Method C). $^1H$ NMR (400 MHz, methanol-$d_4$) δ ppm: 8.33 (s, 1H), 7.69 (s, 1H), 7.58 (d, J=8.0 Hz, 1H), 7.24 (dd, J=1.5, 8.5 Hz, 1H), 6.68 (s, 1H), 6.65-6.61 (m, 1H), 4.60 (s, 2H), 4.43-4.27 (m, 2H), 4.16-4.00 (m, 4H), 3.76-3.62 (m, 1H), 3.62-3.54 (m, 1H), 3.53-3.41 (m, 1H), 3.30-3.06 (m, 1H), 2.54 (s, 3H), 2.48-2.34 (m, 1H), 2.18-1.90 (m, 5H), 1.23-1.03 (m, 2H), 1.01-0.81 (m, 1H), 0.37-0.30 (m, 2H), 0.14-0.06 (m, 2H).

Example 98

((3R,5R)-3-Amino-5-fluoropiperidin-1-yl)(2-(1-(cyclopropylmethyl)-6-(2-hydroxypropan-2-yl)-1H-indol-2-yl)-4-methoxy-3-methylpyrazolo[1,5-a]pyridin-6-yl)methanone

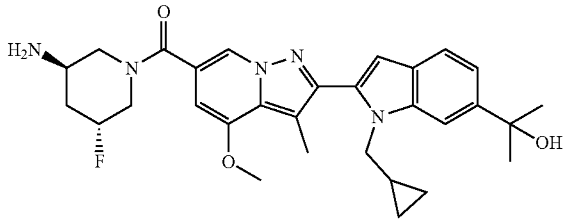 [SMILES: COc1cc(C(=O)N2C[C@H](N)C[C@@H](F)C2)cn2nc(-c3cc4ccc(C(C)(C)O)cc4n3CC3CC3)c(C)c12]

Intermediate 98A ((3R,5R)-3-Amino-5-fluoropiperidin-1-yl)(2-(6-bromo-1-(cyclopropylmethyl)-1H-indol-2-yl)-4-methoxy-3-methylpyrazolo[1,5-a]pyridin-6-yl) methanone

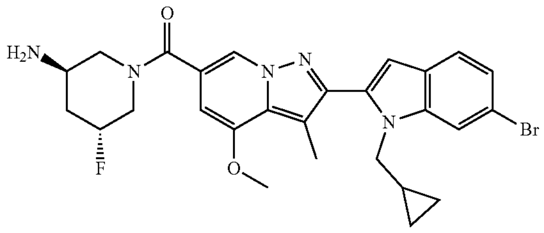 [SMILES: COc1cc(C(=O)N2C[C@H](N)C[C@@H](F)C2)cn2nc(-c3cc4ccc(Br)cc4n3CC3CC3)c(C)c12]

Intermediate 98A was prepared following a procedure similar to the preparation of Intermediate 97A (70 mg, 100%). LCMS m/z: 778.3 $[M+H]^+$.

Intermediate 98B (9H-Fluoren-9-yl)methyl-((3R,5R)-1-(2-(6-bromo-1-(cyclopropylmethyl)-1H-indol-2-yl)-4-methoxy-3-methylpyrazolo[1,5-a]pyridine-6-carbonyl)-5-fluoropiperidin-3-yl)carbamate

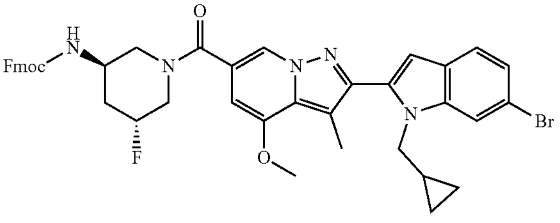

Intermediate 98B was prepared following a procedure similar to the preparation of Intermediate 97B (65 mg, 66%) as an off-white solid. LC-MS m/z: 778.3 $[M+H]^+$.

Intermediate 98C (9H-Fluoren-9-yl)methyl-((3R,5R)-1-(2-(6-acetyl-1-(cyclopropylmethyl)-1H-indol-2-yl)-4-methoxy-3-methylpyrazolo[1,5-a]pyridine-6-carbonyl)-5-fluoropiperidin-3-yl)carbamate

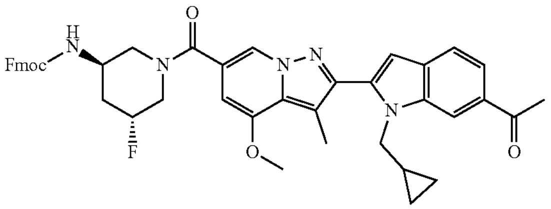

Intermediate 98C was prepared following a procedure similar to the preparation of Intermediate 97C (crude 70 mg) as black syrup. LC-MS m/z: 740.4 $[M+H]^+$.

Intermediate 98D (9H-Fluoren-9-yl)methyl-((3R,5R)-1-(2-(1-(cyclopropylmethyl)-6-(2-hydroxypropan-2-yl)-1H-indol-2-yl)-4-methoxy-3-methylpyrazolo[1,5-a]pyridine-6-carbonyl)-5-fluoropiperidin-3-yl)carbamate

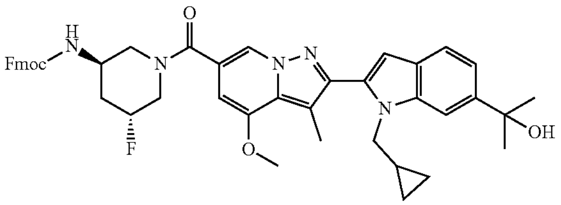

Intermediate 98D was prepared following a procedure similar to the preparation of Intermediate 97D (30 mg, 42%) as a pale yellow solid. LC-MS m/z: 756.2 $[M+H]^+$.

Example 98

Compound of Example 98 was prepared following a procedure similar to the preparation of a compound of Example 97 (1.5 mg, 6%), as a pale yellow solid. LC-MS m/z: 534.2 $[M+H]^+$. HPLC retention time: 6.983 min (Method C). $^1$H NMR (400 MHz, DMSO-$d_6$) δ ppm: 8.34 (s, 1H), 7.65 (s, 1H), 7.52 (d, J=8.5 Hz, 1H), 7.19 (dd, J=1.3, 8.3 Hz, 1H), 6.68 (s, 1H), 6.53 (s, 1H), 5.01-4.93 (m, 2H), 4.35 (br d, J=6.5 Hz, 3H), 3.97 (s, 4H), 3.26-3.09 (m, 1H), 3.08-2.82 (m, 2H), 2.62 (m, 3H), 2.43-2.25 (m, 2H), 2.24-1.99 (m, 1H), 1.51 (s, 6H), 1.17-1.05 (m, 1H), 0.33-0.28 (m, 2H), 0.17-0.12 (m, 2H).

Example 99

((3R,5R)-3-Amino-5-fluoropiperidin-1-yl)(2-(1-(cyclopropylmethyl)-6-(1,1,1-trifluoro-2-hydroxy-propan-2-yl)-1H-indol-2-yl)-4-methoxy-3-methylpyrazolo[1,5-a]pyridin-6-yl)methanone

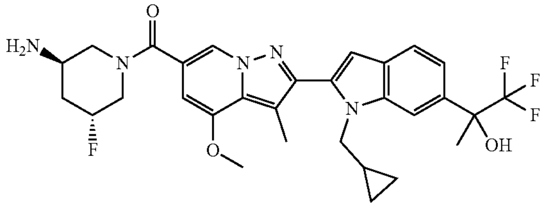 [SMILES: COc1cc(C(=O)N2C[C@H](N)C[C@@H](F)C2)cn2nc(-c3cc4ccc(C(C)(O)C(F)(F)F)cc4n3CC3CC3)c(C)c12]

Intermediate 99A tert-Butyl-((3R,5R)-1-(2-(6-acetyl-1-(cyclopropylmethyl)-1H-indol-2-yl)-4-methoxy-3-methylpyrazolo[1,5-a]pyridine-6-carbonyl)-5-fluoropiperidin-3-yl)carbamate

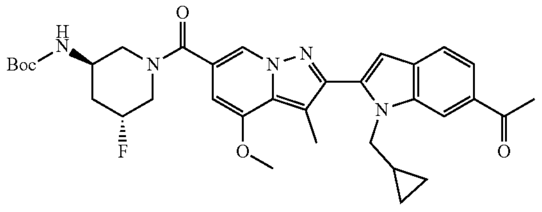 [SMILES: COc1cc(C(=O)N2C[C@H](F)C[C@@H](NC(=O)OC(C)(C)C)C2)cn2nc(-c3cc4ccc(C(C)=O)cc4n3CC3CC3)c(C)c12]

Intermediate 99A was prepared following a procedure similar to the preparation of Intermediate 97C (200 mg, 66%) as a glassy solid. LC-MS m/z: 618.4 $[M+H]^+$.

Intermediate 99B tert-Butyl-((3R,5R)-1-(2-(1-(cyclopropylmethyl)-6-(1,1,1-trifluoro-2-hydroxypropan-2-yl)-1H-indol-2-yl)-4-methoxy-3-methylpyrazolo[1,5-a]pyridine-6-carbonyl)-5-fluoropiperidin-3-yl)carbamate

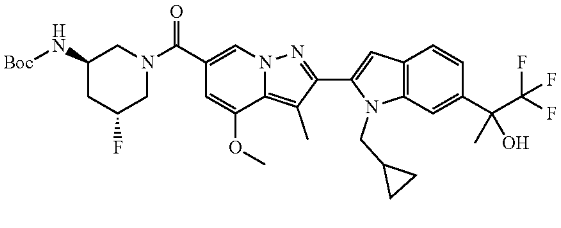 [SMILES: COc1cc(C(=O)N2C[C@H](F)C[C@@H](NC(=O)OC(C)(C)C)C2)cn2nc(-c3cc4ccc(C(C)(O)C(F)(F)F)cc4n3CC3CC3)c(C)c12]

Trimethyl(trifluoromethyl)silane (0.142 ml, 0.283 mmol, 2 M in THF) was added to a solution of Intermediate 99A (35 mg, 0.057 mmol) in DME (0.5 ml) in a 8 ml chemglass vial, followed by the addition of caesium fluoride (1 mg, 6.58 μmol) on the walls of the vial. The vial was closed and the contents were mixed, stirred at a room temperature for 16 hours, and concentrated under vacuum to afford a crude title compound (30 mg, 70%), which was used in the next step without further purification. LC-MS m/z: 760 $[M+H]^+$.

Example 99

2,6-Lutidine (0.018 ml, 0.158 mmol) was added to a stirred solution of Intermediate 99B (30 mg, 0.039 mmol) in DCM (1 ml), and the reaction mixture was cooled to 0° C., followed by the addition of TMS-OTf (0.014 ml, 0.079 mmol). The reaction mixture was stirred at 0° C. for 30 minutes, and additional 28 μl of TMS-OTf was added. The contents were allowed to warm to a room temperature, stirred for 30 minutes, quenched by the addition of 10% $NaHCO_3$ solution, and kept on standby over the weekend. The mixture was extracted with EtOAc (4×10 ml), dried over $Na_2SO_4$, concentrated under vacuum and the crude compound was purified using prep-HPLC. The purified compound was further purified using RP-HPLC to afford the title compound (2.2 mg, 10%). LC-MS m/z: 588 $[M+H]^+$. LC-MS retention time: 1.889 min (Method E). $^1$H NMR (400 MHz, DMSO-$d_6$) δ ppm: 8.39 (s, 1H), 7.80 (s, 1H), 7.61 (d, J=8.3 Hz, 1H), 7.30 (br, d, J=8.3 Hz, 1H), 6.75 (s, 1H), 6.55 (s, 1H), 5.10-4.92 (m,1H), 4.41-4.36 (m, 2H), 3.98 (s, 3H),3.80-3.17 (m, 1H),2.54 (s, 3H), 2.30-2.21 (m, 2H), 1.79 (br, s, 3H), 1.31-1.07 (m, 1H), 0.91-0.77 (m, 2H), 0.36-0.24 (m, 2H),0.16 (br, d, J=5.1 Hz, 2H).

Example 100

((7R)-7-Amino-2-azabicyclo[2.2.1]heptan-2-yl)(2-(1-(cyclopropylmethyl)-6-(2-hydroxypropan-2-yl)-1H-indol-2-yl)-3-methylpyrazolo[1,5-a]pyridin-6-yl)methanone

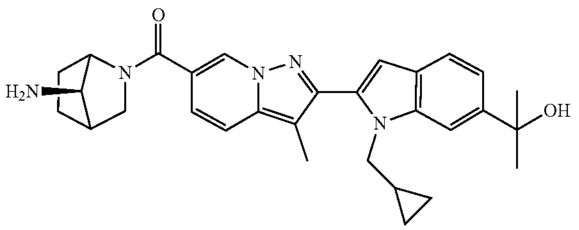 [SMILES: Cc1c(-c2cc3ccc(C(C)(C)O)cc3n2CC2CC2)nn2cc(C(=O)N3CC4CCC3[C@@H]4N)ccc12]

Intermediate 100A tert-Butyl-((7R)-2-(2-(6-acetyl-1-(cyclopropylmethyl)-1H-indol-2-yl)-3-methylpyrazolo[1,5-a]pyridine-6-carbonyl)-2-azabicyclo[2.2.1]heptan-7-yl) carbamate

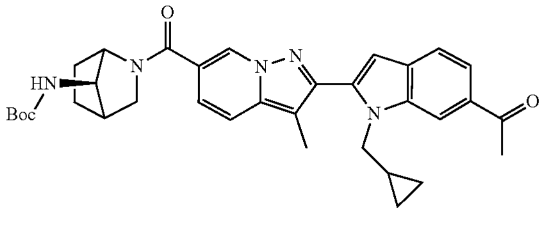 [SMILES: CC(=O)c1ccc2cc(-c3nn4cc(C(=O)N5CC6CCC5[C@@H]6NC(=O)OC(C)(C)C)ccc4c3C)n(CC3CC3)c2c1]

Intermediate 100A was prepared following a procedure similar to the preparation of Intermediate 97C (70 mg, 37%). LC-MS m/z: 582.4 $[M+H]^+$.

Intermediate 100B 1-(2-(6-((7R)-7-Amino-2-azabicyclo[2.2.1]heptane-2-carbonyl)-3-methylpyrazolo[1,5-a]pyridin-2-yl)-1-(cyclopropylmethyl)-1H-indol-6-yl)ethan-1-one

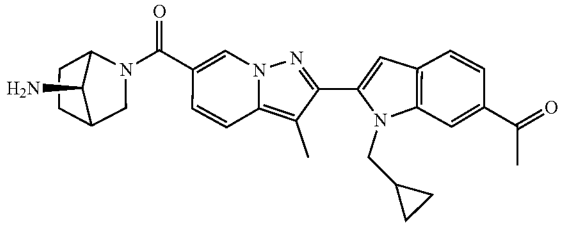 [SMILES: CC(=O)c1ccc2cc(-c3nn4cc(C(=O)N5CC6CCC5[C@@H]6N)ccc4c3C)n(CC3CC3)c2c1]

TFA (9.27 μL, 0.120 mmol) was added to a stirred solution of Intermediate 100A (70 mg, 0.120 mmol) in DCM (0.5 ml). The reaction mixture was stirred at a room temperature for 2 hours, and concentrated under reduced pressure to afford a crude product (30 mg, 52%). LC-MS m/z: 482.3 $[M+H]^+$.

Example 100

Methyl magnesium bromide (0.415 ml, 0.415 mmol) was added to a stirred solution of Intermediate 100B (100 mg, 0.208 mmol) in THF (3 ml) at 0° C. The reaction mixture was stirred for 3 hours, allowed to warm to a room temperature, stirred for 3 hours, quenched with saturated ammonium chloride (50 ml), and extracted with EtOAc (2×100 ml). The combined organic layers were dried over sodium sulphate, filtered, and the filtrate was concentrated under reduced pressure to afford the title compound. The crude compound was purified by prep-HPLC. The purified compound was further purified using RP-HPLC to afford the title compound (1.6 mg, 1.5%). LC-MS m/z: 498.4 [M+H]. HPLC retention time: 5.115 min (Method C). $^1H$ NMR (400 MHz, methanol-$d_4$) δ ppm: 8.73 (s, 1H), 7.74-7.64 (m, 2H), 7.57 (d, J=8.0 Hz, 1H), 7.31 (dd, J=1.0, 9.0 Hz, 1H), 7.24 (d, J=8.6 Hz, 1H), 6.72 (s, 1H), 4.42 (d, J=6.5 Hz, 2H), 4.33 (br s, 1H), 4.01 (s, 1H), 3.84-3.58 (m, 1H), 3.49 (s, 1H), 3.42 (s, 1H), 3.28-3.20 (m, 2H), 3.14 (d, J=1.5 Hz, 1H), 2.43 (s, 3H), 2.40-2.30 (m, 1H), 2.21 (s, 1H), 2.14-2.01 (m, 2H), 1.99-1.91 (m, 1H), 1.90 (s, 1H), 1.64 (s, 7H), 1.29 (s, 6H), 1.18-1.09 (m, 1H), 0.36-0.28 (m, 2H), 0.10 (s, 2H).

Example 101

((7R)-7-Amino-2-azabicyclo[2.2.1]heptan-2-yl)(2-(1-(cyclopropylmethyl)-6-(1,1,1-trifluoro-2-hydroxypropan-2-yl)-1H-indol-2-yl)-3-methylpyrazolo[1,5-a]pyridin-6-yl)methanone

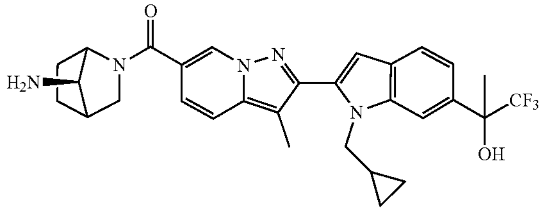 [SMILES: Cc1c(-c2cc3ccc(C(C)(O)C(F)(F)F)cc3n2CC2CC2)nn2cc(C(=O)N3CC4CCC3[C@@H]4N)ccc12]

Intermediate 101A tert-Butyl-((7R)-2-(2-(1-(cyclopropylmethyl)-6-(1,1,1-trifluoro-2-hydroxypropan-2-yl)-1H-indol-2-yl)-3-methylpyrazolo[1,5-a]pyridine-6-carbonyl)-2-azabicyclo[2.2.1]heptan-7-yl)carbamate

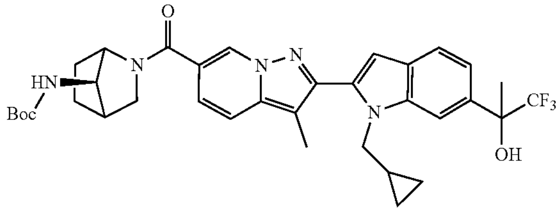 [SMILES: Cc1c(-c2cc3ccc(C(C)(O)C(F)(F)F)cc3n2CC2CC2)nn2cc(C(=O)N3CC4CCC3[C@@H]4NC(=O)OC(C)(C)C)ccc12]

$Me_3SiCF_3$ (430 μl, 0.860 mmol) was added to a stirred solution of Intermediate 100A (50 mg, 0.086 mmol) in THF (1 ml) at −78° C., followed by slow addition of TBAF (215 μl, 0.430 mmol). The reaction mixture was allowed to warm to a room temperature, stirred for 3 hours, quenched with water (100 ml), and extracted with EtOAc (2×100 ml). The combined organic layers were dried over sodium sulphate, filtered, and the filtrate was concentrated under reduced pressure to afford a crude title compound (30 mg, 54%). LC-MS m/z: 652.3 $[M+H]^+$.

Example 101

HCl (1 ml, 4 M in dioxane) was added to a stirred solution of Intermediate 101A (40 mg, 0.061 mmol) in dioxane (0.5 ml) at a room temperature. The reaction mixture was stirred for 2 hours, concentrated under reduced pressure, and the crude product obtained was purified using prep-HPLC. The purified product was further purified using RP-HPLC to afford the title compound (8.6 mg, 23%). LC-MS m/z: 552.3 [M+H]. HPLC retention time: 6.316 min (Method C). $^1H$ NMR (400 MHz, methanol-$d_4$) δ ppm: 8.80 (s, 1H), 8.73 (s, 1H), 7.82 (s, 1H), 7.73-7.59 (m, 2H), 7.36-7.29 (m, 2H), 6.76 (s, 1H), 5.05-4.88 (m, 1H), 4.43 (d, J=6.5 Hz, 2H), 4.33 (s, 1H), 4.00 (s, 1H), 3.72-3.63 (m, 1H), 3.29-3.20 (m, 4H), 2.43 (s, 3H), 2.31 (br s, 1H), 2.14-1.87 (m, 3H), 1.83 (s, 3H), 1.74-1.52 (m, 3H), 1.46-1.24 (m, 3H), 1.14-1.07 (m, 1H), 1.02 (t, J=7.5 Hz, 3H), 0.90 (s, 1H), 0.36-0.28 (m, 2H), 0.15-0.03 (m, 2H).

Example 102

((7R)-7-Amino-2-azabicyclo[2.2.1]heptan-2-yl)(2-(1-(cyclopropylmethyl)-6-(2-hydroxypropan-2-yl)-1H-pyrrolo[2,3-b]pyridin-2-yl)-3-methylpyrazolo[1,5-a]pyridin-6-yl)methanone

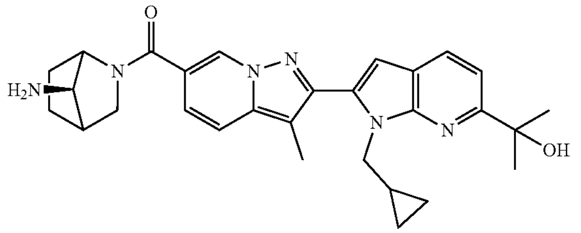 [SMILES: Cc1c(-c2cc3ccc(C(C)(C)O)nc3n2CC2CC2)nn2cc(C(=O)N3CC4CCC3[C@@H]4N)ccc12]

Intermediate 102A tert-Butyl-((7R)-2-(2-(6-acetyl-1-(cyclopropylmethyl)-1H-pyrrolo[2,3-b]pyridin-2-yl)-3-methylpyrazolo[1,5-a]pyridine-6-carbonyl)-2-azabicyclo[2.2.1]heptan-7-yl)carbamate

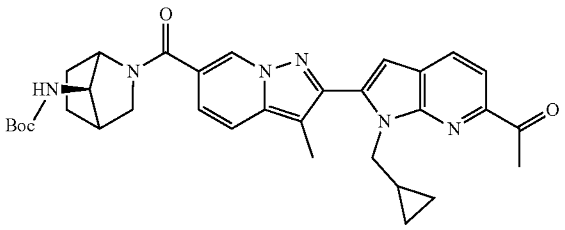 [SMILES: CC(=O)c1ccc2cc(-c3nn4cc(C(=O)N5CC6CCC5[C@@H]6NC(=O)OC(C)(C)C)ccc4c3C)n(CC3CC3)c2n1]

Intermediate 102A was prepared following a procedure similar to the preparation of Intermediate 97C (150 mg, 74%). LC-MS m/z: 583.34 $[M+H]^+$.

Intermediate 102B tert-Butyl-((7R)-2-(2-(1-(cyclopropylmethyl)-6-(2-hydroxypropan-2-yl)-1H-pyrrolo[2,3-b]pyridin-2-yl)-3-methylpyrazolo[1,5-a]pyridine-6-carbonyl)-2-azabicyclo[2.2.1]heptan-7-yl)carbamate

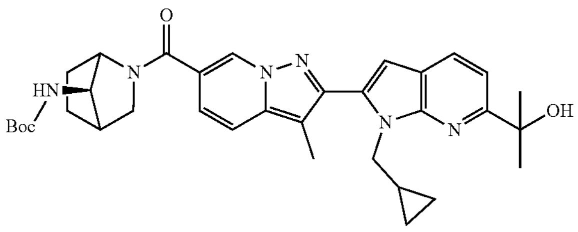 [SMILES: Cc1c(-c2cc3ccc(C(C)(C)O)nc3n2CC2CC2)nn2cc(C(=O)N3CC4CCC3[C@@H]4NC(=O)OC(C)(C)C)ccc12]

Intermediate 102B was prepared following a procedure similar to the preparation of Intermediate 97D (70 mg, 68%) LC-MS m/z: 599.4 $[M+H]^+$.

Example 102

Compound of Example 102 was prepared following a procedure similar to the preparation of a compound of Example 1 (12.7 mg, 22%) LC-MS m/z: 499.4 $[M+H]^+$. HPLC retention time: 5.846 min (Method C). $^1$H NMR (400 MHz, DMSO-$d_6$) δ ppm: 9.14-8.85 (m, 1H), 8.06 (d, J=8.5 Hz, 1H), 7.93-7.79 (m, 1H), 7.54 (d, J=8.5 Hz, 1H), 7.48-7.27 (m, 1H), 6.88 (s, 1H), 4.71-4.47 (m, 2H), 4.36-4.21 (m, 1H), 3.92-3.78 (m, 1H), 3.69-3.56 (m, 2H), 2.73 (s, 2H), 2.54 (s, 3H), 2.52-2.31 (m, 6H), 2.15-1.83 (m, 4H), 1.78-1.70 (m, 1H), 1.59 (s, 6H), 1.39-1.14 (m, 1H), 0.43-0.34 (m, 4H).

Example 103

((7R)-7-Amino-2-azabicyclo[2.2.1]heptan-2-yl)(2-(1-(cyclopropylmethyl)-6-(1,1,1-trifluoro-2-hydroxypropan-2-yl)-1H-pyrrolo[2,3-b]pyridin-2-yl)-3-methylpyrazolo[1,5-a]pyridin-6-yl)methanone

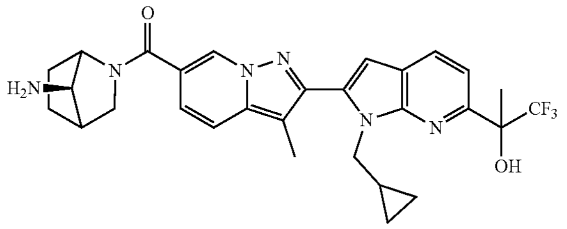 [SMILES: Cc1c(-c2cc3ccc(C(C)(O)C(F)(F)F)nc3n2CC2CC2)nn2cc(C(=O)N3CC4CCC3[C@@H]4N)ccc12]

Intermediate 103A tert-Butyl-((7R)-2-(2-(1-(cyclopropylmethyl)-6-(1,1,1-trifluoro-2-hydroxypropan-2-yl)-1H-pyrrolo[2,3-b]pyridin-2-yl)-3-methylpyrazolo[1,5-a]pyridine-6-carbonyl)-2-azabicyclo[2.2.1]heptan-7-yl)carbamate

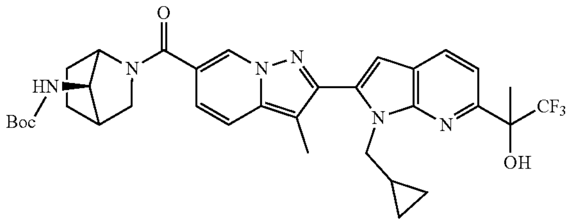 [SMILES: Cc1c(-c2cc3ccc(C(C)(O)C(F)(F)F)nc3n2CC2CC2)nn2cc(C(=O)N3CC4CCC3[C@@H]4NC(=O)OC(C)(C)C)ccc12]

Intermediate 103A was prepared following a procedure similar to the preparation of Intermediate 101A (50 mg, 45%). LC-MS m/z: 653.4 $[M+H]^+$.

Example 103

Compound of Example 103 was prepared following a procedure similar to the preparation of Example 101 (1.9 mg, 3%) LC-MS m/z: 553.4 $[M+H]^+$. HPLC retention time: 6.865 min (Method C). $^1$H NMR (400 MHz, methanol-$d_4$) δ ppm: 9.00-8.80 (m, 1H), 8.10 (d, J=8.5 Hz, 1H), 7.76 (br s, 1H), 7.52 (d, J=8.0 Hz, 1H), 7.39 (br s, 1H), 6.87 (s, 1H), 4.96-4.91 (m, 1H), 4.61 (dd, J=7.0, 3.5 Hz, 2H), 4.48-4.33 (m, 1H), 3.93 (s, 1H), 3.77 (br s, 1H), 2.72-2.84 (m, 2H), 2.49 (s, 3H), 2.23 (s, 1H), 2.01 (br s, 2H), 1.86 (s, 3H), 1.49-1.22 (m, 2H), 1.18 (br s, 1H), 0.35-0.12 (m, 4H).

Example 104

((7R)-7-Amino-2-azabicyclo[2.2.1]heptan-2-yl)(2-(1-(cyclopropylmethyl)-6-(1-hydroxyethyl)-1H-pyrrolo[2,3-b]pyridin-2-yl)-3-methylpyrazolo[1,5-a]pyridin-6-yl)methanone

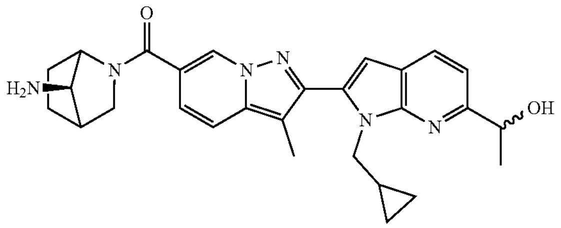 [SMILES: Cc1c(-c2cc3ccc(C(C)O)nc3n2CC2CC2)nn2cc(C(=O)N3CC4CCC3[C@@H]4N)ccc12]

Intermediate 104A tert-Butyl-((7R)-2-(2-(1-(cyclopropylmethyl)-6-(1-hydroxyethyl)-1H-pyrrolo[2,3-b]pyridin-2-yl)-3-methylpyrazolo[1,5-a]pyridine-6-carbonyl)-2-azabicyclo[2.2.1]heptan-7-yl)carbamate

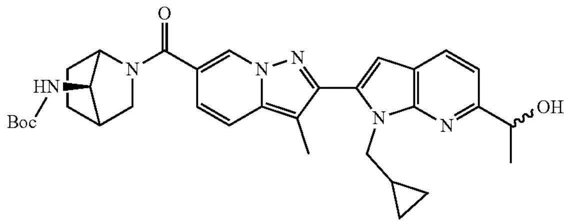 [SMILES: Cc1c(-c2cc3ccc(C(C)O)nc3n2CC2CC2)nn2cc(C(=O)N3CC4CCC3[C@@H]4NC(=O)OC(C)(C)C)ccc12]

Sodium borohydride (4.54 mg, 0.120 mmol) was added to a stirred solution of Intermediate 102A (70 mg, 0.120 mmol) in methanol. The reaction mixture was stirred at a room temperature for 3 hours, quenched with saturated ammonium chloride (100 ml), and extracted with EtOAc (2×100 ml). The combined organic layers were dried over sodium sulphate, filtered, and the filtrate was concentrated under reduced pressure to afford a crude title compound (40 mg, 57%). LC-MS m/z: 585.4 $[M+H]^+$.

Example 104

Compound of Example 104 was prepared following a procedure similar to the preparation of Example 1 (5.6 mg, 10%). LC-MS m/z: 485.4 $[M+H]^+$; HPLC retention time: 7.898 min (Method C). $^1H$ NMR (400 MHz, methanol-$d_4$) δ ppm: 8.89-8.83 (br, s, 1H), 8.03 (d, J=8.5 Hz, 1H), 7.75 (br, s, 1H), 7.37 (br, s, 1H), 7.31 (d, J=8.0 Hz, 1H), 6.80 (s, 1H), 5.10-4.92 (m, 1H), 4.74 (br, s, 1H), 4.60 (d, J=7.0 Hz, 1H), 4.44 (br, s, 1H), 3.92 (br, d, J=6.5 Hz, 1H), 3.77 (br, s, 1H), 3.67 (br, s, 1H), 3.58-3.38 (m, 1H), 2.87-2.63 (m, 1H), 2.48 (s, 3H), 2.21 (br, s, 1H), 1.87-2.02 (br,s, 2H), 1.64-1.53 (m, 3H), 1.42-1.24 (m, 2H), 1.24-1.06 (m, 1H), 0.34-0.18 (m, 4H).

Example 105

((3R,5R)-3-Amino-5-fluoropiperidin-1-yl)(2-(1-(cyclopropylmethyl)-6-(2-hydroxypropan-2-yl)-1H-pyrrolo[2,3-b]pyridin-2-yl)-3-methylpyrazolo[1,5-a]pyridin-6-yl)methanone

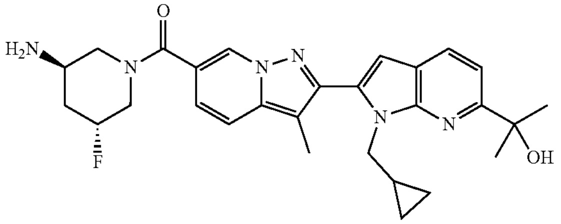 [SMILES: Cc1c(-c2cc3ccc(C(C)(C)O)nc3n2CC2CC2)nn2cc(C(=O)N3C[C@H](N)C[C@@H](F)C3)ccc12]

Intermediate 105A tert-Butyl-((3R,5R)-1-(2-(6-acetyl-1-(cyclopropylmethyl)-1H-pyrrolo[2,3-b]pyridin-2-yl)-3-methylpyrazolo[1,5-a]pyridine-6-carbonyl)-5-fluoropiperidin-3-yl)carbamate

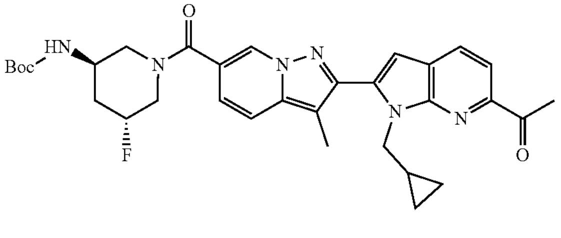 [SMILES: CC(=O)c1ccc2cc(-c3nn4cc(C(=O)N5C[C@H](F)C[C@@H](NC(=O)OC(C)(C)C)C5)ccc4c3C)n(CC3CC3)c2n1]

Intermediate 105A was prepared following a procedure similar to the preparation of Intermediate 97C (400 mg, 79%). LC-MS: 589.3 $[M+H]^+$.

Intermediate 105B tert-Butyl-((3R,5R)-1-(2-(1-(cyclopropylmethyl)-6-(2-hydroxypropan-2-yl)-1H-pyrrolo[2,3-b]pyridin-2-yl)-3-methylpyrazolo[1,5-a]pyridine-6-carbonyl)-5-fluoropiperidin-3-yl)carbamate

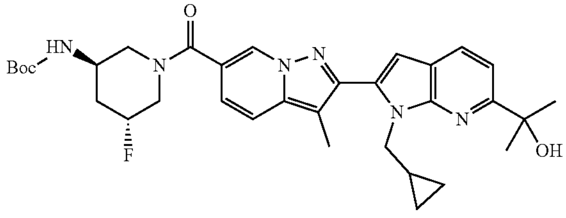 [SMILES: Cc1c(-c2cc3ccc(C(C)(C)O)nc3n2CC2CC2)nn2cc(C(=O)N3C[C@H](F)C[C@@H](NC(=O)OC(C)(C)C)C3)ccc12]

Intermediate 105B was prepared following a procedure similar to the preparation of Intermediate 97D (30 mg, 29%). LC-MS m/z: 605.3 [M+H]$^+$.

Example 105

Compound of Example 105 was prepared following a procedure similar to the preparation of the compound of Example 1 (14 mg, 20%). LC-MS m/z: 505.4 [M+H]$^+$; HPLC retention time: 7.101 min (Method C). $^1$H NMR (400 MHz, methanol-$d_4$) δ ppm: 8.74 (t, J=1.3 Hz, 1H), 8.01 (d, J=8.0 Hz, 1H), 7.75 (d, J=9.4 Hz, 1H), 7.42 (d, J=8.0 Hz, 1H), 7.28 (dd, J=1.5, 9.0 Hz, 1H), 6.78 (s, 1H), 5.06-5.01 (m, 1H), 4.98-4.88 (m, 1H), 4.84-4.73 (m, 2H), 4.57 (d, J=6.5 Hz, 3H), 4.51 (br d, J=3.5 Hz, 1H), 4.47-4.20 (m, 1H),3.63 (s, 1H), 3.55-3.36 (m, 3H), 3.31-3.28 (m, 1H), 3.18-3.14 (m, 1H), 2.99-2.83 (m, 1H), 2.53-2.41 (m, 4H), 1.97 (s, 2H), 1.83-1.64 (m, 8H), 1.39-1.28 (m, 1H), 1.25-1.14 (m, 1H), 0.93 (d, J=6.5 Hz, 1H), 0.36-0.25 (m, 4H)

Examples 106 and 107

Intermediates 106A and 107A tert-Butyl-((3R,5R)-1-(2-(1-(cyclopropylmethyl)-6-(1,1,1-trifluoro-2-hydroxypropan-2-yl)-1H-pyrrolo[2,3-b]pyridin-2-yl)-3-methylpyrazolo[1,5-a]pyridine-6-carbonyl)-5-fluoropiperidin-3-yl)carbamate

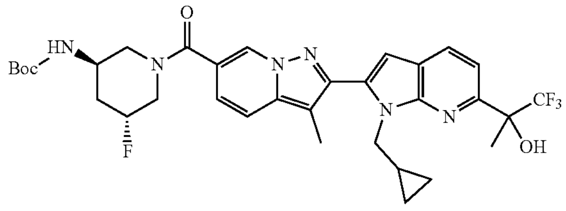 [SMILES: Cc1c(-c2cc3ccc(C(C)(O)C(F)(F)F)nc3n2CC2CC2)nn2cc(C(=O)N3C[C@H](F)C[C@@H](NC(=O)OC(C)(C)C)C3)ccc12]

Intermediates 106A and 107A were obtained following a procedure similar to the preparation of Intermediate 101A. Both the diastereomers were isolated by chiral SFC method. Diastereomer-1: (35 mg, 8%). LC-MS m/z: 659.4 [M+H]$^+$. Diastereomer-2: (35 mg, 8%). LC-MS m/z: 659.4 [M+H]$^+$.

Examples 106 and 107

((3R,5R)-3-Amino-5-fluoropiperidin-1-yl)(2-(1-(cyclopropylmethyl)-6-(1,1,1-trifluoro-2-hydroxypropan-2-yl)-1H-pyrrolo[2,3-b]pyridin-2-yl)-3-methylpyrazolo[1,5-a]pyridin-6-yl)methanone

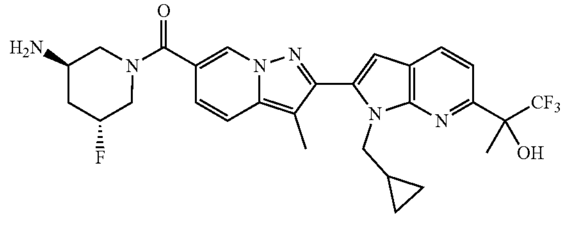 [SMILES: Cc1c(-c2cc3ccc(C(C)(O)C(F)(F)F)nc3n2CC2CC2)nn2cc(C(=O)N3C[C@H](N)C[C@@H](F)C3)ccc12]

TFA was added to the diastereomer 106A (35 mg) in DCM, and the reaction mixture was stirred at a room temperature for 2 hours The volatiles were removed under vacuum and the crude product was purified by HPLC. The purified product was further purified using RP-HPLC to afford a compound of Example 106 (30 mg, 94%). LC-MS m/z: 559.27 [M+H]$^+$; HPLC retention time: 7.046 min (Method C). $^1$H NMR (400 MHz, methanol-$d_4$) δ ppm: 8.79 (s, 1H), 8.10 (d, J=8.0 Hz, 1H), 7.78 (d, J=9.1 Hz, 1H), 7.52 (d, J=8.0 Hz, 1H), 7.30 (dd, J=9.0, 1.5 Hz, 1H), 6.87 (s, 1H), 4.80-4.88 (m, 1H), 4.64-4.50 (m, 2H), 3.72-3.42 (m, 2H), 3.11-2.95 (m, 1H), 2.50 (s, 3H), 1.96 (s, 1H), 1.86 (s, 4H), 1.31 (s, 3H), 1.39-1.15 (m, 1H), 1.24-1.12 (m, 1H), 0.36-0.26 (m, 4H).

Compound of Example 107 was prepared analogous to the compound of Example 106 (21 mg, 66%). LC-MS m/z: 559.27 [M+H]$^+$; HPLC retention time: 7.048 min (Method C). $^1$H NMR (400 MHz, methanol-$d_4$) δ ppm: 8.79 (s, 1H), 8.10 (d, J=8.0 Hz, 1H), 7.78 (d, J=9.1 Hz, 1H), 7.52 (d, J=8.0 Hz, 1H), 7.30 (dd, J=9.0, 1.5 Hz, 1H), 6.87 (s, 1H), 4.80-4.88 (m, 1H), 4.64-4.50 (m, 2H), 3.72-3.42 (m, 2H), 3.11-2.95 (m, 1H), 2.50 (s, 3H), 1.96 (s, 1H), 1.86 (s, 4H), 1.31 (s, 3H), 1.39-1.15 (m, 1H), 1.24-1.12 (m, 1H), 0.36-0.26 (m, 4H).

Example 108

((7R)-7-Amino-2-azabicyclo[2.2.1]heptan-2-yl)(2-(6-chloro-1-(cyclopropylmethyl)-1H-pyrrolo[2,3-b]pyridin-2-yl)-3-methylpyrazolo[1,5-a]pyrimidin-6-yl)methanone

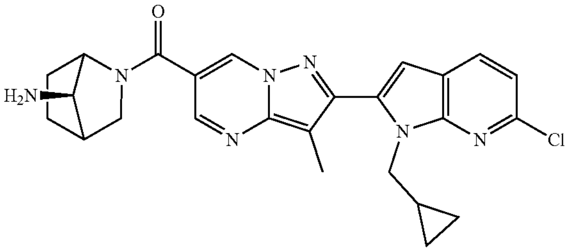 [SMILES: Cc1c(-c2cc3ccc(Cl)nc3n2CC2CC2)nn2cc(C(=O)N3CC4CCC3[C@@H]4N)cnc12]

Intermediate 108A

5-Bromo-4-methyl-1H-pyrazol-3-amine

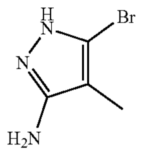

Borane dimethyl sulfide complex (3.04 ml, 32.0 mmol) was added to a stirred solution of ethyl 3-amino-5-bromo-1H-pyrazole-4-carboxylate (3.0 g, 12.82 mmol) in THF (30 ml) at 0° C. The reaction mixture was stirred for 1 hour, heated to 65° C. and stirred further for 16 hours, slowly quenched with methanol (5 ml) at a room temperature and stirred at 65° C. for 1 hour, the volatiles were removed under vacuum, and the residue obtained was washed with saturated brine solution and extracted with DCM (2×50 ml). The combined organic extracts were dried over sodium sulphate, filtered, and the filtrate was evaporated under reduced pressure to afford the title compound (1.55 g, 68%) as a white solid. LC-MS m/z: 176.0 $[M+H]^+$.

Intermediate 108B

Ethyl-2-bromo-3-methylpyrazolo[1,5-a]pyrimidine-6-carboxylate

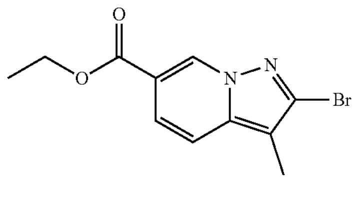 [SMILES: CCOC(=O)c1ccc2c(C)c(Br)nn2c1]

Acetic acid (5 ml) was added to a stirred solution of Intermediate 108A (0.8 g, 4.55 mmol) and Ethyl 2-formyl-3-oxopropanoate (0.655 g, 4.55 mmol) in ethanol (25 ml) at 30° C. The reaction mixture was stirred at 80° C. for 16 hours, evaporated to dryness, quenched with brine solution and extracted with DCM (2×50 ml). The combined organic extracts were dried over sodium sulphate, filtered, and the filtrate was evaporated under reduced pressure to afford the crude product, which was loaded onto a silica gel column (24 g) and purified using EtOAc in hexane (0-100%) in a gradient manner to afford the title compound (460 mg, 36%). LC-MS m/z: 285.9 $[M+H]^+$. $^1H$ NMR (400 MHz, $CDCl_3$) δ ppm: 9.2-9.1 (m, 1H), 8.9-8.8 (m, 1H), 4.5-4.4 (m, 2H), 2.3 (s, 3H), 1.5-1.4 (m, 3H).

Intermediate 108C

2-Bromo-3-methylpyrazolo[1,5-a]pyrimidine-6-carboxylic acid

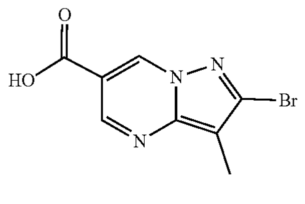

LiOH (388 mg, 16.19 mmol) in water (1 ml) was added to a stirred solution of Intermediate 108B (460 mg, 1.619 mmol) in THF (6.00 ml) and methanol (3 ml). The reaction mixture was stirred at a room temperature for 16 hours, evaporated to dryness, acidified with citric acid solution, and extracted with DCM (2×50 ml). The combined organic extracts were dried over sodium sulphate, filtered, and the filtrate was evaporated under reduced pressure to afford the title compound as a crude product (380 mg, 92%). LC-MS m/z: 257.0 $[M+H]^+$. $^1H$ NMR (400 MHz, MeOD) δ ppm: 9.21-9.20 (d, 1H, J=2.4 Hz), 8.95-8.94 (d, 1H, J=2.8 Hz), 2.4 (s, 3H).

Intermediate 108D tert-Butyl-((7R)-2-(2-bromo-3-methylpyrazolo[1,5-a]pyrimidine-6-carbonyl)-2-azabicyclo[2.2.1]heptan-7-yl)carbamate

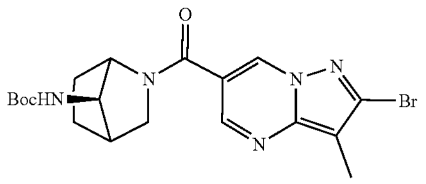 [SMILES: CCC1CN(C(=O)c2cnc3c(C)c(Br)nn3c2)C(CC)[C@@H]1NC(=O)OC(C)(C)C]

HATU (80 mg, 0.211 mmol) and DIPEA (0.092 ml, 0.527 mmol) were added to a stirred solution of Intermediate 108C (45 mg, 0.176 mmol), tert-butyl ((7R)-2-azabicyclo[2.2.1]heptan-7-yl)carbamate (44.8 mg, 0.211 mmol) in DMF (3 ml). The reaction mixture was stirred at a room temperature for 16 hours, evaporated to dryness, quenched with brine solution, and extracted with DCM (2×50 ml). The combined organic extracts were dried over sodium sulphate, filtered, and the filtrate was evaporated under reduced pressure to afford the crude material. The crude material was loaded onto a silica gel column (12 g) and purified using EtOAc in hexane (0-100%) in a gradient manner to afford the title compound (55 mg, 70%). LC-MS m/z: 396.1 [M-54]. $^1H$ NMR (400 MHz, MeOD) δ ppm: 8.73-8.72 (d, 1H, J=2.4 Hz), 8.70-8.69 (d, 1H, J=2.8 Hz), 3.80-3.76 (m, 1H), 3.27-3.23 (m, 1H), 3.15-2.96 (m, 2H), 2.53 (m, 1H), 2.35-2.34 (s, 3H), 1.91-1.61 (m, 4H), 1.40 (s, 9H).

Intermediate 108E tert-Butyl-((7R)-2-(2-(6-chloro-1-(cyclopropylmethyl)-1H-pyrrolo[2,3-b]pyridin-2-yl)-3-methylpyrazolo[1,5-a]pyrimidine-6-carbonyl)-2-azabicyclo[2.2.1]heptan-7-yl)carbamate

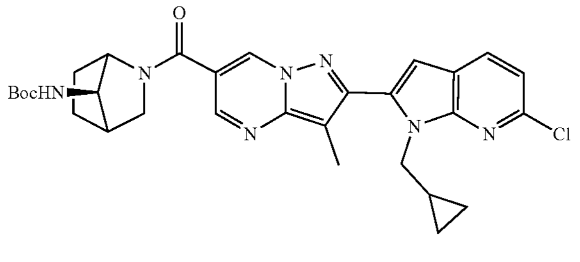 [SMILES: CCC1CN(C(=O)c2cnc3c(C)c(-c4cc5ccc(Cl)nc5n4CC4CC4)nn3c2)C(CC)[C@@H]1NC(=O)OC(C)(C)C]

$Pd(PPh_3)_4$ (10.78 mg, 9.33 μmol) was added to a stirred solution of Intermediate 108D (210 mg, 0.466 mmol), 6-chloro-1-(cyclopropylmethyl)-2-(trimethylstannyl)-1H-pyrrolo[2,3-b]pyridine (Intermediate-7, 215 mg, 0.583 mmol) and CuI (17.76 mg, 0.093 mmol) in dioxane (5 ml), and the reaction mixture was heated to 110° C. and stirred for 3 hours The reaction mixture was evaporated to dryness to afford the crude material. The crude material was loaded onto a silica gel column (12 g) and purified using EtOAc in hexane (0-100%) in a gradient manner to afford the title compound (220 mg, 82%). LC-MS m/z: 576.3 $[M+H]^+$. $^1H$ NMR (400 MHz, MeOD) δ ppm 7.7-7.6 (m, 1H), 7.5-7.3 (m, 1H), 7.2-7.1 (m, 1H), 7.0 (m, 1H), 6.6-6.4 (m, 1H), 4.02-

4.00 (m, 2H), 3.96-3.94 (m, 2H), 3.69-3.66 (m, 2H), 2.16-2.06 (s, 3H), 1.92 (m, 1H), 1.8-1.5 (m, 4H), 0.90-0.85 (m, 1H), 0.65-0.61 (m, 2H), 0.40-0.37 (m, 2H).

Example 108

TFA (0.033 ml, 0.434 mmol) was added to a stirred solution of Intermediate 108E (25 mg, 0.043 mmol) in DCM (5 ml). The reaction mixture was stirred at a room temperature for 16 hours, evaporated to dryness and the crude material was purified using prep-HPLC. The purified product was further purified using RP-HPLC to afford the title compound (5.5 mg, 27%). LC-MS m/z: 476.3 $[M+H]^+$. LC-MS retention time: 2.76 min, (Method H). $^1H$ NMR (400 MHz, DMSO-$d_6$) δ ppm: 9.3-9.1 (m, 1H), 8.7-8.6 (m, 1H), 8.1-8.0 (m, 1H), 7.2-7.1 (m, 1H), 6.9 (s, 1H), 4.7-4.6 (m, 2H), 4.5 (m, 1H), 4.4-4.1 (m, 1H), 3.9-3.5 (m, 2H), 2.6 (s, 3H), 2.55-2.45 (m, 1H), 2.2-2.0 (m, 2H), 1.2-1.1 (m, 1H), 1.0-0.8 (m, 2H), 0.4-0.3 (m, 2H).

Example 109

((7R)-7-Amino-2-azabicyclo[2.2.1]heptan-2-yl)(2-(1-(cyclopropylmethyl)-6-(2-fluoro-3-hydroxyphenyl)-1H-pyrrolo[2,3-b]pyridin-2-yl)-3-methylpyrazolo[1,5-a]pyrimidin-6-yl)methanone

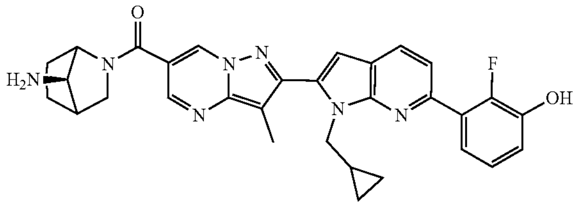 [SMILES: CCC1CN(C(=O)c2cnc3c(C)c(-c4cc5ccc(-c6cccc(O)c6F)nc5n4CC4CC4)nn3c2)C(CC)[C@@H]1N]

Intermediate 109A tert-Butyl-((7R)-2-(2-(1-(cyclopropylmethyl)-6-(2-fluoro-3-hydroxyphenyl)-1H-pyrrolo[2,3-b]pyridin-2-yl)-3-methylpyrazolo[1,5-a]pyrimidine-6-carbonyl)-2-azabicyclo[2.2.1]heptan-7-yl)carbamate

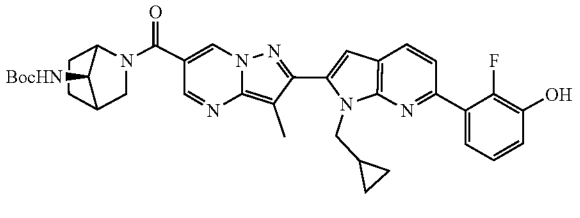 [SMILES: CCC1CN(C(=O)c2cnc3c(C)c(-c4cc5ccc(-c6cccc(O)c6F)nc5n4CC4CC4)nn3c2)C(CC)[C@@H]1NC(=O)OC(C)(C)C]

$Pd(PPh_3)_4$ (3.51 mg, 3.04 μmol) was added to a stirred solution of Intermediate 108E (35 mg, 0.061 mmol), 2-fluoro-3-(4,4,5,5-tetramethyl-1,3,2-dioxaborolan-2-yl) phenol (17.36 mg, 0.073 mmol) and $K_2CO_3$ (20.99 mg, 0.152 mmol) in 1,4-dioxane (4 ml). The reaction mixture was stirred at 85° C. for 3 hours, filtered through a celite bed, and the filtrate was evaporated to dryness to afford a crude material. The crude compound was used in the next step without further purification. LC-MS m/z: 652.4 $[M+H]^+$.

Example 109

TFA (0.047 ml, 0.614 mmol) was added to a stirred solution of Intermediate 109A (40 mg, 0.061 mmol) in DCM (5 ml). The reaction mixture was stirred at a room temperature for 16 hours, evaporated to dryness, and the crude material obtained was purified using RP-HPLC to afford the title compound (1.2 mg, 22%). LC-MS m/z: 552.3 $[M+H]^+$. LC-MS retention time: 1.70 min/1.48 min. (Methods E/F). $^1H$ NMR (400 MHz, DMSO-$d_6$) δ ppm: 9.8 (s, 1H), 9.4-9.2 (m, 1H), 8.7-8.6 (m, 1H), 8.2-8.1 (m, 1H), 7.6-7.5 (m, 1H), 7.4-7.3 (m, 1H), 7.2-7.1 (m, 1H), 7.1-7.0 (m, 2H), 4.7-4.5 (m, 2H), 4.4-4.3 (m, 2H), 3.9-3.8 (m, 1H), 2.3 (s, 3H), 1.9-1.8 (m, 2H), 1.7-1.6 (m, 2H), 1.5 (m, 1H), 1.2-1.1 (m, 1H), 0.9-0.8 (m, 2H), 0.4-0.3 (m, 2H).

Compounds of Examples 110 to 112 in Table 13 were prepared following a procedure similar to the preparation of a compound of Example 109, by Suzuki coupling of Intermediate 108E with appropriate boronate acid.

TABLE 13

| Example | Structure<br>Name<br>Analytical Data: LC-MS m/z $[M + H]^+$; HPLC retention time 1 (HPLC method 1), HPLC retention time 2 (HPLC method 2), |
|---|---|
| 110 | 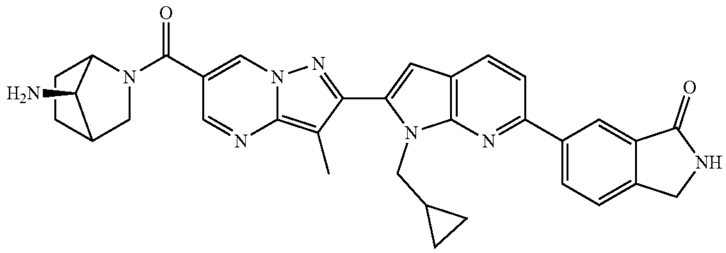 [SMILES: Cc1c(-c2cc3ccc(-c4ccc5c(c4)C(=O)NC5)nc3n2CC2CC2)nn2cc(C(=O)N3CC4CCC3[C@@H]4N)cnc12]<br>6-(2-(6-((7R)-7-Amino-2-azabicyclo[2.2.1]heptane-2-carbonyl)-3-methylpyrazolo[1,5-a]pyrimidin-2-yl)-1-(cyclopropylmethyl)-1H-pyrrolo[2,3-b]pyridin-6-yl)isoindolin-1-one<br>Analytical Data: 573.3, 1.346 min (Method A), 1.341 min (Method B) |

TABLE 13-continued

| Example | Structure<br>Name<br>Analytical Data: LC-MS m/z [M + H]$^+$; HPLC retention time 1 (HPLC method 1), HPLC retention time 2 (HPLC method 2), |
|---|---|
| 111 | 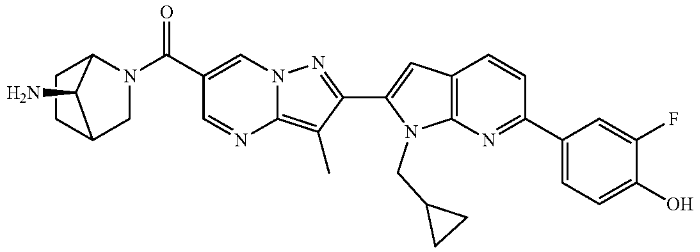 [SMILES: Cc1c(-c2cc3ccc(-c4ccc(O)c(F)c4)nc3n2CC2CC2)nn2cc(C(=O)N3CC4CCC3[C@@H]4N)cnc12]<br>((7R)-7-Amino-2-azabicyclo[2.2.1]heptan-2-yl)(2-(1-(cyclopropylmethyl)-6-(3-fluoro-4-hydroxyphenyl)-1H-pyrrolo[2,3-b]pyridin-2-yl)-3-methylpyrazolo[1,5-a]pyrimidin-6-yl)methanone<br>Analytical Data: 552.3, 1.626 min (Method A), 1.481 min (Method B) |
| 112 | 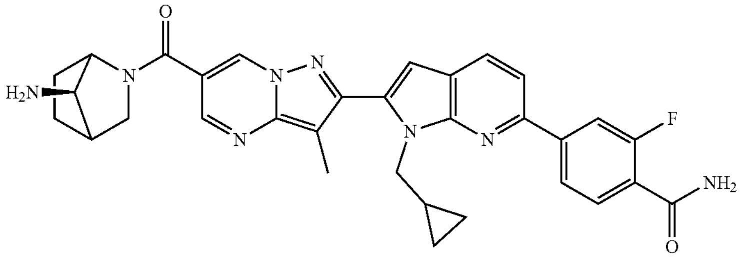 [SMILES: Cc1c(-c2cc3ccc(-c4ccc(C(N)=O)c(F)c4)nc3n2CC2CC2)nn2cc(C(=O)N3CC4CCC3[C@@H]4N)cnc12]<br>4-(2-(6-((7R)-7-Amino-2-azabicyclo[2.2.1]heptane-2-carbonyl)-3-methylpyrazolo[1,5-a]pyrimidin-2-yl)-1-(cyclopropylmethyl)-1H-pyrrolo[2,3-b]pyridin-6-yl)-2-fluorobenzamide<br>Analytical Data: 579.3, 1.567 min (Method A), 1.366 min (Method B) |

Example 113

((7R)-7-Amino-2-azabicyclo[2.2.1]heptan-2-yl)(2-(1-(cyclopropylmethyl)-1H-indol-2-yl)-4-methoxy-3-methylpyrazolo[1,5-a]pyrazin-6-yl)methanone

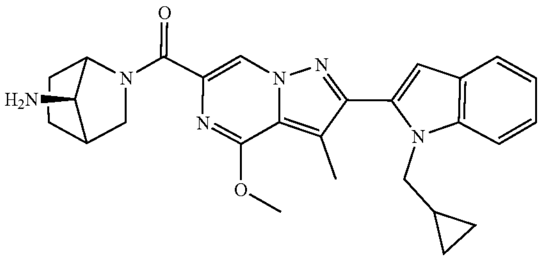 [SMILES: CCC1CN(C(=O)c2cn3nc(-c4cc5ccccc5n4CC4CC4)c(C)c3c(OC)n2)C(CC)[C@@H]1N]

Intermediate 113A

Ethyl-5-bromo-4-methyl-1H-pyrazole-3-carboxylate

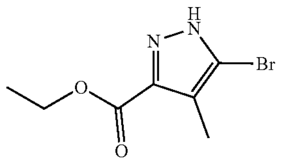

Bromine (3.34 ml, 64.9 mmol) was added to a stirred suspension of ethyl 4-methyl-1H-pyrazole-3-carboxylate (10.0 g, 64.9 mmol) in water (50 ml). The reaction mixture was stirred at a room temperature for 2 hours, diluted with EtOAc (50 ml), washed with saturated $NaHCO_3$ solution (20 ml), brine, dried over sodium sulfate, filtered, and the filtrate was concentrated in vacuum. The crude product thus obtained was purified using a silica gel column (120 g, Redisep® $SiO_2$ column, eluting with 10% EtOAc in n-hexane) to obtain (9.0 g, 60%) of title compound as a white solid. LC-MS m/z: 231.0 [M−H]$^+$. $^1$H NMR (400 MHz, DMSO-$d_6$) δ ppm: 14.08 (br s, 1H), 4.32 (q, J=7.03 Hz, 2H), 2.16 (s, 3H), 1.31 (t, J=7.03 Hz, 3H).

Intermediate 113B

Ethyl-3-bromo-4-methyl-1-(2-oxopropyl)-1H-pyrazole-5-carboxylate (A2115-423)

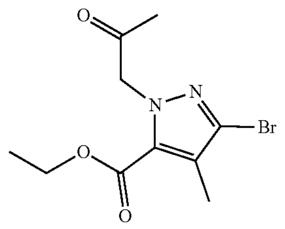 [SMILES: CCOC(=O)c1c(C)c(Br)nn1CC(C)=O]

$K_2CO_3$ (6.40 g, 46.3 mmol) was added to a stirred solution of Intermediate 113A (9.0 g, 38.6 mmol) in DMF (30 ml), followed by the addition of 1-chloropropan-2-one (3.25 ml, 38.6 mmol). The resulting reaction mixture was stirred at a room temperature for 1 hour, diluted with water (20 ml), and extracted with EtOAc (3×30 ml). The combined organic layers were washed with brine, dried over sodium sulfate, filtered, and the filtrate was concentrated under reduced pressure. The crude product thus obtained was purified using a silica gel column (120 g, Redisep® $SiO_2$ column, eluting with 14% EtOAc in n-hexane) to afford the title compound 6.5 g (58%) as off-white solid. LC-MS m/z: 288.9 $[M+H]^+$. $^1H$ NMR (400 MHz, DMSO-$d_6$) δ ppm: 5.38 (s, 2H), 4.26 (q, J=7.03 Hz, 2H), 2.18 (d, J=1.00 Hz, 6H), 1.28 (t, J=7.03 Hz, 3H).

Intermediate 113C

2-Bromo-3,6-dimethylpyrazolo[1,5-c]pyrazin-4(5H)-one

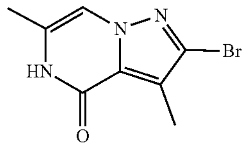

Ammonium acetate (34.7 g, 450 mmol) was added to a stirred solution of Intermediate 113B (6.5 g, 22.48 mmol) in acetic acid (15.0 m). The reaction mixture was stirred at 120° C. for 16 hours, diluted with water (100 ml), and the resulting solids were filtered off and dried under vacuum to obtain 4.2 g (77%) of the title compound as off-white solid. LC-MS m/z: 240.1 $[M-H]^+$. $^1H$ NMR (400 MHz, DMSO-$d_6$) δ ppm: 11.28 (br, s, 1H), 7.42 (s, 1H), 2.34 (s, 3H), 2.07 (s, 3H).

Intermediate 113D

2-Bromo-4-methoxy-3,6-dimethylpyrazolo[1,5-c] pyrazine (A2115-429-1)

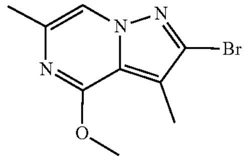

$POCl_3$ (2.310 ml, 24.79 mmol) was added to the Intermediate 113C (2.0 g, 8.26 mmol). The reaction mixture solution was stirred at 115° C. for 2 hours, concentrated to dryness to obtain Intermediate 2-bromo-4-chloro-3,6-dimethylpyrazolo[1,5-a]pyrazine as a brown solid. LC-MS retention time: 1.72 min.; m/z: 259.9 $[M+H]^+$. Sodium methoxide in methanol (5.4 M, 7.65 ml, 41.3 mmol) was added to the crude product obtained above in methanol (5 ml) at 0° C., and the reaction mixture was stirred at a room temperature for 16 hours, diluted with water (20 ml) and extracted with EtOAc (2×20 ml). The combined organic layers were washed with brine, dried over sodium sulfate, filtered, and concentrated in vacuum. The crude product was purified using a silica gel column (24 g, Redisep® $SiO_2$ column, eluting with 14% EtOAc in n-hexane) to afford 1.8 g (85%) of the title compound as a brown solid. LC-MS m/z: 256.0 $[M+H]^+$. $^1H$ NMR (400 MHz, DMSO-$d_6$) δ ppm: 8.12 (s, 1H), 4.01 (s, 3H), 2.43-2.33 (m, 6H).

Intermediate 113E

2-Bromo-4-methoxy-3-methylpyrazolo[1,5-a]pyrazine-6-carbaldehyde

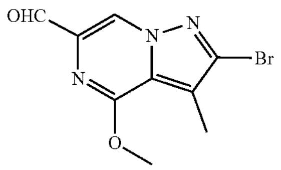

Selenium dioxide (1.430 g, 12.89 mmol) was added to a stirred solution of Intermediate 113D (3.0 g, 11.71 mmol) in 1,4-dioxane (10 ml). The reaction mixture was stirred at 110° C. for 16 hours, filtered through a celite bed, and the filtrate was concentrated to obtain 2 g of the crude title compound, which was used in the next step without further purification. LC-MS m/z: 270.0 $[M+H]^+$.

Intermediate 113F

Methyl-2-bromo-4-methoxy-3-methylpyrazolo[1,5-a]pyrazine-6-carboxylate

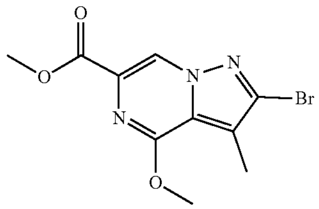 [SMILES: COC(=O)c1cn2nc(Br)c(C)c2c(OC)n1]

Oxone (5.92 g, 9.63 mmol) was added to a stirred solution of Intermediate 113E (2.0 g, 7.41 mmol) in MeOH (8 ml). The reaction mixture was stirred at 70° C. for 6 hours, concentrated under reduced pressure. The residue thus obtained was diluted with water (10 ml), and extracted with EtOAc (2×20 ml). The combined organic layers were washed with brine, dried over sodium sulfate, filtered, and the filtrate was concentrated in vacuum. The crude product thus obtained was purified using a silica gel column (24 g Redisep® $SiO_2$ column, eluting with 14% EtOAc in n-hexane) to afford 0.32 g (14%) of the title compound as off-white solid. LC-MS m/z: 300 $[M+H]^+$. $^1H$ NMR (400 MHz, DMSO-$d_6$) δ ppm: 8.90 (s, 1H), 4.09 (s, 3H), 3.88 (s, 3H), 2.34 (s, 3H).

Intermediate 113G

Methyl-2-(1-(tert-butoxycarbonyl)-1H-indol-2-yl)-4-methoxy-3-methylpyrazolo[1,5-a]pyrazine-6-carboxylate

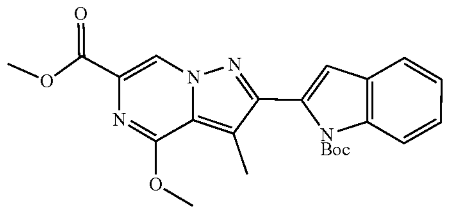 [SMILES: COC(=O)c1cn2nc(-c3cc4ccccc4n3C(=O)OC(C)(C)C)c(C)c2c(OC)n1]

(1-(tert-Butoxycarbonyl)-1H-indol-2-yl)boronic acid (239 mg, 0.916 mmol) and potassium phosphate tribasic in water (2M, 1.041 ml, 2.083 mmol) were added to a stirred solution of Intermediate 113F (250 mg, 0.833 mmol) in 1,4-dioxane (4 ml). The solution was degassed with argon and $Pd(Ph_3)_4$ (67.4 mg, 0.058 mmol) was added to this solution. The reaction mixture was stirred at 100° C. for 10 hours, diluted with water (10 ml), and extracted with 10% MeOH in DCM (2×30 ml). The combined organic layers were washed with brine, dried over sodium sulfate, filtered, and concentrated in vacuum to afford the title compound (280 mg, crude). The crude product was used in the next step without further purification. LC-MS m/z: 437.4 $[M+H]^+$. $^1H$ NMR (400 MHz, DMSO-$d_6$) δ ppm: 9.01(s, 1H), 7.65-7.01 (m, 5H), 4.13 (s, 3H), 3.90 (s, 3H), 2.70 (s, 3H), 1.24 (s, 9H).

Intermediate 113H

Methyl-2-(1H-indol-2-yl)-4-methoxy-3-methylpyrazolo[1,5-a]pyrazine-6-carboxylate

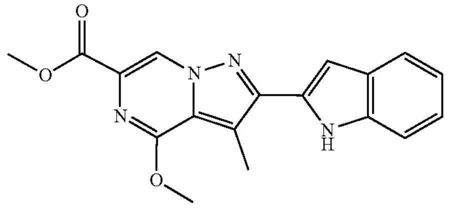 [SMILES: COC(=O)c1cn2nc(-c3cc4ccccc4[nH]3)c(C)c2c(OC)n1]

TFA (0.494 ml, 6.42 mmol) was added to a stirred suspension of Intermediate 113G (280 mg, 0.642 mmol) in DCM (5 ml). The reaction mixture was stirred at a room temperature for 16 hours, concentrated to remove the excess TFA, and the residue thus obtained was diluted with water (5 ml) and extracted with DCM (2×15 ml). The combined organic layers were washed with saturated $NaHCO_3$ solution, brine, dried over sodium sulfate, filtered, and the filtrate was concentrated in vacuum to afford 160 mg (56%) of the title compound as a brown solid. LC-MS m/z: 337.2 $[M+H]^+$. $^1H$ NMR (400 MHz, methanol-$d_4$) δ ppm: 8.82 (s, 1H), 7.68-7.53 (m, 4H), 6.92 (s, 1H), 4.21 (s, 3H), 3.98 (s, 3H), 2.72 (s, 3H).

Intermediate 113I 2-(1-(Cyclopropylmethyl)-1H-indol-2-yl)-4-methoxy-3-methylpyrazolo[1,5-a]pyrazine-6-carboxylic acid

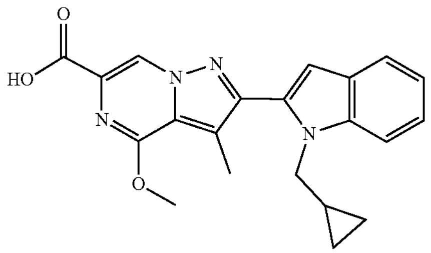 [SMILES: COc1nc(C(=O)O)cn2nc(-c3cc4ccccc4n3CC3CC3)c(C)c12]

Sodium hydride (23.19 mg, 0.580 mmol) was added to a stirred solution of Intermediate 113H (130 mg, 0.387 mmol) in DMF (1 ml). The reaction mixture was stirred at 0° C. for 5 min, followed by the addition of (Bromomethyl)cyclopropane (62.6 mg, 0.464 mmol). The reaction mixture was stirred at a room temperature for 16 hours, diluted with water (5 ml), and extracted with EtOAc (2×10 ml). The combined organic layers were washed with 1N HCl, brine, dried over sodium sulfate, filtered, and the filtrate was concentrated in vacuum to afford the crude title compound (140 mg) as brown solid. LC-MS m/z: 377 $[M+H]^+$. $^1H$ NMR (400 MHz, DMSO-$d_6$) δ ppm: 11.66 (s, 1H), 8.84 (s, 1H), 7.71-7.27 (m, 4H), 6.85 (s, 1H), 4.40 (d, J=6.53 Hz, 2H), 4.14 (s, 3H), 2.73 (s, 3H), 0.86 (s, 1H), 0.25-0.39 (m, 2H), 0.15 (q, J=4.69 Hz, 2H).

Intermediate 113J tert-Butyl-((7R)-2-(2-(1-(cyclopropylmethyl)-1H-indol-2-yl)-4-methoxy-3-methylpyrazolo[1,5-a]pyrazine-6-carbonyl)-2-azabicyclo[2.2.1]heptan-7-yl) carbamate

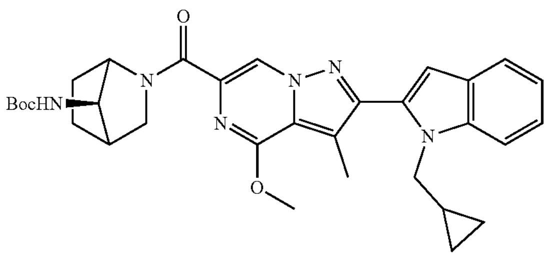 [SMILES: COc1nc(C(=O)N2CC3CCC2[C@@H]3NC(=O)OC(C)(C)C)cn2nc(-c3cc4ccccc4n3CC3CC3)c(C)c12]

HATU (106 mg, 0.279 mmol), tert-butyl ((7R)-2-azabicyclo[2.2.1]heptan-7-yl)carbamate (47.4 mg, 0.223 mmol) and DIPEA (0.065 ml, 0.372 mmol) were added to a stirred solution of Intermediate 113I (70 mg, 0.186 mmol) in DMF (1 ml). The reaction mixture was stirred at a room temperature for 2 hours, diluted with water (5 ml), and extracted with EtOAc (2×10 ml). The combined organic layers were washed with brine, dried over sodium sulfate, filtered, and the filtrate was concentrated in vacuum to afford the crude title compound (70 mg). LC-MS m/z: 571.3 $[M+H]^+$. $^1H$ NMR (400 MHz, DMSO-$d_6$) δ ppm: 8.82 (dd, J=4.27, 1.25 Hz, 1H), 8.67-8.60(m, 1H), 7.61-7.57 (m, 2H), 7.21-7.06

(m, 2H), 6.87 (s, 1H), 4.46-4.36 (m, 3H), 4.16-4.08 (m, 3H), 3.58-3.48 (m, 1H), 3.39-3.35 (m, 1H), 3.29-3.21 (m, 2H), 2.72-2.68 (m, 1H), 2.58-2.55 (m, 2H), 2.46-2.42 (m, 2H), 1.98-1.82 (m, 1H), 1.31-1.48 (m, 9H), 0.92-0.86 (m, 1H), 0.50 (dd, J=8.03, 1.51 Hz, 2H), 0.13-0.33 (m, 2H).

Example 113

TFA (0.094 ml, 1.227 mmol) was added to a stirred solution of Intermediate 113J (70 mg, 0.123 mmol) in DCM (3 ml). The resulting solution was stirred at a room temperature for 16 hours, concentrated, and the crude material thus obtained was purified using preparative LC-MS. The purified product was further purified using RP-HPLC to afford 14.7 mg (25%) of the title compound. LC-MS m/z: 471.3 $[M+H]^+$. LC-MS retention time: 2.067 min (Method G), 1.780 min (Method F). $^1H$ NMR (400 MHz, DMSO-$d_6$) δ ppm: 8.72-8.56 (m, 1H), 7.62 (t, J=7.5 Hz, 2H), 7.22 (t, J=7.6 Hz, 1H), 7.13-7.04 (m, 1H), 6.83 (s, 1H), 4.57 (br, s, 1H), 4.39 (br d, J=6.6 Hz, 2H), 4.16-4.04 (m, 3H), 3.90 (s, 2H), 3.63-3.51 (m, 1H), 3.19 (br, s, 1H), 3.10 (br, d, J=11.7 Hz, 1H), 2.54 (s, 3H), 2.26-2.04 (m,2H), 2.01-1.84 (m, 2H), 1.46-1.34 (m, 1H), 1.15-1.02 (m, 1H), 0.29 (br, d, J=8.1 Hz, 2H), 0.14 (br, d, J=4.6 Hz, 2H).

Example 114

((3R,5R)-3-Amino-5-fluoropiperidin-1-yl)(2-(1-(cyclopropylmethyl)-1H-indol-2-yl)-4-methoxy-3-methylpyrazolo[1,5-a]pyrazin-6-yl)methanone

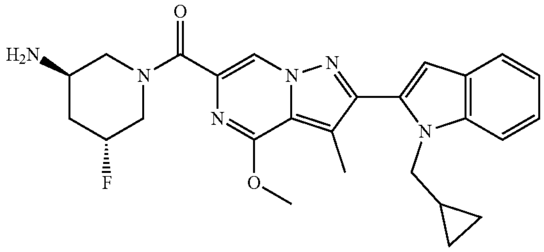 [SMILES: COc1nc(C(=O)N2C[C@H](N)C[C@@H](F)C2)cn2nc(-c3cc4ccccc4n3CC3CC3)c(C)c12]

Compound of Example 114 was prepared following a procedure similar to the preparation of a compound of Example 113, by coupling Intermediate 113I with the appropriate amine. LC-MS m/z: 477.3 $[M+H]^+$, LC-MS retention time: 1.7 min (UPLC).

Example 115

((7R)-7-Amino-2-azabicyclo[2.2.1]heptan-2-yl)(2-(1-(cyclopropylmethyl)-1H-pyrrolo[2,3-b]pyridin-2-yl)-4-methoxy-3-methylpyrazolo[1,5-a]pyrazin-6-yl)methanone

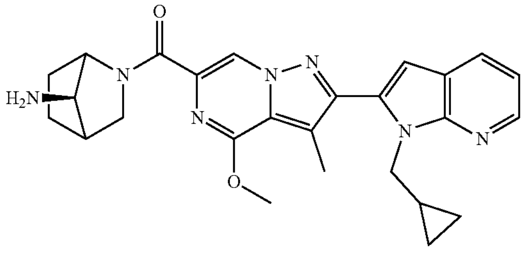 [SMILES: COc1nc(C(=O)N2CC3CCC2[C@@H]3N)cn2nc(-c3cc4cccnc4n3CC3CC3)c(C)c12]

Intermediate 115A

Methyl-2-(1-(cyclopropylmethyl)-1H-pyrrolo[2,3-b]pyridin-2-yl)-4-methoxy-3-methylpyrazolo[1,5-a]pyrazine-6-carboxylate

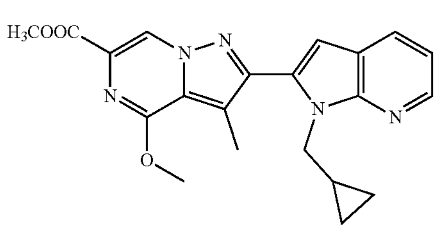

1-(Cyclopropylmethyl)-2-(trimethylstannyl)-1H-pyrrolo[2,3-b]pyridine (Intermediate 7, 167 mg, 0.500 mmol) was added to a stirred solution of Intermediate 113F (150 mg, 0.500 mmol) in 1,4-dioxane (3 ml). The reaction mixture was degassed with argon, followed by the addition of $Pd(Ph_3)_4$ (57.8 mg, 0.050 mmol). The reaction mixture was stirred at 110° C. for 16 hours, diluted with water (5 ml), and extracted with EtOAc (2×10 ml). The combined organic layers were washed with brine, dried over sodium sulfate, filtered and concentrated in vacuum to obtain the crude title compound (200 mg). LC-MS m/z: 392.2 $[M+H]^+$.

Intermediate 115B 2-(1-(Cyclopropylmethyl)-1H-pyrrolo[2,3-b]pyridin-2-yl)-4-methoxy-3-methylpyrazolo[1,5-a]pyrazine-6-carboxylic acid

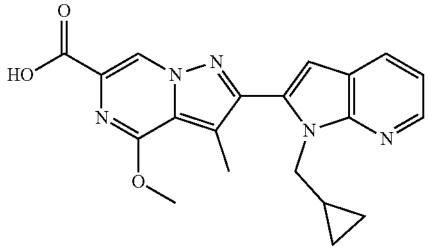 [SMILES: COc1nc(C(=O)O)cn2nc(-c3cc4cccnc4n3CC3CC3)c(C)c12]

Sodium hydroxide in water (1.277 ml, 2.55 mmol) was added to a stirred solution of Intermediate 115A (200 mg, 0.511 mmol) in THF (3 ml). The resulting solution was stirred at a room temperature for 1 hour, acidified with 1N HCl (3.0 ml), and extracted with EtOAc (2×10 ml). The combined organic layers were washed with brine, dried over sodium sulfate, filtered, and the filtrate was concentrated in vacuum. The compound thus obtained was washed with diethyl ether (5 ml) to remove impurities and dried to afford (110 mg) of the title compound. LC-MS m/z: 378.2 $[M+H]^+$. $^1H$ NMR (400 MHz, DMSO-$d_6$) δ ppm: 13.31-13.14 (m, 1H), 8.90 (s, 1H), 8.40(s, 1H), 7.72-7.14 (m, 2H), 6.89 (s, 1H), 4.62-4.48 (m, 2H), 4.36-4.08 (m,3H), 2.43-2.22 (m, 3H), 1.05-0.97 (m, 1H), 0.57-0.32 (m, 2H), 0.30-0.12 (m, 2H).

Intermediate 115C tert-Butyl-((7R)-2-(2-(1-(cyclopropylmethyl)-1H-pyrrolo[2,3-b]pyridin-2-yl)-4-methoxy-3-methylpyrazolo[1,5-a]pyrazine-6-carbonyl)-2-azabicyclo[2.2.1]heptan-7-yl)carbamate

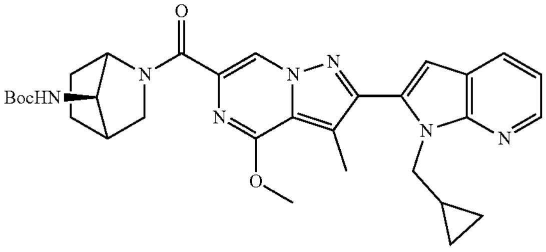 [SMILES: COc1nc(C(=O)N2CC3CCC2[C@@H]3NC(=O)OC(C)(C)C)cn2nc(-c3cc4cccnc4n3CC3CC3)c(C)c12]

HATU (76 mg, 0.199 mmol), tert-butyl ((7R)-2-azabicyclo[2.2.1]heptan-7-yl)carbamate (33.8 mg, 0.159 mmol) and DIPEA (0.046 ml, 0.265 mmol) were added to a stirred solution of Intermediate 115B (50 mg, 0.132 mmol) in DMF (1 ml). The reaction mixture was stirred at a room temperature for 2 hours, diluted with water (5 ml), and extracted with EtOAc (2×10 ml). The combined organic layers were washed with brine, dried over sodium sulfate, filtered, and the filtrate was concentrated in vacuum. The crude product was purified using a silica gel column (24 g, Redisep® $SiO_2$ column, eluting with 4% methanol in DCM to afford the title compound (0.050 g, 66%). LC-MS m/z: 572.3 $[M+H]^+$. $^1H$ NMR (400 MHz, DMSO-$d_6$) δ ppm: 8.68 (s, 1H), 8.35-8.33 (m, 1H), 8.09-8.04 (m, 1H), 7.68-7.51 (m, 1H), 7.20-7.14 (m, 1H), 6.89 (s, 1H), 4.53-4.43 (m, 2H), 4.12 (s, 3H), 4.10-4.06 (m, 1H), 3.72-3.47 (m, 3H), 2.69 (s, 3H), 1.97-1.82 (m, 3H), 1.40-1.29 (m, 9H), 1.26-1.21 (m, 2H), 1.20-1.10 (m, 1H), 0.34-0.16 (m, 4H).

Example 115

TFA (0.067 ml, 0.875 mmol) was added to a stirred solution of Intermediate 115C (50 mg, 0.087 mmol) in DCM (3 ml). The resulting solution was stirred at a room temperature for 16 hours, concentrated, and the crude product thus obtained was purified using preparative LC-MS. The purified product was further purified using RP-HPLC to afford 17.5 mg (42%) of the title compound. LC-MS m/z: 472.3 $[M+H]^+$, retention time: 1.78 min (Method G), 1.338 min (Method F). $^1H$ NMR (400 MHz, DMSO-$d_6$) δ ppm: 8.65 (s, 1H), 8.34 (dd, J=1.5, 4.6 Hz, 1H), 8.06 (dd, J=1.5, 7.8 Hz, 1H), 7.17 (dd, 7.8 Hz, 1H),6.89 (s, 1H), 4.54-4.44 (m, 3H), 4.20 (s, 1H), 4.16-4.05 (m, 3H), 3.60 (d, J=10.3 Hz, 1H), 3.56-3.51 (m, 1H), 3.17 (s, 1H), 3.09 (d, J=11.2 Hz, 1H), 2.61-2.55 (m, 3H), 2.24-2.06 (m, 2H), 2.01-1.83 (m, 2H), 1.64-1.34 (m, 1H), 1.25-1.12 (m, 1H), 0.33-0.16 (m, 4H).

Compounds of Examples 116 and 117 in Table 14 were prepared following a procedure similar to the preparation of a compound of Example 115, by coupling of Intermediate 115B with appropriate amine.

TABLE 14

| Example | Structure<br>Name<br>Analytical Data: LC-MS m/z $[M + H]^+$; HPLC retention time (HPLC method) |
|---|---|
| 116 | 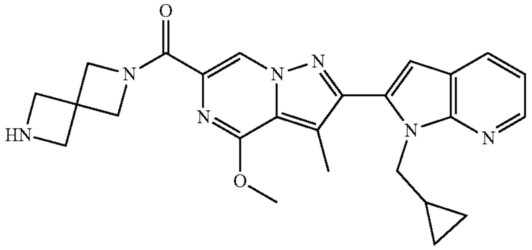 [SMILES: COc1nc(C(=O)N2CC3(CNC3)C2)cn2nc(-c3cc4cccnc4n3CC3CC3)c(C)c12]<br>(2-(1-(Cyclopropylmethyl)-1H-pyrrolo[2,3-b]pyridin-2-yl)-4-methoxy-3-methylpyrazolo[1,5-a]pyrazin-6-yl)(2,6-diazaspiro[3.3]heptan-2-yl)methanone<br>Analytical Data: 472.3, 1.4 min (Method F) |
| 117 | 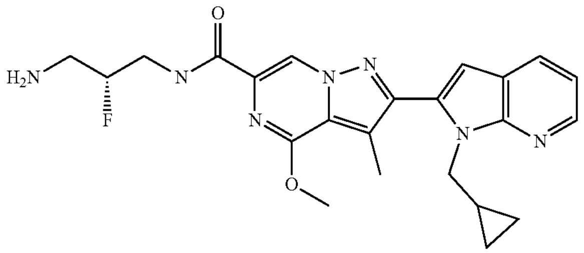 [SMILES: COc1nc(C(=O)NC[C@H](F)CN)cn2nc(-c3cc4cccnc4n3CC3CC3)c(C)c12]<br>(R)-N-(3-Amino-2-fluoropropyl)-2-(1-(cyclopropylmethyl)-1H-pyrrolo[2,3-b]pyridin-2-yl)-4-methoxy-3-methylpyrazolo[1,5-a]pyrazine-6-carboxamide<br>Analytical Data: 452.3, 1.6 min (Method G) |

Example 118

((7R)-7-Amino-2-azabicyclo[2.2.1]heptan-2-yl)(2-(1-(cyclopropylmethyl)-1H-indol-2-yl)-4-methoxy-3-methylbenzo[b]thiophen-6-yl)methanone

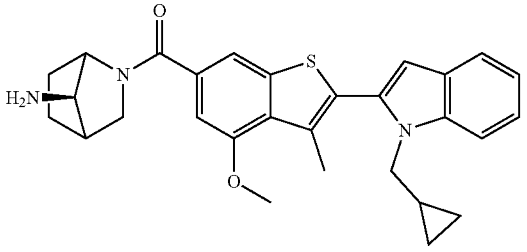 [SMILES: COc1cc(C(=O)N2CC3CCC2[C@@H]3N)cc2sc(-c3cc4ccccc4n3CC3CC3)c(C)c12]

Intermediate 118A

Ethyl-4-methoxy-3-methylbenzo[b]thiophene-6-carboxylate

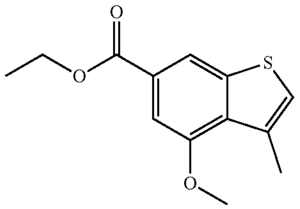 [SMILES: CCOC(=O)c1cc(OC)c2c(C)csc2c1]

$K_2CO_3$ (1.404 g, 10.16 mmol) was added to a stirred solution of ethyl 4-hydroxy-3-methylbenzo[b]thiophene-6-carboxylate (1.2 g, 5.08 mmol; U.S. Pub. 20080280875) in DMF (6 m). The reaction mixture was stirred for 10 min, followed by the addition of methyl iodide (0.381 ml, 6.09 mmol). The reaction mixture was further stirred for 5 hours at a room temperature, poured into water (70 ml, and extracted with EtOAc (2×25 ml). The combined organic layers were washed with water (50 ml) and brine solution (50 ml), dried over $Na_2SO_4$, filtered, and the volatiles were evaporated to dryness under reduced pressure. Residue thus obtained was purified using a silica gel column using a gradient of EtOAc in hexane. The product was isolated at 15% EtOAc in hexane, required fractions were collected and volatiles were evaporated to dryness under reduced pressure to afford the title compound as yellow solid (900 mg, 80%). $^1$H NMR (400 MHz, DMSO-$d_6$) δ ppm: 8.16 (s, 1H), 7.48 (s, 1H), 7.31 (s, 1H), 4.23-4.46 (m, 2H), 3.94 (s, 3H), 2.54-2.59 (m, 3H),1.29-1.44 (m, 3H).

Intermediate 118B

4-Methoxy-3-methylbenzo[b]thiophene-6-carboxylic acid

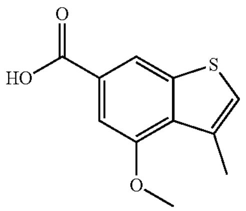

Lithium hydroxide (201 mg, 8.39 mmol) in water (2 ml) was added to a stirred solution of Intermediate 118A (700 mg, 2.80 mmol) in a mixture of ethanol (5 ml) and THF (5 ml). The reaction mixture was stirred at a room temperature for 17 hours, the volatiles were evaporated to dryness under reduced pressure, water (10 ml) was added, and pH of the reaction mixture was adjusted to pH 2 using 1.5 N aqueous HCl. The solids thus obtained were collected by vacuum filtration to afford 4-methoxy-3-methylbenzo[b]thiophene-6-carboxylic acid (620 mg, 80%). LC-MS m/z: 221.1 $[M-H]^+$. $^1$H NMR (400 MHz, DMSO-$d_6$) δ ppm: 12.9 (br, 1H), 8.12 (d, J=1.51 Hz, 1H), 7.45 (s, 1H), 7.32 (d, J=1.00 Hz, 1H), 3.93 (s, 3H), 2.57 (d, J=1.00 Hz, 3H).

Intermediate 118C tert-Butyl-((7R)-2-(4-methoxy-3-methylbenzo[b]thiophene-6-carbonyl)-2-azabicyclo[2.2.1]heptan-7-yl)carbamate

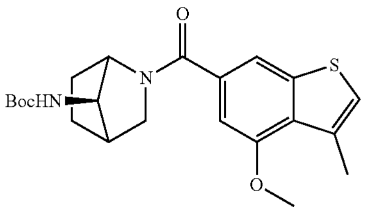 [SMILES: COc1cc(C(=O)N2CC3CCC2[C@@H]3NC(=O)OC(C)(C)C)cc2scc(C)c12]

HATU (1591 mg, 4.18 mmol), DIPEA (1.462 ml, 8.37 mmol) and tert-butyl ((7R)-2-azabicyclo[2.2.1]heptan-7-yl) carbamate (592 mg, 2.79 mmol) were added to a stirred solution of Intermediate 118B (620 mg, 2.79 mmol) in DMF (10 ml). The reaction mixture was stirred further at a room temperature for 17 hours, water (30 ml) was added, and the reaction mixture was extracted with EtOAc (2×25 ml). The combined organic layers were washed with water (25 ml) and brine (50 ml), dried over $Na_2SO_4$, filtered, and the volatiles were evaporated to dryness under reduced pressure to afford the title compound (800 mg, 60%). LC-MS m/z: 417.3 $[M+H]^+$.

Intermediate 118D tert-Butyl-((7R)-2-(2-chloro-4-methoxy-3-methyl-benzo[b]thiophene-6-carbonyl)-2-azabicyclo[2.2.1]heptan-7-yl)carbamate

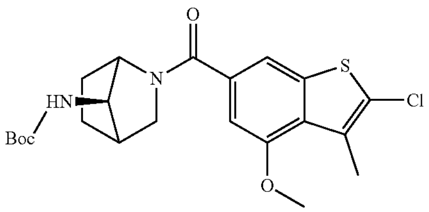 [SMILES: COc1cc(C(=O)N2CC3CCC2[C@@H]3NC(=O)OC(C)(C)C)cc2sc(Cl)c(C)c12]

LDA (0.6 ml, 0.120 mmol) was added to a stirred solution of Intermediate 118C (50 mg, 0.120 mmol) in THF (4 ml) at −78° C., and the reaction mixture was stirred for 30 min. A solution of perchloroethane (28.7 mg, 0.120 mmol) in THF (4 ml) was added and the reaction mixture was further stirred for 5 hours. Later, the reaction mixture was allowed to warm to a room temperature, quenched with aqueous ammonium chloride solution (25 ml), and extracted with EtOAc (2×25 ml). The combined organic layers were washed with water (25 ml) and brine (50 ml), dried over $Na_2SO_4$, filtered, and the volatiles were evaporated to dryness under reduced pressure to afford the title compound (50 mg, 60%). LC-MS m/z: 451.2 $[M+H]^+$.

Intermediate 118E tert-Butyl-((7R)-2-(2-(1-(cyclopropylmethyl)-1H-indol-2-yl)-4-methoxy-3-methylbenzo[b]thiophene-6-carbonyl)-2-azabicyclo[2.2.1]heptan-7-yl)carbamate

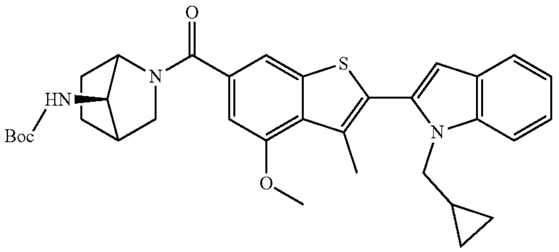 [SMILES: COc1cc(C(=O)N2CC3CCC2[C@@H]3NC(=O)OC(C)(C)C)cc2sc(-c3cc4ccccc4n3CC3CC3)c(C)c12]

A solution of $K_2CO_3$ (92 mg, 0.665 mmol) in water (1 ml) was added to a stirred solution of Intermediate 118D (100 mg, 0.222 mmol) and 1-(cyclopropylmethyl)-2-(4,4,5,5-tetramethyl-1,3,2-dioxaborolan-2-yl)-1H-indole (Intermediate-10, 65.9 mg, 0.222 mmol) in dioxane (3 ml), followed by the addition of tetrakis(triphenylphosphine)palladium(0) under argon atmosphere. The reaction mixture was heated at 120° C. and stirred for 17 hours, allowed to cool to a room temperature, water (10 ml) was added, and extracted with EtOAc (2×15 ml). The combined organic layers were washed with water (15 ml) and brine (20 ml), dried over $Na_2SO_4$, filtered, and the volatiles were evaporated to dryness under reduced pressure to afford the title compound (120 mg, 85%). LC-MS m/z: 586.3 $[M+H]^+$.

Example 118

TFA (0.158 ml, 2.049 mmol) was added to a stirred solution of Intermediate 118E (120 mg, 0.205 mmol) in DCM (2 ml). The reaction mixture was stirred at a room temperature for 17 hours, the volatiles were evaporated to dryness under reduced pressure, and the crude product thus obtained was purified using reverse phase column chromatography. The purified product was further purified using RP-HPLC to afford the title compound (2.2 mg, 2%). LC-MS m/z: 486.3 $[M+H]^+$. LC-MS retention time: 1.8 min (Method F). $^1H$ NMR (400 MHz, DMSO-$d_6$) δ ppm: 7.79-7.54 (m, 3H), 7.23 (t, J=7.7 Hz, 1H), 7.14-7.06 (m, 1H), 7.06-6.88 (m, 1H), 6.64 (s, 1H), 4.07-3.99 (m, 2H), 3.97-3.91 (m, 3H), 3.76-3.71 (m, 1H), 3.61-3.56 (m, 1H), 3.51-3.47 (m, 1H), 3.18 (br, d, J=10.8 Hz, 1H), 2.55 (s, 2H), 2.48-2.41 (m, 3H), 2.04-1.81 (m, 3H), 1.62 (br, d, J=1.0 Hz, 1H), 1.23 (s, 1H), 0.98 (br, s, 1H), 0.38-0.22 (m, 2H), 0.10 (br, d, J=2.9 Hz, 2H).

Example 119

((7R)-7-Amino-2-azabicyclo[2.2.1]heptan-2-yl)(2-(1-(cyclopropylmethyl)-1H-pyrrolo[2,3-b]pyridin-2-yl)-4-methoxy-3-methylbenzo[b]thiophen-6-yl)methanone

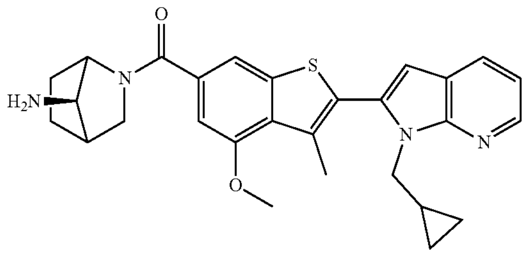 [SMILES: COc1cc(C(=O)N2CC3CCC2[C@@H]3N)cc2sc(-c3cc4cccnc4n3CC3CC3)c(C)c12]

Intermediate 119A tert-Butyl-((7R)-2-(4-methoxy-3-methyl-2-(4,4,5,5-tetramethyl-1,3,2-dioxaborolan-2-yl)benzo[b]thiophene-6-carbonyl)-2-azabicyclo[2.2.1]heptan-7-yl)carbamate

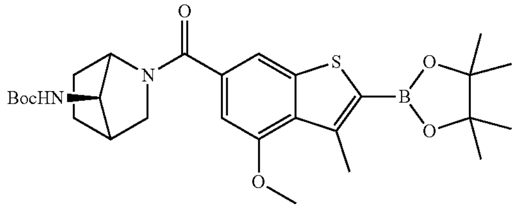 [SMILES: COc1cc(C(=O)N2CC3CCC2[C@@H]3NC(=O)OC(C)(C)C)cc2sc(B3OC(C)(C)C(C)(C)O3)c(C)c12]

LDA (1.2 ml, 0.480 mmol) was added drop wise under argon atmosphere to a stirred solution of Intermediate 118C (200 mg, 0.480 mmol) in THF (4 ml) at −78° C. The reaction mixture was stirred for 45 min, followed by the addition of 2-isopropoxy-4,4,5,5-tetramethyl-1,3,2-dioxaborolane (0.100 ml, 0.480 mmol). The reaction mixture was further stirred for 1 hours, allowed to warm to a room temperature, quenched with aqueous ammonium chloride solution (25 ml), and extracted with EtOAc (2×25 ml). The combined organic layers were washed with water (25 ml) and brine solution (50 ml), dried over $Na_2SO_4$, filtered and the volatiles were evaporated to dryness under reduced pressure to afford the title compound (200 mg, crude). LC-MS m/z: 543 $[M+H]^+$.

Intermediate 119B tert-Butyl-((7R)-2-(2-(1-(cyclopropylmethyl)-1H-pyrrolo[2,3-b]pyridin-2-yl)-4-methoxy-3-methylbenzo[b]thiophene-6-carbonyl)-2-azabicyclo[2.2.1]heptan-7-yl)carbamate

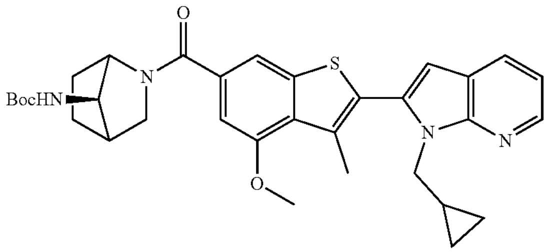 [SMILES: COc1cc(C(=O)N2CC3CCC2[C@@H]3NC(=O)OC(C)(C)C)cc2sc(-c3cc4cccnc4n3CC3CC3)c(C)c12]

A solution of $K_2CO_3$ (184 mg, 1.330 mmol) in water (1 ml) was added to a stirred solution of Intermediate 119A (200 mg, 0.443 mmol) and 1-(cyclopropylmethyl)-2-iodo-1H-pyrrolo[2,3-b]pyridine (132 mg, 0.443 mmol) in dioxane (6 ml), followed by the addition of $PdCl_2$(dppf) (20.23 mg, 0.028 mmol)) under argon atmosphere. The reaction mixture was heated to 85° C. and stirred for 17 hours, allowed to cool to a room temperature, water (10 ml) was added, and extracted with EtOAc (2×15 ml). The combined organic layers were washed with water (15 ml) and brine (20 ml), dried over $Na_2SO_4$, filtered, and the volatiles were evaporated to dryness under reduced pressure to afford the title compound (200 mg, crude). LC-MS m/z: 587.4 $[M+H]^+$.

Example 119

TFA (0.263 ml, 3.41 mmol) was added to a stirred solution of Intermediate 119B (200 mg, 0.341 mmol) in DCM (3 ml). The reaction mixture was stirred at a room temperature for 17 hours, the volatiles were evaporated to dryness under reduced pressure, and the residue thus obtained was purified using prep-HPLC. The purified product was further purified using RP-HPLC to afford the title compound (16.2 mg, 9%). LC-MS m/z: 487.2 $[M+H]^+$. LC-MS retention time: 1.4 min (Method F). $^1$H NMR (400 MHz, DMSO-$d_6$) δ ppm: 8.38-8.27 (m, 1H), 8.10-7.96 (m, 1H), 7.76-7.58 (m, 1H), 7.22-7.10 (m, 1H), 7.03-6.90 (m, 1H), 6.74-6.65 (m, 1H), 4.17-4.09 (m, 2H), 3.99-3.87 (m, 4H), 3.70 (s, 1H), 3.52-3.48 (m, 1H), 3.17 (br, d, J=1.2 Hz, 1H), 3.09-3.00 (m, 1H), 2.58-2.53 (m, 1H), 2.48-2.42 (m, 3H), 2.23-2.09 (m, 1H), 2.03-1.86 (m, 3H), 1.79-1.64 (m, 1H), 1.45-1.30 (m, 1H), 1.07-0.95 (m, 1H), 0.34-0.24 (m, 2H), 0.19-0.10 (m, 2H).

Example 120

6-(2-(6-((7R)-7-Amino-2-azabicyclo[2.2.1]heptane-2-carbonyl)-4-methoxy-3-methylbenzo[b]thiophen-2-yl)-1-(cyclopropylmethyl)-1H-indol-6-yl)isoindolin-1-one

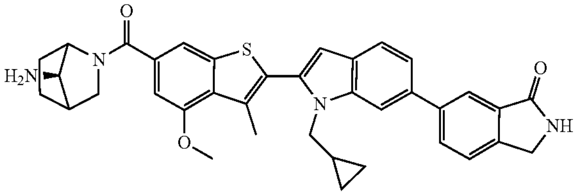 [SMILES: COc1cc(C(=O)N2CC3CCC2[C@@H]3N)cc2sc(-c3cc4ccc(-c5ccc6c(c5)C(=O)NC6)cc4n3CC3CC3)c(C)c12]

Intermediate 120A tert-Butyl-((7R)-2-(2-(6-bromo-1-(cyclopropylmethyl)-1H-indol-2-yl)-4-methoxy-3-methylbenzo[b]thiophene-6-carbonyl)-2-azabicyclo[2.2.1]heptan-7-yl)carbamate

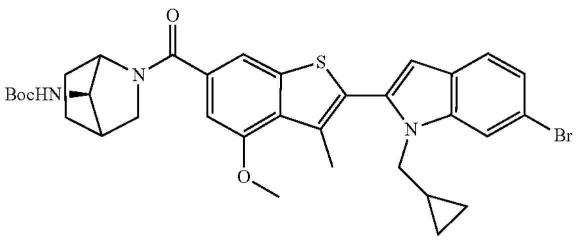 [SMILES: COc1cc(C(=O)N2CC3CCC2[C@@H]3NC(=O)OC(C)(C)C)cc2sc(-c3cc4ccc(Br)cc4n3CC3CC3)c(C)c12]

A solution of $K_2CO_3$ (2.293 g, 16.59 mmol) in water (8 ml) was added to a stirred solution of Intermediate 119A (3 g, 5.53 mmol), 6-bromo-1-(cyclopropylmethyl)-2-iodo-1H-indole (Intermediate-12, 2.079 g, 5.53 mmol) and $PdCl_2$ (dppf)-$CH_2Cl_2$ adduct (0.339 g, 0.415 mmol) in dioxane (50 ml). The reaction mixture was heated to 80° C. and stirred for 14 hours, the volatiles were evaporated to dryness under reduced pressure, water (50 ml) was added to the reaction mixture, and extracted with EtOAc (2×50 ml). The combined organic extracts were washed with water (100 ml) and brine (100 ml), dried over sodium sulphate, filtered, and the filtrate was concentrated to dryness under reduced pressure. Residue thus obtained was purified using a silica gel column using a gradient of EtOAc in hexane. The product was isolated at 45% EtOAc in hexane, required fractions were collected and volatiles were evaporated to dryness under reduced pressure to afford the title compound (1.2 g, 33%). LCMS m/z: 666.4 $[M+2H]^+$.

Intermediate 120B tert-Butyl-((7R)-2-(2-(1-(cyclopropylmethyl)-6-(3-oxoisoindolin-5-yl)-1H-indol-2-yl)-4-methoxy-3-methylbenzo[b]thiophene-6-carbonyl)-2-azabicyclo[2.2.1]heptan-7-yl)carbamate

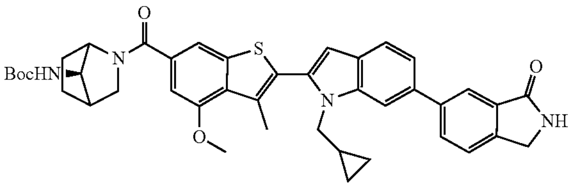 [SMILES: COc1cc(C(=O)N2CC3CCC2[C@@H]3NC(=O)OC(C)(C)C)cc2sc(-c3cc4ccc(-c5ccc6c(c5)C(=O)NC6)cc4n3CC3CC3)c(C)c12]

A solution of $K_2CO_3$ (24.95 mg, 0.181 mmol) in water (1 ml) was added to a stirred solution of Intermediate 120A (40 mg, 0.060 mmol) and 6-(4,4,5,5-tetramethyl-1,3,2-dioxaborolan-2-yl)isoindolin-1-one (15.59 mg, 0.060 mmol) in dioxane (2 ml), followed by the addition of $PdCl_2$(dppf) DCM adduct (3.30 mg, 4.51 μmol) under argon atmosphere. The reaction mixture was heated to 80° C. and stirred for 14 hours, the volatiles were evaporated to dryness under reduced pressure, water (10 ml) was added and the reaction mixture was extracted with EtOAc (2×10 ml). The combined organic extracts were washed with water (20 ml) and brine (20 ml), dried over sodium sulphate, filtered, and the filtrate was evaporated to dryness under reduced pressure to afford title compound (40 mg, crude). LC-MS m/z: 715 $[M-H]^+$.

Example 120

TFA (0.043 ml, 0.558 mmol) was added to a stirred solution of Intermediate 120B (40 mg, 0.056 mmol) in DCM (2 ml). The reaction mixture was stirred at a room temperature for 17 hours, the volatiles were evaporated to dryness under reduced pressure, and the crude product thus obtained was purified using RP-HPLC to afford the title compound (2.8 mg, 8%). LC-MS m/z: 617.4 $[M-H]^+$. LC-MS retention time: 1.5 min (Method F). $^1$H NMR (400 MHz, DMSO-$d_6$) δ ppm: 8.60 (s, 1H), 8.06-7.96 (m, 3H), 7.75-7.65 (m, 2H), 7.63 (s, 1H), 7.48 (d, J=8.3 Hz, 1H), 7.03-6.91 (m, 1H), 6.69 (s,1H), 4.44 (s, 3H), 4.22-4.12 (m, 2H), 3.96 (s, 4H), 3.71 (br, s, 1H), 3.49 (br, d, J=1.5 Hz, 1H), 3.18 (br, d, J=0.7 Hz, 1H), 3.09-3.03 (m, 1H), 2.20 (br, s, 1H),2.04-1.81 (m, 3H), 1.76-1.69 (m, 1H), 1.45-1.36 (m, 1H), 1.23 (s, 2H), 1.10-1.02 (m, 1H), 0.35 (br, d, J=8.1 Hz, 2H), 0.14 (br, d, J=3.2 Hz, 2H).

Compounds of Examples 121 to 129 in Table 15 were prepared following a procedure similar to the preparation of a compound of Example 120, by Suzuki coupling of the Intermediate 120A with appropriate boronic acid.

TABLE 15

| Example | Structure<br>Name<br>Analytical Data: LC-MS m/z $[M + H]^+$; HPLC retention time (HPLC method) |
|---|---|
| 121 | 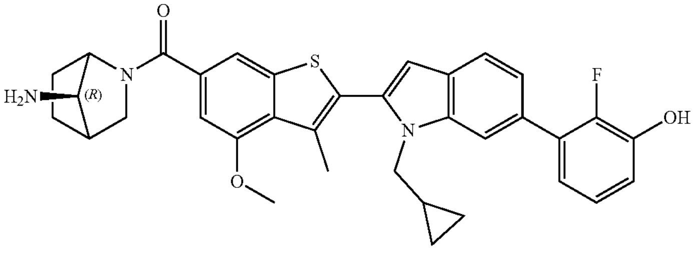<br>((7R)-7-Amino-2-azabicyclo[2.2.1]heptan-2-yl)(2-(1-(cyclopropylmethyl)-6-(2-fluoro-3-hydroxyphenyl)-1H-indol-2-yl)-4-methoxy-3-methylbenzo[b]thiophen-6-yl)methanone<br>Analytical Data: 596.3, 2.075 min (Method E) |
| 122 | 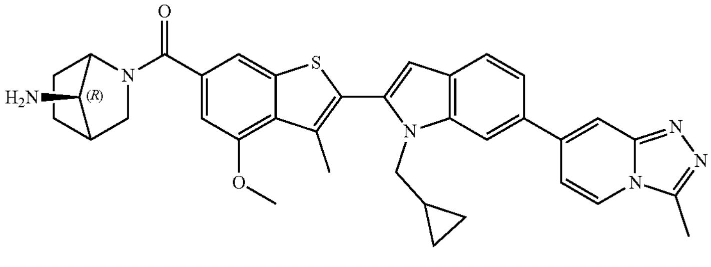<br>((7R)-7-Amino-2-azabicyclo[2.2.1]heptan-2-yl)(2-(1-(cyclopropylmethyl)-6-(3-methyl-[1,2,4]triazolo[4,3-a]pyridin-7-yl)-1H-indol-2-yl)-4-methoxy-3-methylbenzo[b]thiophen-6-yl)methanone<br>Analytical Data: 617.3, 1.7 min (Method E) |
| 123 | 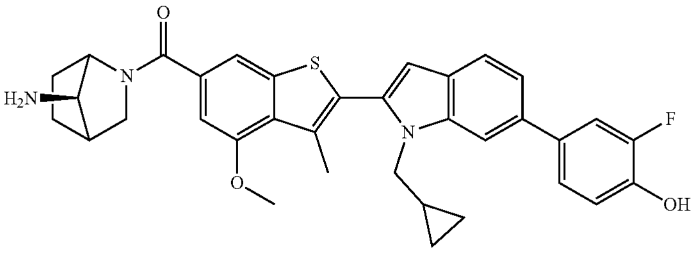 [SMILES: COc1cc(C(=O)N2CC3CCC2[C@@H]3N)cc2sc(-c3cc4ccc(-c5ccc(O)c(F)c5)cc4n3CC3CC3)c(C)c12]<br>((7R)-7-Amino-2-azabicyclo[2.2.1]heptan-2-yl)(2-(1-(cyclopropylmethyl)-6-(3-fluoro-4-hydroxyphenyl)-1H-indol-2-yl)-4-methoxy-3-methylbenzo[b]thiophen-6-yl)methanone<br>Analytical Data: 596.3, 2.0 min (Method E) |
| 124 | 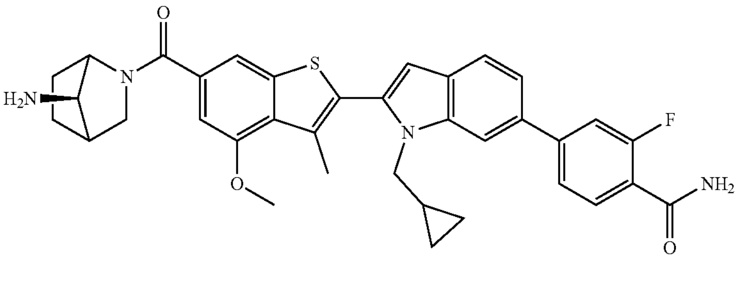 [SMILES: COc1cc(C(=O)N2CC3CCC2[C@@H]3N)cc2sc(-c3cc4ccc(-c5ccc(C(N)=O)c(F)c5)cc4n3CC3CC3)c(C)c12]<br>4-(2-(6-((7R)-7-Amino-2-azabicyclo[2.2.1]heptane-2-carbonyl)-4-methoxy-3-methylbenzo[b]thiophen-2-yl)-1-(cyclopropylmethyl)-1H-indol-6-yl)-2-fluorobenzamide<br>Analytical Data: 623.3, 1.8 min (Method E) |

TABLE 15-continued

| Example | Structure<br>Name<br>Analytical Data: LC-MS m/z [M + H]$^+$; HPLC retention time (HPLC method) |
|---|---|
| 125 | 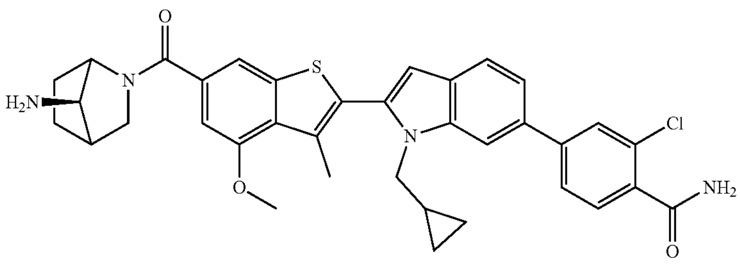 [SMILES: COc1cc(C(=O)N2CC3CCC2[C@@H]3N)cc2sc(-c3cc4ccc(-c5ccc(C(N)=O)c(Cl)c5)cc4n3CC3CC3)c(C)c12]<br>4-(2-(6-((7R)-7-Amino-2-azabicyclo[2.2.1]heptane-2-carbonyl)-4-methoxy-3-methylbenzo[b]thiophen-2-yl)-1-(cyclopropylmethyl)-1H-indol-6-yl)-2-chlorobenzamide<br>Analytical Data: 639.3, 1.8 min (Method E) |
| 126 | 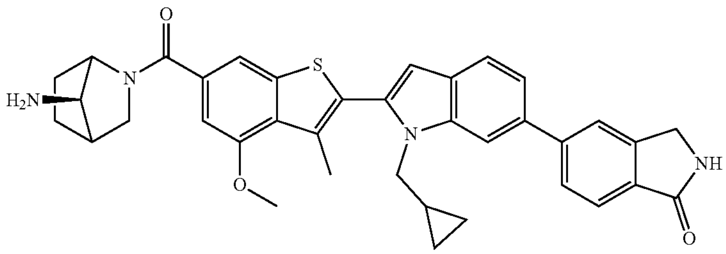 [SMILES: COc1cc(C(=O)N2CC3CCC2[C@@H]3N)cc2sc(-c3cc4ccc(-c5ccc6c(c5)CNC6=O)cc4n3CC3CC3)c(C)c12]<br>5-(2-(6-((7R)-7-Amino-2-azabicyclo[2.2.1]heptane-2-carbonyl)-4-methoxy-3-methylbenzo[b]thiophen-2-yl)-1-(cyclopropylmethyl)-1H-indol-6-yl)isoindolin-1-one<br>Analytical Data: 617.3, 1.7 min (Method E) |
| 127 | 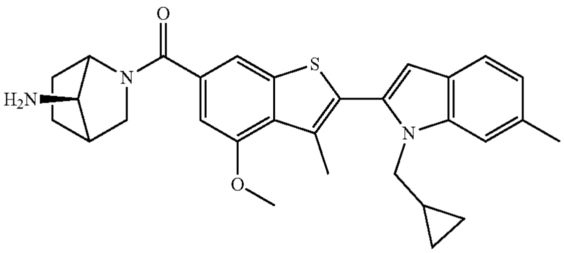 [SMILES: COc1cc(C(=O)N2CC3CCC2[C@@H]3N)cc2sc(-c3cc4ccc(C)cc4n3CC3CC3)c(C)c12]<br>((7R)-7-Amino-2-azabicyclo[2.2.1]heptan-2-yl)(2-(1-(cyclopropylmethyl)-6-methyl-1H-indol-2-yl)-4-methoxy-3-methylbenzo[b]thiophen-6-yl)methanone<br>Analytical Data: 500, 2.3 min (Method E) |
| 128 | 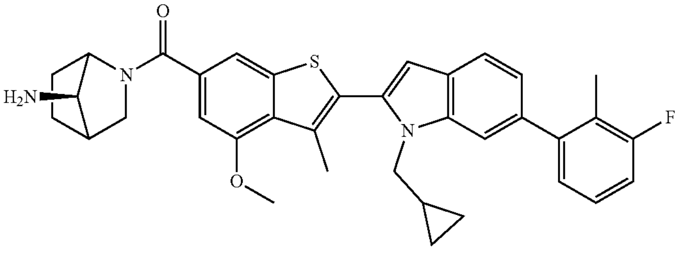 [SMILES: COc1cc(C(=O)N2CC3CCC2[C@@H]3N)cc2sc(-c3cc4ccc(-c5cccc(F)c5C)cc4n3CC3CC3)c(C)c12]<br>((7R)-7-Amino-2-azabicyclo[2.2.1]heptan-2-yl)(2-(1-(cyclopropylmethyl)-6-(3-fluoro-2-methylphenyl)-1H-indol-2-yl)-4-methoxy-3-methylbenzo[b]thiophen-6-yl)methanone<br>Analytical Data: 594.3, 2.6 min (Method E) |

TABLE 15-continued

| Example | Structure<br>Name<br>Analytical Data: LC-MS m/z [M + H]$^+$; HPLC retention time (HPLC method) |
|---|---|
| 129 | 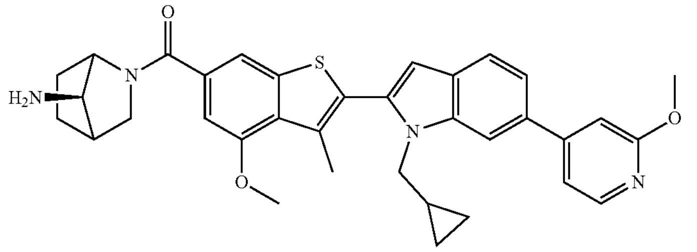 [SMILES: COc1cc(-c2ccc3cc(-c4sc5cc(C(=O)N6CC7CCC6[C@@H]7N)cc(OC)c5c4C)n(CC4CC4)c3c2)ccn1]<br>((7R)-7-Amino-2-azabicyclo[2.2.1]heptan-2-yl)(2-(1-(cyclopropylmethyl)-6-(2-methoxypyridin-4-yl)-1H-indol-2-yl)-4-methoxy-3-methylbenzo[b]thiophen-6-yl)methanone<br>Analytical Data: 593, 2.0 min (Method E) |

Example 130

((7R)-7-Amino-2-azabicyclo[2.2.1]heptan-2-yl)(2-(6-(4-aminopiperidin-1-yl)-1-(cyclopropylmethyl)-1H-indol-2-yl)-4-methoxy-3-methylbenzo[b]thiophen-6-yl)methanone

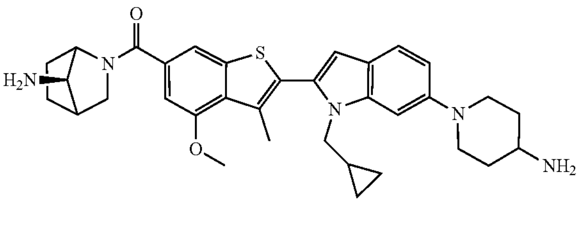 [SMILES: COc1cc(C(=O)N2CC3CCC2[C@@H]3N)cc2sc(-c3cc4ccc(N5CCC(N)CC5)cc4n3CC3CC3)c(C)c12]

Intermediate 130A tert-Butyl-((7R)-2-(2-(6-(4-((tert-butoxycarbonyl)amino)piperidin-1-yl)-1-(cyclopropylmethyl)-1H-indol-2-yl)-4-methoxy-3-methylbenzo[b]thiophene-6-carbonyl)-2-azabicyclo[2.2.1]heptan-7-yl)carbamate

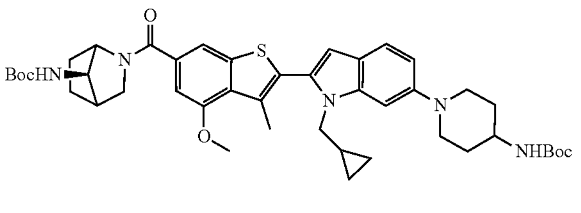 [SMILES: COc1cc(C(=O)N2CC3CCC2[C@@H]3NC(=O)OC(C)(C)C)cc2sc(-c3cc4ccc(N5CCC(NC(=O)OC(C)(C)C)CC5)cc4n3CC3CC3)c(C)c12]

Caesium carbonate (147 mg, 0.451 mmol), RUPHOS (35.1 mg, 0.075 mmol) and $Pd_2(dba)_3$ (13.78 mg, 0.015 mmol) were added to a stirred solution of Intermediate 120A (100 mg, 0.150 mmol) and tert-butyl piperidin-4-ylcarbamate (30.1 mg,0.150 mmol) in dioxane (3 ml). The reaction mixture was degasified with argon for 5 min, stirred at 110° C. for 16 hours, cooled to a room temperature, water (10 ml) was added and the reaction mixture was extracted with EtOAc (2×10 ml). The combined organic extracts were washed with water (20 ml) and brine (20 ml), dried over sodium sulphate, filtered, and volatiles were evaporated to dryness under reduced pressure to afford the title compound 100 mg (crude). LC-MS m/z: 784.5 [M−H]$^+$.

Example 130

TFA (0.5 ml) was added to a stirred solution of Intermediate 130A (100 mg) in DCM (2 ml), and the reaction mixture was stirred at a room temperature for 17 hours. The volatiles were evaporated to dryness under reduced pressure and the residue thus obtained was purified using RP-HPLC to afford the title compound (9.4 mg, 13%). LC-MS m/z: 584.3 [M−H]$^+$. LCMS retention time: 1.5 min (Method E). $^1$H NMR (400 MHz, DMSO-$d_6$) δ ppm: 8.13 (br, d, J=4.2 Hz, 1H), 8.03-7.85 (m, 4H), 7.76-7.59 (m, 1H), 7.45 (d, J=8.3 Hz, 1H), 7.11-7.04 (m, 1H), 7.04-6.93 (m, 1H), 6.90 (br, d, J=7.6 Hz, 1H), 6.50 (s, 1H), 4.56-4.12 (m, 3H), 4.03-3.92 (m, 3H), 3.81-3.73 (m, 2H), 3.63-3.55 (m, 1H), 3.20(br, d, J=11.5 Hz, 1H), 2.87-2.76 (m, 2H), 2.46-2.41 (m, 2H), 2.04-1.81 (m, 4H), 1.74-1.59 (m, 2H), 1.02-0.89 (m, 1H), 0.37-0.26 (m, 2H), 0.14-0.03 (m, 2H).

Example 131

((7R)-7-Amino-2-azabicyclo[2.2.1]heptan-2-yl)(2-(1-(cyclopropylmethyl)-6-(4-methoxypiperidin-1-yl)-1H-indol-2-yl)-4-methoxy-3-methylbenzo[b]thiophen-6-yl)methanone

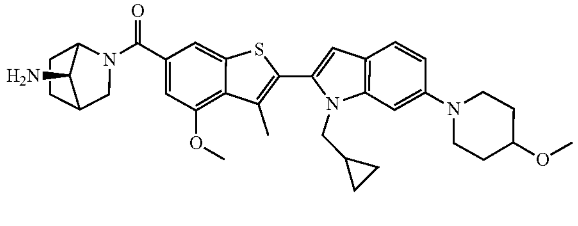 [SMILES: COc1cc(C(=O)N2CC3CCC2[C@@H]3N)cc2sc(-c3cc4ccc(N5CCC(OC)CC5)cc4n3CC3CC3)c(C)c12]

Intermediate 131A tert-Butyl-((7R)-2-(2-(1-(cyclopropylmethyl)-6-(4-methoxypiperidin-1-yl)-1H-indol-2-yl)-4-methoxy-3-methylbenzo[b]thiophene-6-carbonyl)-2-azabicyclo[2.2.1]heptan-7-yl)carbamate

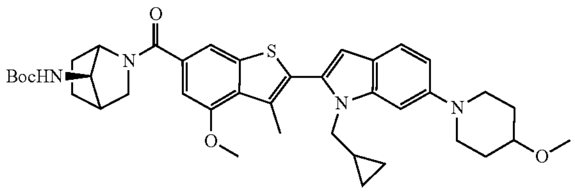 [SMILES: COc1cc(C(=O)N2CC3CCC2[C@@H]3NC(=O)OC(C)(C)C)cc2sc(-c3cc4ccc(N5CCC(OC)CC5)cc4n3CC3CC3)c(C)c12]

2-Dicyclohexylphosphino-2',4',6'-triisopropylbiphenyl (XPHOS, 10.76 mg, 0.023 mmol), potassium tert-butoxide (10.13 mg, 0.090 mmol) and palladium (II) acetate (3.04 mg, 0.014 mmol) were added to a stirred solution of Intermediate 120A (30 mg, 0.045 mmol) and 4-methoxypiperidine (5.20 mg, 0.045 mmol) in dioxane (1 ml). The reaction mixture was degasified under argon for 5 min and then stirred at 110° C. for 16 hours. The reaction mixture was cooled to a room temperature, water (10 ml) was added, and extracted with EtOAc (2×10 ml). The combined organic extracts were washed with water (20 ml) and brine (20 ml), dried over sodium sulphate, filtered, and the filtrate was evaporated to dryness under reduced pressure to afford the title compound 100 mg (crude). LC-MS m/z: 699.5 $[M+H]^+$.

Example 131

TFA (0.5 ml) was added to a stirred solution of Intermediate 131A (100 mg) in DCM (2 ml). The reaction mixture was stirred at a room temperature for 17 hours, the volatiles were evaporated to dryness under reduced pressure, and the crude compound thus obtained was purified using RP-HPLC to afford the title compound (6.6 mg, 18%). LC-MS m/z: 599.3 $[M+H]^+$. LC-MS retention time: 2.1 min (Method E). $^1$H NMR (400 MHz, DMSO-$d_6$) δ ppm: 7.72-7.57 (m, 1H), 7.41 (d, J=8.8 Hz, 1H), 7.03 (s, 1H), 6.99-6.92 (m, 1H), 6.87 (dd, J=9.0, 1.2 Hz, 1H), 6.48(s, 1H), 4.01-3.91 (m, 5H), 3.75 (br, s, 1H), 3.54-3.47 (m, 3H), 3.29 (s, 4H), 3.21 (br, d, J=1.7 Hz, 1H), 3.08 (br, d, J=10.8 Hz, 1H), 2.96-2.86 (m,3H), 2.46-2.42 (m, 3H), 2.28-2.20 (m, 1H), 2.03-1.84 (m, 4H), 1.79-1.53 (m, 3H), 1.46-1.37 (m, 1H), 1.02-0.89 (m, 1H), 0.38-0.25 (m,2H), 0.08 (br, d, J=3.4 Hz, 2H).

Example 132

5-(2-(6-((7R)-7-Amino-2-azabicyclo[2.2.1]heptane-2-carbonyl)-4-methoxy-3-methylbenzo-[b]thiophen-2-yl)-1-(cyclopropylmethyl)-1H-pyrrolo[2,3-b]pyridin-6-yl)isoindolin-1-one

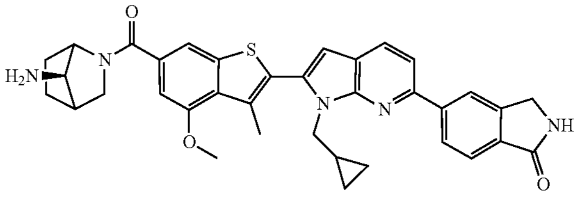 [SMILES: COc1cc(C(=O)N2CC3CCC2[C@@H]3N)cc2sc(-c3cc4ccc(-c5ccc6c(c5)CNC6=O)nc4n3CC3CC3)c(C)c12]

Intermediate 132A tert-Butyl-((7R)-2-(2-(6-chloro-1-(cyclopropylmethyl)-1H-pyrrolo[2,3-b]pyridin-2-yl)-4-methoxy-3-methylbenzo[b]thiophene-6-carbonyl)-2-azabicyclo[2.2.1]heptan-7-yl)carbamate

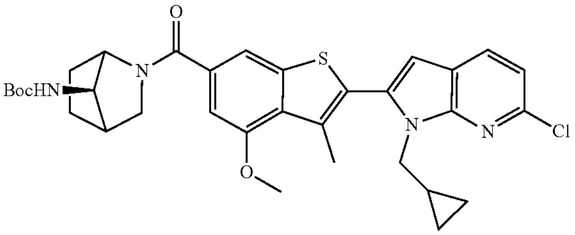 [SMILES: COc1cc(C(=O)N2CC3CCC2[C@@H]3NC(=O)OC(C)(C)C)cc2sc(-c3cc4ccc(Cl)nc4n3CC3CC3)c(C)c12]

6-Chloro-1-(cyclopropylmethyl)-2-iodo-1H-pyrrolo[2,3-b]pyridine (Intermediate 3, 800 mg, 2.406 mmol) and potassium carbonate (831 mg, 6.01 mmol) in water (0.5 ml) were added to a degasified solution of Intermediate 119A (1696 mg, 3.13 mmol) in 1,4-dioxane (15 ml), followed by the addition of $PdCl_2(dppf)$-$CH_2Cl_2$ adduct (118 mg, 0.144 mmol). The resulting solution was stirred at 80° C. for 10 hours, diluted with water (5 m), and extracted with EtOAc (2×10 ml). The combined organic layers were washed with brine (20 ml), dried over sodium sulfate, filtered, and the filtrate was concentrated under reduced pressure. The crude product thus obtained was purified using a silica gel column (24 g, Redisep® $SiO_2$ column, eluting with 80% EtOAc in n-hexane) to afford the title compound (0.55 g, 36%) as a brown solid. LC-MS m/z: 621.3 $[M+H]^+$.

Intermediate 132B tert-Butyl-((7R)-2-(2-(1-(cyclopropylmethyl)-6-(1-oxoisoindolin-5-yl)-1H-pyrrolo[2,3-b]pyridin-2-yl)-4-methoxy-3-methylbenzo[b]thiophene-6-carbonyl)-2-azabicyclo[2.2.1]heptan-7-yl)carbamate

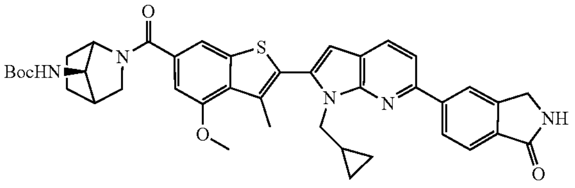 [SMILES: COc1cc(C(=O)N2CC3CCC2[C@@H]3NC(=O)OC(C)(C)C)cc2sc(-c3cc4ccc(-c5ccc6c(c5)CNC6=O)nc4n3CC3CC3)c(C)c12]

5-(4,4,5,5-tetramethyl-1,3,2-dioxaborolan-2-yl)isoindolin-1-one (37.5 mg, 0.145 mmol), potassium phosphate tribasic (64.1 mg, 0.302 mmol) in water (0.3 ml) were added to a degassed solution of Intermediate 132A (75 mg, 0.121 mmol) in 1,4-dioxane (2 ml), followed by the addition of XPHOS Pd G2 (5.30 mg, 7.24 μmol). The resulting solution was heated to 80° C. and stirred for 10 hours, diluted with water (5 ml), and extracted with EtOAc (2×10 ml). The combined organic layers were washed with brine, dried over sodium sulfate, filtered, and the filtrate was concentrated in vacuum. The crude product thus obtained was purified using a silica gel column (12 g, Redisep® $SiO_2$ column, eluting with 80% EtOAc in n-hexane) to afford the title compound (35 mg, 40%) as a brown solid. LC-MS m/z: 718.4 $[M+H]^+$.

Example 132

TFA (0.032 ml, 0.418 mmol) was added to a stirred solution of Intermediate 132B (30 mg, 0.042 mmol) in DCM (5 ml) at a room temperature. The reaction mixture was stirred further for 16 hours, concentrated, and the crude product thus obtained was purified using RP-HPLC to afford the title compound (0.013 g, 48%). LC-MS m/z: 618.3 $[M+H]^+$. HPLC retention time: 6.9 min (Method C). $^1H$ NMR (400 MHz, methanol-$d_4$) δ ppm: 8.34-8.44 (m, 2H), 8.12 (d, J=8.07 Hz, 1H), 7.92 (d, J=7.83 Hz, 1H), 7.82-7.87 (m, 1H), 7.65 (s, 1H), 6.97-7.11 (m, 1H), 6.69 (s, 1H), 4.60 (s, 2H), 4.31 (br, d, J=6.85 Hz, 2H), 4.04 (s, 3H), 3.73-3.83 (m, 1H), 3.56-3.71 (m, 1H), 2.69-2.90 (m, 1H)2.59 (s, 3H), 1.93-2.31 (m, 3H), 1.10-1.24 (m, 1H), 0.40 (br, d, J=8.07 Hz, 2H), 0.25 (br, d, J=5.62 Hz, 2H).

Compounds of Examples 133 to 136 in Table 16 were prepared following a procedure similar to the preparation of a compound of Example 132, by Suzuki coupling of Intermediate 132A with appropriate boronic acid.

TABLE 16

| Example | Structure<br>Name<br>Analytical Data: LC-MS m/z $[M + H]^+$; HPLC retention time (HPLC method) |
|---|---|
| 133 | 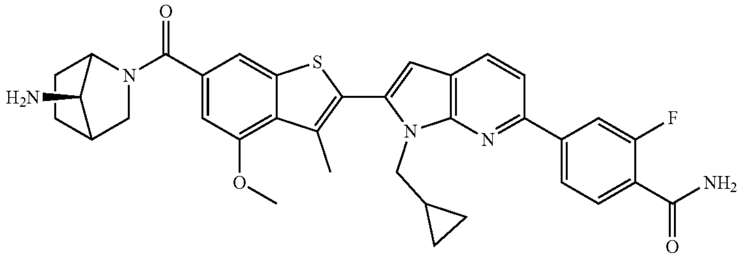 [SMILES: COc1cc(C(=O)N2CC3CCC2[C@@H]3N)cc2sc(-c3cc4ccc(-c5ccc(C(N)=O)c(F)c5)nc4n3CC3CC3)c(C)c12]<br>4-(2-(6-((7R)-7-Amino-2-azabicyclo[2.2.1]heptane-2-carbonyl)-4-methoxy-3-methylbenzo[b]thiophen-2-yl)-1-(cyclopropylmethyl)-1H-pyrrolo[2,3-b]pyridin-6-yl)-2-fluorobenzamide<br>Analytical Data: 624.4, 2.9 min (UPLC) |
| 134 | 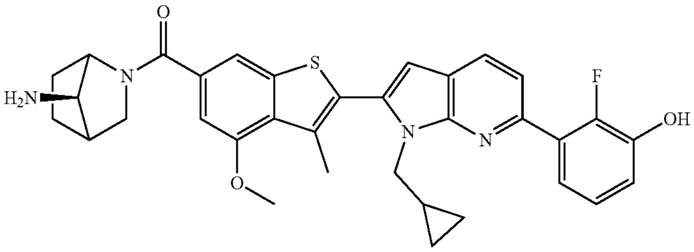 [SMILES: COc1cc(C(=O)N2CC3CCC2[C@@H]3N)cc2sc(-c3cc4ccc(-c5cccc(O)c5F)nc4n3CC3CC3)c(C)c12]<br>((7R)-7-Amino-2-azabicyclo[2.2.1]heptan-2-yl)(2-(1-(cyclopropylmethyl)-6-(2-fluoro-3-hydroxyphenyl)-1H-pyrrolo[2,3-b]pyridin-2-yl)-4-methoxy-3-methylbenzo[b]thiophen-6-yl)methanone<br>Analytical Data: 597.3, 7.5 min (Method C) |
| 135 | 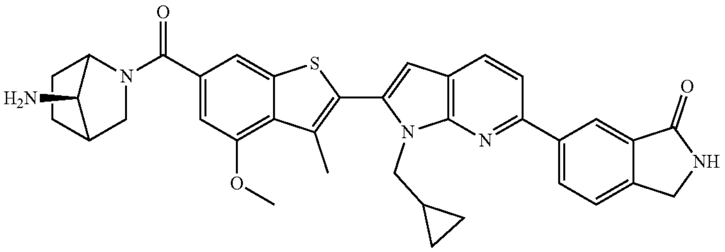 [SMILES: COc1cc(C(=O)N2CC3CCC2[C@@H]3N)cc2sc(-c3cc4ccc(-c5ccc6c(c5)C(=O)NC6)nc4n3CC3CC3)c(C)c12]<br>6-(2-(6-((7R)-7-Amino-2-azabicyclo[2.2.1]heptane-2-carbonyl)-4-methoxy-3-methylbenzo[b]thiophen-2-yl)-1-(cyclopropylmethyl)-1H-pyrrolo[2,3-b]pyridin-6-yl)isoindolin-1-one<br>Analytical Data: 618.2, 7.39 min (Method C) |

TABLE 16-continued

| Example | Structure<br>Name<br>Analytical Data: LC-MS m/z [M + H]$^+$; HPLC retention time (HPLC method) |
|---|---|
| 136 | 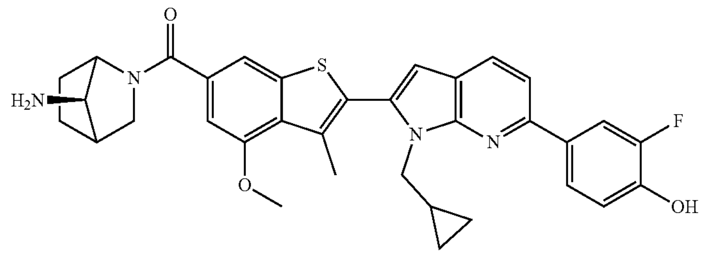 [SMILES: COc1cc(C(=O)N2CC3CCC2[C@@H]3N)cc2sc(-c3cc4ccc(-c5ccc(O)c(F)c5)nc4n3CC3CC3)c(C)c12]<br>((7R)-7-Amino-2-azabicyclo[2.2.1]heptan-2-yl)(2-(1-(cyclopropylmethyl)-6-(3-fluoro-4-hydroxyphenyl)-1H-pyrrolo[2,3-b]pyridin-2-yl)-4-methoxy-3-methylbenzo[b]thiophen-6-yl)methanone<br>Analytical Data: 597.3, 7.0 min (Method C) |

Example 137

((7R)-7-Amino-2-azabicyclo[2.2.1]heptan-2-yl)(2-(1-(cyclopropylmethyl)-6-(4-methoxypiperidin-1-yl)-1H-pyrrolo[2,3-b]pyridin-2-yl)-4-methoxy-3-methylbenzo[b]thiophen-6-yl)methanone

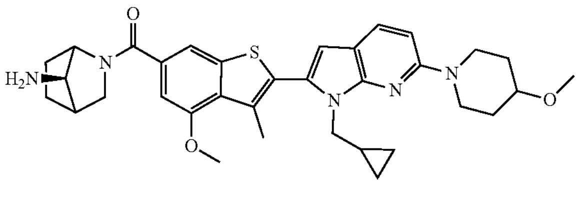 [SMILES: COc1cc(C(=O)N2CC3CCC2[C@@H]3N)cc2sc(-c3cc4ccc(N5CCC(OC)CC5)nc4n3CC3CC3)c(C)c12]

Intermediate 137A tert-Butyl-((7R)-2-(2-(1-(cyclopropylmethyl)-6-(4-methoxypiperidin-1-yl)-1H-pyrrolo[2,3-b]pyridin-2-yl)-4-methoxy-3-methylbenzo[b]thiophene-6-carbonyl)-2-azabicyclo[2.2.1]heptan-7-yl)carbamate

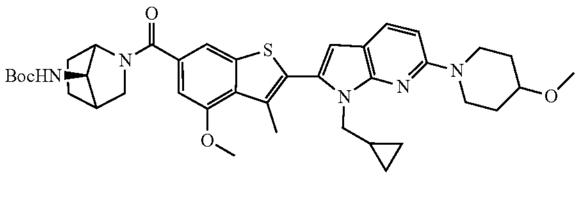 [SMILES: COc1cc(C(=O)N2CC3CCC2[C@@H]3NC(=O)OC(C)(C)C)cc2sc(-c3cc4ccc(N5CCC(OC)CC5)nc4n3CC3CC3)c(C)c12]

4-Methoxypiperidine (19.47 mg, 0.169 mmol), potassium tert-butoxide (25.3 mg, 0.225 mmol), $Pd(OAc)_2$ (7.59 mg, 0.034 mmol), and XPHOS (32.2 mg, 0.068 mmol) were added to a degasified stirred solution of Intermediate 132A (70 mg, 0.113 mmol) in 1,4-dioxane (2 ml). The reaction mixture was heated to 110° C. and stirred for 16 hours, concentrated, diluted with water (5 ml), and extracted with EtOAc (2×10 ml). The combined organic layers were washed with brine, dried over sodium sulfate, filtered, and the filtrate was concentrated in vacuum. The crude product obtained was purified using a silica gel column (12 g, Redisep® $SiO_2$ column, eluting with 5% methanol in DCM) to afford the title compound as brown solid (40 mg, 50%). LC-MS m/z: 700 [M+H]$^+$.

Example 137

TFA (4.40 μl, 0.057 mmol) was added to a stirred solution of Intermediate 137A (40 mg, 0.057 mmol) in DCM (5 ml). The reaction mixture was stirred at a room temperature for 16 hours, concentrated, and the crude compound thus obtained was purified using RP-HPLC to afford the title compound (11 mg, 31%) as off white solid. LC-MS m/z: 600.2 [M+H]$^+$. LCMS retention time: 2.44 min (Method C). $^1$H NMR (400 MHz, methanol-$d_4$) δ ppm: 7.76 (d, J=8.56 Hz, 1H), 7.58 (s, 1H), 7.01-6.98(m, 1H), 6.74 (d, J=8.80 Hz, 1H), 6.42 (s, 1H), 4.17-4.06 (m, 4H), 3.98 (s, 3H), 3.82-3.66 (m, 1H), 3.58-3.49 (m, 1H), 3.39 (s, 3H), 3.35 (s, 1H), 3.29-3.12 (m, 3H), 2.57-2.47 (m, 4H), 2.10-1.91 (m, 5H), 1.77-1.53 (m, 3H), 1.43-1.24 (m, 1H), 1.17-1.02 (m, 1H), 0.37-0.28 (m, 2H), 0.23-0.04 (m, 2H).

Example 138

((3R,5R)-3-Amino-5-fluoropiperidin-1-yl)(2-(1-(cyclopropylmethyl)-1H-pyrrolo[2,3-b]pyridin-2-yl)-4-methoxy-3-methylbenzo[b]thiophen-6-yl)methanone

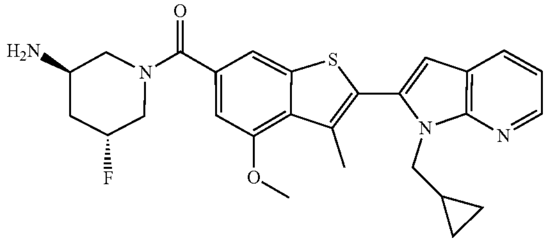 [SMILES: COc1cc(C(=O)N2C[C@H](N)C[C@@H](F)C2)cc2sc(-c3cc4cccnc4n3CC3CC3)c(C)c12]

Intermediate 138A tert-Butyl-((3R,5R)-5-fluoro-1-(4-methoxy-3-methylbenzo[b]thiophene-6-carbonyl)-piperidin-3-yl) carbamate

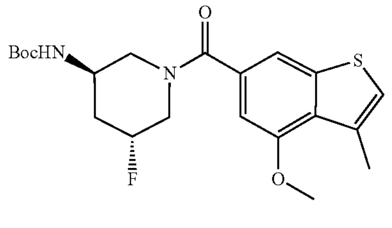 [SMILES: COc1cc(C(=O)N2C[C@H](F)C[C@@H](NC(=O)OC(C)(C)C)C2)cc2scc(C)c12]

HATU (1026 mg, 2.70 mmol) and DIPEA (1.179 ml, 6.75 mmol) in DMF (14 ml) was added to a stirred solution of Intermediate 118B (500 mg, 2.250 mmol), and tert-butyl ((3R,5R)-5-fluoropiperidin-3-yl)carbamate (491 mg, 2.250 mmol). The reaction mixture was stirred at a room temperature for 17 hours, water (30 ml) was added, and extracted with EtOAc (2×25 ml). The combined organic layers were washed with water (25 ml) and brine (50 ml), dried over $Na_2SO_4$, filtered, and the volatiles were evaporated to dryness under reduced pressure. The crude product thus obtained was purified using a silica gel column (40 g, Redisep® $SiO_2$ column, eluting with 40% EtOAc in hexane) to afford the title compound (300 mg, crude). LC-MS m/z: 421.2 $[M-H]^+$.

Intermediate 138B tert-Butyl-((3R,5R)-5-fluoro-1-(4-methoxy-3-methyl-2-(4,4,5,5-tetramethyl-1,3,2-dioxaborolan-2-yl)benzo[b]thiophene-6-carbonyl)piperidin-3-yl) carbamate

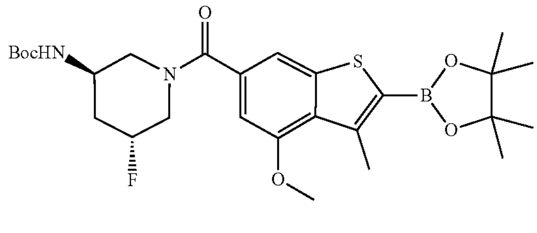 [SMILES: COc1cc(C(=O)N2C[C@H](F)C[C@@H](NC(=O)OC(C)(C)C)C2)cc2sc(B3OC(C)(C)C(C)(C)O3)c(C)c12]

LDA (1 ml, 2 mmol) was added drop wise under argon atmosphere to a stirred solution of Intermediate 138A (200 mg, 0.473 mmol) in THF (13 m) at −78° C., the reaction mixture was stirred for 45 min followed by the addition of 2-Isopropoxy-4,4,5,5-tetramethyl-1,3,2-dioxaborolane (0.4 ml, 0.473 mmol). The reaction mixture was stirred for 1 hour, allowed to warm to a room temperature, quenched with aqueous ammonium chloride solution (25 ml), and extracted with EtOAc (2×25 ml). The combined organic layers were washed with water (25 ml) and brine (50 ml), dried over $Na_2SO_4$, filtered, and the volatiles were evaporated to dryness under reduced pressure to afford the title compound (200 mg, crude). LC-MS m/z: 491.2 $[M-57+H]^+$.

Intermediate 138C tert-Butyl-((3R,5R)-1-(2-(1-(cyclopropylmethyl)-1H-pyrrolo[2,3-b]pyridin-2-yl)-4-methoxy-3-methylbenzo[b]thiophene-6-carbonyl)-5-fluoropiperidin-3-yl)carbamate

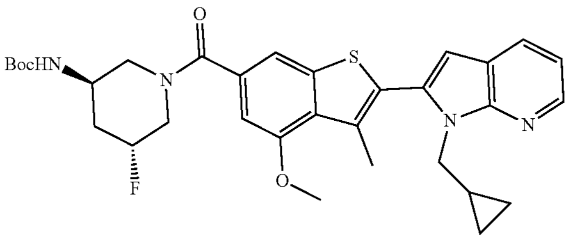 [SMILES: COc1cc(C(=O)N2C[C@H](F)C[C@@H](NC(=O)OC(C)(C)C)C2)cc2sc(-c3cc4cccnc4n3CC3CC3)c(C)c12]

A solution of $K_2CO_3$ (302 mg, 2.188 mmol) in water (1 ml) was added to a stirred solution of Intermediate 138B (400 mg, 0.729 mmol) and 1-(cyclopropylmethyl)-2-iodo-1H-pyrrolo[2,3-b]pyridine (217 mg, 0.729 mmol) in dioxane (4 ml), followed by the addition of tetrakis-(triphenylphosphine)palladium(0) (63.2 mg, 0.055 mmol) under argon atmosphere. The reaction mixture was heated to 85° C. and stirred for 17 hours, allowed to cool to a room temperature, water (10 ml) was added, and extracted with EtOAc (2×15 ml). The combined organic layers were washed with water (15 ml) and brine (20 ml), dried over $Na_2SO_4$, filtered and the volatiles were evaporated to dryness under reduced pressure to afford the title compound (200 mg, 50%). LC-MS m/z: 593.3 $[M+H]^+$.

Example 138

TFA (0.260 ml, 3.37 mmol) was added to a stirred solution of Intermediate 138C (200 mg, 0.337 mmol) in DCM (2 ml). The reaction mixture was stirred at a room temperature for 17 hours, the volatiles were evaporated to dryness under reduced pressure, and the crude product thus obtained was purified using RP-HPLC to afford the title compound (13.8, 8%). LC-MS m/z: 493.3 $[M+H]^+$. LC-MS retention time: 1.8 min (Method E). $^1H$ NMR (400 MHz, DMSO-$d_6$) δ ppm: 8.34 (dd, J=1.6, 4.8 Hz, 1H), 7.63 (s, 1H), 7.31-6.99 (m, 2H), 6.93 (s, 1H), 6.69 (s, 1H), 5.13-4.58 (m, 3H), 4.16 (br, d, J=7.1 Hz, 3H), 3.95 (s, 5H), 3.10-2.79 (m, 1H), 2.41-2.32 (m, 3H), 1.98-1.69 (m, 1H), 1.29-1.09 (m, 1H), 1.06-0.94 (m, 1H),0.36-0.25 (m, 2H), 0.15 (br, d, J=4.6 Hz, 2H).

Example 139

5-(2-(6-((3R,5R)-3-Amino-5-fluoropiperidine-1-carbonyl)-4-methoxy-3-methylbenzo[b]thiophen-2-yl)-1-(cyclopropylmethyl)-1H-pyrrolo[2,3-b]pyridin-6-yl)isoindolin-1-one

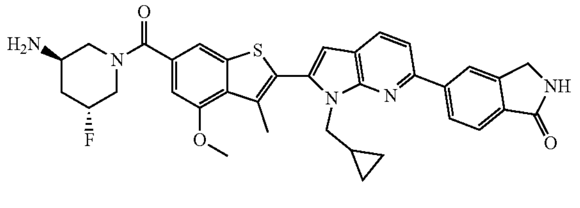 [SMILES: COc1cc(C(=O)N2C[C@H](N)C[C@@H](F)C2)cc2sc(-c3cc4ccc(-c5ccc6c(c5)CNC6=O)nc4n3CC3CC3)c(C)c12]

Intermediate 139A tert-Butyl-((3R,5R)-1-(2-(6-chloro-1-(cyclopropylmethyl)-1H-pyrrolo[2,3-b]pyridin-2-yl)-4-methoxy-3-methylbenzo[b]thiophene-6-carbonyl)-5-fluoropiperidin-3-yl)carbamate

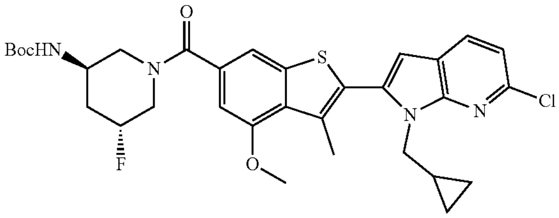 [SMILES: COc1cc(C(=O)N2C[C@H](F)C[C@@H](NC(=O)OC(C)(C)C)C2)cc2sc(-c3cc4ccc(Cl)nc4n3CC3CC3)c(C)c12]

6-Chloro-1-(cyclopropylmethyl)-2-iodo-1H-pyrrolo[2,3-b]pyridine (Intermediate-3, 0.8 g, 2.406 mmol) and $K_2CO_3$ (0.831 g, 6.01 mmol) in water (0.8 ml) were added to a degassed solution of Intermediate 138B (1.583 g, 2.89 mmol) in 1,4-dioxane (3 ml), followed by the addition of $PdCl_2(dppf)-CH_2Cl_2$ adduct (0.118 g, 0.144 mmol). The reaction mixture was heated to 90° C. and stirred for 16 hours, diluted with water (5 ml), and extracted with EtOAc (2×10 ml). The combined organic layers were washed with brine (20 ml), dried over sodium sulphate, filtered, and the filtrate was concentrated under reduced pressure. The crude product thus obtained was purified using a silica gel column (24 g, Redisep® $SiO_2$ column, eluting with 80% EtOAc in n-hexane) to afford the title compound as brown solid (40 mg, 46%). LC-MS m/z: 627 $[M+H]^+$. $^1H$ NMR (400 MHz, DMSO-d6) δ ppm: 8.10 (d, J=8.53 Hz, 1H), 7.63 (s, 1H), 7.25 (d, J=8.03 Hz, 1H), 6.93 (s, 2H), 6.75 (s, 1H), 4.05 (dt, J=14.68, 7.47 Hz, 2H), 3.95 (br, s, 6H), 3.16-3.30 (m, 2H), 2.44-2.48 (m, 4H), 1.99 (s, 1H), 1.41 (br, s, 9H), 1.08 (s, 1H), 0.34 (br, d, J=6.53 Hz, 2H), 0.15 (br, d, J=6.02 Hz, 2H).

Intermediate 139B tert-Butyl-((3R,5R)-1-(2-(1-(cyclopropylmethyl)-6-(1-oxoisoindolin-5-yl)-1H-pyrrolo[2,3-b]pyridin-2-yl)-4-methoxy-3-methylbenzo[b]thiophene-6-carbonyl)-5-fluoropiperidin-3-yl)carbamate

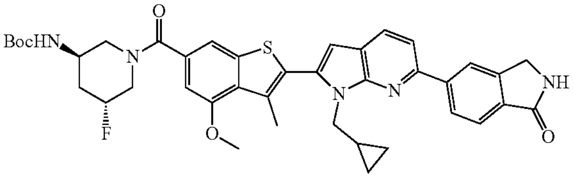 [SMILES: COc1cc(C(=O)N2C[C@H](F)C[C@@H](NC(=O)OC(C)(C)C)C2)cc2sc(-c3cc4ccc(-c5ccc6c(c5)CNC6=O)nc4n3CC3CC3)c(C)c12]

5-(4,4,5,5-Tetramethyl-1,3,2-dioxaborolan-2-yl)isoindolin-1-one (37.2 mg, 0.144 mmol), $K_2CO_3$ (63.5 mg, 0.299 mmol) and XPHOS Pd G2 (5.25 mg, 7.18 μmol) were added to a degassed solution of Intermediate 139A (75 mg, 0.120 mmol) in 1,4-dioxane (2 ml). The reaction mixture stirred at 80° C. for 10 hours, diluted with water (5 ml), and extracted with EtOAc (2×10 ml). The combined organic layers were washed with brine, dried over sodium sulphate, filtered, and concentrated under vacuum. The crude product was purified using a silica gel column (12 g, Redisep® $SiO_2$ column, eluting with 80% EtOAc in n-hexane) to afford the title compound as brown solid (40 mg, 46%). LC-MS m/z: 724 $[M+H]^+$.

Example 139

TFA (0.043 ml, 0.553 mmol) was added to a solution of Intermediate 139B (40 mg, 0.055 mmol) in DCM (3.0 ml). The reaction mixture was stirred at a room temperature for 16 hours, concentrated, and the crude compound was purified using RP-HPLC to afford the title compound (10 mg, 28%) as off-white solid. LC-MS m/z: 624.3 $[M+H]^+$. HPLC retention time: 2.37 min (Method I). $^1H$ NMR (400 MHz, methanol-$d_4$) δ ppm: 8.40 (s, 1H), 8.35 (d, J=8.2 Hz, 1H), 8.11 (d, J=8.3 Hz, 1H), 7.92 (d, J=8.1 Hz, 1H), 7.82 (d, J=8.3 Hz, 1H), 7.56 (d, J=1.0 Hz, 1H), 6.99-6.93 (m, 1H), 6.69 (s, 1H), 4.83-4.73 (m, 3H), 4.62-4.57 (m, 2H), 4.01(s, 3H), 2.58 (s, 3H), 2.45-2.36 (m, 1H), 1.96-1.93 (m, 1H), 1.75-1.57 (m, 1H), 1.47-1.26 (m, 3H), 1.25-1.14 (m, 1H), 0.99-0.88 (m, 1H), 0.43-0.37 (m, 2H), 0.31-0.21 (m, 2H).

Compounds of Examples 140 and 141 in Table 17 were prepared following a procedure similar to the preparation of a compound of Example 139, by Suzuki coupling of Intermediate 139A with appropriate boronic acid.

TABLE 17

| Example | Structure<br>Name<br>Analytical Data: LC-MS m/z $[M + H]^+$; HPLC retention time (HPLC method) |
|---|---|
| 140 | 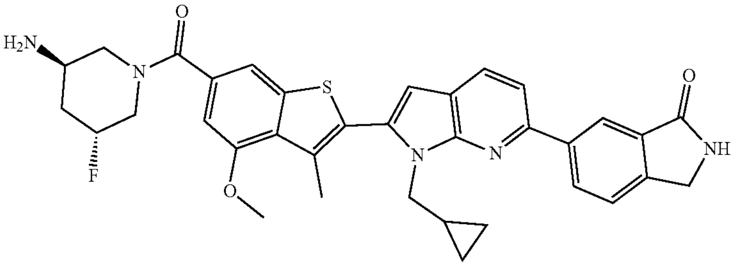 [SMILES: COc1cc(C(=O)N2C[C@H](N)C[C@@H](F)C2)cc2sc(-c3cc4ccc(-c5ccc6c(c5)C(=O)NC6)nc4n3CC3CC3)c(C)c12]<br>6-(2-(6-((3R,5R)-3-Amino-5-fluoropiperidine-1-carbonyl)-4-methoxy-3-methylbenzo[b]thiophen-2-yl)-1-(cyclopropylmethyl)-1H-pyrrolo[2,3-b]pyridin-6-yl)isoindolin-1-one<br>Analytical Data: 624.2, 7.1 min (Method C) |

TABLE 17-continued

| Example | Structure<br>Name<br>Analytical Data: LC-MS m/z [M + H]+; HPLC retention time (HPLC method) |
|---|---|
| 141 | 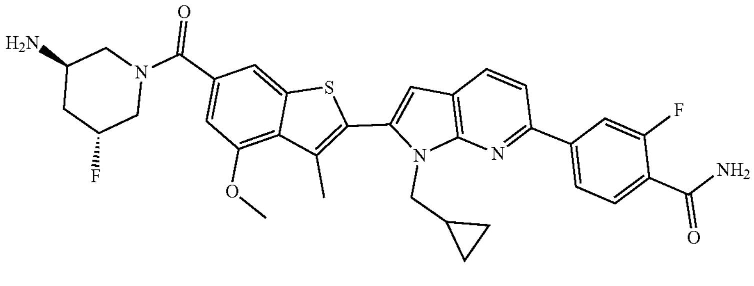 [SMILES: COc1cc(C(=O)N2C[C@H](N)C[C@@H](F)C2)cc2sc(-c3cc4ccc(-c5ccc(C(N)=O)c(F)c5)nc4n3CC3CC3)c(C)c12]<br>4-(2-(6-((3R,5R)-3-Amino-5-fluoropiperidine-1-carbonyl)-4-methoxy-3-methylbenzo[b]thiophen-2-yl)-1-(cyclopropylmethyl)-1H-pyrrolo[2,3-b]pyridin-6-yl)-2-fluorobenzamide<br>Analytical Data: 630.2, 7.3 min (Method C) |

Example 142

((3R,5R)-3-Amino-5-fluoropiperidin-1-yl)(2-(1-(cyclopropylmethyl)-6-(4-methoxypiperidin-1-yl)-1H-pyrrolo[2,3-b]pyridin-2-yl)-4-methoxy-3-methylbenzo[b]thiophen-6-yl)methanone

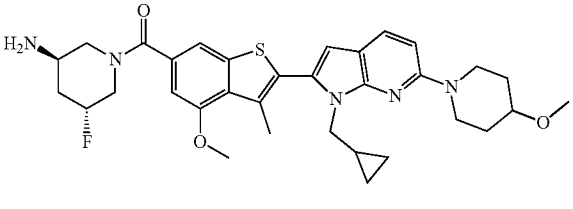 [SMILES: COc1cc(C(=O)N2C[C@H](N)C[C@@H](F)C2)cc2sc(-c3cc4ccc(N5CCC(OC)CC5)nc4n3CC3CC3)c(C)c12]

Intermediate 142A tert-Butyl-((3R,5R)-1-(2-(1-(cyclopropylmethyl)-6-(4-methoxypiperidin-1-yl)-1H-pyrrolo[2,3-b]pyridin-2-yl)-4-methoxy-3-methylbenzo[b]thiophene-6-carbonyl)-5-fluoropiperidin-3-yl)carbamate

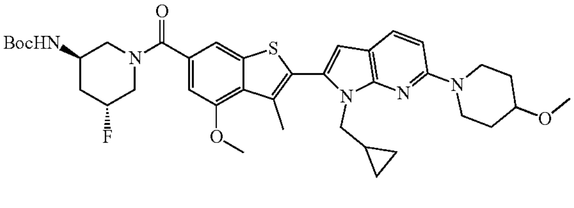 [SMILES: COc1cc(C(=O)N2C[C@H](F)C[C@@H](NC(=O)OC(C)(C)C)C2)cc2sc(-c3cc4ccc(N5CCC(OC)CC5)nc4n3CC3CC3)c(C)c12]

4-Methoxypiperidine (19.28 mg, 0.167 mmol) and potassium tert-butoxide (25.05 mg, 0.223 mmol) were added to a solution of Intermediate139A (70 mg, 0.112 mmol) in 1,4-dioxane (2 ml). The reaction mixture was degasified with argon for 10 min, followed by the addition of XPHOS (31.9 mg, 0.067 mmol) and $Pd(OAc)_2$ (7.52 mg, 0.033 mmol). The resulting reaction mixture was stirred at 110° C. for 12 hours, concentrated, diluted with water (5 ml), and extracted with EtOAc (2×10 ml). The combined organic layers were washed with brine (20 ml), dried over sodium sulfate, filtered, and the filtrate was concentrated under reduced pressure. The crude product was purified using a silica gel column (12 g, Redisep® $SiO_2$ column, eluting with 90% EtOAc in hexane) to afford the title compound as brown solid (40 mg, 51%). LC-MS m/z: 706 [M+H]+.

Example 142

TFA (0.044 ml, 0.567 mmol) was added to a stirred solution of Intermediate 142A (40 mg, 0.057 mmol) in DCM (3 ml). The reaction mixture was stirred at a room temperature for 16 hours, concentrated, and the crude compound was purified using RP-HPLC to afford the title compound (7 mg, 19%) as off-white solid. LC-MS m/z: 606 [M+H]+. LCMS retention time: 2.66 min (Method F). $^1H$ NMR (400 MHz, methanol-$d_4$) δ ppm: 7.76 (d, J=8.8 Hz, 1H), 7.56 (d, J=1.0 Hz, 1H), 6.96 (d, J=1.0 Hz, 1H), 6.75 (d, J=8.8 Hz, 1H), 6.42 (s, 1H), 4.19-4.06 (m, 4H), 4.02-3.98 (m, 3H), 3.52 (br, d, J=4.4 Hz, 2H), 3.68-3.47 (m, 2H), 3.45-3.39 (m, 4H), 3.30-3.15 (m, 2H), 2.54 (s, 3H), 2.03 (br, s, 2H), 1.73-1.56 (m, 2H), 1.51-1.28 (m, 4H), 1.13-1.00 (m, 1H), 0.38-0.27 (m, 2H), 0.18 (d, J=5.9 Hz, 2H).

Example 143

6-(2-(6-((3R,5R)-3-Amino-5-fluoropiperidine-1-carbonyl)-4-methoxy-3-methylbenzo[b]thiophen-2-yl)-1-(cyclopropylmethyl)-1H-indol-6-yl)isoindolin-1-one

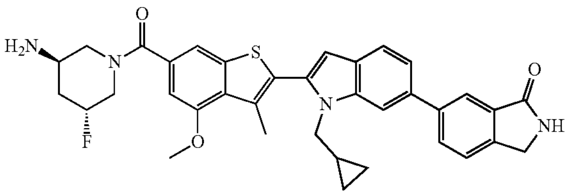 [SMILES: COc1cc(C(=O)N2C[C@H](N)C[C@@H](F)C2)cc2sc(-c3cc4ccc(-c5ccc6c(c5)C(=O)NC6)cc4n3CC3CC3)c(C)c12]

Intermediate 143A tert-Butyl-((3R,5R)-1-(2-(6-bromo-1-(cyclopropylmethyl)-1H-indol-2-yl)-4-methoxy-3-methylbenzo[b]thiophene-6-carbonyl)-5-fluoropiperidin-3-yl) carbamate

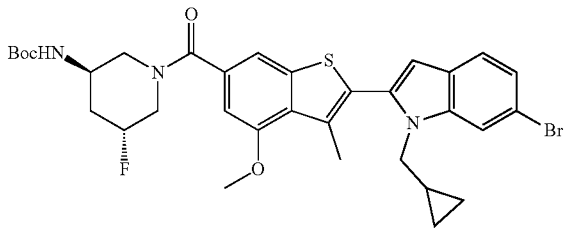

$K_2CO_3$ (287 mg, 2.078 mmol) and $PdCl_2$(dppf) (38.0 mg, 0.052 mmol) were added to a degasified solution of Intermediate 138B (380 mg, 0.693 mmol) and 6-bromo-1-(cyclopropylmethyl)-2-iodo-1H-indole (Intermediate 12, 261 mg, 0.693 mmol) in dioxane (3 ml). The reaction mixture was heated at 80° C. for 17 hours, diluted with water (5 ml), and extracted with EtOAc (2×10 ml). The combined organic layers were washed with brine (20 ml), dried over sodium sulphate, filtered, and the filtrate was concentrated to afford the title compound (180 mg). LC-MS m/z: 670.3 $[M-H]^+$.

Intermediate 143B tert-Butyl-(3R,5R)-1-(2-(1-(cyclopropylmethyl)-6-(3-oxoisoindolin-5-yl)-1H-indol-2-yl)-4-methoxy-3-methylbenzo[b]thiophene-6-carbonyl)-5-fluoropiperidin-3-yl) carbamate

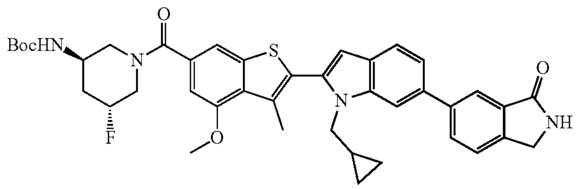 [SMILES: COc1cc(C(=O)N2C[C@H](F)C[C@@H](NC(=O)OC(C)(C)C)C2)cc2sc(-c3cc4ccc(-c5ccc6c(c5)C(=O)NC6)cc4n3CC3CC3)c(C)c12]

$PdCl_2$(dppf) (9.82 mg, 0.013 mmol) and $K_2CO_3$ (55.6 mg, 0.403 mmol) in water (1 ml) were added to a degasified solution Intermediate 143A (90 mg, 0.134 mmol) and 6-(4,4,5,5-tetramethyl-1,3,2-dioxaborolan-2-yl)isoindolin-1-one (34.8 mg, 0.134 mmol) in dioxane (2 ml). The reaction mixture was heated at 80° C. for 17 hours, diluted with water (5 ml), and extracted with EtOAc (2×10 ml). The combined organic layers were washed with brine (20 ml), dried over sodium sulphate, filtered, and the filtrate was concentrated to afford title compound (80 mg). LC-MS m/z: 723.4 $[M-H]^+$.

Example 143

TFA (0.5 ml) was added to a stirred solution of Intermediate 143B (80 mg) in DCM (3 ml). The reaction mixture was stirred at a room temperature for 16 hours, concentrated, and the crude compound obtained was purified using RP-HPLC to afford the title compound (4.8 mg, 7%). LC-MS m/z: 623.3 $[M+H]^+$. LCMS retention time: 1.6 min (Method F).

Example 144

5-(2-(6-((3R,5R)-3-Amino-5-fluoropiperidine-1-carbonyl)-4-methoxy-3-methylbenzo[b]thiophen-2-yl)-1-(cyclopropylmethyl)-1H-indol-6-yl)isoindolin-1-one

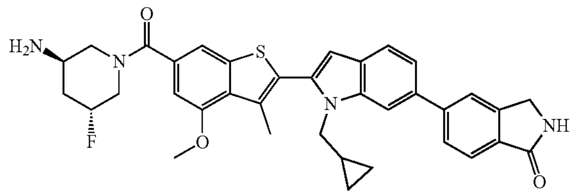

Intermediate 144A tert-Butyl-((3R,5R)-1-(2-(1-(cyclopropylmethyl)-6-(1-oxoisoindolin-5-yl)-1H-indol-2-yl)-4-methoxy-3-methylbenzo[b]thiophene-6-carbonyl)-5-fluoropiperidin-3-yl)carbamate

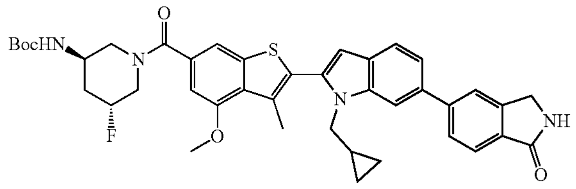 [SMILES: COc1cc(C(=O)N2C[C@H](F)C[C@@H](NC(=O)OC(C)(C)C)C2)cc2sc(-c3cc4ccc(-c5ccc6c(c5)CNC6=O)cc4n3CC3CC3)c(C)c12]

$PdCl_2$(dppf) (9.82 mg, 0.013 mmol) and $K_2CO_3$ (55.6 mg, 0.403 mmol) in water (1 ml) were added to a degasified solution of Intermediate 143A (90 mg, 0.134 mmol) and 5-(4,4,5,5-tetramethyl-1,3,2-dioxaborolan-2-yl)isoindolin-1-one (34.8 mg, 0.134 mmol) in dioxane (2 ml). The reaction mixture was heated at 80° C. for 17 hours, diluted with water (5 ml), and extracted with EtOAc (2×10 ml). The combined organic layers were washed with brine (20 ml), dried over sodium sulphate, filtered, and the filtrate was concentrated to afford the title compound (80 mg). LC-MS m/z: 723.4 $[M-H]^+$.

Example 144

TFA (0.5 ml) was added to a stirred solution of Intermediate 144A (80 mg) in DCM (3 ml) and the reaction mixture was stirred at a room temperature for 16 hours, concentrated and the crude compound thus obtained was purified by using RP-HPLC to afford the title compound (3.2 mg, 6%). LC-MS m/z: 623.3 $[M+H]^+$. LCMS retention time: 1.7 min (Method F). $^1$H NMR (400 MHz, DMSO-$d_6$) δ ppm: 8.55 (s, 1H), 8.01 (s, 1H), 7.97 (s, 1H), 7.89 (d, J=7.8 Hz, 1H), 7.76 (d, J=7.8 Hz, 1H), 7.71 (d, J=8.3 Hz, 1H), 7.58 (s,1H), 7.49 (dd, J=1.0, 8.3 Hz, 1H), 6.90 (s, 1H), 6.69 (s, 1H), 5.08-4.75 (m, 1H), 4.46 (s, 4H), 4.21-4.09 (m, 2H), 3.94 (s, 5H), 3.05-2.80 (m, 2H), 2.19-2.10 (m, 1H), 1.65-1.41 (m, 1H), 1.11-0.97 (m, 1H), 0.41-0.25 (m, 2H), 0.19-0.05 (m, 2H).

Example 145

((7R)-7-Amino-2-azabicyclo[2.2.1]heptan-2-yl)(2-(1-(cyclopropylmethyl)-1H-pyrrolo[2,3-b]pyridin-2-yl)-4-methoxy-3-methylbenzofuran-6-yl)methanone

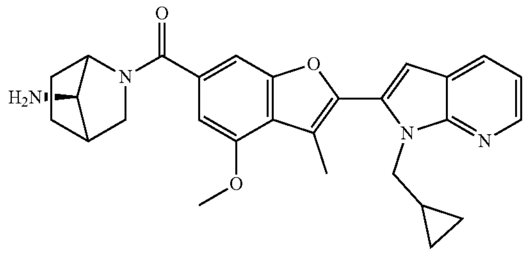 [SMILES: COc1cc(C(=O)N2CC3CCC2[C@@H]3N)cc2oc(-c3cc4cccnc4n3CC3CC3)c(C)c12]

Intermediate 145A

Methyl-3,5-dihydroxy-4-iodobenzoate

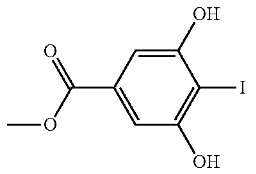

N-Iodosuccinimide (NIS, 26.8 g, 119 mmol) in MeOH (200 ml) was added to a stirred solution of methyl 3,5-dihydroxybenzoate (20 g, 119 mmol) in MeOH (200 ml) at 0° C. The reaction mixture was stirred at a room temperature for 16 hours, quenched with aqueous sodium thiosulphate solution (200 ml), and stirred for 15 min. Organic solvents were removed under reduced pressure, diluted with water (100 ml) and extracted with EtOAc (2×200 ml). The combined organic layers were washed with water (200 ml) and brine (200 ml), dried over sodium sulphate, filtered, and the filtrate was evaporated under reduced pressure to afford a crude compound (40 g). LC-MS m/z: 294.9 $[M+H]^+$. $^1H$ NMR (400 MHz, DMSO-$d_6$) δ ppm: 10.51 (s, 2H), 6.94 (s, 2H), 3.32 (s, 3H).

Intermediate 145B

Methyl-3-(allyloxy)-5-hydroxy-4-iodobenzoate

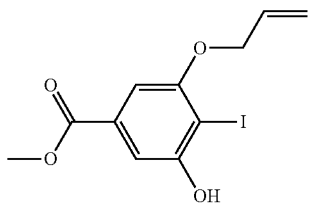 [SMILES: C=CCOc1cc(C(=O)OC)cc(O)c1I]

$K_2CO_3$ (5.44 g, 39.3 mmol) was added to a stirred solution of Intermediate 145A (11.57 g, 39.3 mmol) in DMF (100 ml). The contents were stirred for 10 min, followed by the addition of allyl bromide (3.40 ml, 39.3 mmol) drop wise. The reaction mixture was stirred at a room temperature for 16 hours, filtered, the filtrate was diluted with water (100 ml) and extracted with EtOAc (3×100 ml). The combined organic layers were dried over sodium sulphate, filtered and the filtrate was evaporated under reduced pressure. The crude material was purified using a silica gel column (80 g, Redisep® $SiO_2$ column, eluting with 30% EtOAc in n-hexane) to afford the title compound (9.3 g, 54%) as an off white solid. LC-MS m/z: 335 $[M+H]^+$. $^1H$ NMR (400 MHz, DMSO-$d_6$) δ ppm: 10.73 (s, 1H), 7.13 (d, J=1.51 Hz, 1H), 6.92 (d, J=2.01 Hz, 1H), 5.88-6.16 (m, 1H), 5.51 (dd, J=17.07, 2.01 Hz, 1H), 5.28 (dd, J=10.54, 1.51 Hz, 1H), 4.63-4.69 (m, 1H), 3.32 (s, 2H), 2.52-2.68 (m, 1H).

Intermediate 145C

Methyl-3-(allyloxy)-4-iodo-5-methoxybenzoate

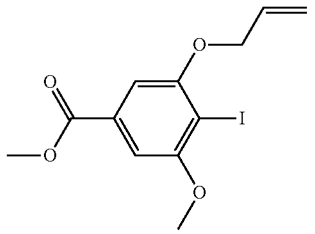 [SMILES: C=CCOc1cc(C(=O)OC)cc(OC)c1I]

$K_2CO_3$ (5.77 g, 41.8 mmol) was added to a stirred solution of Intermediate 145B (9.3 g, 27.8 mmol) in DMF (100 ml), and the contents were stirred for 10 min, followed by the addition of methyl iodide (2.26 ml, 36.2 mmol). The reaction mixture was stirred at a room temperature for 16 hours, filtered, the filtrate was diluted with water (100 ml) and extracted with EtOAc (3×100 ml). The combined organic layers were dried over anhydrous sodium sulphate, filtered, and the volatiles were evaporated under reduced pressure to afford the crude compound. The crude compound was purified using a silica gel column (40 g, Redisep® $SiO_2$ column, eluting with 35% EtOAc in n-hexane) to afford the title compound (5.5 g, 45%) as a colourless oil. LC-MS m/z: 349 $[M+H]^+$. $^1H$ NMR (400 MHz, DMSO-$d_6$) δ ppm: 7.13 (s, 2H), 6.06 (ddt, 1H), 5.45-5.58 (m, 1H), 5.30 (dd, J=10.76, 1.71 Hz, 1H), 4.67-4.77 (m, 2H), 3.89-3.92(m, 3H), 3.32 (s, 2H), 0.01 (s, 1H).

Intermediate 145D

Methyl-4-methoxy-3-methylbenzofuran-6-carboxylate

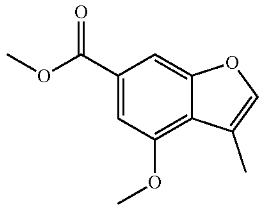 [SMILES: COC(=O)c1cc(OC)c2c(C)coc2c1]

Palladium (II) acetate (0.177 g, 0.790 mmol) was added to a stirred solution of Intermediate 145C (5.5 g, 15.80 mmol), sodium carbonate (4.19 g, 39.5 mmol), sodium formate (1.074 g, 15.80 mmol), and tetrabutylammonium chloride (4.83 g, 17.38 mmol) in DMF (2 ml). The reaction mixture was stirred at 80° C. for 16 hours, filtered through a celite bed, and washed with EtOAc (50 ml). The filtrate was diluted with water (150 ml), and extracted with EtOAc (3×50 ml). The combined organic layers were dried over anhydrous sodium sulphate, filtered, and the filtrate was evaporated under reduced pressure. The crude compound thus obtained was purified using a silica gel column (24 g, Redisep® $SiO_2$ column, eluting with 40-45% EtOAc in n-hexane) to afford the title compound (1.1 g, 29%) as a colourless oil. LC-MS m/z: 221 $[M+H]^+$. $^1H$ NMR (400 MHz, DMSO-$d_6$) δ ppm: 7.83-7.86 (m, 1H), 7.71-7.74 (m, 1H), 7.25-7.31 (m, 1H), 3.94 (s, 4H), 3.84-3.91 (m, 5H), 2.53-2.69 (m, 1H),2.41-2.49 (m, 3H), 2.32 (d, J=1.47 Hz, 5H).

Intermediate 145E

4-Methoxy-3-methylbenzofuran-6-carboxylic acid

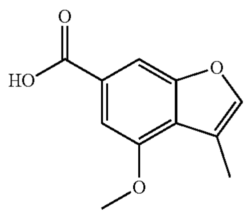

LiOH (1.631 g, 68.1 mmol) in water (5 ml) was added to a stirred solution of Intermediate 145D (5.0 g, 22.70 mmol) in THF (3 ml) and MeOH (3 ml). The reaction mixture was stirred at a room temperature for 3 hours, evaporated under reduced pressure to dryness, and the residue thus obtained was acidified to pH 3 using ice cold 1.5 N HCl. The resulting solids were filtered, washed with water, and vacuum dried to afford the title compound (4.34 g, 93%) as a white solid. LC-MS m/z: 205 $[M-H]^+$. $^1H$ NMR (400 MHz, DMSO-$d_6$) δ ppm: 7.81 (d, J=1.51 Hz, 1H), 7.68 (d, J=1.00 Hz, 1H), 7.27 (s, 1H), 3.92 (s, 3H), 2.45-2.47 (m, 1H), 2.31 (d, J=1.00 Hz, 3H).

Intermediate 145F tert-Butyl-((7R)-2-(4-methoxy-3-methylbenzofuran-6-carbonyl)-2-azabicyclo[2.2.1]heptan-7-yl)carbamate

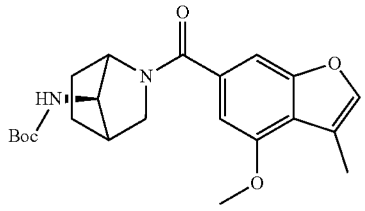 [SMILES: COc1cc(C(=O)N2CC3CCC2[C@@H]3NC(=O)OC(C)(C)C)cc2occ(C)c12]

HATU (4.15 g, 10.91 mmol) in DMF (20 ml) and DIPEA (3.81 ml, 21.82 mmol) were added to a stirred solution of tert-butyl ((7R)-2-azabicyclo[2.2.1]heptan-7-yl)carbamate (1.544 g, 7.27 mmol), 145E (1.5 g, 7.27 mmol). The reaction mixture was stirred at a room temperature for 16 hours, evaporated under reduced pressure to dryness, water (50 ml) was added, and extracted with EtOAc (2×50 ml). The combined organic layers were washed with water (100 ml) and brine (100 ml), dried over anhydrous sodium sulphate, filtered, and the filtrate was evaporated under reduced pressure. The crude compound thus obtained was purified using a silica gel column (24 g, Redisep® $SiO_2$ column, eluting with 10-90% EtOAc in n-hexane) to afford the title compound (2.2 g, 76%) as an off-white solid. LC-MS m/z: 401.3 $[M+H]^+$.

Intermediate 145G tert-Butyl-((7R)-2-(2-chloro-4-methoxy-3-methylbenzofuran-6-carbonyl)-2-azabicyclo[2.2.1]heptan-7-yl)carbamate

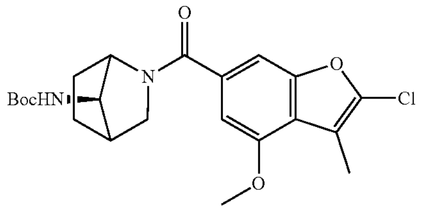 [SMILES: COc1cc(C(=O)N2CC3CCC2[C@@H]3NC(=O)OC(C)(C)C)cc2oc(Cl)c(C)c12]

LDA at −78° C. (0.7 ml, 1.400 mmol) was added to a stirred solution of Intermediate 145F (100 mg, 0.250 mmol) in THF (15 ml) under nitrogen atmosphere. The reaction mixture was stirred for 45 min, followed by the addition of hexachloroethane (65.0 mg, 0.275 mmol) in 2 ml of THF. The reaction mixture was allowed to warm to a room temperature and stirred for 4 hours, quenched with water (50 ml), and extracted with EtOAc (2×50 ml). The combined organic layers were washed with water (30 ml) and brine (30 ml), dried over anhydrous sodium sulphate, filtered, and the filtrate were evaporated to dryness under reduced pressure to afford the crude material (120 mg). LC-MS m/z: 435.3 $[M+H]^+$.

Intermediate 145H tert-Butyl-((7R)-2-(2-(1-(cyclopropylmethyl)-1H-pyrrolo[2,3-b]pyridin-2-yl)-4-methoxy-3-methylbenzofuran-6-carbonyl)-2-azabicyclo[2.2.1]heptan-7-yl) carbamate

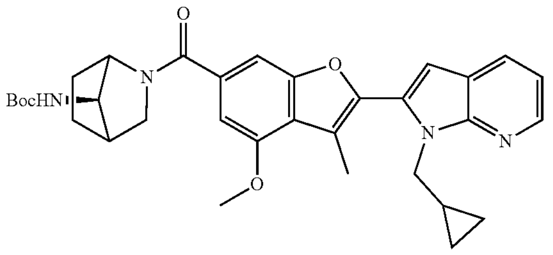 [SMILES: COc1cc(C(=O)N2CC3CCC2[C@@H]3NC(=O)OC(C)(C)C)cc2oc(-c3cc4cccnc4n3CC3CC3)c(C)c12]

$K_2CO_3$ (95 mg, 0.690 mmol) in water (0.75 ml) was added to a stirred solution of Intermediate 145G (100 mg, 0.230 mmol), 1-(cyclopropylmethyl)-2-(4,4,5,5-tetramethyl-1,3,2-dioxaborolan-2-yl)-1H-pyrrolo[2,3-b]pyridine (Intermediate 11, 68.6 mg, 0.230 mmol) and tetrakis(triphenylphosphine)palladium(0) (266 mg, 0.230 mmol) in dioxane (2 ml). The reaction mixture was stirred and heated at 120° C. for 6 hours, evaporated under reduced pressure to dryness, water (10 ml) was added, extracted with EtOAc (2×10 ml). The combined organic layers were washed with water (10 ml) and brine (10 ml), dried over anhydrous sodium sulphate, filtered, and the filtrate was evaporated under reduced pressure to afford the crude compound (100 mg). LC-MS m/z: 571.5 $[M+H]^+$.

Example 145

TFA (0.108 ml, 1.402 mmol) was added to a stirred solution of Intermediate 145H (80 mg, 0.140 mmol) in DCM (2 ml). The reaction mixture was stirred at a room temperature for 6 hours, evaporated under reduce pressure to dryness, and the crude product thus obtained was purified using RP-HPLC to afford the title compound (10 mg, 15%). LC-MS m/z: 471.3 $[M+H]^+$. LC-MS retention time: 1.4 min. (Method F). $^1H$ NMR (400 MHz, DMSO-$d_6$) δ ppm: 8.35 (dd, J=1.5, 4.6 Hz, 1H), 8.07 (dd, J=1.5, 7.8 Hz, 1H), 7.44-6.91 (m, 2H), 6.88 (t, J=2.0 Hz, 2H), 4.36 (d, J=7.1 Hz, 2H), 4.18 (s, 1H), 4.01-3.90 (m, 3H), 3.74 (s, 1H), 3.66-3.50 (m, 1H), 3.21 (s, 1H), 3.10-3.01 (m, 1H), 2.28-2.17 (m, 1H), 2.02-1.65 (m, 3H), 1.50-1.34 (m, 1H), 1.18-1.06 (m, 1H), 0.39-0.29 (m, 2H), 0.27-0.13 (m, 2H).

Example 146

((7R)-7-Amino-2-azabicyclo[2.2.1]heptan-2-yl)(2-(6-chloro-1-(cyclopropylmethyl)-1H-pyrrolo[2,3-b]pyridin-2-yl)-4-methoxy-3-methylbenzofuran-6-yl)methanone

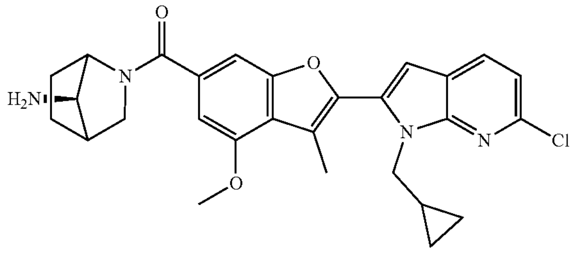 [SMILES: COc1cc(C(=O)N2CC3CCC2[C@@H]3N)cc2oc(-c3cc4ccc(Cl)nc4n3CC3CC3)c(C)c12]

Intermediate 146A tert-Butyl-((7R)-2-(4-methoxy-3-methyl-2-(4,4,5,5-tetramethyl-1,3,2-dioxaborolan-2-yl)benzofuran-6-carbonyl)-2-azabicyclo[2.2.1]heptan-7-yl)carbamate

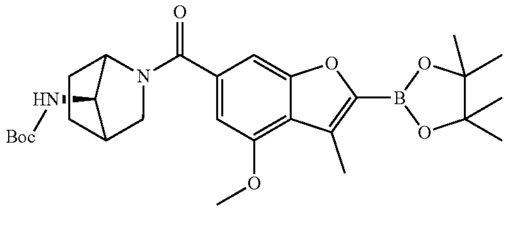 [SMILES: COc1cc(C(=O)N2CC3CCC2[C@@H]3NC(=O)OC(C)(C)C)cc2oc(B3OC(C)(C)C(C)(C)O3)c(C)c12]

LDA (3.75 ml, 7.49 mmol) was drop wise added to a stirred solution of Intermediate 145F (0.6 g, 1.498 mmol) in THF (6 ml) at −78° C. The reaction mixture was stirred for 30 min, followed by the addition of 2-isopropoxy-4,4,5,5-tetramethyl-1,3,2-dioxaborolane (1.254 g, 6.74 mmol). The reaction mixture was stirred at −78° C. for 1 hour, quenched by water at −78° C., and extracted with EtOAc (3×50 ml). The combined organic layers were dried over anhydrous sodium sulphate, filtered, and filtrate was evaporated under reduced pressure to afford the title compound (0.780 g, 99%) as brown oil. LC-MS m/z: 527 $[M-H]^+$.

Intermediate 146B tert-Butyl-((7R)-2-(2-(6-chloro-1-(cyclopropylmethyl)-1H-pyrrolo[2,3-b]pyridin-2-yl)-4-methoxy-3-methylbenzofuran-6-carbonyl)-2-azabicyclo[2.2.1]heptan-7-yl)carbamate

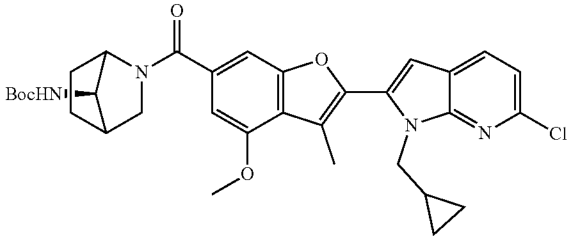 [SMILES: COc1cc(C(=O)N2CC3CCC2[C@@H]3NC(=O)OC(C)(C)C)cc2oc(-c3cc4ccc(Cl)nc4n3CC3CC3)c(C)c12]

$K_2CO_3$ (37.3 mg, 0.270 mmol) in water (0.75 ml) was added to a stirred solution of Intermediate 146A (40 mg, 0.090 mmol), 6-chloro-1-(cyclopropylmethyl)-2-iodo-1H-pyrrolo[2,3-b]pyridine (Intermediate-3, 29.9 mg, 0.090 mmol) and $PdCl_2(dppf)-CH_2Cl_2$ adduct (5.51 mg, 6.75 μmol) in dioxane (3 ml). The reaction mixture was heated to 110° C. and stirred for 6 hours, evaporated under reduced pressure to dryness, water (10 ml) was added, and extracted with EtOAc (2×10 ml). The combined organic layers were washed with water (10 ml) and brine solution (10 ml), dried over anhydrous sodium sulphate, filtered, and the filtrate was evaporated under reduced pressure to afford the crude compound (60 mg). LC-MS m/z: 605.3 $[M+H]^+$.

Example 146

TFA (0.076 ml, 0.992 mmol) was added to a stirred solution of Intermediate 146B (60 mg, 0.099 mmol) in DCM (2 ml). The reaction mixture was stirred at a room temperature for 10 hours, concentrated under reduced pressure, and the crude product thus obtained was purified using RP-HPLC the to afford the title compound (1.9 mg, 3.6%), LC-MS m/z: 505.2 $[M+H]^+$; LC-MS retention time: 1.906/2.216 min. (Method E/F).

Example 147

((3R,5R)-3-Amino-5-fluoropiperidin-1-yl)(2-(1-(cyclopropylmethyl)-1H-pyrrolo[2,3-b]pyridin-2-yl)-4-methoxy-3-methylbenzofuran-6-yl)methanone

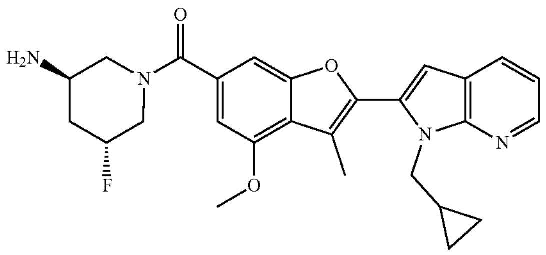 [SMILES: COc1cc(C(=O)N2C[C@H](N)C[C@@H](F)C2)cc2oc(-c3cc4cccnc4n3CC3CC3)c(C)c12]

Intermediate 147A tert-Butyl-((3R,5R)-5-fluoro-1-(4-methoxy-3-methylbenzofuran-6-carbonyl)piperidin-3-yl)carbamate

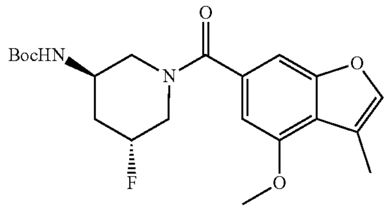 [SMILES: COc1cc(C(=O)N2C[C@H](F)C[C@@H](NC(=O)OC(C)(C)C)C2)cc2occ(C)c12]

HATU (830 mg, 2.182 mmol) in DMF (15 ml) and DIPEA (0.762 ml, 4.36 mmol) were added to a stirred solution of Intermediate 145E (300 mg, 1.455 mmol) and tert-butyl ((3R,5R)-5-fluoropiperidin-3-yl)carbamate (318 mg, 1.455 mmol). The reaction mixture was stirred at a room temperature for 16 hours, evaporated under reduced pressure to dryness, water (50 ml) was added, and extracted with EtOAc (2×50 ml). The combined organic layers were washed with water (100 ml), brine solution (100 ml), dried over anhydrous sodium sulphate, filtered, and the filtrate was concentrated under reduced pressure to afford the crude material. The crude compound was purified using a silica gel column (24 g, Redisep® SiO2 column, eluting with 40-45% EtOAc in n-hexane) to afford the title compound (450 mg, 76%) as an off-white solid. LC-MS m/z: 405.3 $[M-H]^+$.

Intermediate 147B tert-Butyl-((3R,5R)-1-(2-chloro-4-methoxy-3-methylbenzofuran-6-carbonyl)-5-fluoropiperidin-3-yl) carbamate

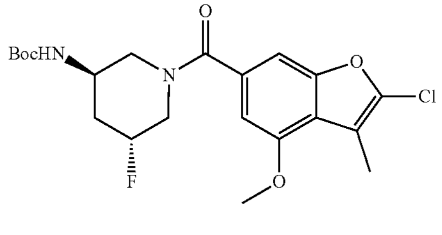 [SMILES: COc1cc(C(=O)N2C[C@H](F)C[C@@H](NC(=O)OC(C)(C)C)C2)cc2oc(Cl)c(C)c12]

LDA (0.7 ml, 1.400 mmol) was added to a stirred solution of Intermediate 147A (110 mg, 0.271 mmol) in THF (10 ml) at −78° C. under nitrogen atmosphere. The reaction mixture was stirred for 1 hour, followed by the addition of hexachloroethane (70.5 mg, 0.298 mmol) in 2 ml of THF at −78° C. The reaction mixture was allowed to warm to a room temperature and stirred for 4 hours, quenched with water, and extracted with EtOAc (2×50 ml). The combined organic layers were washed with water (30 ml) and brine (30 ml), dried over anhydrous sodium sulphate, filtered, and the filtrate was concentrated under reduced pressure to afford the crude compound (112 mg). LC-MS m/z: 441.2 $[M-H]^+$.

Intermediate 147C tert-Butyl-((3R,5R)-1-(2-(1-(cyclopropylmethyl)-1H-pyrrolo[2,3-b]pyridin-2-yl)-4-methoxy-3-methylbenzofuran-6-carbonyl)-5-fluoropiperidin-3-yl) carbamate

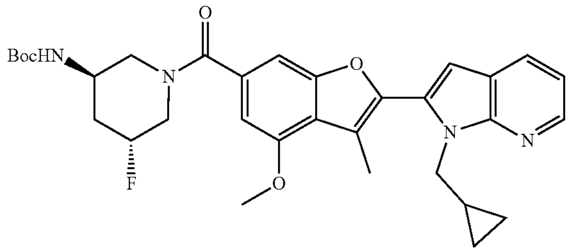 [SMILES: COc1cc(C(=O)N2C[C@H](F)C[C@@H](NC(=O)OC(C)(C)C)C2)cc2oc(-c3cc4cccnc4n3CC3CC3)c(C)c12]

$K_2CO_3$ (103 mg, 0.748 mmol) in water (0.75 ml) was added to a stirred solution of Intermediate 147B (110 mg, 0.249 mmol), 1-(cyclopropylmethyl)-2-(4,4,5,5-tetramethyl-1,3,2-dioxaborolan-2-yl)-1H-pyrrolo[2,3-b]pyridine (Intermediate 11, 74.4 mg, 0.249 mmol), and tetrakis(triphenylphosphine)palladium(0) (288 mg, 0.249 mmol) in dioxane (3 ml), The reaction mixture was stirred and heated at 120° C. for 6 hours, evaporated under reduced pressure to dryness, water (10 ml) was added, and extracted with EtOAc (2×10 ml). The combined organic layers were washed with water (10 ml) and brine (10 ml), dried over anhydrous sodium sulphate, filtered, and the filtrate was concentrated under reduced pressure to afford the crude material. The crude compound was purified using a silica gel column (24 g, Redisep® $SiO_2$ column, eluting with 50-75% EtOAc in n-hexane) to afford the title compound (100 mg). LC-MS m/z: 575.5 $[M-H]^+$.

Example 147

TFA (0.120 ml, 1.561 mmol) was added to a stirred solution of Intermediate 147C (90 mg, 0.156 mmol) in DCM (2 ml) and the reaction mixture was stirred at a room temperature for 5 hours The reaction mixture was evaporated under reduced pressure, and the crude product thus obtained was purified using RP-HPLC to afford the title compound (0.8 mg, 1%). LC-MS m/z: 477.3 $[M+H]^+$. LC-MS retention time: 1.5 min (Method F). $^1H$ NMR (400 MHz, DMSO-$d_6$) δ ppm: 8.35 (dd, J 1.3, 5.0 Hz, 1H), 8.17-7.86 (m, 1H), 7.30 (s, 1H), 7.19 (dd, J=4.5, 7.7 Hz, 1H), 6.88 (s, 1H), 6.84 (s, 1H), 5.04-4.66 (m, 1H), 4.35 (d, J=7.3 Hz, 2H), 3.95 (s, 4H), 2.39-2.33 (m, 1H), 1.93-1.77 (m, 1H), 1.33-1.06 (m, 5H), 0.90-0.77 (m, 1H), 0.41-0.31 (m,2H), 0.28-0.19 (m, 2H).

Example 148

((7R)-7-Amino-2-azabicyclo[2.2.1]heptan-2-yl)(2-(1-(cyclopropylmethyl)-1H-indol-2-yl)-4-methoxy-3-methylbenzofuran-6-yl)methanone

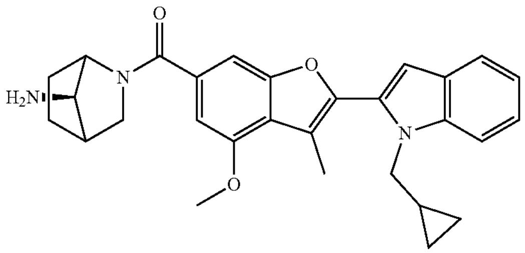 [SMILES: COc1cc(C(=O)N2CC3CCC2[C@@H]3N)cc2oc(-c3cc4ccccc4n3CC3CC3)c(C)c12]

Intermediate 148A tert-Butyl-((7R)-2-(2-(1-(cyclopropylmethyl)-1H-indol-2-yl)-4-methoxy-3-methylbenzofuran-6-carbonyl)-2-azabicyclo[2.2.1]heptan-7-yl)carbamate

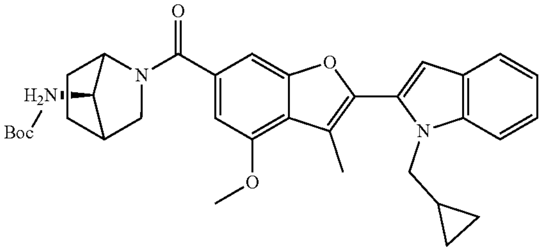 [SMILES: COc1cc(C(=O)N2CC3CCC2[C@@H]3NC(=O)OC(C)(C)C)cc2oc(-c3cc4ccccc4n3CC3CC3)c(C)c12]

A solution of $K_2CO_3$ (95 mg, 0.690 mmol) in water (0.75 ml) was added to a stirred solution of Intermediate 145G (100 mg, 0.230 mmol), 1-(cyclopropylmethyl)-2-(4,4,5,5-tetramethyl-1,3,2-dioxaborolan-2-yl)-1H-indole (Intermediate-10, 68.3 mg, 0.230 mmol), and tetrakis-(triphenylphosphine)palladium(0) (266 mg, 0.230 mmol) in dioxane (2 ml). The reaction mixture was heated to 120° C. and stirred for 6 hours, evaporated under reduced pressure to dryness, water (10 ml) was added, and extracted with EtOAc (2×10 ml). The combined organic layers were washed with water (10 ml) and brine (10 ml), dried over anhydrous sodium sulphate, filtered, and the filtrate was concentrated under reduced pressure to afford the crude compound (100 mg). LC-MS m/z: 570.4 $[M+H]^+$.

Example 148

TFA (0.135 ml, 1.755 mmol) was added to a stirred solution of Intermediate 148A (100 mg, 0.176 mmol) in DCM (2 ml). The reaction mixture was stirred at a room temperature for 16 hours, evaporated under reduced pressure, and the crude product obtained was purified using RP-HPLC to afford the title compound (11.1 mg, 13%). LC-MS m/z: 470.3 $[M+H]^+$. LC-MS retention time: 1.8 min (Method F). $^1H$ NMR (400 MHz, DMSO-$d_6$) δ ppm: 7.64 (dd, J=3.1, 8.2 Hz, 2H), 7.29-7.22 (m, 2H), 7.13-7.09 (m, 1H), 6.91-6.82 (m, 2H), 4.24 (d, J=6.6 Hz, 2H), 4.00-3.91 (m, 3H), 3.70 (s, 1H), 3.67-3.54 (m, 1H), 3.50 (br, d, J=10.8 Hz, 2H), 3.18-3.15 (m, 2H), 3.12-3.01 (m, 1H), 2.21 (br, s, 1H), 2.03-1.85 (m, 2H), 1.84-1.64 (m, 1H), 1.47-1.31 (m, 1H), 1.13-1.04 (m, 1H), 0.37-0.32 (m, 2H), 0.16 (d, J=4.4 Hz, 2H)

Example 149

5-(2-(6-((7R)-7-Amino-2-azabicyclo[2.2.1]heptane-2-carbonyl)-4-methoxy-3-methylbenzofuran-2-yl)-1-(cyclopropylmethyl)-1H-indol-6-yl)isoindolin-1-one

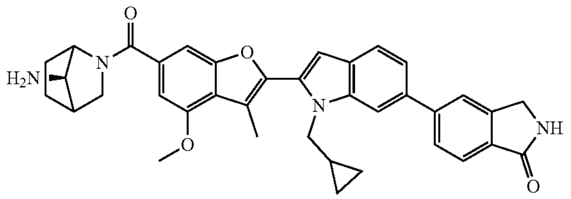 [SMILES: COc1cc(C(=O)N2CC3CCC2[C@@H]3N)cc2oc(-c3cc4ccc(-c5ccc6c(c5)CNC6=O)cc4n3CC3CC3)c(C)c12]

Intermediate 149A tert-Butyl-((7R)-2-(2-(6-bromo-1-(cyclopropylmethyl)-1H-indol-2-yl)-4-methoxy-3-methylbenzofuran-6-carbonyl)-2-azabicyclo[2.2.1]heptan-7-yl)carbamate

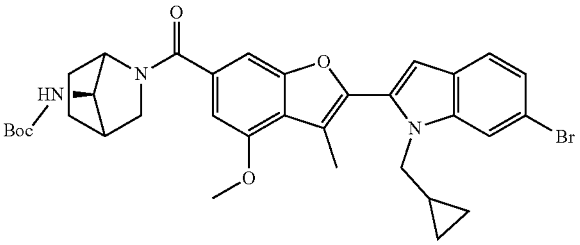 [SMILES: COc1cc(C(=O)N2CC3CCC2[C@@H]3NC(=O)OC(C)(C)C)cc2oc(-c3cc4ccc(Br)cc4n3CC3CC3)c(C)c12]

A solution of $K_2CO_3$ (622 mg, 4.50 mmol) in water (0.027 ml, 1.501 mmol) was added to a stirred and degasified solution of Intermediate 146A (790 mg, 1.501 mmol), 6-bromo-1-(cyclopropylmethyl)-2-iodo-1H-indole (Intermediate-12, 1016 mg, 2.70 mmol) in dioxane (8 ml), followed by the addition of $Pd(PPh_3)_4$ (130 mg, 0.113 mmol). The reaction mixture was heated to 80° C. and stirred for 16 hours, diluted with water (50 ml), and extracted with EtOAc (3×50 ml). The combined organic layers were dried over anhydrous sodium sulphate, filtered, and the filtrate was evaporated under reduced pressure. The crude product was purified using a silica gel column (24 g, Redisep® $SiO_2$ column, eluting with 65% EtOAc in n-hexane) to afford the title compound (700 mg, 72%) as a brown oil. LC-MS m/z: 650 $[M-H]^+$.

Intermediate 149B tert-Butyl-((7R)-2-(2-(1-(cyclopropylmethyl)-6-(1-oxoisoindolin-5-yl)-1H-indol-2-yl)-4-methoxy-3-methylbenzofuran-6-carbonyl)-2-azabicyclo[2.2.1]heptan-7-yl)carbamate

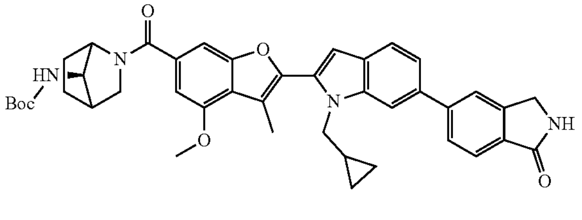 [SMILES: COc1cc(C(=O)N2CC3CCC2[C@@H]3NC(=O)OC(C)(C)C)cc2oc(-c3cc4ccc(-c5ccc6c(c5)CNC6=O)cc4n3CC3CC3)c(C)c12]

A solution of $K_2CO_3$ (60.7 mg, 0.439 mmol) in water (2.64 μl, 0.146 mmol) was added to a stirred and degasified solution of Intermediate 149A (95 mg, 0.146 mmol) and 5-(4,4,5,5-tetramethyl-1,3,2-dioxaborolan-2-yl)isoindolin-1-one (38.0 mg, 0.146 mmol) in dioxane (2 ml). The reaction mixture was degasified with argon, followed by the addition of $PdCl_2$(dppf)-$CH_2Cl_2$ adduct (8.97 mg, 10.99 μmol). The reaction mixture was heated to 80° C. and stirred for 16 hours, diluted with water (50 ml), and extracted with EtOAc (3x50 ml). The combined organic layers were dried over anhydrous sodium sulphate, filtered, and the filtrate was concentrated under reduced pressure. The crude product thus obtained was purified using prep HPLC to afford the title compound as off-white solid (0.040 g, 39%). LC-MS m/z: 701 $[M-H]^+$.

Example 149

TFA (4.52 μL, 0.059 mmol) was added to a stirred solution of Intermediate 149B (40 mg, 0.059 mmol) in DCM (2 ml), and the contents were stirred at a room temperature for 3 hours The reaction mixture was evaporated under reduced pressure and the residue was stirred with aqueous ammonia solution (2 ml). The aqueous solution was decanted and the residue obtained was dried under vacuum and purified using RP-HPLC to afford the title compound (7.33 mg, 30%). LC-MS m/z: 601 $[M+H]^+$. LC-MS retention time: 2.664 min (Method H). $^1$H NMR (400 MHz, DMSO-$d_6$) δ ppm: 8.50-8.60 (m, 1H), 7.89-8.10 (m, 3H), 7.85-8.00 (m, 2H), 7.81-7.97 (m, 1H), 7.70-7.83 (m, 2H), 7.44-7.58 (m,1H), 7.22-7.34 (m, 1H), 6.89 (s, 2H), 4.47 (s, 5H), 4.30 (s, 2H), 4.23-4.39 (m, 1H), 3.97 (s, 4H), 3.66-3.79 (m, 2H), 3.44-3.59 (m, 2H), 2.97-3.17 (m, 3H), 2.53-2.61 (m, 15H), 2.35-2.47 (m, 6H), 2.18-2.29 (m, 2H), 1.83-2.05 (m, 3H), 1.24 (s, 10H), 0.75-0.96 (m, 3H), 0.26-0.43 (m, 1H), 0.15-0.23 (m,2H), 0.01-0.02 (m, 2H), −0.06-0.00 (m, 9H).

Compounds of Examples 150 to 157 in Table 18 were obtained following a procedure similar to the preparation of a compound of Example 149, by Suzuki coupling of Intermediate 149A with appropriate boronic ester or acid.

TABLE 18

| Example | Structure<br>Name<br>Analytical Data: LC-MS m/z $[M + H]^+$; HPLC retention time (HPLC method) |
|---|---|
| 150 | 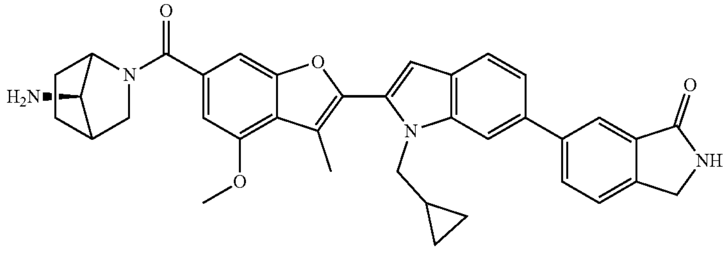 [SMILES: COc1cc(C(=O)N2CC3CCC2[C@@H]3N)cc2oc(-c3cc4ccc(-c5ccc6c(c5)C(=O)NC6)cc4n3CC3CC3)c(C)c12]<br>6-(2-(6-((7R)-7-Amino-2-azabicyclo[2.2.1]-heptane-2-carbonyl)-4-methoxy-3-methylbenzofuran-2-yl)-1-(cyclopropylmethyl)-1H-indol-6-yl)isoindolin-1-one<br>Analytical Data: 601.4, 2.720 min (Method H) |
| 151 | 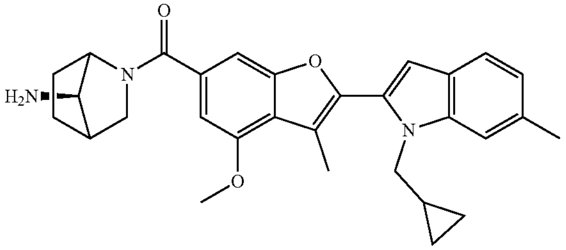 [SMILES: COc1cc(C(=O)N2CC3CCC2[C@@H]3N)cc2oc(-c3cc4ccc(C)cc4n3CC3CC3)c(C)c12]<br>((7R)-7-Amino-2-azabicyclo[2.2.1]heptan-2-yl)(2-(1-(cyclopropylmethyl)-6-methyl-1H-indol-2-yl)-4-methoxy-3-methylbenzofuran-6-yl)methanone<br>Analytical Data: 484.3, 3.512 min (Method H) |

TABLE 18-continued

| Example | Structure<br>Name<br>Analytical Data: LC-MS m/z $[M + H]^+$; HPLC retention time (HPLC method) |
|---|---|
| 152 | 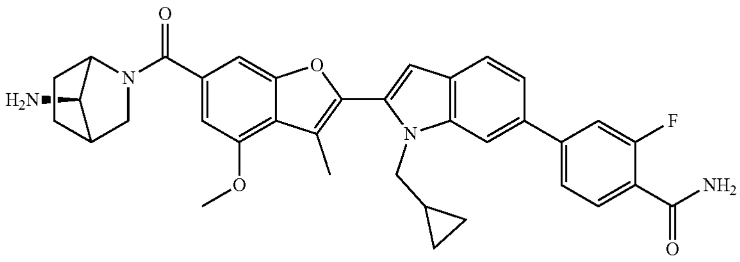 [SMILES: COc1cc(C(=O)N2CC3CCC2[C@@H]3N)cc2oc(-c3cc4ccc(-c5ccc(C(N)=O)c(F)c5)cc4n3CC3CC3)c(C)c12]<br>4-(2-(6-((7R)-7-Amino-2-azabicyclo[2.2.1]heptane-2-carbonyl)-4-methoxy-3-methylbenzofuran-2-yl)-1-(cyclopropylmethyl)-1H-indol-6-yl)-2-fluorobenzamide<br>Analytical Data: 607.4, 2.853 min (Method H) |
| 153 | 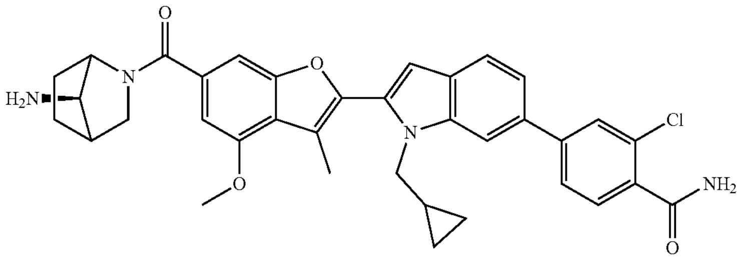 [SMILES: COc1cc(C(=O)N2CC3CCC2[C@@H]3N)cc2oc(-c3cc4ccc(-c5ccc(C(N)=O)c(Cl)c5)cc4n3CC3CC3)c(C)c12]<br>4-(2-(6-((7R)-7-Amino-2-azabicyclo[2.2.1]heptane-2-carbonyl)-4-methoxy-3-methylbenzofuran-2-yl)-1-(cyclopropylmethyl)-1H-indol-6-yl)-2-chlorobenzamide<br>Analytical Data: 623.4, 2.801 min (Method H) |
| 154 | 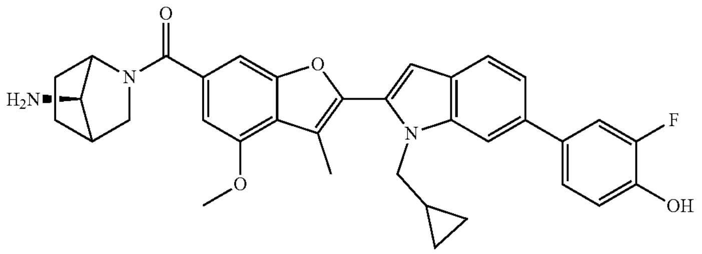 [SMILES: COc1cc(C(=O)N2CC3CCC2[C@@H]3N)cc2oc(-c3cc4ccc(-c5ccc(O)c(F)c5)cc4n3CC3CC3)c(C)c12]<br>((7R)-7-Amino-2-azabicyclo[2.2.1]heptan-2-yl)(2-(1-(cyclopropylmethyl)-6-(3-fluoro-4-hydroxyphenyl)-1H-indol-2-yl)-4-methoxy-3-methylbenzofuran-6-yl)methanone<br>Analytical Data: 580.3, 2.308 min (Method E) |
| 155 | 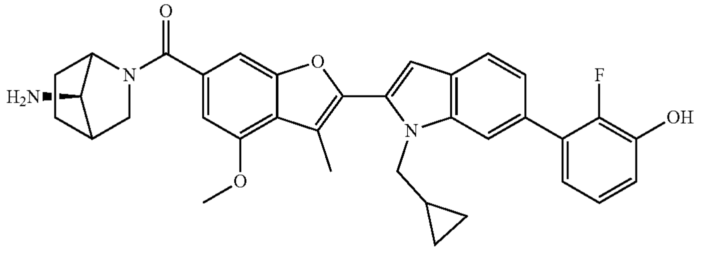 [SMILES: COc1cc(C(=O)N2CC3CCC2[C@@H]3N)cc2oc(-c3cc4ccc(-c5cccc(O)c5F)cc4n3CC3CC3)c(C)c12]<br>((7R)-7-Amino-2-azabicyclo[2.2.1]heptan-2-yl)(2-(1-(cyclopropylmethyl)-6-(3-methyl-[1,2,4]triazolo[4,3-a]pyridin-7-yl)-1H-pyrrolo[2,3-b]pyridin-2-yl)-4-methoxy-3-methylpyrazolo[1,5-a]pyridin-6-yl)methanone<br>Analytical Data: 580.3, 6.998 min (Method D) |

TABLE 18-continued

| Example | Structure<br>Name<br>Analytical Data: LC-MS m/z $[M + H]^+$; HPLC retention time (HPLC method) |
|---|---|
| 156 | 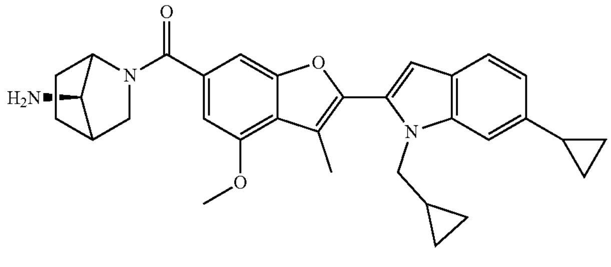 [SMILES: COc1cc(C(=O)N2CC3CCC2[C@@H]3N)cc2oc(-c3cc4ccc(C5CC5)cc4n3CC3CC3)c(C)c12]<br>((7R)-7-Amino-2-azabicyclo[2.2.1]heptan-2-yl)(2-(6-cyclopropyl-1-(cyclopropylmethyl)-1H-indol-2-yl)-4-methoxy-3-methylbenzofuran-6-yl)methanone<br>Analytical Data: 510.3, 2.358 min (Method E) |
| 157 | 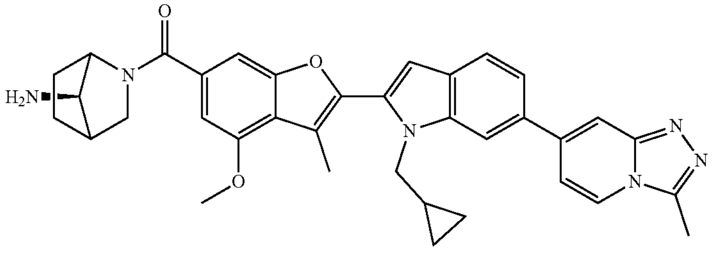 [SMILES: COc1cc(C(=O)N2CC3CCC2[C@@H]3N)cc2oc(-c3cc4ccc(-c5ccn6c(C)nnc6c5)cc4n3CC3CC3)c(C)c12]<br>((7R)-7-Amino-2-azabicyclo[2.2.1]heptan-2-yl)(2-(1-(cyclopropylmethyl)-6-(3-methyl-[1,2,4]triazolo[4,3-a]pyridin-7-yl)-1H-indol-2-yl)-4-methoxy-3-methylbenzofuran-6-yl)methanone<br>Analytical Data: 601.4, 2.616 min (Method H) |

Example 158

3-((7R)-7-Amino-2-azabicyclo[2.2.1]heptan-2-yl)(2-(1-(cyclopropylmethyl)-6-(4-ethoxypiperidin-1-yl)-1H-indol-2-yl)-4-methoxy-3-methylbenzofuran-6-yl)methanone

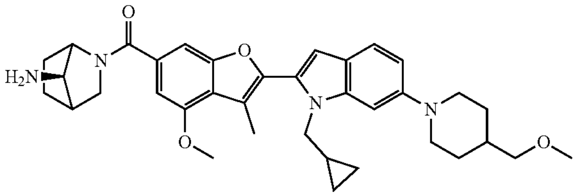 [SMILES: COCC1CCN(c2ccc3cc(-c4oc5cc(C(=O)N6CC7CCC6[C@@H]7N)cc(OC)c5c4C)n(CC4CC4)c3c2)CC1]

Intermediate 158A tert-Butyl-((7R)-2-(2-(1-(cyclopropylmethyl)-6-(4-ethoxypiperidin-1-yl)-1H-indol-2-yl)-4-methoxy-3-methylbenzofuran-6-carbonyl)-2-azabicyclo[2.2.1]heptan-7-yl)carbamate

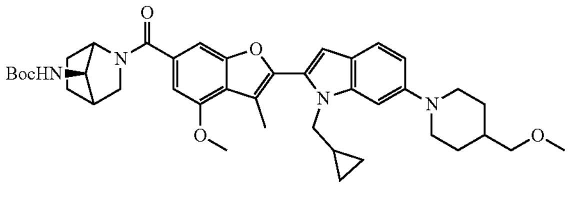 [SMILES: COCC1CCN(c2ccc3cc(-c4oc5cc(C(=O)N6CC7CCC6[C@@H]7NC(=O)OC(C)(C)C)cc(OC)c5c4C)n(CC4CC4)c3c2)CC1]

$Pd(OAc)_2$ (15.58 mg, 0.069 mmol) was added to a stirred and degasified solution of Intermediate 149A (150 mg, 0.231 mmol), 4-ethoxypiperidine (44.8 mg,0.347 mmol), XPHOS (55.1 mg, 0.116 mmol) and KOtBu (51.9 mg, 0.463 mmol) in dioxane (2 ml). The reaction mixture was heated to 110° C. and stirred for 16 hours, filtered through a celite bed, and the filtrate was evaporated under reduced pressure. The crude product thus obtained was purified using prep HPLC to afford the title compound as an off-white solid (20 mg). LC-MS m/z: 697 $[M+H]^+$.

Example 158

TFA (0.022 ml, 0.287 mmol was added to a stirred solution of Intermediate 158A (20 mg, 0.029 mmol) in DCM (1 ml). The reaction mixture was stirred at a room temperature for 3 hours, and evaporated under reduced pressure to afford the crude material, which was purified using RP-HPLC to afford the title compound (4.8 mg, 27%). LC-MS m/z: 597.4$[M+H]^+$. LC-MS retention time: 2.284/1.342 min (Methods E/F). $^1H$ NMR (400 MHz, DMSO-$d_6$) δ ppm: 7.45 (d, J=8.9 Hz, 1H), 7.25 (s, 1H), 7.02 (s, 1H), 6.93-6.85 (m, 2H), 6.67 (s, 1H), 4.22-4.03 (m, 4H), 4.02-3.88 (m, 5H), 3.84 (br, d, J=3.2 Hz, 2H), 3.59-3.38 (m, 13H), 3.30-3.22 (m, 4H), 3.17 (d, J=5.3 Hz, 2H), 3.09 (br, d, J=10.4 Hz, 3H), 3.00-2.74(m, 5H), 2.66-2.53 (m, 4H), 2.47-2.40 (m, 5H), 2.08 (s, 1H), 2.03-1.74 (m, 7H), 1.67-1.53 (m, 4H), 1.50 (br, s, 2H), 1.32-1.20 (m, 9H), 1.20-1.03 (m, 7H), 0.90-0.81 (m, 2H), 0.34 (br, d, J=7.5 Hz, 2H), 0.17-0.09 (m, 2H), 0.01 (s, 1H).

Compounds of Examples 159 and 160 in Table 19 were prepared following a procedure similar to the preparation of a compound of Example 158 by Buchwald coupling of Intermediate 149A with appropriate amines

TABLE 19

| Example | Structure<br>Name<br>Analytical Data: LC-MS m/z [M + H]$^+$; HPLC retention time (HPLC method) |
|---|---|
| 159 | 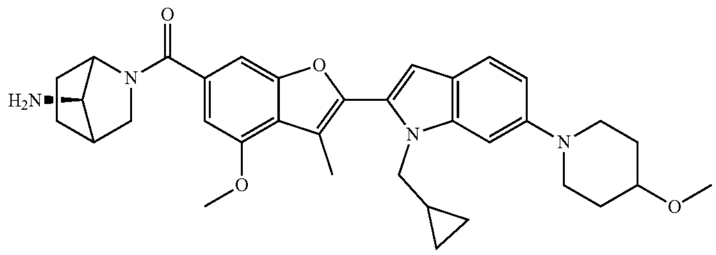 [SMILES: COc1cc(C(=O)N2CC3CCC2[C@@H]3N)cc2oc(-c3cc4ccc(N5CCC(OC)CC5)cc4n3CC3CC3)c(C)c12]<br>((7R)-7-Amino-2-azabicyclo[2.2.1]heptan-2-yl)(2-(1-(cyclopropylmethyl)-6-(4-methoxypiperidin-1-yl)-1H-indol-2-yl)-4-methoxy-3-methylbenzofuran-6-yl)methanone<br>Analytical Data: 583.4, 6.015 min (Method D) |
| 160 | 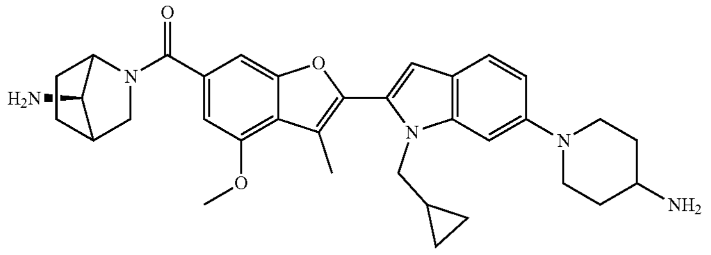 [SMILES: COc1cc(C(=O)N2CC3CCC2[C@@H]3N)cc2oc(-c3cc4ccc(N5CCC(N)CC5)cc4n3CC3CC3)c(C)c12]<br>((7R)-7-Amino-2-azabicyclo[2.2.1]heptan-2-yl)(2-(6-(4-aminopiperidin-1-yl)-1-(cyclopropylmethyl)-1H-indol-2-yl)-4-methoxy-3-methylbenzofuran-6-yl)methanone<br>Analytical Data: 583.4, 8.803 min (Method D) |

Example 161

((3R,5R)-3-Amino-5-fluoropiperidin-1-yl)(2-(1-(cyclopropylmethyl)-1H-indol-2-yl)-4-methoxy-3-methylbenzofuran-6-yl)methanone

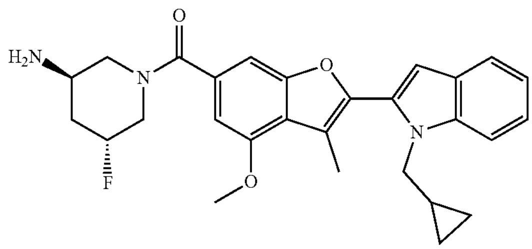 [SMILES: COc1cc(C(=O)N2C[C@H](N)C[C@@H](F)C2)cc2oc(-c3cc4ccccc4n3CC3CC3)c(C)c12]

Intermediate 161A tert-Butyl-((3R,5R)-1-(2-(1-(cyclopropylmethyl)-1H-indol-2-yl)-4-methoxy-3-methylbenzofuran-6-carbonyl)-5-fluoropiperidin-3-yl)carbamate

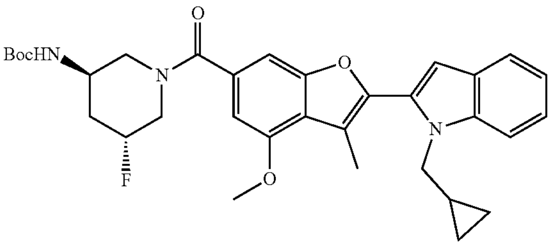 [SMILES: COc1cc(C(=O)N2C[C@H](F)C[C@@H](NC(=O)OC(C)(C)C)C2)cc2oc(-c3cc4ccccc4n3CC3CC3)c(C)c12]

A solution of $K_2CO_3$ (103 mg, 0.748 mmol) in water (0.75 ml) was added to a stirred and degassified solution of Intermediate 147B (110 mg, 0.249 mmol), 1-(cyclopropyl-methyl)-2-(4,4,5,5-tetramethyl-1,3,2-dioxaborolan-2-yl)-1H-indole (Intermediate 10, 74.2 mg, 0.249 mmol) in dioxane (3 ml), followed by the addition of $Pd(PPh_3)_4$ (288 mg, 0.249 mmol). The reaction mixture was heated to 115° C. and stirred for 6 hours, evaporated under reduced pressure to dryness, water (50 ml) was added, and extracted with EtOAc (2×50 ml). The combined organic layers were washed with water (10 ml) and brine (10 ml), dried over anhydrous sodium sulphate, filtered, and the filtrate was evaporated under reduced pressure. The crude compound thus obtained was purified using a silica gel column (24 g, Redisep® $SiO_2$ column, eluting with 75% EtOAc in n-hexane) to afford the title compound (100 mg). LC-MS m/z: 576.4 [M+H]$^+$.

Example 161

TFA (0.120 ml, 1.563 mmol) was added to a stirred solution of Intermediate 161A (90 mg, 0.156 mmol) in DCM (4 ml). The reaction mixture was stirred at a room temperature for 10 hours, and evaporated under reduced pressure to afford the crude material, which was purified using RP-HPLC to afford the title compound (6.4 mg, 8.4%). LC-MS m/z: 476.4 [M+H]$^+$. LC-MS retention time: 1.9 min (Method F). $^1$H NMR (400 MHz, DMSO-$d_6$) δ ppm: 7.64 (dd, J=4.5, 7.7 Hz, 2H), 7.25 (t, J=7.2 Hz, 1H), 7.22 (s, 1H), 7.11 (t, J=7.4 Hz, 1H), 6.82 (s, 1H), 6.82-6.79 (m, 1H), 5.02-4.77 (m, 1H), 4.58-4.40 (m, 1H), 4.23 (d, J=6.8 Hz, 2H), 3.94 (s, 3H), 3.17 (s, 3H), 2.97 (br, t, J=10.4 Hz, 2H), 2.67 (s, 1H), 2.49-2.46 (m, 3H), 2.33 (s, 1H), 2.15 (br, s, 1H), 1.90 (s, 1H), 1.23 (s, 1H), 1.16-0.99 (m, 1H), 0.39-0.29 (m, 2H), 0.18 (q, J=4.7 Hz, 2H).

Example 162

4-(2-(6-((3R,5R)-3-Amino-5-fluoropiperidine-1-carbonyl)-4-methoxy-3-methylbenzofuran-2-yl)-1-(cyclopropylmethyl)-1H-indol-6-yl)-2-chlorobenzamide

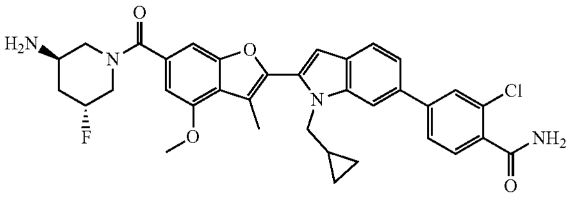 [SMILES: COc1cc(C(=O)N2C[C@H](N)C[C@@H](F)C2)cc2oc(-c3cc4ccc(-c5ccc(C(N)=O)c(Cl)c5)cc4n3CC3CC3)c(C)c12]

Intermediate 162A tert-Butyl-((3R,5R)-5-fluoro-1-(4-methoxy-3-methyl-2-(4,4,5,5-tetramethyl-1,3,2-dioxaborolan-2-yl)benzofuran-6-carbonyl)piperidin-3-yl)carbamate

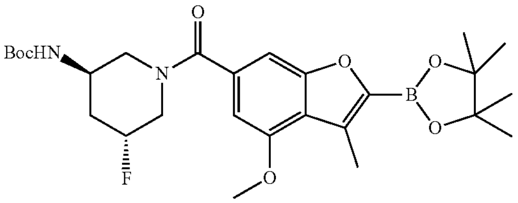 [SMILES: COc1cc(C(=O)N2C[C@H](F)C[C@@H](NC(=O)OC(C)(C)C)C2)cc2oc(B3OC(C)(C)C(C)(C)O3)c(C)c12]

LDA (4.92 ml, 9.84 mmol) was added drop wise to a stirred solution of Intermediate 147A (0.4 g, 0.984 mmol) in THF (4 ml) at −78° C. The reaction mixture was stirred for 30 min, followed by the addition of 2-isopropoxy-4,4,5,5-tetramethyl-1,3,2-dioxaborolane (0.916 g, 4.92 mmol). The reaction mixture was stirred −78° C. for 1 hour, quenched with water at −78° C., and extracted with EtOAc (3×50 ml). The combined organic layers were dried over anhydrous sodium sulphate, filtered, and the filtrate was evaporated under reduced pressure to afford the title compound (0.520 g, 99%) as brown oil. LC-MS m/z=533 [M−H]$^+$.

Intermediate 162B tert-Butyl-((3R,5R)-1-(2-(6-bromo-1-(cyclopropylmethyl)-1H-indol-2-yl)-4-methoxy-3-methylbenzofuran-6-carbonyl)-5-fluoropiperidin-3-yl)carbamate

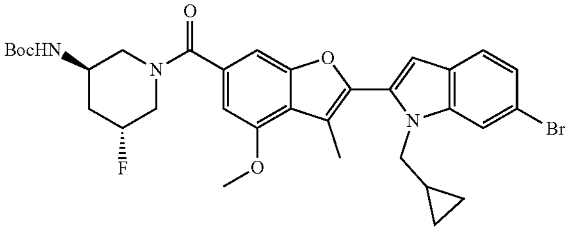 [SMILES: COc1cc(C(=O)N2C[C@H](F)C[C@@H](NC(=O)OC(C)(C)C)C2)cc2oc(-c3cc4ccc(Br)cc4n3CC3CC3)c(C)c12]

A solution of $K_2CO_3$ (37.3 mg, 0.270 mmol) in water (0.75 ml) was added to a stirred and degasified solution of Intermediate 162A (524 mg, 0.984 mmol), 6-bromo-1-(cyclopropylmethyl)-2-iodo-1H-indole (Intermediate-12, 444 mg, 1.181 mmol) in dioxane (8 ml). The reaction mixture was degasified using argon, followed by the addition of $Pd(PPh_3)_4$ (85 mg, 0.074 mmol). The reaction mixture was heated to 80° C. and stirred for 16 hours, evaporated under reduced pressure to dryness, water (50 ml) was added, and extracted with EtOAc (2×50 ml). The combined organic layers were washed with water (20 ml) and brine (20 ml), dried over anhydrous sodium sulphate, filtered, and the filtrate was evaporated under reduced pressure. The crude product thus obtained was purified using a silica gel column (12 g, Redisep® $SiO_2$ column, eluting with 5% MeOH in $CHCl_3$) to afford the title compound as a brown oil (400 mg, 62%). LC-MS m/z=655.3 [M+H]$^+$.

Intermediate 162C tert-Butyl-((3R,5R)-1-(2-(6-(4-carbamoyl-3-chlorophenyl)-1-(cyclopropylmethyl)-1H-indol-2-yl)-4-methoxy-3-methylbenzofuran-6-carbonyl)-5-fluoropiperidin-3-yl)carbamate

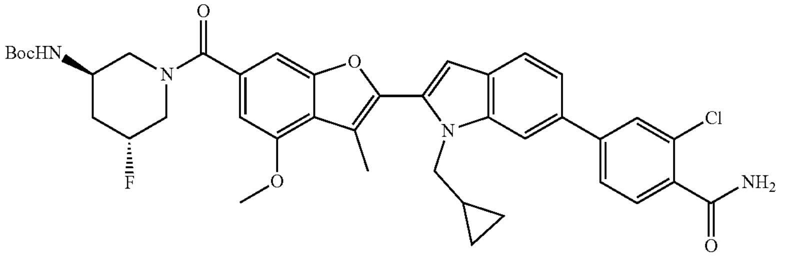 [SMILES: COc1cc(C(=O)N2C[C@H](F)C[C@@H](NC(=O)OC(C)(C)C)C2)cc2oc(-c3cc4ccc(-c5ccc(C(N)=O)c(Cl)c5)cc4n3CC3CC3)c(C)c12]

A solution of $K_2CO_3$ (95 mg, 0.687 mmol) in water (4.13 μl, 0.229 mmol) was added to a stirred and degasified solution of Intermediate 162B (150 mg, 0.229 mmol) and 2-chloro-4-(4,4,5,5-tetramethyl-1,3,2-dioxaborolan-2-yl) benzamide (97 mg, 0.344 mmol) in dioxane (2 ml), followed by addition of $PdCl_2(dppf)$-$CH_2Cl_2$ adduct (14.04 mg, 0.017 mmol). The reaction mixture was heated to 80° C. and stirred for 16 hours, diluted with water (50 ml), and extracted with EtOAc (3×50 ml). The combined organic layers were dried over anhydrous sodium sulphate, filtered, and the filtrate was evaporated under reduced pressure concentrated to afford the crude material, which was purified using preparative HPLC to afford the product as brown oil (0.015 g, 8%). LC/MS m/z: 729 $[M-H]^+$.

Example 162

TFA (0.120 ml, 1.561 mmol was added to a stirred solution of Intermediate 162C (15 mg, 0.020 mmol) in DCM (2 ml). The reaction mixture was stirred at a room temperature for 1 hour, and evaporated under reduced pressure to afford the crude product, which was purified using RP-HPLC to afford the title compound (2.2 mg, 14%). LC-MS m/z: 629 $[M+H]^+$. LC-MS retention time: 1.885/1.687 min (Method E/F).

Example 163

((3R,5R)-3-Amino-5-fluoropiperidin-1-yl)(2-(1-(cyclopropylmethyl)-6-(2-fluoro-3-hydroxyphenyl)-1H-indol-2-yl)-4-methoxy-3-methylbenzofuran-6-yl) methanone

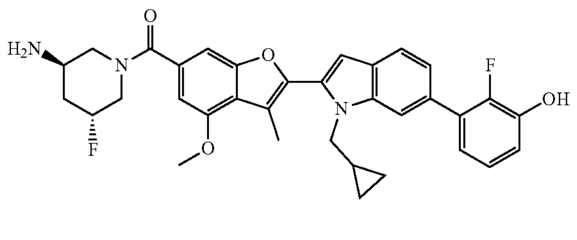 [SMILES: COc1cc(C(=O)N2C[C@H](N)C[C@@H](F)C2)cc2oc(-c3cc4ccc(-c5cccc(O)c5F)cc4n3CC3CC3)c(C)c12]

Compound of Example 163 was prepared following a procedure similar to the preparation of a compound of Example 162, using the Intermediate 162B and the appropriate boronic acid. LC-MS m/z: 586.3 $[M+H]^+$. LC-MS retention time: 2.071 min (Method T).

Example 164

((7R)-7-Amino-2-azabicyclo[2.2.1]heptan-2-yl)(2-(1-(cyclopropylmethyl)-1H-pyrrolo[2,3-b]pyridin-2-yl)-3-methylbenzofuran-6-yl)methanone

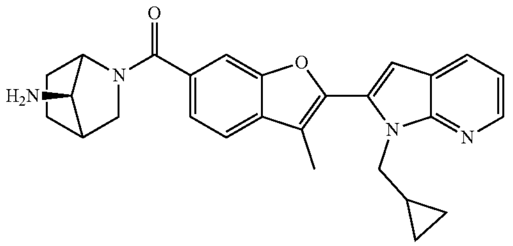 [SMILES: Cc1c(-c2cc3cccnc3n2CC2CC2)oc2cc(C(=O)N3CC4CCC3[C@@H]4N)ccc12]

Intermediate 164A

Methyl-3-(allyloxy)-4-iodobenzoate

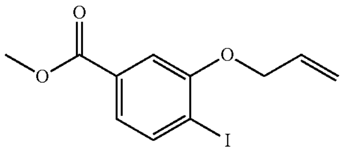

$K_2CO_3$ (5.47 g, 39.6 mmol) and 3-bromoprop-1-ene (3.42 ml, 39.6 mmol) were added to a stirred solution of methyl 3-hydroxy-4-iodobenzoate (5.5 g, 19.78 mmol) in DMF (100 ml). The reaction mixture was stirred at a room temperature for 2 hours, quenched with water (100 ml), and extracted with EtOAc (3×150 ml). The combined organic layers were washed with water (100 ml) and brine (100 ml), dried over anhydrous sodium sulphate, filtered, and the filtrate was evaporated under reduced pressure to afford the crude material, which was purified using flash chromatography (80 g silica gel column,50% EtOAc in pet ether) to afford the title compound as a white solid (6.1 g, 97%). $^1H$ NMR (400 MHz, DMSO-$d_6$) δ ppm: 0.01 (d, J=0.73 Hz, 1H), 3.86 (s, 3H), 4.70-4.75 (m, 2H), 5.31 (dd, J=10.64, 1.10 Hz, 1H), 5.51 (dd, J=17.61, 1.47 Hz, 1H), 6.01-6.11 (m, 1H), 7.33 (dd, J=8.07, 0.98 Hz, 1H), 7.43 (s, 1H), 7.96 (d, J=8.07 Hz, 1H).

Intermediate 164B

Methyl-3-methylbenzofuran-6-carboxylate

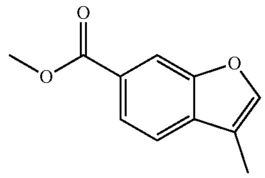

Palladium(II) acetate (0.071 g, 0.314 mmol), sodium carbonate (1.666 g, 15.72 mmol), and tetrabutylammonium chloride hydrate (2.047 g, 6.92 mmol) were added to a stirred and degassified solution of Intermediate 164A (2.0 g, 6.29 mmol) in DMF (30 ml). The reaction mixture was stirred and heated to 80° C. for 48 hours, evaporated under reduced pressure to dryness, water (100 ml) was added, and extracted with EtOAc (2×100 ml). The combined organic layers were washed with water (50 ml) and brine (50 ml), dried over anhydrous sodium sulphate, and evaporated under reduced pressure to afford the crude material, which was purified using flash chromatography (40 g, silica gel column, 25% EtOAc in pet ether) to afford the title compound (1.0 g, 84%) as white solid. LC-MS m/z: 191 [M−H]. $^1H$ NMR (400 MHz, DMSO-$d_6$) δ ppm: 2.25 (d, J=1.51 Hz, 3H), 3.82-3.90 (m, 3H), 7.74 (d, J=8.03 Hz, 1H), 7.89 (d, J=7.88 Hz, 1H), 7.96-8.04 (m, 1H), 8.09 (d, J=1.51 Hz, 1H).

Intermediate 164C

3-Methylbenzofuran-6-carboxylic acid

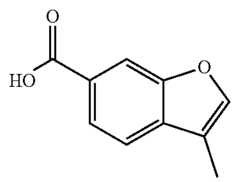

LiOH (0.378 g, 15.77 mmol) in water (5 ml) was added to a stirred solution of Intermediate 164B (1.0 g, 5.26 mmol) in THF (5 ml) and MeOH (5 ml). The reaction mixture was stirred at a room temperature for 12 hours, evaporated under reduced pressure to remove the volatile solvents, and 1.5N HCl solution was added till the solution turned acidic. The solids precipitated were filtered, and dried under high vacuum to afford the title compound (0.85 g, 92%) as a white solid. LC-MS m/z: 175.2 [M−H]. $^1$H NMR (400 MHz, DMSO-$d_6$) δ ppm: 2.24 (d, J=1.00 Hz, 3H), 7.71 (d, J=8.03 Hz, 1H), 7.80-7.92 (m, 1H), 7.97 (d, J=1.51 Hz, 1H), 8.06 (s, 1H).

Intermediate 164D tert-Butyl-((7R)-2-(3-methylbenzofuran-6-carbonyl)-2-azabicyclo[2.2.1]heptan-7-yl)carbamate

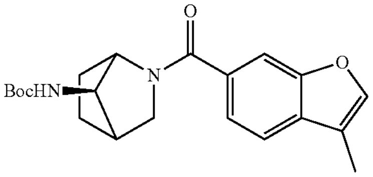 [SMILES: Cc1coc2cc(C(=O)N3CC4CCC3[C@@H]4NC(=O)OC(C)(C)C)ccc12]

HATU (2.75 g, 7.24 mmol) in DMF (20 ml) and DIPEA (1.685 ml, 9.65 mmol) were added to a stirred solution of Intermediate 164C (0.85 g, 4.82 mmol) and tert-butyl ((7R)-2-azabicyclo-[2.2.1]heptan-7-yl)carbamate (1.024 g, 4.82 mmol). The reaction mixture was stirred at a room temperature for 12 hours, diluted with water (200 ml), and extracted with EtOAc (2×100 ml). The combined organic layers were washed with water (50 ml) and brine (50 ml), dried over anhydrous sodium sulphate, filtered, and the filtrate was evaporated under reduced pressure to afford the crude material, which was purified using a silica gel column (24 g, silica gel column,70% EtOAc in pet ether) to afford the title compound (1.5 g, 84%). LC-MS m/z: 371 [M+H]$^+$.

Intermediate 164E ter-Butyl-((7R)-2-(2-chloro-3-methylbenzofuran-6-carbonyl)-2-azabicyclo[2.2.1]heptan-7-yl)carbamate

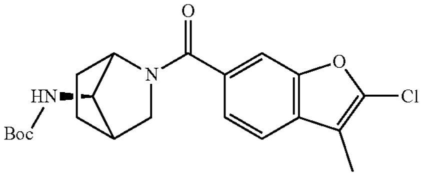 [SMILES: Cc1c(Cl)oc2cc(C(=O)N3CC4CCC3[C@@H]4NC(=O)OC(C)(C)C)ccc12]

1M THF solution of lithium diisopropylamide (0.225 ml, 0.540 mmol) was added to a stirred solution of Intermediate 164D (100 mg, 0.270 mmol) in THF (15 ml) at −78° C. under nitrogen atmosphere. The reaction mixture was stirred for 1 hour, followed by the addition of hexachloroethane (70.3 mg, 0.297 mmol) in 2 ml of THF. The reaction mixture was allowed to warm up to a room temperature and stirred for further 4 hours, quenched with saturated aqueous ammonium chloride solution (50 ml), and extracted with EtOAc (2×50 ml). The combined organic layers were washed with water (100 ml) and brine (100 ml), dried over anhydrous sodium sulphate, filtered, and the filtrate was evaporated under reduced pressure to afford the crude compound (85 mg, 78%) as gummy liquid. LC-MS m/z: 405.1 [M+H]$^+$.

Intermediate 164F tert-Butyl-((7R)-2-(2-(1-(cyclopropylmethyl)-1H-pyrrolo[2,3-b]pyridin-2-yl)-3-methylbenzofuran-6-carbonyl)-2-azabicyclo[2.2.1]heptan-7-yl)carbamate

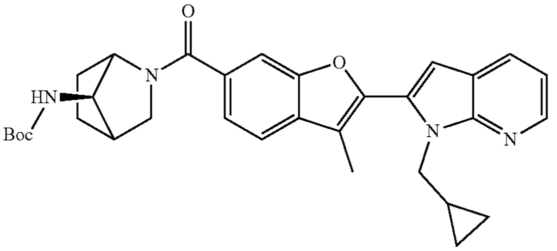 [SMILES: Cc1c(-c2cc3cccnc3n2CC2CC2)oc2cc(C(=O)N3CC4CCC3[C@@H]4NC(=O)OC(C)(C)C)ccc12]

A solution of $K_2CO_3$ (103 mg, 0.748 mmol) in water (0.75 ml) and tetrakis-(triphenylphosphine)palladium(0) (14.27 mg, 0.012 mmol) were added to a stirred and degasified solution of Intermediate 164E (100 mg, 0.247 mmol) and 1-(cyclopropylmethyl)-2-(trimethylstannyl)-1H-pyrrolo[2,3-b]pyridine (Intermediate 7, 83 mg, 0.247 mmol) in dioxane (3 ml). The reaction mixture was heated to 100° C. and stirred for 16 hours, evaporated under reduced pressure to dryness, water (10 ml) was added, and extracted with EtOAc (2×10 ml). The combined organic layers were washed with water (10 ml) and brine (10 ml), dried over anhydrous sodium sulphate, filtered, and the filtrate was evaporated under reduced pressure to afford the crude title compound (40 mg) as a brown oil. LC-MS m/z: 541.3 [M+H]$^+$.

Example 164

TFA (0.057 ml, 0.740 mmol) was added to a stirred solution of Intermediate 164F (40 mg, 0.074 mmol) in DCM (2 ml). The reaction mixture was stirred at a room temperature for 6 hours, evaporated under reduced pressure to afford the crude material, which was purified using RP-HPLC to afford the title compound (1.5 mg, 4%). LC-MS m/z: 441.3 [M+H]$^+$. LC-MS retention time: 1.3 min (Method F). $^1$H NMR (400 MHz, DMSO-$d_6$) δ ppm: 0.26 (br, s, 2H), 0.35 (br, d, J=8.31 Hz, 2H), 0.86 (s, 2H), 1.11-1.27 (m, 16H), 1.30 (br, s, 2H), 1.38 (s, 4H), 1.90 (br, s, 4H), 2.41-2.47 (m, 4H), 3.11-3.28 (m, 4H), 4.43 (br, d, J=7.09 Hz, 2H), 6.96 (s, 2H), 7.17-7.23 (m, 2H), 7.77 (s, 2H), 7.82 (br, s, 1H), 7.86 (s, 2H), 8.09 (br, d, J=7.58 Hz, 2H), 8.37 (br, d, J=4.40 Hz, 1H).

Example 165

((7R)-7-Amino-2-azabicyclo[2.2.1]heptan-2-yl)(2-(6-chloro-1-(cyclopropylmethyl)-1H-pyrrolo[2,3-b]pyridin-2-yl)-3-methylbenzofuran-6-yl)methanone

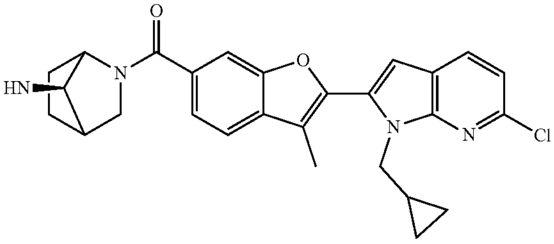 [SMILES: Cc1c(-c2cc3ccc(Cl)nc3n2CC2CC2)oc2cc(C(=O)N3CC4CCC3[C@@H]4N)ccc12]

Intermediate 165A tert-Butyl-((7R)-2-(3-methyl-2-(4,4,5,5-tetramethyl-1,3,2-dioxaborolan-2-yl)benzofuran-6-carbonyl)-2-azabicyclo[2.2.1]heptan-7-yl)carbamate

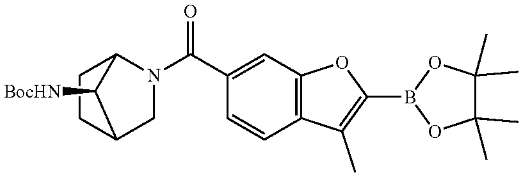 [SMILES: Cc1c(B2OC(C)(C)C(C)(C)O2)oc2cc(C(=O)N3CC4CCC3[C@@H]4NC(=O)OC(C)(C)C)ccc12]

1M THF solution of lithium diisopropylamide (5.40 ml, 10.80 mmol) was added to a stirred solution of Intermediate 164D (1.0 g, 2.70 mmol) in tetrahydrofuran (15 ml) at −78° C. The reaction mixture was stirred for 5 min, followed by the addition of 2-isopropoxy-4,4,5,5-tetramethyl-1,3,2-dioxaborolane (0.826 ml, 4.05 mmol) at −78° C., and the reaction mixture was stirred at the same temperature for another 2 hours. The reaction mixture was quenched with water (30 ml), and extracted with EtOAc (2×50 ml). The combined organic layers were washed with water (50 ml) and brine (50 ml), dried over anhydrous sodium sulphate, filtered, and the filtrate was evaporated under reduced pressure to afford the title compound (1.1 g, 82%) as a gummy liquid. LC-MS m/z: 497.3 $[M+H]^+$.

Intermediate 165B tert-Butyl-((7R)-2-(2-(6-chloro-1-(cyclopropylmethyl)-1H-pyrrolo[2,3-b]pyridin-2-yl)-3-methylbenzofuran-6-carbonyl)-2-azabicyclo[2.2.1]heptan-7-yl)carbamate

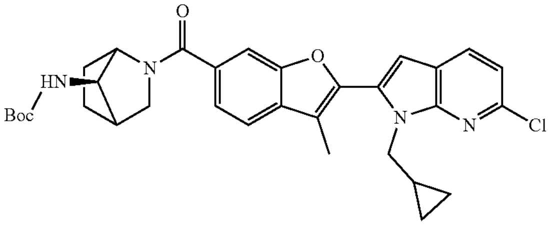 [SMILES: Cc1c(-c2cc3ccc(Cl)nc3n2CC2CC2)oc2cc(C(=O)N3CC4CCC3[C@@H]4NC(=O)OC(C)(C)C)ccc12]

A solution of $K_2CO_3$ (112 mg, 0.812 mmol) and water (1 ml) and tetrakis (triphenylphosphine)palladium(0) (23.45 mg, 0.020 mmol) was added to a stirred and degasified solution of Intermediate 165A (134 mg, 0.271 mmol), 6-chloro-1-(cyclopropylmethyl)-2-iodo-1H-pyrrolo[2,3-b]pyridine (Intermediate 3, 90 mg, 0.271 mmol) in dioxane (3 ml). The reaction mixture was heated to 85° C. and stirred for 16 hours, diluted with water (25 ml), and extracted with EtOAc (2×25 ml). The combined organic layers were washed with water (20 ml) and brine (20 ml), dried over sodium sulphate, filtered, and the filtrate was evaporated under reduced pressure to afford the crude title compound (100 mg) as brown solid. LC-MS m/z: 575 $[M+H]^+$.

Example 165

TFA (0.057 ml, 0.740 mmol) was added to a stirred solution of Intermediate 165B (100 mg, 0.074 mmol) in DCM (2 ml) and the reaction mixture was stirred at a room temperature for 6 hours. The reaction mixture was evaporated under reduced pressure to afford the crude material, which was purified using RP-HPLC to afford the title compound (5.1 mg, 6%). LC-MS m/z: 475 $[M+H]^+$. LC-MS retention time: 2.09/1.787 min (Method E/F). $^1H$ NMR (400 MHz, DMSO-$d_6$) δ ppm: 8.19-8.07 (m, 1H), 7.84-7.67 (m, 2H), 7.52-7.33 (m, 1H), 7.25 (dd, J=0.9, 8.2 Hz, 1H), 7.04-6.92 (m, 1H), 4.36 (d, J=7.1 Hz, 2H), 3.66 (br, d, J=1.7 Hz, 1H), 3.53-3.48 (m, 1H), 3.17 (br, d, J=1.7 Hz, 1H), 3.07 (d, J-11.2 Hz, 1H), 2.45-2.41 (m, 3H), 2.22-2.09 (m, 2H), 2.01-1.86 (m, 3H), 1.75-1.65 (m, 1H), 1.46-1.31 (m, 1H), 1.27-1.20 (m, 2H), 1.19-1.07 (m, 1H), 0.39-0.32 (m, 2H), 0.28-0.21 (m, 2H).

Example 166

6-(2-(6-((7R)-7-Amino-2-azabicyclo[2.2.1]heptane-2-carbonyl)-3-methylbenzofuran-2-yl)-1-(cyclopropylmethyl)-1H-pyrrolo[2,3-b]pyridin-6-yl)isoindolin-1-one

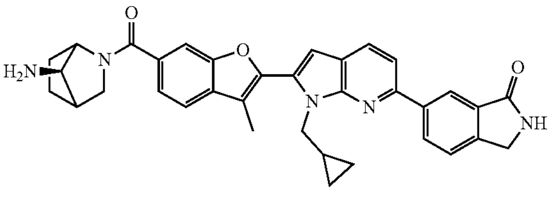 [SMILES: Cc1c(-c2cc3ccc(-c4ccc5c(c4)C(=O)NC5)nc3n2CC2CC2)oc2cc(C(=O)N3CC4CCC3[C@@H]4N)ccc12]

Intermediate 166A tert-Butyl-((7R)-2-(2-(1-(cyclopropylmethyl)-6-(3-oxoisoindolin-5-yl)-1H-pyrrolo[2,3-b]pyridin-2-yl)-3-methylbenzofuran-6-carbonyl)-2-azabicyclo[2.2.1]heptan-7-yl)carbamate

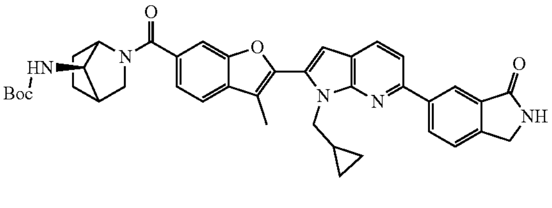 [SMILES: Cc1c(-c2cc3ccc(-c4ccc5c(c4)C(=O)NC5)nc3n2CC2CC2)oc2cc(C(=O)N3CC4CCC3[C@@H]4NC(=O)OC(C)(C)C)ccc12]

Potassium phosphate tribasic anhydrous (111 mg, 0.522 mmol) in water (1 ml) was added to a stirred and degasified solution of Intermediate 165B (100 mg, 0.174 mmol) and 6-(4,4,5,5-tetramethyl-1,3,2-dioxaborolan-2-yl)isoindolin-1-one (45.1 mg, 0.174 mmol) in dioxane (2 ml). The reaction mixture was degasified with argon, followed by the addition of XPHOS Pd G2 (8.29 mg, 0.017 mmol). The reaction mixture was heated to 100° C. and stirred for 2 hours, cooled to a room temperature, water (25 ml) was added, and extracted with EtOAc (2×25 ml). The combined organic layers were washed with water (20 ml) and brine (20 ml), dried over anhydrous sodium sulphate, filtered, and the filtrate was evaporated under reduced pressure to afford the crude compound (100 mg). LC-MS m/z: 672 $[M+H]^+$.

Example 166

TFA (0.115 ml, 1.489 mmol) was added to a stirred solution of Intermediate 165A (100 mg, 0.149 mmol) in DCM (2 ml). The reaction mixture was stirred at a room temperature for 16 hours, evaporated under reduced pressure, and the crude compound was purified using RP-HPLC to afford the title compound (3.1 mg, 3%). LC-MS m/z: 572 $[M+H]^+$. LC-MS retention time: 1.72/1.49 min (Method E/F). $^1H$ NMR (400 MHz, DMSO-$d_6$) δ ppm: 8.66 (s, 1H), 8.49-8.38 (m, 3H), 8.18 (d, J=8.1 Hz, 1H), 8.02-7.62 (m, 7H), 7.50-7.31 (m, 2H), 6.98 (s, 1H), 6.94-6.85 (m, 1H), 4.51 (br, d, J=6.8 Hz, 2H), 4.46 (s, 3H), 4.30-4.18 (m, 1H), 3.71 (d, J=12.0 Hz, 2H), 3.51 (br, s, 1H), 3.16-3.04 (m, 1H), 2.63 (s, 1H), 2.47 (s, 3H), 2.28-2.20 (m, 1H), 2.01-1.82 (m, 3H), 1.77-1.41 (m, 4H), 1.32-1.16 (m, 6H), 0.92-0.82 (m, 2H), 0.60-0.49 (m, 1H), 0.43-0.31 (m, 4H).

Compounds of Examples167 to 172 in Table 20 were prepared following a procedure similar to the preparation of a compound of Example 166, by Suzuki coupling of Intermediate 165B with appropriate boronic acids.

TABLE 20

| Example | Structure<br>Name<br>Analytical Data: LC-MS m/z $[M + H]^+$; HPLC retention time (HPLC method) |
|---|---|
| 167 | 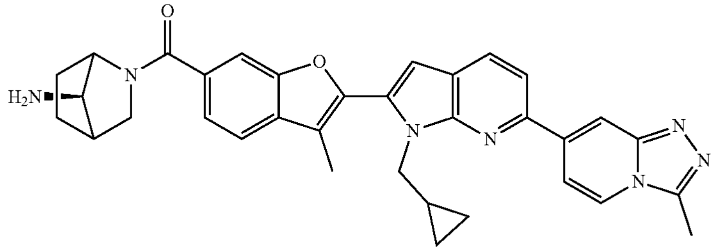 [SMILES: Cc1c(-c2cc3ccc(-c4ccn5c(C)nnc5c4)nc3n2CC2CC2)oc2cc(C(=O)N3CC4CCC3[C@@H]4N)ccc12]<br>((7R)-7-Amino-2-azabicyclo[2.2.1]heptan-2-yl)(2-(1-(cyclopropylmethyl)-6-(3-methyl-[1,2,4]triazolo[4,3-a]pyridin-7-yl)-1H-pyrrolo[2,3-b]pyridin-2-yl)-3-methylbenzofuran-6-yl)methanonecyclopropylmethyl)-1H-indol-6-yl)isoindolin-1-one<br>Analytical Data: 572.3, 1.679 min (Method E) |
| 168 | 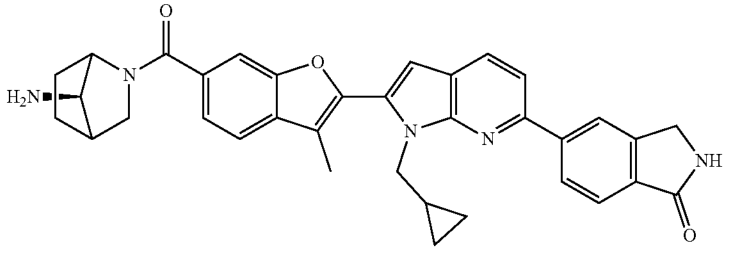 [SMILES: Cc1c(-c2cc3ccc(-c4ccc5c(c4)CNC5=O)nc3n2CC2CC2)oc2cc(C(=O)N3CC4CCC3[C@@H]4N)ccc12]<br>5-(2-(6-((7R)-7-Amino-2-azabicyclo[2.2.1]heptane-2-carbonyl)-3-methylbenzofuran-2-yl)-1-(cyclopropylmethyl)-1H-pyrrolo[2,3-b]pyridin-6-yl)isoindolin-1-one<br>Analytical Data: 572.4, 1.176 min (Method F) |

TABLE 20-continued

| Example | Structure<br>Name<br>Analytical Data: LC-MS m/z [M + H]+; HPLC retention time (HPLC method) |
|---|---|
| 169 | 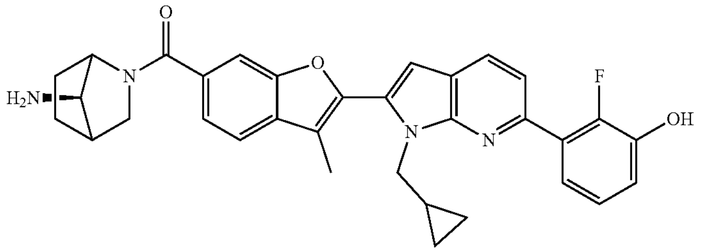 [SMILES: Cc1c(-c2cc3ccc(-c4cccc(O)c4F)nc3n2CC2CC2)oc2cc(C(=O)N3CC4CCC3[C@@H]4N)ccc12]<br>((7R)-7-Amino-2-azabicyclo[2.2.1]heptan-2-yl)(2-(1-(cyclopropylmethyl)-6-(2-fluoro-3-hydroxyphenyl)-1H-pyrrolo[2,3-b]pyridin-2-yl)-3-methylbenzofuran-6-yl)methanone<br>Analytical Data: 551.3, 1.913 min (Method E) |
| 170 | 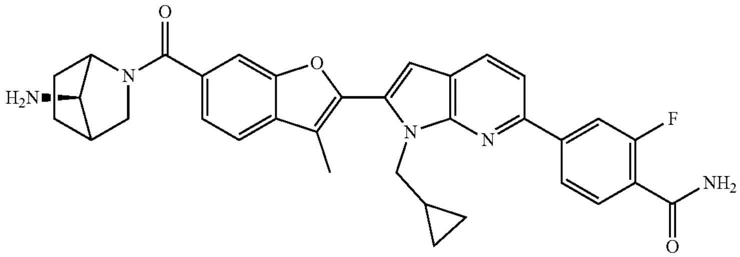 [SMILES: Cc1c(-c2cc3ccc(-c4ccc(C(N)=O)c(F)c4)nc3n2CC2CC2)oc2cc(C(=O)N3CC4CCC3[C@@H]4N)ccc12]<br>4-(2-(6-((7R)-7-amino-2-azabicyclo[2.2.1]heptane-2-carbonyl)-3-methylbenzofuran-2-yl)-1-(cyclopropylmethyl)-1H-pyrrolo[2,3-b]pyridin-6-yl)-2-fluorobenzamide<br>Analytical Data: 578.3, 1.765 min (Method E) |
| 171 | 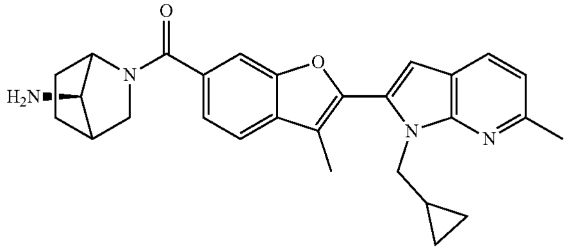 [SMILES: Cc1ccc2cc(-c3oc4cc(C(=O)N5CC6CCC5[C@@H]6N)ccc4c3C)n(CC3CC3)c2n1]<br>((7R)-7-Amino-2-azabicyclo[2.2.1]heptan-2-yl)(2-(1-(cyclopropylmethyl)-6-methyl-1H-pyrrolo[2,3-b]pyridin-2-yl)-3-methylbenzofuran-6-yl)methanone<br>Analytical Data: 455.3, 1.342 min (Method F) |
| 172 | 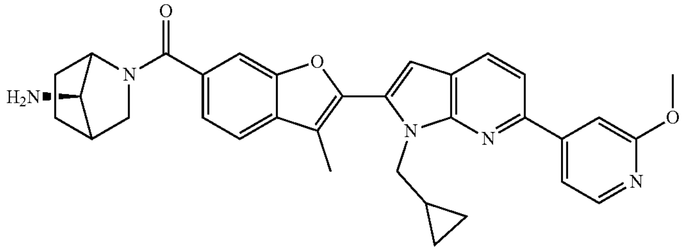 [SMILES: COc1cc(-c2ccc3cc(-c4oc5cc(C(=O)N6CC7CCC6[C@@H]7N)ccc5c4C)n(CC4CC4)c3n2)ccn1]<br>((7R)-7-Amino-2-azabicyclo[2.2.1]heptan-2-yl)(2-(1-(cyclopropylmethyl)-6-(2-methoxypyridin-4-yl)-1H-pyrrolo[2,3-b]pyridin-2-yl)-3-methylbenzofuran-6-yl)methanone<br>Analytical Data: 548.3, 1.704 min (Method F) |

Example 173

((7R)-7-Amino-2-azabicyclo[2.2.1]heptan-2-yl)(2-(1-(cyclopropylmethyl)-6-(3-methoxyazetidin-1-yl)-1H-pyrrolo[2,3-b]pyridin-2-yl)-3-methylbenzofuran-6-yl)methanone

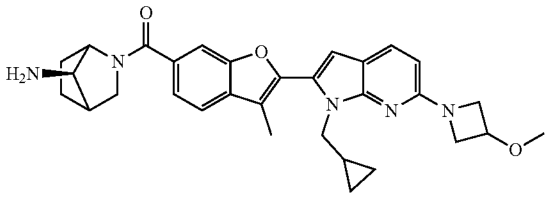 [SMILES: COC1CN(c2ccc3cc(-c4oc5cc(C(=O)N6CC7CCC6[C@@H]7N)ccc5c4C)n(CC4CC4)c3n2)C1]

Intermediate 173A tert-Butyl-((7R)-2-(2-(1-(cyclopropylmethyl)-6-(3-methoxyazetidin-1-yl)-1H-pyrrolo[2,3-b]pyridin-2-yl)-3-methylbenzofuran-6-carbonyl)-2-azabicyclo[2.2.1]heptan-7-yl)carbamate

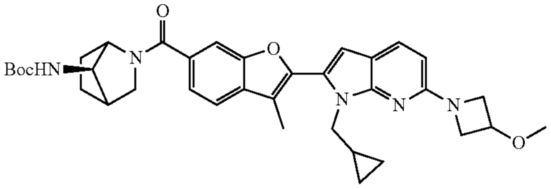 [SMILES: COC1CN(c2ccc3cc(-c4oc5cc(C(=O)N6CC7CCC6[C@@H]7NC(=O)OC(C)(C)C)ccc5c4C)n(CC4CC4)c3n2)C1]

RUPHOS (0.041 g, 0.087 mmol) and caesium carbonate (0.113 g, 0.348 mmol) were added to a stirred and degasified solution of Intermediate 165B (0.1 g, 0.174 mmol), 3-methoxyazetidine (0.015 g, 0.174 mmol) in dioxane (2 ml). The reaction mixture was purged with nitrogen for 5 min, followed by the addition of $Pd_2(dba)_3$ (0.016 g, 0.017 mmol). The reaction mixture was heated to 110° C. and stirred for 12 hours, filtered through a celite bed, washed using EtOAc, and the filtrate was evaporated under reduced pressure to afford a residue. Water (50 ml) was added to the residue obtained and extracted with EtOAc (2×50 ml). The combined organic layers were washed with water (50 ml) and brine (50 ml), dried over anhydrous sodium sulphate, filtered, and the filtrate was evaporated under reduced pressure to afford the crude compound (100 mg). LC-MS m/z: 626 $[M+H]^+$.

Example 173

TFA (0.031 ml, 0.400 mmol) was added to a stirred solution of Intermediate 173A (0.05 g, 0.080 mmol) in DCM (2 ml). The reaction mixture was stirred at a room temperature for 1 hour, evaporated under reduced pressure, and the crude product obtained was purified using RP-HPLC to afford the title compound (9.7 mg, 19%). LC-MS m/z: 526 $[M+H]^+$. LC-MS retention time: 2.024/1.599 min (Method E/F). $^1H$ NMR (400 MHz, DMSO-$d_6$) δ ppm: 7.81 (d, J=8.6 Hz, 1H), 7.75-7.61 (m, 2H), 7.47-7.33 (m, 1H), 6.72 (s, 1H), 6.30 (d, J=8.3 Hz, 1H), 4.39-4.32(m, 1H), 4.27-4.16 (m, 4H), 3.83-3.77 (m, 2H), 3.71-3.49 (m, 2H), 3.27 (s, 3H), 3.20-3.15 (m, 2H), 3.07 (br, d, J=11.0 Hz, 1H), 2.39 (s, 3H),2.24-2.15 (m, 1H), 2.00-1.65 (m, 3H), 1.45-1.32 (m, 1H), 1.20-1.10 (m, 1H), 0.39-0.31 (m, 2H), 0.31-0.22 (m, 2H).

Example 174

((3R,5R)-3-Amino-5-fluoropiperidin-1-yl)(2-(1-(cyclopropylmethyl)-1H-pyrrolo[2,3-b]pyridin-2-yl)-3-methylbenzofuran-6-yl)methanone

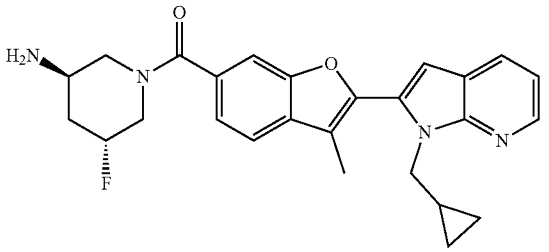 [SMILES: Cc1c(-c2cc3cccnc3n2CC2CC2)oc2cc(C(=O)N3C[C@H](N)C[C@@H](F)C3)ccc12]

Intermediate 174A tert-Butyl-((3R,5R)-5-fluoro-1-(3-methylbenzofuran-6-carbonyl)piperidin-3-yl)carbamate

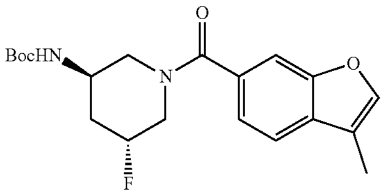 [SMILES: Cc1coc2cc(C(=O)N3C[C@H](F)C[C@@H](NC(=O)OC(C)(C)C)C3)ccc12]

HATU (3.24 g, 8.51 mmol) in DMF (20 ml) and DIPEA (1.983 ml, 11.35 mmol) were added to a stirred solution of Intermediate 164C (1.0 g, 5.68 mmol), tert-butyl ((3R,5R)-5-fluoropiperidin-3-yl) carbamate (1.239 g, 5.68 mmol). The reaction mixture was stirred at a room temperature for 12 hours, quenched with water (200 ml), and extracted with EtOAc (2×200 ml). The combined organic layers were washed with water (100 ml) and brine (100 ml), dried over anhydrous sodium sulphate, filtered, and the filtrate was evaporated under reduced pressure. A crude product thus obtained was purified using flash chromatography (24 g, silica gel column,70% EtOAc in pet ether) to afford the title compound (2.0 g, 94%) as a gummy liquid. LC-MS m/z: 377 $[M+H]^+$.

Intermediate 174B tert-Butyl-((3R,5R)-1-(2-chloro-3-methylbenzofuran-6-carbonyl)-5-fluoropiperidin-3-yl)carbamate

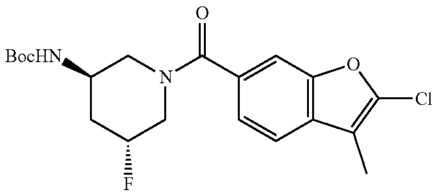 [SMILES: Cc1c(Cl)oc2cc(C(=O)N3C[C@H](F)C[C@@H](NC(=O)OC(C)(C)C)C3)ccc12]

1M THF solution of LDA (0.266 ml, 0.531 mmol) was added to a stirred solution of Intermediate 174A (100 mg, 0.266 mmol) in THF (15 ml) at −78° C. under nitrogen atmosphere and the reaction mixture was stirred for 1 hour, followed by the addition of hexachloroethane (69.2 mg, 0.292 mmol) in 2 ml of THF. The reaction mixture was allowed to warm to a room temperature and stirred for 4 hours, quenched with water (15 ml), and extracted with EtOAc (2×50 ml). The combined organic layers were washed with water (30 ml) and brine (30 ml), dried over anhydrous sodium sulphate, filtered, and the filtrate was evaporated under reduced pressure to afford the crude compound (120 mg) as a brown solid. LC-MS m/z: 409.3 $[M-H]^+$.

Intermediate 174C tert-Butyl-((3R,5R)-1-(2-(1-(cyclopropylmethyl)-1H-pyrrolo[2,3-b]pyridin-2-yl)-3-methylbenzofuran-6-carbonyl)-5-fluoropiperidin-3-yl)carbamate

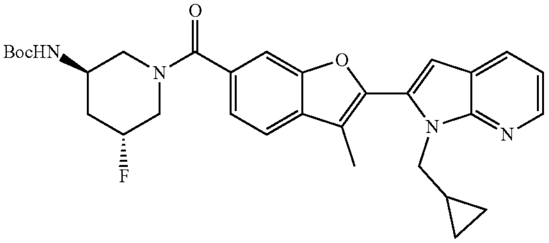

A solution of $K_2CO_3$ (121 mg, 0.876 mmol) in water (0.75 ml) was added to a stirred and degasified solution of Intermediate 174B (120 mg, 0.292 mmol) and 1-(cyclopropylmethyl)-2-(4,4,5,5-tetramethyl-1,3,2-dioxaborolan-2-yl)-1H-pyrrolo[2,3-b]pyridine (87 mg, 0.292 mmol) in dioxane (3 ml). The reaction mixture was degasified with argon, followed by the addition of $Pd(PPh_3)_4$ (338 mg, 0.292 mmol). The reaction mixture was heated to 115° C. and stirred for 6 hours, evaporated under reduced pressure to dryness, water (20 ml) was added, and extracted with EtOAc (2×30 ml). The combined organic layers were washed with water (20 ml) and brine (20 ml), dried over anhydrous sodium sulphate, filtered, and the filtrate was evaporated under reduced pressure to afford the crude compound (100 mg) as brown solid. LC/MS m/z: 547.4 $[M+H]^+$.

Example 174

TFA (0.141 ml, 1.829 mmol) was added to a stirred solution of Intermediate 174C (100 mg, 0.183 mmol) in DCM (2 ml). The reaction mixture was stirred at a room temperature for 7 hours, evaporated under reduced pressure, and the crude product obtained was purified using RP-HPLC to afford the title compound (14.2 mg, 17%). LC-MS m/z: 447.2 $[M+H]^+$. LC-MS retention time: 1.4 min (Method F). $^1H$ NMR (400 MHz, DMSO-$d_6$) δ ppm: 8.37 (dd, J=1.5, 4.6 Hz, 1H), 8.17-7.99 (m, 3H), 7.83 (d, J=8.1 Hz, 1H), 7.73 (s, 1H), 7.40 (dd, J=1.2, 8.1 Hz, 1H), 7.27-7.18 (m, 1H), 7.01 (s, 1H), 6.95 (s, 1H), 5.07-4.85 (m, 1H), 4.81-4.66 (m, 1H), 4.42 (d, J=7.1 Hz, 2H), 3.57 (br, s, 2H), 3.17 (s, 1H), 2.62-2.52 (m, 1H), 2.45 (s, 3H), 2.35 (br, d, J=13.9 Hz, 1H), 2.08 (s, 1H), 1.90 (s, 1H), 1.80 (s, 1H), 1.25-1.14 (m, 1H), 0.38-0.31 (m, 2H), 0.31-0.25 (m, 2H).

Example 175

6-(2-(6-((3R,5R)-3-Amino-5-fluoropiperidine-1-carbonyl)-3-methylbenzofuran-2-yl)-1-(cyclopropylmethyl)-1H-pyrrolo[2,3-b]pyridin-6-yl)isoindolin-1-one

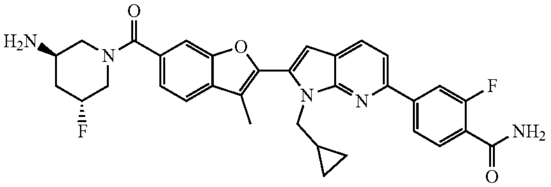 [SMILES: Cc1c(-c2cc3ccc(-c4ccc(C(N)=O)c(F)c4)nc3n2CC2CC2)oc2cc(C(=O)N3C[C@H](N)C[C@@H](F)C3)ccc12]

Intermediate 175A tert-Butyl-((3R,5R)-5-fluoro-1-(3-methyl-2-(4,4,5,5-tetramethyl-1,3,2-dioxaborolan-2-yl)benzofuran-6-carbonyl)piperidin-3-yl)carbamate

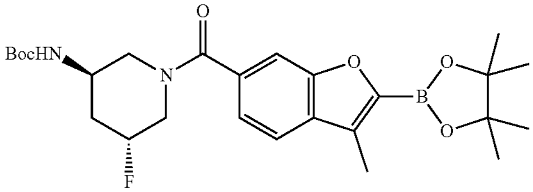 [SMILES: Cc1c(B2OC(C)(C)C(C)(C)O2)oc2cc(C(=O)N3C[C@H](F)C[C@@H](NC(=O)OC(C)(C)C)C3)ccc12]

1M THF solution of LDA (5.31 ml, 10.63 mmol) was added to a stirred solution of Intermediate 174A (1.0 g, 2.66 mmol) in THF (20 ml) at −78° C. The reaction mixture was stirred for 30 min, followed by the addition of 2-isopropoxy-4,4,5,5-tetramethyl-1,3,2-dioxaborolane (1.084 ml, 5.31 mmol) at −78° C. and stirring at −78° C. for 2 hours. The reaction mixture was quenched with water (10 ml), and extracted with EtOAc (2×100 ml). The combined organic layers were washed with water (100 ml) and brine (100 ml), dried over anhydrous sodium sulphate, filtered, and the filtrate was evaporated under reduced pressure to afford the crude material (1.1 g, 82%) as a gummy liquid. LC-MS m/z: 503 $[M+H]^+$.

Intermediate 175B tert-Butyl-((3R,5R)-1-(2-(6-chloro-1-(cyclopropylmethyl)-1H-pyrrolo[2,3-b]pyridin-2-yl)-3-methylbenzofuran-6-carbonyl)-5-fluoropiperidin-3-yl)carbamate

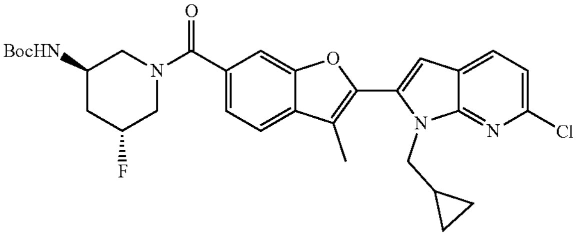 [SMILES: Cc1c(-c2cc3ccc(Cl)nc3n2CC2CC2)oc2cc(C(=O)N3C[C@H](F)C[C@@H](NC(=O)OC(C)(C)C)C3)ccc12]

A solution of $K_2CO_3$ (413 mg, 2.99 mmol) in water (1 ml) was added to a stirred and degasified solution of Intermediate 175A (500 mg, 0.995 mmol) and 6-chloro-1-(cyclopropylmethyl)-2-iodo-1H-pyrrolo[2,3-b]pyridine (Intermediate 3, 331 mg, 0.995 mmol) in dioxane (2 ml), followed by the addition of $PdCl_2$(dppf) (72.8 mg, 0.100 mmol). The reaction mixture was heated to 80° C. and stirred for 17 hours, evaporated under reduced pressure to dryness, water (20 ml) was added, and extracted with EtOAc (2×30 ml). The combined organic layers were washed with water (20 ml) and brine (20 ml), dried over anhydrous sodium sulphate, filtered, and the filtrate was evaporated under reduced pressure to afford the crude (180 mg, 40%) as a brown solid. LC-MS m/z: 581.3 $[M+H]^+$.

Intermediate 175C tert-Butyl-((3R,5R)-1-(2-(1-(cyclopropylmethyl)-6-(3-oxoisoindolin-5-yl)-1H-pyrrolo[2,3-b]pyridin-2-yl)-3-methylbenzofuran-6-carbonyl)-5-fluoropiperidin-3-yl)carbamate

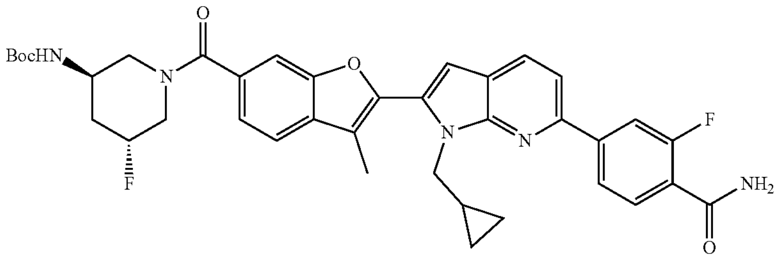 [SMILES: Cc1c(-c2cc3ccc(-c4ccc(C(N)=O)c(F)c4)nc3n2CC2CC2)oc2cc(C(=O)N3C[C@H](F)C[C@@H](NC(=O)OC(C)(C)C)C3)ccc12]

A solution of $K_2CO_3$ (64.2 mg, 0.465 mmol in water (1 ml) was added to a stirred and degasified solution of Intermediate 175B (90 mg, 0.155 mmol) and 2-fluoro-4-(4,4,5,5-tetramethyl-1,3,2-dioxaborolan-2-yl)benzamide (40.1 mg, 0.155 mmol) in dioxane (2 ml), followed by the addition of $PdCl_2$(dppf) (56.7 mg, 0.077 mmol). The reaction mixture was heated to 80° C. and stirred for 16 hours, evaporated under reduced pressure to dryness, water (20 ml) was added, and extracted with EtOAc (2×30 ml). The combined organic layers were washed with water (20 ml) and brine (20 ml), dried over anhydrous sodium sulphate, filtered, and the filtrate was evaporated under reduced pressure to afford the crude product (90 mg) as a brown solid. LC-MS m/z 678.4 $[M+H]^+$.

Example 175

TFA (0.141 ml, 1.829 mmol) was added to a stirred solution of Intermediate 175C (90 mg, 0.183 mmol) in DCM (2 ml). The reaction mixture was stirred at a room temperature for 7 hours, evaporated under reduced pressure, and the crude product thus obtained was purified using RP-HPLC to afford the title compound (6.9 mg, 16%). LC-MS m/z: 578 $[M+H]^+$. LC-MS retention time: 1.803/1.607 min. (Method E/F). $^1$H NMR (400 MHz, DMSO-$d_6$) δ ppm: 8.70-8.58 (m, 2H), 8.49-8.39 (m, 3H), 8.18 (d, J=8.3 Hz, 1H), 8.03-7.82 (m, 2H), 7.81 (d, J=8.1 Hz, 1H), 7.75-7.62 (m, 3H), 7.37 (d, J=7.8 Hz, 1H), 6.98 (s, 1H), 4.56-4.41 (m, 6H), 3.02 (td, J=4.2, 1.6 Hz, 1H), 2.47 (s, 3H), 2.22-2.09 (m, 1H), 1.63-1.42 (m, 1H), 1.32-1.22 (m, 2H), 0.61-0.49 (m, 1H), 0.44-0.31 (m, 4H).

Example 176

((7R)-7-Amino-2-azabicyclo[2.2.1]heptan-2-yl)(2-(1-(cyclopropylmethyl)-1H-indol-2-yl)-3-methylbenzofuran-6-yl)methanone

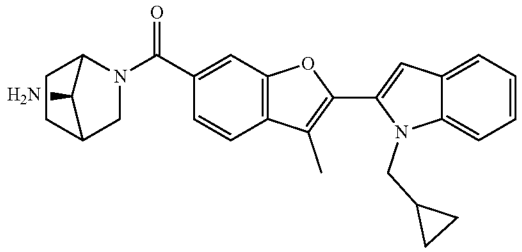

Intermediate 176A tert-Butyl-((7R)-2-(2-(1-(cyclopropylmethyl)-1H-indol-2-yl)-3-methylbenzofuran-6-carbonyl)-2-azabicyclo[2.2.1]heptan-7-yl)carbamate

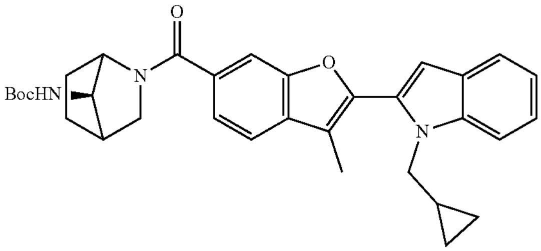 [SMILES: "BocHN" ; Cc1c(-c2cc3ccccc3n2CC2CC2)oc2cc(C(=O)N3CC4CCC3[C@@H]4C)ccc12]

A solution of $K_2CO_3$ (71.7 mg, 0.519 mmol) in water (0.75 ml) was added to a stirred and degasified solution of Intermediate 164E (70 mg, 0.173 mmol) and 1-(cyclopropylmethyl)-2-(4,4,5,5-tetramethyl-1,3,2-dioxaborolan-2-yl)-1H-indole (Intermediate 10, 51.4 mg, 0.173 mmol) in dioxane (2 ml), followed by the addition of $Pd(PPh_3)_4$ (200 mg, 0.173 mmol). The reaction mixture was heated to 120° C. and stirred for 6 hours, evaporated under reduced pressure to dryness, water (25 ml) was added, and extracted with EtOAc (2×25 ml). The combined organic extracts were washed with water (25 ml) and brine (25 ml), dried over anhydrous sodium sulphate, filtered, and the filtrate was evaporated under reduced pressure to afford the title compound (100 mg) as a brown solid. LC/MS m/z: 540.3 $[M+H]^+$.

Example 176

TFA (0.143 ml, 1.853 mmol) was added to a stirred solution of Intermediate 176A (100 mg, 0.185 mmol) in DCM (3 ml). The reaction mixture was stirred at a room temperature for 10 hours, evaporated under reduced pressure, and the crude product thus obtained was purified using RP-HPLC to afford the title compound. LC-MS m/z: 441.2 $[M+H]^+$. LC-MS retention time: 2.9 min. (Method H). $^1H$ NMR (400 MHz, DMSO-$d_6$) δ ppm: 8.29-7.99 (m, 3H), 8.28-7.98 (m, 2H), 7.82-7.67 (m, 2H), 7.54-7.37 (m, 1H), 7.23 (t, J=7.5 Hz, 1H), 7.16 (d, J=9.0 Hz, 1H), 6.8 (s, 1H), 4.55-4.50 (m, 2H), 4.30-4.24 (m, 2H), 4.27 (br, d, J=7.0 Hz, 1H), 4.14 (br, s, 1H), 4.12-4.02 (m, 1H), 3.75-3.41 (m, 2H), 3.25-3.04 (m, 1H), 2.68-2.60 (m, 1H), 2.38 (s, 3H), 1.99-1.82 (m, 3H), 1.74-1.51 (m, 1H), 1.16-0.96 (m, 1H), 0.39-0.27 (m, 2H), 0.15 (br, d, J=4.5 Hz, 2H).

Example 177

6-(2-(6-((7R)-7-Amino-2-azabicyclo[2.2.1]heptane-2-carbonyl)-3-methylbenzofuran-2-yl)-1-(cyclopropylmethyl)-1H-indol-6-yl)isoindolin-1-one

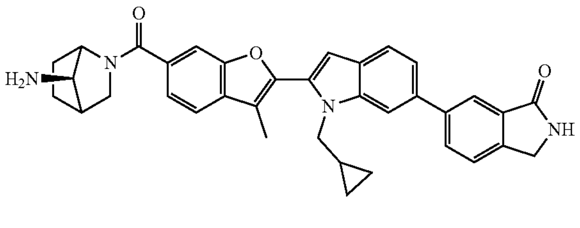 [SMILES: Cc1c(-c2cc3ccc(-c4ccc5c(c4)C(=O)NC5)cc3n2CC2CC2)oc2cc(C(=O)N3CC4CCC3[C@@H]4N)ccc12]

Intermediate 177A tert-Butyl-((7R)-2-(2-(6-bromo-1-(cyclopropylmethyl)-1H-indol-2-yl)-3-methylbenzofuran-6-carbonyl)-2-azabicyclo[2.2.1]heptan-7-yl)carbamate

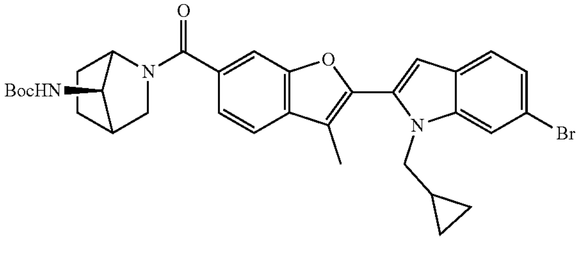 [SMILES: Cc1c(-c2cc3ccc(Br)cc3n2CC2CC2)oc2cc(C(=O)N3CC4CCC3[C@@H]4NC(=O)OC(C)(C)C)ccc12]

A solution of $K_2CO_3$ (0.368 g, 2.66 mmol) in water (0.1 ml) was added to a stirred and degasified solution of Intermediate 165A (0.551 g, 1.330 mmol) and 6-bromo-1-(cyclopropylmethyl)-2-iodo-1H-indole (Intermediate-12, 0.5 g, 1.330 mmol) in dioxane (10 ml), followed by the addition of $Pd(PPh_3)_4$ (0.123 g, 0.106 mmol). The reaction mixture was heated to 80° C. and stirred for 3 hours, filtered through a celite bed using EtOAc, and the filtrate was evaporated under reduced pressure. The crude product thus obtained was purified using flash chromatography (12 g silica gel column,70% EtOAc in pet ether) to afford the pure the title compound (0.28 g, 34%) as a gummy liquid. LC-MS m/z: 620 [M+H].

Intermediate 177B tert-Butyl-((7R)-2-(2-(1-(cyclopropylmethyl)-6-(3-oxoisoindolin-5-yl)-1H-indol-2-yl)-3-methylbenzofuran-6-carbonyl)-2-azabicyclo[2.2.1]heptan-7-yl) carbamate

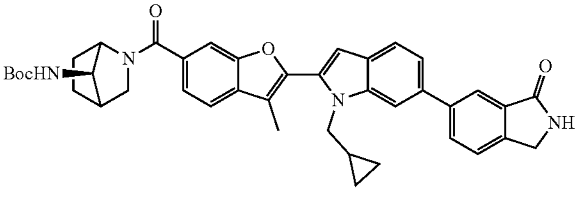 [SMILES: Cc1c(-c2cc3ccc(-c4ccc5c(c4)C(=O)NC5)cc3n2CC2CC2)oc2cc(C(=O)N3CC4CCC3[C@@H]4NC(=O)OC(C)(C)C)ccc12]

A solution of $K_2CO_3$ (0.045 g, 0.323 mmol) in water (0.1 ml) was added to a stirred and degasified solution of Intermediate 177A (0.1 g, 0.162 mmol) and 644,4,5,5-tetramethyl-1,3,2-dioxaborolan-2-yl)isoindolin-1-one (0.050 g, 0.194 mmol) in dioxane (2 ml), followed by the addition of $PdCl_2(dppf)$-$CH_2Cl_2$ adduct (0.013 g, 0.016 mmol). The reaction mixture was heated to 80° C. and stirred for 2 hours, filtered through a celite bed using EtOAc, and the filtrate was evaporated under reduced pressure to afford the title compound (100 mg) as a brown solid. LC-MS m/z: 672 $[M+H]^+$.

Example 177

TFA (0.057 ml, 0.745 mmol) was added to a stirred solution of Intermediate 177B (0.1 g, 0.149 mmol) in DCM (2 ml). The reaction mixture was stirred at a room temperature for 1 hour, evaporated under reduced pressure, and the crude product obtained was purified using RP-HPLC to afford the title compound (5.6 mg, 6.4%). LC-MS m/z: 572 $[M+H]^+$. LC-MS Ret. Time: 1.739/1.532 min (Method E/F). $^1H$ NMR (400 MHz, DMSO-$d_6$) δ ppm: 8.60 (s, 1H), 8.08-7.99 (m, 2H), 7.81-7.65 (m, 2H), 7.54-7.38 (m, 3H), 6.93 (s, 1H), 4.54-4.38 (m, 5H), 3.68 (s, 1H),3.52 (br, d, J-10.0 Hz, 1H), 3.17 (br, s, 2H), 3.07-2.99 (m, 1H), 2.45-2.38 (m, 4H), 2.25-2.12 (m, 1H), 2.03-1.81 (m, 3H), 1.75-1.65 (m, 1H), 1.48-1.30(m, 1H), 1.19-1.04 (m, 1H), 0.41-0.33 (m, 2H), 0.21 (q, J=5.1 Hz, 2H).

Compounds of Examples 178 to 188 in Table 21 were prepared following a procedure similar to the preparation of a compound of Example 177, by Suzuki coupling of Intermediate 177A with appropriate boronic ester or acid.

TABLE 21

| Example | Structure<br>Name<br>Analytical Data: LC-MS m/z [M + H]$^+$; HPLC retention time (HPLC method) |
|---|---|
| 178 | 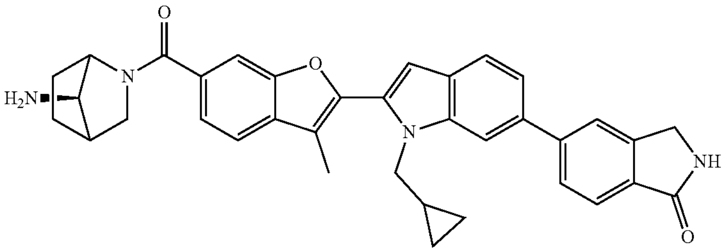 [SMILES: Cc1c(-c2cc3ccc(-c4ccc5c(c4)CNC5=O)cc3n2CC2CC2)oc2cc(C(=O)N3CC4CCC3[C@@H]4N)ccc12]<br>5-(2-(6-((7R)-7-Amino-2-azabicyclo[2.2.1]heptane-2-carbonyl)-3-methylbenzofuran-2-yl)-1-(cyclopropylmethyl)-1H-indol-6-yl)isoindolin-1-one<br>Analytical Data: 571.3, 1.704 min (Method E) |
| 179 | 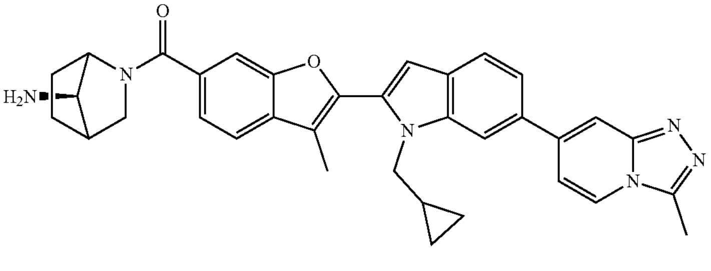 [SMILES: Cc1c(-c2cc3ccc(-c4ccn5c(C)nnc5c4)cc3n2CC2CC2)oc2cc(C(=O)N3CC4CCC3[C@@H]4N)ccc12]<br>((7R)-7-Amino-2-azabicyclo[2.2.1]heptan-2-yl)(2-(1-(cyclopropylmethyl)-6-(3-methyl-[1,2,4]triazolo[4,3-a]pyridin-7-yl)-1H-indol-2-yl)-3-methylbenzofuran-6-yl)methanone<br>Analytical Data: 571.3, 1.578 min (Method E) |
| 180 | 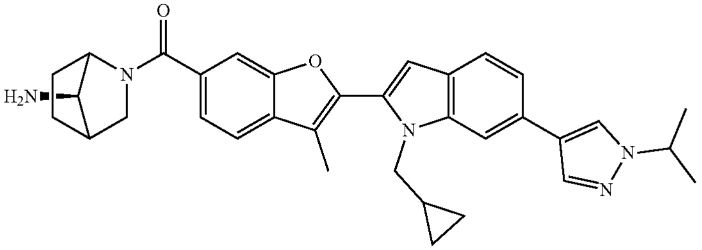 [SMILES: Cc1c(-c2cc3ccc(-c4cnn(C(C)C)c4)cc3n2CC2CC2)oc2cc(C(=O)N3CC4CCC3[C@@H]4N)ccc12]<br>((7R)-7-Amino-2-azabicyclo[2.2.1]heptan-2-yl)(2-(1-(cyclopropylmethyl)-6-(1-isopropyl-1H-pyrazol-4-yl)-1H-indol-2-yl)-3-methylbenzofuran-6-yl)methanone<br>Analytical Data: 548.4, 1.991 min (Method E) |
| 181 | 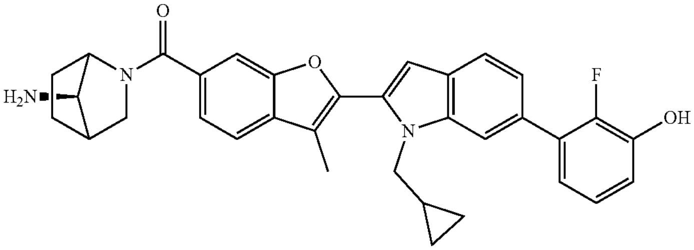 [SMILES: Cc1c(-c2cc3ccc(-c4cccc(O)c4F)cc3n2CC2CC2)oc2cc(C(=O)N3CC4CCC3[C@@H]4N)ccc12]<br>((7R)-7-Amino-2-azabicyclo[2.2.1]heptan-2-yl)(2-(1-(cyclopropylmethyl)-6-(2-fluoro-3-hydroxyphenyl)-1H-indol-2-yl)-3-methylbenzofuran-6-yl)methanone<br>Analytical Data: 550.3, 1.962 min (Method E) |

TABLE 21-continued

| Example | Structure<br>Name<br>Analytical Data: LC-MS m/z $[M + H]^+$; HPLC retention time (HPLC method) |
|---|---|
| 182 | 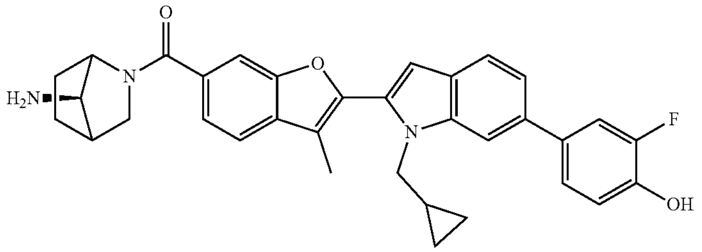 [SMILES: Cc1c(-c2cc3ccc(-c4ccc(O)c(F)c4)cc3n2CC2CC2)oc2cc(C(=O)N3CC4CCC3[C@@H]4N)ccc12]<br>((7R)-7-Amino-2-azabicyclo[2.2.1]heptan-2-yl)(2-(1-(cyclopropylmethyl)-6-(3-fluoro-4-hydroxyphenyl)-1H-indol-2-yl)-3-methylbenzofuran-6-yl)methanone<br>Analytical Data: 550.3, 1.944 min (Method E) |
| 183 | 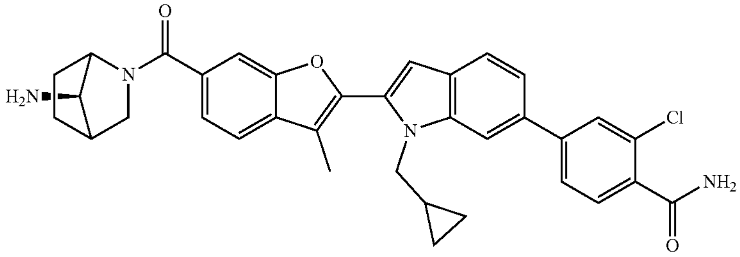 [SMILES: Cc1c(-c2cc3ccc(-c4ccc(C(N)=O)c(Cl)c4)cc3n2CC2CC2)oc2cc(C(=O)N3CC4CCC3[C@@H]4N)ccc12]<br>4-(2-(6-((7R)-7-Amino-2-azabicyclo[2.2.1]heptane-2-carbonyl)-3-methylbenzofuran-2-yl)-1-(cyclopropylmethyl)-1H-indol-6-yl)-2-chlorobenzamide<br>Analytical Data: 593.4, 1.782 min (Method E) |
| 184 | 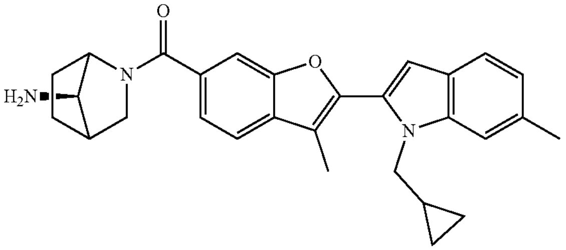 [SMILES: Cc1ccc2cc(-c3oc4cc(C(=O)N5CC6CCC5[C@@H]6N)ccc4c3C)n(CC3CC3)c2c1]<br>((7R)-7-Amino-2-azabicyclo[2.2.1]heptan-2-yl)(2-(1-(cyclopropylmethyl)-6-methyl-1H-indol-2-yl)-3-methylbenzofuran-6-yl)methanone<br>Analytical Data: 454.3, 2.177 min (Method E) |
| 185 | 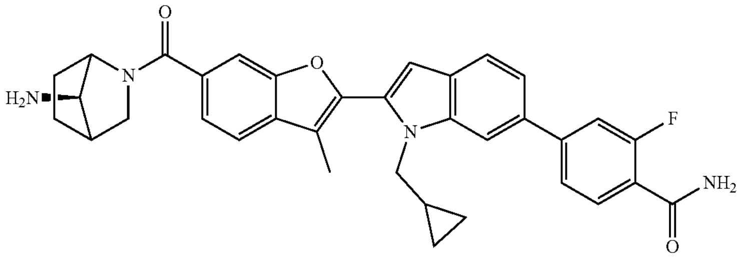 [SMILES: Cc1c(-c2cc3ccc(-c4ccc(C(N)=O)c(F)c4)cc3n2CC2CC2)oc2cc(C(=O)N3CC4CCC3[C@@H]4N)ccc12]<br>4-(2-(6-((7R)-7-Amino-2-azabicyclo[2.2.1]heptane-2-carbonyl)-3-methylbenzofuran-2-yl)-1-(cyclopropylmethyl)-1H-indol-6-yl)-2-fluorobenzamide<br>Analytical Data: 577.3, 1.790 min (Method E) |

TABLE 21-continued

| Example | Structure<br>Name<br>Analytical Data: LC-MS m/z [M + H]$^+$; HPLC retention time (HPLC method) |
|---|---|
| 186 | 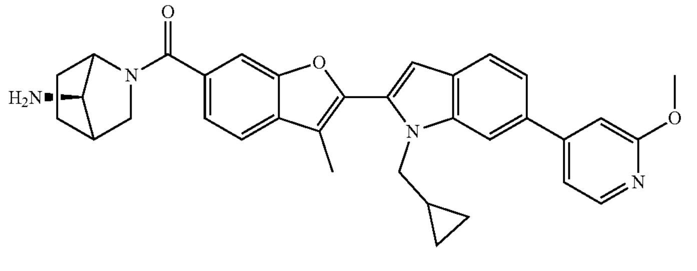 [SMILES: COc1cc(-c2ccc3cc(-c4oc5cc(C(=O)N6CC7CCC6[C@@H]7N)ccc5c4C)n(CC4CC4)c3c2)ccn1]<br>((7R)-7-Amino-2-azabicyclo[2.2.1]heptan-2-yl)(2-(1-(cyclopropylmethyl)-6-(2-methoxypyridin-4-yl)-1H-indol-2-yl)-3-methylbenzofuran-6-yl)methanone<br>Analytical Data: 547.4, 2.146 min (Method E) |
| 187 | 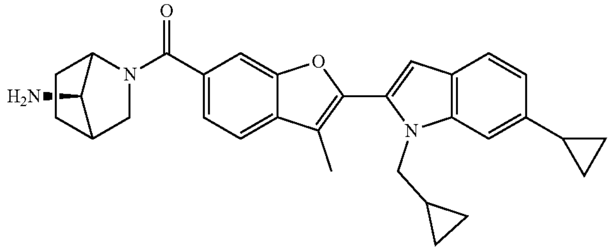 [SMILES: Cc1c(-c2cc3ccc(C4CC4)cc3n2CC2CC2)oc2cc(C(=O)N3CC4CCC3[C@@H]4N)ccc12]<br>((7R)-7-Amino-2-azabicyclo[2.2.1]heptan-2-yl)(2-(6-cyclopropyl-1-(cyclopropylmethyl)-1H-indol-2-yl)-3-methylbenzofuran-6-yl)methanone<br>Analytical Data: 480.3, 2.252 min (Method E) |
| 188 | 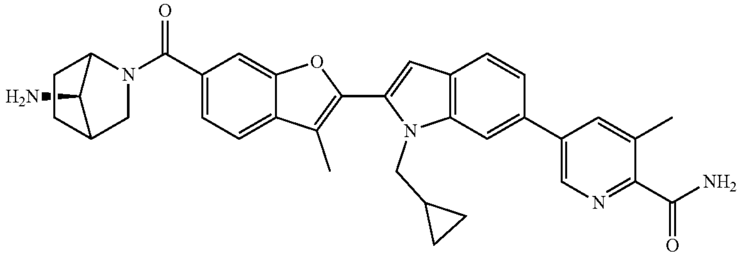 [SMILES: Cc1cc(-c2ccc3cc(-c4oc5cc(C(=O)N6CC7CCC6[C@@H]7N)ccc5c4C)n(CC4CC4)c3c2)cnc1C(N)=O]<br>5-(2-(6-((7R)-7-Amino-2-azabicyclo[2.2.1]heptane-2-carbonyl)-3-methylbenzofuran-2-yl)-1-(cyclopropylmethyl)-1H-indol-6-yl)-3-methylpicolinamide<br>Analytical Data: 574.3, 1.802 min (Method E) |

Example 189

((7R)-7-Amino-2-azabicyclo[2.2.1]heptan-2-yl)(2-(1-(cyclopropylmethyl)-6-(4-methoxypiperidin-1-yl)-1H-indol-2-yl)-3-methylbenzofuran-6-yl)methanone

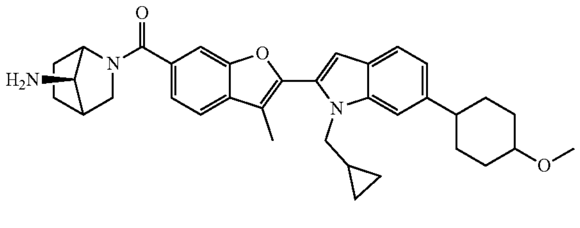 [SMILES: COC1CCC(c2ccc3cc(-c4oc5cc(C(=O)N6CC7CCC6[C@@H]7N)ccc5c4C)n(CC4CC4)c3c2)CC1]

Intermediate 189A tert-Butyl-((7R)-2-(2-(1-(cyclopropylmethyl)-6-(4-methoxypiperidin-1-yl)-1H-indol-2-yl)-3-methylbenzofuran-6-carbonyl)-2-azabicyclo[2.2.1]heptan-7-yl)carbamate

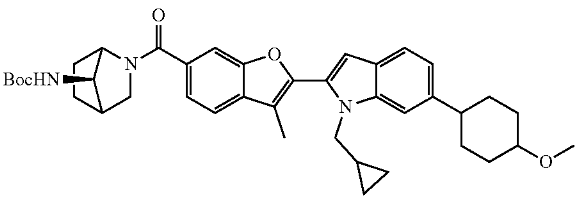 [SMILES: COC1CCC(c2ccc3cc(-c4oc5cc(C(=O)N6CC7CCC6[C@@H]7NC(=O)OC(C)(C)C)ccc5c4C)n(CC4CC4)c3c2)CC1]

Potassium tert-butoxide (0.036 g, 0.323 mmol) and XPHOS (0.039 g, 0.081 mmol) were added to a stirred and degasified solution of Intermediate 177A (0.1 g, 0.162 mmol), 4-methoxy-piperidine (0.019 g, 0.162 mmol) in dioxane (2 ml). The reaction mixture was purged with nitrogen for 5 min, followed by the addition of Palladium(II) acetate (10.89 mg, 0.048 mmol). The reaction mixture was heated to 110° C. and stirred for 12 hours, filtered through a celite bed using EtOAc (50 ml), and the filtrate was evaporated under reduced pressure to afford a residue. Water (50 ml) was added to the residue, and extracted with EtOAc (2×50 ml). The combined organic layers were washed with water (50 ml) and brine (50 ml), dried over anhydrous sodium sulphate, filtered, and the filtrate was evaporated under reduced pressure to afford the title compound (90 mg, 85%) as a brown solid. LC-MS m/z: 653 [M+H].

Example 189

TFA (0.059 ml, 0.766 mmol) was added to a stirred solution of Intermediate 189A (0.1 g, 0.153 mmol) in DCM (2 ml). The reaction mixture was stirred at a room temperature for 1 hour, evaporated under reduced pressure, and the crude product obtained was purified using RP-HPLC to afford the title compound (9.6 mg, 10%). LC-MS m/z: 553 $[M+H]^+$. LC-MS retention time: 2.009/1.117 min (Method E/F). $^1H$ NMR (400 MHz, DMSO-$d_6$) δ ppm: 7.73 (s, 1H), 7.65 (s, 1H), 7.49-7.43 (m, 1H), 7.39 (dd, J=0.7, 7.6 Hz, 1H), 7.03 (d, J=1.0 Hz, 1H), 6.91-6.87 (m, 1H),6.73 (s, 1H), 4.24 (br, d, J=6.8 Hz, 2H), 3.70 (br, d, J=1.2 Hz, 1H), 3.57-3.50 (m, 3H), 3.07 (br, d, J=10.8 Hz, 1H), 2.97-2.91 (m, 2H), 2.37 (s, 4H), 2.26-2.15 (m, 1H), 2.03-1.88 (m, 5H), 1.73-1.54 (m, 3H), 1.12-1.04 (m, 1H), 0.39-0.28 (m, 2H), 0.17 (br, d, J=4.2 Hz, 2H).

Compounds of Examples 190 to 193 in Table 22 were prepared following a procedure similar to the preparation of a compound of Example 189, using the Intermediate 177A and the appropriate amine.

TABLE 22

| Example | Structure<br>Name<br>Analytical Data: LC-MS m/z $[M + H]^+$; HPLC retention time (HPLC method) |
|---|---|
| 190 | 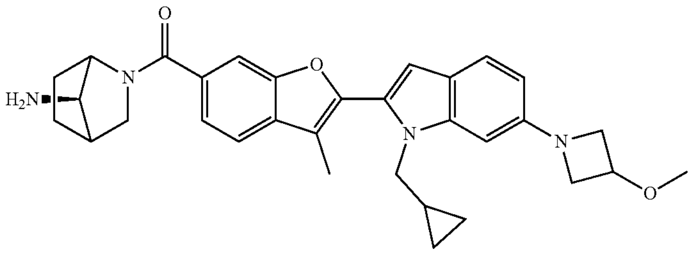 [SMILES: COC1CN(c2ccc3cc(-c4oc5cc(C(=O)N6CC7CCC6[C@@H]7N)ccc5c4C)n(CC4CC4)c3c2)C1]<br>((7R)-7-Amino-2-azabicyclo[2.2.1]heptan-2-yl)(2-(1-(cyclopropylmethyl)-6-(3-methoxyazetidin-1-yl)-1H-indol-2-yl)-3-methylbenzofuran-6-yl)methanone<br>Analytical Data: 525.4, 1.389 min (Method F) |
| 191 | 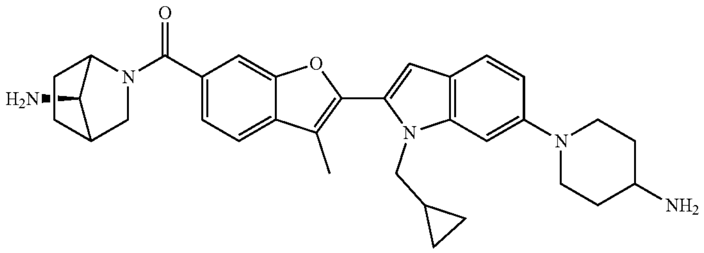 [SMILES: Cc1c(-c2cc3ccc(N4CCC(N)CC4)cc3n2CC2CC2)oc2cc(C(=O)N3CC4CCC3[C@@H]4N)ccc12]<br>((7R)-7-Amino-2-azabicyclo[2.2.1]heptan-2-yl)(2-(6-(4-aminopiperidin-1-yl)-1-(cyclopropylmethyl)-1H-indol-2-yl)-3-methylbenzofuran-6-yl)methanone<br>Analytical Data: 538.3, 1.375 min (Method E) |
| 192 | 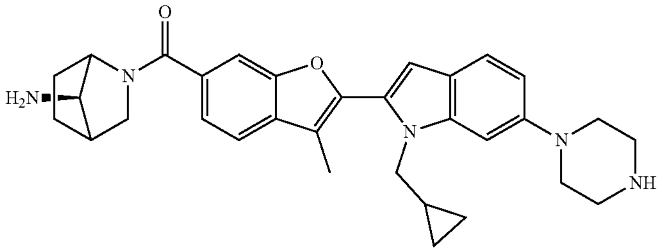 [SMILES: Cc1c(-c2cc3ccc(N4CCNCC4)cc3n2CC2CC2)oc2cc(C(=O)N3CC4CCC3[C@@H]4N)ccc12]<br>((7R)-7-Amino-2-azabicyclo[2.2.1]heptan-2-yl)(2-(1-(cyclopropylmethyl)-6-(piperazin-1-yl)-1H-indol-2-yl)-3-methylbenzofuran-6-yl)methanone<br>Analytical Data: 524.3, 1.377 min (Method E) |

TABLE 22-continued

| Example | Structure<br>Name<br>Analytical Data: LC-MS m/z $[M + H]^+$; HPLC retention time (HPLC method) |
|---|---|
| 193 | 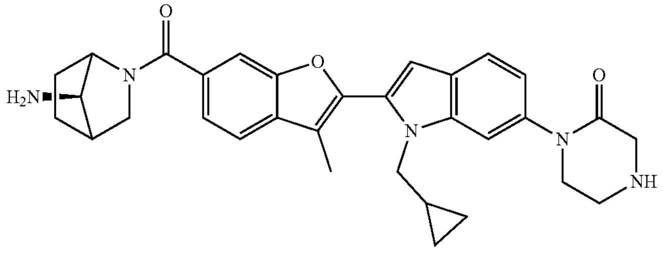 [SMILES: Cc1c(-c2cc3ccc(N4CCNCC4=O)cc3n2CC2CC2)oc2cc(C(=O)N3CC4CCC3[C@@H]4N)ccc12]<br>1-(2-(6-((7R)-7-Amino-2-azabicyclo[2.2.1]heptane-2-carbonyl)-3-methylbenzofuran-2-yl)-1-(cyclopropylmethyl)-1H-indol-6-yl)piperazin-2-one<br>Analytical Data: 538.3, 1.289 min (Method E) |

Example-194

((3R,5R)-3-Amino-5-fluoropiperidin-1-yl)(2-(1-(cyclopropylmethyl)-1H-indol-2-yl)-3-methylbenzofuran-6-yl)methanone

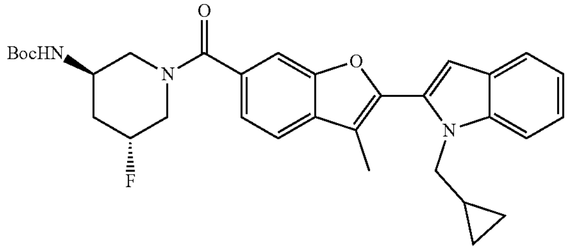 [SMILES: Cc1c(-c2cc3ccccc3n2CC2CC2)oc2cc(C(=O)N3C[C@H](F)C[C@@H](NC(=O)OC(C)(C)C)C3)ccc12]

Intermediate 194A tert-Butyl-((3R,5R)-1-(2-(1-(cyclopropylmethyl)-1H-indol-2-yl)-3-methylbenzofuran-6-carbonyl)-5-fluoropiperidin-3-yl)carbamate

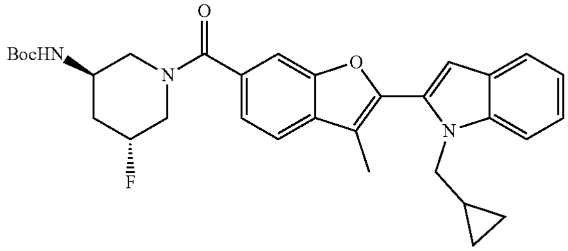 [SMILES: Cc1c(-c2cc3ccccc3n2CC2CC2)oc2cc(C(=O)N3C[C@H](F)C[C@@H](NC(=O)OC(C)(C)C)C3)ccc12]

A solution of $K_2CO_3$ (101 mg, 0.730 mmol) in water (0.75 ml) was added to a stirred and degasified solution of Intermediate 174B (100 mg, 0.243 mmol) and 1-(cyclopropylmethyl)-2-(4,4,5,5-tetramethyl-1,3,2-dioxaborolan-2-yl)-1H-indole (Intermediate 10, 72.3 mg, 0.243 mmol) in dioxane (3 ml). The reaction mixture was degasified with argon, followed by the addition of $Pd(PPh_3)_4$ (281 mg, 0.243 mmol). The reaction mixture was heated to 115° C. and stirred for 6 hours, evaporated under reduced pressure to dryness, water (25 ml) was added, and extracted with EtOAc (2×25 ml). The combined organic layers were washed with water (10 ml) and brine (10 ml), dried over anhydrous sodium sulphate, filtered, and the filtrate was evaporated under reduced pressure to afford the title compound (100 mg) as brown solid. LC-MS m/z: 546.5 $[M+H]^+$.

Example 194

TFA (0.141 ml, 1.833 mmol) was added to a stirred solution of Intermediate 194A (100 mg, 0.183 mmol) in DCM (2 ml). The reaction mixture was stirred at a room temperature for 7 hours, evaporated under reduced pressure, and the crude product obtained was purified using RP-HPLC to afford the title compound (1.3 mg, 1.4%). LC-MS m/z: 446.3 $[M+H]^+$. LC-MS retention time: 1.8 min (Method F). $^1H$ NMR (400 MHz, DMSO-$d_6$) δ ppm: 7.79 (d, J=7.8 Hz, 1H), 7.71-7.63 (m, 3H), 7.37 (dd, J=1.3, 7.9 Hz, 1H), 7.30-7.23 (m, 1H), 7.16-7.06 (m, 1H), 6.90(s, 1H), 5.04-4.82 (m, 1H), 4.73-4.39 (m, 1H), 4.30 (d, J=6.8 Hz, 2H), 3.94-3.83 (m, 1H), 2.86-2.74 (m, 1H), 2.41 (s, 3H), 2.31-2.21 (m, 1H), 1.84-1.64 (m, 1H), 1.24 (s, 2H), 1.18-1.07 (m, 1H), 0.41-0.27 (m, 2H), 0.24-0.11 (m, 2H).

Example 195

5-(2-(6-((3R,5R)-3-Amino-5-fluoropiperidine-1-carbonyl)-3-methylbenzofuran-2-yl)-1-(cyclopropylmethyl)-1H-indol-6-yl)isoindolin-1-one

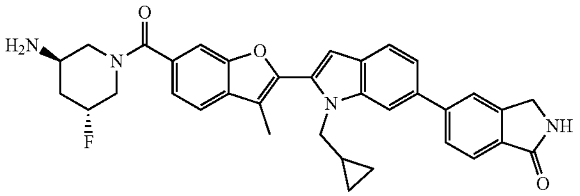 [SMILES: Cc1c(-c2cc3ccc(-c4ccc5c(c4)CNC5=O)cc3n2CC2CC2)oc2cc(C(=O)N3C[C@H](N)C[C@@H](F)C3)ccc12]

Intermediate 195A tert-Butyl-((3R,5R)-1-(2-(6-bromo-1-(cyclopropylmethyl)-1H-indol-2-yl)-3-methylbenzofuran-6-carbonyl)-5-fluoropiperidin-3-yl)carbamate

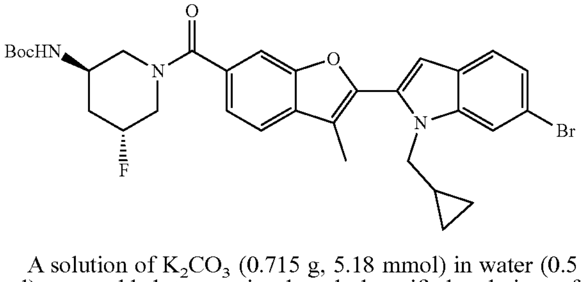

A solution of $K_2CO_3$ (0.715 g, 5.18 mmol) in water (0.5 ml) was added to a stirred and degasified solution of Intermediate 175A (1.3 g, 2.59 mmol) and 6-bromo-1-(cyclopropylmethyl)-2-iodo-1H-indole (Intermediate-12, 0.973 g, 2.59 mmol) in dioxane (12 ml). The reaction mixture was degasified with argon, followed by the addition of $PdCl_2$(dppf)-$CH_2Cl_2$ adduct (0.190 g, 0.233 mmol). The reaction mixture was heated to 80° C. and stirred for 3 hours, diluted with water (100 ml) and extracted with EtOAc (2×100 ml). The combined organic layers were washed with water (100 ml) and brine (100 ml), dried over anhydrous sodium sulphate, filtered, and the filtrate was evaporated under reduced pressure. The crude material was purified using a silica gel column (40 g, silica gel column,70% EtOAc in pet ether) to afford the title compound (1.1 g, 68%) as a gummy liquid. LC-MS m/z: 626 [M+H]$^+$.

Intermediate 195B tert-Butyl-(3R,5R)-1-(2-(1-(cyclopropylmethyl)-6-(1-oxoisoindolin-5-yl)-1H-indol-2-yl)-3-methylbenzofuran-6-carbonyl)-5-fluoropiperidin-3-yl)carbamate

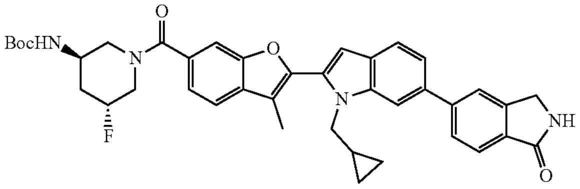 [SMILES: Cc1c(-c2cc3ccc(-c4ccc5c(c4)CNC5=O)cc3n2CC2CC2)oc2cc(C(=O)N3C[C@H](F)C[C@@H](NC(=O)OC(C)(C)C)C3)ccc12]

A solution of $K_2CO_3$ (0.044 g, 0.320 mmol) in water (0.5 ml) was added to a stirred and degasified solution of Intermediate 195A (0.1 g, 0.160 mmol) and 5-(4,4,5,5-tetramethyl-1,3,2-dioxaborolan-2-yl)isoindolin-1-one (0.050 g, 0.192 mmol) in dioxane (2 ml). The reaction mixture was degasified with argon, followed by the addition of $PdCl_2$(dppf)-$CH_2Cl_2$ adduct (0.013 g, 0.016 mmol). The reaction mixture was heated to 80° C. and stirred for 12 hours, filtered through a celite bed using ethyl acetate, and the filtrate was concentrated under reduced pressure to afford the title compound (100 mg, 91%). LC/MS m/z=677.4 [M+H]$^+$.

Example 195

TFA (0.056 ml, 0.732 mmol) was added to a stirred solution of 195B (0.1 g, 0.146 mmol) in DCM (2 ml). The reaction mixture was stirred at a room temperature for 1 hour, evaporated under reduced pressure, and the crude product obtained was purified using RP-HPLC to afford the title compound (2 mg, 2.1%). LC/MS m/z: 577.3 [M+H]$^+$. LC-MS retention time: 1.678/1.529 min (Method E/F); $^1$H NMR (400 MHz, DMSO-$d_6$) δ ppm: 8.55 (s, 1H), 8.03 (s, 1H), 7.98 (s, 1H), 7.90 (br, dd, J=1.1, 8.4 Hz, 2H), 7.83-7.74 (m, 4H), 7.70 (br, d, J=0.7 Hz, 1H),7.52 (d, J=9.0 Hz, 1H), 7.39 (d, J=7.6 Hz, 1H), 6.95 (s, 1H), 4.47 (s, 3H), 4.45-4.39 (m, 2H), 3.01-2.88 (m, 2H), 2.44 (s, 3H), 2.28 (br, t, J=7.5 Hz, 1H),1.92-1.74 (m, 2H), 1.57-1.39 (m, 2H), 1.30-1.08 (m, 14H), 0.90-0.79 (m, 2H), 0.43-0.32 (m, 2H), 0.25-0.17 (m, 2H).

Compounds of Examples 196 to 199 in Table 23 were prepared following a procedure similar to the preparation of a compound of Example 195, using the Intermediate 195A and the appropriate boronic esters or acids

TABLE 23

| Example | Structure<br>Name<br>Analytical Data: LC-MS m/z [M + H]$^+$; HPLC retention time (HPLC method) |
|---|---|
| 196 | 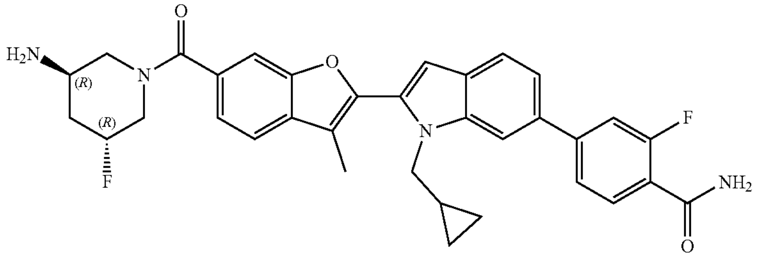<br>4-(2-(6-((3R,5R)-3-Amino-5-fluoropiperidine-1-carbonyl)-3-methylbenzofuran-2-yl)-1-(cyclopropylmethyl)-1H-indol-6-yl)-2-fluorobenzamide<br>Analytical Data: 583.4, 1.755 min (Method E) |

TABLE 23-continued

| Example | Structure<br>Name<br>Analytical Data: LC-MS m/z [M + H]+; HPLC retention time (HPLC method) |
|---|---|
| 197 | 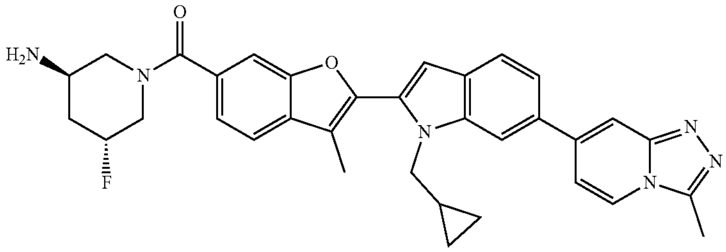 [SMILES: Cc1c(-c2cc3ccc(-c4ccn5c(C)nnc5c4)cc3n2CC2CC2)oc2cc(C(=O)N3C[C@H](N)C[C@@H](F)C3)ccc12]<br>((3R,5R)-3-Amino-5-fluoropiperidin-1-yl)(2-(1-(cyclopropylmethyl)-6-(3-methyl-[1,2,4]triazolo[4,3-a]pyridin-7-yl)-1H-indol-2-yl)-3-methylbenzofuran-6-yl)methanone<br>Analytical Data: 577.3, 1.562 min (Method E) |
| 198 | 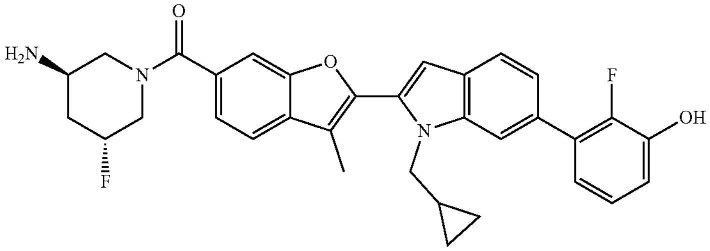 [SMILES: Cc1c(-c2cc3ccc(-c4cccc(O)c4F)cc3n2CC2CC2)oc2cc(C(=O)N3C[C@H](N)C[C@@H](F)C3)ccc12]<br>((3R,5R)-3-Amino-5-fluoropiperidin-1-yl)(2-(1-(cyclopropylmethyl)-6-(2-fluoro-3-hydroxyphenyl)-1H-indol-2-yl)-3-methylbenzofuran-6-yl)methanone<br>Analytical Data: 556.3, 1.933 min (Method E) |
| 199 | 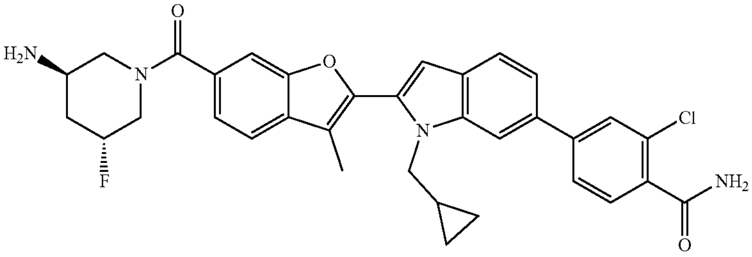 [SMILES: Cc1c(-c2cc3ccc(-c4ccc(C(N)=O)c(Cl)c4)cc3n2CC2CC2)oc2cc(C(=O)N3C[C@H](N)C[C@@H](F)C3)ccc12]<br>4-(2-(6-((3R,5R)-3-Amino-5-fluoropiperidine-1-carbonyl)-3-methylbenzofuran-2-yl)-1-(cyclopropylmethyl)-1H-indol-6-yl)-2-chlorobenzamide<br>Analytical Data: 599.3, 1.741 min (Method E) |

Example 200

((3R,5R)-3-Amino-5-fluoropiperidin-1-yl)(2-(1-(cyclopropylmethyl)-6-(4-methoxypiperidin-1-yl)-1H-indol-2-yl)-3-methylbenzofuran-6-yl)methanone

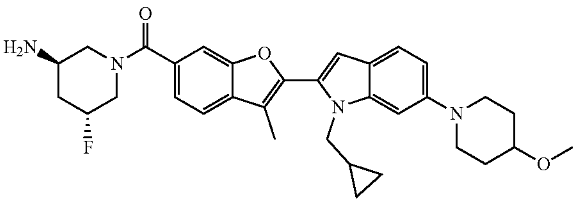 [SMILES: COC1CCN(c2ccc3cc(-c4oc5cc(C(=O)N6C[C@H](N)C[C@@H](F)C6)ccc5c4C)n(CC4CC4)c3c2)CC1]

Intermediate 200A tert-Butyl-((3R,5R)-1-(2-(1-(cyclopropylmethyl)-6-(4-methoxypiperidin-1-yl)-1H-indol-2-yl)-3-methyl-benzofuran-6-carbonyl)-5-fluoropiperidin-3-yl)carbamate

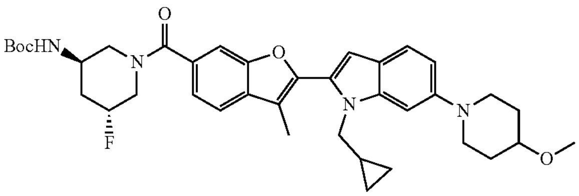 [SMILES: COC1CCN(c2ccc3cc(-c4oc5cc(C(=O)N6C[C@H](F)C[C@@H](NC(=O)OC(C)(C)C)C6)ccc5c4C)n(CC4CC4)c3c2)CC1]

Potassium tert-butoxide (0.036 g, 0.320 mmol), XPHOS (0.038 g, 0.080 mmol) were added to a stirred and degasified solution of Intermediate 195A (0.1 g, 0.160 mmol), (0.018 g, 0.160 mmol) in dioxane (2 ml). The reaction mixture was purged with nitrogen for 5 min, followed by the addition of Palladium(II) acetate (10.89 mg, 0.048 mmol). The reaction mixture heated to 110° C. and stirred for 12 hours, filtered through a celite bed using EtOAc (50 ml), and the filtrate was evaporated under reduced pressure. Water (50 ml) was added to the residue thus obtained, and extracted with EtOAc (2×50 ml). The combined organic layers were washed with water (50 ml) and brine (50 ml), dried over anhydrous sodium sulphate, filtered, and the filtrate was evaporated under reduced pressure to afford the title compound (90 mg, 85%) as brown solid. LC-MS m/z: 659.4 $[M+H]^+$.

Example 200

TFA (0.029 ml, 0.379 mmol) was added to a stirred solution of Intermediate 200A (0.05 g, 0.076 mmol) in DCM (2 ml). The reaction mixture was stirred at a room temperature for 1 hour, evaporated under reduced pressure, and the crude product thus obtained was purified using RP-HPLC to afford the title compound (6.8 mg, 15%). LC-MS m/z: 559 $[M+H]^+$. LC-MS retention time: 1.959/1.161 min, (Method E/F). $^1H$ NMR (400 MHz, DMSO-$d_6$) δ ppm: 8.17-7.91 (m, 2H), 7.77 (d, J=8.3 Hz, 1H), 7.67 (s, 1H), 7.60-7.52 (m, 1H), 7.37 (d, J=7.8 Hz, 1H), 7.07-6.96 (m, 1H),6.80 (s, 1H), 4.26 (br, d, J=6.8 Hz, 2H), 3.57 (br, dd, 4.5 Hz, 3H), 3.31 (s, 6H),3.12-2.87 (m, 2H), 2.38 (s, 5H), 2.11-2.01 (m, 2H), 1.89- 1.58 (m,1H), 1.23 (s, 1H), 1.11 (br, d, J=7.1 Hz, 1H), 0.41-0.30 (m, 2H), 0.19 (d, J=4.6 Hz, 2H).

Compounds of Examples 201 and 202 in Table 24 were prepared following a procedure similar to the preparation of a compound of Example 200, using the Intermediate 195A and the appropriate amine.

TABLE 24

| Example | Structure<br>Name<br>Analytical Data: LC-MS m/z $[M + H]^+$; HPLC retention time (HPLC method) |
|---|---|
| 201 | 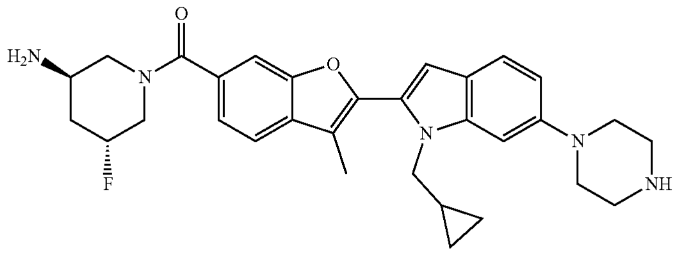 [SMILES: Cc1c(-c2cc3ccc(N4CCNCC4)cc3n2CC2CC2)oc2cc(C(=O)N3C[C@H](N)C[C@@H](F)C3)ccc12]<br>((3R,5R)-3-Amino-5-fluoropiperidin-1-yl)(2-(1-(cyclopropylmethyl)-6-(piperazin-1-yl)-1H-indol-2-yl)-3-methylbenzofuran-6-yl)methanone<br>Analytical Data: LC-MS m/z: 530.3 $[M + H]^+$; HPLC retention time: 1.171 min (Method E) |
| 202 | 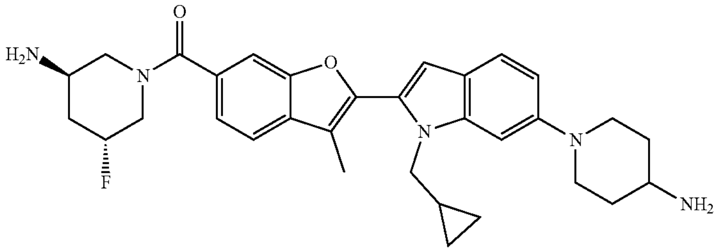 [SMILES: Cc1c(-c2cc3ccc(N4CCC(N)CC4)cc3n2CC2CC2)oc2cc(C(=O)N3C[C@H](N)C[C@@H](F)C3)ccc12]<br>((3R,5R)-3-Amino-5-fluoropiperidin-1-yl)(2-(6-(4-aminopiperidin-1-yl)-1-(cyclopropylmethyl)-1H-indol-2-yl)-3-methylbenzofuran-6-yl)methanone<br>Analytical Data: LC-MS m/z: 544.3$[M + H]^+$; HPLC retention time: 2.007 min (Method E) |

Example 203

((7R)-7-Amino-2-azabicyclo[2.2.1]heptan-2-yl)(2-(1-(cyclopropylmethyl)-6-(2-hydroxypropan-2-yl)-1H-pyrrolo[2,3-b]pyridin-2-yl)-4-methoxy-3-methylbenzofuran-6-yl)methanone

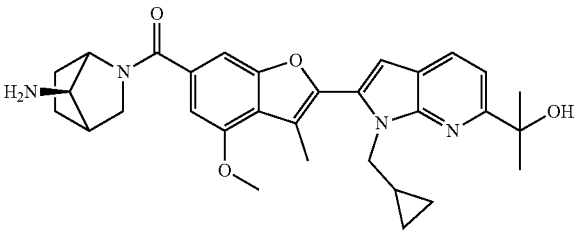 [SMILES: COc1cc(C(=O)N2CC3CCC2[C@@H]3N)cc2oc(-c3cc4ccc(C(C)(C)O)nc4n3CC3CC3)c(C)c12]

Intermediate 203A tert-Butyl-((7R)-2-(2-(6-acetyl-1-(cyclopropylmethyl)-1H-pyrrolo[2,3-b]pyridin-2-yl)-4-methoxy-3-methylbenzofuran-6-carbonyl)-2-azabicyclo[2.2.1]heptan-7-yl)carbamate

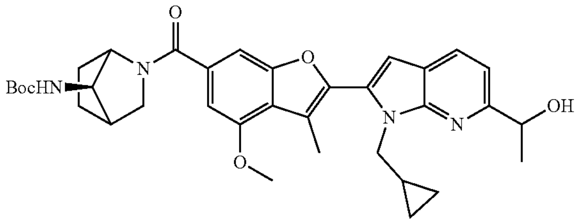

Tributyl (1-ethoxyvinyl)tin (119 mg, 0.331 mmol) and $Pd(PPh_3)_4$ (38.2 mg, 0.033 mmol) were added to a stirred and degasified solution of Intermediate 146B (200 mg, 0.331 mmol) in toluene (5 ml). The reaction mixture was heated to 85° C. and stirred for 14 hours, evaporated under reduced pressure to dryness, and the crude product thus obtained was purified using a silica gel column (12 g, Redisep® $SiO_2$ column, eluting with 45% EtOAc in n-hexane) to afford the title compound (120 mg, 59%) as a brown solid. LC-MS m/z: 613.4 $[M+H]^+$.

Intermediate 203B tert-Butyl-((7R)-2-(2-(1-(cyclopropylmethyl)-6-(2-hydroxypropan-2-yl)-1H-pyrrolo[2,3-b]pyridin-2-yl)-4-methoxy-3-methylbenzofuran-6-carbonyl)-2-azabicyclo[2.2.1]heptan-7-yl)carbamate

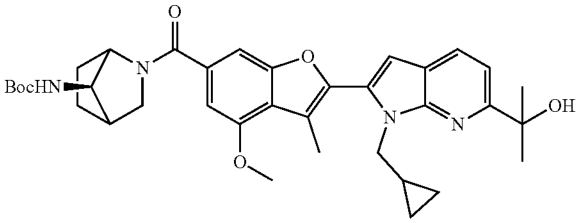 [SMILES: COc1cc(C(=O)N2CC3CCC2[C@@H]3NC(=O)OC(C)(C)C)cc2oc(-c3cc4ccc(C(C)(C)O)nc4n3CC3CC3)c(C)c12]

Methyl magnesium bromide (0.245 ml, 0.490 mmol, 2M in THF) was added to a stirred solution of Intermediate 203A (100 mg, 0.163 mmol) in THF at 0° C. The reaction mixture was stirred for 2 hours, quenched with saturated aqueous ammonium chloride solution (20 ml), and extracted with EtOAc (2×10 ml). The combined organic layers were washed with water (10 ml) and brine (10 ml), dried over anhydrous sodium sulphate, filtered, and the filtrate was evaporated under reduced pressure to afford the crude product (130 mg) as a brown solid. LC-MS m/z: 629.5 $[M+H]^+$.

Example 203

TFA (0.123 ml, 1.590 mmol) was added to a solution of 203B (100 mg, 0.159 mmol) in DCM (3 ml) and the reaction mixture was stirred at a room temperature for 6 hours. The reaction mixture was evaporated under reduced pressure, and the crude product thus obtained was purified using RP-HPLC to afford the title compound (1.21 mg, 1%). LC-MS m/z: 529.3 $[M+H]^+$. LC-MS retention time: 1.921/1.643 min (Method E/F).

Example 204

((7R)-7-Amino-2-azabicyclo[2.2.1]heptan-2-yl)(2-(1-(cyclopropylmethyl)-6-(2-hydroxypropan-2-yl)-1H-indol-2-yl)-3-methylbenzofuran-6-yl)methanone

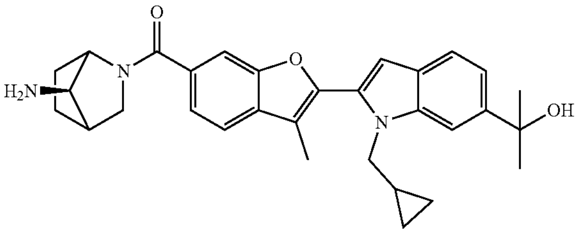 [SMILES: Cc1c(-c2cc3ccc(C(C)(C)O)cc3n2CC2CC2)oc2cc(C(=O)N3CC4CCC3[C@@H]4N)ccc12]

Intermediate 204A tert-Butyl-((7R)-2-(2-(6-acetyl-1-(cyclopropylmethyl)-1H-indol-2-yl)-3-methylbenzofuran-6-carbonyl)-2-azabicyclo[2.2.1]heptan-7-yl)carbamate

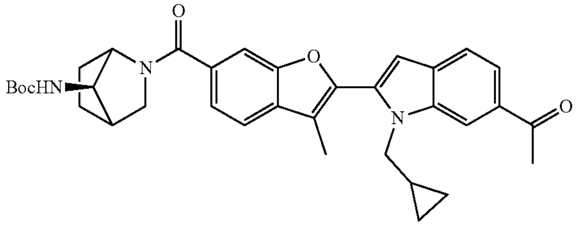 [SMILES: CC(=O)c1ccc2cc(-c3oc4cc(C(=O)N5CC6CCC5[C@@H]6NC(=O)OC(C)(C)C)ccc4c3C)n(CC3CC3)c2c1]

Tributyl(1-ethoxyvinyl)stannane (0.234 g, 0.647 mmol) and $Pd(PPh_3)_2Cl_2$ (0.023 g, 0.032 mmol) were added to a stirred and degasified solution of Intermediate 177A (0.2 g, 0.323 mmol) in toluene (2 ml). The reaction mixture was heated to 90° C. and stirred for 3 hours, evaporated under reduced pressure, and the crude product thus obtained was purified using a silica gel column (4 g, Redisep® $SiO_2$ column, eluting with 70% EtOAc in n-hexane) to afford the title compound (0.13 g, 69%) as gummy liquid. LC-MS m/z: 582.4 $[M+H]^+$.

Intermediate 204B tert-Butyl-((7R)-2-(2-(1-(cyclopropylmethyl)-6-(2-hydroxypropan-2-yl)-1H-indol-2-yl)-3-methylbenzofuran-6-carbonyl)-2-azabicyclo[2.2.1]heptan-7-yl) carbamate

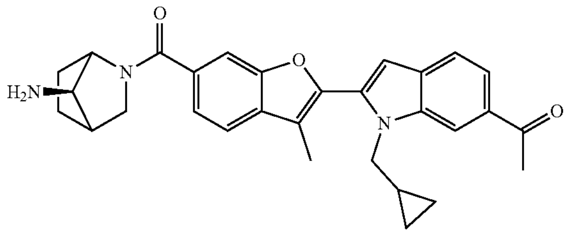 [SMILES: CC(=O)c1ccc2cc(-c3oc4cc(C(=O)N5CC6CCC5[C@@H]6N)ccc4c3C)n(CC3CC3)c2c1]

TFA (0.040 ml, 0.516 mmol) was added to a stirred solution Intermediate 204A (0.06 g, 0.103 mmol) in DCM (2 ml). The reaction mixture was stirred at a room temperature for 1 hour, evaporated under reduced pressure, diluted with 10% sodium bicarbonate solution (20 ml), and extracted with EtOAc (2×20 ml). The combined organic layers were washed with water (20 ml) and brine (20 ml), dried over anhydrous sodium sulphate, filtered, and the filtrate was evaporated under reduced pressure to afford the crude product (50 mg) as a gummy liquid. LC-MS m/z: 482.3 $[M+H]^+$.

Example 204

Methyl magnesium bromide (0.125 ml, 0.125 mmol) was added to a stirred solution of Intermediate 204B (0.05 g, 0.104 mmol) in THF (2 ml) at 0° C. The reaction mixture was stirred at a room temperature for 2 hours, quenched with saturated aqueous ammonium chloride solution (20 ml), and extracted with EtOAc (2×20 ml). The combined organic layers were washed with water (20 ml) and brine (20 ml), dried over anhydrous sodium sulphate, filtered, and the filtrate was evaporated under reduced pressure. The crude product thus obtained was purified using RP-HPLC to afford the title compound (3.5 mg, 6%). LC/MS m/z: 498.4 $[M+H]^+$, retention time: 3.476 min (Method H). $^1H$ NMR (400 MHz, DMSO-$d_6$) δ ppm: 7.76 (s, 1H), 7.73-7.66 (m, 3H), 7.55 (d, J=8.0 Hz, 1H), 7.24 (s, 1H), 6.82 (s, 1H), 5.04 (s, 1H), 4.27 (d, J=7.0 Hz, 2H), 3.51 (s, 4H),2.39-2.36 (m, 4H), 2.29-2.19 (m, 4H), 1.83-1.69 (m, 2H), 1.66(s, 1H), 1.56-1.41 (m, 6H), 1.36 (br, d, J=8.0 Hz, 1H), 1.34-1.10 (m,4H), 0.98-0.77 (m, 1H), 0.39-0.34 (m, 2H), 0.19 (br, d, J=4.0 Hz, 2H).

Compounds of Examples 205 and 206 in Table 25 were prepared following a procedure similar to the preparation of a compound of Example 3, using Suzuki coupling reaction of Intermediate 2E with appropriate boronic acid or boronate esters.

TABLE 25

| Example | Structure<br>Name<br>Analytical Data: LC-MS m/z $[M + H]^+$; HPLC retention time (HPLC method) |
|---|---|
| 205 | 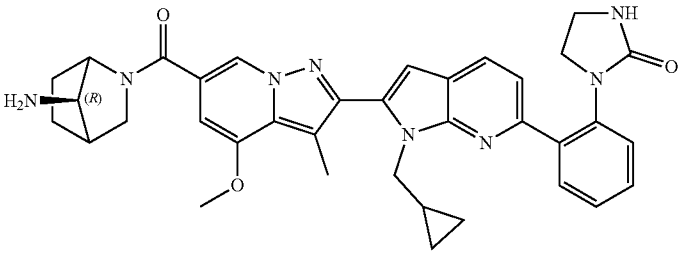<br>1-[2-(2-{6-[(7R)-7-Amino-2-azabicyclo[2.2.1]heptane-2-carbonyl]-4-methoxy-3-methylpyrazolo[1,5-a]pyridin-2-yl}-1-(cyclopropylmethyl)-1H-pyrrolo[2,3-b]pyridin-6-yl)phenyl]imidazolidin-2-one<br>Analytical Data: 631.4; 1.568 min (Method E) |
| 206 | 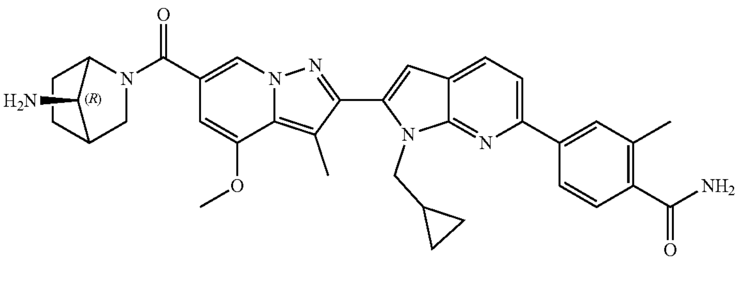<br>4-(2-{6-[(7R)-7-Amino-2-azabicyclo[2.2.1]heptane-2-carbonyl]-4-methoxy-3-methylpyrazolo[1,5-a]pyridin-2-yl}-1-(cyclopropylmethyl)-1H-pyrrolo[2,3-b]pyridin-6-yl)-2-methylbenzamide<br>Analytical Data: 604.4; 1.781 min (Method E) |

Example 207

4-(2-{6-[(3R,5R)-3-Amino-5-fluoropiperidine-1-carbonyl]-4-methoxy-3-methylpyrazolo[1,5-a]pyridin-2-yl}-1-(cyclopropylmethyl)-1H-pyrrolo[2,3-b]pyridin-6-yl)-2-fluoro-5-methylbenzamide

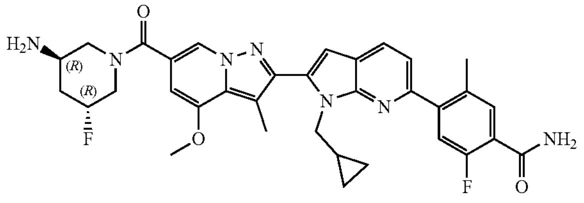

Compound of Example 207 was prepared following a procedure similar to the preparation compound of Example 16, using Intermediate 15A and appropriate boronic acid or boronate ester. LC-MS m/z: 627.3 $[M+H]^+$; HPLC retention time: 1.762 min (HPLC method E).

Example 208

4-(2-{6-[(3R)-3-Aminopiperidine-1-carbonyl]-4-methoxy-3-methylpyrazolo[1,5-a]pyridin-2-yl}-1-(cyclopropylmethyl)-1H-pyrrolo[2,3-b]pyridin-6-yl)-2-fluoro-5-methylbenzamide

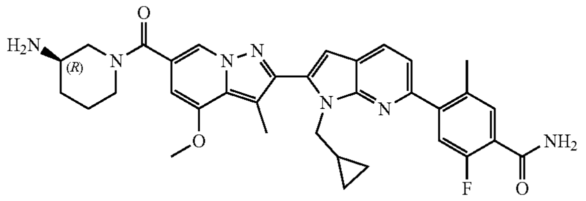

Compound of Example 208 was prepared following a procedure similar to the preparation of compound of Example 3, using Intermediate 2D and tert-butyl (R)-piperidin-3-ylcarbamate in amide formation reaction and the appropriate boronic acid or boronate ester in Suzuki coupling reaction. LC-MS m/z: 609.3 $[M+H]^+$; HPLC retention time: 1.710 min (HPLC Method E).

Compounds of Examples 209 to 226 in Table 26 were prepared following a procedure similar to the preparation of a compound of Example 29, by Suzuki coupling of Intermediate 29A with appropriate boronic acid or boronate ester.

TABLE 26

| Example | Structure<br>Name<br>Analytical Data: LC-MS m/z $[M + H]^+$; HPLC retention time (HPLC method 1) |
| --- | --- |
| 209 | 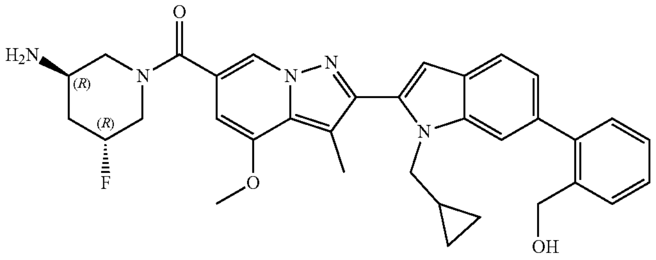<br>[2-(2-{6-[(3R,5R)-3-Amino-5-fluoropiperidine-1-carbonyl]-4-methoxy-3-methylpyrazolo[1,5-a]pyridin-2-yl}-1-(cyclopropylmethyl)-1H-indol-6-yl)phenyl]methanol<br>Analytical Data: 582.3; 1.913 min (Method E) |
| 210 | 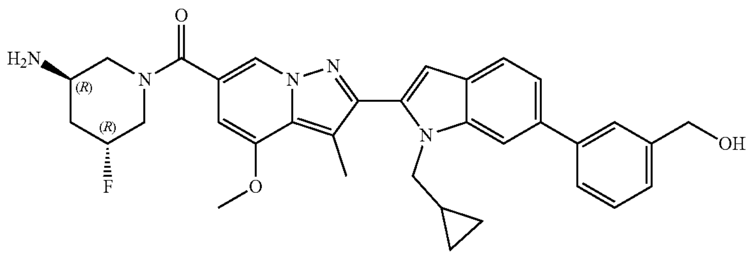<br>[3-(2-{6-[(3R,5R)-3-Amino-5-fluoropiperidine-1-carbonyl]-4-methoxy-3-methylpyrazolo[1,5-a]pyridin-2-yl}-1-(cyclopropylmethyl)-1H-indol-6-yl)phenyl]methanol<br>Analytical Data: 582.3; 1.856 min (Method E) |

TABLE 26-continued

| Example | Structure<br>Name<br>Analytical Data: LC-MS m/z [M + H]$^+$; HPLC retention time (HPLC method 1) |
|---|---|
| 211 | 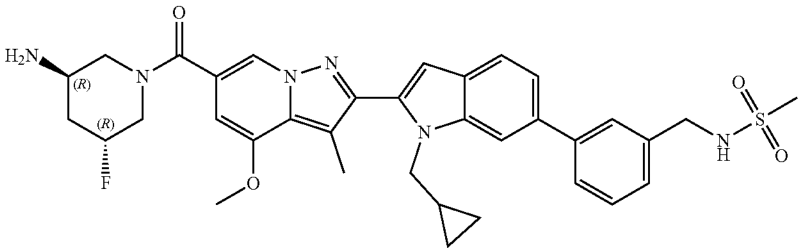<br>N-{[3-(2-{6-[(3R,5R)-3-Amino-5-fluoropiperidine-1-carbonyl]-4-methoxy-3-methylpyrazolo[1,5-a]pyridin-2-yl}-1-(cyclopropylmethyl)-1H-indol-6-yl)phenyl]methyl}methanesulfonamide<br>Analytical Data: 659.3; 1.878 min (Method E) |
| 212 | 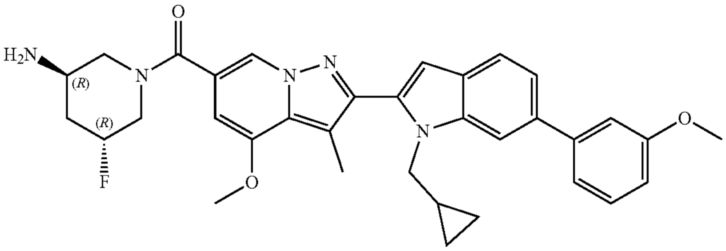<br>(3R,5R)-1-{2-[1-(Cyclopropylmethyl)-6-(3-methoxyphenyl)-1H-indol-2-yl]-4-methoxy-3-methylpyrazolo[1,5-a]pyridine-6-carbonyl}-5-fluoropiperidin-3-amine<br>Analytical Data: 582.3; 2.275 min (Method E) |
| 213 | 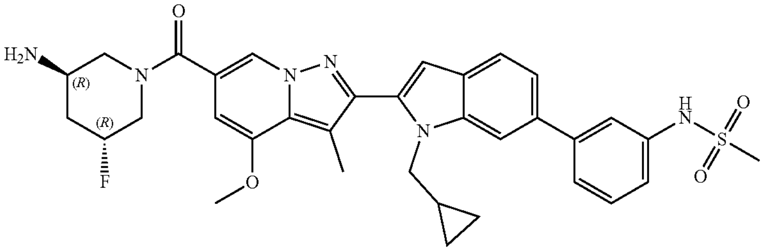<br>N-[3-(2-{6-[(3R,5R)-3-Amino-5-fluoropiperidine-1-carbonyl]-4-methoxy-3-methylpyrazolo[1,5-a]pyridin-2-yl}-1-(cyclopropylmethyl)-1H-indol-6-yl)phenyl]methanesulfonamide<br>Analytical Data: 645.3, 1.871 min (Method E) |
| 214 | 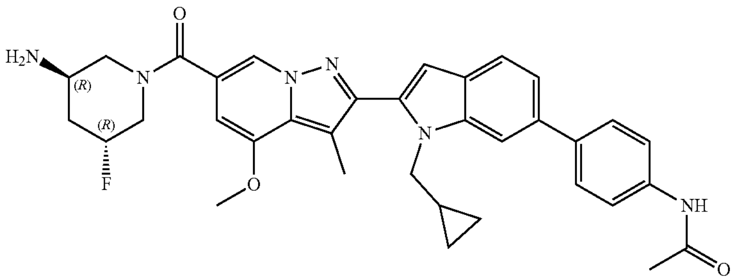<br>N-[4-(2-{6-[(3R,5R)-3-Amino-5-fluoropiperidine-1-carbonyl]-4-methoxy-3-methylpyrazolo[1,5-a]pyridin-2-yl}-1-(cyclopropylmethyl)-1H-indol-6-yl)phenyl]acetamide<br>Analytical Data: 609.3; 1.772 min (Method E) |

TABLE 26-continued

| Example | Structure<br>Name<br>Analytical Data: LC-MS m/z [M + H]$^+$; HPLC retention time (HPLC method 1) |
|---|---|
| 215 | 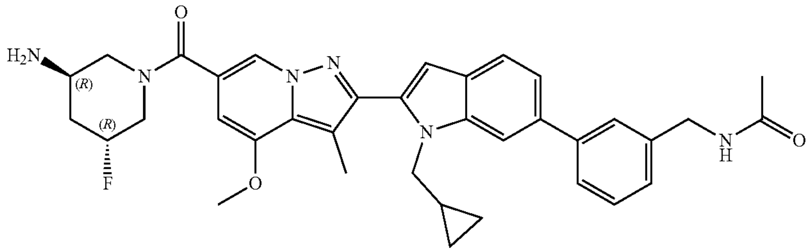<br>N-{[3-(2-{6-[(3R,5R)-3-Amino-5-fluoropiperidine-1-carbonyl]-4-methoxy-3-methylpyrazolo[1,5-a]pyridin-2-yl}-1-(cyclopropylmethyl)-1H-indol-6-yl)phenyl]methyl}acetamide<br>Analytical Data: 623.2.3; 1.782 min (Method E) |
| 216 | 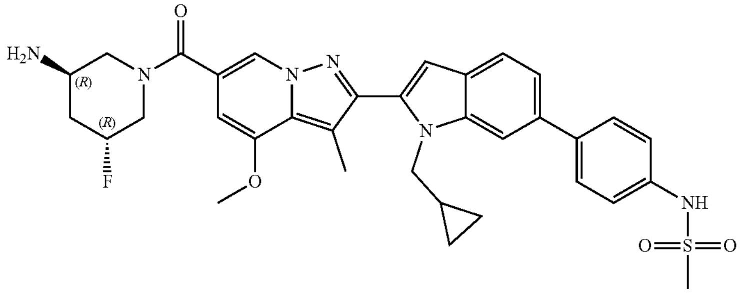<br>N-[4-(2-{6-[(3R,5R)-3-Amino-5-fluoropiperidine-1-carbonyl]-4-methoxy-3-methylpyrazolo[1,5-a]pyridin-2-yl}-1-(cyclopropylmethyl)-1H-indol-6-yl)phenyl]methanesulfonamide<br>Analytical Data: 645.2; 1.828 min (Method E) |
| 217 | 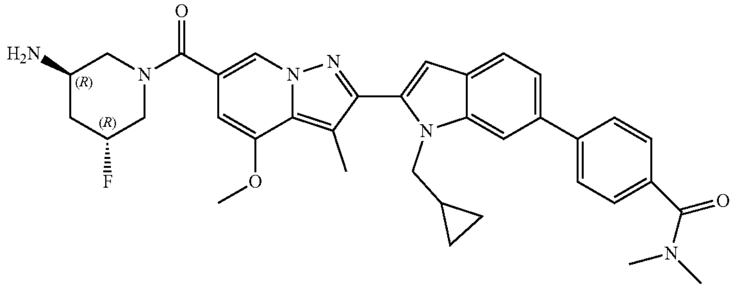<br>4-(2-{6-[(3R,5R)-3-Amino-5-fluoropiperidine-1-carbonyl]-4-methoxy-3-methylpyrazolo[1,5-a]pyridin-2-yl}-1-(cyclopropylmethyl)-1H-indol-6-yl)-N,N-dimethylbenzamide<br>Analytical Data: 623.3; 1.864 min (Method E) |
| 218 | 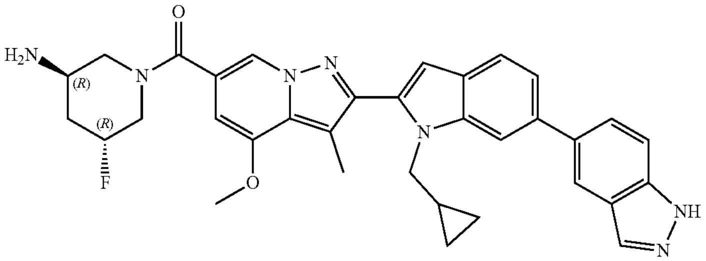<br>(3R,5R)-1-{2-[1-(Cyclopropylmethyl)-6-(1H-indazol-5-yl)-1H-indol-2-yl]-4-methoxy-3-methylpyrazolo[1,5-a]pyridine-6-carbonyl}-5-fluoropiperidin-3-amine<br>Analytical Data: 592.3; 1.819 min (Method E) |

TABLE 26-continued

| Example | Structure<br>Name<br>Analytical Data: LC-MS m/z [M + H]$^+$; HPLC retention time (HPLC method 1) |
|---|---|
| 219 | 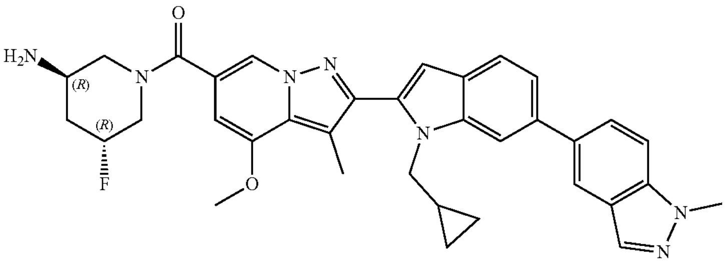<br>(3R,5R)-1-{2-[1-(Cyclopropylmethyl)-6-(1-methyl-1H-indazol-5-yl)-1H-indol-2-yl]-4-methoxy-3-methylpyrazolo[1,5-a]pyridine-6-carbonyl}-5-fluoropiperidin-3-amine<br>Analytical Data: 606.3; 2.054 min (Method E) |
| 220 | 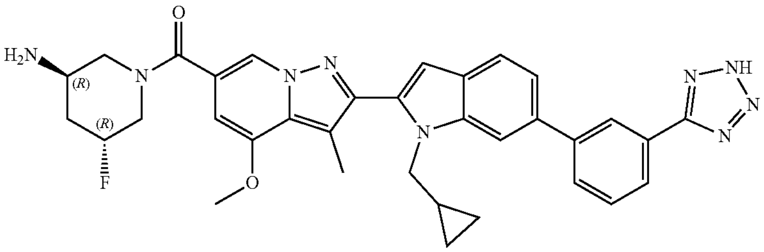<br>(3R,5R)-1-{2-[1-(Cyclopropylmethyl)-6-[3-(2H-1,2,3,4-tetrazol-5-yl)phenyl]-1H-indol-2-yl]-4-methoxy-3-methylpyrazolo[1,5-a]pyridine-6-carbonyl}-5-fluoropiperidin-3-amine<br>Analytical Data: 620.3; 1.455 min (Method E) |
| 221 | 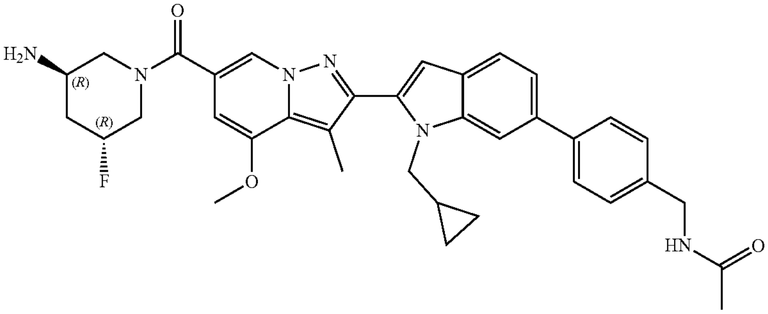<br>N-{[4-(2-{6-[(3R,5R)-3-Amino-5-fluoropiperidine-1-carbonyl]-4-methoxy-3-methylpyrazolo[1,5-a]pyridin-2-yl}-1-(cyclopropylmethyl)-1H-indol-6-yl)phenyl]methyl}acetamide<br>Analytical Data: 623.3; 1.742 min (Method E) |
| 222 | 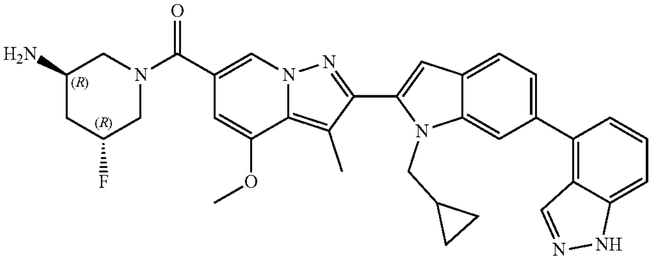<br>(3R,5R)-1-{2-[1-(Cyclopropylmethyl)-6-(1H-indazol-4-yl)-1H-indol-2-yl]-4-methoxy-3-methylpyrazolo[1,5-a]pyridine-6-carbonyl}-5-fluoropiperidin-3-amine<br>Analytical Data: 592.3; 1.876 min (Method E) |

TABLE 26-continued

| Example | Structure<br>Name<br>Analytical Data: LC-MS m/z $[M + H]^+$; HPLC retention time (HPLC method 1) |
|---|---|
| 223 | 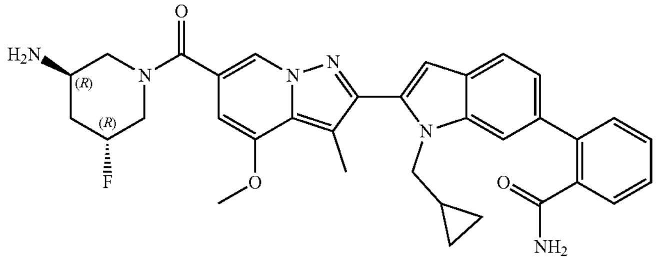<br>2-(2-{6-[(3R,5R)-3-Amino-5-fluoropiperidine-1-carbonyl]-4-methoxy-3-methylpyrazolo[1,5-a]pyridin-2-yl}-1-(cyclopropylmethyl)-1H-indol-6-yl)benzamide<br>Analytical Data: 595.3; 1.653 min (Method E) |
| 224 | 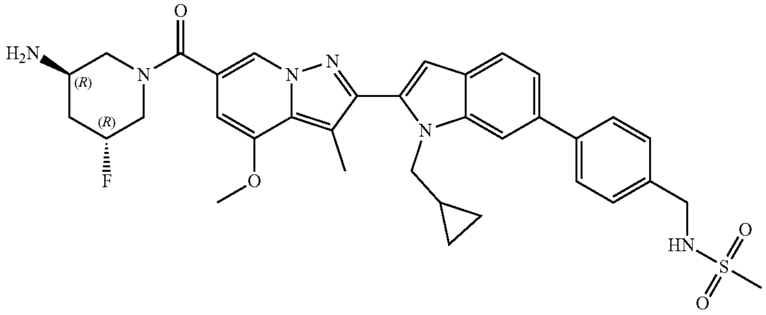<br>N-{[4-(2-{6-[(3R,5R)-3-Amino-5-fluoropiperidine-1-carbonyl]-4-methoxy-3-methylpyrazolo[1,5-a]pyridin-2-yl}-1-(cyclopropylmethyl)-1H-indol-6-yl)phenyl]methyl}methanesulfonamide<br>Analytical Data: 659.2; 1.865 min (Method E) |
| 225 | 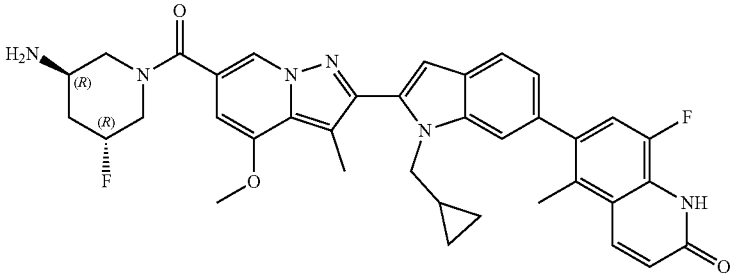<br>6-(2-{6-[(3R,5R)-3-Amino-5-fluoropiperidine-1-carbonyl]-4-methoxy-3-methylpyrazolo[1,5-a]pyridin-2-yl}-1-(cyclopropylmethyl)-1H-indol-6-yl)-8-fluoro-5-methyl-1,2-dihydroquinolin-2-one<br>Analytical Data: 651.3, 1.807 min (Method E) |
| 226 | 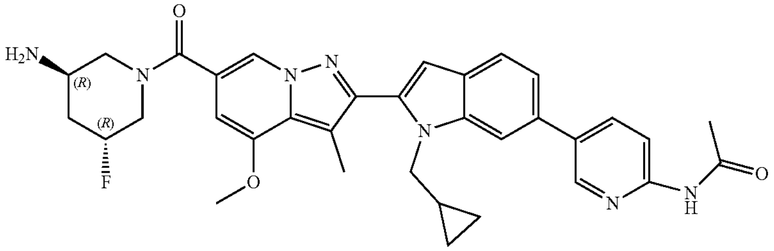<br>N-[5-(2-{6-[(3R,5R)-3-Amino-5-fluoropiperidine-1-carbonyl]-4-methoxy-3-methylpyrazolo[1,5-a]pyridin-2-yl}-1-(cyclopropylmethyl)-1H-indol-6-yl)pyridin-2-yl]acetamide<br>Analytical Data: 610.3; 1.721 min (Method E) |

Compounds of Examples 227 to 240 in Table 27 were prepared following a procedure similar to the preparation of a compound of Example 29, using the Intermediate 23D and tert-butyl (R)-piperidin-3-ylcarbamate in amide formation and the appropriate boronic acid/boronate ester in Suzuki coupling reaction.

TABLE 27

| Example | Structure<br>Name<br>Analytical Data: LC-MS m/z [M + H]$^+$; HPLC retention time (HPLC method 1) |
|---|---|
| 227 | 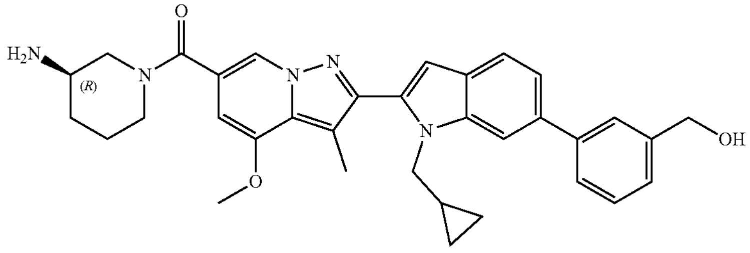<br>[3-(2-{6-[(3R)-3-Aminopiperidine-1-carbonyl]-4-methoxy-3-methylpyrazolo[1,5-a]pyridin-2-yl}-1-(cyclopropylmethyl)-1H-indol-6-yl)phenyl]methanol<br>Analytical Data: 564.3; 1.777 min (Method E) |
| 228 | 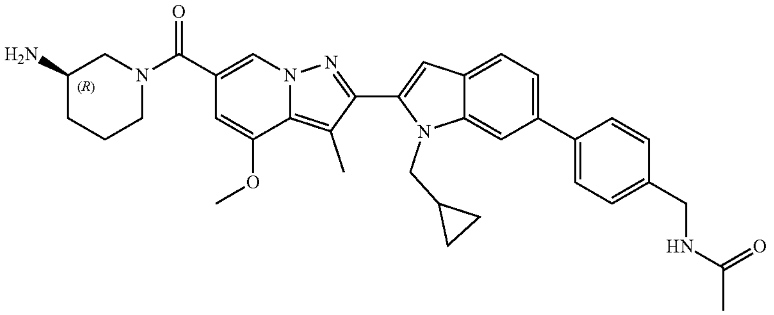<br>N-{[4-(2-{6-[(3R)-3-Aminopiperidine-1-carbonyl]-4-methoxy-3-methylpyrazolo[1,5-a]pyridin-2-yl}-1-(cyclopropylmethyl)-1H-indol-6-yl)phenyl]methyl}acetamide<br>Analytical Data: 605.3; 1.602 min (Method E) |
| 229 | 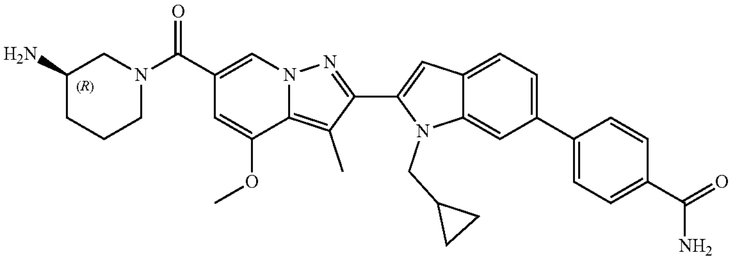<br>4-(2-{6-[(3R)-3-Aminopiperidine-1-carbonyl]-4-methoxy-3-methylpyrazolo[1,5-a]pyridin-2-yl}-1-(cyclopropylmethyl)-1H-indol-6-yl)benzamide<br>Analytical Data: 577.3; 1.557 min (Method E) |

TABLE 27-continued

| Example | Structure<br>Name<br>Analytical Data: LC-MS m/z $[M + H]^+$; HPLC retention time (HPLC method 1) |
|---|---|
| 230 | 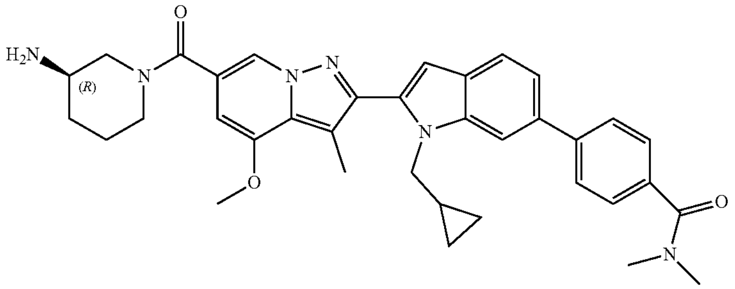<br>4-(2-{6-[(3R)-3-Aminopiperidine-1-carbonyl]-4-methoxy-3-methylpyrazolo[1,5-a]pyridin-2-yl}-1-(cyclopropylmethyl)-1H-indol-6-yl)-N,N-dimethylbenzamide<br>Analytical Data: 605.3; 1.771 min (Method E) |
| 231 | 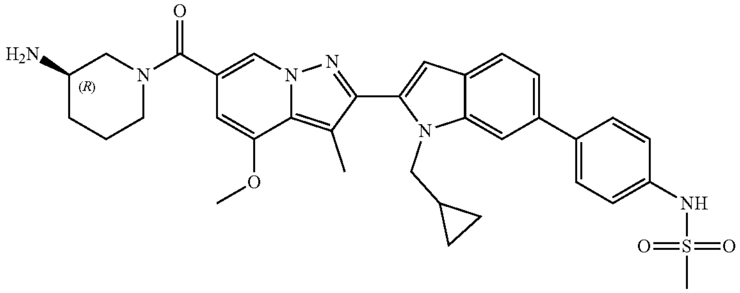<br>N-[4-(2-{6-[(3R)-3-Aminopiperidine-1-carbonyl]-4-methoxy-3-methylpyrazolo[1,5-a]pyridin-2-yl}-1-(cyclopropylmethyl)-1H-indol-6-yl)phenyl]methanesulfonamide<br>Analytical Data: 625.3; 1.743 min (Method E) |
| 232 | 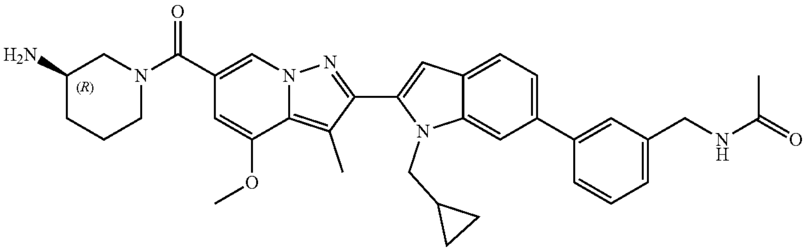<br>N-{[3-(2-{6-[(3R)-3-Aminopiperidine-1-carbonyl]-4-methoxy-3-methylpyrazolo[1,5-a]pyridin-2-yl}-1-(cyclopropylmethyl)-1H-indol-6-yl)phenyl]methyl}acetamide<br>Analytical Data: 605.3, 1.699 min (Method E) |
| 233 | 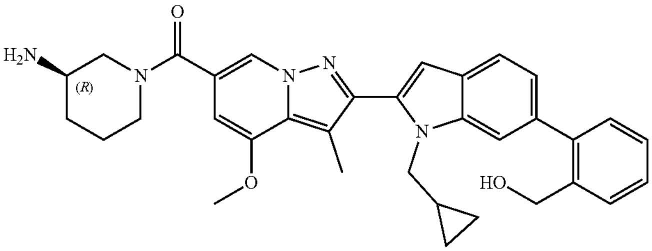<br>[2-(2-{6-[(3R)-3-Aminopiperidine-1-carbonyl]-4-methoxy-3-methylpyrazolo[1,5-a]pyridin-2-yl}-1-(cyclopropylmethyl)-1H-indol-6-yl)phenyl]methanol<br>Analytical Data: 564.3; 1.831 min (Method E) |

TABLE 27-continued

| Example | Structure<br>Name<br>Analytical Data: LC-MS m/z [M + H]+; HPLC retention time (HPLC method 1) |
|---|---|
| 234 | 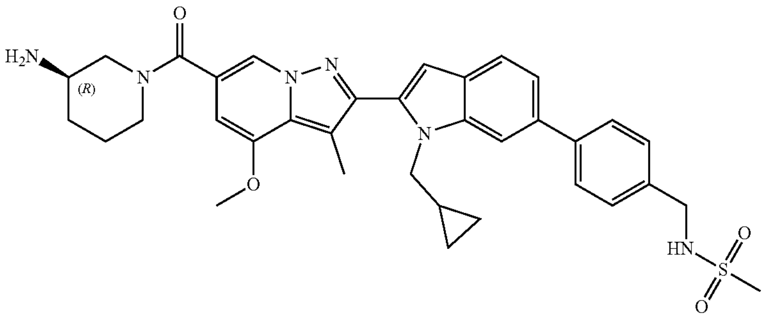<br>N-{[4-(2-{6-[(3R)-3-Aminopiperidine-1-carbonyl]-4-methoxy-3-methylpyrazolo[1,5-a]pyridin-2-yl}-1-(cyclopropylmethyl)-1H-indol-6-yl)phenyl]methyl}methanesulfonamide<br>Analytical Data: 641.2; 1.763 min (Method E) |
| 235 | 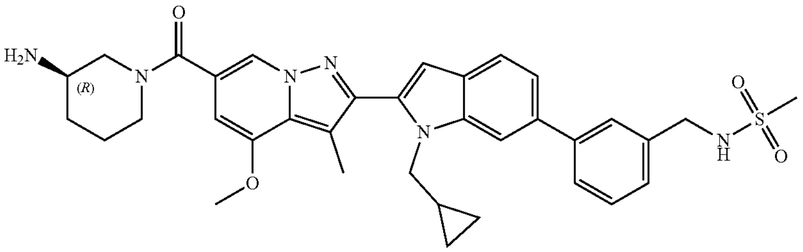<br>N-{[3-(2-{6-[(3R)-3-Aminopiperidine-1-carbonyl]-4-methoxy-3-methylpyrazolo[1,5-a]pyridin-2-yl}-1-(cyclopropylmethyl)-1H-indol-6-yl)phenyl]methyl}methanesulfonamide<br>Analytical Data: 641.3; 1.802 min (Method E) |
| 236 | 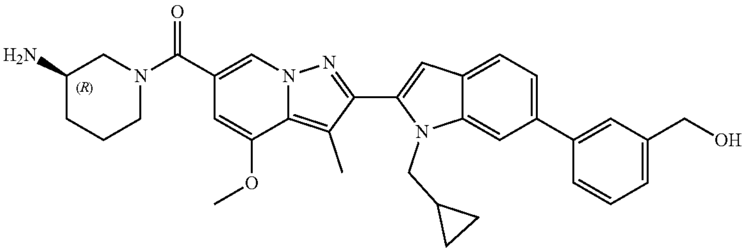<br>[3-(2-{6-[(3R)-3-Aminopiperidine-1-carbonyl]-4-methoxy-3-methylpyrazolo[1,5-a]pyridin-2-yl}-1-(cyclopropylmethyl)-1H-indol-6-yl)phenyl]methanol<br>Analytical Data: 564.2; 1.738 min (Method E) |
| 237 | 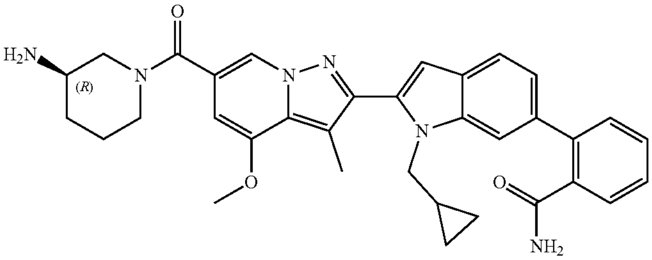<br>2-(2-{6-[(3R)-3-Aminopiperidine-1-carbonyl]-4-methoxy-3-methylpyrazolo[1,5-a]pyridin-2-yl}-1-(cyclopropylmethyl)-1H-indol-6-yl)benzamide<br>Analytical Data: 577.3; 1.573 min (Method E) |

TABLE 27-continued

| Example | Structure<br>Name<br>Analytical Data: LC-MS m/z [M + H]$^+$; HPLC retention time (HPLC method 1) |
|---|---|
| 238 | 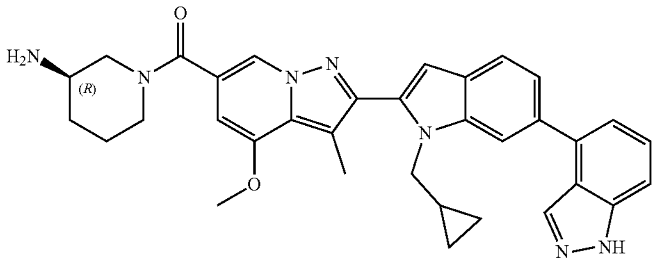<br>(3R)-1-{2-[1-(Cyclopropylmethyl)-6-(1H-indazol-4-yl)-1H-indol-2-yl]-4-methoxy-3-methylpyrazolo[1,5-a]pyridine-6-carbonyl}piperidin-3-amine<br>Analytical Data: 574.3; 1.703 min (Method E) |
| 239 | 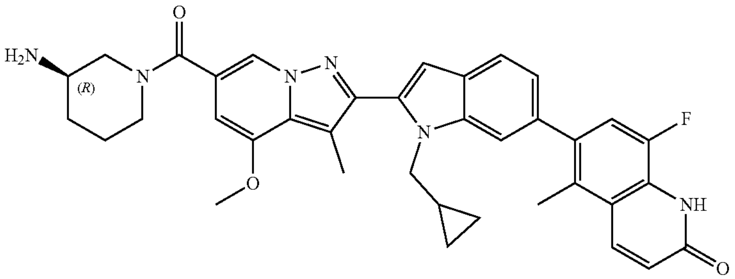<br>6-(2-{6-[(3R)-3-Aminopiperidine-1-carbonyl]-4-methoxy-3-methylpyrazolo[1,5-a]pyridin-2-yl}-1-(cyclopropylmethyl)-1H-indol-6-yl)-8-fluoro-5-methyl-1,2-dihydroquinolin-2-one<br>Analytical Data: 633.3; 1.753 min (Method E) |
| 240 | 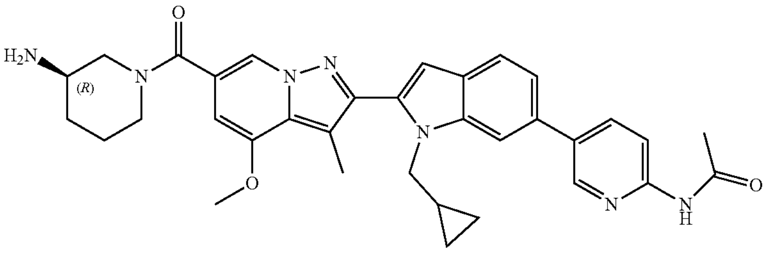<br>N-[5-(2-{6-[(3R)-3-Aminopiperidine-1-carbonyl]-4-methoxy-3-methylpyrazolo[1,5-a]pyridin-2-yl}-1-(cyclopropylmethyl)-1H-indol-6-yl)pyridin-2-yl]acetamide<br>Analytical Data: 592.3; 1.640 min (Method E) |

Compounds of Examples 241 to 247 in Table 28 were prepared following a procedure similar to the preparation of a compound of Example 33, by Buchwald coupling of Intermediate 29A with appropriate amine.

TABLE 28

| Example | Structure<br>Name<br>Analytical Data: LC-MS m/z [M + H]+; HPLC retention time (HPLC method) |
|---|---|
| 241 | 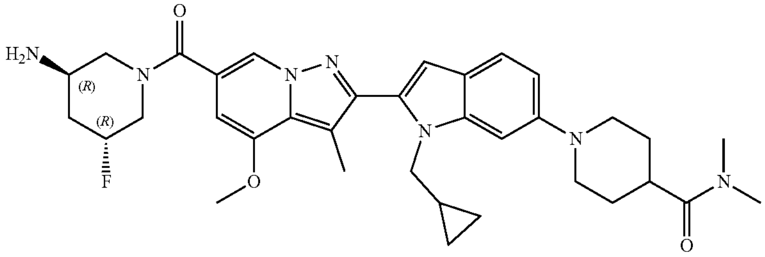<br>(3R,5R)-1-{2-[1-(Cyclopropylmethyl)-6-(4-methanesulfonylpiperidin-1-yl)-1H-indol-2-yl]-4-methoxy-3-methylpyrazolo[1,5-a]pyridine-6-carbonyl}-5-fluoropiperidin-3-amine<br>Analytical Data: 637.2; 1.588 min (Method E) |
| 242 | 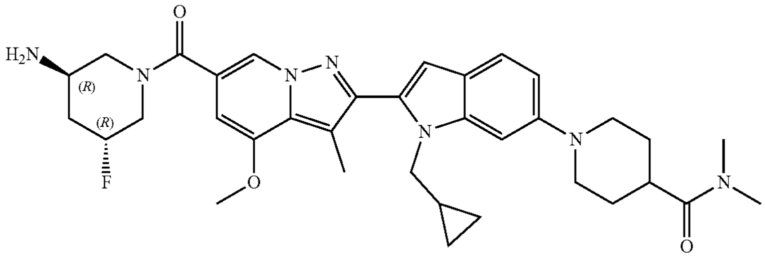<br>1-(2-{6-[(3R,5R)-3-Amino-5-fluoropiperidine-1-carbonyl]-4-methoxy-3-methylpyrazolo[1,5-a]pyridin-2-yl}-1-(cyclopropylmethyl)-1H-indol-6-yl)-N,N-dimethylpiperidine-4-carboxamide<br>Analytical Data: 630.4; 1.634 min (Method E) |
| 243 | 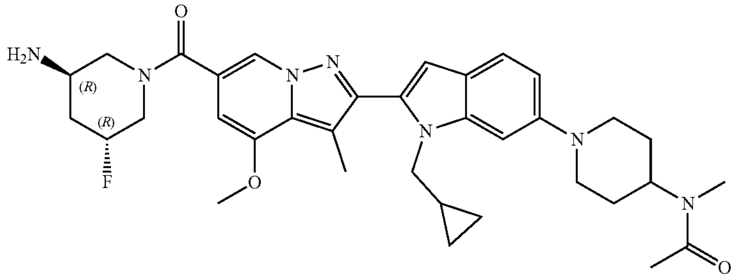<br>N-[1-(2-{6-[(3R,5R)-3-Amino-5-fluoropiperidine-1-carbonyl]-4-methoxy-3-methylpyrazolo[1,5-a]pyridin-2-yl}-1-(cyclopropylmethyl)-1H-indol-6-yl)piperidin-4-yl]-N-methylacetamide<br>Analytical Data: 630.4; 1.423 min (Method E) |
| 244 | 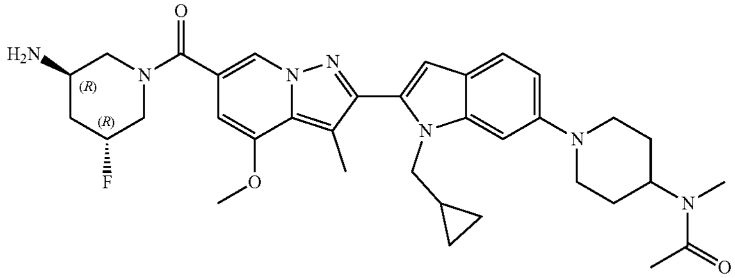<br>N-[1-(2-{6-[(3R,5R)-3-Amino-5-fluoropiperidine-1-carbonyl]-4-methoxy-3-methylpyrazolo[1,5-a]pyridin-2-yl}-1-(cyclopropylmethyl)-1H-indol-6-yl)piperidin-4-yl]-N-methylacetamide<br>Analytical Data: 630.4; 1.617 min (Method E) |

TABLE 28-continued

| Example | Structure<br>Name<br>Analytical Data: LC-MS m/z [M + H]$^+$; HPLC retention time (HPLC method) |
|---|---|
| 245 | 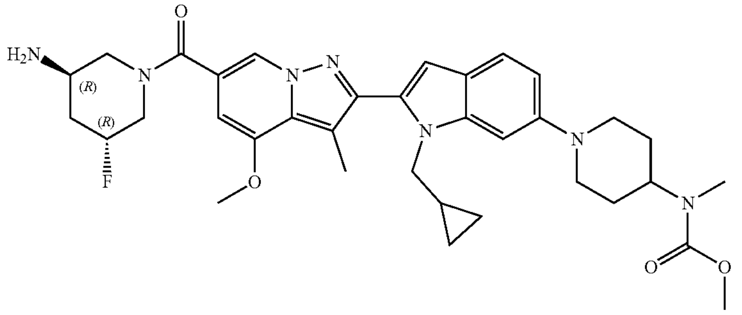<br>Methyl N-[1-(2-{6-[(3R,5R)-3-amino-5-fluoropiperidine-1-carbonyl]-4-methoxy-3-methylpyrazolo[1,5-a]pyridin-2-yl}-1-(cyclopropylmethyl)-1H-indol-6-yl)piperidin-4-yl]-N-methylcarbamate<br>Analytical Data: 646.3; 1.895 min (Method E) |
| 246 | 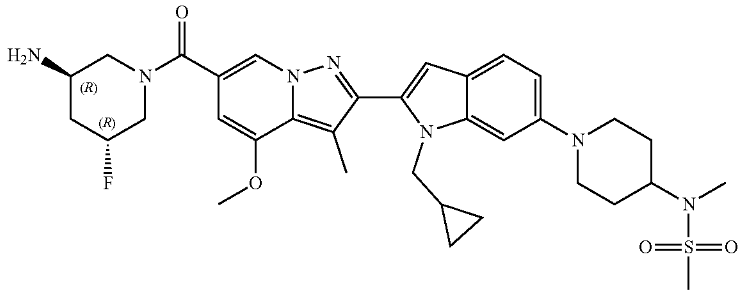<br>N-[1-(2-{6-[(3R,5R)-3-Amino-5-fluoropiperidine-1-carbonyl]-4-methoxy-3-methylpyrazolo[1,5-a]pyridin-2-yl}-1-(cyclopropylmethyl)-1H-indol-6-yl)piperidin-4-yl]-N-methylmethanesulfonamide<br>Analytical Data: 666.3; 1.733 min (Method E) |
| 247 | 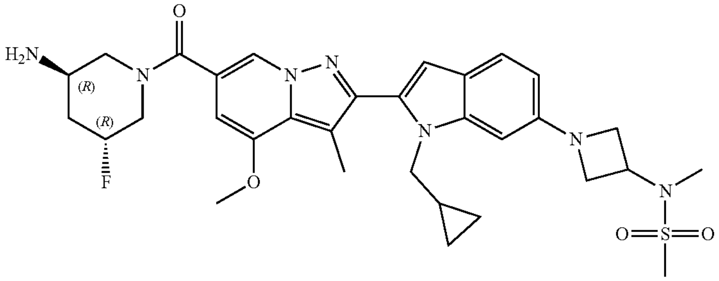<br>N-[1-(2-{6-[(3R,5R)-3-Amino-5-fluoropiperidine-1-carbonyl]-4-methoxy-3-methylpyrazolo[1,5-a]pyridin-2-yl}-1-(cyclopropylmethyl)-1H-indol-6-yl)azetidin-3-yl]-N-methylmethanesulfonamide<br>Analytical Data: 638.3; 1.670 min (Method E) |

Compounds of Examples 248 to 256 in Table 29 were prepared following a procedure similar to the preparation of a compound of Example 33, by using Intermediate 23D and tert-butyl (R)-piperidin-3-ylcarbamate for amide formation and appropriate secondary amine in the Buchwald coupling reaction.

TABLE 29

| Example | Structure<br>Name<br>Analytical Data: LC-MS m/z [M + H]$^+$; HPLC retention time (HPLC method) |
|---|---|
| 248 | 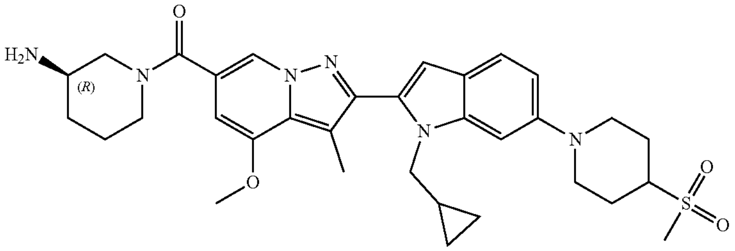<br>(3R)-1-{2-[1-(Cyclopropylmethyl)-6-(4-methanesulfonylpiperidin-1-yl)-1H-indol-2-yl]-4-methoxy-3-methylpyrazolo[1,5-a]pyridine-6-carbonyl}piperidin-3-amine<br>Analytical Data: 619.3; 1.530 min (Method E) |
| 249 | 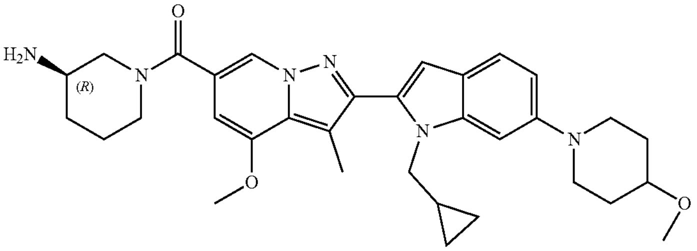<br>(3R)-1-{2-[1-(Cyclopropylmethyl)-6-(4-methoxypiperidin-1-yl)-1H-indol-2-yl]-4-methoxy-3-methylpyrazolo[1,5-a]pyridine-6-carbonyl}piperidin-3-amine<br>Analytical Data: 571.3, 1.837 min (Method E) |
| 250 | 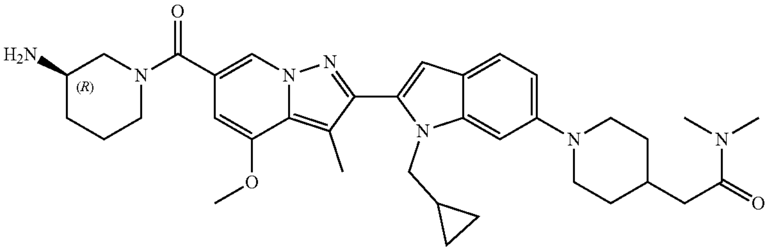<br>2-[1-(2-{6-[(3R)-3-Aminopiperidine-1-carbonyl]-4-methoxy-3-methylpyrazolo[1,5-a]pyridin-2-yl}-1-(cyclopropylmethyl)-1H-indol-6-yl)piperidin-4-yl]-N,N-dimethylacetamide<br>Analytical Data: 626.3; 1.647 min (Method E) |
| 251 | 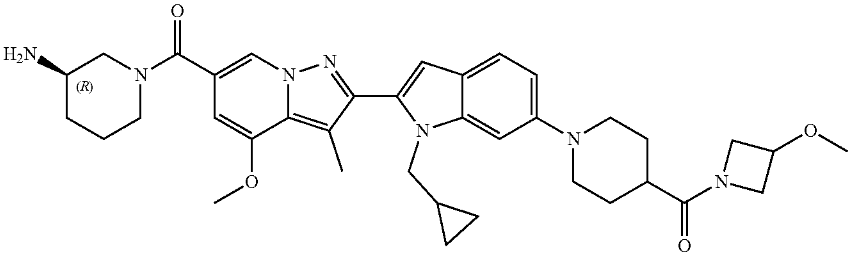<br>(3R)-1-{2-[1-(Cyclopropylmethyl)-6-[4-(3-methoxyazetidine-1-carbonyl)piperidin-1-yl]-1H-indol-2-yl]-4-methoxy-3-methylpyrazolo[1,5-a]pyridine-6-carbonyl}piperidin-3-amine<br>Analytical Data: 654.4; 1.565 min (Method E) |

TABLE 29-continued

| Example | Structure<br>Name<br>Analytical Data: LC-MS m/z [M + H]$^+$; HPLC retention time (HPLC method) |
|---|---|
| 252 | 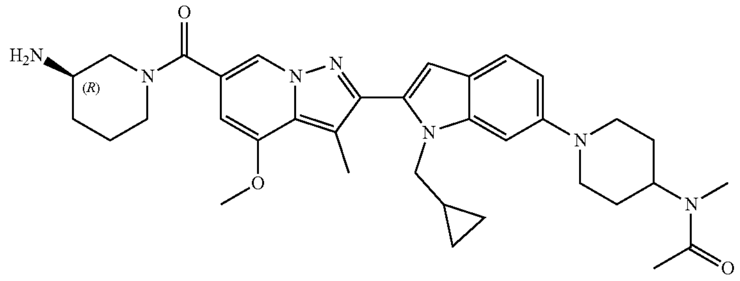<br>N-[1-(2-{6-[(3R)-3-Aminopiperidine-1-carbonyl]-4-methoxy-3-methylpyrazolo[1,5-a]pyridin-2-yl}-1-(cyclopropylmethyl)-1H-indol-6-yl)piperidin-4-yl]-N-methylacetamide<br>Analytical Data: 612.4; 1.571 min (Method E) |
| 253 | 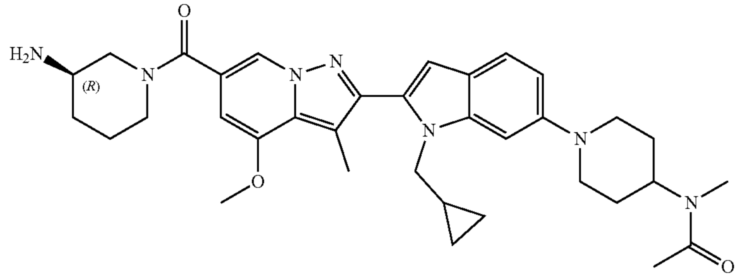<br>N-[1-(2-{6-[(3R)-3-Aminopiperidine-1-carbonyl]-4-methoxy-3-methylpyrazolo[1,5-a]pyridin-2-yl}-1-(cyclopropylmethyl)-1H-indol-6-yl)piperidin-4-yl]-N-methylacetamide<br>Analytical Data: 612.4; 1.566 min (Method E) |
| 254 | 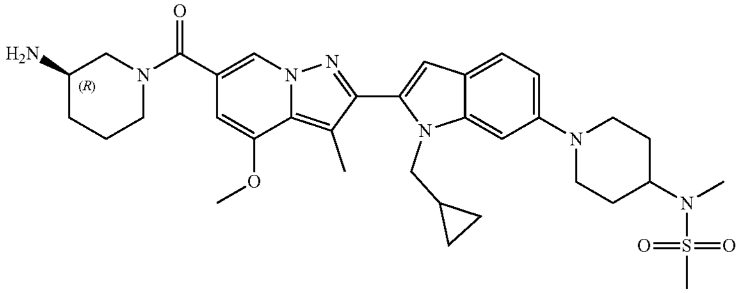<br>N-[1-(2-{6-[(3R)-3-Aminopiperidine-1-carbonyl]-4-methoxy-3-methylpyrazolo[1,5-a]pyridin-2-yl}-1-(cyclopropylmethyl)-1H-indol-6-yl)piperidin-4-yl]-N-methylmethanesulfonamide<br>Analytical Data: 648.3; 1.677 min (Method E) |

TABLE 29-continued

| Example | Structure<br>Name<br>Analytical Data: LC-MS m/z [M + H]+; HPLC retention time (HPLC method) |
|---|---|
| 255 | 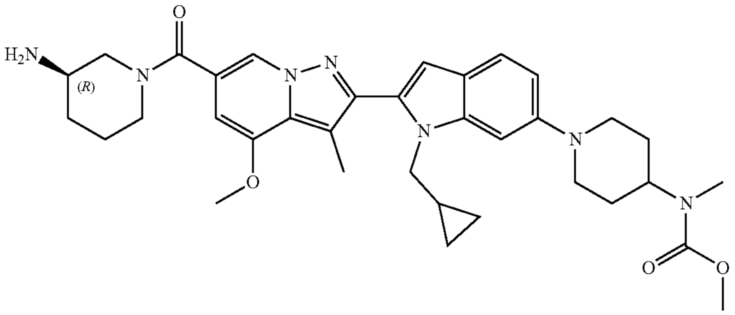<br>Methyl N-[1-(2-{6-[(3R)-3-aminopiperidine-1-carbonyl]-4-methoxy-3-methylpyrazolo[1,5-a]pyridin-2-yl}-1-(cyclopropylmethyl)-1H-indol-6-yl)piperidin-4-yl]-N-methylcarbamate<br>Analytical Data: 628.4; 1.840 min (Method E) |
| 256 | 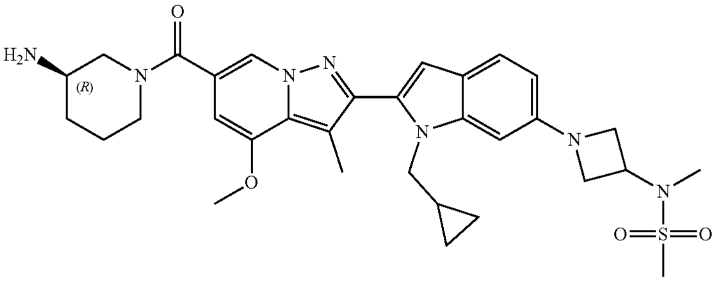<br>N-[1-(2-{6-[(3R)-3-Aminopiperidine-1-carbonyl]-4-methoxy-3-methylpyrazolo[1,5-a]pyridin-2-yl}-1-(cyclopropylmethyl)-1H-indol-6-yl)azetidin-3-yl]-N-methylmethanesulfonamide<br>Analytical Data: 620.3; 1.631 min (Method E) |

Compounds of Examples 257 to 264 in Table 30 were prepared following a procedure similar to the preparation of a compound of Example 40, using Suzuki coupling of Intermediate 39E with appropriate boronic acid or boronate ester.

TABLE 30

| Example | Structure<br>Name<br>Analytical Data: LC-MS m/z [M + H]+; HPLC retention time (HPLC method) |
|---|---|
| 257 | 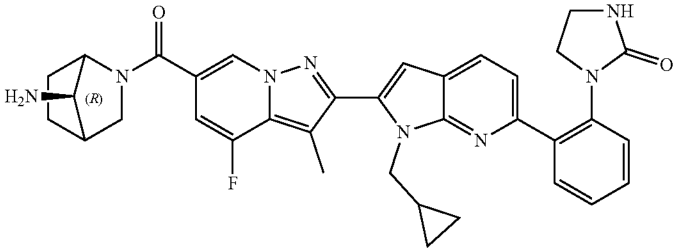<br>1-[2-(2-{6-[(7R)-7-Amino-2-azabicyclo[2.2.1]heptane-2-carbonyl]-4-fluoro-3-methylpyrazolo[1,5-a]pyridin-2-yl}-1-(cyclopropylmethyl)-1H-pyrrolo[2,3-b]pyridin-6-yl)phenyl]imidazolidin-2-one<br>Analytical Data: 619.2; 1.678 min (Method E) |

TABLE 30-continued

| Example | Structure<br>Name<br>Analytical Data: LC-MS m/z $[M + H]^+$; HPLC retention time (HPLC method) |
|---|---|
| 258 | 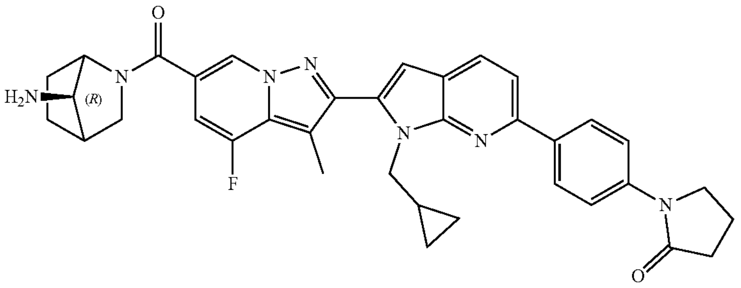<br>1-[4-(2-{6-[(7R)-7-Amino-2-azabicyclo[2.2.1]heptane-2-carbonyl]-4-fluoro-3-methylpyrazolo[1,5-a]pyridin-2-yl}-1-(cyclopropylmethyl)-1H-pyrrolo[2,3-b]pyridin-6-yl)phenyl]pyrrolidin-2-one<br>Analytical Data: 618.3; 1.984 min (Method E) |
| 259 | 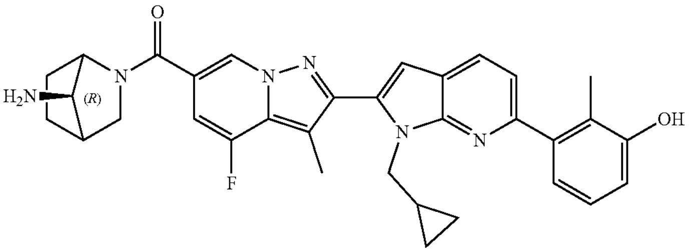<br>3-(2-{6-[(7R)-7-Amino-2-azabicyclo[2.2.1]heptane-2-carbonyl]-4-fluoro-3-methylpyrazolo[1,5-a]pyridin-2-yl}-1-(cyclopropylmethyl)-1H-pyrrolo[2,3-b]pyridin-6-yl)-2-methylphenol<br>Analytical Data: 565.3; 1.900 min (Method E) |
| 260 | 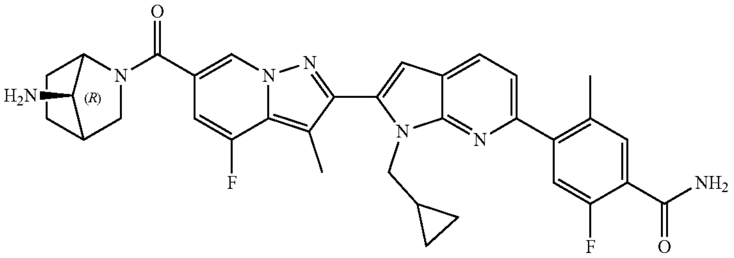<br>4-(2-{6-[(7R)-7-Amino-2-azabicyclo[2.2.1]heptane-2-carbonyl]-4-fluoro-3-methylpyrazolo[1,5-a]pyridin-2-yl}-1-(cyclopropylmethyl)-1H-pyrrolo[2,3-b]pyridin-6-yl)-2-fluoro-5-methylbenzamide<br>Analytical Data: 610.3; 1.760 min (Method E) |
| 261 | 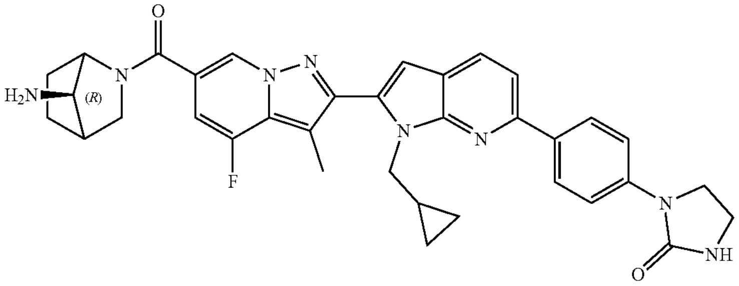<br>1-[4-(2-{6-[(7R)-7-Amino-2-azabicyclo[2.2.1]heptane-2-carbonyl]-4-fluoro-3-methylpyrazolo[1,5-a]pyridin-2-yl}-1-(cyclopropylmethyl)-1H-pyrrolo[2,3-b]pyridin-6-yl)phenyl]imidazolidin-2-one<br>Analytical Data: 619.4; 1.844 min (Method E) |

TABLE 30-continued

| Example | Structure<br>Name<br>Analytical Data: LC-MS m/z $[M + H]^+$; HPLC retention time (HPLC method) |
|---|---|
| 262 | 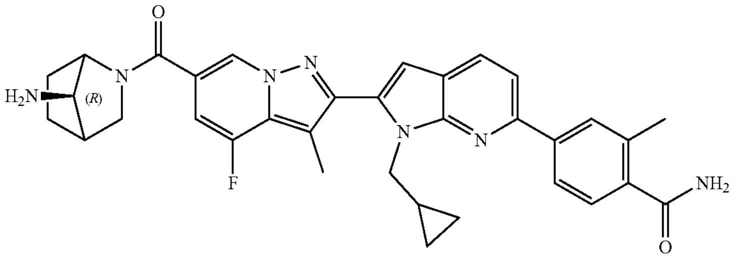<br>4-(2-{6-[(7R)-7-Amino-2-azabicyclo[2.2.1]heptane-2-carbonyl]-4-fluoro-3-methylpyrazolo[1,5-a]pyridin-2-yl}-1-(cyclopropylmethyl)-1H-pyrrolo[2,3-b]pyridin-6-yl)-2-methylbenzamide<br>Analytical Data: 592.4; 1.734 min (Method E) |
| 263 | 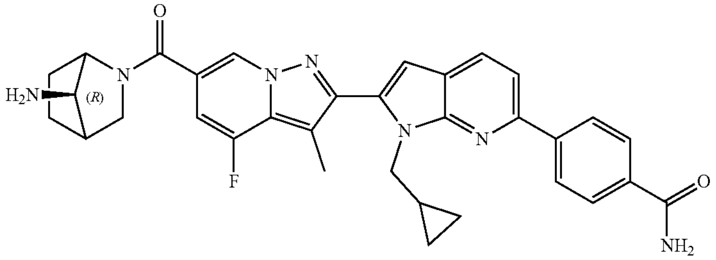<br>4-(2-{6-[(7R)-7-Amino-2-azabicyclo[2.2.1]heptane-2-carbonyl]-4-fluoro-3-methylpyrazolo[1,5-a]pyridin-2-yl}-1-(cyclopropylmethyl)-1H-pyrrolo[2,3-b]pyridin-6-yl)benzamide<br>Analytical Data: 578.3; 1.682 min (Method E) |
| 264 | 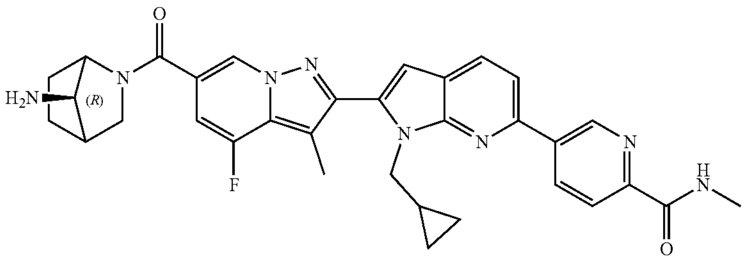<br>5-(2-{6-[(7R)-7-Amino-2-azabicyclo[2.2.1]heptane-2-carbonyl]-4-fluoro-3-methylpyrazolo[1,5-a]pyridin-2-yl}-1-(cyclopropylmethyl)-1H-pyrrolo[2,3-b]pyridin-6-yl)-N-methylpyridine-2-carboxamide<br>Analytical Data: 593.3; 1.783 min (Method E) |

Compounds of Examples 265 to 268 in Table 31 were prepared following a procedure similar to the preparation of a compound of Example 50, using Intermediate 39E and appropriate secondary amine in Buchwald coupling reaction.

TABLE 31

| Example | Structure<br>Name<br>Analytical Data: LC-MS m/z [M + H]+; HPLC retention time (HPLC method) |
|---|---|
| 265 | 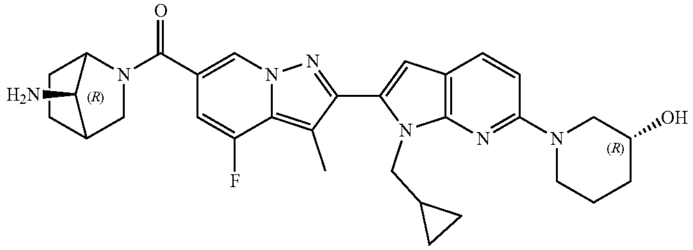<br>((7R)-7-Amino-2-azabicyclo[2.2.1]heptan-2-yl)(2-(1-(cyclopropylmethyl)-6-((R)-3-hydroxypiperidin-1-yl)-1H-pyrrolo[2,3-b]pyridin-2-yl)-4-fluoro-3-methylpyrazolo[1,5-a]pyridin-6-yl)methanone<br>Analytical Data: 558.4; 5.795 min (Method C) |
| 266 | 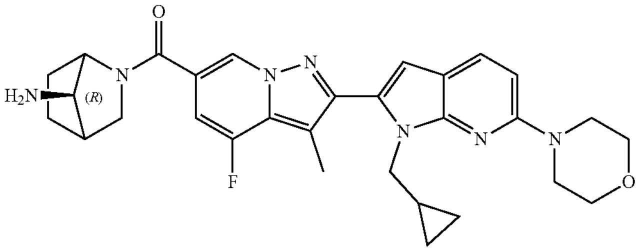<br>(7R)-2-{2-[1-(Cyclopropylmethyl)-6-(morpholin-4-yl)-1H-pyrrolo[2,3-b]pyridin-2-yl]-4-fluoro-3-methylpyrazolo[1,5-a]pyridine-6-carbonyl}-2-azabicyclo[2.2.1]heptan-7-amine<br>Analytical Data: 544.3; 1.668 min (Method E) |
| 267 | 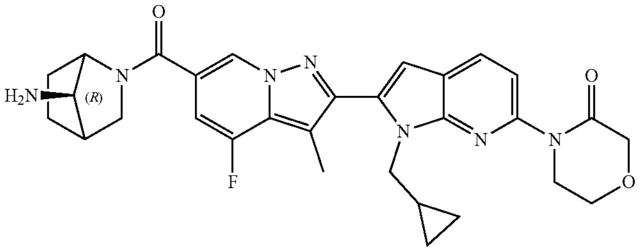<br>4-(2-{6-[(7R)-7-Amino-2-azabicyclo[2.2.1]heptane-2-carbonyl]-4-fluoro-3-methylpyrazolo[1,5-a]pyridin-2-yl}-1-(cyclopropylmethyl)-1H-pyrrolo[2,3-b]pyridin-6-yl)morpholin-3-one<br>Analytical Data: 558.3; 1.595 min (Method E) |
| 268 | 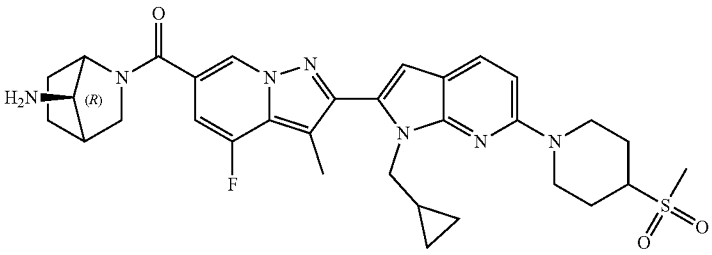<br>(7R)-2-{2-[1-(Cyclopropylmethyl)-6-(4-methanesulfonylpiperidin-1-yl)-1H-pyrrolo[2,3-b]pyridin-2-yl]-4-fluoro-3-methylpyrazolo[1,5-a]pyridine-6-carbonyl}-2-azabicyclo[2.2.1]heptan-7-amine<br>Analytical Data: 620.2; 1.713 min (Method E) |

Compounds of Examples 269 to 273 in Table 32 were prepared following a procedure similar to the preparation of a compound of Example 50, using Intermediate 39D and tert-butyl (R)-piperidin-3-ylcarbamate in amide formation and with appropriate secondary amine in Buchwald coupling reaction.

TABLE 32

| Example | Structure<br>Name<br>Analytical Data: LC-MS m/z [M + H]+; HPLC retention time (HPLC method) |
|---|---|
| 269 | 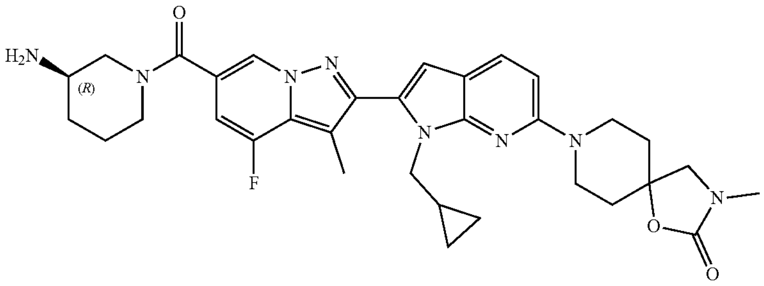<br>8-(2-{6-[(3R)-3-Aminopiperidine-1-carbonyl]-4-fluoro-3-methylpyrazolo[1,5-a]pyridin-2-yl}-1-(cyclopropylmethyl)-1H-pyrrolo[2,3-b]pyridin-6-yl)-3-methyl-1-oxa-3,8-diazaspiro[4.5]decan-2-one<br>Analytical Data: 615.3; 1.703 min (Method E) |
| 270 | 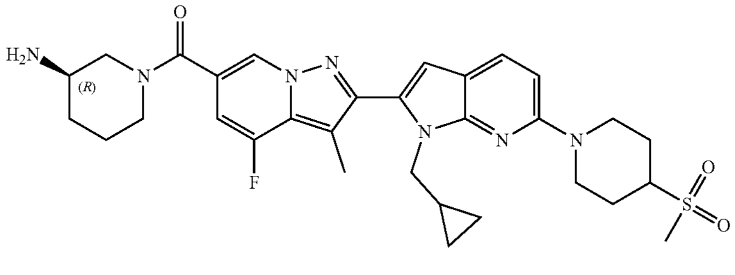<br>(3R)-1-{2-[1-(Cyclopropylmethyl)-6-(4-methanesulfonylpiperidin-1-yl)-1H-pyrrolo[2,3-b]pyridin-2-yl]-4-fluoro-3-methylpyrazolo[1,5-a]pyridine-6-carbonyl}piperidin-3-amine<br>Analytical Data: 608.3; 1.558 min (Method E) |
| 271 | 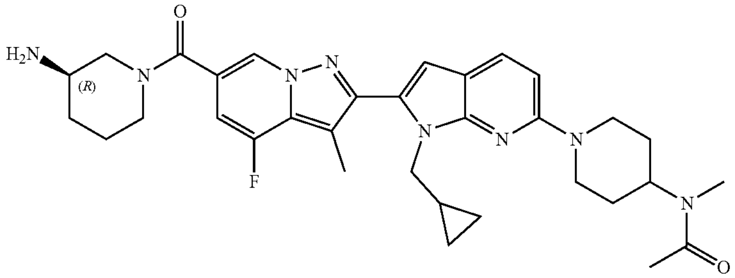<br>N-[1-(2-{6-[(3R)-3-Aminopiperidine-1-carbonyl]-4-fluoro-3-methylpyrazolo[1,5-a]pyridin-2-yl}-1-(cyclopropylmethyl)-1H-pyrrolo[2,3-b]pyridin-6-yl)piperidin-4-yl]-N-methylacetamide<br>Analytical Data: 601.3; 1.618 min (Method E) |
| 272 | 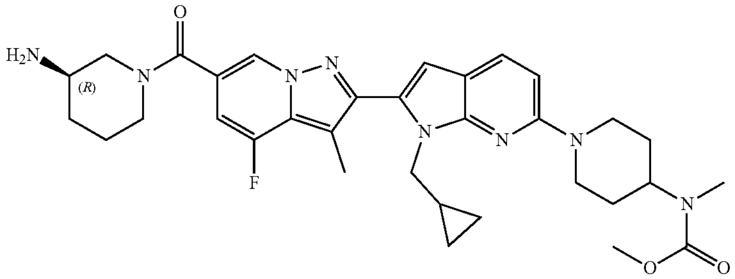<br>Methyl N-[1-(2-{6-[(3R)-3-aminopiperidine-1-carbonyl]-4-fluoro-3-methylpyrazolo[1,5-a]pyridin-2-yl}-1-(cyclopropylmethyl)-1H-pyrrolo[2,3-b]pyridin-6-yl)piperidin-4-yl]-N-methylcarbamate<br>Analytical Data: 617.3; 1.905min (Method E) |

TABLE 32-continued

| Example | Structure<br>Name<br>Analytical Data: LC-MS m/z $[M + H]^+$; HPLC retention time (HPLC method) |
|---|---|
| 273 | 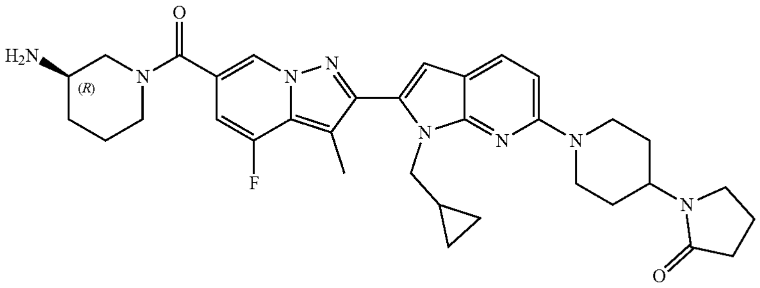<br>1-[1-(2-{6-[(3R)-3-Aminopiperidine-1-carbonyl]-4-fluoro-3-methylpyrazolo[1,5-a]pyridin-2-yl}-1-(cyclopropylmethyl)-1H-pyrrolo[2,3-b]pyridin-6-yl)piperidin-4-yl]pyrrolidin-2-one<br>Analytical Data: 613.3; 1.640 min (Method E) |

Compounds of Examples 274 and 275 in Table 33 were prepared following a procedure similar to the preparation of a compound of Example 50, using Intermediate 39E with appropriate primary alcohol in Buchwald coupling reaction.

TABLE 33

| Example | Structure<br>Name<br>Analytical Data: LC-MS m/z $[M + H]^+$; HPLC retention time (HPLC method) |
|---|---|
| 274 | 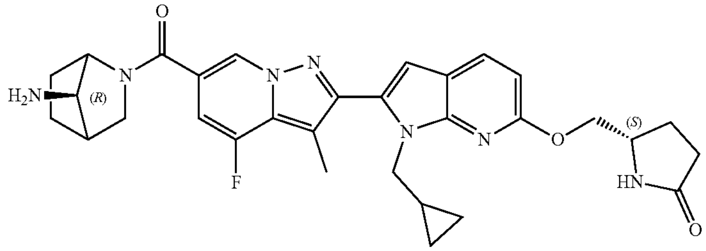<br>(5S)-5-{[(2-{6-[(7R)-7-Amino-2-azabicyclo[2.2.1]heptane-2-carbonyl]-4-fluoro-3-methylpyrazolo[1,5-a]pyridin-2-yl}-1-(cyclopropylmethyl)-1H-pyrrolo[2,3-b]pyridin-6-yl)oxy]methyl}pyrrolidin-2-one<br>Analytical Data: 572.2; 1.453 min (Method E) |
| 275 | 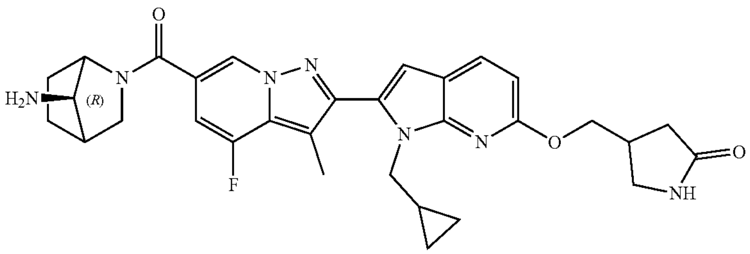<br>4-{[(2-{6-[(7R)-7-Amino-2-azabicyclo[2.2.1]heptane-2-carbonyl]-4-fluoro-3-methylpyrazolo[1,5-a]pyridin-2-yl}-1-(cyclopropylmethyl)-1H-pyrrolo[2,3-b]pyridin-6-yl)oxy]methyl}pyrrolidin-2-one (mixture of diastereomers)<br>Analytical Data: 572.4; 1.519 min (Method E) |

Example 276

(3R)-1-{4-Chloro-2-[1-(cyclopropylmethyl)-6-(4-methoxypiperidin-1-yl)-1H-pyrrolo[2,3-b]pyridin-2-yl]-3-methylpyrazolo[1,5-a]pyridine-6-carbonyl}piperidin-3-amine

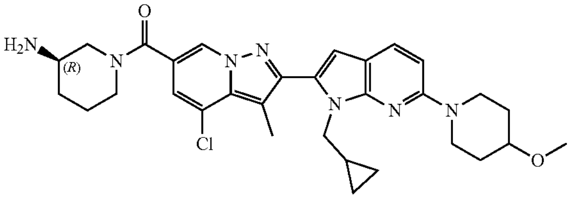

Compound of Example 276 was prepared following a procedure similar to the preparation of a compound of Example 50, using Intermediate 24 to carboxylic acid and tert-butyl (R)-piperidin-3-ylcarbamate in amide formation and with appropriate secondary amine in Buchwald coupling reaction. LC-MS m/z: 576.3 $[M+H]^+$; HPLC retention time: 1.649 min (method F)

Compounds of Examples 277 to 288 in Table 34 were prepared following a procedure similar to the preparation of a compound of Example 54, by using Intermediate 39D and tert-butyl (R)-piperidin-3-ylcarbamate in amide formation and appropriate boronic acid or boronate ester in Suzuki coupling reaction.

TABLE 34

| Example | Structure<br>Name<br>Analytical Data: LC-MS m/z $[M + H]^+$; HPLC retention time (HPLC method) |
|---|---|
| 277 | 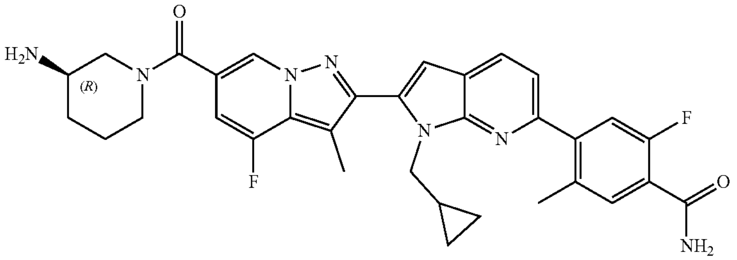<br>4-(2-{6-[(3R)-3-Aminopiperidine-1-carbonyl]-4-fluoro-3-methylpyrazolo[1,5-a]pyridin-2-yl}-1-(cyclopropylmethyl)-1H-pyrrolo[2,3-b]pyridin-6-yl)-2-fluoro-5-methylbenzamide<br>Analytical Data: 598.3; 1.689 min (Method E) |
| 278 | 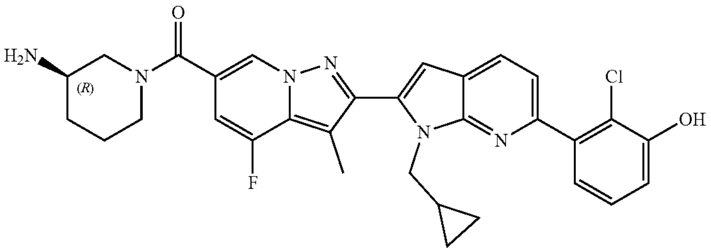<br>3-(2-{6-[(3R)-3-Aminopiperidine-1-carbonyl]-4-fluoro-3-methylpyrazolo[1,5-a]pyridin-2-yl}-1-(cyclopropylmethyl)-1H-pyrrolo[2,3-b]pyridin-6-yl)-2-chlorophenol<br>Analytical Data: 573.2; 1.777 min (Method E) |
| 279 | 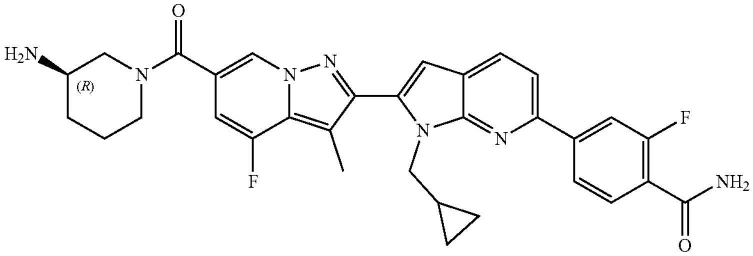<br>4-(2-{6-[(3R)-3-Aminopiperidine-1-carbonyl]-4-fluoro-3-methylpyrazolo[1,5-a]pyridin-2-yl}-1-(cyclopropylmethyl)-1H-pyrrolo[2,3-b]pyridin-6-yl)-2-fluorobenzamide<br>Analytical Data: 584.3; 1.603 min (Method E) |

TABLE 34-continued

| Example | Structure<br>Name<br>Analytical Data: LC-MS m/z [M + H]$^+$; HPLC retention time (HPLC method) |
|---|---|
| 280 | 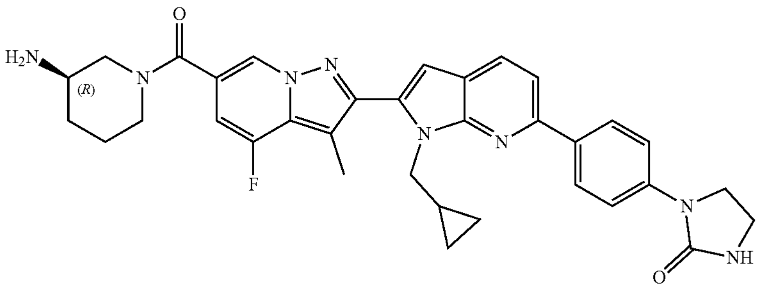<br>1-[4-(2-{6-[(3R)-3-Aminopiperidine-1-carbonyl]-4-fluoro-3-methylpyrazolo[1,5-a]pyridin-2-yl}-1-(cyclopropylmethyl)-1H-pyrrolo[2,3-b]pyridin-6-yl)phenyl]imidazolidin-2-one<br>Analytical Data: 607.3; 1.710 min (Method E) |
| 281 | 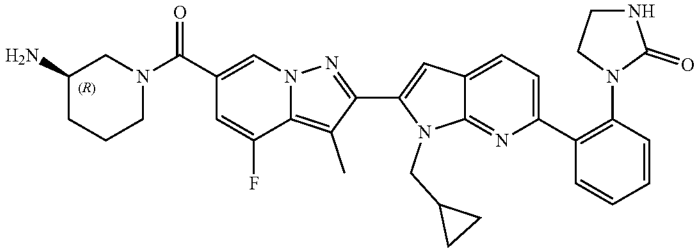<br>1-[2-(2-{6-[(3R)-3-Aminopiperidine-1-carbonyl]-4-fluoro-3-methylpyrazolo[1,5-a]pyridin-2-yl}-1-(cyclopropylmethyl)-1H-pyrrolo[2,3-b]pyridin-6-yl)phenyl]imidazolidin-2-one<br>Analytical Data: 607.3; 1.554 min (Method E) |
| 282 | 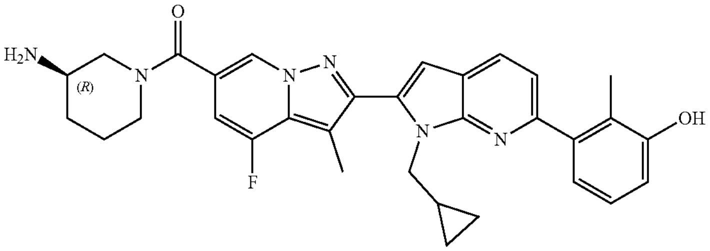<br>3-(2-{6-[(3R)-3-Aminopiperidine-1-carbonyl]-4-fluoro-3-methylpyrazolo[1,5-a]pyridin-2-yl}-1-(cyclopropylmethyl)-1H-pyrrolo[2,3-b]pyridin-6-yl)-2-methylphenol<br>Analytical Data: 555.3; 1.782 min (Method E) |
| 283 | 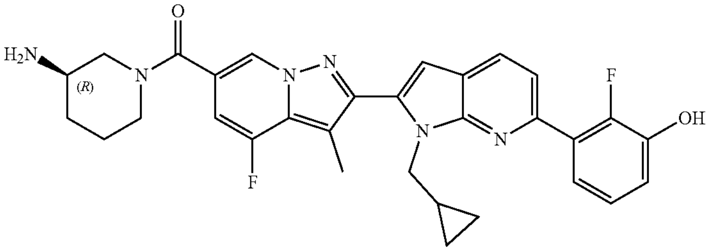<br>3-(2-{6-[(3R)-3-Aminopiperidine-1-carbonyl]-4-fluoro-3-methylpyrazolo[1,5-a]pyridin-2-yl}-1-(cyclopropylmethyl)-1H-pyrrolo[2,3-b]pyridin-6-yl)-2-fluorophenol<br>Analytical Data: 557.3; 1.735 min (Method E) |

TABLE 34-continued

| Example | Structure<br>Name<br>Analytical Data: LC-MS m/z [M + H]$^+$; HPLC retention time (HPLC method) |
|---|---|
| 284 | 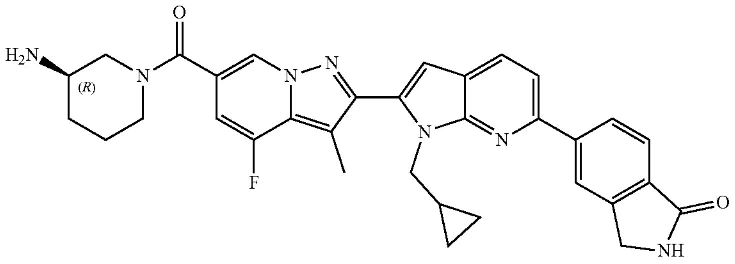<br>5-(2-{6-[(3R)-3-Aminopiperidine-1-carbonyl]-4-fluoro-3-methylpyrazolo[1,5-a]pyridin-2-yl}-1-(cyclopropylmethyl)-1H-pyrrolo[2,3-b]pyridin-6-yl)-2,3-dihydro-1H-isoindol-1-one<br>Analytical Data: 578.3; 1.533 min (Method E) |
| 285 | 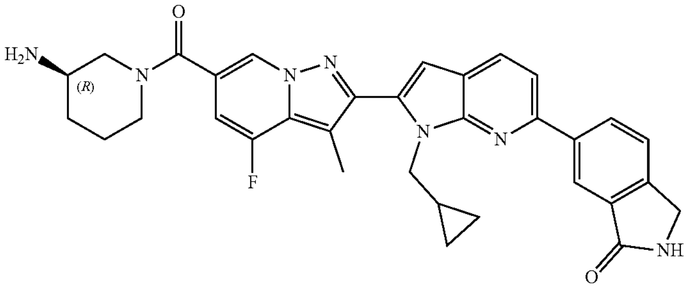<br>6-(2-{6-[(3R)-3-Aminopiperidine-1-carbonyl]-4-fluoro-3-methylpyrazolo[1,5-a]pyridin-2-yl}-1-(cyclopropylmethyl)-1H-pyrrolo[2,3-b]pyridin-6-yl)-2,3-dihydro-1H-isoindol-1-one<br>Analytical Data: 578.3, 1.625 min (Method E) |
| 286 | 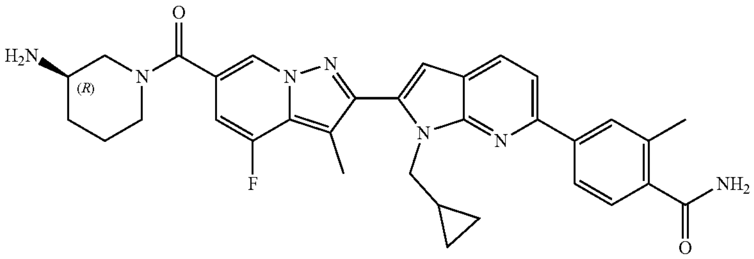<br>4-(2-{6-[(3R)-3-Aminopiperidine-1-carbonyl]-4-fluoro-3-methylpyrazolo[1,5-a]pyridin-2-yl}-1-(cyclopropylmethyl)-1H-pyrrolo[2,3-b]pyridin-6-yl)-2-methylbenzamide<br>Analytical Data: 580.3; 1.618 min (Method E) |
| 287 | 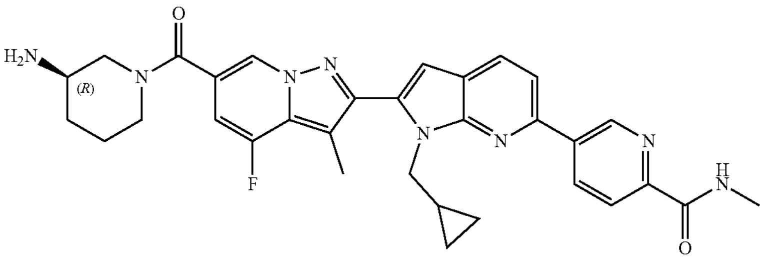<br>5-(2-{6-[(3R)-3-Aminopiperidine-1-carbonyl]-4-fluoro-3-methylpyrazolo[1,5-a]pyridin-2-yl}-1-(cyclopropylmethyl)-1H-pyrrolo[2,3-b]pyridin-6-yl)-N-methylpyridine-2-carboxamide<br>Analytical Data: 581.2; 1.693 min (Method E) |

TABLE 34-continued

| Example | Structure<br>Name<br>Analytical Data: LC-MS m/z [M + H]$^+$; HPLC retention time (HPLC method) |
|---|---|
| 288 | 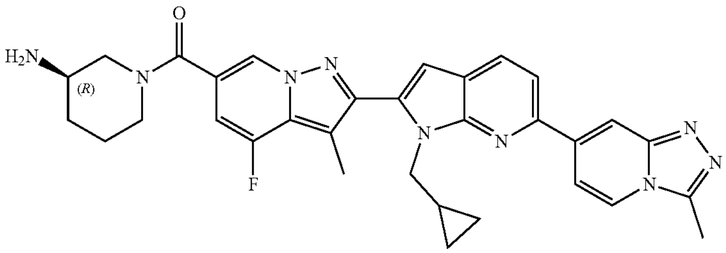<br>(3R)-1-{2-[1-(Cyclopropylmethyl)-6-{3-methyl-[1,2,4]triazolo[4,3-a]pyridin-7-yl}-1H-pyrrolo[2,3-b]pyridin-2-yl]-4-fluoro-3-methylpyrazolo[1,5-a]pyridine-6-carbonyl}piperidin-3-amine<br>Analytical Data: 578.3; 1.441 min (Method E) |

Example 289

(3R,5R)-1-{4-Chloro-2-[6-chloro-1-(cyclopropylmethyl)-1H-pyrrolo[2,3-b]pyridin-2-yl]-3-methylpyrazolo[1,5-a]pyridine-6-carbonyl}-5-fluoropiperidin-3-amine

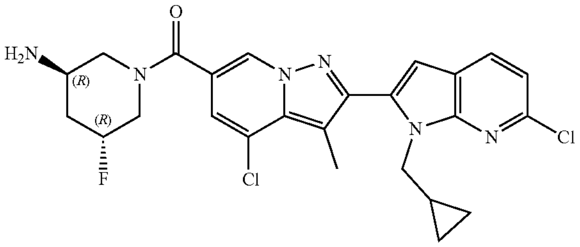

Compound of Example 289 was prepared following a procedure similar to the preparation of a compound of Example 53 by using Intermediate 24 to carboxylic acid and tert-butyl ((3R,5R)-5-fluoropiperidin-3-yl)carbamate in amide formation. LC-MS m/z: 515.1 [M+H]$^+$; HPLC retention time: 2.048 min (Method E).

Example 290

(3R,5R)-1-{4-Chloro-2-[1-(cyclopropylmethyl)-6-(1H-indazol-5-yl)-1H-pyrrolo[2,3-b]pyridin-2-yl]-3-methylpyrazolo[1,5-a]pyridine-6-carbonyl}-5-fluoropiperidin-3-amine

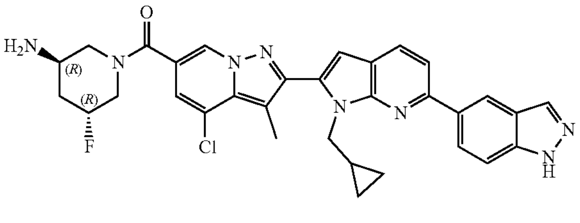

Compound of Example 290 was prepared following a procedure similar to the preparation of a compound of Example 54 by using Intermediate 24 to carboxylic acid and tert-butyl ((3R,5R)-5-fluoropiperidin-3-yl)carbamate in amide formation and appropriate boronic acid or boronate ester in Suzuki coupling reaction. LC-MS m/z: 597.2 [M+H]$^+$; HPLC retention time: 1.878 min (Method E).

Example 291

(3R)-1-{4-Chloro-2-[6-chloro-1-(cyclopropylmethyl)-1H-pyrrolo[2,3-b]pyridin-2-yl]-3-methylpyrazolo[1,5-a]pyridine-6-carbonyl}piperidin-3-amine

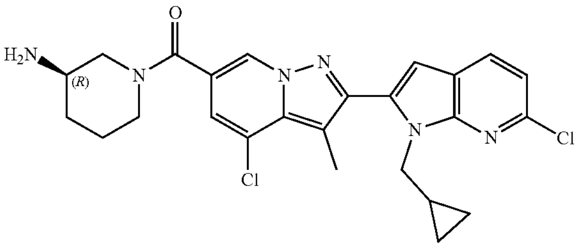

Compound of Example 291 was prepared following a procedure similar to the preparation of a compound of Example 53, by using Intermediate 24 to carboxylic acid and tert-butyl (R)-piperidin-3-ylcarbamate in amide formation. LC-MS m/z: 497.1 [M+H]$^+$; HPLC retention time: 1.992 min (Method E).

Example 292

(3R)-1-{4-chloro-2-[1-(Cyclopropylmethyl)-6-(1H-indazol-5-yl)-1H-pyrrolo[2,3-b]pyridin-2-yl]-3-methylpyrazolo[1,5-a]pyridine-6-carbonyl}piperidin-3-amine

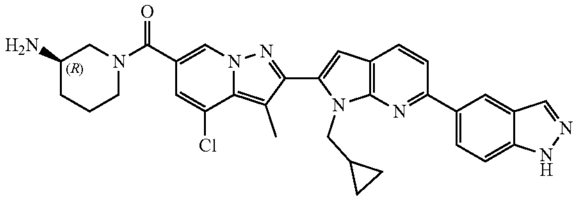

Compound of Example 292 was prepared following a procedure similar to the preparation of a compound of Example 54 by using Intermediate 24 to carboxylic acid and tert-butyl (R)-piperidin-3-ylcarbamate in amide formation and appropriate boronic acid or boronate ester in Suzuki coupling reaction. LC-MS m/z: 579.2 $[M+H]^+$; HPLC retention time: 1.787 min (Method E)

Compounds of Examples 293 to 295 in Table 35 were prepared following a procedure similar to the preparation of a compound of Example 58, by Suzuki coupling of Intermediate 58E with appropriate boronic acid.

TABLE 35

| Example | Structure<br>Name<br>Analytical Data: LC-MS m/z $[M + H]^+$; HPLC retention time (HPLC method) |
|---|---|
| 293 | 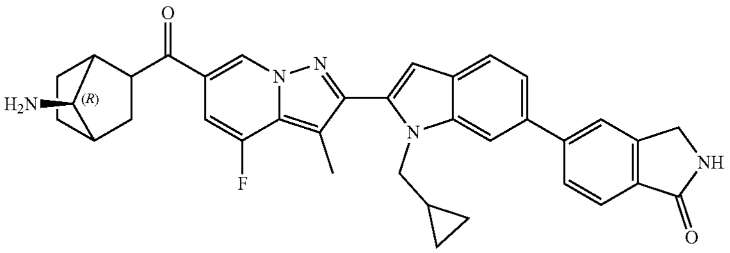<br>5-(2-{6-[(7R)-7-Amino-2-azabicyclo[2.2.1]heptane-2-carbonyl]-4-fluoro-3-methylpyrazolo[1,5-a]pyridin-2-yl}-1-(cyclopropylmethyl)-1H-indol-6-yl)-2,3-dihydro-1H-isoindol-1-one<br>Analytical Data: 589.3; 1.808 min (Method E) |
| 294 | 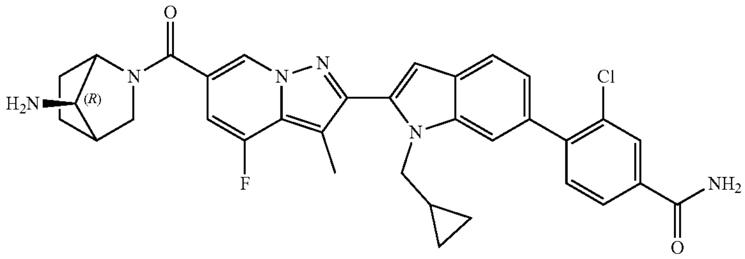<br>4-(2-{6-[(7R)-7-Amino-2-azabicyclo[2.2.1]heptane-2-carbonyl]-4-fluoro-3-methylpyrazolo[1,5-a]pyridin-2-yl}-1-(cyclopropylmethyl)-1H-indol-6-yl)-3-chlorobenzamide<br>Analytical Data: 611.3; 1.880 min (Method E) |
| 295 | 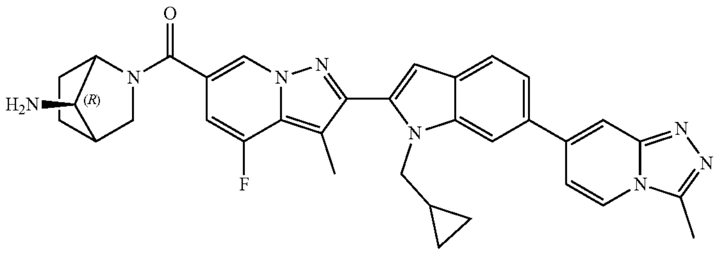<br>(7R)-2-{2-[1-(Cyclopropylmethyl)-6-{3-methyl-[1,2,4]triazolo[4,3-a]pyridin-7-yl}-1H-indol-2-yl]-4-fluoro-3-methylpyrazolo[1,5-a]pyridine-6-carbonyl}-2-azabicyclo[2.2.1]heptan-7-amine<br>Analytical Data: 589.4; 1.784 min (Method D) |

Example 296

(7R)-2-{2-[1-(Cyclopropylmethyl)-6-(3-methoxyazetidin-1-yl)-1H-indol-2-yl]-4-fluoro-3-methylpyrazolo[1,5-a]pyridine-6-carbonyl}-2-azabicyclo[2.2.1]heptan-7-amine

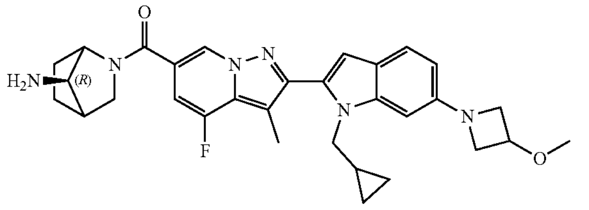

Compound of Example 296 was prepared following a procedure similar to the preparation of a compound of Example 50, by using Intermediate 58E and appropriate secondary amine in Buchwald coupling reaction. LC-MS m/z: 543.3 $[M+H]^+$; HPLC retention time: 2.028 min (Method E).

Compounds of Examples 297 to 308 in Table 36 were prepared following a procedure similar to the preparation of a compound of Example 64, by Suzuki coupling of Intermediate 64E with appropriate boronic acid.

TABLE 36

| Example | Structure<br>Name<br>Analytical Data: LC-MS m/z $[M + H]^+$; HPLC retention time (HPLC method) |
|---|---|
| 297 | 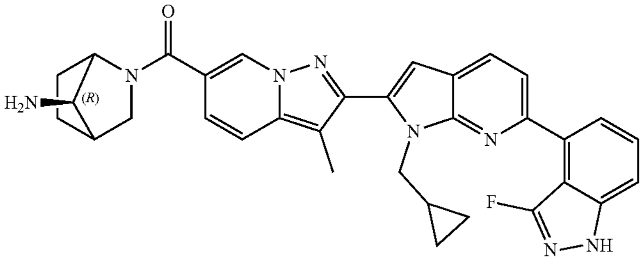<br>(7R)-2-{2-[1-(Cyclopropylmethyl)-6-(3-fluoro-1H-indazol-4-yl)-1H-pyrrolo[2,3-b]pyridin-2-yl]-3-methylpyrazolo[1,5-a]pyridine-6-carbonyl}-2-azabicyclo[2.2.1]heptan-7-amine<br>Analytical Data: 575.3; 1.56 min (Method E) |
| 298 | 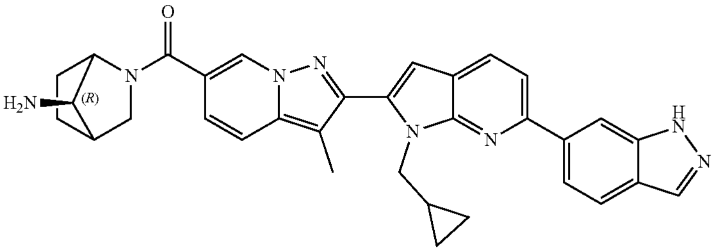<br>(7R)-2-{2-[1-(Cyclopropylmethyl)-6-(1H-indazol-6-yl)-1H-pyrrolo[2,3-b]pyridin-2-yl]-3-methylpyrazolo[1,5-a]pyridine-6-carbonyl}-2-azabicyclo[2.2.1]heptan-7-amine<br>Analytical Data: 557.2, 1.754 min (Method E) |
| 299 | 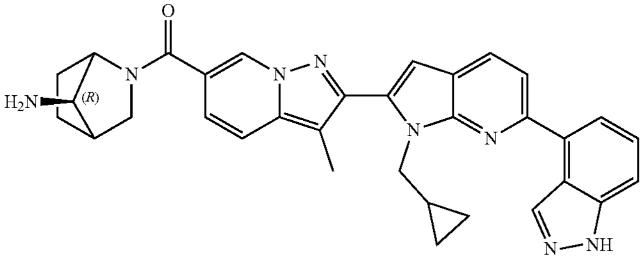<br>(7R)-2-{2-[1-(Cyclopropylmethyl)-6-(1H-indazol-4-yl)-1H-pyrrolo[2,3-b]pyridin-2-yl]-3-methylpyrazolo[1,5-a]pyridine-6-carbonyl}-2-azabicyclo[2.2.1]heptan-7-amine<br>Analytical Data: 557.2; 1.749 min (Method E) |

TABLE 36-continued

| Example | Structure<br>Name<br>Analytical Data: LC-MS m/z $[M + H]^+$; HPLC retention time (HPLC method) |
|---|---|
| 300 | 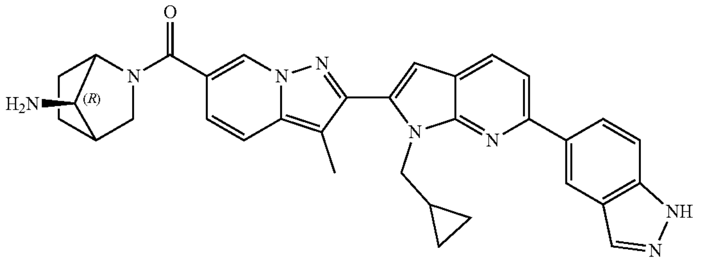<br>(7R)-2-{2-[1-(Cyclopropylmethyl)-6-(1H-indazol-5-yl)-1H-pyrrolo[2,3-b]pyridin-2-yl]-3-methylpyrazolo[1,5-a]pyridine-6-carbonyl}-2-azabicyclo[2.2.1]heptan-7-amine<br>Analytical Data: 557.2; 1.702 min (Method E) |
| 301 | 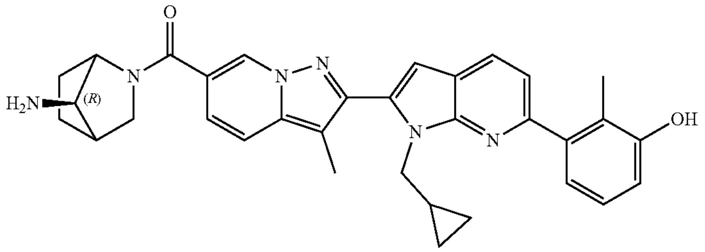<br>3-(2-{6-[(7R)-7-Amino-2-azabicyclo[2.2.1]heptane-2-carbonyl]-3-methylpyrazolo[1,5-a]pyridin-2-yl}-1-(cyclopropylmethyl)-1H-pyrrolo[2,3-b]pyridin-6-yl)-2-methylphenol<br>Analytical Data: 547.3; 1.491 min (Method E) |
| 302 | 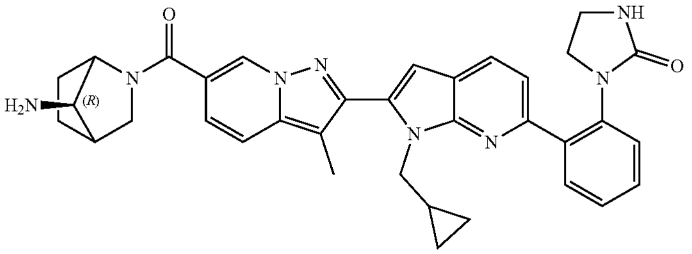<br>1-[2-(2-{6-[(7R)-7-Amino-2-azabicyclo[2.2.1]heptane-2-carbonyl]-3-methylpyrazolo[1,5-a]pyridin-2-yl}-1-(cyclopropylmethyl)-1H-pyrrolo[2,3-b]pyridin-6-yl)phenyl]imidazolidin-2-one<br>Analytical Data: 601.3; 1.395 min (Method E) |
| 303 | 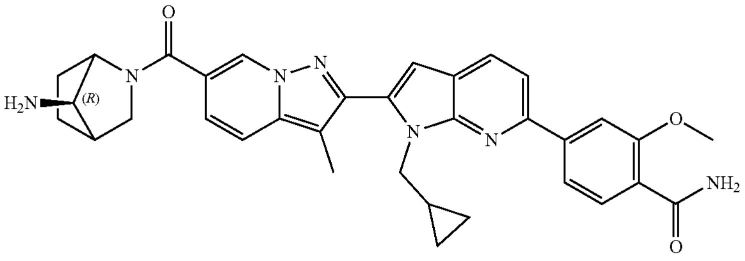<br>4-(2-{6-[(7R)-7-Amino-2-azabicyclo[2.2.1]heptane-2-carbonyl]-3-methylpyrazolo[1,5-a]pyridin-2-yl}-1-(cyclopropylmethyl)-1H-pyrrolo[2,3-b]pyridin-6-yl)-2-methoxybenzamide<br>Analytical Data: 590.3; 1.752 min (Method E) |

TABLE 36-continued

| Example | Structure<br>Name<br>Analytical Data: LC-MS m/z [M + H]+; HPLC retention time (HPLC method) |
|---|---|
| 304 | 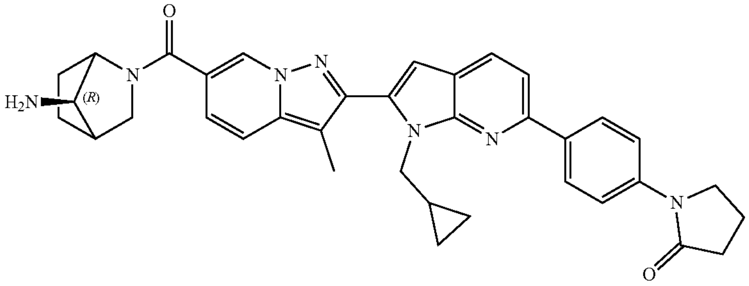<br>1-[4-(2-{6-[(7R)-7-Amino-2-azabicyclo[2.2.1]heptane-2-carbonyl]-3-methylpyrazolo[1,5-a]pyridin-2-yl}-1-(cyclopropylmethyl)-1H-pyrrolo[2,3-b]pyridin-6-yl)phenyl]pyrrolidin-2-one<br>Analytical Data: 600.4; 1.875 min (Method E) |
| 305 | 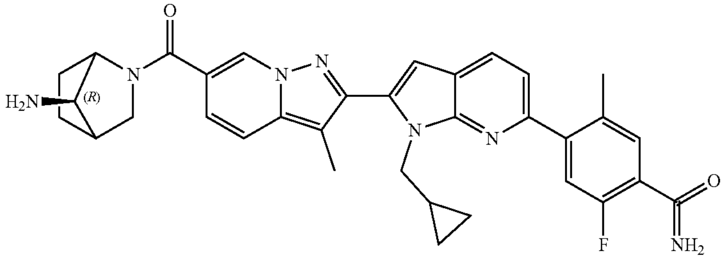<br>4-(2-{6-[(7R)-7-Amino-2-azabicyclo[2.2.1]heptane-2-carbonyl]-3-methylpyrazolo[1,5-a]pyridin-2-yl}-1-(cyclopropylmethyl)-1H-pyrrolo[2,3-b]pyridin-6-yl)-2-fluoro-5-methylbenzamide<br>Analytical Data: 592.3; 1.433 min (Method E) |
| 306 | 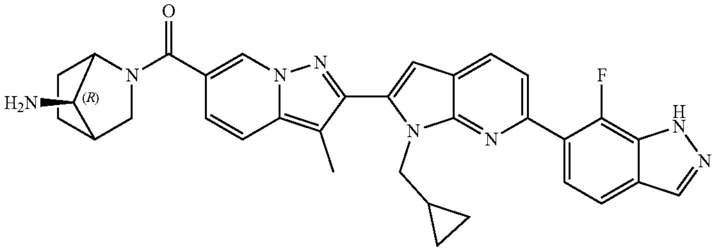<br>(7R)-2-{2-[1-(Cyclopropylmethyl)-6-(7-fluoro-1H-indazol-6-yl)-1H-pyrrolo[2,3-b]pyridin-2-yl]-3-methylpyrazolo[1,5-a]pyridine-6-carbonyl}-2-azabicyclo[2.2.1]heptan-7-amine<br>Analytical Data: 575.3, 2.036 min (Method E) |
| 307 | 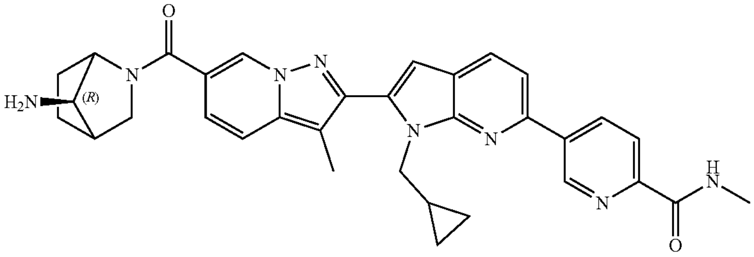<br>5-(2-{6-[(7R)-7-Amino-2-azabicyclo[2.2.1]heptane-2-carbonyl]-3-methylpyrazolo[1,5-a]pyridin-2-yl}-1-(cyclopropylmethyl)-1H-pyrrolo[2,3-b]pyridin-6-yl)-N-methylpyridine-2-carboxamide<br>Analytical Data: 575.4; 1.508 min (Method E) |

TABLE 36-continued

| Example | Structure<br>Name<br>Analytical Data: LC-MS m/z [M + H]$^+$; HPLC retention time (HPLC method) |
|---|---|
| 308 | 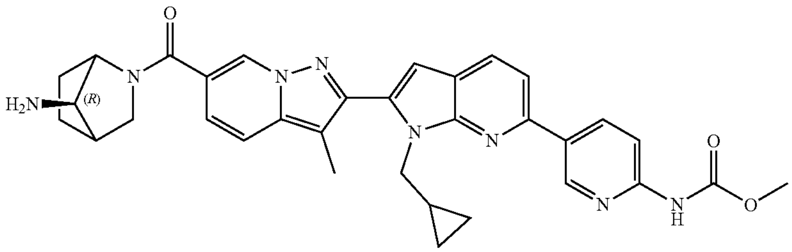<br>Methyl N-[5-(2-{6-[(7R)-7-amino-2-azabicyclo[2.2.1]heptane-2-carbonyl]-3-methylpyrazolo[1,5-a]pyridin-2-yl}-1-(cyclopropylmethyl)-1H-pyrrolo[2,3-b]pyridin-6-yl)pyridin-2-yl]carbamate<br>Analytical Data: 591.4; 1.748 min (Method E) |

Compounds of Examples 309 to 317 in Table 37 were prepared following a procedure similar to the preparation of a compound of Example 64, by using Intermediate 64D and tert-butyl (R)-piperidin-3-ylcarbamate in amide formation and appropriate boronic acid/boronate ester in Suzuki coupling.

TABLE 37

| Example | Structure<br>Name<br>Analytical Data: LC-MS m/z [M + H]$^+$; HPLC retention time (HPLC method) |
|---|---|
| 309 | 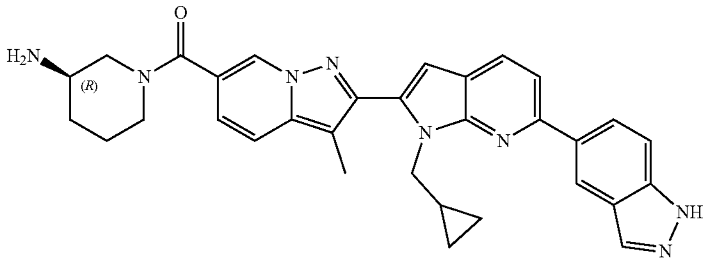<br>(3R)-1-{2-[1-(Cyclopropylmethyl)-6-(1H-indazol-5-yl)-1H-pyrrolo[2,3-b]pyridin-2-yl]-3-methylpyrazolo[1,5-a]pyridine-6-carbonyl}piperidin-3-amine<br>Analytical Data: 545.3; 1.523 min (Method E) |
| 310 | 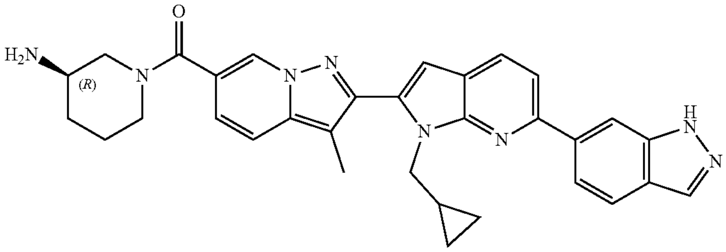<br>(3R)-1-{2-[1-(Cyclopropylmethyl)-6-(1H-indazol-6-yl)-1H-pyrrolo[2,3-b]pyridin-2-yl]-3-methylpyrazolo[1,5-a]pyridine-6-carbonyl}piperidin-3-amine<br>Analytical Data: 545.3; 1.608 min (Method E) |

TABLE 37-continued

| Example | Structure<br>Name<br>Analytical Data: LC-MS m/z [M + H]$^+$; HPLC retention time (HPLC method) |
|---|---|
| 311 | 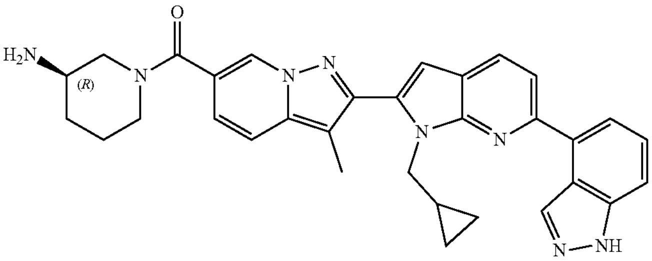<br>(3R)-1-{2-[1-(Cyclopropylmethyl)-6-(1H-indazol-4-yl)-1H-pyrrolo[2,3-b]pyridin-2-yl]-3-methylpyrazolo[1,5-a]pyridine-6-carbonyl}piperidin-3-amine<br>Analytical Data: 545.3; 1.581 min (Method E) |
| 312 | 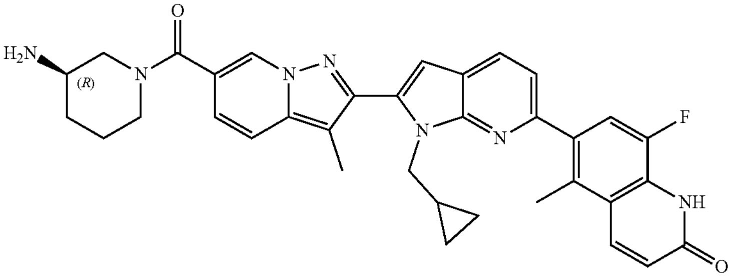<br>6-(2-{6-[(3R)-3-Aminopiperidine-1-carbonyl]-3-methylpyrazolo[1,5-a]pyridin-2-yl}-1-(cyclopropylmethyl)-1H-pyrrolo[2,3-b]pyridin-6-yl)-8-fluoro-5-methyl-1,2-dihydroquinolin-2-one<br>Analytical Data: 604.4; 1.454 min (Method E) |
| 313 | 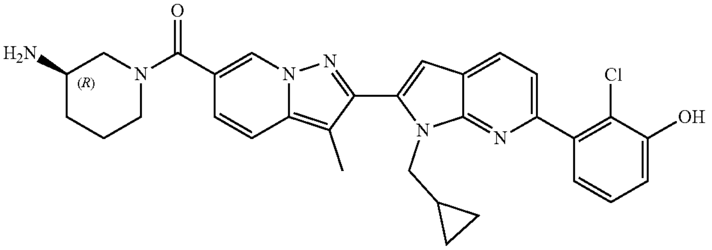<br>3-(2-{6-[(3R)-3-Aminopiperidine-1-carbonyl]-3-methylpyrazolo[1,5-a]pyridin-2-yl}-1-(cyclopropylmethyl)-1H-pyrrolo[2,3-b]pyridin-6-yl)-2-chlorophenol<br>Analytical Data: 555.3; 1.606 min (Method E) |
| 314 | 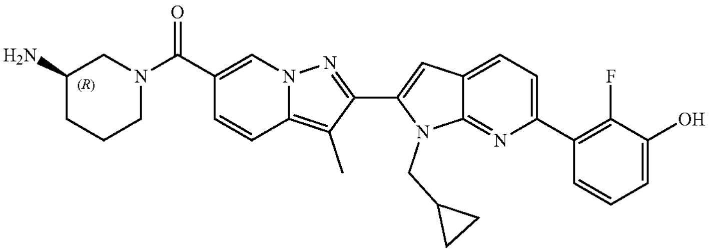<br>3-(2-{6-[(3R)-3-Aminopiperidine-1-carbonyl]-3-methylpyrazolo[1,5-a]pyridin-2-yl}-1-(cyclopropylmethyl)-1H-pyrrolo[2,3-b]pyridin-6-yl)-2-fluorophenol<br>Analytical Data: 539.3; 1.579 min (Method E) |

TABLE 37-continued

| Example | Structure<br>Name<br>Analytical Data: LC-MS m/z $[M + H]^+$; HPLC retention time (HPLC method) |
|---|---|
| 315 | 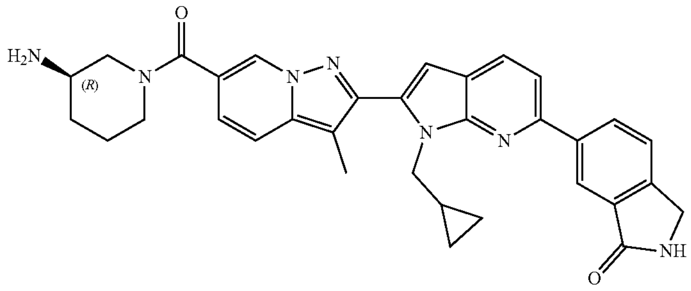<br>a]pyridin-2-yl}-1-(cyclopropylmethyl)-1H-pyrrolo[2,3-b]pyridin-6-yl)-2,3-dihydro-1H-isoindol-1-one<br>Analytical Data: 560.4; 1.507 min (Method E) |
| 316 | 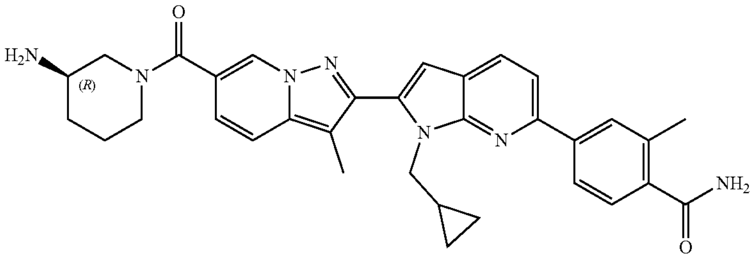<br>4-(2-{6-[(3R)-3-Aminopiperidine-1-carbonyl]-3-methylpyrazolo[1,5-a]pyridin-2-yl}-1-(cyclopropylmethyl)-1H-pyrrolo[2,3-b]pyridin-6-yl)-2-methylbenzamide<br>Analytical Data: 562.4; 1.415 min (Method E) |
| 317 | 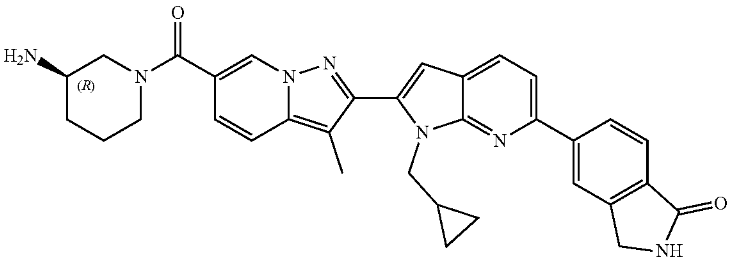<br>5-(2-{6-[(3R)-3-Aminopiperidine-1-carbonyl]-3-methylpyrazolo[1,5-a]pyridin-2-yl}-1-(cyclopropylmethyl)-1H-pyrrolo[2,3-b]pyridin-6-yl)-2,3-dihydro-1H-isoindol-1-one<br>Analytical Data: 560.4; 1.391 min (Method E) |

Compounds of Examples 318 to 320 in Table 38 were prepared following a procedure similar to the preparation of a compound of Example 76, by Buchwald coupling of Intermediate 64E with appropriate amines.

TABLE 38

| Example | Structure<br>Name<br>Analytical Data: LC-MS m/z [M + H]+; HPLC retention time (HPLC method) |
|---|---|
| 318 | 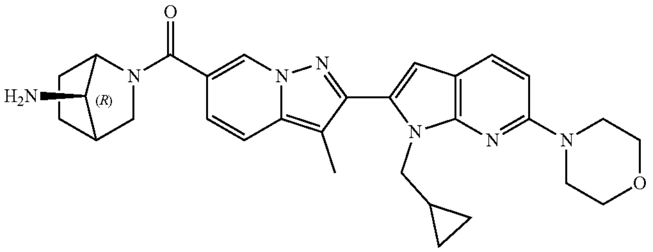<br>(7R)-2-{2-[1-(Cyclopropylmethyl)-6-(morpholin-4-yl)-1H-pyrrolo[2,3-b]pyridin-2-yl]-3-methylpyrazolo[1,5-a]pyridine-6-carbonyl}-2-azabicyclo[2.2.1]heptan-7-amine<br>Analytical Data: 526.3, 1.782 min (Method E) |
| 319 | 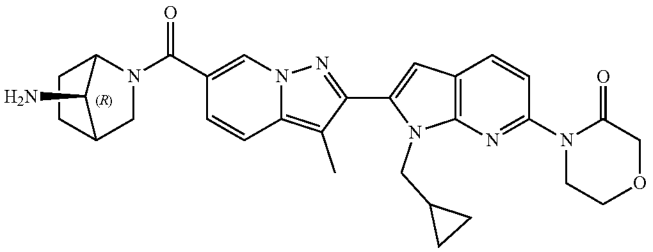<br>4-(2-{6-[(7R)-7-Amino-2-azabicyclo[2.2.1]heptane-2-carbonyl]-3-methylpyrazolo[1,5-a]pyridin-2-yl}-1-(cyclopropylmethyl)-1H-pyrrolo[2,3-b]pyridin-6-yl)morpholin-3-one<br>Analytical Data: 540.4; 1.458 min (Method E) |
| 320 | 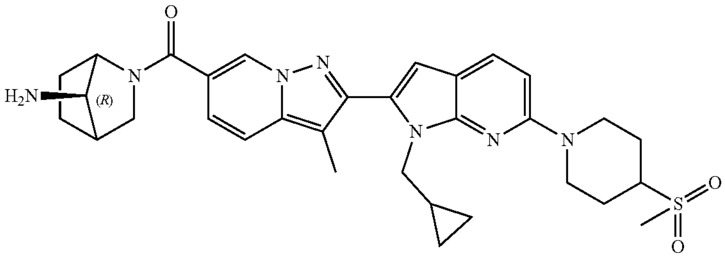<br>(7R)-2-{2-[1-(Cyclopropylmethyl)-6-(4-methanesulfonylpiperidin-1-yl)-1H-pyrrolo[2,3-b]pyridin-2-yl]-3-methylpyrazolo[1,5-a]pyridine-6-carbonyl}-2-azabicyclo[2.2.1]heptan-7-amine<br>Analytical Data: 602.2; 1.326 min (Method E) |

Compounds of Examples 321 to 324 in Table 39 were prepared following a procedure similar to the preparation of a compound of Example 81, by Suzuki coupling of Intermediate 81A with appropriate boronic acid.

TABLE 39

| Example | Structure<br>Name<br>Analytical Data: LC-MS m/z $[M + H]^+$; HPLC retention time (HPLC method) |
|---|---|
| 321 | 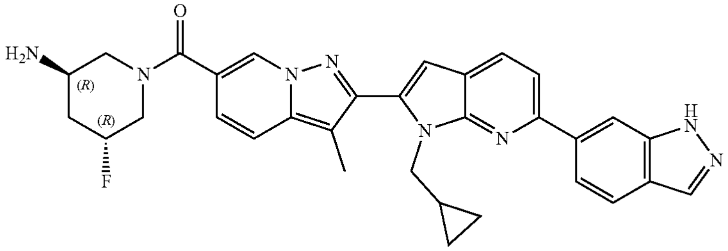<br>(3R,5R)-1-{2-[1-(Cyclopropylmethyl)-6-(1H-indazol-6-yl)-1H-pyrrolo[2,3-b]pyridin-2-yl]-3-methylpyrazolo[1,5-a]pyridine-6-carbonyl}-5-fluoropiperidin-3-amine<br>Analytical Data: 563.3; 2.191 min (Method E) |
| 322 | 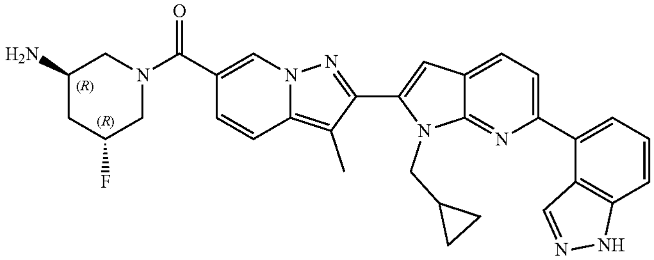<br>(3R,5R)-1-{2-[1-(Cyclopropylmethyl)-6-(1H-indazol-4-yl)-1H-pyrrolo[2,3-b]pyridin-2-yl]-3-methylpyrazolo[1,5-a]pyridine-6-carbonyl}-5-fluoropiperidin-3-amine<br>Analytical Data: 563.2; 1.744 min (Method E) |
| 323 | 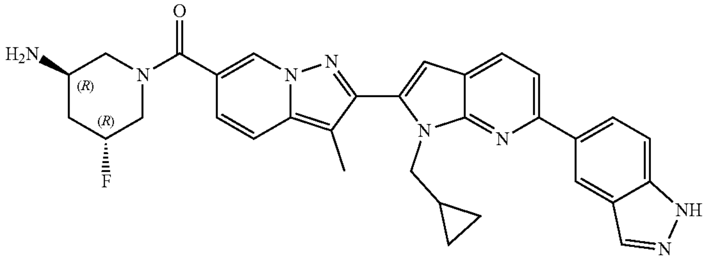<br>(3R,5R)-1-{2-[1-(Cyclopropylmethyl)-6-(1H-indazol-5-yl)-1H-pyrrolo[2,3-b]pyridin-2-yl]-3-methylpyrazolo[1,5-a]pyridine-6-carbonyl}-5-fluoropiperidin-3-amine<br>Analytical Data: 563.3; 1.670 min (Method E) |
| 324 | 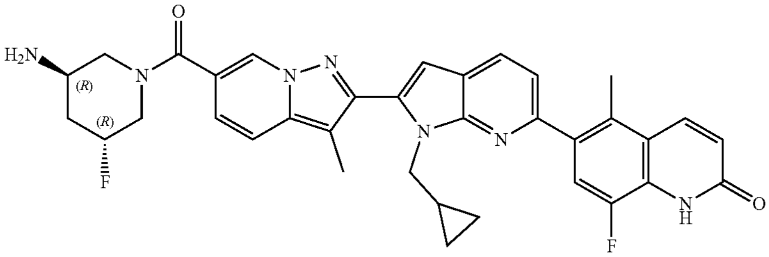<br>6-(2-{6-[(3R,5R)-3-Amino-5-fluoropiperidine-1-carbonyl]-3-methylpyrazolo[1,5-a]pyridin-2-yl}-1-(cyclopropylmethyl)-1H-pyrrolo[2,3-b]pyridin-6-yl)-8-fluoro-5-methyl-1,2-dihydroquinolin-2-one<br>Analytical Data: 622.3; 1.461 min (Method E) |

Example 325

Methyl N-[1-(2-{6-[(3R,5R)-3-amino-5-fluoropiperidine-1-carbonyl]-3-methylpyrazolo[1,5-a]pyridin-2-yl}-1-(cyclopropylmethyl)-1H-pyrrolo[2,3-b]pyridin-6-yl)piperidin-4-yl]-N-methylcarbamate

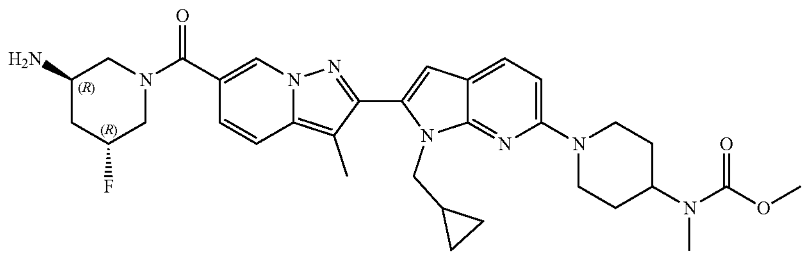

Compound of Example 325 was prepared following a procedure similar to the preparation of a compound of Example 87, by Buchwald coupling of Intermediate 81A with appropriate secondary amine. LC-MS m/z: 617 $[M+H]^+$; HPLC retention time: 1.530 min (Method E).

Compounds of Examples 326 to 341 in Table 40 were prepared following a procedure similar to the preparation of a compound of Example 89, by Suzuki coupling of Intermediate 89E with appropriate boronic acid or boronate ester.

TABLE 40

| Example | Structure<br>Name<br>Analytical Data: LC-MS m/z $[M + H]^+$; HPLC retention time (HPLC method) |
|---|---|
| 326 | 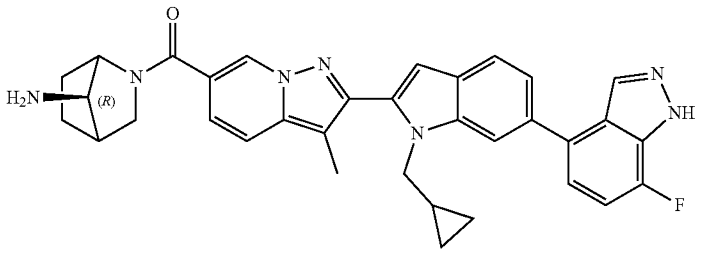<br>(7R)-2-{2-[1-(Cyclopropylmethyl)-6-(7-fluoro-1H-indazol-4-yl)-1H-indol-2-yl]-3-methylpyrazolo[1,5-a]pyridine-6-carbonyl}-2-azabicyclo[2.2.1]heptan-7-amine<br>Analytical Data: 574.3; 2.144 min (Method E) |
| 327 | 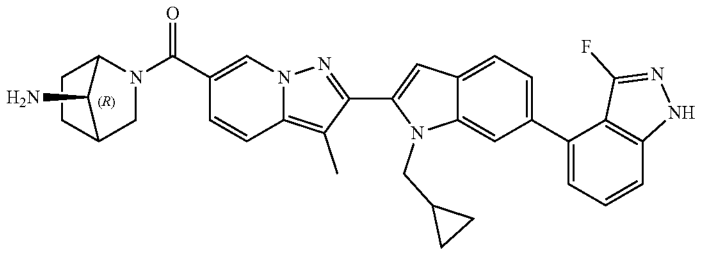<br>(7R)-2-{2-[1-(Cyclopropylmethyl)-6-(3-fluoro-1H-indazol-4-yl)-1H-indol-2-yl]-3-methylpyrazolo[1,5-a]pyridine-6-carbonyl}-2-azabicyclo[2.2.1]heptan-7-amine<br>Analytical Data:5 74.3; 2.173 min (Method E) |

TABLE 40-continued

| Example | Structure<br>Name<br>Analytical Data: LC-MS m/z [M + H]$^+$; HPLC retention time (HPLC method) |
|---|---|
| 328 | 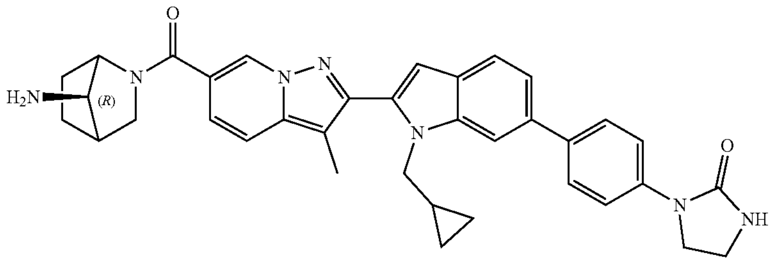<br>1-[4-(2-{6-[(7R)-7-Amino-2-azabicyclo[2.2.1]heptane-2-carbonyl]-3-methylpyrazolo[1,5-a]pyridin-2-yl}-1-(cyclopropylmethyl)-1H-indol-6-yl)phenyl]imidazolidin-2-one<br>Analytical Data: 600.4; 1.762 min (Method E) |
| 329 | 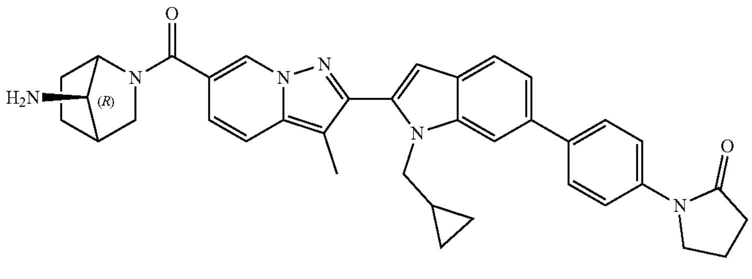<br>1-[4-(2-{6-[(7R)-7-Amino-2-azabicyclo[2.2.1]heptane-2-carbonyl]-3-methylpyrazolo[1,5-a]pyridin-2-yl}-1-(cyclopropylmethyl)-1H-indol-6-yl)phenyl]pyrrolidin-2-one<br>Analytical Data: 599.4; 1.883 min (Method E) |
| 330 | 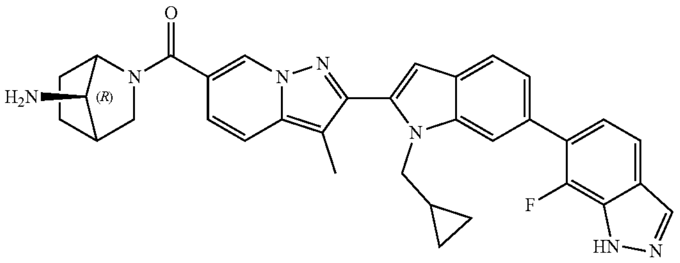<br>(7R)-2-{2-[1-(Cyclopropylmethyl)-6-(7-fluoro-1H-indazol-6-yl)-1H-indol-2-yl]-3-methylpyrazolo[1,5-a]pyridine-6-carbonyl}-2-azabicyclo[2.2.1]heptan-7-amine<br>Analytical Data: 574.4; 2.053 min (Method E) |
| 331 | 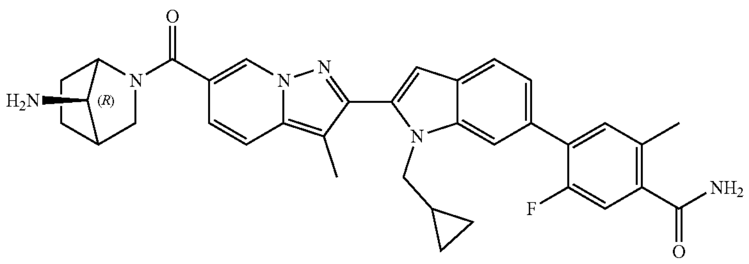<br>4-(2-{6-[(7R)-7-Amino-2-azabicyclo[2.2.1]heptane-2-carbonyl]-3-methylpyrazolo[1,5-a]pyridin-2-yl}-1-(cyclopropylmethyl)-1H-indol-6-yl)-5-fluoro-2-methylbenzamide<br>Analytical Data: 591.2; 1.481 min (Method E) |

TABLE 40-continued

| Example | Structure<br>Name<br>Analytical Data: LC-MS m/z [M + H]+; HPLC retention time (HPLC method) |
|---|---|
| 332 | 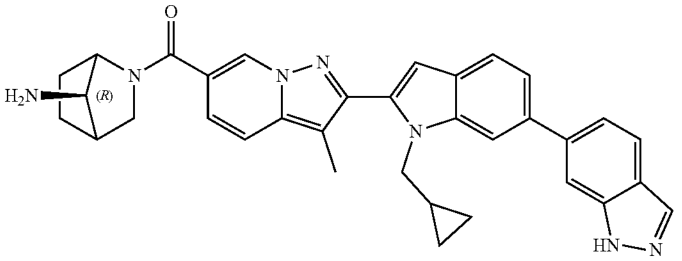<br>(7R)-2-{2-[1-(Cyclopropylmethyl)-6-(1H-indazol-6-yl)-1H-indol-2-yl]-3-methylpyrazolo[1,5-a]pyridine-6-carbonyl}-2-azabicyclo[2.2.1]heptan-7-amine<br>Analytical Data: 556.2; 1.772 min (Method E) |
| 333 | 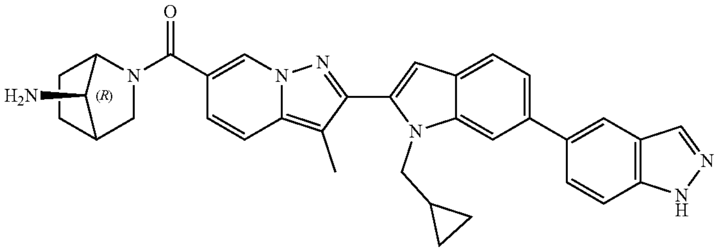<br>(7R)-2-{2-[1-(Cyclopropylmethyl)-6-(1H-indazol-5-yl)-1H-indol-2-yl]-3-methylpyrazolo[1,5-a]pyridine-6-carbonyl}-2-azabicyclo[2.2.1]heptan-7-amine<br>Analytical Data: 556.2; 1.703 min (Method E) |
| 334 | 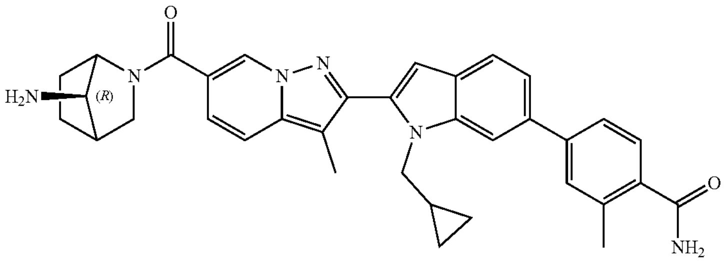<br>4-(2-{6-[(7R)-7-Amino-2-azabicyclo[2.2.1]heptane-2-carbonyl]-3-methylpyrazolo[1,5-a]pyridin-2-yl}-1-(cyclopropylmethyl)-1H-indol-6-yl)-2-methylbenzamide<br>Analytical Data: 573.2; 1.383 min (Method E) |
| 335 | 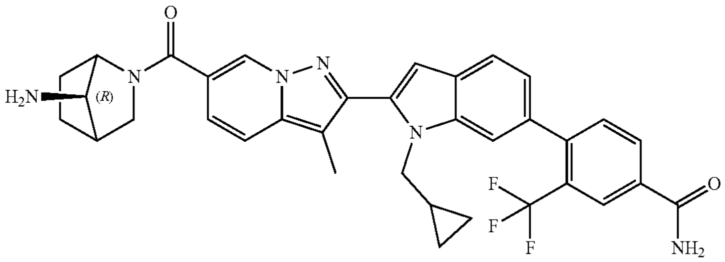<br>4-(2-{6-[(7R)-7-Amino-2-azabicyclo[2.2.1]heptane-2-carbonyl]-3-methylpyrazolo[1,5-a]pyridin-2-yl}-1-(cyclopropylmethyl)-1H-indol-6-yl)-3-(trifluoromethyl)benzamide<br>Analytical Data: 627.3; 1.493 min (Method E) |

TABLE 40-continued

| Example | Structure<br>Name<br>Analytical Data: LC-MS m/z [M + H]$^+$; HPLC retention time (HPLC method) |
|---|---|
| 336 | 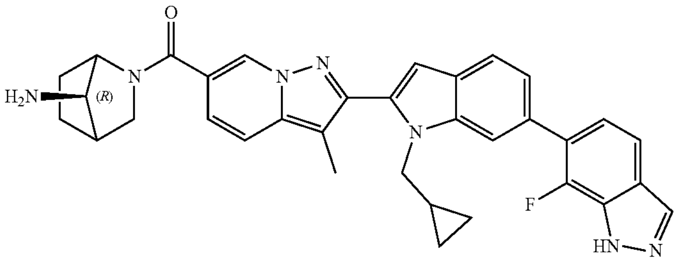<br>(7R)-2-{2-[1-(Cyclopropylmethyl)-6-(7-fluoro-1H-indazol-6-yl)-1H-indol-2-yl]-3-methylpyrazolo[1,5-a]pyridine-6-carbonyl}-2-azabicyclo[2.2.1]heptan-7-amine<br>Analytical Data: 574.3; 2.128 min (Method E) |
| 337 | 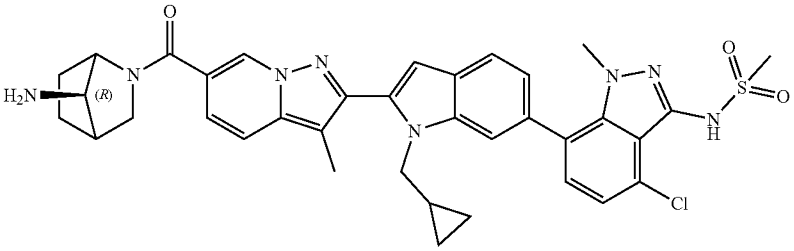<br>N-[7-(2-{6-[(7R)-7-Amino-2-azabicyclo[2.2.1]heptane-2-carbonyl]-3-methylpyrazolo[1,5-a]pyridin-2-yl}-1-(cyclopropylmethyl)-1H-indol-6-yl)-4-chloro-1-methyl-1H-indazol-3-yl]methanesulfonamide<br>Analytical Data: 698.3; 2.217 min (Method E) |
| 338 | 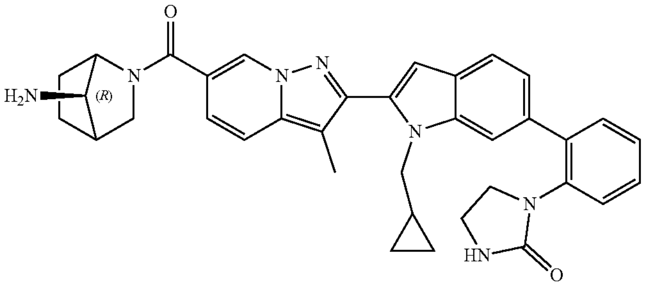<br>1-[2-(2-{6-[(7R)-7-Amino-2-azabicyclo[2.2.1]heptane-2-carbonyl]-3-methylpyrazolo[1,5-a]pyridin-2-yl}-1-(cyclopropylmethyl)-1H-indol-6-yl)phenyl]imidazolidin-2-one<br>Analytical Data: 601.4; 1.825 min (Method E) |
| 339 | 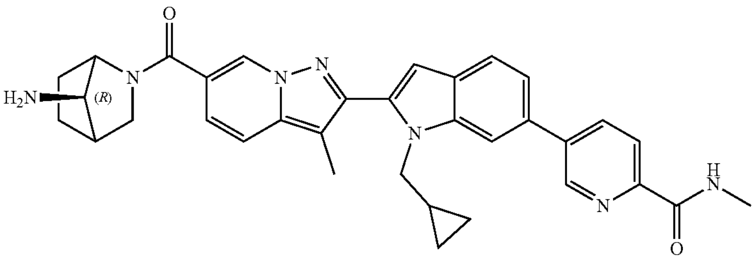<br>4-(2-{6-[(7R)-7-Amino-2-azabicyclo[2.2.1]heptane-2-carbonyl]-3-methylpyrazolo[1,5-a]pyridin-2-yl}-1-(cyclopropylmethyl)-1H-indol-6-yl)-2-chlorobenzamide<br>Analytical Data: 594.2; 1.755 min (Method E) |

TABLE 40-continued

| Example | Structure<br>Name<br>Analytical Data: LC-MS m/z [M + H]$^+$; HPLC retention time (HPLC method) |
|---|---|
| 340 | 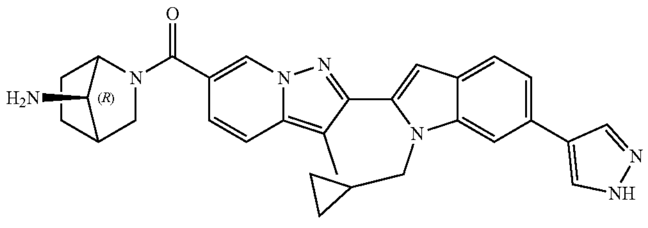<br>5-(2-{6-[(7R)-7-Amino-2-azabicyclo[2.2.1]heptane-2-carbonyl]-3-methylpyrazolo[1,5-a]pyridin-2-yl}-1-(cyclopropylmethyl)-1H-indol-6-yl)-N-methylpyridine-2-carboxamide<br>Analytical Data: 574.2; 1.441 min (Method E) |
| 341 | 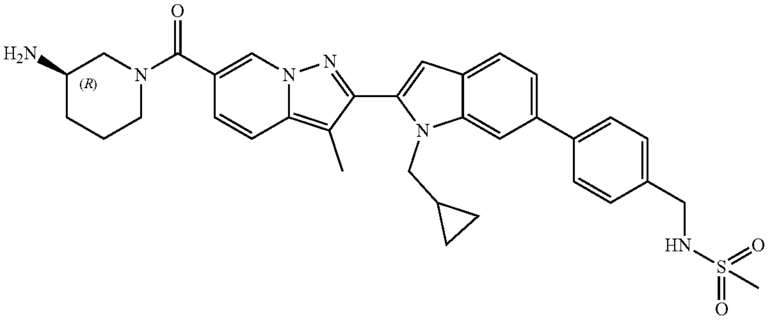<br>(7R)-2-{2-[1-(Cyclopropylmethyl)-6-(1H-pyrazol-4-yl)-1H-indol-2-yl]-3-methylpyrazolo[1,5-a]pyridine-6-carbonyl}-2-azabicyclo[2.2.1]heptan-7-amine<br>Analytical Data: 506.2; 1.554 min (Method E) |

Compounds of Examples 342 to 349 in Table 41 were prepared following a procedure similar to the preparation of a compound of Example 92, by using Intermediate 89D and tert-butyl (R)-piperidin-3-ylcarbamate in amide formation and with appropriate boronic acid or boronate ester in Suzuki coupling reaction.

TABLE 41

| Example | Structure<br>Name<br>Analytical Data: LC-MS m/z [M + H]$^+$; HPLC retention time (HPLC method) |
|---|---|
| 342 | 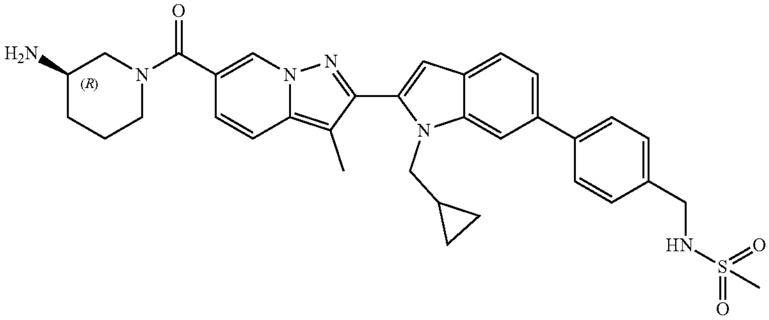<br>N-{[4-(2-{6-[(3R)-3-Aminopiperidine-1-carbonyl]-3-methylpyrazolo[1,5-a]pyridin-2-yl}-1-(cyclopropylmethyl)-1H-indol-6-yl)phenyl]methyl}methanesulfonamide<br>Analytical Data: 611.2; 1.571 min (Method E) |

TABLE 41-continued

| Example | Structure<br>Name<br>Analytical Data: LC-MS m/z [M + H]$^+$; HPLC retention time (HPLC method) |
|---|---|
| 343 | 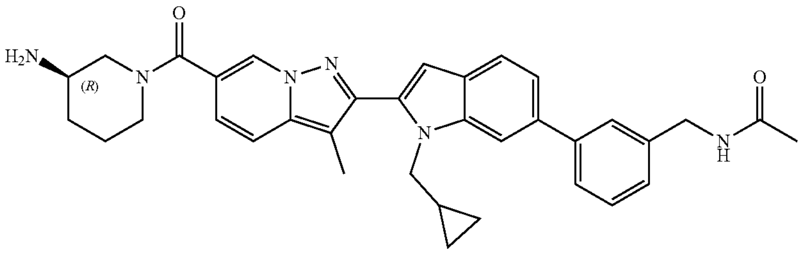<br>N-{[3-(2-{6-[(3R)-3-Aminopiperidine-1-carbonyl]-3-methylpyrazolo[1,5-a]pyridin-2-yl}-1-(cyclopropylmethyl)-1H-indol-6-yl)phenyl]methyl}acetamide<br>Analytical Data: 575.3; 1.584 min (Method E) |
| 344 | 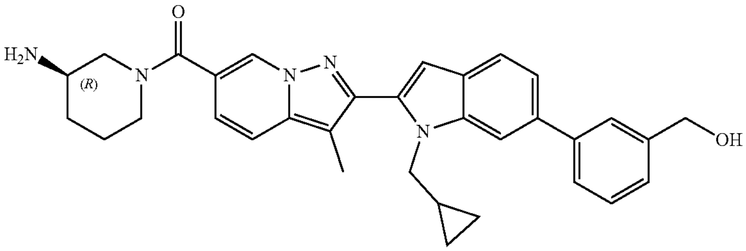<br>[3-(2-{6-[(3R)-3-Aminopiperidine-1-carbonyl]-3-methylpyrazolo[1,5-a]pyridin-2-yl}-1-(cyclopropylmethyl)-1H-indol-6-yl)phenyl]methanol<br>Analytical Data: 534.3; 1.556 min (Method E) |
| 345 | 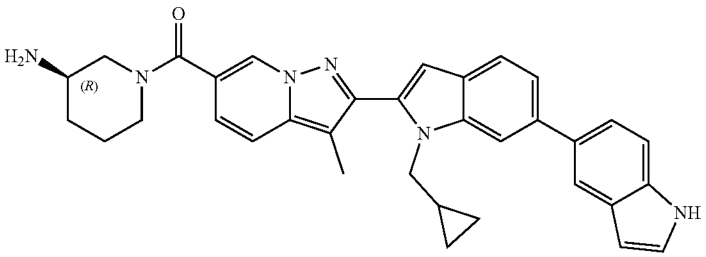<br>(3R)-1-{2-[1'-(Cyclopropylmethyl)-1H,1'H-[5,6'-biindole]-2'-yl]-3-methylpyrazolo[1,5-a]pyridine-6-carbonyl}piperidin-3-amine<br>Analytical Data: 543.2; 1.869 min (Method E) |
| 346 | 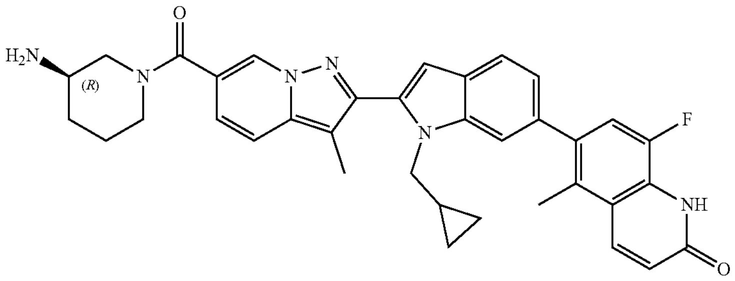<br>6-(2-{6-[(3R)-3-Aminopiperidine-1-carbonyl]-3-methylpyrazolo[1,5-a]pyridin-2-yl}-1-(cyclopropylmethyl)-1H-indol-6-yl)-8-fluoro-5-methyl-1,2-dihydroquinolin-2-one<br>Analytical Data: 603.3; 1.535 min (Method E) |

TABLE 41-continued

| Example | Structure<br>Name<br>Analytical Data: LC-MS m/z [M + H]$^+$; HPLC retention time (HPLC method) |
|---|---|
| 347 | 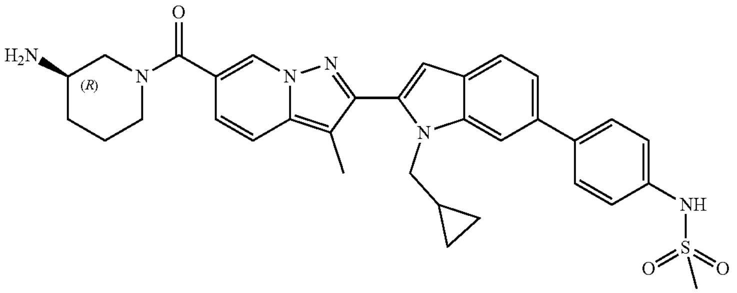<br>N-[4-(2-{6-[(3R)-3-Aminopiperidine-1-carbonyl]-3-methylpyrazolo[1,5-a]pyridin-2-yl}-1-(cyclopropylmethyl)-1H-indol-6-yl)phenyl]methanesulfonamide<br>Analytical Data: 597.3; 1.625 min (Method E) |
| 348 | 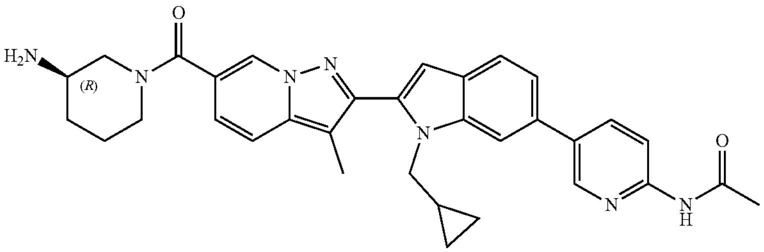<br>N-[5-(2-{6-[(3R)-3-Aminopiperidine-1-carbonyl]-3-methylpyrazolo[1,5-a]pyridin-2-yl}-1-(cyclopropylmethyl)-1H-indol-6-yl)pyridin-2-yl]acetamide<br>Analytical Data: 562.3; 1.625 min (Method E) |
| 349 | 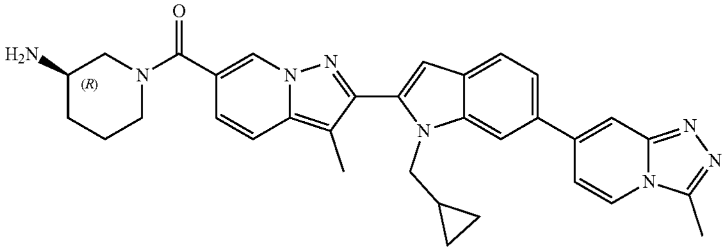<br>(R)-(3-Aminopiperidin-1-yl)(2-(1-(cyclopropylmethyl)-6-(3-methyl-[1,2,4]triazolo[4,3-a]pyridin-7-yl)-1H-indol-2-yl)-3-methylpyrazolo[1,5-a]pyridin-6-yl)methanone<br>Analytical Data: 559.3; 1.452 min (Method E) |

Compounds of Examples 350 and 351 in Table 42 were prepared following a procedure similar to the preparation of a compound of Example 91, by Buchwald coupling of Intermediate 89E with appropriate secondary amine.

TABLE 42

| Example | Structure<br>Name<br>Analytical Data: LC-MS m/z [M + H]$^+$; HPLC retention time (HPLC method) |
|---|---|
| 350 | 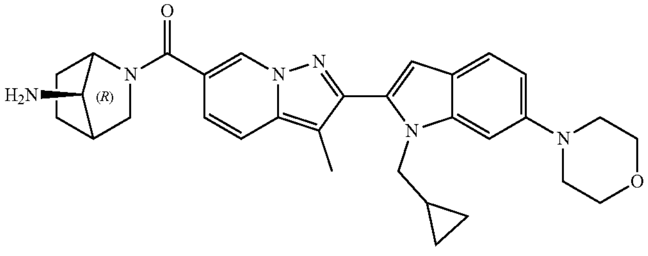<br>(7R)-2-{2-[1-(Cyclopropylmethyl)-6-(morpholin-4-yl)-1H-indol-2-yl]-3-methylpyrazolo[1,5-a]pyridine-6-carbonyl}-2-azabicyclo[2.2.1]heptan-7-amine<br>Analytical Data: 525.3; 1.755 min (Method E) |
| 351 | 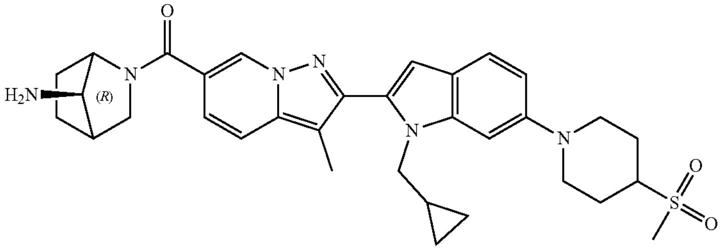<br>(7R)-2-{2-[1-(Cyclopropylmethyl)-6-(4-methanesulfonylpiperidin-1-yl)-1H-indol-2-yl]-3-methylpyrazolo[1,5-a]pyridine-6-carbonyl}-2-azabicyclo[2.2.1]heptan-7-amine<br>Analytical Data: 601.3; 1.500 min (Method E) |

Compounds of Examples 352 to 357 in Table 43 were prepared following a procedure similar to the preparation of a compound of Example 91, by using Intermediate 89D and tert-butyl ((3R,5R)-5-fluoropiperidin-3-yl)carbamate in amide formation and with appropriate secondary amine in Buchwald coupling reaction.

TABLE 43

| Example | Structure<br>Name<br>Analytical Data: LC-MS m/z [M + H]$^+$; HPLC retention time (HPLC method) |
|---|---|
| 352 | 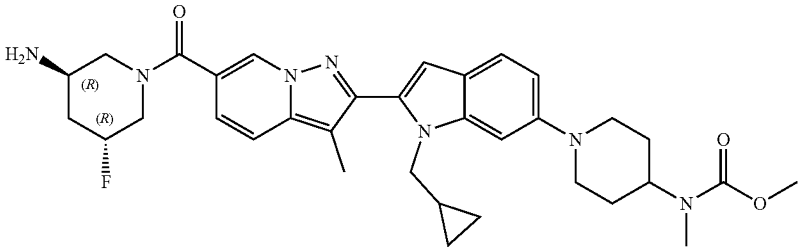<br>Methyl N-[1-(2-{6-[(3R,5R)-3-amino-5-fluoropiperidine-1-carbonyl]-3-methylpyrazolo[1,5-a]pyridin-2-yl}-1-(cyclopropylmethyl)-1H-indol-6-yl)piperidin-4-yl]-N-methylcarbamate<br>Analytical Data: 616.3; 1.830 min (Method E) |

TABLE 43-continued

| Example | Structure<br>Name<br>Analytical Data: LC-MS m/z [M + H]$^+$; HPLC retention time (HPLC method) |
|---|---|
| 353 | 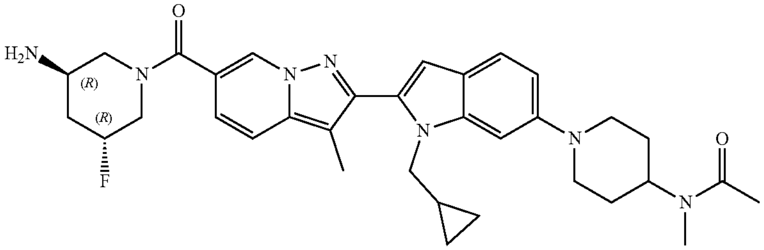<br>N-[1-(2-{6-[(3R,5R)-3-Amino-5-fluoropiperidine-1-carbonyl]-3-methylpyrazolo[1,5-a]pyridin-2-yl}-1-(cyclopropylmethyl)-1H-indol-6-yl)piperidin-4-yl]-N-methylacetamide<br>Analytical Data: 600.4, 1.059 min (Method E) |
| 354 | 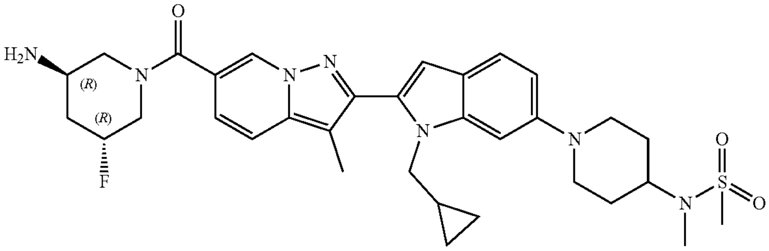<br>N-[1-(2-{6-[(3R,5R)-3-Amino-5-fluoropiperidine-1-carbonyl]-3-methylpyrazolo[1,5-a]pyridin-2-yl}-1-(cyclopropylmethyl)-1H-indol-6-yl)piperidin-4-yl]-N-methylmethanesulfonamide<br>Analytical Data: 636.2; 1.656 min (Method E) |
| 355 | 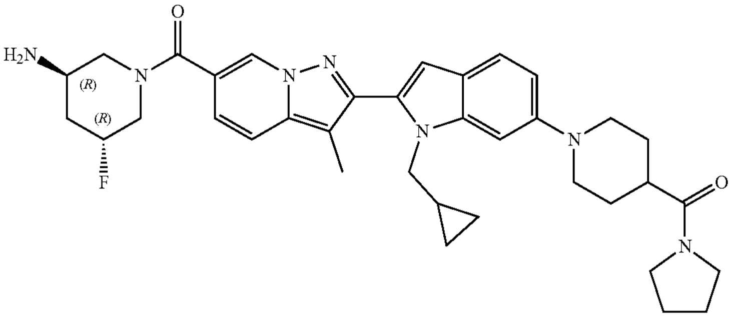<br>(3R,5R)-1-{2-[1-(Cyclopropylmethyl)-6-[4-(pyrrolidine-1-carbonyl)piperidin-1-yl]-1H-indol-2-yl]-3-methylpyrazolo[1,5-a]pyridine-6-carbonyl}-5-fluoropiperidin-3-amine<br>Analytical Data: 626.4; 1.636 min (Method E) |
| 356 | 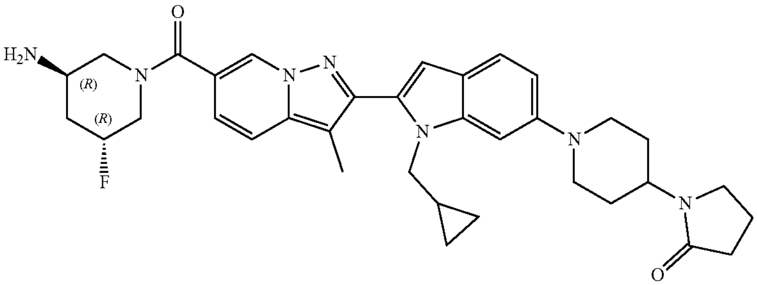<br>1-[1-(2-{6-[(3R,5R)-3-Amino-5-fluoropiperidine-1-carbonyl]-3-methylpyrazolo[1,5-a]pyridin-2-yl}-1-(cyclopropylmethyl)-1H-indol-6-yl)piperidin-4-yl]pyrrolidin-2-one<br>Analytical Data: 612.3; 1.512 min (Method E) |

TABLE 43-continued

| Example | Structure<br>Name<br>Analytical Data: LC-MS m/z $[M + H]^+$; HPLC retention time (HPLC method) |
|---|---|
| 357 | 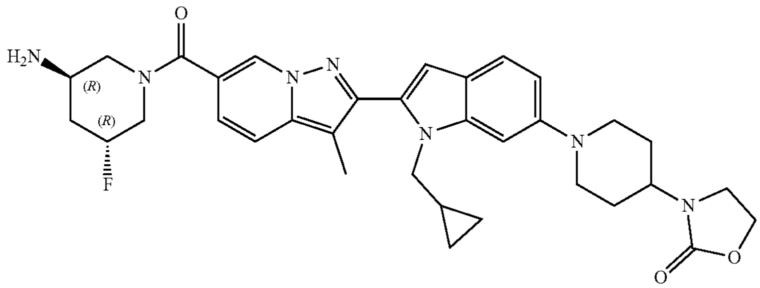<br>3-[1-(2-{6-[(3R,5R)-3-Amino-5-fluoropiperidine-1-carbonyl]-3-methylpyrazolo[1,5-a]pyridin-2-yl}-1-(cyclopropylmethyl)-1H-indol-6-yl)piperidin-4-yl]-1,3-oxazolidin-2-one<br>Analytical Data: 614.3; 1.479 min (Method E) |

Compounds of Examples 358 to 366 in Table 44 were prepared following a procedure similar to the preparation of a compound of Example 91, by using Intermediate 89D and tert-butyl (R)-piperidin-3-ylcarbamate in amide formation and with appropriate secondary amine in Buchwald coupling reaction.

TABLE 44

| Example | Structure<br>Name<br>Analytical Data: LC-MS m/z $[M + H]^+$; HPLC retention time (HPLC method) |
|---|---|
| 358 | 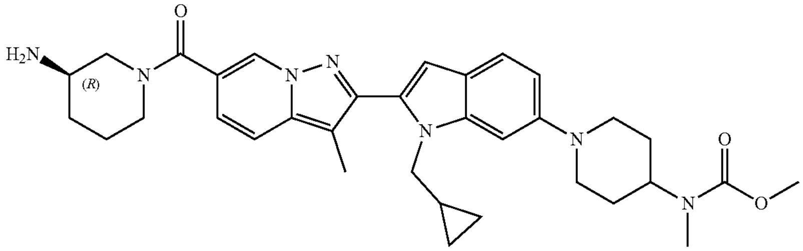<br>Methyl N-[1-(2-{6-[(3R)-3-aminopiperidine-1-carbonyl]-3-methylpyrazolo[1,5-a]pyridin-2-yl}-1-(cyclopropylmethyl)-1H-indol-6-yl)piperidin-4-yl]-N-methylcarbamate<br>Analytical Data: 598.4; 1.170 min (Method E) |
| 359 | 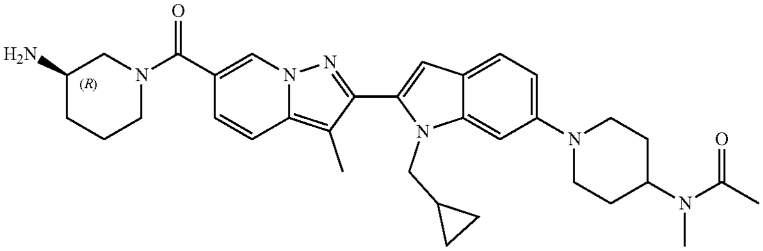<br>N-[1-(2-{6-[(3R)-3-Aminopiperidine-1-carbonyl]-3-methylpyrazolo[1,5-a]pyridin-2-yl}-1-(cyclopropylmethyl)-1H-indol-6-yl)piperidin-4-yl]-N-methyl acetamide<br>Analytical Data: 582.4; 1.488 min (Method E) |

TABLE 44-continued

| Example | Structure<br>Name<br>Analytical Data: LC-MS m/z [M + H]$^+$; HPLC retention time (HPLC method) |
|---|---|
| 360 | 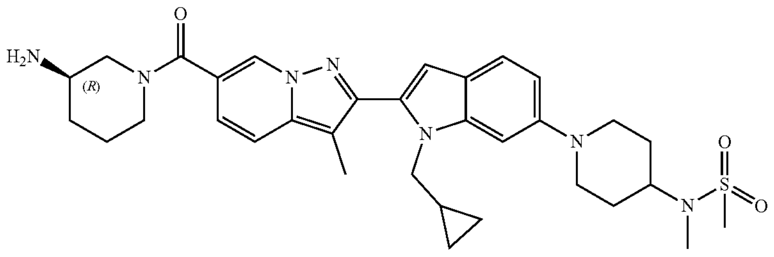<br>N-[1-(2-{6-[(3R)-3-Aminopiperidine-1-carbonyl]-3-methylpyrazolo[1,5-a]pyridin-2-yl}-1-(cyclopropylmethyl)-1H-indol-6-yl)piperidin-4-yl]-N-methylmethanesulfonamide<br>Analytical Data: 618.4; 1.063 min (Method E) |
| 361 | 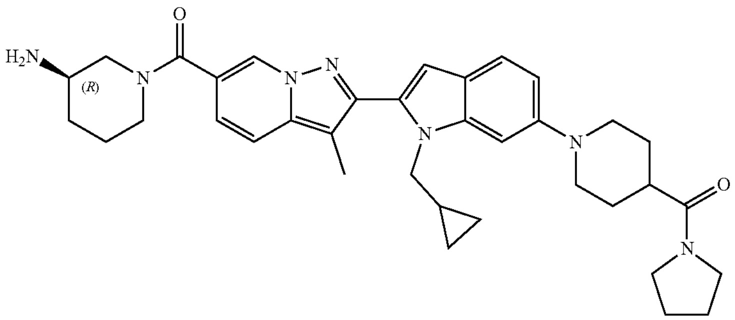<br>(3R)-1-{2-[1-(Cyclopropylmethyl)-6-[4-(pyrrolidine-1-carbonyl)piperidin-1-yl]-1H-indol-2-yl]-3-methylpyrazolo[1,5-a]pyridine-6-carbonyl}piperidin-3-amine<br>Analytical Data: 608.3; 1.591 min (Method E) |
| 362 | 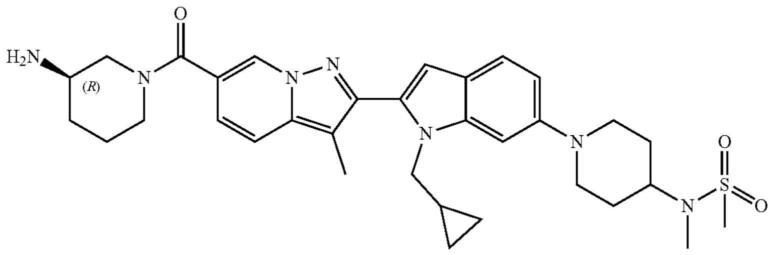<br>N-[1-(2-{6-[(3R)-3-Aminopiperidine-1-carbonyl]-3-methylpyrazolo[1,5-a]pyridin-2-yl}-1-(cyclopropylmethyl)-1H-indol-6-yl)piperidin-4-yl]-N-methylmethanesulfonamide<br>Analytical Data: 618.4; 1.063 min (Method E) |
| 363 | 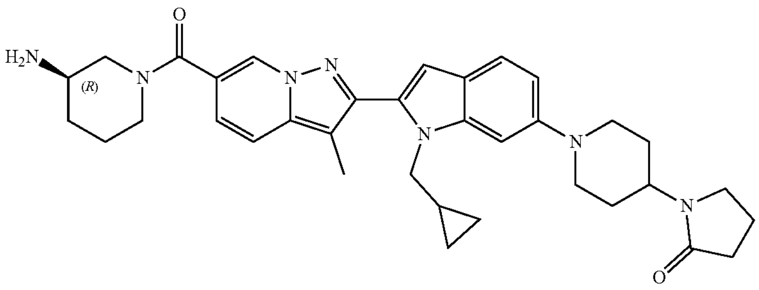<br>1-[1-(2-{6-[(3R)-3-Aminopiperidine-1-carbonyl]-3-methylpyrazolo[1,5-a]pyridin-2-yl}-1-(cyclopropylmethyl)-1H-indol-6-yl)piperidin-4-yl]pyrrolidin-2-one<br>Analytical Data: 594.3; 1.448 min (Method E) |

TABLE 44-continued

| Example | Structure<br>Name<br>Analytical Data: LC-MS m/z $[M + H]^+$; HPLC retention time (HPLC method) |
|---|---|
| 364 | 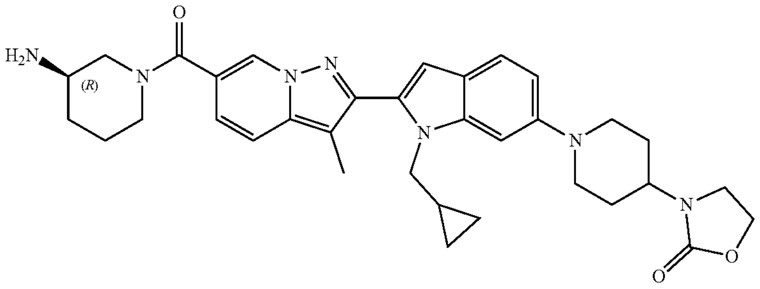<br>3-[1-(2-{6-[(3R)-3-Aminopiperidine-1-carbonyl]-3-methylpyrazolo[1,5-a]pyridin-2-yl}-1-(cyclopropylmethyl)-1H-indol-6-yl)piperidin-4-yl]-1,3-oxazolidin-2-one<br>Analytical Data: 596.3; 1.412 min (Method E) |
| 365 | 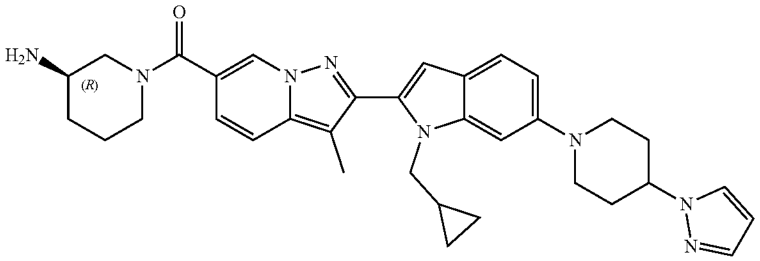<br>(3R)-1-{2-[1-(Cyclopropylmethyl)-6-[4-(1H-pyrazol-1-yl)piperidin-1-yl]-1H-indol-2-yl]-3-methylpyrazolo[1,5-a]pyridine-6-carbonyl}piperidin-3-amine<br>Analytical Data: 577.3; 1.628 min (Method E) |
| 366 | 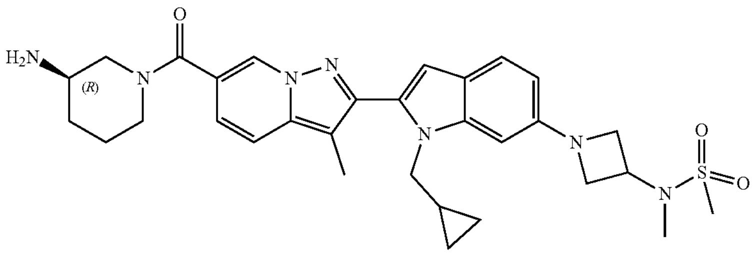<br>N-[1-(2-{6-[(3R)-3-Aminopiperidine-1-carbonyl]-3-methylpyrazolo[1,5-a]pyridin-2-yl}-1-(cyclopropylmethyl)-1H-indol-6-yl)azetidin-3-yl]-N-methylmethanesulfonamide<br>Analytical Data: 590.3; 1.522 min (Method E) |

Compounds of Examples 367 to 379 in Table 45 were prepared following a procedure similar to the preparation of a compound of Example 92, by Suzuki coupling of Intermediate 92A with appropriate boronic acid or boronate ester.

TABLE 45

| Example | Structure<br>Name<br>Analytical Data: LC-MS m/z [M + H]+; HPLC retention time (HPLC method) |
|---|---|
| 367 | 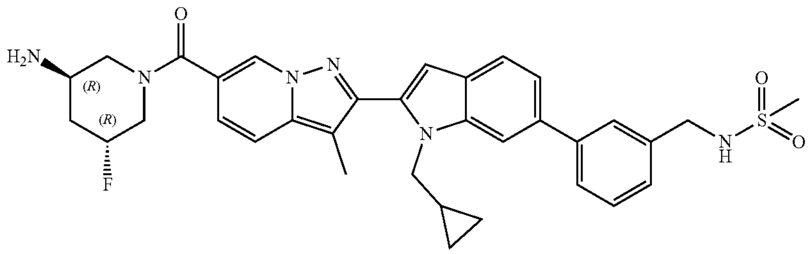<br>N-{[3-(2-{6-[(3R,5R)-3-Amino-5-fluoropiperidine-1-carbonyl]-3-methylpyrazolo[1,5-a]pyridin-2-yl}-1-(cyclopropylmethyl)-1H-indol-6-yl)phenyl]methyl}methanesulfonamide<br>Analytical Data: 629.2; 1.775 min (Method E) |
| 368 | 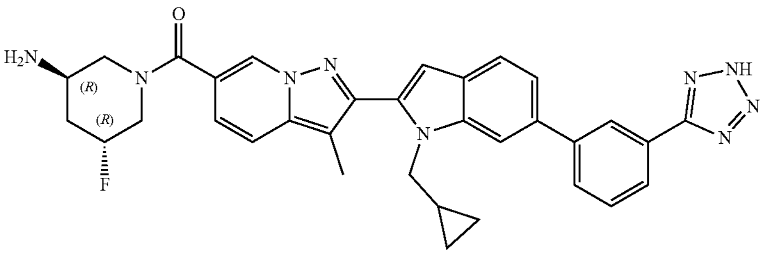<br>(3R,5R)-1-{2-[1-(Cyclopropylmethyl)-6-[3-(2H-1,2,3,4-tetrazol-5-yl)phenyl]-1H-indol-2-yl]-3-methylpyrazolo[1,5-a]pyridine-6-carbonyl}-5-fluoropiperidin-3-amine<br>Analytical Data: 590.3; 1.369 min (Method E) |
| 369 | 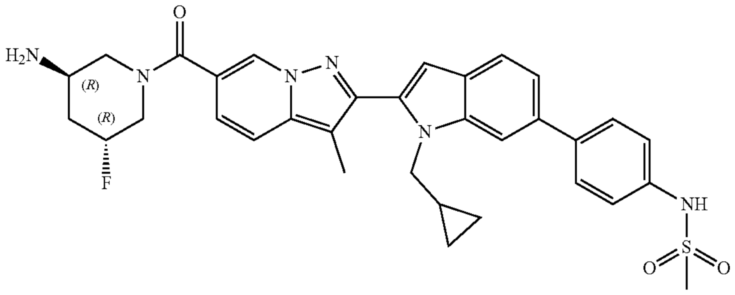<br>N-[4-(2-{6-[(3R,5R)-3-Amino-5-fluoropiperidine-1-carbonyl]-3-methylpyrazolo[1,5-a]pyridin-2-yl}-1-(cyclopropylmethyl)-1H-indol-6-yl)phenyl]methanesulfonamide<br>Analytical Data: 615.2; 1.713 min (Method E) |
| 370 | 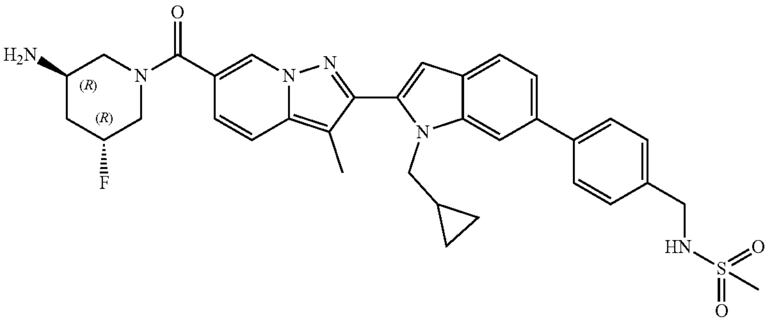<br>N-{[4-(2-{6-[(3R,5R)-3-Amino-5-fluoropiperidine-1-carbonyl]-3-methylpyrazolo[1,5-a]pyridin-2-yl}-1-(cyclopropylmethyl)-1H-indol-6-yl)phenyl]methyl}methanesulfonamide<br>Analytical Data: 629.3; 1.738 min (Method E) |

TABLE 45-continued

| Example | Structure<br>Name<br>Analytical Data: LC-MS m/z $[M + H]^+$; HPLC retention time (HPLC method) |
|---|---|
| 371 | 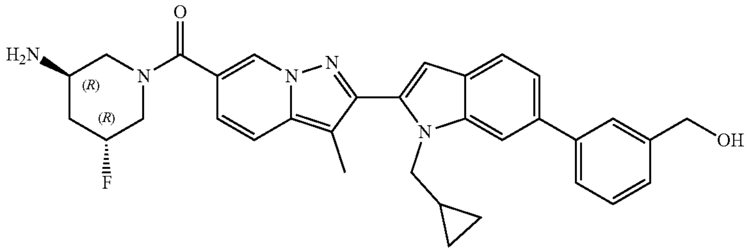<br>[3-(2-{6-[(3R,5R)-3-Amino-5-fluoropiperidine-1-carbonyl]-3-methylpyrazolo[1,5-a]pyridin-2-yl}-1-(cyclopropylmethyl)-1H-indol-6-yl)phenyl]methanol<br>Analytical Data: 552.3; 1.742 min (Method E) |
| 372 | 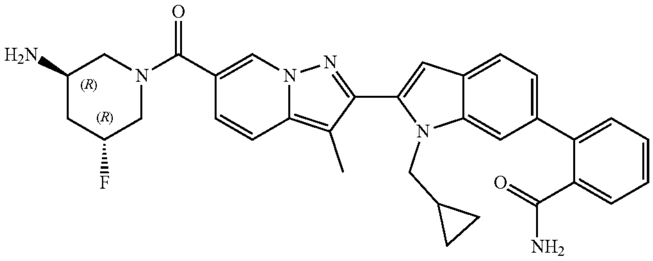<br>2-(2-{6-[(3R,5R)-3-Amino-5-fluoropiperidine-1-carbonyl]-3-methylpyrazolo[1,5-a]pyridin-2-yl}-1-(cyclopropylmethyl)-1H-indol-6-yl)benzamide<br>Analytical Data: 565.3; 1.536 min (Method E) |
| 373 | 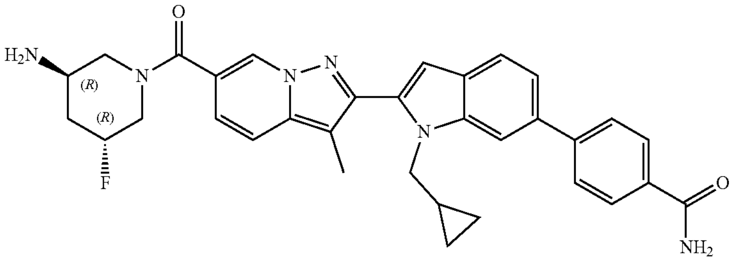<br>4-(2-{6-[(3R,5R)-3-Amino-5-fluoropiperidine-1-carbonyl]-3-methylpyrazolo[1,5-a]pyridin-2-yl}-1-(cyclopropylmethyl)-1H-indol-6-yl)benzamide<br>Analytical Data: 565.2; 1.531 min (Method E) |
| 374 | 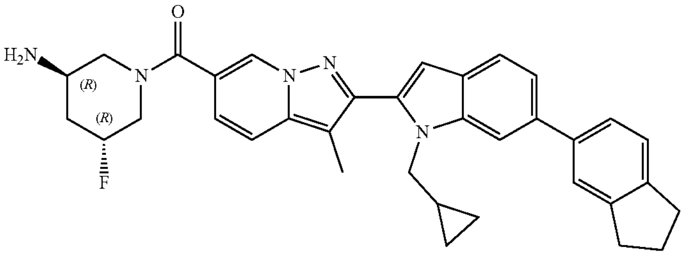<br>(3R,5R)-1-{2-[1'-(Cyclopropylmethyl)-1H,1'H-[5,6'-biindole]-2'-yl]-3-methylpyrazolo[1,5-a]pyridine-6-carbonyl}-5-fluoropiperidin-3-amine<br>Analytical Data: 561.2; 1.943 min (Method E) |

TABLE 45-continued

| Example | Structure<br>Name<br>Analytical Data: LC-MS m/z [M + H]$^+$; HPLC retention time (HPLC method) |
|---|---|
| 375 | 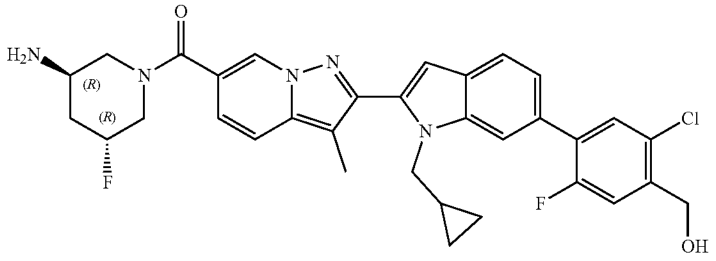<br>[4-(2-{6-[(3R,5R)-3-Amino-5-fluoropiperidine-1-carbonyl]-3-methylpyrazolo[1,5-a]pyridin-2-yl}-1-(cyclopropylmethyl)-1H-indol-6-yl)-2-chloro-5-fluorophenyl]methanol<br>Analytical Data: 604.3; 1.915 min (Method E) |
| 376 | 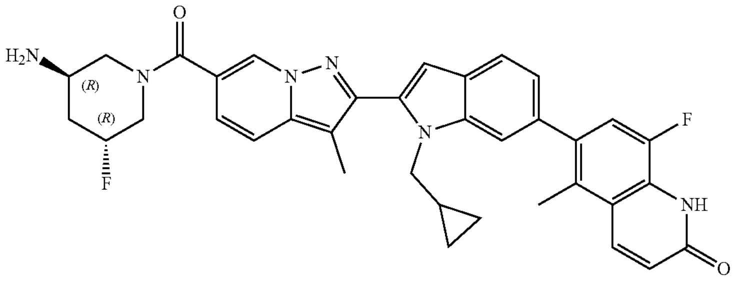<br>6-(2-{6-[(3R,5R)-3-Amino-5-fluoropiperidine-1-carbonyl]-3-methylpyrazolo[1,5-a]pyridin-2-yl}-1-(cyclopropylmethyl)-1H-indol-6-yl)-8-fluoro-5-methyl-1,2-dihydroquinolin-2-one<br>Analytical Data: 621.3; 1.557 min (Method E) |
| 377 | 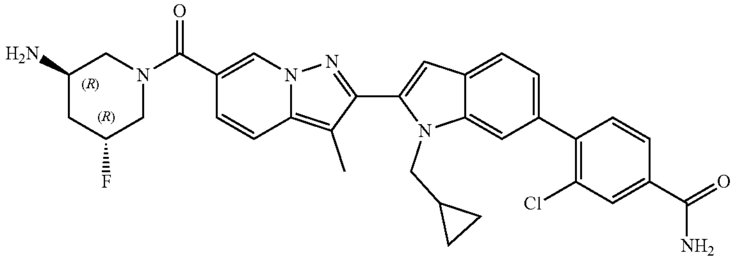<br>4-(2-{6-[(3R,5R)-3-Amino-5-fluoropiperidine-1-carbonyl]-3-methylpyrazolo[1,5-a]pyridin-2-yl}-1-(cyclopropylmethyl)-1H-indol-6-yl)-3-chlorobenzamide<br>Analytical Data: 599.3; 1.676 min (Method E) |
| 378 | 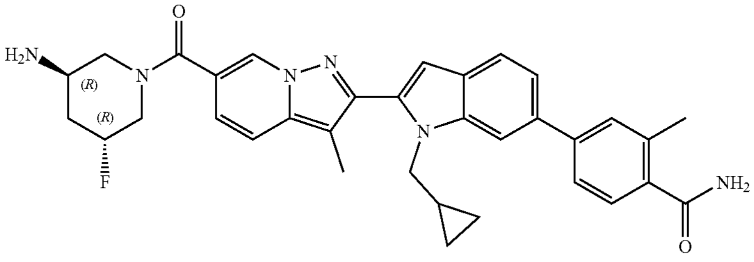<br>4-(2-{6-[(3R,5R)-3-Amino-5-fluoropiperidine-1-carbonyl]-3-methylpyrazolo[1,5-a]pyridin-2-yl}-1-(cyclopropylmethyl)-1H-indol-6-yl)-2-methylbenzamide<br>Analytical Data: 579.4; 1.523 min (Method E) |

TABLE 45-continued

| Example | Structure<br>Name<br>Analytical Data: LC-MS m/z $[M + H]^+$; HPLC retention time (HPLC method) |
|---|---|
| 379 | 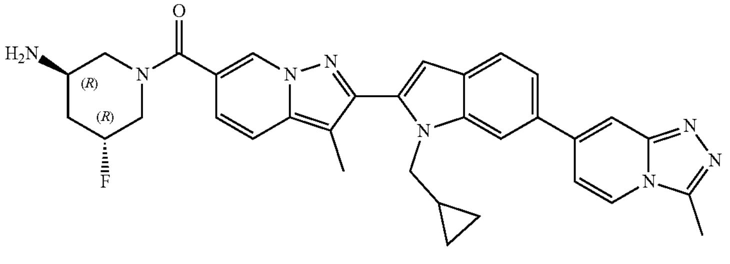<br>(3R,5R)-1-{2-[1-(Cyclopropylmethyl)-6-{3-methyl-[1,2,4]triazolo[4,3-a]pyridin-7-yl}-1H-indol-2-yl]-3-methylpyrazolo[1,5-a]pyridine-6-carbonyl}-5-fluoropiperidin-3-amine<br>Analytical Data: 577.3; 1.501 min (Method E) |

Example 380

2-(2-{6-[(3R)-3-Aminopiperidine-1-carbonyl]-3-methylpyrazolo[1,5-a]pyridin-2-yl}-1-(cyclopropylmethyl)-1H-pyrrolo[2,3-b]pyridin-6-yl)propan-2-ol (Homochiral)

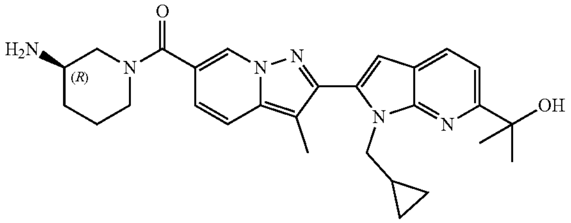

Compound of Example 380 was obtained by amide formation of Intermediate 64D with tert-butyl (R)-piperidin-3-ylcarbamate followed the similar preparation of a compound of Example 100. LC-MS m/z: 487.4 $[M+H]^+$; HPLC retention time: 1.453 min (Method E).

Example 381

2-(2-{6-[(7R)-7-Amino-2-azabicyclo[2.2.1]heptane-2-carbonyl]-3-methylpyrazolo[1,5-a]pyridin-2-yl}-1-(cyclopropylmethyl)-1H-pyrrolo[2,3-b]pyridin-6-yl)-1,1-difluoropropan-2-ol (Diastereomeric mixture)

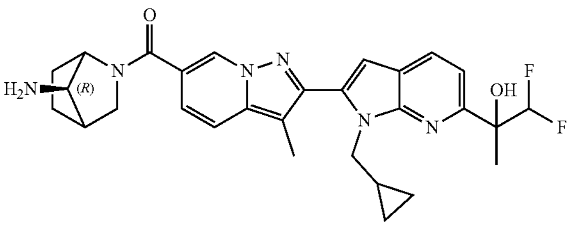

Compound of Example 381 was prepared following a procedure similar to the preparation of a compound of Example 101, by using Intermediate 100A with (Difluoromethyl)trimethylsilane reagent. LC-MS m/z: 535.2 $[M+H]^+$; HPLC retention time: 1.503 min (Method E).

Example 382

2-(2-{6-[(3R)-3-Aminopiperidine-1-carbonyl]-3-methylpyrazolo[1,5-a]pyridin-2-yl}-1-(cyclopropylmethyl)-1H-pyrrolo[2,3-b]pyridin-6-yl)-1,1,1-trifluoropropan-2-ol (Diastereomeric mixture)

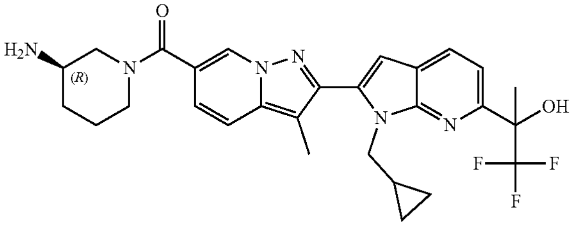

Compound of Example 382 was obtained by amide formation of Intermediate 64D with tert-butyl (R)-piperidin-3-ylcarbamate followed with the similar preparation of a compound of Example 101. LC-MS m/z: 541.3 $[M+H]^+$; HPLC retention time: 1.746 min (Method E).

Example 383

2-(2-{6-[(7R)-7-Amino-2-azabicyclo[2.2.1]heptane-2-carbonyl]-4-fluoro-3-methylpyrazolo[1,5-a]pyridin-2-yl}-1-(cyclopropylmethyl)-1H-pyrrolo[2,3-b]pyridin-6-yl)-1,1,1-trifluoropropan-2-ol

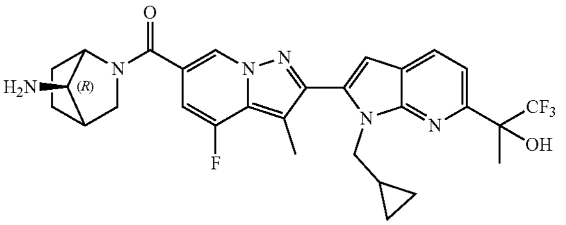

Compound of Example 383 obtained following a procedure similar to the preparation of Example 101, from Intermediate 39E. Analytical Data: LC-MS m/z: 571.3 $[M+H]^+$; HPLC retention time: 2.147 min (Method E).

Example 384

1-(2-{6-[(7R)-7-Amino-2-azabicyclo[2.2.1]heptane-2-carbonyl]-4-fluoro-3-methylpyrazolo[1,5-a]pyridin-2-yl}-1-(cyclopropylmethyl)-1H-pyrrolo[2,3-b]pyridin-6-yl)-1-cyclopropylethan-1-ol

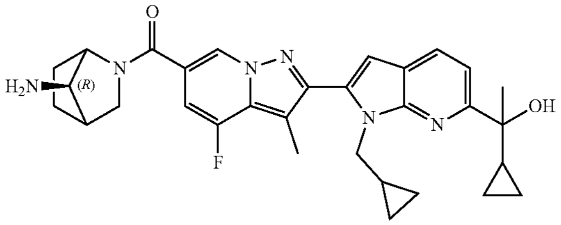

Compound of Example 384 was prepared following a procedure similar to the preparation of Example 102, from Intermediate 39E and using cyclopropyl magnesium bromide in Grignard addition reaction. LC-MS m/z: 543.2 $[M+H]^+$; HPLC retention time: 1.812 min (Method E).

Example 385

1-(2-{6-[(3R)-3-Aminopiperidine-1-carbonyl]-3-methylpyrazolo[1,5-a]pyridin-2-yl}-1-(cyclopropylmethyl)-1H-pyrrolo[2,3-b]pyridin-6-yl)ethan-1-ol (Diastereomeric mixture)

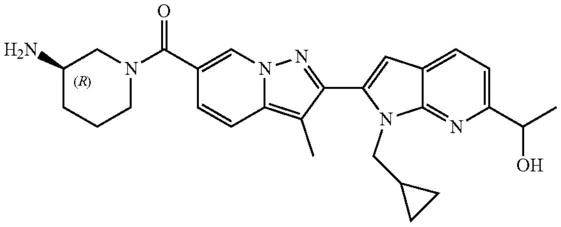

Compound of Example 385 was obtained by amide formation of Intermediate 64D with tert-butyl (R)-piperidin-3-ylcarbamate following the procedure to the preparation of Example 104. LC-MS m/z: 473.3 $[M+H]^+$; HPLC retention time: 1.259 min (Method E).

Examples 386 and 387

((R)-3-Aminopiperidin-1-yl)(2-(1-(cyclopropylmethyl)-7-(1-(tetrahydro-2H-pyran-2-carbonyl)piperidin-4-yl)-1H-indol-2-yl)-4-methoxy-3-methylpyrazolo[1,5-a]pyridin-6-yl)methanone (isomer 1)

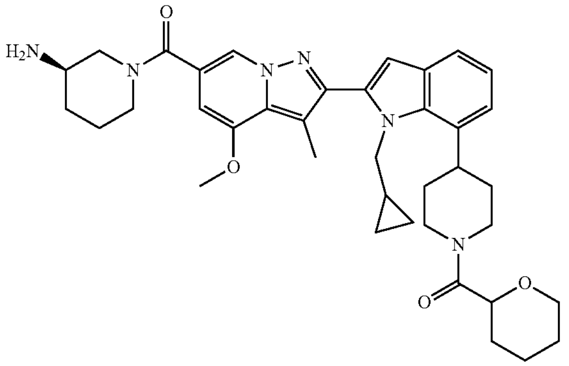 [SMILES: COc1cc(C(=O)N2CCC[C@@H](N)C2)cn2nc(-c3cc4cccc(C5CCN(C(=O)C6CCCCO6)CC5)c4n3CC3CC3)c(C)c12]

Intermediate 386A

Methyl 2-(7-(1-(tert-butoxycarbonyl)piperidin-4-yl)-1-(cyclopropylmethyl)-1H-indol-2-yl)-4-methoxy-3-methylpyrazolo[1,5-a]pyridine-6-carboxylate

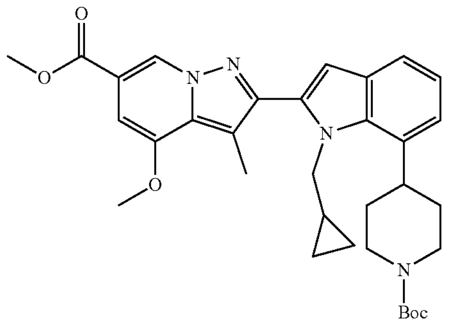 [SMILES: COC(=O)c1cc(OC)c2c(C)c(-c3cc4cccc(C5CCN(C(=O)OC(C)(C)C)CC5)c4n3CC3CC3)nn2c1]

Intermediate 1 (1.042 g, 5.69 mmol) and copper(I) iodide (0.542 g, 2.84 mmol) were added to a stirred solution of Intermediate 30 (2.5 g, 5.69 mmol) in DMF (5 ml). The reaction mixture was heated to 80° C. for 48 hours, allowed to cool to a room temperature, diluted with water (100 m), and extracted with ethyl acetate (2×100 ml). The combined organic layers were dried over sodium sulphate, filtered, and concentrated under reduced pressure to obtain a crude product, which was purified using silica a gel column (0-20% ethyl acetate in hexane) to afford methyl 2-(7-(1-(tert-butoxycarbonyl)piperidin-4-yl)-1-(cyclopropylmethyl)-1H-indol-2-yl)-4-methoxy-3-methylpyrazolo[1,5-a]pyridine-6-carboxylate (1.6 g, 49%). LC-MS 573.3 $[M+H]^+$; $^1H$ NMR (400 MHz, chloroform-d) δ ppm: 8.84-8.86 (s, 1H), 7.53-7.61 (m, 1H), 7.14-7.19 (m, 2H), 6.87 (s, 1H), 6.77 (s, 1H), 4.44 (d, J=6.50 Hz, 2H), 4.04 (s, 3H), 4.01-3.97 (m, 4H), 3.93 (s, 3H), 2.89-3.00 (m, 1H), 2.55 (s, 3H), 2.08-2.05 (m, 2H), 1.76-1.94 (m, 2H), 1.53 (s, 9H), 0.88-1.03 (m, 1H), 0.17-0.33 (m, 2H), 0.18-0.06 (m, 2H).

Intermediate 386B

Methyl 2-(1-(cyclopropylmethyl)-7-(piperidin-4-yl)-1H-indol-2-yl)-4-methoxy-3-methylpyrazolo[1,5-a]pyridine-6-carboxylate

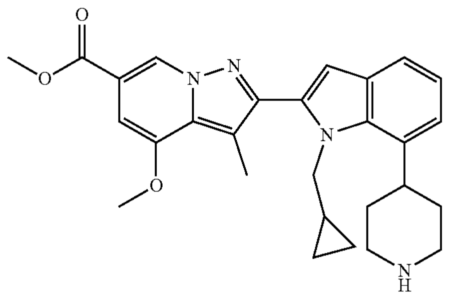 [SMILES: COC(=O)c1cc(OC)c2c(C)c(-c3cc4cccc(C5CCNCC5)c4n3CC3CC3)nn2c1]

TFA (0.210 ml, 2.73 mmol) was added to a stirred solution of Intermediate 386A (1.6 g, 2.73 mmol) in DCM (15 ml) at 0° C. The reaction mixture was stirred for 3 hours at a room temperature, and concentrated under reduced pressure to obtain methyl 2-(1-(cyclopropylmethyl)-7-(piperidin-4-yl)-1H-indol-2-yl)-4-methoxy-3-methylpyrazolo[1,5-a]pyridine-6-carboxylate (1.1 g, 85%). LC-MS m/z: 473.4 $[M+H]^+$.

Intermediate 386C

Methyl 2-(1-(cyclopropylmethyl)-7-(1-(tetrahydro-2H-pyran-2-carbonyl)piperidin-4-yl)-1H-indol-2-yl)-4-methoxy-3-methylpyrazolo[1,5-a]pyridine-6-carboxylate

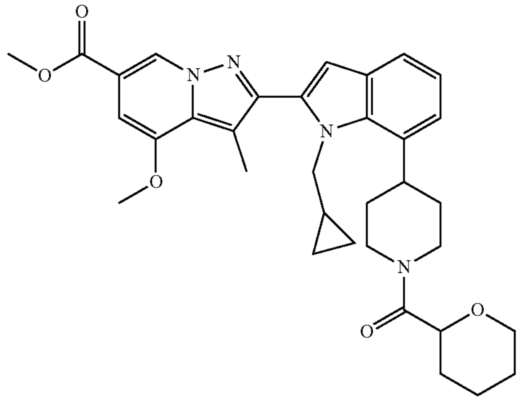 [SMILES: COC(=O)c1cc(OC)c2c(C)c(-c3cc4cccc(C5CCN(C(=O)C6CCCCO6)CC5)c4n3CC3CC3)nn2c1]

Racemic tetrahydro-2H-pyran-2-carboxylic acid (55.1 mg, 0.423 mmol), DIPEA (0.222 ml, 1.270 mmol) and HATU (241 mg, 0.635 mmol) were added to a stirred solution of Intermediate 386B (200 mg, 0.423 mmol) in DMF (2 ml). The reaction mixture was stirred for 3 hours, quenched with water, the solids obtained were filtered and dried in vacuo to obtain methyl 2-(1-(cyclopropylmethyl)-7-(1-(tetrahydro-2H-pyran-2-carbonyl) piperidin-4-yl)-1H-indol-2-yl)-4-methoxy-3-methylpyrazolo[1,5-a]pyridine-6-carboxylate (180 mg, 73%). LC-MS m/z: 585.4 $[M+H]^+$.

Intermediate 386D 2-(1-(Cyclopropylmethyl)-7-(1-(tetrahydro-2H-pyran-2-carbonyl)piperidin-4-yl)-1H-indol-2-yl)-4-methoxy-3-methylpyrazolo[1,5-a]pyridine-6-carboxylic acid

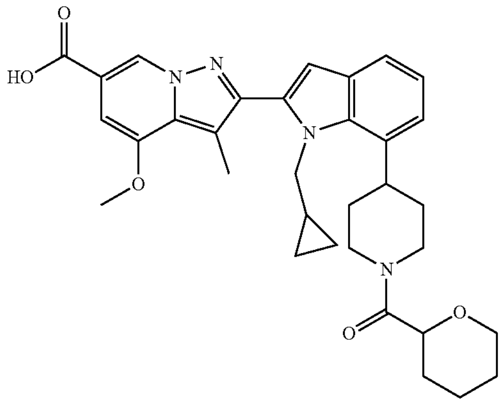 [SMILES: COc1cc(C(=O)O)cn2nc(-c3cc4cccc(C5CCN(C(=O)C6CCCCO6)CC5)c4n3CC3CC3)c(C)c12]

LiOH (7.37 mg, 0.308 mmol) was added to a stirred solution of Intermediate 386C (180 mg, 0.308 mmol) in a mixture of solvents [THF (1 ml), methanol (1.0 ml) and water (1 ml)]. The reaction mixture was stirred for 4 hours, concentrated under reduced pressure to obtain crude salts, which were acidified with 1 N HCl. The solids thus obtained were filtered through Buchner funnel and dried under vacuo to obtain 2-(1-(cyclopropylmethyl)-7-(1-(tetrahydro-2H-pyran-2-carbonyl)piperidin-4-yl)-1H-indol-2-yl)-4-methoxy-3-methylpyrazolo[1,5-a]pyridine-6-carboxylic acid (160 mg, 91%). LC-MS m/z: 571.2 $[M+H]^+$.

Intermediate 386E & Intermediate 386F tert-Butyl ((3R)-1-(2-(1-(cyclopropylmethyl)-7-(1-(tetrahydro-2H-pyran-2-carbonyl)piperidin-4-yl)-1H-indol-2-yl)-4-methoxy-3-methylpyrazolo[1,5-a]pyridine-6-carbonyl)piperidin-3-yl)carbamate

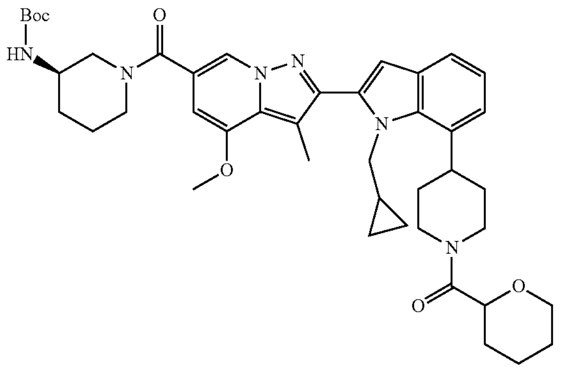 [SMILES: COc1cc(C(=O)N2CCC[C@@H](NC(=O)OC(C)(C)C)C2)cn2nc(-c3cc4cccc(C5CCN(C(=O)C6CCCCO6)CC5)c4n3CC3CC3)c(C)c12]

tert-Butyl (R)-piperidin-3-ylcarbamate (35.1 mg, 0.175 mmol), DIPEA (0.092 ml, 0.526 mmol) and HATU (100 mg, 0.263 mmol) were added to a stirred solution of Intermediate 386D (100 mg, 0.175 mmol) in DMF (1 ml). The reaction mixture was stirred for 3 hours, quenched with water (50 ml), and the solids obtained were filtered and dried to obtain a crude product, which was purified by SFC chiral purification to afford corresponding homochiral isomers. (Preparative SFC Conditions Column/dimensions: Whelk (R, R) (250×30) mm, 5u % $CO_2$: 60%, Co solvent: 40% of 5 mM Ammonium Acetate in [MeOH+ACN(1:1)], total flow: 170.0 g/min, back Pressure: 100 bar, temperature: 40° C., UV: 225 nm.

Isomer 1 (Intermediate 386E): tert-butyl ((3R)-1-(2-(1-(cyclopropylmethyl)-7-(1-(tetrahydro-2H-pyran-2-carbonyl)piperidin-4-yl)-1H-indol-2-yl)-4-methoxy-3-methylpyrazolo[1,5-a]pyridine-6-carbonyl)piperidin-3-yl) carbamate (40 mg, 61%). LC-MS m/z: 753.7 $[M+H]^+$.

Isomer 2 (Intermediate 386F): tert-butyl ((3R)-1-(2-(1-(cyclopropylmethyl)-7-(1-(tetrahydro-2H-pyran-2-carbonyl)piperidin-4-yl)-1H-indol-2-yl)-4-methoxy-3-methylpyrazolo[1,5-a]pyridine-6-carbonyl)piperidin-3-yl) carbamate (40 mg, 61%). LC-MS m/z: 753.7 $[M+H]^+$.

Example 386

((R)-3-Aminopiperidin-1-yl)(2-(1-(cyclopropylmethyl)-7-(1-(tetrahydro-2H-pyran-2-carbonyl)piperidin-4-yl)-1H-indol-2-yl)-4-methoxy-3-methylpyrazolo[1,5-a]pyridin-6-yl)methanone (isomer 1)

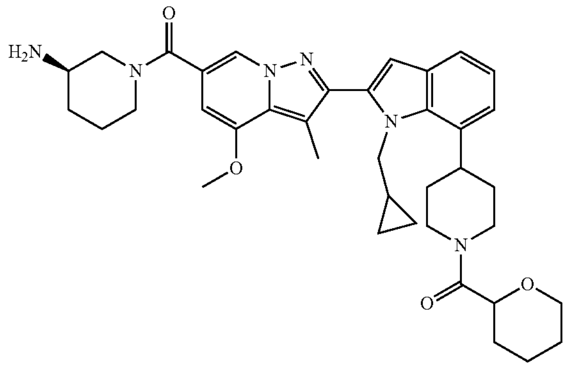 [SMILES: COc1cc(C(=O)N2CCC[C@@H](N)C2)cn2nc(-c3cc4cccc(C5CCN(C(=O)C6CCCCO6)CC5)c4n3CC3CC3)c(C)c12]

TFA (0.053 mmol) was added to a stirred solution of 386E (40 mg, 0.053 mmol) in DCM (1 ml) at 0° C. The reaction mixture was allowed to warm to a room temperature and stirred for 3 hours, concentrated in vacuo to obtain a crude product, which was purified using preparative LC/MS with the following conditions: Column: Waters X Bridge C18, 150 mm×19 mm, 5-μm particles; mobile phase A: 5:95 acetonitrile:water with 0.1% trifluoroacetic acid; mobile phase B: 95:5 acetonitrile:water with 0.1% trifluoroacetic acid; gradient: a 0-minute hold at 20% B, 20-40% B over 20 minutes, then a 5-minute hold at 100% B; flow rate: 20 ml/min, column temperature: 25° C. Fraction collection was triggered by signals. Fractions containing the desired product were combined and dried via centrifugal evaporation. The purified material was diluted with a 1:1 mixture of ethylene dichloride and methanol (EDM), treated with Si-Pyridine and shaken for a minimum of 2 hours, the resulting mixture was filtered and dried via centrifugal evaporation to afford ((R)-3-aminopiperidin-1-yl) (2-(1-(cyclopropylmethyl)-7-(1-(tetrahydro-2H-pyran-2-carbonyl)piperidin-4-yl)-1H-indol-2-yl)-4-methoxy-3-methylpyrazolo[1,5-a]pyridin-6-yl)methanone (isomer 1, 3 mg, 8%). LC-MS m/z: 653.5 $[M+H]^+$. LCMS retention time: 1.825 min (method E). $^1$H NMR (400 MHz, DMSO-$d_6$) δ ppm: 8.46 (s, 1H), 7.49 (d, J=6.69 Hz, 1H), 7.08 (m, 2H), 6.72 (s, 1H), 6.62 (s, 1H), 4.62-4.57 (m, 1H), 4.41 (d, J=6.11 Hz, 2H), 4.24-4.14 (m, 2H), 3.99 (s, 3H), 3.93-3.85 (m, 2H), 3.68-3.58 (m, 1H), 3.55-3.45 (m, 1H), 3.30-3.20 (m, 4H), 2.53-2.56 (m, 2H), 2.47 (s, 3H), 2.05-1.95 (m, 4H), 1.87-1.72 (m, 4H), 1.70-1.55 (m, 6H), 1.53-1.44 (m, 2H), 1.0-0.9 (m, 1H), 0.23 (d, J=8.31 Hz, 2H),−0.18 (m, 2H).

Example 387

((R)-3-Aminopiperidin-1-yl)(2-(1-(cyclopropylmethyl)-7-(1-(tetrahydro-2H-pyran-2-carbonyl)piperidin-4-yl)-1H-indol-2-yl)-4-methoxy-3-methylpyrazolo[1,5-a]pyridin-6-yl)methanone (isomer 2)

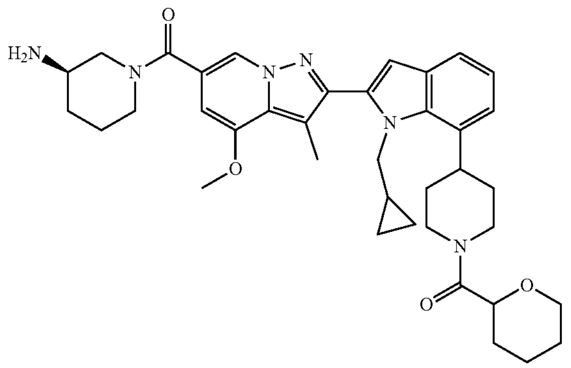 [SMILES: COc1cc(C(=O)N2CCC[C@@H](N)C2)cn2nc(-c3cc4cccc(C5CCN(C(=O)C6CCCCO6)CC5)c4n3CC3CC3)c(C)c12]

Compound of Example 387 was prepared in a similar fashion like Example 386 using the intermediate 386F.

Compounds of Examples 388 to 412 in Table 46 were prepared following a procedure similar to the preparation of a compound of Example 386, by acid amine coupling of Intermediate 386B with appropriate carboxylic acid and amines.

TABLE 46

| Example | Structure<br>Name<br>Analytical Data: LC-MS m/z $[M + H]^+$; HPLC retention time (HPLC method) |
|---|---|
| 388 | 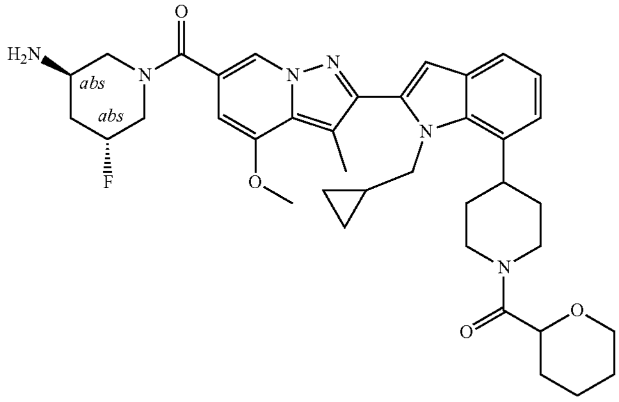 [SMILES: COc1cc(C(=O)N2C[C@H](N)C[C@@H](F)C2)cn2nc(-c3cc4cccc(C5CCN(C(=O)C6CCCCO6)CC5)c4n3CC3CC3)c(C)c12]<br>((3R,5R)-3-Amino-5-fluoropiperidin-1-yl)(2-(1-(cyclopropylmethyl)-7-(1-(tetrahydro-2H-pyran-2-carbonyl)piperidin-4-yl)-1H-indol-2-yl)-4-methoxy-3-methylpyrazolo[1,5-a]pyridin-6-yl)methanone (isomer 1)<br>Analytical Data: 671.; 1.953 min (Method E) |
| 389 | 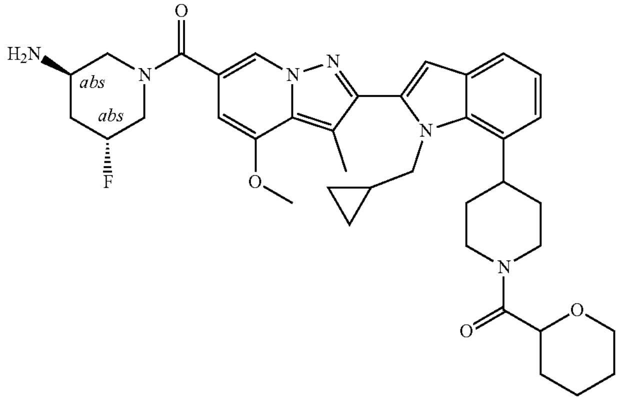 [SMILES: COc1cc(C(=O)N2C[C@H](N)C[C@@H](F)C2)cn2nc(-c3cc4cccc(C5CCN(C(=O)C6CCCCO6)CC5)c4n3CC3CC3)c(C)c12]<br>((3R,5R)-3-Amino-5-fluoropiperidin-1-yl)(2-(1-(cyclopropylmethyl)-7-(1-(tetrahydro-2H-pyran-2-carbonyl)piperidin-4-yl)-1H-indol-2-yl)-4-methoxy-3-methylpyrazolo[1,5-a]pyridin-6-yl)methanone (isomer 2)<br>Analytical Data: 671.4; 1.951 min (Method E) |
| 390 | 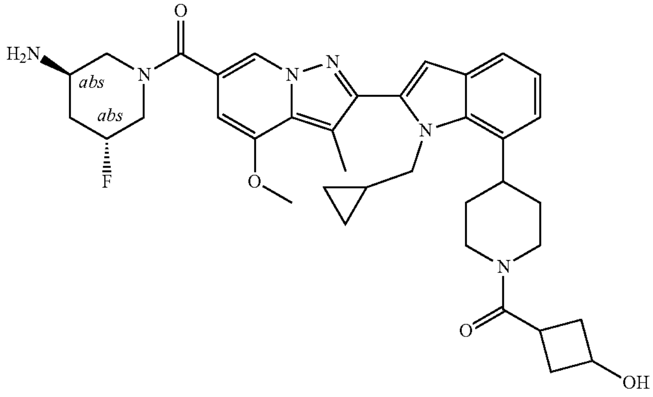 [SMILES: COc1cc(C(=O)N2C[C@H](N)C[C@@H](F)C2)cn2nc(-c3cc4cccc(C5CCN(C(=O)C6CC(O)C6)CC5)c4n3CC3CC3)c(C)c12]<br>((3R,5R)-3-Amino-5-fluoropiperidin-1-yl)(2-(1-(cyclopropylmethyl)-7-(1-(3-hydroxycyclobutane-1-carbonyl)piperidin-4-yl)-1H-indol-2-yl)-4-methoxy-3-methylpyrazolo[1,5-a]pyridin-6-yl)methanone (isomer 1)<br>Analytical Data: 657.3; 1.502 min (Method E) |

TABLE 46-continued

| Example | Structure<br>Name<br>Analytical Data: LC-MS m/z [M + H]+; HPLC retention time (HPLC method) |
|---|---|
| 391 | 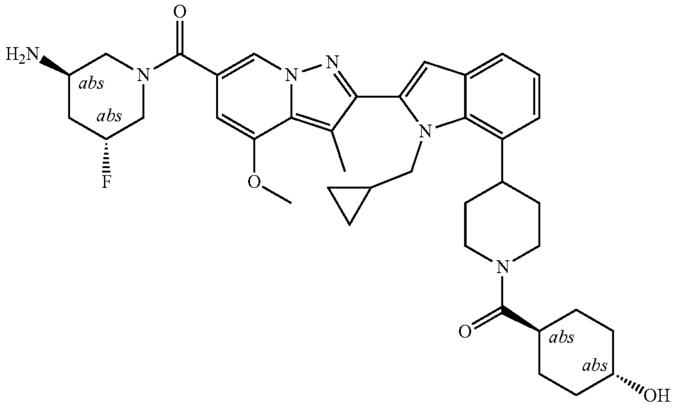 [SMILES: COc1cc(C(=O)N2C[C@H](N)C[C@@H](F)C2)cn2nc(-c3cc4cccc(C5CCN(C(=O)[C@H]6CC[C@H](O)CC6)CC5)c4n3CC3CC3)c(C)c12]<br>((3R,5R)-3-Amino-5-fluoropiperidin-1-yl)(2-(1-(cyclopropylmethyl)-7-(1-((1r,4r)-4-hydroxycyclohexane-1-carbonyl)piperidin-4-yl)-1H-indol-2-yl)-4-methoxy-3-methylpyrazolo[1,5-a]pyridin-6-yl)methanone<br>Analytical Data: 685.3; 1.625 min (Method E) |
| 392 | 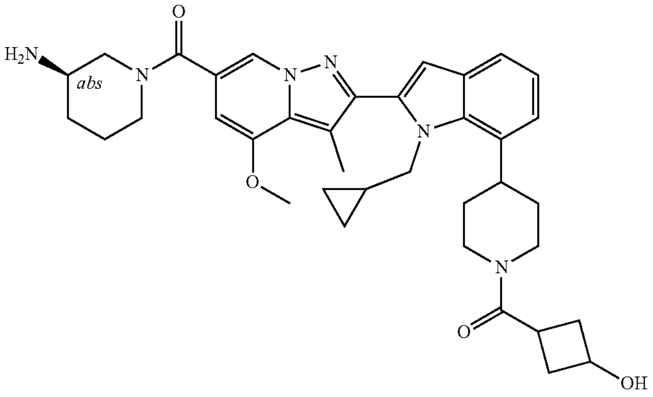 [SMILES: COc1cc(C(=O)N2CCC[C@@H](N)C2)cn2nc(-c3cc4cccc(C5CCN(C(=O)C6CC(O)C6)CC5)c4n3CC3CC3)c(C)c12]<br>(R)-(3-Aminopiperidin-1-yl)(2-(1-(cyclopropylmethyl)-7-(1-(3-hydroxycyclobutane-1-carbonyl)piperidin-4-yl)-1H-indol-2-yl)-4-methoxy-3-methylpyrazolo[1,5-a]pyridin-6-yl)methanone (isomer 1)<br>Analytical Data: 639.3; 1.512 min (Method E) |
| 393 | 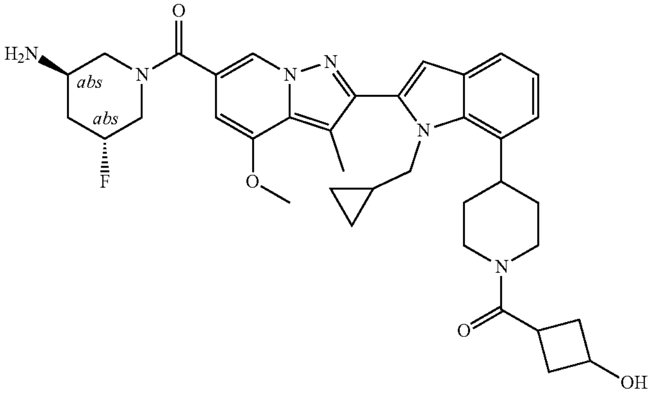 [SMILES: COc1cc(C(=O)N2C[C@H](N)C[C@@H](F)C2)cn2nc(-c3cc4cccc(C5CCN(C(=O)C6CC(O)C6)CC5)c4n3CC3CC3)c(C)c12]<br>((3R,5R)-3-Amino-5-fluoropiperidin-1-yl)(2-(1-(cyclopropylmethyl)-7-(1-(3-hydroxycyclobutane-1-carbonyl)piperidin-4-yl)-1H-indol-2-yl)-4-methoxy-3-methylpyrazolo[1,5-a]pyridin-6-yl)methanone (isomer 2)<br>Analytical Data: 657.3; 1.534 min (Method E) |

TABLE 46-continued

| Example | Structure<br>Name<br>Analytical Data: LC-MS m/z $[M + H]^+$; HPLC retention time (HPLC method) |
|---|---|
| 394 | 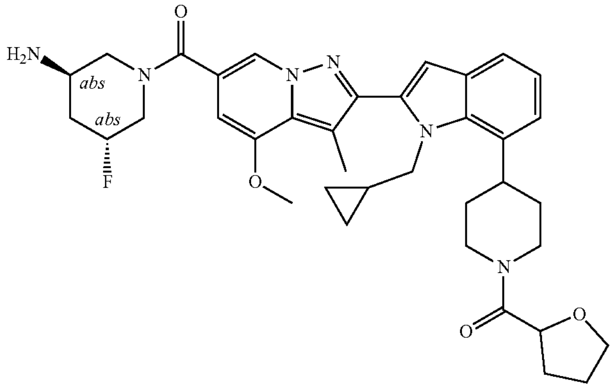 [SMILES: COc1cc(C(=O)N2C[C@H](N)C[C@@H](F)C2)cn2nc(-c3cc4cccc(C5CCN(C(=O)C6CCCO6)CC5)c4n3CC3CC3)c(C)c12]<br>((3R,5R)-3-Amino-5-fluoropiperidin-1-yl)(2-(1-(cyclopropylmethyl)-7-(1-(tetrahydrofuran-2-carbonyl)piperidin-4-yl)-1H-indol-2-yl)-4-methoxy-3-methylpyrazolo[1,5-a]pyridin-6-yl)methanone (isomer 1)<br>Analytical Data: 657.3; 1.664 min (Method E) |
| 395 | 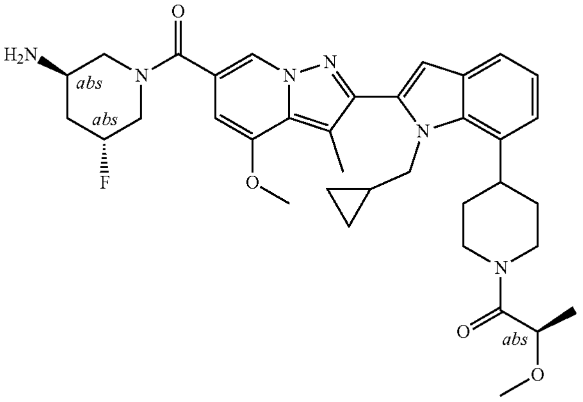 [SMILES: COc1cc(C(=O)N2C[C@H](N)C[C@@H](F)C2)cn2nc(-c3cc4cccc(C5CCN(C(=O)[C@@H](C)OC)CC5)c4n3CC3CC3)c(C)c12]<br>(R)-1-(4-(2-(6-((3R,5R)-3-Amino-5-fluoropiperidine-1-carbonyl)-4-methoxy-3-methylpyrazolo[1,5-a]pyridin-2-yl)-1-(cyclopropylmethyl)-1H-indol-7-yl)piperidin-1-yl)-2-methoxypropan-1-one<br>Analytical Data: 645.3; 1.735 min (Method E) |
| 396 | 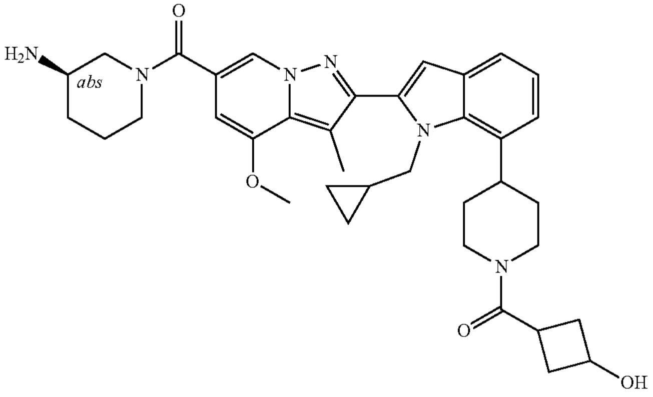 [SMILES: COc1cc(C(=O)N2CCC[C@@H](N)C2)cn2nc(-c3cc4cccc(C5CCN(C(=O)C6CC(O)C6)CC5)c4n3CC3CC3)c(C)c12]<br>(R)-(3-Aminopiperidin-1-yl)(2-(1-(cyclopropylmethyl)-7-(1-(3-hydroxycyclobutane-1-carbonyl)piperidin-4-yl)-1H-indol-2-yl)-4-methoxy-3-methylpyrazolo[1,5-a]pyridin-6-yl)methanone (isomer 1)<br>Analytical Data: 639.3; 1.520 min (Method E) |

TABLE 46-continued

| Example | Structure<br>Name<br>Analytical Data: LC-MS m/z [M + H]+; HPLC retention time (HPLC method) |
|---|---|
| 397 | 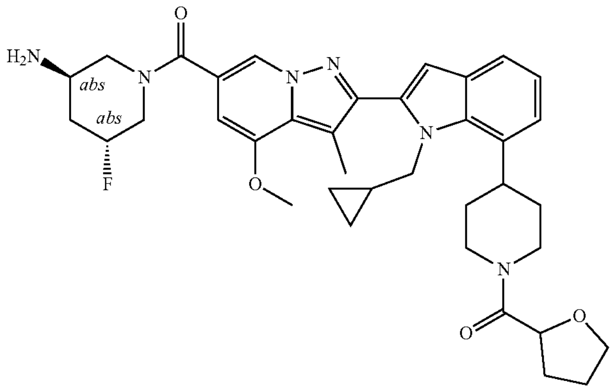 [SMILES: COc1cc(C(=O)N2C[C@H](N)C[C@@H](F)C2)cn2nc(-c3cc4cccc(C5CCN(C(=O)C6CCCO6)CC5)c4n3CC3CC3)c(C)c12]<br>((3R,5R)-3-Amino-5-fluoropiperidin-1-yl)(2-(1-(cyclopropylmethyl)-7-(1-(tetrahydrofuran-2-carbonyl)piperidin-4-yl)-1H-indol-2-yl)-4-methoxy-3-methylpyrazolo[1,5-a]pyridin-6-yl)methanone (isomer 2)<br>Analytical Data: 657.3; 1.676 min (Method E) |
| 398 | 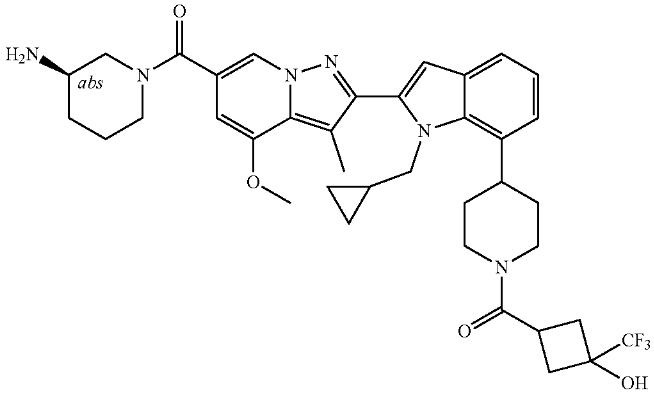 [SMILES: COc1cc(C(=O)N2CCC[C@@H](N)C2)cn2nc(-c3cc4cccc(C5CCN(C(=O)C6CC(O)(C(F)(F)F)C6)CC5)c4n3CC3CC3)c(C)c12]<br>(R)-(3-Aminopiperidin-1-yl)(2-(1-(cyclopropylmethyl)-7-(1-(3-hydroxy-3-(trifluoromethyl)cyclobutane-1-carbonyl)piperidin-4-yl)-1H-indol-2-yl)-4-methoxy-3-methylpyrazolo[1,5-a]pyridin-6-yl)methanone (mixture of diastereomers)<br>Analytical Data: 707.3; 1.774 min (Method E) |
| 399 | 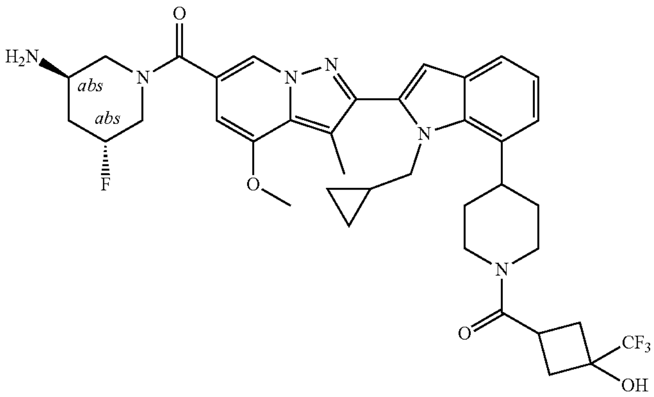 [SMILES: COc1cc(C(=O)N2C[C@H](N)C[C@@H](F)C2)cn2nc(-c3cc4cccc(C5CCN(C(=O)C6CC(O)(C(F)(F)F)C6)CC5)c4n3CC3CC3)c(C)c12]<br>((3R,5R)-3-Amino-5-fluoropiperidin-1-yl)(2-(1-(cyclopropylmethyl)-7-(1-(3-hydroxy-3-(trifluoromethyl)cyclobutane-1-carbonyl)piperidin-4-yl)-1H-indol-2-yl)-4-methoxy-3-methylpyrazolo[1,5-a]pyridin-6-yl)methanone (mixture of diastereomers)<br>Analytical Data: 725.3; 1.793 min (Method E) |

TABLE 46-continued

| Example | Structure<br>Name<br>Analytical Data: LC-MS m/z [M + H]$^+$; HPLC retention time (HPLC method) |
|---|---|
| 400 | 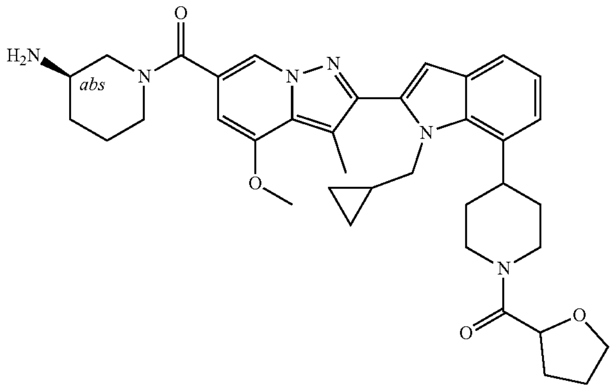 [SMILES: COc1cc(C(=O)N2CCC[C@@H](N)C2)cn2nc(-c3cc4cccc(C5CCN(C(=O)C6CCCO6)CC5)c4n3CC3CC3)c(C)c12]<br>((R)-3-Aminopiperidin-1-yl)(2-(1-(cyclopropylmethyl)-7-(1-(tetrahydrofuran-2-carbonyl)piperidin-4-yl)-1H-indol-2-yl)-4-methoxy-3-methylpyrazolo[1,5-a]pyridin-6-yl)methanone (mixture of diastereomers)<br>Analytical Data: 639.3; 1.657 min (Method E) |
| 401 | 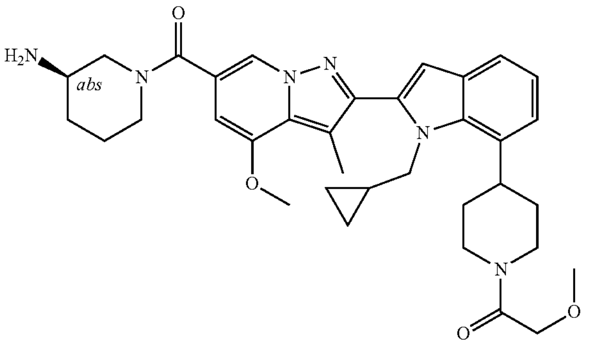 [SMILES: COCC(=O)N1CCC(c2cccc3cc(-c4nn5cc(C(=O)N6CCC[C@@H](N)C6)cc(OC)c5c4C)n(CC4CC4)c23)CC1]<br>(R)-1-(4-(2-(6-(3-Aminopiperidine-1-carbonyl)-4-methoxy-3-methylpyrazolo[1,5-a]pyridin-2-yl)-1-(cyclopropylmethyl)-1H-indol-7-yl)piperidin-1-yl)-2-methoxyethan-1-one<br>Analytical Data: 613.3; 1.565 min (Method E) |
| 402 | 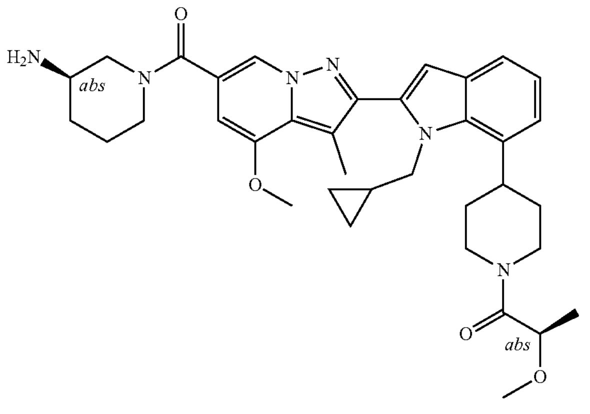 [SMILES: COc1cc(C(=O)N2CCC[C@@H](N)C2)cn2nc(-c3cc4cccc(C5CCN(C(=O)[C@@H](C)OC)CC5)c4n3CC3CC3)c(C)c12]<br>(R)-1-(4-(2-(6-((R)-3-Aminopiperidine-1-carbonyl)-4-methoxy-3-methylpyrazolo[1,5-a]pyridin-2-yl)-1-(cyclopropylmethyl)-1H-indol-7-yl)piperidin-1-yl)-2-methoxypropan-1-one<br>Analytical Data: 627.3; 1.603 min (Method E) |

TABLE 46-continued

| Example | Structure<br>Name<br>Analytical Data: LC-MS m/z [M + H]$^+$; HPLC retention time (HPLC method) |
|---|---|
| 403 | 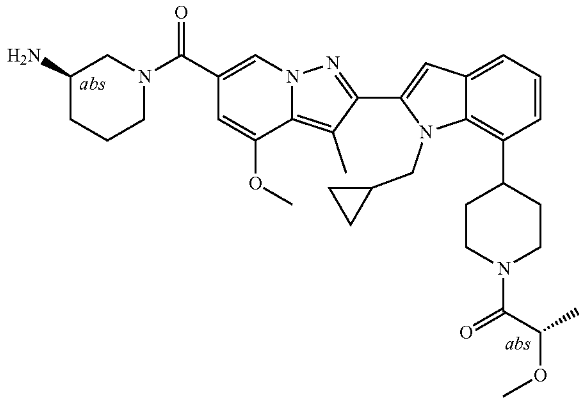 [SMILES: COc1cc(C(=O)N2CCC[C@@H](N)C2)cn2nc(-c3cc4cccc(C5CCN(C(=O)[C@H](C)OC)CC5)c4n3CC3CC3)c(C)c12]<br>(S)-1-(4-(2-(6-((R)-3-Aminopiperidine-1-carbonyl)-4-methoxy-3-methylpyrazolo[1,5-a]pyridin-2-yl)-1-(cyclopropylmethyl)-1H-indol-7-yl)piperidin-1-yl)-2-methoxypropan-1-one<br>Analytical Data: 627.3; 1.698 min (Method E) |
| 404 | 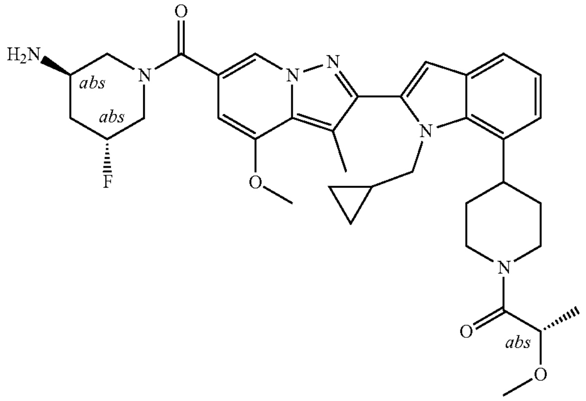 [SMILES: COc1cc(C(=O)N2C[C@H](N)C[C@@H](F)C2)cn2nc(-c3cc4cccc(C5CCN(C(=O)[C@H](C)OC)CC5)c4n3CC3CC3)c(C)c12]<br>(S)-1-(4-(2-(6-((3R,5R)-3-Amino-5-fluoropiperidine-1-carbonyl)-4-methoxy-3-methylpyrazolo[1,5-a]pyridin-2-yl)-1-(cyclopropylmethyl)-1H-indol-7-yl)piperidin-1-yl)-2-methoxypropan-1-one<br>Analytical Data: 645.3; 1.751 min (Method E) |
| 405 | 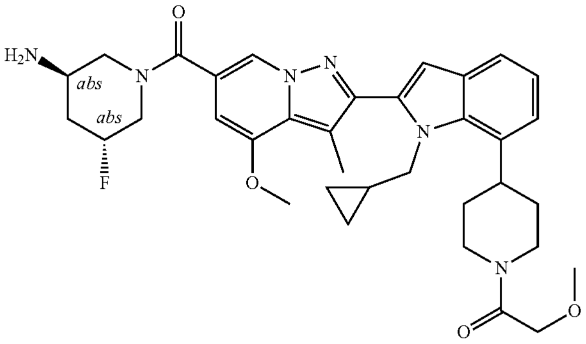 [SMILES: COCC(=O)N1CCC(c2cccc3cc(-c4nn5cc(C(=O)N6C[C@H](N)C[C@@H](F)C6)cc(OC)c5c4C)n(CC4CC4)c23)CC1]<br>1-(4-(2-(6-((3R,5R)-3-Amino-5-fluoropiperidine-1-carbonyl)-4-methoxy-3-methylpyrazolo[1,5-a]pyridin-2-yl)-1-(cyclopropylmethyl)-1H-indol-7-yl)piperidin-1-yl)-2-methoxyethan-1-one<br>Analytical Data: 631.3; 1.681 min (Method E) |

TABLE 46-continued

| Example | Structure<br>Name<br>Analytical Data: LC-MS m/z [M + H]+; HPLC retention time (HPLC method) |
|---|---|
| 406 | 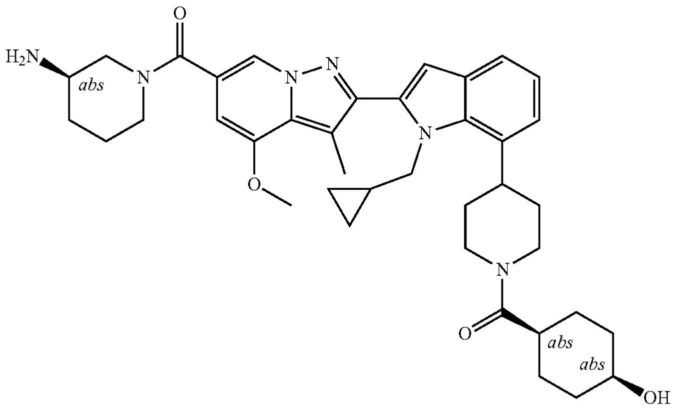 [SMILES: COc1cc(C(=O)N2CCC[C@@H](N)C2)cn2nc(-c3cc4cccc(C5CCN(C(=O)[C@H]6CC[C@@H](O)CC6)CC5)c4n3CC3CC3)c(C)c12]<br>((R)-3-Aminopiperidin-1-yl)(2-(1-(cyclopropylmethyl)-7-(1-((1s,4s)-4-hydroxycyclohexane-1-carbonyl)piperidin-4-yl)-1H-indol-2-yl)-4-methoxy-3-methylpyrazolo[1,5-a]pyridin-6-yl)methanone<br>Analytical Data: 667.3; 1.672 min (Method E) |
| 407 | 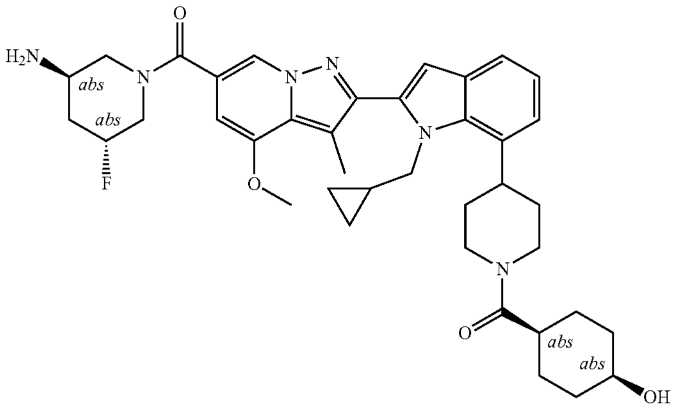 [SMILES: COc1cc(C(=O)N2C[C@H](N)C[C@@H](F)C2)cn2nc(-c3cc4cccc(C5CCN(C(=O)[C@H]6CC[C@@H](O)CC6)CC5)c4n3CC3CC3)c(C)c12]<br>((3R,5R)-3-Amino-5-fluoropiperidin-1-yl)(2-(1-(cyclopropylmethyl)-7-(1-((1s,4s)-4-hydroxycyclohexane-1-carbonyl)piperidin-4-yl)-1H-indol-2-yl)-4-methoxy-3-methylpyrazolo[1,5-a]pyridin-6-yl)methanone<br>Analytical Data: 685.3; 1.721 min (Method E) |
| 408 | 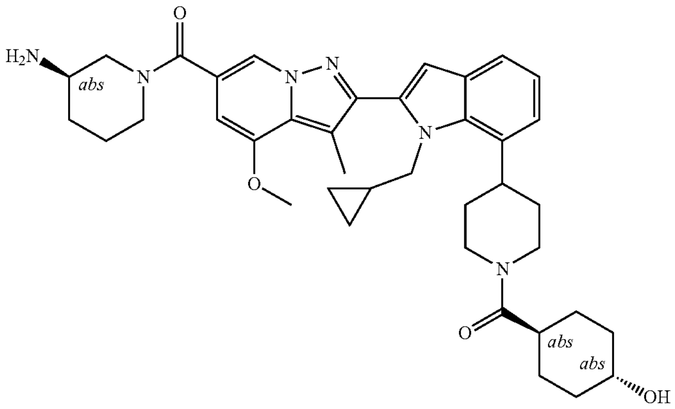 [SMILES: COc1cc(C(=O)N2CCC[C@@H](N)C2)cn2nc(-c3cc4cccc(C5CCN(C(=O)[C@H]6CC[C@H](O)CC6)CC5)c4n3CC3CC3)c(C)c12]<br>((R)-3-Aminopiperidin-1-yl)(2-(1-(cyclopropylmethyl)-7-(1-((1r,4r)-4-hydroxycyclohexane-1-carbonyl)piperidin-4-yl)-1H-indol-2-yl)-4-methoxy-3-methylpyrazolo[1,5-a]pyridin-6-yl)methanone<br>Analytical Data: 667.3; 1.583 min (Method E) |

TABLE 46-continued

| Example | Structure<br>Name<br>Analytical Data: LC-MS m/z [M + H]$^+$; HPLC retention time (HPLC method) |
|---|---|
| 409 | 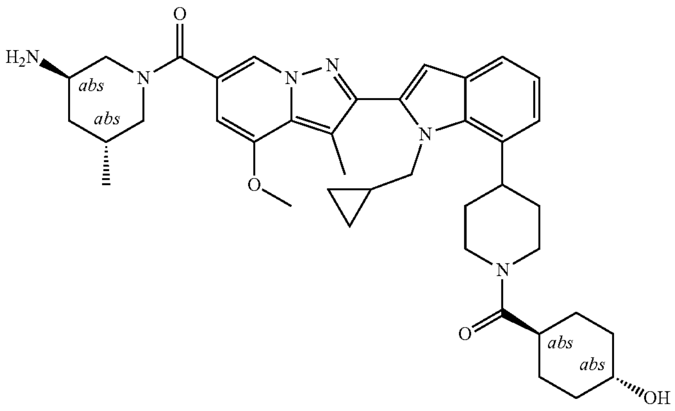 [SMILES: COc1cc(C(=O)N2C[C@H](C)C[C@@H](N)C2)cn2nc(-c3cc4cccc(C5CCN(C(=O)[C@H]6CC[C@H](O)CC6)CC5)c4n3CC3CC3)c(C)c12]<br>((3R,5R)-3-Amino-5-fluoropiperidin-1-yl)(2-(1-(cyclopropylmethyl)-7-(1-((1r,4r)-4-hydroxycyclohexane-1-carbonyl)piperidin-4-yl)-1H-indol-2-yl)-4-methoxy-3-methylpyrazolo[1,5-a]pyridin-6-yl)methanone<br>Analytical Data: 685.3; 1.625 min (Method E) |
| 410 | 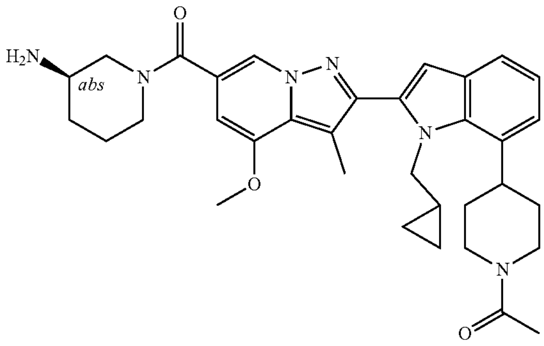 [SMILES: COc1cc(C(=O)N2CCC[C@@H](N)C2)cn2nc(-c3cc4cccc(C5CCN(C(C)=O)CC5)c4n3CC3CC3)c(C)c12]<br>(R)-1-(4-(2-(6-(3-Aminopiperidine-1-carbonyl)-4-methoxy-3-methylpyrazolo[1,5-a]pyridin-2-yl)-1-(cyclopropylmethyl)-1H-indol-7-yl)piperidin-1-yl)ethan-1-one<br>Analytical Data: 583.4; 1.641 min (Method E) |
| 411 | 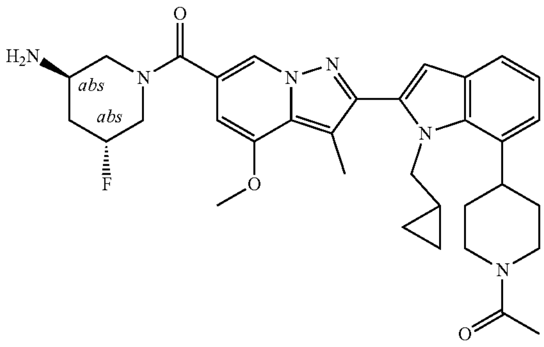 [SMILES: COc1cc(C(=O)N2C[C@H](N)C[C@@H](F)C2)cn2nc(-c3cc4cccc(C5CCN(C(C)=O)CC5)c4n3CC3CC3)c(C)c12]<br>1-(4-(2-(6-((3R,5R)-3-Amino-5-fluoropiperidine-1-carbonyl)-4-methoxy-3-methylpyrazolo[1,5-a]pyridin-2-yl)-1-(cyclopropylmethyl)-1H-indol-7-yl)piperidin-1-yl)ethan-1-one<br>Analytical Data: 601.4; 1.696 min (Method E) |

TABLE 46-continued

| Example | Structure<br>Name<br>Analytical Data: LC-MS m/z [M + H]$^+$; HPLC retention time (HPLC method) |
|---|---|
| 412 | 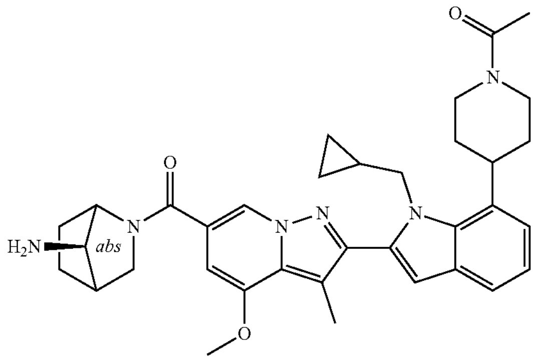 [SMILES: COc1cc(C(=O)N2CC3CCC2[C@@H]3N)cn2nc(-c3cc4cccc(C5CCN(C(C)=O)CC5)c4n3CC3CC3)c(C)c12]<br>1-(4-(2-(6-((7R)-7-Amino-2-azabicyclo[2.2.1]heptane-2-carbonyl)-4-methoxy-3-methylpyrazolo[1,5-a]pyridin-2-yl)-1-(cyclopropylmethyl)-1H-indol-7-yl)piperidin-1-yl)ethan-1-one<br>Analytical Data: 595.4; 8.079 min (Method D) |

Example 413

(R)-1-(4-(2-(6-(3-Aminopiperidine-1-carbonyl)-4-fluoro-3-methylpyrazolo[1,5-a]pyridin-2-yl)-1-(cyclopropylmethyl)-1H-indol-7-yl)piperidin-1-yl)ethan-1-one

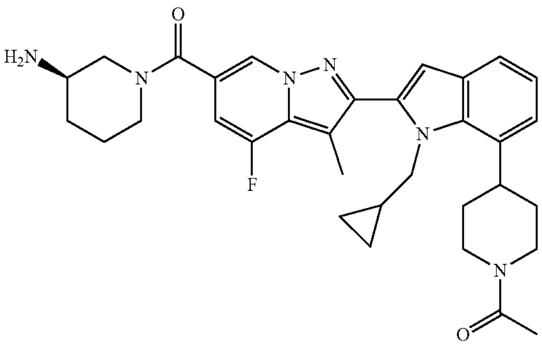 [SMILES: CC(=O)N1CCC(c2cccc3cc(-c4nn5cc(C(=O)N6CCC[C@@H](N)C6)cc(F)c5c4C)n(CC4CC4)c23)CC1]

Intermediate 413A

Methyl 2-(7-(1-(tert-butoxycarbonyl)piperidin-4-yl)-1-(cyclopropylmethyl)-1H-indol-2-yl)-4-fluoro-3-methylpyrazolo[1,5-a]pyridine-6-carboxylate

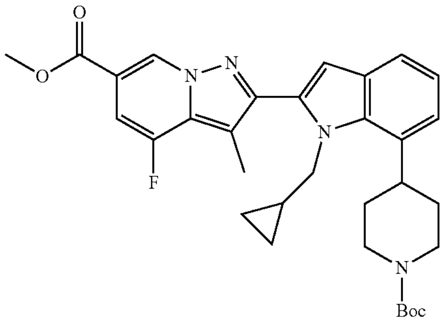 [SMILES: COC(=O)c1cc(F)c2c(C)c(-c3cc4cccc(C5CCN(C(=O)OC(C)(C)C)CC5)c4n3CC3CC3)nn2c1]

Copper(I) iodide (0.260 g, 1.365 mmol) was added to a stirred solution of Intermediate 9 (3.11 g, 18.20 mmol) and Intermediate 30 (2.0 g, 4.55 mmol) in DMF (40 ml). The reaction mixture was heated to 80° C. for 16 hours, filtered through a celite bed, and washed with ethyl acetate. The combined filtrate was washed with water (2×100 ml), followed by 10% sodium bicarbonate solution. The organic layer was dried over anhydrous sodium sulphate and evaporated under reduced pressure to obtain a crude product, which was purified using a silica gel column (0-15% ethyl acetate in pet ether) to afford methyl 2-(7-(1-(tert-butoxycarbonyl)piperidin-4-yl)-1-(cyclopropylmethyl)-1H-indol-2-yl)-4-fluoro-3-methylpyrazolo[1,5-a]pyridine-6-carboxylate (0.38 g, 15%) as a gummy liquid. LC-MS m/z: 561.4 [M+H]$^+$. $^1$H NMR (400 MHz, DMSO-$d_6$) δ ppm: 9.14 (s, 1H), 9.15-9.13 (m, 1H), 7.52 (dd, J=1.3, 7.8 Hz, 1H), 7.42-7.35 (m, 1H), 7.22-7.04 (m, 3H), 6.85 (s, 1H), 4.44 (d, J=6.5 Hz, 2H), 4.15 (br, s, 2H), 3.94-3.90 (m, 3H), 2.49-2.46 (m, 4H), 2.41 (s, 1H), 2.00-1.83 (m, 3H), 1.78-1.56 (m, 3H), 1.53-1.35 (m, 9H), 1.26 (br, d, J=8.5 Hz, 2H), 0.99-0.80 (m, 1H), 0.25-0.21 (m, 2H), −0.01-−0.18 (m, 2H).

Intermediate 413B

Methyl 2-(1-(cyclopropylmethyl)-7-(piperidin-4-yl)-1H-indol-2-yl)-4-fluoro-3-methylpyrazolo[1,5-a]pyridine-6-carboxylate

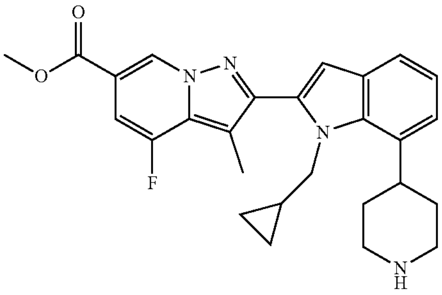 [SMILES: COC(=O)c1cc(F)c2c(C)c(-c3cc4cccc(C5CCNCC5)c4n3CC3CC3)nn2c1]

TFA (0.254 ml, 3.30 mmol) was added to a stirred solution of Intermediate 413A (0.37 g, 0.660 mmol) in DCM (2 ml). The reaction mixture was stirred for 1 hour, and concentrated under reduced pressure to obtain a crude product, which was neutralized using 10% sodium bicarbonate solution and the contents were extracted with ethyl acetate (4×25 ml). The combined organic layers were washed with water and brine solution, dried over anhydrous sodium sulphate, and evaporated under reduced pressure to obtain methyl 2-(1-(cyclopropylmethyl)-7-(piperidin-4-yl)-1H-indol-2-yl)-4-fluoro-3-methylpyrazolo[1,5-a]pyridine-6-carboxylate (0.29 g, 95%). LC-MS m/z: 461.3 [M+H]+.

Intermediate 413C

Methyl 2-(7-(1-acetylpiperidin-4-yl)-1-(cyclopropylmethyl)-1H-indol-2-yl)-4-fluoro-3-methylpyrazolo[1,5-a]pyridine-6-carboxylate

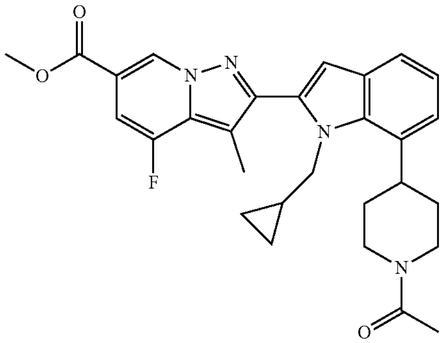 [SMILES: COC(=O)c1cc(F)c2c(C)c(-c3cc4cccc(C5CCN(C(C)=O)CC5)c4n3CC3CC3)nn2c1]

Triethylamine (0.039 ml, 0.282 mmol) was added to a stirred solution of Intermediate 413B (0.13 g, 0.282 mmol) in DCM (3 ml), followed by the addition of acetic anhydride (0.029 g, 0.282 mmol) at 0° C. The reaction mixture was allowed to warm to a room temperature and stirred for 1 hour, diluted with water, and extracted with DCM (3×15 ml). The combined organic layers were washed with water and brine solution, dried over anhydrous sodium sulphate, and evaporated under reduced pressure to obtain methyl 2-(7-(1-acetylpiperidin-4-yl)-1-(cyclopropylmethyl)-1H-indol-2-yl)-4-fluoro-3-methylpyrazolo[1,5-a]pyridine-6-carboxylate (0.12 g, 85%) as gummy liquid, which was used further without purification. LC-MS m/z: 503.4 [M+H]+.

Intermediate 413D 2-(7-(1-Acetylpiperidin-4-yl)-1-(cyclopropylmethyl)-1H-indol-2-yl)-4-fluoro-3-methylpyrazolo[1,5-a]pyridine-6-carboxylic acid

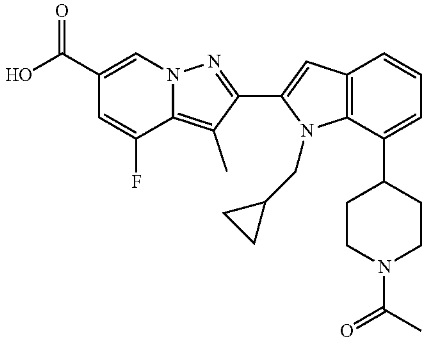 [SMILES: CC(=O)N1CCC(c2cccc3cc(-c4nn5cc(C(=O)O)cc(F)c5c4C)n(CC4CC4)c23)CC1]

Intermediate 413D (0.1 g, 94%) was prepared following a procedure similar to the preparation of Intermediate 386D. LC-MS m/z: 489.4 [M+H]+

Intermediate 413E tert-butyl (R)-(1-(2-(7-(1-acetylpiperidin-4-yl)-1-(cyclopropylmethyl)-1H-indol-2-yl)-4-fluoro-3-methylpyrazolo[1,5-a]pyridine-6-carbonyl)piperidin-3-yl)carbamate

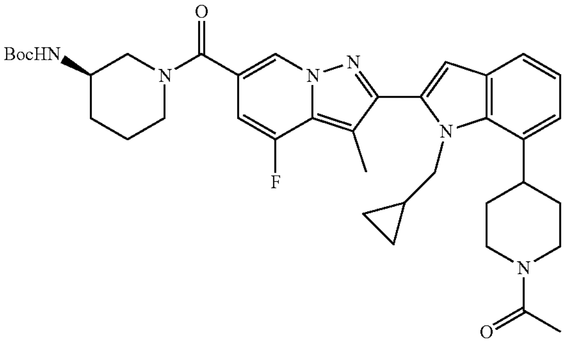 [SMILES: CC(=O)N1CCC(c2cccc3cc(-c4nn5cc(C(=O)N6CCC[C@@H](NC(=O)OC(C)(C)C)C6)cc(F)c5c4C)n(CC4CC4)c23)CC1]

Intermediate 413E was prepared following a procedure similar to the preparation of Intermediate 386E (0.07 g, 85%) as a gummy liquid. LC-MS m/z: 671.5[M+H]+

Example 413

(R)-1-(4-(2-(6-(3-aminopiperidine-1-carbonyl)-4-fluoro-3-methylpyrazolo[1,5-a]pyridin-2-yl)-1-(cyclopropylmethyl)-1H-indol-7-yl)piperidin-1-yl)ethan-1-one

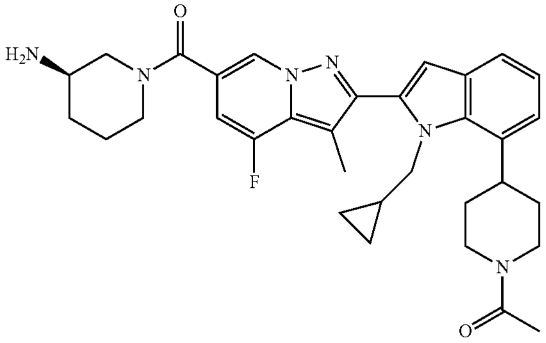 [SMILES: CC(=O)N1CCC(c2cccc3cc(-c4nn5cc(C(=O)N6CCC[C@@H](N)C6)cc(F)c5c4C)n(CC4CC4)c23)CC1]

(R)-1-(4-(2-(6-(3-aminopiperidine-1-carbonyl)-4-fluoro-3-methylpyrazolo[1,5-a]pyridin-2-yl)-1-(cyclopropylmethyl)-1H-indol-7-yl)piperidin-1-yl)ethan-1-one was prepared starting from intermediate 413 E following a procedure similar to the preparation of Example 386. LC-MS m/z: 571.3 [M+H]+. LCMS retention time: 1.64 min (method E). $^1$H NMR (400 MHz, DMSO-$d_6$) δ ppm: 8.74 (s, 1H), 7.51 (dd, J=7.50, 1.00 Hz, 1H), 7.04-7.22 (m, 3H), 6.79 (s, 1H), 4.43 (d, J=6.00 Hz, 2H), 4.1-3.9 (m, 2H), 3.70-3.55 (m, 2H), 3.20-3.07 (m, 2H), 3.07-2.86 (m, 2H), 2.85-2.62 (m, 2H), 2.07 (s, 3H), 2.05-1.95 (m, 2H), 1.92 (s, 3H), 1.90-1.77 (m, 2H), 1.75-1.35 (m, 4H), 1.24-1.22 (m, 2H), 0.97-0.93 (m, 1H), 0.26-0.22 (m, 2H), −0.17-−0.13 (m, 2H).

Compounds of Examples 414 to 429 in Table 47 were prepared following a procedure similar to the preparation of a compound of Example 413, by acid amine coupling of Intermediate 413B with appropriate carboxylic acid followed by ester hydrolysis and the coupling of resulting carboxylic acid with appropriate amines

TABLE 47

| Example | Structure Name<br>Analytical Data: LC-MS m/z [M + H]$^+$; HPLC retention time (HPLC method 1) |
|---|---|
| 414 | 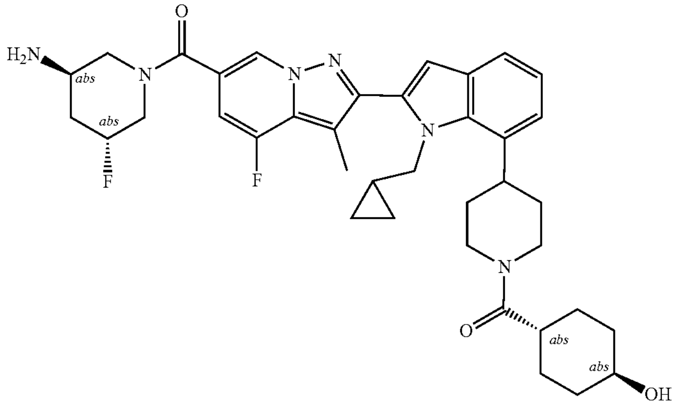 [SMILES: Cc1c(-c2cc3cccc(C4CCN(C(=O)[C@H]5CC[C@H](O)CC5)CC4)c3n2CC2CC2)nn2cc(C(=O)N3C[C@H](N)C[C@@H](F)C3)cc(F)c12]<br>((3R,5R)-3-Amino-5-fluoropiperidin-1-yl)(2-(1-(cyclopropylmethyl)-7-(1-((1r,4r)-4-hydroxycyclohexane-1-carbonyl)piperidin-4-yl)-1H-indol-2-yl)-4-fluoro-3-methylpyrazolo[1,5-a]pyridin-6-yl)methanone<br>Analytical data 673.3; 1.70 min (Method E) |
| 415 | 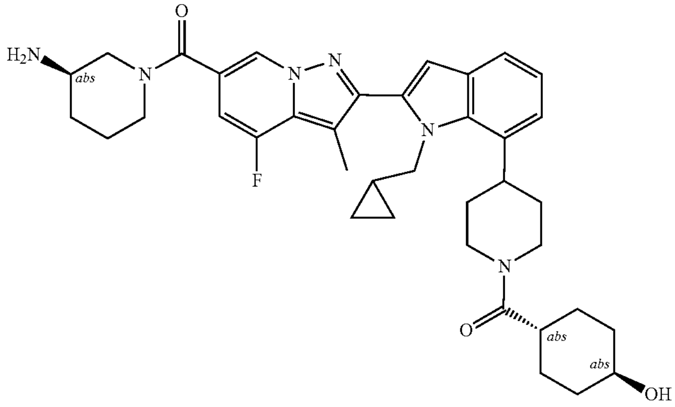 [SMILES: Cc1c(-c2cc3cccc(C4CCN(C(=O)[C@H]5CC[C@H](O)CC5)CC4)c3n2CC2CC2)nn2cc(C(=O)N3CCC[C@@H](N)C3)cc(F)c12]<br>((R)-3-Aminopiperidin-1-yl)(2-(1-(cyclopropylmethyl)-7-(1-((1r,4r)-4-hydroxycyclohexane-1-carbonyl)piperidin-4-yl)-1H-indol-2-yl)-4-fluoro-3-methylpyrazolo[1,5-a]pyridin-6-yl)methanone<br>Analytical data: 655.4; 1.63 min (Method E) |
| 416 | 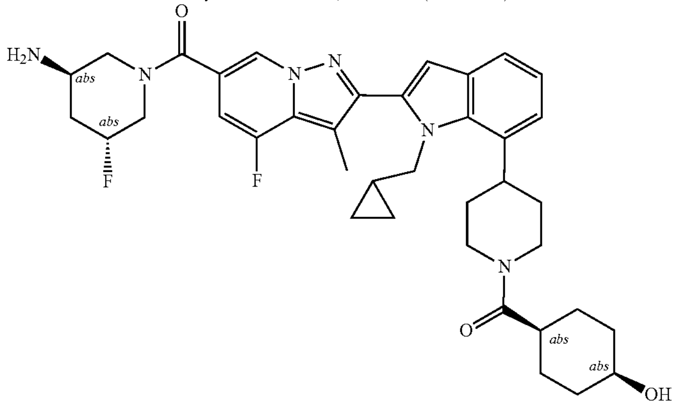<br>((3R,5R)-3-Amino-5-fluoropiperidin-1-yl)(2-(1-(cyclopropylmethyl)-7-(1-((1s,4s)-4-hydroxycyclohexane-1-carbonyl)piperidin-4-yl)-1H-indol-2-yl)-4-fluoro-3-methylpyrazolo[1,5-a]pyridin-6-yl)methanone<br>Analytical data: 673.3; 1.78 min (Method E) |

TABLE 47-continued

| Example | Structure Name<br>Analytical Data: LC-MS m/z [M + H]$^+$; HPLC retention time (HPLC method 1) |
|---|---|
| 417 | 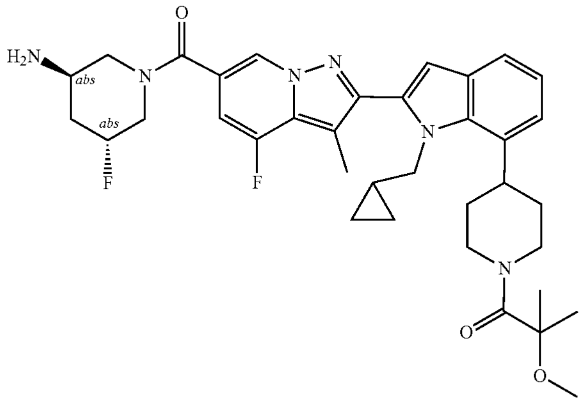 [SMILES: COC(C)(C)C(=O)N1CCC(c2cccc3cc(-c4nn5cc(C(=O)N6C[C@H](N)C[C@@H](F)C6)cc(F)c5c4C)n(CC4CC4)c23)CC1]<br>1-(4-(2-(6-((3R,5R)-3-Amino-5-fluoropiperidin-1-carbonyl)-4-fluoro-3-methylpyrazolo[1,5-a]pyridin-2-yl)-1-(cyclopropylmethyl)-1H-indol-7-yl)piperidin-1-yl)-2-methoxy-2-methylpropan-1-one<br>Analytical data: 647.3; 2.0 min (Method E) |
| 418 | 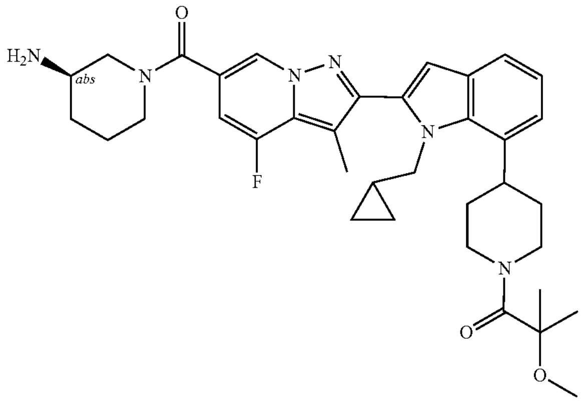 [SMILES: COC(C)(C)C(=O)N1CCC(c2cccc3cc(-c4nn5cc(C(=O)N6CCC[C@@H](N)C6)cc(F)c5c4C)n(CC4CC4)c23)CC1]<br>(R)-1-(4-(2-(6-(3-Aminopiperidin-1-carbonyl)-4-fluoro-3-methylpyrazolo[1,5-a]pyridin-2-yl)-1-(cyclopropylmethyl)-1H-indol-7-yl)piperidin-1-yl)-2-methoxy-2-methylpropan-1-one<br>Analytical data: 629.4; 1.96 min (Method E) |
| 419 | 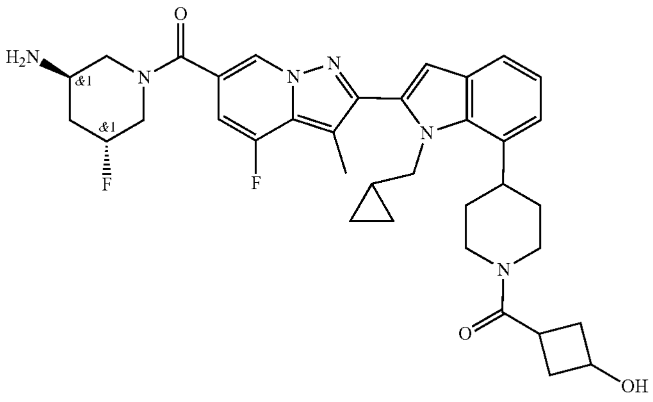 [SMILES: Cc1c(-c2cc3cccc(C4CCN(C(=O)C5CC(O)C5)CC4)c3n2CC2CC2)nn2cc(C(=O)N3C[C@H](N)C[C@@H](F)C3)cc(F)c12]<br>((3R,5R)-3-Amino-5-fluoropiperidin-1-yl)(2-(1-(cyclopropylmethyl)-7-(1-(3-hydroxycyclobutane-1-carbonyl)piperidin-4-yl)-1H-indol-2-yl)-4-fluoro-3-methylpyrazolo[1,5-a]pyridin-6-yl)methanone (mixture of diastereomers)<br>Analytical data: 645.4; 1.51 min (Method E) |

TABLE 47-continued

| Example | Structure Name<br>Analytical Data: LC-MS m/z [M + H]$^+$; HPLC retention time (HPLC method 1) |
|---|---|
| 420 | 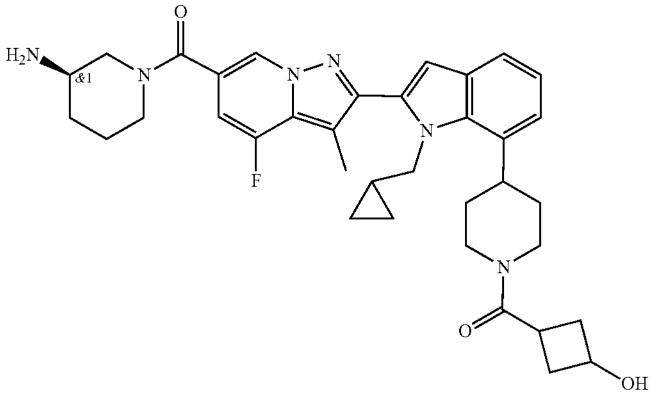 [SMILES: Cc1c(-c2cc3cccc(C4CCN(C(=O)C5CC(O)C5)CC4)c3n2CC2CC2)nn2cc(C(=O)N3CCC[C@@H](N)C3)cc(F)c12]<br>(R)-(3-Aminopiperidin-1-yl)(2-(1-(cyclopropylmethyl)-7-(1-(3-hydroxycyclobutane-1-carbonyl)piperidin-4-yl)-1H-indol-2-yl)-4-fluoro-3-methylpyrazolo[1,5-a]pyridin-6-yl)methanone (mixture of diastereomers)<br>Analytical data: 627.4; 1.58 min (Method E) |
| 421 | 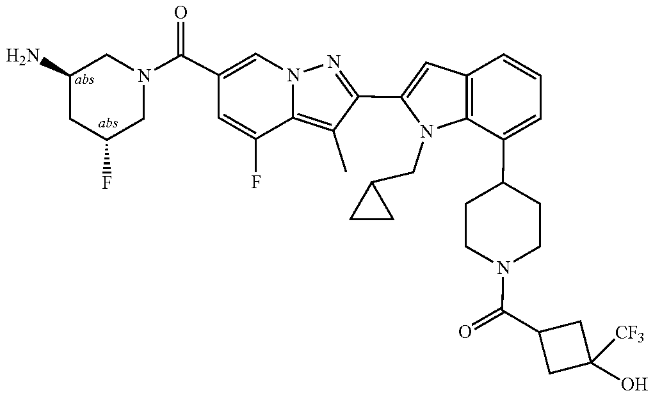 [SMILES: Cc1c(-c2cc3cccc(C4CCN(C(=O)C5CC(O)(C(F)(F)F)C5)CC4)c3n2CC2CC2)nn2cc(C(=O)N3C[C@H](N)C[C@@H](F)C3)cc(F)c12]<br>((3R,5R)-3-Amino-5-fluoropiperidin-1-yl)(2-(1-(cyclopropylmethyl)-7-(1-(3-hydroxy-3-(trifluoromethyl)cyclobutane-1-carbonyl)piperidin-4-yl)-1H-indol-2-yl)-4-fluoro-3-methylpyrazolo[1,5-a]pyridin-6-yl)methanone (mixture of diastereomers)<br>Analytical data: 713.3; 1.93 min (Method E) |
| 422 | 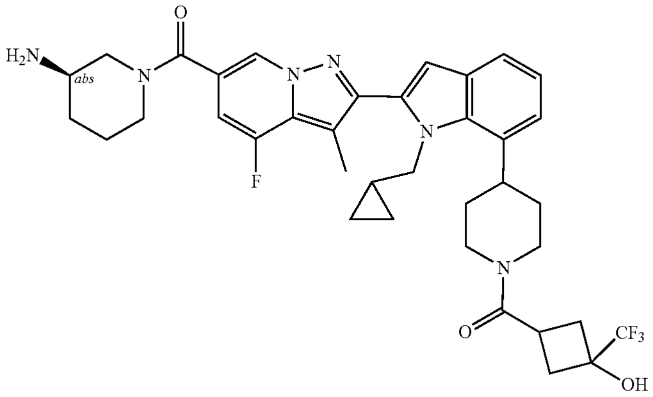 [SMILES: Cc1c(-c2cc3cccc(C4CCN(C(=O)C5CC(O)(C(F)(F)F)C5)CC4)c3n2CC2CC2)nn2cc(C(=O)N3CCC[C@@H](N)C3)cc(F)c12]<br>(R)-(3-Aminopiperidin-1-yl)(2-(1-(cyclopropylmethyl)-7-(1-(3-hydroxy-3-(trifluoromethyl)cyclobutane-1-carbonyl)piperidin-4-yl)-1H-indol-2-yl)-4-fluoro-3-methylpyrazolo[1,5-a]pyridin-6-yl)methanone (mixture of diastereomers)<br>Analytical data: 695.3; 1.89 min (Method E) |

TABLE 47-continued

| Example | Structure Name<br>Analytical Data: LC-MS m/z [M + H]$^+$; HPLC retention time (HPLC method 1) |
|---|---|
| 423 | 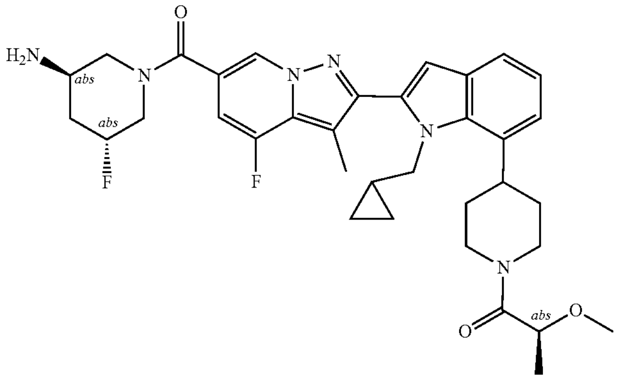 [SMILES: CO[C@@H](C)C(=O)N1CCC(c2cccc3cc(-c4nn5cc(C(=O)N6C[C@H](N)C[C@@H](F)C6)cc(F)c5c4C)n(CC4CC4)c23)CC1]<br>(S)-1-(4-(2-(6-((3R,5R)-3-Amino-5-fluoropiperidine-1-carbonyl)-4-fluoro-3-methylpyrazolo[1,5-a]pyridin-2-yl)-1-(cyclopropylmethyl)-1H-indol-7-yl)piperidin-1-yl)-2-methoxypropan-1-one<br>Analytical data: 633.3; 1.78 min (Method E) |
| 424 | 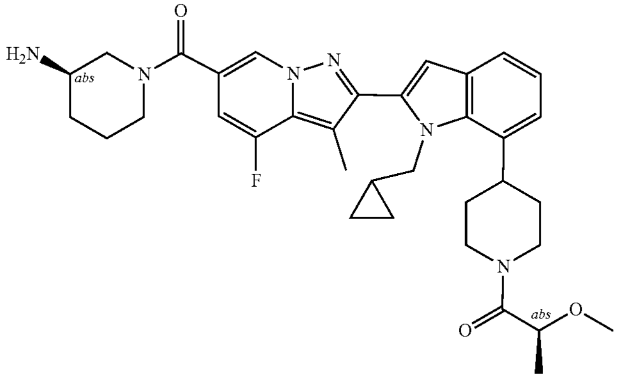 [SMILES: CO[C@@H](C)C(=O)N1CCC(c2cccc3cc(-c4nn5cc(C(=O)N6CCC[C@@H](N)C6)cc(F)c5c4C)n(CC4CC4)c23)CC1]<br>(S)-1-(4-(2-(6-((R)-3-Aminopiperidine-1-carbonyl)-4-fluoro-3-methylpyrazolo[1,5-a]pyridin-2-yl)-1-(cyclopropylmethyl)-1H-indol-7-yl)piperidin-1-yl)-2-methoxypropan-1-one<br>Analytical data: 615.4; 1.71 min (Method E) |
| 425 | 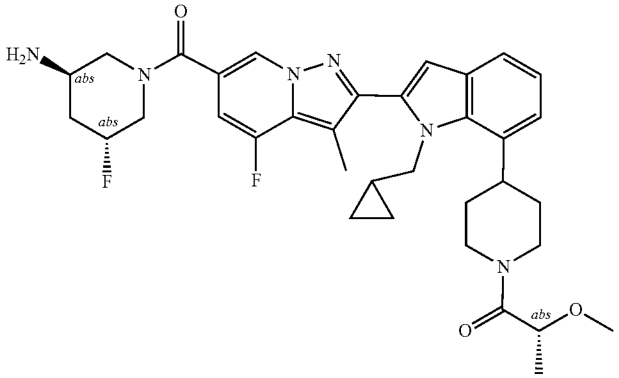 [SMILES: CO[C@H](C)C(=O)N1CCC(c2cccc3cc(-c4nn5cc(C(=O)N6C[C@H](N)C[C@@H](F)C6)cc(F)c5c4C)n(CC4CC4)c23)CC1]<br>(R)-1-(4-(2-(6-((3R,5R)-3-Amino-5-fluoropiperidine-1-carbonyl)-4-fluoro-3-methylpyrazolo[1,5-a]pyridin-2-yl)-1-(cyclopropylmethyl)-1H-indol-7-yl)piperidin-1-yl)-2-methoxypropan-1-one<br>Analytical data: 633.4; 1.64 min (Method E) |

TABLE 47-continued

| Example | Structure Name<br>Analytical Data: LC-MS m/z [M + H]$^+$; HPLC retention time (HPLC method 1) |
|---|---|
| 426 | 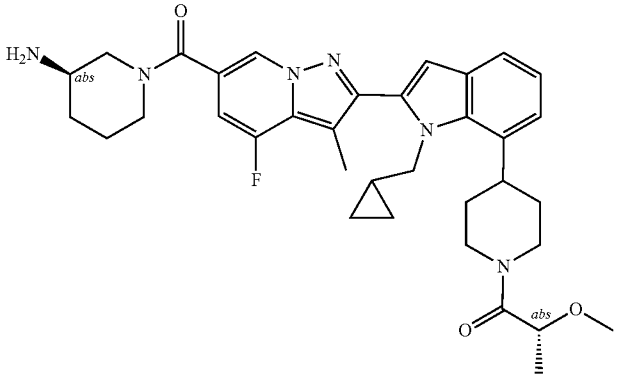 [SMILES: CO[C@H](C)C(=O)N1CCC(c2cccc3cc(-c4nn5cc(C(=O)N6CCC[C@@H](N)C6)cc(F)c5c4C)n(CC4CC4)c23)CC1]<br>(R)-1-(4-(2-(6-((R)-3-Aminopiperidine-1-carbonyl)-4-fluoro-3-methylpyrazolo[1,5-a]pyridin-2-yl)-1-(cyclopropylmethyl)-1H-indol-7-yl)piperidin-1-yl)-2-methoxypropan-1-one<br>Analytical data: 615.4; 1.72 min (Method E) |
| 427 | 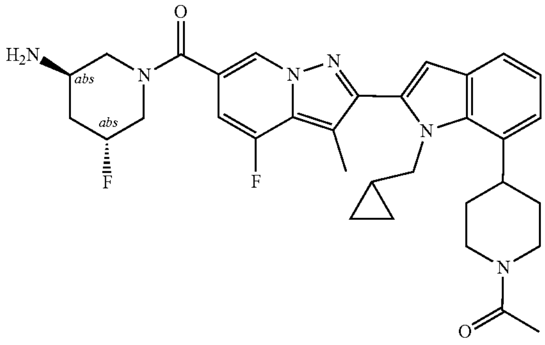 [SMILES: CC(=O)N1CCC(c2cccc3cc(-c4nn5cc(C(=O)N6C[C@H](N)C[C@@H](F)C6)cc(F)c5c4C)n(CC4CC4)c23)CC1]<br>1-(4-(2-(6-((3R,5R)-3-Amino-5-fluoropiperidine-1-carbonyl)-4-fluoro-3-methylpyrazolo[1,5-a]pyridin-2-yl)-1-(cyclopropylmethyl)-1H-indol-7-yl)piperidin-1-yl)ethan-1-one<br>Analytical data: 589.3; 1.70 min (Method E) |
| 428 | 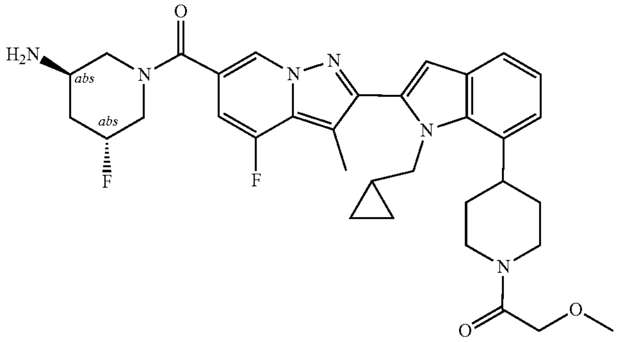 [SMILES: COCC(=O)N1CCC(c2cccc3cc(-c4nn5cc(C(=O)N6C[C@H](N)C[C@@H](F)C6)cc(F)c5c4C)n(CC4CC4)c23)CC1]<br>1-(4-(2-(6-((3R,5R)-3-Amino-5-fluoropiperidine-1-carbonyl)-4-fluoro-3-methylpyrazolo[1,5-a]pyridin-2-yl)-1-(cyclopropylmethyl)-1H-indol-7-yl)piperidin-1-yl)-2-methoxyethan-1-one<br>Analytical data: 619.3; 1.69 min (Method E) |

TABLE 47-continued

| Example | Structure Name<br>Analytical Data: LC-MS m/z [M + H]$^+$; HPLC retention time (HPLC method 1) |
|---|---|
| 429 | 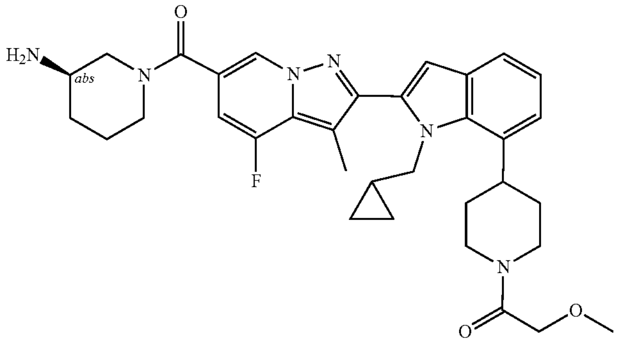 [SMILES: COCC(=O)N1CCC(c2cccc3cc(-c4nn5cc(C(=O)N6CCC[C@@H](N)C6)cc(F)c5c4C)n(CC4CC4)c23)CC1]<br>(R)-1-(4-(2-(6-(3-Aminopiperidine-1-carbonyl)-4-fluoro-3-methylpyrazolo[1,5-a]pyridin-2-yl)-1-(cyclopropylmethyl)-1H-indol-7-yl)piperidin-1-yl)-2-methoxyethan-1-one<br>Analytical data: 601.3; 1.62 min (Method E) |

Example 430

Ethyl 2-(7-(1-(tert-butoxycarbonyl)piperidin-4-yl)-1-(cyclopropylmethyl)-1H-indol-2-yl)-3-methylpyrazolo[1,5-a]pyridine-6-carboxylate

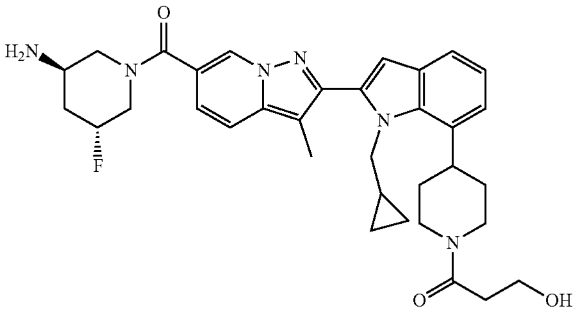 [SMILES: Cc1c(-c2cc3cccc(C4CCN(C(=O)CCO)CC4)c3n2CC2CC2)nn2cc(C(=O)N3C[C@H](N)C[C@@H](F)C3)ccc12]

Intermediate 430A

Ethyl 2-(7-(1-(tert-butoxycarbonyl)piperidin-4-yl)-1-(cyclopropylmethyl)-1H-indol-2-yl)-3-methylpyrazolo[1,5-a]pyridine-6-carboxylate

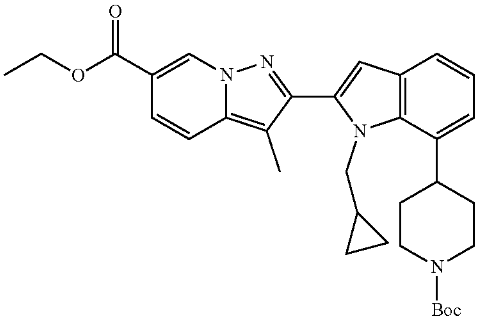 [SMILES: CCOC(=O)c1ccc2c(C)c(-c3cc4cccc(C5CCN(C(=O)OC(C)(C)C)CC5)c4n3CC3CC3)nn2c1]

Intermediate 430A (2.1 g, 47%) was prepared following a procedure similar to the preparation of Intermediate 386A. LC-MS m/z: 557.3 [M+H]$^+$

Intermediate 430B

Ethyl 2-(1-(cyclopropylmethyl)-7-(piperidin-4-yl)-1H-indol-2-yl)-3-methylpyrazolo[1,5-a]pyridine-6-carboxylate

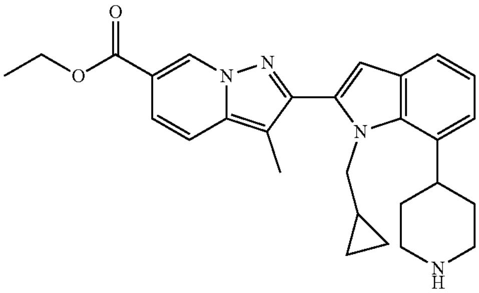 [SMILES: CCOC(=O)c1ccc2c(C)c(-c3cc4cccc(C5CCNCC5)c4n3CC3CC3)nn2c1]

Intermediate 430B (1.4 g, 81%) was prepared starting from Intermediate 430A following a procedure similar to the preparation of Intermediate 386B. LC-MS m/z: 457.3 [M+H]$^+$ Intermediate 430C 1-(4-(2-(6-((3R,5R)-3-amino-5-fluoropiperidine-1-carbonyl)-3-methylpyrazolo[1,5-a]pyridin-2-yl)-1-(cyclopropylmethyl)-1H-indol-7-yl)piperidin-1-yl)-3-hydroxypropan-1-one

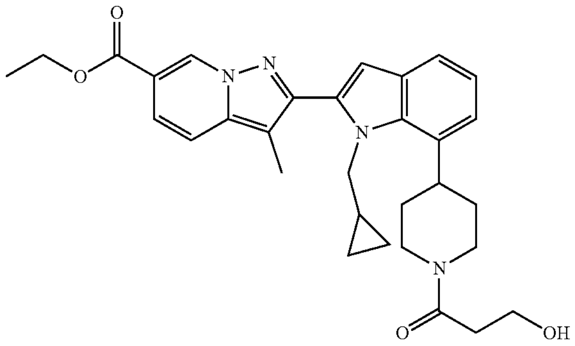 [SMILES: CCOC(=O)c1ccc2c(C)c(-c3cc4cccc(C5CCN(C(=O)CCO)CC5)c4n3CC3CC3)nn2c1]

3-Hydroxypropanoic acid (59.2 mg, 0.657 mmol), DIPEA (0.344 ml, 1.971 mmol) and HATU (375 mg, 0.986 mmol) were added to a stirred solution of Intermediate 430B (300 mg, 0.657 mmol) in DMF (1 ml). The reaction was continued for 3 hours. The reaction mixture was cooled to 0° C., and quenched with ice cold water to obtain a solid, which was filtered through Buchner funnel and dried under reduced vacuum to afford the title compound ethyl 2-(1-(cyclopropylmethyl)-7-(1-(3-hydroxypropanoyl)piperidin-4-yl)-1H-indol-2-yl)-3-methylpyrazolo[1,5-a]pyridine-6-carboxylate (172 mg, 50%). LC-MS m/z: 529.3 $[M+H]^+$.

Intermediate 430D 2-(1-(cyclopropylmethyl)-7-(1-(3-hydroxypropanoyl)piperidin-4-yl)-1H-indol-2-yl)-3-methylpyrazolo[1,5-a]pyridine-6-carboxylic acid

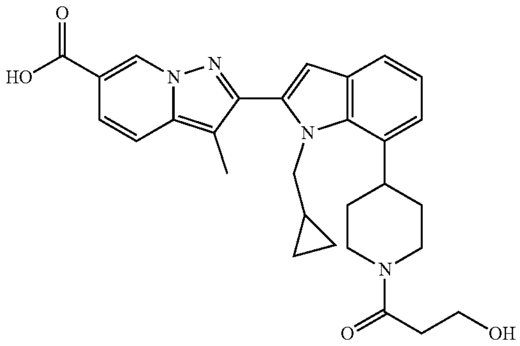 [SMILES: Cc1c(-c2cc3cccc(C4CCN(C(=O)CCO)CC4)c3n2CC2CC2)nn2cc(C(=O)O)ccc12]

Intermediate 430D (140 mg, 92%) was prepared starting from Intermediate 430C following a procedure similar to the preparation of Intermediate 386D. LC-MS m/z: 501.4 $[M+H]^+$.

Intermediate 430E tert-Butyl ((3R,5R)-1-(2-(1-(cyclopropylmethyl)-7-(1-(3-hydroxypropanoyl)piperidin-4-yl)-1H-indol-2-yl)-3-methylpyrazolo[1,5-a]pyridine-6-carbonyl)-5-fluoropiperidin-3-yl)carbamate

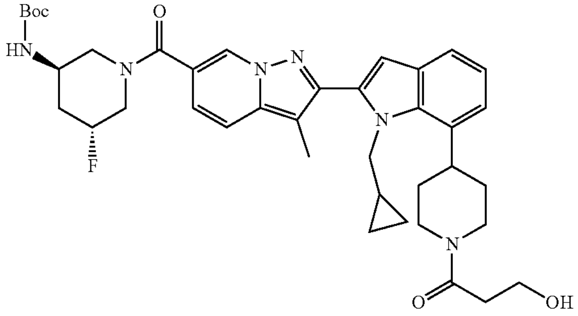 [SMILES: Cc1c(-c2cc3cccc(C4CCN(C(=O)CCO)CC4)c3n2CC2CC2)nn2cc(C(=O)N3C[C@H](F)C[C@@H](NC(=O)OC(C)(C)C)C3)ccc12]

Intermediate 430E (60 mg, 86%) was prepared starting from Intermediate 430D following a procedure similar to the preparation of Intermediate 386E. LC-MS m/z: 645.4 $[M-tBu]^+$.

Example 430

1-(4-(2-(6-((3R,5R)-3-amino-5-fluoropiperidine-1-carbonyl)-3-methylpyrazolo[1,5-a]pyridin-2-yl)-1-(cyclopropylmethyl)-1H-indol-7-yl)piperidin-1-yl)-3-hydroxypropan-1-one

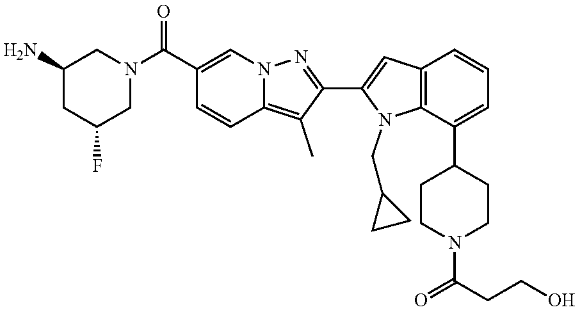 [SMILES: Cc1c(-c2cc3cccc(C4CCN(C(=O)CCO)CC4)c3n2CC2CC2)nn2cc(C(=O)N3C[C@H](N)C[C@@H](F)C3)ccc12]

HCl (4 M in dioxane) (0.043 ml, 0.171 mmol) was added to a stirred solution of Intermediate 430E (60 mg, 0.086 mmol) in 1,4-dioxane (1 ml) at 0° C. The reaction was continued for 3 hours. The reaction mixture was concentrated in vacuo to obtain a crude compound, which was purified using preparative LC/MS with the following conditions: Column: Waters X Bridge C18, 150 mm×19 mm, 5-μm particles; mobile phase A: 5:95 acetonitrile:water with 0.1% trifluoroacetic acid; mobile phase B: 95:5 acetonitrile: water with 0.1% trifluoroacetic acid; gradient: a 0-minute hold at 15% B, 15-30% B over 20 minutes, then a 5-minute hold at 100% B; flow rate: 20 ml/min; column temperature: 25° C. Fraction collection was triggered by signals. Fractions containing the desired product were combined and dried using centrifugal evaporation. The purified material was then diluted with a 1:1 mixture of ethylene dichloride and methanol (EDM), treated with Si-Pyridine and shaken for a minimum of 2 hours. The resulting mixture was filtered, and dried via centrifugal evaporation to afford 1-(4-(2-(6-((3R,5R)-3-amino-5-fluoropiperidine-1-carbonyl)-3-methylpyrazolo[1,5-a]pyridin-2-yl)-1-(cyclopropylmethyl)-1H-indol-7-yl)piperidin-1-yl)-3-hydroxypropan-1-one (6.9 mg, 11%). LC-MS m/z: 601.3 $[M+H]^+$. LCMS retention time: 1.504 min (method E). $^1H$ NMR (400 MHz, DMSO-$d_6$) δ ppm: 8.76 (s, 1H), 7.80 (d, J=9.29 Hz, 1H), 7.50 (d, J=7.58 Hz, 1H), 7.23 (d, J=9.15 Hz, 1H), 7.07-7.14 (m, 2H), 6.78 (s, 1H), 6.32 (br, s, 1H), 4.50 (d, J=6.36 Hz, 2H), 3.67 (m, 4H), 3.39-3.54 (m, 4H), 3.25 (m, 3H), 2.80-2.60 (m, 2H), 2.38 (s, 3H), 2.25-2.10 (m, 2H), 2.08-1.90 (m, 2H), 1.85-1.75 (m, 2H), 1.70-1.50 (m, 2H),1.26-1.22 (m, 2H), 0.98-0.90 (m, 1H), 0.22 (d, J=8.07 Hz, 2H), −0.17 (d, J=5.14 Hz, 2H).

Compounds of Examples 431 to 479 in Table 48 were prepared following a procedure similar to the preparation of a compound of Example 430, by acid amine coupling of Intermediate 430B with appropriate carboxylic acid followed by ester hydrolysis and amide coupling of resulting carboxylic acid with appropriate amines.

TABLE 48

| Example | Structure Name<br>Analytical Data: LC-MS m/z $[M + H]^+$; HPLC retention time (HPLC method) |
|---|---|
| 431 | 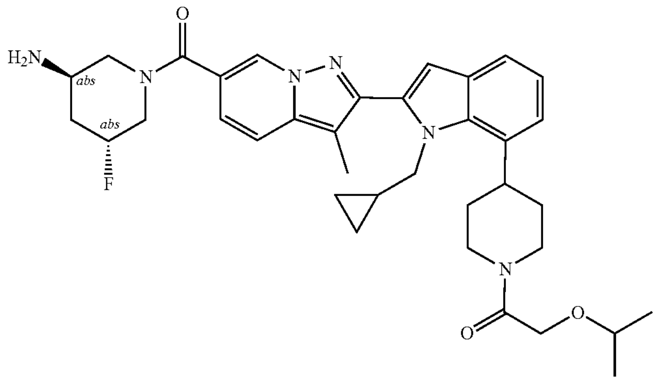 [SMILES: Cc1c(-c2cc3cccc(C4CCN(C(=O)COC(C)C)CC4)c3n2CC2CC2)nn2cc(C(=O)N3C[C@H](N)C[C@@H](F)C3)ccc12]<br>1-(4-(2-(6-((3R,5R)-3-amino-5-fluoropiperidine-1-carbonyl)-3-methylpyrazolo[1,5-a]pyridin-2-yl)-1-(cyclopropylmethyl)-1H-indol-7-yl)piperidin-1-yl)-2-isopropoxyethan-1-one<br>Analytical Data: 629.4; 1.842 min (Method E) |
| 432 | 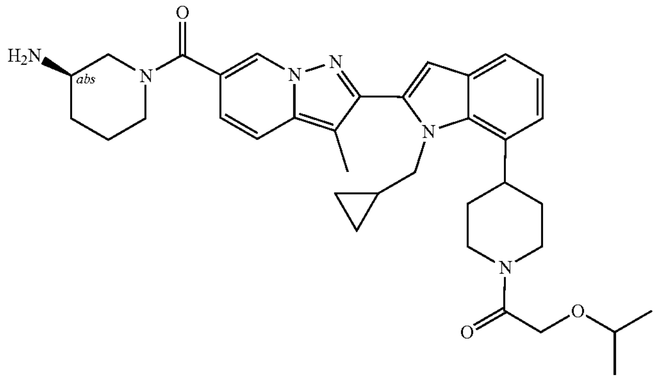 [SMILES: Cc1c(-c2cc3cccc(C4CCN(C(=O)COC(C)C)CC4)c3n2CC2CC2)nn2cc(C(=O)N3CCC[C@@H](N)C3)ccc12]<br>(R)-1-(4-(2-(6-(3-aminopiperidine-1-carbonyl)-3-methylpyrazolo[1,5-a]pyridin-2-yl)-1-(cyclopropylmethyl)-1H-indol-7-yl)piperidin-1-yl)-2-isopropoxyethan-1-one<br>Analytical Data: 611.5; 1.760 min (Method E) |

TABLE 48-continued

| Example | Structure Name<br>Analytical Data: LC-MS m/z [M + H]+; HPLC retention time (HPLC method) |
|---|---|
| 433 | 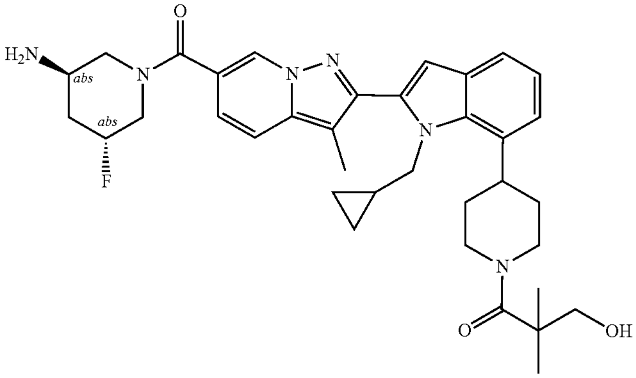 [SMILES: Cc1c(-c2cc3cccc(C4CCN(C(=O)C(C)(C)CO)CC4)c3n2CC2CC2)nn2cc(C(=O)N3C[C@H](N)C[C@@H](F)C3)ccc12]<br>1-(4-(2-(6-((3R,5R)-3-amino-5-fluoropiperidine-1-carbonyl)-3-methylpyrazolo[1,5-a]pyridin-2-yl)-1-(cyclopropylmethyl)-1H-indol-7-yl)piperidin-1-yl)-3-hydroxy-2,2-dimethylpropan-1-one<br>Analytical Data: 629.3; 1.748 min (Method E) |
| 434 | 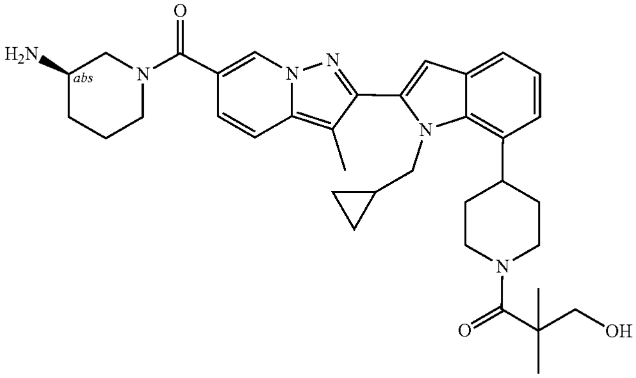 [SMILES: Cc1c(-c2cc3cccc(C4CCN(C(=O)C(C)(C)CO)CC4)c3n2CC2CC2)nn2cc(C(=O)N3CCC[C@@H](N)C3)ccc12]<br>(R)-1-(4-(2-(6-(3-aminopiperidine-1-carbonyl)-3-methylpyrazolo[1,5-a]pyridin-2-yl)-1-(cyclopropylmethyl)-1H-indol-7-yl)piperidin-1-yl)-3-hydroxy-2,2-dimethylpropan-1-one<br>Analytical Data: 611.4; 1.663 min (Method E) |
| 435 | 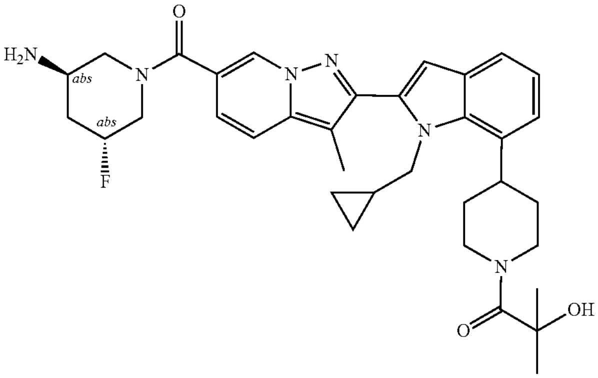 [SMILES: Cc1c(-c2cc3cccc(C4CCN(C(=O)C(C)(C)O)CC4)c3n2CC2CC2)nn2cc(C(=O)N3C[C@H](N)C[C@@H](F)C3)ccc12]<br>1-(4-(2-(6-((3R,5R)-3-amino-5-fluoropiperidine-1-carbonyl)-3-methylpyrazolo[1,5-a]pyridin-2-yl)-1-(cyclopropylmethyl)-1H-indol-7-yl)piperidin-1-yl)-2-hydroxy-2-methylpropan-1-one<br>Analytical Data: 615.3; 1.694 min (Method E) |

TABLE 48-continued

| Example | Structure Name<br>Analytical Data: LC-MS m/z $[M + H]^+$; HPLC retention time (HPLC method) |
|---|---|
| 436 | 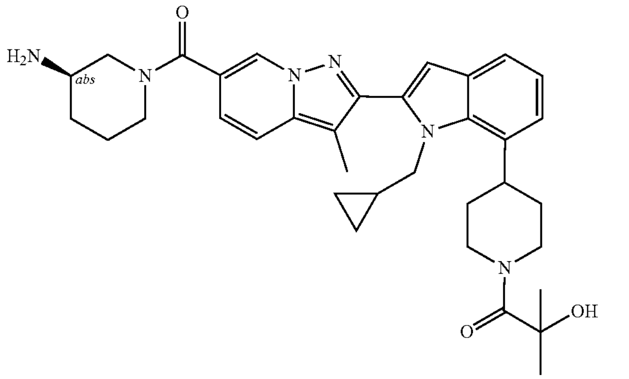 [SMILES: Cc1c(-c2cc3cccc(C4CCN(C(=O)C(C)(C)O)CC4)c3n2CC2CC2)nn2cc(C(=O)N3CCC[C@@H](N)C3)ccc12]<br>(R)-1-(4-(2-(6-(3-aminopiperidine-1-carbonyl)-3-methylpyrazolo[1,5-a]pyridin-2-yl)-1-(cyclopropylmethyl)-1H-indol-7-yl)piperidin-1-yl)-2-hydroxy-2-methylpropan-1-one<br>Analytical Data: 597.3; 1.597 min (Method E) |
| 437 | 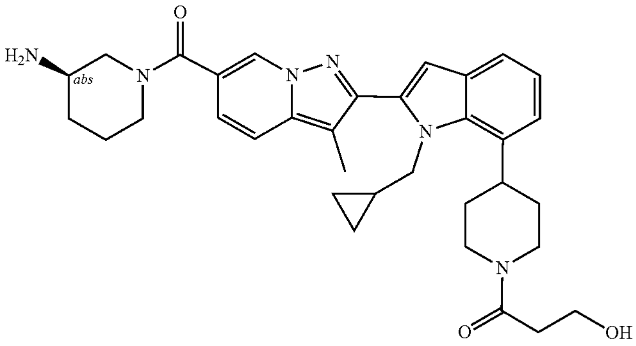 [SMILES: Cc1c(-c2cc3cccc(C4CCN(C(=O)CCO)CC4)c3n2CC2CC2)nn2cc(C(=O)N3CCC[C@@H](N)C3)ccc12]<br>(R)-1-(4-(2-(6-(3-aminopiperidine-1-carbonyl)-3-methylpyrazolo[1,5-a]pyridin-2-yl)-1-(cyclopropylmethyl)-1H-indol-7-yl)piperidin-1-yl)-3-hydroxypropan-1-one<br>Analytical Data: 583.4; 1.377 min (Method E) |
| 438 | 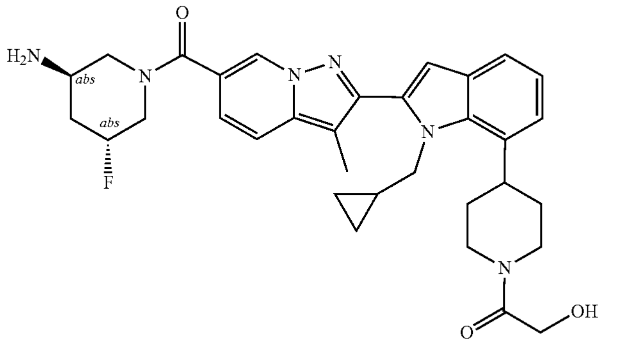 [SMILES: Cc1c(-c2cc3cccc(C4CCN(C(=O)CO)CC4)c3n2CC2CC2)nn2cc(C(=O)N3C[C@H](N)C[C@@H](F)C3)ccc12]<br>1-(4-(2-(6-((3R,5R)-3-amino-5-fluoropiperidine-1-carbonyl)-3-methylpyrazolo[1,5-a]pyridin-2-yl)-1-(cyclopropylmethyl)-1H-indol-7-yl)piperidin-1-yl)-2-hydroxyethan-1-one<br>Analytical Data: 587.3; 1.544 min (Method E) |

TABLE 48-continued

| Example | Structure Name<br>Analytical Data: LC-MS m/z [M + H]$^+$; HPLC retention time (HPLC method) |
|---|---|
| 439 | 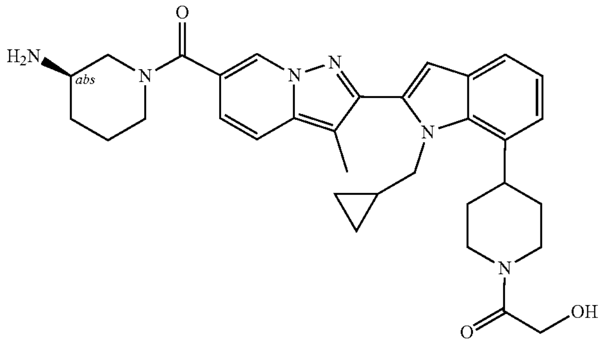 [SMILES: Cc1c(-c2cc3cccc(C4CCN(C(=O)CO)CC4)c3n2CC2CC2)nn2cc(C(=O)N3CCC[C@@H](N)C3)ccc12]<br>(R)-1-(4-(2-(6-(3-aminopiperidine-1-carbonyl)-3-methylpyrazolo[1,5-a]pyridin-2-yl)-1-(cyclopropylmethyl)-1H-indol-7-yl)piperidin-1-yl)-2-hydroxyethan-1-one<br>Analytical Data: 569.3; 1.464 min (Method E) |
| 440 | 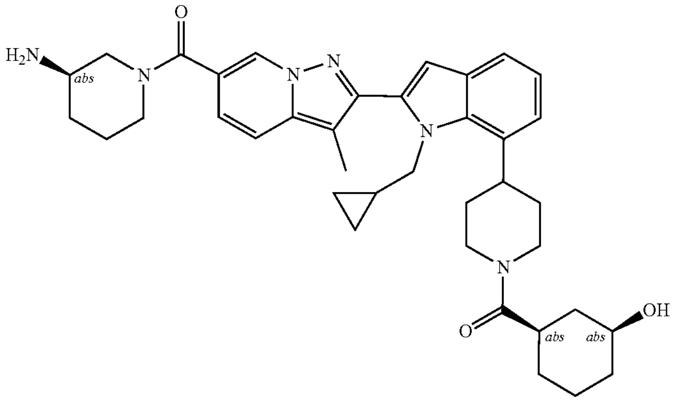 [SMILES: Cc1c(-c2cc3cccc(C4CCN(C(=O)[C@@H]5CCC[C@H](O)C5)CC4)c3n2CC2CC2)nn2cc(C(=O)N3CCC[C@@H](N)C3)ccc12]<br>((R)-3-aminopiperidin-1-yl)(2-(1-(cyclopropylmethyl)-7-(1-((1R,3S)-3-hydroxycyclohexane-1-carbonyl)piperidin-4-yl)-1H-indol-2-yl)-3-methylpyrazolo[1,5-a]pyridin-6-yl)methanone<br>Analytical Data: 637.4; 1.521 min (Method E) |
| 441 | 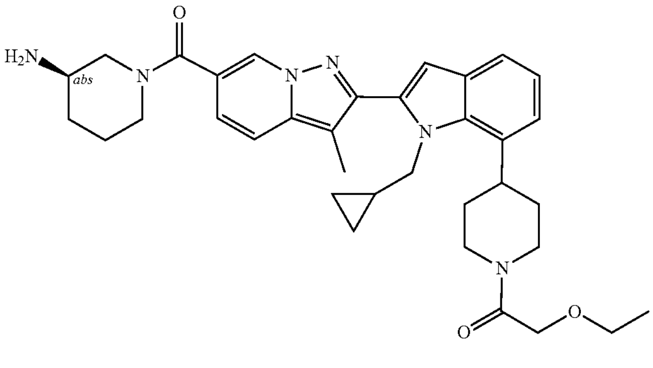 [SMILES: CCOCC(=O)N1CCC(c2cccc3cc(-c4nn5cc(C(=O)N6CCC[C@@H](N)C6)ccc5c4C)n(CC4CC4)c23)CC1]<br>(R)-1-(4-(2-(6-(3-aminopiperidine-1-carbonyl)-3-methylpyrazolo[1,5-a]pyridin-2-yl)-1-(cyclopropylmethyl)-1H-indol-7-yl)piperidin-1-yl)-2-ethoxyethan-1-one<br>Analytical Data: 597.3; 1.561 min (Method E) |

TABLE 48-continued

| Example | Structure Name<br>Analytical Data: LC-MS m/z [M + H]+; HPLC retention time (HPLC method) |
|---|---|
| 442 | 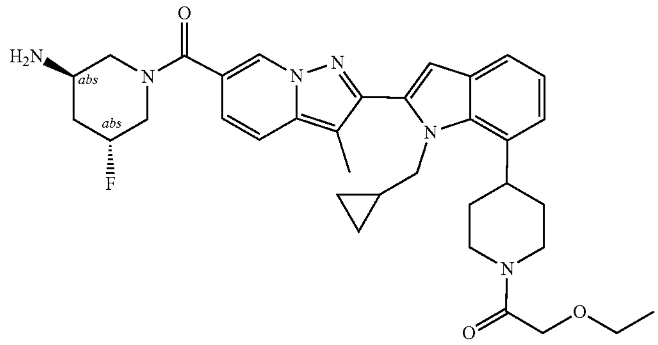 [SMILES: CCOCC(=O)N1CCC(c2cccc3cc(-c4nn5cc(C(=O)N6C[C@H](N)C[C@@H](F)C6)ccc5c4C)n(CC4CC4)c23)CC1]<br>1-(4-(2-(6-((3R,5R)-3-amino-5-fluoropiperidine-1-carbonyl)-3-methylpyrazolo[1,5-a]pyridin-2-yl)-1-(cyclopropylmethyl)-1H-indol-7-yl)piperidin-1-yl)-2-ethoxyethan-1-one<br>Analytical Data: 615.3; 1.576 min (Method E) |
| 443 | 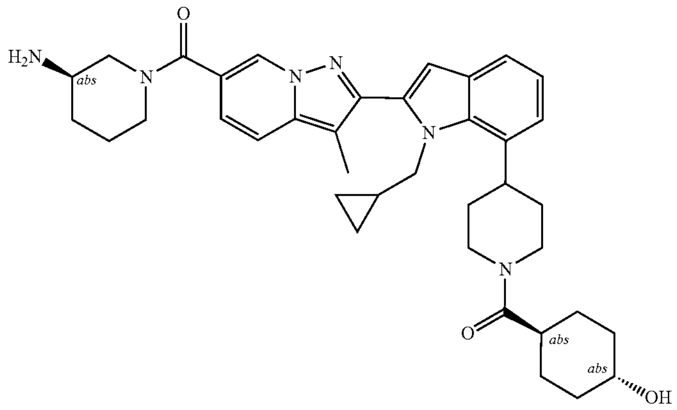 [SMILES: Cc1c(-c2cc3cccc(C4CCN(C(=O)[C@H]5CC[C@H](O)CC5)CC4)c3n2CC2CC2)nn2cc(C(=O)N3CCC[C@@H](N)C3)ccc12]<br>((R)-3-aminopiperidin-1-yl)(2-(1-(cyclopropylmethyl)-7-(1-((1r,4r)-4-hydroxycyclohexane-1-carbonyl)piperidin-4-yl)-1H-indol-2-yl)-3-methylpyrazolo[1,5-a]pyridin-6-yl)methanone<br>Analytical Data: 637.3; 1.497 min (Method E) |
| 444 | 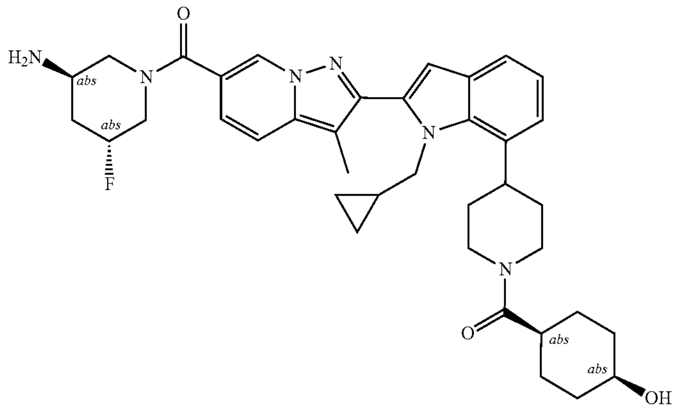 [SMILES: Cc1c(-c2cc3cccc(C4CCN(C(=O)[C@H]5CC[C@@H](O)CC5)CC4)c3n2CC2CC2)nn2cc(C(=O)N3C[C@H](N)C[C@@H](F)C3)ccc12]<br>((3R,5R)-3-amino-5-fluoropiperidin-1-yl)(2-(1-(cyclopropylmethyl)-7-(1-((1s,4s)-4-hydroxycyclohexane-1-carbonyl)piperidin-4-yl)-1H-indol-2-yl)-3-methylpyrazolo[1,5-a]pyridin-6-yl)methanone<br>Analytical Data: 655.4; 1.637 min (Method E) |

TABLE 48-continued

| Example | Structure Name<br>Analytical Data: LC-MS m/z [M + H]+; HPLC retention time (HPLC method) |
|---|---|
| 445 | 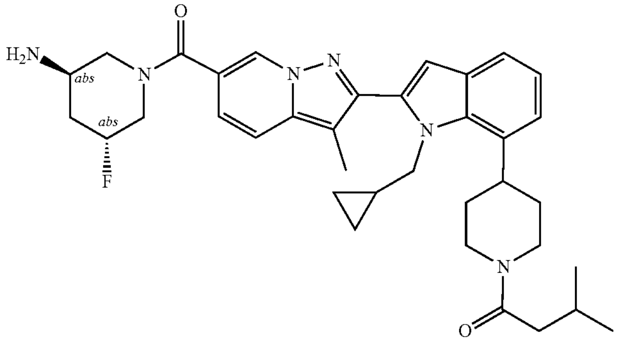 [SMILES: Cc1c(-c2cc3cccc(C4CCN(C(=O)CC(C)C)CC4)c3n2CC2CC2)nn2cc(C(=O)N3C[C@H](N)C[C@@H](F)C3)ccc12]<br>1-(4-(2-(6-((3R,5R)-3-amino-5-fluoropiperidine-1-carbonyl)-3-methylpyrazolo[1,5-a]pyridin-2-yl)-1-(cyclopropylmethyl)-1H-indol-7-yl)piperidin-1-yl)-3-methylbutan-1-one<br>Analytical Data: 613.4; 1.918 min (Method E) |
| 446 | 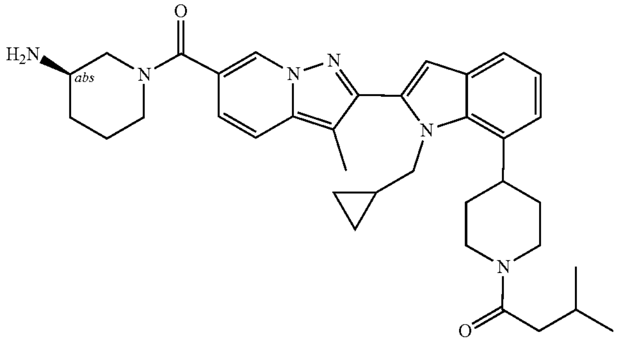 [SMILES: Cc1c(-c2cc3cccc(C4CCN(C(=O)CC(C)C)CC4)c3n2CC2CC2)nn2cc(C(=O)N3CCC[C@@H](N)C3)ccc12]<br>(R)-1-(4-(2-(6-(3-aminopiperidine-1-carbonyl)-3-methylpyrazolo[1,5-a]pyridin-2-yl)-1-(cyclopropylmethyl)-1H-indol-7-yl)piperidin-1-yl)-3-methylbutan-1-one<br>Analytical Data: 595.4; 1.861 min (Method E) |
| 447 | 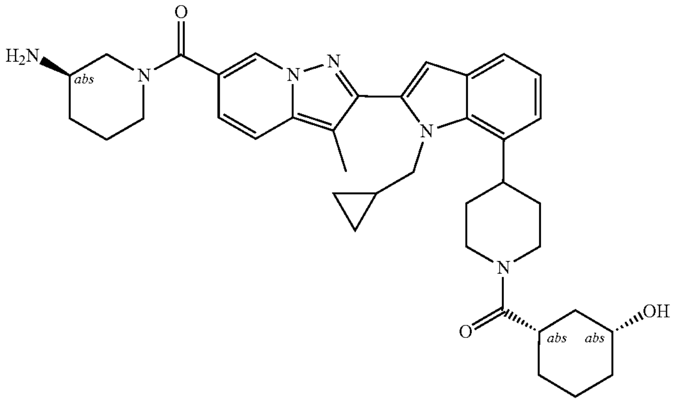 [SMILES: Cc1c(-c2cc3cccc(C4CCN(C(=O)[C@H]5CCC[C@@H](O)C5)CC4)c3n2CC2CC2)nn2cc(C(=O)N3CCC[C@@H](N)C3)ccc12]<br>((R)-3-aminopiperidin-1-yl)(2-(1-(cyclopropylmethyl)-7-(1-((1S,3R)-3-hydroxycyclohexane-1-carbonyl)piperidin-4-yl)-1H-indol-2-yl)-3-methylpyrazolo[1,5-a]pyridin-6-yl)methanone<br>Analytical Data: 637.4; 1.58 min (Method E) |

TABLE 48-continued

| Example | Structure Name<br>Analytical Data: LC-MS m/z [M + H]+; HPLC retention time (HPLC method) |
|---|---|
| 448 | 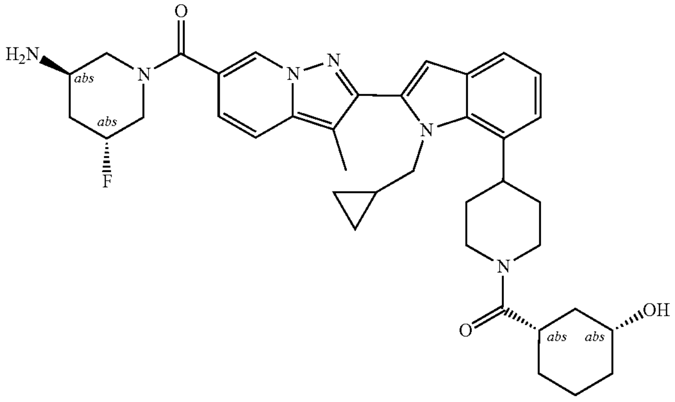 [SMILES: Cc1c(-c2cc3cccc(C4CCN(C(=O)[C@H]5CCC[C@@H](O)C5)CC4)c3n2CC2CC2)nn2cc(C(=O)N3C[C@H](N)C[C@@H](F)C3)ccc12]<br>((3R,5R)-3-amino-5-fluoropiperidin-1-yl)(2-(1-(cyclopropylmethyl)-7-(1-((1S,3R)-3-hydroxycyclohexane-1-carbonyl)piperidin-4-yl)-1H-indol-2-yl)-3-methylpyrazolo[1,5-a]pyridin-6-yl)methanone<br>Analytical Data: 655.4; 1.492 min (Method E) |
| 449 | 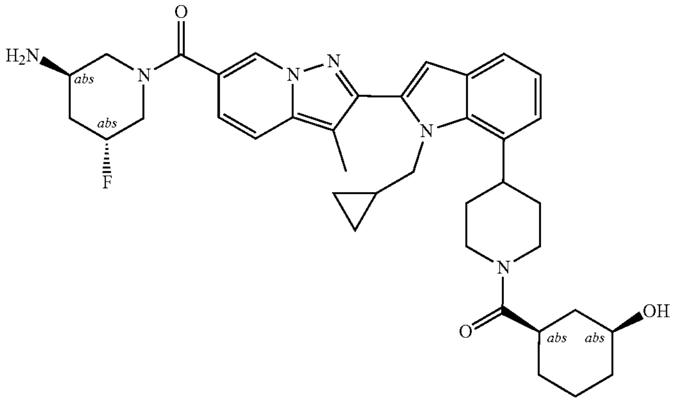 [SMILES: Cc1c(-c2cc3cccc(C4CCN(C(=O)[C@@H]5CCC[C@H](O)C5)CC4)c3n2CC2CC2)nn2cc(C(=O)N3C[C@H](N)C[C@@H](F)C3)ccc12]<br>((3R,5R)-3-amino-5-fluoropiperidin-1-yl)(2-(1-(cyclopropylmethyl)-7-(1-((1R,3S)-3-hydroxycyclohexane-1-carbonyl)piperidin-4-yl)-1H-indol-2-yl)-3-methylpyrazolo[1,5-a]pyridin-6-yl)methanone<br>Analytical Data: 655.4; 1.494 min (Method E) |
| 450 | 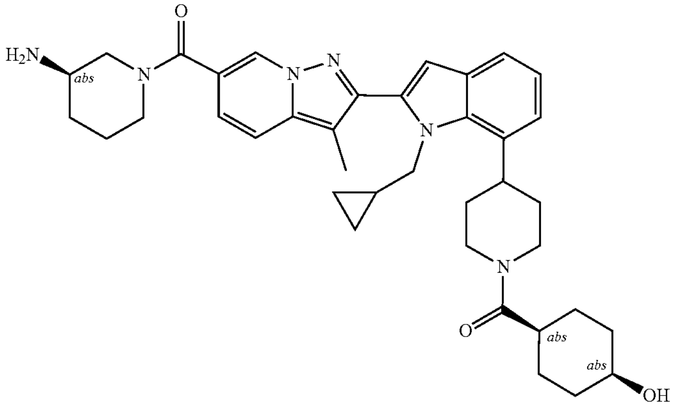 [SMILES: Cc1c(-c2cc3cccc(C4CCN(C(=O)[C@H]5CC[C@@H](O)CC5)CC4)c3n2CC2CC2)nn2cc(C(=O)N3CCC[C@@H](N)C3)ccc12]<br>((R)-3-aminopiperidin-1-yl)(2-(1-(cyclopropylmethyl)-7-(1-((2s,4s)-4-hydroxycyclohexane-1-carbonyl)piperidin-4-yl)-1H-indol-2-yl)-3-methylpyrazolo[1,5-a]pyridin-6-yl)methanone<br>Analytical Data: 637.5; 1.499 min (Method E) |

TABLE 48-continued

| Example | Structure Name<br>Analytical Data: LC-MS m/z [M + H]+; HPLC retention time (HPLC method) |
|---|---|
| 451 | 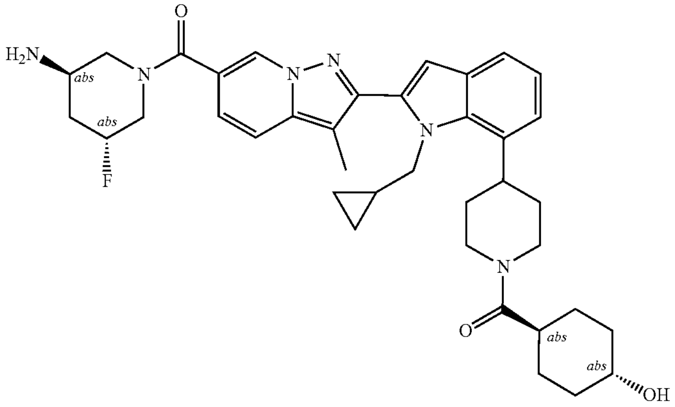 [SMILES: Cc1c(-c2cc3cccc(C4CCN(C(=O)[C@H]5CC[C@H](O)CC5)CC4)c3n2CC2CC2)nn2cc(C(=O)N3C[C@H](N)C[C@@H](F)C3)ccc12]<br>((3R,5R)-3-amino-5-fluoropiperidin-1-yl)(2-(1-(cyclopropylmethyl)-7-(1-((1r,4r)-4-hydroxycyclohexane-1-carbonyl)piperidin-4-yl)-1H-indol-2-yl)-3-methylpyrazolo[1,5-a]pyridin-6-yl)methanone<br>Analytical Data: 655.4; 1.546 min (Method) |
| 452 | 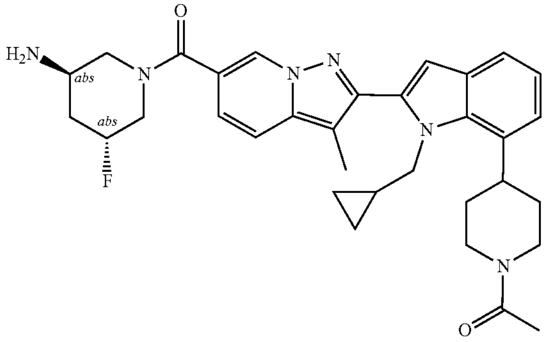 [SMILES: CC(=O)N1CCC(c2cccc3cc(-c4nn5cc(C(=O)N6C[C@H](N)C[C@@H](F)C6)ccc5c4C)n(CC4CC4)c23)CC1]<br>1-(4-(2-(6-((3R,5R)-3-amino-5-fluoropiperidine-1-carbonyl)-3-methylpyrazolo[1,5-a]pyridin-2-yl)-1-(cyclopropylmethyl)-1H-indol-7-yl)piperidin-1-yl)ethan-1-one<br>Analytical Data: 571.4; 1.907 min (Method E) |
| 453 | 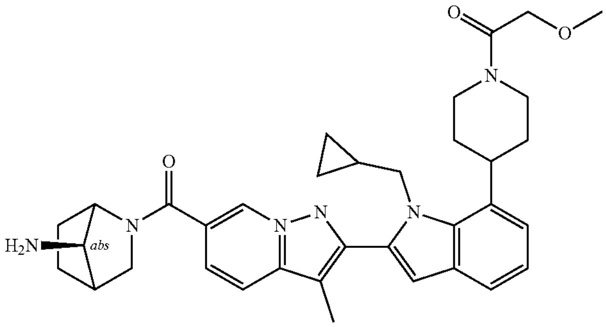<br>1-(4-(2-(6-((7R)-7-amino-2-azabicyclo[2.2.1]heptane-2-carbonyl)-3-methylpyrazolo[1,5-a]pyridin-2-yl)-1-(cyclopropylmethyl)-1H-indol-7-yl)piperidin-1-yl)-2-methoxyethan-1-one<br>Analytical Data: 595.4; 8.066 min (Method D) |

TABLE 48-continued

| Example | Structure Name<br>Analytical Data: LC-MS m/z $[M + H]^+$; HPLC retention time (HPLC method) |
|---|---|
| 454 | 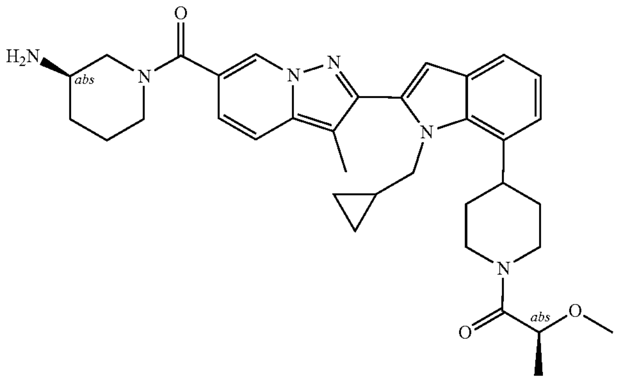 [SMILES: CO[C@@H](C)C(=O)N1CCC(c2cccc3cc(-c4nn5cc(C(=O)N6CCC[C@@H](N)C6)ccc5c4C)n(CC4CC4)c23)CC1]<br>(S)-1-(4-(2-(6-((R)-3-aminopiperidine-1-carbonyl)-3-methylpyrazolo[1,5-a]pyridin-2-yl)-1-(cyclopropylmethyl)-1H-indol-7-yl)piperidin-1-yl)-2-methoxypropan-1-one<br>Analytical Data: 597.3; 1.520 min (Method E) |
| 455 | 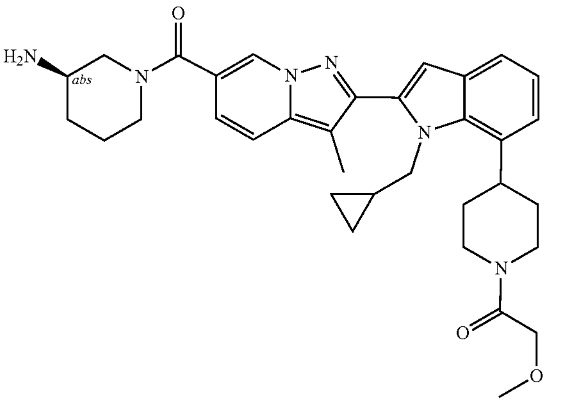 [SMILES: COCC(=O)N1CCC(c2cccc3cc(-c4nn5cc(C(=O)N6CCC[C@@H](N)C6)ccc5c4C)n(CC4CC4)c23)CC1]<br>(R)-1-(4-(2-(6-(3-aminopiperidine-1-carbonyl)-3-methylpyrazolo[1,5-a]pyridin-2-yl)-1-(cyclopropylmethyl)-1H-indol-7-yl)piperidin-1-yl)-2-methoxyethan-1-one<br>Analytical Data: 583.3; 1.505 min (Method E) |
| 456 | 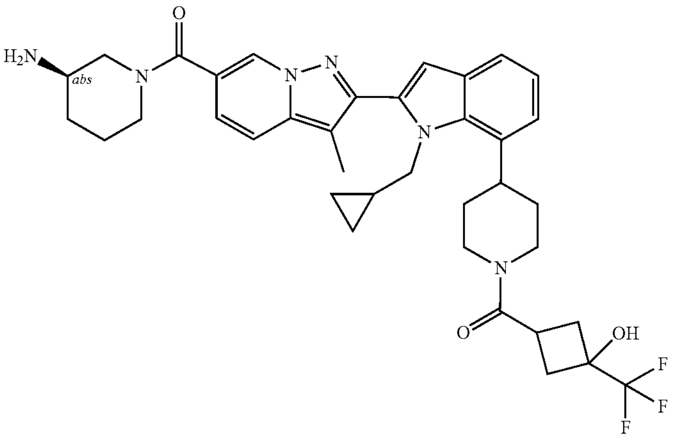 [SMILES: Cc1c(-c2cc3cccc(C4CCN(C(=O)C5CC(O)(C(F)(F)F)C5)CC4)c3n2CC2CC2)nn2cc(C(=O)N3CCC[C@@H](N)C3)ccc12]<br>(R)-(3-aminopiperidin-1-yl)(2-(1-(cyclopropylmethyl)-7-(1-(3-hydroxy-3-(trifluoromethyl)cyclobutane-1-carbonyl)piperidin-4-yl)-1H-indol-2-yl)-3-methylpyrazolo[1,5-a]pyridin-6-yl)methanone (mixture of diastereomers)<br>Analytical Data: 677.4; 1.779 min (Method E) |

TABLE 48-continued

| Example | Structure Name<br>Analytical Data: LC-MS m/z [M + H]$^+$; HPLC retention time (HPLC method) |
|---|---|
| 457 | 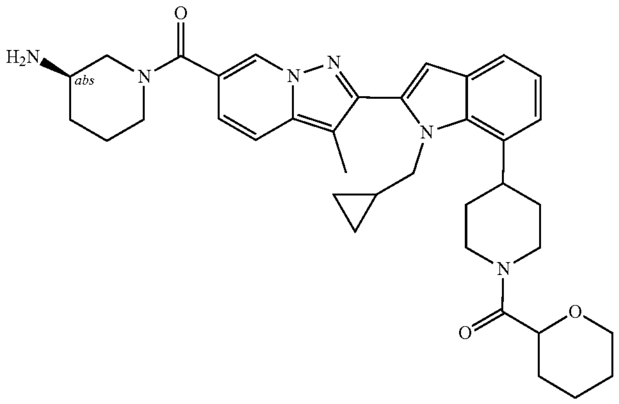 [SMILES: Cc1c(-c2cc3cccc(C4CCN(C(=O)C5CCCCO5)CC4)c3n2CC2CC2)nn2cc(C(=O)N3CCC[C@@H](N)C3)ccc12]<br>((R)-3-aminopiperidin-1-yl)(2-(1-(cyclopropylmethyl)-7-(1-(tetrahydro-2H-pyran-4-carbonyl)piperidin-4-yl)-1H-indol-2-yl)-3-methylpyrazolo[1,5-a]pyridin-6-yl)methanone (mixture of diastereomers)<br>Analytical Data: 623.3; 1.735 min (Method) |
| 458 | 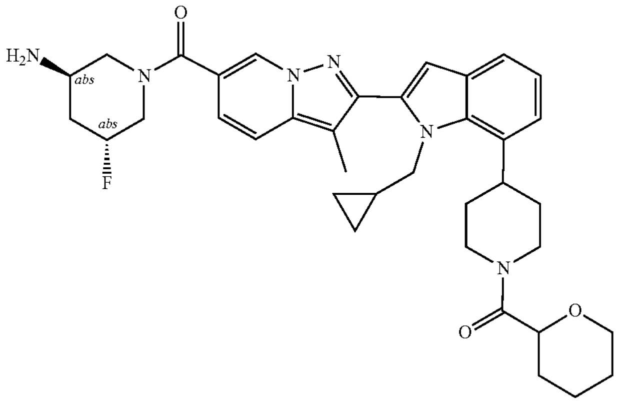 [SMILES: Cc1c(-c2cc3cccc(C4CCN(C(=O)C5CCCCO5)CC4)c3n2CC2CC2)nn2cc(C(=O)N3C[C@H](N)C[C@@H](F)C3)ccc12]<br>((3R,5R)-3-amino-5-fluoropiperidin-1-yl)(2-(1-(cyclopropylmethyl)-7-(1-(tetrahydro-2H-pyran-2-carbonyl)piperidin-4-yl)-1H-indol-2-yl)-3-methyltetrahydro[1,5-a]pyridin-6-yl)methanone (mixture of diastereomers)<br>Analytical Data: 641.5; 1.792 min (Method E) |
| 459 | 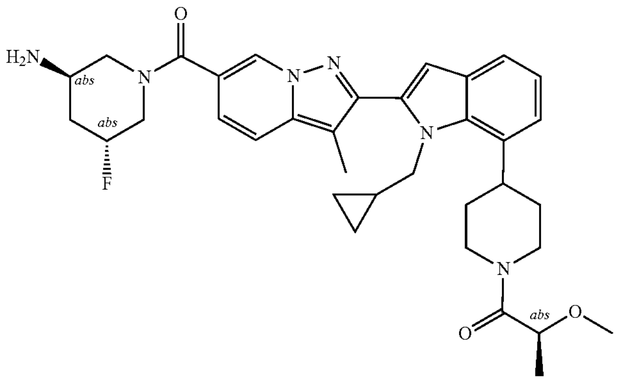 [SMILES: CO[C@@H](C)C(=O)N1CCC(c2cccc3cc(-c4nn5cc(C(=O)N6C[C@H](N)C[C@@H](F)C6)ccc5c4C)n(CC4CC4)c23)CC1]<br>(S)-1-(4-(2-(6-((3R,5R)-3-amino-5-fluoropiperidine-1-carbonyl)-3-methylpyrazolo[1,5-a]pyridin-2-yl)-1-(cyclopropylmethyl)-1H-indol-7-yl)piperidin-1-yl)-2-methoxypropan-1-one<br>Analytical Data: 615.3; 1.649 min (Method E) |

TABLE 48-continued

| Example | Structure Name<br>Analytical Data: LC-MS m/z $[M + H]^+$; HPLC retention time (HPLC method) |
| --- | --- |
| 460 | 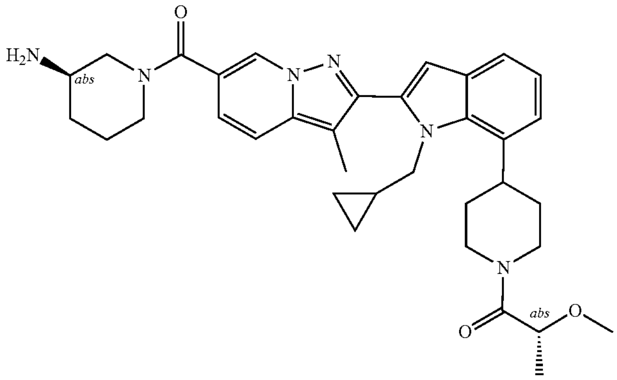 [SMILES: CO[C@H](C)C(=O)N1CCC(c2cccc3cc(-c4nn5cc(C(=O)N6CCC[C@@H](N)C6)ccc5c4C)n(CC4CC4)c23)CC1]<br>(R)-1-(4-(2-(6-((R)-3-aminopiperidine-1-carbonyl)-3-methylpyrazolo[1,5-a]pyridin-2-yl)-1-(cyclopropylmethyl)-1H-indol-7-yl)piperidin-1-yl)-2-methoxypropan-1-one<br>Analytical Data: 597.4; 1.521 min (Method E) |
| 461 | 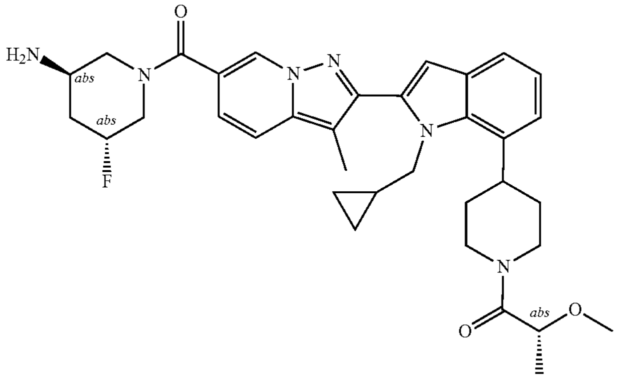 [SMILES: CO[C@H](C)C(=O)N1CCC(c2cccc3cc(-c4nn5cc(C(=O)N6C[C@H](N)C[C@@H](F)C6)ccc5c4C)n(CC4CC4)c23)CC1]<br>(R)-1-(4-(2-(6-((3R,5R)-3-amino-5-fluoropiperidine-1-carbonyl)-3-methylpyrazolo[1,5-a]pyridin-2-yl)-1-(cyclopropylmethyl)-1H-indol-7-yl)piperidin-1-yl)-2-methoxypropan-1-one<br>Analytical Data: 615.3; 1.538 min (Method E) |
| 462 | 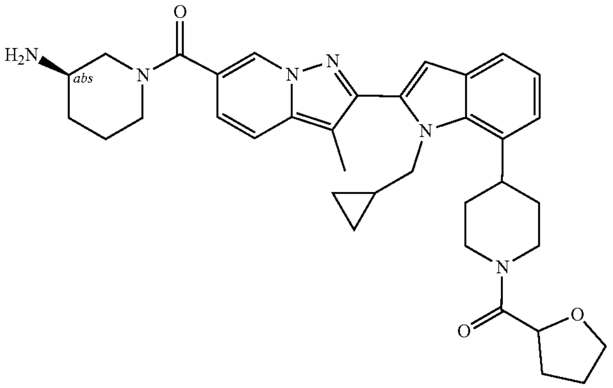 [SMILES: Cc1c(-c2cc3cccc(C4CCN(C(=O)C5CCCO5)CC4)c3n2CC2CC2)nn2cc(C(=O)N3CCC[C@@H](N)C3)ccc12]<br>((R)-3-aminopiperidin-1-yl)(2-(1-(cyclopropylmethyl)-7-(1-(tetrahydrofuran-2-carbonyl)piperidin-4-yl)-1H-indol-2-yl)-3-methylpyrazolo[1,5-a]pyridin-6-yl)methanone (mixture of diastereomers)<br>Analytical Data: 609.3; 1.708 min (Method E) |

TABLE 48-continued

| Example | Structure Name<br>Analytical Data: LC-MS m/z [M + H]+; HPLC retention time (HPLC method) |
|---|---|
| 463 | 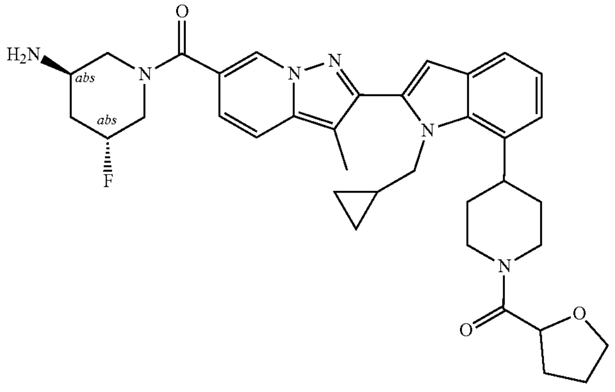 [SMILES: Cc1c(-c2cc3cccc(C4CCN(C(=O)C5CCCO5)CC4)c3n2CC2CC2)nn2cc(C(=O)N3C[C@H](N)C[C@@H](F)C3)ccc12]<br>((3R,5R)-3-amino-5-fluoropiperidin-1-yl)(2-(1-(cyclopropylmethyl)-7-(1-(tetrahydrofuran-2-carbonyl)piperidin-4-yl)-1H-indol-2-yl)-3-methylpyrazolo[1,5-a]pyridin-6-yl)methanone (mixture of diastereomers)<br>Analytical Data: 627.3; 1.770 min (Method E) |
| 464 | 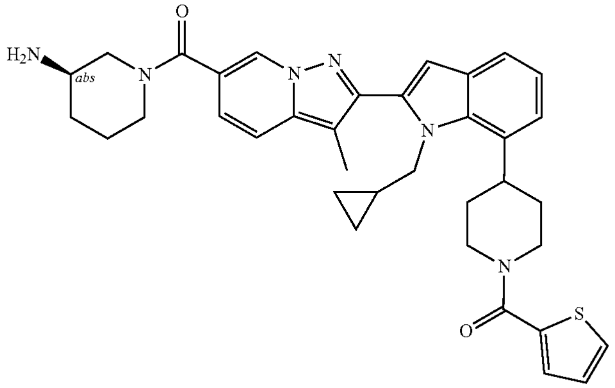 [SMILES: Cc1c(-c2cc3cccc(C4CCN(C(=O)c5cccs5)CC4)c3n2CC2CC2)nn2cc(C(=O)N3CCC[C@@H](N)C3)ccc12]<br>(R)-(3-aminopiperidin-1-yl)(2-(1-(cyclopropylmethyl)-7-(1-(thiophene-2-carbonyl)piperidin-4-yl)-1H-indol-2-yl)-3-methylpyrazolo[1,5-a]pyridin-6-yl)methanone<br>Analytical Data: 621.3; 1.819 min (Method E) |
| 465 | 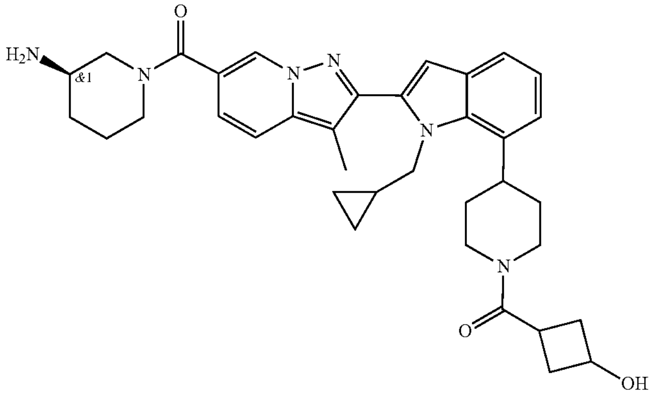 [SMILES: Cc1c(-c2cc3cccc(C4CCN(C(=O)C5CC(O)C5)CC4)c3n2CC2CC2)nn2cc(C(=O)N3CCC[C@@H](N)C3)ccc12]<br>(R)-(3-aminopiperidin-1-yl)(2-(1-(cyclopropylmethyl)-7-(1-(3-hydroxycyclobutane-1-carbonyl)piperidin-4-yl)-1H-indol-2-yl)-3-methylpyrazolo[1,5-a]pyridin-6-yl)methanone (mixture of diastereomers)<br>Analytical Data: 609.3; 1.390 min (Method E) |

TABLE 48-continued

| Example | Structure Name<br>Analytical Data: LC-MS m/z [M + H]$^+$; HPLC retention time (HPLC method) |
|---|---|
| 466 | 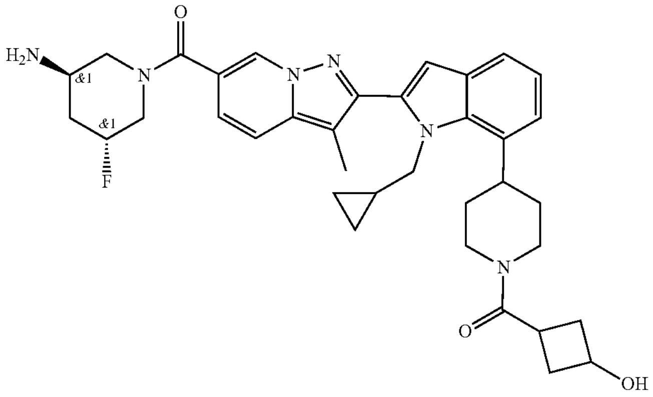 [SMILES: Cc1c(-c2cc3cccc(C4CCN(C(=O)C5CC(O)C5)CC4)c3n2CC2CC2)nn2cc(C(=O)N3C[C@H](N)C[C@@H](F)C3)ccc12]<br>((3R,5R)-3-amino-5-fluoropiperidin-1-yl)(2-(1-(cyclopropylmethyl)-7-(1-(3-hydroxycyclobutane-1-carbonyl)piperidin-4-yl)-1H-indol-2-yl)-3-methylpyrazolo[1,5-a]pyridin-6-yl)methanone (mixture of diastereomers)<br>Analytical Data: 627.3; 1.406 min (Method E) |
| 467 | 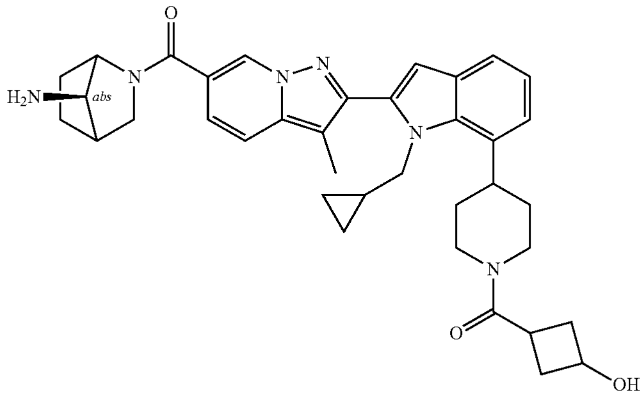 [SMILES: Cc1c(-c2cc3cccc(C4CCN(C(=O)C5CC(O)C5)CC4)c3n2CC2CC2)nn2cc(C(=O)N3CC4CCC3[C@@H]4N)ccc12]<br>(4-(2-(6-((7R)-7-amino-2-azabicyclo[2.2.1]heptane-2-carbonyl)-3-methylpyrazolo[1,5-a]pyridin-2-yl)-1-(cyclopropylmethyl)-1H-indol-7-yl)piperidin-1-yl)(3-hydroxycyclobutyl)methanone (mixture of diastereomers)<br>Analytical Data: 621.3; 1.371 min (Method E) |
| 468 | 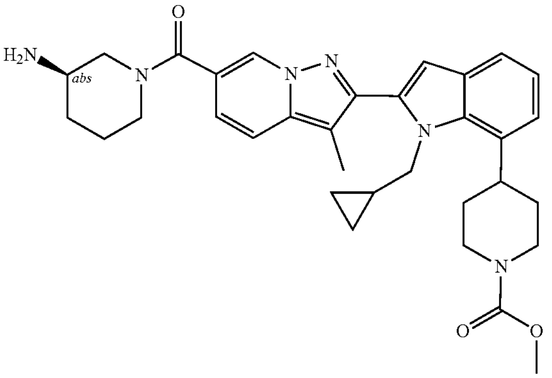 [SMILES: COC(=O)N1CCC(c2cccc3cc(-c4nn5cc(C(=O)N6CCC[C@@H](N)C6)ccc5c4C)n(CC4CC4)c23)CC1]<br>Methyl (R)-4-(2-(6-(3-aminopiperidine-1-carbonyl)-3-methylpyrazolo[1,5-a]pyridin-2-yl)-1-(cyclopropylmethyl)-1H-indol-7-yl)piperidine-1-carboxylate<br>Analytical Data: 569.3; 1.671 min (Method E) |

TABLE 48-continued

| Example | Structure Name<br>Analytical Data: LC-MS m/z [M + H]+; HPLC retention time (HPLC method) |
|---|---|
| 469 | 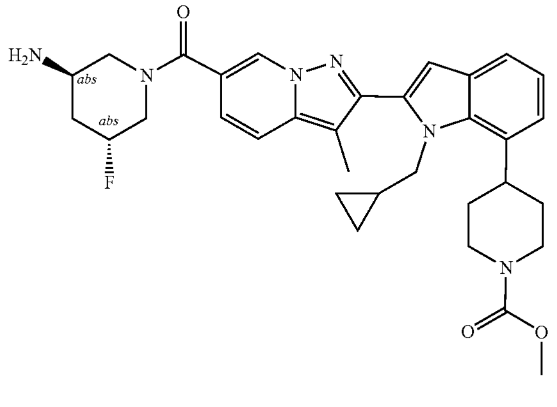 [SMILES: COC(=O)N1CCC(c2cccc3cc(-c4nn5cc(C(=O)N6C[C@H](N)C[C@@H](F)C6)ccc5c4C)n(CC4CC4)c23)CC1]<br>Methyl 4-(2-(6-((3R,5R)-3-amino-5-fluoropiperidine-1-carbonyl)-3-methylpyrazolo[1,5-a]pyridin-2-yl)-1-(cyclopropylmethyl)-1H-indol-7-yl)piperidine-1-carboxylate<br>Analytical Data: 587.3; 1.699 min (Method E) |
| 470 | 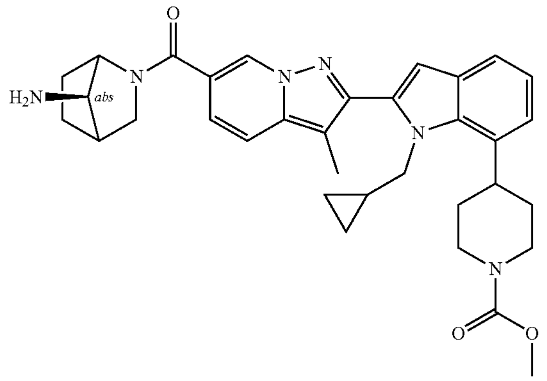 [SMILES: COC(=O)N1CCC(c2cccc3cc(-c4nn5cc(C(=O)N6CC7CCC6[C@@H]7N)ccc5c4C)n(CC4CC4)c23)CC1]<br>Methyl 4-(2-(6-((7R)-7-amino-2-azabicyclo[2.2.1]heptane-2-carbonyl)-3-methylpyrazolo[1,5-a]pyridin-2-yl)-1-(cyclopropylmethyl)-1H-indol-7-yl)piperidine-1-carboxylate<br>Analytical Data: 581.3; 1.646 min (Method E) |
| 471 | 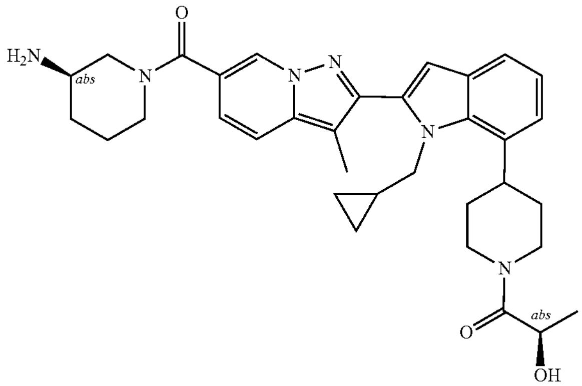 [SMILES: Cc1c(-c2cc3cccc(C4CCN(C(=O)[C@@H](C)O)CC4)c3n2CC2CC2)nn2cc(C(=O)N3CCC[C@@H](N)C3)ccc12]<br>(R)-1-(4-(2-(6-((R)-3-aminopiperidine-1-carbonyl)-3-methylpyrazolo[1,5-a]pyridin-2-yl)-1-(cyclopropylmethyl)-1H-indol-7-yl)piperidin-1-yl)-2-hydroxypropan-1-one<br>Analytical Data: 583.3; 1.428 min (Method E) |

TABLE 48-continued

| Example | Structure Name<br>Analytical Data: LC-MS m/z [M + H]+; HPLC retention time (HPLC method) |
|---|---|
| 472 | 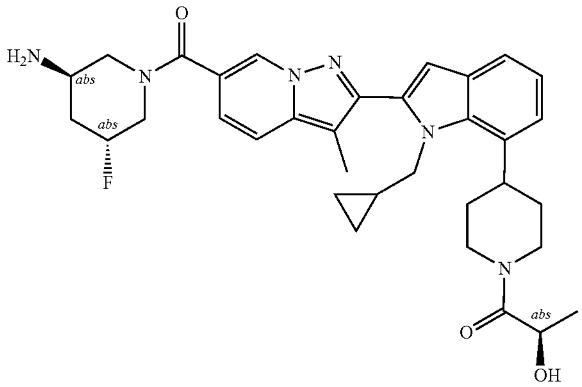 [SMILES: Cc1c(-c2cc3cccc(C4CCN(C(=O)[C@@H](C)O)CC4)c3n2CC2CC2)nn2cc(C(=O)N3C[C@H](N)C[C@@H](F)C3)ccc12]<br>(R)-1-(4-(2-(6-((3R,5R)-3-amino-5-fluoropiperidine-1-carbonyl)-3-methylpyrazolo[1,5-a]pyridin-2-yl)-1-(cyclopropylmethyl)-1H-indol-7-yl)piperidin-1-yl)-2-hydroxypropan-1-one<br>Analytical Data: 601.3; 1.554 min (Method E) |
| 473 | 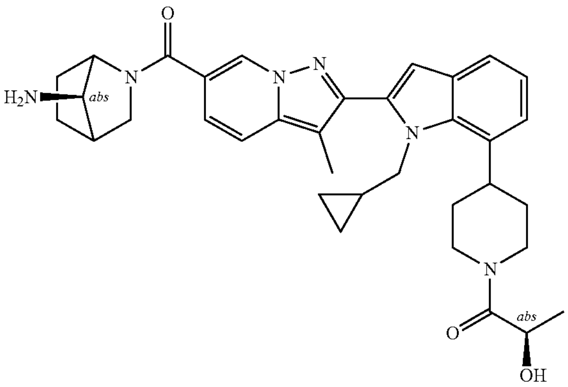 [SMILES: Cc1c(-c2cc3cccc(C4CCN(C(=O)[C@@H](C)O)CC4)c3n2CC2CC2)nn2cc(C(=O)N3CC4CCC3[C@@H]4N)ccc12]<br>(2R)-1-(4-(2-(6-((7R)-7-Amino-2-azabicyclo[2.2.1]heptane-2-carbonyl)-3-methylpyrazolo[1,5-a]pyridin-2-yl)-1-(cyclopropylmethyl)-1H-indol-7-yl)piperidin-1-yl)-2-hydroxypropan-1-one<br>Analytical Data: 595.3; 1.406 min (Method E) |
| 474 | 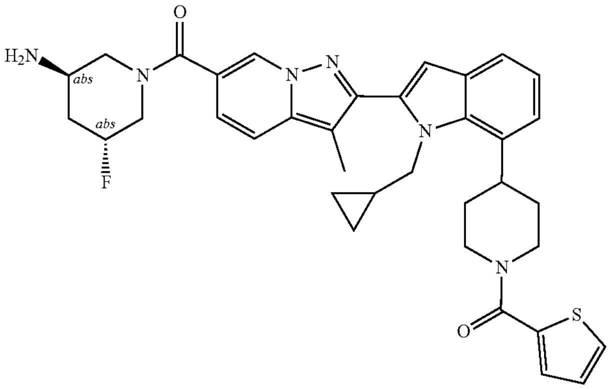 [SMILES: Cc1c(-c2cc3cccc(C4CCN(C(=O)c5cccs5)CC4)c3n2CC2CC2)nn2cc(C(=O)N3C[C@H](N)C[C@@H](F)C3)ccc12]<br>((3R,5R)-3-Amino-5-fluoropiperidin-1-yl)(2-(1-(cyclopropylmethyl)-7-(1-(thiophene-2-carbonyl)piperidin-4-yl)-1H-indol-2-yl)-3-methylpyrazolo[1,5-a]pyridin-6-yl)methanone<br>Analytical Data: 639.2; 1.749 min (Method E) |

TABLE 48-continued

| Example | Structure Name<br>Analytical Data: LC-MS m/z [M + H]+; HPLC retention time (HPLC method) |
|---|---|
| 475 | 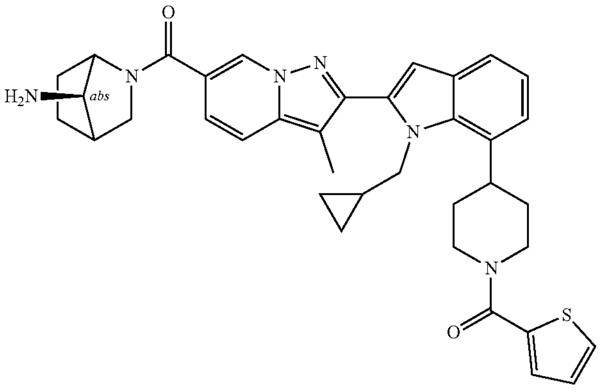 [SMILES: Cc1c(-c2cc3cccc(C4CCN(C(=O)c5cccs5)CC4)c3n2CC2CC2)nn2cc(C(=O)N3CC4CCC3[C@@H]4N)ccc12]<br>(4-(2-(6-((7R)-7-Amino-2-azabicyclo[2.2.1]heptane-2-carbonyl)-3-methylpyrazolo[1,5-a]pyridin-2-yl)-1-(cyclopropylmethyl)-1H-indol-7-yl)piperidin-1-yl)(thiophen-2-yl)methanone<br>Analytical Data: 633.2; 1.911 min (Method E) |
| 476 | 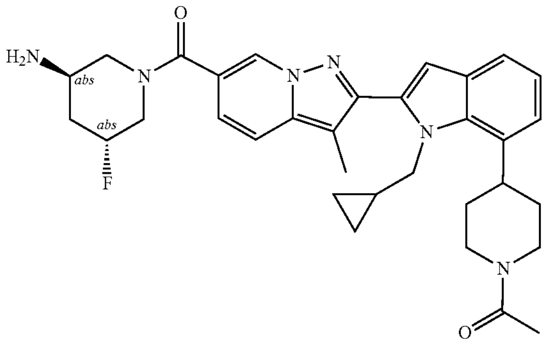 [SMILES: CC(=O)N1CCC(c2cccc3cc(-c4nn5cc(C(=O)N6C[C@H](N)C[C@@H](F)C6)ccc5c4C)n(CC4CC4)c23)CC1]<br>1-(4-(2-(6-((3R,5R)-3-Amino-5-fluoropiperidine-1-carbonyl)-3-methylpyrazolo[1,5-a]pyridin-2-yl)-1-(cyclopropylmethyl)-1H-indol-7-yl)piperidin-1-yl)ethan-1-one<br>Analytical Data: 571.4; 1.60 min (Method E) |
| 477 | 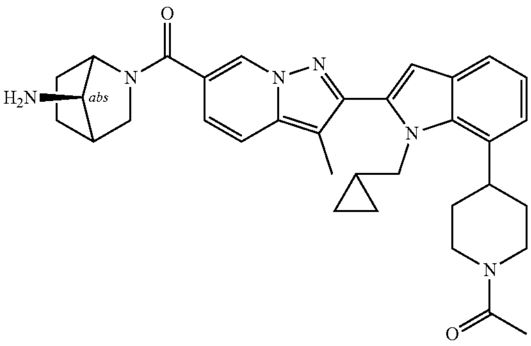 [SMILES: CC(=O)N1CCC(c2cccc3cc(-c4nn5cc(C(=O)N6CC7CCC6[C@@H]7N)ccc5c4C)n(CC4CC4)c23)CC1]<br>1-(4-(2-(6-((7R)-7-Amino-2-azabicyclo[2.2.1]heptane-2-carbonyl)-3-methylpyrazolo[1,5-a]pyridin-2-yl)-1-(cyclopropylmethyl)-1H-indol-7-yl)piperidin-1-yl)ethan-1-one<br>Analytical Data: 565.4; 1.640 min (Method E) |

TABLE 48-continued

| Example | Structure Name<br>Analytical Data: LC-MS m/z $[M + H]^+$; HPLC retention time (HPLC method) |
|---|---|
| 478 | 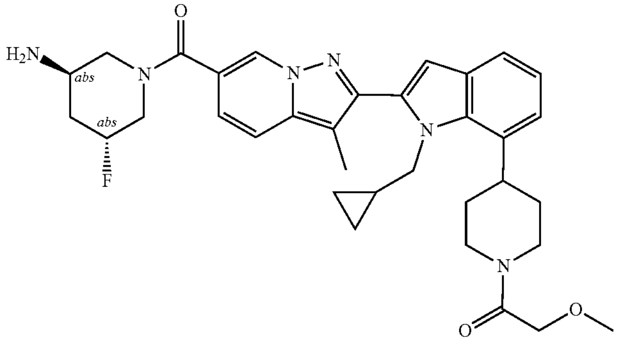 [SMILES: COCC(=O)N1CCC(c2cccc3cc(-c4nn5cc(C(=O)N6C[C@H](N)C[C@@H](F)C6)ccc5c4C)n(CC4CC4)c23)CC1]<br>1-(4-(2-(6-((3R,5R)-3-Amino-5-fluoropiperidine-1-carbonyl)-3-methylpyrazolo[1,5-a]pyridin-2-yl)-1-(cyclopropylmethyl)-1H-indol-7-yl)piperidin-1-yl)-2-methoxyethan-1-one<br>Analytical Data: 601.4; 5.680 min (Method D) |
| 479 | 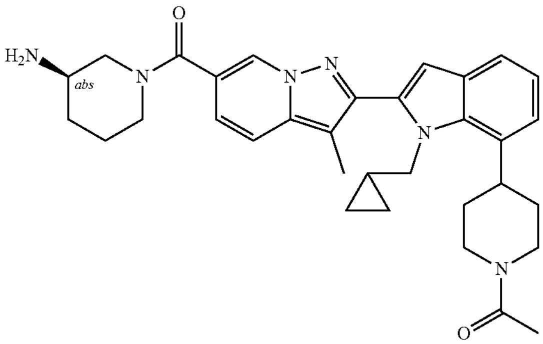 [SMILES: CC(=O)N1CCC(c2cccc3cc(-c4nn5cc(C(=O)N6CCC[C@@H](N)C6)ccc5c4C)n(CC4CC4)c23)CC1]<br>(R)-1-(4-(2-(6-(3-Aminopiperidine-1-carbonyl)-3-methylpyrazolo[1,5-a]pyridin-2-yl)-1-(cyclopropylmethyl)-1H-indol-7-yl)piperidin-1-yl)ethan-1-one<br>Analytical Data: 553.4; 1.484 min (Method E) |

Example 480

(R)-1-(4-(2-(6-(3-aminopiperidine-1-carbonyl)-4-methoxy-3-methylpyrazolo[1,5-a]pyridin-2-yl)-1-(cyclopropylmethyl)-5-fluoro-1H-indol-7-yl)piperidin-1-yl)-2-Methoxyethan-1-one

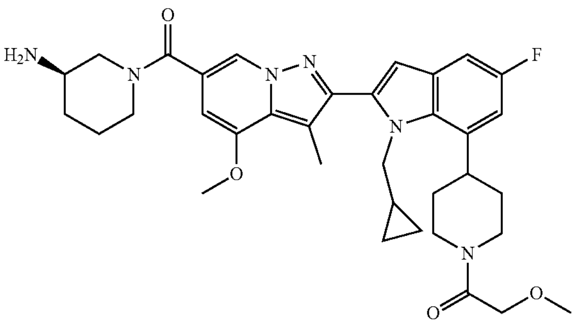 [SMILES: COCC(=O)N1CCC(c2cc(F)cc3cc(-c4nn5cc(C(=O)N6CCC[C@@H](N)C6)cc(OC)c5c4C)n(CC4CC4)c23)CC1]

Intermediate 480A methyl 2-(7-(1-(tert-butoxycarbonyl)piperidin-4-yl)-1-(cyclopropylmethyl)-5-fluoro-1H-indol-2-yl)-4-methoxy-3-methylpyrazolo[1,5-a]pyridine-6-carboxylate

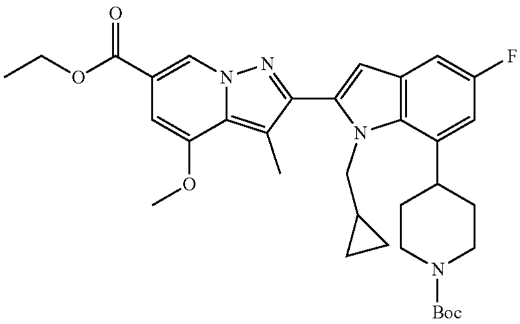 [SMILES: CCOC(=O)c1cc(OC)c2c(C)c(-c3cc4cc(F)cc(C5CCN(C(=O)OC(C)(C)C)CC5)c4n3CC3CC3)nn2c1]

To a stirred solution of Intermediate 36 (900 mg, 1.967 mmol) in DMF (5 ml) was added Intermediate 1 (360 mg, 1.967 mmol) and copper(I) iodide (187 mg, 0.984 mmol) and heated to 80° C. for 48 hours The reaction mixture was quenched with $NaHCO_3$ (300 ml) and extracted with ethyl acetate (2×300 ml). The combined organic layers were dried over sodium sulphate, filtered and concentrated under reduced vacuum pressure to give crude product. Purified using a silica gel column using 0-20% ethyl acetate in hexane to afford methyl 2-(7-(1-(tert-butoxycarbonyl)piperidin-4-yl)-1-(cyclopropylmethyl)-5-fluoro-1H-indol-2-yl)-4-methoxy-3-methylpyrazolo[1,5-a]pyridine-6-carboxylate (600 mg, 52%). LC-MS m/z: 591.2 $[M+H]^+$ Intermediate 480B Methyl 2-(1-(cyclopropylmethyl)-5-fluoro-7-(piperidin-4-yl)-1H-indol-2-yl)-4-methoxy-3-methylpyrazolo[1,5-a]pyridine-6-carboxylate

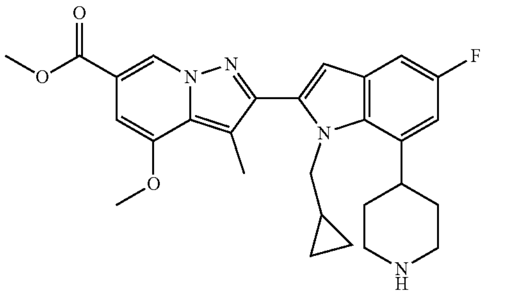 [SMILES: COC(=O)c1cc(OC)c2c(C)c(-c3cc4cc(F)cc(C5CCNCC5)c4n3CC3CC3)nn2c1]

TFA (0.078 ml, 1.016 mmol) was added to stirred solution of Intermediate 480A (600 mg, 1.016 mmol) in DCM (5 ml) at 0° C. The reaction mixture was allowed to warm to a room temperature and stirred for 3 hours, concentrated under reduced pressure to obtain a crude title compound methyl 2-(1-(cyclopropylmethyl)-5-fluoro-7-(piperidin-4-yl)-1H-indol-2-yl)-4-methoxy-3-methylpyrazolo[1,5-a]pyridine-6-carboxylate (470 mg, 94%). LC-MS m/z: 491.3 $[M+H]^+$.

Intermediate 480C

Methyl 2-(1-(cyclopropylmethyl)-5-fluoro-7-(1-(2-methoxyacetyl)piperidin-4-yl)-1H-indol-2-yl)-4-methoxy-3-methylpyrazolo[1,5-a]pyridine-6-carboxylate

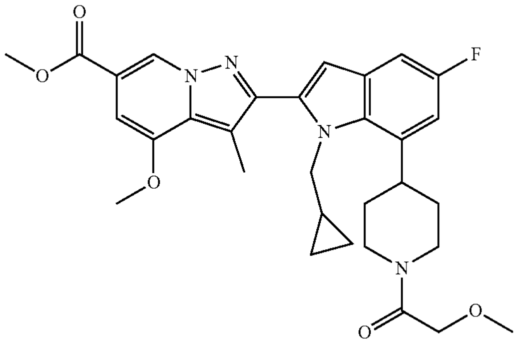

DIPEA (0.128 ml, 0.734 mmol) and HATU (140 mg, 0.367 mmol) were added to a stirred solution of Intermediate 480B (24.24 mg, 0.269 mmol). The reaction was continued for 3 hours. The reaction mixture was quenched with water (50 ml), and the solids obtained were filtered and dried in vacuo to obtain the title compound methyl 2-(1-(cyclopropylmethyl)-5-fluoro-7-(1-(2-methoxyacetyl)piperidin-4-yl)-1H-indol-2-yl)-4-methoxy-3-methylpyrazolo[1,5-a]pyridine-6-carboxylate (110 mg, 80%). LC-MS m/z: 563.3 $[M+H]^+$.

Intermediate 480D 2-(1-(Cyclopropylmethyl)-5-fluoro-7-(1-(2-methoxyacetyl)piperidin-4-yl)-1H-indol-2-yl)-4-methoxy-3-methylpyrazolo[1,5-a]pyridine-6-carboxylic acid

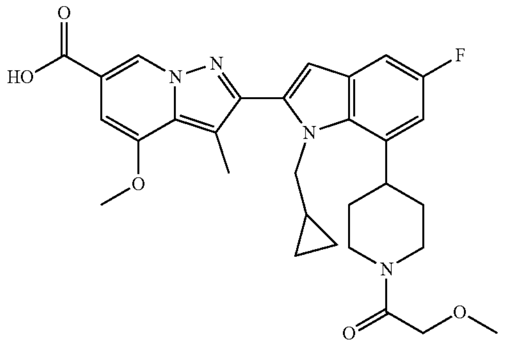 [SMILES: COCC(=O)N1CCC(c2cc(F)cc3cc(-c4nn5cc(C(=O)O)cc(OC)c5c4C)n(CC4CC4)c23)CC1]

LiOH (13.83 mg, 0.578 mmol) was added to a stirred solution of Intermediate 480C (130 mg, 0.231 mmol) in a mixture of solvents: THF (1 ml), MeOH (1 ml) and water (1 ml). The reaction mixture was stirred for 3 hours, concentrated under reduced pressure to obtain a crude residue, which was acidified with 1 N HCl. The solids precipitated were filtered through Buchner funnel, and dried in vacuum to afford the title compound 2-(1-(cyclopropylmethyl)-5-fluoro-7-(1-(2-methoxyacetyl)piperidin-4-yl)-1H-indol-2-yl)-4-methoxy-3-methylpyrazolo[1,5-a]pyridine-6-carboxylic acid (105 mg, 83%). LC-MS m/z: 549.2 $[M+H]^+$.

Intermediate 480E tert-Butyl (R)-(1-(2-(1-(cyclopropylmethyl)-5-fluoro-7-(1-(2-methoxyacetyl)piperidin-4-yl)-1H-indol-2-yl)-4-methoxy-3-methylpyrazolo[1,5-a]pyridine-6-carbonyl)piperidin-3-yl)carbamate

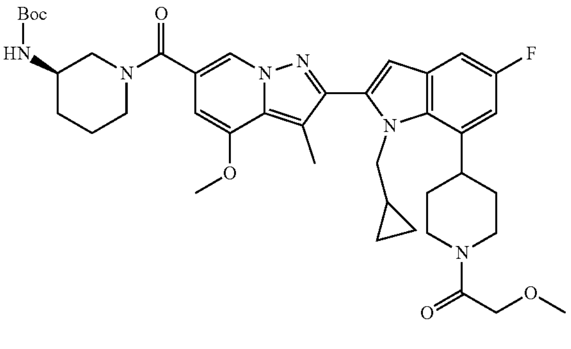 [SMILES: COCC(=O)N1CCC(c2cc(F)cc3cc(-c4nn5cc(C(=O)N6CCC[C@@H](NC(=O)OC(C)(C)C)C6)cc(OC)c5c4C)n(CC4CC4)c23)CC1]

tert-Butyl (R)-piperidin-3-ylcarbamate (18.25 mg, 0.091 mmol), DIPEA (0.048 ml, 0.273 mmol) and HATU (52.0 mg, 0.137 mmol) were added to a stirred solution of Intermediate 480D (50 mg, 0.091 mmol) in DMF (1 ml). The reaction mixture was stirred for 3 hours, quenched with ice cold water, and the solids obtained were filtered through Buchner funnel and dried under reduced pressure to afford the title compound tert-butyl (R)-(1-(2-(1-(cyclopropylmethyl)-5-fluoro-7-(1-(2-methoxyacetyl)piperidin-4-yl)-1H-indol-2-yl)-4-methoxy-3-methylpyrazolo[1,5-a]pyridine-6-carbonyl)piperidin-3-yl)carbamate (43 mg, 65%). LC-MS m/z: 731.2 $[M+H]^+$.

Example 480

(R)-1-(4-(2-(6-(3-Aminopiperidine-1-carbonyl)-4-methoxy-3-methylpyrazolo[1,5-a]pyridin-2-yl)-1-(cyclopropylmethyl)-5-fluoro-1H-indol-7-yl)piperidin-1-yl)-2-methoxyethan-1-one

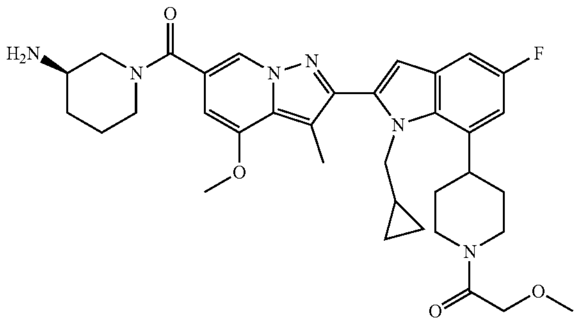 [SMILES: COCC(=O)N1CCC(c2cc(F)cc3cc(-c4nn5cc(C(=O)N6CCC[C@@H](N)C6)cc(OC)c5c4C)n(CC4CC4)c23)CC1]

TFA (10.54 μl, 0.137 mmol) was added to a solution of Intermediate 480E (50 mg, 0.068 mmol) in DCM (1 ml) at 0° C. The reaction mixture was stirred for 3 hours, and concentrated in vacuum to obtain a crude compound, which was purified using preparative LC/MS with the following conditions: Column: Waters XBridge C18, 150 mm×19 mm, 5-μm particles; mobile phase A: 5:95 acetonitrile:water with 0.1% trifluoroacetic acid; mobile phase B: 95:5 acetonitrile: water with 0.1% trifluoroacetic acid; gradient: a 0-minute hold at 15% B, 15-30% B over 20 minutes, then a 5-minute hold at 100% B; flow rate: 20 ml/min; column temperature: 25° C. Fraction collection was triggered by signals. Fractions containing the desired product were combined and dried using centrifugal evaporation. The purified material was then diluted with a 1:1 mixture of ethylene dichloride and methanol (EDM), treated with Si-Pyridine and shaken for a minimum of 2 hours. The resulting mixture was filtered and dried using centrifugal evaporation to afford (R)-1-(4-(2-(6-(3-aminopiperidine-1-carbonyl)-4-methoxy-3-methylpyrazolo[1,5-a]pyridin-2-yl)-1-(cyclopropylmethyl)-5-fluoro-1H-indol-7-yl)piperidin-1-yl)-2-methoxyethan-1-one.

Compounds of Examples 481 to 483 in Table 49 were prepared following a procedure similar to the preparation of a compound of Example 480, by acid amine coupling of Intermediate 480B with appropriate carboxylic acid followed by ester hydrolysis and the resulting carboxylic acid with appropriate amines.

TABLE 49

| Example | Structure<br>Name<br>Analytical Data: LC-MS m/z $[M + H]^+$; HPLC retention time (HPLC method 1) |
|---|---|
| 481 | 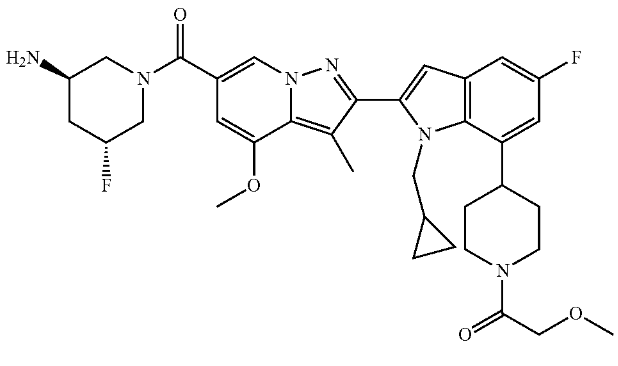<br>A2C37-742<br>1-(4-(2-(6-((3R,5R)-3-Amino-5-fluoropiperidine-1-carbonyl)-4-methoxy-3-methylpyrazolo[1,5-a]pyridin-2-yl)-1-(cyclopropylmethyl)-5-fluoro-1H-indol-7-yl)piperidin-1-yl)-2-methoxyethan-1-one<br>Analytical Data: 633.2; 1.911 min (Method E) |

TABLE 49-continued

| Example | Structure<br>Name<br>Analytical Data: LC-MS m/z $[M + H]^+$; HPLC retention time (HPLC method 1) |
|---|---|
| 482 | 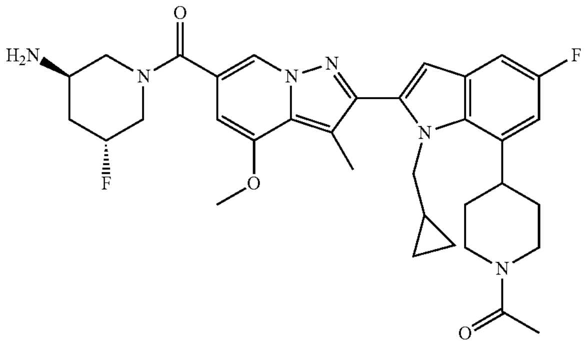<br>A2C37-744<br>1-(4-(2-(6-((3R,5R)-3-Amino-5-fluoropiperidine-1-carbonyl)-4-methoxy-3-methylpyrazolo[1,5-a]pyridin-2-yl)-1-(cyclopropylmethyl)-5-fluoro-1H-indol-7-yl)piperidin-1-yl)ethan-1-one<br>Analytical Data: 619.3; 1.703 min (Method E) |
| 483 | 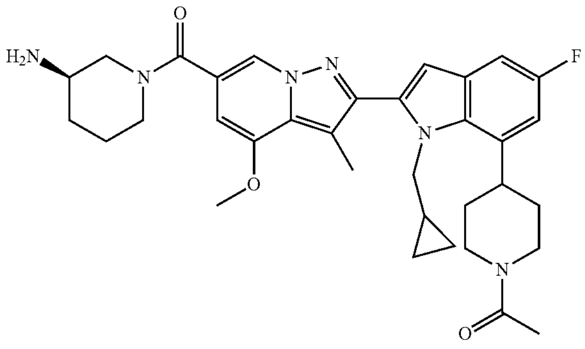<br>A2C37-745<br>(R)-1-(4-(2-(6-(3-Aminopiperidine-1-carbonyl)-4-methoxy-3-methylpyrazolo[1,5-a]pyridin-2-yl)-1-(cyclopropylmethyl)-5-fluoro-1H-indol-7-yl)piperidin-1-yl)ethan-1-one<br>Analytical Data: 601.3; 1.629 min (Method E) |

Example 484

((R)-3-Aminopiperidin-1-yl)(2-(1-(cyclopropylmethyl)-5-fluoro-7-(1-((1r,4r)-4-hydroxycyclohexane-1-carbonyl)piperidin-4-yl)-1H-indol-2-yl)-3-methylpyrazolo[1,5-a]pyridin-6-yl)methanone

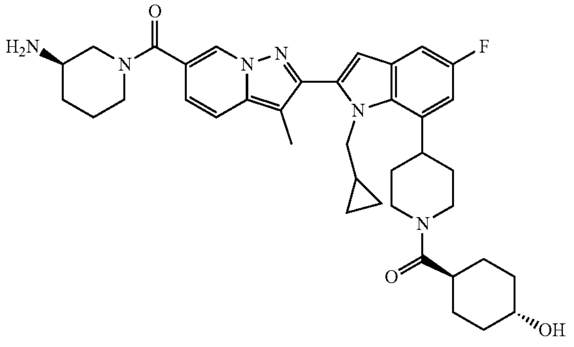 [SMILES: Cc1c(-c2cc3cc(F)cc(C4CCN(C(=O)[C@H]5CC[C@H](O)CC5)CC4)c3n2CC2CC2)nn2cc(C(=O)N3CCC[C@@H](N)C3)ccc12]

Intermediate 484A

Ethyl 2-(7-(1-(tert-butoxycarbonyl)piperidin-4-yl)-1-(cyclopropylmethyl)-5-fluoro-1H-indol-2-yl)-3-methylpyrazolo[1,5-a]pyridine-6-carboxylate

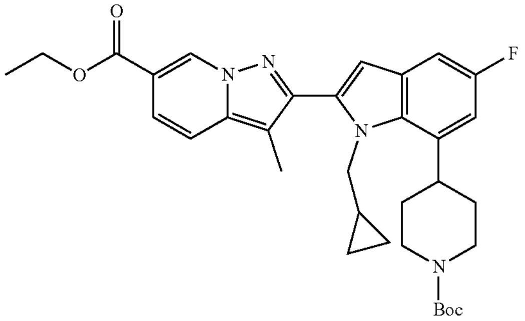 [SMILES: CCOC(=O)c1ccc2c(C)c(-c3cc4cc(F)cc(C5CCN(C(=O)OC(C)(C)C)CC5)c4n3CC3CC3)nn2c1]

Intermediate 484A (3.0 g, 68%) was prepared following a procedure similar to the preparation of Intermediate 386A. LC-MS m/z: 575.5 $[M+H]^+$.

Intermediate 484B

Ethyl 2-(1-(cyclopropylmethyl)-5-fluoro-7-(piperidin-4-yl)-1H-indol-2-yl)-3-methylpyrazolo[1,5-a]pyridine-6-carboxylate

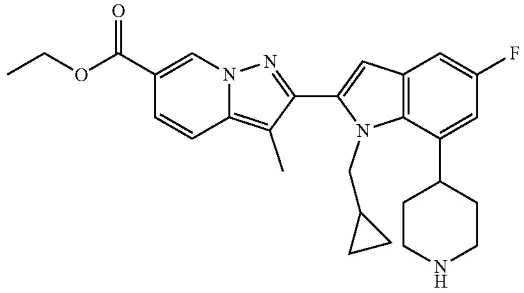 [SMILES: CCOC(=O)c1ccc2c(C)c(-c3cc4cc(F)cc(C5CCNCC5)c4n3CC3CC3)nn2c1]

Intermediate 484B (500 mg, 76%) was obtained from intermediate 484A following a procedure similar to the preparation of Intermediate 386B. LC-MS m/z: 475.4 [M+H]+.

Intermediate 484C

Ethyl 2-(1-(cyclopropylmethyl)-5-fluoro-7-(1-((1r,4r)-4-hydroxycyclohexane-1-carbonyl)piperidin-4-yl)-1H-indol-2-yl)-3-methylpyrazolo[1,5-a]pyridine-6-carboxylate

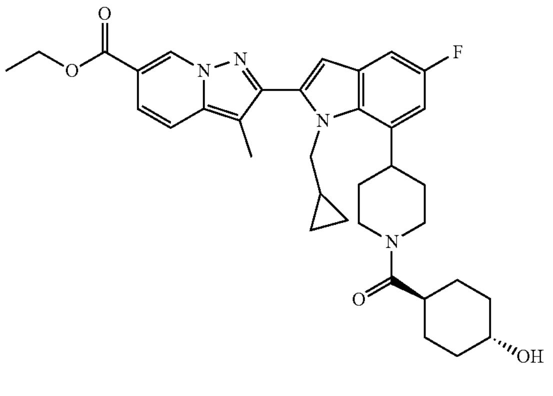 [SMILES: CCOC(=O)c1ccc2c(C)c(-c3cc4cc(F)cc(C5CCN(C(=O)[C@H]6CC[C@H](O)CC6)CC5)c4n3CC3CC3)nn2c1]

(1s,4s)-4-Hydroxycyclohexane-1-carboxylic acid (30.4 mg, 0.211 mmol), DIPEA (0.110 ml, 0.632 mmol) and HATU (120 mg, 0.316 mmol) were added to a stirred solution of Intermediate 484B (100 mg, 0.211 mmol) in DMF (2 ml). The reaction mixture was stirred 3 hours, quenched with water (50 ml), and extracted with ethyl acetate (2×50 ml). The combined organic layers were dried over sodium sulphate, filtered, and concentrated under reduced pressure to give afford crude ethyl 2-(1-(cyclopropylmethyl)-5-fluoro-7-(1-((1s,4s)-4-hydroxycyclohexane-1-carbonyl)piperidin-4-yl)-1H-indol-2-yl)-3-methylpyrazolo[1,5-a]pyridine-6-carboxylate (100 mg, 79%). LC-MS m/z: 601.8 $[M+H]^+$.

Intermediate 484D 2-(1-(cyclopropylmethyl)-5-fluoro-7-(1-((1r,4r)-4-hydroxycyclohexane-1-carbonyl)piperidin-4-yl)-1H-indol-2-yl)-3-methylpyrazolo[1,5-a]pyridine-6-carboxylic acid

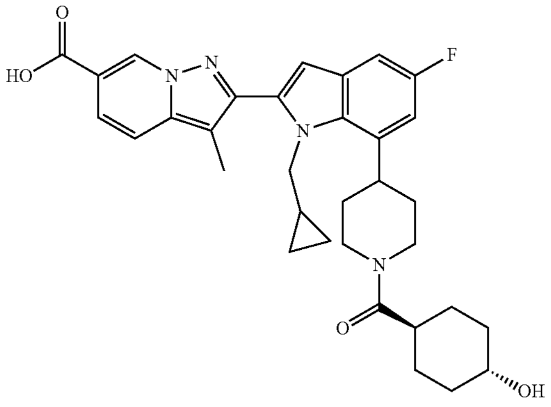 [SMILES: Cc1c(-c2cc3cc(F)cc(C4CCN(C(=O)[C@H]5CC[C@H](O)CC5)CC4)c3n2CC2CC2)nn2cc(C(=O)O)ccc12]

LiOH (3.99 mg, 0.166 mmol) was added to a stirred solution of Intermediate 484C (100 mg, 0.166 mmol) in a mixture of solvents: THF (1 ml), methanol (1 ml) and water (1 ml).The reaction mixture was stirred for 4 hours, concentrated in vacuo and the salts obtained were neutralized using 1 N HCl. The solids obtained was filtered through a Buchner funnel, and dried under reduced pressure to afford 2-(1-(cyclopropylmethyl)-5-fluoro-7-(1-((1r,4r)-4-hydroxycyclohexane-1-carbonyl)piperidin-4-yl)-1H-indol-2-yl)-3-methylpyrazolo[1,5-a]pyridine-6-carboxylic acid (90 mg, 94%). LC-MS m/z: 573.5 $[M+H]^+$.

Intermediate 484E tert-butyl ((R)-1-(2-(1-(cyclopropylmethyl)-5-fluoro-7-(1-((1r,4r)-4-hydroxycyclohexane-1-carbonyl)piperidin-4-yl)-1H-indol-2-yl)-3-methylpyrazolo[1,5-a]pyridine-6-carbonyl)piperidin-3-yl)carbamate

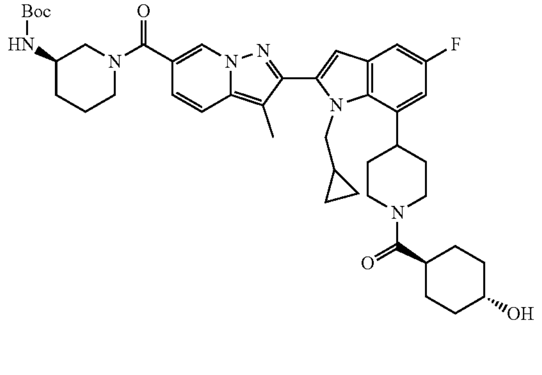 [SMILES: Cc1c(-c2cc3cc(F)cc(C4CCN(C(=O)[C@H]5CC[C@H](O)CC5)CC4)c3n2CC2CC2)nn2cc(C(=O)N3CCC[C@@H](NC(=O)OC(C)(C)C)C3)ccc12]

Intermediate 484E (100 mg, 76%) was prepared starting from Intermediate 484D following a procedure similar to the preparation of Intermediate 386E. LC-MS m/z: 755.6 $[M+H]^+$.

Example 484

((R)-3-Aminopiperidin-1-yl)(2-(1-(cyclopropylmethyl)-5-fluoro-7-(1-((1r,4r)-4-hydroxycyclohexane-1-carbonyl)piperidin-4-yl)-1H-indol-2-yl)-3-methylpyrazolo[1,5-a]pyridin-6-yl)methanone

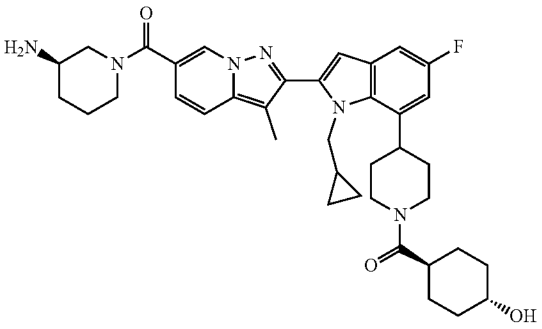 [SMILES: Cc1c(-c2cc3cc(F)cc(C4CCN(C(=O)[C@H]5CC[C@H](O)CC5)CC4)c3n2CC2CC2)nn2cc(C(=O)N3CCC[C@@H](N)C3)ccc12]

TFA (0.106 mmol) was added to a stirred solution of Intermediate 484E (80 mg, 0.106 mmol) in DCM (1 ml) at 0° C. The reaction mixture was stirred for 3 hours, concentrated in vacuo to obtain a crude compound, which was purified using preparative LC/MS with the following conditions: Column: Waters X Bridge C18, 19×150 mm, 5 μm particles; mobile phase A: 10 mM ammonium acetate; mobile phase B: acetonitrile; gradient: 12-47% B over 25 minutes, then a 5-minute hold at 100% B; flow rate: 15 ml/min. Fractions containing the desired product were combined, and dried using centrifugal evaporation. The purified material was then diluted with a 1:1 mixture of ethylene dichloride and methanol (EDM), treated with Si-Pyridine, and shaken for a minimum of 2 hours, filtered, and dried via centrifugal evaporation to afford ((R)-3-aminopiperidin-1-yl)(2-(1-(cyclopropylmethyl)-5-fluoro-7-(1-((1s,4s)-4-hydroxycyclohexane-1-carbonyl)piperidin-4-yl)-1H-indol-2-yl)-3-methylpyrazolo[1,5-a]pyridin-6-yl)methanone (7.3 mg, 10%). LCMS m/z: 655.4 $[M+H]^+$. LCMS retention time: 1.52 min (method E); 1H NMR (400 MHz, DMSO-$d_6$) δ ppm: 8.86 (s, 1H), 8.13-7.90 (m, 2H), 7.82 (d, J=9.3 Hz, 1H), 7.33-7.10 (m, 3H), 7.04-6.93 (m, 2H), 6.78 (s,1H), 4.70-4.62 (m, 1H), 4.50-4.26 (m, 3H), 4.17-3.94 (m, 3H), 3.84-3.79 (m, 1H), 3.64-3.59 (m, 1H), 3.31-3.16 (m, 5H), 2.95-2.61 (m,4H), 2.37 (s, 3H), 2.06-1.94 (m, 3H), 1.87-1.35 (m, 7H), 0.98-0.88 (m, 1H), 0.23 (br, d, J=8.8 Hz, 2H), 0.12-0.28 (m, 2H).

Compounds of Examples 485 to 509 in Table 50 were prepared following a procedure similar to the preparation of a compound of Example 484, by acid amine coupling of Intermediate 484B with appropriate carboxylic acid followed by ester hydrolysis and coupling with appropriate amines

TABLE 50

| Example | Structure<br>Name<br>Analytical Data: LC-MS m/z [M + H]+; HPLC retention time (HPLC method) |
|---|---|
| 485 | 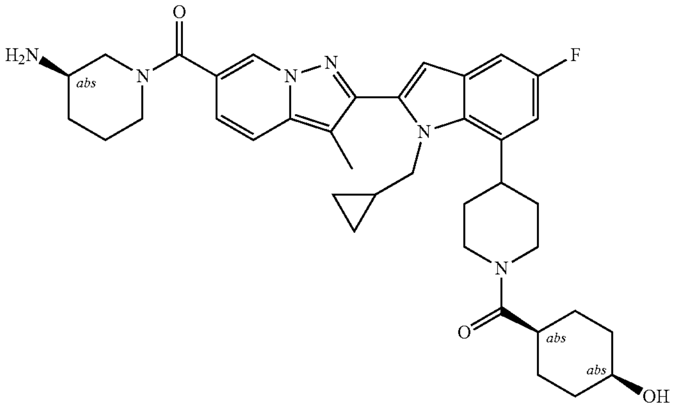 [SMILES: Cc1c(-c2cc3cc(F)cc(C4CCN(C(=O)[C@H]5CC[C@@H](O)CC5)CC4)c3n2CC2CC2)nn2cc(C(=O)N3CCC[C@@H](N)C3)ccc12]<br>((R)-3-Aminopiperidin-1-yl)(2-(1-(cyclopropylmethyl)-5-fluoro-7-(1-((1s,4s)-4-hydroxycyclohexane-1-carbonyl)piperidin-4-yl)-1H-indol-2-yl)-3-methylpyrazolo[1,5-a]pyridin-6-yl)methanone<br>Analytical Data: 655.4; 1.650 min (Method E) |
| 486 | 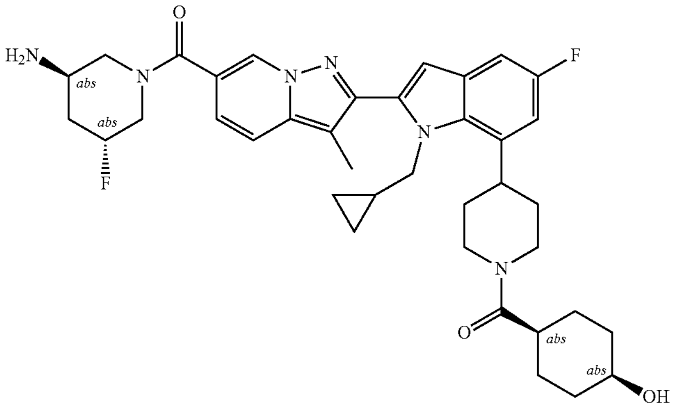 [SMILES: Cc1c(-c2cc3cc(F)cc(C4CCN(C(=O)[C@H]5CC[C@@H](O)CC5)CC4)c3n2CC2CC2)nn2cc(C(=O)N3C[C@H](N)C[C@@H](F)C3)ccc12]<br>((3R,5R)-3-Amino-5-fluoropiperidin-1-yl)(2-(1-(cyclopropylmethyl)-5-fluoro-7-(1-((1s,4s)-4-hydroxycyclohexane-1-carbonyl)piperidin-4-yl)-1H-indol-2-yl)-3-methylpyrazolo[1,5-a]pyridin-6-yl)methanone<br>Analytical Data: 673.4; 1.623 min (Method E) |
| 487 | 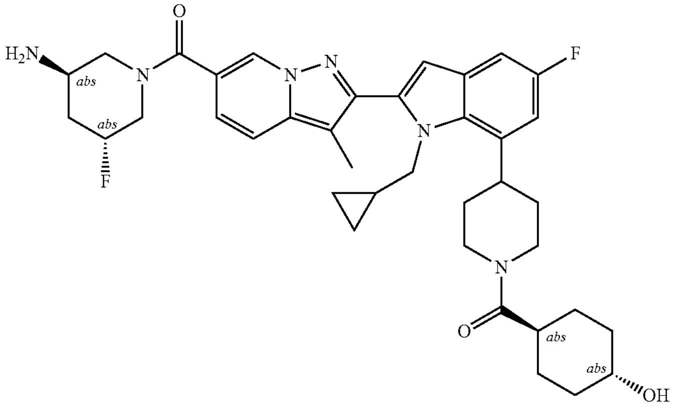 [SMILES: Cc1c(-c2cc3cc(F)cc(C4CCN(C(=O)[C@H]5CC[C@H](O)CC5)CC4)c3n2CC2CC2)nn2cc(C(=O)N3C[C@H](N)C[C@@H](F)C3)ccc12]<br>((3R,5R)-3-Amino-5-fluoropiperidin-1-yl)(2-(1-(cyclopropylmethyl)-5-fluoro-7-(1-((1r,4r)-4-hydroxycyclohexane-1-carbonyl)piperidin-4-yl)-1H-indol-2-yl)-3-methylpyrazolo[1,5-a]pyridin-6-yl)methanone<br>Analytical Data: 673.4; 1.627 min (Method E) |

TABLE 50-continued

| Example | Structure<br>Name<br>Analytical Data: LC-MS m/z [M + H]+; HPLC retention time (HPLC method) |
|---|---|
| 488 | 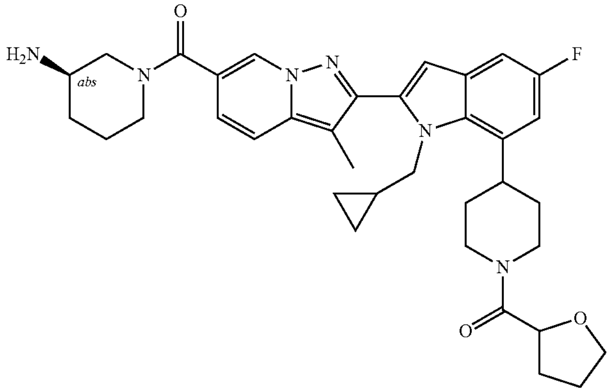 [SMILES: Cc1c(-c2cc3cc(F)cc(C4CCN(C(=O)C5CCCO5)CC4)c3n2CC2CC2)nn2cc(C(=O)N3CCC[C@@H](N)C3)ccc12]<br>((R)-3-Aminopiperidin-1-yl)(2-(1-(cyclopropylmethyl)-5-fluoro-7-(1-(tetrahydrofuran-2-carbonyl)piperidin-4-yl)-1H-indol-2-yl)-3-methylpyrazolo[1,5-a]pyridin-6-yl)methanone (isomer 1)<br>Analytical Data: 627.4; 1.942 min (Method E) |
| 489 | 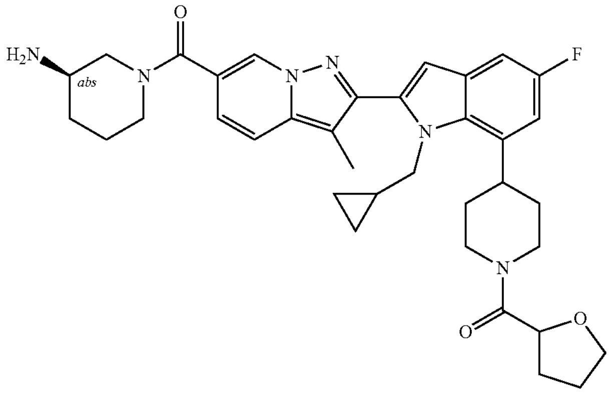 [SMILES: Cc1c(-c2cc3cc(F)cc(C4CCN(C(=O)C5CCCO5)CC4)c3n2CC2CC2)nn2cc(C(=O)N3CCC[C@@H](N)C3)ccc12]<br>((R)-3-Aminopiperidin-1-yl)(2-(1-(cyclopropylmethyl)-5-fluoro-7-(1-(tetrahydrofuran-2-carbonyl)piperidin-4-yl)-1H-indol-2-yl)-3-methylpyrazolo[1,5-a]pyridin-6-yl)methanone (isomer 2)<br>Analytical Data: 627.4; 1.942 min (Method E) |
| 490 | 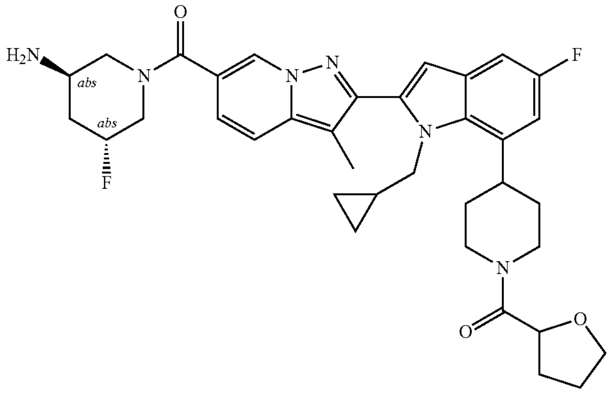 [SMILES: Cc1c(-c2cc3cc(F)cc(C4CCN(C(=O)C5CCCO5)CC4)c3n2CC2CC2)nn2cc(C(=O)N3C[C@H](N)C[C@@H](F)C3)ccc12]<br>((3R,5R)-3-Amino-5-fluoropiperidin-1-yl)(2-(1-(cyclopropylmethyl)-5-fluoro-7-(1-(tetrahydrofuran-2-carbonyl)piperidin-4-yl)-1H-indol-2-yl)-3-methylpyrazolo[1,5-a]pyridin-6-yl)methanone (isomer 1)<br>Analytical Data: 645.45; 1.979 min (Method E) |

TABLE 50-continued

| Example | Structure<br>Name<br>Analytical Data: LC-MS m/z [M + H]$^+$; HPLC retention time (HPLC method) |
|---|---|
| 491 | 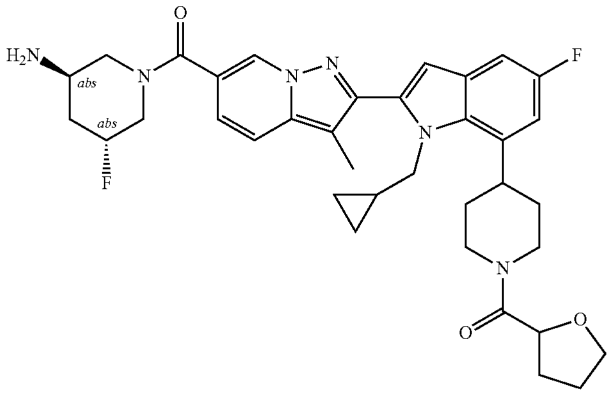 [SMILES: Cc1c(-c2cc3cc(F)cc(C4CCN(C(=O)C5CCCO5)CC4)c3n2CC2CC2)nn2cc(C(=O)N3C[C@H](N)C[C@@H](F)C3)ccc12]<br>((3R,5R)-3-Amino-5-fluoropiperidin-1-yl)(2-(1-(cyclopropylmethyl)-5-fluoro-7-(1-(tetrahydrofuran-2-carbonyl)piperidin-4-yl)-1H-indol-2-yl)-3-methylpyrazolo[1,5-a]pyridin-6-yl)methanone (isomer 2)<br>Analytical Data: 645.45; 1.979 min (Method E) |
| 492 | 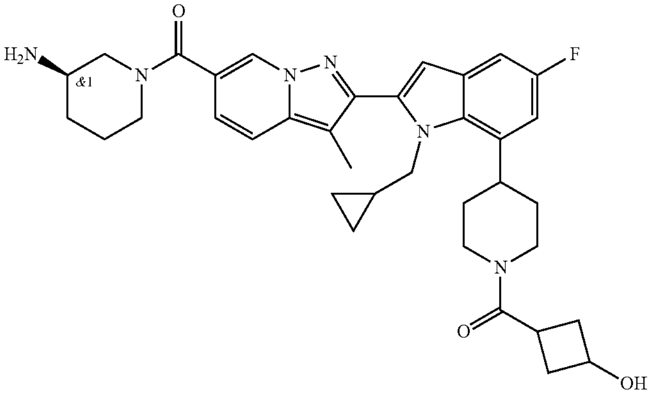 [SMILES: Cc1c(-c2cc3cc(F)cc(C4CCN(C(=O)C5CC(O)C5)CC4)c3n2CC2CC2)nn2cc(C(=O)N3CCC[C@@H](N)C3)ccc12]<br>(R)-(3-Aminopiperidin-1-yl)(2-(1-(cyclopropylmethyl)-5-fluoro-7-(1-(3-hydroxycyclobutane-1-carbonyl)piperidin-4-yl)-1H-indol-2-yl)-3-methylpyrazolo[1,5-a]pyridin-6-yl)methanone (mixture of diastereomers)<br>Analytical Data: 627.3; 1.509 min (Method E) |
| 493 | 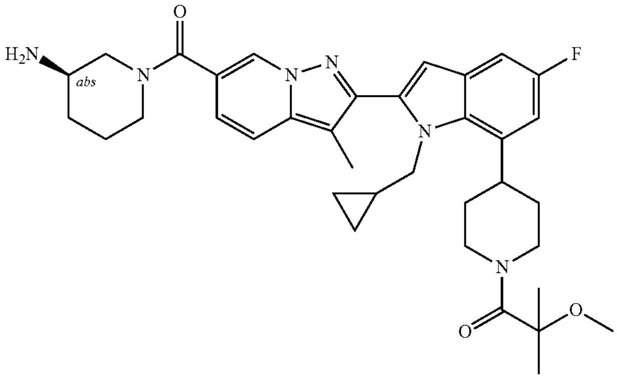 [SMILES: COC(C)(C)C(=O)N1CCC(c2cc(F)cc3cc(-c4nn5cc(C(=O)N6CCC[C@@H](N)C6)ccc5c4C)n(CC4CC4)c23)CC1]<br>(R)-1-(4-(2-(6-(3-Aminopiperidine-1-carbonyl)-3-methylpyrazolo[1,5-a]pyridin-2-yl)-1-(cyclopropylmethyl)-5-fluoro-1H-indol-7-yl)piperidin-1-yl)-2-methoxy-2-methylpropan-1-one<br>Analytical Data: 629.3; 1.868 min (Method E) |

TABLE 50-continued

| Example | Structure<br>Name<br>Analytical Data: LC-MS m/z [M + H]+; HPLC retention time (HPLC method) |
|---|---|
| 494 | 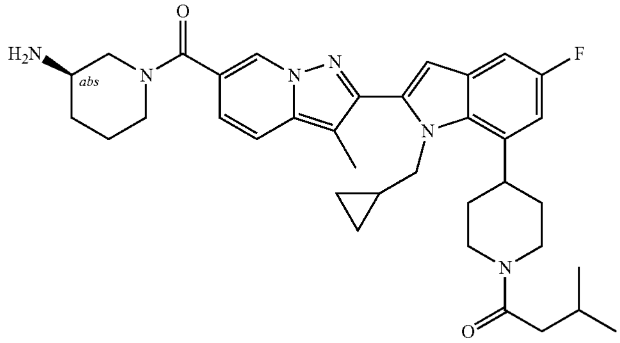 [SMILES: Cc1c(-c2cc3cc(F)cc(C4CCN(C(=O)CC(C)C)CC4)c3n2CC2CC2)nn2cc(C(=O)N3CCC[C@@H](N)C3)ccc12]<br>1-(4-(2-(6-((3R,5R)-3-Amino-5-fluoropiperidine-1-carbonyl)-3-methylpyrazolo[1,5-a]pyridin-2-yl)-1-(cyclopropylmethyl)-5-fluoro-1H-indol-7-yl)piperidin-1-yl)-3-methylbutan-1-one<br>Analytical Data: 613.3; 1.780 min (Method E) |
| 495 | 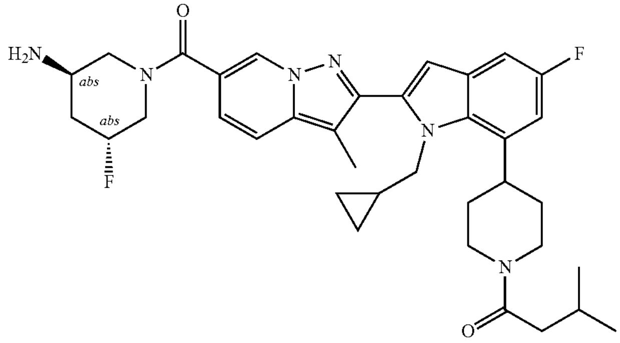 [SMILES: Cc1c(-c2cc3cc(F)cc(C4CCN(C(=O)CC(C)C)CC4)c3n2CC2CC2)nn2cc(C(=O)N3C[C@H](N)C[C@@H](F)C3)ccc12]<br>1-(4-(2-(6-((3R,5R)-3-Amino-5-fluoropiperidine-1-carbonyl)-3-methylpyrazolo[1,5-a]pyridin-2-yl)-1-(cyclopropylmethyl)-5-fluoro-1H-indol-7-yl)piperidin-1-yl)-3-methylbutan-1-one<br>Analytical Data: 631.3; 1.810 min (Method E) |
| 496 | 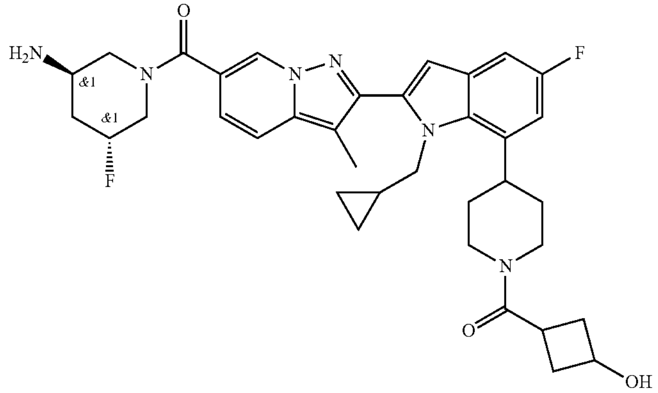 [SMILES: Cc1c(-c2cc3cc(F)cc(C4CCN(C(=O)C5CC(O)C5)CC4)c3n2CC2CC2)nn2cc(C(=O)N3C[C@H](N)C[C@@H](F)C3)ccc12]<br>((3R,5R)-3-Amino-5-fluoropiperidin-1-yl)(2-(1-(cyclopropylmethyl)-5-fluoro-7-(1-(3-hydroxycyclobutane-1-carbonyl)piperidin-4-yl)-1H-indol-2-yl)-3-methylpyrazolo[1,5-a]pyridin-6-yl)methanone (mixture of diastereomers)<br>Analytical Data: 645.3; 1.447 min (Method E) |

TABLE 50-continued

| Example | Structure<br>Name<br>Analytical Data: LC-MS m/z $[M + H]^+$; HPLC retention time (HPLC method) |
|---|---|
| 497 | 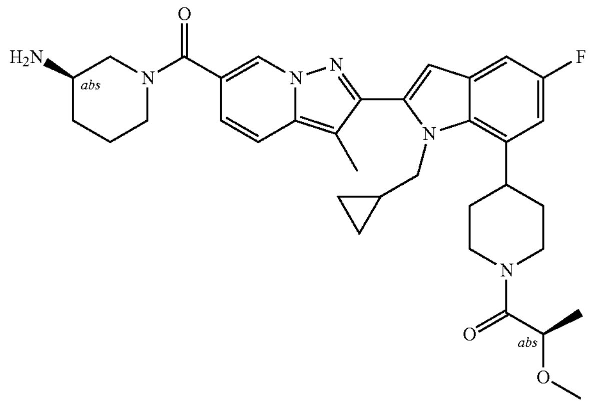 [SMILES: CO[C@H](C)C(=O)N1CCC(c2cc(F)cc3cc(-c4nn5cc(C(=O)N6CCC[C@@H](N)C6)ccc5c4C)n(CC4CC4)c23)CC1]<br>(R)-1-(4-(2-(6-((R)-3-Aminopiperidine-1-carbonyl)-3-methylpyrazolo[1,5-a]pyridin-2-yl)-1-(cyclopropylmethyl)-5-fluoro-1H-indol-7-yl)piperidin-1-yl)-2-methoxypropan-1-one<br>Analytical Data: 615.3; 1.551 min (Method E) |
| 498 | 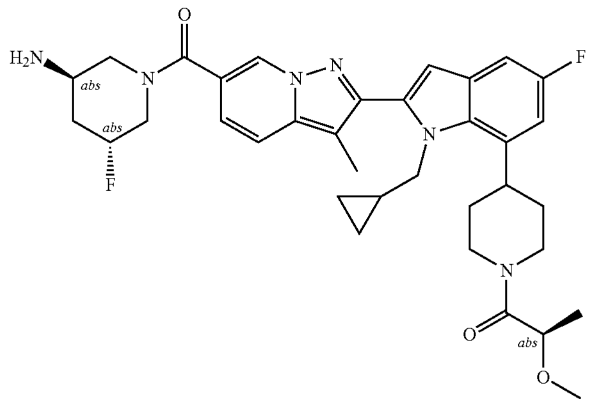 [SMILES: CO[C@H](C)C(=O)N1CCC(c2cc(F)cc3cc(-c4nn5cc(C(=O)N6C[C@H](N)C[C@@H](F)C6)ccc5c4C)n(CC4CC4)c23)CC1]<br>(R)-1-(4-(2-(6-((3R,5R)-3-Amino-5-fluoropiperidine-1-carbonyl)-3-methylpyrazolo[1,5-a]pyridin-2-yl)-1-(cyclopropylmethyl)-5-fluoro-1H-indol-7-yl)piperidin-1-yl)-2-methoxypropan-1-one<br>Analytical Data: 633.3; 1.693 min (Method E) |
| 499 | 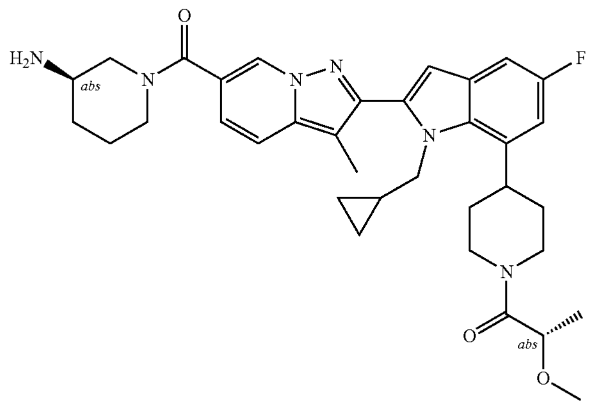 [SMILES: CO[C@@H](C)C(=O)N1CCC(c2cc(F)cc3cc(-c4nn5cc(C(=O)N6CCC[C@@H](N)C6)ccc5c4C)n(CC4CC4)c23)CC1]<br>(S)-1-(4-(2-(6-((R)-3-Aminopiperidine-1-carbonyl)-3-methylpyrazolo[1,5-a]pyridin-2-yl)-1-(cyclopropylmethyl)-5-fluoro-1H-indol-7-yl)piperidin-1-yl)-2-methoxypropan-1-one<br>Analytical Data: 615.3; 1.545 min (Method E) |

TABLE 50-continued

| Example | Structure<br>Name<br>Analytical Data: LC-MS m/z [M + H]+; HPLC retention time (HPLC method) |
|---|---|
| 500 | 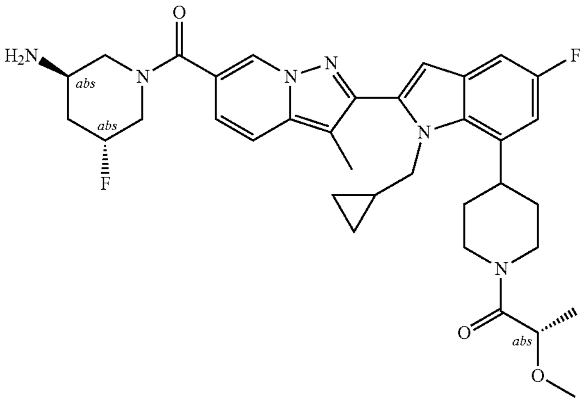 [SMILES: CO[C@@H](C)C(=O)N1CCC(c2cc(F)cc3cc(-c4nn5cc(C(=O)N6C[C@H](N)C[C@@H](F)C6)ccc5c4C)n(CC4CC4)c23)CC1]<br>(S)-1-(4-(2-(6-((3R,5R)-3-Amino-5-fluoropiperidine-1-carbonyl)-3-methylpyrazolo[1,5-a]pyridin-2-yl)-1-(cyclopropylmethyl)-5-fluoro-1H-indol-7-yl)piperidin-1-yl)-2-methoxypropan-1-one<br>Analytical Data: 633.3; 1.564 min (Method E) |
| 501 | 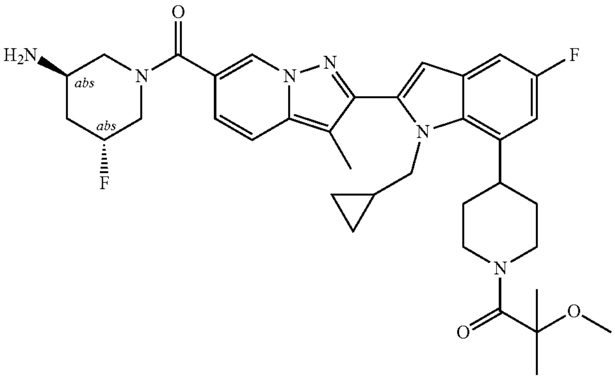 [SMILES: COC(C)(C)C(=O)N1CCC(c2cc(F)cc3cc(-c4nn5cc(C(=O)N6C[C@H](N)C[C@@H](F)C6)ccc5c4C)n(CC4CC4)c23)CC1]<br>1-(4-(2-(6-((3R,5R)-3-Amino-5-fluoropiperidine-1-carbonyl)-3-methylpyrazolo[1,5-a]pyridin-2-yl)-1-(cyclopropylmethyl)-5-fluoro-1H-indol-7-yl)piperidin-1-yl)-2-methoxy-2-methylpropan-1-one<br>Analytical Data: 647.3; 1.908 min (Method) |
| 502 | 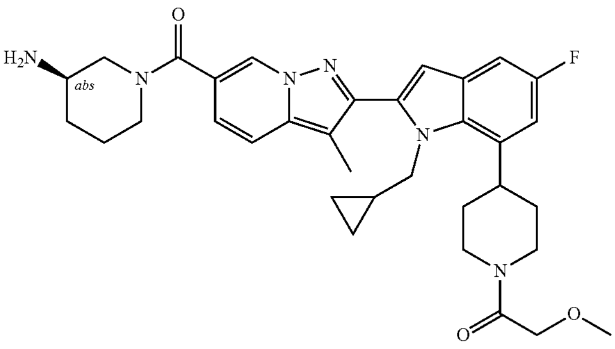 [SMILES: COCC(=O)N1CCC(c2cc(F)cc3cc(-c4nn5cc(C(=O)N6CCC[C@@H](N)C6)ccc5c4C)n(CC4CC4)c23)CC1]<br>(R)-1-(4-(2-(6-(3-Aminopiperidine-1-carbonyl)-3-methylpyrazolo[1,5-a]pyridin-2-yl)-1-(cyclopropylmethyl)-5-fluoro-1H-indol-7-yl)piperidin-1-yl)-2-methoxyethan-1-one<br>Analytical Data: 601.3; 1.513 min (Method E) |

TABLE 50-continued

| Example | Structure<br>Name<br>Analytical Data: LC-MS m/z [M + H]$^+$; HPLC retention time (HPLC method) |
|---|---|
| 503 | 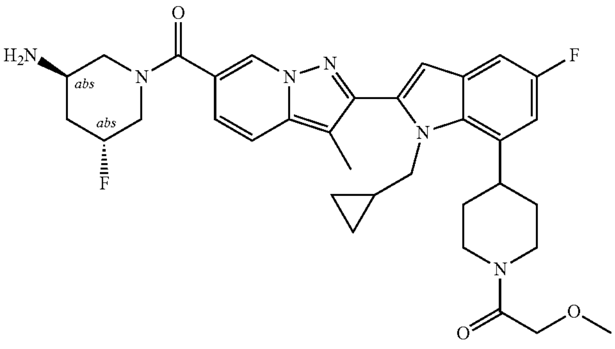 [SMILES: COCC(=O)N1CCC(c2cc(F)cc3cc(-c4nn5cc(C(=O)N6C[C@H](N)C[C@@H](F)C6)ccc5c4C)n(CC4CC4)c23)CC1]<br>1-(4-(2-(6-((3R,5R)-3-Amino-5-fluoropiperidine-1-carbonyl)-3-methylpyrazolo[1,5-a]pyridin-2-yl)-1-(cyclopropylmethyl)-5-fluoro-1H-indol-7-yl)piperidin-1-yl)-2-methoxyethan-1-one<br>Analytical Data: 619.3; 1.529 min (Method E) |
| 504 | 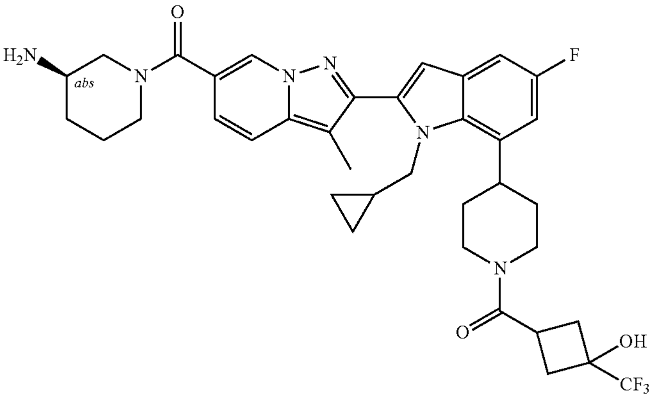 [SMILES: Cc1c(-c2cc3cc(F)cc(C4CCN(C(=O)C5CC(O)(C(F)(F)F)C5)CC4)c3n2CC2CC2)nn2cc(C(=O)N3CCC[C@@H](N)C3)ccc12]<br>(R)-(3-Aminopiperidin-1-yl)(2-(1-(cyclopropylmethyl)-5-fluoro-7-(1-(3-hydroxy-3-(trifluoromethyl)cyclobutane-1-carbonyl)piperidin-4-yl)-1H-indol-2-yl)-3-methylpyrazolo[1,5-a]pyridin-6-yl)methanone<br>Analytical Data: 695.3; 1.712 min (Method E) |
| 505 | 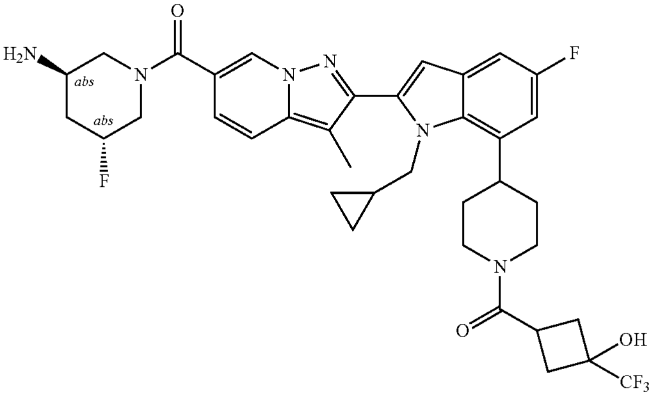 [SMILES: Cc1c(-c2cc3cc(F)cc(C4CCN(C(=O)C5CC(O)(C(F)(F)F)C5)CC4)c3n2CC2CC2)nn2cc(C(=O)N3C[C@H](N)C[C@@H](F)C3)ccc12]<br>((3R,5R)-3-Amino-5-fluoropiperidin-1-yl)(2-(1-(cyclopropylmethyl)-5-fluoro-7-(1-(3-hydroxy-3-(trifluoromethyl)cyclobutane-1-carbonyl)piperidin-4-yl)-1H-indol-2-yl)-3-methylpyrazolo[1,5-a]pyridin-6-yl)methanone (mixture of diastereomers)<br>Analytical Data: 713.3; 1.726 min (Method E) |

TABLE 50-continued

| Example | Structure<br>Name<br>Analytical Data: LC-MS m/z [M + H]$^+$; HPLC retention time (HPLC method) |
|---|---|
| 506 | 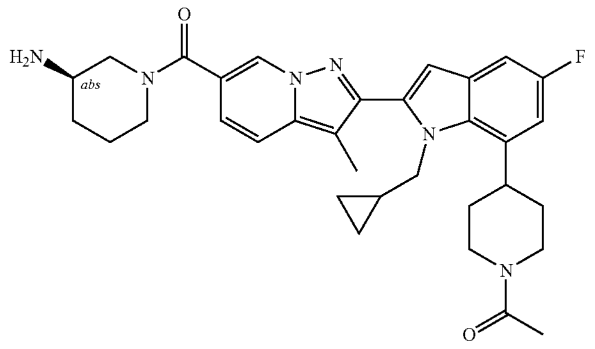 [SMILES: CC(=O)N1CCC(c2cc(F)cc3cc(-c4nn5cc(C(=O)N6CCC[C@@H](N)C6)ccc5c4C)n(CC4CC4)c23)CC1]<br>(R)-1-(4-(2-(6-(3-Aminopiperidine-1-carbonyl)-3-methylpyrazolo[1,5-a]pyridin-2-yl)-1-(cylcopropylmethyl)-5-fluoro-1H-indol-7-yl)piperidin-1-yl)ethan-1-one<br>Analytical Data: 571.3; 1.508 min (Method E) |
| 507 | 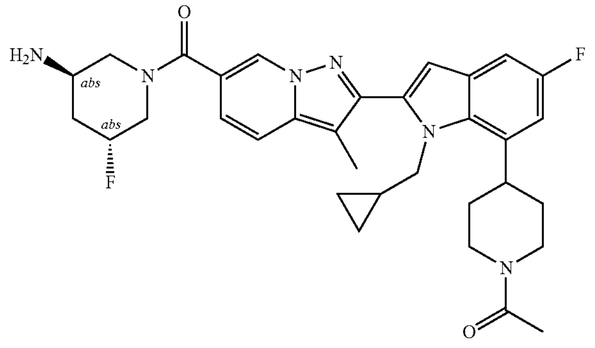 [SMILES: CC(=O)N1CCC(c2cc(F)cc3cc(-c4nn5cc(C(=O)N6C[C@H](N)C[C@@H](F)C6)ccc5c4C)n(CC4CC4)c23)CC1]<br>1-(4-(2-(6-((3R,5R)-3-Amino-5-fluoropiperidine-1-carbonyl)-3-methylpyrazolo[1,5-a]pyridin-2-yl)-1-(cyclopropylmethyl)-5-fluoro-1H-indol-7-yl)piperidin-1-yl)ethan-1-one<br>Analytical Data: 589.2; 1.573 min (Method E) |
| 508 | 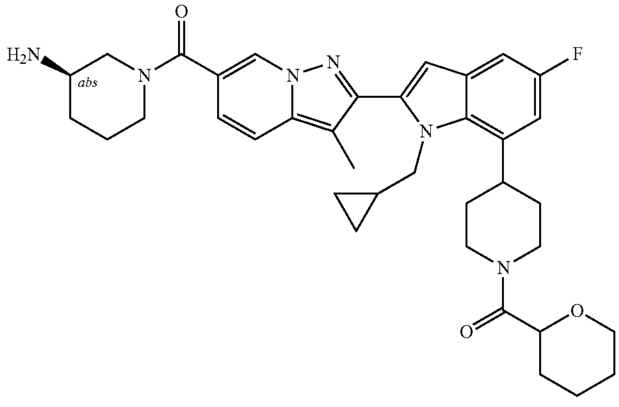 [SMILES: Cc1c(-c2cc3cc(F)cc(C4CCN(C(=O)C5CCCCO5)CC4)c3n2CC2CC2)nn2cc(C(=O)N3CCC[C@@H](N)C3)ccc12]<br>((R)-3-Aminopiperidin-1-yl)(2-(1-(cyclopropylmethyl)-5-fluoro-7-(1-(tetrahydro-2H-pyran-2-carbonyl)piperidin-4-yl)-1H-indol-2-yl)-3-methylpyrazolo[1,5-a]pyridin-6-yl)methanone (mixture of diastereomers)<br>Analytical Data: 641.4; 1.732 min (Method E) |

TABLE 50-continued

| Example | Structure<br>Name<br>Analytical Data: LC-MS m/z $[M + H]^+$; HPLC retention time (HPLC method) |
|---|---|
| 509 | 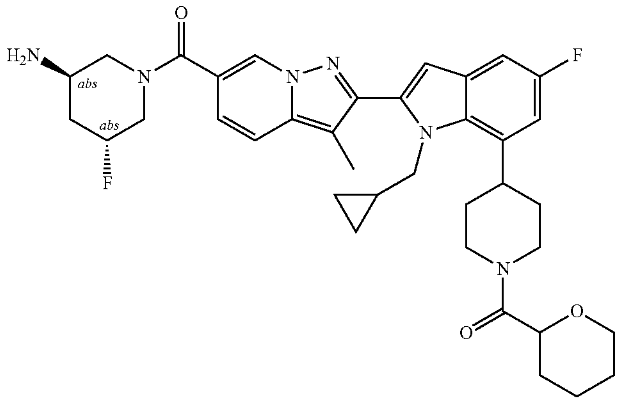 [SMILES: Cc1c(-c2cc3cc(F)cc(C4CCN(C(=O)C5CCCCO5)CC4)c3n2CC2CC2)nn2cc(C(=O)N3C[C@H](N)C[C@@H](F)C3)ccc12]<br>((3R,5R)-3-Amino-5-fluoropiperidin-1-yl)(2-(1-(cyclopropylmethyl)-5-fluoro-7-(1-(tetrahydro-2H-pyran-2-carbonyl)piperidin-4-yl)-1H-indol-2-yl)-3-methylpyrazolo[1,5-a]pyridin-6-yl)methanone (mixture of diastereomers)<br>Analytical Data: 659.3 ; 1.711 min (Method E) |

Example 510

(R)-1-(4-(2-(6-(3-Aminopiperidine-1-carbonyl)-4-methoxy-3-methylpyrazolo[1,5-a]pyridin-2-yl)-1-(cyclopropylmethyl)-1H-pyrrolo[2,3-c]pyridin-7-yl)piperidin-1-yl)-2-methoxyethan-1-one

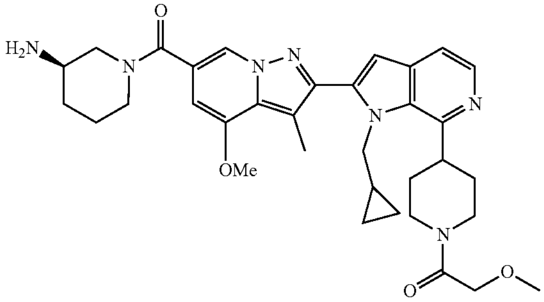 [SMILES: COCC(=O)N1CCC(c2nccc3cc(-c4nn5cc(C(=O)N6CCC[C@@H](N)C6)cc(OC)c5c4C)n(CC4CC4)c23)CC1]

Intermediate 510A methyl 2-(7-(1-(tert-butoxycarbonyl)piperidin-4-yl)-1-(cyclopropylmethyl)-1H-pyrrolo[2,3-c]pyridin-2-yl)-4-methoxy-3-methylpyrazolo[1,5-a]pyridine-6-carboxylate

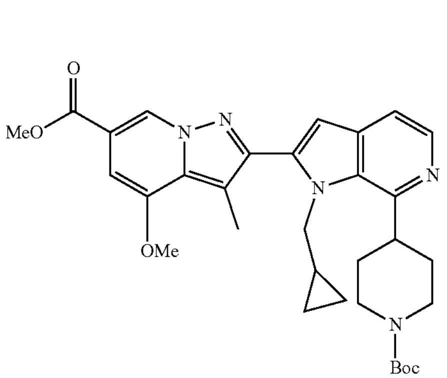 [SMILES: COC(=O)c1cc(OC)c2c(C)c(-c3cc4ccnc(C5CCN(C(=O)OC(C)(C)C)CC5)c4n3CC3CC3)nn2c1]

1-Amino-3-methoxy-5-(methoxycarbonyl)pyridin-1-ium 2,4 dinitro phenolate salt (2.120 g, 5.79 mmol) and copper(I) iodide (0.110 g, 0.579 mmol) were added to a stirred solution of Intermediate 44 (0.85 g, 1.929 mmol) in DMF (3 ml). The reaction mixture was stirred at 80° C. for 30 hours, allowed to cool to a room temperature, diluted with water (20 ml), quenched with saturated $NaHCO_3$ solution (10 ml), and extracted with ethyl acetate (3×20 ml). The combined organic layers were washed with brine, dried over sodium sulfate, filtered, and concentrated in vacuum to obtain a crude product, which was purified using a silica gel column, eluting with 0-70% ethyl acetate in hexane to afford methyl 2-(7-(1-(tert-butoxycarbonyl)piperidin-4-yl)-1-(cyclopropylmethyl)-1H-pyrrolo[2,3-c]pyridin-2-yl)-4-methoxy-3-methylpyrazolo[1,5-a]pyridine-6-carboxylate (520 mg, 47%). LC-MS m/z: 574.3 $[M+H]^+$.

Intermediate 510B

Methyl 2-(1-(cyclopropylmethyl)-7-(piperidin-4-yl)-1H-pyrrolo[2,3-c]pyridin-2-yl)-4-methoxy-3-methylpyrazolo[1,5-a]pyridine-6-carboxylate

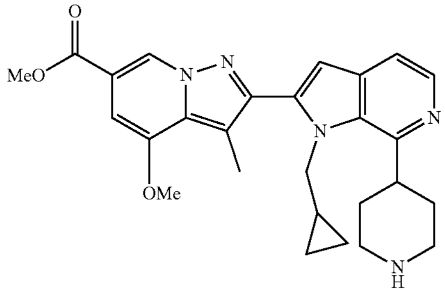 [SMILES: COC(=O)c1cc(OC)c2c(C)c(-c3cc4ccnc(C5CCNCC5)c4n3CC3CC3)nn2c1]

TFA (0.698 ml, 9.06 mmol) was added to a stirred solution of Intermediate 510A (520 mg, 0.906 mmol) in dichloromethane (10 ml). The reaction mixture was stirred at a room temperature for 16 hours, the salts thus obtained were treated with $NaHCO_3$ solution, and extracted with ethyl acetate (2×25 ml). The combined organic layers were washed with brine, dried over sodium sulfate, filtered, and concentrated in vacuum to afford methyl 2-(1-(cyclopropylmethyl)-7-(piperidin-4-yl)-1H-pyrrolo[2,3-c]pyridin-2-yl)-4-methoxy-3-methylpyrazolo[1,5-a]pyridine-6-carboxylate (410 mg, 96%). LC-MS m/z: 474.2 $[M+H]^+$.

Intermediate 510C

Methyl 2-(1-(cyclopropylmethyl)-7-(1-(2-methoxyacetyl)piperidin-4-yl)-1H-pyrrolo[2,3-c]pyridin-2-yl)-4-methoxy-3-methylpyrazolo[1,5-a]pyridine-6-carboxylate

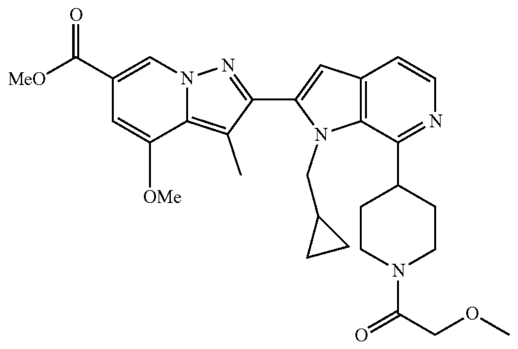 [SMILES: COCC(=O)N1CCC(c2nccc3cc(-c4nn5cc(C(=O)OC)cc(OC)c5c4C)n(CC4CC4)c23)CC1]

HATU (181 mg, 0.475 mmol) and 2-methoxyacetic acid (42.8 mg, 0.475 mmol) followed by DIPEA (0.138 ml, 0.792 mmol) were added to a stirred solution of Intermediate 510B (150 mg, 0.317 mmol) in DMF (2.0 ml). The reaction mixture was stirred for 2 hours, diluted with water (5 ml), quenched with saturated $NaHCO_3$ solution (10 ml), and extracted with ethyl acetate (3×25 ml). The combined organic layers were washed with brine, dried over sodium sulfate, filtered, and concentrated in vacuum to afford methyl 2-(1-(cyclopropylmethyl)-7-(1-(2-methoxyacetyl)piperidin-4-yl)-1H-pyrrolo[2,3-c]pyridin-2-yl)-4-methoxy-3-methylpyrazolo[1,5-a]pyridine-6-carboxylate (130 mg, 75%) LC-MS m/z: 546.3 $[M+H]^+$.

Intermediate 510D 2-(1-(Cyclopropylmethyl)-7-(1-(2-methoxyacetyl)piperidin-4-yl)-1H-pyrrolo[2,3-c]pyridin-2-yl)-4-methoxy-3-methylpyrazolo[1,5-a]pyridine-6-carboxylic acid

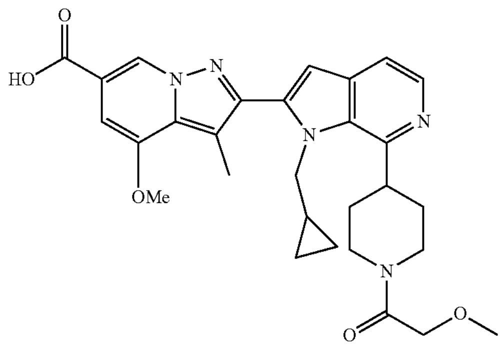 [SMILES: COCC(=O)N1CCC(c2nccc3cc(-c4nn5cc(C(=O)O)cc(OC)c5c4C)n(CC4CC4)c23)CC1]

LiOH (30.7 mg, 1.283 mmol) was added to a stirred solution of Intermediate 510C (140 mg, 0.257 mmol) in THF (5 ml), MeOH (1 ml), water (2 ml). The reaction mixture stirred for 4 hours, diluted with water (5 ml) and 1N HCl (2 ml), and extracted with ethyl acetate (2×25 ml). The combined organic layers were washed with brine, dried over sodium sulfate, filtered, and concentrated in vacuum to afford 2-(1-(cyclopropylmethyl)-7-(1-(2-methoxyacetyl)piperidin-4-yl)-1H-pyrrolo[2,3-c]pyridin-2-yl)-4-methoxy-3-methylpyrazolo[1,5-a]pyridine-6-carboxylic acid (90 mg, 66%). LC-MS m/z: 532.2 $[M+H]^+$.

Intermediate 510E (R)-1-(4-(2-(6-(3-Aminopiperidine-1-carbonyl)-4-methoxy-3-methylpyrazolo[1,5-a]pyridin-2-yl)-1-(cyclopropylmethyl)-1H-pyrrolo[2,3-c]pyridin-7-yl)piperidin-1-yl)-2-methoxyethan-1-one

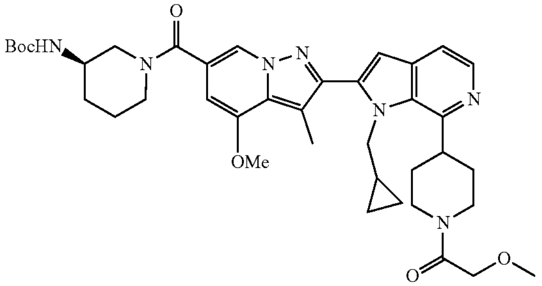 [SMILES: COCC(=O)N1CCC(c2nccc3cc(-c4nn5cc(C(=O)N6CCC[C@@H](NC(=O)OC(C)(C)C)C6)cc(OC)c5c4C)n(CC4CC4)c23)CC1]

tert-Butyl (R)-piperidin-3-ylcarbamate (25.4 mg, 0.127 mmol), HATU (48.3 mg, 0.127 mmol) followed by DIPEA (0.037 ml, 0.212 mmol) were added to a stirred solution of Intermediate 510D (45 mg, 0.085 mmol) in DMF (1.0 ml). The reaction mixture was stirred 16 hours, diluted with water (5 ml), and extracted with ethyl acetate (2×10 ml). The combined organic layers were washed with brine, dried over sodium sulfate, filtered, and concentrated in vacuum to afford tert-butyl (R)-(1-(2-(1-(cyclopropylmethyl)-7-(1-(2-methoxyacetyl)piperidin-4-yl)-1H-pyrrolo[2,3-c]pyridin-2-yl)-4-methoxy-3-methylpyrazolo[1,5-a]pyridine-6-carbonyl)piperidin-3-yl)carbamate (40 mg, 66%). LC-MS m/z: 714.3 $[M+H]^+$.

Example 510

(R)-1-(4-(2-(6-(3-Aminopiperidine-1-carbonyl)-4-methoxy-3-methylpyrazolo[1,5-a]pyridin-2-yl)-1-(cyclopropylmethyl)-1H-pyrrolo[2,3-c]pyridin-7-yl)piperidin-1-yl)-2-methoxyethan-1-one

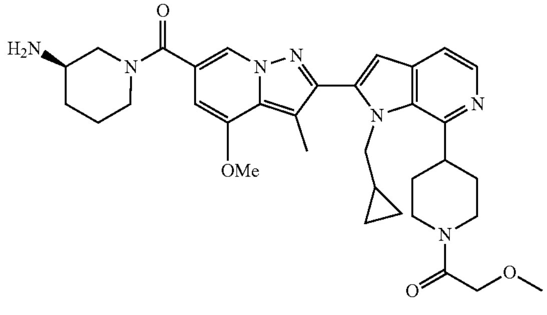 [SMILES: COCC(=O)N1CCC(c2nccc3cc(-c4nn5cc(C(=O)N6CCC[C@@H](N)C6)cc(OC)c5c4C)n(CC4CC4)c23)CC1]

TFA (0.043 ml, 0.560 mmol) was added to a stirred solution of Intermediate 510E (40 mg, 0.056 mmol) in dichloromethane (5 ml) at 0° C. The reaction mixture was allowed to warm to room a temperature and stirred for 3 hours, concentrated in vacuum to obtain a crude compound, which was purified using preparative LC/MS with the following conditions: Column: Waters X Bridge C18, 150×19 mm, 5 μm particles; mobile phase A: 5:95 acetonitrile:water with 0.1% trifluoroacetic acid; mobile phase B: 95:5 acetonitrile:water with 0.1% trifluoroacetic acid; gradient: a 0-minute hold at 20% B, 20-40% B over 20 minutes, then a 5-minute hold at 100% B; flow rate: 20 ml/min; column temperature: 25° C. Fraction collection was triggered by signals. Fractions containing the desired product were combined and dried via centrifugal evaporation. The purified material was then diluted with a 1:1 mixture of ethylene dichloride and methanol (EDM), treated with Si-Pyridine, and shaken for a minimum of 2 hours, filtered and dried using centrifugal evaporation to afford (R)-1-(4-(2-(6-(3-aminopiperidine-1-carbonyl)-4-methoxy-3-methylpyrazolo[1,5-a]pyridin-2-yl)-1-(cyclopropylmethyl)-1H-pyrrolo[2,3-c]pyridin-7-yl)piperidin-1-yl)-2-methoxyethan-1-one. LC-MS m/z: 614.3 $[M+H]^+$. Retention time: 1.188 min (Method E).

Example 511

1-(4-(2-(6-((3R,5R)-3-Amino-5-fluoropiperidine-1-carbonyl)-4-methoxy-3-methylpyrazolo[1,5-a]pyridin-2-yl)-1-(cyclopropylmethyl)-1H-pyrrolo[2,3-c]pyridin-7-yl)piperidin-1-yl)-2-methoxyethan-1-one

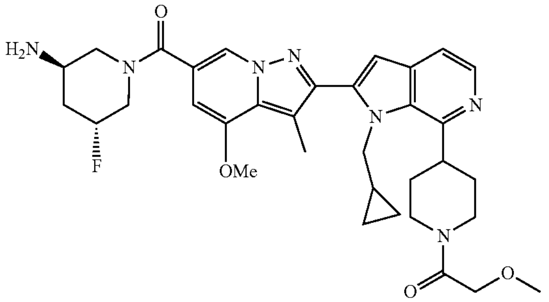 [SMILES: COCC(=O)N1CCC(c2nccc3cc(-c4nn5cc(C(=O)N6C[C@H](N)C[C@@H](F)C6)cc(OC)c5c4C)n(CC4CC4)c23)CC1]

Compound of Example 511 was prepared following a procedure similar to the preparation of a compound of Example 510, by acid amine coupling of Intermediate 510B with appropriate carboxylic acid followed by ester hydrolysis and coupling with appropriate amine. LC-MS m/z $[M+H]^+$: 632.3. HPLC retention time: 1.309 min (Method E)

Example 512

(R)-1-(4-(2-(6-(3-Aminopiperidine-1-carbonyl)-3-methylpyrazolo[1,5-a]pyridin-2-yl)-1-(cyclopropylmethyl)-1H-pyrrolo[2,3-c]pyridin-7-yl)piperidin-1-yl)-2-methoxyethan-1-one

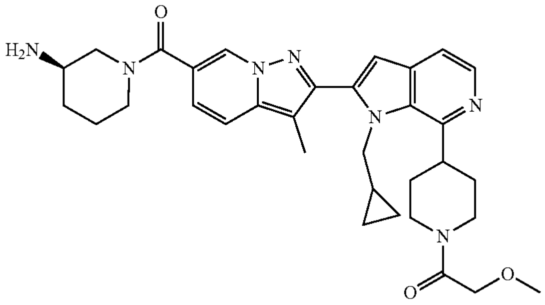 [SMILES: COCC(=O)N1CCC(c2nccc3cc(-c4nn5cc(C(=O)N6CCC[C@@H](N)C6)ccc5c4C)n(CC4CC4)c23)CC1]

Intermediate 512A

Ethyl 2-(7-(1-(tert-butoxycarbonyl)piperidin-4-yl)-1-(cyclopropylmethyl)-1H-pyrrolo[2,3-c]pyridin-2-yl)-3-methylpyrazolo[1,5-a]pyridine-6-carboxylate

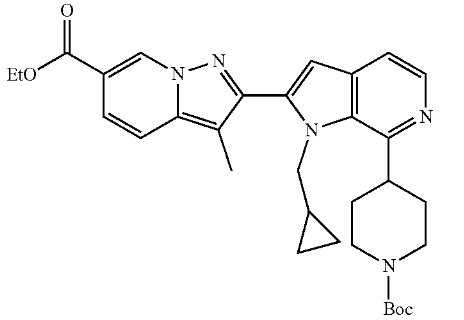 [SMILES: CCOC(=O)c1ccc2c(C)c(-c3cc4ccnc(C5CCN(C(=O)OC(C)(C)C)CC5)c4n3CC3CC3)nn2c1]

Intermediate 512A (480 mg, 45%) was prepared by following a similar procedure depicted for Intermediate 386A using the intermediates 44 and 8. LC-MS m/z: 558.3 $[M+H]^+$; $^1H$ NMR (300 MHz, DMSO-$d_6$) δ ppm:9.21 (s, 1H), 8.18-8.12 (m, 1H), 7.87 (d, J=9.4 Hz, 1H), 7.64 (d, J=9.4 Hz, 1H), 7.48 (d, J=5.3 Hz, 1H), 6.89 (s, 1H), 4.62-4.52 (m, 2H), 4.46-4.29 (m, 2H), 4.21-4.01 (m, 2H), 3.11-2.81 (m, 2H), 2.38 (s, 3H), 1.93-1.79 (m, 4H), 1.59-1.50 (m, 1H), 1.44 (s, 9H), 1.39-1.34 (m, 3H),1.09-0.95 (m, 1H), 0.32-0.21 (m, 2H), −0.11-−0.18 (m, 2H).

Intermediate 512B

Ethyl 2-(1-(cyclopropylmethyl)-7-(piperidin-4-yl)-1H-pyrrolo[2,3-c]pyridin-2-yl)-3-methylpyrazolo[1,5-a]pyridine-6-carboxylate

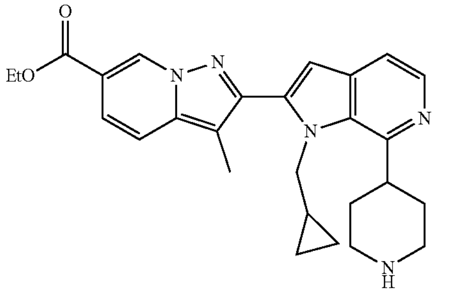 [SMILES: CCOC(=O)c1ccc2c(C)c(-c3cc4ccnc(C5CCNCC5)c4n3CC3CC3)nn2c1]

Intermediate 512B (320 mg, 81%) was prepared in similar fashion to Intermediate 510B. LC-MS m/z: 458.3 [M+H]$^+$.

Intermediate 512C ethyl 2-(1-(cyclopropylmethyl)-7-(1-(2-methoxyacetyl)piperidin-4-yl)-1H-pyrrolo[2,3-c]pyridin-2-yl)-3-methylpyrazolo[1,5-a]pyridine-6-carboxylate

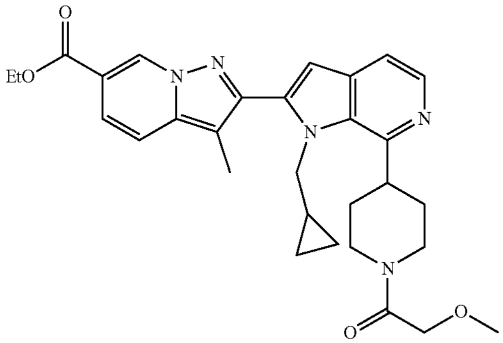 [SMILES: CCOC(=O)c1ccc2c(C)c(-c3cc4ccnc(C5CCN(C(=O)COC)CC5)c4n3CC3CC3)nn2c1]

Intermediate 512C (130 mg, 0, 75%) was prepared in similar fashion to intermediate 510C. LC-MS m/z: 530.3 [M+H]$^+$.

Intermediate 512D 2-(1-(cyclopropylmethyl)-7-(1-(2-methoxyacetyl)piperidin-4-yl)-1H-pyrrolo[2,3-c]pyridin-2-yl)-3-methylpyrazolo[1,5-a]pyridine-6-carboxylic acid

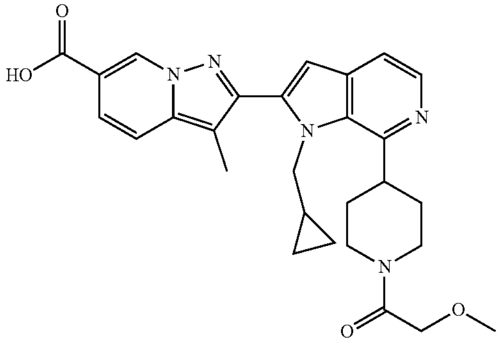 [SMILES: COCC(=O)N1CCC(c2nccc3cc(-c4nn5cc(C(=O)O)ccc5c4C)n(CC4CC4)c23)CC1]

Intermediate 512D (90 mg, 68%) was prepared in similar fashion to intermediate 510D. LC-MS m/z: 502.2 [M+H]$^+$ Intermediate 512E tert-butyl (R)-(1-(2-(1-(cyclopropylmethyl)-7-(1-(2-methoxyacetyl)piperidin-4-yl)-1H-pyrrolo[2,3-c]pyridin-2-yl)-3-methylpyrazolo[1,5-a]pyridine-6-carbonyl)piperidin-3-yl)carbamate

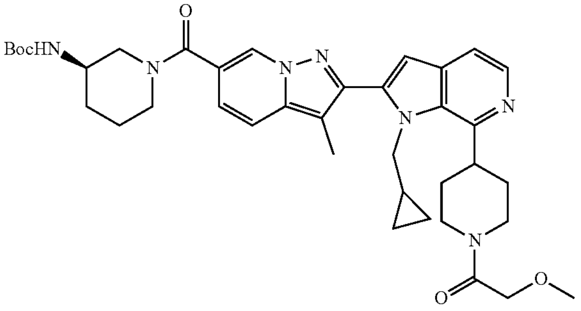 [SMILES: COCC(=O)N1CCC(c2nccc3cc(-c4nn5cc(C(=O)N6CCC[C@@H](NC(=O)OC(C)(C)C)C6)ccc5c4C)n(CC4CC4)c23)CC1]

Intermediate 512E (40 mg, 65%). was prepared in similar fashion to intermediate 510E. LC-MS m/z: 684.3 [M+H]$^+$ Example 512

(R)-1-(4-(2-(6-(3-Aminopiperidine-1-carbonyl)-3-methylpyrazolo[1,5-a]pyridin-2-yl)-1-(cyclopropylmethyl)-1H-pyrrolo[2,3-c]pyridin-7-yl)piperidin-1-yl)-2-methoxyethan-1-one

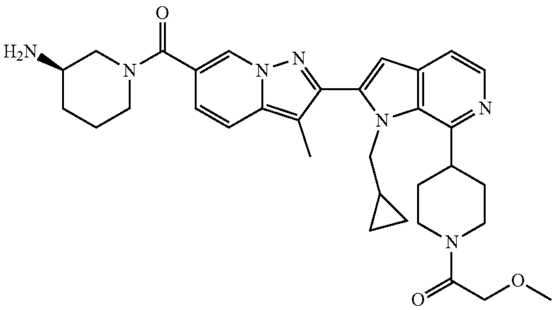 [SMILES: COCC(=O)N1CCC(c2nccc3cc(-c4nn5cc(C(=O)N6CCC[C@@H](N)C6)ccc5c4C)n(CC4CC4)c23)CC1]

Prepared in similar fashion to Example 510. LC-MS m/z: 584.3 [M+H]$^+$ 1.128 min (Method E)

Example 513

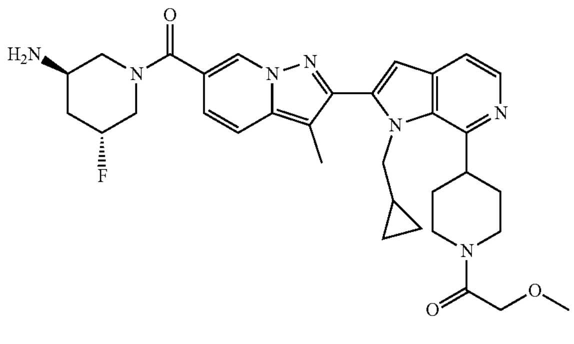 [SMILES: COCC(=O)N1CCC(c2nccc3cc(-c4nn5cc(C(=O)N6C[C@H](N)C[C@@H](F)C6)ccc5c4C)n(CC4CC4)c23)CC1]

1-(4-(2-(6-((3R,5R)-3-Amino-5-fluoropiperidine-1-carbonyl)-3-methylpyrazolo[1,5-a]pyridin-2-yl)-1-(cyclopropylmethyl)-1H-pyrrolo[2,3-c]pyridin-7-yl) piperidin-1-yl)-2-methoxyethan-1-one Compounds of Example 513 in Table 52 was prepared following a procedure similar to the preparation of a compound of Example 512, by acid amine coupling of Intermediate 512B with appropriate carboxylic acid followed by ester hydrolysis and coupling with appropriate amines Analytical Data: LC-MS m/z [M+H]+; HPLC retention time (HPLC method Analytical Data: 602.3, 1.188 min (Method E)

Example 514

((3R,5R)-3-Amino-5-fluoropiperidin-1-yl)(2-(1-(cyclopropylmethyl)-7-(1-((1R,4R)-4-hydroxycyclohexane-1-carbonyl)azetidin-3-yl)-1H-indol-2-yl)-4-methoxy-3-methylpyrazolo[1,5-a]pyridin-6-yl) methanone

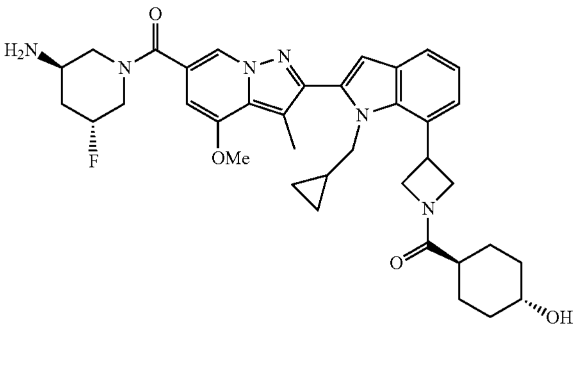 [SMILES: COc1cc(C(=O)N2C[C@H](N)C[C@@H](F)C2)cn2nc(-c3cc4cccc(C5CN(C(=O)[C@H]6CC[C@H](O)CC6)C5)c4n3CC3CC3)c(C)c12]

Intermediate 514A

Methyl 2-(7-(1-(tert-butoxycarbonyl)azetidin-3-yl)-1-(cyclopropylmethyl)-1H-indol-2-yl)-4-methoxy-3-methylpyrazolo[1,5-a]pyridine-6-carboxylate

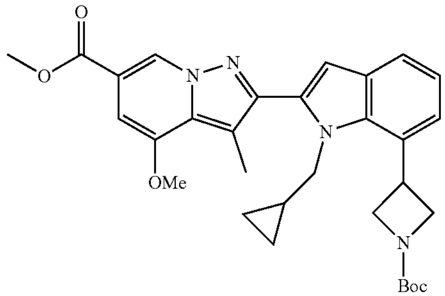 [SMILES: COC(=O)c1cc(OC)c2c(C)c(-c3cc4cccc(C5CN(C(=O)OC(C)(C)C)C5)c4n3CC3CC3)nn2c1]

Intermediate 1 (3.20 g, 8.75 mmol) was added to a stirred solution of Intermediate 49 (1.2 g, 2.92 mmol) and CuI (0.167 g, 0.875 mmol) in DMF (10 ml). The reaction mixture was stirred at 80° C. for 30 hours, diluted with water (20 ml), and extracted with ethyl acetate (3×30 ml). The combined organic layers were washed with brine, dried over sodium sulfate, filtered, and concentrated in vacuum. The crude compound thus obtained was purified using a silica gel column, eluting with 0-20% ethyl acetate in hexane to afford methyl 2-(7-(1-(tert-butoxycarbonyl)azetidin-3-yl)-1-(cyclopropylmethyl)-1H-indol-2-yl)-4-methoxy-3-methylpyrazolo[1,5-a]pyridine-6-carboxylate (1.3 g, 82%). LC-MS m/z: 545.4 $[M+H]^+$.

Intermediate 514B

Methyl 2-(7-(azetidin-3-yl)-1-(cyclopropylmethyl)-1H-indol-2-yl)-4-methoxy-3-methylpyrazolo[1,5-a]pyridine-6-carboxylate

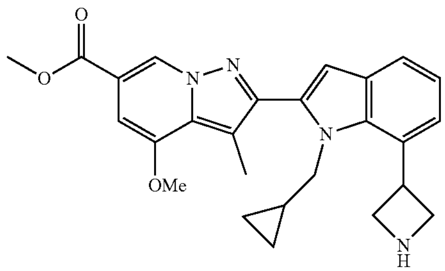 [SMILES: COC(=O)c1cc(OC)c2c(C)c(-c3cc4cccc(C5CNC5)c4n3CC3CC3)nn2c1]

TFA (1.839 ml, 23.87 mmol) was added to a stirred solution of Intermediate 514A (1.3 g, 2.387 mmol) in dichloromethane (20 ml). The reaction mixture was stirred at a room temperature for 16 hours, diluted with water (10 ml), and saturated sodium bicarbonate solution (10 ml), and extracted with ethyl acetate (3×20 ml). The combined organic layers were washed with brine, dried over sodium sulfate, filtered, and concentrated in vacuum to afford methyl 2-(7-(azetidin-3-yl)-1-(cyclopropylmethyl)-1H-indol-2-yl)-4-methoxy-3-methylpyrazolo[1,5-a]pyridine-6-carboxylate (1 g, 94%). LC-MS m/z: 445.4 $[M+H]^+$.

Intermediate 514C

Methyl 2-(1-(cyclopropylmethyl)-7-(1-((1R,4R)-4-hydroxycyclohexane-1-carbonyl)azetidin-3-yl)-1H-indol-2-yl)-4-methoxy-3-methylpyrazolo[1,5-a]pyridine-6-carboxylate

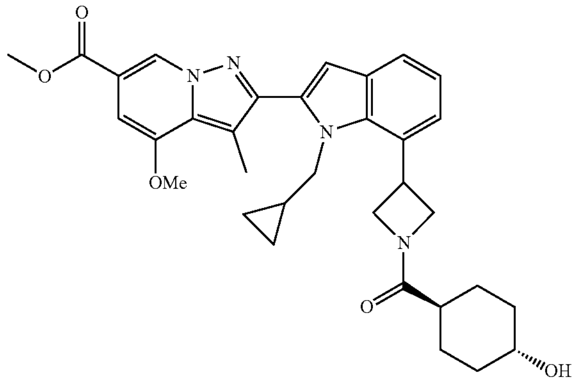 [SMILES: COC(=O)c1cc(OC)c2c(C)c(-c3cc4cccc(C5CN(C(=O)[C@H]6CC[C@H](O)CC6)C5)c4n3CC3CC3)nn2c1]

(1R,4R)-4-Hydroxycyclohexane-1-carboxylic acid (63.2 mg, 0.439 mmol) was added to a stirred solution of Intermediate 514B (150 mg, 0.337 mmol) in DMF (3 ml), followed by HATU (192 mg, 0.506 mmol) and DIPEA (0.118 ml, 0.675 mmol). The reaction mixture was stirred at a room temperature for 16 hours, diluted with water (20 ml), and extracted with ethyl acetate (3×30 ml). The combined organic layers were washed with brine, dried over sodium sulfate, filtered, and concentrated in vacuum. The crude product was purified using a silica gel column, eluting with 0-5% methanol in dichloromethane to afford methyl 2-(1-(cyclopropylmethyl)-7-(1-((1R,4R)-4-hydroxycyclohexane-1-carbonyl)azetidin-3-yl)-1H-indol-2-yl)-4-methoxy-3-methylpyrazolo[1,5-a]pyridine-6-carboxylate (110 mg, 57%). LC-MS m/z: 571.4 $[M+H]^+$.

Intermediate 514D 2-(1-(cyclopropylmethyl)-7-(1-((1r,4r)-4-hydroxycyclohexane-1-carbonyl)azetidin-3-yl)-1H-indol-2-yl)-4-methoxy-3-methylpyrazolo[1,5-a]pyridine-6-carboxylic acid

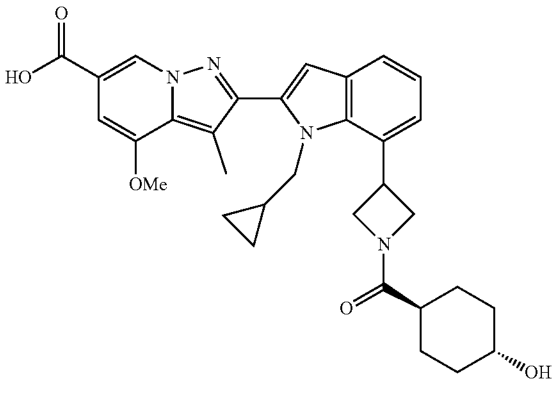 [SMILES: COc1cc(C(=O)O)cn2nc(-c3cc4cccc(C5CN(C(=O)[C@H]6CC[C@H](O)CC6)C5)c4n3CC3CC3)c(C)c12]

LiOH (25.2 mg, 1.051 mmol) was added to a stirred solution of Intermediate 514C (120 mg, 0.210 mmol) in THF (3 ml), water (0.5 ml), and MeOH (1 ml). The reaction mixture was stirred at a room temperature for 16 hours, diluted with water (5 ml) and 1N HCl (5 ml), and extracted with ethyl acetate (3×30 ml). The combined organic layers were washed with brine, dried over sodium sulfate, filtered, and concentrated in vacuum to get 2-(1-(cyclopropylmethyl)-7-(1-((1R,4R)-4-hydroxycyclohexane-1-carbonyl)azetidin-3-yl)-1H-indol-2-yl)-4-methoxy-3-methylpyrazolo[1,5-a]pyridine-6-carboxylic acid (90 mg, 77%). LC-MS m/z: 557.4 $[M+H]^+$.

Intermediate 514E tert-Butyl ((3R,5R)-1-(2-(1-(cyclopropylmethyl)-7-(1-((1R,4R)-4-hydroxycyclohexane-1-carbonyl)azetidin-3-yl)-1H-indol-2-yl)-4-methoxy-3-methylpyrazolo[1,5-a]pyridine-6-carbonyl)-5-fluoropiperidin-3-yl)carbamate

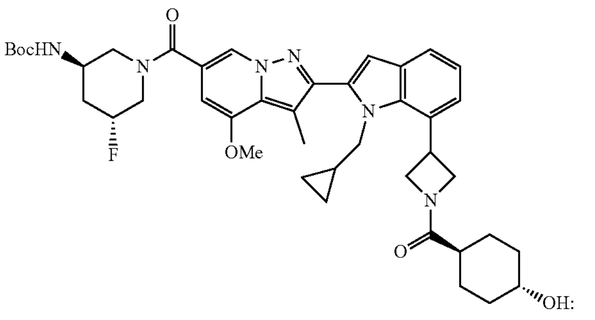

tert-Butyl ((3R,5R)-5-fluoropiperidin-3-yl)carbamate (21.17 mg, 0.097 mmol), HATU (46.1 mg, 0.121 mmol) followed by DIPEA (0.042 ml, 0.243 mmol) were added to a stirred solution of Intermediate 514D (45 mg, 0.081 mmol) in DMF (0.5 ml). The reaction mixture was stirred at a room temperature for 16 hours, diluted with water (5 ml) and 1 N HCl (5 ml), and extracted with ethyl acetate (3×30 ml). The combined organic layers were washed with brine, dried over sodium sulfate, filtered, and concentrated in vacuum to afford tert-butyl ((3R,5R)-1-(2-(1-(cyclopropylmethyl)-7-(1-((1R,4R)-4-hydroxycyclohexane-1-carbonyl)azetidin-3-yl)-1H-indol-2-yl)-4-methoxy-3-methylpyrazolo[1,5-a]pyridine-6-carbonyl)-5-fluoropiperidin-3-yl)carbamate (40 mg, 65%). LC-MS m/z: 757.6 $[M+H]^+$.

Example 514

((3R,5R)-3-Amino-5-fluoropiperidin-1-yl)(2-(1-(cyclopropylmethyl)-7-(14(1R,4R)-4-hydroxycyclohexane-1-carbonyl)azetidin-3-yl)-1H-indol-2-yl)-4-methoxy-3-methylpyrazolo[1,5-a]pyridin-6-yl)methanone

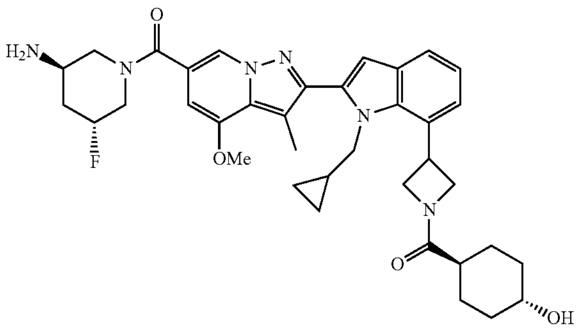 [SMILES: COc1cc(C(=O)N2C[C@H](N)C[C@@H](F)C2)cn2nc(-c3cc4cccc(C5CN(C(=O)[C@H]6CC[C@H](O)CC6)C5)c4n3CC3CC3)c(C)c12]

TFA (0.041 ml, 0.528 mmol) was added to a stirred solution of Intermediate 514E (40 mg, 0.053 mmol) in $CH_2Cl_2$ (3.0 ml). The reaction mixture was stirred at a room temperature for 6 hours, concentrated, and the crude material was purified using preparative LC/MS with the following conditions: Column: Waters X Bridge C18, 19×150 mm, 5 μm particles; mobile phase A: 10 mM ammonium acetate; mobile phase B: acetonitrile; gradient: 12-48% B over 25 minutes, then a 5-minute hold at 100% B; flow rate: 15 ml/min. Fractions containing the desired product were combined and dried using centrifugal evaporation. The purified material was then diluted with a 1:1 mixture of DCM and methanol, treated with Si-Pyridine, and shaken for a minimum of 2 hours. The resulting mixture was filtered and dried using centrifugal evaporation to afford ((3R,5R)-3-amino-5-fluoropiperidin-1-yl)(2-(1-(cyclopropylmethyl)-7-(1-((1r,4r)-4-hydroxycyclohexane-1-carbonyl)azetidin-3-yl)-1H-indol-2-yl)-4-methoxy-3-methylpyrazolo[1,5-a]pyridin-6-yl)methanone (11.2 mg, 32%). LC-MS m/z: 657.4 $[M+H]^+$. LCMS retention time: 1.537 min (method E). $^1H$ NMR (400 MHz, DMSO-$d_6$) δ ppm: 8.36 (s, 1H), 7.58-7.49 (m, 1H), 7.37 (d, J=7.3 Hz, 1H), 7.16 (t, J=7.6 Hz, 1H), 6.76 (s, 1H), 6.54 (d, J=0.8 Hz, 1H), 5.02-4.88 (m, 1H), 4.74-4.68 (m, 1H), 4.68-4.59 (m, 1H), 4.54 (br, d, J=3.0 Hz, 1H), 4.41-4.31 (m, 5H), 4.01 (br, dd, J=6.1, 9.4 Hz, 2H), 3.97 (s, 3H), 3.10-3.03 (m, 2H), 2.48 (s, 3H), 2.20 (tt, J=3.4, 11.6 Hz, 2H), 1.89-1.80 (m, 3H), 1.76-1.49 (m, 3H), 1.43-1.30 (m,2H), 1.23-1.11 (m, 3H), 0.83-0.72 (m, 1H), 0.16 (d, J=8.3 Hz, 2H), −0.16-−0.34 (m, 2H)

Compounds of Examples 515 to 529 in Table 51 were prepared following a procedure similar to the preparation of a compound of Example 514, by acid amine coupling of Intermediate 514B with appropriate carboxylic acid followed by ester hydrolysis and coupling with appropriate amines

TABLE 51

| Example | Structure<br>Name<br>Analytical Data: LC-MS m/z [M + H]+; HPLC retention time (HPLC method) |
|---|---|
| 515 | 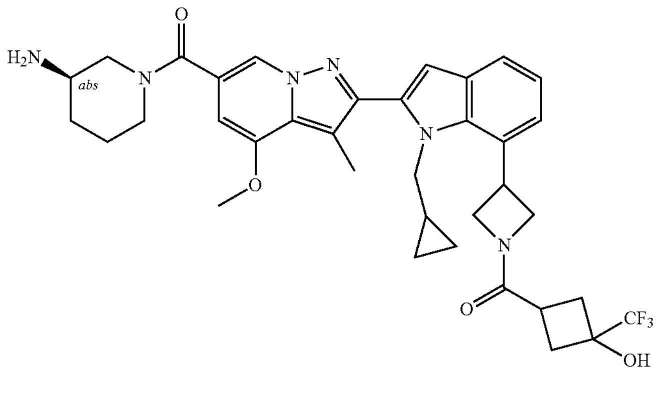 [SMILES: COc1cc(C(=O)N2CCC[C@@H](N)C2)cn2nc(-c3cc4cccc(C5CN(C(=O)C6CC(O)(C(F)(F)F)C6)C5)c4n3CC3CC3)c(C)c12]<br>(R)-(3-Aminopiperidin-1-yl)(2-(1-(cyclopropylmethyl)-7-(1-(3-hydroxy-3-(trifluoromethyl)cyclobutane-1-carbonyl)azetidin-3-yl)-1H-indol-2-yl)-4-methoxy-3-methylpyrazolo[1,5-a]pyridin-6-yl)methanone (mixture of diastereomers)<br>Analytical Data: 679.3, 1.754 min (Method E) |

TABLE 51-continued

| Example | Structure<br>Name<br>Analytical Data: LC-MS m/z [M + H]+; HPLC retention time (HPLC method) |
|---|---|
| 516 | 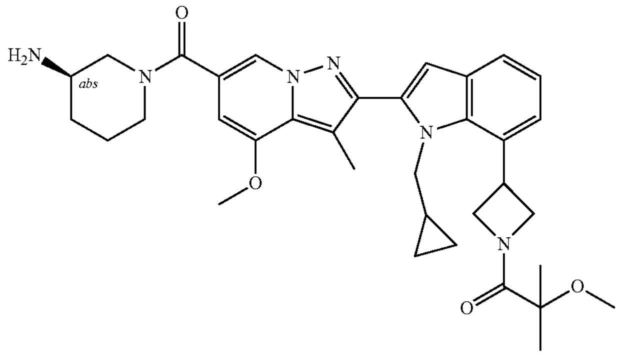 [SMILES: COc1cc(C(=O)N2CCC[C@@H](N)C2)cn2nc(-c3cc4cccc(C5CN(C(=O)C(C)(C)OC)C5)c4n3CC3CC3)c(C)c12]<br>(R)-1-(3-(2-(6-(3-Aminopiperidine-1-carbonyl)-4-methoxy-3-methylpyrazolo[1,5-a]pyridin-2-yl)-1-(cyclopropylmethyl)-1H-indol-7-yl)azetidin-1-yl)-2-methoxy-2-methylpropan-1-one<br>Analytical Data: 613.3, 1.733 min (Method E) |
| 517 | 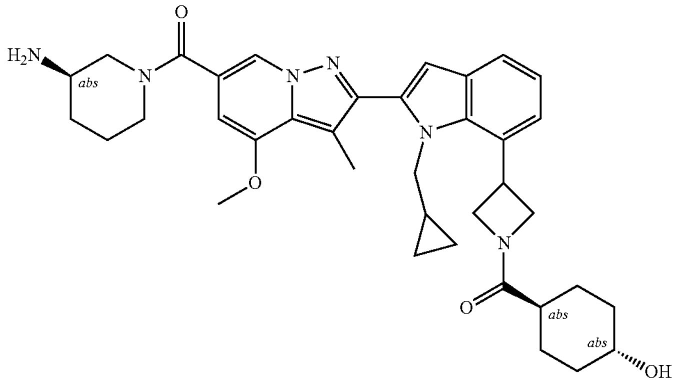 [SMILES: COc1cc(C(=O)N2CCC[C@@H](N)C2)cn2nc(-c3cc4cccc(C5CN(C(=O)[C@H]6CC[C@H](O)CC6)C5)c4n3CC3CC3)c(C)c12]<br>((R)-3-Aminopiperidin-1-yl)(2-(1-(cyclopropylmethyl)-7-(1-((1r,4r)-4-hydroxycyclohexane-1-carbonyl)azetidin-3-yl)-1H-indol-2-yl)-4-methoxy-3-methylpyrazolo[1,5-a]pyridin-6-yl)methanone<br>Analytical Data: 639.4, 1.489 min (Method E) |
| 518 | 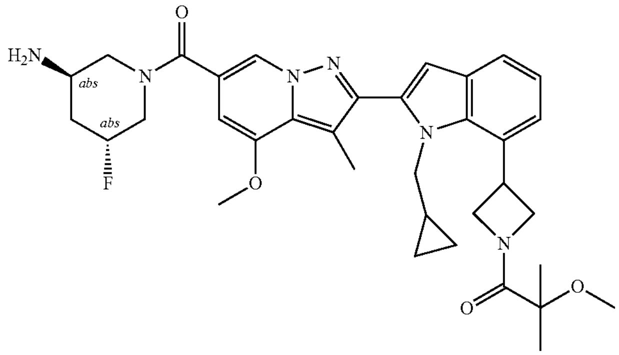 [SMILES: COc1cc(C(=O)N2C[C@H](N)C[C@@H](F)C2)cn2nc(-c3cc4cccc(C5CN(C(=O)C(C)(C)OC)C5)c4n3CC3CC3)c(C)c12]<br>1-(3-(2-(6-((3R,5R)-3-Amino-5-fluoropiperidine-1-carbonyl)-4-methoxy-3-methylpyrazolo[1,5-a]pyridin-2-yl)-1-(cyclopropylmethyl)-1H-indol-7-yl)azetidin-1-yl)-2-methoxy-2-methylpropan-1-one<br>Analytical Data: 631.3, 1.788 min (Method E) |

TABLE 51-continued

| Example | Structure<br>Name<br>Analytical Data: LC-MS m/z [M + H]+; HPLC retention time (HPLC method) |
|---|---|
| 519 | 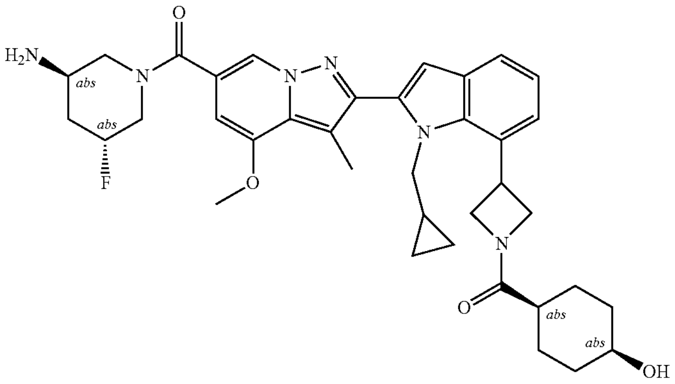 [SMILES: COc1cc(C(=O)N2C[C@H](N)C[C@@H](F)C2)cn2nc(-c3cc4cccc(C5CN(C(=O)[C@H]6CC[C@@H](O)CC6)C5)c4n3CC3CC3)c(C)c12]<br>((3R,5R)-3-Amino-5-fluoropiperidin-1-yl)(2-(1-(cyclopropylmethyl)-7-(1-((1s,4s)-4-hydroxycyclohexane-1-carbonyl)azetidin-3-yl)-1H-indol-2-yl)-4-methoxy-3-methylpyrazolo[1,5-a]pyridin-6-yl)methanone<br>Analytical Data: 657.4, 1.630 min (Method E) |
| 520 | 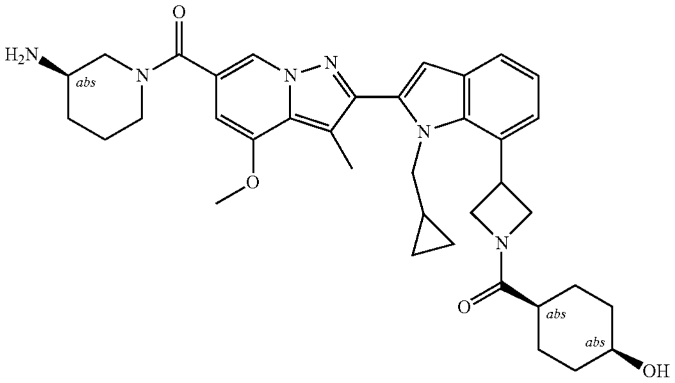 [SMILES: COc1cc(C(=O)N2CCC[C@@H](N)C2)cn2nc(-c3cc4cccc(C5CN(C(=O)[C@H]6CC[C@@H](O)CC6)C5)c4n3CC3CC3)c(C)c12]<br>((R)-3-Aminopiperidin-1-yl)(2-(1-(cyclopropylmethyl)-7-(1-((1s,4s)-4-hydroxycyclohexane-1-carbonyl)azetidin-3-yl)-1H-indol-2-yl)-4-methoxy-3-methylpyrazolo[1,5-a]pyridin-6-yl)methanone<br>Analytical Data: 639.4, 1.581 min (Method E) |
| 521 | 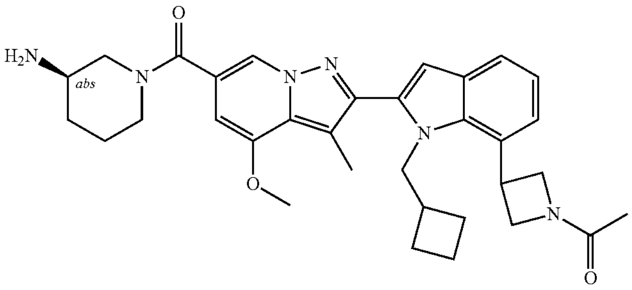 [SMILES: COc1cc(C(=O)N2CCC[C@@H](N)C2)cn2nc(-c3cc4cccc(C5CN(C(C)=O)C5)c4n3CC3CCC3)c(C)c12]<br>(R)-1-(3-(2-(6-(3-Aminopiperidine-1-carbonyl)-4-methoxy-3-methylpyrazolo[1,5-a]pyridin-2-yl)-1-(cyclopropylmethyl)-1H-indol-7-yl)azetidin-1-yl)ethan-1-one<br>Analytical Data: 555.3, 1.506 min (Method E) |

TABLE 51-continued

| Example | Structure<br>Name<br>Analytical Data: LC-MS m/z [M + H]+; HPLC retention time (HPLC method) |
|---|---|
| 522 | 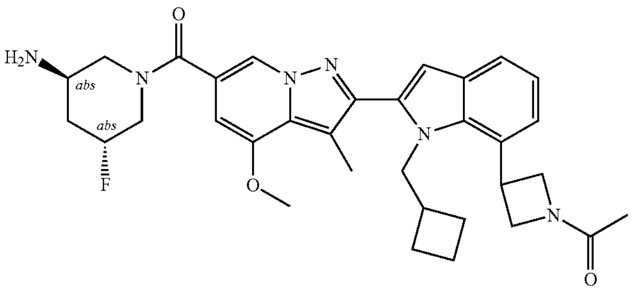 [SMILES: COc1cc(C(=O)N2C[C@H](N)C[C@@H](F)C2)cn2nc(-c3cc4cccc(C5CN(C(C)=O)C5)c4n3CC3CCC3)c(C)c12]<br>1-(3-(2-(6-((3R,5R)-3-Amino-5-fluoropiperidine-1-carbonyl)-4-methoxy-3-methylpyrazolo[1,5-a]pyridin-2-yl)-1-(cyclopropylmethyl)-1H-indol-7-yl)azetidin-1-yl)ethan-1-one<br>Analytical Data: 573.3, 1.593 min (Method E) |
| 523 | 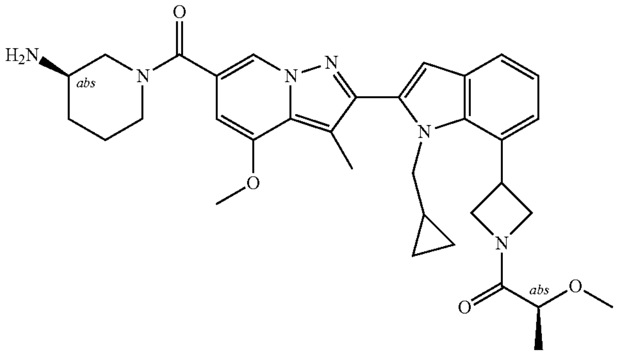 [SMILES: COc1cc(C(=O)N2CCC[C@@H](N)C2)cn2nc(-c3cc4cccc(C5CN(C(=O)[C@H](C)OC)C5)c4n3CC3CC3)c(C)c12]<br>(S)-1-(3-(2-(6-((R)-3-Aminopiperidine-1-carbonyl)-4-methoxy-3-methylpyrazolo[1,5-a]pyridin-2-yl)-1-(cyclopropylmethyl)-1H-indol-7-yl)azetidin-1-yl)-2-methoxypropan-1-one<br>Analytical Data: 599.3, 1.605 min (Method E) |
| 524 | 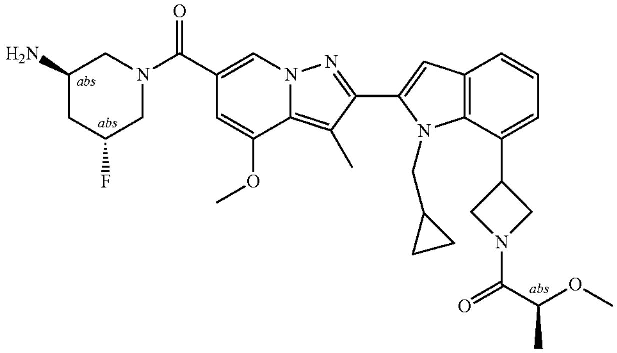 [SMILES: COc1cc(C(=O)N2C[C@H](N)C[C@@H](F)C2)cn2nc(-c3cc4cccc(C5CN(C(=O)[C@H](C)OC)C5)c4n3CC3CC3)c(C)c12]<br>(S)-1-(3-(2-(6-((3R,5R)-3-Amino-5-fluoropiperidine-1-carbonyl)-4-methoxy-3-methylpyrazolo[1,5-a]pyridin-2-yl)-1-(cyclopropylmethyl)-1H-indol-7-yl)azetidin-1-yl)-2-methoxypropan-1-one<br>Analytical Data: 617.3, 1.638 min (Method E) |

TABLE 51-continued

| Example | Structure<br>Name<br>Analytical Data: LC-MS m/z [M + H]+; HPLC retention time (HPLC method) |
|---|---|
| 525 | 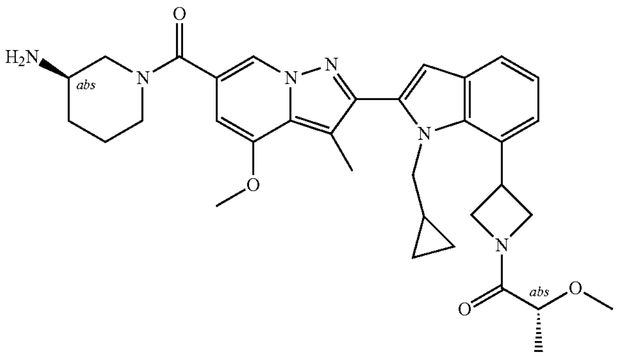 [SMILES: COc1cc(C(=O)N2CCC[C@@H](N)C2)cn2nc(-c3cc4cccc(C5CN(C(=O)[C@@H](C)OC)C5)c4n3CC3CC3)c(C)c12]<br>(R)-1-(3-(2-(6-((R)-3-Aminopiperidine-1-carbonyl)-4-methoxy-3-methylpyrazolo[1,5-a]pyridin-2-yl)-1-(cyclopropylmethyl)-1H-indol-7-yl)azetidin-1-yl)-2-methoxypropan-1-one<br>Analytical Data: 599.3, 1.613 min (Method E) |
| 526 | 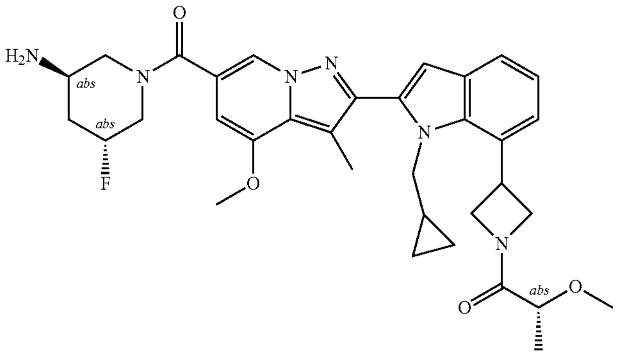 [SMILES: COc1cc(C(=O)N2C[C@H](N)C[C@@H](F)C2)cn2nc(-c3cc4cccc(C5CN(C(=O)[C@@H](C)OC)C5)c4n3CC3CC3)c(C)c12]<br>(R)-1-(3-(2-(6-((3R,5R)-3-Amino-5-fluoropiperidine-1-carbonyl)-4-methoxy-3-methylpyrazolo[1,5-a]pyridin-2-yl)-1-(cyclopropylmethyl)-1H-indol-7-yl)azetidin-1-yl)-2-methoxypropan-1-one<br>Analytical Data: 617.3, 1.533 min (Method F) |
| 527 | 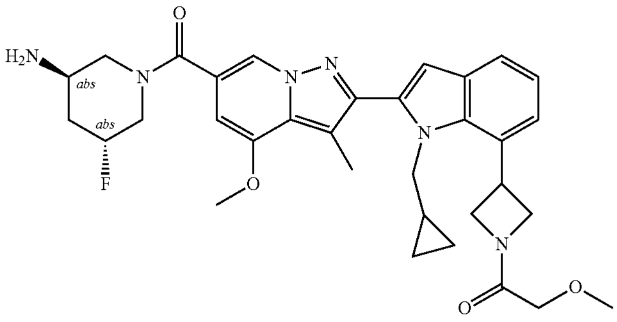 [SMILES: COCC(=O)N1CC(c2cccc3cc(-c4nn5cc(C(=O)N6C[C@H](N)C[C@@H](F)C6)cc(OC)c5c4C)n(CC4CC4)c23)C1]<br>1-(3-(2-(6-((3R,5R)-3-Amino-5-fluoropiperidine-1-carbonyl)-4-methoxy-3-methylpyrazolo[1,5-a]pyridin-2-yl)-1-(cyclopropylmethyl)-1H-indol-7-yl)azetidin-1-yl)-2-methoxyethan-1-one<br>Analytical Data: 603.2, 1.597 min (Method E) |

TABLE 51-continued

| Example | Structure<br>Name<br>Analytical Data: LC-MS m/z [M + H]+; HPLC retention time (HPLC method) |
|---|---|
| 528 | 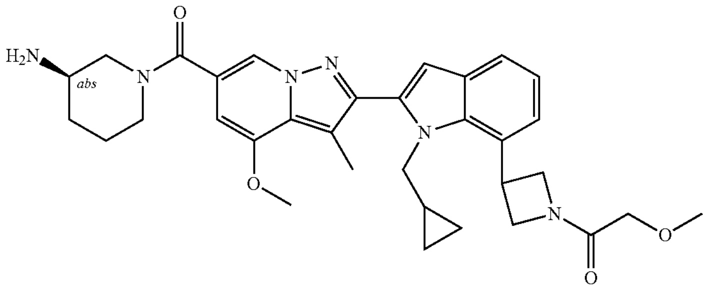 [SMILES: COCC(=O)N1CC(c2cccc3cc(-c4nn5cc(C(=O)N6CCC[C@@H](N)C6)cc(OC)c5c4C)n(CC4CC4)c23)C1]<br>(R)-1-(3-(2-(6-(3-Aminopiperidine-1-carbonyl)-4-methoxy-3-methylpyrazolo[1,5-a]pyridin-2-yl)-1-(cyclopropylmethyl)-1H-indol-7-yl)azetidin-1-yl)-2-methoxyethan-1-one<br>Analytical Data: 585.3, 1.607 min (Method E) |
| 529 | 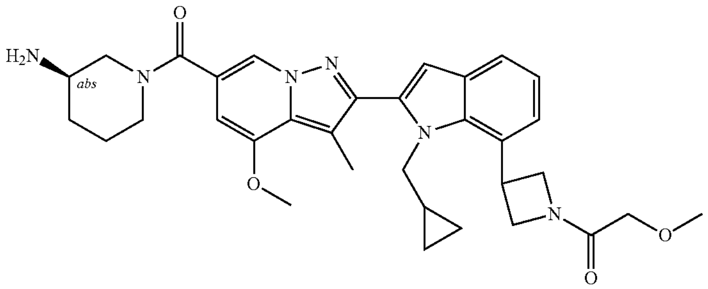 [SMILES: COCC(=O)N1CC(c2cccc3cc(-c4nn5cc(C(=O)N6CCC[C@@H](N)C6)cc(OC)c5c4C)n(CC4CC4)c23)C1]<br>(R)-1-(3-(2-(6-(3-Aminopiperidine-1-carbonyl)-4-methoxy-3-methylpyrazolo[1,5-a]pyridin-2-yl)-1-(cyclopropylmethyl)-1H-indol-7-yl)azetidin-1-yl)-2-methoxyethan-1-one<br>Analytical Data: 585.3, 1.540 min (Method E) |

Example 530

((R)-3-Aminopiperidin-1-yl)(2-(1-(cyclopropylmethyl)-7-(1-((1r,4r)-4-hydroxycyclohexane-1-carbonyl)azetidin-3-yl)-1H-indol-2-yl)-3-methylpyrazolo[1,5-a]pyridin-6-yl)methanone

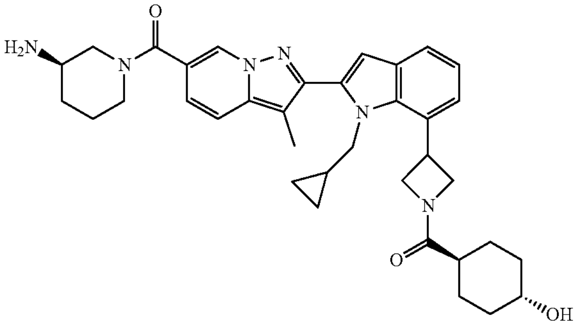 [SMILES: Cc1c(-c2cc3cccc(C4CN(C(=O)[C@H]5CC[C@H](O)CC5)C4)c3n2CC2CC2)nn2cc(C(=O)N3CCC[C@@H](N)C3)ccc12]

Intermediate 530A

Ethyl 2-(7-(1-(tert-butoxycarbonyl)azetidin-3-yl)-1-(cyclopropylmethyl)-1H-indol-2-yl)-3-methylpyrazolo[1,5-a]pyridine-6-carboxylate

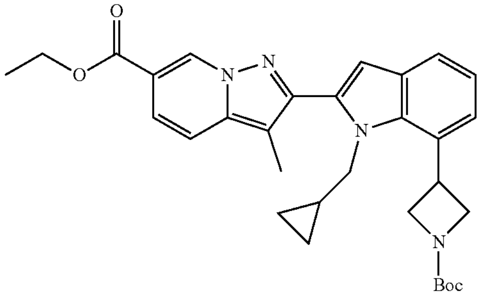 [SMILES: CCOC(=O)c1ccc2c(C)c(-c3cc4cccc(C5CN(C(=O)OC(C)(C)C)C5)c4n3CC3CC3)nn2c1]

Intermediate 8 (3.83 g, 10.94 mmol) and copper(I) iodide (0.208 g, 1.08 mmol) were added to a stirred solution of Intermediate 49 (1.5 g, 3.65 mmol) in (10 ml). The reaction mixture was stirred at 80° C. for 30 hours, diluted with water (15 ml), and extracted with ethyl acetate (3×30 ml). The combined organic layers were washed with brine, dried over sodium sulphate, filtered, and concentrated in vacuum. The crude product was purified using a silica gel column, eluting 20% ethyl acetate in hexane to afford (110 mg, 57%) ethyl 2-(7-(1-(tert-butoxycarbonyl)azetidin-3-yl)-1-(cyclopropylmethyl)-1H-indol-2-yl)-3-methylpyrazolo[1,5-a]pyridine-6-carboxylate. LC-MS m/z: 529.3 $[M+H]^+$.

Intermediate 530B

Ethyl 2-(7-(azetidin-3-yl)-1-(cyclopropylmethyl)-1H-indol-2-yl)-3-methylpyrazolo[1,5-a]pyridine-6-carboxylate

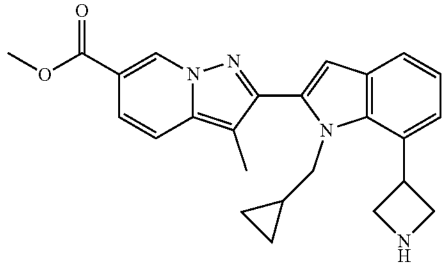 [SMILES: COC(=O)c1ccc2c(C)c(-c3cc4cccc(C5CNC5)c4n3CC3CC3)nn2c1]

TFA (1.749 ml, 22.70 mmol) was added to a stirred solution of Intermediate 530A (1.2 g, 2.270 mmol) in dichloromethane (5 ml). The reaction mixture was stirred at a room temperature for 16 hours, concentrated, diluted with water (10 ml), washed with saturated $NaHCO_3$ solution (10 ml), and extracted with dichloromethane (3×20 ml). The combined organic layers were washed with brine, dried over sodium sulphate, filtered, and concentrated in vacuum to afford ethyl 2-(7-(azetidin-3-yl)-1-(cyclopropylmethyl)-1H-indol-2-yl)-3-methylpyrazolo[1,5-a]pyridine-6-carboxylate (crude 1.0 g). LC-MS m/z: 429.4 $[M+H]^+$.

Intermediate 530C

Ethyl 2-(1-(cyclopropylmethyl)-7-(1-((1R,4R)-4-hydroxycyclohexane-1-carbonyl)azetidin-3-yl)-1H-indol-2-yl)-3-methylpyrazolo[1,5-a]pyridine-6-carboxylate

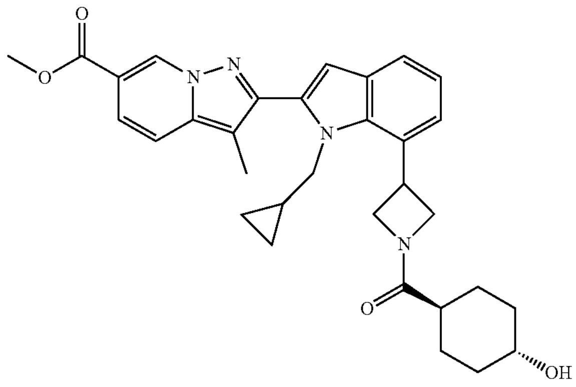 [SMILES: COC(=O)c1ccc2c(C)c(-c3cc4cccc(C5CN(C(=O)[C@H]6CC[C@H](O)CC6)C5)c4n3CC3CC3)nn2c1]

(1R,4R)-4-Hydroxycyclohexane-1-carboxylic acid (87 mg, 0.607 mmol), HATU (266 mg, 0.700 mmol) followed by DIPEA (0.245 ml, 1.400 mmol) were added to a stirred solution of Intermediate 530B (200 mg, 0.467 mmol) in DMF (5 ml). The reaction mixture was stirred at a room temperature for 1 hour, diluted with water (5 ml), and extracted with ethyl acetate (3×10 ml). The combined organic layers were washed with brine, dried over sodium sulphate, filtered, and concentrated in vacuum. The crude product thus obtained was purified using a silica gel column, eluting 2% methanol in dichloromethane to afford (130 mg, 50%) ethyl 2-(1-(cyclopropylmethyl)-7-(1-((1R,4R)-4-hydroxycyclohexane-1-carbonyl)azetidin-3-yl)-1H-indol-2-yl)-3-methylpyrazolo[1,5-a]pyridine-6-carboxylate. LC-MS m/z: 555.4 $[M+H]^+$.

Intermediate 530D 2-(1-(cyclopropylmethyl)-7-(1-((1R,4R)-4-hydroxycyclohexane-1-carbonyl)azetidin-3-yl)-1H-indol-2-yl)-3-methylpyrazolo[1,5-a]pyridine-6-carboxylic acid

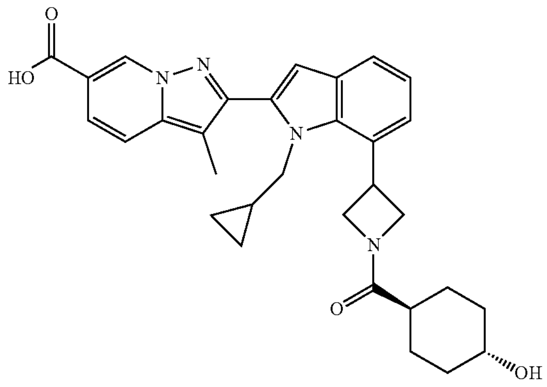 [SMILES: Cc1c(-c2cc3cccc(C4CN(C(=O)[C@H]5CC[C@H](O)CC5)C4)c3n2CC2CC2)nn2cc(C(=O)O)ccc12]

LiOH (17.27 mg, 0.721 mmol) was added to a stirred solution of Intermediate 530C (80 mg, 0.144 mmol) in THF (3 ml), methanol (1 ml), and water (0.5 ml). The reaction mixture was stirred at a room temperature for 16 hours, diluted with water (5 ml) and 1 N HCl (5 ml), and extracted with ethyl acetate (3×10 ml). The combined organic layers were washed with brine, dried over sodium sulphate, filtered, and concentrated in vacuum to afford (crude 80 mg) 2-(1-(cyclopropylmethyl)-7-(1-((1r,4r)-4-hydroxycyclohexane-1-carbonyl)azetidin-3-yl)-1H-indol-2-yl)-3-methylpyrazolo[1,5-a]pyridine-6-carboxylic acid. LC-MS m/z: 527.3 $[M+H]^+$.

Intermediate 530E tert-Butyl ((R)-1-(2-(1-(cyclopropylmethyl)-7-(1-((1R,4R)-4-hydroxycyclohexane-1-carbonyl)azetidin-3-yl)-1H-indol-2-yl)-3-methylpyrazolo[1,5-a]pyridine-6-carbonyl)piperidin-3-yl)carbamate

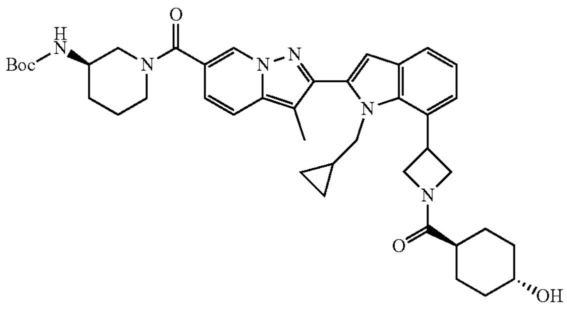 [SMILES: Cc1c(-c2cc3cccc(C4CN(C(=O)[C@H]5CC[C@H](O)CC5)C4)c3n2CC2CC2)nn2cc(C(=O)N3CCC[C@@H](NC(=O)OC(C)(C)C)C3)ccc12]

tert-Butyl (R)-piperidin-3-ylcarbamate (18.25 mg, 0.091 mmol), HATU (57.8 mg, 0.152 mmol), DIPEA (0.040 ml, 0.228 mmol) was added to a stirred solution of Intermediate 530D (40 mg, 0.076 mmol) in DMF (1 ml). The reaction mixture was stirred at a room temperature for 3 hours, diluted with water (5 ml) and 1N HCl (5 ml), and extracted with ethyl acetate (3×10 ml). The combined organic layers were washed with brine, dried over sodium sulphate, filtered, and concentrated in vacuum to afford tert-butyl ((R)-1-(2-(1-(cyclopropylmethyl)-7-(1-((1R,4R)-4-hydroxycyclohexane-1-carbonyl)azetidin-3-yl)-1H-indol-2-yl)-3-methylpyrazolo[1,5-a]pyridine-6-carbonyl)piperidin-3-yl) carbamate (40 mg, 74%). LC-MS m/z: 709.6 $[M+H]^+$.

Example 530

((R)-3-Aminopiperidin-1-yl)(2-(1-(cyclopropylmethyl)-7-(1-((1R,4R)-4-hydroxycyclohexane-1-carbonyl)azetidin-3-yl)-1H-indol-2-yl)-3-methylpyrazolo[1,5-a]pyridin-6-yl)methanone

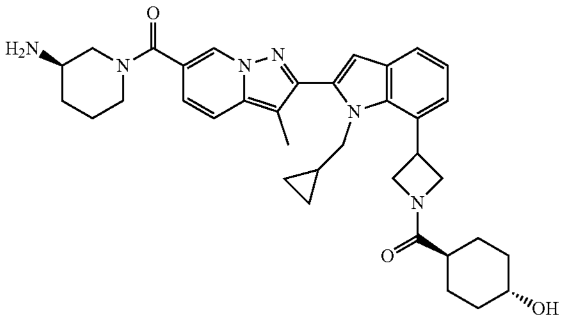 [SMILES: Cc1c(-c2cc3cccc(C4CN(C(=O)[C@H]5CC[C@H](O)CC5)C4)c3n2CC2CC2)nn2cc(C(=O)N3CCC[C@@H](N)C3)ccc12]

TFA (0.043 ml, 0.564 mmol) was added to a stirred solution of Intermediate 530E (40 mg, 0.056 mmol) in DCM (3 ml). The reaction mixture was stirred for 16 hours, concentrated in vacuum to obtain a crude compound, which was purified using a preparative LC/MS with the following conditions: Column: Waters XBridge C18, 150×19 mm, 5 μm particles; mobile phase A: 5:95 acetonitrile:water with 0.1% trifluoroacetic acid; mobile phase B: 95:5 acetonitrile: water with 0.1% trifluoroacetic acid; gradient: a 0-minute hold at 15% B, 15-30% B over 20 minutes, then a 5-minute hold at 100% B; flow rate: 20 ml/min; column temperature: 25° C. Fraction collection was triggered by signals. Fractions containing the desired product were combined and dried using centrifugal evaporation. The purified material was then diluted with a 1:1 mixture of ethylene dichloride and methanol (EDM), treated with Si-Pyridine, and shaken for a minimum of 2 hours. The resulting mixture was filtered and dried using centrifugal evaporation to afford ((R)-3-aminopiperidin-1-yl)(2-(1-(cyclopropylmethyl)-7-(1-((1R,4R)-4-hydroxycyclohexane-1-carbonyl)azetidin-3-yl)-1H-indol-2-yl)-3-methylpyrazolo[1,5-a]pyridin-6-yl) methanone (6.9 mg, 11%). LC-MS m/z: 609.3 $[M+H]^+$. LCMS retention time: 1.411 min (method E). $^1H$ NMR (400 MHz, DMSO-$d_6$) δ ppm: 8.86 (s, 1H), 7.99 (br, s, 2H), 7.81 (dd, J=0.7, 9.0 Hz, 1H), 7.57 (d, J=7.8 Hz, 1H), 7.38 (d, J=7.6 Hz, 1H),7.28 (dd, J=1.5, 9.0 Hz, 1H), 7.17 (t, J=7.6 Hz, 1H),7.16-6.98 (m, 1H), 6.83 (s, 1H), 4.75-4.61 (m, 2H), 4.58-4.52 (m, 1H), 4.47-4.31 (m, 4H), 4.02 (br, s, 2H),3.82-3.74 (m,1H), 3.29-3.19 (m, 3H), 2.39 (s, 3H), 2.24-2.16 (m, 1H), 2.06-1.95 (m, 1H), 1.90-1.55 (m, 7H), 1.43-1.29 (m, 2H), 1.23-1.06 (m, 2H),0.84-0.74 (m, 1H), 0.17 (br, d, J=8.1 Hz, 2H), 0.16-0.32 (m, 2H).

Compounds of Examples 531 to 565 in Table 52 were prepared following a procedure similar to the preparation of a compound of Example 530, by acid amine coupling of Intermediate 530B with appropriate carboxylic acid followed by ester hydrolysis and coupling with appropriate amines

TABLE 52

| Example | Structure<br>Name<br>Analytical Data: LC-MS m/z $[M + H]^+$; HPLC retention time (HPLC method) |
|---|---|
| 531 | 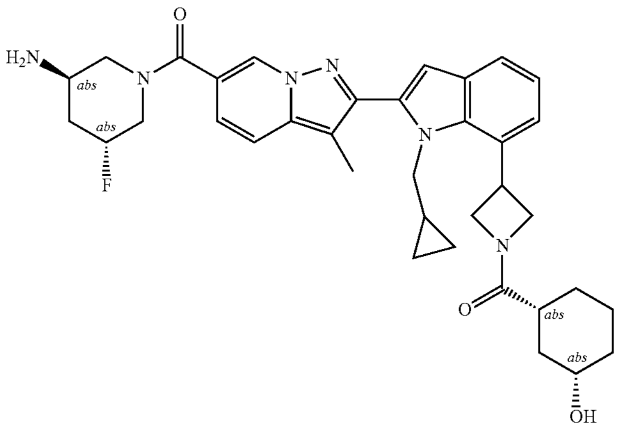 [SMILES: Cc1c(-c2cc3cccc(C4CN(C(=O)[C@@H]5CCC[C@H](O)C5)C4)c3n2CC2CC2)nn2cc(C(=O)N3C[C@H](N)C[C@@H](F)C3)ccc12]<br>((3R,5R)-3-Amino-5-fluoropiperidin-1-yl)(2-(1-(cyclopropylmethyl)-7-(1-((1R,3S)-3-hydroxycyclohexane-1-carbonyl)azetidin-3-yl)-1H-indol-2-yl)-3-methylpyrazolo[1,5-a]pyridin-6-yl)methanone<br>Analytical Data: 627.3, 1.510 min (Method E) |

TABLE 52-continued

| Example | Structure<br>Name<br>Analytical Data: LC-MS m/z [M + H]+; HPLC retention time (HPLC method) |
|---|---|
| 532 | 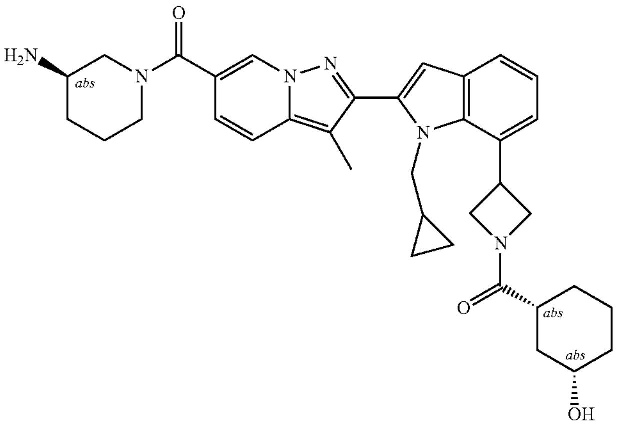 [SMILES: Cc1c(-c2cc3cccc(C4CN(C(=O)[C@@H]5CCC[C@H](O)C5)C4)c3n2CC2CC2)nn2cc(C(=O)N3CCC[C@@H](N)C3)ccc12]<br>((R)-3-Aminopiperidin-1-yl)(2-(1-(cyclopropylmethyl)-7-(1-((1R,3S)-3-hydroxycyclohexane-1-carbonyl)azetidin-3-yl)-1H-indol-2-yl)-3-methylpyrazolo[1,5-a]pyridin-6-yl)methanone<br>Analytical Data: 609.3, 1.446 min (Method E) |
| 533 | 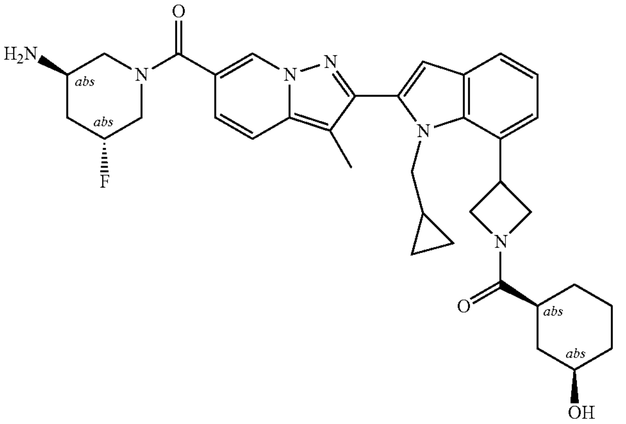 [SMILES: Cc1c(-c2cc3cccc(C4CN(C(=O)[C@H]5CCC[C@@H](O)C5)C4)c3n2CC2CC2)nn2cc(C(=O)N3C[C@H](N)C[C@@H](F)C3)ccc12]<br>((3R,5R)-3-Amino-5-fluoropiperidin-1-yl)(2-(1-(cyclopropylmethyl)-7-(1-((1S,3R)-3-hydroxycyclohexane-1-carbonyl)azetidin-3-yl)-1H-indol-2-yl)-3-methylpyrazolo[1,5-a]pyridin-6-yl)methanone<br>Analytical Data: 627.3, 1.499 min (Method E) |
| 534 | 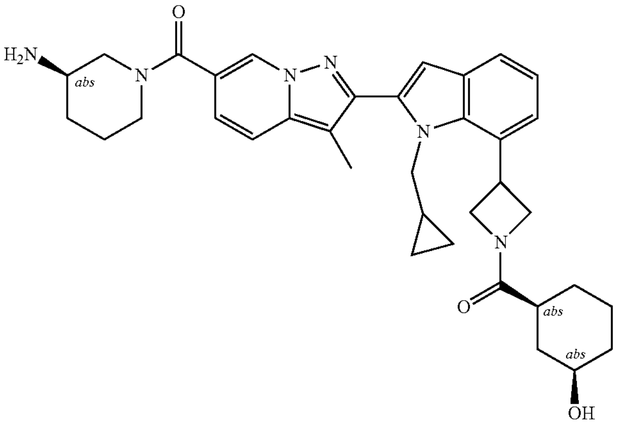 [SMILES: Cc1c(-c2cc3cccc(C4CN(C(=O)[C@H]5CCC[C@@H](O)C5)C4)c3n2CC2CC2)nn2cc(C(=O)N3CCC[C@@H](N)C3)ccc12]<br>((R)-3-Aminopiperidin-1-yl)(2-(1-(cyclopropylmethyl)-7-(1-((1S,3R)-3-hydroxycyclohexane-1-carbonyl)azetidin-3-yl)-1H-indol-2-yl)-3-methylpyrazolo[1,5-a]pyridin-6-yl)methanone<br>Analytical Data: 609.3, 1.446 min (Method E) |

TABLE 52-continued

| Example | Structure<br>Name<br>Analytical Data: LC-MS m/z $[M + H]^+$; HPLC retention time (HPLC method) |
|---|---|
| 535 | 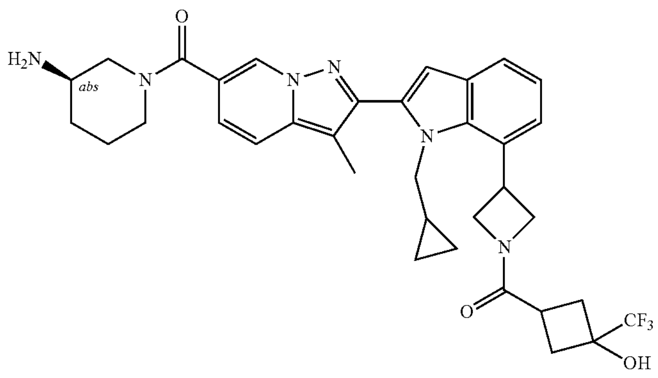 [SMILES: Cc1c(-c2cc3cccc(C4CN(C(=O)C5CC(O)(C(F)(F)F)C5)C4)c3n2CC2CC2)nn2cc(C(=O)N3CCC[C@@H](N)C3)ccc12]<br>(R)-(3-Aminopiperidin-1-yl)(2-(1-(cyclopropylmethyl)-7-(1-(3-hydroxy-3-(trifluoromethyl)cyclobutane-1-carbonyl)azetidin-3-yl)-1H-indol-2-yl)-3-methylpyrazolo[1,5-a]pyridin-6-yl)methanone (mixture of diastereomers)<br>Analytical Data: 649.3, 1.656 min (Method E) |
| 536 | 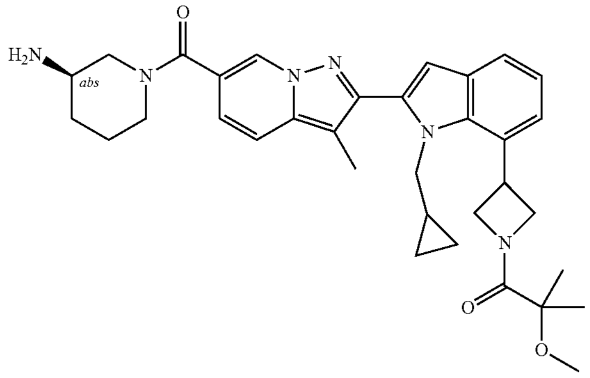 [SMILES: COC(C)(C)C(=O)N1CC(c2cccc3cc(-c4nn5cc(C(=O)N6CCC[C@@H](N)C6)ccc5c4C)n(CC4CC4)c23)C1]<br>(R)-1-(3-(2-(6-(3-Aminopiperidine-1-carbonyl)-3-methylpyrazolo[1,5-a]pyridin-2-yl)-1-(cyclopropylmethyl)-1H-indol-7-yl)azetidin-1-yl)-2-methoxy-2-methylpropan-1-one<br>Analytical Data: 583.3, 1.616 min (Method E) |
| 537 | 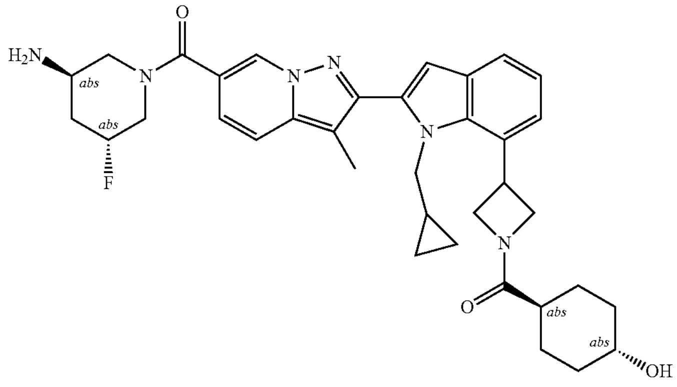 [SMILES: Cc1c(-c2cc3cccc(C4CN(C(=O)[C@H]5CC[C@H](O)CC5)C4)c3n2CC2CC2)nn2cc(C(=O)N3C[C@H](N)C[C@@H](F)C3)ccc12]<br>((3R,5R)-3-Amino-5-fluoropiperidin-1-yl)(2-(1-(cyclopropylmethyl)-7-(1-((1r,4r)-4-hydroxycyclohexane-1-carbonyl)azetidin-3-yl)-1H-indol-2-yl)-3-methylpyrazolo[1,5-a]pyridin-6-yl)methanone<br>Analytical Data: 627.3, 1.458 min (Method E) |

TABLE 52-continued

| Example | Structure<br>Name<br>Analytical Data: LC-MS m/z $[M + H]^+$; HPLC retention time (HPLC method) |
|---|---|
| 538 | 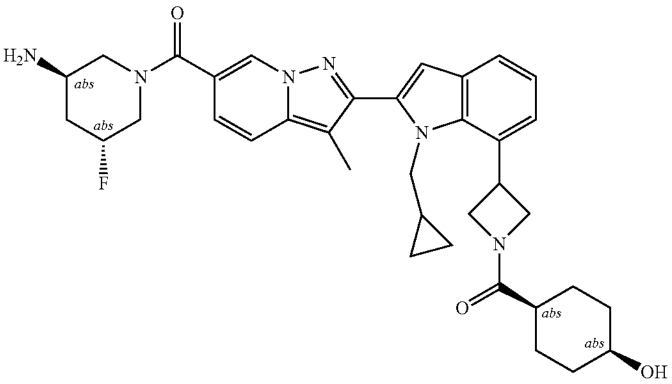 [SMILES: Cc1c(-c2cc3cccc(C4CN(C(=O)[C@H]5CC[C@@H](O)CC5)C4)c3n2CC2CC2)nn2cc(C(=O)N3C[C@H](N)C[C@@H](F)C3)ccc12]<br>((3R,5R)-3-Amino-5-fluoropiperidin-1-yl)(2-(1-(cyclopropylmethyl)-7-(1-((1s,4s)-4-hydroxycyclohexane-1-carbonyl)azetidin-3-yl)-1H-indol-2-yl)-3-methylpyrazolo[1,5-a]pyridin-6-yl)methanone<br>Analytical Data: 627.3, 1.498 min (Method E) |
| 539 | 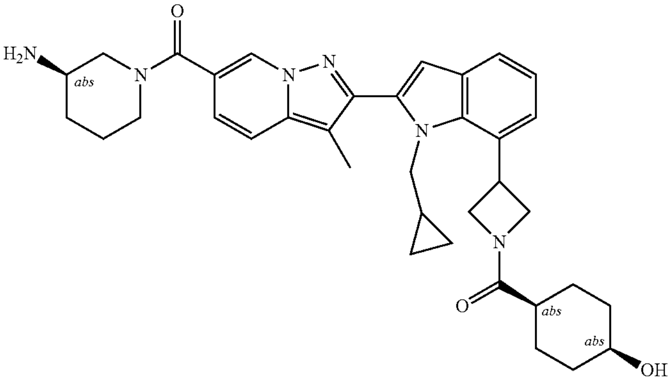 [SMILES: Cc1c(-c2cc3cccc(C4CN(C(=O)[C@H]5CC[C@@H](O)CC5)C4)c3n2CC2CC2)nn2cc(C(=O)N3CCC[C@@H](N)C3)ccc12]<br>((R)-3-Aminopiperidin-1-yl)(2-(1-(cyclopropylmethyl)-7-(1-((1s,4s)-4-hydroxycyclohexane-1-carbonyl)azetidin-3-yl)-1H-indol-2-yl)-3-methylpyrazolo[1,5-a]pyridin-6-yl)methanone<br>Analytical Data: 609.3, 1.440 min (Method E) |
| 540 | 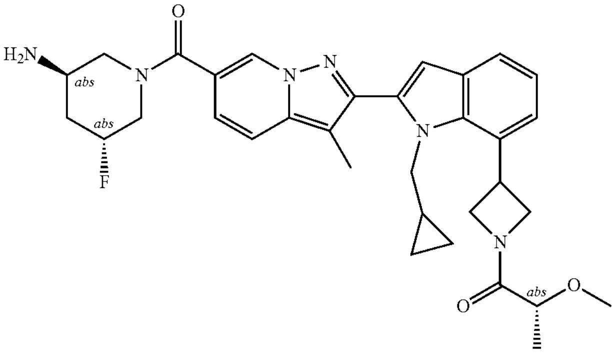 [SMILES: CO[C@H](C)C(=O)N1CC(c2cccc3cc(-c4nn5cc(C(=O)N6C[C@H](N)C[C@@H](F)C6)ccc5c4C)n(CC4CC4)c23)C1]<br>(R)-1-(3-(2-(6-((3R,5R)-3-Amino-5-fluoropiperidine-1-carbonyl)-3-methylpyrazolo[1,5-a]pyridin-2-yl)-1-(cyclopropylmethyl)-1H-indol-7-yl)azetidin-1-yl)-2-methoxypropan-1-one<br>Analytical Data: 587.2, 1.488 min (Method E) |

TABLE 52-continued

| Example | Structure<br>Name<br>Analytical Data: LC-MS m/z [M + H]$^+$; HPLC retention time (HPLC method) |
|---|---|
| 541 | 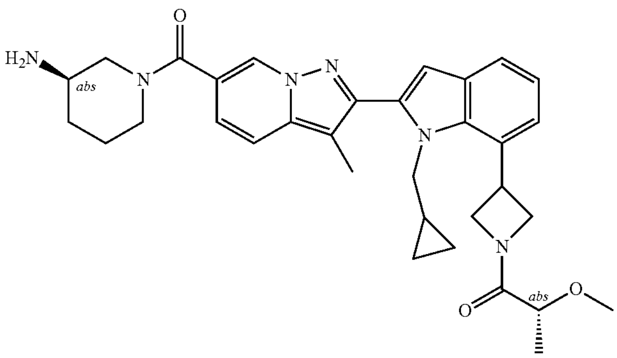 [SMILES: CO[C@H](C)C(=O)N1CC(c2cccc3cc(-c4nn5cc(C(=O)N6CCC[C@@H](N)C6)ccc5c4C)n(CC4CC4)c23)C1]<br>(R)-1-(3-(2-(6-((R)-3-Aminopiperidine-1-carbonyl)-3-methylpyrazolo[1,5-a]pyridin-2-yl)-1-(cyclopropylmethyl)-1H-indol-7-yl)azetidin-1-yl)-2-methoxypropan-1-one<br>Analytical data: 569.3, 1.443 min (Method E) |
| 542 | 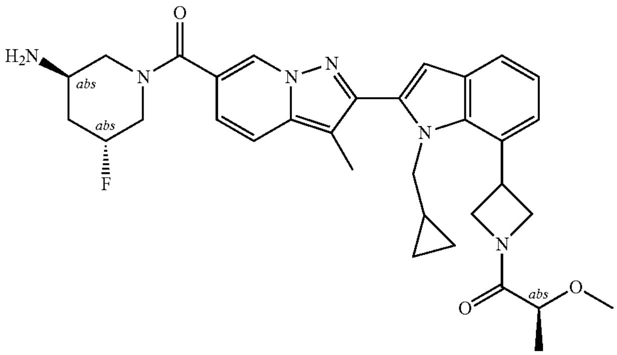 [SMILES: CO[C@@H](C)C(=O)N1CC(c2cccc3cc(-c4nn5cc(C(=O)N6C[C@H](N)C[C@@H](F)C6)ccc5c4C)n(CC4CC4)c23)C1]<br>(S)-1-(3-(2-(6-((3R,5R)-3-Amino-5-fluoropiperidine-1-carbonyl)-3-methylpyrazolo[1,5-a]pyridin-2-yl)-1-(cyclopropylmethyl)-1H-indol-7-yl)azetidin-1-yl)-2-methoxypropan-1-one<br>Analytical Data: 587.3, 1.486 min (Method E) |
| 543 | 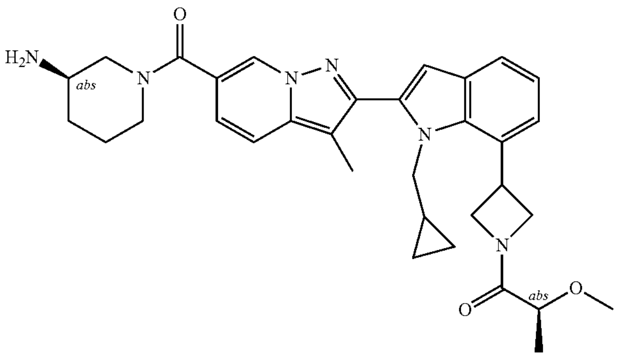 [SMILES: CO[C@@H](C)C(=O)N1CC(c2cccc3cc(-c4nn5cc(C(=O)N6CCC[C@@H](N)C6)ccc5c4C)n(CC4CC4)c23)C1]<br>(S)-1-(3-(2-(6-((R)-3-aminopiperidine-1-carbonyl)-3-methylpyrazolo[1,5-a]pyridin-2-yl)-1-(cyclopropylmethyl)-1H-indol-7-yl)azetidin-1-yl)-2-methoxypropan-1-one<br>Analytical Data: 569.3, 1.441 min (Method E) |

TABLE 52-continued

| Example | Structure<br>Name<br>Analytical Data: LC-MS m/z [M + H]$^+$; HPLC retention time (HPLC method) |
|---|---|
| 544 | 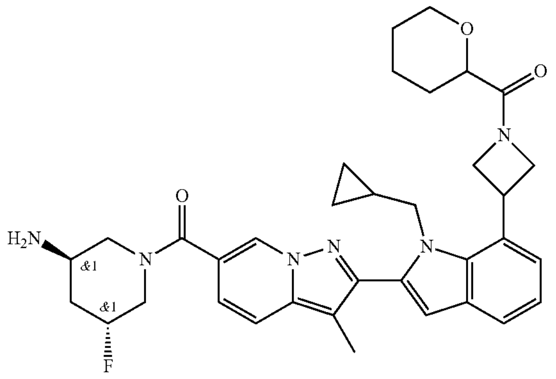 [SMILES: Cc1c(-c2cc3cccc(C4CN(C(=O)C5CCCCO5)C4)c3n2CC2CC2)nn2cc(C(=O)N3C[C@H](N)C[C@@H](F)C3)ccc12]<br>((3R,5R)-3-Amino-5-fluoropiperidin-1-yl)(2-(1-(cyclopropylmethyl)-7-(1-(tetrahydro-2H-pyran-2-carbonyl)azetidin-3-yl)-1H-indol-2-yl)-3-methylpyrazolo[1,5-a]pyridin-6-yl)methanone (mixture of diastereomers)<br>Analytical Data: 613.3, 1.653 min (Method E) |
| 545 | 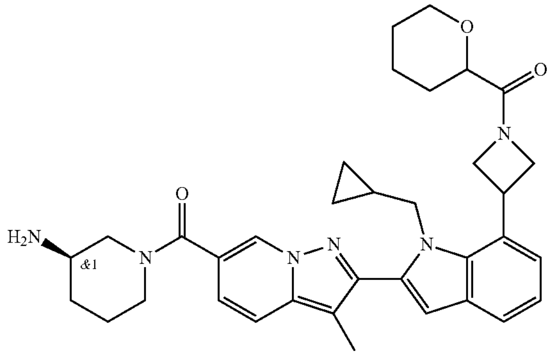 [SMILES: Cc1c(-c2cc3cccc(C4CN(C(=O)C5CCCCO5)C4)c3n2CC2CC2)nn2cc(C(=O)N3CCC[C@@H](N)C3)ccc12]<br>((R)-3-Aminopiperidin-1-yl)(2-(1-(cyclopropylmethyl)-7-(1-(tetrahydro-2H-pyran-2-carbonyl)azetidin-3-yl)-1H-indol-2-yl)-3-methylpyrazolo[1,5-a]pyridin-6-yl)methanone (mixture of diastereomers)<br>Analytical Data: 595.3, 1.732 min (Method E) |
| 546 | 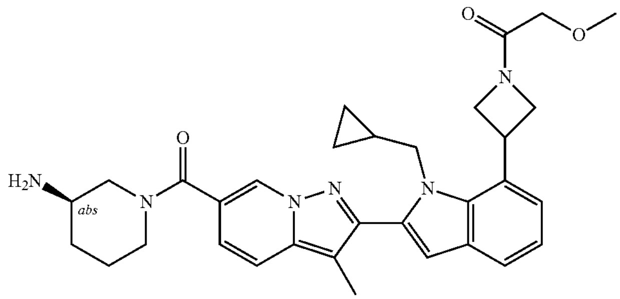 [SMILES: COCC(=O)N1CC(c2cccc3cc(-c4nn5cc(C(=O)N6CCC[C@@H](N)C6)ccc5c4C)n(CC4CC4)c23)C1]<br>(R)-1-(3-(2-(6-(3-Aminopiperidine-1-carbonyl)-3-methylpyrazolo[1,5-a]pyridin-2-yl)-1-(cyclopropylmethyl)-1H-indol-7-yl)azetidin-1-yl)-2-methoxyethan-1-one<br>Analytical Data: 555.4, 6.864 min (Method D) |

TABLE 52-continued

| Example | Structure<br>Name<br>Analytical Data: LC-MS m/z [M + H]$^+$; HPLC retention time (HPLC method) |
|---|---|
| 547 | 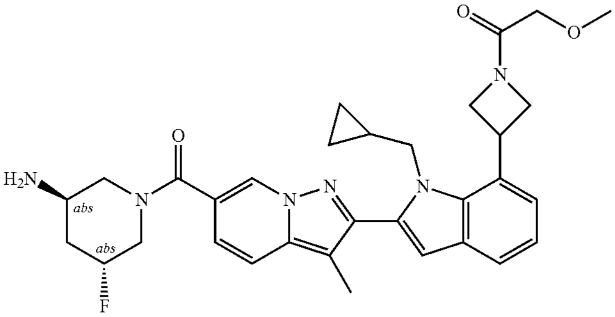 [SMILES: COCC(=O)N1CC(c2cccc3cc(-c4nn5cc(C(=O)N6C[C@H](N)C[C@@H](F)C6)ccc5c4C)n(CC4CC4)c23)C1]<br>1-(3-(2-(6-((3R,5R)-3-Amino-5-fluoropiperidine-1-carbonyl)-3-methylpyrazolo[1,5-a]pyridin-2-yl)-1-(cyclopropylmethyl)-1H-indol-7-yl)azetidin-1-yl)-2-methoxyethan-1-one<br>Analytical Data: 573.2, 6.996 min (Method C) |
| 548 | 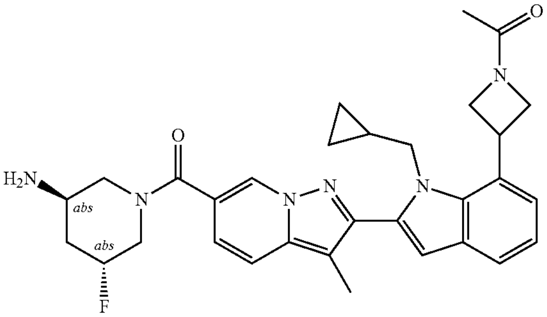 [SMILES: CC(=O)N1CC(c2cccc3cc(-c4nn5cc(C(=O)N6C[C@H](N)C[C@@H](F)C6)ccc5c4C)n(CC4CC4)c23)C1]<br>1-(3-(2-(6-((3R,5R)-3-Amino-5-fluoropiperidine-1-carbonyl)-3-methylpyrazolo[1,5-a]pyridin-2-yl)-1-(cyclopropylmethyl)-1H-indol-7-yl)azetidin-1-yl)ethan-1-one<br>Analytical Data: 544.2, 7.161 min (Method D) |
| 549 | 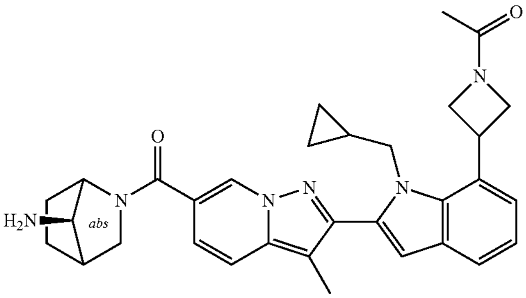 [SMILES: CC(=O)N1CC(c2cccc3cc(-c4nn5cc(C(=O)N6CC7CCC6[C@@H]7N)ccc5c4C)n(CC4CC4)c23)C1]<br>1-(3-(2-(6-((7R)-7-Amino-2-azabicyclo[2.2.1]heptane-2-carbonyl)-3-methylpyrazolo[1,5-a]pyridin-2-yl)-1-(cyclopropylmethyl)-1H-indol-7-yl)azetidin-1-yl)ethan-1-one<br>Analytical Data: 537.4, 6.854 min (Method D) |

Example 550

(R)-5-(((2-(6-((3R,5R)-3-amino-5-fluoropiperidine-1-carbonyl)-4-methoxy-3-methylpyrazolo[1,5-a]pyridin-2-yl)-1-(cyclopropylmethyl)-1H-indol-7-yl)oxy)methyl)pyrrolidin-2-one

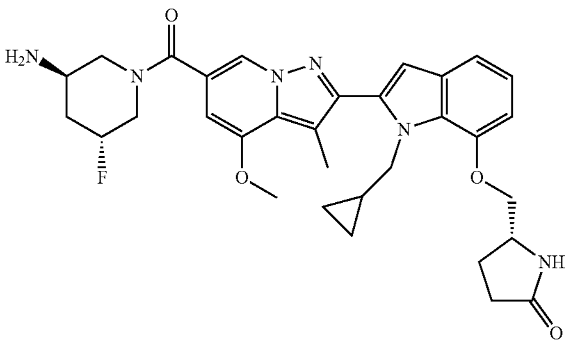 [SMILES: COc1cc(C(=O)N2C[C@H](N)C[C@@H](F)C2)cn2nc(-c3cc4cccc(OC[C@H]5CCC(=O)N5)c4n3CC3CC3)c(C)c12]

Intermediate 550A

Methyl 2-(7-(benzyloxy)-1-(cyclopropylmethyl)-1H-indol-2-yl)-4-methoxy-3-methylpyrazolo[1,5-a]pyridine-6-carboxylate

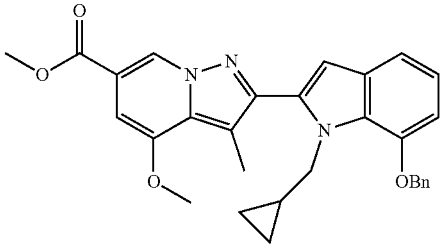 [SMILES: COC(=O)c1cc(OC)c2c(C)c(-c3cc4cccc(OCc5ccccc5)c4n3CC3CC3)nn2c1]

Intermediate 50 (1.9 g, 5.24 mmol was added to a stirred solution of Intermediate 1 (2.28 g, 5.24 mmol) and copper(I) iodide (0.263 g, 1.380 mmol) in DMF (10 ml). The reaction mixture was heated to 80° C. for 48 hours, quenched with water (100 ml) and extracted with ethyl acetate (2×100 ml). The combined organic layer was dried over sodium sulphate, filtered, and concentrated under reduced vacuum to obtain a crude product, which was purified using a silica gel column (10-20% of ethyl acetate in hexane) to afford methyl 2-(7-(benzyloxy)-1-(cyclopropylmethyl)-1H-indol-2-yl)-4-methoxy-3-methylpyrazolo[1,5-a]pyridine-6-carboxylate (500 mg, 37%). LC-MS m/z: 496.2 $[M+H]^+$ Intermediate 550B Methyl 2-(1-(cyclopropylmethyl)-7-hydroxy-1H-indol-2-yl)-4-methoxy-3-methylpyrazolo[1,5-a]pyridine-6-carboxylate

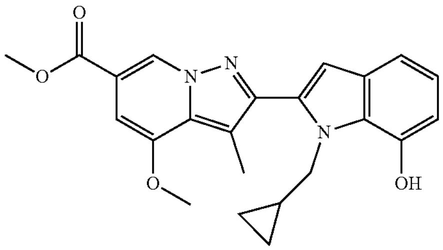 [SMILES: COC(=O)c1cc(OC)c2c(C)c(-c3cc4cccc(O)c4n3CC3CC3)nn2c1]

A solution of Intermediate 550A (500 mg, 1.009 mmol) in ethyl acetate (3 ml) was degassed with nitrogen for 5 min, followed by the addition of Pd/C (107 mg, 0.101 mmol). The reaction mixture was stirred under $H_2$ atmosphere for 4 hours, filtered through a celite bed, and washed with methanol. The combined filtrate was concentrated under reduced pressure to afford crude methyl 2-(1-(cyclopropylmethyl)-7-hydroxy-1H-indol-2-yl)-4-methoxy-3-methylpyrazolo[1,5-a]pyridine-6-carboxylate (350 mg, 86%) LC-MS m/z: 406.3 $[M+H]^+$. $^1H$ NMR (300 MHz, DMSO-$d_6$) δ ppm: 9.77 (s, 1H), 8.85 (s, 1H), 7.05 (d, J=7.6 Hz, 1H), 6.90-6.81 (m, 2H), 6.67 (s, 1H), 6.60 (d, J=7.2 Hz, 1H), 4.56 (br, d, J=6.4 Hz, 2H), 4.09-3.94 (m, 3H), 3.90 (s, 3H), 3.32-3.17 (m, 3H), 1.02 (br, s, 1H), 0.26-0.12 (m, 2H),0.05-0.01 (m, 2H)

Intermediate 550C

Indol-2-yl)-4-methoxy-3-methylpyrazolo[1,5-a]pyridine-6-carboxylate AR NO-A2C37-163

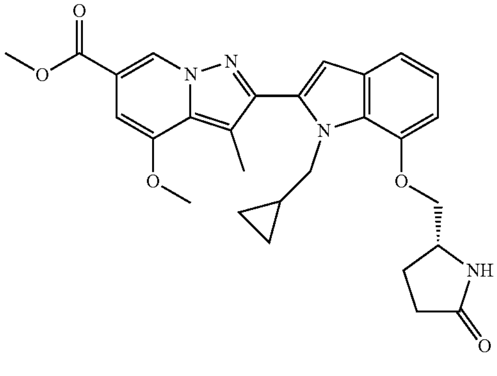 [SMILES: COC(=O)c1cc(OC)c2c(C)c(-c3cc4cccc(OC[C@H]5CCC(=O)N5)c4n3CC3CC3)nn2c1]

Cesium carbonate (241 mg, 0.740 mmol), tetrabutylammonium iodide (27.3 mg, 0.074 mmol) and (R)-(5-oxopyrrolidin-2-yl)methyl 4-methylbenzenesulfonate (66.4 mg, 0.247 mmol) were added to a stirred solution of Intermediate 550B (100 mg, 0.247 mmol) in DMF (1 ml). The reaction mixture was heated to 60° C. for 16 hours, quenched with water (100 ml), and extracted with ethyl acetate (2×100 ml). The combined organic layers were dried over sodium sulphate, filtered, and concentrated under reduced pressure to afford methyl (R)-2-(1-(cyclopropylmethyl)-7-((5-oxopyrrolidin- 2-yl)methoxy)-1H-indol-2-yl)-4-methoxy-3-methylpyrazolo[1,5-a]pyridine-6-carboxylate (105 mg, 85%). LC-MS m/z: 503.4 [M+H]$^+$.

Intermediate 550D (R)-2-(1-(Cyclopropylmethyl)-7-((5-oxopyrrolidin-2-yl)methoxy)-1H-indol-2-yl)-4-methoxy-3-methylpyrazolo[1,5-a]pyridine-6-carboxylic acid

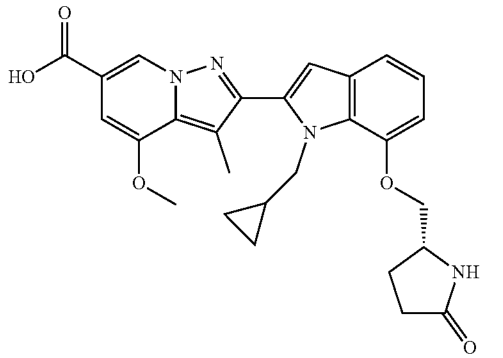 [SMILES: COc1cc(C(=O)O)cn2nc(-c3cc4cccc(OC[C@H]5CCC(=O)N5)c4n3CC3CC3)c(C)c12]

LiOH (4.76 mg, 0.199 mmol) was added to a stirred solution of Intermediate 550C (100 mg, 0.199 mmol) in THF (1 ml), methanol (1.0 ml) and water (1 ml). The reaction mixture was stirred for 16 hours, concentrated under reduced pressure, then acidified with 1 N HCl, and the solids thus obtained were filtered through a Buchner funnel and dried under reduced pressure to afford (R)-2-(1-(cyclopropylmethyl)-7-((5-oxopyrrolidin-2-yl)methoxy)-1H-indol-2-yl)-4-methoxy-3-methylpyrazolo[1,5-a]pyridine-6-carboxylic acid (90 mg, 93%). LC-MS m/z: 489.3 [M+H]$^+$ Intermediate 550E tert-butyl ((3R,5R)-1-(2-(1-(cyclopropylmethyl)-7-(((R)-5-oxopyrrolidin-2-yl)methoxy)-1H-indol-2-yl)-4-methoxy-3-methylpyrazolo[1,5-a]pyridine-6-carbonyl)-5-fluoropiperidin-3-yl)carbamate

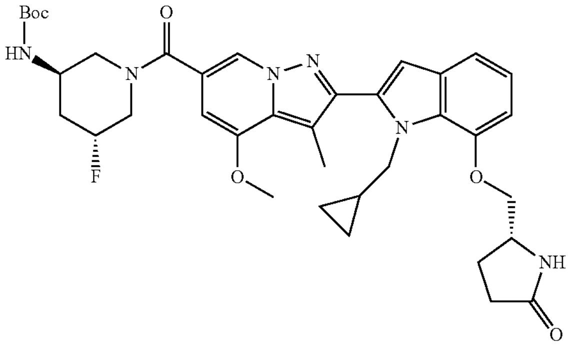 [SMILES: COc1cc(C(=O)N2C[C@H](F)C[C@@H](NC(=O)OC(C)(C)C)C2)cn2nc(-c3cc4cccc(OC[C@H]5CCC(=O)N5)c4n3CC3CC3)c(C)c12]

tert-Butyl ((3R,5R)-5-fluoropiperidin-3-yl)carbamate (22.34 mg, 0.102 mmol), DIPEA (0.054 ml, 0.307 mmol), HATU (58.4 mg, 0.154 mmol) were added to a stirred solution of Intermediate 550D (50 mg, 0.102 mmol) in DMF (1 ml). The reaction mixture was stirred 3 hours, quenched with water (50 ml), and extracted with ethyl acetate (2×50 ml). The combined organic layers were dried over sodium sulphate, filtered, and concentrated under reduced pressure to afford tert-butyl ((3R,5R)-1-(2-(1-(cyclopropylmethyl)-7-(((R)-5-oxopyrrolidin-2-yl)methoxy)-1H-indol-2-yl)-4-methoxy-3-methylpyrazolo[1,5-a]pyridine-6-carbonyl)-5-fluoropiperidin-3-yl)carbamate (50 mg, 71%). LC-MS m/z: 689.3 [M+H]$^+$.

Example 550

(R)-5-(((2-(6-((3R,5R)-3-Amino-5-fluoropiperidine-1-carbonyl)-4-methoxy-3-methylpyrazolo[1,5-a]pyridin-2-yl)-1-(cyclopropylmethyl)-1H-indol-7-yl)oxy)methyl)pyrrolidin-2-one

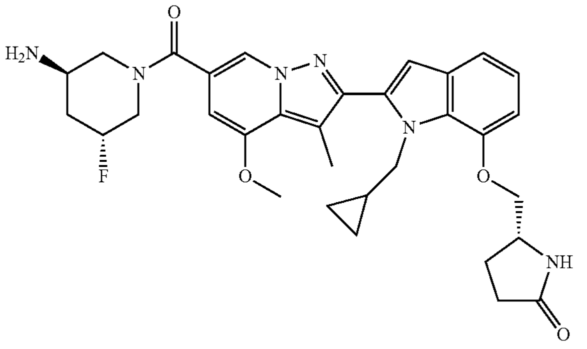 [SMILES: COc1cc(C(=O)N2C[C@H](N)C[C@@H](F)C2)cn2nc(-c3cc4cccc(OC[C@H]5CCC(=O)N5)c4n3CC3CC3)c(C)c12]

TFA (0.087 mmol) was added to a stirred solution of tert-butyl ((3R,5R)-1-(2-(1-(cyclopropylmethyl)-7-(((R)-5-oxopyrrolidin-2-yl)methoxy)-1H-indol-2-yl)-4-methoxy-3-methylpyrazolo[1,5-a]pyridine-6-carbonyl)-5-fluoropiperidin-3-yl)carbamate (60 mg, 0.087 mmol) in DCM (1 ml) at 0° C. The reaction mixture was allowed it to warm to a room temperature and stirred for 3 hours, concentrated in vacuo to afford a crude compound, which was purified using preparative HPLC to afford (R)-5-(((2-(6-((3R,5R)-3-Amino-5-fluoropiperidine-1-carbonyl)-4-methoxy-3-methylpyrazolo[1,5-a]pyridin-2-yl)-1-(cyclopropylmethyl)-1H-indol-7-yl)oxy)methyl)pyrrolidin-2-one (11.2 mg, 19%). LC-MS m/z: 589.2 [M+H]$^+$. LCMS retention time: 1.498 min (method E). $^1$H NMR (400 MHz, DMSO-$d_6$) δ ppm: 8.36 (s, 1H), 7.87 (s, 1H), 7.21 (d, J=8.0 Hz, 1H), 6.99 (t, J=8.0 Hz, 1H), 6.76 (d, J=8.0 Hz, 1H), 6.67 (s, 1H), 6.54 (s, 1H), 5.05-4.86 (m, 1H), 4.52 (br, dd, J=3.1, 7.0 Hz, 2H), 4.15-4.00 (m, 4H), 3.98 (s, 3H), 3.09-3.01 (m, 3H), 2.47 (s, 3H), 2.31-2.14 (m, 4H), 2.07-1.99 (m, 1H), 1.68-1.49 (m, 1H), 1.07-0.98 (m, 1H), 0.22-0.13 (m, 2H), −0.05 (q, J=4.8 Hz, 2H).

Compounds of Examples 551 to 565 in Table 53 were prepared following a procedure similar to the preparation of a compound of Example 550 in Table 55, by displacement reaction of Intermediate 550B with appropriate tosylate followed by ester hydrolysis and coupling with appropriate amines

TABLE 53

| Example | Structure<br>Name<br>Analytical Data: LC-MS m/z [M + H]+; HPLC retention time (HPLC method) |
|---|---|
| 551 | 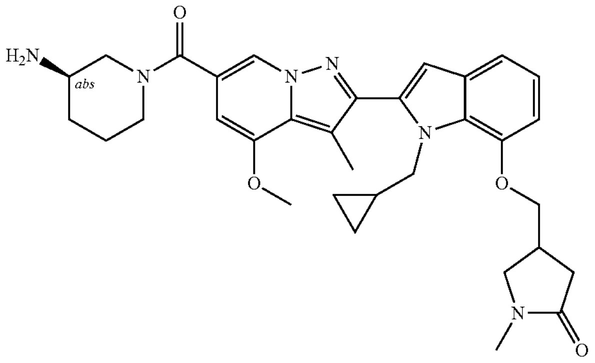 [SMILES: COc1cc(C(=O)N2CCC[C@@H](N)C2)cn2nc(-c3cc4cccc(OCC5CC(=O)N(C)C5)c4n3CC3CC3)c(C)c12]<br>4-(((2-(6-((R)-3-Aminopiperidine-1-carbonyl)-4-methoxy-3-methylpyrazolo[1,5-a]pyridin-2-yl)-1-(cyclopropylmethyl)-1H-indol-7-yl)oxy)methyl)-1-methylpyrrolidin-2-one (isomer 1)<br>Analytical Data: 585.3, 1.624 min (Method E) |
| 552 | 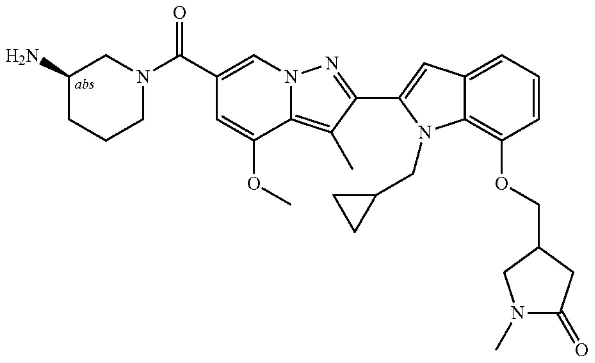 [SMILES: COc1cc(C(=O)N2CCC[C@@H](N)C2)cn2nc(-c3cc4cccc(OCC5CC(=O)N(C)C5)c4n3CC3CC3)c(C)c12]<br>4-(((2-(6-((R)-3-Aminopiperidine-1-carbonyl)-4-methoxy-3-methylpyrazolo[1,5-a]pyridin-2-yl)-1-(cyclopropylmethyl)-1H-indol-7-yl)oxy)methyl)-1-methylpyrrolidin-2-one (isomer 1)<br>Analytical Data: 585.3, 1.629 min (Method E) |
| 553 | 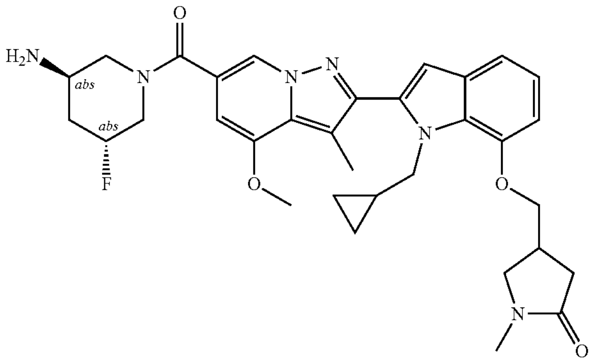 [SMILES: COc1cc(C(=O)N2C[C@H](N)C[C@@H](F)C2)cn2nc(-c3cc4cccc(OCC5CC(=O)N(C)C5)c4n3CC3CC3)c(C)c12]<br>4-(((2-(6-((3R,5R)-3-Amino-5-fluoropiperidine-1-carbonyl)-4-methoxy-3-methylpyrazolo[1,5-a]pyridin-2-yl)-1-(cyclopropylmethyl)-1H-indol-7-yl)oxy)methyl)-1-methylpyrrolidin-2-one (isomer 1)<br>Analytical Data: 603.3, 1.645 min (Method E) |

TABLE 53-continued

| Example | Structure<br>Name<br>Analytical Data: LC-MS m/z [M + H]+; HPLC retention time (HPLC method) |
|---|---|
| 554 | 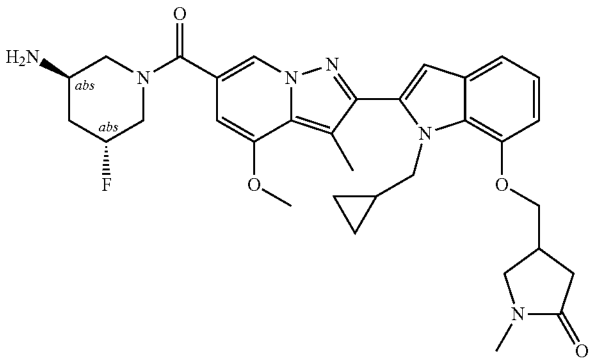 [SMILES: COc1cc(C(=O)N2C[C@H](N)C[C@@H](F)C2)cn2nc(-c3cc4cccc(OCC5CC(=O)N(C)C5)c4n3CC3CC3)c(C)c12]<br>4-(((2-(6-((3R,5R)-3-Amino-5-fluoropiperidine-1-carbonyl)-4-methoxy-3-methylpyrazolo[1,5-a]pyridin-2-yl)-1-(cyclopropylmethyl)-1H-indol-7-yl)oxy)methyl)-1-methylpyrrolidin-2-one (isomer 2)<br>Analytical Data: 603.3, 1.640 min (Method E) |
| 555 | 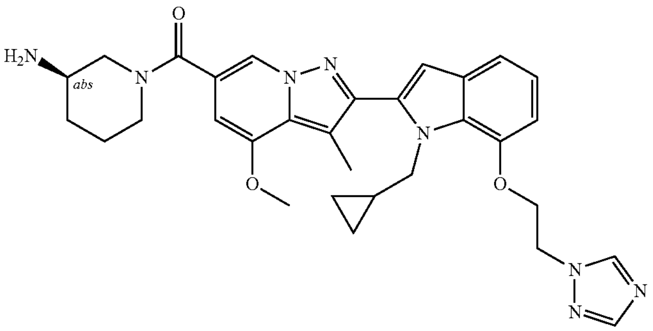 [SMILES: COc1cc(C(=O)N2CCC[C@@H](N)C2)cn2nc(-c3cc4cccc(OCCn5cncn5)c4n3CC3CC3)c(C)c12]<br>(R)-(2-(7-(2-(1H-1,2,4-Triazol-1-yl)ethoxy)-1-(cyclopropylmethyl)-1H-indol-2-yl)-4-methoxy-3-methylpyrazolo[1,5-a]pyridin-6-yl)(3-aminopiperidin-1-yl)methanone<br>Analytical Data: 569.2, 1.482 min (Method E) |
| 556 | 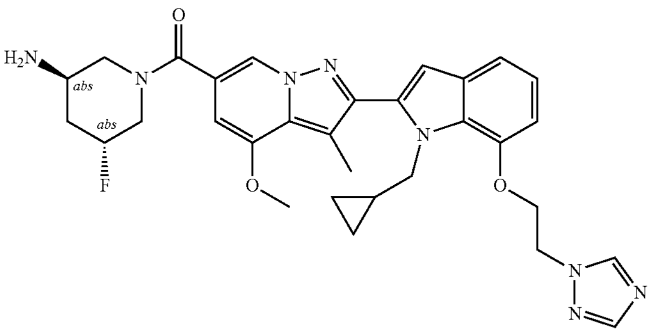 [SMILES: COc1cc(C(=O)N2C[C@H](N)C[C@@H](F)C2)cn2nc(-c3cc4cccc(OCCn5cncn5)c4n3CC3CC3)c(C)c12]<br>(2-(7-(2-(1H-1,2,4-Triazol-1-yl)ethoxy)-1-(cyclopropylmethyl)-1H-indol-2-yl)-4-methoxy-3-methylpyrazolo[1,5-a]pyridin-6-yl)((3R,5R)-3-amino-5-fluoropiperidin-1-yl)methanone<br>Analytical Data: 587.3, 1.629 min (Method E) |

TABLE 53-continued

| Example | Structure<br>Name<br>Analytical Data: LC-MS m/z [M + H]+; HPLC retention time (HPLC method) |
|---|---|
| 557 | 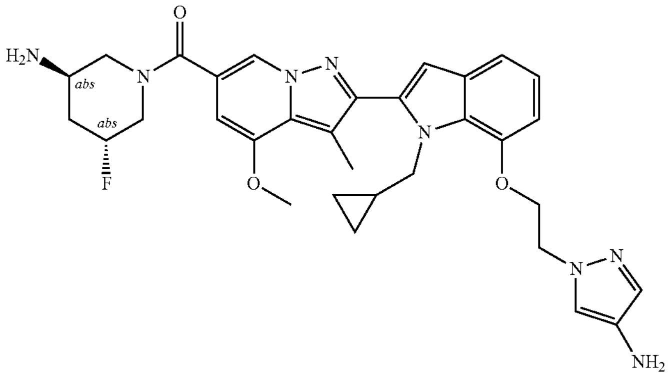 [SMILES: COc1cc(C(=O)N2C[C@H](N)C[C@@H](F)C2)cn2nc(-c3cc4cccc(OCCn5cc(N)cn5)c4n3CC3CC3)c(C)c12]<br>(2-(7-(2-(4-Amino-1H-pyrazol-1-yl)ethoxy)-1-(cyclopropylmethyl)-1H-indol-2-yl)-4-methoxy-3-methylpyrazolo[1,5-a]pyridin-6-yl)((3R,5R)-3-amino-5-fluoropiperidin-1-yl)methanone<br>Analytical Data: 601.2, 1.558 min<br>(Method E) |
| 558 | 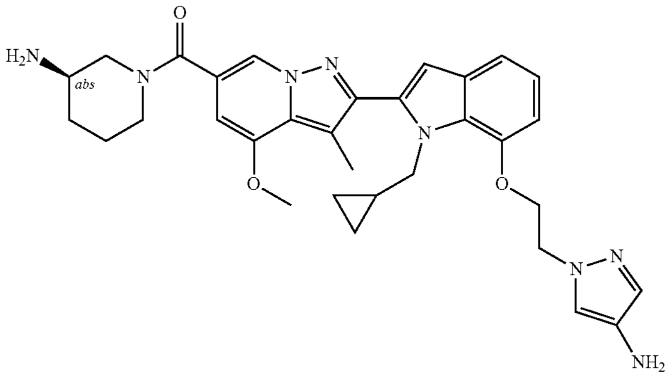 [SMILES: COc1cc(C(=O)N2CCC[C@@H](N)C2)cn2nc(-c3cc4cccc(OCCn5cc(N)cn5)c4n3CC3CC3)c(C)c12]<br>(R)-(2-(7-(2-(4-Amino-1H-pyrazol-1-yl)ethoxy)-1-(cyclopropylmethyl)-1H-indol-2-yl)-4-methoxy-3-methylpyrazolo[1,5-a]pyridin-6-yl)(3-aminopiperidin-1-yl)methanone<br>Analytical Data: 583.2, 1.264 min<br>(Method E) |
| 559 | 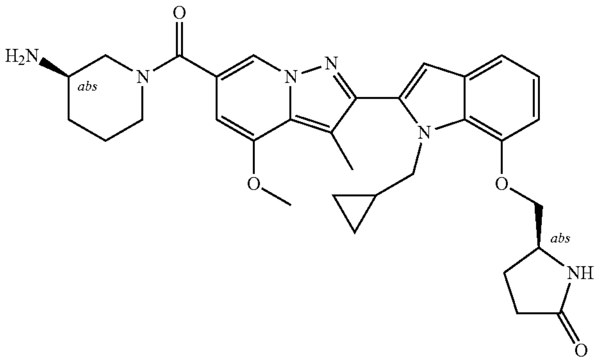 [SMILES: COc1cc(C(=O)N2CCC[C@@H](N)C2)cn2nc(-c3cc4cccc(OC[C@@H]5CCC(=O)N5)c4n3CC3CC3)c(C)c12]<br>(S)-5-(((2-(6-((R)-3-Aminopiperidine-1-carbonyl)-4-methoxy-3-methylpyrazolo[1,5-a]pyridin-2-yl)-1-(cyclopropylmethyl)-1H-indol-7-yl)oxy)methyl)pyrrolidin-2-one<br>Analytical Data: 571.3, 1.470 min (Method E) |

TABLE 53-continued

| Example | Structure<br>Name<br>Analytical Data: LC-MS m/z [M + H]+; HPLC retention time (HPLC method) |
|---|---|
| 560 | 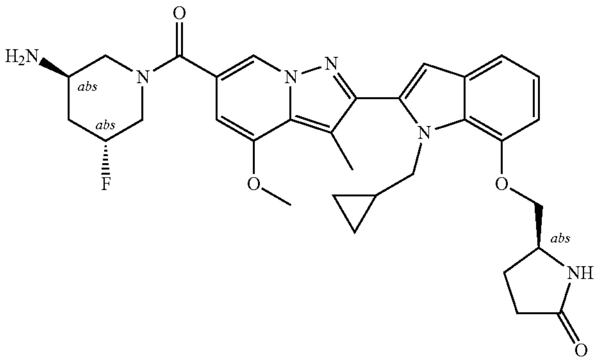 [SMILES: COc1cc(C(=O)N2C[C@H](N)C[C@@H](F)C2)cn2nc(-c3cc4cccc(OC[C@@H]5CCC(=O)N5)c4n3CC3CC3)c(C)c12]<br>(S)-5-(((2-(6-((3R,5R)-3-Amino-5-fluoropiperidine-1-carbonyl)-4-methoxy-3-methylpyrazolo[1,5-a]pyridin-2-yl)-1-(cyclopropylmethyl)-1H-indol-7-yl)oxy)methyl)pyrrolidin-2-one<br>Analytical Data: 589.2, 1.489 min<br>(Method E) |
| 561 | 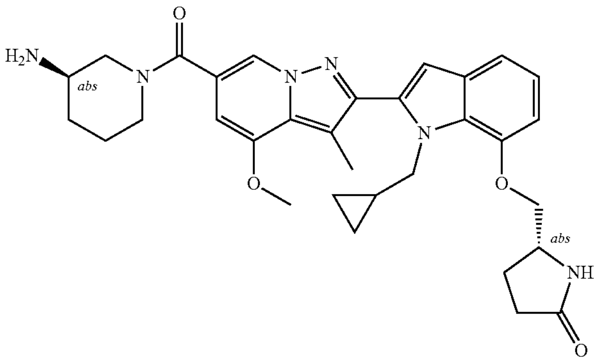 [SMILES: COc1cc(C(=O)N2CCC[C@@H](N)C2)cn2nc(-c3cc4cccc(OC[C@H]5CCC(=O)N5)c4n3CC3CC3)c(C)c12]<br>(R)-5-(((2-(6-((R)-3-Aminopiperidine-1-carbonyl)-4-methoxy-3-methylpyrazolo[1,5-a]pyridin-2-yl)-1-(cyclopropylmethyl)-1H-indol-7-yl)oxy)methyl)pyrrolidin-2-one<br>Analytical Data: 571.2, 1.465 min (Method E) |
| 562 | 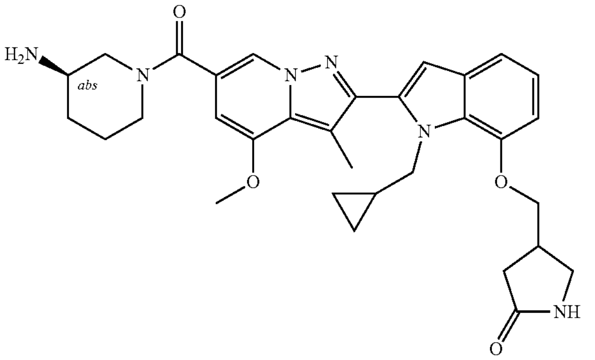 [SMILES: COc1cc(C(=O)N2CCC[C@@H](N)C2)cn2nc(-c3cc4cccc(OCC5CNC(=O)C5)c4n3CC3CC3)c(C)c12]<br>4-(((2-(6-((R)-3-Aminopiperidine-1-carbonyl)-4-methoxy-3-methylpyrazolo[1,5-a]pyridin-2-yl)-1-(cyclopropylmethyl)-1H-indol-7-yl)oxy)methyl)pyrrolidin-2-one (isomer 1) Analytical Data: 571.2, 1.471 min<br>(Method E) |

TABLE 53-continued

| Example | Structure<br>Name<br>Analytical Data: LC-MS m/z [M + H]+; HPLC retention time (HPLC method) |
|---|---|
| 563 | 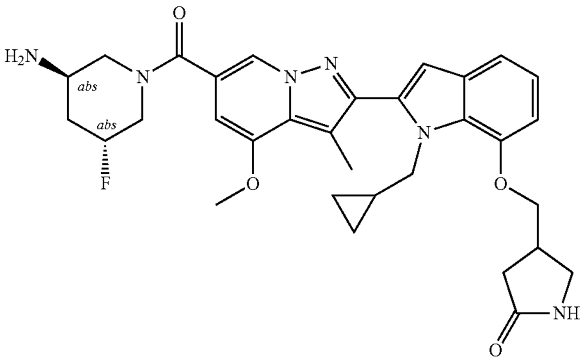 [SMILES: COc1cc(C(=O)N2C[C@H](N)C[C@@H](F)C2)cn2nc(-c3cc4cccc(OCC5CNC(=O)C5)c4n3CC3CC3)c(C)c12]<br>4-(((2-(6-((3R,5R)-3-Amino-5-fluoropiperidine-1-carbonyl)-4-methoxy-3-methylpyrazolo[1,5-a]pyridin-2-yl)-1-(cyclopropylmethyl)-1H-indol-7-yl)oxy)methyl)pyrrolidin-2-one (isomer 1)<br>Analytical Data: 589.3, 1.492 min (Method E) |
| 564 | 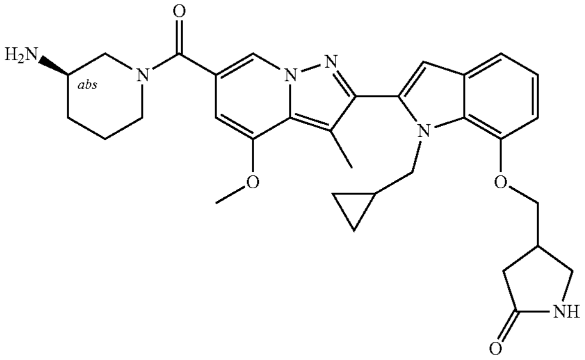 [SMILES: COc1cc(C(=O)N2CCC[C@@H](N)C2)cn2nc(-c3cc4cccc(OCC5CNC(=O)C5)c4n3CC3CC3)c(C)c12]<br>4-(((2-(6-((R)-3-Aminopiperidine-1-carbonyl)-4-methoxy-3-methylpyrazolo[1,5-a]pyridin-2-yl)-1-(cyclopropylmethyl)-1H-indol-7-yl)oxy)methyl)pyrrolidin-2-one (isomer 2)<br>Analytical Data: 571.2, 1.476 min<br>(Method E) |
| 565 | 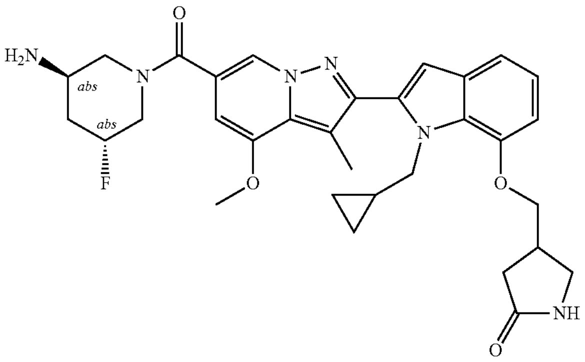 [SMILES: COc1cc(C(=O)N2C[C@H](N)C[C@@H](F)C2)cn2nc(-c3cc4cccc(OCC5CNC(=O)C5)c4n3CC3CC3)c(C)c12]<br>4-(((2-(6-((3R,5R)-3-Amino-5-fluoropiperidine-1-carbonyl)-4-methoxy-3-methylpyrazolo[1,5-a]pyridin-2-yl)-1-(cyclopropylmethyl)-1H-indol-7-yl)oxy)methyl)pyrrolidin-2-one (isomer 2)<br>Analytical Data: 589.3, 1.484 min (Method E) |

Example 566

4-(((2-(6-((R)-3-Aminopiperidine-1-carbonyl)-4-fluoro-3-methylpyrazolo[1,5-a]pyridin-2-yl)-1-(cyclopropylmethyl)-1H-indol-7-yl)oxy)methyl)pyrrolidin-2-one (isomer 1)

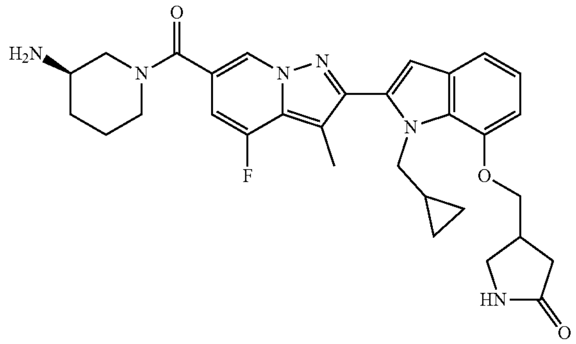 [SMILES: Cc1c(-c2cc3cccc(OCC4CNC(=O)C4)c3n2CC2CC2)nn2cc(C(=O)N3CCC[C@@H](N)C3)cc(F)c12]

Intermediate 566A methyl 2-(7-(benzyl oxy)-1-(cyclopropylmethyl)-1H-indol-2-yl)-4-fluoro-3-methylpyrazolo[1,5-a]pyridine-6-carboxylate

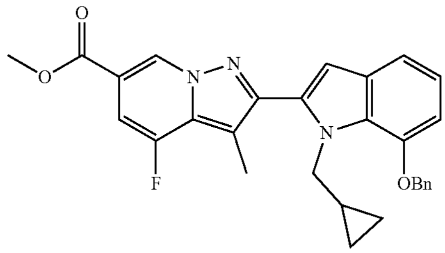 [SMILES: COC(=O)c1cc(F)c2c(C)c(-c3cc4cccc(OCc5ccccc5)c4n3CC3CC3)nn2c1]

Intermediate 566A (0.7 g, 26%) was prepared following a procedure similar to the preparation of Intermediate 530A as a gummy liquid. LC-MS m/z: 484.3 $[M+H]^+$ Intermediate 566B Methyl 2-(1-(cyclopropylmethyl)-7-hydroxy-1H-indol-2-yl)-4-fluoro-3-methylpyrazolo[1,5-a]pyridine-6-carboxylate

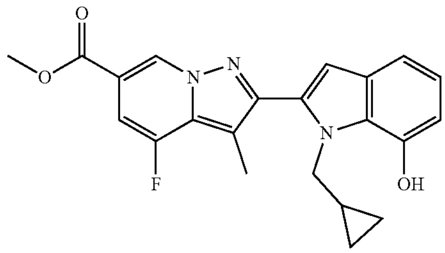 [SMILES: COC(=O)c1cc(F)c2c(C)c(-c3cc4cccc(O)c4n3CC3CC3)nn2c1]

Intermediate 566B (0.31 g, 85%) was prepared following a procedure similar to the preparation of Intermediate 530B. LC-MS m/z: 394.3 $[M+H]^+$; $^1H$ NMR (400 MHz, DMSO-$d_6$) δ ppm:9.13 (d, J=1.0 Hz, 1H), 7.38 (d, J=11.5 Hz, 1H), 7.07 (d, J=8.0 Hz, 1H), 6.87 (t, J=7.8 Hz, 1H), 6.75 (s, 1H), 6.62 (d, J=7.5 Hz, 1H), 4.61 (d, J=6.5 Hz, 2H), 3.91 (s, 3H), 2.49-2.47 (m, 3H), 1.05-1.02(m, 1H), 0.28-0.14 (m, 2H), 0.10-0.03 (m, 2H).

Intermediate 566C

Methyl 2-(1-(cyclopropylmethyl)-7-((5-oxopyrrolidin-3-yl)methoxy)-1H-indol-2-yl)-4-fluoro-3-methylpyrazolo[1,5-a]pyridine-6-carboxylate

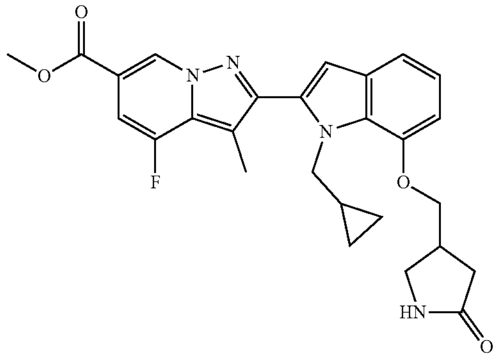 [SMILES: COC(=O)c1cc(F)c2c(C)c(-c3cc4cccc(OCC5CNC(=O)C5)c4n3CC3CC3)nn2c1]

Cesium carbonate (0.124 g, 0.381 mmol) and (5-oxopyrrolidin-3-yl)methyl 4-methylbenzenesulfonate (0.068 g, 0.254 mmol) were added to a stirred solution of Intermediate 566B (0.1 g, 0.254 mmol) in DMF (3 ml). The reaction mixture was stirred at 60° C. for 2 hours, diluted with water, and the solids obtained were filtered and dried under reduced pressure to afford crude methyl 2-(1-(cyclopropylmethyl)-7-((5-oxopyrrolidin-3-yl)methoxy)-1H-indol-2-yl)-4-fluoro-3-methylpyrazolo[1,5-a]pyridine-6-carboxylate (0.12 g, 96%) as a brown solid. LC-MS m/z: 491.3 $[M+H]^+$.

Intermediate 566D 2-(1-(Cyclopropylmethyl)-7-((5-oxopyrrolidin-3-yl)methoxy)-1H-indol-2-yl)-4-fluoro-3-methylpyrazolo[1,5-a]pyridine-6-carboxylic acid

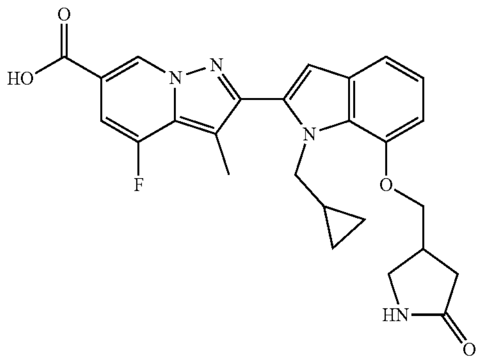 [SMILES: Cc1c(-c2cc3cccc(OCC4CNC(=O)C4)c3n2CC2CC2)nn2cc(C(=O)O)cc(F)c12]

LiOH (0.029 g, 1.223 mmol) was added to a stirred solution of Intermediate 566C (0.12 g, 0.245 mmol) in ethanol (1 ml), THF (1 ml), and water (1 ml). The reaction mixture was stirred for 2 hours, concentrated, and the residue obtained was neutralized using 1.5 N HCl solution. The solids thus obtained were filtered and dried under high vacuum to afford 2-(1-(cyclopropylmethyl)-7-((5-oxopyrrolidin-3-yl)methoxy)-1H-indol-2-yl)-4-fluoro-3-methylpyrazolo[1,5-a]pyridine-6-carboxylic acid (0.11 g, 94%) as a white solid. LC-MS m/z: 477.3 $[M+H]^+$ Intermediate 566E tert-Butyl ((3R)-1-(2-(1-(cyclopropylmethyl)-7-((5-oxopyrrolidin-3-yl)methoxy)-1H-indol-2-yl)-4-fluoro-3-methylpyrazolo[1,5-a]pyridine-6-carbonyl)piperidin-3-yl)carbamate

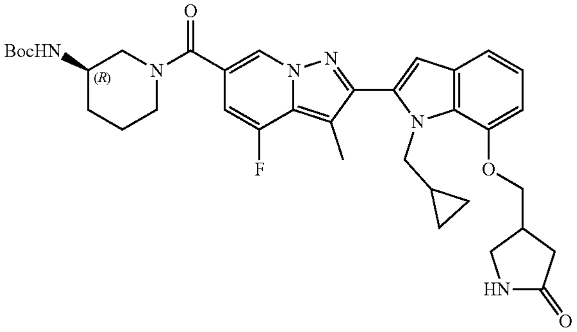

Intermediate 566E (0.07 g, 84%) was prepared following a procedure similar to the preparation of Intermediate 530E. LC-MS m/z: 659.5 $[M+H]^+$ Example 566

4-(((2-(6-((R)-3-aminopiperidine-1-carbonyl)-4-fluoro-3-methylpyrazolo[1,5-a]pyridin-2-yl)-1-(cyclopropylmethyl)-1H-indol-7-yl)oxy)methyl)pyrrolidin-2-one. (isomer 1) LC-MS m/z: 559.2 $[M+H]^+$. LCMS retention time: 1.52 min (method E); $^1$H NMR (400 MHz, DMSO-$d_6$) δ ppm: 8.78 (s, 1H), 8.13 (br.s, 1H), 7.62 (s,1H), 7.26-7.12 (m, 3H), 7.00 (t, J=8.0 Hz, 1H), 6.79 (d, J=8.0 Hz, 1H), 6.75 (s, 1H), 4.52 (d, J=6.8 Hz, 2H), 4.17 (d, J=6.3 Hz, 2H), 4.10-4.00 (m, 1H), 3.54-3.49 (m, 1H), 3.25-3.10 (m, 3H), 3.03-2.94 (m, 1H), 2.53-2.50 (m, 1H), 2.46 (s, 3H), 2.44-2.38 (m, 2H), 2.19 (dd, J=7.3, 16.8 Hz, 1H), 2.06-1.97 (m, 2H), 1.84-1.72 (m, 1H), 1.69-1.51 (m, 1H),1.07-0.95 (m, 1H), 0.27-0.13 (m, 2H), 0.00--0.07 (m, 2H).

Compounds of Examples 567 to 572 in Table 54 were prepared following a procedure similar to the preparation of a compound of Example 566, by displacement reaction of Intermediate 566B with appropriate tosylate followed by ester hydrolysis and coupling with appropriate amines.

TABLE 54

| Example | Structure<br>Name<br>Analytical Data: LC-MS m/z $[M + H]^+$; HPLC retention time (HPLC method) |
|---|---|
| 567 | 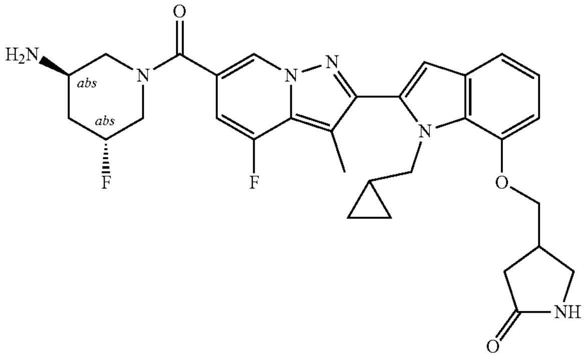 [SMILES: Cc1c(-c2cc3cccc(OCC4CNC(=O)C4)c3n2CC2CC2)nn2cc(C(=O)N3C[C@H](N)C[C@@H](F)C3)cc(F)c12]<br>4-(((2-(6-((3R,5R)-3-Amino-5-fluoropiperidine-1-carbonyl)-4-fluoro-3-methylpyrazolo[1,5-a]pyridin-2-yl)-1-(cyclopropylmethyl)-1H-indol-7-yl)oxy)methyl)pyrrolidin-2-one (isomer 1)<br>Analytical Data: 577.3; 1.493 min (Method E) |

TABLE 54-continued

| Example | Structure<br>Name<br>Analytical Data: LC-MS m/z [M + H]$^+$; HPLC retention time (HPLC method) |
|---|---|
| 568 | 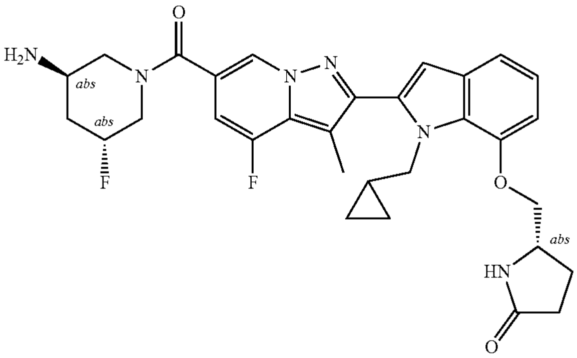 [SMILES: Cc1c(-c2cc3cccc(OC[C@@H]4CCC(=O)N4)c3n2CC2CC2)nn2cc(C(=O)N3C[C@H](N)C[C@@H](F)C3)cc(F)c12]<br>(S)-5-(((2-(6-((3R,5R)-3-Amino-5-fluoropiperidine-1-carbonyl)-4-fluoro-3-methylpyrazolo[1,5-a]pyridin-2-yl)-1-(cyclopropylmethyl)-1H-indol-7-yl)oxy)methyl)pyrrolidin-2-one<br>Analytical Data: 577.2; 1.650 min (Method E) |
| 569 | 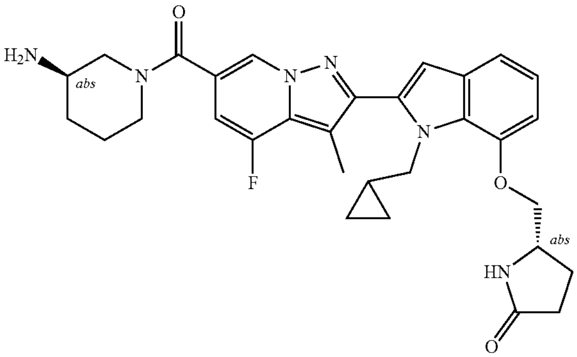 [SMILES: Cc1c(-c2cc3cccc(OC[C@@H]4CCC(=O)N4)c3n2CC2CC2)nn2cc(C(=O)N3CCC[C@@H](N)C3)cc(F)c12]<br>(S)-5-(((2-(6-((R)-3-Aminopiperidine-1-carbonyl)-4-fluoro-3-methylpyrazolo[1,5-a]pyridin-2-yl)-1-(cyclopropylmethyl)-1H-indol-7-yl)oxy)methyl)pyrrolidin-2-one<br>Analytical Data: 559.2; 1.588 min (Method E) |
| 570 | 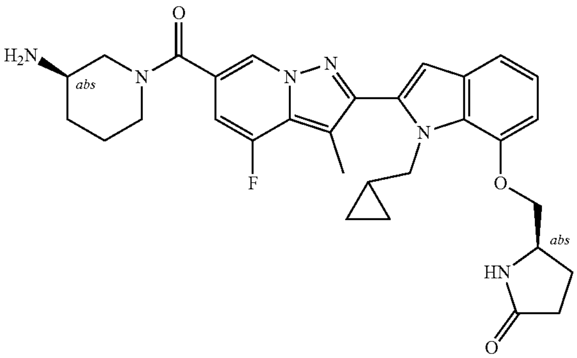 [SMILES: Cc1c(-c2cc3cccc(OC[C@H]4CCC(=O)N4)c3n2CC2CC2)nn2cc(C(=O)N3CCC[C@@H](N)C3)cc(F)c12]<br>(R)-5-(((2-(6-((R)-3-Aminopiperidine-1-carbonyl)-4-fluoro-3-methylpyrazolo[1,5-a]pyridin-2-yl)-1-(cyclopropylmethyl)-1H-indol-7-yl)oxy)methyl)pyrrolidin-2-one<br>Analytical Data: 559.2, 1.588 min (Method E) |

TABLE 54-continued

| Example | Structure<br>Name<br>Analytical Data: LC-MS m/z $[M + H]^+$; HPLC retention time (HPLC method) |
|---|---|
| 571 | 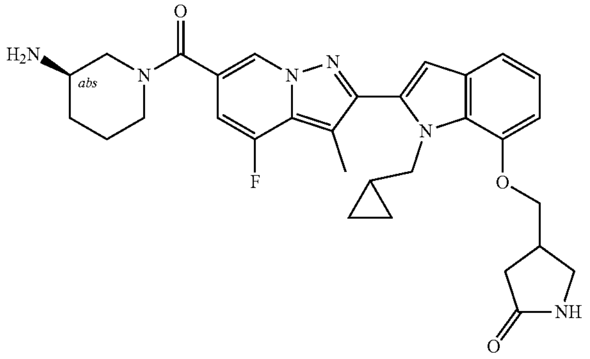 [SMILES: Cc1c(-c2cc3cccc(OCC4CNC(=O)C4)c3n2CC2CC2)nn2cc(C(=O)N3CCC[C@@H](N)C3)cc(F)c12]<br>4-(((2-(6-((R)-3-Aminopiperidine-1-carbonyl)-4-fluoro-3-methylpyrazolo[1,5-a]pyridin-2-yl)-1-(cyclopropylmethyl)-1H-indol-7-yl)oxy)methyl)pyrrolidin-2-one (isomer 2)<br>Analytical Data: 559.2, 1.52 min (Method E) |
| 572 | 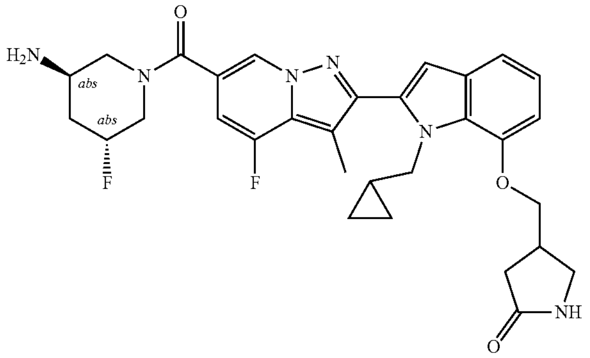 [SMILES: Cc1c(-c2cc3cccc(OCC4CNC(=O)C4)c3n2CC2CC2)nn2cc(C(=O)N3C[C@H](N)C[C@@H](F)C3)cc(F)c12]<br>4-(((2-(6-((3R,5R)-3-Amino-5-fluoropiperidine-1-carbonyl)-4-fluoro-3-methylpyrazolo[1,5-a]pyridin-2-yl)-1-(cyclopropylmethyl)-1H-indol-7-yl)oxy)methyl)pyrrolidin-2-one (isomer 2)<br>Analytical Data: 577.2, 1.58 min (Method E) |

Example 573

4-(((2-(6-((3R,5R)-3-Amino-5-fluoropiperidine-1-carbonyl)-3-methylpyrazolo[1,5-a]pyridin-2-yl)-1-(cyclopropylmethyl)-1H-indol-7-yl)oxy)methyl)pyrrolidin-2-one (isomer 1)

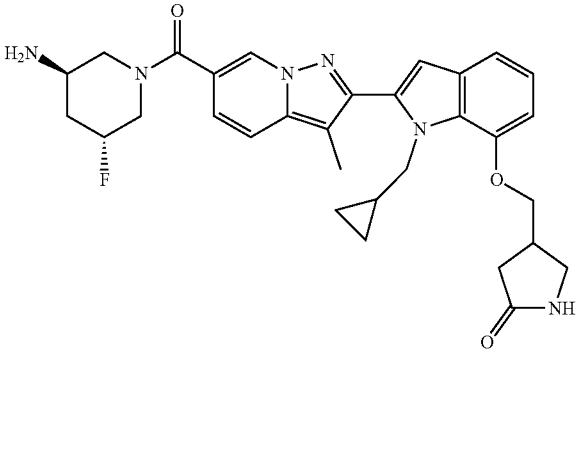 [SMILES: Cc1c(-c2cc3cccc(OCC4CNC(=O)C4)c3n2CC2CC2)nn2cc(C(=O)N3C[C@H](N)C[C@@H](F)C3)ccc12]

Intermediate 573A

Ethyl 2-(7-(benzyloxy)-1-(cyclopropylmethyl)-1H-indol-2-yl)-3-methylpyrazolo[1,5-a]pyridine-6-carboxylate

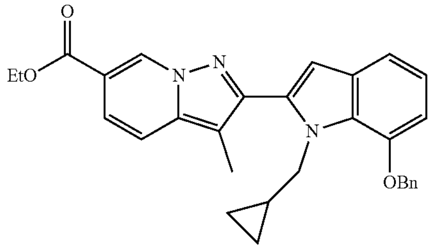 [SMILES: CCOC(=O)c1ccc2c(C)c(-c3cc4cccc(OCc5ccccc5)c4n3CC3CC3)nn2c1]

Intermediate 573A (850 mg, 32%) was prepared following a procedure similar to the preparation of Intermediate 550A. LC-MS m/z: 480.2 $[M+H]^+$ Intermediate 573B Ethyl 2-(1-(cyclopropylmethyl)-7-hydroxy-1H-indol-2-yl)-3-methylpyrazolo[1,5-a]pyridine-6-carboxylate

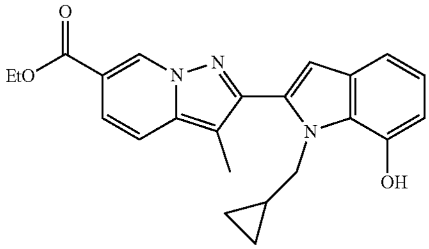 [SMILES: CCOC(=O)c1ccc2c(C)c(-c3cc4cccc(O)c4n3CC3CC3)nn2c1]

Intermediate 573B (450 mg, 65%) was prepared following a procedure similar to the preparation of Intermediate 550B. LC-MS m/z: 390.4 $[M+H]^+$ Intermediate 573C Ethyl 2-(1-(cyclopropylmethyl)-7-((5-oxopyrrolidin-3-yl)methoxy)-1H-indol-2-yl)-3-methylpyrazolo[1,5-a]pyridine-6-carboxylate

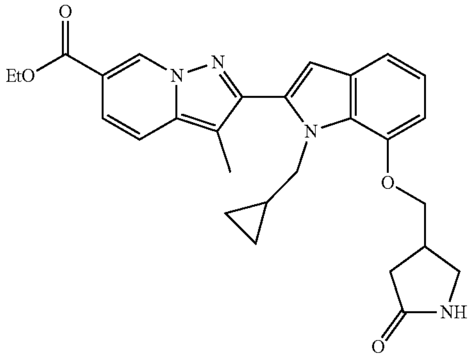

Cesium carbonate (251 mg, 0.770 mmol) and tetrabutylammonium iodide (28.5 mg, 0.077 mmol) and (5-oxopyrrolidin-3-yl)methyl 4-methylbenzenesulfonate (69.2 mg, 0.257 mmol) were added to a stirred solution of 573B (100 mg, 0.257 mmol) in DMF (1 ml). The reaction mixture was heated for at 60° C. 16 hours, quenched with water (100 ml), and extracted with ethyl acetate (2×100 ml). The combined the organic layers were dried over sodium sulphate, filtered, and concentrated under reduced pressure to afford crude ethyl 2-(1-(cyclopropylmethyl)-7-((5-oxopyrrolidin-3-yl)methoxy)-1H-indol-2-yl)-3-methylpyrazolo[1,5-a]pyridine-6-carboxylate (110 mg, 88%). LC-MS m/z: 487.3 $[M+H]^+$ Intermediate 573D 2-(1-(Cyclopropylmethyl)-7-((5-oxopyrrolidin-3-yl)methoxy)-1H-indol-2-yl)-3-methylpyrazolo[1,5-a]pyridine-6-carboxylic acid

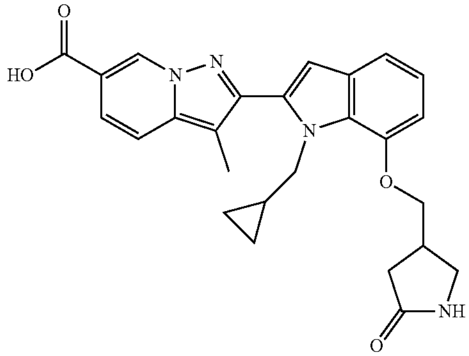 [SMILES: Cc1c(-c2cc3cccc(OCC4CNC(=O)C4)c3n2CC2CC2)nn2cc(C(=O)O)ccc12]

LiOH (5.91 mg, 0.247 mmol) was added to a stirred solution of Intermediate 573D (120 mg, 0.247 mmol) in THF (1 ml), methanol (1 ml), and water (1 ml). The reaction mixture was stirred for 16 hours, concentrated under reduced pressure to afford the crude salts, which were acidified with 1 N HCl. The solids obtained were filtered through a Buchner funnel and dried in vacuo to afford 2-(1-(cyclopropylmethyl)-7-((5-oxopyrrolidin-3-yl)methoxy)-1H-indol-2-yl)-3-methylpyrazolo[1,5-a]pyridine-6-carboxylic acid (100 mg, 88%). LC-MS m/z: 459.2 $[M+H]^+$ Intermediate 573E tert-Butyl ((3R,5R)-1-(2-(1-(cyclopropylmethyl)-7-((5-oxopyrrolidin-3-yl)methoxy)-1H-indol-2-yl)-3-methylpyrazolo[1,5-a]pyridine-6-carbonyl)-5-fluoropiperidin-3-yl)carbamate

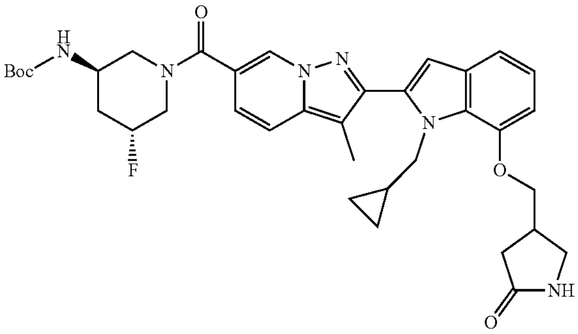 [SMILES: Cc1c(-c2cc3cccc(OCC4CNC(=O)C4)c3n2CC2CC2)nn2cc(C(=O)N3C[C@H](F)C[C@@H](NC(=O)OC(C)(C)C)C3)ccc12]

tert-Butyl ((3R,5R)-5-fluoropiperidin-3-yl)carbamate (23.80 mg, 0.109 mmol), DIPEA (0.057 ml, 0.327 mmol) and HATU (62.2 mg, 0.164 mmol) were added to a stirred solution of Intermediate 573D (50 mg, 0.109 mmol) in DMF (1 ml). The reaction mixture was stirred for 3 hours, diluted with water (50 ml), and extracted with ethyl acetate (2×50 ml). The combined organic layers were dried over sodium sulphate, filtered, and concentrated under reduced pressure to afford crude tert-butyl ((3R,5R)-1-(2-(1-(cyclopropylmethyl)-7-((5-oxopyrrolidin-3-yl)methoxy)-1H-indol-2-yl)-3-methylpyrazolo[1,5-a]pyridine-6-carbonyl)-5-fluoropiperidin-3-yl)carbamate (60 mg, 84%). LC-MS m/z: 659.3 [M+H]$^+$.

Example 573

4-(((2-(6-((3R,5R)-3-Amino-5-fluoropiperidine-1-carbonyl)-3-methylpyrazolo[1,5-a]pyridin-2-yl)-1-(cyclopropylmethyl)-1H-indol-7-yl)oxy)methyl) pyrrolidin-2-one (isomer 1)

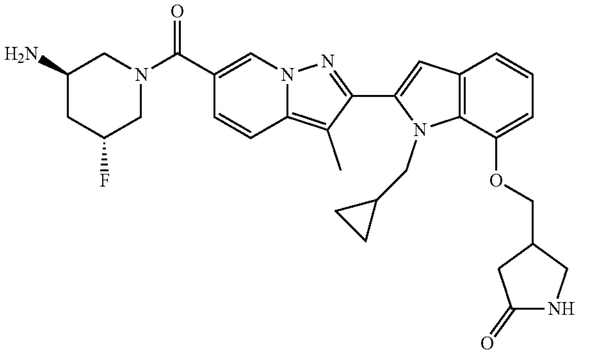 [SMILES: Cc1c(-c2cc3cccc(OCC4CNC(=O)C4)c3n2CC2CC2)nn2cc(C(=O)N3C[C@H](N)C[C@@H](F)C3)ccc12]

4-(((2-(6-((3R,5R)-3-amino-5-fluoropiperidine-1-carbonyl)-3-methylpyrazolo[1,5-a]pyridin-2-yl)-1-(cyclopropylmethyl)-1H-indol-7-yl)oxy)methyl)pyrrolidin-2-one (isomer 1) (21.7 mg, 42%). LC-MS m/z: 559.2 [M+H]$^+$. LCMS retention time: 1.384 min (method E). $^1$H NMR (400 MHz, DMSO-$d_6$) δ ppm: 8.75 (s, 1H), 7.79 (d, J=9.0 Hz, 1H), 7.62 (s, 1H), 7.23-7.17 (m, 2H), 6.99 (t, J=8.0 Hz, 1H), 6.77 (d, J=8.0 Hz, 1H), 6.73 (s, 1H), 5.03-4.98 (m, 1H), 4.60 (d, J=8.0 Hz, 2H), 4.16 (d, J=4.0 Hz, 2H), 3.50 (br, d, J=6.4 Hz, 1H), 3.23-2.94 (m, 5H), 2.44-2.39 (m, 1H), 2.37(s, 3H), 2.23-2.11 (m, 2H), 1.60-1.42 (m, 1H), 1.07-0.97 (m, 1H), 0.22-0.14 (m, 2H), 0.00--0.06 (m, 2H).

Compounds of Examples 574 to 590 in Table 55 were obtained following a procedure similar to the preparation of a compound of Example 573, by displacement reaction of Intermediate 573B with appropriate tosylate followed by ester hydrolysis and coupling with appropriate amines.

TABLE 55

| Example | Structure<br>Name<br>Analytical Data: LC-MS m/z [M + H]$^+$; HPLC retention time (HPLC method) |
|---|---|
| 574 | 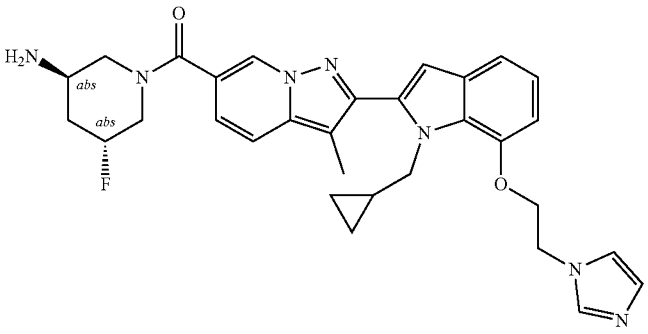 [SMILES: Cc1c(-c2cc3cccc(OCCn4ccnc4)c3n2CC2CC2)nn2cc(C(=O)N3C[C@H](N)C[C@@H](F)C3)ccc12]<br>(2-(7-(2-(1H-Imidazol-1-yl)ethoxy)-1-(cyclopropylmethyl)-1H-indol-2-yl)-3-methylpyrazolo[1,5-a]pyridin-6-yl)((3R,5R)-3-amino-5-fluoropiperidin-1-yl)methanone<br>Analytical Data: 556.3, 1.272 min (Method E) |
| 575 | 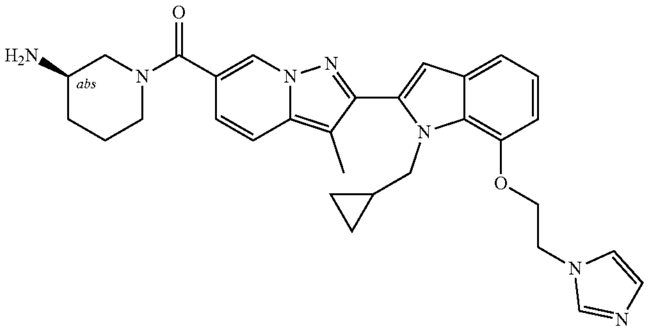 [SMILES: Cc1c(-c2cc3cccc(OCCn4ccnc4)c3n2CC2CC2)nn2cc(C(=O)N3CCC[C@@H](N)C3)ccc12]<br>(R)-(2-(7-(2-(1H-lmidazol-1-yl)ethoxy)-1-(cyclopropylmethyl)-1H-indol-2-yl)-3-methylpyrazolo[1,5-a]pyridin-6-yl)(3-aminopiperidin-1-yl)methanone<br>Analytical Data: 538.3, 1.278 min (Method E) |

TABLE 55-continued

| Example | Structure<br>Name<br>Analytical Data: LC-MS m/z $[M + H]^+$; HPLC retention time (HPLC method) |
|---|---|
| 576 | 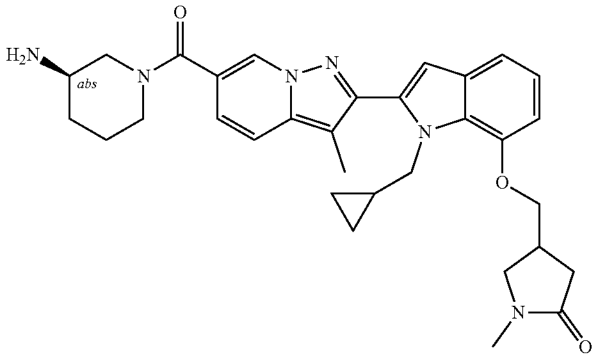 [SMILES: Cc1c(-c2cc3cccc(OCC4CC(=O)N(C)C4)c3n2CC2CC2)nn2cc(C(=O)N3CCC[C@@H](N)C3)ccc12]<br>4-(((2-(6-((R)-3-Aminopiperidine-1-carbonyl)-3-methylpyrazolo[1,5-a]pyridin-2-yl)-1-(cyclopropylmethyl)-1H-indol-7-yl)oxy)methyl)-1-methylpyrrolidin-2-one (isomer 1)<br>Analytical Data: 555.3, 1.531 min (Method E) |
| 577 | 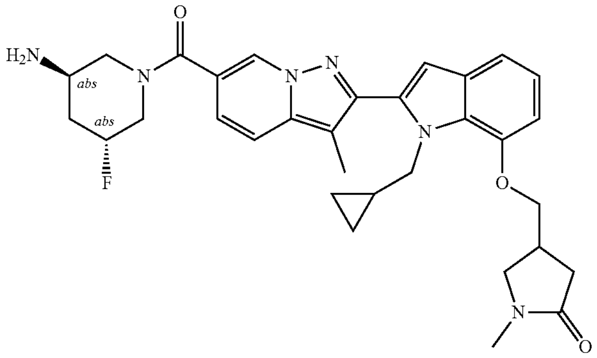 [SMILES: Cc1c(-c2cc3cccc(OCC4CC(=O)N(C)C4)c3n2CC2CC2)nn2cc(C(=O)N3C[C@H](N)C[C@@H](F)C3)ccc12]<br>4-(((2-(6-((3R,5R)-3-Amino-5-fluoropiperidine-1-carbonyl)-3-methylpyrazolo[1,5-a]pyridin-2-yl)-1-(cyclopropylmethyl)-1H-indol-7-yl)oxy)methyl)-1-methylpyrrolidin-2-one (isomer 1)<br>Analytical Data: 573.2, 1.544 min (Method E) |
| 578 | 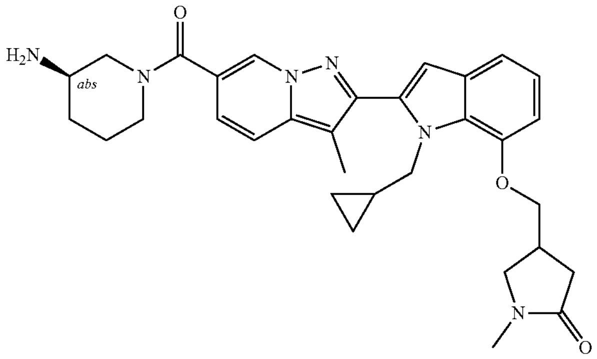 [SMILES: Cc1c(-c2cc3cccc(OCC4CC(=O)N(C)C4)c3n2CC2CC2)nn2cc(C(=O)N3CCC[C@@H](N)C3)ccc12]<br>4-(((2-(6-((R)-3-Aminopiperidine-1-carbonyl)-3-methylpyrazolo[1,5-a]pyridin-2-yl)-1-(cyclopropylmethyl)-1H-indol-7-yl)oxy)methyl)-1-methylpyrrolidin-2-one (isomer 2)<br>Analytical Data: 555.3, 1.524 min (Method E) |

TABLE 55-continued

| Example | Structure<br>Name<br>Analytical Data: LC-MS m/z [M + H]+; HPLC retention time (HPLC method) |
|---|---|
| 579 | 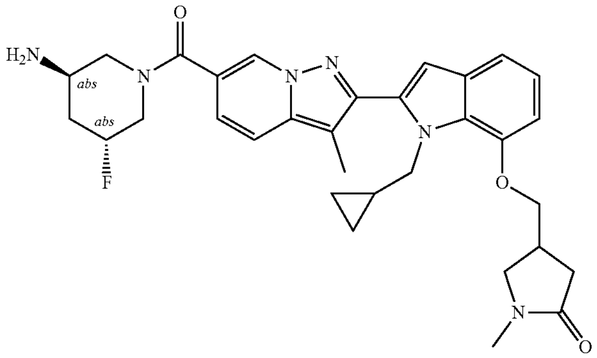 [SMILES: Cc1c(-c2cc3cccc(OCC4CC(=O)N(C)C4)c3n2CC2CC2)nn2cc(C(=O)N3C[C@H](N)C[C@@H](F)C3)ccc12]<br>4-(((2-(6-((3R,5R)-3-Amino-5-fluoropiperidine-1-carbonyl)-3-methylpyrazolo[1,5-a]pyridin-2-yl)-1-(cyclopropylmethyl)-1H-indol-7-yl)oxy)methyl)-1-methylpyrrolidin-2-one (isomer 2)<br>Analytical Data: 573.2, 1.546 min (Method E) |
| 580 | 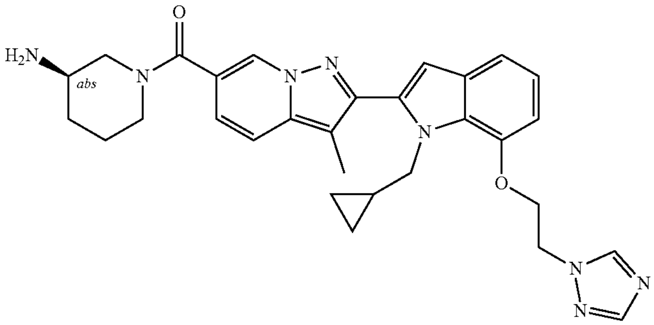 [SMILES: Cc1c(-c2cc3cccc(OCCn4cncn4)c3n2CC2CC2)nn2cc(C(=O)N3CCC[C@@H](N)C3)ccc12]<br>(R)-(2-(7-(2-(1H-1,2,4-Triazol-1-yl)ethoxy)-1-(cyclopropylmethyl)-1H-indol-2-yl)-3-methylpyrazolo[1,5-a]pyridin-6-yl)(3-aminopiperidin-1-yl)methanone<br>Analytical Data: 539.3, 1.384 min (Method E) |
| 581 | 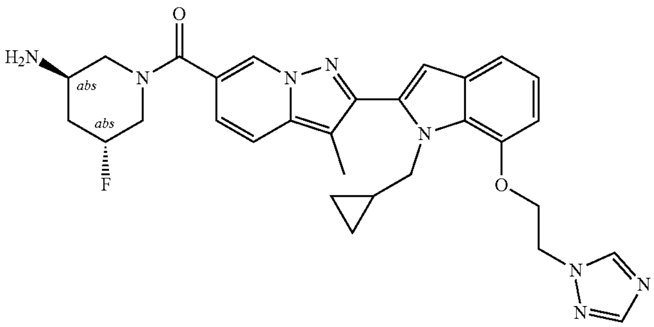 [SMILES: Cc1c(-c2cc3cccc(OCCn4cncn4)c3n2CC2CC2)nn2cc(C(=O)N3C[C@H](N)C[C@@H](F)C3)ccc12]<br>(2-(7-(2-(1H-1,2,4-Triazol-1-yl)ethoxy)-1-(cyclopropylmethyl)-1H-indol-2-yl)-3-methylpyrazolo[1,5-a]pyridin-6-yl)((3R, 5R)-3-amino-5-fluoropiperidin-1-yl)methanone<br>Analytical Data: 557.2, 1.516 min (Method E) |

TABLE 55-continued

| Example | Structure<br>Name<br>Analytical Data: LC-MS m/z $[M + H]^+$; HPLC retention time (HPLC method) |
|---|---|
| 582 | 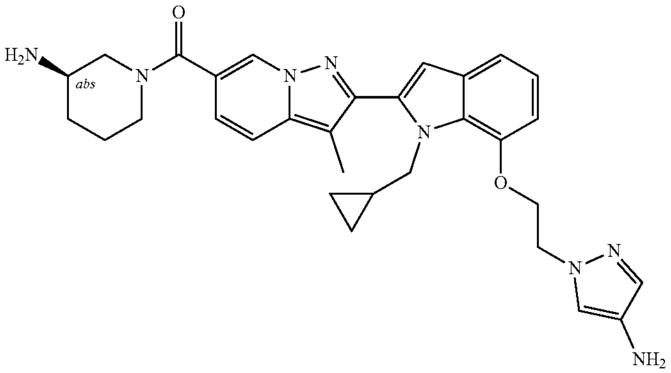 [SMILES: Cc1c(-c2cc3cccc(OCCn4cc(N)cn4)c3n2CC2CC2)nn2cc(C(=O)N3CCC[C@@H](N)C3)ccc12]<br>(R)-(2-(7-(2-(4-Amino-1H-pyrazol-1-yl)ethoxy)-1-(cyclopropylmethyl)-1H-indol-2-yl)-3-methylpyrazolo[1,5-a]pyridin-6-yl)(3-aminopiperidin-1-yl)methanone<br>Analytical Data: 553.3, 1.410 min (Method E) |
| 583 | 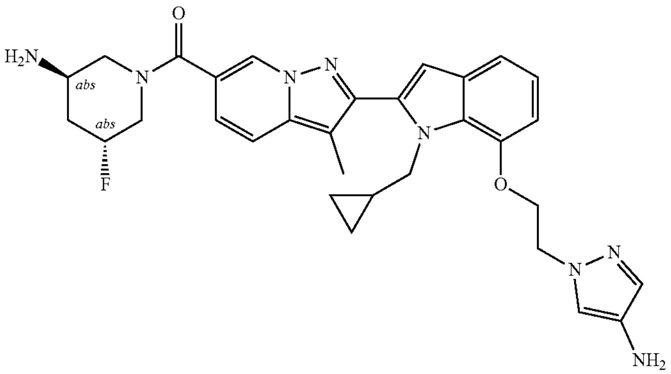 [SMILES: Cc1c(-c2cc3cccc(OCCn4cc(N)cn4)c3n2CC2CC2)nn2cc(C(=O)N3C[C@H](N)C[C@@H](F)C3)ccc12]<br>(2-(7-(2-(4-Amino-1H-pyrazol-1-yl)ethoxy)-1-(cyclopropylmethyl)-1H-indol-2-yl)-3-methylpyrazolo[1,5-a]pyridin-6-yl)((3R,5R)-3-amino-5-fluoropiperidin-1-yl)methanone<br>Analytical Data: 571.3, 1.473 min (Method E) |
| 584 | 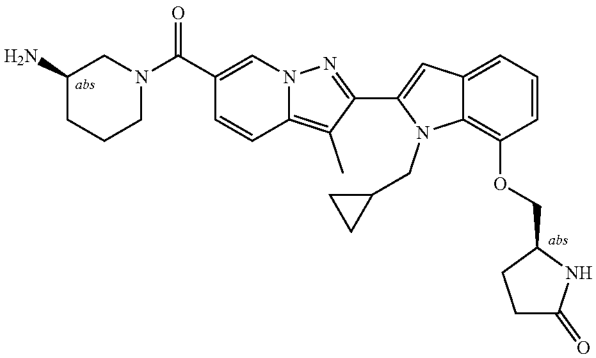 [SMILES: Cc1c(-c2cc3cccc(OC[C@@H]4CCC(=O)N4)c3n2CC2CC2)nn2cc(C(=O)N3CCC[C@@H](N)C3)ccc12]<br>(S)-5-(((2-(6-((R)-3-Aminopiperidine-1-carbonyl)-3-methylpyrazolo[1,5-a]pyridin-2-yl)-1-(cyclopropylmethyl)-1H-indol-7-yl)oxy)methyl)pyrrolidin-2-one<br>Analytical Data: 541.3, 1.402 min (Method E) |

TABLE 55-continued

| Example | Structure<br>Name<br>Analytical Data: LC-MS m/z [M + H]$^+$; HPLC retention time (HPLC method) |
|---|---|
| 585 | 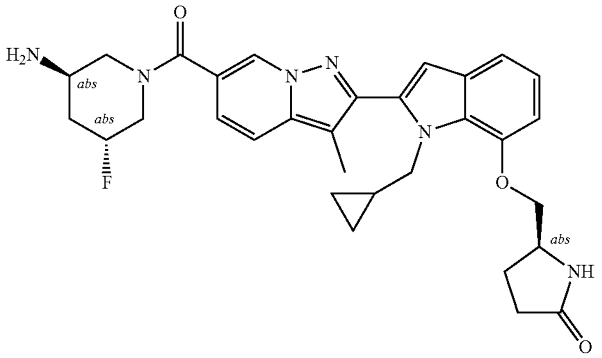 [SMILES: Cc1c(-c2cc3cccc(OC[C@@H]4CCC(=O)N4)c3n2CC2CC2)nn2cc(C(=O)N3C[C@H](N)C[C@@H](F)C3)ccc12]<br>(S)-5-(((2-(6-((3R,5R)-3-Amino-5-fluoropiperidine-1-carbonyl)-3-methylpyrazolo[1,5-a]pyridin-2-yl)-1-(cyclopropylmethyl)-1H-indol-7-yl)oxy)methyl)pyrrolidin-2-one<br>Analytical Data: 559.3, 1.386 min (Method E) |
| 586 | 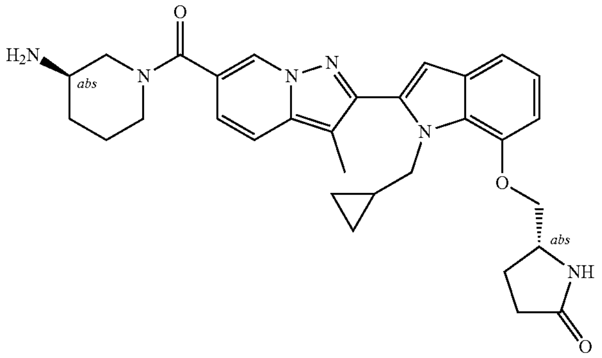 [SMILES: Cc1c(-c2cc3cccc(OC[C@H]4CCC(=O)N4)c3n2CC2CC2)nn2cc(C(=O)N3CCC[C@@H](N)C3)ccc12]<br>(R)-5-(((2-(6-((R)-3-Aminopiperidine-1-carbonyl)-3-methylpyrazolo[1,5-a]pyridin-2-yl)-1-(cyclopropylmethyl)-1H-indol-7-yl)oxy)methyl)pyrrolidin-2-one<br>Analytical Data: 541.3, 1.373 min (Method E) |
| 587 | 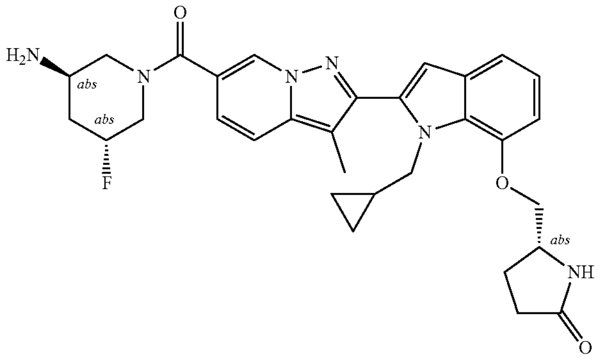 [SMILES: Cc1c(-c2cc3cccc(OC[C@H]4CCC(=O)N4)c3n2CC2CC2)nn2cc(C(=O)N3C[C@H](N)C[C@@H](F)C3)ccc12]<br>(R)-5-(((2-(6-((3R,5R)-3-Amino-5-fluoropiperidine-1-carbonyl)-3-methylpyrazolo[1,5-a]pyridin-2-yl)-1-(cyclopropylmethyl)-1H-indol-7-yl)oxy)methyl)pyrrolidin-2-one<br>Analytical Data: 559.2 , 1.388 min (Method E) |

TABLE 55-continued

| Example | Structure<br>Name<br>Analytical Data: LC-MS m/z $[M + H]^+$; HPLC retention time (HPLC method) |
|---|---|
| 588 | 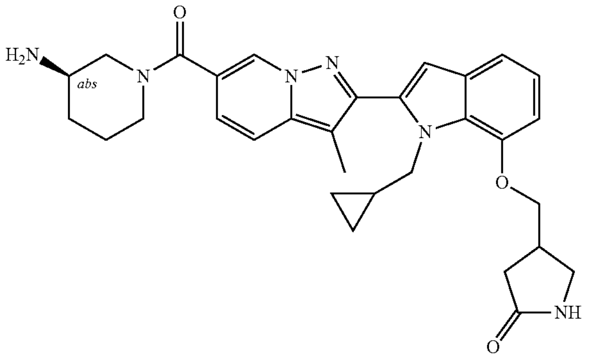 [SMILES: Cc1c(-c2cc3cccc(OCC4CNC(=O)C4)c3n2CC2CC2)nn2cc(C(=O)N3CCC[C@@H](N)C3)ccc12]<br>4-(((2-(6-((R)-3-Aminopiperidine-1-carbonyl)-3-methylpyrazolo[1,5-a]pyridin-2-yl)-1-(cyclopropylmethyl)-1H-indol-7-yl)oxy)methyl)pyrrolidin-2-one (isomer 1)<br>Analytical Data: 541.2 , 1.375 min (Method E) |
| 589 | 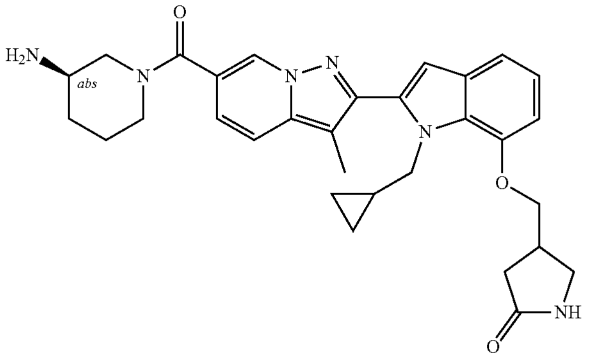 [SMILES: Cc1c(-c2cc3cccc(OCC4CNC(=O)C4)c3n2CC2CC2)nn2cc(C(=O)N3CCC[C@@H](N)C3)ccc12]<br>4-(((2-(6-((R)-3-Aminopiperidine-1-carbonyl)-3-methylpyrazolo[1,5-a]pyridin-2-yl)-1-(cyclopropylmethyl)-1H-indol-7-yl)oxy)methyl)pyrrolidin-2-one (isomer 2)<br>Analytical Data: 541.3, 1.372 min (Method E) |
| 590 | 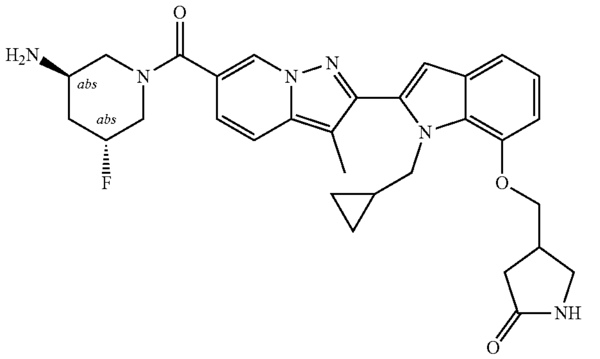 [SMILES: Cc1c(-c2cc3cccc(OCC4CNC(=O)C4)c3n2CC2CC2)nn2cc(C(=O)N3C[C@H](N)C[C@@H](F)C3)ccc12]<br>4-(((2-(6-((3R,5R)-3-Amino-5-fluoropiperidine-1-carbonyl)-3-methylpyrazolo[1,5-a]pyridin-2-yl)-1-(cyclopropylmethyl)-1H-indol-7-yl)oxy)methyl)pyrrolidin-2-one (isomer 2)<br>Analytical Data: 559.2, 1.382 min. Method E) |

Example 591

4-(((2-(6-((R)-3-Aminopiperidine-1-carbonyl)-4-methoxy-3-methylpyrazolo[1,5-a]pyridin-2-yl)-1-(cyclopropylmethyl)-1H-pyrrolo[2,3-c]pyridin-7-yl)oxy)methyl)pyrrolidin-2-one (isomer 1)

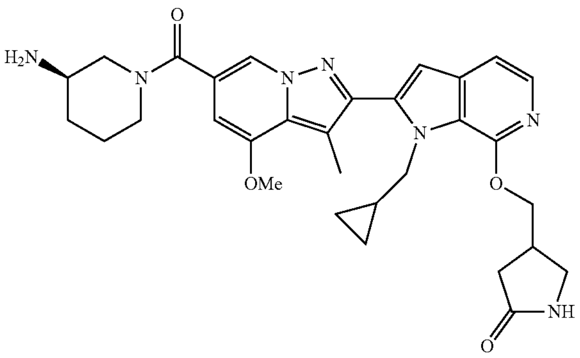 [SMILES: COc1cc(C(=O)N2CCC[C@@H](N)C2)cn2nc(-c3cc4ccnc(OCC5CNC(=O)C5)c4n3CC3CC3)c(C)c12]

Intermediate 591A

Methyl 2-(7-chloro-1-(cyclopropylmethyl)-1H-pyrrolo[2,3-c]pyridin-2-yl)-4-methoxy-3-methylpyrazolo[1,5-a]pyridine-6-carboxylate

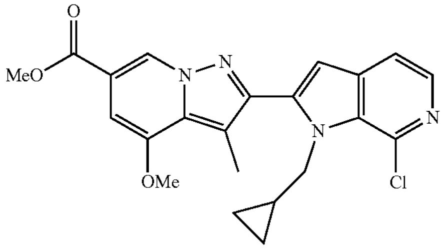 [SMILES: COC(=O)c1cc(OC)c2c(C)c(-c3cc4ccnc(Cl)c4n3CC3CC3)nn2c1]

1-Amino-3-methoxy-5-(methoxycarbonyl)pyridin-1-ium (2.261 g, 12.34 mmol) was added to a stirred solution of (E)-7-chloro-1-(cyclopropylmethyl)-2-(2-nitroprop-1-en-1-yl)-1H-pyrrolo[2,3-c]pyridine (1.2 g, 4.11 mmol) in DMF (10 ml). The reaction mixture was stirred at 80° C. for 30 hours, diluted with water (20 ml), and extracted with ethyl acetate (3×30 ml). The combined organic layers were washed with brine, dried over sodium sulfate, filtered, and concentrated in vacuum. The crude product thus obtained was purified using a silica gel column, eluting with 0-20% ethyl acetate in n-hexane to afford (820 mg, 47%) of methyl 2-(7-chloro-1-(cyclopropylmethyl)-1H-pyrrolo[2,3-c]pyridin-2-yl)-4-methoxy-3-methylpyrazolo[1,5-a]pyridine-6-carboxylate as brown solid. LC-MS m/z: 425.2 $[M+H]^+$.

Intermediate 591B 2-(7-chloro-1-(cyclopropylmethyl)-1H-pyrrolo[2,3-c]pyridin-2-yl)-4-methoxy-3-methylpyrazolo[1,5-a]pyridine-6-carboxylic acid

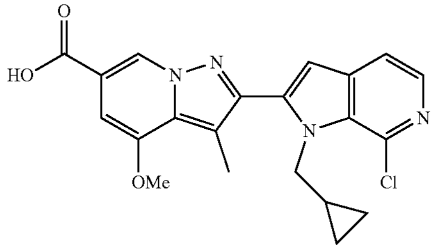 [SMILES: COc1cc(C(=O)O)cn2nc(-c3cc4ccnc(Cl)c4n3CC3CC3)c(C)c12]

Intermediate 591B (0.62 g, 92%) was prepared following a similar procedure depicted for example 550A. LC-MS m/z: 411.1 $[M+H]^+$; $^1$H NMR (400 MHz, DMSO-$d_6$) δ ppm: 8.82 (s, 1H), 8.02 (d, J=5.5 Hz, 1H), 7.68 (d, J=5.5 Hz, 1H), 6.99 (s, 1H), 6.91 (s, 1H), 4.69 (d, J=7.0 Hz, 2H), 4.02 (s, 3H), 2.47 (s, 3H), 1.06-1.03 (m, 1H), 0.29-0.22 (m, 2H), −0.02-−0.05(m, 2H).

Intermediate 591C tert-butyl (R)-(1-(2-(7-chloro-1-(cyclopropylmethyl)-1H-pyrrolo[2,3-c]pyridin-2-yl)-4-methoxy-3-methylpyrazolo[1,5-a]pyridine-6-carbonyl)piperidin-3-yl)carbamate

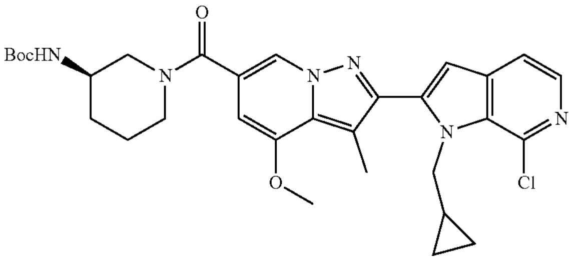 [SMILES: COc1cc(C(=O)N2CCC[C@@H](NC(=O)OC(C)(C)C)C2)cn2nc(-c3cc4ccnc(Cl)c4n3CC3CC3)c(C)c12]

tert-Butyl (R)-piperidin-3-ylcarbamate (175 mg, 0.876 mmol), HATU (416 mg, 1.095 mmol), DIPEA (0.383 ml, 2.191 mmol) was added to a stirred solution of 2-(7-chloro-1-(cyclopropylmethyl)-1H-pyrrolo[2,3-c]pyridin-2-yl)-4-methoxy-3-methylpyrazolo[1,5-a]pyridine-6-carboxylic acid (300 mg, 0.730 mmol) in DMF (5 ml). The reaction mixture was stirred at a room temperature for 6 hours, diluted with water (10 ml), and extracted with ethyl acetate (20 ml). The combined organic layers were washed with brine, dried over sodium sulfate, filtered, and concentrated in vacuum. The crude product thus obtained was purified using comb flash chromatography (12 g, Redisep® $SiO_2$ column, eluting with 0-10% methanol in dichloromethane to afford tert-butyl (R)-(1-(2-(7-chloro-1-(cyclopropylmethyl)-1H-pyrrolo[2,3-c]pyridin-2-yl)-4-methoxy-3-methylpyrazolo[1,5-a]pyridine-6-carbonyl)piperidin-3-yl)carbamate (380 mg,88%) as brown solid. LC-MS m/z: 593.5 $[M+H]^+$ Intermediate 591D tert-Butyl ((3R)-1-(2-(1-(cyclopropylmethyl)-7-((5-oxopyrrolidin-3-yl)methoxy)-1H-pyrrolo[2,3-c]pyridin-2-yl)-4-methoxy-3-methylpyrazolo[1,5-a]pyridine-6-carbonyl)piperidin-3-yl)carbamate

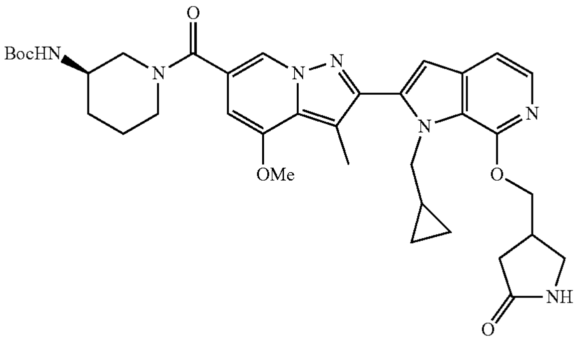 [SMILES: COc1cc(C(=O)N2CCC[C@@H](NC(=O)OC(C)(C)C)C2)cn2nc(-c3cc4ccnc(OCC5CNC(=O)C5)c4n3CC3CC3)c(C)c12]

Racemic 4-(hydroxymethyl)pyrrolidin-2-one (88 mg, 0.674 mmol), $Cs_2CO_3$ (412 mg, 1.264 mmol), S-BINAP (52.5 mg, 0.084 mmol) and $Pd_2(dba)_3$ (38.6 mg, 0.042 mmol) were added to a stirred solution of tert-butyl (R)-(1-(2-(7-chloro-1-(cyclopropylmethyl)-1H-pyrrolo[2,3-c]pyridin-2-yl)-4-methoxy-3-methylpyrazolo[1,5-a]pyridine-6-carbonyl)piperidin-3-yl)carbamate (250 mg, 0.421 mmol) in Toluene (3 ml). The reaction mixture was stirred at 95° C. for 16 hours, diluted with water (10 ml), and extracted with ethyl acetate (2×20 ml). The combined organic layers were washed with brine, dried over sodium sulfate, filtered, and concentrated in vacuum. The crude product thus obtained was purified using a silica gel column, eluting with 0-8% Methanol in dichloromethane) to afford racemic compound, which was separated using a chiral SFC. Isomer 01: tert-butyl ((3R)-1-(2-(1-(cyclopropylmethyl)-7-((5-oxopyrrolidin-3-yl)methoxy)-1H-pyrrolo[2,3-c]pyridin-2-yl)-4-methoxy-3-methylpyrazolo[1,5-a]pyridine-6-carbonyl)piperidin-3-yl)carbamate (30 mg, 10%); isomer 02: tert-butyl ((3R)-1-(2-(1-(cyclopropylmethyl)-7-((5-oxopyrrolidin-3-yl)methoxy)-1H-pyrrolo[2,3-c]pyridin-2-yl)-4-methoxy-3-methylpyrazolo[1,5-a]pyridine-6-carbonyl)piperidin-3-yl)carbamate (30 mg, 10%). LC-MS m/z: 672.4 $[M+H]^+$ (Method H).

Example 591

4-(((2-(6-((R)-3-Aminopiperidine-1-carbonyl)-4-methoxy-3-methylpyrazolo[1,5-a]pyridin-2-yl)-1-(cyclopropylmethyl)-1H-pyrrolo[2,3-c]pyridin-7-yl)oxy)methyl)pyrrolidin-2-one (isomer 1)

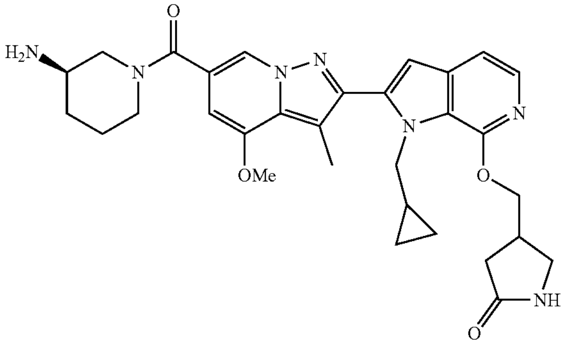 [SMILES: COc1cc(C(=O)N2CCC[C@@H](N)C2)cn2nc(-c3cc4ccnc(OCC5CNC(=O)C5)c4n3CC3CC3)c(C)c12]

TFA (0.034 ml, 0.447 mmol) was added to a stirred solution of tert-butyl ((3R)-1-(2-(1-(cyclopropylmethyl)-7-((5-oxopyrrolidin-3-yl)methoxy)-1H-pyrrolo[2,3-c]pyridin-2-yl)-4-methoxy-3-methylpyrazolo[1,5-a]pyridine-6-carbonyl)piperidin-3-yl)carbamate (30 mg, 0.045 mmol) in dichloromethane (5 ml). The reaction mixture was stirred at a room temperature for 16 hours, concentrated, and the crude product thus obtained was purified using a preparative LC/MS with the following conditions: Column: Waters XBridge C18, 19×150 mm, 5 μm particles, mobile phase A: 10 mM ammonium acetate; mobile phase B: acetonitrile; gradient: 12-48% B over 25 minutes, then a 5-minute hold at 100% B; flow rate: 15 ml/min. Fractions containing the desired product were combined and dried using centrifugal evaporation. The purified material was then diluted with a 1:1 mixture of DCM and methanol, treated with Si-Pyridine, and shaken for a minimum of 2 hours. The resulting mixture was filtered and dried using centrifugal evaporation to afford 4-(((2-(6-((R)-3-aminopiperidine-1-carbonyl)-4-methoxy-3-methylpyrazolo[1,5-a]pyridin-2-yl)-1-(cyclopropylmethyl)-1H-pyrrolo[2,3-c]pyridin-7-yl)oxy)methyl)pyrrolidin-2-one (isomer 1) (18.8 mg, 74%). LC-MS m/z: 572.2 $[M+H]^+$. Retention time: 1.309 min (Method E). $^1H$ NMR (400 MHz, DMSO-$d_6$) δ ppm: 8.40 (s, 1H), 7.69 (d, J=5.4 Hz, 1H), 7.60 (s, 1H), 7.23 (d, J=5.4 Hz, 1H), 6.75 (s, 1H), 6.59 (s, 1H), 4.53-4.45 (m,4H), 3.98 (s, 3H), 3.49-3.47 (m, 1H), 3.22-3.19 (m, 2H), 3.06-2.95 (m, 3H), 2.80-2.73 (m, 1H), 2.46 (s, 3H), 2.41-2.35 (m, 1H), 2.21-2.13 (m, 1H), 1.72-1.70 (m, 1H), 1.50-1.48 (m, 1H), 1.33-1.26 (m, 1H), 1.09-1.01 (m, 1H), 0.28-0.20 (m, 2H), 0.06-0.01 (m, 2H).

Compounds of Examples 592 to 608 in Table 56 were prepared following a procedure similar to the preparation of a compound of Example 591, by Buchwald etherification reaction of Intermediate 591C with appropriate alcohols

TABLE 56

| Example | Structure<br>Name<br>Analytical Data: LC-MS m/z [M + H]+; HPLC retention time (HPLC method) |
|---|---|
| 592 | 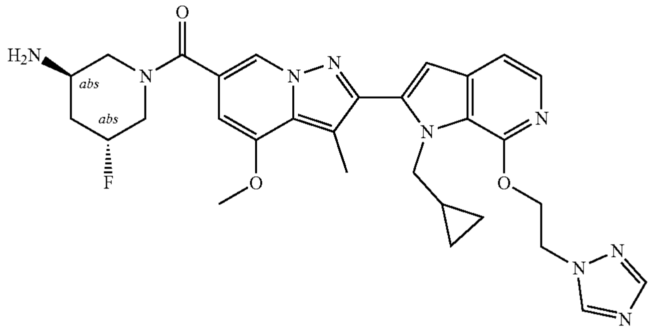 [SMILES: COc1cc(C(=O)N2C[C@H](N)C[C@@H](F)C2)cn2nc(-c3cc4ccnc(OCCn5cncn5)c4n3CC3CC3)c(C)c12]<br>(2-(7-(2-(1H-1,2,4-Triazol-1-yl)ethoxy)-1-(cyclopropylmethyl)-1H-pyrrolo[2,3-c]pyridin-2-yl)-4-methoxy-3-methylpyrazolo[1,5-a]pyridin-6-yl)((3R,5R)-3-amino-5-fluoropiperidin-1-yl)methanone<br>Analytical Data: 588.3, 1.476 min (Method E) |
| 593 | 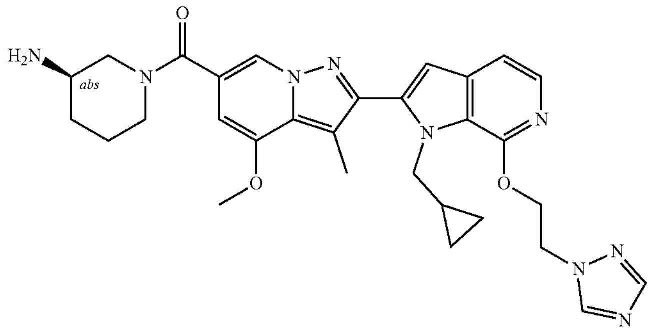 [SMILES: COc1cc(C(=O)N2CCC[C@@H](N)C2)cn2nc(-c3cc4ccnc(OCCn5cncn5)c4n3CC3CC3)c(C)c12]<br>(R)-(2-(7-(2-(1H-1,2,4-Triazol-1-yl)ethoxy)-1-(cyclopropylmethyl)-1H-pyrrolo[2,3-c]pyridin-2-yl)-4-methoxy-3-methylpyrazolo[1,5-a]pyridin-6-yl)(3-aminopiperidin-1-yl)methanone<br>Analytical Data: 570.2, 1.405 min (Method E) |
| 594 | 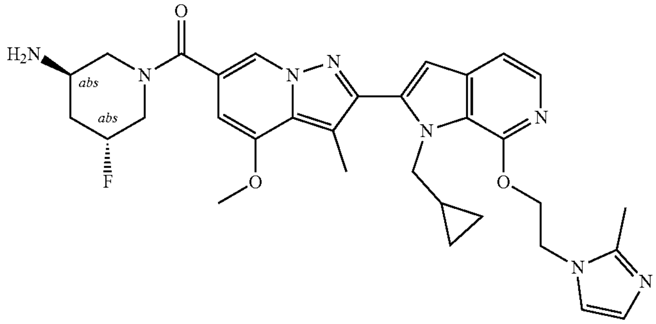 [SMILES: COc1cc(C(=O)N2C[C@H](N)C[C@@H](F)C2)cn2nc(-c3cc4ccnc(OCCn5ccnc5C)c4n3CC3CC3)c(C)c12]<br>((3R,5R)-3-Amino-5-fluoropiperidin-1-yl)(2-(1-(cyclopropylmethyl)-7-(2-(2-methyl-1H-imidazol-1-yl)ethoxy)-1H-pyrrolo[2,3-c]pyridin-2-yl)-4-methoxy-3-methylpyrazolo[1,5-a]pyridin-6-yl)methanone<br>Analytical Data: 601.3, 1.513 min (Method E) |

TABLE 56-continued

| Example | Structure<br>Name<br>Analytical Data: LC-MS m/z [M + H]+; HPLC retention time (HPLC method) |
|---|---|
| 595 | 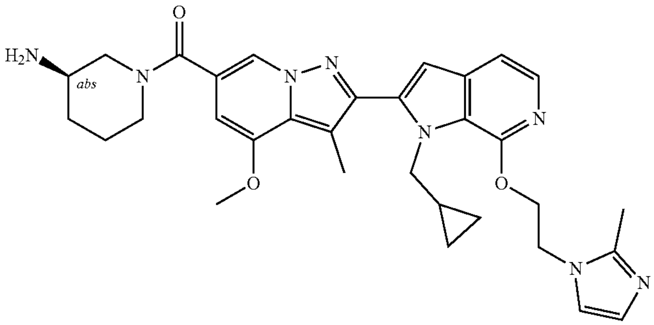 [SMILES: COc1cc(C(=O)N2CCC[C@@H](N)C2)cn2nc(-c3cc4ccnc(OCCn5ccnc5C)c4n3CC3CC3)c(C)c12]<br>(R)-(3-Aminopiperidin-1-yl)(2-(1-(cyclopropylmethyl)-7-(2-(2-methyl-1H-imidazol-1-yl)ethoxy)-1H-pyrrolo[2,3-c]pyridin-2-yl)-4-methoxy-3-methylpyrazolo[1,5-a]pyridin-6-yl)methanone<br>Analytical Data: 571.3, 1.398 min (Method E) |
| 596 | 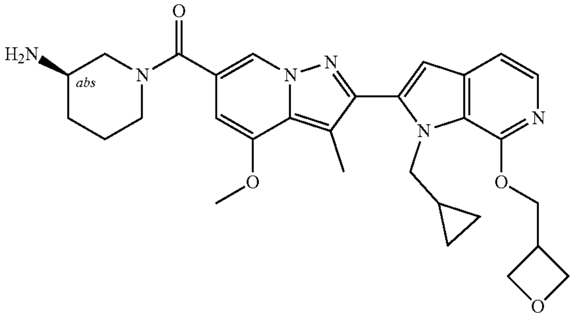 [SMILES: COc1cc(C(=O)N2CCC[C@@H](N)C2)cn2nc(-c3cc4ccnc(OCC5COC5)c4n3CC3CC3)c(C)c12]<br>(R)-(3-Aminopiperidin-1-yl)(2-(1-(cyclopropylmethyl)-7-(oxetan-3-ylmethoxy)-1H-pyrrolo[2,3-c]pyridin-2-yl)-4-methoxy-3-methylpyrazolo[1,5-a]pyridin-6-yl)methanone<br>Analytical Data: 545.3, 0.982 min (Method E) |
| 597 | 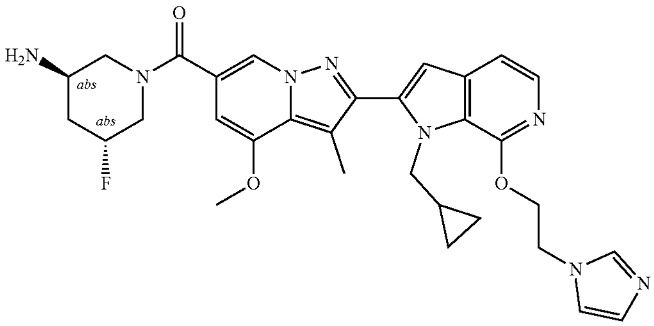 [SMILES: COc1cc(C(=O)N2C[C@H](N)C[C@@H](F)C2)cn2nc(-c3cc4ccnc(OCCn5ccnc5)c4n3CC3CC3)c(C)c12]<br>(2-(7-(2-(1H-Imidazol-1-yl)ethoxy)-1-(cyclopropylmethyl)-1H-pyrrolo[2,3-c]pyridin-2-yl)-4-methoxy-3-methylpyrazolo[1,5-a]pyridin-6-yl)((3R,5R)-3-amino-5-fluoropiperidin-1-yl)methanone<br>Analytical Data: 587.3, 1.530 min (Method E) |

TABLE 56-continued

| Example | Structure<br>Name<br>Analytical Data: LC-MS m/z [M + H]+; HPLC retention time (HPLC method) |
|---|---|
| 598 | 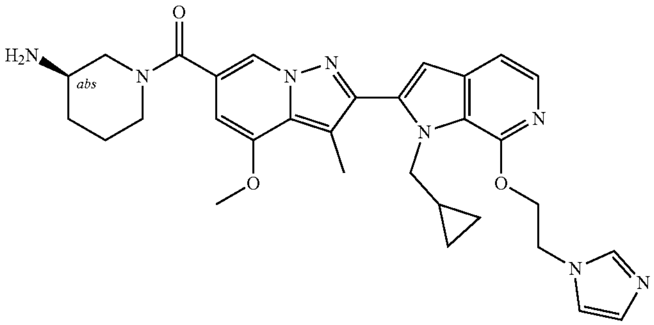 [SMILES: COc1cc(C(=O)N2CCC[C@@H](N)C2)cn2nc(-c3cc4ccnc(OCCn5ccnc5)c4n3CC3CC3)c(C)c12]<br>(R)-(2-(7-(2-(1H-Imidazol-1-yl)ethoxy)-1-(cyclopropylmethyl)-1H-pyrrolo[2,3-c]pyridin-2-yl)-4-methoxy-3-methylpyrazolo[1,5-a]pyridin-6-yl)(3-aminopiperidin-1-yl)methanone<br>Analytical Data: 569.3, 1.467 min (Method E) |
| 599 | 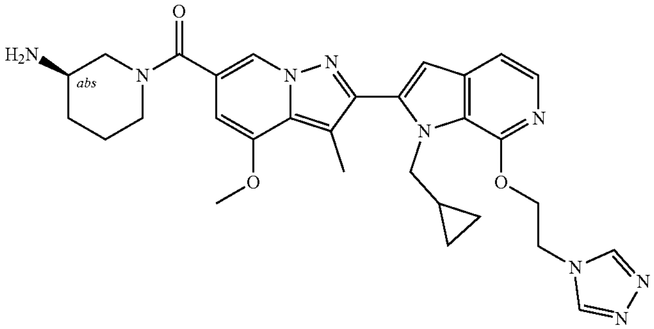 [SMILES: COc1cc(C(=O)N2CCC[C@@H](N)C2)cn2nc(-c3cc4ccnc(OCCn5cnnc5)c4n3CC3CC3)c(C)c12]<br>(R)-(2-(7-(2-(4H-1,2,4-Triazol-4-yl)ethoxy)-1-(cyclopropylmethyl)-1H-pyrrolo[2,3-c]pyridin-2-yl)-4-methoxy-3-methylpyrazolo[1,5-a]pyridin-6-yl)(3-aminopiperidin-1-yl)methanone<br>Analytical Data: 570.3, 1.313 min (Method E) |
| 600 | 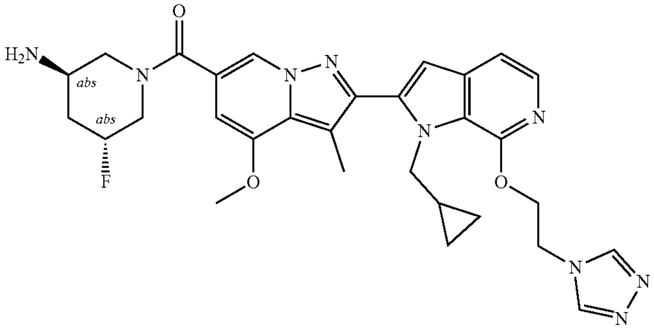 [SMILES: COc1cc(C(=O)N2C[C@H](N)C[C@@H](F)C2)cn2nc(-c3cc4ccnc(OCCn5cnnc5)c4n3CC3CC3)c(C)c12]<br>(2-(7-(2-(4H-1,2,4-Triazol-4-yl)ethoxy)-1-(cyclopropylmethyl)-1H-pyrrolo[2,3-c]pyridin-2-yl)-4-methoxy-3-methylpyrazolo[1,5-a]pyridin-6-yl)((3R,5R)-3-amino-5-fluoropiperidin-1-yl)methanone<br>Analytical Data: 588.2, 1.369 min (Method E) |

TABLE 56-continued

| Example | Structure<br>Name<br>Analytical Data: LC-MS m/z [M + H]+; HPLC retention time (HPLC method) |
|---|---|
| 601 | 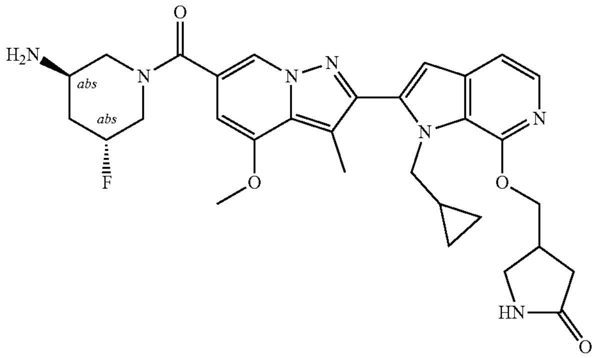 [SMILES: COc1cc(C(=O)N2C[C@H](N)C[C@@H](F)C2)cn2nc(-c3cc4ccnc(OCC5CNC(=O)C5)c4n3CC3CC3)c(C)c12]<br>4-(((2-(6-((3R,5R)-3-Amino-5-fluoropiperidine-1-carbonyl)-4-methoxy-3-methylpyrazolo[1,5-a]pyridin-2-yl)-1-(cyclopropylmethyl)-1H-pyrrolo[2,3-c]pyridin-7-yl)oxy)methyl)pyrrolidin-2-one (isomer 1)<br>Analytical Data: 590.3, 1.434 min (Method E) |
| 602 | 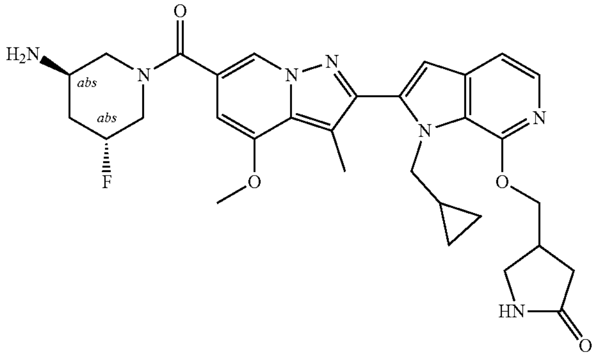 [SMILES: COc1cc(C(=O)N2C[C@H](N)C[C@@H](F)C2)cn2nc(-c3cc4ccnc(OCC5CNC(=O)C5)c4n3CC3CC3)c(C)c12]<br>4-(((2-(6-((3R,5R)-3-Amino-5-fluoropiperidine-1-carbonyl)-4-methoxy-3-methylpyrazolo[1,5-a]pyridin-2-yl)-1-(cyclopropylmethyl)-1H-pyrrolo[2,3-c]pyridin-7-yl)oxy)methyl)pyrrolidin-2-one (isomer 2)<br>Analytical Data: 590.2, 1.436 min (Method E) |
| 603 | 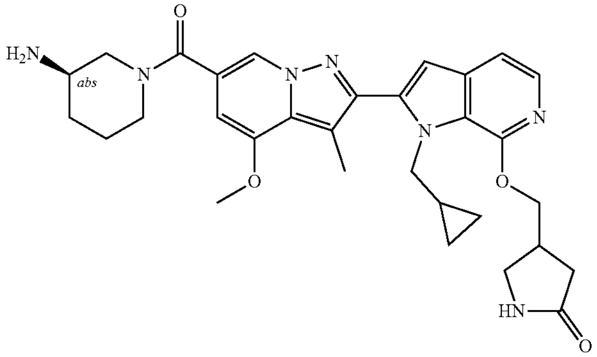 [SMILES: COc1cc(C(=O)N2CCC[C@@H](N)C2)cn2nc(-c3cc4ccnc(OCC5CNC(=O)C5)c4n3CC3CC3)c(C)c12]<br>4-(((2-(6-((R)-3-Aminopiperidine-1-carbonyl)-4-methoxy-3-methylpyrazolo[1,5-a]pyridin-2-yl)-1-(cyclopropylmethyl)-1H-pyrrolo[2,3-c]pyridin-7-yl)oxy)methyl)pyrrolidin-2-one (isomer 2)<br>Analytical Data: 572.2, 1.312 min (Method E) |

TABLE 56-continued

| Example | Structure<br>Name<br>Analytical Data: LC-MS m/z [M + H]+; HPLC retention time (HPLC method) |
|---|---|
| 604 | 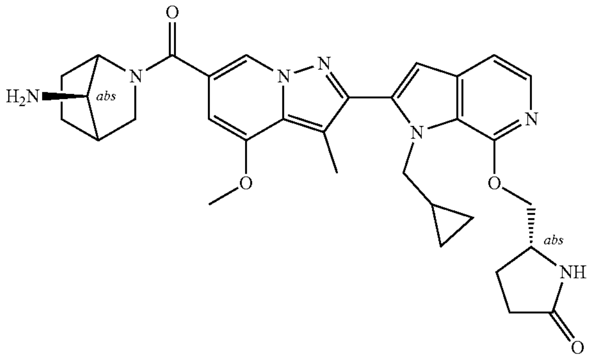 [SMILES: COc1cc(C(=O)N2CC3CCC2[C@@H]3N)cn2nc(-c3cc4ccnc(OC[C@H]5CCC(=O)N5)c4n3CC3CC3)c(C)c12]<br>(5R)-5-(((2-(6-((7R)-7-Amino-2-azabicyclo[2.2.1]heptane-2-carbonyl)-4-methoxy-3-methylpyrazolo[1,5-a]pyridin-2-yl)-1-(cyclopropylmethyl)-1H-pyrrolo[2,3-c]pyridin-7-yl)oxy)methyl)pyrrolidin-2-one<br>Analytical Data: 584.3, 1.438 min (Method E) |
| 605 | 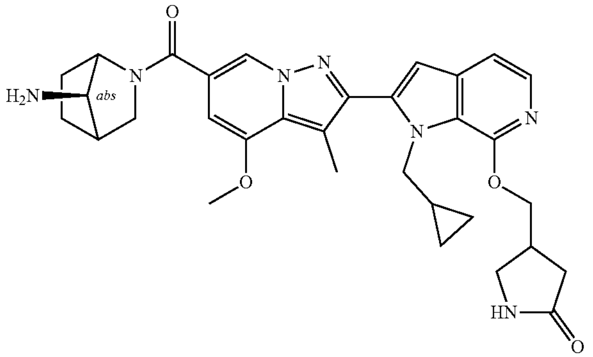 [SMILES: COc1cc(C(=O)N2CC3CCC2[C@@H]3N)cn2nc(-c3cc4ccnc(OCC5CNC(=O)C5)c4n3CC3CC3)c(C)c12]<br>4-(((2-(6-((7R)-7-Amino-2-azabicyclo[2.2.1]heptane-2-carbonyl)-4-methoxy-3-methylpyrazolo[1,5-a]pyridin-2-yl)-1-(cyclopropylmethyl)-1H-pyrrolo[2,3-c]pyridin-7-yl)oxy)methyl)pyrrolidin-2-one (isomer 1)<br>Analytical Data: 584.3, 8.372 min (Method C) |
| 606 | 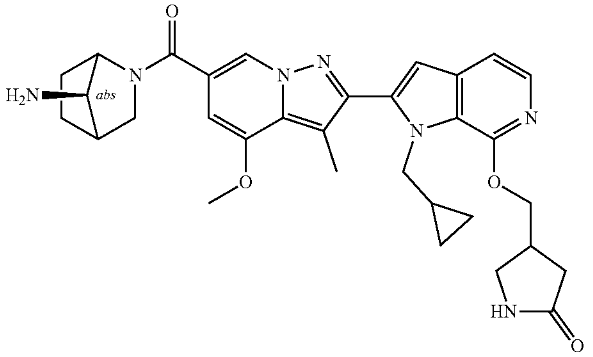 [SMILES: COc1cc(C(=O)N2CC3CCC2[C@@H]3N)cn2nc(-c3cc4ccnc(OCC5CNC(=O)C5)c4n3CC3CC3)c(C)c12]<br>4-(((2-(6-((7R)-7-Amino-2-azabicyclo[2.2.1]heptane-2-carbonyl)-4-methoxy-3-methylpyrazolo[1,5-a]pyridin-2-yl)-1-(cyclopropylmethyl)-1H-pyrrolo[2,3-c]pyridin-7-yl)oxy)methyl)pyrrolidin-2-one (isomer 2)<br>Analytical Data: 584.3, 8.335 min (Method C) |

TABLE 56-continued

| Example | Structure<br>Name<br>Analytical Data: LC-MS m/z [M + H]+; HPLC retention time (HPLC method) |
|---|---|
| 607 | 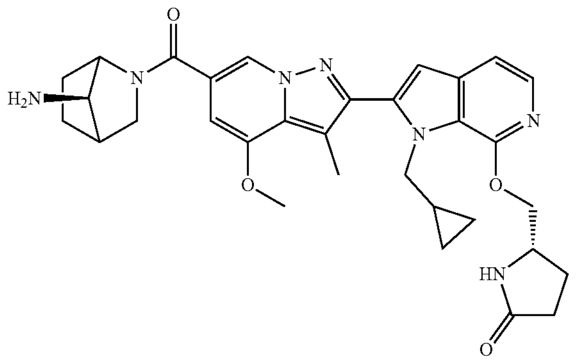 [SMILES: COc1cc(C(=O)N2CC3CCC2[C@@H]3N)cn2nc(-c3cc4ccnc(OC[C@@H]5CCC(=O)N5)c4n3CC3CC3)c(C)c12]<br>(5R)-5-(((2-(6-((7S)-7-Amino-2-azabicyclo[2.2.1]heptane-2-carbonyl)-4-methoxy-3-methylpyrazolo[1,5-a]pyridin-2-yl)-1-(cyclopropylmethyl)-1H-pyrrolo[2,3-c]pyridin-7-yl)oxy)methyl)pyrrolidin-2-one<br>Analytical Data: 584.4, 1.505 min (Method E) |
| 608 | 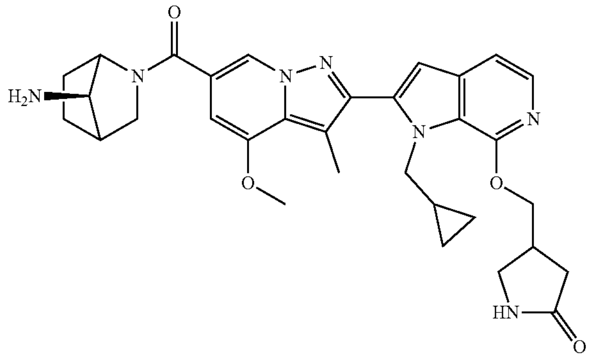 [SMILES: COc1cc(C(=O)N2CC3CCC2[C@@H]3N)cn2nc(-c3cc4ccnc(OCC5CNC(=O)C5)c4n3CC3CC3)c(C)c12]<br>4-(((2-(6-((7R)-7-Amino-2-azabicyclo[2.2.1]heptane-2-carbonyl)-4-methoxy-3-methylpyrazolo[1,5-a]pyridin-2-yl)-1-(cyclopropylmethyl)-1H-pyrrolo[2,3-c]pyridin-7-yl)oxy)methyl)pyrrolidin-2-one (mixture of diastereomers)<br>Analytical Data: 584.3, 1.456 min (Method E) |

Example 609

(R)-(2-(7-(2-(4H-1,2,4-Triazol-4-yl)ethoxy)-1-(cyclopropylmethyl)-1H-pyrrolo[2,3-c]pyridin-2-yl)-3-methylpyrazolo[1,5-a]pyridin-6-yl)(3-aminopiperidin-1-yl)methanone

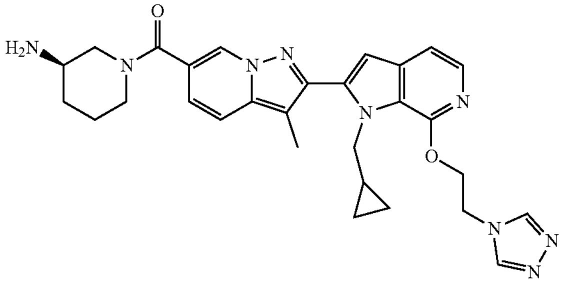 [SMILES: Cc1c(-c2cc3ccnc(OCCn4cnnc4)c3n2CC2CC2)nn2cc(C(=O)N3CCC[C@@H](N)C3)ccc12]

Intermediate 609A

Ethyl 2-(7-chloro-1-(cyclopropylmethyl)-1H-pyrrolo[2,3-c]pyridin-2-yl)-3-methylpyrazolo[1,5-a]pyridine-6-carboxylate

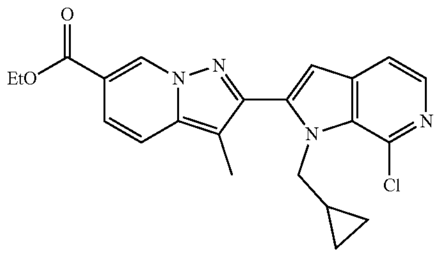 [SMILES: CCOC(=O)c1ccc2c(C)c(-c3cc4ccnc(Cl)c4n3CC3CC3)nn2c1]

1-Amino-3-(ethoxycarbonyl)pyridin-1-ium (2.063 g, 12.34 mmol) was added to a stirred solution of (E)-7-chloro-1-(cyclopropylmethyl)-2-(2-nitroprop-1-en-1-yl)-1H-pyrrolo[2,3-c]pyridine (1.2 g, 4.11 mmol) in DMF (3 ml). The reaction mixture was stirred at 80° C. for 30 hours, diluted with water (20 ml), and extracted with ethyl acetate (3×20 ml). The combined organic layers were washed with brine, dried over sodium sulfate, filtered, and concentrated in vacuum. A crude product thus obtained was purified using a silica gel column, eluting with 0-20% ethyl acetate in hexane to afford ethyl 2-(7-chloro-1-(cyclopropylmethyl)-1H-pyrrolo[2,3-c]pyridin-2-yl)-3-methylpyrazolo[1,5-a]pyridine-6-carboxylate (1.0 g, 60%) as brown solid. LC-MS m/z: 409.3 $[M+H]^+$; $^1H$ NMR (300 MHz, DMSO-$d_6$) δ ppm:9.24 (s, 1H), 8.30 (td, J=2.1, 7.9 Hz, 1H), 8.07-7.97 (m,1H), 7.88 (d, J=9.3 Hz, 1H), 7.71-7.55 (m, 3H), 7.05 (s, 1H), 4.78 (d, J=6.8 Hz, 2H), 4.42-4.31 (m, 2H), 2.38 (s, 3H), 1.40-1.30 (m, 3H), 1.08-1.03 (m, 1H), 0.40-0.19 (m, 2H), −0.01-−0.04 (m, 2H).

Intermediate 609B 2-(7-Chloro-1-(cyclopropylmethyl)-1H-pyrrolo[2,3-c]pyridin-2-yl)-3-methylpyrazolo[1,5-a]pyridine-6-carboxylic acid

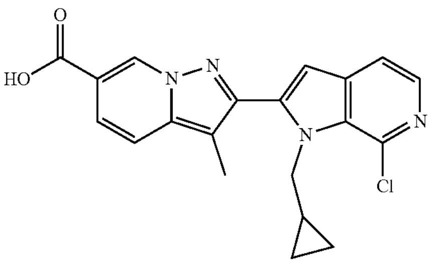 [SMILES: Cc1c(-c2cc3ccnc(Cl)c3n2CC2CC2)nn2cc(C(=O)O)ccc12]

2-(7-Chloro-1-(cyclopropylmethyl)-1H-pyrrolo[2,3-c]pyridin-2-yl)-3-methylpyrazolo[1,5-a]pyridine-6-carboxylic acid (0.55 g, 82%) was prepared using procedure similar to the preparation of Intermediate 510D as a brown solid as a brown solid. LC-MS m/z: 381.3 $[M+H]^+$; $^1H$ NMR (300 MHz, DMSO-$d_6$) δ ppm:9.16 (s, 1H), 8.02 (d, J=5.3 Hz, 1H), 7.85 (d, J=9.4 Hz, 1H), 7.69 (d, J=5.3 Hz, 1H), 7.64 (dd, 9.4 Hz, 1H), 7.04 (s, 1H), 4.77 (d, J=6.8 Hz, 2H), 2.38 (s, 3H), 1.23 (s, 1H), 1.18-0.96 (m, 1H), 0.25 (br, d, J=7.9 Hz, 2H), −0.01-−0.06 (m,2H).

Intermediate 609C tert-Butyl (R)-(1-(2-(7-chloro-1-(cyclopropylmethyl)-1H-pyrrolo[2,3-c]pyridin-2-yl)-3-methylpyrazolo[1,5-a]pyridine-6-carbonyl)piperidin-3-yl)carbamate

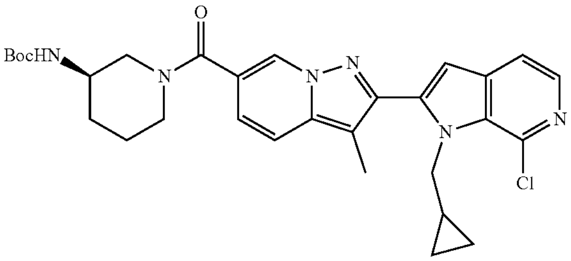 [SMILES: Cc1c(-c2cc3ccnc(Cl)c3n2CC2CC2)nn2cc(C(=O)N3CCC[C@@H](NC(=O)OC(C)(C)C)C3)ccc12]

Intermediate 609C was prepared following a procedure similar to the preparation of Intermediate 386E (200 mg, 90%). LC-MS m/z: 563.3 $[M+H]^+$.

Intermediate 609D tert-Butyl (R)-(1-(2-(7-(2-(4H-1,2,4-triazol-4-yl)ethoxy)-1-(cyclopropylmethyl)-1H-pyrrolo[2,3-c]pyridin-2-yl)-3-methylpyrazolo[1,5-a]pyridine-6-carbonyl)piperidin-3-yl)carbamate

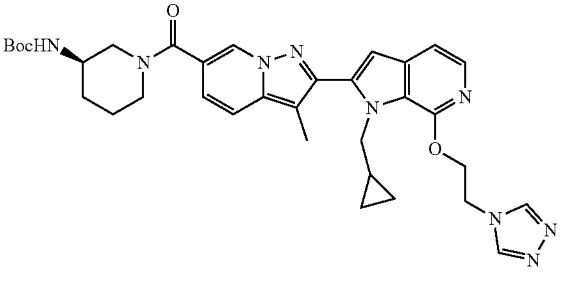 [SMILES: Cc1c(-c2cc3ccnc(OCCn4cnnc4)c3n2CC2CC2)nn2cc(C(=O)N3CCC[C@@H](NC(=O)OC(C)(C)C)C3)ccc12]

2-(4H-1,2,4-Triazol-4-yl)ethan-1-ol (30.1 mg, 0.266 mmol), $Cs_2CO_3$ (174 mg, 0.533 mmol), S-BINAP (22.12 mg, 0.036 mmol) and $Pd_2(dba)_3$ (16.26 mg, 0.018 mmol) were added to a stirred solution of tert-butyl (R)-(1-(2-(7-chloro-1-(cyclopropylmethyl)-1H-pyrrolo[2,3-c]pyridin-2-yl)-3-methylpyrazolo[1,5-a]pyridine-6-carbonyl)piperidin-3-yl)carbamate (100 mg, 0.178 mmol) in 1,4-dioxane (3 ml). The reaction mixture was degassed with argon for 5 and then stirred at 85° C. for 16 hours, diluted with water (20 ml), and extracted with ethyl acetate (20 ml). The combined organic layers were washed with brine, dried over sodium sulfate, filtered, and concentrated in vacuum. A crude product thus obtained was purified using a silica gel column eluting with 0-8% MeOH in dichloromethane to afford (40 mg, 35%) tert-butyl (R)-(1-(2-(7-(2-(4H-1,2,4-triazol-4-yl)ethoxy)-1-(cyclopropylmethyl)-1H-pyrrolo[2,3-c]pyridin-2-yl)-3-methylpyrazolo[1,5-a]pyridine-6-carbonyl)piperidin-3-yl)carbamate. LCMS m/z: 640.6 $[M+H]^+$ Example 609

(R)-(2-(7-(2-(4H-1,2,4-Triazol-4-yl)ethoxy)-1-(cyclopropylmethyl)-1H-pyrrolo[2,3-c]pyridin-2-yl)-3-methylpyrazolo[1,5-a]pyridin-6-yl)(3-aminopiperidin-1-yl)methanone

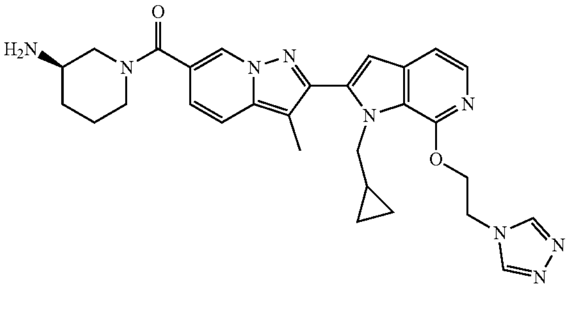 [SMILES: Cc1c(-c2cc3ccnc(OCCn4cnnc4)c3n2CC2CC2)nn2cc(C(=O)N3CCC[C@@H](N)C3)ccc12]

HCl in dioxane (4.0 M) (0.019 ml, 0.625 mmol) was added to a stirred solution of tert-butyl (R)-(1-(2-(7-(2-(4H-1,2,4-triazol-4-yl)ethoxy)-1-(cyclopropylmethyl)-1H-pyrrolo[2,3-c]pyridin-2-yl)-3-methylpyrazolo[1,5-a]pyridine-6-carbonyl)piperidin-3-yl)carbamate (40 mg, 0.063 mmol) in 1,4-dioxane (1 ml). The reaction mixture was stirred at a room temperature for 1 hour, concentrated, and the crude product thus obtained was purified using a preparative LC/MS with the following conditions: Column: Waters XBridge C18, 19×150 mm, 5 μm particles; mobile phase A: 10 mM ammonium acetate; mobile phase B: acetonitrile; gradient: 10-30% B over 20 minutes, then a 5-minute hold at 100% B; flow rate: 20 ml/min. Fractions containing the desired product were combined and dried using centrifugal evaporation. The purified material was then diluted with a 1:1 mixture of ethylene dichloride and methanol (EDM), treated with Si-Pyridine, and shaken for a minimum of 2 hours The resulting mixture was filtered and dried using centrifugal evaporation to afford (R)-(2-(7-(2-(4H-1,2,4-triazol-4-yl)ethoxy)-1-(cyclopropylmethyl)-1H-pyrrolo[2,3-c]pyridin-2-yl)-3-methylpyrazolo[1,5-a]pyridin-6-yl)(3-aminopiperidin-1-yl)methanone (8.9 mg, 26%). LC-MS m/z: 540.2 $[M+H]^+$, LCMS retention time 1.195 min. $^1H$ NMR (400 MHz, DMSO-$d_6$) δ ppm: 8.84 (s, 1H), 8.64 (s, 2H), 7.82 (s, 1H), 7.70 (d, J=5.4 Hz, 1H), 7.27-7.24 (m, 2H), 6.79 (s, 1H), 4.85 (br, d, J=6.1 Hz, 2H), 4.57 (dd, J=3.9, 6.1 Hz, 2H), 4.43-4.41 (m, 2H), 3.29-3.03 (m, 3H), 2.89-2.84 (m, 1H), 2.53-2.53 (m, 1H), 2.36 (s, 3H), 1.92-1.89 (m, 2H), 1.24-1.00 (m, 2H), 0.82-0.80 (m, 1H), 0.17-0.14 (m, 2H), −0.10-−0.13 (m, 2H)

Compounds of Examples 610 to 619 in Table 57 were obtained following a procedure similar to the preparation of a compound of Example 610, by Buchwald etherification reaction of Intermediate 609C with appropriate alcohols

TABLE 57

| Example | Structure<br>Name<br>Analytical Data: LC-MS m/z [M + H]+; HPLC retention time (HPLC method) |
|---|---|
| 610 | 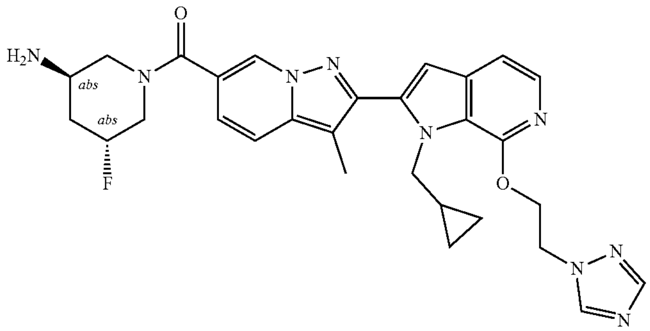 [SMILES: Cc1c(-c2cc3ccnc(OCCn4cncn4)c3n2CC2CC2)nn2cc(C(=O)N3C[C@H](N)C[C@@H](F)C3)ccc12]<br>(2-(7-(2-(1H-1,2,4-Triazol-1-yl)ethoxy)-1-(cyclopropylmethyl)-1H-pyrrolo[2,3-c]pyridin-2-yl)-3-methylpyrazolo[1,5-a]pyridin-6-yl)((3R,5R)-3-amino-5-fluoropiperidin-1-yl)methanone<br>Analytical Data: 558.3, 1.357 min (Method E) |
| 611 | 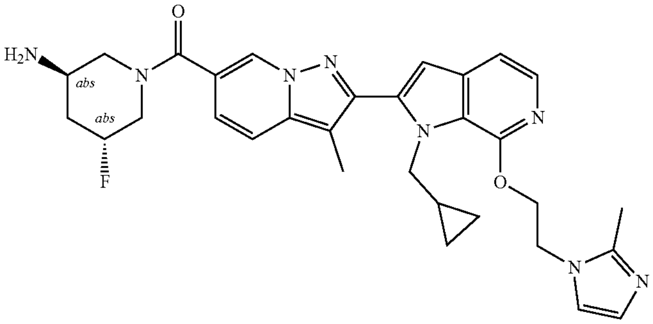 [SMILES: Cc1c(-c2cc3ccnc(OCCn4ccnc4C)c3n2CC2CC2)nn2cc(C(=O)N3C[C@H](N)C[C@@H](F)C3)ccc12]<br>((3R,5R)-3-Amino-5-fluoropiperidin-1-yl)(2-(1-(cyclopropylmethyl)-7-(2-(2-methyl-1H-imidazol-1-yl)ethoxy)-1H-pyrrolo[2,3-c]pyridin-2-yl)-3-methylpyrazolo[1,5-a]pyridin-6-yl)methanone<br>Analytical Data: 571.3, 1.398 min (Method E) |

TABLE 57-continued

| Example | Structure<br>Name<br>Analytical Data: LC-MS m/z [M + H]+; HPLC retention time (HPLC method) |
|---|---|
| 612 | 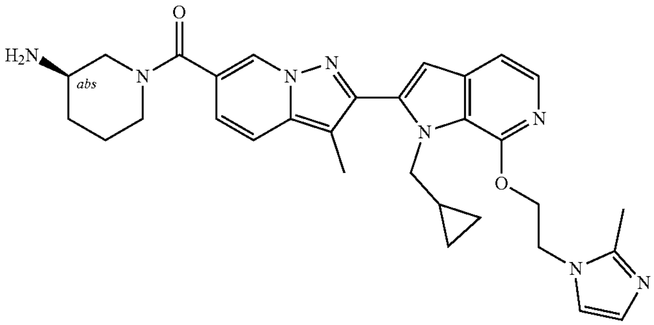 [SMILES: Cc1c(-c2cc3ccnc(OCCn4ccnc4C)c3n2CC2CC2)nn2cc(C(=O)N3CCC[C@@H](N)C3)ccc12]<br>(R)-(3-Aminopiperidin-1-yl)(2-(1-(cyclopropylmethyl)-7-(2-(2-methyl-1H-imidazol-1-yl)ethoxy)-1H-pyrrolo[2,3-c]pyridin-2-yl)-3-methylpyrazolo[1,5-a]pyridin-6-yl)methanone<br>Analytical Data: 553.3, 1.337 min (Method E) |
| 613 | 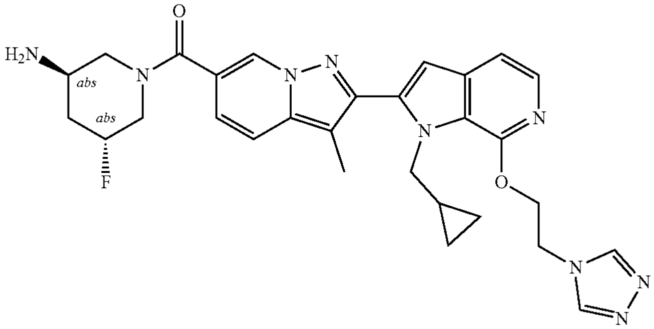 [SMILES: Cc1c(-c2cc3ccnc(OCCn4cnnc4)c3n2CC2CC2)nn2cc(C(=O)N3C[C@H](N)C[C@@H](F)C3)ccc12]<br>(2-(7-(2-(4H-1,2,4-Triazol-4-yl)ethoxy)-1-(cyclopropylmethyl)-1H-pyrrolo[2,3-c]pyridin-2-yl)-3-methylpyrazolo[1,5-a]pyridin-6-yl)((3R,5R)-3-amino-5-fluoropiperidin-1-yl)methanone<br>Analytical Data: 558.2, 1.262 min (Method E) |
| 614 | 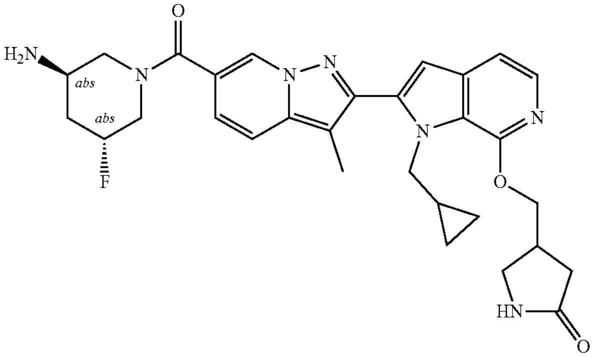 [SMILES: Cc1c(-c2cc3ccnc(OCC4CNC(=O)C4)c3n2CC2CC2)nn2cc(C(=O)N3C[C@H](N)C[C@@H](F)C3)ccc12]<br>4-(((2-(6-((3R,5R)-3-Amino-5-fluoropiperidine-1-carbonyl)-3-methylpyrazolo[1,5-a]pyridin-2-yl)-1-(cyclopropylmethyl)-1H-pyrrolo[2,3-c]pyridin-7-yl)oxy)methyl)pyrrolidin-2-one (isomer 1)<br>Analytical Data: 560.3, 1.340 min (Method E) |

TABLE 57-continued

| Example | Structure<br>Name<br>Analytical Data: LC-MS m/z [M + H]+; HPLC retention time (HPLC method) |
|---|---|
| 615 | 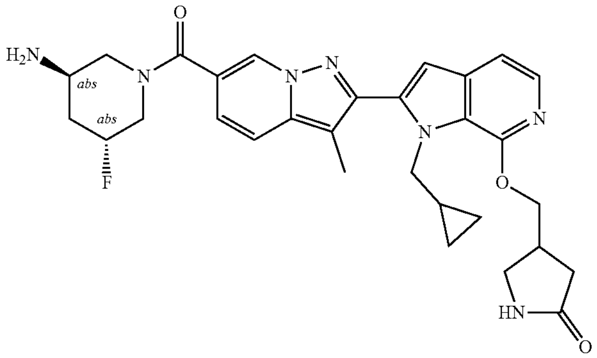 [SMILES: Cc1c(-c2cc3ccnc(OCC4CNC(=O)C4)c3n2CC2CC2)nn2cc(C(=O)N3C[C@H](N)C[C@@H](F)C3)ccc12]<br>4-(((2-(6-((3R,5R)-3-Amino-5-fluoropiperidine-1-carbonyl)-3-methylpyrazolo[1,5-a]pyridin-2-yl)-1-(cyclopropylmethyl)-1H-pyrrolo[2,3-c]pyridin-7-yl)oxy)methyl)pyrrolidin-2-one (isomer 2)<br>Analytical Data: 560.2, 1.329 min (Method E) |
| 616 | 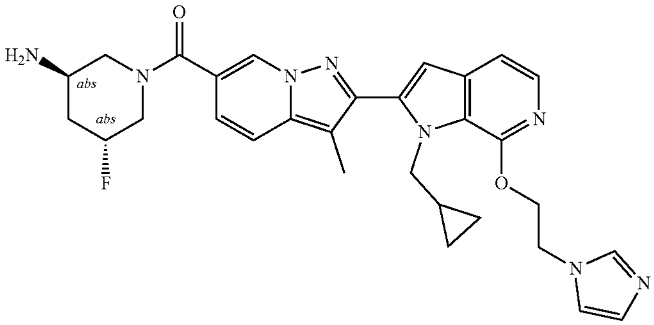 [SMILES: Cc1c(-c2cc3ccnc(OCCn4ccnc4)c3n2CC2CC2)nn2cc(C(=O)N3C[C@H](N)C[C@@H](F)C3)ccc12]<br>(2-(7-(2-(1H-Imidazol-1-yl)ethoxy)-1-(cyclopropylmethyl)-1H-pyrrolo[2,3-c]pyridin-2-yl)-3-methylpyrazolo[1,5-a]pyridin-6-yl)((3R,5R)-3-amino-5-fluoropiperidin-1-yl)methanone<br>Analytical Data: 557.2, 1.414 min (Method E) |
| 617 | 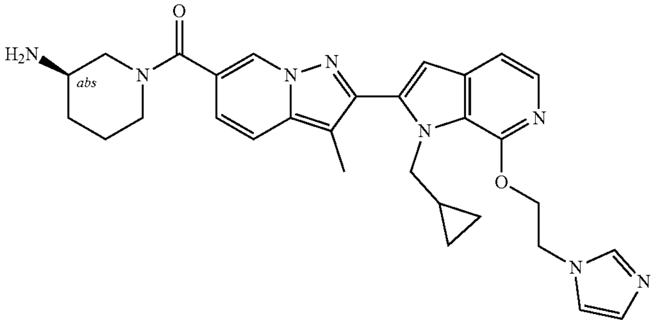 [SMILES: Cc1c(-c2cc3ccnc(OCCn4ccnc4)c3n2CC2CC2)nn2cc(C(=O)N3CCC[C@@H](N)C3)ccc12]<br>(R)-(2-(7-(2-(1H-Imidazol-1-yl)ethoxy)-1-(cyclopropylmethyl)-1H-pyrrolo[2,3-c]pyridin-2-yl)-3-methylpyrazolo[1,5-a]pyridin-6-yl)(3-aminopiperidin-1-yl)methanone<br>Analytical Data: 539.2, 1.349 min (Method E) |

TABLE 57-continued

| Example | Structure<br>Name<br>Analytical Data: LC-MS m/z [M + H]+; HPLC retention time (HPLC method) |
|---|---|
| 618 | 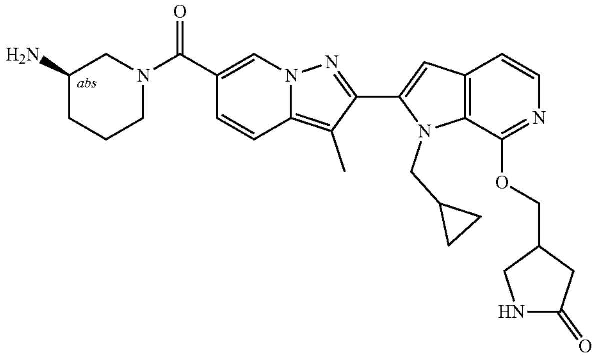 [SMILES: Cc1c(-c2cc3ccnc(OCC4CNC(=O)C4)c3n2CC2CC2)nn2cc(C(=O)N3CCC[C@@H](N)C3)ccc12]<br>4-(((2-(6-((R)-3-Aminopiperidine-1-carbonyl)-3-methylpyrazolo[1,5-a]pyridin-2-yl)-1-(cyclopropylmethyl)-1H-pyrrolo[2,3-c]pyridin-7-yl)oxy)methyl)pyrrolidin-2-one (isomer 1)<br>Analytical Data: 542.2, 1.256 min (Method E) |
| 619 | 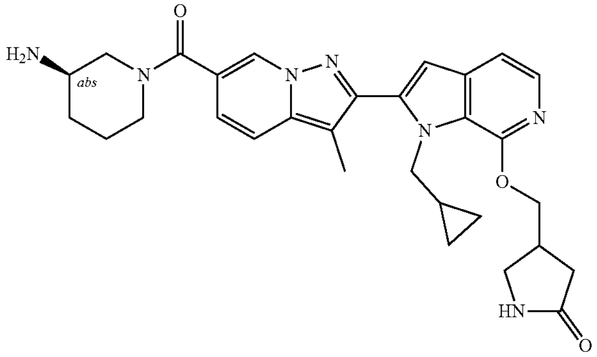 [SMILES: Cc1c(-c2cc3ccnc(OCC4CNC(=O)C4)c3n2CC2CC2)nn2cc(C(=O)N3CCC[C@@H](N)C3)ccc12]<br>4-(((2-(6-((R)-3-Aminopiperidine-1-carbonyl)-3-methylpyrazolo[1,5-a]pyridin-2-yl)-1-(cyclopropylmethyl)-1H-pyrrolo[2,3-c]pyridin-7-yl)oxy)methyl)pyrrolidin-2-one (isomer 2)<br>Analytical Data: 542.2, 1.255 min (Method E) |

Example 620

(2-(7-(2-(4H-1,2,4-Triazol-4-yl)ethoxy)-1-methyl-1H-pyrrolo[2,3-c]pyridin-2-yl)-4-methoxy-3-methylpyrazolo[1,5-a]pyridin-6-yl)((3R,5R)-3-amino-5-fluoropiperidin-1-yl)methanone

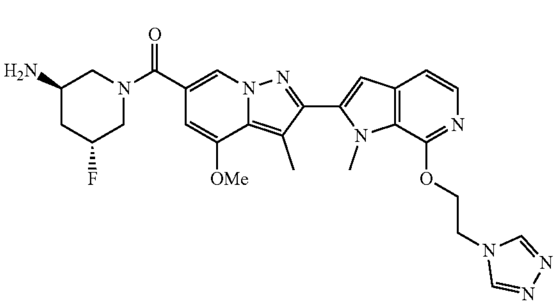 [SMILES: COc1cc(C(=O)N2C[C@H](N)C[C@@H](F)C2)cn2nc(-c3cc4ccnc(OCCn5cnnc5)c4n3C)c(C)c12]

Intermediate 620A

Methyl 2-(7-chloro-1-methyl-1H-pyrrolo[2,3-c]pyridin-2-yl)-4-methoxy-3-methylpyrazolo[1,5-a]pyridine-6-carboxylate

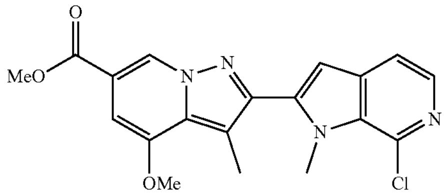 [SMILES: COC(=O)c1cc(OC)c2c(C)c(-c3cc4ccnc(Cl)c4n3C)nn2c1]

Intermediate 1 (4.37 g, 23.84 mmol) and copper(I) iodide (0.454 g, 2.384 mmol) were added to a solution of 7-chloro-1-methyl-2-(2-nitroprop-1-en-1-yl)-1H-pyrrolo[2,3-c]pyridine (2 g, 7.95 mmol) in DMF (10 ml). The reaction mixture was stirred for 16 hours, diluted with ethyl acetate (100 ml), washed with water (3×50 ml), dried over $Na_2SO_4$, and concentrated to afford a crude compound, which was purified using a silica gel column using 0-30% ethyl acetate in Hexane to afford methyl 2-(7-chloro-1-methyl-1H-pyrrolo

[2,3-c]pyridin-2-yl)-4-methoxy-3-methylpyrazolo[1,5-a] pyridine-6-carboxylate (1.4 g, 46%) as brown solid. LC-MS m/z: 385.3 [M+H]+.

Intermediate 620B 2-(7-Chloro-1-methyl-1H-pyrrolo[2,3-c]pyridin-2-yl)-4-methoxy-3-methylpyrazolo[1,5-a]pyridine-6-carboxylic acid

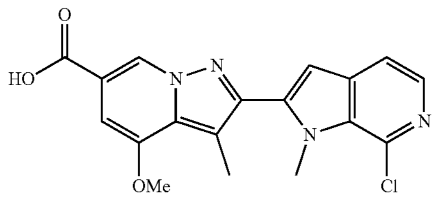 [SMILES: COc1cc(C(=O)O)cn2nc(-c3cc4ccnc(Cl)c4n3C)c(C)c12]

Intermediate 620B was prepared following a procedure similar to the preparation of Intermediate 519B (600 mg, 45%) as Off white solid. LC-MS m/z: 371.3 [M+H]+.

Intermediate 620C tert-Butyl ((3R,5R)-1-(2-(7-chloro-1-methyl-1H-pyrrolo[2,3-c]pyridin-2-yl)-4-methoxy-3-methylpyrazolo[1,5-a]pyridine-6-carbonyl)-5-fluoropiperidin-3-yl)carbamate

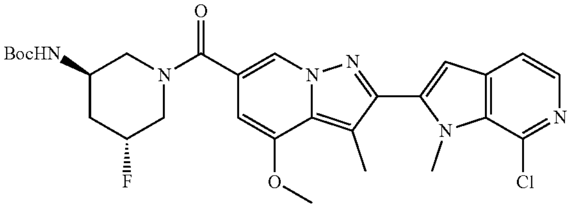 [SMILES: COc1cc(C(=O)N2C[C@H](F)C[C@@H](NC(=O)OC(C)(C)C)C2)cn2nc(-c3cc4ccnc(Cl)c4n3C)c(C)c12]

Intermediate 620C was prepared following a procedure similar to the preparation of Intermediate 519C (600 mg, 78%) as a brown solid. LC-MS m/z: 571.3 [M+H]+.

Intermediate 620D tert-Butyl ((3R,5R)-1-(2-(7-(2-(4H-1,2,4-triazol-4-yl)ethoxy)-1-methyl-1H-pyrrolo[2,3-c]pyridin-2-yl)-4-methoxy-3-methylpyrazolo[1,5-a]pyridine-6-carbonyl)-5-fluoropiperidin-3-yl)carbamate

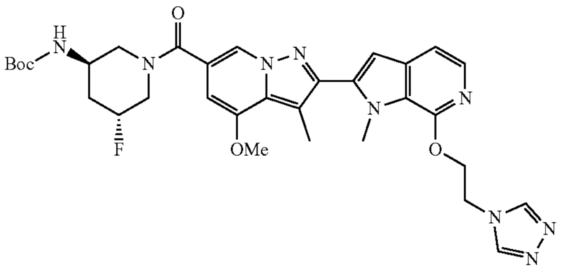 [SMILES: COc1cc(C(=O)N2C[C@H](F)C[C@@H](NC(=O)OC(C)(C)C)C2)cn2nc(-c3cc4ccnc(OCCn5cnnc5)c4n3C)c(C)c12]

Intermediate 620D was prepared following a procedure similar to the preparation of Intermediate 519D (50 mg, 63%) as a brown solid. LC-MS m/z: 648.3 [M+H]+.

Example 620

(2-(7-(2-(4H-1,2,4-Triazol-4-yl)ethoxy)-1-methyl-1H-pyrrolo[2,3-c]pyridin-2-yl)-4-methoxy-3-methylpyrazolo[1,5-a]pyridin-6-yl)((3R,5R)-3-amino-5-fluoropiperidin-1-yl)methanone

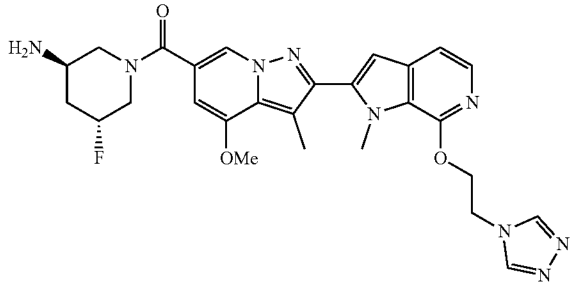 [SMILES: COc1cc(C(=O)N2C[C@H](N)C[C@@H](F)C2)cn2nc(-c3cc4ccnc(OCCn5cnnc5)c4n3C)c(C)c12]

TFA (0.1 ml) was added to a solution of Intermediate 620D (20 mg, 0.031 mmol) in dichloromethane (5 ml), and the reaction mixture was stirred for 1 hour. The reaction mixture was concentrated to obtain a crude compound, which was purified using a preparative LC/MS with the following conditions: Column: Waters XBridge C18, 19×150 mm, 5-μm particles; mobile phase A: 10 mM ammonium acetate; mobile phase B: acetonitrile; gradient: 9-32% B over 25 minutes, then a 5-minute hold at 100% B; flo rate w: 20 ml/min. Fractions containing the desired product were combined and dried via centrifugal evaporation. The purified material was then diluted with a 1:1 mixture of ethylene dichloride and methanol (EDM), treated with Si-Pyridine, and shaken for a minimum of 2 hours. The resulting mixture was filtered and dried using centrifugal evaporation to afford (2-(7-(2-(4H-1,2,4-triazol-4-yl)ethoxy)-1-methyl-1H-pyrrolo[2,3-c]pyridin-2-yl)-4-methoxy-3-methylpyrazolo[1,5-a]pyridin-6-yl)((3R,5R)-3-amino-5-fluoropiperidin-1-yl)methanone (3.2 mg, %). LC-MS m/z: 548.3 [M+H]+; LCMS retention time: 1.180 min [method E]

Example 621

((3R,5R)-3-Amino-5-fluoropiperidin-1-yl) (2-(3-(cyclopropylmethyl)-4-(1-(2-hydroxyethyl)-1H-pyrazol-4-yl)benzo[b]thiophen-2-yl)-4-methoxy-3-methylpyrazolo[1,5-a]pyridin-6-yl)methanone

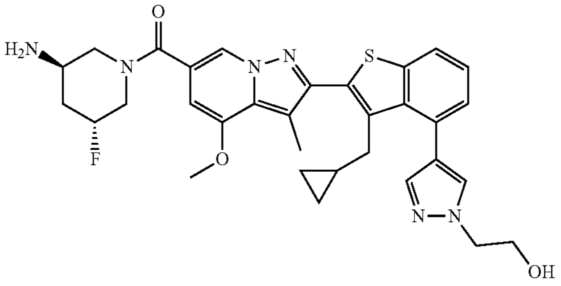 [SMILES: COc1cc(C(=O)N2C[C@H](N)C[C@@H](F)C2)cn2nc(-c3sc4cccc(-c5cnn(CCO)c5)c4c3CC3CC3)c(C)c12]

Intermediate 621A

Methyl 2-(4-bromo-3-(cyclopropylmethyl)benzo[b]thiophen-2-yl)-4-methoxy-3-methylpyrazolo[1,5-a]pyridine-6-carboxylate

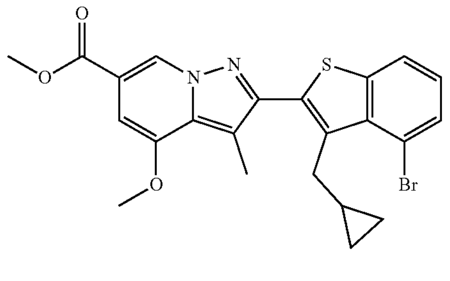 [SMILES: COC(=O)c1cc(OC)c2c(C)c(-c3sc4cccc(Br)c4c3CC3CC3)nn2c1]

CuI (0.541 g, 2.84 mmol) was added to a stirred solution of Intermediate 62 (1 g, 2.84 mmol) and Intermediate 1(1.040 g, 5.68 mmol) in DMF (5 ml). The reaction mixture was stirred for 3 hours at 80° C., the volatiles were evaporated to dryness under reduced pressure, water (100 ml) was added, and extracted with ethyl acetate (2×100 ml). The combined organic extracts were washed with water (100 ml) and brine solution (100 ml), dried over sodium sulphate, filtered, and volatiles were evaporated to dryness under reduced pressure. Residue thus obtained was purified using a silica gel column using a 50% ethyl acetate in hexane to afford methyl 2-(4-bromo-3-(cyclopropylmethyl)benzo[b]thiophen-2-yl)-4-methoxy-3-methylpyrazolo[1,5-a]pyridine-6-carboxylate (500 mg, 36%). LC-MS m/z: 485.3 $[M+H]^+$.

Intermediate 621B 2-(4-Bromo-3-(cyclopropylmethyl)benzo[b]thiophen-2-yl)-4-methoxy-3-methylpyrazolo[1,5-a]pyridine-6-carboxylic acid

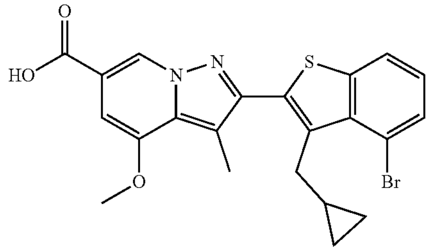 [SMILES: COc1cc(C(=O)O)cn2nc(-c3sc4cccc(Br)c4c3CC3CC3)c(C)c12]

Lithium hydroxide (74.0 mg, 3.09 mmol) in water (1 ml) was added to a stirred solution of Intermediate 621A (500 mg, 1.030 mmol) in THF (10 ml). The reaction mixture was stirred at a room temperature for 16 hours, the volatiles were evaporated to dryness under reduced pressure. A residue thus obtained was dissolved in water (15 ml), cooled to 0° C. and the pH was adjusted to pH 5 using 1.5 N HCl solution. The solids thus obtained were collected by vacuum filtration, and dried under vacuum at ambient temperature to afford 2-(4-bromo-3-(cyclopropylmethyl)benzo[b]thiophen-2-yl)-4-methoxy-3-methylpyrazolo[1,5-a]pyridine-6-carboxylic acid (400 mg, 82%). LC-MS m/z: 472.9 $[M+H]^+$.

Intermediate 621C tert-Butyl ((3R,5R)-1-(2-(4-bromo-3-(cyclopropylmethyl)benzo[b]thiophen-2-yl)-4-methoxy-3-methylpyrazolo[1,5-a]pyridine-6-carbonyl)-5-fluoropiperidin-3-yl)carbamate

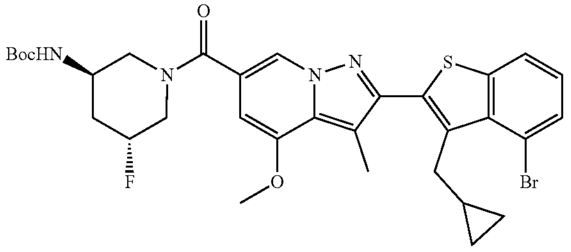 [SMILES: COc1cc(C(=O)N2C[C@H](F)C[C@@H](NC(=O)OC(C)(C)C)C2)cn2nc(-c3sc4cccc(Br)c4c3CC3CC3)c(C)c12]

HATU (605 mg, 1.591 mmol) and DIPEA (0.556 ml, 3.18 mmol) were added to a stirred solution of Intermediate 621B (400 mg, 0.849 mmol), tert-butyl ((3R,5R)-5-fluoropiperidin-3-yl)carbamate (185 mg, 0.849 mmol) in DMF (2 ml). The reaction mixture was stirred at a room temperature for 16 hours, the volatiles were evaporated to dryness under reduced pressure, water (50 ml) was added, and extracted with ethyl acetate (2×50 ml). The combined organic extracts were washed with water (100 ml) and brine solution (100 ml), dried over sodium sulphate, filtered, and volatiles were evaporated to dryness under reduced pressure. A residue thus obtained was purified using a silica gel column (gradient of ethyl acetate in hexane), and the product was isolated at 40% ethyl acetate in hexane. Required fractions were collected and volatiles were evaporated to dryness under reduced pressure to afford tert-butyl ((3R,5R)-1-(2-(4-bromo-3-(cyclopropylmethyl)benzo[b]thiophen-2-yl)-4-methoxy-3-methylpyrazolo[1,5-a]pyridine-6-carbonyl)-5-fluoropiperidin-3-yl)carbamate (400 mg, 70%). LC-MS m/z: 673.1 $[M+H]^+$.

Intermediate 621D tert-Butyl ((3R,5R)-1-(2-(3-(cyclopropylmethyl)-4-(1-(2-hydroxyethyl)-1H-pyrazol-4-yl)benzo[b]thiophen-2-yl)-4-methoxy-3-methylpyrazolo[1,5-a]pyridine-6-carbonyl)-5-fluoropiperidin-3-yl)carbamate

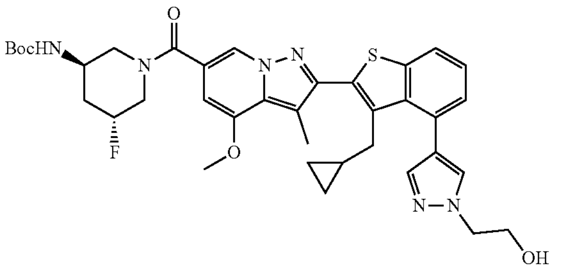 [SMILES: COc1cc(C(=O)N2C[C@H](F)C[C@@H](NC(=O)OC(C)(C)C)C2)cn2nc(-c3sc4cccc(-c5cnn(CCO)c5)c4c3CC3CC3)c(C)c12]

$K_2CO_3$ (30.9 mg, 0.223 mmol) and $PdCl_2$(dppf) (10.89 mg, 0.015 mmol) were added to a stirred solution Intermediate 621C (50 mg, 0.074 mmol) and 2-(4-(4,4,5,5-tetramethyl-1,3,2-dioxaborolan-2-yl)-1H-pyrazol-1-yl)ethan-1-ol (17.73 mg, 0.074 mmol) in 1,4-dioxane (2 ml) under argon atmosphere. The reaction mixture was heated at 80° C. for 2 hours, the volatiles were evaporated to dryness under reduced pressure, water (10 ml) was added, and extracted with ethyl acetate (2×10 ml). The combined organic extracts were washed with water (10 ml) and brine solution (10 ml), organic layer was dried over sodium sulphate, filtered, and volatiles were evaporated to dryness under reduced pressure to afford tert-butyl ((3R,5R)-1-(2-(3-(cyclopropylmethyl)-4-(1-(2-hydroxyethyl)-1H-pyrazol-4-yl)benzo[b]thiophen-2-yl)-4-methoxy-3-methylpyrazolo[1,5-a]pyridine-6-carbonyl)-5-fluoropiperidin-3-yl)carbamate (40 mg, 76%). LC-MS m/z: 703.3 $[M+H]^+$.

Example 621

((3R,5R)-3-Amino-5-fluoropiperidin-1-yl)(2-(3-(cyclopropylmethyl)-4-(1-(2-hydroxyethyl)-1H-pyrazol-4-yl)benzo[b]thiophen-2-yl)-4-methoxy-3-methylpyrazolo[1,5-a]pyridin-6-yl)methanone

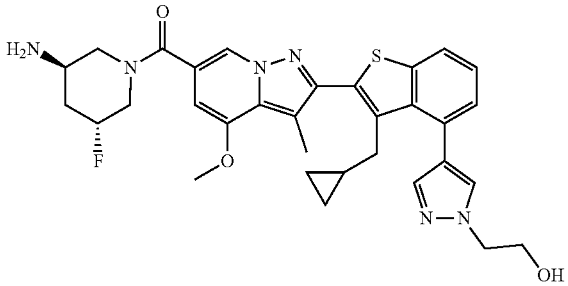 [SMILES: COc1cc(C(=O)N2C[C@H](N)C[C@@H](F)C2)cn2nc(-c3sc4cccc(-c5cnn(CCO)c5)c4c3CC3CC3)c(C)c12]

TFA (0.044 ml, 0.569 mmol) was added to a stirred solution of Intermediate 621D (40 mg, 0.057 mmol) in DCM (2 ml). The reaction mixture was stirred for 1 hour at a room temperature, the volatiles were evaporated to dryness under reduced pressure, and the crude compound thus obtained was purified using reverse phase HPLC to afford ((3R,5R)-3-amino-5-fluoropiperidin-1-yl) (2-(3-(cyclopropylmethyl)-4-(1-(2-hydroxyethyl)-1H-pyrazol-4-yl)benzo[b]thiophen-2-yl)-4-methoxy-3-methylpyrazolo[1,5-a]pyridin-6-yl) methanone (7.1 mg, 20%), LC-MS m/z: 603.3 $[M+H]^+$. LCMS retention time: 1.558 min (method E).

Example 622

(R)-(3-aminopiperidin-1-yl)(2-(1-(cyclopropylmethyl)-1H-indol-2-yl)-3-(2-hydroxyethyl)-4-methoxybenzo[b]thiophen-6-yl)methanone

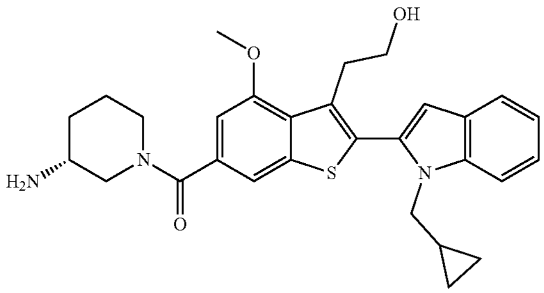 [SMILES: COc1cc(C(=O)N2CCC[C@@H](N)C2)cc2sc(-c3cc4ccccc4n3CC3CC3)c(CCO)c12]

Intermediate 622A tert-butyldiphenyl(2-(thiophen-3-yl)ethoxy)silane

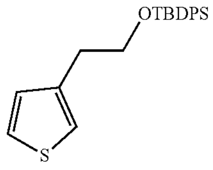

To a stirred solution of 2-(thiophen-3-yl)ethanol (10 g, 78.1 mmol) in DCM (500 mL) was added imidazole (15.9 g, 234.3 mmol) at 0° C. under nitrogen atmosphere. Then to this was added TBDPSCl (23.5 g, 85.9 mmol) at 0° C. The reaction was stirred at room temperature for 2 h. The reaction was monitored by TLC and LCMS. The resulting solution was diluted with water (300 mL), then extracted with DCM (2×300 mL). The combined organic extracts were dried over anhydrous sodium sulphate concentrated under vacuum. The crude product was purified by silica gel column chromatography (petroleum ether:ethyl acetate=20:1) to afford the title compound (27 g, 94.7%) as colorless oil. LCMS (ESI, m/z): 367 $[M+H]^+$.

Intermediate 622B (2-(2-bromothiophen-3-yl)ethoxy)(tert-butyl)diphenylsilane

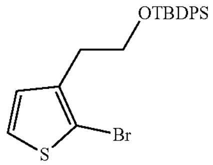

To a stirred solution of Intermediate 622A (5 g, 13.6 mmol) in MeCN (100 mL) was added NBS (3.6 g, 20.4 mmol) at 0° C. under nitrogen atmosphere. The reaction was stirred at room temperature for 12 h. The reaction was monitored by TLC and LCMS. The resulting solution was diluted with water (100 mL), then extracted with ethyl acetate (2×100 mL). The combined organic extracts were dried over anhydrous sodium sulphate concentrated under vacuum. The crude product was purified by silica gel column chromatography (petroleum ether:ethyl acetate=20:1) to afford the title compound (5.5 g, 90.7%) as a yellow solid. LCMS (ESI, m/z): 445 $[M+H]^+$.

Intermediate 622C 5-bromo-4-(2-(tert-butyldiphenylsilyloxy)ethyl)thiophene-2-carbaldehyde

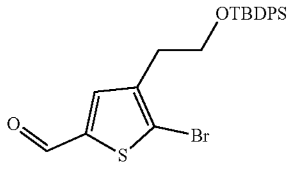

To a stirred solution of Intermediate 622B (5.5 g, 12.3 mmol) in THF (50 mL) was added nBuLi (1 M in hexane) (18.5 g, 18.4 mmol) at −78° C. under nitrogen atmosphere. The reaction was stirred at −78° C. for 0.5 h. Then to this was added $Et_2NH$ (1.8 g, 24.6 mmol) and DMF (1.1 g, 14.8 mmol) −78° C. under nitrogen atmosphere. The reaction was stirred at 0° C. for 2 h under nitrogen atmosphere. The reaction was monitored by TLC and LCMS. The resulting solution was diluted $NH_4Cl$ (100 mL, aq.), then extracted with ethyl acetate (2×100 mL). The combined organic extracts were dried over anhydrous sodium sulphate concentrated under vacuum. The crude product was purified by silica gel column chromatography (petroleum ether:ethyl acetate=10:1) to afford the title compound (4.9 g, 84%) as yellow oil. LCMS (ESI, m/z): 472 $[M+H]^+$.

Intermediate 622D (Z)-4-(5-bromo-4-(2-((tert-butyldiphenylsilyl)oxy)ethyl)thiophen-2-yl)-3-(ethoxycarbonyl)but-3-enoic acid

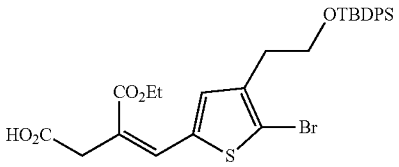

To a stirred solution of Intermediate 622C (4.9 g, 10.4 mmol) in tert-butanol (200 mL) was added diethyl butanedioate (7.2 g, 41.6 mmol) and t-BuOK (1 M in THF) (21 mL, 20.8 mmol). The resulting mixture was stirred at 50° C. for 1 h under nitrogen atmosphere. LCMS showed the reaction was complete, and the mixture was diluted with water (100 mL), then adjusted to pH 6-7 with HCl (2 M). The resulting mixture was extracted with ethyl acetate (2×200 mL). The combined organic extracts were washed with brine (2×50 mL), dried over anhydrous sodium sulfate, and concentrated under vacuum. The residue was purified by silica gel column chromatography (petroleum ether:ethyl acetate=5:1) to obtain the title compound (4 g, 64.5%) as yellow oil. LCMS (ESI, m/z): 601 $[M+H]^+$.

Intermediate 622E ethyl 4-acetoxy-2-bromo-3-(2-((tert-butyldiphenylsilyl)oxy)ethyl)benzo[b]thiophene-6-carboxylate

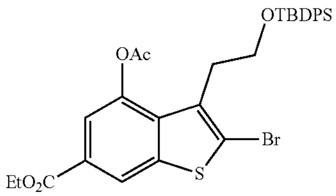

To a stirred solution of Intermediate 622D (4 g, 6.6 mmol) in $Ac_2O$ (50 mL) was added NaOAc (2.4 g, 29.7 mmol). The resulting mixture was stirred at 70° C. for 1 h under nitrogen atmosphere. LCMS showed the reaction was complete, and the solids were filtered out. The resulting mixture was concentrated. The residue was purified by silica gel column chromatography (petroleum ether:ethyl acetate=5:1) to obtain the title compound (2.5 g, 60.9%) as yellow oil. LCMS (ESI, m/z): 625 $[M+H]^+$.

Intermediate 622F ethyl 2-bromo-3-(2-((tert-butyldiphenylsilyl)oxy)ethyl)-4-hydroxybenzo[b]thiophene-6-carboxylate

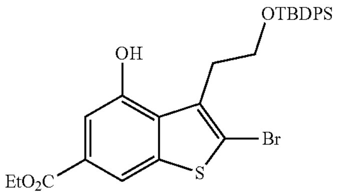

To a stirred solution of Intermediate 622E (2.5 g, 4 mmol) in Ethanol (50 mL) was added $K_2CO_3$ (1.1 g, 8 mmol). The resulting mixture was stirred at 70° C. for 1 h under nitrogen atmosphere. LCMS showed the reaction was complete, and the solids were filtered out. The resulting mixture was concentrated. The residue was purified by silica gel column chromatography (petroleum ether:ethyl acetate=2:1) to obtain the title compound (2 g, 85.8%) as a white solid. LCMS (ESI, m/z): 583 $[M+H]^+$.

Intermediate 622G ethyl 2-bromo-3-(2-((tert-butyldiphenylsilyl)oxy)ethyl)-4-methoxybenzo[b]thiophene-6-carboxylate

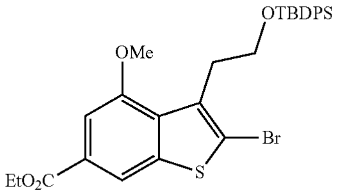

To a stirred solution of Intermediate 622F ATN-81-252615-6 (2 g, 3.4 mmol) in DMF (30 mL) was added $K_2CO_3$ (1.4 g, 10.2 mmol) and MeI (719 mg, 5.1 mmol). The resulting mixture was stirred at room temperature for 30 min. LCMS showed the reaction was complete, and the solids were filtered out. The resulting mixture was concentrated. The residue was purified by silica gel column chromatography (petroleum ether:ethyl acetate=5:1) to obtain the title compound (2 g, 97.6%) as a white solid. LCMS (ESI, m/z): 597 $[M+H]^+$.

Intermediate 622H tert-butyl 2-(3-(2-((tert-butyldiphenylsilyl)oxy)ethyl)-6-(ethoxycarbonyl)-4-methoxybenzo[b]thiophen-2-yl)-1H-indole-1-carboxylate

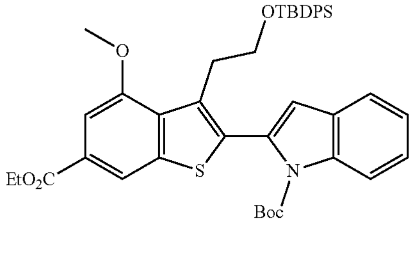

To a stirred solution of Intermediate 622G (150 mg, 0.25 mmol) in 1,4-dioxane (8 mL) and water (1.5 mL), was added 1-(tert-butoxycarbonyl)-1H-indol-2-ylboronic (130 mg, 0.5 mmol), $Pd(dppf)Cl_2 \cdot CH_2Cl_2$ (43 mg, 0.05 mmol) and $K_3PO_4$ (212 mg, 1 mmol) at room temperature under nitrogen atmosphere. The reaction was stirred at 90° C. for 2 h. The reaction was monitored by TLC and LCMS. The reaction mixture was cooled to room temperature. The resulting solution was diluted with 50 mL of water, then extracted with ethyl acetate (2×50 mL). The combined organic extracts were washed with water (50 mL) and brine (50 mL), dried over anhydrous sodium sulfate, concentrated under vacuum. The crude product was purified by Prep-TLC (petroleum ether/ethyl acetate=3:2) to afford the title compound (150 mg, 81.5%) as a yellow solid. LCMS (ESI, m/z): 734 [M+H]$^+$.

Intermediate 622I ethyl 3-(2-((tert-butyldiphenylsilyl)oxy)ethyl)-2-(1H-indol-2-yl)-4-methoxybenzo[b]thiophene-6-carboxylate

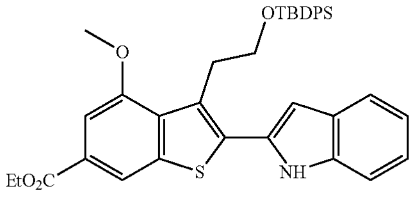

To a stirred solution of Intermediate 622H (150 g, 0.20 mmol) in DCM (10 mL) was added silica gel (1.5 g). The mixture was concentrated under vacuum. The residue was stirred at 90° C. for 2 h under vacuum. The reaction was monitored by LCMS. The mixture was filtered through a Celite pad and washed with DCM/MeOH=15:1 (80 mL). The combined organic extract was concentrated under vacuum to afford the title compound (110 mg, 85.2%) as yellow solid. LCMS (ESI, m/z): 634 [M+H]$^+$.

Intermediate 622J ethyl 3-(2-((tert-butyldiphenylsilyl)oxy)ethyl)-2-(1-(cyclopropylmethyl)-1H-indol-2-yl)-4-methoxybenzo[b]thiophene-6-carboxylate

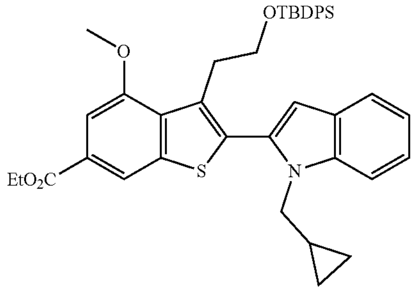

To a stirred solution of Intermediate 622I (110 mg, 0.17 mmol) in DMF (3 mL) was added bromomethylcyclopropane (47 mg, 0.35 mmol) and $Cs_2CO_3$ (115 mg, 0.35 mmol). The reaction was stirred at 50° C. for 1 h. The reaction was monitored by LCMS. The mixture was quenched with water (15 mL), extracted with ethyl acetate (2×30 mL). The organic layer was washed with brine (2×50 mL) and concentrated under vacuum. The crude product was purified by column chromatography (petroleum ether/ethyl acetate=3/1) to afford the title compound (100 mg, 83.8%) as a yellow solid. LCMS (ESI, m/z): 688 [M+H]$^+$.

Intermediate 622K 2-(1-(cyclopropylmethyl)-1H-indol-2-yl)-3-(2-hydroxyethyl)-4-methoxybenzo[b]thiophene-6-carboxylic acid

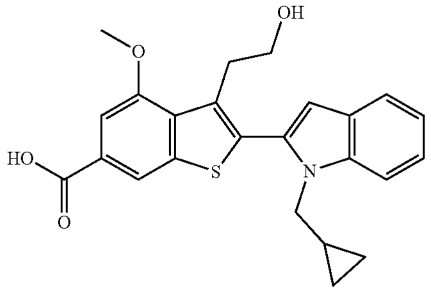 [SMILES: COc1cc(C(=O)O)cc2sc(-c3cc4ccccc4n3CC3CC3)c(CCO)c12]

To a solution of Intermediate 622J (100 mg, 0.15 mmol) in MeOH (4 mL) and water (1 ml) were added NaOH (35 mg, 0.9 mmol) at room temperature under nitrogen atmosphere. The resulting mixture was stirred at 50° C. for 16 h. The reaction was monitored by TLC and LCMS. The pH value of the solution was adjusted to 2-3 with HCl (1M). The residue was purified by flash column chromatography on C18 silica (Mobile Phase A: water (0.5% TFA), Mobile Phase B: ACN; Flow rate: 40 mL/min; Gradient: 45% B to 50% B in 2.5 min; 254/210 nm) to afford the title compound (50 mg, 81.9%) as yellow oil. LCMS (ESI, m/z): 422 [M+H]$^+$.

Intermediate 622L tert-butyl (R)-(1-(2-(1-(cyclopropylmethyl)-1H-indol-2-yl)-3-(2-hydroxyethyl)-4-methoxybenzo[b]thiophene-6-carbonyl)piperidin-3-yl)carbamate

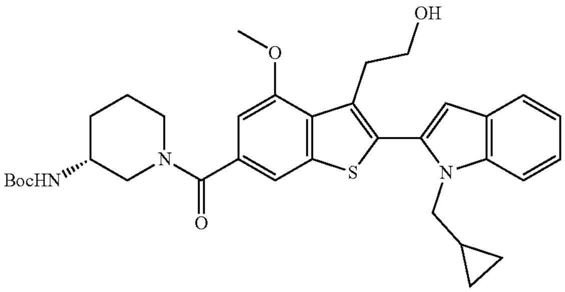 [SMILES: COc1cc(C(=O)N2CCC[C@@H](NC(=O)OC(C)(C)C)C2)cc2sc(-c3cc4ccccc4n3CC3CC3)c(CCO)c12]

To a stirred solution of Intermediate 622K (50 mg, 0.12 mmol) in DMF (3 mL) was added tert-butyl (R)-piperidin-3-ylcarbamate (35 mg, 0.18 mmol), HATU (67.65 mg, 0.18 mmol) and DIEA (0.06 mL, 0.36 mmol) at 0° C. The resulting mixture was stirred at room temperature for 1 h. The mixture was quenched with $NH_4Cl$ (sat. aq) (10 mL) at 0° C., and extracted with ethyl acetate (2×30 mL). The combined organic extracts were washed with brine (50 mL), dried over anhydrous sodium sulfate, and concentrated under vacuum. The obtained orange sticky oil was purified by column chromatography (DCM/MeOH=20/1) to afford the title compound (65 mg, 90%) as a yellow oil. LCMS (ESI, m/z): 604 $[M+H]^+$.

Example 622

(R)-(3-aminopiperidin-1-yl)(2-(1-(cyclopropylmethyl)-1H-indol-2-yl)-3-(2-hydroxyethyl)-4-methoxybenzo[b]thiophen-6-yl)methanone

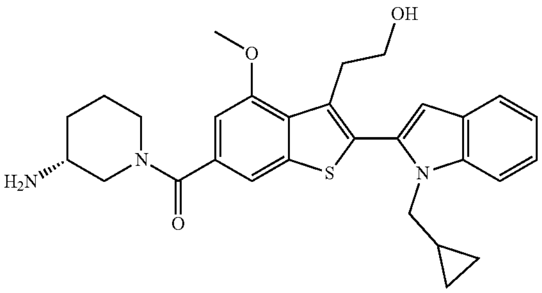 [SMILES: COc1cc(C(=O)N2CCC[C@@H](N)C2)cc2sc(-c3cc4ccccc4n3CC3CC3)c(CCO)c12]

To a stirred solution of Intermediate 622L (65 mg, 0.11 mmol) in DCM (2.5 mL) was added TFA (0.7 mL) at room temperature. The resulting mixture was stirred at room temperature for 1 h. The reaction was monitored by TLC and LCMS. The mixture was concentrated under vacuum. The obtained orange sticky oil was purified using preparative RP-HPLC to afford the title compound (11.3 mg, 44%) as a pink solid. LCMS m/z: 504.3 $[M+H]^+$. LCMS retention time: 1.583 min. (Method J). $^1H$ NMR (400 MHz, DMSO-$d_6$) δ 8.12-7.84 (m, 3H), 7.68-7.54 (m, 3H), 7.24 (t, J=7.6 Hz, 1H), 7.12 (t, J=7.5 Hz, 1H), 7.00 (s, 1H), 6.71 (s, 1H), 4.05 (d, J=6.8 Hz, 2H), 3.98 (s, 3H), 3.76-3.44 (m, 4H), 3.60 (t, J=7.6 Hz, 3H), 3.22-3.15 (m, 1H), 3.05 (t, J=7.5 Hz, 2H), 2.08-2.00 (m, 1H), 1.81-1.71 (m, 1H), 1.64-1.53 (m, 2H), 1.06-0.98 (m, 1H), 0.42-0.30 (m, 2H), 0.21-0.11 (m, 2H).

Example 623

((3R,5R)-3-amino-5-fluoropiperidin-1-yl)(2-(1-(cyclopropylmethyl)-1H-indol-2-yl)-3-(2-hydroxyethyl)-4-methoxybenzo[b]thiophen-6-yl)methanone

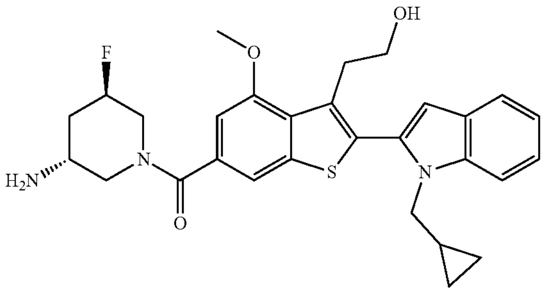 [SMILES: COc1cc(C(=O)N2C[C@H](N)C[C@@H](F)C2)cc2sc(-c3cc4ccccc4n3CC3CC3)c(CCO)c12]

Example 623 was prepared by a similar method to Example 622 from common Intermediate 622J. The compound was purified using preparative RP-HPLC to afford the title compound (22.3 mg, 46%) as a white solid. LCMS m/z: 522.25 $[M+H]^+$. LCMS retention time: 2.648 min. (Method J). $^1H$ NMR (400 MHz, DMSO-$d_6$) δ 8.38-8.12 (m, 3H), 7.66-7.59 (m, 3H), 7.23 (t, J=7.1 Hz, 1H), 7.11 (t, J=7.6 Hz, 1H), 6.96 (s, 1H), 6.71 (s, 1H), 5.13-4.69 (m, 2H), 4.62 (t, J=5.6 Hz, 1H), 4.04 (d, J=6.8 Hz, 2H), 3.97 (s, 3H), 3.63-3.54 (m, 2H), 3.44-3.36 (m, 2H), 3.24-3.92 (m, 2H), 3.04 (t, J=7.4 Hz, 2H), 2.44-2.31 (m, 1H), 2.03-1.77 (m, 1H), 1.09-0.95 (m, 1H), 0.43-0.29 (m, 2H), 0.22-0.11 (m, 2H).

Example 624

((3R,5R)-3-amino-5-fluoropiperidin-1-yl)(2-(1-(cyclopropylmethyl)-6-methoxy-1H-indol-2-yl)-3-(2-hydroxyethyl)-4-methoxybenzo[b]thiophen-6-yl)methanone

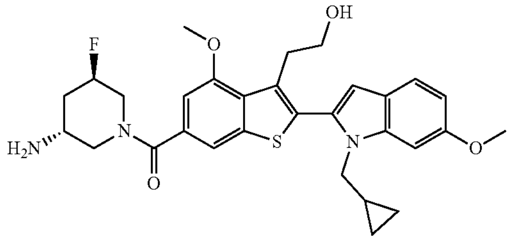 [SMILES: COc1ccc2cc(-c3sc4cc(C(=O)N5C[C@H](N)C[C@@H](F)C5)cc(OC)c4c3CCO)n(CC3CC3)c2c1]

Example 624 was prepared by a similar method to Example 622 from common Intermediate 622G. The compound was purified using preparative RP-HPLC to afford the title compound (10.2 mg, 29.8%) as a white solid. LCMS m/z: 552.25 $[M+H]^+$. LCMS retention time: 2.501 min. (Method J). $^1H$ NMR (400 MHz, DMSO-$d_6$) δ 8.40-8.10 (m, 3H), 7.62 (s, 1H), 7.48 (d, J=8.6 Hz, 1H), 7.14 (s, 1H), 6.95 (s, 1H), 6.77 (dd, J=8.6, 2.2 Hz, 1H), 6.63 (s, 1H), 5.14-4.56 (m, 3H), 4.02 (d, J=6.8 Hz, 2H), 3.98 (s, 3H), 3.84 (s, 3H), 3.59 (t, J=8.0 Hz, 2H), 3.49-3.35 (m, 2H), 3.05 (t, J=7.5 Hz, 2H), 2.45-2.34 (m, 1H), 2.08-1.81 (m, 1H), 1.08-0.96 (m, 1H), 0.41-0.31 (m, 2H), 0.22-0.12 (m, 2H).

Example 625

(R)-(3-(2-aminoethyl)-2-(1-(cyclopropylmethyl)-1H-indol-2-yl)-4-methoxybenzo[b]thiophen-6-yl)(3-aminopiperidin-1-yl)methanone

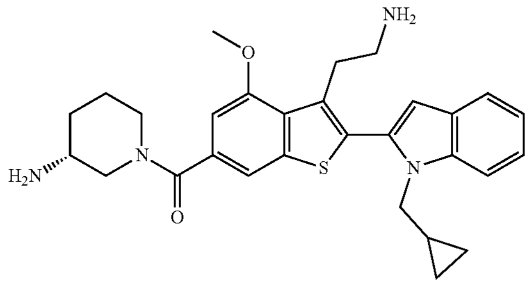 [SMILES: COc1cc(C(=O)N2CCC[C@@H](N)C2)cc2sc(-c3cc4ccccc4n3CC3CC3)c(CCN)c12]

Intermediate 625A (R)-2-(6-(3-((tert-butoxycarbonyl)amino)piperidine-1-carbonyl)-2-(1-(cyclopropylmethyl)-1H-indol-2-yl)-4-methoxybenzo[b]thiophen-3-yl)ethyl methanesulfonate

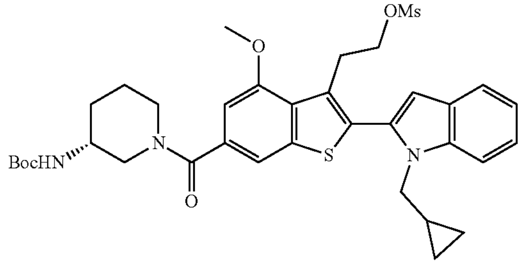 [SMILES: COc1cc(C(=O)N2CCC[C@@H](NC(=O)OC(C)(C)C)C2)cc2sc(-c3cc4ccccc4n3CC3CC3)c(CCOS(C)(=O)=O)c12]

To a stirred solution of Intermediate 622L (80 mg, 0.13 mmol) in DCM (2 mL) was added TEA (54 mg, 0.53 mmol) and MSCI (31 mg, 0.27 mmol) at 0° C. The resulting reaction solution was stirred at this temperature for 1 h. The reaction was monitored by TLC and LCMS. It was then quenched with saturated aqueous $NaHCO_3$ (15 mL), extracted with DCM (2×30 mL). The organic layer was washed with brine (30 mL), dried over anhydrous sodium sulfate and concentrated under vacuum. The residue was purified by column chromatography (MeOH/DCM=1/50) to afford the title compound (78 mg, 86%) as a colorless oil. LCMS (ESI, m/z): 682 $[M+H]^+$.

Intermediate 625B tert-butyl (R)-(1-(3-(2-azidoethyl)-2-(1-(cyclopropylmethyl)-1H-indol-2-yl)-4-methoxybenzo[b]thiophene-6-carbonyl)piperidin-3-yl)carbamate

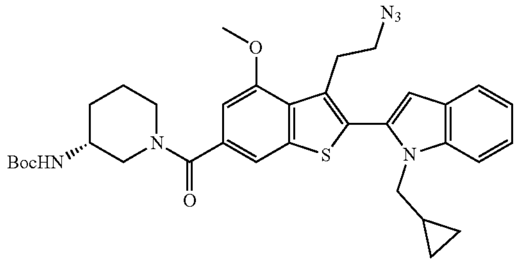 [SMILES: COc1cc(C(=O)N2CCC[C@@H](NC(=O)OC(C)(C)C)C2)cc2sc(-c3cc4ccccc4n3CC3CC3)c(CCN=[N+]=[N-])c12]

To a stirred solution of Intermediate 625A (78 mg, 0.11 mmol) in DMF (1.5 mL) was added $NaN_3$ (18 mg, 0.29 mmol) at room temperature. The resulting reaction mixture was heated to 70° C. for 5 h. The reaction was monitored by TLC and LCMS. The mixture was cooled to room temperature. It was extracted with ethyl acetate (2×30 mL). The combined organic extracts were washed with water (50 mL) and brine (50 mL), dried over anhydrous sodium sulfate, concentrated under vacuum. The residue was purified by Prep-TLC (petroleum ether/ethyl acetate=2:1) to afford title compound (62 mg, 86%) as a colorless oil. LCMS (ESI, m/z): 629 $[M+H]^+$.

Intermediate 625C tert-butyl (R)-(1-(3-(2-aminoethyl)-2-(1-(cyclopropylmethyl)-1H-indol-2-yl)-4-methoxybenzo[b]thiophene-6-carbonyl)piperidin-3-yl)carbamate

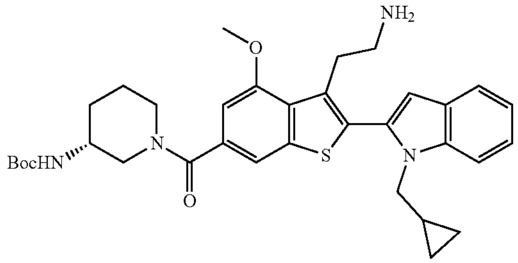 [SMILES: COc1cc(C(=O)N2CCC[C@@H](NC(=O)OC(C)(C)C)C2)cc2sc(-c3cc4ccccc4n3CC3CC3)c(CCN)c12]

To a stirred solution of Intermediate 625B (52 mg, 0.08 mmol) in methanol (5 mL) was added Pd/C (10 mg) under nitrogen atmosphere. The resulting mixture was stirred at room temperature for 2 h under an atmosphere of hydrogen. The reaction was monitored by TLC and LCMS. The solution was filtered through a celite pad and the pad was washed with methanol (50 mL). The filtrate was evaporated to dryness to give crude product which was purified by Prep-TLC (DCM/MeOH=5:1) to afford the title compound (30 mg, 60%) as a colorless oil. LCMS (ESI, m/z): 603 $[M+H]^+$.

Example 625

(R)-(3-(2-aminoethyl)-2-(1-(cyclopropylmethyl)-1H-indol-2-yl)-4-methoxybenzo[b]thiophen-6-yl)(3-aminopiperidin-1-yl)methanone

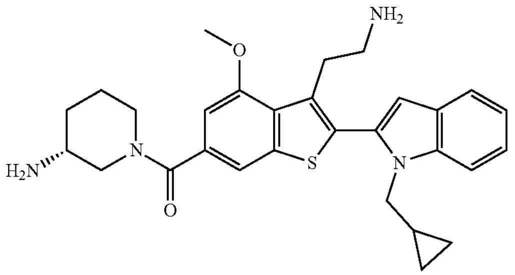 [SMILES: COc1cc(C(=O)N2CCC[C@@H](N)C2)cc2sc(-c3cc4ccccc4n3CC3CC3)c(CCN)c12]

To a stirred solution of Intermediate 625C (30 mg, 0.05 mmol) in DCM (2 mL) was added TFA (0.6 mL) at 0° C. The resulting mixture was stirred at room temperature for 1 h. The reaction was monitored by TLC and LCMS. The reaction solution was concentrated under vacuum. The obtained orange sticky oil was purified by preparative RP-HPLC to afford the title compound (20.5 mg, 82%) as a light yellow solid. LCMS m/z: 503.3 $[M+H]^+$. LCMS retention time: 1.379 min. (Method J). $^1H$ NMR (400 MHz, DMSO-$d_6$) δ 8.08-7.90 (m, 3H), 7.87-7.77 (m, 3H), 7.71-7.62 (m, 3H), 7.26 (t, J=8.0 Hz, 1H), 7.14 (t, J=7.5 Hz, 1H), 7.03 (s, 1H), 6.77 (s, 1H), 4.16-3.96 (m, 3H), 4.02 (s, 3H), 3.32-3.22 (m, 2H), 3.20-3.12 (m, 4H), 3.08-2.96 (m, 3H), 2.07-2.00 (m, 1H), 1.79-1.72 (m, 1H), 1.66-1.55 (m, 2H), 1.04-0.96 (m, 1H), 0.42-0.33 (m, 2H), 0.20-0.14 (m, 2H).

Example 626

(R)-(3-aminopiperidin-1-yl)(2-(1-(cyclopropylmethyl)-1H-indol-2-yl)-4-(2-hydroxyethyl)-3-methylbenzo[b]thiophen-6-yl)methanone

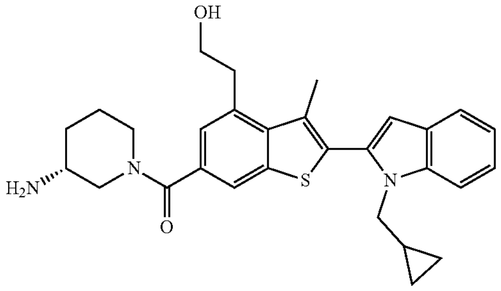 [SMILES: Cc1c(-c2cc3ccccc3n2CC2CC2)sc2cc(C(=O)N3CCC[C@@H](N)C3)cc(CCO)c12]

Intermediate 626A (Z)-3-ethoxycarbonyl-4-(4-methyl-2-thienyl)but-3-enoic acid

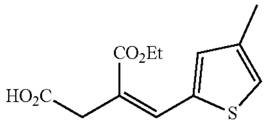 [SMILES: CCOC(=O)/C(=C\c1cc(C)cs1)CC(=O)O]

To a stirred solution of 4-methylthiophene-2-carbaldehyde (5 g, 39.63 mmol) in tert-butanol (20 mL) were added t-BuOK (1 M in THF) (47 mL, 47.55 mmol) and diethyl butanedioate (13.8 g, 79.25 mmol) in portions at room temperature under nitrogen atmosphere. The resulting mixture was stirred at 50° C. for 2 h. LCMS showed the reaction was complete, and the mixture was diluted with water (100 mL), then adjusted to pH 6-7 with HCl (2 M). The resulting mixture was extracted with ethyl acetate (2×200 mL). The combined organic extracts were washed with brine (2×50 mL), dried over anhydrous sodium sulfate, and concentrated under vacuum. The crude product was purified by silica column chromatography (Petroleum ether/ethyl acetate=10:1) to afford the title compound (8 g, 79%) as a yellow solid. LCMS (ESI, m/z): 255 $[M+H]^+$.

Intermediate 626B

Ethyl 4-acetoxy-3-methyl-benzothiophene-6-carboxylate

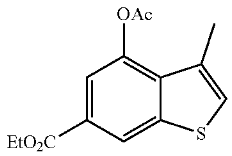

To a stirred solution of Intermediate 626A (8 g, 31.46 mmol) in Acetic anhydride (50 mL) were added NaOAc (11.6 g, 141.57 mmol) in portions at room temperature under nitrogen atmosphere. The resulting mixture was stirred at 70° C. for 2 h. The reaction was monitored by TLC and LCMS. LCMS showed the reaction was complete, and the solids were filtered out. The resulting mixture was concentrated. The crude product was purified by silica column chromatography (petroleum ether/ethyl acetate=10:1) to afford the title compound (6 g, 68%) as a yellow solid. LCMS (ESI, m/z): 279 $[M+H]^+$.

Intermediate 626C

Ethyl 4-hydroxy-3-methylbenzo[b]thiophene-6-carboxylate

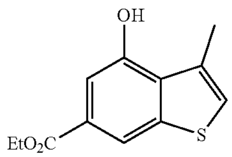 [SMILES: CCOC(=O)c1cc(O)c2c(C)csc2c1]

To a stirred solution of Intermediate 626B (6 g, 21.56 mmol) in Ethanol (50 mL) were added $K_2CO_3$ (5.9 g, 43.12 mmol) in portions at room temperature under nitrogen atmosphere. The resulting mixture was stirred at 70° C. for 2 h. LCMS showed the reaction was complete, and the solids were filtered out. The resulting mixture was concentrated. The crude product was purified by silica column chromatography (Petroleum ether/ethyl acetate=2:1) to afford the title compound (4 g, 78%) as a yellow solid. LCMS (ESI, m/z): 237 $[M+H]^+$.

Intermediate 626D

Ethyl 3-methyl-4-(trifluoromethylsulfonyloxy)benzo[b]thiophene-6-carboxylate

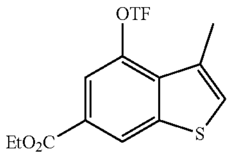

To a stirred solution of Intermediate 626C (4 g, 16.93 mmol) in DCM (50 mL) were added $Et_3N$ (7.1 mL, 50.79 mmol) and $Tf_2O$ (4.27 mL, 25.39 mmol) in portions at 0° C. under nitrogen atmosphere. The resulting mixture was stirred at room temperature for 2 h. The reaction was monitored by TLC and LCMS. The reaction was quenched by adding water (100 mL) and extracted with DCM (3×100 mL). The combined organic extracts were washed with brine (2×100 mL), dried over anhydrous sodium sulfate, and concentrated under vacuum. The crude product was purified by silica column chromatography (Petroleum ether/ethyl acetate=4:1) to afford the title compound (3.9 g, 62%) as a yellow solid. LCMS (ESI, m/z): 369 $[M+H]^+$.

Intermediate 626E

Ethyl 3-methyl-4-vinylbenzo[b]thiophene-6-carboxylate

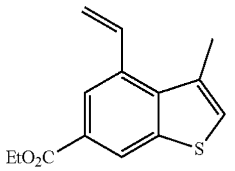

To a stirred solution of Intermediate 626D (3.9 g, 10.59 mmol) in 1,4-Dioxane (80 mL) and Water (16 mL) were added 4,4,5,5-tetramethyl-2-vinyl-1,3,2-dioxaborolane (3.3 g, 21.18 mmol), $Pd(PPh_3)_4$ (0.86 g, 0.74 mmol) and $K_3PO_4$ (8.98 g, 42.35 mmol) in portions at room temperature under nitrogen atmosphere. The resulting mixture was stirred at 80° C. for 4 h under nitrogen atmosphere. The reaction was monitored by TLC and LCMS. The reaction was quenched by adding water (100 mL) and extracted with ethyl acetate (3×100 mL). The combined organic extracts were washed with brine (2×200 mL), dried over anhydrous sodium sulfate, and concentrated under vacuum. The crude product was purified by silica column chromatography (Petroleum ether/ethyl acetate=4:1) to afford the title compound (2.38 g, 91%) as a yellow oil. LCMS (ESI, m/z): 247 $[M+H]^+$.

Intermediate 626F

Ethyl 4-(2-hydroxyethyl)-3-methylbenzo[b]thiophene-6-carboxylate

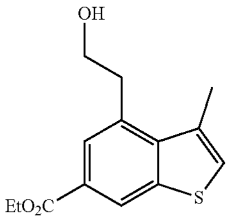 [SMILES: CCOC(=O)c1cc(CCO)c2c(C)csc2c1]

To a stirred solution of Intermediate 626E (500 mg, 2.03 mmol) in THF (10 mL) were added $BH_3$ (1 M in THF) (4 mL) in portions at 0° C. under nitrogen atmosphere. The resulting mixture was stirred at room temperature for 2 h. The reaction was monitored by TLC and LCMS. The reaction was quenched by adding water (30 mL) at 0° C. and extracted with ethyl acetate (3×30 mL). The combined organic extracts were washed with brine (2×50 mL), dried over anhydrous sodium sulfate, and concentrated under vacuum. The crude product was purified by silica column chromatography (Petroleum ether/ethyl acetate=2:1) to afford the title compound (300 mg, 55%) as a yellow solid. LCMS (ESI, m/z): 265 $[M+H]^+$.

Intermediate 626G

Ethyl 2-bromo-4-(2-hydroxyethyl)-3-methylbenzo[b]thiophene-6-carboxylate

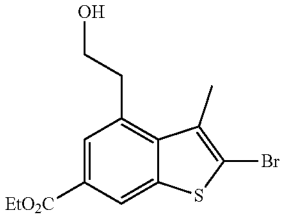 [SMILES: CCOC(=O)c1cc(CCO)c2c(C)c(Br)sc2c1]

To a stirred solution of Intermediate 626F (300 mg, 1.13 mmol) in chloroform (10 mL) was added $Br_2$ (190 mg, 1.19 mmol) in portions at 0° C. under nitrogen atmosphere. The resulting mixture was stirred at room temperature for 0.5 h. The reaction was monitored by TLC and LCMS. The reaction was quenched by adding water (20 mL) and extracted with DCM (3×30 mL). The combined organic extracts were washed with brine (2×50 mL), dried over anhydrous sodium sulfate, and concentrated under vacuum. The crude product was purified by silica column chromatography (petroleum ether/ethyl acetate=2:1) to afford the title compound (260 mg, 66%) as a yellow oil. LCMS (ESI, m/z): 343 $[M+H]^+$.

Intermediate 626H

Ethyl 2-bromo-4-(2-((tert-butyldiphenylsilyl)oxy)ethyl)-3-methylbenzo[b]thiophene-6-carboxylate

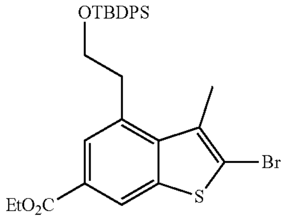

To a stirred solution of Intermediate 626G (260 mg, 0.76 mmol) in DCM (5 mL) were added imidazole (206 mg, 3.03 mmol) and TBDPSCl (0.24 mL, 0.91 mmol) in portions at room temperature under nitrogen atmosphere. The resulting mixture was stirred at room temperature for 2 h. The reaction was monitored by TLC and LCMS. The reaction was quenched by adding water (30 mL) and extracted with DCM (3x30 mL). The combined organic extracts were dried over anhydrous sodium sulphate and concentrated under vacuum. The crude product was purified by silica column chromatography (Petroleum ether/ethyl acetate=10:1) to afford the title compound (400 mg, 90%) as a yellow solid. LCMS (ESI, m/z): 581 $[M+H]^+$.

Intermediate 626I tert-Butyl 2-(4-(2-((tert-butyldiphenylsilyl)oxy)ethyl)-6-(ethoxycarbonyl)-3-methylbenzo[b]thiophen-2-yl)-1H-indole-1-carboxylate

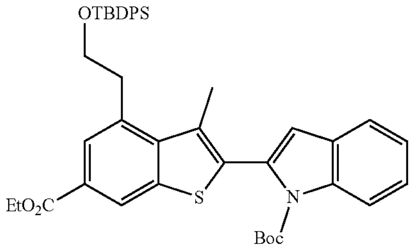

To a stirred solution of Intermediate 626H (400 mg, 0.69 mmol) in 1,4-dioxane (5 mL) and water (1 mL) were added $Pd(PPh_3)_4$ (60 mg, 0.05 mmol), $K_3PO_4$ (440 mg, 2.06 mmol) and (1-tert-butoxycarbonylindol-2-yl)boronic acid (197 mg, 0.76 mmol) at room temperature under nitrogen atmosphere. The resulting mixture was stirred at 80° C. for 4 h under nitrogen atmosphere. The reaction was monitored by TLC and LCMS. The reaction was quenched by adding water (20 mL) and extracted with ethyl acetate (3x20 mL). The combined organic extracts were dried over anhydrous sodium sulphate and concentrated under vacuum. The crude product was purified by silica column chromatography (petroleum ether/ethyl acetate=4:1) to afford the title compound (490 mg, 99%) as a yellow oil. LCMS (ESI, m/z): 718 $[M+H]^+$.

Intermediate 626J

Ethyl 4-(2-(tert-butyldiphenylsilyloxy)ethyl)-2-(1H-indol-2-yl)-3-methylbenzo[b]thiophene-6-carboxylate

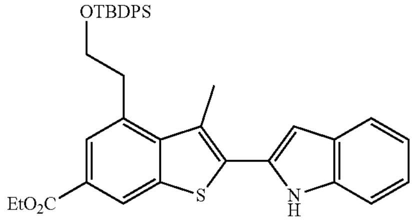

Intermediate 626I (490 mg, 0.68 mmol) and silica gel (5 g) was dissolved in moderate DCM. Prior to the sealed stirring, the reagent should evaporate the solvent, and react under vacuum condition at 90° C. in oil bath. After 30 min stirring, the LCMS and TLC revealed that the reaction was complete. The crude product was finally purified by column chromatography using ethyl acetate as the eluent to afford the title compound (420 mg, 97%) as yellow solid. LCMS (ESI, m/z): 618 $[M+H]^+$.

Intermediate 626K 2-(1-(Cyclopropylmethyl)-1H-indol-2-yl)-4-(2-hydroxyethyl)-3-methylbenzo[b]thiophene-6-carboxylic acid

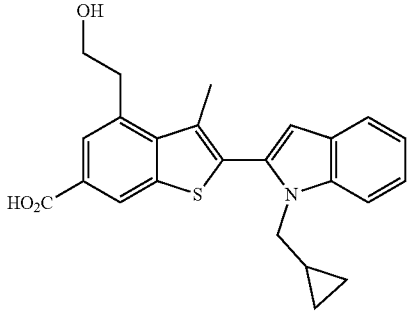 [SMILES: Cc1c(-c2cc3ccccc3n2CC2CC2)sc2cc(C(=O)O)cc(CCO)c12]

To a stirred solution of Intermediate 626J (460 mg, 0.74 mmol) in DMF (10 mL) were added NaH (53 mg, 2.23 mmol) at 0° C. The resulting mixture was stirred at 0° C. for 0.5 h. Then to this was added bromomethylcyclopropane (150 mg, 1.12 mmol) in portions at 0° C. under nitrogen atmosphere. The resulting mixture was stirred at room temperature for 2 h. The reaction was monitored by TLC and LCMS. The reaction was quenched by adding water (5 mL). The mixture was purified directly by flash column chromatography on C18 silica (Mobile Phase A: water (0.5% TFA), Mobile Phase B: acetonitrile; Flow rate: 100 mL/min; Gradient: 30% B to 40% B in 2 min; UV: 254/210 nm) to obtain the title compound (130 mg, 43%) as a yellow oil. LCMS (ESI, m/z): 406 $[M+H]^+$.

Intermediate 626L tert-Butyl (R)-(1-(2-(1-(cyclopropylmethyl)-1H-indol-2-yl)-4-(2-hydroxyethyl)-3-methylbenzo[b]thiophene-6-carbonyl)piperidin-3-yl)carbamate

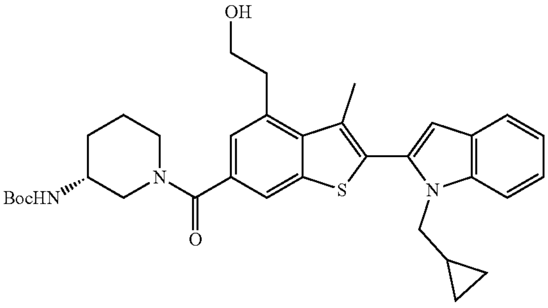 [SMILES: Cc1c(-c2cc3ccccc3n2CC2CC2)sc2cc(C(=O)N3CCC[C@@H](NC(=O)OC(C)(C)C)C3)cc(CCO)c12]

To a stirred solution of Intermediate 626K (60 mg, 0.15 mmol) in DMF (1.5 mL) were added tert-butyl (R)-piperidin-3-ylcarbamate (44 mg, 0.22 mmol), HATU (84 mg, 0.22 mmol) and DIEA (0.04 mL, 0.44 mmol) in portions at room temperature under nitrogen atmosphere. The resulting mixture was stirred at room temperature for 2 h. The reaction was monitored by LCMS. The reaction was then quenched by adding water (20 mL) and extracted with ethyl acetate (3×20 mL). The combined organic extracts were washed with brine (2×40 mL), dried over anhydrous sodium sulphate and concentrated under vacuum. The crude product was purified by silica column chromatography (DCM/methanol=20:1) to afford the title compound (75 mg, 86%) as a yellow solid. LCMS (ESI, m/z): 588 $[M+H]^+$.

Example 626

(R)-(3-Aminopiperidin-1-yl)(2-(1-(cyclopropylmethyl)-1H-indol-2-yl)-4-(2-hydroxyethyl)-3-methylbenzo[b]thiophen-6-yl)methanone

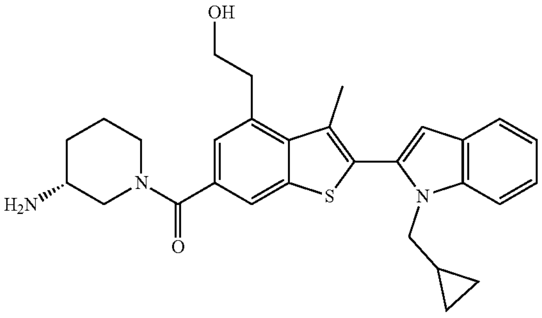 [SMILES: Cc1c(-c2cc3ccccc3n2CC2CC2)sc2cc(C(=O)N3CCC[C@@H](N)C3)cc(CCO)c12]

To a stirred solution of Intermediate 626L (70 mg, 0.12 mmol) in DCM (3 mL) was added TFA (1 mL) at room temperature under nitrogen atmosphere. The resulting mixture was stirred at room temperature for 0.5 h. The reaction solution was concentrated in vacuo and product was purified using preparative RP-HPLC to afford the title compound (29.6 mg, 50%) as a white solid. LCMS m/z: 488.25 $[M+H]^+$. LCMS retention time: 1.736 min. (Method J). $^1H$ NMR (400 MHz, DMSO-$d_6$+$D_2O$) δ 7.91 (s, 1H), 7.62 (d, J=7.9 Hz, 1H), 7.59 (d, J=8.2 Hz, 1H), 7.29 (s, 1H), 7.24 (t, J=7.2 Hz, 1H), 7.11 (t, J=7.5 Hz, 1H), 6.63 (s, 1H), 4.34-4.16 (m, 1H), 4.00 (t, J=6.7 Hz, 3H), 3.71 (t, J=7.0 Hz, 2H), 3.57-3.40 (m, 1H), 3.32 (t, J=7.0 Hz, 2H), 3.28-3.11 (m, 3H), 2.49 (s, 3H), 2.09-1.97 (m, 1H), 1.81-1.47 (m, 3H), 1.01-0.89 (m, 1H), 0.36-0.27 (m, 2H), 0.11-0.01 (m, 2H).

Example 627

(R)-(3-Aminopiperidin-1-yl)(2-(1-(cyclopropylmethyl)-1H-indol-2-yl)-4-(hydroxymethyl)-3-methylbenzo[b]thiophen-6-yl)methanone

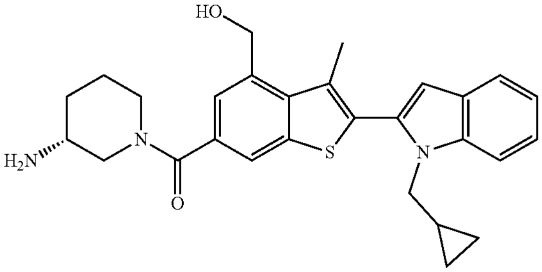 [SMILES: Cc1c(-c2cc3ccccc3n2CC2CC2)sc2cc(C(=O)N3CCC[C@@H](N)C3)cc(CO)c12]

Intermediate 627A

Ethyl 4-(hydroxymethyl)-3-methylbenzo[b]thiophene-6-carboxylate

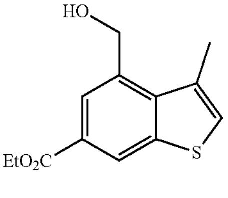 [SMILES: CCOC(=O)c1cc(CO)c2c(C)csc2c1]

To a stirred solution of Intermediate 626D (500 mg, 1.36 mmol) in 1,4-Dioxane (10 mL) and water (2 mL) were added potassium; acetoxymethyl(trifluoro)boranuide (488 mg, 2.71 mmol), $Pd_2(dba)_3$ (124 mg, 0.14 mmol), Ruphos (126 mg, 0.27 mmol) and $Na_2CO_3$ (431 mg, 4.07 mmol) in portions at room temperature under nitrogen atmosphere. The resulting mixture was stirred at 100° C. for 12 h under nitrogen atmosphere. The reaction was monitored by LCMS. The reaction was then quenched by adding water (20 mL) and extracted with ethyl acetate (2×20 mL). The combined organic extracts were washed with brine (2×30 mL), dried over anhydrous sodium sulphate and concentrated under vacuum. The crude product was purified by silica column chromatography (petroleum ether/ethyl acetate=2:1) to afford the title compound (260 mg, 76%) as a yellow solid. LCMS (ESI, m/z): 251 $[M+H]^+$.

Intermediate 627B

Ethyl 4-(((tert-butyldiphenylsilyl)oxy)methyl)-3-methylbenzo[b]thiophene-6-carboxylate

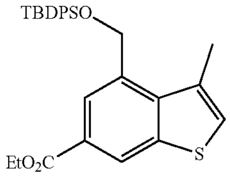

To a stirred solution of Intermediate 627A (260 mg, 1.04 mmol) in DCM (5 mL) were added imidazole (282 mg, 4.15 mmol) and TBDPSCl (0.32 mL, 1.25 mmol) in portions at room temperature under nitrogen atmosphere. The resulting mixture was stirred at room temperature for 2 h. The reaction was monitored by TLC and LCMS. The reaction was quenched by adding water (30 mL) and extracted with DCM (3x30 mL). The combined organic extracts were dried over anhydrous sodium sulphate and concentrated under vacuum. The crude product was purified by silica column chromatography (petroleum ether/ethyl acetate=4:1) to afford the title compound (400 mg, 78%) as a yellow solid. LCMS (ESI, m/z): 489 $[M+H]^+$.

Intermediate 627C

Ethyl 2-bromo-4-(((tert-butyldiphenylsilyl)oxy) methyl)-3-methylbenzo[b]thiophene-6-carboxylate

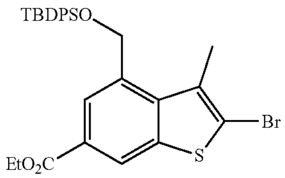

To a stirred solution of Intermediate 627B (400 mg, 0.82 mmol) in chloroform (5 mL) were added $Br_2$ (0.11 mL, 0.9 mmol) in portions at room temperature under nitrogen atmosphere. The resulting mixture was stirred at room temperature for 2 h. The reaction was monitored by TLC and LCMS. The reaction was quenched by adding water (30 mL) and extracted with ethyl acetate (3x30 mL). The combined organic extracts were dried over anhydrous sodium sulphate and concentrated under vacuum. The crude product was purified by silica column chromatography (petroleum ether/ethyl acetate=4:1) to afford the title compound (360 mg, 77%) as a yellow solid. LCMS (ESI, m/z): 567 $[M+H]^+$.

Intermediate 627D tert-Butyl 2-(4-(((tert-butyldiphenylsilyl)oxy) methyl)-6-(ethoxycarbonyl)-3-methylbenzo[b]thiophen-2-yl)-1H-indole-1-carboxylate

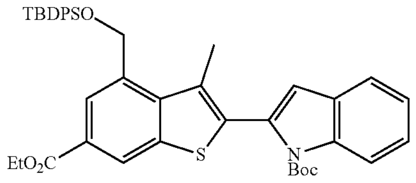

To a stirred solution of Intermediate 627C (360 mg, 0.63 mmol) in 1,4-dioxane (10 mL) and water (2 mL) were added (1-tert-butoxycarbonylindol-2-yl)boronic acid (331 mg, 1.27 mmol), $K_3PO_4$ (403 mg, 1.9 mmol) and $Pd(PPh_3)_4$ (53 mg, 0.06 mmol) in portions at room temperature under nitrogen atmosphere. The resulting mixture was stirred at 80° C. for 4 h under nitrogen atmosphere. The reaction was monitored by TLC and LCMS. The reaction was quenched by adding water (30 mL) and extracted with ethyl acetate (3x30 mL). The combined organic extracts were dried over anhydrous sodium sulphate and concentrated under vacuum. The crude product was purified by silica column chromatography (petroleum ether/ethyl acetate=4:1) to afford the title compound (400 mg, 89%) as a yellow solid. LCMS (ESI, m/z): 704 $[M+H]^+$.

Intermediate 627E

Ethyl 4-(((tert-butyldiphenylsilyl)oxy)methyl)-2-(1H-indol-2-yl)-3-methylbenzo[b]thiophene-6-carboxylate

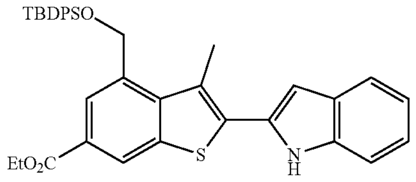

Intermediate 627D (400 mg, 0.57 mmol) and silica gel (4 g) was dissolved in moderate DCM. Prior to the sealed stirring, the reagent should evaporate the solvent, and react under vacuum condition at 90° C. in oil bath. After 30 min stirring, the LCMS and TLC revealed that the reaction was complete. The crude product was finally purified by column chromatography using ethyl acetate as the eluent to afford the title compound (250 mg, 72.8%) as yellow solid. LCMS (ESI, m/z): 604 $[M+H]^+$.

Intermediate 627F 2-(1-(Cyclopropylmethyl)-1H-indol-2-yl)-4-(hydroxymethyl)-3-methylbenzo[b]thiophene-6-carboxylic acid

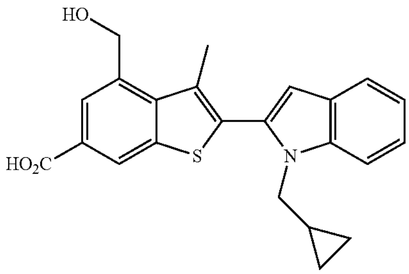 [SMILES: Cc1c(-c2cc3ccccc3n2CC2CC2)sc2cc(C(=O)O)cc(CO)c12]

To a stirred solution of Intermediate 627E (100 mg, 0.17 mmol) in DMF (3 mL) was added NaH (13 mg, 0.33 mmol) in portions at 0° C. and was warmed to room temperature under nitrogen atmosphere. The resulting mixture was stirred at room temperature for 0.5 h. Then was added bromomethylcyclopropane (44 mg, 0.33 mmol) in portions at 0° C. and was warmed to room temperature under nitrogen atmosphere. The resulting mixture was stirred at room temperature for 2 h. LCMS showed no starting material. Then the mixture was added methanol (1 mL) and NaOH (6 mg, 0.17 mmol) by turns. The resulting mixture was stirred at room temperature for 30 min TLC showed the reaction was complete, and the mixture was concentrated to clean up methanol and then adjusted to pH 5-6 with hydrochloric acid and extracted with ethyl acetate (2×20 mL). The combined organic extracts were washed with brine (20 mL), dried over anhydrous sodium sulphate and concentrated under vacuum. The crude product was purified by silica column chromatography (DCM/methanol=10:1) to afford the title compound (41 mg, 63.2%) as yellow oil. LCMS (ESI, m/z): 392 $[M+H]^+$.

Intermediate 627G tert-Butyl (R)-(1-(2-(1-(cyclopropylmethyl)-1H-indol-2-yl)-4-(hydroxymethyl)-3-methylbenzo[b]thiophene-6-carbonyl)piperidin-3-yl)carbamate

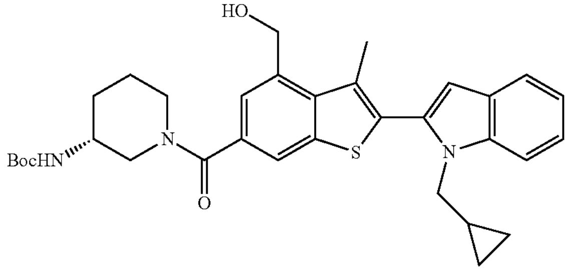 [SMILES: Cc1c(-c2cc3ccccc3n2CC2CC2)sc2cc(C(=O)N3CCC[C@@H](NC(=O)OC(C)(C)C)C3)cc(CO)c12]

To a stirred solution of Intermediate 627F (41 mg, 0.10 mmol) in DMF (3 mL) were added HATU (59 mg, 0.16 mmol) in portions at room temperature under nitrogen atmosphere. The resulting mixture was stirred at room temperature for 0.5 h. Then to this was added DIEA (40 mg, 0.31 mmol) and tert-butyl (R)-piperidin-3-ylcarbamate (31 mg, 0.16 mmol) in portions at 0° C. The resulting mixture was stirred at room temperature for 1 h. The reaction was monitored by LCMS. The reaction was then quenched by adding water (20 mL) and extracted with ethyl acetate (2×20 mL). The combined organic extracts were washed with brine (2×30 mL), dried over anhydrous sodium sulphate and concentrated under vacuum. The crude product was purified by silica column chromatography (DCM/methanol=30:1) to afford the title compound (39 mg, 64.9%) as light-yellow oil. LCMS (ESI, m/z): 574 $[M+H]^+$.

Example 627

(R)-(3-Aminopiperidin-1-yl)(2-(1-(cyclopropylmethyl)-1H-indol-2-yl)-4-(hydroxymethyl)-3-methylbenzo[b]thiophen-6-yl)methanone

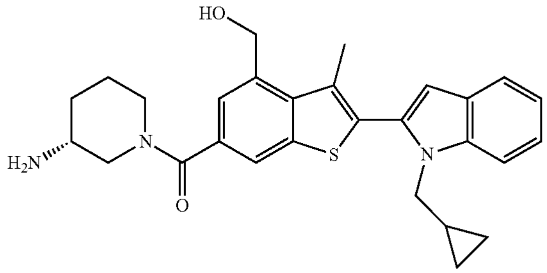 [SMILES: Cc1c(-c2cc3ccccc3n2CC2CC2)sc2cc(C(=O)N3CCC[C@@H](N)C3)cc(CO)c12]

To a stirred solution of Intermediate 627G (39 mg, 0.07 mmol) in DCM (2 mL) was added TFA (0.5 mL) in portions at room temperature under nitrogen atmosphere. The resulting mixture was stirred at room temperature for 0.5 h. The reaction was monitored by LCMS and the mixture was concentrated in vacuo. Then added a little amount water, methanol and sodium methoxide stirring for 20 min. TLC and LCMS showed the reaction was complete, and the product was purified using preparative RP-HPLC to afford the title compound (12.4 mg, 38.4%) as white solid. LCMS m/z: 474.30 $[M+H]^+$. LCMS retention time: 1.737 min. (Method J). $^1H$ NMR (400 MHz, $CD_3OD-d_4$): δ 7.97 (d, J=1.3 Hz, 1H), 7.60 (d, J=7.9 Hz, 1H), 7.57-7.49 (m, 2H), 7.28-7.21 (m, 1H), 7.10 (t, J=7.3 Hz, 1H), 6.61 (s, 1H), 5.16 (s, 2H), 4.05 (d, J=6.7 Hz, 2H), 3.50-3.35 (m, 2H), 2.60 (s, 3H), 2.25-2.16 (m, 1H), 1.88-1.68 (m, 3H), 1.11-1.01 (m, 1H), 0.41-0.32 (m, 2H), 0.11-0.04 (m, 2H).

Example 628

((3R,5R)-3-Amino-5-fluoropiperidin-1-yl)(2-(1-(cyclopropylmethyl)-6-methoxy-1H-indol-2-yl)-3-(2-hydroxyethyl)-4-methoxybenzofuran-6-yl)methanone

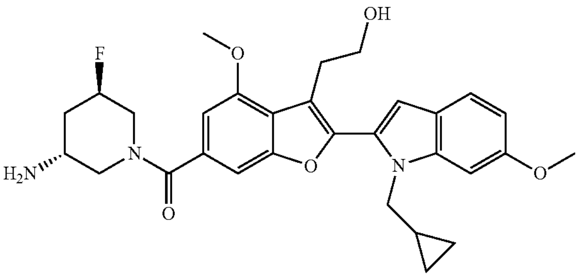 [SMILES: COc1ccc2cc(-c3oc4cc(C(=O)N5C[C@H](N)C[C@@H](F)C5)cc(OC)c4c3CCO)n(CC3CC3)c2c1]

Intermediate 628A (Z)-4-(4-Bromofuran-2-yl)-3-(ethoxycarbonyl)but-3-enoic acid

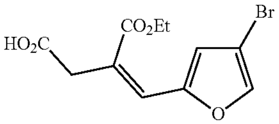 [SMILES: CCOC(=O)/C(=C\c1cc(Br)co1)CC(=O)O]

To a solution of 4-bromofuran-2-carbaldehyde (5 g, 28.7 mmol) in tert-butanol (200 mL) was added diethyl butanedioate (20 g, 114.8 mmol) and t-BuOK (1 M in THF) (57 mL, 57.4 mmol). The resulting mixture was stirred at 50° C. for 1 h under nitrogen atmosphere. The reaction was monitored by LCMS. The mixture was diluted with water (150 mL), then adjusted to pH 6-7 with HCl (2 M). The resulting mixture was extracted with ethyl acetate (2×200 mL). The combined organic extracts were washed with brine (2×300 mL), dried over anhydrous sodium sulfate and concentrated under vacuum. The residue was purified by silica gel column chromatography (petroleum ether/ethyl acetate=5:1) to afford the title compound (5.2 g, 60%) as yellow oil. LCMS (ESI, m/z): 303 $[M+H]^+$.

Intermediate 628B

Ethyl 4-acetoxy-3-bromobenzofuran-6-carboxylate

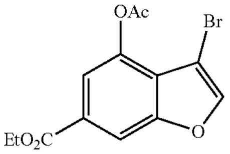 [SMILES: CCOC(=O)c1cc(OC(C)=O)c2c(Br)coc2c1]

To a solution of Intermediate 628A (5.2 g, 17.1 mmol) in $Ac_2O$ (60 mL) was added NaOAc (6.3 g, 77.4 mmol). The resulting mixture was stirred at 70° C. for 1 h under nitrogen atmosphere. The reaction was monitored by LCMS. The solids were filtered out. The resulting mixture was concentrated under vacuum. The residue was purified by silica gel column chromatography (petroleum ether/ethyl acetate=5:1) to afford the title compound (3.4 g, 61%) as yellow oil. LCMS (ESI, m/z): 327 $[M+H]^+$.

Intermediate 628C

Ethyl 3-bromo-4-hydroxybenzofuran-6-carboxylate

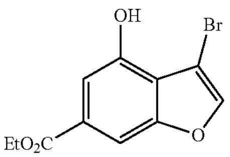

To a solution of Intermediate 628B (3.4 g, 10.4 mmol) in ethanol (50 mL) was added $K_2CO_3$ (2.9 g, 20.8 mmol). The resulting mixture was stirred at 70° C. for 1 h under nitrogen atmosphere. The reaction was monitored by LCMS. The solids were filtered out. The resulting mixture was concentrated under vacuum. The residue was purified by silica gel column chromatography (petroleum ether/ethyl acetate=2:1) to afford the title compound (2 g, 67%) as a yellow solid. LC/MS m/z: 285 $[M+H]^+$.

Intermediate 628D

Ethyl 3-bromo-4-methoxybenzofuran-6-carboxylate

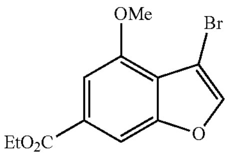 [SMILES: CCOC(=O)c1cc(OC)c2c(Br)coc2c1]

To a solution of Intermediate 628C (2 g, 7 mmol) in DMF (25 mL) was added $K_2CO_3$ (2.9 g, 21 mmol) and MeI (1.5 g, 10.5 mmol). The resulting mixture was stirred at room temperature for 1 h. The reaction was monitored by LCMS. The solids were filtered out. The resulting mixture was concentrated. The residue was purified by silica gel column chromatography (petroleum ether/ethyl acetate=5:1) to afford the title compound (1.8 g, 86%) as a white solid. LC/MS m/z: 299 $[M+H]^+$.

Intermediate 628E

Ethyl 4-methoxy-3-vinylbenzofuran-6-carboxylate

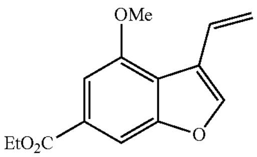 [SMILES: C=Cc1coc2cc(C(=O)OCC)cc(OC)c12]

To a solution of Intermediate 628D (1.8 g, 6 mmol) in 1,4-Dioxane (30 mL) and Water (6 mL) were added 4,4,5,5-tetramethyl-2-vinyl-1,3,2-dioxaborolane (1.8 g, 12 mmol), $Pd(PPh_3)_4$ (693 mg, 0.6 mmol) and $K_3PO_4$ (5.9 g, 24 mmol) in portions at room temperature under nitrogen atmosphere. The resulting mixture was stirred at 80° C. for 4 h under nitrogen atmosphere. The reaction was monitored by TLC and LCMS. The reaction was quenched by adding water (50 mL) and extracted with ethyl acetate (3×50 mL). The combined organic extracts were washed with brine (2×100 mL), dried over anhydrous sodium sulphate and concentrated under vacuum. The crude product was purified by silica column chromatography (petroleum ether/ethyl acetate=5:1) to afford the title compound (1.2 g, 81%) as a yellow solid. LC/MS m/z: 247 $[M+H]^+$.

Intermediate 628F

Ethyl 3-(2-hydroxyethyl)-4-methoxybenzofuran-6-carboxylate

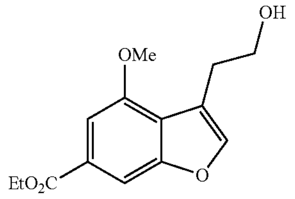 [SMILES: CCOC(=O)c1cc(OC)c2c(CCO)coc2c1]

To a solution of Intermediate 628E (1.2 g, 4.8 mmol) in THF (30 mL) was added $BH_3$ (1 M in THF) (5.7 mL, 5.7 mmol) in portions at 0° C. under nitrogen atmosphere. The resulting mixture was stirred at room temperature for 2 h. Then to this was added $H_2O_2$ (30%) (3 mL) dropwise at 0° C. under nitrogen atmosphere. The resulting mixture was stirred at room temperature for 1 h. The reaction was monitored by TLC and LCMS. The reaction was quenched by adding $Na_2SO_3$ (aq.) (40 mL) at 0° C. and extracted with ethyl acetate (2×50 mL). The combined organic extracts were washed with NaOH (1 M) (50 mL), dried over anhydrous sodium sulphate and concentrated under vacuum. The crude product was purified by silica column chromatography (petroleum ether/ethyl acetate=2:1) to afford the title compound (700 mg, 55%) as a yellow solid. LC/MS m/z: 265 $[M+H]^+$.

Intermediate 628G

Ethyl 2-bromo-3-(2-hydroxyethyl)-4-methoxybenzofuran-6-carboxylate

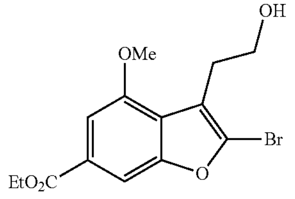 [SMILES: CCOC(=O)c1cc(OC)c2c(CCO)c(Br)oc2c1]

To a solution of Intermediate 628F (700 mg, 2.6 mmol) in Chloroform (10 mL) was added $Br_2$ (437 mg, 2.7 mmol) in portions at 0° C. under nitrogen atmosphere. The resulting mixture was stirred at room temperature for 0.5 h. The reaction was monitored by TLC and LCMS. The reaction was quenched by adding water (30 mL) and extracted with DCM (3×30 mL). The combined organic extracts were washed with brine (2×50 mL), dried over anhydrous sodium sulphate and concentrated under vacuum. The crude product was purified by silica column chromatography (petroleum ether/ethyl acetate=2:1) to afford the title compound (600 mg, 67%) as a yellow oil. LC/MS m/z: 343 $[M+H]^+$.

Intermediate 628H

Ethyl 2-bromo-3-(2-((tert-butyldiphenylsilyl)oxy)ethyl)-4-methoxybenzofuran-6-carboxylate

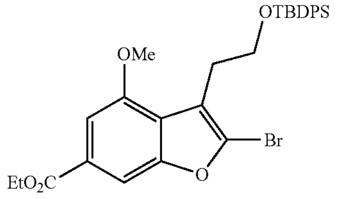

To a solution of Intermediate 628G (600 mg, 1.7 mmol) in DCM (10 mL) were added imidazole (578 mg, 8.5 mmol) and TBDPSCl (560 mg, 2 mmol) in portions at 0° C. under nitrogen atmosphere. The resulting mixture was stirred at room temperature for 2 h. The reaction was monitored by TLC and LCMS. The reaction was quenched by adding water (30 mL) and extracted with DCM (3×30 mL). The combined organic extracts were dried over anhydrous sodium sulphate and concentrated under vacuum. The crude product was purified by silica column chromatography (petroleum ether/ethyl acetate=10:1) to afford the title compound (950 mg, 96%) as a yellow solid. LC/MS m/z: 581 $[M+H]^+$.

Intermediate 628I tert-Butyl 2-(3-(2-((tert-butyldiphenylsilyl)oxy)ethyl)-6-(ethoxycarbonyl)-4-methoxybenzofuran-2-yl)-6-methoxy-1H-indole-1-carboxylate

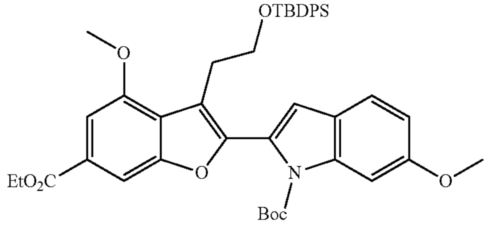

To a solution of Intermediate 628H (150 mg, 0.26 mmol) in THF (2 ml) and water (1 ml) were added (1-tert-butoxycarbonyl-6-methoxy-indol-2-yl)boronic acid (90 mg, 0.31 mmol), $Pd(PPh_3)_4$ (29 mg, 0.03 mmol) and $Na_2CO_3$ (54 mg, 0.52 mmol) under a nitrogen atmosphere. The resulting mixture was stirred at 80° C. for 6 h. The reaction was monitored by LCMS. The reaction was extracted with ethyl acetate (3×1 ml). The combined organic extracts were washed with water (3 ml) and brine (3 ml), dried over anhydrous sodium sulfate and concentrated under vacuum. The crude product was purified by column chromatography (petroleum ether/ethyl acetate=10:1) to afford the title compound (165 mg, 85%) as white solid. LC/MS m/z: 748 $[M+H]^+$.

Intermediate 628J

Ethyl 3-(2-((tert-butyldiphenylsilyl)oxy)ethyl)-4-methoxy-2-(6-methoxy-1H-indol-2-yl)benzofuran-6-carboxylate

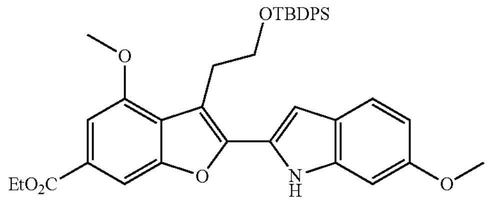

To a solution of Intermediate 628I (180 mg, 0.24 mmol) in DCM was added silica gel (2 g) and stirred evenly. Then DCM was removed under vacuum. The resulting solid mixture was stirred at 90° C. for 1 h. The reaction was monitored by LCMS. The crude product was purified by column chromatography (petroleum ether/ethyl acetate=1:2) to afford the title compound (150 mg, 96%) as a white solid. LC/MS m/z: 648 $[M+H]^+$.

Intermediate 628K

Ethyl 3-(2-((tert-butyldiphenylsilyl)oxy)ethyl)-2-(1-(cyclopropylmethyl)-6-methoxy-1H-indol-2-yl)-4-methoxybenzofuran-6-carboxylate

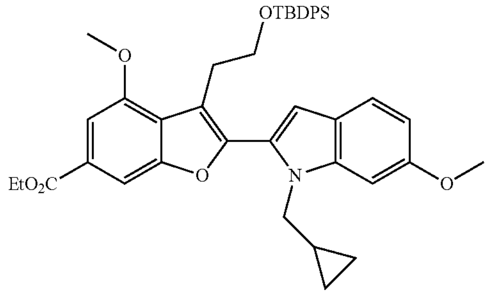

To a solution of Intermediate 628J (70 mg, 0.11 mmol) in DMF (2 ml) was added NaH (8 mg, 0.22 mmol) in portions at 0° C. The resulting mixture was stirred at room temperature for 0.5 h. To the above mixture was added bromomethylcyclopropane (21 mg, 0.16 mmol) drop wise at 0° C. The resulting mixture was stirred for 2 h at room temperature. The reaction was monitored by LCMS. The reaction was quenched by adding water (10 ml), extracted with ethyl acetate (3×10 ml). The combined organic extracts were washed with water (30 ml) and brine (30 ml), dried over anhydrous sodium sulfate and concentrated under vacuum. The crude product was purified by column chromatography (petroleum ether/ethyl acetate=1:1) to afford the title compound (75 mg, 97%) as a yellow solid. LC/MS m/z: 702 $[M+H]^+$.

Intermediate 628L

Ethyl 2-(1-(cyclopropylmethyl)-6-methoxy-1H-indol-2-yl)-3-(2-hydroxyethyl)-4-methoxybenzofuran-6-carboxylate

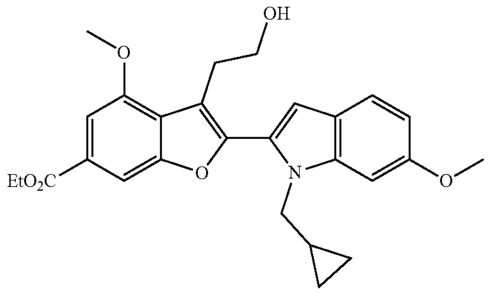 [SMILES: CCOC(=O)c1cc(OC)c2c(CCO)c(-c3cc4ccc(OC)cc4n3CC3CC3)oc2c1]

To a solution of Intermediate 628K (75 mg, 0.11 mmol) in THF (2 ml) was added 1 M TBAF in THF (1 ml). The resulting mixture was stirred at room temperature for overnight. The reaction was monitored by LCMS. the mixture was concentrated under vacuum. The crude product was purified by column chromatography (petroleum ether/ethyl acetate=5:1) to afford the title compound (45 mg, 88%) as a white solid. LC/MS m/z: 464 $[M+H]^+$ Intermediate 628M 2-(1-(Cyclopropylmethyl)-6-methoxy-1H-indol-2-yl)-3-(2-hydroxyethyl)-4-methoxybenzofuran-6-carboxylic acid

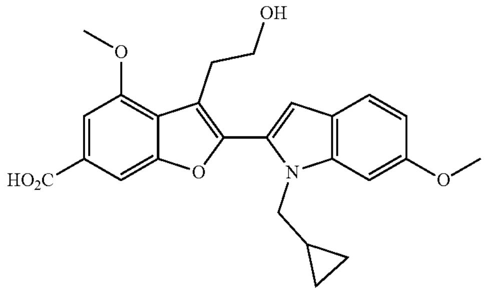 [SMILES: COc1ccc2cc(-c3oc4cc(C(=O)O)cc(OC)c4c3CCO)n(CC3CC3)c2c1]

To a solution of Intermediate 628L (93 mg, 0.20 mmol) in methanol (2 ml) was added a solution of NaOH (80 mg, 2.01 mmol) in water (1 ml). The resulting mixture was stirred at 50° C. for 1 h. The reaction was monitored by LCMS. The reaction was quenched by adding water (5 ml), adjusted to pH 6-7 with 1M HCl (0.7 ml), extracted with ethyl acetate (3×5 ml). The combined organic extracts were washed with brine (15 ml), dried over anhydrous sodium sulfate and concentrated under vacuum. The crude product was purified by column chromatography (petroleum ether/ethyl acetate=1:3) to afford the title compound (78 mg, 90%) as a yellow solid. LC/MS m/z: 436 $[M+H]^+$ Intermediate 628N tert-Butyl ((3R,5R)-1-(2-(1-(cyclopropylmethyl)-6-methoxy-1H-indol-2-yl)-3-(2-hydroxyethyl)-4-methoxybenzofuran-6-carbonyl)-5-fluoropiperidin-3-yl)carbamate

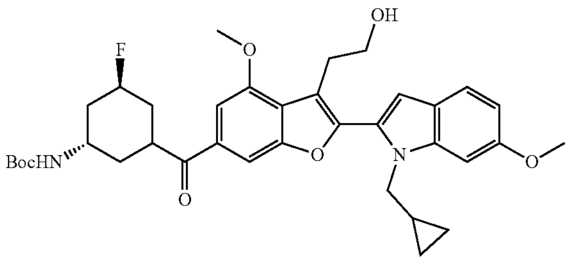 [SMILES: COc1ccc2cc(-c3oc4cc(C(=O)C5C[C@H](F)C[C@@H](NC(=O)OC(C)(C)C)C5)cc(OC)c4c3CCO)n(CC3CC3)c2c1]

To a solution of Intermediate 628M (45 mg, 0.10 mmol) in DMF (2 ml) was added HATU (58 mg, 0.16 mmol). The resulting mixture was stirred at room temperature for 0.5 h. Then to this above mixture was added DIEA (0.05 ml, 0.31 mmol) and tert-butyl ((3R,5R)-5-fluoropiperidin-3-yl)carbamate (27 mg, 0.12 mmol) at 0° C. under nitrogen atmosphere. The resulting mixture was stirred at room temperature for 1 h. The reaction was monitored by LCMS. The reaction was quenched by adding water (5 ml), extracted with ethyl acetate (10 ml). The combined organic extracts were washed with water (10 ml) and brine (10 ml), dried over anhydrous sodium sulfate and concentrated under vacuum. The crude product was purified by column chromatography (petroleum ether/ethyl acetate=1:2) to afford the title compound (45 mg, 71%) as yellow oil. LC/MS m/z: 636 $[M+H]^+$ Example 628

((3R,5R)-3-Amino-5-fluoropiperidin-1-yl)(2-(1-(cyclopropylmethyl)-6-methoxy-1H-indol-2-yl)-3-(2-hydroxyethyl)-4-methoxybenzofuran-6-yl)methanone

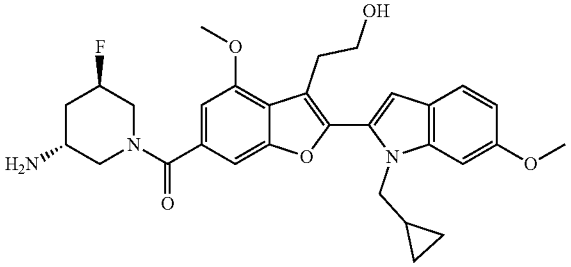 [SMILES: COc1ccc2cc(-c3oc4cc(C(=O)N5C[C@H](N)C[C@@H](F)C5)cc(OC)c4c3CCO)n(CC3CC3)c2c1]

To a solution of Intermediate 628N (45 mg, 0.07 mmol) in DCM (2 ml) was added TFA (1 ml). The resulting mixture was stirred at room temperature for 0.5 h. The reaction was monitored by LCMS. The solvent was evaporated under vacuum. The crude product was purified by preparative to afford the title compound (13.5 mg, 36%). LC-MS m/z: 536.2 $[M+H]^+$. LC-MS retention time: 2.528 min. (Method K). $^1H$ NMR (300 MHz, DMSO-$d_6$) δ ppm 8.23 (s, 3H), 7.28 (s, 1H), 7.22 (d, J=8.0 Hz, 1H), 7.03 (t, J=7.9 Hz, 1H), 6.91 (s, 1H), 6.86 (s, 1H), 6.80 (d, J=8.0 Hz, 1H), 5.08-4.86 (m, 1H), 4.82-4.65 (m, 2H), 4.34 (d, J=7.0 Hz, 2H), 3.96 (s, 3H), 3.94 (s, 3H), 3.73 (t, J=12.0 Hz, 2H), 3.49-3.27 (m, 4H), 2.95 (t, J=12.0 Hz, 2H), 2.45-2.31 (m, 1H), 2.00-1.80 (m, 1H), 1.08-0.98 (m, 1H), 0.33-0.21 (m, 2H), 0.12-0.04 (m, 2H).

Example 629

((3R,5R)-3-amino-5-fluoropiperidin-1-yl)(2-(1-(cyclopropylmethyl)-1H-pyrrolo[2,3-b]pyridin-2-yl)-3-(2-hydroxyethyl)-4-methoxybenzofuran-6-yl)methanone

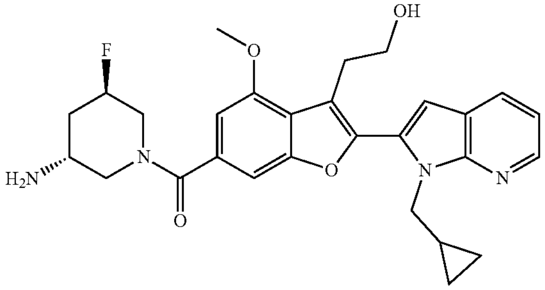 [SMILES: COc1cc(C(=O)N2C[C@H](N)C[C@@H](F)C2)cc2oc(-c3cc4cccnc4n3CC3CC3)c(CCO)c12]

Example 629 was prepared by a similar method to Example 628 from common Intermediate 628H. The compound was purified by preparative RP-HPLC to afford the title compound (31.2 mg, 51%). LC-MS m/z: 507.3 $[M+H]^+$. LC-MS retention time: 2.217 min. (Method K). $^1H$ NMR (400 MHz, DMSO-$d_6$) δ ppm 8.35-8.34 (m, 1H), 8.15-8.12 (m, 1H), 7.27-7.21 (m, 2H), 7.05 (s, 1H), 6.82 (s, 1H), 5.18-4.64 (m, 2H), 4.30 (d, J=6.8 Hz, 2H), 3.93 (s, 4H), 3.75-3.72 (m, 2H), 3.42-3.34 (m, 2H), 3.03-3.00 (m, 3H), 2.49-2.37 (m, 1H), 1.94-1.77 (m, 1H), 1.09-1.05 (m, 1H), 0.33-0.29 (m, 2H), 0.20-0.16 (m, 2H).

Example 630

((3R,5R)-3-amino-5-fluoropiperidin-1-yl)(2-(1-(cyclopropylmethyl)-1H-indol-2-yl)-3-(2-hydroxyethyl)-4-methoxybenzofuran-6-yl)methanone

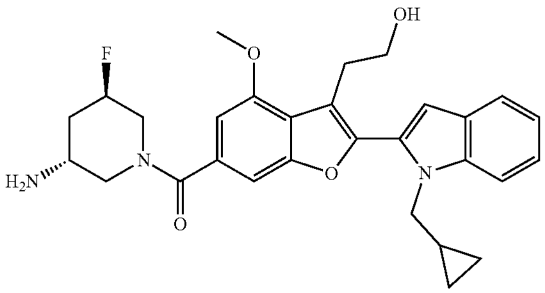

Example 630 was prepared by a similar method to Example 628 from common Intermediate 628H. The compound was purified by preparative RP-HPLC to afford the title compound (7.7 mg, 22%) as a white solid. LC-MS m/z: 506.2 $[M+H]^+$. LC-MS retention time: 2.119 min. (Method K). $^1H$ NMR (400 MHz, DMSO-$d_6$) δ ppm 7.63 (d, J=7.6

Hz, 2H), 7.27-7.22 (m, 2H), 7.13-7.11 (m, 1H), 7.09-6.97 (m, 1H), 6.82 (s, 1H), 4.78-4.72 (m, 2H), 4.63-4.37 (m, 1H), 4.20 (d, J=6.8 Hz, 2H), 3.95 (s, 4H), 3.77-3.72 (m, 2H), 3.01-2.67 (m, 5H), 2.14-1.95 (m, 3H), 1.64-1.37 (m, 1H), 1.12-1.07 (m, 1H), 0.37-0.33 (m, 2H), 0.20-0.16 (m, 2H).

Example 631

(2-(1-(cyclopropylmethyl)-1H-indol-2-yl)-3-(2-hydroxyethyl)-4-methoxybenzofuran-6-yl)((3R,5R)-3-fluoro-5-(methylamino)piperidin-1-yl)methanone

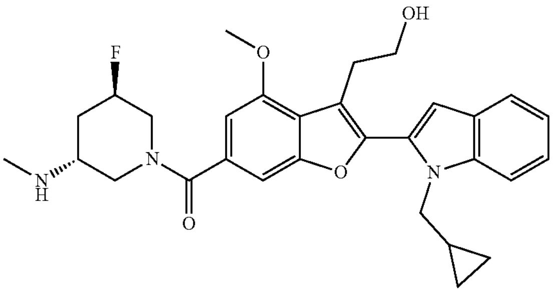 [SMILES: CN[C@@H]1C[C@@H](F)CN(C(=O)c2cc(OC)c3c(CCO)c(-c4cc5ccccc5n4CC4CC4)oc3c2)C1]

Intermediate 631A ethyl 3-(2-((tert-butyldiphenylsilyl)oxy)ethyl)-2-(1H-indol-2-yl)-4-methoxybenzofuran-6-carboxylate

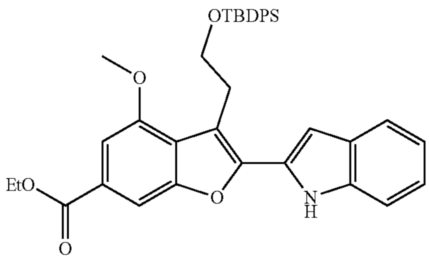

To a solution of Intermediate 628H (142 mg, 0.48 mmol) and 2-(4,4,5,5-tetramethyl-1,3,2-dioxaborolan-2-yl)-1H-indole (175 mg, 0.72 mmol) in THF (7 ml) and water (1.5 ml) was added $Na_2CO_3$ (126 mg, 1.19 mmol) and Pd(dppf)$Cl_2$ (20 mg, 0.03 mmol). The mixture was stirred at 80° C. for 18 h under nitrogen atmosphere. The reaction was monitored by LCMS. The resulting solution was concentrated under vacuum. The crude product was purified by column chromatography (petroleum ether/ethyl acetate=5:1) to afford the title compound (210 mg, 71%) as a yellow oil. LC/MS m/z: 618 $[M+H]^+$.

Intermediate 631B ethyl 3-(2-((tert-butyldiphenylsilyl)oxy)ethyl)-2-(1-(cyclopropylmethyl)-1H-indol-2-yl)-4-methoxybenzofuran-6-carboxylate

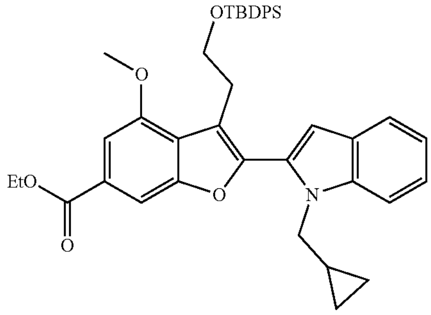

To a solution of Intermediate 631A (210 mg, 0.34 mmol) in DMF (3 ml), was added $Cs_2CO_3$ (223 mg, 0.68 mmol) and (bromomethyl)cyclopropane (69 mg, 0.51 mmol). The mixture was stirred at 50° C. for 1 h. The reaction was monitored by LCMS. The mixture was purified by flash column chromatography on C18 silica to afford the title compound (220 mg, 96%) as a yellow oil. LC/MS m/z: 672 $[M+H]^+$.

Intermediate 631C 3-(2-((tert-butyldiphenylsilyl)oxy)ethyl)-2-(1-(cyclopropylmethyl)-1H-indol-2-yl)-4-methoxybenzofuran-6-carboxylic acid

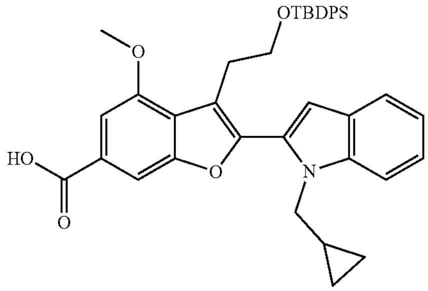

To a solution of Intermediate 631B (220 mg, 0.33 mmol) in THF (3 ml) and methanol (0.20 ml) was added NaOH (39 mg, 1.64 mmol). The mixture was stirred at room temperature for 1 h. The reaction was monitored by LCMS. The resulting solution was adjusted to pH 6-7 with 1 M HCl. The mixture was extracted with DCM/MeOH (10:1) (3×10 ml). The combined organic extracts were washed with brine (30 ml), dried over anhydrous sodium sulfate and concentrated under vacuum to afford the title compound (200 mg, 94%) as a yellow oil. LC/MS m/z: 644 $[M+H]^+$.

Intermediate 631D tert-butyl ((3R,5R)-1-(3-(2-((tert-butyldiphenylsilyl)oxy)ethyl)-2-(1-(cyclopropylmethyl)-1H-indol-2-yl)-4-methoxybenzofuran-6-carbonyl)-5-fluoropiperidin-3-yl)carbamate

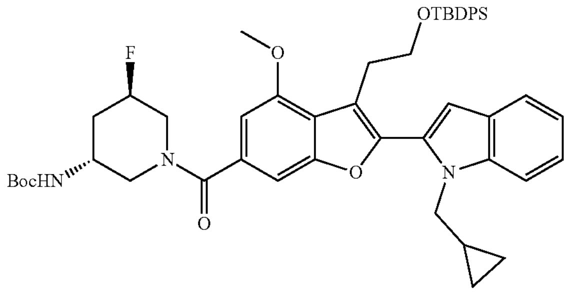

To a solution of Intermediate 631C (200 mg, 0.31 mmol) and DIEA (0.16 ml, 0.93 mmol) in DMF (5 ml) was added HATU (177 mg, 0.47 mmol) at room temperature. The mixture was stirred at room temperature for 10 minute. Then the above resulting mixture was added into a solution of tert-butyl ((3R,5R)-5-fluoropiperidin-3-yl)carbamate (67.8 mg, 0.31 mmol) in DMF (1 ml) with drop wise at room temperature. The resulting mixture was stirred at room temperature for 1 h. The reaction was monitored by LCMS. The reaction was then quenched by adding water (20 ml) and extracted with ethyl acetate (20 ml). The combined organic extracts were washed with water (2×20 ml) and brine (2×20 ml), dried over anhydrous sodium sulfate and concentrated under vacuum. The crude product was purified by column chromatography (ethyl acetate) to afford the title compound (180 mg, 69%) as a yellow solid. LC/MS m/z: 844 $[M+H]^+$.

Intermediate 631E tert-butyl ((3R,5R)-1-(3-(2-((tert-butyldiphenylsilyl)oxy)ethyl)-2-(1-(cyclopropylmethyl)-1H-indol-2-yl)-4-methoxybenzofuran-6-carbonyl)-5-fluoropiperidin-3-yl)(methyl)carbamate

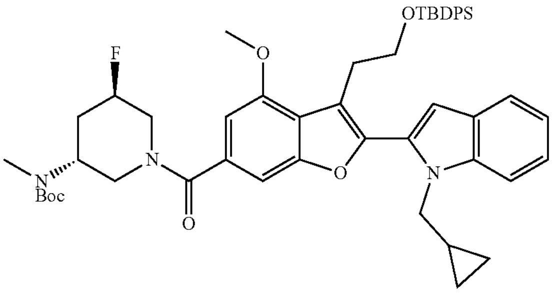

To a solution of Intermediate 631D (110 mg, 0.13 mmol) in DMF (3 ml) was added NaH (10 mg, 0.39 mmol) in portions at 0° C. The resulting mixture was stirred at room temperature for 0.5 h. To the above mixture was added MeI (0.01 ml, 0.20 mmol) drop wise at 0° C. The resulting mixture was stirred at room temperature for 1 h under nitrogen atmosphere. The reaction was monitored by LCMS. The reaction was quenched by adding water (10 ml), extracted with ethyl acetate (10 ml). The combined organic extracts were washed with water (2×10 ml) and brine (2×10 ml), dried over anhydrous sodium sulfate and concentrated under vacuum. The crude product was purified by column chromatography (ethyl acetate) to afford the title compound (100 mg, 90%) as a yellow solid. LC/MS m/z: 858 $[M+H]^+$.

Example 631

(2-(1-(cyclopropylmethyl)-1H-indol-2-yl)-3-(2-hydroxyethyl)-4-methoxybenzofuran-6-yl)((3R,5R)-3-fluoro-5-(methylamino)piperidin-1-yl)methanone

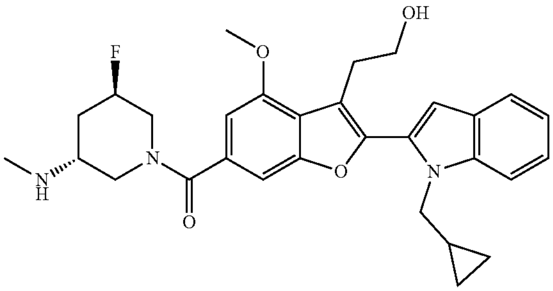 [SMILES: CN[C@@H]1C[C@@H](F)CN(C(=O)c2cc(OC)c3c(CCO)c(-c4cc5ccccc5n4CC4CC4)oc3c2)C1]

To a solution of Intermediate 631E (100 mg, 0.13 mmol) in THF (2 ml) was added HF-Py (13 mg, 0.13 mmol) at 0° C. The resulting solution was stirred at room temperature for 1 h. The reaction was monitored by LCMS. The resulting solution was concentrated under vacuum. The crude product thus obtained was purified using RP-HPLC to afford the title compound (33.9 mg, 50%) as a white solid. LC-MS m/z: 520 $[M+H]^+$. LC-MS retention time: 1.640 min. (Method K). $^1H$ NMR (400 MHz, Methanol-$d_4$) δ ppm 7.64 (s, 1H), 7.53 (d, J=8 Hz, 1H), 7.29-7.25 (m, 2H), 7.14-7.1 (m, 1H), 6.92 (s, 2H), 5.07-4.88 (m, 2H), 4.24 (d, J=6.8 Hz, 3H), 4.04 (s, 3H), 3.94-3.9 (m, 2H), 3.63-3.50 (m, 2H), 3.18-3.15 (m, 2H), 3.15-3.01 (m, 1H), 2.88-2.83 (m, 3H), 2.65 (s, 1H), 2.00-1.16 (m, 1H), 1.17-1.14 (m, 1H), 0.42-0.38 (m, 2H), 0.19-0.16 (m, 2H).

Example 632

((3R,5R)-3-amino-5-fluoropiperidin-1-yl)(2-(1-(cyclopropylmethyl)-7-methoxy-1H-indol-2-yl)-3-(2-hydroxyethyl)-4-methoxybenzofuran-6-yl)methanone

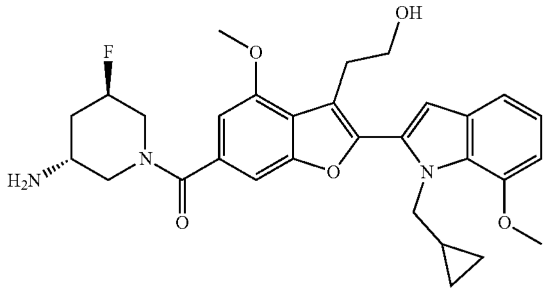 [SMILES: COc1cc(C(=O)N2C[C@H](N)C[C@@H](F)C2)cc2oc(-c3cc4cccc(OC)c4n3CC3CC3)c(CCO)c12]

Example 632 was prepared by a similar procedure to Example 628 from common Intermediate 628H. The compound was purified by RP-HPLC to afford the title compound (18.9 mg, 50%). LC-MS m/z: 536.2 [M+H]$^+$. LC-MS retention time: 1.622 min. (Method K). $^1$H NMR (300 MHz, DMSO-d$_6$) δ ppm 8.23 (s, 3H), 7.28 (s, 1H), 7.22 (d, J=8.0 Hz, 1H), 7.03 (t, J=7.9 Hz, 1H), 6.91 (s, 1H), 6.86 (s, 1H), 6.80 (d, J=8.0 Hz, 1H), 5.08-4.86 (m, 1H), 4.82-4.65 (m, 2H), 4.34 (d, J=7.0 Hz, 2H), 3.96 (s, 3H), 3.94 (s, 3H), 3.73 (t, J=12.0 Hz, 2H), 3.49-3.27 (m, 4H), 2.95 (t, J=12.0 Hz, 2H), 2.45-2.31 (m, 1H), 2.00-1.80 (m, 1H), 1.08-0.98 (m, 1H), 0.33-0.21 (m, 2H), 0.12-0.04 (m, 2H)

Example 633

4-(((2-(6-((3R,5R)-3-amino-5-fluoropiperidine-1-carbonyl)-3-(2-hydroxyethyl)-4-methoxybenzofuran-2-yl)-1-(cyclopropylmethyl)-1H-indol-7-yl)oxy)methyl)pyrrolidin-2-one

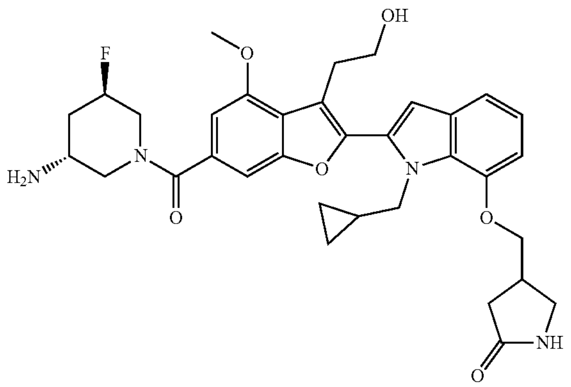 [SMILES: COc1cc(C(=O)N2C[C@H](N)C[C@@H](F)C2)cc2oc(-c3cc4cccc(OCC5CNC(=O)C5)c4n3CC3CC3)c(CCO)c12]

Intermediate 633A 7-(benzyloxy)-2-(4,4,5,5-tetramethyl-1,3,2-dioxaborolan-2-yl)-1H-indole

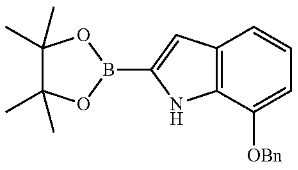 [SMILES: CC1(C)OB(c2cc3cccc(OCc4ccccc4)c3[nH]2)OC1(C)C]

To a solution of 7-(benzyloxy)-1H-indole (500 mg, 2.24 mmol) in hexane (20 ml), was added 4,4,5,5-tetramethyl-1,3,2-dioxaborolane (28 mg, 0.22 mmol), 4,4,5,5-tetramethyl-2-(4,4,5,5-tetramethyl-1,3,2-dioxaborolan-2-yl)-1,3,2-dioxaborolane (514 mg, 2.02 mmol), 4,4-Di-tert-butyl-2,2-dipyridyl (29 mg, 0.11 mmol) and Bis(1,5-cyclooctadiene) di-μ-methoxydiiridium(I) (73 mg, 0.11 mmol) under nitrogen atmosphere. The mixture was stirred at room temperature for overnight. The reaction was monitored by LCMS. The resulting solution was concentrated under vacuum. The crude product was purified by column chromatography (petroleum ether/ethyl acetate=10:1) to afford the title compound (400 mg, 51%) as a yellow solid. LC/MS m/z: 350 [M+H]$^+$.

Intermediate 633B ethyl 2-(7-(benzyloxy)-1H-indol-2-yl)-3-(2-((tert-butyldiphenylsilyl)oxy)ethyl)-4-methoxybenzofuran-6-carboxylate

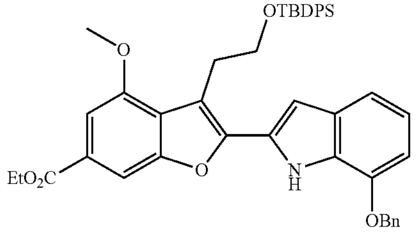

To a solution of Intermediate 633A (400 mg, 1.14 mmol) in THF (10 ml) and $H_2O$ (2 ml), was added Intermediate 628H (793 mg, 1.37 mmol), $Pd(PPh_3)_4$ (127 mg, 0.11 mmol) and $Na_2CO_3$ (242 mg, 2.28 mmol) under nitrogen atmosphere. The resulting solution was stirred at 80° C. for overnight. The reaction was monitored by LCMS. The reaction was then quenched by adding water (30 ml) and extracted with ethyl acetate (30 ml), washed with brine (10 ml), dried over anhydrous sodium sulfate and concentrated under vacuum. The crude product was purified by column chromatography (petroleum ether/ethyl acetate=5:1) to afford the title compound (650 mg, 98%) as a yellow solid. LC/MS m/z: 724 [M+H]$^+$.

Intermediate 633C ethyl 2-(7-(benzyloxy)-1-(cyclopropylmethyl)-1H-indol-2-yl)-3-(2-((tert-butyldiphenylsilyl)oxy)ethyl)-4-methoxybenzofuran-6-carboxylate

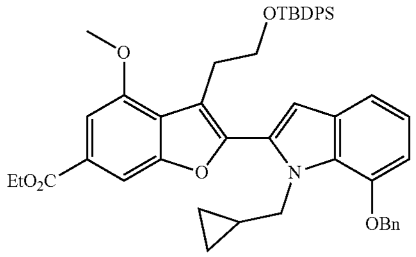

To a solution of Intermediate 633B (650 mg, 0.89 mmol) in DMF (8 ml), was added (bromomethyl)cyclopropane (180 mg, 1.33 mmol) and $Cs_2CO_3$ (870 mg, 2.67 mmol). The resulting solution was stirred at 50° C. for 1 h. The reaction was monitored by LCMS. The reaction was then quenched by adding water (30 ml) and extracted with ethyl acetate (30 ml), washed with water (2×30 ml) and brine (2×30 ml), dried over anhydrous sodium sulfate and concentrated under vacuum. The crude product was purified by column chromatography (petroleum ether/ethyl acetate=10:1) to afford the title compound (623 mg, 90%) as a light yellow solid. LC/MS m/z: 778 [M+H]$^+$.

Intermediate 633D ethyl 3-(2-((tert-butyldiphenylsilyl)oxy)ethyl)-2-(1-(cyclopropylmethyl)-7-hydroxy-1H-indol-2-yl)-4-methoxybenzofuran-6-carboxylate

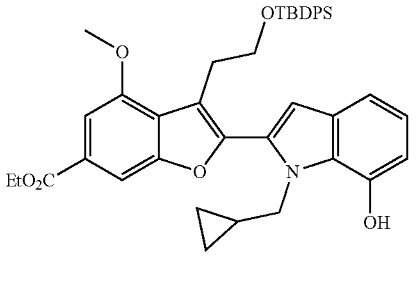

To a solution of Intermediate 633C (623 mg, 0.80 mmol) in methanol (10 ml), was added Pd/C (125 mg) under nitrogen atmosphere. The mixture was stirred at room temperature for overnight under hydrogen atmosphere. Solids were filtered out and the solvent was evaporated under vacuum. The crude product was purified by column chromatography (petroleum ether/ethyl acetate=5:1) to afford the title compound (396 mg, 72%) as a yellow solid. LC/MS m/z: 688 $[M+H]^+$.

Intermediate 633E ethyl 3-(2-((tert-butyldiphenylsilyl)oxy)ethyl)-2-(1-(cyclopropylmethyl)-7-((5-oxopyrrolidin-3-yl)methoxy)-1H-indol-2-yl)-4-methoxybenzofuran-6-carboxylate

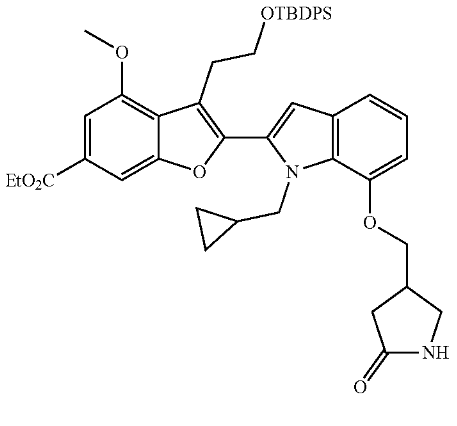

To a solution of Intermediate 633D (180 mg, 0.26 mmol) in acetone (3 ml), was added 4-(bromomethyl)pyrrolidin-2-one (93 mg, 0.52 mmol) and $Cs_2CO_3$ (256 mg, 0.78 mmol) under nitrogen atmosphere. The mixture was stirred at 60° C. for overnight. The reaction was monitored by LCMS. The reaction mixture was concentrated under vacuum. The crude product was purified by column chromatography (DCM/MeOH=10:1) to afford (130 mg, 64%) as a yellow solid. LC/MS m/z: 785 $[M+H]^+$.

Intermediate 633F 3-(2-((tert-butyldiphenylsilyl)oxy)ethyl)-2-(1-(cyclopropylmethyl)-7-((5-oxopyrrolidin-3-yl)methoxy)-1H-indol-2-yl)-4-methoxybenzofuran-6-carboxylic acid

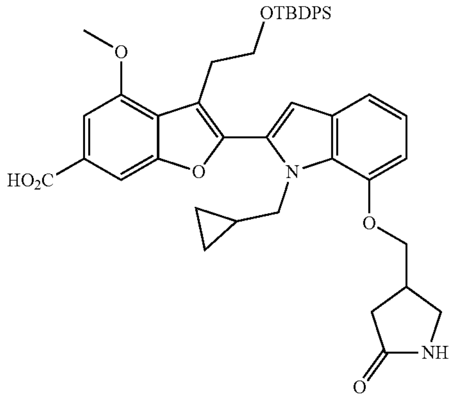

To a solution of Intermediate 633E (125 mg, 0.16 mmol) in THF (1.2 ml) and water (0.4 ml) was added LiOH (11 mg, 0.48 mmol). The resulting mixture was stirred at 50° C. for overnight. The reaction was monitored by LCMS. The resulting solution was adjusted to pH 5-6 with HCl (1 M). The mixture was extracted with DCM/MeOH (10:1) (3×10 ml). The combined organic extracts were washed with brine (30 ml), dried over anhydrous sodium sulfate and concentrated under vacuum to afford the title compound (110 mg, 91%) as a yellow oil. LC/MS m/z: 757 $[M+H]^+$.

Intermediate 633G tert-butyl ((3R,5R)-1-(3-(2-((tert-butyldiphenylsilyl)oxy)ethyl)-2-(1-(cyclopropylmethyl)-7-((5-oxopyrrolidin-3-yl)methoxy)-1H-indol-2-yl)-4-methoxybenzofuran-6-carbonyl)-5-fluoropiperidin-3-yl)carbamate

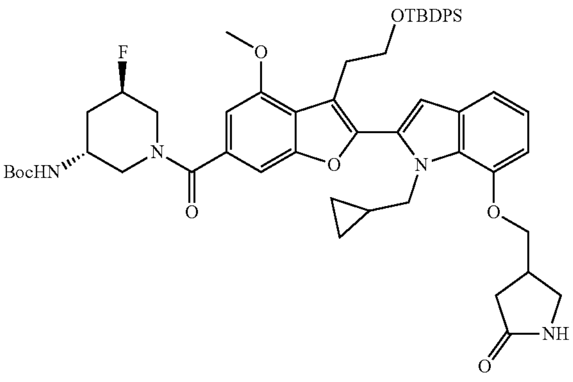

To a solution of Intermediate 633F (110 mg, 0.14 mmol) in DMF (2 ml) was added HATU (94 mg, 0.25 mmol). The resulting mixture was stirred at room temperature for 30 minute. To the above mixture was added DIEA (0.1 ml, 0.57 mmol) and tert-butyl ((3R,5R)-5-fluoropiperidin-3-yl)carbamate (47 mg, 0.21 mmol). The mixture was stirred at room temperature for 1 h. The reaction was monitored by LCMS. The reaction was then quenched by adding water (10 ml) and extracted with ethyl acetate (2×10 ml). The combined organic extracts were washed with water (2×20 ml) and brine (2×20 ml), dried over anhydrous sodium sulfate and concentrated under vacuum. The crude product was purified by column chromatography (DCM/MeOH=15:1) to afford the title compound (127 mg, 95%) as a yellow solid. LC/MS m/z: 957 $[M+H]^+$.

Intermediate 633H tert-butyl ((3R,5R)-1-(2-(1-(cyclopropylmethyl)-7-((5-oxopyrrolidin-3-yl)methoxy)-1H-indol-2-yl)-3-(2-hydroxyethyl)-4-methoxybenzofuran-6-carbonyl)-5-fluoropiperidin-3-yl)carbamate

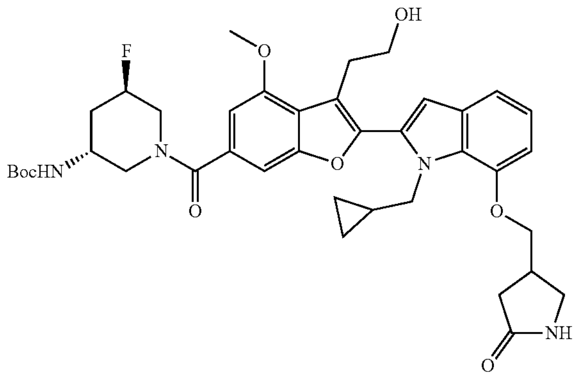 [SMILES: COc1cc(C(=O)N2C[C@H](F)C[C@@H](NC(=O)OC(C)(C)C)C2)cc2oc(-c3cc4cccc(OCC5CNC(=O)C5)c4n3CC3CC3)c(CCO)c12]

To a solution of Intermediate 633G (127 mg, 0.13 mmol) in THF (1 ml), was added TBAF (1 M in THF) (2 ml). The resulting solution was stirred at room temperature for overnight. The reaction was monitored by LCMS. The reaction was then quenched by adding water (10 ml) and extracted with ethyl acetate (10 ml), washed with water (5×10 ml) and brine (5×10 ml), dried over anhydrous sodium sulfate and concentrated under vacuum. The crude product was purified by column chromatography (DCM/MeOH=10:1) to afford the title compound (76 mg, 81%) as a yellow solid. LC/MS m/z: 719 $[M+H]^+$.

Example 633

4-(((2-(6-((3R,5R)-3-amino-5-fluoropiperidine-1-carbonyl)-3-(2-hydroxyethyl)-4-methoxybenzofuran-2-yl)-1-(cyclopropylmethyl)-1H-indol-7-yl)oxy)methyl)pyrrolidin-2-one

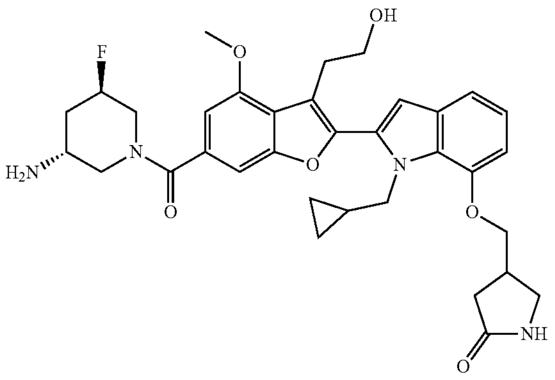 [SMILES: COc1cc(C(=O)N2C[C@H](N)C[C@@H](F)C2)cc2oc(-c3cc4cccc(OCC5CNC(=O)C5)c4n3CC3CC3)c(CCO)c12]

To a solution of Intermediate 633H (70 mg, 0.1 mmol) in DCM (2 ml), was added TFA (0.7 ml). The resulting solution was stirred for 0.5 h at room temperature. The reaction was monitored by LCMS. The solvent was evaporated under vacuum. The mixture product was diluted with MeOH and basified to PH 8 with saturated sodium bicarbonate solution. The resulting solution was stirred at room temperature for 0.5 h. The reaction was monitored by LCMS. The reaction was then quenched by adding water (10 ml) and extracted with DCM/MeOH (10:1) (3×10 ml). The combined organic extracts were washed with brine (20 ml), dried over anhydrous sodium sulfate and concentrated under vacuum. The crude product was purified by RP-HPLC to afford the title compound (39.9 mg, 64%) as a white solid. LC-MS m/z: 619.4 $[M+H]^+$. LC-MS retention time: 1.480 min. (Method K). $^1H$ NMR (300 MHz, DMSO-$d_6$+$D_2O$) δ 7.25 (t, J=8.4 Hz, 2H), 7.02 (t, J=7.8 Hz, 1H), 6.91 (s, 1H), 6.82 (t, J=7.8 Hz, 2H), 5.19-4.63 (m, 2H), 4.33 (d, J=6.0 Hz, 2H), 4.16 (d, J=6.3 Hz, 2H), 3.96 (s, 3H), 3.73 (t, J=6.9 Hz, 2H), 3.54-3.37 (m, 4H), 3.25-3.19 (m, 1H), 2.98-2.94 (m, 4H), 2.52-2.37 (m, 2H), 2.23-2.13 (m, 1H), 1.99-1.71 (m, 1H), 1.10-0.97(m, 1H), 0.32-0.23 (m, 2H). 0.07--0.02 (m, 2H).

Compounds of Examples 634 to 639 in Table 58 were obtained following a procedure similar to the preparation of a compound of Example 633 by alkylation of Intermediate 633D with appropriate alkyl halides.

TABLE 58

| Example | Structure | Name Analytical Data: LC-MS m/z [M + H]+; LC-MS retention time (LC-MS method); $^1$H NMR (MHz, solvent) |
|---|---|---|
| 634 | 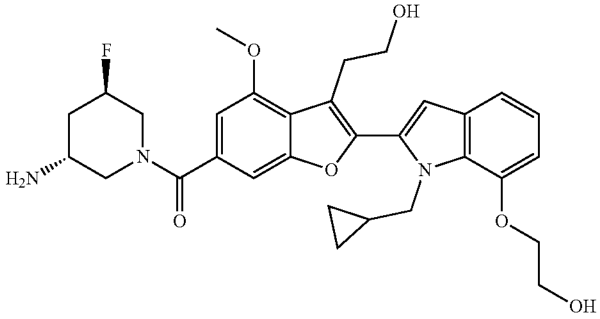 [SMILES: COc1cc(C(=O)N2C[C@H](N)C[C@@H](F)C2)cc2oc(-c3cc4cccc(OCCO)c4n3CC3CC3)c(CCO)c12] | ((3R,5R)-3-amino-5-fluoropiperidin-1-yl)(2-(1-(cyclopropylmethyl)-7-(2-hydroxyethoxy)-1H-indol-2-yl)-3-(2-hydroxyethyl)-4-methoxybenzofuran-6-yl)methanone Analytical Data: 566.1, 1.477 min. (Method K); (400MHz, DMSO-$d_6$) δ ppm 8.34 (s, 3H), 7.28 (s, 1H), 7.21 (d, J = 7.6 Hz, 1H), 6.99 (t, J = 7.8 Hz, 1H), 6.90 (s, 1H), 6.86 (s, 1H), 6.78 (d, J = 7.6 Hz, 1H), 5.04-4.77 (m, 4H), 4.42 (d, J = 6.8 Hz, 2H), 4.18-4.15 (m, 2H), 3.97 (s, 3H), 3.83-3.72 (m, 4H), 3.44-3.36 (m, 3H), 3.05-2.90 (m, 3H), 2.46-2.39 (m, 1H), 2.01-1.83 (m, 1H), 1.09-1.05 (m, 1H), 0.27-0.15 (m, 4H). |
| 635 | 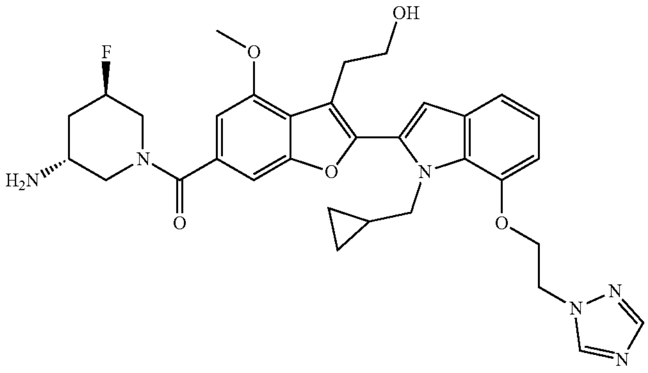 [SMILES: COc1cc(C(=O)N2C[C@H](N)C[C@@H](F)C2)cc2oc(-c3cc4cccc(OCCn5cncn5)c4n3CC3CC3)c(CCO)c12] | (2-(7-(2-(1H-1,2,4-triazol-1-yl)ethoxy)-1-(cyclopropylmethyl)-1H-indol-2-yl)-3-(2-hydroxyethyl)-4-methoxybenzofuran-6-yl)((3R,5R)-3-amino-5-fluoropiperidin-1-yl)methanone Analytical Data: 617.3; 1.426 min. (Method K); (400 MHz, DMSO-$d_6$): δ ppm 8.75 (s, 1H), 8.51-8.21 (m, 3H), 8.09 (s, 1H), 7.27 (s, 1H), 7.22 (d, J = 7.8 Hz, 1H), 7.01 (t, J = 7.8 Hz, 1H), 6.89 (s, 1H), 6.87-6.81 (m, 2H), 5.16-4.85 (m, 1H), 4.78-4.71 (m, 2H), 4.64-4.51 (m, 4H), 4.14 (d, J = 6.6 Hz, 2H), 4.05-3.98 (m, 1H), 3.95 (s, 3H), 3.72 (t, J = 7.0 Hz, 2H), 3.48-3.30 (m, 2H), 3.07-2.87 (m, 3H), 2.46-2.31 (m, 1H), 2.04-1.80 (m, 1H), 0.84-0.73 (m, 1H), 0.21-0.11 (m, 2H), −0.05-−0.14 (m, 2H). |

TABLE 58-continued

| Example | Structure | Name Analytical Data: LC-MS m/z [M + H]+; LC-MS retention time (LC-MS method); $^1$H NMR (MHz, solvent) |
|---|---|---|
| 636 | 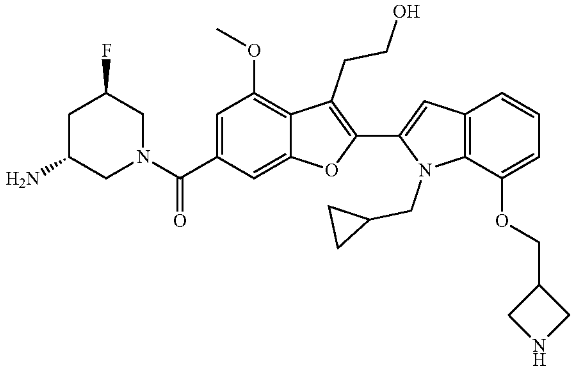 [SMILES: COc1cc(C(=O)N2C[C@H](N)C[C@@H](F)C2)cc2oc(-c3cc4cccc(OCC5CNC5)c4n3CC3CC3)c(CCO)c12] | ((3R,5R)-3-amino-5-fluoropiperidin-1-yl)(2-(7-(azetidin-3-ylmethoxy)-1-(cyclopropylmethyl)-1H-indol-2-yl)-3-(2-hydroxyethyl)-4-methoxybenzofuran-6-yl)methanone Analytical Data: 519.2; 1.325 min. (Method K); (400 MHz, DMSO-$d_6$): δ ppm 9.20 (s, 2H), 8.43-8.12 (m, 3H), 7.27-7.22 (m, 2H), 7.03 (t, J = 7.8 Hz, 1H), 6.92 (s, 1H), 6.88-6.78 (m, 2H), 5.20-4.51 (m, 4H), 4.44-4.24 (m, 4H), 4.16-4.04 (m, 2H), 3.97 (s, 3H), 3.95-3.87 (m, 3H), 3.75 (t, J = 7.0 Hz, 2H), 3.41-3.28 (m, 2H), 3.00-2.92 (m, 3H), 2.44-2.36 (m, 1H), 2.04-1.84 (m, 1H), 1.09-1.01 (m, 1H), 0.32-0.23 (m, 2H), 0.08-0.01 (m, 2H). |
| 637 | 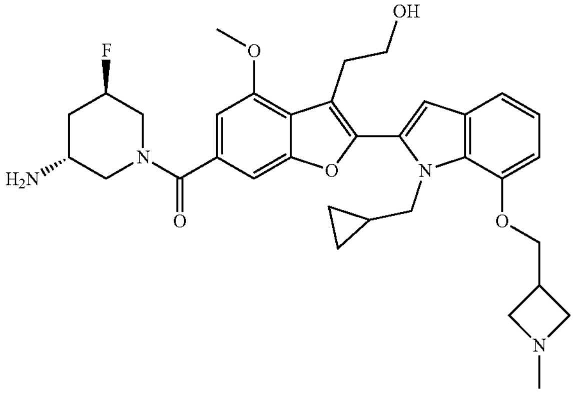 [SMILES: COc1cc(C(=O)N2C[C@H](N)C[C@@H](F)C2)cc2oc(-c3cc4cccc(OCC5CN(C)C5)c4n3CC3CC3)c(CCO)c12] | ((3R,5R)-3-amino-5-fluoropiperidin-1-yl)(2-(1-(cyclopropylmethyl)-7-((1-methylazetidin-3-yl)methoxy)-1H-indol-2-yl)-3-(2-hydroxyethyl)-4-methoxybenzofuran-6-yl)methanone Analytical Data: 605.3; 1.337 min. (Method K); (400 MHz, DMSO-$d_6$): δ ppm 10.7-10.9 (m, 1H), 8.62-8.15 (m, 3H), 7.29-7.22 (m, 2H), 7.05 (t, J = 7.8 Hz, 1H), 6.91 (s, 1H), 6.88-6.75 (m, 2H), 5.31-4.58 (m, 3H), 4.45 (d, J = 7.4 Hz, 1H), 4.37-4.21 (m, 4H), 4.17-3.99 (m, 4H), 3.96 (s, 3H), 3.72-3.67 (m, 3H), 3.34-3.22 (m, 3H), 3.01-2.89 (m, 2H), 2.87-2.79 (m, 3H), 2.43-2.31 (m, 1H), 2.03-1.81 (m, 1H), 1.12-1.00 (m, 1H), 0.34-0.22 (m, 2H), 0.07-0.01 (m, 2H). |

TABLE 58-continued

| Example | Structure | Name Analytical Data: LC-MS m/z [M + H]+; LC-MS retention time (LC-MS method); $^1$H NMR (MHz, solvent) |
|---|---|---|
| 638 | 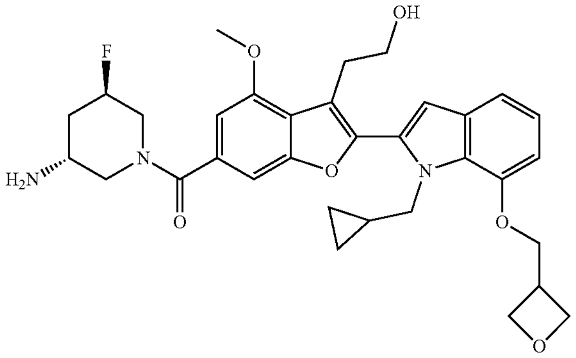 [SMILES: COc1cc(C(=O)N2C[C@H](N)C[C@@H](F)C2)cc2oc(-c3cc4cccc(OCC5COC5)c4n3CC3CC3)c(CCO)c12] | ((3R,5R)-3-amino-5-fluoropiperidin-1-yl)(2-(1-(cyclopropylmethyl)-7-(oxetan-3-ylmethoxy)-1H-indol-2-yl)-3-(2-hydroxyethyl)-4-methoxybenzofuran-6-yl)methanone Analytical Data: 592.1; 1.538 min. (Method K); (400 MHz, DMSO-$d_6$) δ ppm 8.61-8.32 (m, 3H), 7.28-7.23 (m, 1H), 7.04-7.01 (m, 1H), 6.91 (d, J = 2 Hz, 1H), 6.86-6.82 (m, 3H), 4.81-4.77 (m, 2H), 4.58-4.55 (m, 1H), 4.39-4.36 (m, 3H), 4.27-4.18 (m, 2H), 3.97 (s, 3H), 3.93-3.87 (m, 2H), 3.74-3.67 (m, 2H), 3.40-3.33 (m, 3H), 2.98-2.95 (m, 3H), 2.42-2.37 (m, 2H), 1.97-1.87 (m, 1H), 1.09-1.05 (m, 1H), 0.29-0.25 (m, 2H), 0.05-0.04 (m, 2H). |
| 639 | 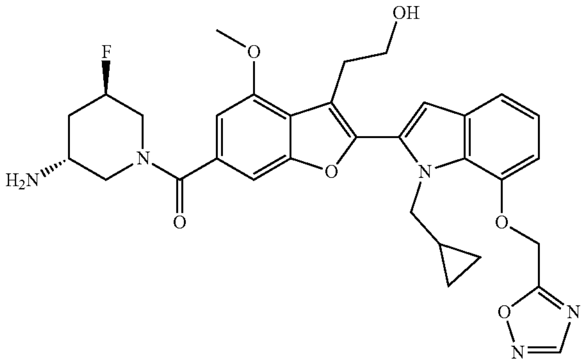 [SMILES: COc1cc(C(=O)N2C[C@H](N)C[C@@H](F)C2)cc2oc(-c3cc4cccc(OCc5ncno5)c4n3CC3CC3)c(CCO)c12] | (2-(7-((1,2,4-oxadiazol-5-yl)methoxy)-1-(cyclopropylmethyl)-1H-indol-2-yl)-3-(2-hydroxyethyl)-4-methoxybenzofuran-6-yl)((3R,5R)-3-amino-5-fluoropiperidin-1-yl)methanone Analytical Data: 602.3; 1.074 min. (Method K); (400 MHz, DMSO-$d_6$) δ ppm 8.37-8.02 (m, 2H), 7.29-7.25 (m, 2H), 7.02-7.01 (m, 1H), 6.99-6.87 (m, 2H), 6.67 (d, J = 7.6 Hz, 1H), 4.92-4.72 (m, 4H), 4.45 (d, J = 6.8 Hz, 2H), 3.97 (s, 4H), 3.75-3.72 (m, 3H), 3.68-3.51 (m, 3H), 3.05-2.95 (m, 3H), 2.38-2.33 (m, 1H), 1.97-1.83 (m, 1H), 1.24-1.08 (m, 1H), 0.25-0.23 (m, 2H), 0.15-0.13 (m, 2H) |

6. BIOLOGICAL ASSAYS

Compounds of the present invention were assayed as inhibitors of PAD4 using the assay protocols described below.

RFMS Human PAD4 Functional Assay 1:

Compounds were solubilized in 100% DMSO to achieve all) mM compound concentration. Compound stock solutions were stored at RT. A series of dilutions were prepared in DMSO and mixed 8 times with 20 µL mixing volume. Final top concentration of compound in the assay is 50 µM. Final assay conditions were as follows:

Reaction volume: 26 µl

Assay buffer: 25 mM hepes, pH 7.5, 5 mM NaCl, 1 mM DTT, 0.2 mg/ml BSA, 0.01% CHAPS, 50 µM Calcium, and 5 µM TPEN Final concentrations: 5 nM hPAD4 enzyme, 250 µM BASE, and 0.5% DMSO Total incubation time: 30 mins compound and enzyme preincubation at 37° C., 90 min enzyme/substrate reaction, 30 min reaction with phenyl glyoxal at 37° C.

Stop solution: 40 µl 5% TCA in ACN 0.13 µL of compound solution was added to 13 µL of 10 nM PAD4 in assay buffer. After 30 min 13 µl of 500 µM of BAEE was added in 25 mM hepes, pH 7.5, 5 mM NaCl, 1 mM DTT, 0.2 mg/ml BSA, 0.01% CHAPS, 50 μM Calcium, 5 μM TPEN was added and the reaction incubated for 90 min at 37° C. The enzymatic reaction was quenched by addition of 15 μl of 6.1N TCA, 100% Final Concentration is 20%, 35 μl of 8.5 mM phenyl glyoxal (final concentration 4 mM) is then added and the reaction is incubated for 30 min at 37° C.

After 30 minutes the plates are spun down to remove all precipitate. The enzyme reaction was quenched with an equal volume of methanol containing internal standard (modified citrulline). Samples were loaded onto the Rapid Fire RF300 system (Agilent) wherein they were first sipped for 1000 ms and then directly loaded to a C18 separations cartridge using a mixture of acetonitrile containing 0.01% formic acid for 3000 ms desalting. The flow rate of the mobile phase was 1.5 ml/min. Once the samples were eluted from the cartridge, a mobile phase of acetonitrile containing 0.01% formic acid was used to move the samples into the mass spectrometer for 4000 ms at a flow rate of 1.25 ml/min/Sciex API5500 triple quadrupole mass spectrometer (Applied Biosystems) equipped with ESI was used to analyze the peptidyl citrulline and internal standard ions.

MRM transition of product and internal standard were monitored at m/z 424.5 to 350.4 and m/z 293 to 247 respectively. The dwell time for each transition was set at 200 ms, and the ESI voltage was used at 5500 with a source temperature of 400° C. Extracted ion peaks for each transition were integrated using the Rapid Fire Integrator software. Peak area of analyte was normalized with internal standard.).

For a given compound example, Table 59 below shows the human PAD4 (hPAD4) $IC_{50}$ in the rapid-fire mass spectrum (RFMS) assay.

TABLE 59

| PAD4 Activity | |
|---|---|
| Example | hPAD4 RFMS $IC_{50}$ (μM) |
| 1 | 0.280 |
| 2 | 0.380 |
| 3 | 0.060 |
| 4 | 0.068 |
| 5 | 0.027 |
| 6 | 0.032 |
| 7 | 0.412 |
| 8 | 0.037 |
| 9 | 0.120 |
| 10 | 0.159 |
| 11 | 1.373 |
| 12 | 2.324 |
| 13 | 0.163 |
| 14 | 0.906 |
| 15 | 0.526 |
| 16 | 0.407 |
| 17 | 0.075 |
| 18 | 0.570 |
| 19 | 0.168 |
| 20 | 0.116 |
| 21 | 0.091 |
| 22 | 2.155 |
| 23 | 0.108 |
| 24 | 0.031 |
| 25 | 0.017 |
| 26 | 0.449 |
| 27 | 0.022 |
| 28 | NA |
| 29 | 1.020 |
| 30 | 0.084 |
| 31 | 0.065 |
| 32 | 0.414 |

TABLE 59-continued

| PAD4 Activity | |
|---|---|
| Example | hPAD4 RFMS $IC_{50}$ (μM) |
| 33 | 0.534 |
| 34 | 0.042 |
| 35 | 0.139 |
| 36 | 0.782 |
| 37 | 3.614 |
| 38 | 0.158 |
| 39 | 0.087 |
| 40 | 0.025 |
| 41 | 0.085 |
| 42 | 0.009 |
| 43 | 0.150 |
| 44 | 1.485 |
| 45 | 0.101 |
| 46 | 0.041 |
| 47 | 1.482 |
| 48 | 0.326 |
| 49 | 0.036 |
| 50 | 0.074 |
| 51 | 0.109 |
| 52 | 0.882 |
| 53 | 0.446 |
| 54 | 0.358 |
| 55 | 0.543 |
| 56 | 0.468 |
| 57 | 0.781 |
| 58 | 0.083 |
| 59 | 0.291 |
| 60 | 0.083 |
| 61 | NA |
| 62 | 0.028 |
| 63 | 0.227 |
| 64 | 0.055 |
| 65 | 0.025 |
| 66 | 0.059 |
| 67 | 0.023 |
| 68 | 0.026 |
| 69 | 0.019 |
| 70 | 0.015 |
| 71 | 0.022 |
| 72 | 0.067 |
| 73 | 0.605 |
| 74 | 0.425 |
| 75 | 0.166 |
| 76 | 0.096 |
| 77 | 0.077 |
| 78 | 0.143 |
| 79 | 0.212 |
| 80 | 1.609 |
| 81 | 0.384 |
| 82 | 0.368 |
| 83 | 0.384 |
| 84 | 0.610 |
| 85 | 0.327 |
| 86 | 0.219 |
| 87 | 2.316 |
| 88 | 1.678 |
| 89 | 0.048 |
| 90 | 0.012 |
| 91 | 0.602 |
| 92 | 0.672 |
| 93 | 0.220 |
| 94 | 0.934 |
| 95 | 0.133 |
| 96 | 0.588 |
| 97 | 0.030 |
| 98 | 0.014 |
| 99 | 0.307 |
| 100 | 0.036 |
| 101 | 0.011 |
| 102 | 0.012 |
| 103 | 0.034 |
| 104 | 0.025 |
| 105 | 0.107 |
| 106 | 0.208 |
| 107 | 0.240 |
| 108 | 0.907 |

TABLE 59-continued

PAD4 Activity

| Example | hPAD4 RFMS $IC_{50}$ (μM) |
|---|---|
| 109 | 0.292 |
| 110 | 1.037 |
| 111 | 15.000 |
| 112 | 0.572 |
| 113 | 0.283 |
| 114 | 3.975 |
| 115 | 3.371 |
| 116 | 22.841 |
| 117 | 15.000 |
| 118 | 0.157 |
| 119 | 0.084 |
| 120 | 0.250 |
| 121 | 1.499 |
| 122 | 0.068 |
| 123 | 0.896 |
| 123 | 0.286 |
| 125 | 0.413 |
| 126 | 0.122 |
| 127 | 0.098 |
| 128 | 4.344 |
| 129 | 0.376 |
| 130 | 0.038 |
| 131 | 0.146 |
| 132 | 0.476 |
| 133 | 0.129 |
| 134 | 0.212 |
| 135 | 0.233 |
| 136 | 0.705 |
| 137 | 0.071 |
| 138 | 0.252 |
| 139 | 0.198 |
| 140 | 0.346 |
| 141 | 0.179 |
| 142 | 0.642 |
| 143 | 0.588 |
| 144 | 0.164 |
| 145 | 0.285 |
| 146 | 1.210 |
| 147 | 0.954 |
| 148 | 0.442 |
| 149 | 0.111 |
| 150 | 0.187 |
| 151 | 0.325 |
| 152 | 0.192 |
| 153 | 0.628 |
| 154 | 1.013 |
| 155 | 1.070 |
| 156 | 0.173 |
| 157 | 0.095 |
| 158 | 1.252 |
| 159 | 1.213 |
| 160 | 0.048 |
| 161 | 0.487 |
| 162 | 2.288 |
| 163 | 5.588 |
| 164 | 0.625 |
| 165 | 0.198 |
| 166 | 0.056 |
| 167 | 0.045 |
| 168 | 0.047 |
| 169 | 0.181 |
| 170 | 0.135 |
| 171 | 0.076 |
| 172 | 8.773 |
| 173 | 0.090 |
| 174 | 0.204 |
| 175 | 0.83 |
| 176 | 0.229 |
| 177 | 0.069 |
| 178 | 0.153 |
| 179 | 0.035 |
| 180 | 0.220 |
| 181 | 0.269 |
| 182 | 0.923 |
| 183 | 0.088 |
| 184 | 0.050 |
| 185 | 0.025 |
| 186 | 0.056 |
| 187 | 1.550 |
| 188 | 0.081 |
| 189 | 0.030 |
| 190 | 0.058 |
| 191 | 0.020 |
| 192 | 0.093 |
| 193 | 0.334 |
| 194 | 1.800 |
| 195 | 0.363 |
| 196 | 0.384 |
| 197 | 0.317 |
| 198 | 3.263 |
| 199 | 3.363 |
| 201 | 1.967 |
| 202 | 1.063 |
| 203 | 0.012 |
| 204 | 0.039 |
| 205 | 0.06 |
| 206 | 0.07 |
| 207 | 0.15 |
| 208 | 0.14 |
| 209 | 1.08 |
| 210 | 0.49 |
| 211 | 1.05 |
| 212 | 1.69 |
| 213 | 0.68 |
| 214 | 0.15 |
| 215 | 0.61 |
| 216 | 0.27 |
| 217 | 0.26 |
| 218 | 0.55 |
| 219 | 0.46 |
| 220 | 4.34 |
| 221 | 0.51 |
| 222 | 1.01 |
| 223 | 0.13 |
| 224 | 1.07 |
| 225 | 0.08 |
| 226 | 0.05 |
| 227 | 0.95 |
| 228 | 0.93 |
| 229 | 0.13 |
| 230 | 0.32 |
| 231 | 0.46 |
| 232 | 0.90 |
| 233 | 0.62 |
| 234 | 1.14 |
| 235 | 0.25 |
| 236 | 0.95 |
| 237 | 0.25 |
| 238 | 0.42 |
| 239 | 0.07 |
| 240 | 0.18 |
| 241 | 0.02 |
| 242 | 0.09 |
| 243 | 4.12 |
| 244 | 0.07 |
| 245 | 0.07 |
| 246 | 0.13 |
| 247 | 0.12 |
| 248 | 0.06 |
| 249 | 0.08 |
| 250 | 0.09 |
| 251 | 0.18 |
| 252 | 0.79 |
| 253 | 0.29 |
| 254 | 0.32 |
| 255 | 0.25 |
| 256 | 0.33 |
| 257 | 0.06 |
| 258 | 0.22 |
| 259 | 0.02 |
| 260 | 0.22 |
| 261 | 0.42 |

TABLE 59-continued

| PAD4 Activity | |
|---|---|
| Example | hPAD4 RFMS $IC_{50}$ (μM) |
| 262 | 0.12 |
| 263 | 0.09 |
| 264 | 0.01 |
| 265 | 0.11 |
| 266 | 0.28 |
| 267 | 0.05 |
| 268 | 0.04 |
| 269 | 0.54 |
| 270 | 2.11 |
| 271 | 2.07 |
| 272 | 3.81 |
| 273 | 2.42 |
| 274 | 0.27 |
| 275 | 0.12 |
| 276 | 2.77 |
| 277 | 0.22 |
| 278 | 0.39 |
| 279 | 0.20 |
| 280 | 1.09 |
| 281 | 0.14 |
| 282 | 0.17 |
| 283 | 0.33 |
| 284 | 1.86 |
| 285 | 1.27 |
| 286 | 0.54 |
| 287 | 1.28 |
| 288 | 0.08 |
| 289 | 3.58 |
| 290 | 2.72 |
| 291 | 5.89 |
| 292 | 2.35 |
| 293 | 0.08 |
| 294 | 0.20 |
| 295 | 0.02 |
| 296 | 0.85 |
| 297 | 0.19 |
| 298 | 0.21 |
| 299 | 0.02 |
| 300 | 0.10 |
| 301 | 0.03 |
| 302 | 0.12 |
| 303 | 0.24 |
| 304 | 0.01 |
| 305 | 0.04 |
| 306 | 0.03 |
| 307 | 0.07 |
| 308 | 0.05 |
| 309 | 0.40 |
| 310 | 0.40 |
| 311 | 0.21 |
| 312 | 0.06 |
| 313 | 0.10 |
| 314 | 0.04 |
| 315 | 0.34 |
| 316 | 0.25 |
| 317 | 0.51 |
| 318 | 0.31 |
| 319 | 0.05 |
| 320 | 0.15 |
| 321 | 15.00 |
| 322 | 0.50 |
| 323 | 0.14 |
| 324 | 0.11 |
| 325 | 1.54 |
| 326 | 0.20 |
| 327 | 0.07 |
| 328 | 0.12 |
| 329 | 0.05 |
| 330 | 0.15 |
| 331 | 0.06 |
| 332 | 0.02 |
| 333 | 0.02 |
| 334 | 0.12 |
| 335 | 0.06 |
| 336 | 0.15 |
| 337 | 0.02 |

TABLE 59-continued

| PAD4 Activity | |
|---|---|
| Example | hPAD4 RFMS $IC_{50}$ (μM) |
| 338 | 0.05 |
| 339 | 0.03 |
| 340 | 0.08 |
| 341 | 0.04 |
| 342 | 0.93 |
| 343 | 0.05 |
| 344 | 0.47 |
| 345 | 0.79 |
| 346 | 0.06 |
| 347 | 0.29 |
| 348 | 0.14 |
| 349 | 0.10 |
| 350 | 0.03 |
| 351 | 0.10 |
| 352 | 0.81 |
| 353 | 0.61 |
| 354 | 0.15 |
| 355 | 0.02 |
| 356 | 2.78 |
| 357 | 0.05 |
| 358 | 0.42 |
| 359 | 0.24 |
| 360 | 0.45 |
| 361 | 0.30 |
| 362 | 0.43 |
| 363 | 2.28 |
| 364 | 1.09 |
| 365 | 0.72 |
| 366 | 0.87 |
| 367 | 1.00 |
| 368 | 2.80 |
| 369 | 0.02 |
| 370 | 0.13 |
| 371 | 1.07 |
| 372 | 0.19 |
| 373 | 0.20 |
| 374 | 2.84 |
| 375 | 1.36 |
| 376 | 0.12 |
| 377 | 0.09 |
| 378 | 0.45 |
| 379 | 0.16 |
| 380 | 0.14 |
| 381 | 0.02 |
| 382 | 0.15 |
| 383 | 0.04 |
| 384 | 0.20 |
| 385 | 0.27 |
| 386 | 0.08 |
| 387 | 0.23 |
| 388 | 0.07 |
| 389 | 0.03 |
| 390 | 0.005 |
| 391 | 0.01 |
| 392 | 0.003 |
| 393 | 0.25 |
| 394 | 0.01 |
| 395 | 0.14 |
| 396 | 0.11 |
| 397 | 0.04 |
| 398 | 0.04 |
| 399 | 0.05 |
| 400 | 0.66 |
| 401 | 0.02 |
| 402 | 0.06 |
| 403 | 0.46 |
| 404 | 0.03 |
| 405 | 0.02 |
| 406 | 0.09 |
| 407 | 0.03 |
| 408 | 0.04 |
| 409 | 0.04 |
| 410 | 0.09 |
| 411 | 0.11 |
| 412 | 0.01 |
| 413 | 0.03 |

TABLE 59-continued

| PAD4 Activity | |
|---|---|
| Example | hPAD4 RFMS $IC_{50}$ (μM) |
| 414 | 0.26 |
| 415 | 0.46 |
| 416 | 0.56 |
| 417 | 5.06 |
| 418 | 1.71 |
| 419 | 8.25 |
| 420 | 0.29 |
| 421 | 0.08 |
| 422 | 0.40 |
| 423 | 0.15 |
| 424 | 0.08 |
| 425 | 0.05 |
| 426 | 0.05 |
| 427 | 0.02 |
| 428 | 0.03 |
| 429 | 0.04 |
| 430 | 0.08 |
| 431 | 0.13 |
| 432 | 0.20 |
| 433 | 0.14 |
| 434 | 0.25 |
| 435 | 0.38 |
| 436 | 0.30 |
| 437 | 0.11 |
| 438 | 0.03 |
| 439 | 0.03 |
| 440 | 0.06 |
| 441 | 0.06 |
| 442 | 0.03 |
| 443 | 0.13 |
| 444 | 0.01 |
| 445 | 0.16 |
| 446 | 0.13 |
| 447 | 0.17 |
| 448 | 0.07 |
| 449 | 0.05 |
| 450 | 0.05 |
| 451 | 0.01 |
| 452 | 0.03 |
| 453 | 0.01 |
| 454 | 0.55 |
| 455 | 0.27 |
| 456 | 0.03 |
| 457 | 0.03 |
| 458 | 0.08 |
| 459 | 0.14 |
| 460 | 0.07 |
| 461 | 0.08 |
| 462 | 0.03 |
| 463 | 0.10 |
| 464 | 0.18 |
| 465 | 0.13 |
| 466 | 0.19 |
| 467 | 0.02 |
| 468 | 0.10 |
| 469 | 0.18 |
| 470 | 0.01 |
| 471 | 0.09 |
| 472 | 0.06 |
| 473 | 0.003 |
| 474 | 0.07 |
| 475 | 0.02 |
| 476 | 0.03 |
| 477 | 0.02 |
| 478 | 0.13 |
| 479 | 0.39 |
| 480 | 0.14 |
| 481 | 0.12 |
| 482 | 0.06 |
| 483 | 0.15 |
| 484 | 0.15 |
| 485 | 0.15 |
| 486 | 0.07 |
| 487 | 0.20 |
| 488 | 0.25 |
| 489 | 0.07 |

TABLE 59-continued

| PAD4 Activity | |
|---|---|
| Example | hPAD4 RFMS $IC_{50}$ (μM) |
| 490 | 0.15 |
| 491 | 1.31 |
| 492 | 0.13 |
| 493 | 0.11 |
| 494 | 0.02 |
| 495 | 0.33 |
| 496 | 0.02 |
| 497 | 0.04 |
| 498 | 0.07 |
| 499 | 0.15 |
| 500 | 0.24 |
| 501 | 0.13 |
| 502 | 0.07 |
| 503 | 0.06 |
| 504 | 0.11 |
| 505 | 0.06 |
| 506 | 0.07 |
| 507 | 0.17 |
| 508 | 0.04 |
| 509 | 0.35 |
| 511 | 0.01 |
| 514 | 0.06 |
| 515 | 0.06 |
| 516 | 1.04 |
| 517 | 0.06 |
| 518 | 0.26 |
| 519 | 0.04 |
| 520 | 0.22 |
| 521 | 6.05 |
| 522 | 15.00 |
| 523 | 0.40 |
| 524 | 0.28 |
| 525 | 0.09 |
| 526 | 0.26 |
| 527 | 0.05 |
| 528 | 15.00 |
| 529 | 1.53 |
| 530 | 0.03 |
| 531 | 0.58 |
| 532 | 1.01 |
| 533 | 0.52 |
| 534 | 0.44 |
| 535 | 0.07 |
| 536 | 2.52 |
| 537 | 0.07 |
| 538 | 0.04 |
| 539 | 0.13 |
| 540 | 1.10 |
| 541 | 2.53 |
| 542 | 0.58 |
| 543 | 0.63 |
| 544 | 1.07 |
| 545 | 0.26 |
| 546 | 0.56 |
| 547 | 0.49 |
| 548 | 0.17 |
| 549 | 0.01 |
| 550 | 0.05 |
| 551 | 0.16 |
| 552 | 0.10 |
| 553 | 0.09 |
| 554 | 0.06 |
| 555 | 0.03 |
| 556 | 0.02 |
| 557 | 0.01 |
| 558 | 0.10 |
| 559 | 0.08 |
| 560 | 0.16 |
| 561 | 0.64 |
| 562 | 0.14 |
| 563 | 0.07 |
| 564 | 0.04 |
| 565 | 0.02 |
| 566 | 0.01 |
| 567 | 0.02 |
| 568 | 0.06 |

TABLE 59-continued

| PAD4 Activity | |
|---|---|
| Example | hPAD4 RFMS $IC_{50}$ (μM) |
| 569 | 0.02 |
| 570 | 0.18 |
| 571 | 0.03 |
| 572 | 0.08 |
| 573 | 0.11 |
| 574 | 0.02 |
| 575 | 0.06 |
| 576 | 0.19 |
| 577 | 0.15 |
| 578 | 0.19 |
| 579 | 0.24 |
| 580 | 0.06 |
| 581 | 0.03 |
| 582 | 0.30 |
| 583 | 1.61 |
| 584 | 0.05 |
| 585 | 0.07 |
| 586 | 0.15 |
| 587 | 1.12 |
| 588 | 0.23 |
| 589 | 0.06 |
| 590 | 0.03 |
| 591 | 0.03 |
| 592 | 0.03 |
| 593 | 0.11 |
| 594 | 0.39 |
| 595 | 1.28 |
| 596 | 7.39 |
| 597 | 0.01 |
| 598 | 0.02 |
| 599 | 0.02 |
| 600 | 0.03 |
| 601 | 0.03 |
| 602 | 0.03 |
| 603 | 0.10 |
| 604 | 0.03 |
| 605 | 0.07 |
| 606 | 0.05 |
| 607 | 0.05 |
| 608 | 0.01 |
| 609 | 0.04 |
| 610 | 0.43 |
| 611 | 1.56 |
| 612 | 2.96 |
| 613 | 0.25 |
| 614 | 0.06 |
| 615 | 0.07 |
| 616 | 0.02 |
| 617 | 0.01 |
| 618 | 0.05 |
| 619 | 0.04 |
| 620 | 0.45 |
| 621 | 0.14 |

RFMS Human PAD4 Functional Assay 2:

Compound Preparation:

Stock compounds were dissolved and stored in 100% DMSO. Compound solutions were prepared via serial dilution at 3-fold intervals in DMSO with top compound concentration at 20 μM in each assay. 0.25 μl of compound solution was transferred from the compound plate to the assay plate by using an acoustic dispenser.

Final Assay Conditions:

Total reaction volume: 25 μl

Assay buffer: 100 HEPES pH 7.4, 200 mM NaCl, 2 mM $CaCl_2$, 5 mM DTT 35 nM recombinant human PAD4

500 μM TSTGGRQGSHH peptide 1.2% DMSO

Stop solution: 10% formic acid

Reaction mixtures were incubated at room temperature for 30 minutes. 10 μl each of the reaction mixtures was then mixed with 40 μl of 10% formic acid in a microtiter plate. The plate was frozen at −80° C. before shipping out on dry ice for RapidFire mass spectroscopy analysis.

Thawed samples were loaded onto the Rapid Fire 300 system (Agilent) wherein they were first sipped for 250 ms and then loaded onto an Agilent "C" (C18) cartridge using a mobile phase of water containing 0.09% formic acid/0.01% trifluoroacetic acid for 3000 ms desalting flowing at a rate of 1.5 ml/min. Once the samples were loaded and washed, a mobile phase of acetonitrile containing 0.09% formic acid/0.01% trifluoroacetic acid was used to elute the samples directly onto a Sciex API4000 triple quadrupole mass spectrometer for 3000 ms at a flow rate of 1.25 ml/min.

MRM transitions for substrate and product were monitored in positive ESI mode at m/z=562.3/969.7 and m/z=562.8/541.3 respectively. The dwell time for each transition was set at 100 ms, and the ESI voltage was used at 5500 with a source temperature of 650° C. Extracted ion peaks for each transition were integrated using the Rapid Fire Integrator software.

For a given compound example, the Table 60 below shows the human PAD4 (hPAD4) $IC_{50}$ in the rapid-fire mass spectrum (RFMS) assay.

TABLE 60

| PAD4 Activity | |
|---|---|
| Example | hPAD4 RFMS $IC_{50}$ μM |
| 622 | 1.20 |
| 623 | 0.395 |
| 624 | 0.383 |
| 625 | 2.04 |
| 626 | 0.849 |
| 627 | 0.879 |
| 628 | 0.322 |
| 629 | 0.785 |
| 630 | 0.288 |
| 631 | 7.58 |
| 632 | 0.327 |
| 633 | 0.179 |
| 634 | 0.209 |
| 635 | 0.216 |
| 636 | 0.277 |
| 637 | 0.621 |
| 638 | 0.295 |
| 639 | 0.243 |

The invention claimed is:

1. A compound of Formula (Ia):

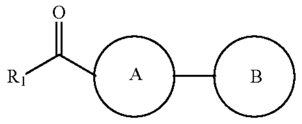

(Ia)

or a pharmaceutically acceptable salt thereof, wherein:

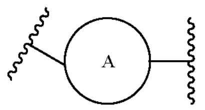

is selected from

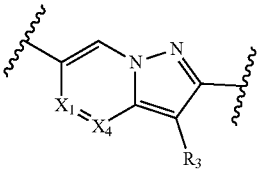

and

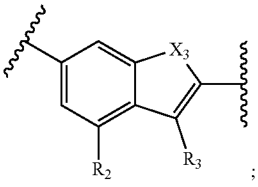

;

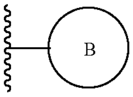

is selected from

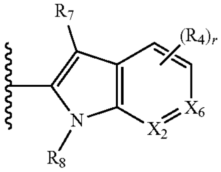

and

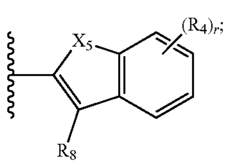

$X_1$ is independently selected from $CR_2$, and N;

$X_2$ is independently selected from $CR_4$, and N;

$X_3$ is independently selected from O, and S;

$X_4$ is independently selected from $CR_2$, and N; provided $X_1$ and $X_4$ are not both N;

$X_5$ is independently selected from O and S;

$X_6$ is independently selected from $CR_4$, and N; provided 1) $X_2$ and $X_6$ are not both N; 2) when $X_2$ and $X_6$ are both $CR_4$, one of $R_4$ is H;

$R_1$ is independently selected from —NH—$C_{1-5}$ alkyl optionally substituted with one or more substituents selected from F, Cl, and $NH_2$, 4-10 membered heterocyclyl, and —NH-4-10 membered heterocyclyl, wherein said heterocyclyl is optionally substituted with one or more substituents selected from F, Cl, CN, $C_{1-3}$ alkyl, =N—$OR_b$, —$(CH_2)_rOR_b$, —$(CH_2)_rNR_aR_a$, —$NR_aC$(=NH)$C_{1-3}$ alkyl, —$NR_aC$(=O)$OR_b$, carbocyclyl, and heterocyclyl;

$R_2$ is independently selected from H, F, Cl, $C_{1-4}$ alkyl optionally substituted with one or more substituents selected from F, Cl, and OH, and —$OC_{1-4}$ alkyl;

$R_3$ is independently selected from H, F, Cl, CN, —C(=O)$OR_b$, and $C_{1-3}$ alkyl optionally substituted with one or more substituents selected from F, Cl, OH, $NH_2$, and $N_3$;

$R_4$ is independently selected from H, F, Cl, Br, —C(=O)$R_b$, $C_{1-6}$ alkyl optionally substituted with one or more substituents selected from F, Cl, OH, and $C_{3-6}$ cycloalkyl, —NH—$C_{1-6}$ alkyl optionally substituted with one or more substituents selected from F, Cl, OH, and $C_{3-6}$ cycloalkyl, —$(CH_2)_r$-aryl substituted with one or more $R_5$, —O—$C_{1-6}$ alkyl substituted with one or more $R_5$, —$(CH_2)_r$—$C_{3-12}$ cycloalkyl substituted with one or more $R_5$, and —$(CH_2)_r$-4-10 membered heterocyclyl comprising carbon atoms and 1-5 heteroatoms selected from N, $NR_6$, O, and S and substituted with one or more $R_5$;

$R_5$ is independently selected from H, F, Cl, Br, CN, =O, $C_{1-4}$ alkyl optionally substituted with one or more $R_e$, $C_{2-4}$ alkenyl optionally substituted with one or more $R_e$, $C_{2-4}$ alkynyl optionally substituted with one or more $R_e$, —$(CR_dR_d)_rOR_b$, —$(CR_dR_d)_rS(O)_pR_c$, —$(CR_dR_d)_rS(O)_pNR_aR_a$, —$(CR_dR_d)_rNR_aS(O)_pR_c$, —$(CR_dR_d)_rNR_aR_a$, —$(CR_dR_d)_rNR_aC$(=O)$R_b$, —$(CR_dR_d)_rNR_aC$(=O)$OR_b$, —$(CR_dR_d)_rNR_aC$(=O)$NR_aR_a$, —$(CR_dR_d)_rC$(=O)$R_b$, —$(CR_dR_d)_rC$(=O)$OR_b$, —$(CR_dR_d)_rC$(=O)$NR_aR_a$, —$(CR_dR_d)_rOC$(=O)$R_b$, —$(CR_dR_d)_rOC$(=O)$OR_b$, $(CR_dR_d)_rO(CH_2)_rC$(=O)$NR_aR_a$, $C_{3-6}$ cycloalkyl optionally substituted with one or more $R_e$, aryl optionally substituted with one or more $R_e$, and heterocyclyl optionally substituted with one or more $R_e$;

$R_6$ is independently selected from H, $C_{1-6}$ alkyl optionally substituted with one or more $R_e$, —$S(O)_pR_c$, —$S(O)_pNR_aR_a$, —C(=O)$R_b$, —C(=O)$OR_b$, —C(=O)$NR_aR_a$, $C_{3-6}$ cycloalkyl optionally substituted with one or more $R_e$, aryl optionally substituted with one or more $R_e$, and heterocyclyl optionally substituted with one or more $R_e$;

$R_7$ is independently selected from H, F, and Cl;

$R_8$ is independently selected from H, and $C_{1-6}$ alkyl optionally substituted with one or more substituents selected from F, Cl, and $C_{3-6}$ cycloalkyl;

$R_a$ is independently selected from H, $C_{1-6}$ alkyl optionally substituted with one or more $R_e$, $C_{2-6}$ alkenyl optionally substituted with one or more $R_e$, $C_{2-6}$ alkynyl optionally substituted with one or more $R_e$, —$(CH_2)_rC_{3-10}$ carbocyclyl optionally substituted with one or more $R_e$, and —$(CH_2)_r$-heterocyclyl optionally substituted with one or more $R_e$; or $R_a$ and $R_a$ together with the nitrogen atom to which they are both attached form a heterocyclic ring optionally substituted with one or more $R_e$;

$R_b$ is independently selected from H, $C_{1-6}$ alkyl optionally substituted with one or more $R_e$, $C_{2-6}$ alkenyl optionally substituted with one or more $R_e$, $C_{2-6}$ alkynyl optionally substituted with one or more $R_e$, —$(CH_2)_r$—$C_{3-10}$ carbocyclyl optionally substituted with one or more $R_e$, and —$(CH_2)_r$-heterocyclyl optionally substituted with one or more $R_e$;

$R_c$ is independently selected from $C_{1-6}$ alkyl optionally substituted with one or more $R_e$, $C_{2-6}$ alkenyl optionally substituted with one or more $R_e$, $C_{2-6}$ alkynyl optionally substituted with one or more $R_e$, —$(CH_2)_r$—$C_{3-10}$ carbocyclyl optionally substituted with one or more $R_e$, and —$(CH_2)_r$-heterocyclyl optionally substituted with one or more $R_e$;

$R_d$ is independently selected from H, and $C_{1-6}$ alkyl optionally substituted with one or more $R_e$;

$R_e$ is independently selected from F, Cl, Br, CN, $NH_2$, —NH—$C_{1-4}$ alkyl, —N($C_{1-4}$ alkyl)$_2$, =O, OH, —$OC_{1-6}$ alkyl, —$CO_2H$, $C_{1-6}$ alkyl optionally substituted with one or more $R_f$, $C_{2-6}$ alkenyl, $C_{2-6}$ alkynyl, —$(CH_2)_r$—$C_{3-6}$ cycloalkyl optionally substituted with one or more $R_f$, —$(CH_2)_r$-aryl optionally substituted with one or more $R_f$, and —$(CH_2)_r$-heterocyclyl optionally substituted with one or more $R_f$;

$R_f$ is independently selected from F, Cl, Br, CN, OH, $OC_{1-5}$ alkyl, $C_{1-5}$ alkyl optionally substituted with OH, $C_{2-5}$ alkenyl, $C_{2-5}$ alkynyl, $C_{3-6}$ cycloalkyl, and phenyl;

p, at each occurrence, is independently selected from zero, 1, and 2; and r, at each occurrence, is independently selected from zero, 1, 2, 3, and 4.

2. The compound according to claim 1, having Formulae (IIa)-(XIII):
(IIa)
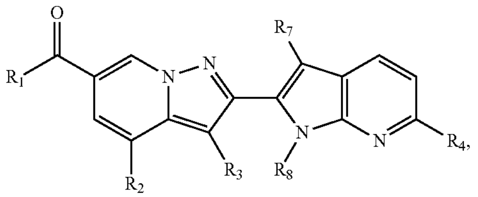
(IIIa)
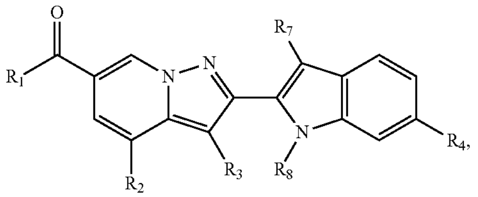
(IVa)
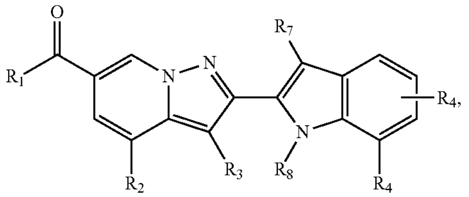
(Va)
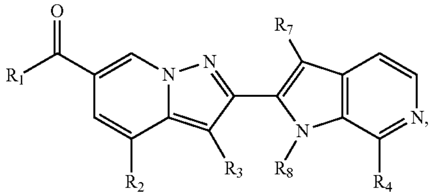
(VIa)
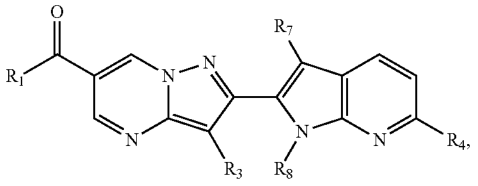
(VII)
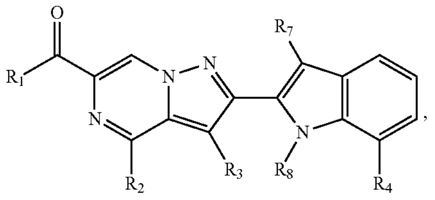
(VIII)
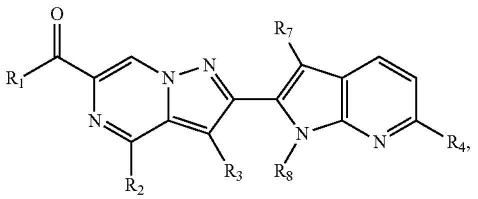
-continued
(IX)
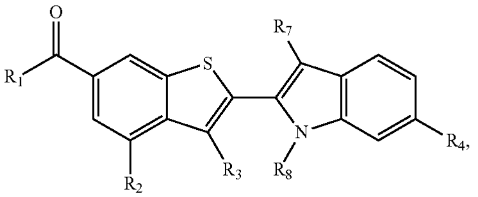
(X)
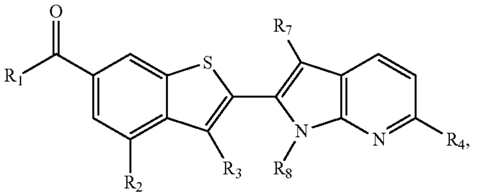
(XI)
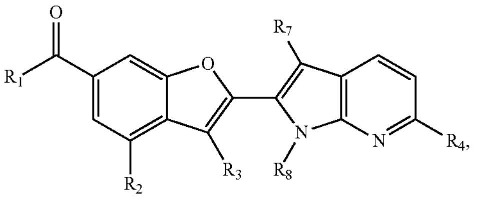
(XII)
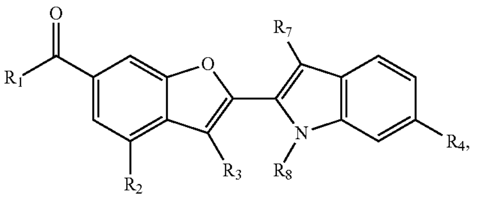
or
(XIII)
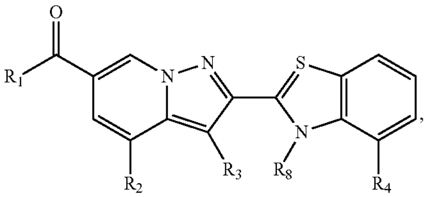
or a pharmaceutically acceptable salt thereof.
3. The compound according to claim 2, having Formula (IIa):
(IIa)
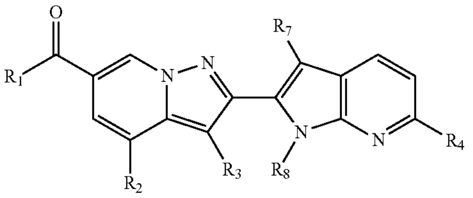

or a pharmaceutically acceptable salt thereof, wherein:

$R_1$ is independently selected from

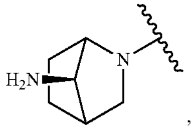
,
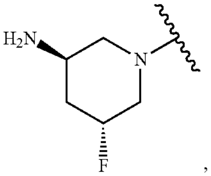
,
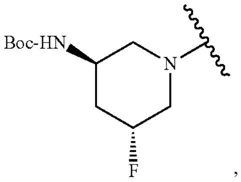
,
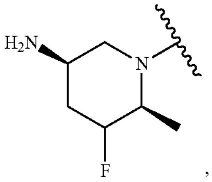
,
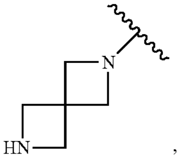
,
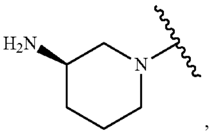
, and
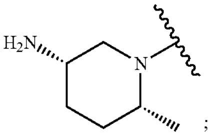
;

$R_2$ is independently selected from H, F, Cl, $C_{1-3}$ alkyl optionally substituted with one or more substituents selected from F, Cl, and OH, and $OC_{1-3}$ alkyl;

$R_3$ is independently selected from H, F, Cl, and $C_{1-3}$ alkyl optionally substituted with one or more substituents selected from F, Cl, and OH;

$R_4$ is independently selected from H, F, Cl, —C(═O)$R_b$, $C_{1-6}$ alkyl optionally substituted with one or more substituents selected from F, Cl, OH, and $C_{3-6}$ cycloalkyl, —NH—$C_{1-6}$ alkyl optionally substituted with one or more substituents selected from F, Cl, OH, and $C_{3-6}$ cycloalkyl, —$(CH_2)_r$-aryl substituted with one or more $R_5$, —O—$C_{1-6}$ alkyl substituted with one or more $R_5$, —$(CH_2)_r$—$C_{3-12}$ cycloalkyl substituted with one or more $R_5$, and —$(CH_2)_r$-4-10 membered heterocyclyl comprising carbon atoms and 1-5 heteroatoms selected from N, $NR_6$, O, and S and substituted with one or more $R_5$;

$R_5$ is independently selected from H, F, Cl, ═O, $C_{1-4}$ alkyl optionally substituted with one or more $R_e$, —$(CH_2)_r$O$R_b$, —$(CH_2)_r$S(O)$_p$$R_c$, —$(CH_2)_r$S(O)$_p$N$R_a$$R_a$, —$(CH_2)_r$N$R_a$S(O)$_p$$R_c$, —$(CH_2)_r$N$R_a$$R_a$, —$(CH_2)_r$N$R_a$C(═O)$R_b$, —$(CH_2)_r$N$R_a$C(═O)O$R_b$, —$(CH_2)_r$N$R_a$C(═O)N$R_a$$R_a$, —$(CH_2)_r$C(═O)$R_b$, —$(CH_2)_r$C(═O)O$R_b$, —$(CH_2)_r$C(═O)N$R_a$$R_a$, —$(CH_2)_r$OC(═O)$R_b$, —$(CH_2)_r$OC(═O)O$R_b$, —$(CH_2)_r$O$(CH_2)_r$C(═O)N$R_a$$R_a$, $C_{3-6}$ cycloalkyl optionally substituted with one or more $R_e$, aryl optionally substituted with one or more $R_e$, and heterocyclyl optionally substituted with one or more $R_e$;

$R_6$ is independently selected from H, $C_{1-6}$ alkyl optionally substituted with one or more $R_e$, C(═O)$R_b$, —C(═O)N$R_a$$R_a$, $C_{3-6}$ cycloalkyl optionally substituted with one or more $R_e$, aryl optionally substituted with one or more $R_e$, and heterocyclyl optionally substituted with one or more $R_e$;

$R_7$ is independently selected from H, F, and Cl;

$R_8$ is independently selected from H, and $C_{1-6}$ alkyl optionally substituted with one or more substituents selected from F, Cl, and $C_{3-6}$ cycloalkyl;

$R_a$ is independently selected from H, and $C_{1-6}$ alkyl optionally substituted with one or more $R_e$; or $R_a$ and $R_a$ together with the nitrogen atom to which they are both attached form a heterocyclic ring optionally substituted with one or more $R_e$;

$R_b$ is independently selected from H, $C_{1-6}$ alkyl optionally substituted with one or more $R_e$, —$(CH_2)_r$—$C_{3-10}$ carbocyclyl optionally substituted with one or more $R_e$, and —$(CH_2)_r$-heterocyclyl optionally substituted with one or more $R_e$;

$R_c$ is independently selected from $C_{1-6}$ alkyl optionally substituted with one or more $R_e$, —$(CH_2)_r$—$C_{3-10}$ carbocyclyl optionally substituted with one or more $R_e$, and —$(CH_2)_r$-heterocyclyl optionally substituted with one or more $R_e$;

$R_e$ is independently selected from F, Cl, Br, $NH_2$, —NH—$C_{1-4}$ alkyl, —N($C_{1-4}$ alkyl)$_2$, ═O, OH, —O$C_{1-6}$ alkyl, $C_{1-6}$ alkyl optionally substituted with one or more $R_f$, —$(CH_2)_r$—$C_{3-6}$ cycloalkyl optionally substituted with one or more $R_f$, —$(CH_2)_r$-aryl optionally substituted with one or more $R_f$, and —$(CH_2)_r$-heterocyclyl optionally substituted with one or more $R_f$;

$R_f$ is independently selected from F, CI, OH, O$C_{1-5}$ alkyl, $C_{1-5}$ alkyl optionally substituted with OH, $C_{3-6}$ cycloalkyl, and phenyl;

p, at each occurrence, is independently selected from zero, 1, and 2; and r, at each occurrence, is independently selected from zero, 1, 2, 3, and 4.

4. The compound according to claim 1, having Formula (IIIa):

(IIIa)

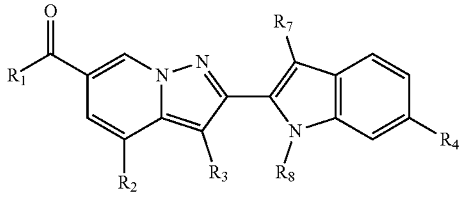

or a pharmaceutically acceptable salt thereof, wherein:

$R_1$ is independently selected from

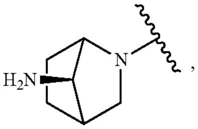
,
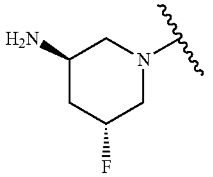
,
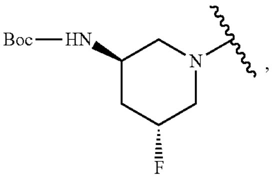
,
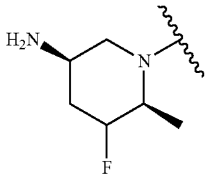
,

-continued

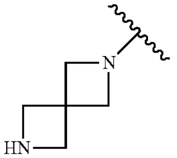,
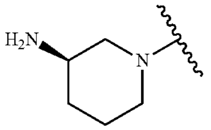, and
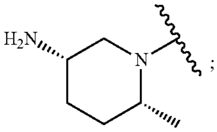;

$R_2$ is independently selected from H, F, Cl, $C_{1-3}$ alkyl optionally substituted with one or more substituents selected from F, Cl, and OH, and $OC_{1-3}$ alkyl;

$R_3$ is independently selected from H, F, Cl, and $C_{1-3}$ alkyl optionally substituted with one or more substituents selected from F, Cl, and OH;

$R_4$ is independently selected from H, F, Cl, $-C(=O)R_b$, $C_{1-6}$ alkyl optionally substituted with one or more substituents selected from F, Cl, OH, and $C_{3-6}$ cycloalkyl, $-NH-C_{1-6}$ alkyl optionally substituted with one or more substituents selected from F, Cl, OH, and $C_{3-6}$ cycloalkyl, $-(CH_2)_r$-aryl substituted with one or more $R_5$, $-O-C_{1-6}$ alkyl substituted with one or more $R_5$, $-(CH_2)_r-C_{3-12}$ cycloalkyl substituted with one or more $R_5$, and $-(CH_2)_r$-4-10 membered heterocyclyl comprising carbon atoms and 1-5 heteroatoms selected from N, $NR_6$, O, and S and substituted with one or more $R_5$;

$R_5$ is independently selected from H, F, Cl, =O, $C_{1-4}$ alkyl optionally substituted with one or more $R_e$, $-(CH_2)_rOR_b$, $-(CH_2)_rS(O)_pR_c$, $-(CH_2)_rS(O)_pNR_aR_a$, $-(CH_2)_rNR_aS(O)_pR_c$, $-(CH_2)_rNR_aR_a$, $-(CH_2)_rNR_aC(=O)R_b$, $-(CH_2)_rNR_aC(=O)OR_b$, $-(CH_2)_rNR_aC(=O)NR_aR_a$, $-(CH_2)_rC(=O)R_b$, $-(CH_2)_rC(=O)OR_b$, $-(CH_2)_rC(=O)NR_aR_a$, $-(CH_2)_rOC(=O)R_b$, $-(CH_2)_rOC(=O)OR_b$, $-(CH_2)_rO(CH_2)_rC(=O)NR_aR_a$, $C_{3-6}$ cycloalkyl optionally substituted with one or more $R_e$, aryl optionally substituted with one or more $R_e$, and heterocyclyl optionally substituted with one or more $R_e$;

$R_6$ is independently selected from H, $C_{1-6}$ alkyl optionally substituted with one or more $R_e$, $-C(=O)R_b$, $-C(=O)OR_b$, $-C(=O)NR_aR_a$, $C_{3-6}$ cycloalkyl optionally substituted with one or more $R_e$, aryl optionally substituted with one or more $R_e$, and heterocyclyl optionally substituted with one or more $R_e$;

$R_7$ is independently selected from H, F, and Cl;

$R_8$ is independently selected from H, and $C_{1-6}$ alkyl optionally substituted with one or more substituents selected from F, Cl, and $C_{3-6}$ cycloalkyl;

$R_a$ is independently selected from H, and $C_{1-6}$ alkyl optionally substituted with one or more $R_e$; or $R_a$ and $R_a$ together with the nitrogen atom to which they are both attached form a heterocyclic ring optionally substituted with one or more $R_e$;

$R_b$ is independently selected from H, $C_{1-6}$ alkyl optionally substituted with one or more $R_e$, $-(CH_2)_r-C_{3-10}$ carbocyclyl optionally substituted with one or more $R_e$, and $-(CH_2)_r$ heterocyclyl optionally substituted with one or more $R_e$;

$R_c$ is independently selected from $C_{1-6}$ alkyl optionally substituted with one or more $R_e$, $-(CH_2)_r-C_{3-10}$ carbocyclyl optionally substituted with one or more $R_e$, and $-(CH_2)_r$-heterocyclyl optionally substituted with one or more $R_e$;

$R_e$ is independently selected from F, Cl, Br, CN, $NH_2$, $-NH-C_{1-4}$ alkyl, $-N(C_{1-4}\ alkyl)_2$, =O, OH, $-OC_{1-6}$ alkyl, $C_{1-6}$ alkyl optionally substituted with one or more $R_f$, $-(CH_2)_r-C_{3-6}$ cycloalkyl optionally substituted with one or more $R_f$, $-(CH_2)_r$-aryl optionally substituted with one or more $R_f$, and $-(CH_2)_r$-heterocyclyl optionally substituted with one or more $R_f$;

$R_f$ is independently selected from F, Cl, OH, $OC_{1-5}$ alkyl, $C_{1-5}$ alkyl optionally substituted with OH, $C_{3-6}$ cycloalkyl, and phenyl;

p, at each occurrence, is independently selected from zero, 1, and 2; and r, at each occurrence, is independently selected from zero, 1, 2, 3, and 4.

5. The compound according to claim 3, or a pharmaceutically acceptable salt thereof, wherein:

$R_1$ is independently selected from

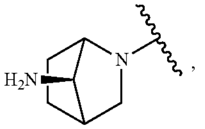,
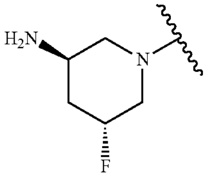, and
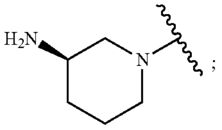;

$R_2$ is independently selected from H, F, Cl, $CH_3$, and $OCH_3$;

$R_3$ is independently selected from H, F, Cl, $CH_3$, and $CH_2OH$;

$R_4$ is independently selected from H, F, Cl, $C_{1-5}$ alkyl optionally substituted with one or more substituents selected from F, Cl, OH, and $C_{3-6}$ cycloalkyl, $-(CH_2)_r$-aryl substituted with one or more $R_5$, $-O-C_{1-6}$ alkyl substituted with one or more $R_5$, $-(CH_2)_r-C_{3-12}$ cycloalkyl substituted with one or more $R_5$, and $-(CH_2)_r$-4-10 membered heterocyclyl comprising carbon atoms and 1-5 heteroatoms selected from N, $NR_6$, O, and S and substituted with one or more $R_5$;

$R_5$ is independently selected from H, F, Cl, =O, $C_{1-4}$ alkyl optionally substituted with one or more $R_e$, $-(CH_2)_rOR_b$, $-(CH_2)_rS(O)_2R_c$, $-(CH_2)_rS(O)_pNR_aR_a$, $-(CH_2)_rNR_aS(O)_2R_c$, $-(CH_2)_rNR_aR_a$, $-(CH_2)_rNR_aC(=O)R_b$, $-(CH_2)_rNR_aC(=O)OR_b$, $-(CH_2)_rNR_aC(=O)NR_aR_a$, $(CH_2)_rC(=O)R_b$, $-(CH_2)_rC(=O)OR_b$, $-(CH_2)_rC(=O)NR_aR_a$, $-(CH_2)_rOC(=O)R_b$, $-(CH_2)_rOC(=O)OR_b$, $-(CH_2)_rO(CH_2)_rC(=O)NR_aR_a$, $C_{3-6}$ cycloalkyl optionally substituted with one or more $R_e$, aryl optionally substituted with one or more $R_e$, and heterocyclyl optionally substituted with one or more $R_e$;

$R_6$ is independently selected from H and $C_{1-65}$ alkyl optionally substituted with one or more $R_e$;

$R_7$ is H;

$R_8$ is $C_{1-3}$ alkyl substituted with one $C_{3-6}$ cycloalkyl;

$R_a$ is independently selected from H, and $C_{1-4}$ alkyl;

$R_b$ is independently selected from H, $C_{1-4}$ alkyl;

$R_c$ is $C_{1-4}$ alkyl; and r, at each occurrence, is independently selected from zero, 1, and 2.
6. The compound according to claim 5, or a pharmaceutically acceptable salt thereof, wherein:
$R_4$ is independently selected from H, F, Cl, $C_{1-5}$ alkyl optionally substituted with one or more substituents selected from F, Cl, and OH, $C_{3-6}$ cycloalkyl,
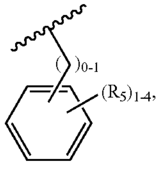 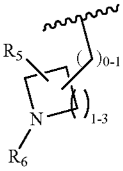, 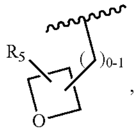,
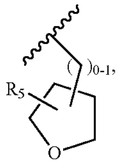 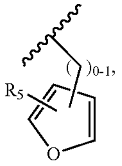 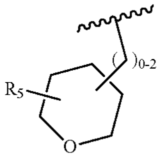
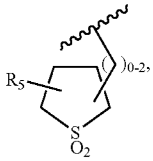 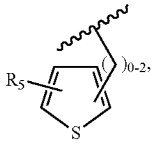 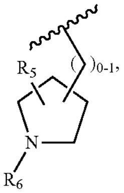
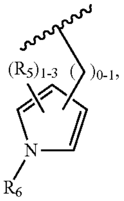 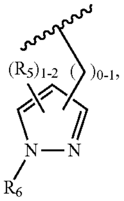 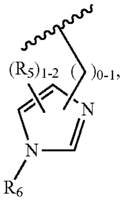
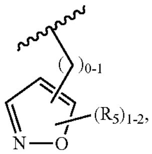 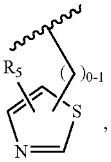, 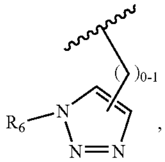,
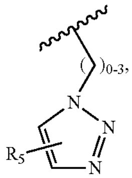 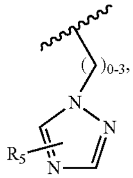 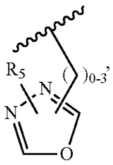 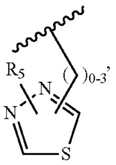
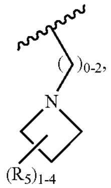 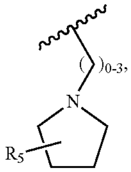 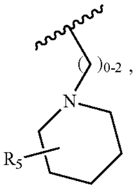
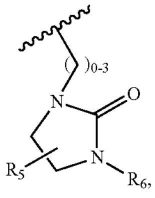 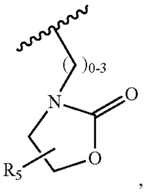, 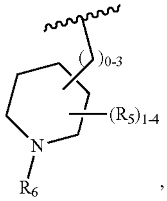,
-continued
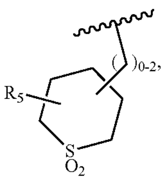 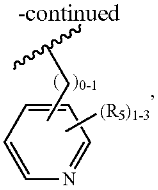 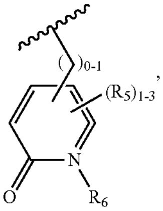
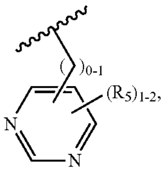 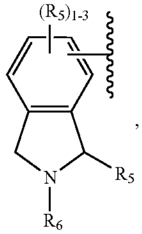,
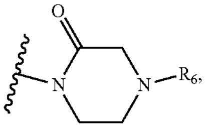 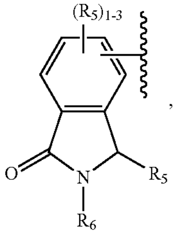,
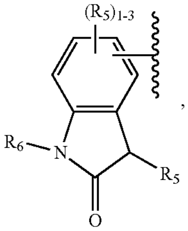, 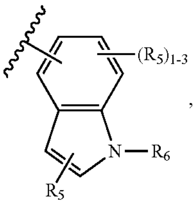,
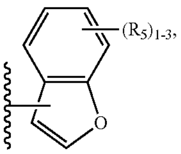 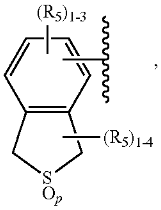,
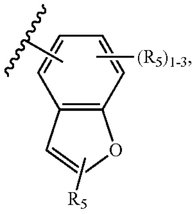 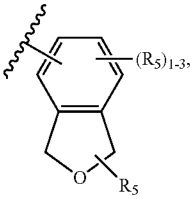
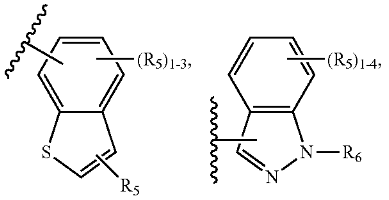
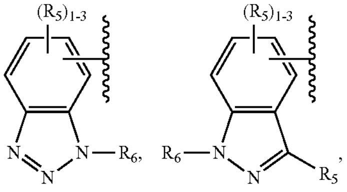

-continued
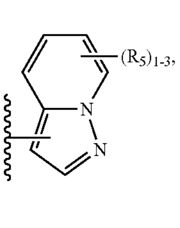
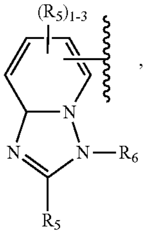
,
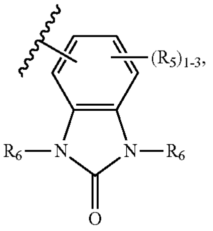
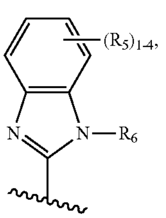
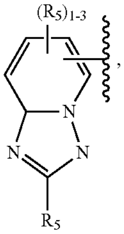
,
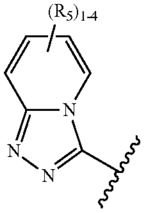
,
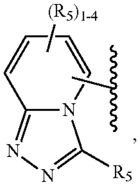
,
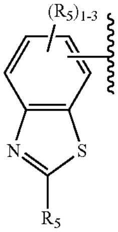
,
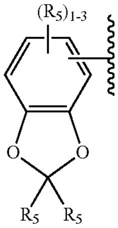
,
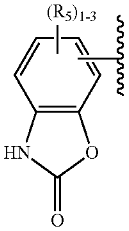
,
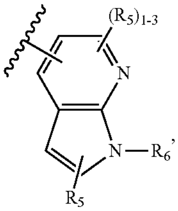
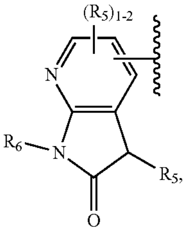
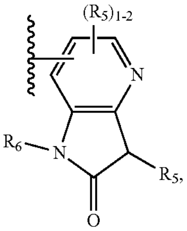
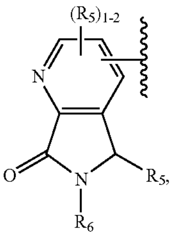
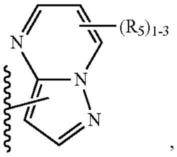
,
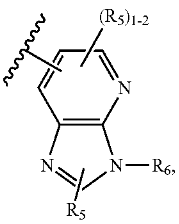
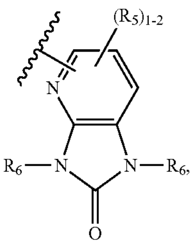
-continued
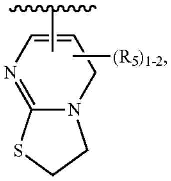
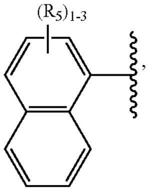
,
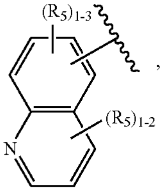
,
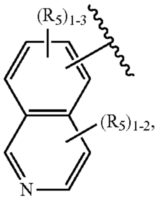
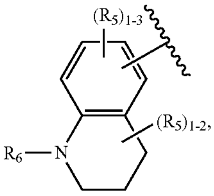
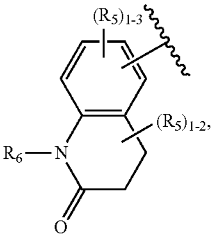
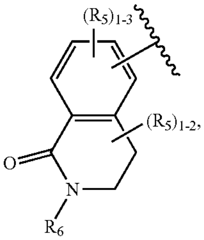
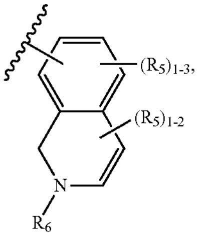
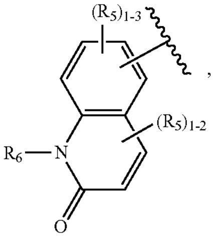
,
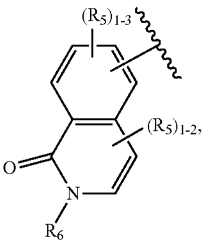
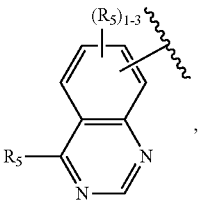
,
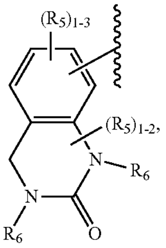
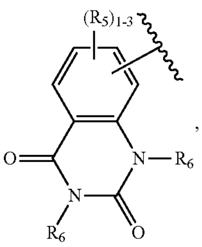
,
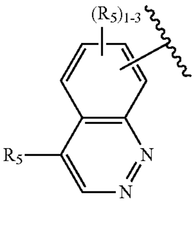
,
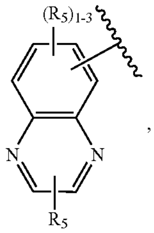
,
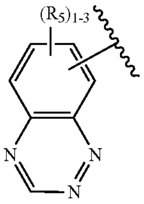
, -continued

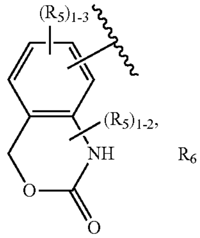
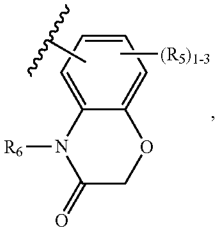
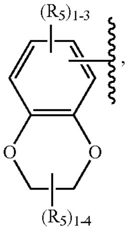
and
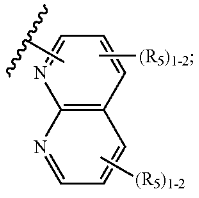

$R_5$ is independently selected from H, F, Cl, =O, $C_{1-4}$ alkyl optionally substituted with one or more $R_e$, $-(CH_2)_rOR_b$, $-(CH_2)_rS(O)_pR_c$, $-(CH_2)_rS(O)_pNR_aR_a$, $-(CH_2)_rNR_aS(O)_pR_c$, $-(CH_2)_rNR_aR_a$, $-(CH_2)_rNR_aC(=O)R_b$, $-(CH_2)_rNR_aC(=O)OR_b$, $-(CH_2)_rNR_aC(=O)NR_aR_a$, $-(CH_2)_rC(=O)R_b$, $-(CH_2)_rC(=O)OR_b$, $-(CH_2)_rC(=O)NR_aR_a$, $-(CH_2)_rOC(=O)R_b$, $-(CH_2)_rOC(=O)OR_b$, $-(CH_2)_rO(CH_2)_rC(=O)NR_aR_a$, $C_{3-6}$ cycloalkyl optionally substituted with one or more $R_e$, aryl optionally substituted with one or more $R_e$, and heterocyclyl optionally substituted with one or more $R_e$; and $R_6$ is independently selected from H and $C_{1-5}$ alkyl.

7. The compound according to claim 6, or a pharmaceutically acceptable salt thereof, wherein:

$R_4$ is independently selected from

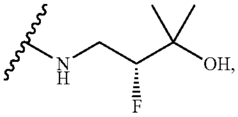
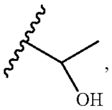
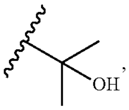
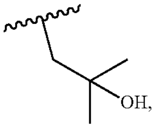
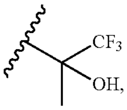
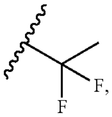
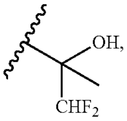
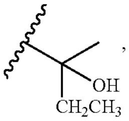
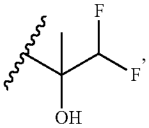
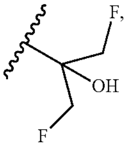
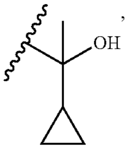
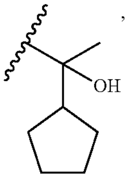
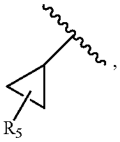
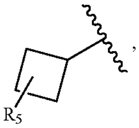
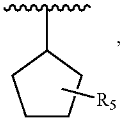

-continued

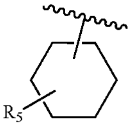
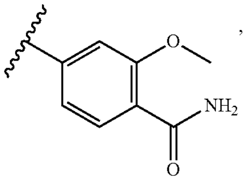
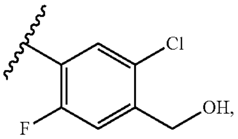
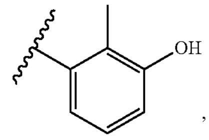
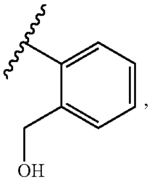
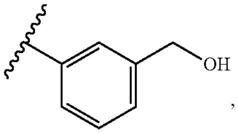
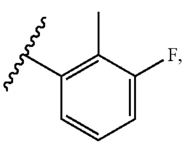
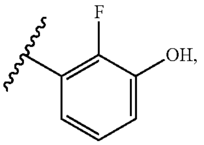
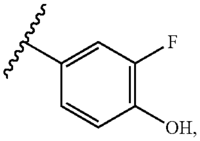
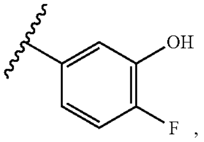
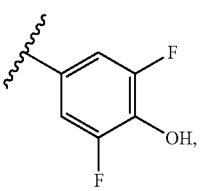
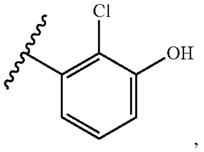
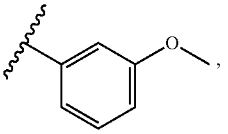
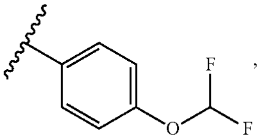
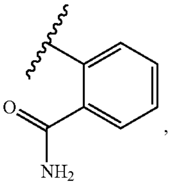
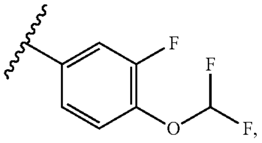
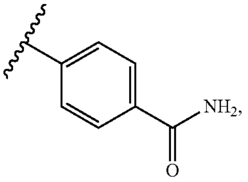
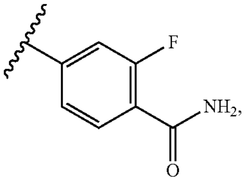
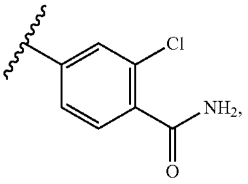
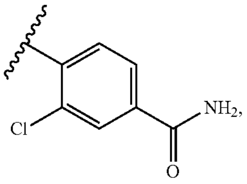

-continued
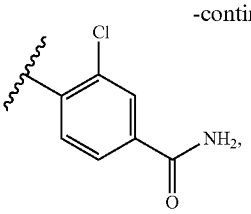,
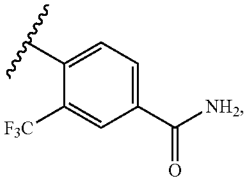,
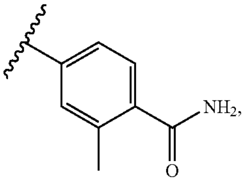,
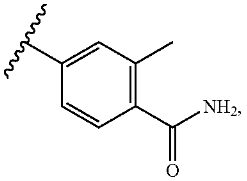,
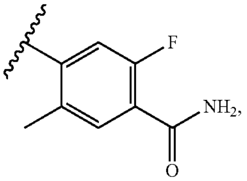,
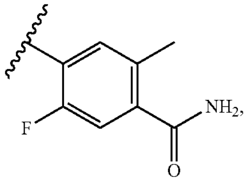,
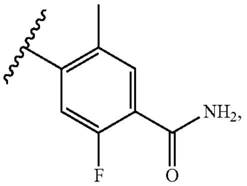,
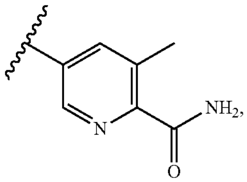,
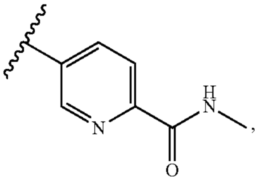,
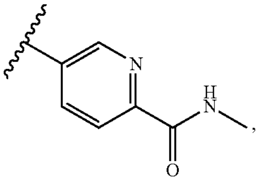,
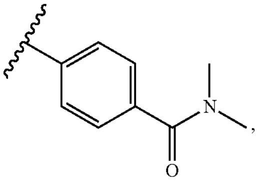,
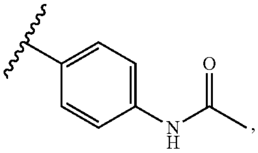,
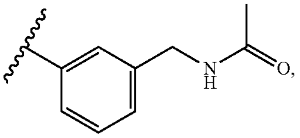,
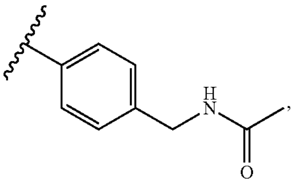,
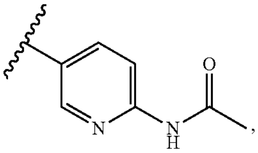,
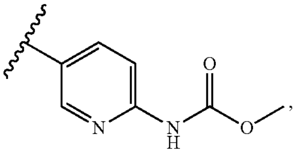,
-continued
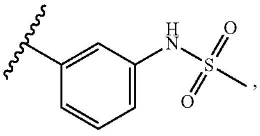,
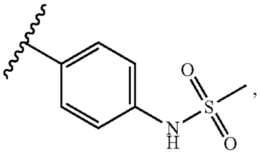,
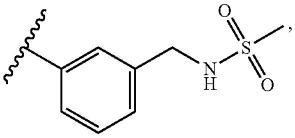,
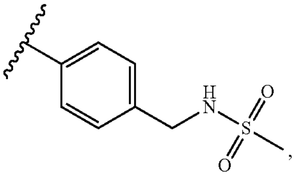,
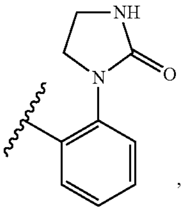,
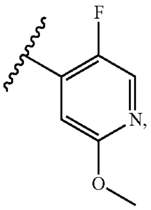,
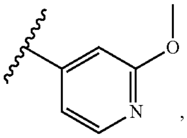,
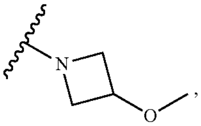,
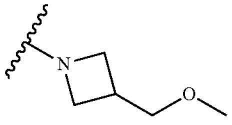,
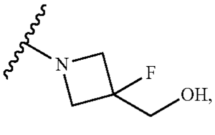,
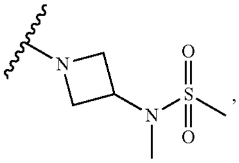,
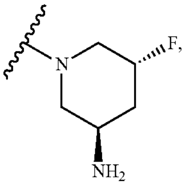,
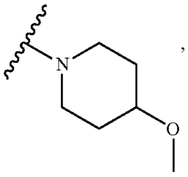,
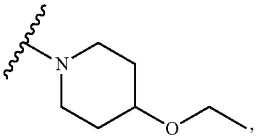,
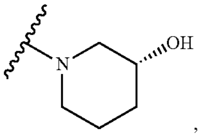,
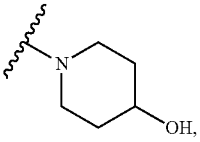,
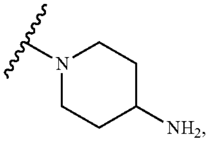, -continued
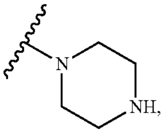
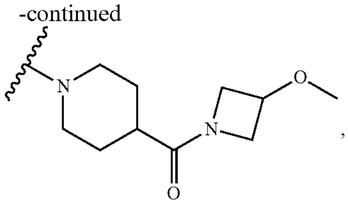
,
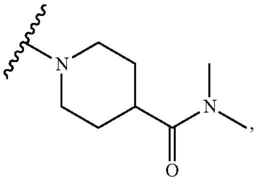
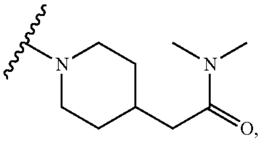
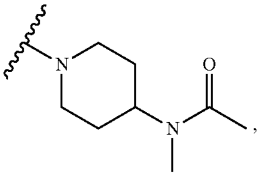
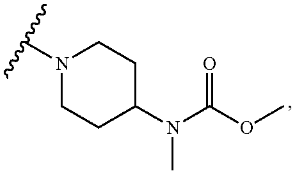
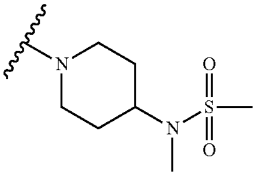
,
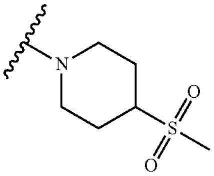
,
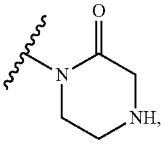
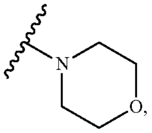
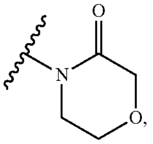
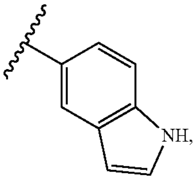
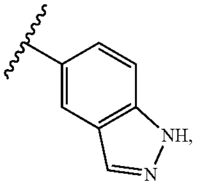
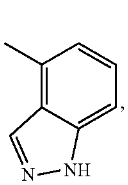
,
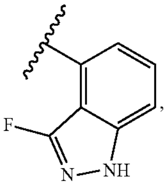
,
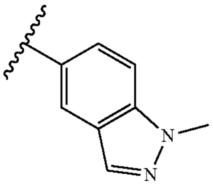
,
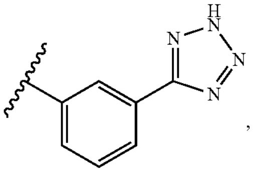
,
-continued
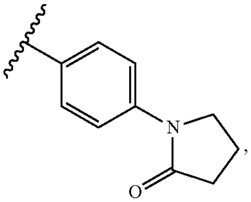
,
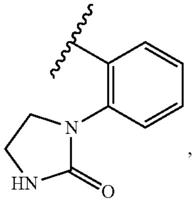
,
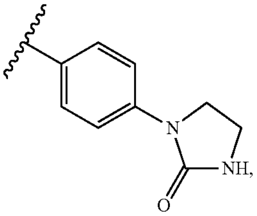
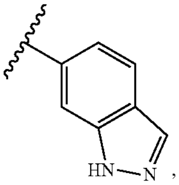
,
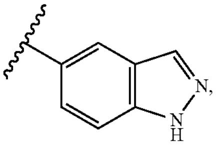
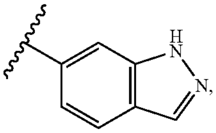
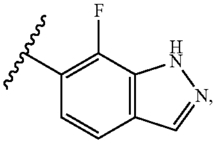
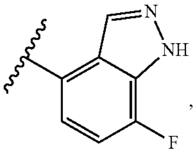
,
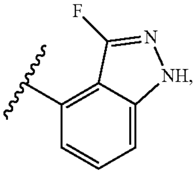
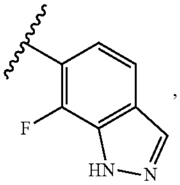
,
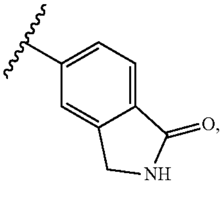
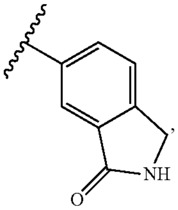
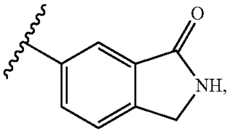
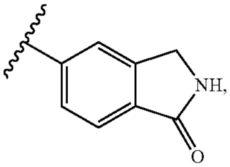
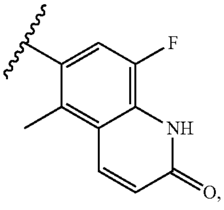
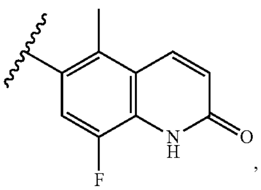
,
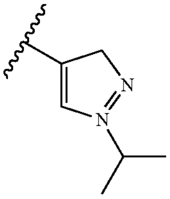
,
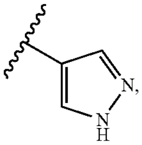

-continued

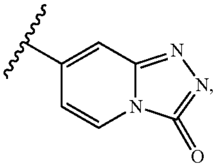,

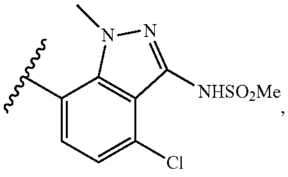,

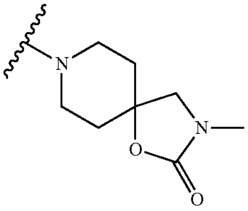,

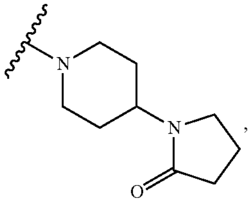,

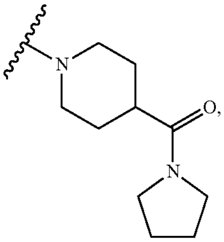,

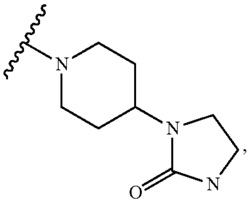, and

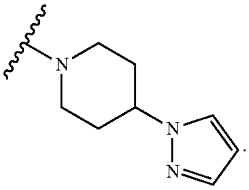.

8. The compound according to claim 1, having Formula (IVa):

(IVa)

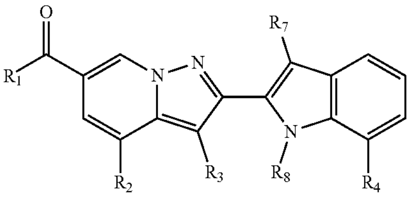

or a pharmaceutically acceptable salt thereof, wherein:

$R_1$ is independently selected from

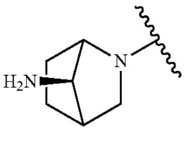,

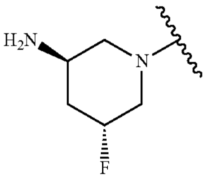,

-continued

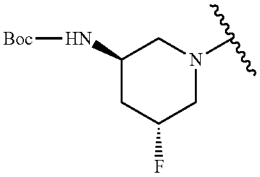,

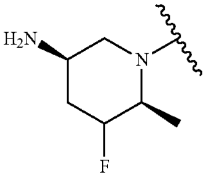,

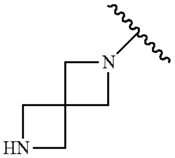,

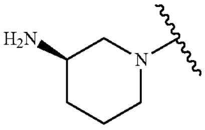, and

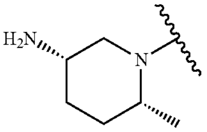;

$R_2$ is independently selected from H, F, Cl, $C_{1-3}$ alkyl optionally substituted with one or more substituents selected from F, Cl, and OH, and $OC_{1-3}$ alkyl;

$R_3$ is independently selected from H, F, Cl, and $C_{1-3}$ alkyl optionally substituted with one or more substituents selected from F, Cl, and OH;

$R_4$ is independently selected from H, F, Cl, $—C(=O)R_b$, $C_{1-6}$ alkyl optionally substituted with one or more substituents selected from F, Cl, OH, and $C_{3-6}$ cycloalkyl, $—NH—C_{1-6}$ alkyl optionally substituted with one or more substituents selected from F, Cl, OH, and $C_{3-6}$ cycloalkyl, $—(CH_2)_r$-aryl substituted with one or more $R_5$, $—O—C_{1-6}$ alkyl substituted with one or more $R_5$, $—(CH_2)_r—C_{3-12}$ cycloalkyl substituted with one or more $R_5$, and $—(CH_2)_r$-4-10 membered heterocyclyl comprising carbon atoms and 1-5 heteroatoms selected from N, $NR_6$, O, and S and substituted with one or more $R_5$;

$R_5$ is independently selected from H, F, Cl, =O, $C_{1-4}$ alkyl optionally substituted with one or more $R_e$, $—(CH_2)_rOR_b$, $—(CH_2)_rS(O)_pR_c$, $—(CH_2)_rS(O)_pNR_aR_a$, $—(CH_2)_rNR_aS(O)_pR_c$, $—(CH_2)_rNR_aR_a$, $—(CH_2)_rNR_aC(=O)R_b$, $—(CH_2)_rNR_aC(=O)OR_b$, $—(CH_2)_rNR_aC(=O)NR_aR_a$, $—(CH_2)_rC(=O)R_b$, $—(CH_2)_rC(=O)OR_b$, $—(CH_2)_rC(=O)NR_aR_a$, $—(CH_2)_rOC(=O)R_b$, $—(CH_2)_rOC(=O)OR_b$, $—(CH_2)_rO(CH_2)_rC(=O)NR_aR_a$, $C_{3-6}$ cycloalkyl optionally substituted with one or more $R_e$, aryl optionally substituted with one or more $R_e$, and heterocyclyl optionally substituted with one or more $R_e$;

$R_6$ is independently selected from H, $C_{1-6}$ alkyl optionally substituted with one or more $R_e$, $—S(O)_pR_c$, $—S(O)_pNR_aR_a$, $—C(=O)R_b$, $—C(=O)OR_b$, $—C(=O)NR_aR_a$, $C_{3-6}$ cycloalkyl optionally substituted with one or more $R_e$, aryl optionally substituted with one or more $R_e$, and heterocyclyl optionally substituted with one or more $R_e$;

$R_7$ is independently selected from H, F, and Cl;

$R_8$ is independently selected from H, and $C_{1-6}$ alkyl optionally substituted with one or more substituents selected from F, Cl, and $C_{3-6}$ cycloalkyl;

$R_a$ is independently selected from H, $C_{1-6}$ alkyl optionally substituted with one or more $R_e$, $—(CH_2)_r—C_{3-10}$ carbocyclyl optionally substituted with one or more $R_e$, and $—(CH_2)_r$-heterocyclyl optionally substituted with one or more $R_e$; or $R_a$ and $R_a$ together with the nitrogen atom to which they are both attached form a heterocyclic ring optionally substituted with one or more $R_e$;

$R_b$ is independently selected from H, $C_{1-6}$ alkyl optionally substituted with one or more $R_e$, $-(CH_2)_r-C_{3-10}$ carbocyclyl optionally substituted with one or more $R_e$, and $-(CH_2)_r$ heterocyclyl optionally substituted with one or more $R_e$;

$R_c$ is independently selected from $C_{1-6}$ alkyl optionally substituted with one or more $R_e$, $-(CH_2)_r-C_{3-10}$ carbocyclyl optionally substituted with one or more $R_e$, and $-(CH_2)_r$-heterocyclyl optionally substituted with one or more $R_e$;

$R_e$ is independently selected from F, Cl, Br, $NH_2$, $-NH-C_{1-4}$ alkyl, $-N(C_{1-4}\ alkyl)_2$, $=O$, OH, $-OC_{1-6}$ alkyl, $C_{1-6}$ alkyl optionally substituted with one or more $R_f$, $-(CH_2)_r-C_{3-6}$ cycloalkyl optionally substituted with one or more $R_f$, $-(CH_2)_r$-aryl optionally substituted with one or more $R_f$, and $-(CH_2)_r$-heterocyclyl optionally substituted with one or more $R_f$;

$R_f$ is independently selected from F, Cl, OH, $OC_{1-5}$ alkyl, $C_{1-5}$ alkyl optionally substituted with OH, $C_{2-5}$ alkenyl, $C_{2-5}$ alkynyl, $C_{3-6}$ cycloalkyl, and phenyl;

p, at each occurrence, is independently selected from zero, 1, and 2; and r, at each occurrence, is independently selected from zero, 1, 2, 3, and 4.

9. The compound according to claim 8, or a pharmaceutically acceptable salt thereof, wherein:

$R_1$ is independently selected from

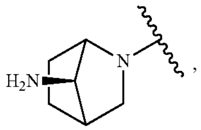

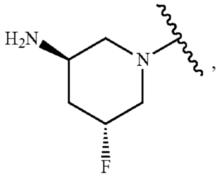

and

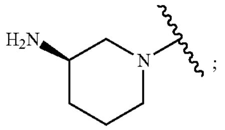

$R_2$ is independently selected from H, F, Cl, and $OCH_3$;

$R_3$ is independently selected from F, Cl, and $CH_3$;

$R_4$ is independently selected from H,

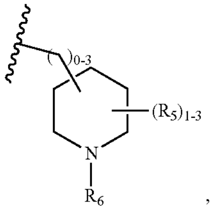

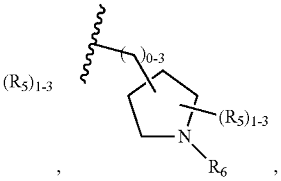

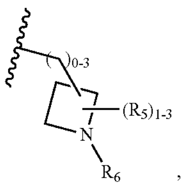

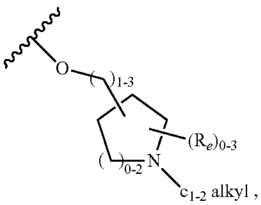

-continued

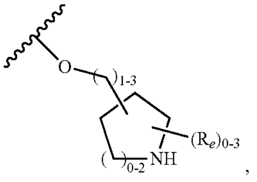

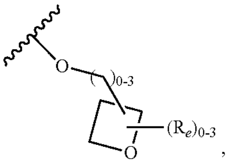

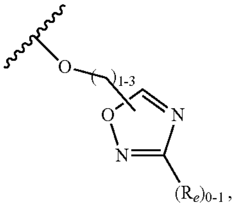

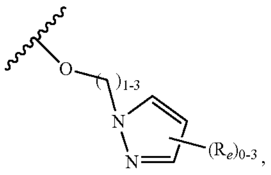

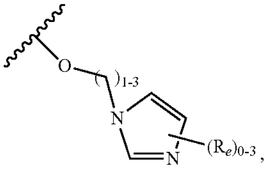

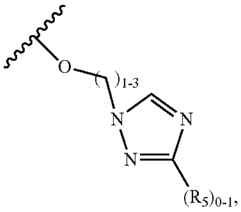

and

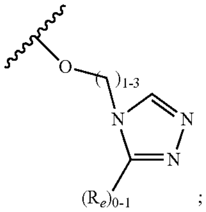

$R_5$ is independently selected from H, $=O$, $C_{1-4}$ alkyl, OH, and $NH_2$;

$R_6$ is independently selected from H, $C_{1-5}$ alkyl optionally substituted with one or more $R_e$, and $-C(=O)R_b$;

$R_7$ is H;

$R_8$ is $C_{1-2}$ alkyl optionally substituted with cyclopropyl;

$R_b$ is independently selected from H, $C_{1-6}$ alkyl optionally substituted with one or more $R_e$, $-(CH_2)_r-C_{3-10}$ carbocyclyl optionally substituted with one or more $R_e$, and $-(CH_2)_r$ heterocyclyl optionally substituted with one or more $R_e$;

$R_e$ is independently selected from $NH_2$ and $C_{1-5}$ alkyl optionally substituted with one or more $R_f$; and $R_f$ is independently selected from F, Cl, OH, and $OC_{1-5}$ alkyl.

10. The compound according to claim 9, or a pharmaceutically acceptable salt thereof, wherein:

$R_4$ is independently selected from

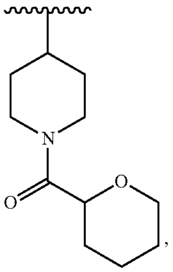

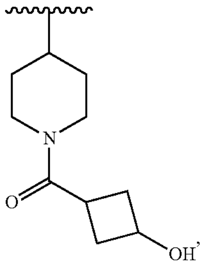

-continued
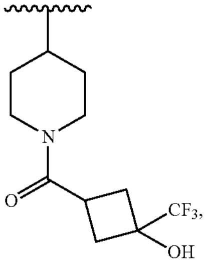
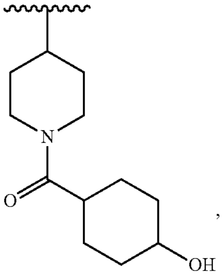
,
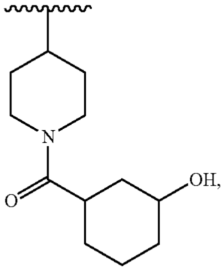
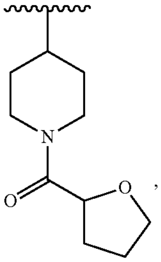
,
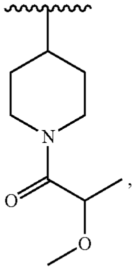
,
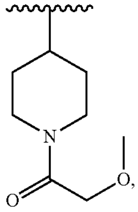
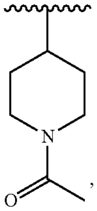
,
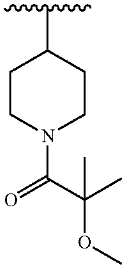
,
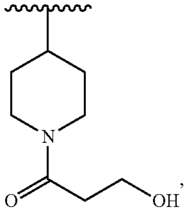
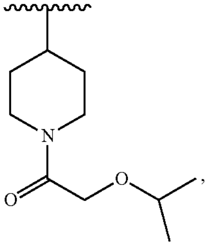
,
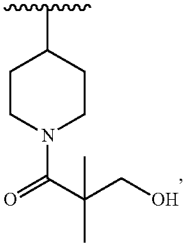
,
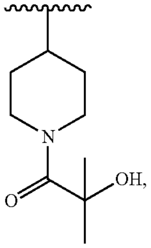
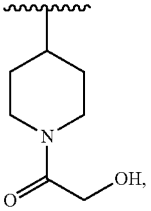
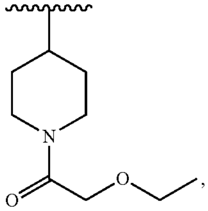
,
-continued
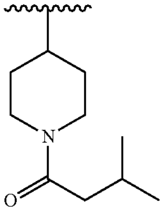
,
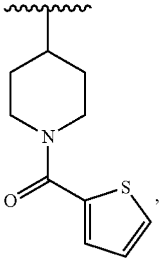
,
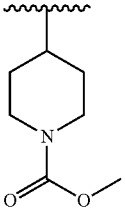
,
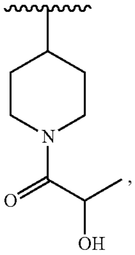
,
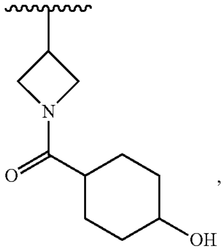
,
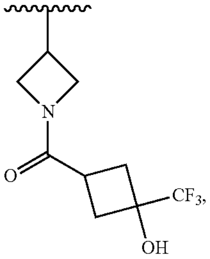
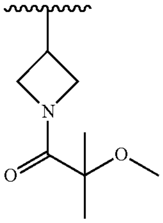
,
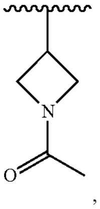
,
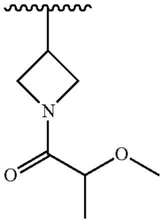
,
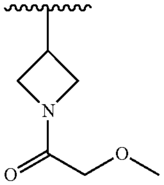
,
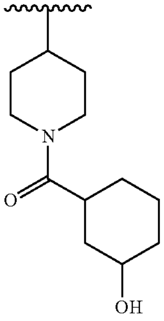
,
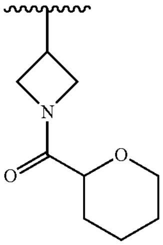
,
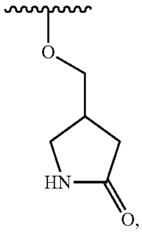
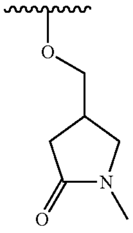
,
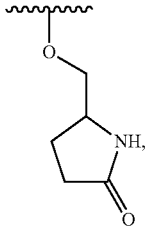
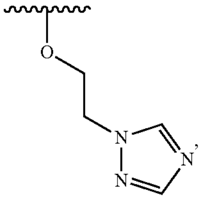

-continued

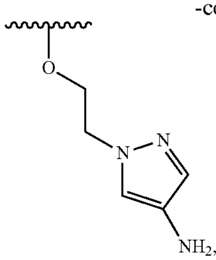

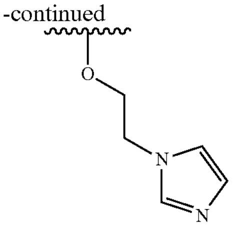

,

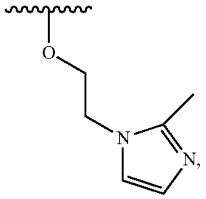

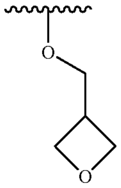

, and

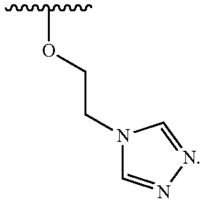

11. The compound according to claim 1, having Formula (Va):

(Va)

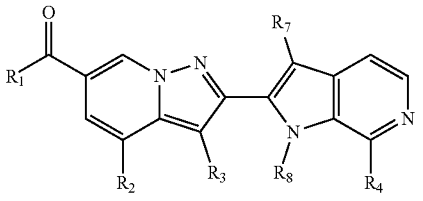

or a pharmaceutically acceptable salt thereof, wherein:

$R_1$ is independently selected from

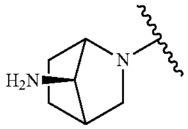

,

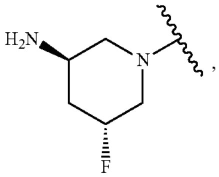

, and

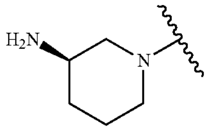

;

$R_2$ is independently selected from H, F, Cl, $CH_3$, and $OCH_3$;

$R_3$ is independently selected from H, F, Cl, CN, $CH_3$, and $CH_2OH$;

$R_4$ is independently selected from H, F, Cl, —C(═O)$R_b$, $C_{1-6}$ alkyl optionally substituted with one or more substituents selected from F, Cl, OH, and $C_{3-6}$ cycloalkyl, —NH—$C_{1-6}$ alkyl optionally substituted with one or more substituents selected from F, Cl, OH, and $C_{3-6}$ cycloalkyl, —$(CH_2)_r$-aryl substituted with one or more $R_5$, —O—$C_{1-6}$ alkyl substituted with one or more $R_5$, —$(CH_2)_r$—$C_{3-12}$ cycloalkyl substituted with one or more $R_5$, and —$(CH_2)_r$-4-10 membered heterocyclyl comprising carbon atoms and 1-5 heteroatoms selected from N, $NR_6$, O, and S and substituted with one or more $R_5$;

$R_5$ is independently selected from H, F, Cl, ═O, $C_{1-4}$ alkyl optionally substituted with one or more $R_e$, —$(CH_2)_r$O$R_b$, —$(CH_2)_r$S(O)$_p$$R_c$, —$(CH_2)_r$S(O)$_p$N$R_a$$R_a$, —$(CH_2)_r$N$R_a$S(O)$_p$$R_c$, —$(CH_2)_r$N$R_a$$R_a$, —$(CH_2)_r$N$R_a$C(═O)$R_b$, —$(CH_2)_r$N$R_a$C(═O)O$R_b$, —$(CH_2)_r$N$R_a$C(═O)N$R_a$$R_a$, —$(CH_2)_r$C(═O)$R_b$, —$(CH_2)_r$C(═O)O$R_b$, —$(CH_2)_r$C(═O)N$R_a$$R_a$, —$(CH_2)_r$OC(═O)$R_b$, —$(CH_2)_r$OC(═O)O$R_b$, —$(CH_2)_r$O$(CH_2)_r$C(═O)N$R_a$$R_a$, $C_{3-6}$ cycloalkyl optionally substituted with one or more $R_e$, aryl optionally substituted with one or more $R_e$, and heterocyclyl optionally substituted with one or more $R_e$;

$R_6$ is independently selected from H, $C_{1-6}$ alkyl optionally substituted with one or more $R_e$, —C(═O)$R_b$, —C(═O)O$R_b$, —C(═O)N$R_a$$R_a$, $C_{3-6}$ cycloalkyl optionally substituted with one or more $R_e$, aryl optionally substituted with one or more $R_e$, and heterocyclyl optionally substituted with one or more $R_e$;

$R_7$ is independently selected from H, F, and Cl;

$R_8$ is independently selected from H, and $C_{1-6}$ alkyl optionally substituted with one or more substituents selected from F, Cl, and $C_{3-6}$ cycloalkyl;

$R_a$ is independently selected from H, $C_{1-6}$ alkyl optionally substituted with one or more $R_e$, —$(CH_2)_r$—$C_{3-10}$ carbocyclyl optionally substituted with one or more $R_e$, and —$(CH_2)_r$ heterocyclyl optionally substituted with one or more $R_e$; or $R_a$ and $R_a$ together with the nitrogen atom to which they are both attached form a heterocyclic ring optionally substituted with one or more $R_e$;

$R_b$ is independently selected from H, $C_{1-6}$ alkyl optionally substituted with one or more $R_e$, —$(CH_2)_r$—$C_{3-10}$ carbocyclyl optionally substituted with one or more $R_e$, and —$(CH_2)_r$ heterocyclyl optionally substituted with one or more $R_e$;

$R_c$ is independently selected from $C_{1-6}$ alkyl optionally substituted with one or more $R_e$, —$(CH_2)_r$—$C_{3-10}$ carbocyclyl optionally substituted with one or more $R_e$, and —$(CH_2)_r$-heterocyclyl optionally substituted with one or more $R_e$;

$R_e$ is independently selected from F, Cl, Br, $NH_2$, —NH—$C_{1-4}$ alkyl, —N($C_{1-4}$ alkyl)$_2$, ═O, OH, —O$C_{1-6}$ alkyl, —$CO_2$H, $C_{1-6}$ alkyl optionally substituted with one or more $R_f$, —$(CH_2)_r$—$C_{3-6}$ cycloalkyl optionally substituted with one or more $R_f$, —$(CH_2)_r$-aryl optionally substituted with one or more $R_f$, and —$(CH_2)_r$-heterocyclyl optionally substituted with one or more $R_f$;

$R_f$ is independently selected from F, Cl, Br, CN, OH, $C_{1-5}$ alkyl optionally substituted with OH, $C_{2-5}$ alkenyl, $C_{2-5}$ alkynyl, $C_{3-6}$ cycloalkyl, and phenyl;

p, at each occurrence, is independently selected from zero, 1, and 2; and r, at each occurrence, is independently selected from zero, 1, 2, 3, and 4.

12. The compound according to claim 11, or a pharmaceutically acceptable salt thereof, wherein;
$R_1$ is independently selected from
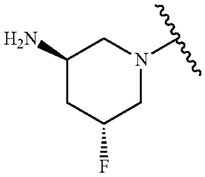, and 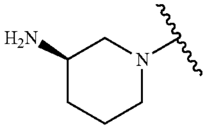;
$R_2$ is $CH_3$;
$R_3$ is $CH_3$;
$R_4$ is independently selected from
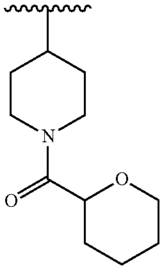, 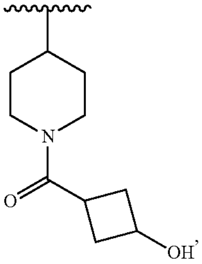, 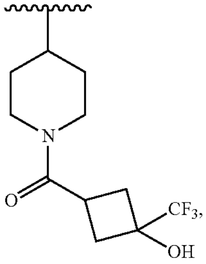 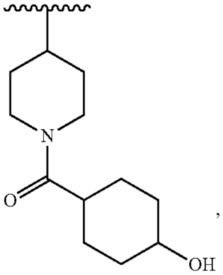, 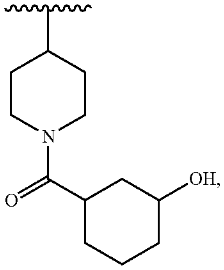 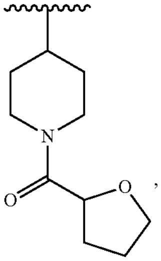, 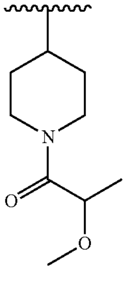, 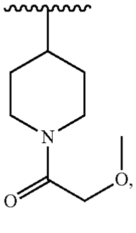 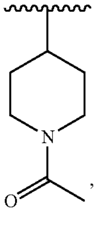,
-continued
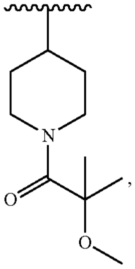, 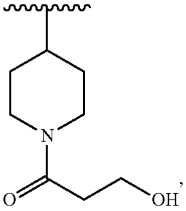, 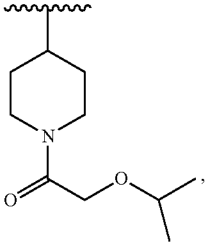, 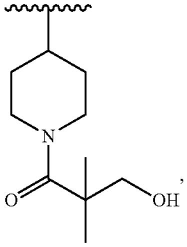, 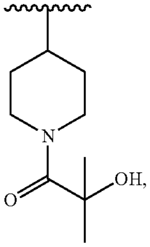 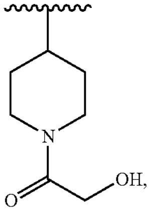 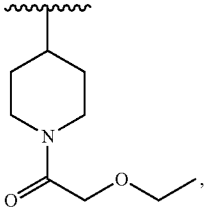 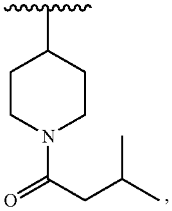, 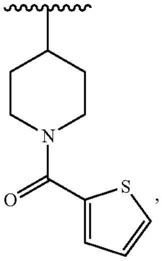, 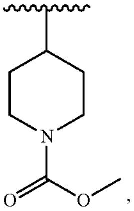, 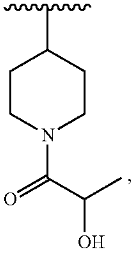, 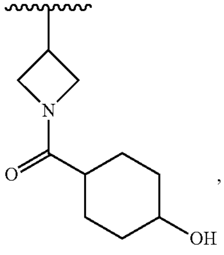, 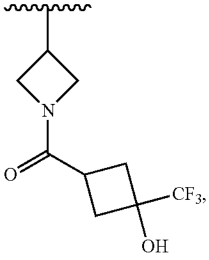 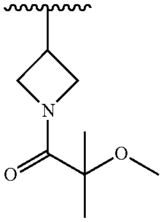, 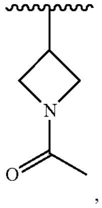, -continued

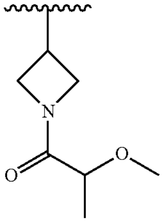, 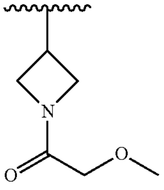,

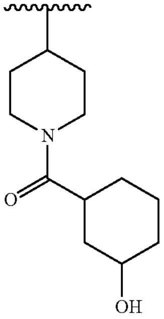, 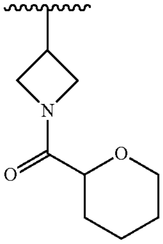, 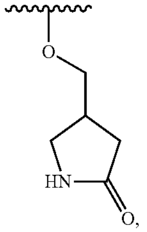

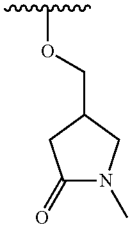, 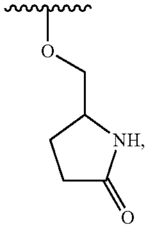 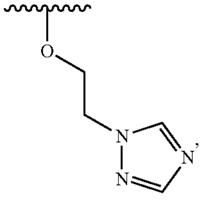

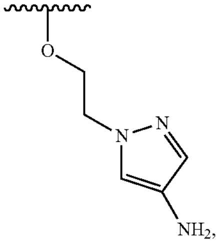 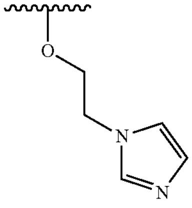,

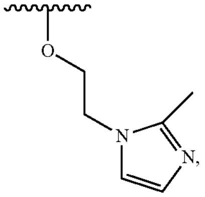 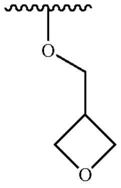,

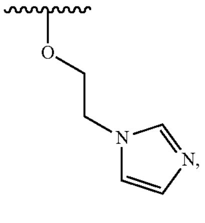 and 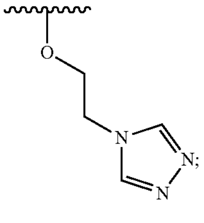

$R_7$ is H; and $R_8$ is $C_{1-2}$ alkyl optionally substituted with cyclopropyl.

13. The compound according to claim 1, having Formula (VIa):

(VIa)

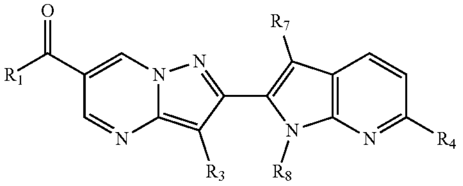

or a pharmaceutically acceptable salt thereof, wherein:

$R_1$ is independently selected from

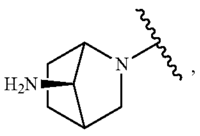, 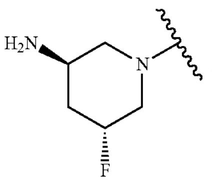, and

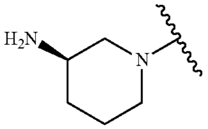;

$R_3$ is independently selected from H, F, and $CH_3$;

$R_4$ is independently selected from H, F, Cl, $—C(=O)R_b$, $C_{1-6}$ alkyl optionally substituted with one or more substituents selected from F, Cl, OH, and $C_{3-6}$ cycloalkyl, $—NH—C_{1-6}$ alkyl optionally substituted with one or more substituents selected from F, Cl, OH, and $C_{3-6}$ cycloalkyl, $—(CH_2)_r$-aryl substituted with one or more $R_5$, $—O—C_{1-6}$ alkyl substituted with one or more $R_5$, $—(CH_2)_r—C_{3-12}$ cycloalkyl substituted with one or more $R_5$, and $—(CH_2)_r$-4-10 membered heterocyclyl comprising carbon atoms and 1-5 heteroatoms selected from N, $NR_6$, O, and S and substituted with one or more $R_5$;

$R_5$ is independently selected from H, F, Cl, Br, CN, =O, $C_{1-4}$ alkyl optionally substituted with one or more $R_e$, $C_{2-4}$ alkenyl optionally substituted with one or more $R_e$, $C_{2-4}$ alkynyl optionally substituted with one or more $R_e$, $—(CH_2)_rOR_b$, $—(CH_2)_rS(O)_pR_c$, $—(CH_2)_rS(O)_pNR_aR_a$, $—(CH_2)_rNR_aS(O)_pR_c$, $—(CH_2)_rNR_aR_a$, $—(CH_2)_rNR_aC(=O)R_b$, $—(CH_2)_rN-R_aC(=O)OR_b$, $—(CH_2)_rNR_aC(=O)NR_aR_a$, $—(CH_2)_rC(=O)R_b$, $—(CH_2)_rC(=O)OR_b$, $—(CH_2)_rC(=O)NR_aR_a$, $—(CH_2)OC(=O)R_b$, $—(CH_2)_rOC(=O)OR_b$, $—(CH_2)_rO(CH_2)_rC(=O)NR_aR_a$, $C_{3-6}$ cycloalkyl optionally substituted with one or more $R_e$, aryl optionally substituted with one or more $R_e$, and heterocyclyl optionally substituted with one or more $R_e$;

$R_6$ is independently selected from H, $C_{1-6}$ alkyl optionally substituted with one or more $R_e$, $—C(=O)R_b$, $—C(=O)OR_b$, $—C(=O)NR_aR_a$, $C_{3-6}$ cycloalkyl optionally substituted with one or more $R_e$, aryl optionally substituted with one or more $R_e$, and heterocyclyl optionally substituted with one or more $R_e$;

$R_7$ is independently selected from H, F, and Cl;

$R_8$ is independently selected from H, and $C_{1-6}$ alkyl optionally substituted with one or more substituents selected from F, Cl, and $C_{3-6}$ cycloalkyl;

$R_a$ is independently selected from H, $C_{1-6}$ alkyl optionally substituted with one or more $R_e$, $C_{2-6}$ alkenyl optionally substituted with one or more Re, $C_{2-6}$ alkynyl optionally substituted with one or more $R_e$, —$(CH_2)_r$—$C_{3-10}$ carbocyclyl optionally substituted with one or more $R_e$, and —$(CH_2)_r$-heterocyclyl optionally substituted with one or more $R_e$; or $R_a$ and $R_a$ together with the nitrogen atom to which they are both attached form a heterocyclic ring optionally substituted with one or more $R_e$;

$R_b$ is independently selected from H, $C_{1-6}$ alkyl optionally substituted with one or more $R_e$, $C_{2-6}$ alkenyl optionally substituted with one or more $R_e$, $C_{2-6}$ alkynyl optionally substituted with one or more $R_e$, —$(CH_2)_r$—$C_{3-10}$ carbocyclyl optionally substituted with one or more $R_e$, and —$(CH_2)_r$ heterocyclyl optionally substituted with one or more $R_e$;

$R_c$ is independently selected from $C_{1-6}$ alkyl optionally substituted with one or more $R_e$, $C_{2-6}$ alkenyl optionally substituted with one or more $R_e$, $C_{2-6}$ alkynyl optionally substituted with one or more $R_e$, —$(CH_2)_r$—$C_{3-10}$ carbocyclyl optionally substituted with one or more $R_e$, and —$(CH_2)_r$-heterocyclyl optionally substituted with one or more $R_e$;

$R_e$ is independently selected from F, Cl, Br, CN, $NH_2$, —NH—$C_{1-4}$ alkyl, —$N(C_{1-4}\ alkyl)_2$, =O, OH, —$OC_{1-6}$ alkyl, —$CO_2H$, $C_{1-6}$ alkyl optionally substituted with one or more $R_f$, $C_{2-6}$ alkenyl, $C_{2-6}$ alkynyl, —$(CH_2)_r$—$C_{3-6}$ cycloalkyl optionally substituted with one or more $R_f$, —$(CH_2)_r$-aryl optionally substituted with one or more $R_f$, and —$(CH_2)_r$-heterocyclyl optionally substituted with one or more $R_f$;

$R_f$ is independently selected from F, Cl, Br, CN, OH, $C_{1-5}$ alkyl optionally substituted with OH, $C_{2-5}$ alkenyl, $C_{2-5}$ alkynyl, $C_{3-6}$ cycloalkyl, and phenyl;

p, at each occurrence, is independently selected from zero, 1, and 2; and r, at each occurrence, is independently selected from zero, 1, 2, 3, and 4.

14. The compound according to claim 13, or a pharmaceutically acceptable salt thereof, wherein;

$R_1$ is independently selected from

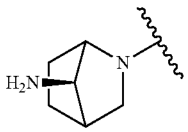 and 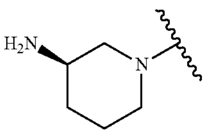 ;

$R_3$ is $CH_3$;

$R_4$ is independently selected from F, Cl,

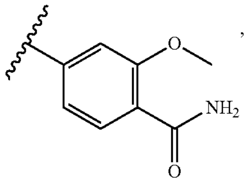 ,

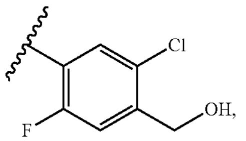 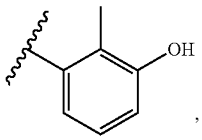 ,

-continued

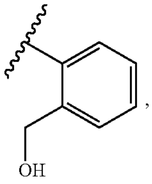 , 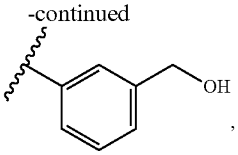 ,

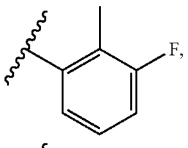 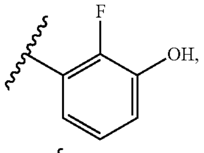

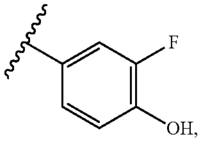 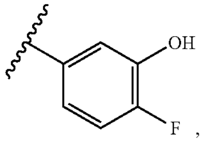 ,

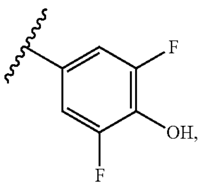 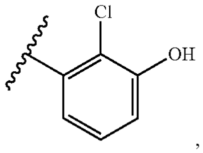 ,

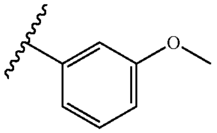 , 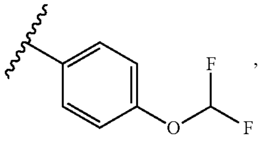 ,

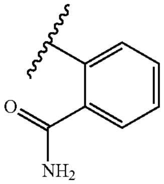 , 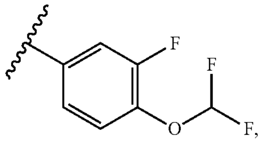

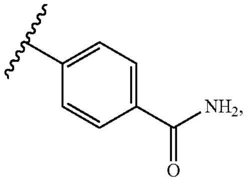 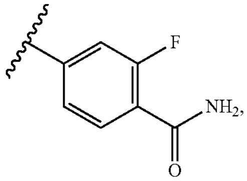

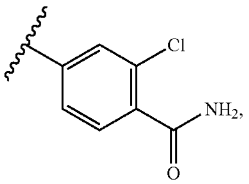 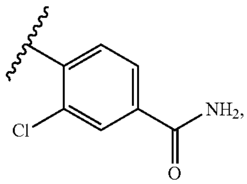

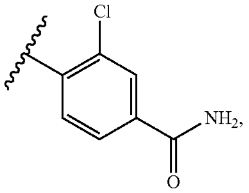 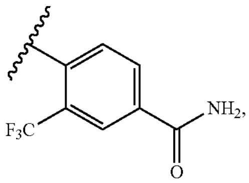

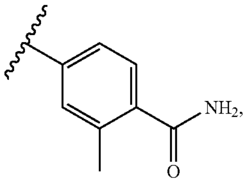 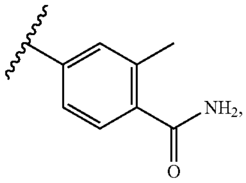

-continued

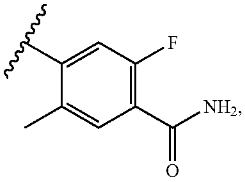
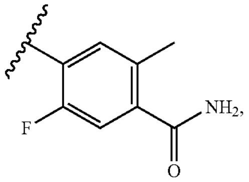
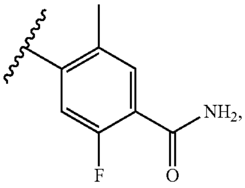
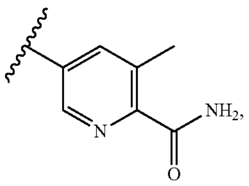
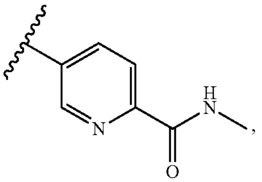
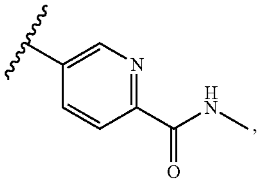
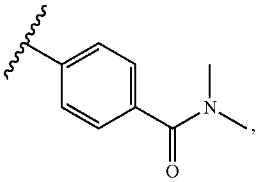
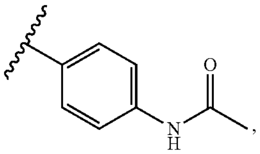
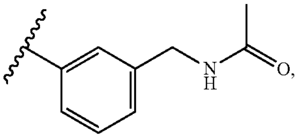
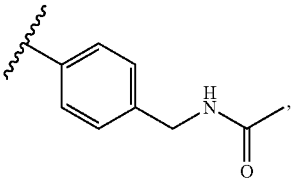
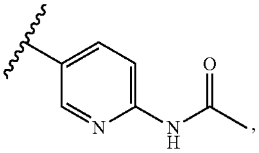
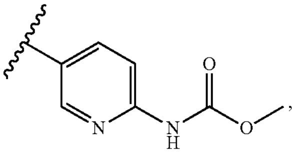
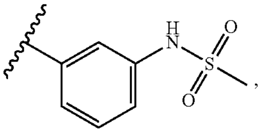
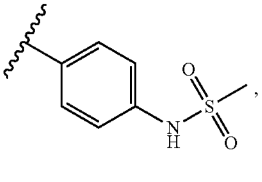

-continued

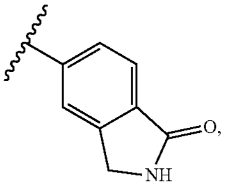
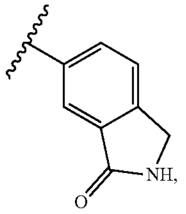
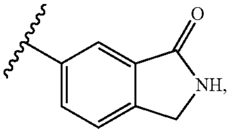
and
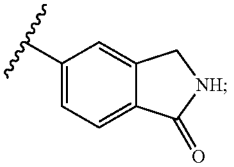

$R_7$ is H; and $R_8$ is $C_{1-2}$ alkyl optionally substituted with cyclopropyl.

15. The compound according to claim 1, having Formula (VII):

(VII)

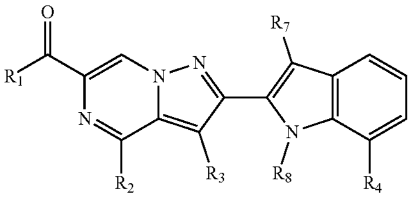

or a pharmaceutically acceptable salt thereof, wherein:

$R_1$ is independently selected from

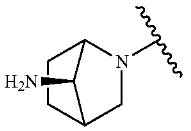
,
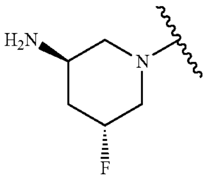
, and
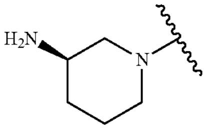
;

$R_2$ is independently selected from H, F, Cl, $CH_3$, and $OCH_3$;

$R_3$ is independently selected from H, F, and $CH_3$;

$R_4$ is independently selected from H, F, Cl, Br, —C(═O)$R_b$, $C_{1-6}$ alkyl optionally substituted with one or more substituents selected from F, Cl, OH, and $C_{3-6}$ cycloalkyl, —NH—$C_{1-6}$ alkyl optionally substituted with one or more substituents selected from F, Cl, OH, and $C_{3-6}$ cycloalkyl, —$(CH_2)_r$-aryl substituted with one or more $R_5$, —O—$C_{1-6}$ alkyl substituted with one or more $R_5$, —$(CH_2)_r$—$C_{3-12}$ cycloalkyl substituted with one or more $R_5$, and —$(CH_2)_r$-4-10 membered heterocyclyl comprising carbon atoms and 1-5 heteroatoms selected from N, $NR_6$, O, and S and substituted with one or more $R_5$;

$R_5$ is independently selected from H, F, Cl, Br, CN, ═O, $C_{1-4}$ alkyl optionally substituted with one or more $R_e$, $C_{2-4}$ alkenyl optionally substituted with one or more $R_e$, $C_{2-4}$ alkynyl optionally substituted with one or more $R_e$, —$(CH_2)_rOR_b$, —$(CH_2)_rS(O)_pR_c$, —$(CH_2)_rS(O)_pNR_aR_a$, —$(CH_2)_rNR_aS(O)_pR_c$, —$(CH_2)_rNR_aR_a$, —$(CH_2)_rNR_aC(=O)R_b$, —$(CH_2)_rN$-$R_aC(=O)OR_b$, —$(CH_2)_rNR_aC(=O)NR_aR_a$, —$(CH_2)_rC(=O)R_b$, —$(CH_2)_rC(=O)OR_b$, —$(CH_2)_rC(=O)NR_aR_a$, —$(CH_2)_rOC(=O)R_b$, —$(CH_2)_rOC(=O)OR_b$, —$(CH_2)_rO(CH_2)_rC(=O)NR_aR_a$, $C_{3-6}$ cycloalkyl optionally substituted with one or more $R_e$, aryl optionally substituted with one or more $R_e$, and heterocyclyl optionally substituted with one or more $R_e$;

$R_6$ is independently selected from H, $C_{1-6}$ alkyl optionally substituted with one or more $R_e$, —$S(O)_pR_c$, —$S(O)_pNR_aR_a$, —$C(=O)R_b$, —$C(=O)OR_b$, —$C(=O)NR_aR_a$, $C_{3-6}$ cycloalkyl optionally substituted with one or more $R_e$, aryl optionally substituted with one or more $R_e$, and heterocyclyl optionally substituted with one or more $R_e$;

$R_7$ is independently selected from H, F, and Cl;

$R_8$ is independently selected from H, and $C_{1-6}$ alkyl optionally substituted with one or more substituents selected from F, Cl, and $C_{3-6}$ cycloalkyl;

$R_a$ is independently selected from H, $C_{1-6}$ alkyl optionally substituted with one or more $R_e$, $C_{2-6}$ alkenyl optionally substituted with one or more $R_e$, $C_{2-6}$ alkynyl optionally substituted with one or more $R_e$, —$(CH_2)_r$—$C_{3-10}$ carbocyclyl optionally substituted with one or more $R_e$, and —$(CH_2)_r$-heterocyclyl optionally substituted with one or more $R_e$; or $R_a$ and $R_a$ together with the nitrogen atom to which they are both attached form a heterocyclic ring optionally substituted with one or more $R_e$;

$R_b$ is independently selected from H, $C_{1-6}$ alkyl optionally substituted with one or more $R_e$, $C_{2-6}$ alkenyl optionally substituted with one or more $R_e$, $C_{2-6}$ alkynyl optionally substituted with one or more $R_e$, —$(CH_2)_r$—$C_{3-10}$ carbocyclyl optionally substituted with one or more $R_e$, and —$(CH_2)_r$ heterocyclyl optionally substituted with one or more $R_e$;

$R_c$ is independently selected from $C_{1-6}$ alkyl optionally substituted with one or more $R_e$, $C_{2-6}$ alkenyl optionally substituted with one or more $R_e$, $C_{2-6}$ alkynyl optionally substituted with one or more $R_e$, —$(CH_2)_r$—$C_{3-10}$ carbocyclyl optionally substituted with one or more $R_e$, and —$(CH_2)_r$-heterocyclyl optionally substituted with one or more $R_e$;

$R_e$ is independently selected from F, Cl, Br, CN, $NH_2$, —NH—$C_{1-4}$ alkyl, —$N(C_{1-4}\ alkyl)_2$, =O, OH, —$OC_{1-6}$ alkyl, —$CO_2H$, $C_{1-6}$ alkyl optionally substituted with one or more $R_f$, $C_{2-6}$ alkenyl, $C_{2-6}$ alkynyl, —$(CH_2)_r$—$C_{3-6}$ cycloalkyl optionally substituted with one or more $R_f$, —$(CH_2)_r$-aryl optionally substituted with one or more $R_f$, and —$(CH_2)_r$-heterocyclyl optionally substituted with one or more $R_f$;

$R_f$ is independently selected from F, Cl, Br, CN, OH, $C_{1-5}$ alkyl optionally substituted with OH, $C_{2-5}$ alkenyl, $C_{2-5}$ alkynyl, $C_{3-6}$ cycloalkyl, and phenyl;

p, at each occurrence, is independently selected from zero, 1, and 2; and r, at each occurrence, is independently selected from zero, 1, 2, 3, and 4.

16. The compound according to claim 1, having Formula (VIII):

(VIII)

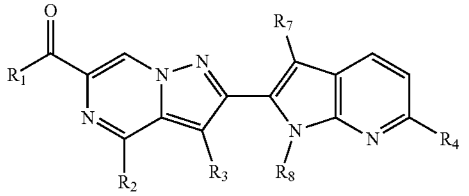

or a pharmaceutically acceptable salt thereof, wherein:

$R_1$ is independently selected from

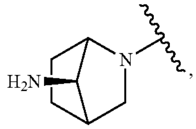, 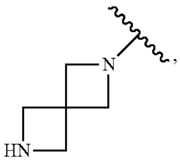, and 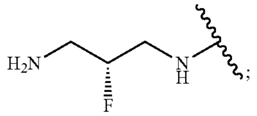;

$R_2$ is independently selected from H, F, and $OCH_3$;

$R_3$ is independently selected from H, F, and $CH_3$;

$R_4$ is independently selected from H, F, Cl, Br, —$C(=O)R_b$, $C_{1-6}$ alkyl optionally substituted with one or more substituents selected from F, Cl, OH, and $C_{3-6}$ cycloalkyl, —NH—$C_{1-6}$ alkyl optionally substituted with one or more substituents selected from F, Cl, OH, and $C_{3-6}$ cycloalkyl, —$(CH_2)_r$-aryl substituted with one or more $R_5$, —O—$C_{1-6}$ alkyl substituted with one or more $R_5$, —$(CH_2)_r$—$C_{3-12}$ cycloalkyl substituted with one or more $R_5$, and —$(CH_2)_r$-4-10 membered heterocyclyl comprising carbon atoms and 1-5 heteroatoms selected from N, $NR_6$, O, and S and substituted with one or more $R_5$;

$R_5$ is independently selected from H, F, Cl, Br, CN, =O, $C_{1-4}$ alkyl optionally substituted with one or more $R_e$, $C_{2-4}$ alkenyl optionally substituted with one or more $R_e$, $C_{2-4}$ alkynyl optionally substituted with one or more $R_e$, —$(CH_2)_rOR_b$, —$(CH_2)_rS(O)_pR_c$, —$(CH_2)_rS(O)_pNR_aR_a$, —$(CH_2)_rNR_aS(O)_pR_c$, —$(CH_2)_rNR_aR_a$, —$(CH_2)_rNR_aC(=O)R_b$, —$(CH_2)_rN$-$R_aC(=O)OR_b$, —$(CH_2)_rNR_aC(=O)NR_aR_a$, —$(CH_2)_rC(=O)R_b$, —$(CH_2)_rC(=O)OR_b$, —$(CH_2)_rC(=O)NR_aR_a$, —$(CH_2)_rOC(=O)R_b$, —$(CH_2)_rOC(=O)OR_b$, —$(CH_2)_rO(CH_2)_rC(=O)NR_aR_a$, $C_{3-6}$ cycloalkyl optionally substituted with one or more $R_e$, aryl optionally substituted with one or more $R_e$, and heterocyclyl optionally substituted with one or more $R_e$;

$R_6$ is independently selected from H, $C_{1-6}$ alkyl optionally substituted with one or more $R_e$, —$C(=O)R_b$, —$C(=O)OR_b$, —$C(=O)NR_aR_a$, $C_{3-6}$ cycloalkyl optionally substituted with one or more $R_e$, aryl optionally substituted with one or more $R_e$, and heterocyclyl optionally substituted with one or more $R_e$;

$R_7$ is independently selected from H, F, and Cl;

$R_8$ is independently selected from H, and $C_{1-6}$ alkyl optionally substituted with one or more substituents selected from F, Cl, and $C_{3-6}$ cycloalkyl;

$R_a$ is independently selected from H, $C_{1-6}$ alkyl optionally substituted with one or more $R_e$, $C_{2-6}$ alkenyl optionally substituted with one or more Re, $C_{2-6}$ alkynyl optionally substituted with one or more $R_e$, —$(CH_2)_r$—$C_{3-10}$ carbocyclyl optionally substituted with one or more $R_e$, and —$(CH_2)_r$-heterocyclyl optionally substituted with one or more $R_e$; or $R_a$ and $R_a$ together with the nitrogen atom to which they are both attached form a heterocyclic ring optionally substituted with one or more $R_e$;

$R_b$ is independently selected from H, $C_{1-6}$ alkyl optionally substituted with one or more $R_e$, $C_{2-6}$ alkenyl optionally substituted with one or more $R_e$, $C_{2-6}$ alkynyl optionally substituted with one or more $R_e$, —$(CH_2)_r$—$C_{3-10}$ carbocyclyl optionally substituted with one or more $R_e$, and —$(CH_2)_r$- heterocyclyl optionally substituted with one or more $R_e$;

$R_c$ is independently selected from $C_{1-6}$ alkyl optionally substituted with one or more $R_e$, $C_{2-6}$ alkenyl optionally substituted with one or more $R_e$, $C_{2-6}$ alkynyl optionally substituted with one or more $R_e$, —$(CH_2)_r$—$C_{3-10}$ carbocyclyl optionally substituted with one or more $R_e$, and —$(CH_2)_r$-heterocyclyl optionally substituted with one or more $R_e$;

$R_d$ is independently selected from H, and $C_{1-6}$ alkyl optionally substituted with one or more $R_e$;

$R_e$ is independently selected from F, Cl, Br, CN, $NH_2$, —NH—$C_{1-4}$ alkyl, —N($C_{1-4}$ alkyl)$_2$, =O, OH, —$OC_{1-6}$ alkyl, —$CO_2H$, $C_{1-6}$ alkyl optionally substituted with one or more $R_f$, $C_{2-6}$ alkenyl, $C_{2-6}$ alkynyl, —$(CH_2)_r$—$C_{3-6}$ cycloalkyl optionally substituted with one or more $R_f$, —$(CH_2)_r$-aryl optionally substituted with one or more $R_f$, and —$(CH_2)_r$-heterocyclyl optionally substituted with one or more $R_f$;

$R_f$ is independently selected from F, Cl, Br, CN, OH, $C_{1-5}$ alkyl optionally substituted with OH, $C_{2-5}$ alkenyl, $C_{2-5}$ alkynyl, $C_{3-6}$ cycloalkyl, and phenyl;

p, at each occurrence, is independently selected from zero, 1, and 2; and r, at each occurrence, is independently selected from zero, 1, 2, 3, and 4.

17. The compound according to claim 1, having Formula (IX):

(IX)

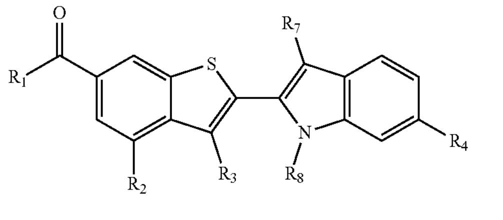

or a pharmaceutically acceptable salt thereof, wherein:

$R_1$ is independently selected from

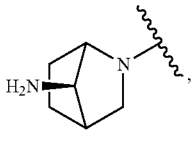,

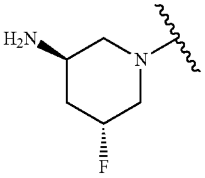, and

-continued

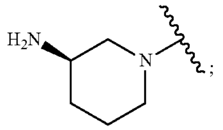;

$R_2$ is independently selected from H, F, $CH_3$, $CH_2OH$, $CH_2CH_2OH$, and $OCH_3$;

$R_3$ is independently selected from H, F, Cl, $CH_3$, $CH_2OH$, $CH_2CH_2OH$, $CH_2NH_3$, $CH_2CH_2NH_2$, and $CH_2CH_2N_3$;

$R_4$ is independently selected from H, F, Cl, Br, —C(=O)$R_b$, $C_{1-6}$ alkyl optionally substituted with one or more substituents selected from F, Cl, OH, and $C_{3-6}$ cycloalkyl, —NH—$C_{1-6}$ alkyl optionally substituted with one or more substituents selected from F, Cl, OH, and $C_{3-6}$ cycloalkyl, —$(CH_2)_r$-aryl substituted with one or more $R_5$, —O—$C_{1-6}$ alkyl substituted with one or more $R_5$, —$(CH_2)_r$—$C_{3-12}$ cycloalkyl substituted with one or more $R_5$, and —$(CH_2)_r$-4-10 membered heterocyclyl comprising carbon atoms and 1-5 heteroatoms selected from N, $NR_6$, O, and S and substituted with one or more $R_5$;

$R_5$ is independently selected from H, F, Cl, Br, CN, =O, $C_{1-4}$ alkyl optionally substituted with one or more $R_e$, $C_{2-4}$ alkenyl optionally substituted with one or more $R_e$, $C_{2-4}$ alkynyl optionally substituted with one or more $R_e$, —$(CH_2)_r$$OR_b$, —$(CH_2)_r$S(O)$_p$$R_c$, —$(CH_2)_r$S(O)$_p$$NR_aR_a$, —$(CH_2)_r$$NR_a$S(O)$_p$$R_c$, —$(CH_2)_r$$NR_aR_a$, —$(CH_2)_r$$NR_a$C(=O)$R_b$, —$(CH_2)_r$$NR_a$C(=O)$OR_b$, —$(CH_2)_r$$NR_a$C(=O)$NR_aR_a$, —$(CH_2)_r$C(=O)$R_b$, —$(CH_2)_r$C(=O)$OR_b$, —$(CH_2)_r$C(=O)$NR_aR_a$, —$(CH_2)_r$OC(=O)$R_b$, —$(CH_2)_r$OC(=O)$OR_b$, —$(CH_2)_r$O$(CH_2)_r$C(=O)$NR_aR_a$, $C_{3-6}$ cycloalkyl optionally substituted with one or more $R_e$, aryl optionally substituted with one or more $R_e$, and heterocyclyl optionally substituted with one or more $R_e$;

$R_6$ is independently selected from H, $C_{1-6}$ alkyl optionally substituted with one or more $R_e$, —S(O)$_p$$R_c$, —S(O)$_p$$NR_aR_a$, —C(=O)$R_b$, —C(=O)$OR_b$, —C(=O)$NR_aR_a$, $C_{3-6}$ cycloalkyl optionally substituted with one or more $R_e$, aryl optionally substituted with one or more $R_e$, and heterocyclyl optionally substituted with one or more $R_e$;

$R_7$ is independently selected from H, F, and Cl;

$R_8$ is independently selected from H, and $C_{1-6}$ alkyl optionally substituted with one or more substituents selected from F, Cl, and $C_{3-6}$ cycloalkyl;

$R_a$ is independently selected from H, $C_{1-6}$ alkyl optionally substituted with one or more $R_e$, $C_{2-6}$ alkenyl optionally substituted with one or more Re, $C_{2-6}$ alkynyl optionally substituted with one or more $R_e$, —$(CH_2)_r$—$C_{3-10}$ carbocyclyl optionally substituted with one or more $R_e$, and —$(CH_2)_r$-heterocyclyl optionally substituted with one or more $R_e$; or $R_a$ and $R_a$ together with the nitrogen atom to which they are both attached form a heterocyclic ring optionally substituted with one or more $R_e$;

$R_b$ is independently selected from H, $C_{1-6}$ alkyl optionally substituted with one or more $R_e$, $C_{2-6}$ alkenyl optionally substituted with one or more $R_e$, $C_{2-6}$ alkynyl optionally substituted with one or more $R_e$, —$(CH_2)_r$—$C_{3-10}$ carbocyclyl optionally substituted with one or more $R_e$, and —$(CH_2)_r$- heterocyclyl optionally substituted with one or more $R_e$;

$R_c$ is independently selected from $C_{1-6}$ alkyl optionally substituted with one or more $R_e$, $C_{2-6}$ alkenyl optionally substituted with one or more $R_e$, $C_{2-6}$ alkynyl optionally substituted with one or more $R_e$, $—(CH_2)_r—C_{3-10}$ carbocyclyl optionally substituted with one or more $R_e$, and $—(CH_2)_r$-heterocyclyl optionally substituted with one or more $R_e$;

$R_e$ is independently selected from F, Cl, Br, CN, $NH_2$, $—NH—C_{1-4}$ alkyl, $—N(C_{1-4}\ alkyl)_2$, $=O$, OH, $—OC_{1-6}$ alkyl, $—CO_2H$, $C_{1-6}$ alkyl optionally substituted with one or more $R_f$, $C_{2-6}$ alkenyl, $C_{2-6}$ alkynyl, $—(CH_2)_r—C_{3-6}$ cycloalkyl optionally substituted with one or more $R_f$, $—(CH_2)_r$-aryl optionally substituted with one or more $R_f$, and $—(CH_2)_r$-heterocyclyl optionally substituted with one or more $R_f$;

$R_f$ is independently selected from F, Cl, Br, CN, OH, $C_{1-5}$ alkyl optionally substituted with OH, $C_{2-5}$ alkenyl, $C_{2-5}$ alkynyl, $C_{3-6}$ cycloalkyl, and phenyl;

p, at each occurrence, is independently selected from zero, 1, and 2; and r, at each occurrence, is independently selected from zero, 1, 2, 3, and 4.

18. The compound according to claim 1, having Formula (X):

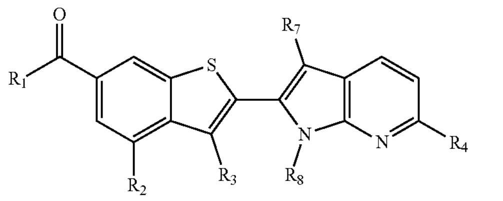

(X)

or a pharmaceutically acceptable salt thereof, wherein:

$R_1$ is independently selected from

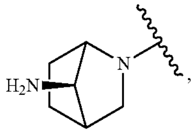

,

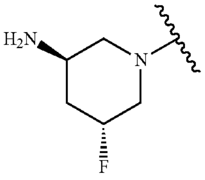

, and

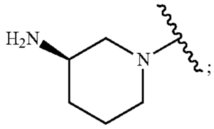

;

$R_2$ is independently selected from H, $FCH_3$, $CH_2OH$, $CH_2CH_2OH$, and $OCH_3$;

$R_3$ is independently selected from H, F, $CH_3$, $CH_2OH$, $CH_2CH_2OH$, $CH_2NH_3$, $CH_2CH_2NH_2$, and $CH_2CH_2N_3$;

$R_4$ is independently selected from H, F, Cl, Br, $—C(=O)R_b$, $C_{1-6}$ alkyl optionally substituted with one or more substituents selected from F, Cl, OH, and $C_{3-6}$ cycloalkyl, $—NH—C_{1-6}$ alkyl optionally substituted with one or more substituents selected from F, Cl, OH, and $C_{3-6}$ cycloalkyl, $—(CH_2)_r$-aryl substituted with one or more $R_5$, $—O—C_{1-6}$ alkyl substituted with one or more $R_5$, $—(CH_2)_r—C_{3-12}$ cycloalkyl substituted with one or more $R_5$, and $—(CH_2)_r$-4-10 membered heterocyclyl comprising carbon atoms and 1-5 heteroatoms selected from N, $NR_6$, O, and S and substituted with one or more $R_5$;

$R_5$ is independently selected from H, F, Cl, Br, CN, $=O$, $C_{1-4}$ alkyl optionally substituted with one or more $R_e$, $C_{2-4}$ alkenyl optionally substituted with one or more $R_e$, $C_{2-4}$ alkynyl optionally substituted with one or more $R_e$, $—(CH_2)_rOR_b$, $—(CH_2)_rS(O)_pR_c$, $—(CH_2)_rS(O)_pNR_aR_a$, $—(CH_2)_rNR_aS(O)_pR_c$, $—(CH_2)_rNR_aR_a$, $—(CH_2)_rNR_aC(=O)R_b$, $—(CH_2)_rNR_aC(=O)OR_b$, $—(CH_2)_rNR_aC(=O)NR_aR_a$, $—(CH_2)_rC(=O)R_b$, $—(CH_2)_rC(=O)OR_b$, $—(CH_2)_rC(=O)NR_aR_a$, $—(CH_2)_rOC(=O)R_b$, $—(CH_2)_rOC(=O)OR_b$, $—(CH_2)_rO(CH_2)_rC(=O)NR_aR_a$, $C_{3-6}$ cycloalkyl optionally substituted with one or more $R_e$, aryl optionally substituted with one or more $R_e$, and heterocyclyl optionally substituted with one or more $R_e$;

$R_6$ is independently selected from H, $C_{1-6}$ alkyl optionally substituted with one or more $R_e$, $—S(O)_pR_c$, $—S(O)_pNR_aR_a$, $—C(=O)R_b$, $—C(=O)OR_b$, $—C(=O)NR_aR_a$, $C_{3-6}$ cycloalkyl optionally substituted with one or more $R_e$, aryl optionally substituted with one or more $R_e$, and heterocyclyl optionally substituted with one or more $R_e$;

$R_7$ is independently selected from H, F, and Cl;

$R_8$ is independently selected from H, and $C_{1-6}$ alkyl optionally substituted with one or more substituents selected from F, Cl, and $C_{3-6}$ cycloalkyl;

$R_a$ is independently selected from H, $C_{1-6}$ alkyl optionally substituted with one or more $R_e$, $C_{2-6}$ alkenyl optionally substituted with one or more $R_e$, $C_{2-6}$ alkynyl optionally substituted with one or more $R_e$, $—(CH_2)_r—C_{3-10}$ carbocyclyl optionally substituted with one or more $R_e$, and $—(CH_2)_r$-heterocyclyl optionally substituted with one or more $R_e$; or $R_a$ and $R_a$ together with the nitrogen atom to which they are both attached form a heterocyclic ring optionally substituted with one or more $R_e$;

$R_b$ is independently selected from H, $C_{1-6}$ alkyl optionally substituted with one or more $R_e$, $C_{2-6}$ alkenyl optionally substituted with one or more $R_e$, $C_{2-6}$ alkynyl optionally substituted with one or more $R_e$, $—(CH_2)_r—C_{3-10}$ carbocyclyl optionally substituted with one or more $R_e$, and $—(CH_2)_r$ heterocyclyl optionally substituted with one or more $R_e$;

$R_c$ is independently selected from $C_{1-6}$ alkyl optionally substituted with one or more $R_e$, $C_{2-6}$ alkenyl optionally substituted with one or more $R_e$, $C_{2-6}$ alkynyl optionally substituted with one or more $R_e$, $—(CH_2)_r—C_{3-10}$ carbocyclyl optionally substituted with one or more $R_e$, and $—(CH_2)_r$-heterocyclyl optionally substituted with one or more $R_e$;

$R_e$ is independently selected from F, Cl, Br, CN, $NH_2$, $—NH—C_{1-4}$ alkyl, $—N(C_{1-4}\ alkyl)_2$, $=O$, OH, $—OC_{1-6}$ alkyl, $—CO_2H$, $C_{1-6}$ alkyl optionally substituted with one or more $R_f$, $C_{2-6}$ alkenyl, $C_{2-6}$ alkynyl, $—(CH_2)_r—C_{3-6}$ cycloalkyl optionally substituted with one or more $R_f$, $—(CH_2)_r$-aryl optionally substituted with one or more $R_f$, and $—(CH_2)_r$-heterocyclyl optionally substituted with one or more $R_f$;

$R_f$ is independently selected from F, Cl, Br, CN, OH, $C_{1-5}$ alkyl optionally substituted with OH, $C_{2-5}$ alkenyl, $C_{2-5}$ alkynyl, $C_{3-6}$ cycloalkyl, and phenyl;

p, at each occurrence, is independently selected from zero, 1, and 2; and r, at each occurrence, is independently selected from zero, 1, 2, 3, and 4.

19. The compound according to claim 1, having Formula (XI):

(XI)

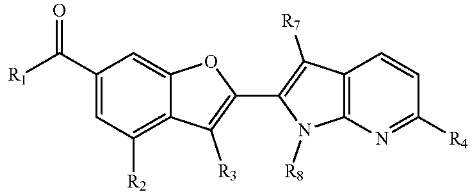

or a pharmaceutically acceptable salt thereof, wherein:

$R_1$ is independently selected from

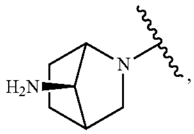, 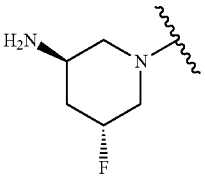, and

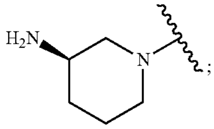;

$R_2$ is independently selected from H, F, $CH_3$, $CH_2OH$, $CH_2CH_2OH$, and $OCH_3$;

$R_3$ is independently selected from H, F, $CH_3$, $CH_2OH$, $CH_2CH_2OH$, $CH_2NH_3$, $CH_2CH_2NH_2$, and $CH_2CH_2N_3$;

$R_4$ is independently selected from H, F, Cl, Br, —C(═O)$R_b$, $C_{1-6}$ alkyl optionally substituted with one or more substituents selected from F, Cl, OH, and $C_{3-6}$ cycloalkyl, —NH—$C_{1-6}$ alkyl optionally substituted with one or more substituents selected from F, Cl, OH, and $C_{3-6}$ cycloalkyl, —$(CH_2)_r$-aryl substituted with one or more $R_5$, —O—$C_{1-6}$ alkyl substituted with one or more $R_5$, —$(CH_2)_r$—$C_{3-12}$ cycloalkyl substituted with one or more $R_5$, and —$(CH_2)_r$-4-10 membered heterocyclyl comprising carbon atoms and 1-5 heteroatoms selected from N, $NR_6$, O, and S and substituted with one or more $R_5$;

$R_5$ is independently selected from H, F, Cl, Br, CN, ═O, $C_{1-4}$ alkyl optionally substituted with one or more $R_e$, $C_{2-4}$ alkenyl optionally substituted with one or more $R_e$, $C_{2-4}$ alkynyl optionally substituted with one or more $R_e$, —$(CH_2)_r$$OR_b$, —$(CH_2)_r$$S(O)_p$$R_c$, —$(CH_2)_r$$S(O)_p$$NR_aR_a$, —$(CH_2)_r$$NR_a$$S(O)_p$$R_c$, —$(CH_2)_r$$NR_aR_a$, —$(CH_2)_r$$NR_a$C(═O)$R_b$, —$(CH_2)_r$N-$R_a$C(═O)$OR_b$, —$(CH_2)_r$$NR_a$C(═O)$NR_aR_a$, —$(CH_2)_r$C(═O)$R_b$, —$(CH_2)_r$C(═O)$OR_b$, —$(CH_2)_r$C(═O)$NR_aR_a$, —$(CH_2)_r$OC(═O)$R_b$, —$(CH_2)_r$OC(═O)$OR_b$, —$(CH_2)_r$O$(CH_2)$, —C(═O)$NR_aR_a$, $C_{3-6}$ cycloalkyl optionally substituted with one or more $R_e$, aryl optionally substituted with one or more $R_e$, and heterocyclyl optionally substituted with one or more $R_e$;

$R_6$ is independently selected from H, $C_{1-6}$ alkyl optionally substituted with one or more $R_e$, —$S(O)_p$$R_c$, —$S(O)_p$$NR_aR_a$, —C(═O)$R_b$, —C(═O)$OR_b$, —C(═O)$NR_aR_a$, $C_{3-6}$ cycloalkyl optionally substituted with one or more $R_e$, aryl optionally substituted with one or more $R_e$, and heterocyclyl optionally substituted with one or more $R_e$;

$R_7$ is independently selected from H, F, and Cl;

$R_8$ is independently selected from H, and $C_{1-6}$ alkyl optionally substituted with one or more substituents selected from F, Cl, and $C_{3-6}$ cycloalkyl;

$R_a$ is independently selected from H, $C_{1-6}$ alkyl optionally substituted with one or more $R_e$, $C_{2-6}$ alkenyl optionally substituted with one or more $R_e$, $C_{2-6}$ alkynyl optionally substituted with one or more $R_e$, —$(CH_2)_r$—$C_{3-10}$ carbocyclyl optionally substituted with one or more $R_e$, and —$(CH_2)_r$-heterocyclyl optionally substituted with one or more $R_e$; or $R_a$ and $R_a$ together with the nitrogen atom to which they are both attached form a heterocyclic ring optionally substituted with one or more $R_e$;

$R_b$ is independently selected from H, $C_{1-6}$ alkyl optionally substituted with one or more $R_e$, $C_{2-6}$ alkenyl optionally substituted with one or more $R_e$, $C_{2-6}$ alkynyl optionally substituted with one or more $R_e$, —$(CH_2)_r$—$C_{3-10}$ carbocyclyl optionally substituted with one or more $R_e$, and —$(CH_2)_r$ heterocyclyl optionally substituted with one or more $R_e$;

$R_c$ is independently selected from $C_{1-6}$ alkyl optionally substituted with one or more $R_e$, $C_{2-6}$ alkenyl optionally substituted with one or more $R_e$, $C_{2-6}$ alkynyl optionally substituted with one or more $R_e$, —$(CH_2)_r$—$C_{3-10}$ carbocyclyl optionally substituted with one or more $R_e$, and —$(CH_2)_r$-heterocyclyl optionally substituted with one or more $R_e$;

$R_d$ is independently selected from H, and $C_{1-6}$ alkyl optionally substituted with one or more $R_e$;

$R_e$ is independently selected from F, Cl, Br, CN, $NH_2$, —NH—$C_{1-4}$ alkyl, —N($C_{1-4}$ alkyl) 2, ═O, OH, —$OC_{1-6}$ alkyl, —$CO_2H$, $C_{1-6}$ alkyl optionally substituted with one or more $R_f$, $C_{2-6}$ alkenyl, $C_{2-6}$ alkynyl, —$(CH_2)_r$—$C_{3-6}$ cycloalkyl optionally substituted with one or more $R_f$, —$(CH_2)_r$-aryl optionally substituted with one or more $R_f$, and —$(CH_2)_r$-heterocyclyl optionally substituted with one or more $R_f$;

$R_f$ is independently selected from F, Cl, Br, CN, OH, $C_{1-5}$ alkyl optionally substituted with OH, $C_{2-5}$ alkenyl, $C_{2-5}$ alkynyl, $C_{3-6}$ cycloalkyl, and phenyl;

p, at each occurrence, is independently selected from zero, 1, and 2; and r, at each occurrence, is independently selected from zero, 1, 2, 3, and 4.

20. The compound according to claim 1, having Formula (XII):

(XII)

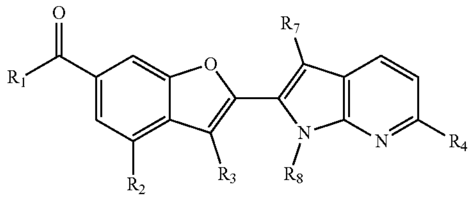

or a pharmaceutically acceptable salt thereof, wherein:

$R_1$ is independently selected from

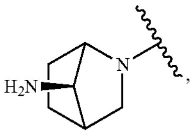, 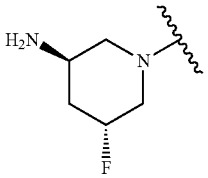,

-continued

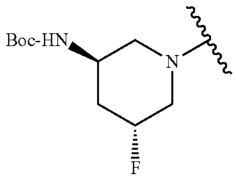, and 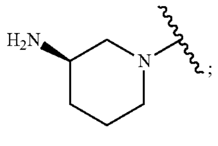;

$R_2$ is independently selected from H, F, $CH_3$, $CH_2OH$, $CH_2CH_2OH$ and $OCH_3$;

$R_3$ is independently selected from H, F, and $CH_3$, $CH_2OH$, $CH_2CH_2OH$, $CH_2NH_3$, $CH_2CH_2NH_2$, and $CH_2CH_2N_3$;

$R_4$ is independently selected from H, F, Cl, Br, —C(═O)$R_b$, $C_{1-6}$ alkyl optionally substituted with one or more substituents selected from F, Cl, OH, and $C_{3-6}$ cycloalkyl, —NH—$C_{1-6}$ alkyl optionally substituted with one or more substituents selected from F, Cl, OH, and $C_{3-6}$ cycloalkyl, —$(CH_2)_r$-aryl substituted with one or more $R_5$, —O—$C_{1-6}$ alkyl substituted with one or more $R_5$, —$(CH_2)_r$—$C_{3-12}$ cycloalkyl substituted with one or more $R_5$, and —$(CH_2)_r$-4-10 membered heterocyclyl comprising carbon atoms and 1-5 heteroatoms selected from N, $NR_6$, O, and S and substituted with one or more $R_5$;

$R_5$ is independently selected from H, F, Cl, Br, CN, ═O, $C_{1-4}$ alkyl optionally substituted with one or more $R_e$, $C_{2-4}$ alkenyl optionally substituted with one or more $R_e$, $C_{2-4}$ alkynyl optionally substituted with one or more $R_e$, —$(CH_2)_r$$OR_b$, —$(CH_2)_r$$S(O)_pR_c$, —$(CH_2)_r$$S(O)_pNR_aR_a$, —$(CH_2)_r$$NR_aS(O)_pR_c$, —$(CH_2)_r$$NR_aR_a$, —$(CH_2)_r$$NR_aC$(═O)$R_b$, —$(CH_2)_r$N-$R_aC$(═O)$OR_b$, —$(CH_2)_r$$NR_aC$(═O)$NR_aR_a$, —$(CH_2)_r$C(═O)$R_b$, —$(CH_2)_r$C(═O)$OR_b$, —$(CH_2)_r$C(═O)$NR_aR_a$, —$(CH_2)_r$OC(═O)$R_b$, —$(CH_2)_r$OC(═O)$OR_b$, —$(CH_2)_r$O$(CH_2)_r$C(═O)$NR_aR_a$, $C_{3-6}$ cycloalkyl optionally substituted with one or more $R_e$, aryl optionally substituted with one or more $R_e$, and heterocyclyl optionally substituted with one or more $R_e$;

$R_6$ is independently selected from H, $C_{1-6}$ alkyl optionally substituted with one or more $R_e$, —$S(O)_pR_c$, —$S(O)_pNR_aR_a$, —C(═O)$R_b$, —C(═O)$OR_b$, —C(═O)$NR_aR_a$, $C_{3-6}$ cycloalkyl optionally substituted with one or more $R_e$, aryl optionally substituted with one or more $R_e$, and heterocyclyl optionally substituted with one or more $R_e$;

$R_7$ is independently selected from H, F, and Cl;

$R_8$ is independently selected from H, and $C_{1-6}$ alkyl optionally substituted with one or more substituents selected from F, Cl, and $C_{3-6}$ cycloalkyl;

$R_a$ is independently selected from H, $C_{1-6}$ alkyl optionally substituted with one or more $R_e$, $C_{2-6}$ alkenyl optionally substituted with one or more $R_e$, $C_{2-6}$ alkynyl optionally substituted with one or more $R_e$, —$(CH_2)_r$—$C_{3-10}$ carbocyclyl optionally substituted with one or more $R_e$, and —$(CH_2)_r$-heterocyclyl optionally substituted with one or more $R_e$; or $R_a$ and $R_a$ together with the nitrogen atom to which they are both attached form a heterocyclic ring optionally substituted with one or more $R_e$;

$R_b$ is independently selected from H, $C_{1-6}$ alkyl optionally substituted with one or more $R_e$, $C_{2-6}$ alkenyl optionally substituted with one or more $R_e$, $C_{2-6}$ alkynyl optionally substituted with one or more $R_e$, —$(CH_2)_r$—$C_{3-10}$ carbocyclyl optionally substituted with one or more $R_e$, and —$(CH_2)_r$ heterocyclyl optionally substituted with one or more $R_e$;

$R_c$ is independently selected from $C_{1-6}$ alkyl optionally substituted with one or more $R_e$, $C_{2-6}$ alkenyl optionally substituted with one or more $R_e$, $C_{2-6}$ alkynyl optionally substituted with one or more $R_e$, —$(CH_2)_r$—$C_{3-10}$ carbocyclyl optionally substituted with one or more $R_e$, and —$(CH_2)_r$-heterocyclyl optionally substituted with one or more $R_e$;

$R_d$ is independently selected from H, and $C_{1-6}$ alkyl optionally substituted with one or more $R_e$;

$R_e$ is independently selected from F, Cl, Br, CN, $NH_2$, —NH—$C_{1-4}$ alkyl, —N($C_{1-4}$ alkyl)$_2$, ═O, OH, —$OC_{1-6}$ alkyl, —$CO_2H$, $C_{1-6}$ alkyl optionally substituted with one or more $R_f$, $C_{2-6}$ alkenyl, $C_{2-6}$ alkynyl, —$(CH_2)_r$—$C_{3-6}$ cycloalkyl optionally substituted with one or more $R_f$, —$(CH_2)_r$-aryl optionally substituted with one or more $R_f$, and —$(CH_2)_r$-heterocyclyl optionally substituted with one or more $R_f$;

$R_f$ is independently selected from F, Cl, Br, CN, OH, $C_{1-5}$ alkyl optionally substituted with OH, $C_{2-5}$ alkenyl, $C_{2-5}$ alkynyl, $C_{3-6}$ cycloalkyl, and phenyl;

p, at each occurrence, is independently selected from zero, 1, and 2; and r, at each occurrence, is independently selected from zero, 1, 2, 3, and 4.

21. The compound according to claim 1, or a pharmaceutically acceptable salt thereof, wherein;

$R_4$ is independently selected from H, F, Cl, Br,

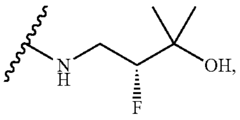 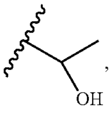, 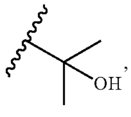,

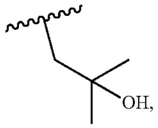 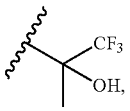 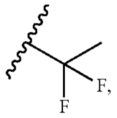

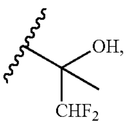 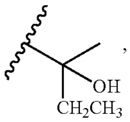, 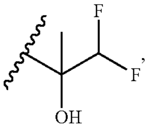,

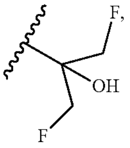 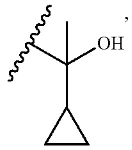, 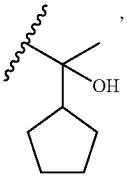,

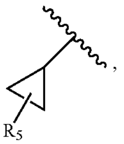, 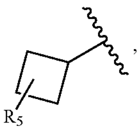, 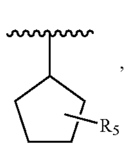,

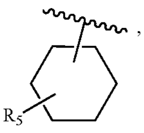, 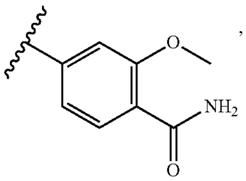,

-continued
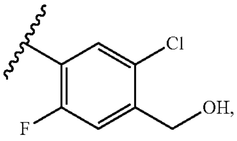 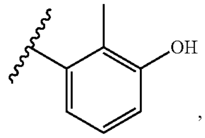 ,
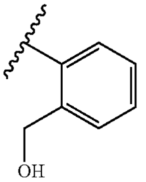 , 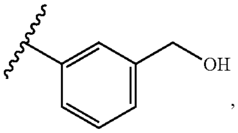 ,
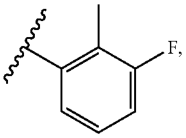 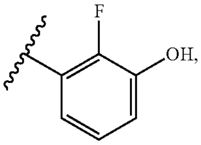
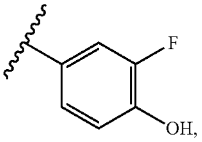 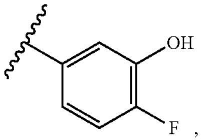 ,
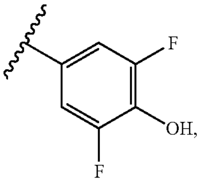 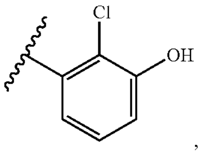 ,
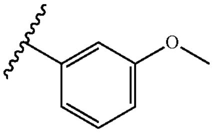 , 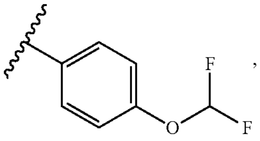 ,
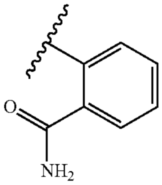 , 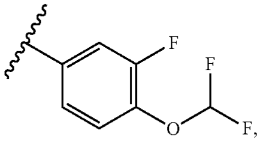
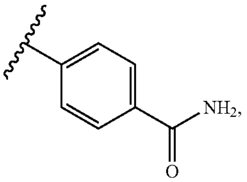 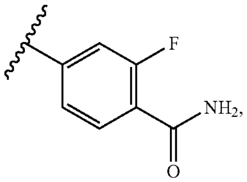
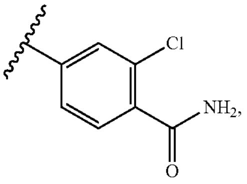 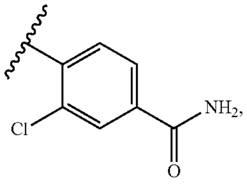
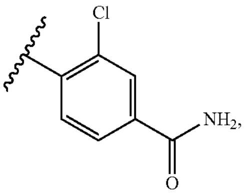 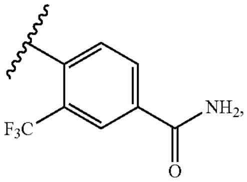
-continued
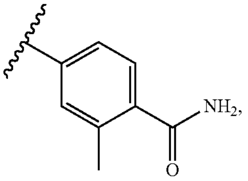 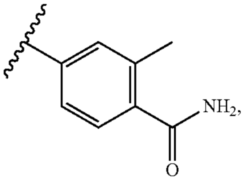
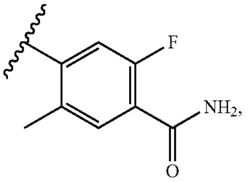 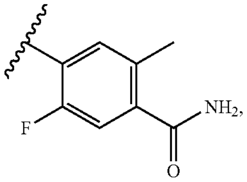
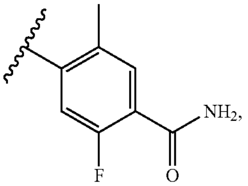 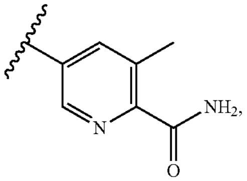
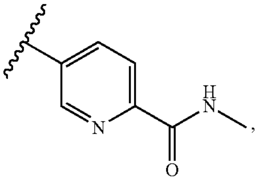 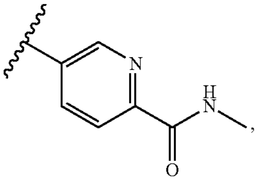
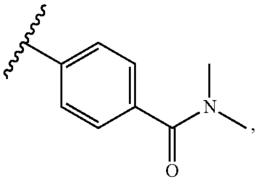 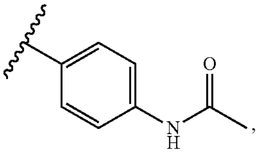
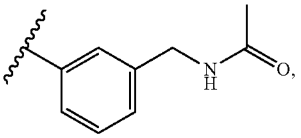
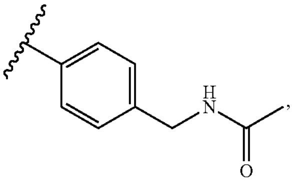
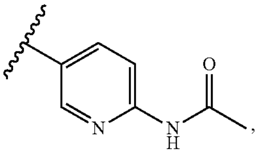
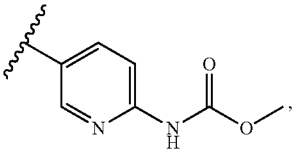
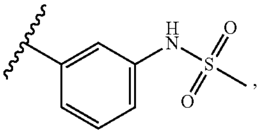

-continued
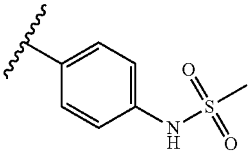,
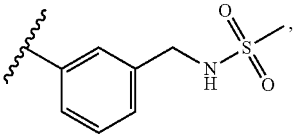,
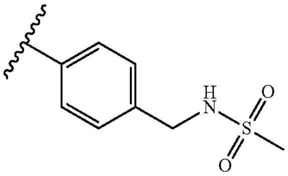, 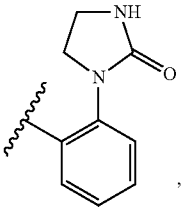,
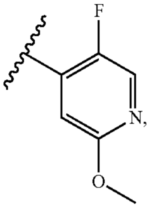 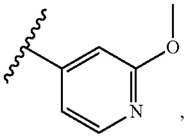,
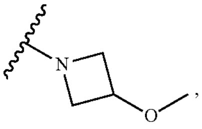, 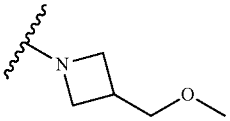,
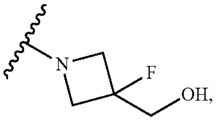 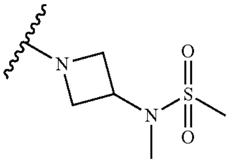,
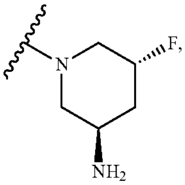 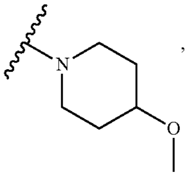,
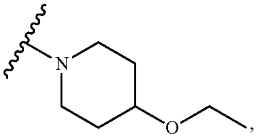 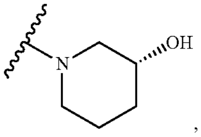,
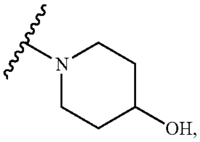 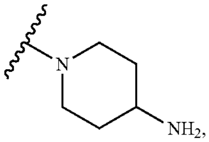
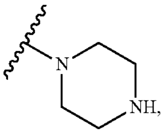 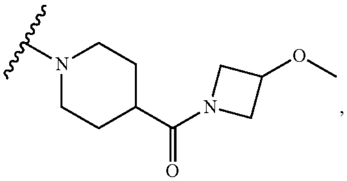,
-continued
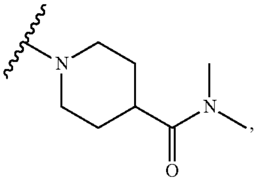
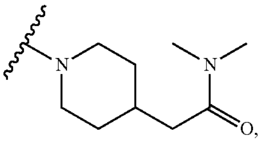
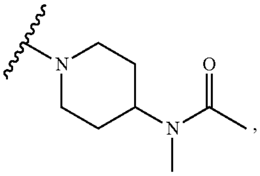
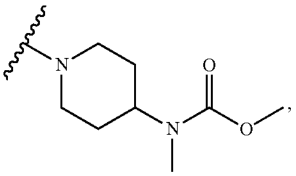
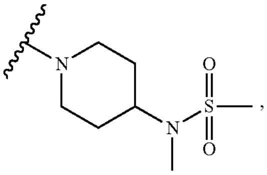, 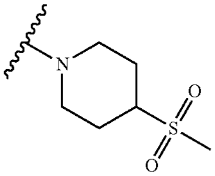,
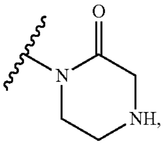 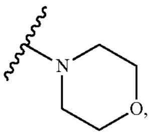 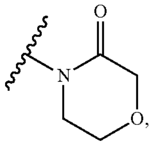
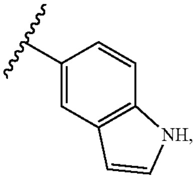 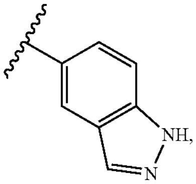
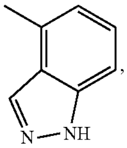, 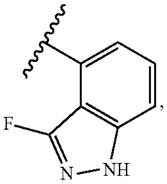,
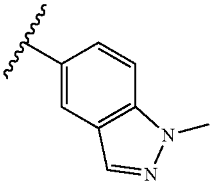, 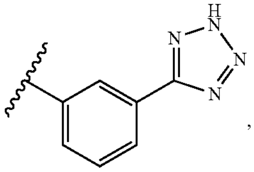, -continued
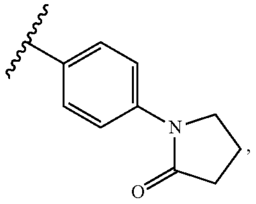
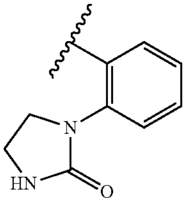
,
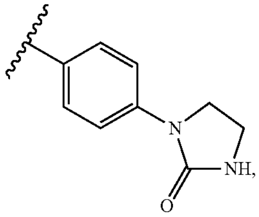
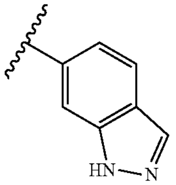
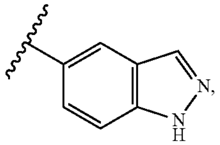
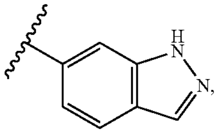
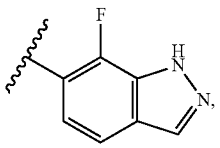
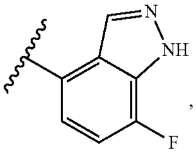
,
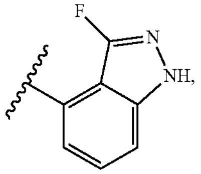
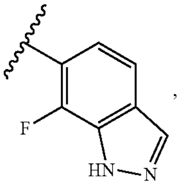
,
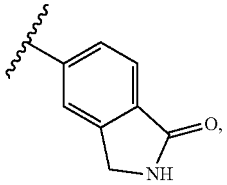
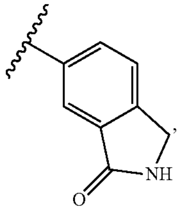
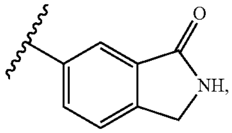
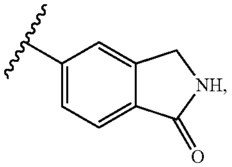
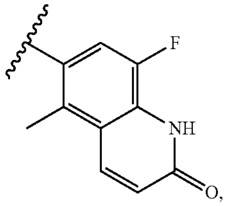
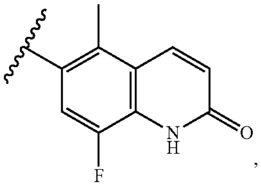
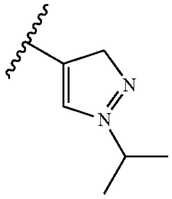
,
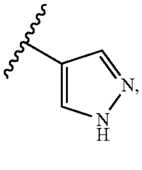
-continued
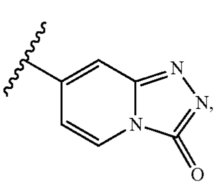
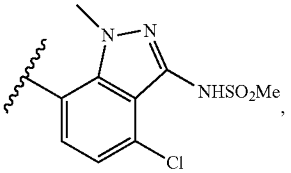
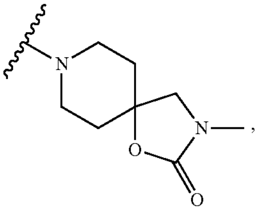
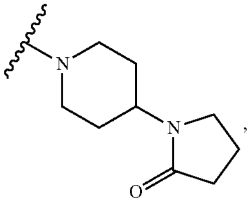
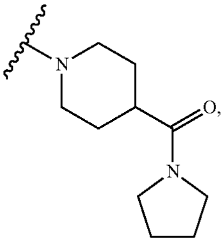
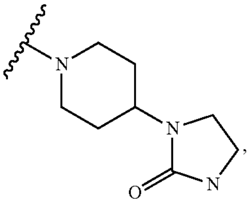
, and
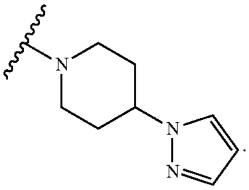
22. The compound according to claim 1, having Formula (XIII):
(XIII)
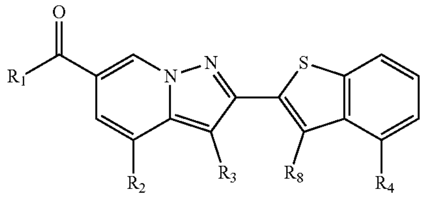
or a pharmaceutically acceptable salt thereof, wherein: $R_1$ is independently selected from
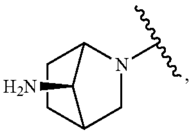
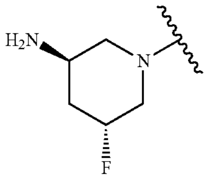
, and -continued

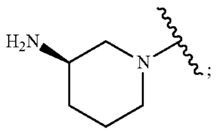

$R_2$ is independently selected from H, F, $CH_3$, and $OCH_3$;

$R_3$ is independently selected from H, F, and $CH_3$;

$R_4$ is independently selected from H, F, Cl, Br, —C(═O)$R_b$, $C_{1-6}$ alkyl optionally substituted with one or more substituents selected from F, Cl, OH, and $C_{3-6}$ cycloalkyl, —NH—$C_{1-6}$ alkyl optionally substituted with one or more substituents selected from F, Cl, OH, and $C_{3-6}$ cycloalkyl, —$(CH_2)_r$-aryl substituted with one or more $R_5$, —O—$C_{1-6}$ alkyl substituted with one or more $R_5$, —$(CH_2)_r$—$C_{3-12}$ cycloalkyl substituted with one or more $R_5$, and —$(CH_2)_r$-4-10 membered heterocyclyl comprising carbon atoms and 1-5 heteroatoms selected from N, $NR_6$, O, and S and substituted with one or more $R_5$;

$R_5$ is independently selected from H, F, Cl, Br, CN, ═O, $C_{1-4}$ alkyl optionally substituted with one or more $R_e$, $C_{2-4}$ alkenyl optionally substituted with one or more $R_e$, $C_{2-4}$ alkynyl optionally substituted with one or more $R_e$, —$(CH_2)_r$$OR_b$, —$(CH_2)_r$S$(O)_p$$R_c$, —$(CH_2)_r$S$(O)_p$$NR_aR_a$, —$(CH_2)_r$$NR_a$S$(O)_p$$R_c$, —$(CH_2)_r$$NR_aR_a$, —$(CH_2)_r$$NR_a$C(═O)$R_b$, —$(CH_2)_r$N-$R_a$C(═O)$OR_b$, —$(CH_2)_r$$NR_a$C(═O)$NR_aR_a$, —$(CH_2)_r$C(═O)$R_b$, —$(CH_2)_r$C(═O)$OR_b$, —$(CH_2)_r$C(═O)$NR_aR_a$, —$(CH_2)_r$OC(═O)$R_b$, —$(CH_2)_r$OC(═O)$OR_b$, —$(CH_2)_r$O$(CH_2)_r$C(═O)$NR_aR_a$, $C_{3-6}$ cycloalkyl optionally substituted with one or more $R_e$, aryl optionally substituted with one or more $R_e$, and heterocyclyl optionally substituted with one or more $R_e$, $R_6$ is independently selected from H, $C_{1-6}$ alkyl optionally substituted with one or more $R_e$, —S$(O)_p$$R_c$, —S$(O)_p$$NR_aR_a$, —C(═O)$R_b$, —C(═O)$OR_b$, —C(═O)$NR_aR_a$, $C_{3-6}$ cycloalkyl optionally substituted with one or more $R_e$, aryl optionally substituted with one or more $R_e$, and heterocyclyl optionally substituted with one or more $R_e$;

$R_7$ is independently selected from H, F, and Cl;

$R_8$ is independently selected from H, and $C_{1-6}$ alkyl optionally substituted with one or more substituents selected from F, Cl, and $C_{3-6}$ cycloalkyl;

$R_a$ is independently selected from H, $C_{1-6}$ alkyl optionally substituted with one or more $R_e$, $C_{2-6}$ alkenyl optionally substituted with one or more $R_e$, $C_{2-6}$ alkynyl optionally substituted with one or more $R_e$, —$(CH_2)_r$—$C_{3-10}$ carbocyclyl optionally substituted with one or more $R_e$, and —$(CH_2)_r$- heterocyclyl optionally substituted with one or more $R_e$; or $R_a$ and $R_a$ together with the nitrogen atom to which they are both attached form a heterocyclic ring optionally substituted with one or more $R_e$;

$R_b$ is independently selected from H, $C_{1-6}$ alkyl optionally substituted with one or more $R_e$, $C_{2-6}$ alkenyl optionally substituted with one or more $R_e$, $C_{2-6}$ alkynyl optionally substituted with one or more $R_e$, —$(CH_2)_r$—$C_{3-10}$ carbocyclyl optionally substituted with one or more $R_e$, and —$(CH_2)_r$- heterocyclyl optionally substituted with one or more $R_e$;

$R_c$ is independently selected from $C_{1-6}$ alkyl optionally substituted with one or more $R_e$, $C_{2-6}$ alkenyl optionally substituted with one or more $R_e$, $C_{2-6}$ alkynyl optionally substituted with one or more $R_e$, —$(CH_2)_r$—$C_{3-10}$ carbocyclyl optionally substituted with one or more $R_e$, and —$(CH_2)_r$-heterocyclyl optionally substituted with one or more $R_e$;

$R_d$ is independently selected from H, and $C_{1-6}$ alkyl optionally substituted with one or more $R_e$;

$R_e$ is independently selected from F, Cl, Br, CN, $NH_2$, —NH—$C_{1-4}$ alkyl, —N$(C_{1-4}$ alkyl$)_2$, ═O, OH, —$OC_{1-6}$ alkyl, —$CO_2H$, $C_{1-6}$ alkyl optionally substituted with one or more $R_f$, $C_{2-6}$ alkenyl, $C_{2-6}$ alkynyl, —$(CH_2)_r$—$C_{3-6}$ cycloalkyl optionally substituted with one or more $R_f$, —$(CH_2)_r$-aryl optionally substituted with one or more $R_f$, and —$(CH_2)_r$-heterocyclyl optionally substituted with one or more $R_f$;

$R_f$ is independently selected from F, Cl, Br, CN, OH, $C_{1-5}$ alkyl optionally substituted with OH, $C_{2-5}$ alkenyl, $C_{2-5}$ alkynyl, $C_{3-6}$ cycloalkyl, and phenyl;

p, at each occurrence, is independently selected from zero, 1, and 2; and r, at each occurrence, is independently selected from zero, 1, 2, 3, and 4.

23. The compound according to claim 1, having Formula (XIV):

(XIV)

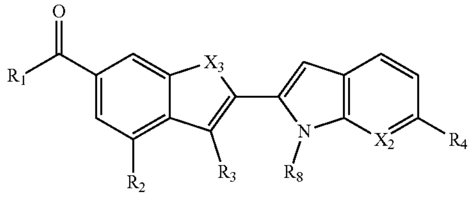

or a pharmaceutically acceptable salt thereof, wherein:

$X_2$ is independently selected from $CR_4$ and N;

$X_3$ is independently selected from O and S;

$R_1$ is independently selected from

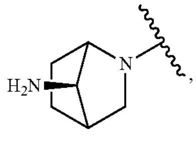 , 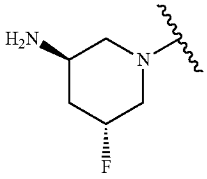 , and

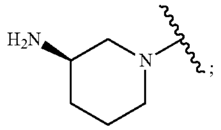

$R_2$ is independently selected from $CH_2OH$, $CH_2CH_2OH$ and $OCH_3$;

$R_3$ is independently selected from $CH_2OH$, $CH_2CH_2OH$, $CH_2NH_2$, $CH_2CH_2NH_2$, and $CH_2CH_2N_3$;

$R_4$ is independently selected from H and —O—$C_{1-4}$ alkyl substituted with one or more $R_5$; provided $R_4$ is not both —O—$C_{1-4}$ alkyl substituted with one or more $R_5$;

$R_5$ is independently selected from OH and heterocyclyl optionally substituted with one or more $R_e$;

$R_8$ is independently selected from H, and $C_{1-6}$ alkyl optionally substituted with $C_{3-6}$ cycloalkyl; and $R_e$ is independently selected from $NH_2$ and $C_{1-3}$ alkyl.

24. The compound according to claim 23, having Formula (XV):

(XV)

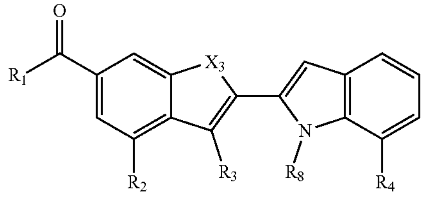

or a pharmaceutically acceptable salt thereof, wherein:

$R_4$ is independently selected from H, $OCH_3$, $OCH_2CH_2OH$,

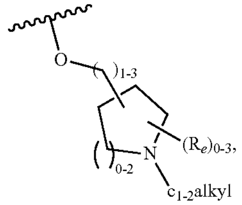

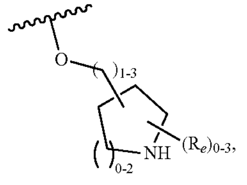

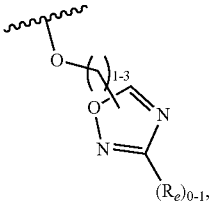

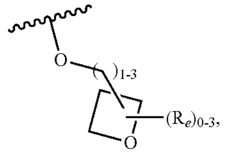

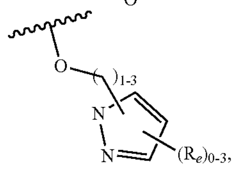

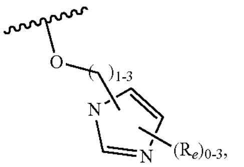

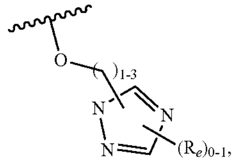

and

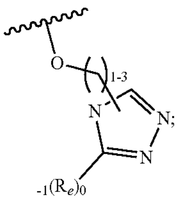

$R_8$ is $C_{1-3}$ alkyl substituted with $C_{3-6}$ cycloalkyl; and $R_e$ is independently selected from $NH_2$ and $C_{1-2}$ alkyl.

25. The compound according to claim 1, selected from:

5-(2-(6-((7R)-7-Amino-2-azabicyclo[2.2.1]-heptane-2-carbonyl)-4-methoxy-3-methylpyrazolo[1,5-a]pyridin-2-yl)-1-(cyclopropylmethyl)-1H-pyrrolo[2,3-b]pyridin-6-yl)isoindolin-1-one;

((7R)-7-Amino-2-azabicyclo[2.2.1]-heptan-2-yl)(2-(6-cyclopropyl-1-(cyclopropylmethyl)-1H-pyrrolo[2,3-b]pyridin-2-yl)-4-methoxy-3-methylpyrazolo[1,5-a]pyridin-6-yl)methanone;

5-(2-(6-((7R)-7-Amino-2-azabicyclo[2.2.1]-heptane-2-carbonyl)-4-methoxy-3-methylpyrazolo[1,5-a]pyridin-2-yl)-1-(cyclopropylmethyl)-1H-indol-6-yl)isoindolin-1-one;

((7R)-7-Amino-2-azabicyclo[2.2.1]heptan-2-yl)(2-(1-(cyclopropylmethyl)-6-(3-methyl-[1,2,4]triazolo[4,3-a]pyridin-7-yl)-1H-indol-2-yl)-4-methoxy-3-methylpyrazolo[1,5-a]pyridin-6-yl)methanone;

((7R)-7-Amino-2-azabicyclo[2.2.1]heptan-2-yl)(2-(1-(cyclopropylmethyl)-6-methyl-1H-indol-2-yl)-4-methoxy-3-methylpyrazolo[1,5-a]pyridin-6-yl)methanone;

3((7R)-7-Amino-2-azabicyclo[2.2.1]heptan-2-yl)(2-(1-(cyclopropylmethyl)-6-methyl-1H-pyrrolo[2,3-b]pyridin-2-yl)-4-fluoro-3-methylpyrazolo[1,5-a]pyridin-6-yl)methanone;

5-(2-(6-((7R)-7-Amino-2-azabicyclo[2.2.1]heptane-2-carbonyl)-4-fluoro-3-methylpyrazolo[1,5-a]pyridin-2-yl)-1-(cyclopropylmethyl)-1H-pyrrolo[2,3-b]pyridin-6-yl)isoindolin-1-one;

6-(2-(6-((7R)-7-Amino-2-azabicyclo[2.2.1]heptane-2-carbonyl)-4-fluoro-3-methylpyrazolo[1,5-a]pyridin-2-yl)-1-(cyclopropylmethyl)-1H-pyrrolo[2,3-b]pyridin-6-yl)isoindolin-1-one;

((7R)-7-Amino-2-azabicyclo[2.2.1]heptan-2-yl)(2-(1-(cyclopropylmethyl)-6-(2-fluoro-3-hydroxyphenyl)-1H-pyrrolo[2,3-b]pyridin-2-yl)-4-fluoro-3-methylpyrazolo[1,5-a]pyridin-6-yl)methanone;

((7R)-7-Amino-2-azabicyclo[2.2.1]heptan-2-yl)(2-(1-(cyclopropylmethyl)-6-(3-methyl-[1,2,4]triazolo[4,3-a]pyridin-7-yl)-1H-indol-2-yl)-4-fluoro-3-methylpyrazolo[1,5-a]pyridin-6-yl)methanone;

6-(2-(6-((7R)-7-Amino-2-azabicyclo[2.2.1]heptane-2-carbonyl)-3-methylpyrazolo[1,5-a]pyridin-2-yl)-1-(cyclopropylmethyl)-1H-pyrrolo[2,3-b]pyridin-6-yl)isoindolin-1-one;

((7R)-7-Amino-2-azabicyclo[2.2.1]heptan-2-yl)(2-(1-(cyclopropylmethyl)-6-(3-fluoro-4-hydroxyphenyl)-1H-pyrrolo[2,3-b]pyridin-2-yl)-3-methylpyrazolo[1,5-a]pyridin-6-yl)methanone;

((7R)-7-Amino-2-azabicyclo[2.2.1]heptan-2-yl)(2-(1-(cyclopropylmethyl)-6-(2-fluoro-3-hydroxyphenyl)-1H-pyrrolo[2,3-b]pyridin-2-yl)-3-methylpyrazolo[1,5-a]pyridin-6-yl)methanone;

4-(2-(6-((7R)-7-Amino-2-azabicyclo[2.2.1]heptane-2-carbonyl)-3-methylpyrazolo[1,5-a]pyridin-2-yl)-1-(cyclopropylmethyl)-1H-pyrrolo[2,3-b]pyridin-6-yl)-2-fluorobenzamide;

((7R)-7-Amino-2-azabicyclo[2.2.1]heptan-2-yl)(2-(1-(cyclopropylmethyl)-6-(3-methyl-[1,2,4]triazolo[4,3-a]pyridin-7-yl)-1H-pyrrolo[2,3-b]pyridin-2-yl)-3-methylpyrazolo[1,5-a]pyridin-6-yl)methanone;

((7R)-7-Amino-2-azabicyclo[2.2.1]heptan-2-yl)(2-(6-cyclopropyl-1-(cyclopropylmethyl)-1H-pyrrolo[2,3-b]pyridin-2-yl)-3-methylpyrazolo[1,5-a]pyridin-6-yl)methanone;

6-(2-(6-((7R)-7-Amino-2-azabicyclo[2.2.1]heptane-2-carbonyl)-3-methylpyrazolo[1,5-a]pyridin-2-yl)-1-(cyclopropylmethyl)-1H-indol-6-yl)isoindolin-1-one;

5-(2-(6-((7R)-7-Amino-2-azabicyclo[2.2.1]heptane-2-carbonyl)-3-methylpyrazolo[1,5-a]pyridin-2-yl)-1-(cyclopropylmethyl)-1H-indol-6-yl)isoindolin-1-one;

((7R)-7-Amino-2-azabicyclo[2.2.1]heptan-2-yl)(2-(1-(cyclopropylmethyl)-6-(2-hydroxypropan-2-yl)-1H-indol-2-yl)-4-methoxy-3-methylpyrazolo[1,5-a]pyridin-6-yl)methanone;

((3R,5R)-3-Amino-5-fluoropiperidin-1-yl)(2-(1-(cyclopropylmethyl)-6-(2-hydroxypropan-2-yl)-1H-indol-2-yl)-4-methoxy-3-methylpyrazolo[1,5-a]pyridin-6-yl)methanone;

((7R)-7-Amino-2-azabicyclo[2.2.1]heptan-2-yl)(2-(1-(cyclopropylmethyl)-6-(2-hydroxypropan-2-yl)-1H-indol-2-yl)-3-methylpyrazolo[1,5-a]pyridin-6-yl)methanone;

((7R)-7-Amino-2-azabicyclo[2.2.1]heptan-2-yl)(2-(1-(cyclopropylmethyl)-6-(1,1,1-trifluoro-2-hydroxypropan-2-yl)-1H-indol-2-yl)-3-methylpyrazolo[1,5-a]pyridin-6-yl)methanone;

((7R)-7-Amino-2-azabicyclo[2.2.1]heptan-2-yl)(2-(1-(cyclopropylmethyl)-6-(2-hydroxypropan-2-yl)-1H-pyrrolo[2,3-b]pyridin-2-yl)-3-methylpyrazolo[1,5-a]pyridin-6-yl)methanone;

((7R)-7-Amino-2-azabicyclo[2.2.1]heptan-2-yl)(2-(1-(cyclopropylmethyl)-6-(1,1,1-trifluoro-2-hydroxypropan-2-yl)-1H-pyrrolo[2,3-b]pyridin-2-yl)-3-methylpyrazolo[1,5-a]pyridin-6-yl)methanone;

((7R)-7-Amino-2-azabicyclo[2.2.1]heptan-2-yl)(2-(1-(cyclopropylmethyl)-6-(1-hydroxyethyl)-1H-pyrrolo[2,3-b]pyridin-2-yl)-3-methylpyrazolo[1,5-a]pyridin-6-yl)methanone;

((7R)-7-Amino-2-azabicyclo[2.2.1]heptan-2-yl)(2-(6-(4-aminopiperidin-1-yl)-1-(cyclopropylmethyl)-1H-indol-2-yl)-4-methoxy-3-methylbenzo[b]thiophen-6-yl)methanone;

((7R)-7-Amino-2-azabicyclo[2.2.1]heptan-2-yl)(2-(6-(4-aminopiperidin-1-yl)-1-(cyclopropylmethyl)-1H-indol-2-yl)-4-methoxy-3-methylbenzofuran-6-yl)methanone;

((7R)-7-Amino-2-azabicyclo[2.2.1]heptan-2-yl)(2-(1-(cyclopropylmethyl)-6-(3-methyl-[1,2,4]triazolo[4,3-a]pyridin-7-yl)-1H-pyrrolo[2,3-b]pyridin-2-yl)-3-methylbenzofuran-6-yl) methanonecyclopropylmethyl)-1H-indol-6-yl) isoindolin-1-one;

5-(2-(6-((7R)-7-Amino-2-azabicyclo[2.2.1]heptane-2-carbonyl)-3-methylbenzofuran-2-yl)-1-(cyclopropylmethyl)-1H-pyrrolo[2,3-b]pyridin-6-yl)isoindolin-1-one;

((7R)-7-Amino-2-azabicyclo[2.2.1]heptan-2-yl)(2-(1-(cyclopropylmethyl)-6-(3-methyl-[1,2,4]triazolo[4,3-a]pyridin-7-yl)-1H-indol-2-yl)-3-methylbenzofuran-6-yl)methanone;

((7R)-7-Amino-2-azabicyclo[2.2.1]heptan-2-yl)(2-(1-(cyclopropylmethyl)-6-methyl-1H-indol-2-yl)-3-methylbenzofuran-6-yl)methanone;

4-(2-(6-((7R)-7-Amino-2-azabicyclo[2.2.1]heptane-2-carbonyl)-3-methylbenzofuran-2-yl)-1-(cyclopropylmethyl)-1H-indol-6-yl)-2-fluorobenzamide;

((7R)-7-Amino-2-azabicyclo[2.2.1]heptan-2-yl)(2-(1-(cyclopropylmethyl)-6-(2-methoxypyridin-4-yl)-1H-indol-2-yl)-3-methylbenzofuran-6-yl)methanone;

((7R)-7-Amino-2-azabicyclo[2.2.1]heptan-2-yl)(2-(1-(cyclopropylmethyl)-6-(4-methoxypiperidin-1-yl)-1H-indol-2-yl)-3-methylbenzofuran-6-yl)methanone;

((7R)-7-Amino-2-azabicyclo[2.2.1]heptan-2-yl)(2-(6-(4-aminopiperidin-1-yl)-1-(cyclopropylmethyl)-1H-indol-2-yl)-3-methylbenzofuran-6-yl)methanone;

((7R)-7-Amino-2-azabicyclo[2.2.1]heptan-2-yl)(2-(1-(cyclopropylmethyl)-6-(2-hydroxypropan-2-yl)-1H-pyrrolo[2,3-b]pyridin-2-yl)-4-methoxy-3-methylbenzofuran-6-yl)methanone;

((7R)-7-Amino-2-azabicyclo[2.2.1]heptan-2-yl)(2-(1-(cyclopropylmethyl)-6-(2-hydroxypropan-2-yl)-1H-indol-2-yl)-3-methylbenzofuran-6-yl)methanone;

N-[5-(2-{6-[(3R,5R)-3-Amino-5-fluoropiperidine-1-carbonyl]-4-methoxy-3-methylpyrazolo[1,5-a]pyridin-2-yl}-1-(cyclopropylmethyl)-1H-indol-6-yl) pyridin-2-yl] acetamide;

(3R,5R)-1-{2-[1-(Cyclopropylmethyl)-6-(4-methanesulfonylpiperidin-1-yl)-1H-indol-2-yl]-4-methoxy-3-methylpyrazolo[1,5-a]pyridine-6-carbonyl}-5-fluoropiperidin-3-amine;

3-(2-{6-[(7R)-7-Amino-2-azabicyclo[2.2.1]heptane-2-carbonyl]-4-fluoro-3-methylpyrazolo[1,5-a]pyridin-2-yl}-1-(cyclopropylmethyl)-1H-pyrrolo[2,3-b]pyridin-6-yl)-2-methylphenol;

5-(2-{6-[(7R)-7-Amino-2-azabicyclo[2.2.1]heptane-2-carbonyl]-4-fluoro-3-methylpyrazolo[1,5-a]pyridin-2-yl}-1-(cyclopropylmethyl)-1H-pyrrolo[2,3-b]pyridin-6-yl)-N-methylpyridine-2-carboxamide;

4-(2-{6-[(7R)-7-Amino-2-azabicyclo[2.2.1]heptane-2-carbonyl]-4-fluoro-3-methylpyrazolo[1,5-a]pyridin-2-yl}-1-(cyclopropylmethyl)-1H-pyrrolo[2,3-b]pyridin-6-yl) morpholin-3-one;

(7R)-2-{2-[1-(Cyclopropylmethyl)-6-(4-methanesulfonylpiperidin-1-yl)-1H-pyrrolo[2,3-b]pyridin-2-yl]-4-fluoro-3-methylpyrazolo[1,5-a]pyridine-6-carbonyl}-2-azabicyclo[2.2.1]heptan-7-amine;

(7R)-2-{2-[1-(Cyclopropylmethyl)-6-{3-methyl-[1,2,4]triazolo[4,3-a]pyridin-7-yl}-1H-indol-2-yl]-4-fluoro-3-methylpyrazolo[1,5-a]pyridine-6-carbonyl}-2-azabicyclo[2.2.1]heptan-7-amine;

(7R)-2-{2-[1-(Cyclopropylmethyl)-6-(1H-indazol-4-yl)-1H-pyrrolo[2,3-b]pyridin-2-yl]-3-methylpyrazolo[1,5-a]pyridine-6-carbonyl}-2-azabicyclo[2.2.1]heptan-7-amine;

3-(2-{6-[(7R)-7-Amino-2-azabicyclo[2.2.1]heptane-2-carbonyl]-3-methylpyrazolo[1,5-a]pyridin-2-yl}-1-(cyclopropylmethyl)-1H-pyrrolo[2,3-b]pyridin-6-yl)-2-methylphenol;

1-[4-(2-{6-[(7R)-7-Amino-2-azabicyclo[2.2.1]heptane-2-carbonyl]-3-methylpyrazolo[1,5-a]pyridin-2-yl}-1-(cyclopropylmethyl)-1H-pyrrolo[2,3-b]pyridin-6-yl) phenyl]pyrrolidin-2-one;

4-(2-{6-[(7R)-7-Amino-2-azabicyclo[2.2.1]heptane-2-carbonyl]-3-methylpyrazolo[1,5-a]pyridin-2-yl}-1-(cyclopropylmethyl)-1H-pyrrolo[2,3-b]pyridin-6-yl)-2-fluoro-5-methylbenzamide;

(7R)-2-{2-[1-(Cyclopropylmethyl)-6-(7-fluoro-1H-indazol-6-yl)-1H-pyrrolo[2,3-b]pyridin-2-yl]-3-methylpyrazolo[1,5-a]pyridine-6-carbonyl}-2-azabicyclo[2.2.1]heptan-7-amine;

Methyl N-[5-(2-{6-[(7R)-7-amino-2-azabicyclo[2.2.1]heptane-2-carbonyl]-3-methylpyrazolo[1,5-a]pyridin-2-yl}-1-(cyclopropylmethyl)-1H-pyrrolo[2,3-b]pyridin-6-yl) pyridin-2-yl]carbamate;

4-(2-{6-[(7R)-7-Amino-2-azabicyclo[2.2.1]heptane-2-carbonyl]-3-methylpyrazolo[1,5-a]pyridin-2-yl}-1-(cyclopropylmethyl)-1H-pyrrolo[2,3-b]pyridin-6-yl) morpholin-3-one;

1-[4-(2-{6-[(7R)-7-Amino-2-azabicyclo[2.2.1]heptane-2-carbonyl]-3-methylpyrazolo[1,5-a]pyridin-2-yl}-1-(cyclopropylmethyl)-1H-indol-6-yl)phenyl]pyrrolidin-2-one;

(7R)-2-{2-[1-(Cyclopropylmethyl)-6-(1H-indazol-6-yl)-1H-indol-2-yl]-3-methylpyrazolo[1,5-a]pyridine-6-carbonyl}-2-azabicyclo[2.2.1]heptan-7-amine;

(7R)-2-{2-[1-(Cyclopropylmethyl)-6-(1H-indazol-5-yl)-1H-indol-2-yl]-3-methylpyrazolo[1,5-a]pyridine-6-carbonyl}-2-azabicyclo[2.2.1]heptan-7-amine;

N-[7-(2-{6-[(7R)-7-Amino-2-azabicyclo[2.2.1]heptane-2-carbonyl]-3-methylpyrazolo[1,5-a]pyridin-2-yl}-1-(cyclopropylmethyl)-1H-indol-6-yl)-4-chloro-1-methyl-1H-indazol-3-yl]methanesulfonamide;

1-[2-(2-{6-[(7R)-7-Amino-2-azabicyclo[2.2.1]heptane-2-carbonyl]-3-methylpyrazolo[1,5-a]pyridin-2-yl}-1-(cyclopropylmethyl)-1H-indol-6-yl)phenyl]imidazolidin-2-one;

4-(2-{6-[(7R)-7-Amino-2-azabicyclo[2.2.1]heptane-2-carbonyl]-3-methylpyrazolo[1,5-a]pyridin-2-yl}-1-(cyclopropylmethyl)-1H-indol-6-yl)-2-chlorobenzamide;

(7R)-2-{2-[1-(Cyclopropylmethyl)-6-(1H-pyrazol-4-yl)-1H-indol-2-yl]-3-methylpyrazolo[1,5-a]pyridine-6-carbonyl}-2-azabicyclo[2.2.1]heptan-7-amine;

(7R)-2-{2-[1-(Cyclopropylmethyl)-6-(morpholin-4-yl)-1H-indol-2-yl]-3-methylpyrazolo[1,5-a]pyridine-6-carbonyl}-2-azabicyclo[2.2.1]heptan-7-amine;

(3R,5R)-1-{2-[1-(Cyclopropylmethyl)-6-[4-(pyrrolidine-1-carbonyl) piperidin-1-yl]-1H-indol-2-yl]-3-methylpyrazolo[1,5-a]pyridine-6-carbonyl}-5-fluoropiperidin-3-amine;

3-[1-(2-{6-[(3R,5R)-3-Amino-5-fluoropiperidine-1-carbonyl]-3-methylpyrazolo[1,5-a]pyridin-2-yl}-1-(cyclopropylmethyl)-1H-indol-6-yl) piperidin-4-yl]-1,3-oxazolidin-2-one;

2-(2-{6-[(7R)-7-Amino-2-azabicyclo[2.2.1]heptane-2-carbonyl]-3-methylpyrazolo[1,5-a]pyridin-2-yl}-1-(cyclopropylmethyl)-1H-pyrrolo[2,3-b]pyridin-6-yl)-1,1-difluoropropan-2-ol;

2-(2-{6-[(7R)-7-Amino-2-azabicyclo[2.2.1]heptane-2-carbonyl]-4-fluoro-3-methylpyrazolo[1,5-a]pyridin-2-yl}-1-(cyclopropylmethyl)-1H-pyrrolo[2,3-b]pyridin-6-yl)-1,1,1-trifluoropropan-2-ol;

((3R,5R)-3-Amino-5-fluoropiperidin-1-yl)(2-(1-(cyclopropylmethyl)-7-(1-(tetrahydro-2H-pyran-2-carbonyl) piperidin-4-yl)-1H-indol-2-yl)-4-methoxy-3-methylpyrazolo[1,5-a]pyridin-6-yl)methanone;

((3R,5R)-3-Amino-5-fluoropiperidin-1-yl)(2-(1-(cyclopropylmethyl)-7-(1-(3-hydroxycyclobutane-1-carbonyl) piperidin-4-yl)-1H-indol-2-yl)-4-methoxy-3-methylpyrazolo[1,5-a]pyridin-6-yl)methanone;

((3R,5R)-3-Amino-5-fluoropiperidin-1-yl)(2-(1-(cyclopropylmethyl)-7-(1-((1r,4r)-4-hydroxycyclohexane-1-carbonyl) piperidin-4-yl)-1H-indol-2-yl)-4-methoxy-3-methylpyrazolo[1,5-a]pyridin-6-yl)methanone;

(R)-(3-Aminopiperidin-1-yl)(2-(1-(cyclopropylmethyl)-7-(1-(3-hydroxycyclobutane-1-carbonyl) piperidin-4-yl)-1H-indol-2-yl)-4-methoxy-3-methylpyrazolo[1,5-a]pyridin-6-yl)methanone;

((3R,5R)-3-Amino-5-fluoropiperidin-1-yl)(2-(1-(cyclopropylmethyl)-7-(1-(tetrahydrofuran-2-carbonyl) piperidin-4-yl)-1H-indol-2-yl)-4-methoxy-3-methylpyrazolo[1,5-a]pyridin-6-yl)methanone;

((3R,5R)-3-Amino-5-fluoropiperidin-1-yl)(2-(1-(cyclopropylmethyl)-7-(1-(tetrahydrofuran-2-carbonyl) piperidin-4-yl)-1H-indol-2-yl)-4-methoxy-3-methylpyrazolo[1,5-a]pyridin-6-yl) methanone;

(R)-(3-Aminopiperidin-1-yl)(2-(1-(cyclopropylmethyl)-7-(1-(3-hydroxy-3-(trifluoromethyl)cyclobutane-1-carbonyl) piperidin-4-yl)-1H-indol-2-yl)-4-methoxy-3-methylpyrazolo[1,5-a]pyridin-6-yl)methanone;

((3R,5R)-3-Amino-5-fluoropiperidin-1-yl)(2-(1-(cyclopropylmethyl)-7-(1-(3-hydroxy-3-(trifluoromethyl)cyclobutane-1-carbonyl) piperidin-4-yl)-1H-indol-2-yl)-4-methoxy-3-methylpyrazolo[1,5-a]pyridin-6-yl) methanone;

(R)-1-(4-(2-(6-(3-Aminopiperidine-1-carbonyl)-4-methoxy-3-methylpyrazolo[1,5-a]pyridin-2-yl)-1-(cyclopropylmethyl)-1H-indol-7-yl) piperidin-1-yl)-2-methoxyethan-1-one;

(S)-1-(4-(2-(6-((3R,5R)-3-Amino-5-fluoropiperidine-1-carbonyl)-4-methoxy-3-methylpyrazolo[1,5-a]pyridin-2-yl)-1-(cyclopropylmethyl)-1H-indol-7-yl) piperidin-1-yl)-2-methoxypropan-1-one;

1-(4-(2-(6-((3R,5R)-3-Amino-5-fluoropiperidine-1-carbonyl)-4-methoxy-3-methylpyrazolo[1,5-a]pyridin-2-yl)-1-(cyclopropylmethyl)-1H-indol-7-yl) piperidin-1-yl)-2-methoxyethan-1-one;

((3R,5R)-3-Amino-5-fluoropiperidin-1-yl)(2-(1-(cyclopropylmethyl)-7-(1-((1s,4s)-4-hydroxycyclohexane-1-carbonyl) piperidin-4-yl)-1H-indol-2-yl)-4-methoxy-3-methylpyrazolo[1,5-a]pyridin-6-yl)methanone;

((R)-3-Aminopiperidin-1-yl)(2-(1-(cyclopropylmethyl)-7-(1-((1r,4r)-4-hydroxycyclohexane-1-carbonyl) piperidin-4-yl)-1H-indol-2-yl)-4-methoxy-3-methylpyrazolo[1,5-a]pyridin-6-yl)methanone;

((3R,5R)-3-Amino-5-fluoropiperidin-1-yl)(2-(1-(cyclopropylmethyl)-7-(1-((1r,4r)-4-hydroxycyclohexane-1-carbonyl) piperidin-4-yl)-1H-indol-2-yl)-4-methoxy-3-methylpyrazolo[1,5-a]pyridin-6-yl)methanone;

1-(4-(2-(6-((7R)-7-Amino-2-azabicyclo[2.2.1]heptane-2-carbonyl)-4-methoxy-3-methylpyrazolo[1,5-a]pyridin-2-yl)-1-(cyclopropylmethyl)-1H-indol-7-yl) piperidin-1-yl) ethan-1-one;

(R)-1-(4-(2-(6-(3-Aminopiperidine-1-carbonyl)-4-fluoro-3-methylpyrazolo[1,5-a]pyridin-2-yl)-1-(cyclopropylmethyl)-1H-indol-7-yl) piperidin-1-yl) ethan-1-one;

(R)-1-(4-(2-(6-((3R,5R)-3-Amino-5-fluoropiperidine-1-carbonyl)-4-fluoro-3-methylpyrazolo[1,5-a]pyridin-2-yl)-1-(cyclopropylmethyl)-1H-indol-7-yl) piperidin-1-yl)-2-methoxypropan-1-one;

(R)-1-(4-(2-(6-((R)-3-Aminopiperidine-1-carbonyl)-4-fluoro-3-methylpyrazolo[1,5-a]pyridin-2-yl)-1-(cyclopropylmethyl)-1H-indol-7-yl) piperidin-1-yl)-2-methoxypropan-1-one;

1-(4-(2-(6-((3R,5R)-3-Amino-5-fluoropiperidine-1-carbonyl)-4-fluoro-3-methylpyrazolo[1,5-a]pyridin-2-yl)-1-(cyclopropylmethyl)-1H-indol-7-yl) piperidin-1-yl) ethan-1-one;

1-(4-(2-(6-((3R,5R)-3-Amino-5-fluoropiperidine-1-carbonyl)-4-fluoro-3-methylpyrazolo[1,5-a]pyridin-2-yl)-1-(cyclopropylmethyl)-1H-indol-7-yl) piperidin-1-yl)-2-methoxyethan-1-one;

1-(4-(2-(6-((3R,5R)-3-amino-5-fluoropiperidine-1-carbonyl)-3-methylpyrazolo[1,5-a]pyridin-2-yl)-1-(cyclopropylmethyl)-1H-indol-7-yl) piperidin-1-yl)-2-hydroxyethan-1-one;

(R)-1-(4-(2-(6-(3-aminopiperidine-1-carbonyl)-3-methylpyrazolo[1,5-a]pyridin-2-yl)-1-(cyclopropylmethyl)-1H-indol-7-yl) piperidin-1-yl)-2-hydroxyethan-1-one;

1-(4-(2-(6-((3R,5R)-3-amino-5-fluoropiperidine-1-carbonyl)-3-methylpyrazolo[1,5-a]pyridin-2-yl)-1-(cyclopropylmethyl)-1H-indol-7-yl) piperidin-1-yl)-2-ethoxyethan-1-one;

((3R,5R)-3-amino-5-fluoropiperidin-1-yl)(2-(1-(cyclopropylmethyl)-7-(1-((1s,4s)-4-hydroxycyclohexane-1-carbonyl) piperidin-4-yl)-1H-indol-2-yl)-3-methylpyrazolo[1,5-a]pyridin-6-yl)methanone;

((3R,5R)-3-amino-5-fluoropiperidin-1-yl)(2-(1-(cyclopropylmethyl)-7-(1-((1R,3S)-3-hydroxycyclohexane-1-carbonyl) piperidin-4-yl)-1H-indol-2-yl)-3-methylpyrazolo[1,5-a]pyridin-6-yl)methanone;

((R)-3-aminopiperidin-1-yl)(2-(1-(cyclopropylmethyl)-7-(1-((1s,4s)-4-hydroxycyclohexane-1-carbonyl) piperidin-4-yl)-1H-indol-2-yl)-3-methylpyrazolo[1,5-a]pyridin-6-yl)methanone;

((3R,5R)-3-amino-5-fluoropiperidin-1-yl)(2-(1-(cyclopropylmethyl)-7-(1-((1r,4r)-4-hydroxycyclohexane-1-carbonyl) piperidin-4-yl)-1H-indol-2-yl)-3-methylpyrazolo[1,5-a]pyridin-6-yl)methanone;

1-(4-(2-(6-((3R,5R)-3-amino-5-fluoropiperidine-1-carbonyl)-3-methylpyrazolo[1,5-a]pyridin-2-yl)-1-(cyclopropylmethyl)-1H-indol-7-yl) piperidin-1-yl) ethan-1-one;

1-(4-(2-(6-((7R)-7-amino-2-azabicyclo[2.2.1]heptane-2-carbonyl)-3-methylpyrazolo[1,5-a]pyridin-2-yl)-1-(cyclopropylmethyl)-1H-indol-7-yl) piperidin-1-yl)-2-methoxyethan-1-one;

(R)-(3-aminopiperidin-1-yl)(2-(1-(cyclopropylmethyl)-7-(1-(3-hydroxy-3-(trifluoromethyl)cyclobutane-1-carbonyl) piperidin-4-yl)-1H-indol-2-yl)-3-methylpyrazolo[1,5-a]pyridin-6-yl)methanone;

((R)-3-aminopiperidin-1-yl)(2-(1-(cyclopropylmethyl)-7-(1-(tetrahydro-2H-pyran-2-carbonyl) piperidin-4-yl)-1H-indol-2-yl)-3-methylpyrazolo[1,5-a]pyridin-6-yl) methanone;

((R)-3-aminopiperidin-1-yl)(2-(1-(cyclopropylmethyl)-7-(1-(tetrahydrofuran-2-carbonyl) piperidin-4-yl)-1H-indol-2-yl)-3-methylpyrazolo[1,5-a]pyridin-6-yl)methanone;

(4-(2-(6-((7R)-7-amino-2-azabicyclo[2.2.1]heptane-2-carbonyl)-3-methylpyrazolo[1,5-a]pyridin-2-yl)-1-(cyclopropylmethyl)-1H-indol-7-yl) piperidin-1-yl)(3-hydroxycyclobutyl)methanone;

Methyl 4-(2-(6-((7R)-7-amino-2-azabicyclo[2.2.1]heptane-2-carbonyl)-3-methylpyrazolo[1,5-a]pyridin-2-yl)-1-(cyclopropylmethyl)-1H-indol-7-yl) piperidine-1-carboxylate;

(2R)-1-(4-(2-(6-((7R)-7-Amino-2-azabicyclo[2.2.1]heptane-2-carbonyl)-3-methylpyrazolo[1,5-a]pyridin-2-yl)-1-(cyclopropylmethyl)-1H-indol-7-yl) piperidin-1-yl)-2-hydroxypropan-1-one;

(4-(2-(6-((7R)-7-Amino-2-azabicyclo[2.2.1]heptane-2-carbonyl)-3-methylpyrazolo[1,5-a]pyridin-2-yl)-1-(cyclopropylmethyl)-1H-indol-7-yl) piperidin-1-yl) (thiophen-2-yl)methanone;

1-(4-(2-(6-((3R,5R)-3-Amino-5-fluoropiperidine-1-carbonyl)-3-methylpyrazolo[1,5-a]pyridin-2-yl)-1-(cyclopropylmethyl)-1H-indol-7-yl) piperidin-1-yl) ethan-1-one;

1-(4-(2-(6-((7R)-7-Amino-2-azabicyclo[2.2.1]heptane-2-carbonyl)-3-methylpyrazolo[1,5-a]pyridin-2-yl)-1-(cyclopropylmethyl)-1H-indol-7-yl) piperidin-1-yl) ethan-1-one;

1-(4-(2-(6-((3R,5R)-3-Amino-5-fluoropiperidine-1-carbonyl)-3-methylpyrazolo[1,5-a]pyridin-2-yl)-1-(cyclopropylmethyl)-5-fluoro-1H-indol-7-yl) piperidin-1-yl)-3-methylbutan-1-one;

((3R,5R)-3-Amino-5-fluoropiperidin-1-yl)(2-(1-(cyclopropylmethyl)-5-fluoro-7-(1-(3-hydroxycyclobutane-1-carbonyl) piperidin-4-yl)-1H-indol-2-yl)-3-methylpyrazolo[1,5-a]pyridin-6-yl)methanone;

(R)-1-(4-(2-(6-((R)-3-Aminopiperidine-1-carbonyl)-3-methylpyrazolo[1,5-a]pyridin-2-yl)-1-(cyclopropylmethyl)-5-fluoro-1H-indol-7-yl) piperidin-1-yl)-2-methoxypropan-1-one;

((R)-3-Aminopiperidin-1-yl)(2-(1-(cyclopropylmethyl)-5-fluoro-7-(1-(tetrahydro-2H-pyran-2-carbonyl) piperidin-4-yl)-1H-indol-2-yl)-3-methylpyrazolo[1,5-a]pyridin-6-yl)methanone;

1-(4-(2-(6-((3R,5R)-3-Amino-5-fluoropiperidine-1-carbonyl)-4-methoxy-3-methylpyrazolo[1,5-a]pyridin-2-yl)-1-(cyclopropylmethyl)-1H-pyrrolo[2,3-c]pyridin-7-yl) piperidin-1-yl)-2-methoxyethan-1-one;

((3R,5R)-3-Amino-5-fluoropiperidin-1-yl)(2-(1-(cyclopropylmethyl)-7-(1-((1s,4s)-4-hydroxycyclohexane-1-carbonyl) azetidin-3-yl)-1H-indol-2-yl)-4-methoxy-3-methylpyrazolo[1,5-a]pyridin-6-yl)methanone;

1-(3-(2-(6-((3R,5R)-3-Amino-5-fluoropiperidine-1-carbonyl)-4-methoxy-3-methylpyrazolo[1,5-a]pyridin-2-yl)-1-(cyclopropylmethyl)-1H-indol-7-yl) azetidin-1-yl)-2-methoxyethan-1-one;

((R)-3-Aminopiperidin-1-yl)(2-(1-(cyclopropylmethyl)-7-(1-((1r,4r)-4-hydroxycyclohexane-1-carbonyl) azetidin-3-yl)-1H-indol-2-yl)-3-methylpyrazolo[1,5-a]pyridin-6-yl)methanone;

1-(3-(2-(6-((7R)-7-Amino-2-azabicyclo[2.2.1]heptane-2-carbonyl)-3-methylpyrazolo[1,5-a]pyridin-2-yl)-1-(cyclopropylmethyl)-1H-indol-7-yl) azetidin-1-yl) ethan-1-one;

4-(((2-(6-((R)-3-Aminopiperidine-1-carbonyl)-4-methoxy-3-methylpyrazolo[1,5-a]pyridin-2-yl)-1-(cyclopropylmethyl)-1H-indol-7-yl)oxy)methyl)pyrrolidin-2-one;

(R)-(2-(7-(2-(1H-1,2,4-Triazol-1-yl) ethoxy)-1-(cyclopropylmethyl)-1H-indol-2-yl)-4-methoxy-3-methylpyrazolo[1,5-a]pyridin-6-yl)(3-aminopiperidin-1-yl) methanone;

(2-(7-(2-(1H-1,2,4-Triazol-1-yl) ethoxy)-1-(cyclopropylmethyl)-1H-indol-2-yl)-4-methoxy-3-methylpyrazolo [1,5-a]pyridin-6-yl)((3R,5R)-3-amino-5-fluoropiperidin-1-yl)methanone;

(2-(7-(2-(4-Amino-1H-pyrazol-1-yl) ethoxy)-1-(cyclopropylmethyl)-1H-indol-2-yl)-4-methoxy-3-methylpyrazolo[1,5-a]pyridin-6-yl)((3R,5R)-3-amino-5-fluoropiperidin-1-yl)methanone;

4-(((2-(6-((R)-3-Aminopiperidine-1-carbonyl)-4-methoxy-3-methylpyrazolo[1,5-a]pyridin-2-yl)-1-(cyclopropylmethyl)-1H-indol-7-yl)oxy)methyl)pyrrolidin-2-one;

4-(((2-(6-((3R,5R)-3-Amino-5-fluoropiperidine-1-carbonyl)-4-methoxy-3-methylpyrazolo[1,5-a]pyridin-2-yl)-1-(cyclopropylmethyl)-1H-indol-7-yl)oxy)methyl) pyrrolidin-2-one;

4-(((2-(6-((R)-3-Aminopiperidine-1-carbonyl)-4-fluoro-3-methylpyrazolo[1,5-a]pyridin-2-yl)-1-(cyclopropylmethyl)-1H-indol-7-yl)oxy)methyl)pyrrolidin-2-one;

4-(((2-(6-((3R,5R)-3-Amino-5-fluoropiperidine-1-carbonyl)-4-fluoro-3-methylpyrazolo[1,5-a]pyridin-2-yl)-1-(cyclopropylmethyl)-1H-indol-7-yl)oxy)methyl)pyrrolidin-2-one;

(S)-5-(((2-(6-((R)-3-Aminopiperidine-1-carbonyl)-4-fluoro-3-methylpyrazolo[1,5-a]pyridin-2-yl)-1-(cyclopropylmethyl)-1H-indol-7-yl)oxy)methyl) pyrrolidin-2-one;

4-(((2-(6-((R)-3-Aminopiperidine-1-carbonyl)-4-fluoro-3-methylpyrazolo[1,5-a]pyridin-2-yl)-1-(cyclopropylmethyl)-1H-indol-7-yl)oxy)methyl)pyrrolidin-2-one;

(2-(7-(2-(1H-Imidazol-1-yl)ethoxy)-1-(cyclopropylmethyl)-1H-indol-2-yl)-3-methylpyrazolo[1,5-a]pyridin-6-yl)((3R,5R)-3-amino-5-fluoropiperidin-1-yl)methanone;

(2-(7-(2-(1H-1,2,4-Triazol-1-yl)ethoxy)-1-(cyclopropylmethyl)-1H-indol-2-yl)-3-methylpyrazolo[1,5-a]pyridin-6-yl)((3R,5R)-3-amino-5-fluoropiperidin-1-yl) methanone;

(S)-5-(((2-(6-((R)-3-Aminopiperidine-1-carbonyl)-3-methylpyrazolo[1,5-a]pyridin-2-yl)-1-(cyclopropylmethyl)-1H-indol-7-yl)oxy)methyl)pyrrolidin-2-one;

4-(((2-(6-((3R,5R)-3-Amino-5-fluoropiperidine-1-carbonyl)-3-methylpyrazolo[1,5-a]pyridin-2-yl)-1-(cyclopropylmethyl)-1H-indol-7-yl)oxy)methyl)pyrrolidin-2-one;

4-(((2-(6-((R)-3-Aminopiperidine-1-carbonyl)-4-methoxy-3-methylpyrazolo[1,5-a]pyridin-2-yl)-1-(cyclopropylmethyl)-1H-pyrrolo[2,3-c]pyridin-7-yl)oxy)methyl)pyrrolidin-2-one;

(2-(7-(2-(1H-1,2,4-Triazol-1-yl)ethoxy)-1-(cyclopropylmethyl)-1H-pyrrolo[2,3-c]pyridin-2-yl)-4-methoxy-3-methylpyrazolo[1,5-a]pyridin-6-yl)((3R,5R)-3-amino-5-fluoropiperidin-1-yl)methanone;

(2-(7-(2-(1H-Imidazol-1-yl)ethoxy)-1-(cyclopropylmethyl)-1H-pyrrolo[2,3-c]pyridin-2-yl)-4-methoxy-3-methylpyrazolo[1,5-a]pyridin-6-yl)((3R,5R)-3-amino-5-fluoropiperidin-1-yl) methanone;

(R)-(2-(7-(2-(1H-Imidazol-1-yl) ethoxy)-1-(cyclopropylmethyl)-1H-pyrrolo[2,3-c]pyridin-2-yl)-4-methoxy-3-methylpyrazolo[1,5-a]pyridin-6-yl)(3-aminopiperidin-1-yl)methanone;

(R)-(2-(7-(2-(4H-1,2,4-Triazol-4-yl)ethoxy)-1-(cyclopropylmethyl)-1H-pyrrolo[2,3-c]pyridin-2-yl)-4-methoxy-3-methylpyrazolo[1,5-a]pyridin-6-yl)(3-aminopiperidin-1-yl)methanone;

(2-(7-(2-(4H-1,2,4-Triazol-4-yl) ethoxy)-1-(cyclopropylmethyl)-1H-pyrrolo[2,3-c]pyridin-2-yl)-4-methoxy-3-methylpyrazolo[1,5-a]pyridin-6-yl)((3R,5R)-3-amino-5-fluoropiperidin-1-yl)methanone;

4-(((2-(6-((3R,5R)-3-Amino-5-fluoropiperidine-1-carbonyl)-4-methoxy-3-methylpyrazolo[1,5-a]pyridin-2-yl)-1-(cyclopropylmethyl)-1H-pyrrolo[2,3-c]pyridin-7-yl)oxy)methyl)pyrrolidin-2-one;

4-(((2-(6-((3R,5R)-3-Amino-5-fluoropiperidine-1-carbonyl)-4-methoxy-3-methylpyrazolo[1,5-a]pyridin-2-yl)-1-(cyclopropylmethyl)-1H-pyrrolo[2,3-c]pyridin-7-yl)oxy)methyl)pyrrolidin-2-one;

(5R)-5-(((2-(6-((7R)-7-Amino-2-azabicyclo[2.2.1]heptane-2-carbonyl)-4-methoxy-3-methylpyrazolo[1,5-a]pyridin-2-yl)-1-(cyclopropylmethyl)-1H-pyrrolo[2,3-c]pyridin-7-yl)oxy)methyl)pyrrolidin-2-one;

4-(((2-(6-((7R)-7-Amino-2-azabicyclo[2.2.1]heptane-2-carbonyl)-4-methoxy-3-methylpyrazolo[1,5-a]pyridin-2-yl)-1-(cyclopropylmethyl)-1H-pyrrolo[2,3-c]pyridin-7-yl)oxy)methyl)pyrrolidin-2-one;

(5R)-5-(((2-(6-((7S)-7-Amino-2-azabicyclo[2.2.1]heptane-2-carbonyl)-4-methoxy-3-methylpyrazolo[1,5-a]pyridin-2-yl)-1-(cyclopropylmethyl)-1H-pyrrolo[2,3-c]pyridin-7-yl)oxy)methyl)pyrrolidin-2-one;

4-(((2-(6-((7R)-7-Amino-2-azabicyclo[2.2.1]heptane-2-carbonyl)-4-methoxy-3-methylpyrazolo[1,5-a]pyridin-2-yl)-1-(cyclopropylmethyl)-1H-pyrrolo[2,3-c]pyridin-7-yl)oxy)methyl)pyrrolidin-2-one;

(R)-(2-(7-(2-(4H-1,2,4-Triazol-4-yl) ethoxy)-1-(cyclopropylmethyl)-1H-pyrrolo[2,3-c]pyridin-2-yl)-3-methylpyrazolo[1,5-a]pyridin-6-yl)(3-aminopiperidin-1-yl) methanone;

(2-(7-(2-(1H-Imidazol-1-yl) ethoxy)-1-(cyclopropylmethyl)-1H-pyrrolo[2,3-c]pyridin-2-yl)-3-methylpyrazolo[1,5-a]pyridin-6-yl)((3R,5R)-3-amino-5-fluoropiperidin-1-yl)methanone;

(R)-(2-(7-(2-(1H-Imidazol-1-yl) ethoxy)-1-(cyclopropylmethyl)-1H-pyrrolo[2,3-c]pyridin-2-yl)-3-methylpyrazolo[1,5-a]pyridin-6-yl)(3-aminopiperidin-1-yl)methanone;

4-(((2-(6-((R)-3-Aminopiperidine-1-carbonyl)-3-methylpyrazolo[1,5-a]pyridin-2-yl)-1-(cyclopropylmethyl)-1H-pyrrolo[2,3-c]pyridin-7-yl)oxy)methyl)pyrrolidin-2-one;

4-(((2-(6-((R)-3-Aminopiperidine-1-carbonyl)-3-methylpyrazolo[1,5-a]pyridin-2-yl)-1-(cyclopropylmethyl)-1H-pyrrolo[2,3-c]pyridin-7-yl)oxy)methyl)pyrrolidin-2-one;

or a pharmaceutically acceptable salt thereof.

26. A pharmaceutical composition comprising a compound according to claim 1, or a stereoisomer, an enantiomer, a diastereomer, a tautomer, or a pharmaceutically acceptable salt thereof, and one or more pharmaceutically acceptable carriers.

27. A method for treating a disease or a disorder associated with PAD4 enzyme activity, comprising administering to a subject in need of such treatment a therapeutically effective amount of at least one compound according to claim 1, or a stereoisomer, an enantiomer, a diastereomer, a tautomer, or a pharmaceutically acceptable salt thereof.

28. A method for treating a disease or a disorder associated with PAD4 enzyme activity, comprising administering to a subject in need of such treatment a therapeutically effective amount of a composition according to claim 26.

29. The method according to claim 27, wherein the disease or the disorder associated with PAD4 enzyme activity is selected from rheumatoid arthritis, Alzheimer's disease, multiple sclerosis, lupus, Parkinson's disease, and cancer.

* * * * *